(12) United States Patent
Mainolfi et al.

(10) Patent No.: US 12,091,411 B2
(45) Date of Patent: Sep. 17, 2024

(54) IRAK DEGRADERS AND USES THEREOF

(71) Applicant: Kymera Therapeutics, Inc., Watertown, MA (US)

(72) Inventors: Nello Mainolfi, Belmont, MA (US); Chris De Savi, Watertown, MA (US); Matthew M. Weiss, Boston, MA (US); Xiao Zhu, Winchester, MA (US); Xiaozhang Zheng, Lexington, MA (US); Bruce C. Follows, Watertown, MA (US)

(73) Assignee: Kymera Therapeutics, Inc., Watertown, MA (US)

( * ) Notice: Subject to any disclaimer, the term of this patent is extended or adjusted under 35 U.S.C. 154(b) by 0 days.

(21) Appl. No.: 18/162,365

(22) Filed: Jan. 31, 2023

(65) Prior Publication Data

US 2023/0365562 A1 Nov. 16, 2023

Related U.S. Application Data

(60) Provisional application No. 63/374,297, filed on Sep. 1, 2022, provisional application No. 63/365,741, filed on Jun. 2, 2022, provisional application No. 63/363,687, filed on Apr. 27, 2022, provisional application No. 63/269,581, filed on Mar. 18, 2022, provisional application No. 63/268,341, filed on Feb. 22, 2022, provisional application No. 63/267,372, filed on Jan. 31, 2022.

(51) Int. Cl.
*C07D 471/10* (2006.01)
*A61K 45/06* (2006.01)

(52) U.S. Cl.
CPC .......... *C07D 471/10* (2013.01); *A61K 45/06* (2013.01)

(58) Field of Classification Search
CPC ................................................. C07D 471/10
See application file for complete search history.

(56) References Cited

U.S. PATENT DOCUMENTS

| | | |
|---|---|---|
| 4,045,485 A | 8/1977 | Fried et al. |
| 4,650,750 A | 3/1987 | Giese |
| 4,709,016 A | 11/1987 | Giese |
| 5,217,866 A | 6/1993 | Summerton et al. |
| 5,360,811 A | 11/1994 | Tegeler et al. |
| 5,360,819 A | 11/1994 | Giese |
| 5,516,931 A | 5/1996 | Giese et al. |
| 5,602,273 A | 2/1997 | Giese et al. |
| 5,604,104 A | 2/1997 | Giese et al. |
| 5,610,020 A | 3/1997 | Giese et al. |
| 5,650,270 A | 7/1997 | Giese et al. |
| 5,721,246 A | 2/1998 | Yoshino et al. |
| 6,306,663 B1 | 10/2001 | Kenten et al. |
| 6,552,065 B2 | 4/2003 | Remiszewski et al. |
| 6,559,280 B2 | 5/2003 | Kenten et al. |
| 6,627,754 B2 | 9/2003 | Blumenkopf et al. |
| 6,949,537 B2 | 9/2005 | Garlich et al. |
| 7,041,298 B2 | 5/2006 | Deshaies et al. |
| 7,071,189 B2 | 7/2006 | Kawashima et al. |
| 7,074,620 B2 | 7/2006 | Kenten et al. |
| 7,173,015 B2 | 2/2007 | Schreiber et al. |
| 7,208,157 B2 | 4/2007 | Dashaies et al. |
| 7,273,920 B2 | 9/2007 | Kenten et al. |
| 7,307,077 B2 | 12/2007 | Kawashima et al. |
| 7,390,799 B2 | 6/2008 | Bruncko et al. |
| 7,402,325 B2 | 7/2008 | Addington |
| 7,449,458 B2 | 11/2008 | Bhamidipati et al. |
| 7,501,496 B1 | 3/2009 | Endl et al. |
| 7,514,444 B2 | 4/2009 | Honigberg et al. |
| 7,528,143 B2 | 5/2009 | Noronha et al. |
| 7,557,210 B2 | 7/2009 | Singh et al. |
| 7,598,257 B2 | 10/2009 | Rodgers et al. |
| 7,622,496 B2 | 11/2009 | Larsen et al. |
| 7,667,039 B2 | 2/2010 | Garcia-Echeverria et al. |
| 7,713,943 B2 | 5/2010 | Klippel-Giese et al. |
| 7,781,433 B2 | 8/2010 | Chuckowree et al. |
| 7,932,260 B2 | 4/2011 | Fowler et al. |
| 7,989,622 B2 | 8/2011 | Bajjalieh et al. |
| 8,138,347 B2 | 3/2012 | Knight et al. |
| 8,185,616 B2 | 5/2012 | Nagata et al. |
| 8,217,035 B2 | 7/2012 | Burger et al. |
| 8,338,439 B2 | 12/2012 | Singh et al. |
| 8,486,941 B2 | 7/2013 | Burns et al. |
| 8,906,682 B2 | 12/2014 | June et al. |
| 9,334,320 B2 | 5/2016 | Okun et al. |
| 9,500,653 B2 | 11/2016 | Crews et al. |
| 9,632,089 B2 | 4/2017 | Crews et al. |
| 9,694,084 B2 | 7/2017 | Bradner et al. |
| 9,750,816 B2 | 9/2017 | Bradner et al. |
| 9,770,512 B2 | 9/2017 | Bradner et al. |
| 9,821,068 B2 | 11/2017 | Bradner et al. |
| 9,969,710 B2 | 5/2018 | Jorand-Lebrun et al. |
| 10,125,114 B2 | 11/2018 | Bradner et al. |
| 10,294,229 B2 | 5/2019 | Gardner et al. |
| 10,336,744 B2 | 7/2019 | Harling et al. |

(Continued)

FOREIGN PATENT DOCUMENTS

CN 105085620 B 5/2018
WO WO1996007655 A1 3/1996

(Continued)

OTHER PUBLICATIONS

Adams, et al., "Big opportunities for small molecules in immuno-oncology," Nature Reviews: Drug Discovery, 2015, 14(9):603-622.

(Continued)

*Primary Examiner* — Matthew P Coughlin
*Assistant Examiner* — Meghan C Heasley
(74) *Attorney, Agent, or Firm* — Dechert LLP; Andrea L.C. Reid; Todd K. Macklin

(57) ABSTRACT

The present invention provides compounds, compositions thereof, and methods of using the same.

9 Claims, No Drawings

(56) References Cited

U.S. PATENT DOCUMENTS

| | | |
|---|---|---|
| 10,874,743 B2 | 12/2020 | Mainolfi et al. |
| 11,065,231 B2 | 7/2021 | Crew et al. |
| 11,117,889 B1 | 9/2021 | Mainolfi et al. |
| 11,292,792 B2 | 4/2022 | Ji et al. |
| 11,318,205 B1 | 5/2022 | Mainolfi et al. |
| 11,352,350 B2 | 6/2022 | Mainolfi et al. |
| 11,358,948 B2 | 6/2022 | Mainolfi et al. |
| 11,512,080 B2 | 11/2022 | Mainolfi et al. |
| 11,542,261 B2 | 1/2023 | Starczynowski et al. |
| 11,591,332 B2 | 2/2023 | Weiss et al. |
| 11,685,750 B2 | 6/2023 | Zheng et al. |
| 11,707,457 B2 | 7/2023 | Weiss |
| 11,723,980 B2 | 8/2023 | Mainolfi et al. |
| 11,773,103 B2 | 10/2023 | Rong et al. |
| 2001/0053782 A1 | 12/2001 | Blumenkopf et al. |
| 2002/0042427 A1 | 4/2002 | Tang et al. |
| 2002/0068063 A1 | 6/2002 | Deshaies et al. |
| 2002/0183360 A1 | 12/2002 | Muller et al. |
| 2003/0045552 A1 | 3/2003 | Robarge et al. |
| 2003/0136944 A1 | 7/2003 | Takehara et al. |
| 2004/0029902 A1 | 2/2004 | Singh et al. |
| 2004/0048859 A1 | 3/2004 | Germann et al. |
| 2004/0106569 A1 | 6/2004 | Klippel-Giese et al. |
| 2004/0116421 A1 | 6/2004 | Kawashima et al. |
| 2004/0242631 A1 | 12/2004 | Garlich et al. |
| 2005/0014802 A1 | 1/2005 | Attardo et al. |
| 2005/0075306 A1 | 4/2005 | Schreiber et al. |
| 2006/0211657 A1 | 9/2006 | Singh et al. |
| 2007/0098719 A1 | 5/2007 | Smith et al. |
| 2007/0135461 A1 | 6/2007 | Rodgers et al. |
| 2007/0191405 A1 | 8/2007 | Noronha et al. |
| 2008/0076768 A1 | 3/2008 | Chuckowree et al. |
| 2008/0108636 A1 | 5/2008 | Honigberg et al. |
| 2008/0194579 A1 | 8/2008 | Garcia-Echeverria et al. |
| 2008/0275067 A1 | 11/2008 | Fowler et al. |
| 2009/0055944 A1 | 2/2009 | Korman et al. |
| 2009/0136494 A1 | 5/2009 | Ponath et al. |
| 2009/0233903 A1 | 9/2009 | Rodgers et al. |
| 2010/0087440 A1 | 4/2010 | Bajjalieh et al. |
| 2010/0150892 A1 | 6/2010 | Han |
| 2010/0197671 A1 | 8/2010 | Burns et al. |
| 2010/0197686 A1 | 8/2010 | Xing et al. |
| 2010/0203056 A1 | 8/2010 | Irving et al. |
| 2010/0233183 A1 | 9/2010 | Triebel et al. |
| 2010/0234377 A1 | 9/2010 | Aicher et al. |
| 2010/0247554 A1 | 9/2010 | Lemke et al. |
| 2010/0249092 A1 | 9/2010 | Singh et al. |
| 2010/0249126 A1 | 9/2010 | Burger et al. |
| 2010/0279316 A1 | 11/2010 | Gorelik et al. |
| 2011/0008331 A1 | 1/2011 | Triebel |
| 2011/0053941 A1 | 3/2011 | Mautino et al. |
| 2011/0136796 A1 | 6/2011 | Mautino et al. |
| 2011/0165156 A1 | 7/2011 | Dimoudis et al. |
| 2011/0196150 A1 | 8/2011 | Man et al. |
| 2011/0223611 A1 | 9/2011 | Salamone et al. |
| 2011/0274683 A1 | 11/2011 | Wong et al. |
| 2012/0015962 A1 | 1/2012 | Arora et al. |
| 2012/0189639 A1 | 7/2012 | Schebye et al. |
| 2012/0277217 A1 | 11/2012 | Mautino et al. |
| 2012/0283238 A1 | 11/2012 | Romero et al. |
| 2012/0329997 A1 | 12/2012 | Fertig et al. |
| 2013/0005949 A1 | 1/2013 | Fertig et al. |
| 2013/0149236 A1 | 6/2013 | Johnson et al. |
| 2013/0190340 A1 | 7/2013 | Hedstrom et al. |
| 2013/0231328 A1 | 9/2013 | Harriman et al. |
| 2013/0274241 A1 | 10/2013 | Jorand-Lebrun et al. |
| 2014/0018343 A1 | 1/2014 | Romero et al. |
| 2014/0018357 A1 | 1/2014 | Harriman et al. |
| 2014/0018361 A1 | 1/2014 | Harriman et al. |
| 2014/0066625 A1 | 3/2014 | Mautino et al. |
| 2014/0079699 A1 | 3/2014 | Wong et al. |
| 2014/0079706 A1 | 3/2014 | Cannarile et al. |
| 2014/0093511 A1 | 4/2014 | Lonberg et al. |
| 2014/0155379 A1 | 6/2014 | Ho et al. |
| 2014/0194404 A1 | 7/2014 | McElroy et al. |
| 2014/0302523 A1 | 10/2014 | Crews et al. |
| 2014/0329799 A1 | 11/2014 | Seganish et al. |
| 2014/0336363 A1 | 11/2014 | Fertig et al. |
| 2014/0341917 A1 | 11/2014 | Nastri et al. |
| 2014/0356322 A1 | 12/2014 | Crews et al. |
| 2015/0011532 A1 | 1/2015 | Paidi et al. |
| 2015/0018344 A1 | 1/2015 | Paidi et al. |
| 2015/0025093 A1 | 1/2015 | Romero et al. |
| 2015/0045347 A1 | 2/2015 | Dodd et al. |
| 2015/0094305 A1 | 4/2015 | Romero et al. |
| 2015/0133451 A1 | 5/2015 | Yoshida et al. |
| 2015/0141396 A1 | 5/2015 | Crosignani et al. |
| 2015/0191464 A1 | 7/2015 | Santella et al. |
| 2015/0225410 A1 | 8/2015 | Castro et al. |
| 2015/0225449 A1 | 8/2015 | Donnell et al. |
| 2015/0274708 A1 | 10/2015 | Seganish et al. |
| 2015/0274738 A1 | 10/2015 | Gray et al. |
| 2015/0284382 A1 | 10/2015 | Bhide et al. |
| 2015/0284405 A1 | 10/2015 | Trzupek et al. |
| 2015/0291562 A1 | 10/2015 | Crew et al. |
| 2015/0299224 A1 | 10/2015 | Seganish et al. |
| 2015/0329498 A1 | 11/2015 | Romero et al. |
| 2015/0374678 A1 | 12/2015 | Chamberlain et al. |
| 2015/0376167 A1 | 12/2015 | Jorand-Lebrun et al. |
| 2015/0376206 A1 | 12/2015 | Jorand-Lebrun et al. |
| 2016/0002265 A1 | 1/2016 | Jenkins et al. |
| 2016/0022642 A1 | 1/2016 | Crews et al. |
| 2016/0045607 A1 | 2/2016 | Crew et al. |
| 2016/0058872 A1 | 3/2016 | Crew et al. |
| 2016/0145252 A1 | 5/2016 | Jorand-Lebrun et al. |
| 2016/0176916 A1 | 6/2016 | Bradner et al. |
| 2016/0214972 A1 | 7/2016 | Jin et al. |
| 2016/0235730 A1 | 8/2016 | Bradner et al. |
| 2016/0235731 A1 | 8/2016 | Bradner et al. |
| 2016/0243247 A1 | 8/2016 | Bradner et al. |
| 2016/0256468 A1 | 9/2016 | Schafer et al. |
| 2016/0272596 A1 | 9/2016 | Chen et al. |
| 2016/0272639 A1 | 9/2016 | Crew et al. |
| 2016/0311833 A1 | 10/2016 | Bothe et al. |
| 2016/0311839 A1 | 10/2016 | Kelley et al. |
| 2016/0326151 A1 | 11/2016 | Gummadi et al. |
| 2016/0340366 A1 | 11/2016 | Gummadi et al. |
| 2017/0001990 A1 | 1/2017 | Chen et al. |
| 2017/0008896 A1 | 1/2017 | Dahmann et al. |
| 2017/0008904 A1 | 1/2017 | Crew et al. |
| 2017/0022189 A1 | 1/2017 | Zhang |
| 2017/0037004 A1 | 2/2017 | Crew et al. |
| 2017/0065719 A1 | 3/2017 | Qian et al. |
| 2017/0121321 A1 | 5/2017 | Crews et al. |
| 2017/0152263 A1 | 6/2017 | Gummadi et al. |
| 2017/0152273 A1 | 6/2017 | Merchant et al. |
| 2017/0204093 A1 | 7/2017 | Chan et al. |
| 2017/0247388 A1 | 8/2017 | Altman et al. |
| 2017/0281784 A1 | 10/2017 | Wang et al. |
| 2017/0327469 A1 | 11/2017 | Crew et al. |
| 2017/0369476 A1 | 12/2017 | Chen et al. |
| 2018/0009779 A1 | 1/2018 | Bradner et al. |
| 2018/0015087 A1 | 1/2018 | Liu et al. |
| 2018/0051027 A1 | 2/2018 | Lim et al. |
| 2018/0051028 A1 | 2/2018 | Lim et al. |
| 2018/0051029 A1 | 2/2018 | Lim et al. |
| 2018/0051030 A1 | 2/2018 | Lim et al. |
| 2018/0051035 A1 | 2/2018 | Lim et al. |
| 2018/0085465 A1 | 3/2018 | Bradner et al. |
| 2018/0118733 A1 | 3/2018 | Harling et al. |
| 2018/0127432 A1 | 5/2018 | Trzupek et al. |
| 2018/0134684 A1 | 5/2018 | Bradner et al. |
| 2018/0147202 A1 | 5/2018 | Crew et al. |
| 2018/0169097 A1 | 6/2018 | Hammerman et al. |
| 2018/0186799 A1 | 7/2018 | Gardner et al. |
| 2018/0194724 A1 | 7/2018 | Kemp et al. |
| 2018/0201609 A1 | 7/2018 | Gummadi et al. |
| 2018/0208605 A1 | 7/2018 | Gummadi et al. |
| 2018/0228907 A1 | 8/2018 | Crew et al. |
| 2018/0230157 A1 | 8/2018 | Bacon et al. |
| 2018/0298015 A1 | 10/2018 | Bryan et al. |
| 2018/0327419 A1 | 11/2018 | Bradner et al. |
| 2018/0370988 A1 | 12/2018 | Gummadi et al. |
| 2019/0071415 A1 | 3/2019 | Bradner et al. |

(56) References Cited

U.S. PATENT DOCUMENTS

| | | |
|---|---|---|
| 2019/0076539 A1 | 3/2019 | Phillips et al. |
| 2019/0076540 A1 | 3/2019 | Phillips et al. |
| 2019/0076541 A1 | 3/2019 | Phillips et al. |
| 2019/0076542 A1 | 3/2019 | Phillips et al. |
| 2019/0105322 A1 | 4/2019 | Macdonald et al. |
| 2019/0151295 A1 | 5/2019 | Crew et al. |
| 2019/0151457 A1 | 5/2019 | Bradner et al. |
| 2019/0192532 A1 | 6/2019 | Bradner et al. |
| 2019/0192668 A1 | 6/2019 | Mainolfi et al. |
| 2019/0276474 A1 | 9/2019 | Chan et al. |
| 2019/0374528 A1 | 12/2019 | Gray et al. |
| 2020/0010468 A1 | 1/2020 | Ji et al. |
| 2020/0103418 A1 | 4/2020 | Hackney et al. |
| 2020/0306273 A1 | 10/2020 | Yang et al. |
| 2020/0347045 A1 | 11/2020 | Mainolfi et al. |
| 2020/0377469 A1 | 12/2020 | Mainolfi et al. |
| 2021/0002296 A1 | 1/2021 | Mainolfi et al. |
| 2021/0147382 A1 | 5/2021 | Bellenie et al. |
| 2021/0228562 A1 | 7/2021 | Weiss |
| 2021/0323952 A1 | 10/2021 | Mainolfi et al. |
| 2021/0395273 A1 | 12/2021 | Zheng et al. |
| 2022/0054453 A1 | 2/2022 | Walker |
| 2022/0273668 A1 | 9/2022 | Gollob et al. |
| 2022/0274993 A1 | 9/2022 | Rong et al. |
| 2022/0306631 A1 | 9/2022 | Ji et al. |
| 2022/0324854 A1 | 10/2022 | Mainolfi et al. |
| 2022/0340570 A1 | 10/2022 | Weiss et al. |
| 2023/0038512 A1 | 2/2023 | Mainolfi et al. |
| 2023/0069104 A1 | 3/2023 | Mainolfi et al. |
| 2023/0089916 A1 | 3/2023 | Mainolfi et al. |
| 2023/0096599 A1 | 3/2023 | Zheng et al. |
| 2023/0101353 A1 | 3/2023 | Mainolfi et al. |
| 2023/0106066 A1 | 4/2023 | Mainolfi et al. |
| 2023/0122219 A1 | 4/2023 | Weiss et al. |
| 2023/0132715 A1 | 5/2023 | Ji et al. |
| 2023/0144292 A1 | 5/2023 | Weiss |
| 2023/0190940 A1 | 6/2023 | Zhang et al. |
| 2023/0219945 A1 | 7/2023 | Mainolfi et al. |
| 2023/0234936 A1* | 7/2023 | Feng ............... C07D 471/10 514/256 |
| 2023/0234950 A1 | 7/2023 | Mainolfi et al. |
| 2023/0234953 A1 | 7/2023 | Weiss et al. |
| 2023/0241075 A1 | 8/2023 | Campbell et al. |
| 2023/0250110 A1 | 8/2023 | Zheng |
| 2023/0257399 A1 | 8/2023 | Leong et al. |
| 2023/0277519 A1 | 9/2023 | Gollob et al. |
| 2023/0303526 A1 | 9/2023 | Mainolfi et al. |

FOREIGN PATENT DOCUMENTS

| | | |
|---|---|---|
| WO | 0110858 A1 | 2/2001 |
| WO | WO2001042246 A2 | 6/2001 |
| WO | WO2002020740 A2 | 3/2002 |
| WO | WO2002088112 A1 | 11/2002 |
| WO | WO2003063794 A2 | 8/2003 |
| WO | WO2004019973 A1 | 3/2004 |
| WO | WO2004089925 A1 | 10/2004 |
| WO | WO2004106328 A1 | 12/2004 |
| WO | WO2005007623 A2 | 1/2005 |
| WO | WO2005113554 A2 | 12/2005 |
| WO | WO2006029879 A2 | 3/2006 |
| WO | WO2006078846 A1 | 7/2006 |
| WO | WO2006105021 A2 | 10/2006 |
| WO | WO2006122806 A2 | 11/2006 |
| WO | WO2007005874 A2 | 1/2007 |
| WO | WO2007016176 A2 | 2/2007 |
| WO | WO2007044729 A2 | 4/2007 |
| WO | WO2007053452 A1 | 5/2007 |
| WO | WO2007070514 A1 | 6/2007 |
| WO | WO2007084786 A1 | 7/2007 |
| WO | WO2007129161 A2 | 11/2007 |
| WO | WO2008039218 A2 | 4/2008 |
| WO | WO2008109943 A1 | 9/2008 |
| WO | WO2008118802 A1 | 10/2008 |
| WO | WO2008132601 A1 | 11/2008 |
| WO | WO2009009116 A2 | 1/2009 |
| WO | WO2009044273 A2 | 4/2009 |
| WO | WO2009073620 A2 | 6/2009 |
| WO | WO2009114512 A1 | 9/2009 |
| WO | WO2009132238 A2 | 10/2009 |
| WO | WO2010019570 A2 | 2/2010 |
| WO | WO2010077634 A1 | 7/2010 |
| WO | WO2011028683 A1 | 3/2011 |
| WO | WO2011043371 A1 | 4/2011 |
| WO | WO2011056652 A1 | 5/2011 |
| WO | WO2011070024 A1 | 6/2011 |
| WO | WO2011090760 A1 | 7/2011 |
| WO | WO2011107553 A1 | 9/2011 |
| WO | WO2011109400 A2 | 9/2011 |
| WO | WO2011131407 A1 | 10/2011 |
| WO | WO2011140249 A2 | 11/2011 |
| WO | WO2012003281 A2 | 1/2012 |
| WO | WO2012007375 A1 | 1/2012 |
| WO | WO2012032433 A1 | 3/2012 |
| WO | WO2012068546 A1 | 5/2012 |
| WO | WO2012078559 A2 | 6/2012 |
| WO | WO2012084704 A1 | 6/2012 |
| WO | WO2012097013 A1 | 7/2012 |
| WO | WO2012129258 A1 | 9/2012 |
| WO | WO2012142237 A1 | 10/2012 |
| WO | WO2012145493 A1 | 10/2012 |
| WO | WO2013042137 A1 | 3/2013 |
| WO | WO2013066729 A1 | 5/2013 |
| WO | WO2013079174 A1 | 6/2013 |
| WO | WO2013087699 A1 | 6/2013 |
| WO | WO2013106535 A1 | 7/2013 |
| WO | WO2013106612 A1 | 7/2013 |
| WO | WO2013106614 A1 | 7/2013 |
| WO | WO2013106641 A1 | 7/2013 |
| WO | WO2013106643 A2 | 7/2013 |
| WO | WO2013106646 A2 | 7/2013 |
| WO | WO2013119716 A1 | 8/2013 |
| WO | WO2013132044 A1 | 9/2013 |
| WO | WO2013169264 A1 | 11/2013 |
| WO | WO2014008218 A1 | 1/2014 |
| WO | WO2014008992 A1 | 1/2014 |
| WO | WO2014011902 A1 | 1/2014 |
| WO | WO2014011906 A2 | 1/2014 |
| WO | WO2014011911 A2 | 1/2014 |
| WO | WO2014036357 A1 | 3/2014 |
| WO | WO2014044622 A1 | 3/2014 |
| WO | WO2014058685 A1 | 4/2014 |
| WO | WO2014058691 A1 | 4/2014 |
| WO | WO2014063061 A1 | 4/2014 |
| WO | WO2014074660 A1 | 5/2014 |
| WO | WO2014074675 A1 | 5/2014 |
| WO | WO2014108452 A1 | 7/2014 |
| WO | WO2014121931 A1 | 8/2014 |
| WO | WO2014121942 A1 | 8/2014 |
| WO | WO2014142237 A1 | 9/2014 |
| WO | WO2014143672 A1 | 9/2014 |
| WO | WO2015048281 A1 | 4/2015 |
| WO | WO2015068856 A1 | 5/2015 |
| WO | WO2015071393 A1 | 5/2015 |
| WO | WO2015091426 A1 | 6/2015 |
| WO | WO2015103453 A1 | 7/2015 |
| WO | WO2015104662 A1 | 7/2015 |
| WO | WO2015104688 A1 | 7/2015 |
| WO | WO2015150995 A1 | 10/2015 |
| WO | WO2015160845 A2 | 10/2015 |
| WO | WO2015164374 A1 | 10/2015 |
| WO | WO2015193846 A1 | 12/2015 |
| WO | WO2016011390 A1 | 1/2016 |
| WO | WO2016053769 A1 | 4/2016 |
| WO | WO2016053770 A1 | 4/2016 |
| WO | WO2016053771 A1 | 4/2016 |
| WO | WO2016053772 A1 | 4/2016 |
| WO | WO2016081679 A1 | 5/2016 |
| WO | WO2016105518 A1 | 6/2016 |
| WO | WO2016118666 A1 | 7/2016 |
| WO | WO2016144844 A1 | 9/2016 |
| WO | WO2016144846 A1 | 9/2016 |
| WO | WO2016144847 A1 | 9/2016 |

(56) References Cited

FOREIGN PATENT DOCUMENTS

| | | |
|---|---|---|
| WO | WO2016144848 A1 | 9/2016 |
| WO | WO2016144849 A1 | 9/2016 |
| WO | WO2016149668 A1 | 9/2016 |
| WO | WO2016169989 A1 | 10/2016 |
| WO | WO2016172560 A1 | 10/2016 |
| WO | WO2016174183 A1 | 11/2016 |
| WO | WO2016197032 A1 | 12/2016 |
| WO | WO2016197114 A1 | 12/2016 |
| WO | WO2016210034 A1 | 12/2016 |
| WO | WO2017004133 A1 | 1/2017 |
| WO | WO2017004134 A1 | 1/2017 |
| WO | WO2017007612 A1 | 1/2017 |
| WO | WO2017009798 A1 | 1/2017 |
| WO | WO2017009806 A1 | 1/2017 |
| WO | WO2017011371 A1 | 1/2017 |
| WO | WO2017011590 A1 | 1/2017 |
| WO | WO2017030814 A1 | 2/2017 |
| WO | WO2017033093 A1 | 3/2017 |
| WO | WO2017049068 A1 | 3/2017 |
| WO | WO2017059280 A1 | 4/2017 |
| WO | WO2017079267 A1 | 5/2017 |
| WO | WO2017108723 A2 | 6/2017 |
| WO | WO2017117473 A1 | 7/2017 |
| WO | WO2017117474 A1 | 7/2017 |
| WO | WO2017127430 A1 | 7/2017 |
| WO | WO2017161119 A1 | 9/2017 |
| WO | WO2017176708 A1 | 10/2017 |
| WO | WO2017176957 A1 | 10/2017 |
| WO | WO2017176958 A1 | 10/2017 |
| WO | WO2017197036 A1 | 11/2017 |
| WO | WO2017197046 A1 | 11/2017 |
| WO | WO2017197051 A1 | 11/2017 |
| WO | WO2017197055 A1 | 11/2017 |
| WO | WO2017197056 A1 | 11/2017 |
| WO | WO2017201449 A1 | 11/2017 |
| WO | WO2017205762 A1 | 11/2017 |
| WO | WO2017205766 A1 | 11/2017 |
| WO | WO2017207385 A1 | 12/2017 |
| WO | WO2017211924 A1 | 12/2017 |
| WO | WO2018052058 A1 | 3/2018 |
| WO | WO2018089736 A1 | 5/2018 |
| WO | WO2018098367 A1 | 5/2018 |
| WO | WO2018119441 A1 | 6/2018 |
| WO | WO2018144649 A1 | 8/2018 |
| WO | WO2018209012 A1 | 11/2018 |
| WO | WO2018237026 A1 | 12/2018 |
| WO | WO2019043214 A1 | 3/2019 |
| WO | WO2019060693 A1 | 3/2019 |
| WO | WO2019060742 A1 | 3/2019 |
| WO | WO2019084026 A1 | 5/2019 |
| WO | WO2019084030 A1 | 5/2019 |
| WO | WO2019099868 A2 | 5/2019 |
| WO | WO2019099926 A1 | 5/2019 |
| WO | 2019111218 A1 | 6/2019 |
| WO | WO2019133531 A1 | 7/2019 |
| WO | WO2019140380 A1 | 7/2019 |
| WO | WO2019140387 A1 | 7/2019 |
| WO | WO2019160915 A1 | 8/2019 |
| WO | WO2019165229 A1 | 8/2019 |
| WO | WO2019236483 A1 | 12/2019 |
| WO | WO2020010177 A1 | 1/2020 |
| WO | WO2020010210 A1 | 1/2020 |
| WO | WO2020010227 A1 | 1/2020 |
| WO | WO2020018788 A1 | 1/2020 |
| WO | 2020092907 A1 | 5/2020 |
| WO | WO2020113233 A1 | 6/2020 |
| WO | WO2020251969 A1 | 12/2020 |
| WO | WO2020251971 A1 | 12/2020 |
| WO | WO2020251972 A1 | 12/2020 |
| WO | WO2020251974 A1 | 12/2020 |
| WO | WO2020264490 A1 | 12/2020 |
| WO | WO2020264499 A1 | 12/2020 |
| WO | WO2021011631 A1 | 1/2021 |
| WO | WO2021011634 A1 | 1/2021 |
| WO | WO2021011868 A1 | 1/2021 |
| WO | WO2021011871 A1 | 1/2021 |
| WO | 2021018118 A1 | 2/2021 |
| WO | WO2021053555 A1 | 3/2021 |
| WO | WO2021119159 A1 | 6/2021 |
| WO | WO2021127190 A1 | 6/2021 |
| WO | WO2021127278 A1 | 6/2021 |
| WO | WO2021127283 A2 | 6/2021 |
| WO | 2021158634 A1 | 8/2021 |
| WO | 2021222366 A1 | 11/2021 |
| WO | 2021247897 A1 | 12/2021 |
| WO | 2021247899 A1 | 12/2021 |
| WO | 2021257914 A1 | 12/2021 |
| WO | WO-2022028547 A1 * | 2/2022 ........... C07D 239/22 |
| WO | 2022087216 A1 | 4/2022 |
| WO | 2022125790 A1 | 6/2022 |
| WO | 2022147465 A1 | 7/2022 |
| WO | 2022174268 A1 | 8/2022 |
| WO | 2022174269 A1 | 8/2022 |
| WO | 2022236339 A1 | 11/2022 |
| WO | 2023076556 A1 | 5/2023 |
| WO | 2023137439 A1 | 7/2023 |
| WO | 2023147594 A2 | 8/2023 |
| WO | 2023192586 A1 | 10/2023 |

OTHER PUBLICATIONS

Aruri et al., "Metal-free Cross-Dehydrogenative Coupling of HN-azoles with a-C(sp3)-H Amides via C—H Activation and Its Mechanistic and Application Studies," The Journal of Organic Chemistry, 2016, 82(2):1000-1012.

Balasubramanian et al., "Abstract 3646: Novel IRAK-4 inhibitors exhibit highly potent anti-proliferative activity in DLBCL cell lines with activating MYD88 L265P mutation," AACR 106th Annual Meeting 2015; Apr. 18-22, 2015; Philadelphia, PA.

Berge et al., "Pharmaceutical salts," J Pharm Sci., 1977, 66(1):1-19.

Berndsen et al., "New insights into ubiquitin E3 ligase mechanism," Nat Struct Mol Biol., 2014, 21(4):301-307.

Blake et al., "Studies with deuterated drugs," J Pharm Sci. 1975;64(3):367-391.

Boichenko et al., "A FRET-Based Assay for the Identification and Characterization of Cereblon Ligands," J Med Chem. 2016, 59(2):770-774.

Buckley et al., "IRAK-4 inhibitors. Part 1: a series of amides," Bioorg Med Chem Lett. 2008, 18(11):3211-3214.

Buckley et al., "IRAK-4 inhibitors. Part II: a structure-based assessment of imidazo[1,2-a]pyridine binding," Bioorg Med Chem Lett., 2008, 18(11):3291-3295.

Buckley et al., "IRAK-4 inhibitors. Part III: A series of imidazo[1,2-a]pyridines," Bioorg Med Chem Lett., 2008, 18(12):3656-3660.

Cameron et al., "Loss of Interleukin Receptor-Associated Kinase 4 Signaling Suppresses Amyloid Pathology and Alters Microglial Phenotype in a Mouse Model of Alzheimer's Disease," J Neurosci., 2012, 32(43):15112-23.

Cario, "Therapeutic Impact of Toll-like Receptors on Inflammatory Bowel Diseases: A Multiple-edged Sword," Inflamm Bowel Dis., 2008, 14(3):411-421.

CAS STN Abstract, RN 1787975-60-3 (Pub. Jun. 24, 2015).
CAS STN Abstract, RN 1795294-81-3 (Pub. Jul. 6, 2015).
CAS STN Abstract, RN 1795451-20-5 (Pub. Jul. 6, 2015).
CAS STN Abstract, RN 1795527-49-9 (Pub. Jul. 6, 2015).
CAS STN Abstract, RN 1871221-08-7 (Pub. Feb. 21, 2016).
CAS STN Abstract, RN 1878956-45-6 (Pub. Mar. 3, 2016).
CAS STN Abstract, RN 1878983-55-1 (Pub. Mar. 3, 2016).
CAS STN Abstract, RN 742039-47-0 (Pub. Sep. 10, 2004).
CAS STN Abstract, RN 779303-42-3 (Pub. Nov. 12, 2004).

Chang et al., "What is the functional role of the thalidomide binding protein cereblon?" Int J Biochem Mol Biol. 2011;2(3):287-94.

Charrier et al., "Desulfonylative Radical Ring Closure onto Aromatics. A Modular Route to Benzazepin-2-ones and 5-Arylpiperidin-2-ones," Org. Lett., 2012, 14(8):2018-2021.

Chaudhary et al., "Recent Advances in the Discovery of Small Molecule Inhibitors of Interleukin-1 Receptor-Associated Kinase 4 (IRAK4) as a Therapeutic Target for Inflammation and Oncology Disorders," J Med Chem., 2015, 58(1):96-110.

(56) References Cited

OTHER PUBLICATIONS

Chiang et al., "Immune Complex-Mediated Cell Activation from Systemic Lupus Erythematosus and Rheumatoid Arthritis Patients Elaborate Different Requirements for IRAK1/4 Kinase Activity across human Cell Types," J Immunol., 2011, 186(2):1279-1288.
Chou and Talalay, "Quantitative analysis of dose-effect relationships: the combined effects of multiple drugs or enzyme inhibitors," Adv Enzyme Regul. 1984, 22:27-55.
Cohen, "Targeting protein kinases for the development of anti-inflammatory drugs," Curr Opin Cell Biol., 2009, 21(2):17-24.
Connolly et al., "Complexities of TGF-beta Targeted Cancer Therapy," Int J Biol Sci., 2012, 8(7):964-978.
Contino-Pepin et al., "Preliminary biological evaluations of new thalidomide analogues for multiple sclerosis application," Bioorg Med Chem Lett., 2009, 19(3):878-881.
Crews, "Targeting the Undruggable Proteome: The Small Molecules of My Dreams," Chem Biol., 2010, 17(6):551-555.
Cushing et al., "Interleukin 1/Toll-like receptor-induced autophosphorylation activates interleukin 1 receptor-associated kinase 4 and controls cytokine induction in a cell type-specific manner," J Biol Chem. 2014;289(15):10865-10875.
Cushing et al., "IRAK4 kinase controls Toll-like receptor induced inflammation through the transcription factor IRF5 in primary human monocytes," J Biol Chem. 2017, 292(45):18689-18698.
Dalbeth et al., "Hyperuricaemia and gout: state of the art and future perspectives," Ann Rheum Dis. 2014, 73(9):1598-600.
De Nardo et al. "Interleukin-1 receptor-associated kinase 4 (IRAK4) plays a dual role in myddosome formation and Toll-like receptor signaling," J Biol Chem. 2018, 293(39):15195-15207.
Degorce et al., "Optimization of permeability in a series of pyrrolotriazine inhibitors of IRAK4," Bioorg Med Chem., 2018, 26(4):913-924.
Deshaies and Joazeiro, "RING domain E3 ubiquitin ligases," Annu Rev Biochem., 2009, 78:399-434.
Devi et al., "Medicinal Attributes of Imidazo[1,2-a]pyridine Derivatives: An Update," Curr Top Med Chem, 2016, 16(26):2963-2994.
Dinarello, "IL-1: Discoveries, controversies and future directions," Eur J Immunol. 2010, 40(3):599-606.
Dinarello, "Interleukin 1 and interleukin 18 as mediators of inflammation and the aging process," Am J Clin Nutr., 2006, 83(suppl):447S-455S.
Dinarello, "Interleukin-18 and the Pathogenesis of Inflammatory Diseases," Semin Nephrol., 2007, 27(1):98-114.
Dudhgaonkar et al., "Selective IRAK4 Inhibition Attenuates Disease in Murine Lupus Models and Demonstrates Steroid Sparing Activity," J Immunol., 2017, 198(3):1308-1319.
Dunne et al., "IRAK1 and IRAK4 Promote Phosphorylation, Ubiquitation, and Degradation of MyD88 Adaptor-like (Mal)," J Biol Chem., 2010, 285(24):18276-82.
El-Gamal et al., "Recent Advances of Colony-Stimulating Factor-1 Receptor (CSF-1R) Kinase and Its Inhibitors," J Med Chem., 2018, 61(13):5450-5466.
Fischer et al., "Structure of the DDB1-CRBN E3 ubiquitin ligase in complex with thalidomide," Nature, 2014, 512(7512):49-53.
Fisher et al., "The complexities inherent in attempts to decrease drug clearance by blocking sites of CYP-mediated metabolism," Curr Opin Drug Discov Devel., 2006, 9(1):101-109.
Flannery et al., "The interleukin-1 receptor-associated kinases: Critical regulators of innate immune signaling," Biochem Pharmacol. 2010, 80(12):1981-91.
Foster, "Deuterium isotope effects in the metabolism of drugs and xenobiotics: implications for drug design," Advances in Drug Research, 1985, 14:1-40.
Fukuto et al., "Determination of the mechanism of demethylenation of (methylenedioxy)phenyl compounds by cytochrome P450 using deuterium isotope effects," J Med Chem., 1991, 34(9):2871-2876.
Gearing, "Targeting toll-like receptors for drug development: a summary of commercial approaches," Immunol Cell Biol., 2007; 85(6):490-494.

Geyer and Müller-Ladner, "Actual status of antiinterleukin-1 therapies in rheumatic diseases," Curr Opin Rheumatol. 2010;22(3):246-251.
Gottipati et al., "IRAK1: A critical signaling mediator of innate immunity," Cell Signal, 2008, 20(2):269-76.
Hagner et al., "CC-122, a pleiotropic pathway modifier, mimics an interferon response and has antitumor activity in DLBCL," Blood, 2015, 126(6):779-789.
Heightman et al., "Structure-Activity and Structure-Conformation Relationships of Aryl Propionic Acid Inhibitors of the Kelch-like ECH-Associated Protein 1/Nuclear Factor Erythroid 2-Related Factor 2 (KEAP1/NRF2) Protein-Protein Interaction," J. Med. Chem., 2019, 62(9): 4683-4702.
Hennessy et al., "Targeting Toll-like receptors: emerging therapeutics?" Nat Rev Drug Discov., 2010, 9(4):293-307.
Hines et al., "MDM2-Recruiting PROTAC Offers Superior, Synergistic Antiproliferative Activity via Simultaneous Degradation of BRD4 and Stabilization of p53," Cancer Res., 2019, 79(1):251-262.
Hoffman et al., "Efficacy and Safety of Rilonacept (Interleukin-1 Trap) in Patients with Cryopyrin-Associated Periodic Syndromes," Arthritis Rheum., 2008, 58(8):2443-2445.
Iannello et al., "Role of Interleukin-18 in the Development and Pathogenesis of AIDS," AIDS Rev., 2009, 11(3):115-125.
Iconomou and Saunders, "Systematic approaches to identify E3 ligase substrates," Biochem J. 2016;473(22):4083-4101.
Iriyama et al., "Clinical significance of genetic mutations of CD79B, CARD11, MYD88, and EZH2 genes in diffuse large B-cell lymphoma patients" 53rd ASH Annual Meeting, San Diego, California, Dec. 10-13, 2011.
Ito et al., "Identification of a primary target of thalidomide teratogenicity," Science, 2010, 327(5971):1345-1350.
Kargbo, "Protac Degradation of IRAK4 for the Treatment of Cancer," ACS Med. Chem. Lett., 2019, 10(10):1370-1371.
Kelly et al., "Selective interleukin-1 receptor-associated kinase 4 inhibitors for the treatment of autoimmune disorders and lymphoid malignancy," J Exp Med., 2015, 212(13):2189-2201.
Kester et al., "Optimization of Benzodiazepinones as Selective Inhibitors of the X-Linked Inhibitor of Apoptosis Protein (XIAP) Second Baculovirus IAP Repeat (BIR2) Domain," J Med Chem., 2013, 56(20):7788-7803.
Kim et al., "A critical role for IRAK4 kinase activity in Toll-like receptor-mediated innate immunity," J Exp Med., 2007, 204(5):1025-1036.
Kondo et al., "Renoprotective effects of novel interleukin-1 receptor-associated kinase 4 inhibitor AS2444697 through anti-inflammatory action in 5/6 nephrectomized rats," Naunyn Schmiedebergs Arch Pharmacol., 2014, 387(10):909-919.
Kou et al., "Effects of RuPeng15 Powder (RPP15) on Monosodium Urate Crystal-Induced Gouty Arthritis in Rats," Evid Based Complement Alternat Med. 2015;2015:527019.
Koziczak-Holbro et al., "IRAK-4 Kinase Activity Is Required for Interleukin-1 (IL-1) Receptor- and Toll-like Receptor 7-mediated Signaling and Gene Expression," J Biol Chem., 2007, 282(18):13552-13560.
Krönke et al., "Lenalidomide causes selective degradation of IKZF1 and IKZF3 in multiple myeloma cells" Science, 2014, 343(6168):301-305.
Ku et al., "Selective predisposition to bacterial infections in IRAK-4-deficient children: IRAK-4-dependent TLRs are otherwise redundant in protective immunity," J Exp Med., 2007, 204(10):2407-2422.
Kubo-Murai et al., "IRAK-4-dependent Degradation of IRAK-1 is a Negative Feedback Signal for TLR-mediated NF-kB Activation," J Biochem. 2008; 143(3):295-302.
Küppers, "IRAK inhibition to shut down TLR signaling in autoimmunity and MyD88-dependent lymphomas," J Exp Med., 2015, 212(13):2184.
Kushner et al., "Pharmacological uses and perspectives of heavy water and deuterated compounds," Can J Physiol Pharmacol., 1999, 77(2):79-88.
Lebakken et al., "A Fluorescence Lifetime Based Binding Assay to Characterize Kinase Inhibitors," J Biomol Screen. 2007, 12(6):828-841.

(56) References Cited

OTHER PUBLICATIONS

Lee et al., "Discovery of Clinical Candidate 1-{[2S,3S,4S)-3-ethyl-4-fluoro-5-oxopyrrolidin-2-yl]methoxy}-7-methoxyisoquinoine-6-carboxamide (PF-06650833), a Potent, Selective Inhibitor of Interleukin-1 Receptor Associated Kinase 4 9IRAK4), by Fragment-Based Drug Design," J Med Chem. 2017;60(13):5521-5542.

Li et al., "Genome-wide and functional annotation of human E3 ubiquitin ligases identifies MULAN, a mitochondrial E3 that regulates the organelle's dynamics and signaling, " PLoS One. 2008;3(1):e1487.

Li et al., "IRAK-4: A novel member of the IRAK family with the properties of an IRAK-kinase," Proc Natl Acad Sci USA., 2002, 99(8):5567-5572.

Li et al., "Targeting interleukin-1 receptor-associated kinase for human hepatocellular carcinoma," J Exp Clin Cancer Res., 2016, 35(1):140.

Li, "IRAK4 in TLR/IL-1R signaling: Possible clinical applications," Eur J Immunol., 2008, 38(3):614-618.

Lim et al., "Discovery of 5-Amino-N-(1H-pyrazol-4-yl)pyrazolo[1,5-a]pyrimidine-3-carboxamide Inhibitors of IRAK4," ACS Med Chem Lett. 2015, 6(6):683-688.

Lin et al., "Helical assembly in the MyD88-IRAK4-IRAK2 complex in TLR /IL-1R signalling," Nature, 2010, 465(7300):885-890.

Lu et al., "Discovery of a Keap1-dependent peptide PROTAC to knockdown Tau by ubiquitination-proteasome degradation pathway," Euro J Med Chem., 2018, 46:251-259.

Lu et al., "Hijacking the E3 Ubiquitin Ligase Cereblon to Efficiently Target BRD4," Chem Biol, 2015, 2(6):755-763.

Lu et al., "The myeloma drug lenalidomide promotes the cereblon-dependent destruction of Ikaros proteins," Science, 2014, 343(6168):305-309.

Lust et al., "Induction of a Chronic Disease State in patients With Smoldering of Indolent Multiple Myeloma by Targeting Interleukin 1β-Induced Interleukin 6 Production and the Myeloma Proliferative Component," Mayo Clin Proc., 2009, 84(2):114-122.

Martinon et al., "Gout-associated uric acid crystals activate the NALP3 inflammasome," Nature, 2006, 440(7081):237-241.

Maschera et al., "Overexpression of an enzymatically inactive interleukin-1-receptor-associated kinase activates nuclear factor-kB," Biochem J., 1999, 339(Pt2):227-231.

Matyskiela et al., "A Cereblon Modulator (CC-220) with Improved Degradation of Ikaros and Aiolos," J Med Chem., 2018, 61(2):535-542.

McElroy et al., "Discovery and hit-to-lead optimization of 2,6-diaminopyrimidine Inhibitors of interleukin-1 receptor-associated kinase 4," Bioorg Med Chem Lett., 2015, 25(9):1836-1841.

McElroy et al., "Potent and Selective Amidopyrazole Inhibitors of IRAK4 That Are Efficacious in a Rodent Model of Inflammation," ACS Med Chem Lett., 2015, 6(6):677-682.

Moynagh, "The Pellino Family: IRAK E3 ligases with emerging roles in innate immune signalling," Trends Immunol. 2009, 30(1):33-42.

Muller et al., "Amino-Substituted Thalidomide Analogs: Potent Inhibitors of TNF-? Production," Bioorg Med Chem Lett, 1999, 9(11):1625-1630.

Ngo et al., "Oncogenically active MYD88 mutations in human lymphoma," Nature, 2011, 470(7332):115-119.

Nunes et al., "Targeting IRAK4 for Degradation with PROTACTSs," ACS Med Chem Lett., 2019, 10(7):1081-1085.

Ohoka et al., "In Vivo Knockdown of Pathogenic Proteins via Specific and Nongenetic Inhibitor of Apoptosis Protein (IAP)-dependent Protein Erasers (SNIPERs)," J Bio Chem., 2017, 292(11):4556-4570.

Ohoka et al., "Development of Small Molecule Chimeras That Recruit AhR E3 Ligase to Target Proteins," ACS Chem. Biol., 2019, 14(12):2822-2832.

Okazaki et al., "A rheostat for immune responses: the unique properties of PD-1 and their advantages for clinical application," Nat. Immunol. 2013, 14(12):1212-1218.

Patra and Choi, "Recent Progress in the Molecular Recognition and Therapeutic Importance of Interleukin-1 Receptor-Associated Kinase 4," Molecules. 2016, 21(11):1529.

PCT International Preliminary Report on Patentability from PCT/US2018/067304, dated Jun. 30, 2020.
PCT International Preliminary Report on Patentability from PCT/US2019/040462, dated Jan. 21, 2021.
PCT International Search Report and Written Opinion from PCT/US2018/052181, dated Feb. 26, 2019.
PCT International Search Report and Written Opinion from PCT/US2018/052242, dated Jan. 30, 2019.
PCT International Search Report and Written Opinion from PCT/US2018/067304, dated Apr. 30, 2019.
PCT International Search Report and Written Opinion from PCT/US2019/013481, dated Mar. 15, 2019.
PCT International Search Report and Written Opinion from PCT/US2019/013491, dated Mar. 18, 2019.
PCT International Search Report and Written Opinion from PCT/US2019/040462, dated Sep. 20, 2019.
PCT International Search Report and Written Opinion from PCT/US2019/040520, dated Nov. 13, 2019.
PCT International Search Report and Written Opinion from PCT/US2019/040545, dated Oct. 21, 2019.
PCT International Search Report and Written Opinion from PCT/US2019/064070, dated Apr. 6, 2020.
PCT International Search Report and Written Opinion from PCT/US2020/026869, dated Jul. 27, 2020.
PCT International Search Report and Written Opinion from PCT/US2020/036913, dated Oct. 26, 2020.
PCT International Search Report and Written Opinion from PCT/US2020/036916, dated Oct. 26, 2020.
PCT International Search Report and Written Opinion from PCT/US2020/036918, dated Oct. 26, 2020.
PCT International Search Report and Written Opinion from PCT/US2020/036921, dated Oct. 26, 2020.
PCT International Search Report and Written Opinion from PCT/US2020/040101, dated Nov. 10, 2020.
PCT International Search Report and Written Opinion from PCT/US2020/040125, dated Nov. 13, 2020.
PCT International Search Report and Written Opinion from PCT/US2020/042105, dated Nov. 20, 2020.
PCT International Search Report and Written Opinion from PCT/US2020/042109, dated Dec. 10, 2020.
PCT International Search Report and Written Opinion from PCT/US2020/042530, dated Oct. 16, 2020.
PCT International Search Report and Written Opinion from PCT/US2020/042534, dated Oct. 26, 2020.
PCT International Search Report and Written Opinion from PCT/US2020/064061, dated Apr. 9, 2021.
PCT International Search Report and Written Opinion from PCT/US2020/065628, dated May 28, 2021.
PCT International Search Report and Written Opinion from PCT/US2020/065752, dated Mar. 25, 2021.
PCT International Search Report and Written Opinion from PCT/US2020/065757, dated May 28, 2021.
PCT International Search Report and Written Opinion from PCT/US2020/066859, dated May 4, 2021.
PCT International Search Report and Written Opinion from PCT/US2021/062640, dated Feb. 8, 2022.
PCT International Search Report and Written Opinion from PCT/US2023/060645, dated Mar. 31, 2023.
PCT International Search Report and Written Opinion from PCT/US2021/035745, dated Sep. 27, 2021.
PCT International Search Report and Written Opinion from PCT/US2021/035747, dated Sep. 27, 2021.
PCT International Search Report and Written Opinion from PCT/US2022/070662, dated Apr. 18, 2022.
PCT International Search Report and Written Opinion from PCT/US2022/070664, dated May 3, 2022.
Picard et al., "Clinical features and outcome of patients with IRAK-4 and MyD88 deficiency," Medicine (Baltimore). 2010, 89(6):403-425.

(56) References Cited

OTHER PUBLICATIONS

Picard et al., "Inherited human IRAK-4 deficiency: an update," Immunol Res., 2007, 38(1-3):347-52.

Piya et al., "BRD4 Proteolysis Targeting Chimera (PROTAC) Leads to Sustained Degradation of BRD4 with Broad Activity Against Acute Leukemias and Overcomes Stroma Mediated Resistance by Modulating Surface Expression of CXCR4," Blood, 2016, 126(23): 675-676.

Powers et al., "Discovery and initial SAR of inhibitors of interleukin-1 receptor-associated kinase-4," Bioorg Med Chem Lett., 2006;16(11):2842-2845.

Priyadarshini et al., "Copper catalyzed oxidative cross-coupling of aromatic amines with 2-pyrrolidinone: a facile synthesis of N-aryl-r-amino-r-lactams," Tetrahedron. 2014;70(36):6068-6074.

Pubmed Compound Summary for CID 101524675, "(2R)-3-Fluoro-2-(2-methylpropyl)-3-phenyl-1,3-azasilinan-6-one," U.S. National Library of Medicine, created Dec. 18, 2015, https://pubchem.ncbi.nlm.nih.gov/compound/101524675. Date Accessed: Sep. 5, 2019 (5 pages).

Pubmed Compound Summary for CID 102164987, "3-[(4S)-2,5-Dioxo-4-phenylimidazolidine-1-yl]-2,6-piperidinedione," U.S. National Library of Medicine, created Dec. 24, 2015, https://pubchem.ncbi.nlm.nih.gov/compound/102164987. Date Accessed: Feb. 25, 2020 (7 pages).

Pubmed Compound Summary for CID 110491408, 3-(5-Amino-2-oxo-3H-benzimidazol-1-yl)piperidine-2,6-dione, U.S. Library of Medicine, created Jan. 18, 2016, https://pubchem.ncbi.nlm.nih.gov/compound/110491408. Date Accessed: Feb. 25, 2020 (7 pages).

Pubmed Compound Summary for CID 110491555, 3-(6-Amino-2-oxo-3H-benzimidazol-1-yl)piperidine-2,6-dione, U.S. Library of Medicine, created Jan. 18, 2016, https://pubchem.ncbi.nlm.nih.gov/compound/110491555. Date Accessed: Feb. 25, 2020 (7 pages).

Pubmed Compound Summary for CID 115370667, "5-(2-Oxoimidazolidin-1-yl)piperidin-2-one." U.S. National Library of Medicine, created Oct. 22, 2012, https://pubchem.ncbi.nlm.nih.gov/compound/115370667. Date Accessed: Feb. 25, 2020 (10 pages).

Pubmed Compound Summary for CID 138728787, "3-(6-Ethylpyrido[2,3-b]indol-9-yl)piperidine-2,6-dione," U.S. National Library of Medicine, created Jul. 20, 2019, https://pubchem.ncbi.nlm.nih.gov/compound/138728787. Date Accessed: Sep. 5, 2019 (6 pages).

Pubmed Compound Summary for CID 17607528, "4-(Carbazol-9-ylmethyl)-1,3-oxazolidin-2-one," U.S. National Library of Medicine, Nov. 13, 2007, https://pubchem.ncbi.nlm.nih.gov/compound/17607528. Date Accessed: Feb. 25, 2020 (6 pages).

Pubmed Compound Summary for CID 5426, "Thalidomide," created Mar. 25, 2005.

Pubmed Compound Summary for CID 63661260, "5-[2-(1-Chloroethyl)benzimidazol-1-yl]piperidin-2-one," U.S. National Library of Medicine, created Oct. 22, 2012, https://pubchem.ncbi.nlm.nih.gov/compound/63661260. Date Accessed: Sep. 4, 2019 (6 pages).

Pubmed Compound Summary for CID 63661460, "6-Oxo-1-(6-oxopiperidin-3-yl)piperidine-3-carboxylic acid," U.S. National Library of Medicine, created Oct. 22, 2012, https://pubchem.ncbi.nlm.nih.gov/compound/63661460. Date Accessed: Feb. 25, 2020 (7 pages).

Pubmed Compound Summary for CID 65967733, "3-(2,5-Dioxo-3-phenylpyrrolidin-1-yl)piperidine-2,6-dione," U.S. National Library of Medicine, created Dec. 24, 2015, https://pubchem.ncbi.nlm.nih.gov/compound/65967733. Date Accessed: Feb. 25, 2020 (7 pages).

Pubmed Compound Summary for CID 65968760, "1-(2,6-Dioxopiperidin-3-yl)benzimidazole-5-carboxylic acid," U.S. National Library of Medicine, created Oct. 24, 2012, https://pubchem.ncbi.nlm.nih.gov/compound/65968760. Date Accessed: Sep. 4, 2019 (6 pages).

Pubmed Compound Summary for CID 67258040, "[1-(9H-Fluoren-9-yl)-1-(6-oxopiperidin-3-yl)ethyl] hydrogen carbonate," U.S. National Library of Medicine, Nov. 30, 2012, https://pubchem.ncbi.nlm.nih.gov/compound/67258040. Date Accessed: Feb. 25, 2020 (9 pages).

Pubmed Compound Summary for CID 83543479, "5(Aminomethyl)-5-(1H-indol-3-yl)piperidin-2-one," U.S. National Library of Medicine, created Oct. 20, 2014, https://pubchem.ncbi.nlm.nih.gov/compound/83543479. Date Accessed: Feb. 25, 2020 (6 pages).

Pubmed Compound Summary for CID 84036945, 1-Piperidin-3-yl-3H-indol-2-one, U.S. Library of Medicine, created Oct. 20, 2014, https://pubchem.ncbi.nlm.nih.gov/compound/84036945. Date Accessed: Feb. 25, 2020 (7 pages).

Pubmed Compound Summary for CID 86793742, 3-[(6-chloro-1H-1,3-benzodiazol-2-yl)sulfanyl]piperidine-2,6-dione, created Feb. 7, 2015, https://pubchem.ncbi.nlm.nih.gov/compound/86793742. Date Accessed: Jan. 10, 2022.

Pubmed Compound Summary for CID 91648396, 3-[(4-Fluorophenyl)sulfanyl]piperidine-2,6-dione, created Mar. 20, 2015, https://pubchem.ncbi.nlm.nih.gov/compound/91648396#section=Structures. Date Accessed: Jan. 10, 2022.

Pubmed Compound Summary for CID 99784232, (3S)-3-(4-fluorophenyl)sulfanylpiperidine-2,6-dione, created Dec. 11, 2015, https://pubchem.ncbi.nlm.nih.gov/compound/99784232. Date Accessed: Jan. 10, 2022.

Raina et al., "Chemical Inducers of Targeted Protein Degradation," J Biol Chem. 2010, 285(15):11057-110560.

Ramirez et al., "Defining causative factors contributing in the activation of hedgehog signaling in diffuse large B-cell lymphoma," Leuk. Res. 2012;36(10):1267-73.

Rokosz et al., "Kinase inhibitors as drugs for chronic inflammatory and immunological diseases: progress and challenges," Expert Opin Ther Targets. 2008;12(7):883-903.

Ronnebaum et al., "Synthesis of 1, 2, 3-triazole 'click' analogues of thalidomide," Tetrahedron. 2016;72(40): 6136-6141.

Ross et al., "Bispecific T cell engager (BITE®) antibody constructs can mediate bystander tumor cell killing," PLoS ONE. 2017; 12(8): e0183390.

Rostovtsev et al., "A Stepwise Huisgen Cycloaddition Process: Copper(I)-Catalyzed Regioselective "Ligation" of Azides and Terminal Alkynes," Angew Chem Int Ed Engl. 2002, 41(14):2596-2599.

Rusnac et al., "Recognition of the Diglycine C-End Degron by CRL2 KLHDC2 Ubiquitin Ligase," Mol. Cell. 2018, 72(5):813-822.e4.

Schnnekloth et al., "Chemical Approaches to Controlling Intracellular Protein Degradation," Chembiochem, 2005, 6(1):40-46.

Scott et al., "Discovery and Optimization of Pyrrolopyrimidine Inhibitors of Interleukin-1 Receptor Associated Kinase 4 (IRAK4) for the Treatment of Mutant MYD88L265P Diffuse Large B-Cell Lymphoma," J Med Chem. 2017, 60(24):10071-10091.

Seganish et al., "Discovery and Structure Enabled Synthesis of 2,6-diaminopyrimidine-4-one IRAK4 Inhibitors," ACS Med Chem Lett. 2015, 6(8):942-947.

Seganish et al., "Initial optimization and series evolution of diaminopyrimidine inhibitors of interleukin-1 receptor associated kinase 4," Bioorg Med Chem Lett. 2015, 25(16):3203-3207.

Seitz et al., "Sulfenylation and Halogenation of Di- and Trianions Derived from Substituted Glutarimides," Synthetic Communications, 1977, 7(6):367-374.

Sen et al., "Transcriptional signaling by double-stranded RNA: role of TLR3," Cytokine Growth Factor Rev., 2005, 16(1):1-14.

Shanmugasundaram et al., "A modular PROTAC design for target destruction using a degradation signal based on a single amino acid," J Biol Chem. 2019, 294(41):15172-15175.

Smith et al., "Identification of quinazoline based inhibitors of IRAK4 for the treatment of inflammation," Bioorg Med Chem Lett., 2017, 27(12):2721-2726.

So et al., "A pilot study of IL-1 inhibition by anakinra in acute gout," Arthritis Res Ther., 2007, 9(2):R28.

Song et al., "The kinase activities of interleukin-e receptor associated kinase (IRAK)-1 and 4 are redundant in the control of inflammatory cytokine expression in human cells," Mol Immunol. 2009, 46(7):1458-66.

Spradin et al., "Harnessing the Anti-Cancer Natural Product Nimbolide for Targeted Protein Degradation," bioRxiv.org, https://www.biorxiv.org/content/biorxiv/early/2019/04/09/436998.full.pdf. Date Accessed, Oct. 3, 2019.

Spratt et al., "RBR E3 ubiquitin ligases: new structures, new insights, new question," Biochem J., 2014, 458(3):421-437.

(56) References Cited

OTHER PUBLICATIONS

Stewart et al., "Efforts toward elucidating Thalidomide's molecular target: an expedient synthesis of the first Thalidomide biotin analogue," Organic & Biomolecular Chemistry, 2010, 8(18): 4059-4062.
Sun et al., "Carbohydrate and protein immobilization onto solid surfaces by sequential Diels-Alder and azide-alkyne cycloadditions," Bioconjug Chem., 2006, 17(1):52-57.
Suzuki et al., "IRAK-4 as the central TIR signaling mediator in innate immunity," Trends Immunol. 2002, 23(10):503-506.
Suzuki et al., "Severe impairment of interleukin-1 and Toll-like receptor signalling in mice lacking IRAK-4," Nature, 2002, 416(6882):750-756.
Swantek et al., "IL-1 Receptor-Associated Kinase Modulates Host Responsiveness to Endotoxin," Journal of Immunology, 2000, 164(8):4301-4316.
Terkeltaub et al., "The interleukin 1 inhibitor rilonacept in treatment of chronic gouty arthritis: results of a placebo-controlled, monosequence crossover, non-randomised, single-blind pilot study," Ann Rheum Dis. 2009, 68(10):1613-1617.
Terkeltaub, "Update on gout: new therapeutic strategies and options," Nat Rev Rheumatol. 2010, 6(1):30-38.
Tong et al., "Targeted Protein Degradation via a Covalent Reversible Degrader Based on Bardoxolone", ChemRxiv. First Posted Online: Apr. 2, 2020, 23 pages.
Toogood, "Small molecule immuno-oncology therapeutic agents," Bioorg. Med. Chem. Lett., 2018, 28(3):319-329.
Torres et al., "Hyperalgesia, synovitis and multiple biomarkers of inflammation are suppressed by interleukin 1 inhibition in a novel animal model of gouty arthritis," Ann Rheum Dis., 2009, 68(10):1602-1608.
Toure and Crews, "Small-Molecule PROTACS: New Approaches to Protein Degradation," Angew Chem Int Ed Engl., 2016, 55(6):1966-1973.
Treon et al., "Whole genome sequencing reveals a widely expressed mutation (MYD88 L265P) with oncogenic activity in Waldenström's Macroglobulinemia" 53rd ASH Annual Meeting, San Diego, California, Dec. 10-13, 2011 [abstract].
Trøseid et al., "The role of interleukin-18 in the metabolic syndrome," Cardiovasc Diabetol., 2010, 9:11.
Tumey et al., "Identification and optimization of indolo [2,3-c]quinoline inhibitors of IRAK4," Bioorg Med Chem Lett., 2014, 24(9):2066-2072.
Uehara et al., "Selective degradation of splicing factor CAPERα by anticancer sulfonamides," Nat Chem Biol., 2017, 13(6):675-680.
Varfolomeev et al., "IAP antagonists induce autoubiquitination of c-IAPs, NF-kappaB activation, and TNFalpha-dependent apoptosis," Cell, 2007, 131(4):669-681.
Vollmer et al., "The mechanism of activation of IRAK1 and IRAK4 by interleukin-1 and Toll-like receptor agonists," Biochem J., 2017, 474(12):2027-2038.
Wang et al., "Crystal Structure of IRAK-4 Kinase in Complex with Inhibitors: Serine/Threonine Kinase with Tyrosine as a Gatekeeper," Structure, 2006, 14(12):1835-1844.
Wang et al., "Discovery of potent, selective, and orally bioavailable inhibitors of interleukin-1 receptor-associated kinase 4," Bioorg Med Chem Lett, 2015, 25(23):5546-5550.
Wang et al., "IRAK-4 Inhibitors for Inflammation," Curr Top Med Chem., 2009, 9(8):724-37.
Wang et al., "Roles of F-box proteins in cancer," Nat Rev Cancer., 2014, 14(4):233-47.
Ward et al., "Covalent Ligand Screening Uncovers a RNF4 E3 Ligase Recruiter for Targeted Protein Degradation Applications," bioRxiv.org, https://www.biorxiv.org/content/biorxiv/early/2018/11/16/439125.full.pdf. Date Accessed, Oct. 3, 2019 (24 pages).
Weaver, "Epidemiology of gout," Cleve Clin J Med., 2008, 75(Suppl 5):S9-12.
Winter et al., "Selective Target Protein Degradation via Phthalimide Conjugation," Science., 2015, 348(6241):1376-1381.
Xia and Chen, "Iron-catalyzed N-alkylation of azoles via cleavage of an sp3 C—H bond adjacent to a nitrogen atom," J Org Chem., 2012, 77(20):9366-9373.
Xu et al., "A somatic variant in MYD88 (L256P) revealed by whole genome sequencing differentiates lymphoplasmacytic lymphoma from marginal zone lymphomas" 53rd ASH Annual Meeting, San Diego, California, Dec. 10-13, 2011.
Yang et al., "Disruption of MYD88 pathway signaling leads to loss of constitutive IRAK1, NK-kB and JAK/STAT signaling and induces apoptosis of cells expressing the MYD88 L265P mutation in Waldenström's Macroglobulinemia" 53rd ASH Annual Meeting, San Diego, California, Dec. 10-13, 2011.
Yang et al., "Exploiting synthetic lethality for the therapy of ABC diffuse large B cell lymphoma," Cancer Cell, 2012, 21(6):723-737.
Zhang et al., "Constitutive IRAK4 Activation Underlies Poor Prognosis and Chemoresistance in Pancreatic Ductal Adenocarcinoma," Clin Cancer Res., 2017, 23(7):1748-1759.
Zhang et al., "Electrophilic PROTACs that degrade nuclear proteins by engaging DCAF16," bioRxiv.org, https://www.biorxiv.org/content/biorxiv/early/2018/10/15/443804.full.pdf. Date Accessed, Oct. 3, 2019.
Zhou et al., "Targets of curcumin," Curr Drug Targets., 2011, 12(3): 332-347.
Zinc 170596280, Date Added Aug. 8, 2015, https://zinc.docking.org/substances/ZINC000170596280/. Date Accessed: Jan. 10, 2022.
Zou et al., "PD-L1 (B7-H1) and PD-1 pathway blockage for cancer therapy: Mechanisms, response biomarkers, and combinations," Sci Transl. Med. 2016;8(328):328rv4.
PCT International Search Report and Written Opinion from PCT/US2023/061673, dated Jul. 25, 2023.
"Acute Leukemia", Merck Manual (Online Edition), 2013, 6 pages.
Ali et al., "Design, synthesis, molecular modelling and biological evaluation of novel 3-(2-naphthyl)-1-phenyl-1H-pyrazole derivatives as potent antioxidants and 15-Lipoxygenase inhibitors", Journal of Enzyme Inhibition and Medicinal Chemistry, 2020, 35(1):847-863.
Collins, "Chemical approaches to targeted protein degradation through modulation of the ubiquitin-proteasome pathway", Biochemical Journal, 2017, 474(7):1127-1147.
Damasio, "Alzheimer's Disease and related dementias", Cecil Textbook of Medicine, 20th Edition, 1996, 2:1992-1996.
Dorwald F. A. Side Reactions in Organic Synthesis, 2005, Wiley: VCH, Weinheim p. I? of Preface p. 1-15.
Gura T., "Systems for identifying new drugs are often faulty," Science, 1997, 278(5340):1041-1042.
Harvey, et al., "Management of organic impurities in small molecule medicinal products: Deriving safe limits for use in early development", Regulatory Toxicology and Pharmacology, 2017, 84:116-123.
Huang et al., "A Chemoproteomic Approach to Query the Degradable Kinome Using a Multi-kinase Degrader", Cell Chem Biol., 2018, 25(1):88-99.
J. G. Cannon, Chapter Nineteen in Burger's Medicinal Chemistry and Drug Discovery, Fifth Edition, vol. I: Principles and Practice, Wiley-Interscience 1995, pp. 783-802, 784.
Johnson et al., "Relationships between drug activity in NCI preclinical in vitro and in vivo models and early clinical trials," British Journal of Cancer, 2001, 84(10):1424-1431.
Layzer, Robert B., "Degenerative diseases of the nervous system", Cecil Textbook of Medicine, 20th Edition, 1996, 2:2050-2057.
Pearce et al., "Failure modes in anticancer drug discovery and development," Cancer Drug Design and Discovery, Edited by Stephen Neidle, Chapter 18, 2008, pp. 424-435.
Simone, Joseph V., "Oncology: Introduction", Cecil Textbook of Medicine, 20th Edition, 1996, 1:1004-1010.
Slavin et al., "Identification of highly potent and selective Interlukin-1 receptor associated kinase 4 (IRAK4) degraders for the treatment suppurativa", Feb. 2020, 1 page. Retrived from https://www.kymeratx.com/wp-content/uploads/2020/07/EHSF_Kymera_2020_Final.pdf.
Stieger et al., "Recrystallization of Active Pharmaceutical Ingredients", Crystallization—Science and Technology, 2012, pp. 183-201.

(56) References Cited

OTHER PUBLICATIONS

Troup, "Current strategies for the design of PROTAC linkers: a critical review", Explor Target Antitumor Ther., 2020, 1(5):273-312.
Tinworth et al., "Small molecule-mediated protein knockdown as a new approach to drug discovery", Med. Chem. Commun., 2016, 7:2206-2216.
Venkatesh et al., "Role of the development scientist in compound lead selection and optimization", J Pharm Sci., 2000, 89(2):145-154.
PCT International Search Report and Written Opinion from PCT/US2021/071048, dated Nov. 5, 2021, 09 pages.
PCT International Search Report and Written Opinion from PCT/US2021/073186, dated May 3, 2022, 16 pages.
PCT International Search Report and Written Opinion from PCT/US2023/017087, dated Jun. 12, 2023, 08 pages.
PCT International Search Report and Written Opinion from PCT/US2021/016377, dated Jun. 15, 2021, 11 pages.
PCT International Preliminary Report on Patentability from PCT/US2018/052181, dated Apr. 2, 2020, 8 pages.
PCT International Preliminary Report on Patentability from PCT/US2019/013491, dated Jul. 23, 2020, 7 pages.
PCT International Preliminary Report on Patentability from PCT/US2019/064070, dated Jun. 10, 2021, 7 pages.
PCT International Preliminary Report on Patentability from PCT/US2020/040101, dated Jan. 6, 2022, 8 pages.
PCT International Preliminary Report on Patentability from PCT/US2020/040125, dated Jan. 6, 2022, 8 pages.
PCT International Preliminary Report on Patentability from PCT/US2020/042530, dated Jan. 27, 2022, 6 pages.
PCT International Preliminary Report on Patentability from PCT/US2020/064061, dated Jun. 23, 2022, 13 pages.
PCT International Preliminary Report on Patentability from PCT/US2020/065752, dated Jun. 30, 2022, 7 pages.
PCT International Preliminary Report on Patentability from PCT/US2020/065757 dated Jun. 30, 2022, 9 pages.
PCT International Preliminary Report on Patentability from PCT/US2021/016377, dated Aug. 18, 2022, 8 pages.
PCT International Preliminary Report on Patentability from PCT/US2021/029578, dated Nov. 10, 2022, 7 pages.
PCT International Preliminary Report on Patentability from PCT/US2021/035745, dated Dec. 15, 2022, 6 pages.
PCT International Preliminary Report on Patentability from PCT/US2021/035747, dated Dec. 15, 2022, 6 pages.
PCT International Preliminary Report on Patentability from PCT/US2021/037952, dated Dec. 29, 2022, 9 pages.
PCT International Preliminary Report on Patentability from PCT/US2021/055971, dated May 4, 2023, 06 pages.
PCT International Preliminary Report on Patentability from PCT/US2021/062640, dated Jun. 22, 2023, 06 pages.
PCT International Preliminary Report on Patentability from PCT/US2021/071048, dated Feb. 9, 2023, 07 pages.
PCT International Preliminary Report on Patentability from PCT/US2021/073186, dated Jul. 13, 2023, 12 pages.
PCT International Preliminary Report on Patentability from PCT/US2022/070662, dated Aug. 24, 2023, 6 pages.
PCT International Preliminary Report on Patentability from PCT/US2022/070664, dated Aug. 24, 2023, 7 pages.
PCT International Preliminary Report on Patentability from PCT/US2020/065628, dated Jun. 30, 2022, 9 pages.
PCT International Search Report and Written Opinion from PCT/US2021/029578, dated Aug. 6, 2021, 09 pages.
PCT International Search Report and Written Opinion from PCT/US2022/048163, dated Mar. 10, 2023, 11 pages.
PCT International Search Report and Written Opinion from PCT/US2022/072194, dated Sep. 6, 2022, 10 pages.
PCT International Search Report and Written Opinion from PCT/US2021/037952, dated Sep. 29, 2021, 11 pages.
PCT International Search Report and Written Opinion from PCT/US2021/055971, dated Feb. 2, 2022, 08 pages.

* cited by examiner

IRAK DEGRADERS AND USES THEREOF

REFERENCE TO RELATED APPLICATIONS

This application claims the benefit of priority to U.S. Provisional Appl. No. 63/267,372, filed Jan. 31, 2022, U.S. Provisional Appl. No. 63/268,341, filed Feb. 22, 2022, U.S. Provisional Appl. No. 63/269,581, filed Mar. 18, 2022, U.S. Provisional Appl. No. 63/363,687, filed Apr. 27, 2022, U.S. Provisional Appl. No. 63/365,741, filed Jun. 2, 2022, and U.S. Provisional Appl. No. 63/374,297, filed Sep. 1, 2022, the entirety of each of which is herein incorporated by reference.

TECHNICAL FIELD OF THE INVENTION

The present invention relates to compounds and methods useful for the modulation of one or more interleukin-1 receptor-associated kinases ("IRAK") via ubiquitination and/or degradation by compounds according to the present invention. The invention also provides pharmaceutically acceptable compositions comprising compounds of the present invention and methods of using said compositions in the treatment of various disorders.

BACKGROUND OF THE INVENTION

Ubiquitin-Proteasome Pathway (UPP) is a critical pathway that regulates key regulator proteins and degrades misfolded or abnormal proteins. UPP is central to multiple cellular processes, and if defective or imbalanced, it leads to pathogenesis of a variety of diseases. The covalent attachment of ubiquitin to specific protein substrates is achieved through the action of E3 ubiquitin ligases.

There are over 600 E3 ubiquitin ligases which facilitate the ubiquitination of different proteins in vivo, which can be divided into four families: HECT-domain E3s, U-box E3s, monomeric RING E3s and multi-subunit E3s. See generally Li et al. (PLOS One, 2008, 3, 1487) titled "Genome-wide and functional annotation of human E3 ubiquitin ligases identifies MULAN, a mitochondrial E3 that regulates the organelle's dynamics and signaling."; Berndsen et al. (Nat. Struct. Mol. Biol., 2014, 21, 301-307) titled "New insights into ubiquitin E3 ligase mechanism"; Deshaies et al. (Ann. Rev. Biochem., 2009, 78, 399-434) titled "RING domain E3 ubiquitin ligases."; Spratt et al. (Biochem. 2014, 458, 421-437) titled "RBR E3 ubiquitin ligases: new structures, new insights, new questions."; and Wang et al. (Nat. Rev. Cancer, 2014, 14, 233-347) titled "Roles of F-box proteins in cancer."

UPP plays a key role in the degradation of short-lived and regulatory proteins important in a variety of basic cellular processes, including regulation of the cell cycle, modulation of cell surface receptors and ion channels, and antigen presentation. The pathway has been implicated in several forms of malignancy, in the pathogenesis of several genetic diseases (including cystic fibrosis, Angelman's syndrome, and Liddle syndrome), in immune surveillance/viral pathogenesis, and in the pathology of muscle wasting. Many diseases are associated with an abnormal UPP and negatively affect cell cycle and division, the cellular response to stress and to extracellular modulators, morphogenesis of neuronal networks, modulation of cell surface receptors, ion channels, the secretory pathway, DNA repair and biogenesis of organelles.

Aberrations in the process have recently been implicated in the pathogenesis of several diseases, both inherited and acquired. These diseases fall into two major groups: (a) those that result from loss of function with the resultant stabilization of certain proteins, and (b) those that result from gain of function, i.e. abnormal or accelerated degradation of the protein target.

The UPP is used to induce selective protein degradation, including use of fusion proteins to artificially ubiquitinate target proteins and synthetic small-molecule probes to induce proteasome-dependent degradation. Bifunctional compounds composed of a target protein-binding ligand and an E3 ubiquitin ligase ligand, induced proteasome-mediated degradation of selected proteins via their recruitment to E3 ubiquitin ligase and subsequent ubiquitination. These drug-like molecules offer the possibility of temporal control over protein expression. Such compounds are capable of inducing the inactivation of a protein of interest upon addition to cells or administration to an animal or human, and could be useful as biochemical reagents and lead to a new paradigm for the treatment of diseases by removing pathogenic or oncogenic proteins (Crews C, Chemistry & Biology, 2010, 17(6):551-555; Schnnekloth J S Jr., Chembiochem, 2005, 6(1):40-46).

An ongoing need exists in the art for effective treatments for disease, especially inflammatory diseases. However, non-specific effects, and the inability to target and modulate certain classes of proteins altogether, such as regulatory proteins, remain as obstacles to the development of effective therapeutic agents. As such, small molecule therapeutic agents that leverage E3 ligase mediated protein degradation to target proteins such as interleukin-1 receptor-associated kinases ("IRAK") hold promise as therapeutic agents. Accordingly, there remains a need to find compounds that are IRAK degraders useful as therapeutic agents.

SUMMARY OF THE INVENTION

The present application relates novel bifunctional compounds, which function to recruit IRAK kinases to E3 ubiquitin ligase for degradation, and methods of preparation and uses thereof. In particular, the present disclosure provides bifunctional compounds, which find utility as modulators of targeted ubiquitination of IRAK kinases, which are then degraded and/or otherwise inhibited by the bifunctional compounds as described herein. An advantage of the compounds provided herein is that a broad range of pharmacological activities is possible, consistent with the degradation/inhibition of IRAK kinases. In addition, the description provides methods of using an effective amount of the compounds as described herein for the treatment or amelioration of a disease condition, such as cancer or an inflammatory disorder.

It has now been found that compounds of this invention, and pharmaceutically acceptable compositions thereof, are effective for the modulation of targeted ubiquitination. Such compounds have the formula I-a to I-ii:

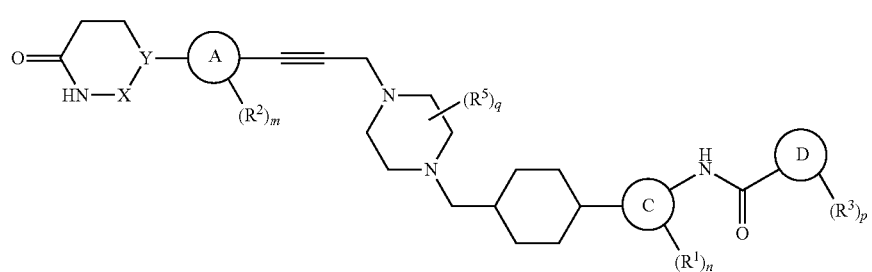
I-a
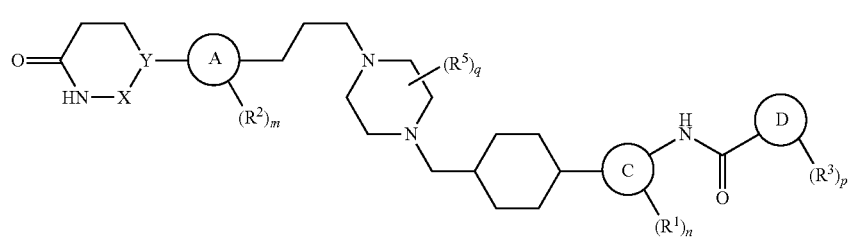
I-b
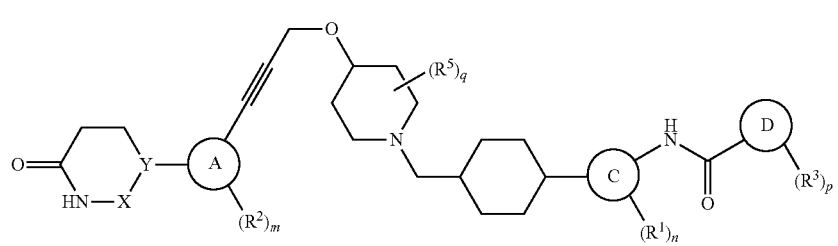
I-c
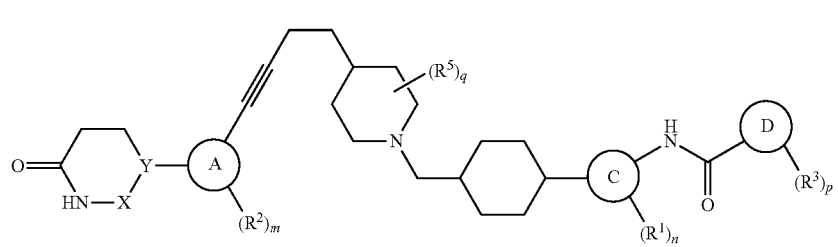
I-d
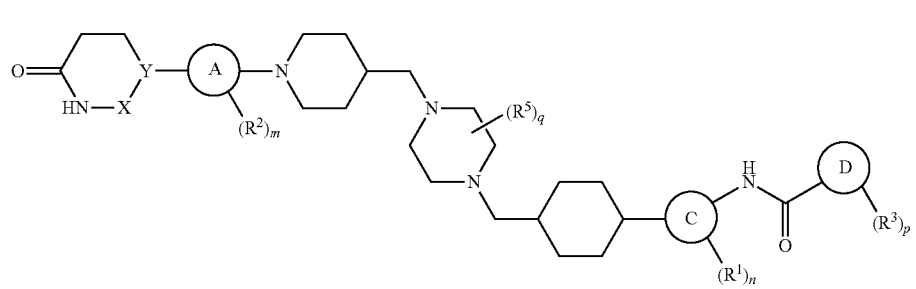
I-e
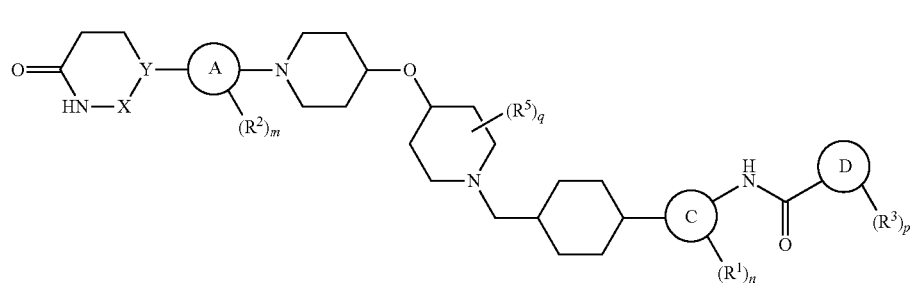
I-f

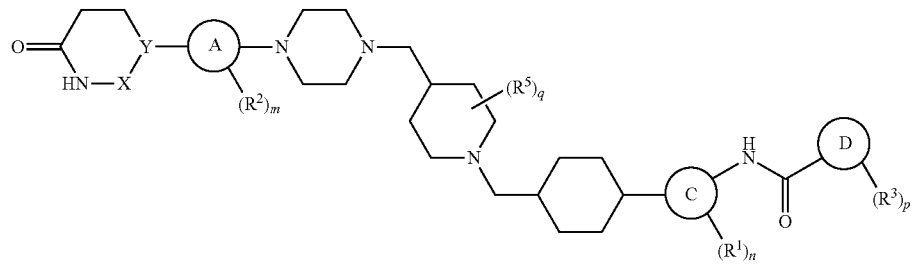
I-g
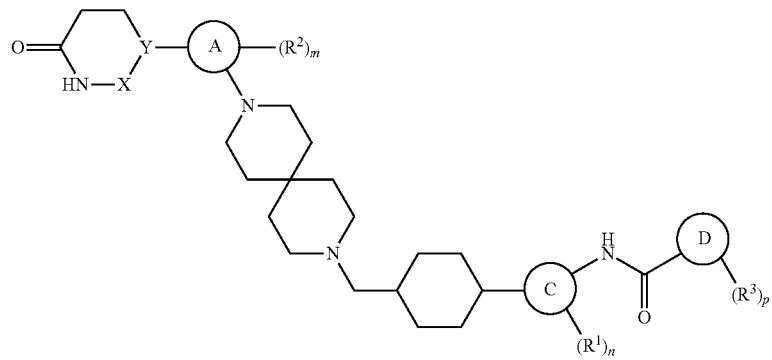
I-h
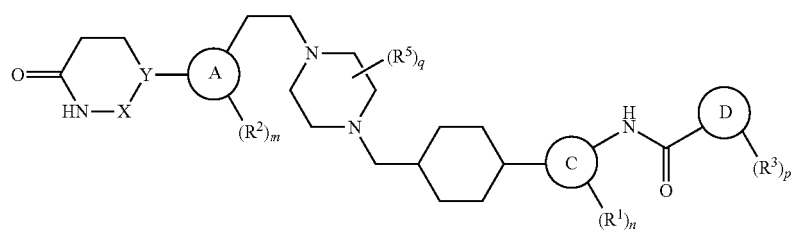
I-i
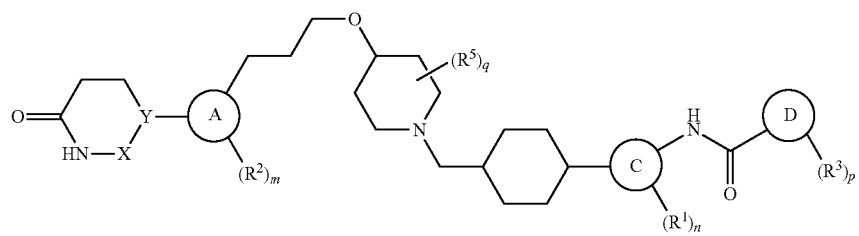
I-j
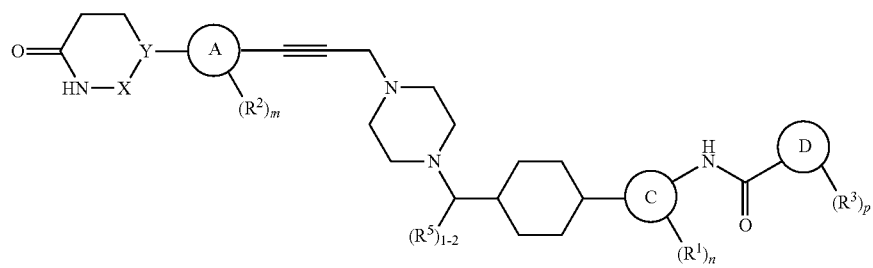
I-k
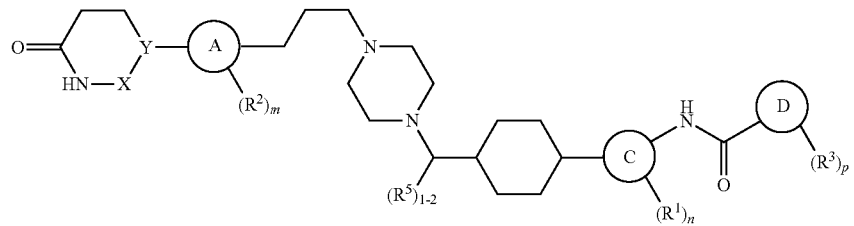
I-l -continued
I-m
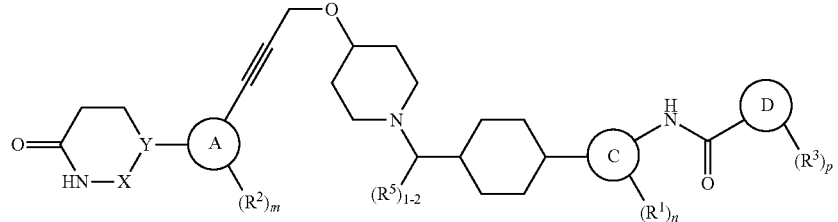
I-n
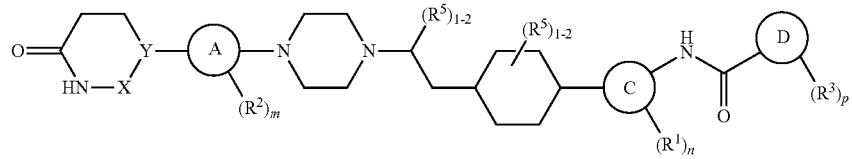
I-o
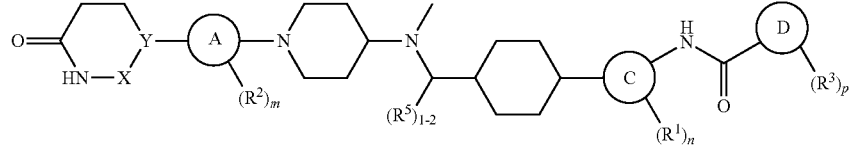
I-p
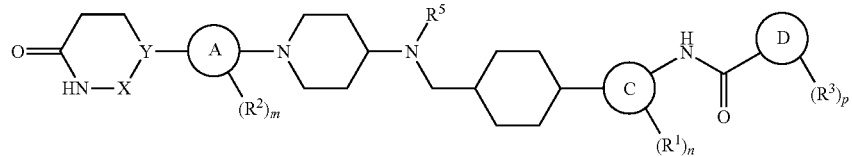
I-q
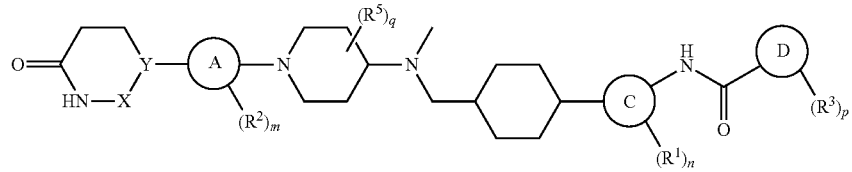
I-r
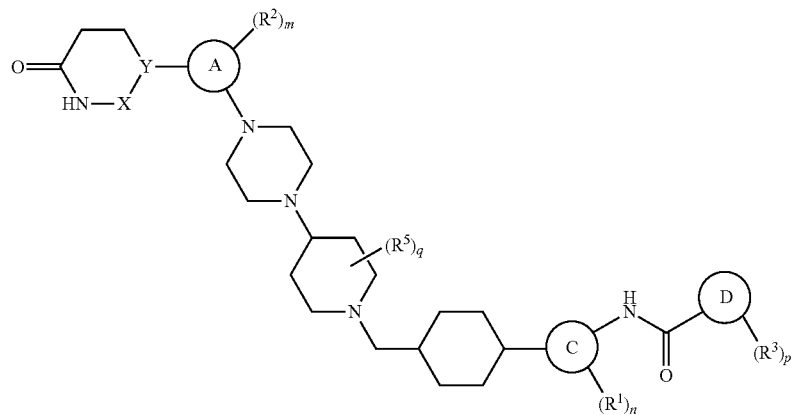
I-s
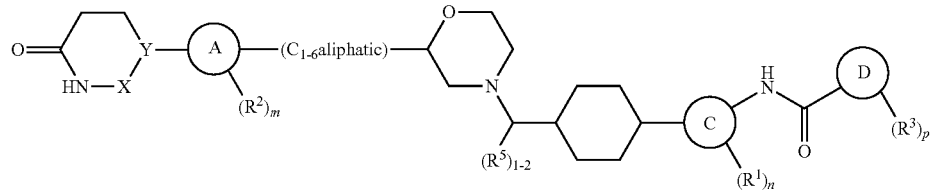

-continued
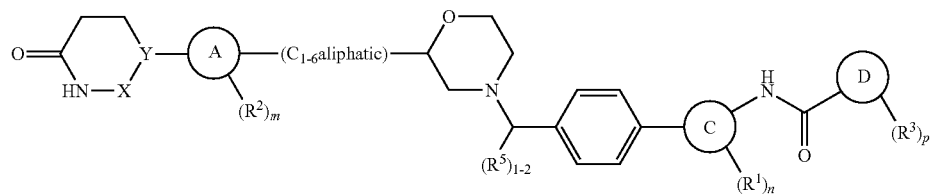
I-t
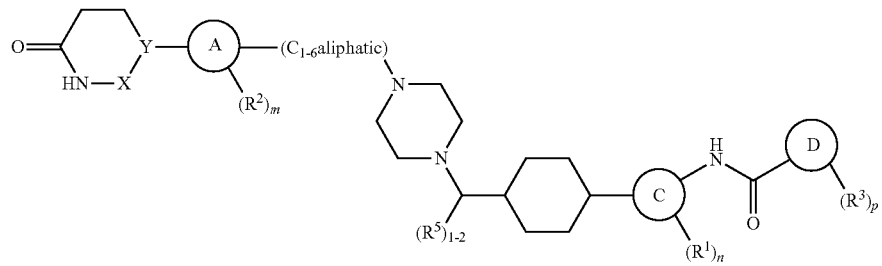
I-u
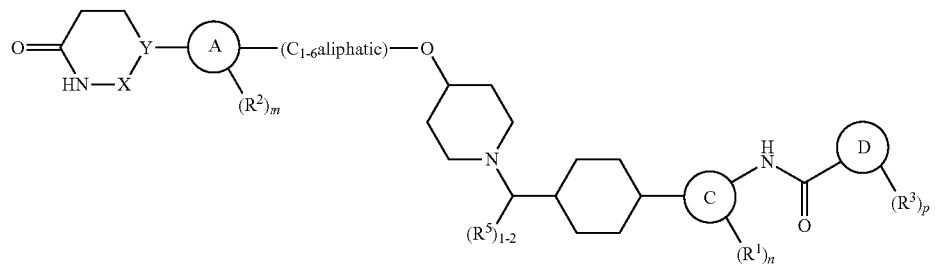
I-v
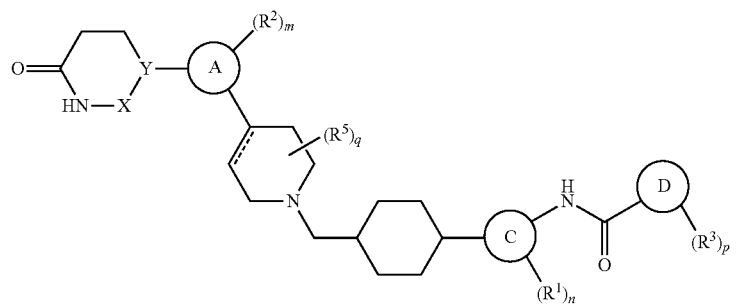
I-w
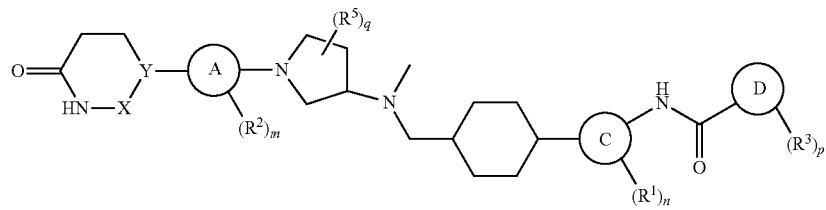
I-x
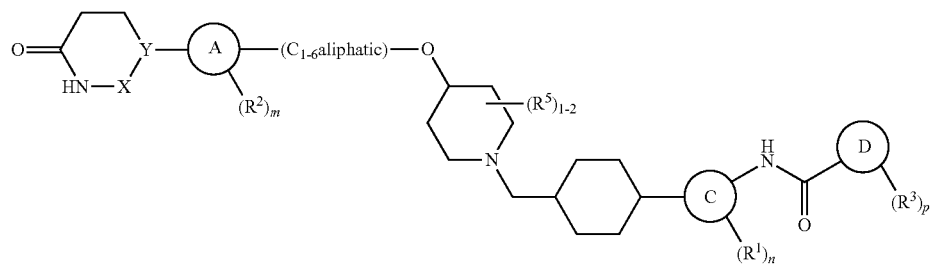
I-y -continued
I-z
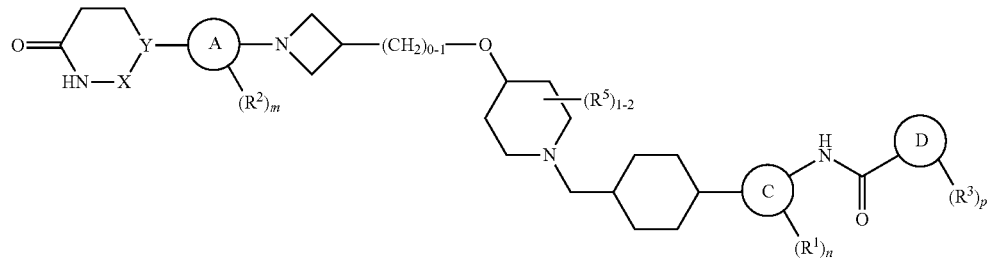
I-aa
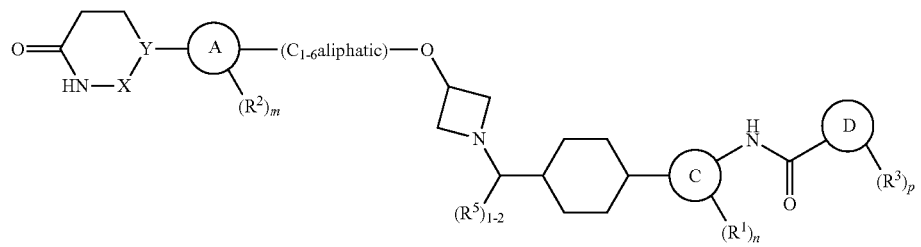
I-bb
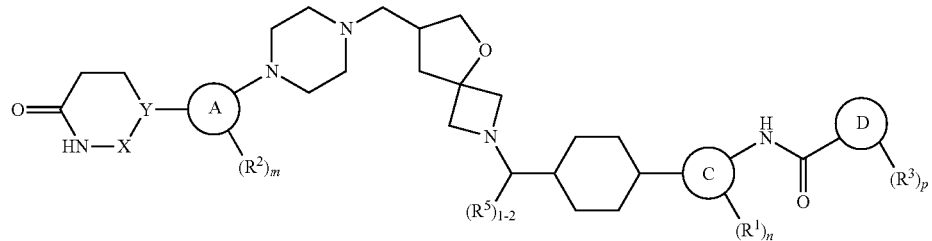
I-cc
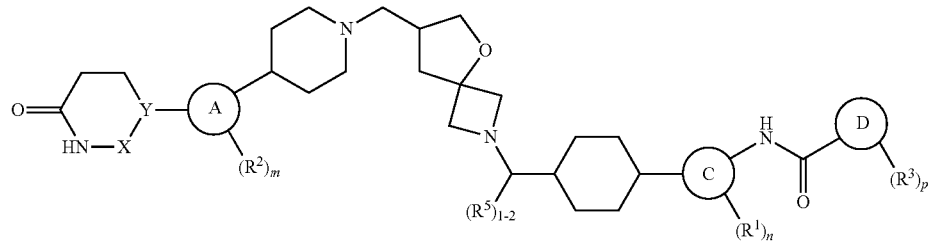
I-dd
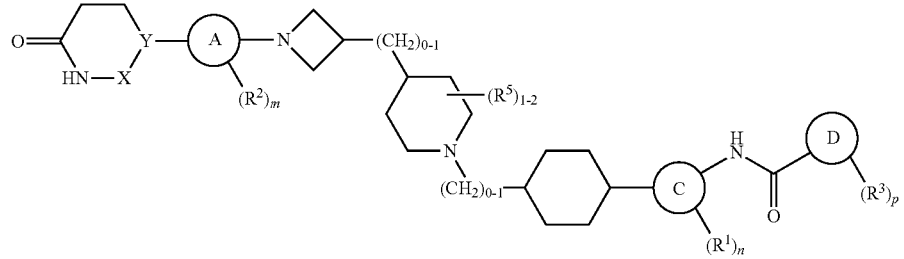
I-ee
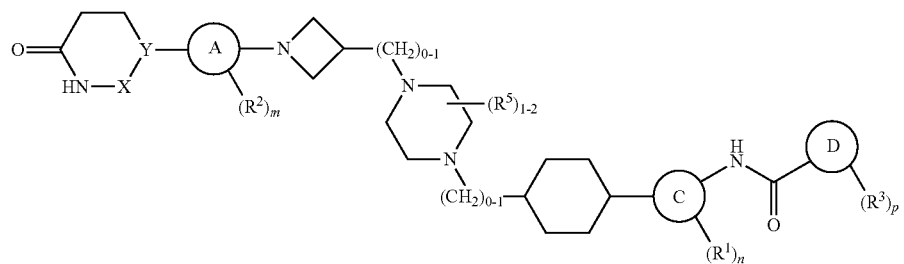

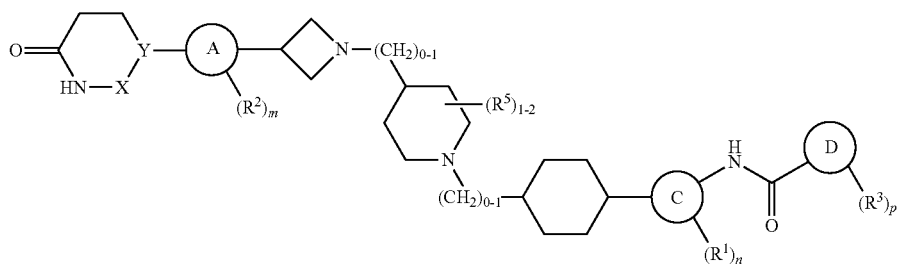

I-ff

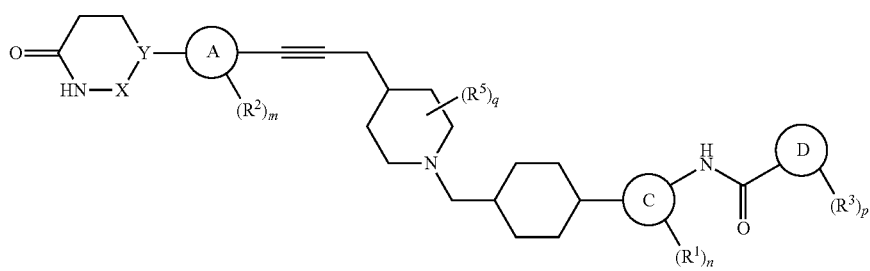

I-gg

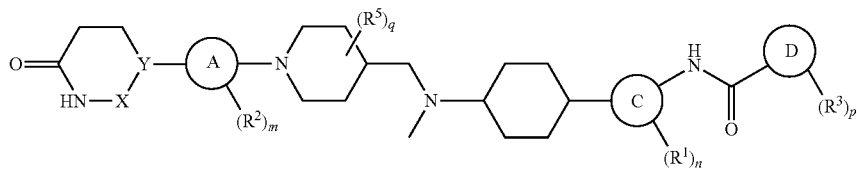

I-hh

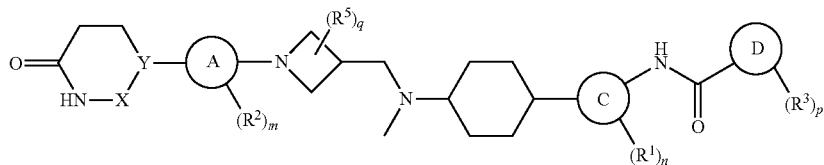

I-ii or a pharmaceutically acceptable salt thereof, wherein each variable is as defined and described herein.

Compounds of the present invention, and pharmaceutically acceptable compositions thereof, are useful for treating a variety of diseases, disorders or conditions, associated with regulation of signaling pathways implicating IRAK kinases. Such diseases, disorders, or conditions include those described herein.

Compounds provided by this invention are also useful for the study of IRAK enzymes in biological and pathological phenomena; the study of intracellular signal transduction pathways occurring in bodily tissues; and the comparative evaluation of new IRAK inhibitors or IRAK degraders or other regulators of kinases, signaling pathways, and cytokine levels in vitro or in vivo.

DETAILED DESCRIPTION OF CERTAIN EMBODIMENTS

1. General Description of Certain Embodiments of the Invention

Compounds of the present invention, and compositions thereof, are useful as degraders and/or inhibitors of one or more IRAK protein kinases. In some embodiments, a provided compound degrades and/or inhibits IRAK4.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms.

In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

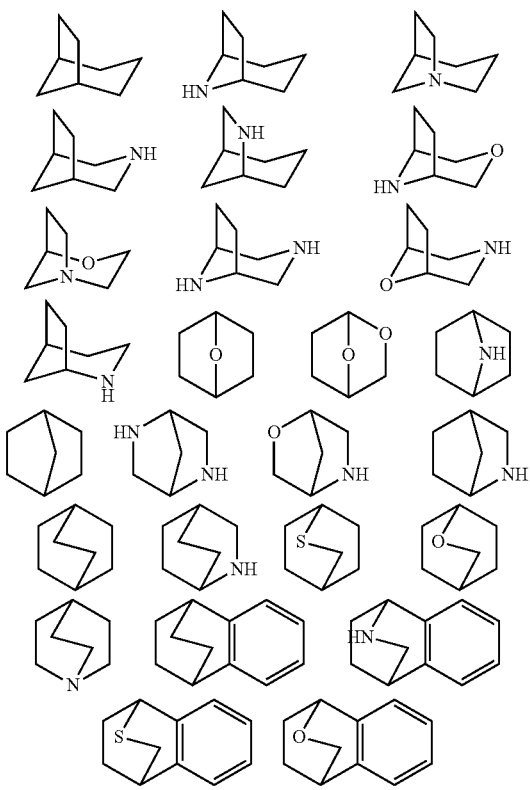

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

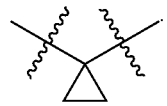 [SMILES: *C1(*)CC1]

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. A heteroaryl ring may include one or more oxo (=O) or thioxo (=S) substituent. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be monocyclic, bicyclic, bridged bicyclic, or spirocyclic. A heterocyclic ring may include one or more oxo (=O) or thioxo (=S) substituent. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —$O(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with R°; —$(CH_2)_{0-4}O(CH_2)_{0-1}Ph$ which may be substituted with R°; —CH=CHPh, which may be substituted with R°; —$(CH_2)_{0-4}O(CH_2)_{0-1}$-pyridyl which may be substituted with R°; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —C(S)R°; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR$—, $SC(S)SR°$; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°)_2$; $SiR°_3$; —$(C_{1-4}$ straight or branched alkylene)O—$N(R°)_2$; or —$(C_{1-4}$ straight or branched alkylene)C(O)O—$N(R°)_2$, wherein each R° may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —$(CH_2)_{0-2}R^●$, -(haloR$^●$), —$(CH_2)_{0-2}OH$, —$(CH_2)_{0-2}OR^●$, —$(CH_2)_{0-2}CH(OR^●)_2$; —$O(haloR^●)$, —CN, —$N_3$, —$(CH_2)_{0-2}C(O)R^●$, —$(CH_2)_{0-2}C(O)OH$, —$(CH_2)_{0-2}C(O)OR^●$, —$(CH_2)_{0-2}SR^●$, —$(CH_2)_{0-2}SH$, —$(CH_2)_{0-2}NH_2$, —$(CH_2)_{0-2}NHR^●$, —$(CH_2)_{0-2}NR^●_2$, —$NO_2$, —$SiR^●_3$, —$OSiR^●_3$, —$C(O)SR^●$, —$(C_{1-4}$ straight or branched alkylene)C(O)OR$^●$, or —$SSR^●$ wherein each R$^●$ is unsubstituted or where preceded by "halo" is substituted only with one or more halogens, and is independently selected from $C_{1-4}$ aliphatic, —$CH_2$Ph, —O($CH_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$)$_{2-3}$O—, or —S(C(R*$_2$))$_{2-3}$S—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$2, or —NO$_2$, wherein each R$^\bullet$ is unsubstituted or where preceded by "halo" is substituted only with one or more halogens, and is independently $C_{1-4}$ aliphatic, —$CH_2$Ph, —O($CH_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently $C_{1-4}$ aliphatic, —$CH_2$Ph, —O($CH_2$)$_{0-1}$Ph, or a 5-6-membered saturated, partially unsaturated, or aryl ring having 0-4 heteroatoms independently selected from nitrogen, oxygen, or sulfur.

As used herein, the term "provided compound" refers to any genus, subgenus, and/or species set forth herein.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$($C_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

As used herein, the term "inhibitor" is defined as a compound that binds to and/or inhibits an IRAK kinase with measurable affinity. In certain embodiments, an inhibitor has an IC$_{50}$ and/or binding constant of less than about 50 µM, less than about 1 µM, less than about 500 nM, less than about 100 nM, less than about 10 nM, or less than about 1 nM.

As used herein, the term "degrader" is defined as a heterobifunctional or monovalent compound that binds to and/or inhibits both an IRAK kinase and an E3 ligase with measurable affinity resulting in the ubiquitination and subsequent degradation of the IRAK kinase. In certain embodiments, a degrader has an DC$_{50}$ of less than about 50 µM, less than about 1 µM, less than about 500 nM, less than about 100 nM, less than about 10 nM, or less than about 1 nM.

A compound of the present invention may be tethered to a detectable moiety. It will be appreciated that such compounds are useful as imaging agents. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57.

As used herein, the term "detectable moiety" is used interchangeably with the term "label" and relates to any moiety capable of being detected, e.g., primary labels and secondary labels. Primary labels, such as radioisotopes (e.g., tritium, $^{32}P$, $^{33}P$, $^{35}S$, or $^{14}C$), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360, 8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably inhibit," as used herein, means a measurable change in an IRAK protein kinase activity between a sample comprising a compound of the present invention, or composition thereof, and an IRAK protein kinase, and an equivalent sample comprising an IRAK protein kinase, in the absence of said compound, or composition thereof. 3. Description of Exemplary Embodiments:

As described above, in certain embodiments, the present invention provides a compound of formula I-a to I-ii:

I-a

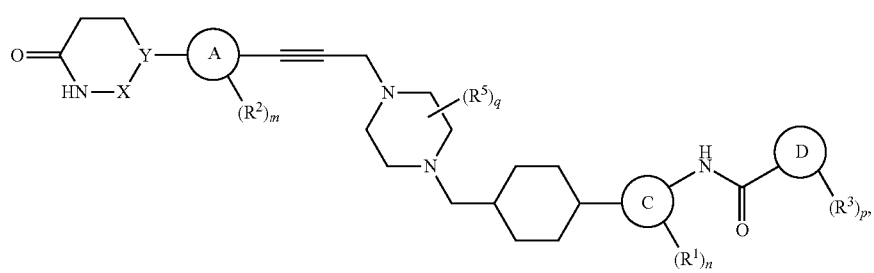

I-b
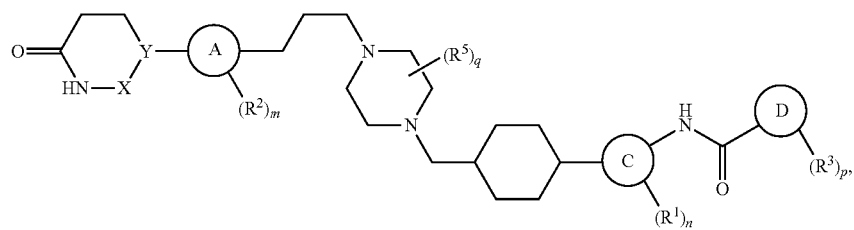
I-c
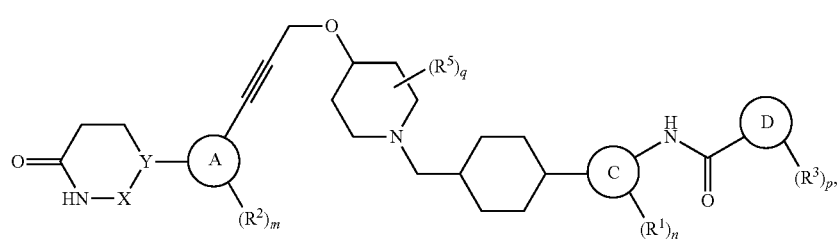
I-d
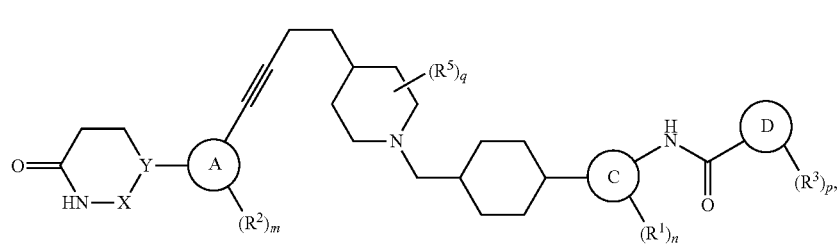
I-e
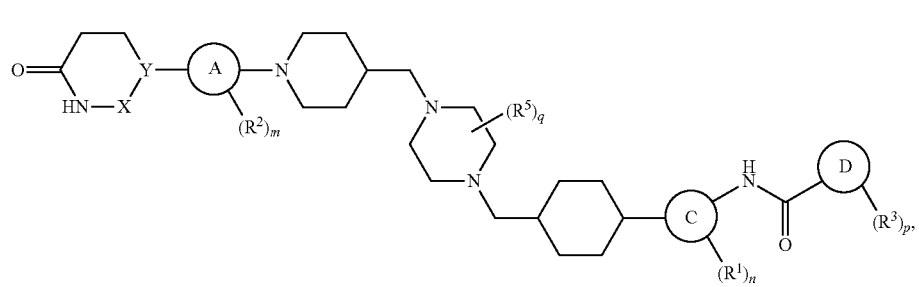
I-f
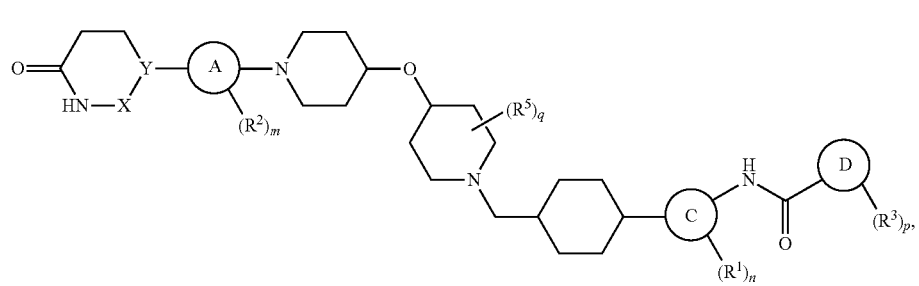
I-g
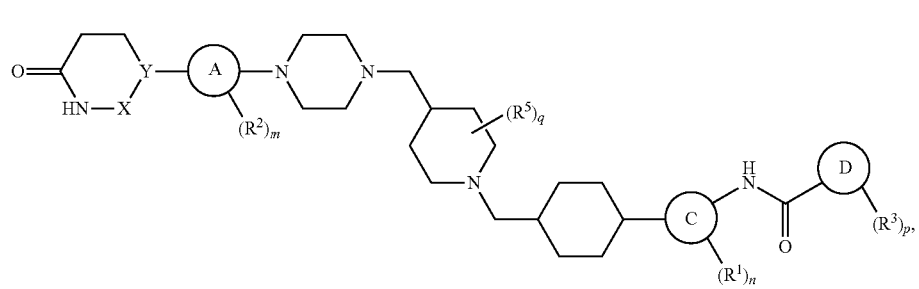

-continued
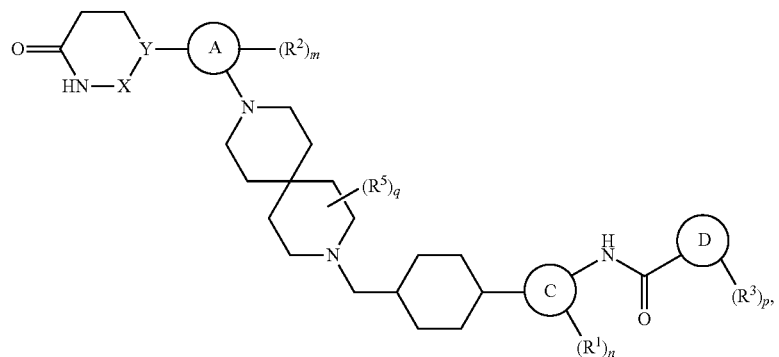
I-h
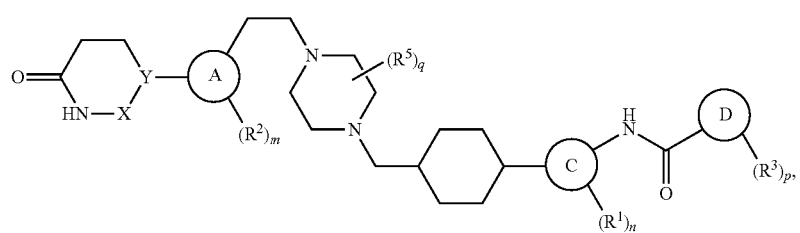
I-i
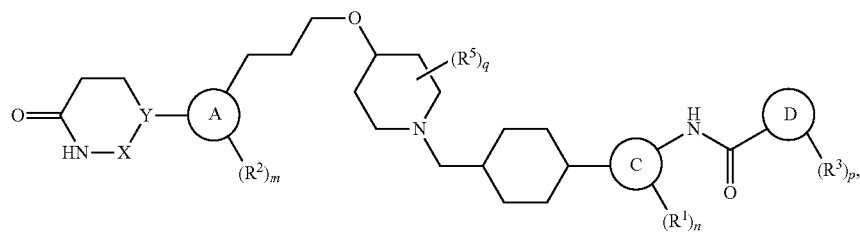
I-j
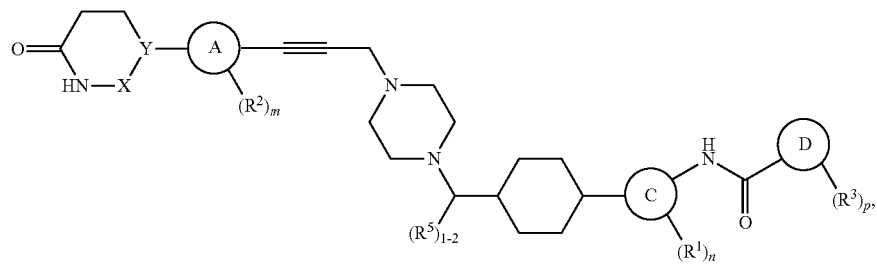
I-k
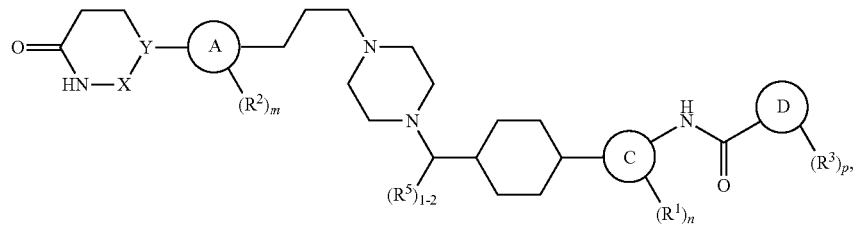
I-l
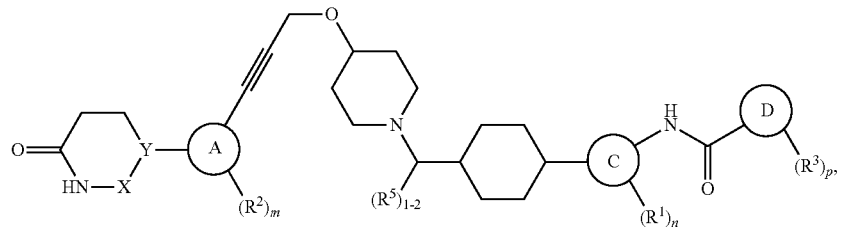
I-m

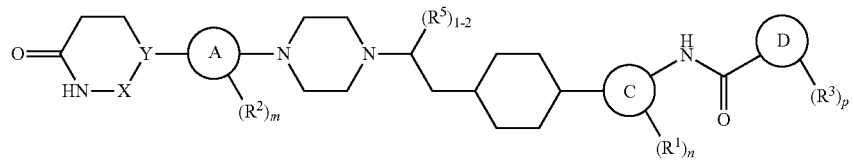
I-n
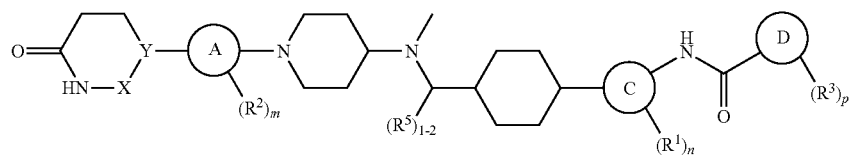
I-o
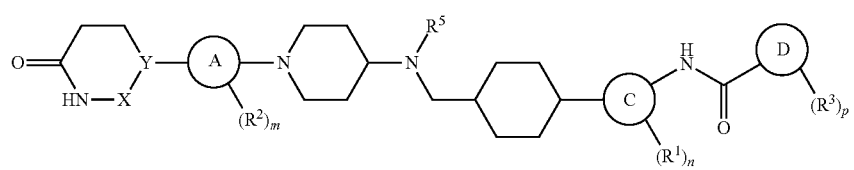
I-p
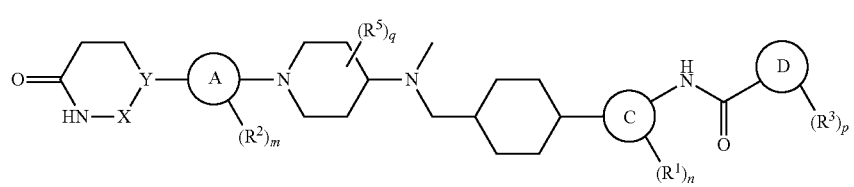
I-q
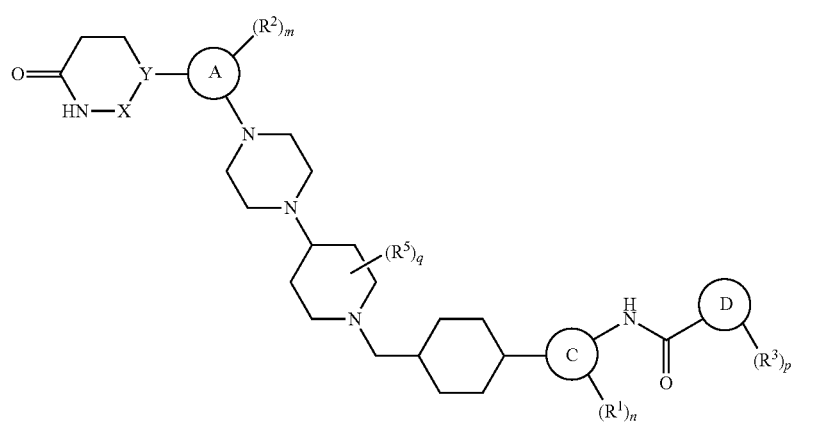
I-r
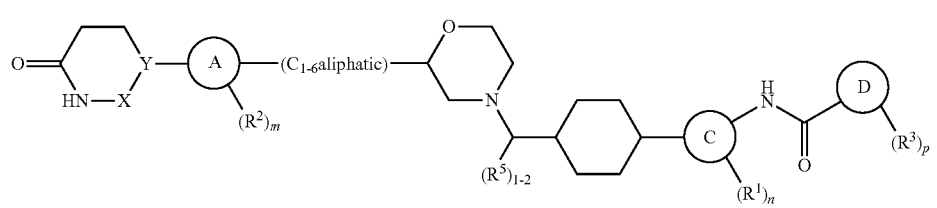
I-s
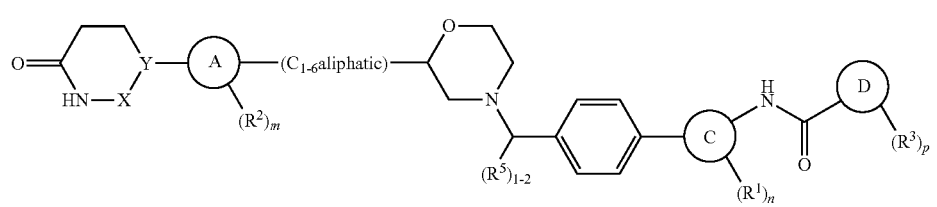
I-t I-u
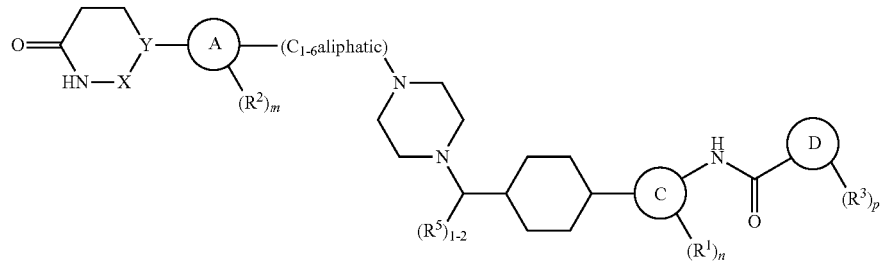
I-v
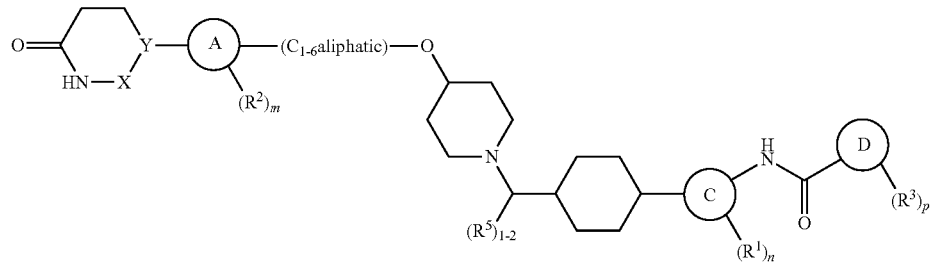
I-w
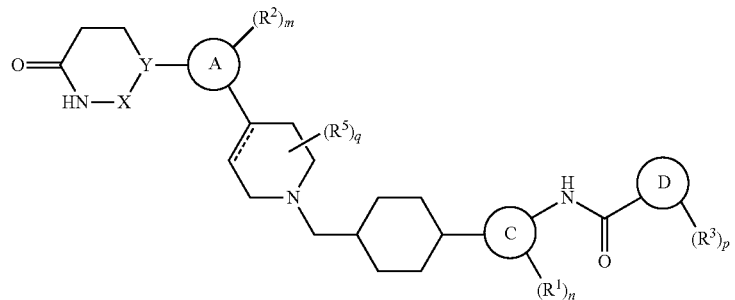
I-x
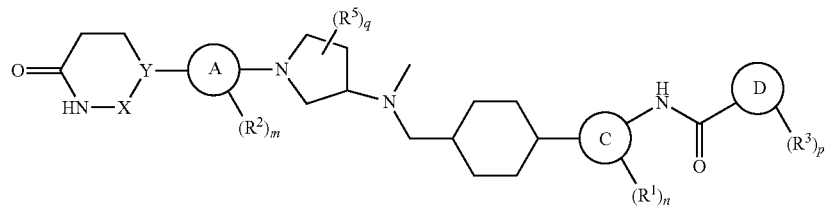
I-y
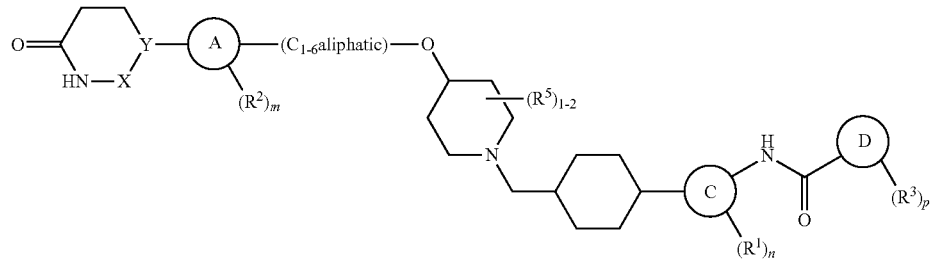
I-z
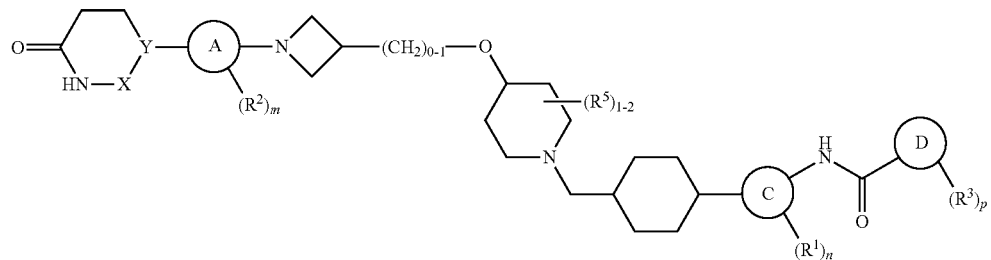

I-aa
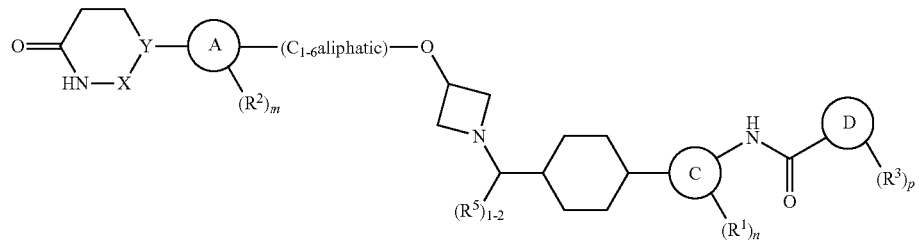
I-bb
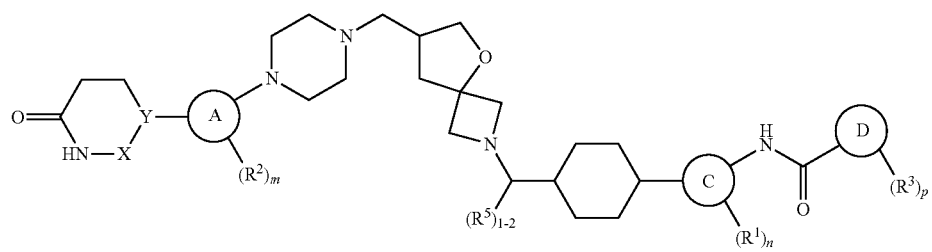
I-cc
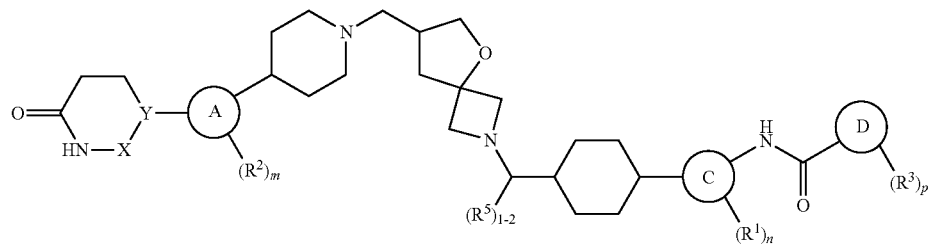
I-dd
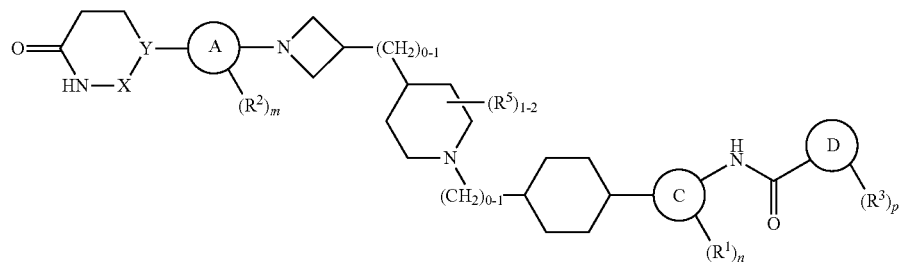
I-ee
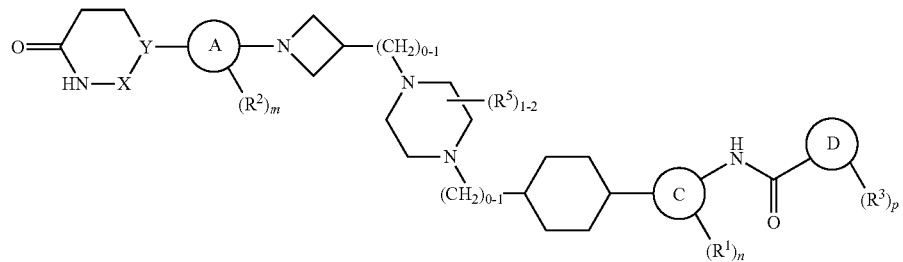
I-ff
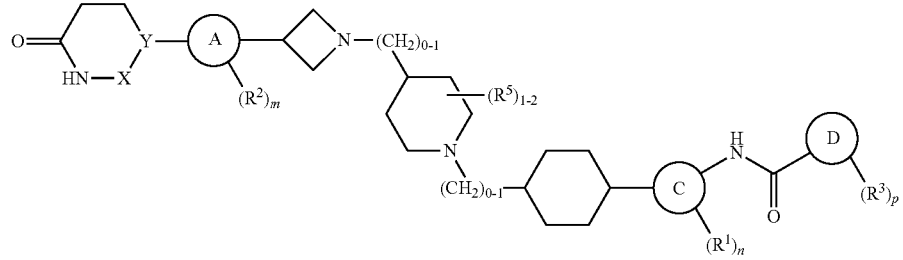

-continued

I-gg

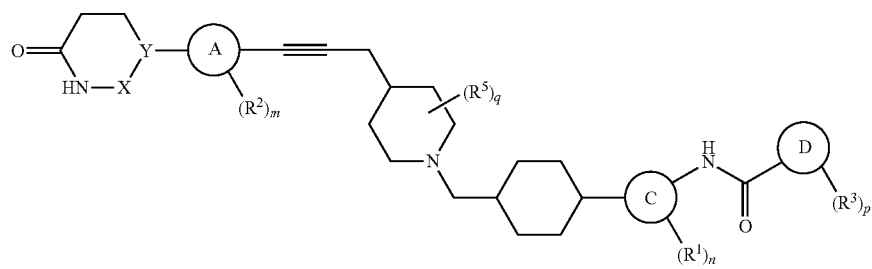

I-hh

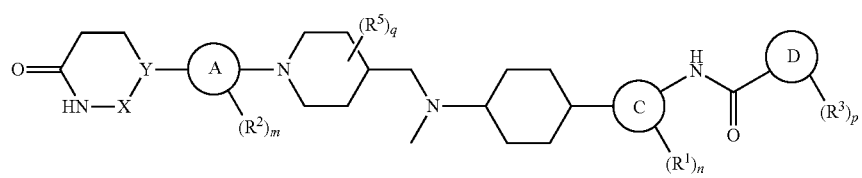

I-ii

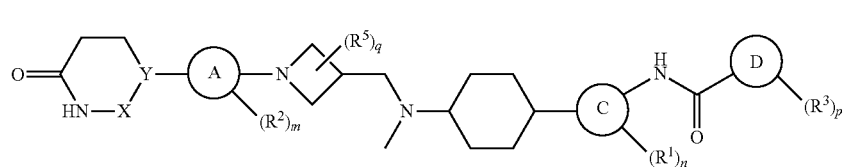

or a pharmaceutically acceptable salt thereof, wherein:

X is a bivalent moiety selected from —CH$_2$— or —C(O)—;

Y is a nitrogen or CH;

Ring A is a ring selected from phenylenyl, naphthylenyl, pyridinylenyl,

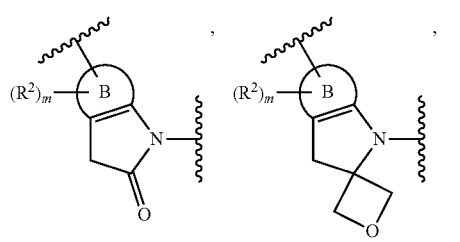

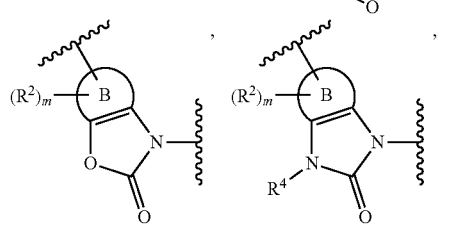

, and

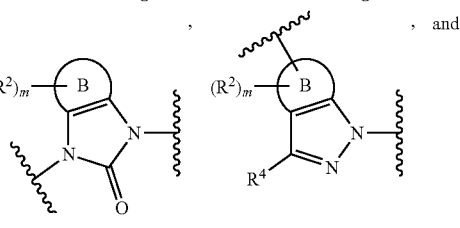

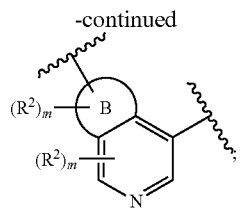

Ring B is a fused ring selected from benzo or a 5-6 membered heteroaryl containing 1-4 heteroatoms independently selected from nitrogen, oxygen, and sulfur;

R$^4$ is hydrogen, C$_{1-5}$ alkyl, or C$_{3-6}$ cycloalkyl;

each of R$^1$, R$^2$, and R$^3$ is independently hydrogen, R$^A$, halogen, —CN, —NO$_2$, —OR, —SR, —NR$_2$, —SiR$_3$, —S(O)$_2$R, —S(O)$_2$NR$_2$, —S(O)R, —C(O)R, —C(O)OR, —C(O)NR$_2$, —C(O)N(R)OR, —CR$_2$N(R)C(O)R, —CR$_2$N(R)C(O)NR$_2$, —CFR$_2$, —CF$_2$R, —CF$_3$, —CR$_2$(OR), —CR$_2$(NR$_2$), —OC(O)R, —OC(O)NR$_2$, —OP(O)R$_2$, —OP(O)(OR)$_2$, —OP(O)(OR)NR$_2$, —OP(O)(NR$_2$)$_2$, —N(R)C(O)OR, —N(R)C(O)R, —N(R)C(O)NR$_2$, —N(R)S(O)$_2$R, —N(R)P(O)R$_2$, —N(R)P(O)(OR)$_2$, —N(R)P(O)(OR)NR$_2$, —N(R)P(O)(NR$_2$)$_2$, or —N(R)S(O)$_2$R;

each R is independently hydrogen, or an optionally substituted group selected from C$_{1-6}$ aliphatic, phenyl, a 3-7 membered saturated or partially unsaturated carbocyclic or heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same carbon or nitrogen are optionally taken together with their intervening atoms to form a 4-11 membered saturated or partially unsaturated monocyclic, bicyclic, bridged bicyclic, or spirocyclic carbocyclic or heterocyclic ring having 1-3 heteroatoms, in addition to the carbon or nitrogen from which the two R groups are attached, independently selected from nitrogen, oxygen, and sulfur;

each $R^A$ is independently an optionally substituted group selected from $C_{1-6}$ aliphatic, phenyl, a 4-7 membered saturated or partially unsaturated carbocyclic or heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$R^5$ is hydrogen, halo, —CN, —OR, oxo, $C_{1-6}$ alkyl, —$CR_2OR$, —$OC_{1-6}$ alkyl, $C_{1-6}$ haloalkyl, —$OC_{1-6}$ haloalkyl, or $C_{3-6}$ cycloalkyl, or:

two $R^5$ groups on the same carbon atom combine to form, with the carbon atom from which the two R groups are attached, a 3-7 membered saturated or partially unsaturated carbocyclic or heterocyclic ring having 1-3 heteroatoms independently selected from nitrogen, oxygen, and sulfur, or two $R^5$ groups on two different carbon atoms combine to form, with the intervening atoms connecting the two $R^5$ groups, a 3-7 membered saturated or partially unsaturated carbocyclic or heterocyclic ring having 1-3 heteroatoms independently selected from nitrogen, oxygen, and sulfur;

each of Ring C and Ring D is independently a ring selected from phenyl or a 5-9 membered heteroaryl ring having 1-3 heteroatoms independently selected from nitrogen, oxygen, and sulfur; and each of m, n, p, and q are independently 0, 1, 2, 3 or 4.

As defined above and described herein, X is a bivalent moiety selected from —$CH_2$— and —C(O)—.

In some embodiments, X is —$CH_2$—. In some embodiments, X is —C(O)—.

In some embodiments, X is selected from those depicted in Table 1 below.

As defined above and described herein, Y is a nitrogen atom or CH.

In some embodiments, Y is a nitrogen atom. In some embodiments, Y is CH.

In some embodiments, Y is selected from those depicted in Table 1 below.

As defined above and described herein, Ring A is a ring selected from phenylenyl, naphthylenyl, pyridinylenyl,

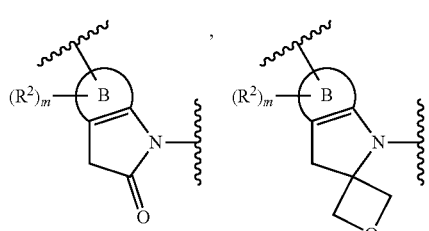

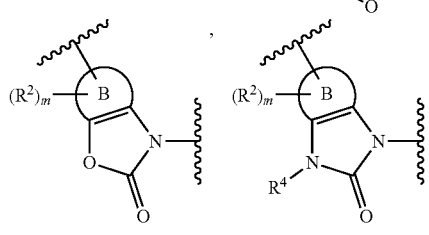

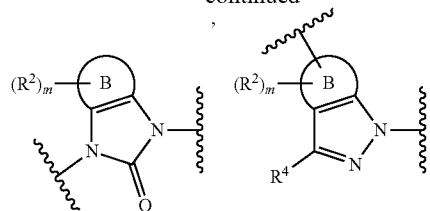

In some embodiments, Ring A is phenylenyl. In some embodiments, Ring A is naphthylenyl. In some embodiments, Ring A is pyridinylenyl. In some embodiments, Ring A is

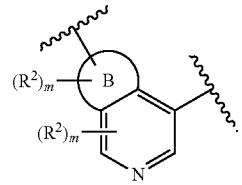

In some embodiments, Ring A is

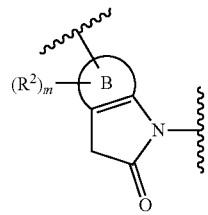

In some embodiments, Ring A is

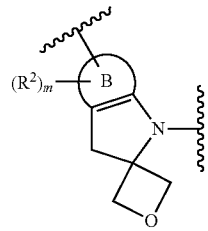

In some embodiments, Ring A is

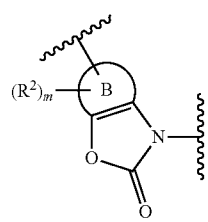

In some embodiments, Ring A is

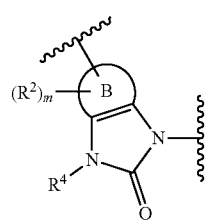

In some embodiments, Ring A is

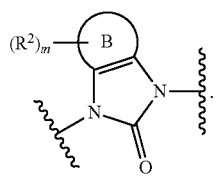

In some embodiments, Ring A is

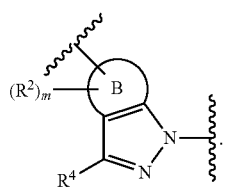

In some embodiments, Ring A is

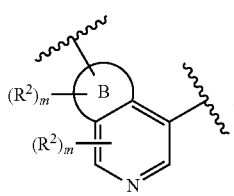

In other embodiments Ring A is a 6-10 membered monocyclic or bicyclic heteroaryl containing 1-4 heteroatoms independently selected from nitrogen, oxygen, and sulfur.

In some embodiments, Ring A is selected from those depicted in Table 1 below.

As defined above and described herein, Ring B is a fused ring selected from benzo or a 5-6 membered heteroaryl containing 1-4 heteroatoms independently selected from nitrogen, oxygen, and sulfur.

In some embodiments, Ring B is benzo. In some embodiments, Ring B is a 5-6 membered heteroaryl containing 1-4 heteroatoms independently selected from nitrogen, oxygen, and sulfur.

In some embodiments, Ring B is selected from those depicted in Table 1 below.

In some embodiments, Ring A and Ring B are

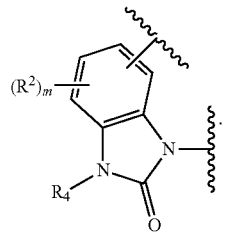

In some embodiments, Ring A and Ring B are

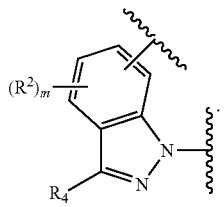

In some embodiments, Ring A and Ring B are

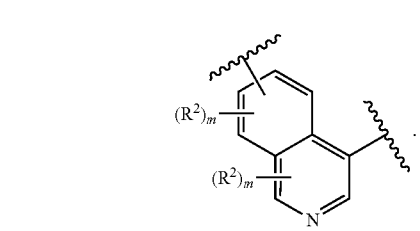

As defined above and described herein, each of Ring C and Ring D is independently a ring selected from phenyl or a 5-9 membered heteroaryl ring having 1-3 heteroatoms independently selected from nitrogen, oxygen, and sulfur.

In some embodiments, Ring C is phenyl. In some embodiments, Ring C is a 5-9 membered heteroaryl ring having 1-3 heteroatoms independently selected from nitrogen, oxygen, and sulfur. In some embodiments, Ring C is a 5-membered heteroaryl ring having 1-3 heteroatoms independently selected from nitrogen, oxygen, and sulfur. In some embodiments, Ring C is a 6-membered heteroaryl ring having 1-3 heteroatoms independently selected from nitrogen, oxygen, and sulfur. In some embodiments, Ring C is a 9-membered heteroaryl ring having 1-3 heteroatoms independently selected from nitrogen, oxygen, and sulfur. In some embodiments, Ring C is a 9-membered heteroaryl ring having 2 nitrogens. In some embodiments, Ring C is a 9-membered heteroaryl ring having 3 nitrogens.

In some embodiments, Ring C is phenyl. In some embodiments, Ring C is pyridyl. In some embodiments, Ring C is pyrazolyl. In some embodiments, Ring C is indazolyl. In some embodiments, Ring C is benzothiazolyl.

In some embodiments, Ring C is

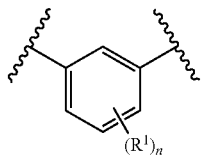

In some embodiments, Ring C is

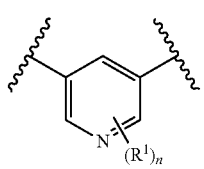

In some embodiments, Ring C is
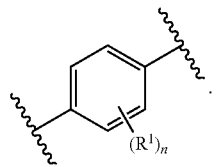
In some embodiments, Ring C is
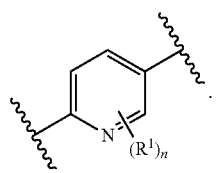
In some embodiments, Ring C is
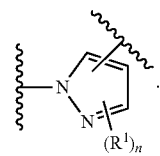
In some embodiments, Ring C is
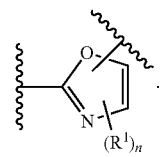
In some embodiments, Ring C is
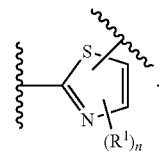
In some embodiments, Ring C is
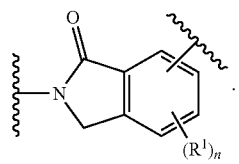
In some embodiments, Ring C is
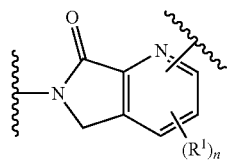
In some embodiments, Ring C
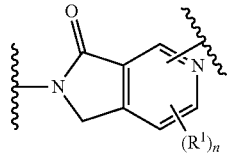
In some embodiments, Ring C is
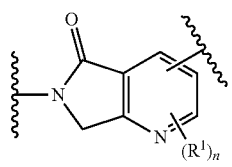
In some embodiments, Ring
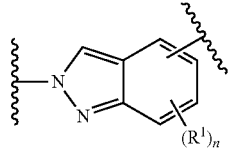
In some embodiments, Ring C is
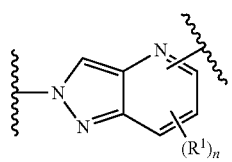
In some embodiments, Ring C is
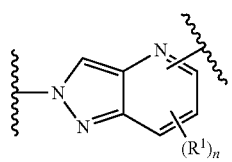

In some embodiments, Ring C is

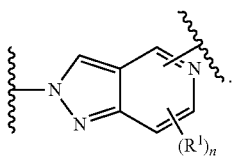

In some embodiments, Ring C is

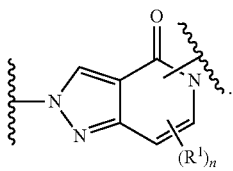

In some embodiments, Ring C is

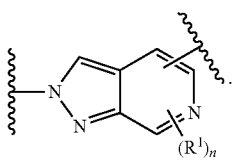

In some embodiments, Ring C is

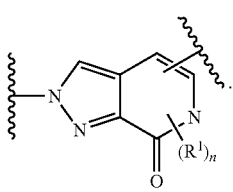

In some embodiments, Ring C is

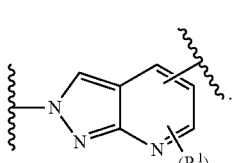

In some embodiments, Ring C is

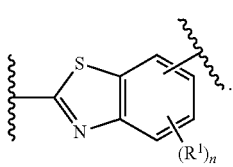

In some embodiments, Ring C is

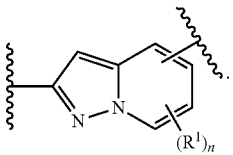

In some embodiments, Ring C is

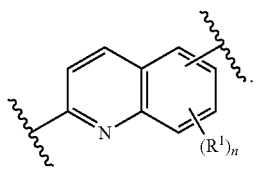

In some embodiments, Ring D is phenyl. In some embodiments, Ring D is a 5-9 membered heteroaryl ring having 1-3 heteroatoms independently selected from nitrogen, oxygen, and sulfur. In some embodiments, Ring D is a 6-membered heteroaryl ring having 1-3 heteroatoms independently selected from nitrogen, oxygen, and sulfur. In some embodiments, Ring D is a 9-membered heteroaryl ring having 1-3 heteroatoms independently selected from nitrogen, oxygen, and sulfur. In some embodiments, Ring D is a 9-membered heteroaryl ring having 2 nitrogens. In some embodiments, Ring D is a 9-membered heteroaryl ring having 3 nitrogens.

In some embodiments, Ring D is phenyl. In some embodiments, Ring D is pyridyl. In some embodiments, Ring D is pyrazinyl. In some embodiments, Ring D is pyrazolo[1,5-a]pyrimidinyl. In some embodiments, Ring D is pyrrolo[1,2-a]pyrimidine.

In some embodiments, Ring D is

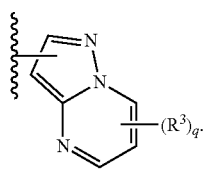

In some embodiments, Ring D is

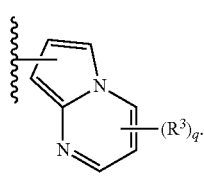

In some embodiments, Ring C and Ring D are selected from those depicted in Table 1 below.

As defined above and described herein, each of $R^1$, $R^2$, and $R^3$ is independently hydrogen, $R^A$, halogen, —CN, —NO$_2$, —OR, —SR, —NR$_2$, —SiR$_3$, —S(O)$_2$R, —S(O)$_2$NR$_2$, —S(O)R, —C(O)R, —C(O)OR, —C(O)NR$_2$, —C(O)N(R)OR, —C(R)$_2$N(R)C(O)R, —C(R)$_2$N(R)C(O)NR$_2$, —CFR$_2$, —CF$_2$R, —CF$_3$, —CR$_2$(OR), —CR$_2$(NR$_2$), —OC(O)R, —OC(O)NR$_2$, —OP(O)R$_2$, —OP(O)(OR)$_2$, —OP(O)(OR)NR$_2$, —OP(O)(NR$_2$)$_2$, —N(R)C(O)OR, —N(R)C(O)R, —N(R)C(O)NR₂, —N(R)S(O)₂R, —N(R)P(O)R₂, —N(R)P(O)(OR)₂, —N(R)P(O)(OR)NR₂, —N(R)P(O)(NR₂)₂, or —N(R)S(O)₂R.

In some embodiments, one or more of $R^1$, $R^2$, and $R^3$ is hydrogen. In some embodiments, one or more of $R^1$, $R^2$, and $R^3$ is deuterium. In some embodiments, one or more of $R^1$, $R^2$, and $R^3$ is $R^A$. In some embodiments, one or more of $R^1$, $R^2$, and $R^3$ is halogen. In some embodiments, one or more of $R^1$, $R^2$, and $R^3$ is $R^A$. In some embodiments, one or more of $R^1$, $R^2$, and $R^3$ is —CN. In some embodiments, one or more of $R^1$, $R^2$, and $R^3$ is —NO₂. In some embodiments, one or more of $R^1$, $R^2$, and $R^3$ is —OR. In some embodiments, one or more of $R^1$, $R^2$, and $R^3$ is —Si(OH)₂R. In some embodiments, one or more of $R^1$, $R^2$, and $R^3$ is —Si(OH)R₂. In some embodiments, one or more of $R^1$, $R^2$, and $R^3$ is —SR. In some embodiments, one or more of $R^1$, $R^2$, and $R^3$ is —NR₂. In some embodiments, one or more of $R^1$, $R^2$, and $R^3$ is —SiR₃. In some embodiments, one or more of $R^1$, $R^2$, and $R^3$ is —S(O)₂R. In some embodiments, one or more of $R^1$, $R^2$, and $R^3$ is —S(O)₂NR₂. In some embodiments, one or more of $R^1$, $R^2$, and $R^3$ is —S(O)R. In some embodiments, one or more of $R^1$, $R^2$, and $R^3$ is —C(O)R. In some embodiments, one or more of $R^1$, $R^2$, and $R^3$ is —C(O)OR. In some embodiments, one or more of $R^1$, $R^2$, and $R^3$ is —C(O)NR₂. In some embodiments, one or more of $R^1$, $R^2$, and $R^3$ is —C(O)N(R)OR. In some embodiments, one or more of $R^1$, $R^2$, and $R^3$ is —CR₂N(R)C(O)R. In some embodiments, one or more of $R^1$, $R^2$, and $R^3$ is —CR₂N(R)C(O)NR₂. In some embodiments, one or more of $R^1$, $R^2$, and $R^3$ is —CFR₂. In some embodiments, one or more of $R^1$, $R^2$, and $R^3$ is —CF₂R. In some embodiments, one or more of $R^1$, $R^2$, and $R^3$ is —CF₃. In some embodiments, one or more of $R^1$, $R^2$, and $R^3$ is —CR₂(OR). In some embodiments, one or more of $R^1$, $R^2$, and $R^3$ is —CR₂(NR₂). In some embodiments, one or more of $R^1$, $R^2$, and $R^3$ is —OC(O)R. In some embodiments, one or more of $R^1$, $R^2$, and $R^3$ is —OC(O)NR₂. In some embodiments, one or more of $R^1$, $R^2$, and $R^3$ is —OP(O)R₂. In some embodiments, one or more of $R^1$, $R^2$, and $R^3$ is —OP(O)(OR)₂. In some embodiments, one or more of $R^1$, $R^2$, and $R^3$ is —OP(O)(OR)NR₂. In some embodiments, $R^2$ is independently —OP(O)(NR₂)₂—. In some embodiments, one or more of $R^1$, $R^2$, and $R^3$ is —N(R)C(O)OR. In some embodiments, one or more of $R^1$, $R^2$, and $R^3$ is —N(R)C(O)R. In some embodiments, one or more of $R^1$, $R^2$, and $R^3$ is —N(R)C(O)NR₂. In some embodiments, one or more of $R^1$, $R^2$, and $R^3$ is —N(R)P(O)R₂. In some embodiments, one or more of $R^1$, $R^2$, and $R^3$ is —N(R)P(O)(OR)₂. In some embodiments, one or more of $R^1$, $R^2$, and $R^3$ is —N(R)P(O)(OR)NR₂. In some embodiments, one or more of $R^1$, $R^2$, and $R^3$ is —N(R)P(O)(NR₂)₂. In some embodiments, one or more of $R^1$, $R^2$, and $R^3$ is —N(R)S(O)₂R.

In some embodiments, $R^1$ is fluoro. In some embodiments, $R^1$ is chloro. In some embodiments, $R^1$ is $C_{1-6}$alkyl. In some embodiments, $R^1$ is methyl. In some embodiments, $R^1$ is —C(OH)Me₂. In some embodiments, $R^1$ is —CHF₂. In some embodiments, $R^1$ is —CF₃. In some embodiments, $R^1$ is —OC$_{1-6}$alkyl. In some embodiments, $R^1$ is —OMe. In some embodiments, $R^1$ is

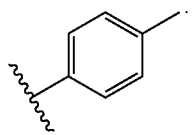

In some embodiments, $R^1$ is

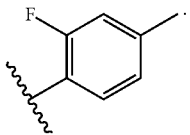 [SMILES: *c1ccc(C)cc1F ; "."]

In some embodiments, $R^1$ is N

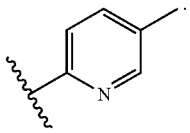

In some embodiments, $R^2$ is fluoro. In some embodiments, $R^2$ is chloro. In some embodiments, $R^2$ is $C_{1-6}$alkyl. In some embodiments, $R^2$ is methyl. In some embodiments, $R^3$ is —C(OH)Me₂. In some embodiments, $R^2$ is —CHF₂. In some embodiments, $R^3$ is —CF₃. In some embodiments, $R^2$ is —OC$_{1-6}$alkyl. In some embodiments, $R^2$ is —OMe.

In some embodiments, $R^3$ is fluoro. In some embodiments, $R^3$ is chloro. In some embodiments, $R^3$ is —CN. In some embodiments, $R^3$ is $C_{1-6}$alkyl. In some embodiments, $R^3$ is methyl. In some embodiments, $R^3$ is ethyl. In some embodiments, $R^3$ is isopropyl. In some embodiments, $R^3$ is t-butyl. In some embodiments, $R^3$ is —CH₂OMe. In some embodiments, $R^3$ is —C(OMe)Me₂. In some embodiments, $R^3$ is —C(CN)Me₂. In some embodiments, $R^3$ is $C_{3-6}$cycloalkyl. In some embodiments, $R^3$ is cyclopropyl. In some embodiments, $R^3$ is cyclobutyl. In some embodiments, $R^3$ is —CHF₂. In some embodiments, $R^3$ is —CF₃. In some embodiments, $R^3$ is —OCF₃. In some embodiments, $R^3$ is —OCHF₂. In some embodiments, $R^3$ is —OC$_{1-6}$alkyl. In some embodiments, $R^3$ is —OiPr. In some embodiments, $R^3$ is —OC$_{3-6}$cycloalkyl. In some embodiments, $R^3$ is

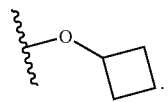

In some embodiments, $R^3$ is

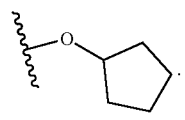 [SMILES: *OC1CCCC1 ; "."]

In some embodiments, $R^3$ is

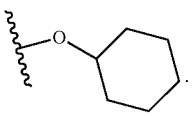

In some embodiments, $R^3$ is —OMe. In some embodiments, $R^3$ is —NMe₂. In some embodiments, $R^3$ is

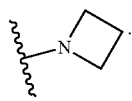
In some embodiments, R³ is
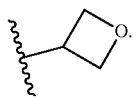 [SMILES: *C1COC1]
In some embodiments, R³ is
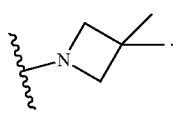 [SMILES: *N1CC(C)(C)C1 ; "."]
In some embodiments, R³ is
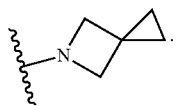
In some embodiments, R³ is
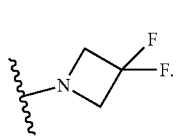 [SMILES: *N1CC(F)(F)C1]
In some embodiments, R³ is
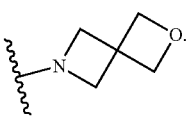
In some embodiments, R³ is
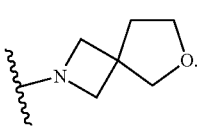 [SMILES: *N1CC2(CCOC2)C1]
In some embodiments, R³ is
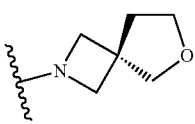
In some embodiments, R³ is
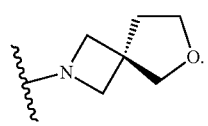
In some embodiments, R³ is
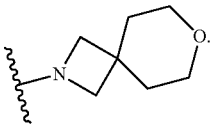 [SMILES: *N1CC2(CCOCC2)C1]
In some embodiments, R³ is
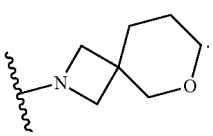 [SMILES: *N1CC2(CCCOC2)C1]
In some embodiments, R³ is
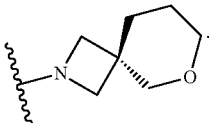
In some embodiments, R³ is
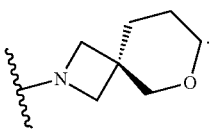
In some embodiments, R³ is
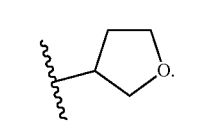 [SMILES: *C1CCOC1]

In some embodiments, R³ is

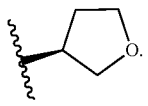

In some embodiments, R³ is

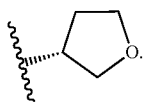

In some embodiments, R³ is

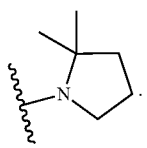

In some embodiments, R³ is

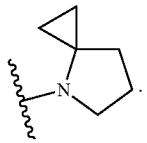

In some embodiments, R³ is

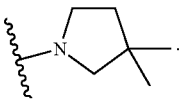 [SMILES: *N1CCC(C)(C)C1]

In some embodiments, R³ is

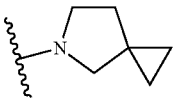

In some embodiments, R³ is

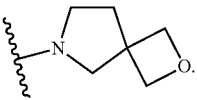 [SMILES: *N1CCC2(COC2)C1]

In some embodiments, R³ is

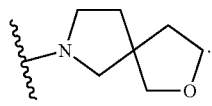 [SMILES: *N1CCC2(CCOC2)C1]

In some embodiments, R³ is

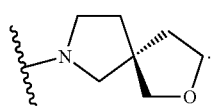 [SMILES: *N1CC[C@]2(CCOC2)C1]

In some embodiments, R³ is

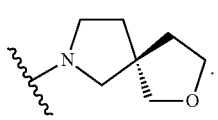 [SMILES: *N1CC[C@@]2(CCOC2)C1]

In some embodiments, R³ is

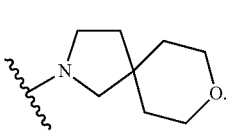 [SMILES: *N1CCC2(CCOCC2)C1]

In some embodiments, R³ is

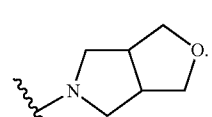

In some embodiments, R³ is

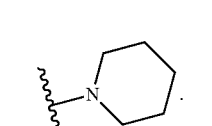

In some embodiments, R³ is

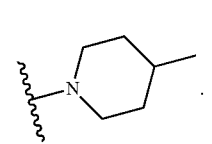 [SMILES: *N1CCC(C)CC1]

In some embodiments, R³ is

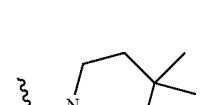

In some embodiments, R³ is
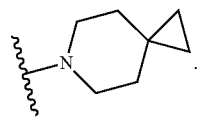
In some embodiments, R³ is
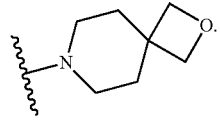 [SMILES: *N1CCC2(CC1)COC2]
In some embodiments, R³ is
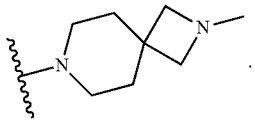 [SMILES: *N1CCC2(CC1)CN(C)C2]
In some embodiments, R³ is
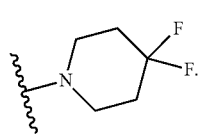
In some embodiments, R³ is
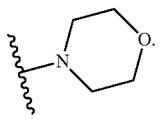
In some embodiments, R³ is
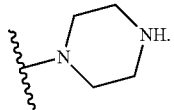 [SMILES: *N1CCNCC1]
In some embodiments, R³ is
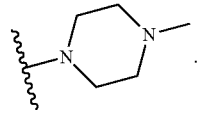 [SMILES: *N1CCN(C)CC1]
In some embodiments, R³ is
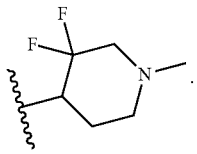 [SMILES: *C1CCN(C)CC1(F)F]
In some embodiments, R³ is
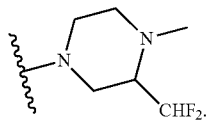
In some embodiments, R³ is
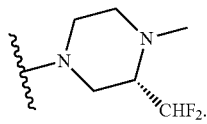
In some embodiments, R³ is
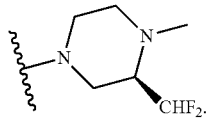
In some embodiments, R³ is
In some embodiments, R³ is
In some embodiments, R³ is
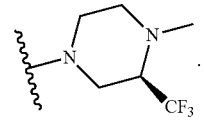

In some embodiments, R³ is
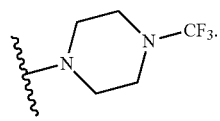 [SMILES: *N1CCN(C(F)(F)F)CC1]
In some embodiments, R³ is
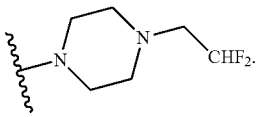 [SMILES: *N1CCN(CC(F)F)CC1]
In some embodiments, R³ is
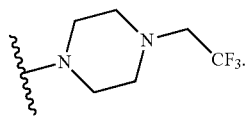 [SMILES: *N1CCN(CC(F)(F)F)CC1]
In some embodiments, R³ is
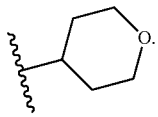
In some embodiments, R³ is
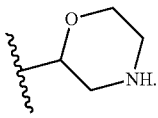 [SMILES: *C1CNCCO1]
In some embodiments, R³ is
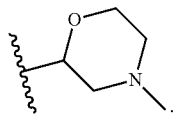
In some embodiments, R³ is
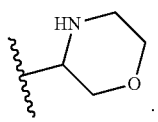
In some embodiments, R³ is
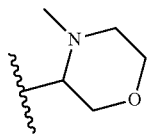
In some embodiments, R³ is
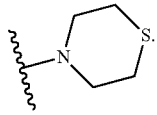
In some embodiments, R³ is
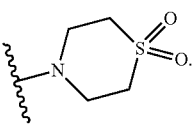 [SMILES: *N1CCS(=O)(=O)CC1]
In some embodiments, R³ is
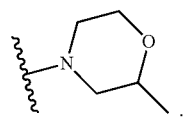 [SMILES: *N1CCOC(C)C1]
In some embodiments, R³ is
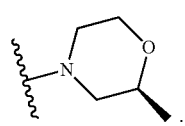 [SMILES: *N1CCO[C@@H](C)C1]
In some embodiments, R³ is
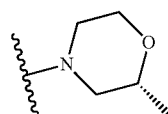
In some embodiments, R³ is
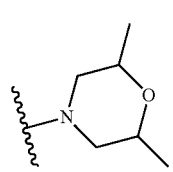

In some embodiments, R³ is
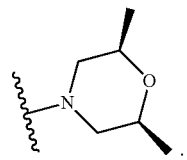 [SMILES: *N1C[C@@H](C)O[C@@H](C)C1]
In some embodiments, R³ is
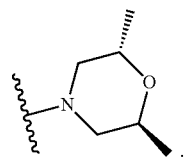 [SMILES: *N1C[C@H](C)O[C@@H](C)C1]
In some embodiments, R³ is
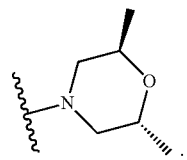
In some embodiments, R³ is
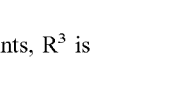
In some embodiments, R³ is
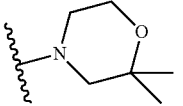
In some embodiments, R³ is
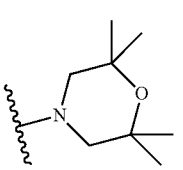
In some embodiments, R³ is
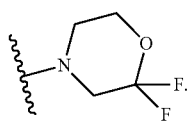 [SMILES: *N1CCOC(F)(F)C1]
In some embodiments, R³ is
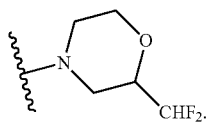
In some embodiments, R³ is
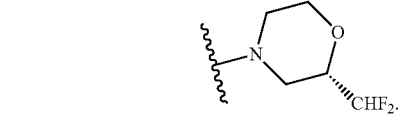 [SMILES: *N1CCO[C@H](C(F)F)C1]
In some embodiments, R³ is
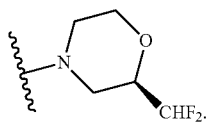
In some embodiments, R³ is
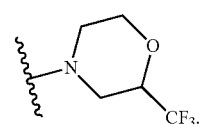
In some embodiments, R³ is
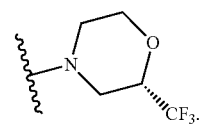
In some embodiments, R³ is
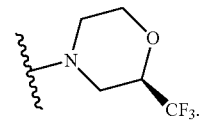
In some embodiments, R³ is
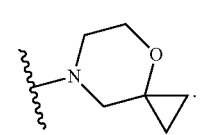

In some embodiments, $R^3$ is

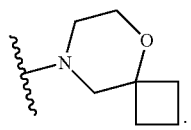

In some embodiments, $R^3$ is

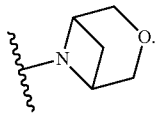

In some embodiments, $R^3$ is

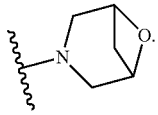

In some embodiments, $R^3$ is

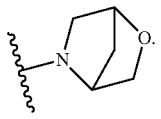

In some embodiments, $R^3$ is

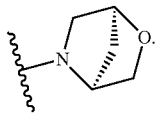

In some embodiments, $R^3$ is

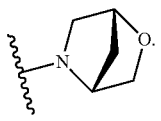

In some embodiments, $R^3$ is

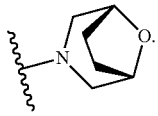

In some embodiments, $R^3$ is

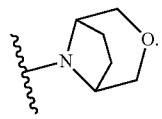

In some embodiments, $R^3$ is

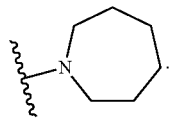

In some embodiments, $R^3$ is

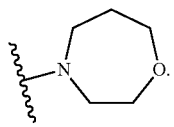

In some embodiments, $R^3$ is —SMe. In some embodiments, $R^3$ is —SCF$_3$. In some embodiments, $R^3$ is —SOCF$_3$. In some embodiments, $R^3$ is —SO$_2$CF$_3$.

In some embodiments, $R^1$, $R^2$, and $R^3$ are selected from those depicted in Table 1 below.

As defined above and described herein, $R^4$ is hydrogen, $C_{1-5}$ alkyl, or $C_{3-6}$ cycloalkyl.

In some embodiments, $R^4$ is hydrogen. In some embodiments, $R^4$ is $C_{1-5}$ alkyl. In some embodiments, $R^4$ is $C_{3-6}$ cycloalkyl.

In some embodiments, $R^4$ is methyl. In some embodiments, $R^4$ is ethyl. In some embodiments, $R^4$ is cyclopropyl.

In some embodiments, $R^4$ is selected from those depicted in Table 1 below.

As defined above and described herein, $R^5$ is hydrogen, halo, —CN, —OR, oxo, $C_{1-6}$ alkyl, —CR$_2$OR, —OC$_{1-6}$ alkyl, $C_{1-6}$ haloalkyl, —OC$_{1-6}$ haloalkyl, or $C_{3-6}$ cycloalkyl, two $R^5$ groups on the same carbon atom combine to form, with the carbon atom from which the two $R^5$ groups are attached, a 3-7 membered saturated or partially unsaturated carbocyclic or heterocyclic ring having 1-3 heteroatoms independently selected from nitrogen, oxygen, and sulfur, or two $R^5$ groups on two different carbon atoms combine to form, with the intervening atoms connecting the two $R^5$ groups, a 3-7 membered saturated or partially unsaturated carbocyclic or heterocyclic ring having 1-3 heteroatoms independently selected from nitrogen, oxygen, and sulfur.

In some embodiments, $R^5$ is hydrogen. In some embodiments, $R^5$ is halo. In some embodiments, $R^5$ is —CN. In some embodiments, $R^5$ is —OR. In some embodiments, $R^5$ is oxo. In some embodiments, $R^5$ is $C_{1-6}$ alkyl. In some embodiments, $R^5$ is —CR$_2$OR. In some embodiments, $R^5$ is —OC$_{1-6}$ alkyl. In some embodiments, $R^5$ is $C_{1-6}$ haloalkyl. In some embodiments, $R^5$ is —OC$_{1-6}$ haloalkyl. In some embodiments, $R^5$ is $C_{3-6}$ cycloalkyl. In some embodiments, two $R^5$ groups on the same carbon atom combine to form, with the carbon atom from which the two $R^5$ groups are attached, a 3-7 membered saturated or partially unsaturated carbocyclic or heterocyclic ring having 1-3 heteroatoms independently selected from nitrogen, oxygen, and sulfur. In some embodiments, two $R^5$ groups on two different carbon atoms combine to form, with the intervening atoms connecting the two R⁵ groups, a 3-7 membered saturated or partially unsaturated carbocyclic or heterocyclic ring having 1-3 heteroatoms independently selected from nitrogen, oxygen, and sulfur.

In some embodiments, R⁵ is fluoro. In some embodiments, R⁵ is geminal difluoro. In some embodiments, R⁵ is methyl. In some embodiments, R⁵ is —OH. In some embodiments, R⁵ is —OMe. In some embodiments, R⁵ is —CMe₂OH. In some embodiments, R⁵ is —CF₃. In some embodiments, R⁵ is —CHF₂. In some embodiments, R⁵ is —CH₂CF₃. In some embodiments, R⁵ is —CH₂CHF₂.

In some embodiments, two R⁵ groups on two different carbon atoms combine to form —R⁵— of a 3-7 membered rated or partially unsaturated carbocyclic or heterocyclic ring having 1-3 heteroatoms independently selected from nitrogen, oxygen, and sulfur, wherein —R⁵— is —CH₂—, —O—, —CH₂CH₂—, —CH₂O—, or —CH₂OCH₂—. In some embodiments, two R⁵ groups on two different carbon atoms combine to form —R⁵— of a bridged bicycle (e.g., 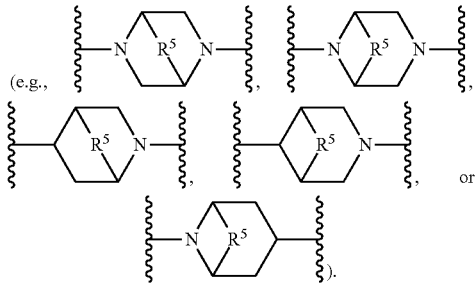 ).

In some embodiments,

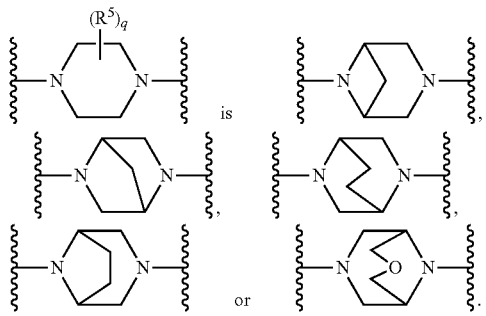 is

In some embodiments,

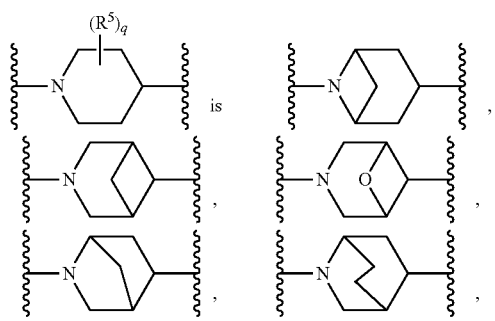

-continued

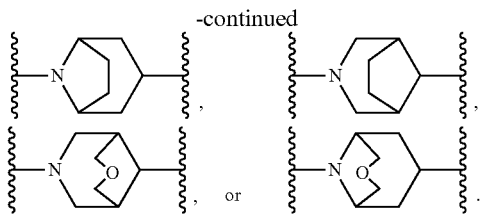

In some embodiments, R⁵ is selected from those depicted in Table 1 below.

As defined above and described herein, each R is independently hydrogen, or an optionally substituted group selected from C₁₋₆ aliphatic, phenyl, a 3-7 membered saturated or partially unsaturated carbocyclic or heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur, or two R groups on the same carbon or nitrogen are optionally taken together with their intervening atoms to form a 4-11 membered saturated or partially unsaturated monocyclic, bicyclic, bridged bicyclic, or spirocyclic carbocyclic or heterocyclic ring having 1-3 heteroatoms, in addition to the carbon or nitrogen from which the two R groups are attached, independently selected from nitrogen, oxygen, and sulfur.

In some embodiments, R is hydrogen. In some embodiments, R is an optionally substituted C₁₋₆ aliphatic. In some embodiments, R is C₁₋₆ alkyl (e.g., methyl, ethyl, isopropyl, etc.). In some embodiments, R is C₁₋₆ haloalkyl (e.g., —CF₃, CHF₂, etc.). In some embodiments, R is an optionally substituted phenyl. In some embodiments, R is an optionally substituted 3-7 membered saturated or partially unsaturated carbocyclic ring. In some embodiments, R is an optionally substituted 3-7 membered saturated or partially unsaturated heterocyclic ring having 1-2 heteroatoms independently selected from nitrogen, oxygen, and sulfur. In some embodiments, R is an optionally substituted 5-6 membered heteroaryl ring having 1-4 heteroatoms independently selected from nitrogen, oxygen, and sulfur. In some embodiments, two R groups on the same carbon or nitrogen are optionally taken together with their intervening atoms to form an optionally substituted 4-11 membered saturated or partially unsaturated monocyclic, bicyclic, bridged bicyclic, or spirocyclic carbocyclic or heterocyclic ring having 1-3 heteroatoms, in addition to the carbon or nitrogen from which the two R groups are attached, independently selected from nitrogen, oxygen, and sulfur.

In some embodiments, R is selected from those depicted in Table 1 below.

As defined above and described herein, each R^A is independently an optionally substituted group selected from C₁₋₆ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur.

In some embodiments, R^A is an optionally substituted C₁₋₆ aliphatic. In some embodiments, R^A is C₁₋₆ alkyl (e.g., methyl, ethyl, isopropyl, etc.). In some embodiments, R^A is C₁₋₆ haloalkyl (e.g., —CF₃, CHF₂, etc.). In some embodiments, R^A is an optionally substituted phenyl. In some embodiments, R^A is an optionally substituted 3-7 membered saturated or partially unsaturated carbocyclic ring. In some embodiments, R^A is an optionally substituted 4-7 membered saturated or partially unsaturated heterocyclic ring having 1-2 heteroatoms independently selected from nitrogen, oxygen, and sulfur. In some embodiments, $R^A$ is an optionally substituted 5-6 membered heteroaryl ring having 1-4 heteroatoms independently selected from nitrogen, oxygen, and sulfur.

In some embodiments, $R^A$ is selected from those depicted in Table 1 below.

As defined above and described herein, each of m, n, p, and q are independently 0, 1, 2, 3 or 4.

In some embodiments, one or more of m, n, p, and q is 0. In some embodiments, one or more of m, n, p, and q is 1. In some embodiments, one or more of m, n, p, and q is 2. In some embodiments, m is 3. In some embodiments, one or more of m, n, p, and q is 4.

In some embodiments, m, n, p, and q are selected from those depicted in Table 1 below.

In some embodiments, the —($C_{1-6}$ aliphatic)- in formula I-s to I-u is —$CH_2$—, —$CH_2CH_2$—, —$CH_2CH_2CH_2$—,

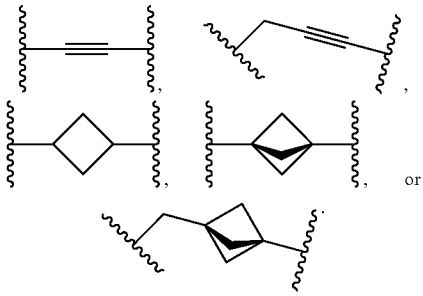

In some embodiments, —($C_{1-6}$ aliphatic)- in formula I-s and I-t is selected from those depicted in Table 1 below.

In some embodiments, the present invention provides a compound of formula I-a, wherein m is 1 and $R^2$ is —$OC_{1-6}$ alkyl as shown, to provide a compound of formula I-a-1:

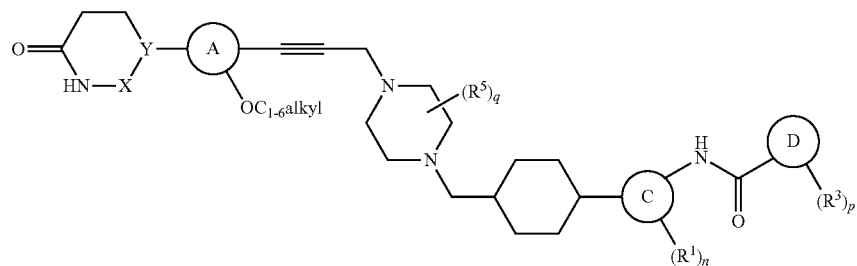

I-a-1 or a pharmaceutically acceptable salt thereof, wherein each of $R^1$, $R^3$, $R^5$, Ring A, Ring C, Ring D, X, Y, n, p, and q is as defined above and described in embodiments herein, both singly and in combination.

In some embodiments, the present invention provides a compound of formula I-a, wherein m is 1 and $R^2$ is halo as shown, to provide a compound of formula I-a-2:

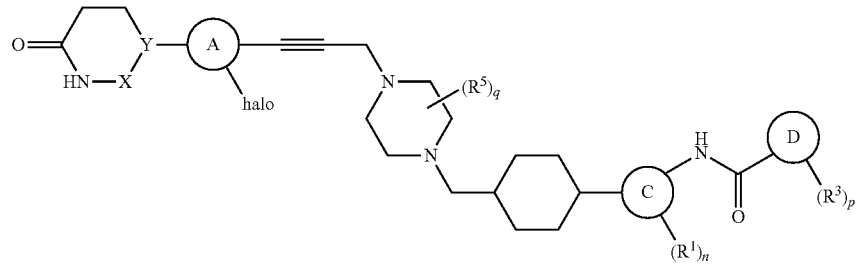

I-a-2 or a pharmaceutically acceptable salt thereof, wherein each of $R^1$, $R^3$, $R^5$, Ring A, Ring C, Ring D, X, Y, n, p, and q is as defined above and described in embodiments herein, both singly and in combination.

In some embodiments, the present invention provides a compound of formula I-a, wherein q is 1 and $R^5$ is $C_{1-6}$ alkyl as shown, to provide a compound of formula I-a-3:

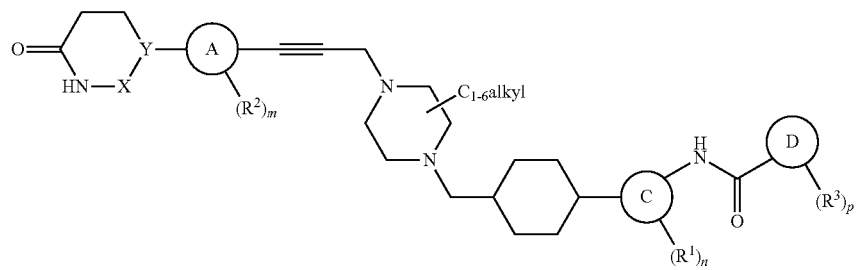

I-a-3 or a pharmaceutically acceptable salt thereof, wherein each of $R^1$, $R^2$, $R^3$, Ring A, Ring C, Ring D, X, Y, m, n, and p is as defined above and described in embodiments herein, both singly and in combination.

In some embodiments, the present invention provides a compound of formula I-b, wherein m is 1 and $R^2$ is $-OC_{1-6}$ alkyl as shown, to provide a compound of formula I-b-1:

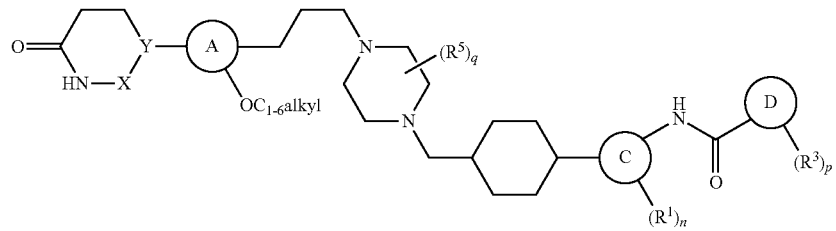

I-b-1 or a pharmaceutically acceptable salt thereof, wherein each of $R^1$, $R^3$, $R^5$, Ring A, Ring C, Ring D, X, Y, n, p, and q is as defined above and described in embodiments herein, both singly and in combination.

In some embodiments, the present invention provides a compound of formula I-b, wherein m is 1 and $R^2$ is halo as shown, to provide a compound of formula I-b-2:

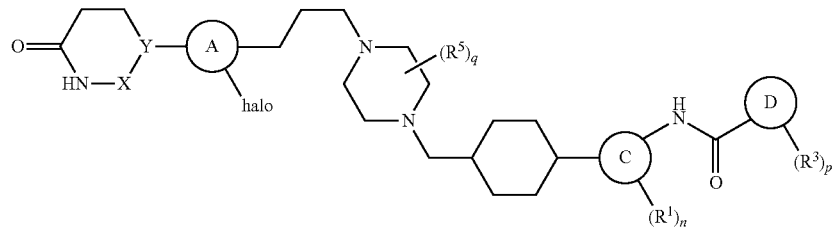

I-b-2 or a pharmaceutically acceptable salt thereof, wherein each of $R^1$, $R^3$, $R^5$, Ring A, Ring C, Ring D, X, Y, n, p, and q is as defined above and described in embodiments herein, both singly and in combination.

In some embodiments, the present invention provides a compound of formula I-b, wherein q is 1 and $R^5$ is $C_{1-6}$ alkyl as shown, to provide a compound of formula I-b-3:

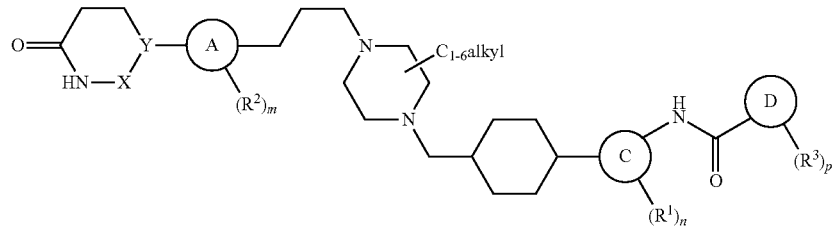

I-b-3 or a pharmaceutically acceptable salt thereof, wherein each of $R^1$, $R^2$, $R^3$, Ring A, Ring C, Ring D, X, Y, m, n, and p is as defined above and described in embodiments herein, both singly and in combination.

In some embodiments, the present invention provides a compound of formula I-c, wherein m is 1 and $R^2$ is —$OC_{1-6}$alkyl as shown, to provide a compound of formula I-c-1:

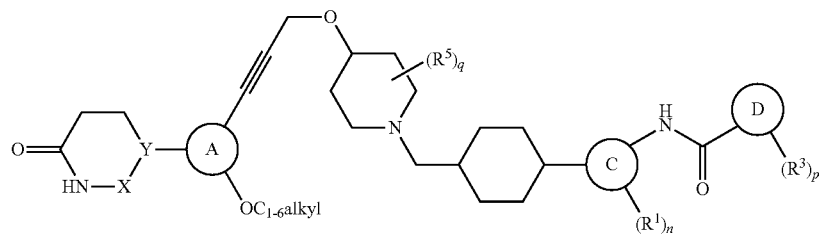

I-c-1 or a pharmaceutically acceptable salt thereof, wherein each of $R^1$, $R^3$, $R^5$, Ring A, Ring C, Ring D, X, Y, m, n, and p is as defined above and described in embodiments herein, both singly and in combination.

In some embodiments, the present invention provides a compound of formula I-c, wherein m is 1 and $R^2$ is halo as shown, to provide a compound of formula I-c-2:

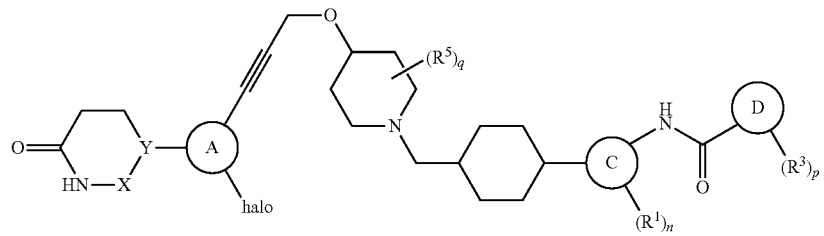

I-c-2 or a pharmaceutically acceptable salt thereof, wherein each of $R^1$, $R^3$, $R^5$, Ring A, Ring C, Ring D, X, Y, m, n, and p is as defined above and described in embodiments herein, both singly and in combination.

In some embodiments, the present invention provides a compound of formula I-c, wherein q is 1 and $R^5$ is $C_{1-6}$ alkyl as shown, to provide a compound of formula I-c-3:

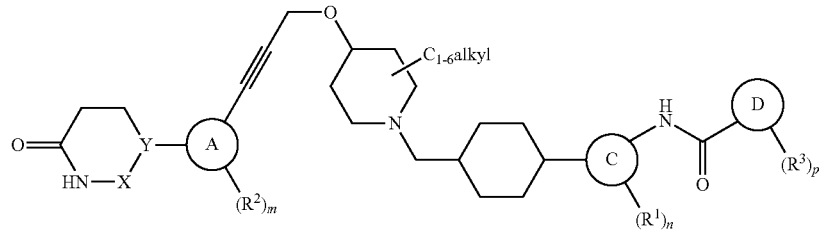

I-c-3 or a pharmaceutically acceptable salt thereof, wherein each of $R^1$, $R^2$, $R^3$, Ring A, Ring C, Ring D, X, Y, m, n, and p is as defined above and described in embodiments herein, both singly and in combination.

In some embodiments, the present invention provides a compound of formula I-c, wherein q is 1 and $R^5$ is halo as shown, to provide a compound of formula I-c-4:

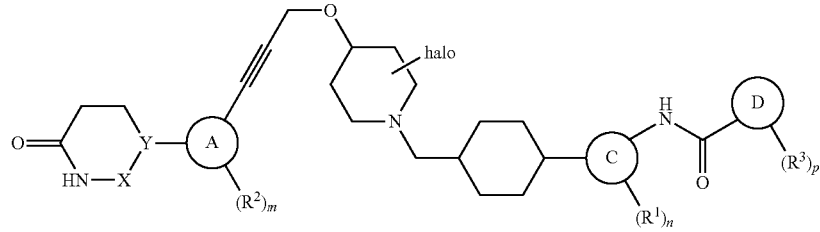

I-c-4 or a pharmaceutically acceptable salt thereof, wherein each of $R^1$, $R^2$, $R^3$, Ring A, Ring C, Ring D, X, Y, m, n, and p is as defined above and described in embodiments herein, both singly and in combination.

In some embodiments, the present invention provides a compound of formula I-c, wherein Ring is phenylenyl as shown, to provide a compound of formula I-c-5:

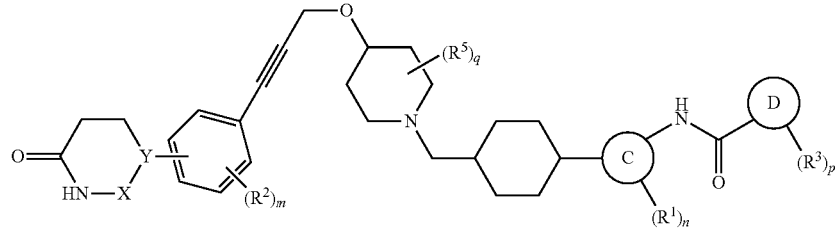

I-c-5 or a pharmaceutically acceptable salt thereof, wherein each of $R^1$, $R^2$, $R^3$, $R^5$, Ring C, Ring D, X, Y, m, n, p, and q is as defined above and described in embodiments herein, both singly and in combination.

In some embodiments, the present invention provides a compound of formula I-c, wherein

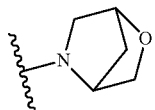

Ring is phenylenyl, p is 1, and R³ is as shown, to provide a compound of formula I-c-6:

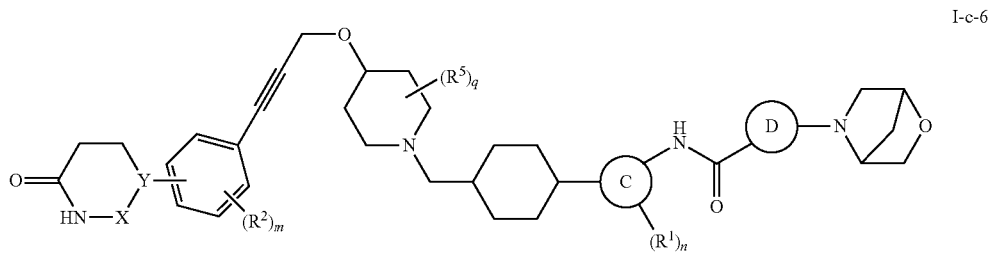

I-c-6 or a pharmaceutically acceptable salt thereof, wherein each of $R^1$, $R^3$, $R^5$, Ring C, Ring D, X, Y, m, n, p, and q is as defined above and described in embodiments herein, both singly and in combination.

In some embodiments, the present invention provides a compound of formula I-d, wherein m is 1 and $R^2$ is —$OC_{1-6}$ alkyl as shown, to provide a compound of formula I-d-1:

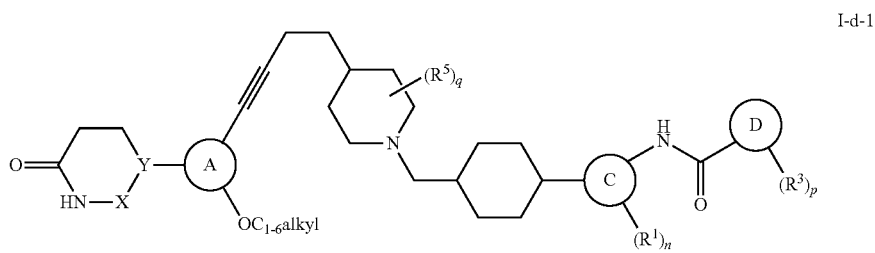

I-d-1 or a pharmaceutically acceptable salt thereof, wherein each of $R^1$, $R^3$, $R^5$, Ring A, Ring C, Ring D, X, Y, m, n, and p is as defined above and described in embodiments herein, both singly and in combination.

In some embodiments, the present invention provides a compound of formula I-d, wherein m is 1 and $R^2$ is halo as shown, to provide a compound of formula I-d-2:

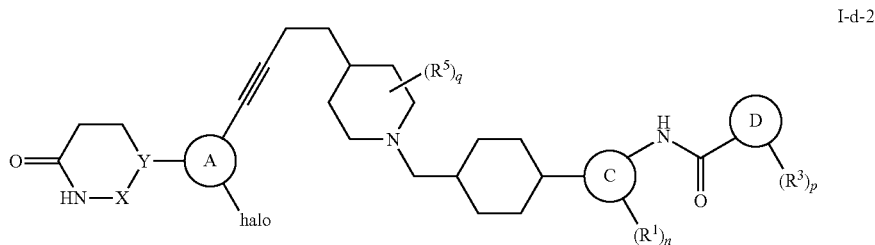

I-d-2 or a pharmaceutically acceptable salt thereof, wherein each of $R^1$, $R^3$, $R^5$, Ring A, Ring C, Ring D, X, Y, m, n, and p is as defined above and described in embodiments herein, both singly and in combination.

In some embodiments, the present invention provides a compound of formula I-d, wherein q is 1 and $R^5$ is $C_{1-6}$ alkyl as shown, to provide a compound of formula I-d-3:

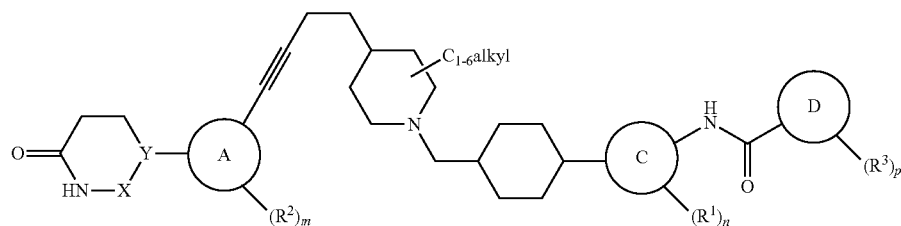

I-d-3 or a pharmaceutically acceptable salt thereof, wherein each of $R^1$, $R^2$, $R^3$, Ring A, Ring C, Ring D, X, Y, m, n, and p is as defined above and described in embodiments herein, both singly and in combination.

In some embodiments, the present invention provides a compound of formula I-d, wherein q is 1 and $R^5$ is halo as shown, to provide a compound of formula I-d-4:

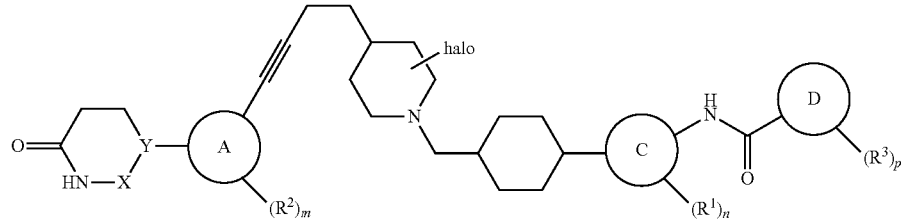

I-d-4 or a pharmaceutically acceptable salt thereof, wherein each of $R^1$, $R^2$, $R^3$, Ring A, Ring C, Ring D, X, Y, m, n, and p is as defined above and described in embodiments herein, both singly and in combination.

In some embodiments, the present invention provides a compound of formula I-h, wherein m is 1 and $R^2$ is —$OC_{1-6}$ alkyl as shown, to provide a compound of formula I-h-1:

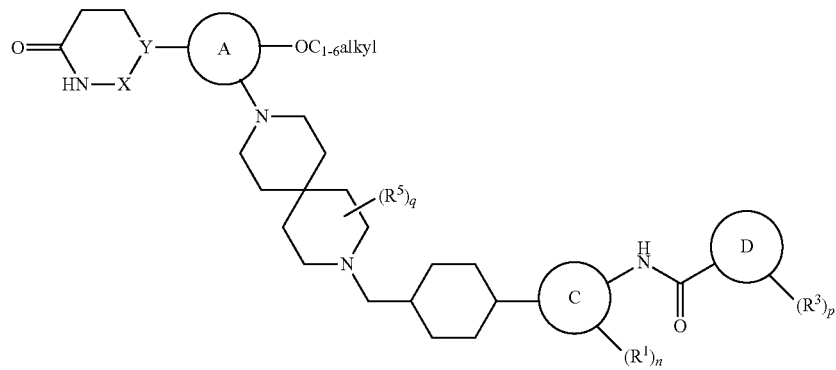

I-h-1 or a pharmaceutically acceptable salt thereof, wherein each of $R^1$, $R^3$, $R^5$, Ring A, Ring C, Ring D, X, Y, n, p, and q is as defined above and described in embodiments herein, both singly and in combination.

In some embodiments, the present invention provides a compound of formula I-h, wherein m is 1 and $R^2$ is halo as shown, to provide a compound of formula I-h-2:

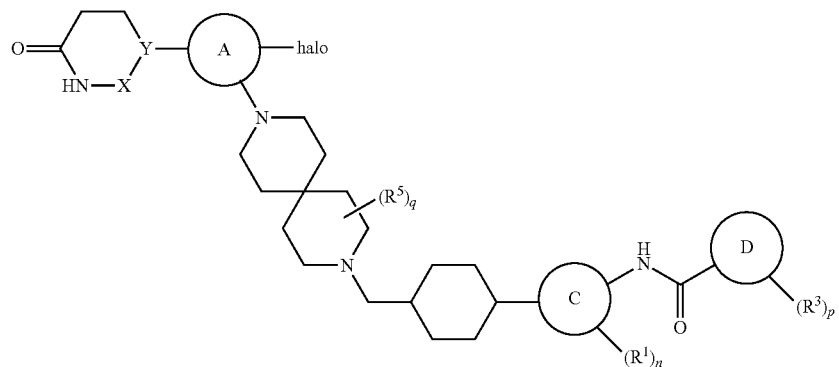

I-h-2 or a pharmaceutically acceptable salt thereof, wherein each of $R^1$, $R^3$, $R^5$, Ring A, Ring C, Ring D, X, Y, n, p, and q is as defined above and described in embodiments herein, both singly and in combination.

In some embodiments, the present invention provides a compound of formula I-r, wherein wherein q is 1-2 and $R^5$ is halo as shown, to provide a compound of formula I-r-1:

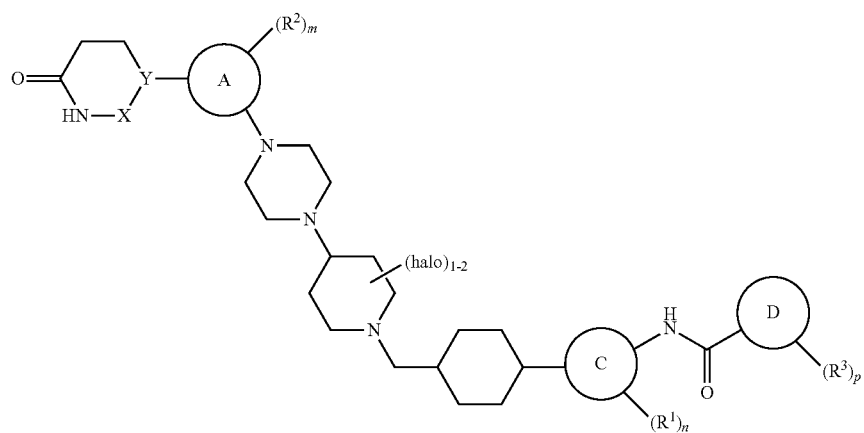

I-r-1 or a pharmaceutically acceptable salt thereof, wherein each of $R^1$, $R^3$, Ring A, Ring C, Ring D, X, Y, n, m, and p is as defined above and described in embodiments herein, both singly and in combination.

In some embodiments, the present invention provides a compound of formula I-r, wherein wherein $R^5$ is geminal difluoro as shown, to provide a compound of formula I-r-2:

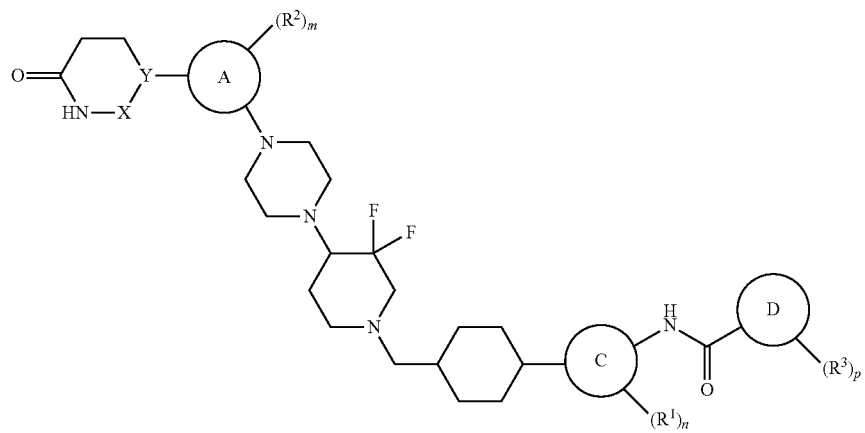

I-r-2 or a pharmaceutically acceptable salt thereof, wherein each of $R^1$, $R^3$, Ring A, Ring C, Ring D, X, Y, n, m, and p is as defined above and described in embodiments herein, both singly and in combination.

In some embodiments, the present invention provides a compound of formula I-r, wherein wherein q is 1-2, Ring C is

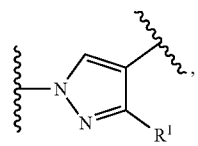

and $R^5$ is halo as shown, to provide a compound of formula I-r-3:

or a pharmaceutically acceptable salt thereof, wherein each of $R^1$, $R^3$, Ring A, Ring D, X, Y, n, m, and p is as defined above and described in embodiments herein, both singly and in combination.

In some embodiments, the present invention provides a compound of formula I-r, wherein wherein q is 1-2, Ring C is

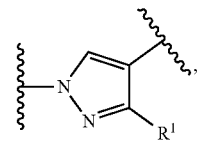

and $R^5$ is geminal difluoro as shown, to provide a compound of formula I-r-4:

I-r-3

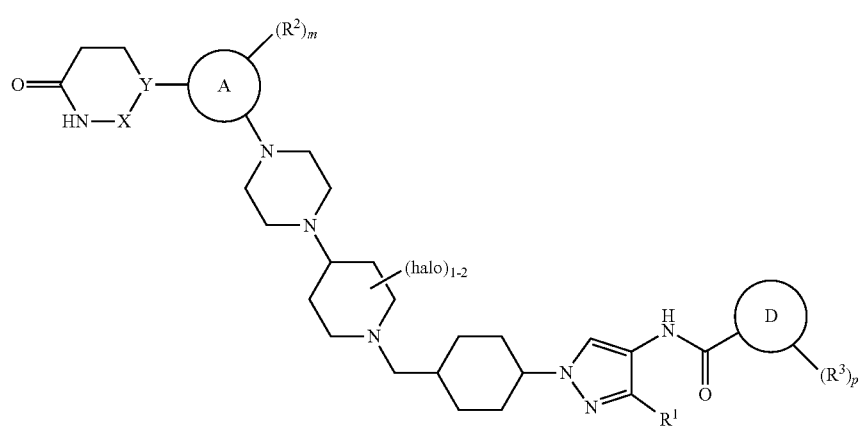

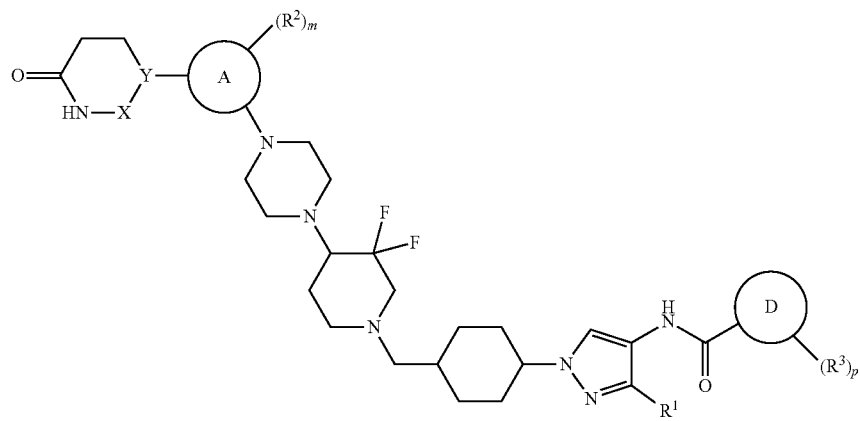

I-r-4 or a pharmaceutically acceptable salt thereof, wherein each of $R^1$, $R^3$, Ring A, Ring D, X, Y, n, m, and p is as defined above and described in embodiments herein, both singly and in combination.

In some embodiments, the present invention provides a compound of formula I-q, wherein wherein q is 1-2 and $R^5$ is halo as shown, to provide a compound of formula I-q-1:

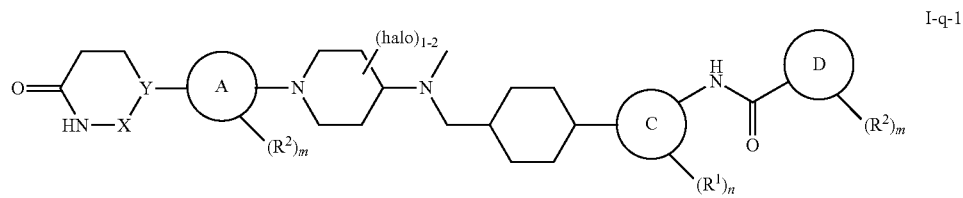

I-q-1 or a pharmaceutically acceptable salt thereof, wherein each of $R^1$, $R^3$, Ring A, Ring C, Ring D, X, Y, n, m, and p is as defined above and described in embodiments herein, both singly and in combination.

In some embodiments, the present invention provides a compound of formula I-u, wherein —($C_{1-6}$ aliphatic)- is

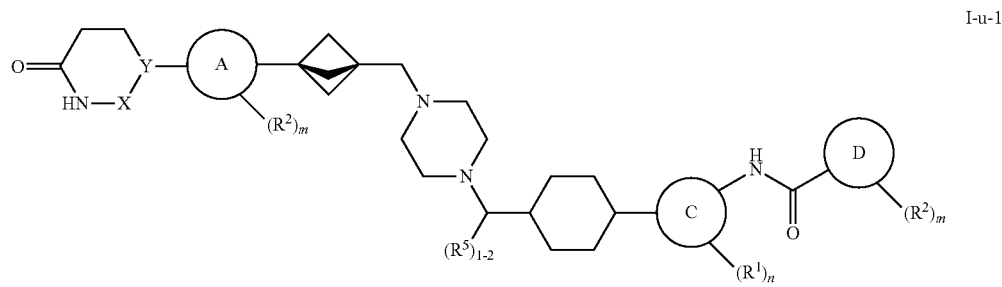

I-u-1 as shown, to provide a compound of formula I-u-1:

or a pharmaceutically acceptable salt thereof, wherein each of $R^1$, $R^3$, $R^5$, Ring A, Ring C, Ring D, X, Y, n, and p is as defined above and described in embodiments herein, both singly and in combination.

In some embodiments, the present invention provides a compound of formula I-w, wherein wherein q is 1-2 and $R^5$ is halo as shown, to provide a compound of formula I-w-1:

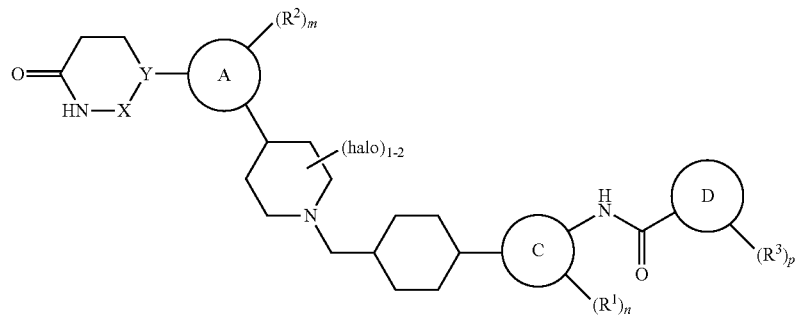

I-w-1 or a pharmaceutically acceptable salt thereof, wherein each of $R^1$, $R^3$, Ring A, Ring C, Ring D, X, Y, n, m, and p is as defined above and described in embodiments herein, both singly and in combination.

In some embodiments, the present invention provides a compound of formula I-w, wherein wherein q is 1-2 and $R^5$ is halo as shown, to provide a compound of formula I-w-2:

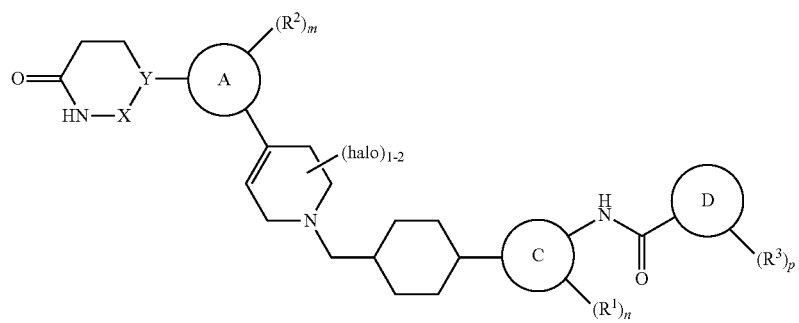

I-w-2 or a pharmaceutically acceptable salt thereof, wherein each of $R^1$, $R^3$, Ring A, Ring C, Ring D, X, Y, n, m, and p is as defined above and described in embodiments herein, both singly and in combination.

In some embodiments, the present invention provides a compound of formula I-w, wherein wherein $R^5$ is geminal difluoro as shown, to provide a compound of formula I-w-3:

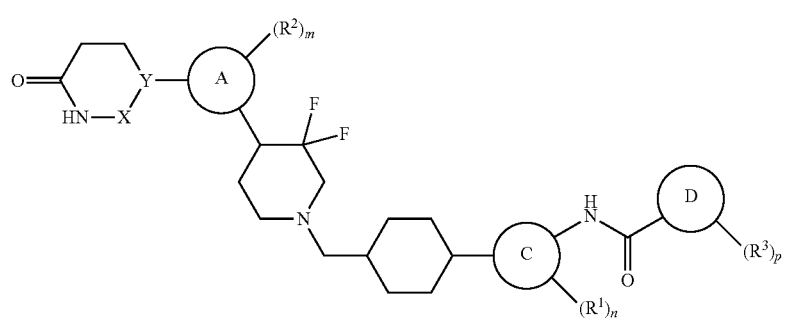

I-w-3 or a pharmaceutically acceptable salt thereof, wherein each of $R^1$, $R^3$, Ring A, Ring C, Ring D, X, Y, n, m, and p is as defined above and described in embodiments herein, both singly and in combination.

In some embodiments, the present invention provides a compound of formula I-w, wherein wherein q is 1-2, Ring C is

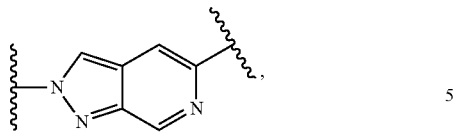

and R⁵ is halo as shown, to provide a compound of formula I-w-4:

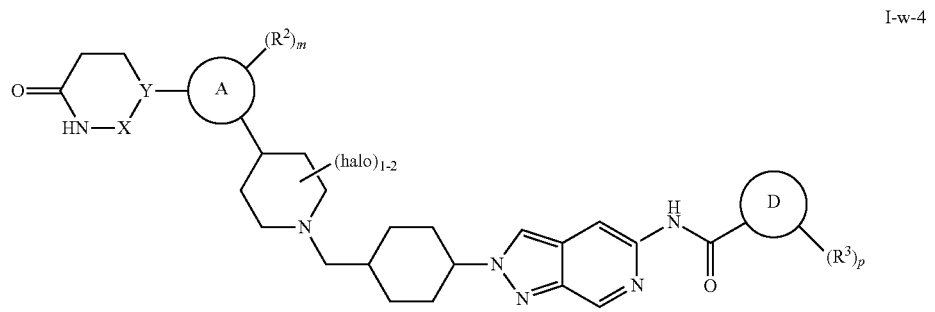

or a pharmaceutically acceptable salt thereof, wherein each of $R^3$, Ring A, Ring D, X, Y, m, and p is as defined above and described in embodiments herein, both singly and in combination.

In some embodiments, the present invention provides a compound of formula I-w, wherein wherein Ring C is

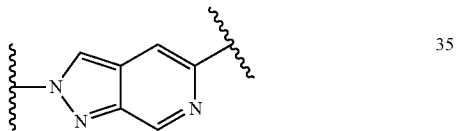

and R⁵ is geminal difluoro as shown, to provide a compound of formula I-w-5:

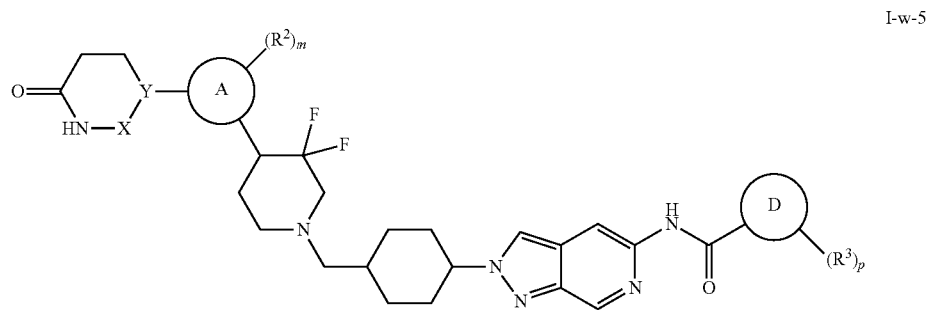

or a pharmaceutically acceptable salt thereof, wherein each of $R^3$, Ring A, Ring D, X, Y, m, and p is as defined above and described in embodiments herein, both singly and in combination.

In some embodiments, the present invention provides a compound of formula I-w, wherein wherein R⁵ is fluoro as shown, to provide a compound of formula I-w-6:

I-w-6

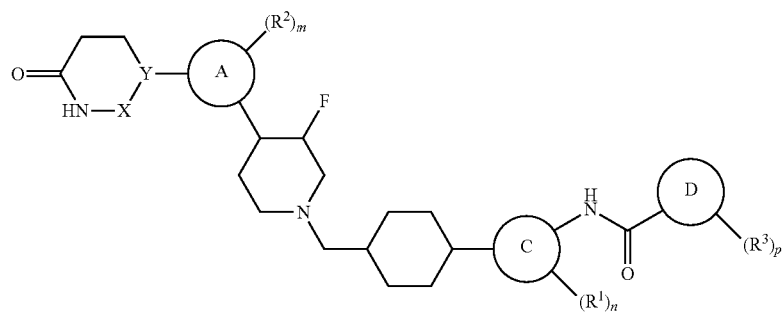

or a pharmaceutically acceptable salt thereof, wherein each of $R^1$, $R^3$, Ring A, Ring C, Ring D, X, Y, n, m, and p is as defined above and described in embodiments herein, both singly and in combination.

In some embodiments, the present invention provides a compound of formula I-y, wherein wherein $C_{1-6}$ aliphatic is

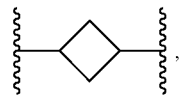

q is 1-2 and $R^5$ is halo as shown, to provide a compound of formula I-y-1:

I-y-1

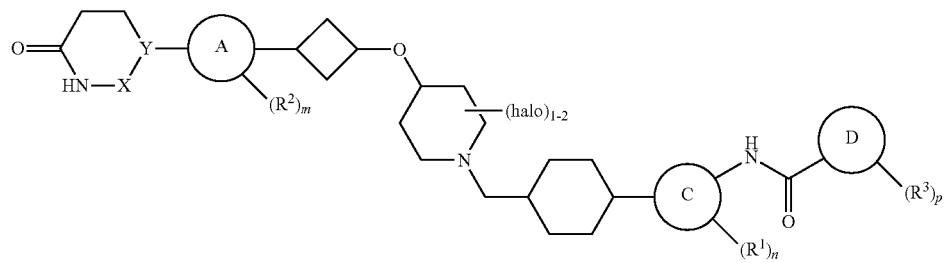

or a pharmaceutically acceptable salt thereof, wherein each of $R^1$, $R^3$, Ring A, Ring C, Ring D, X, Y, n, m, and p is as defined above and described in embodiments herein, both singly and in combination.

In some embodiments, the present invention provides a compound of formula I-z, wherein wherein q is 1-2 and $R^5$ is halo as shown, to provide a compound of formula I-z-1:

I-z-1

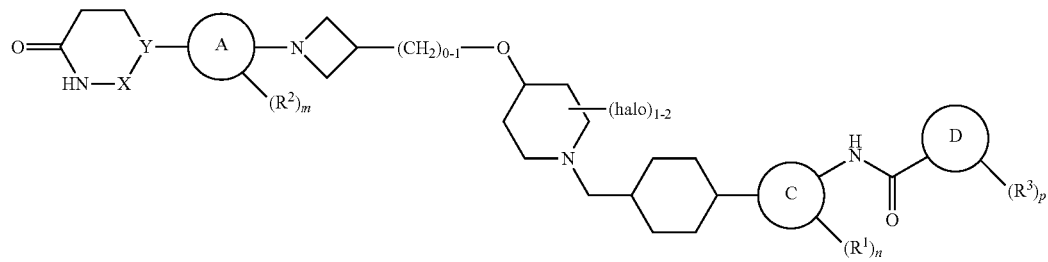

or a pharmaceutically acceptable salt thereof, wherein each of $R^1$, $R^3$, Ring A, Ring C, Ring D, X, Y, n, m, and p is as defined above and described in embodiments herein, both singly and in combination.

Exemplary compounds of the invention are set forth in Table 1, below.
TABLE 1
Exemplary Compounds
| I-# | Structure |
|---|---|
| I-1 | 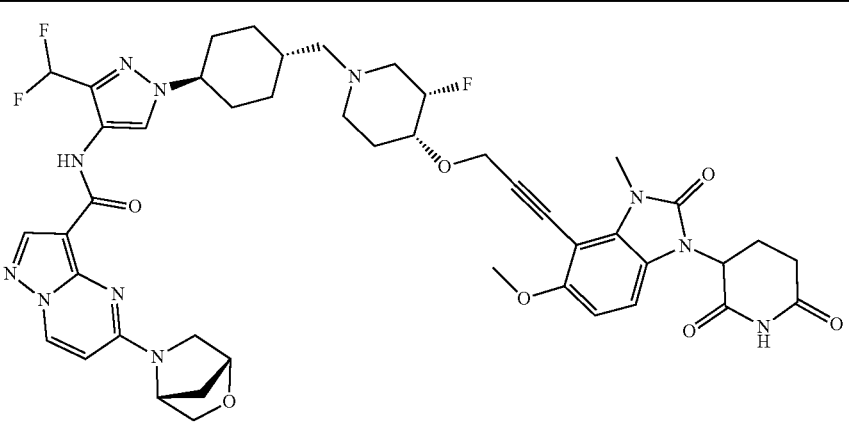 |
| I-2 | 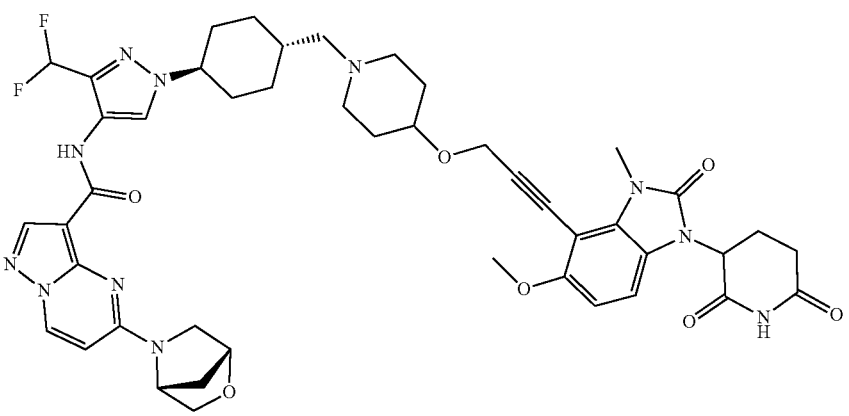 [SMILES: COc1ccc2c(c1C#CCOC1CCN(C[C@H]3CC[C@H](n4cc(NC(=O)c5cnn6ccc(N7C[C@H]8C[C@@H]7CO8)nc56)c(C(F)F)n4)CC3)CC1)n(C)c(=O)n2C1CCC(=O)NC1=O] |
| I-3 | 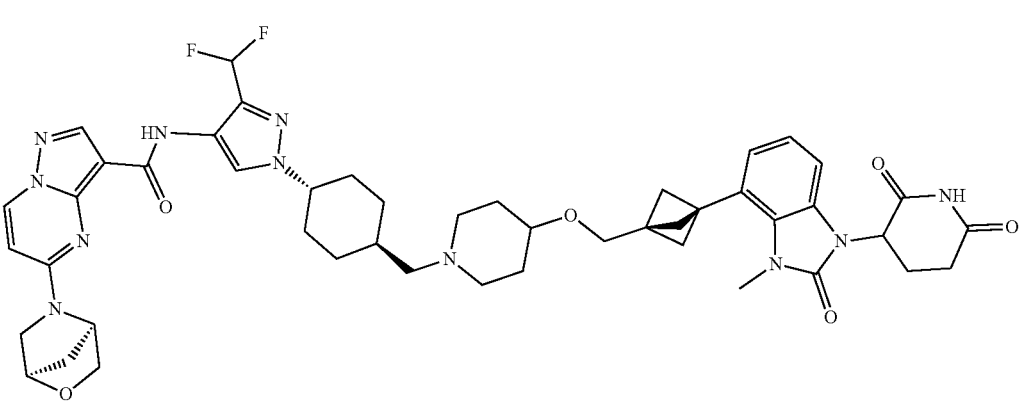 [SMILES: Cn1c(=O)n(C2CCC(=O)NC2=O)c2cccc([C@]34C[C@](COC5CCN(C[C@H]6CC[C@H](n7cc(NC(=O)c8cnn9ccc(N%10C[C@H]%11C[C@@H]%10CO%11)nc89)c(C(F)F)n7)CC6)CC5)(C3)C4)c21] |

TABLE 1-continued

Exemplary Compounds

| I-# | Structure |
|---|---|
| I-4 | 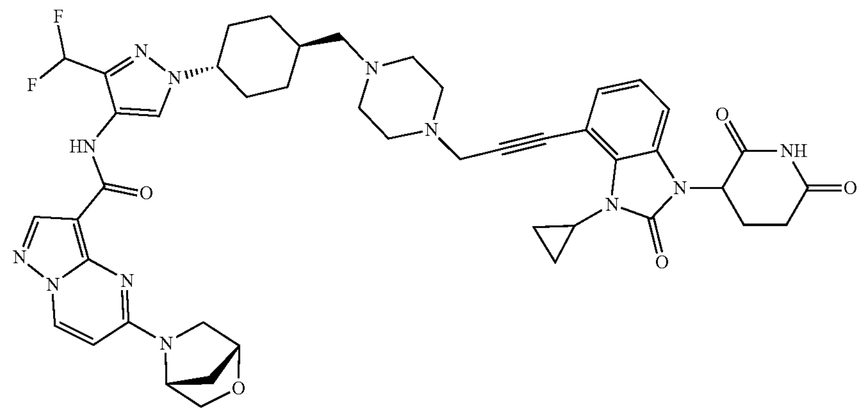 [SMILES: O=C1CCC(n2c(=O)n(C3CC3)c3c(C#CCN4CCN(C[C@H]5CC[C@H](n6cc(NC(=O)c7cnn8ccc(N9C[C@H]%10C[C@@H]9CO%10)nc78)c(C(F)F)n6)CC5)CC4)cccc32)C(=O)N1] |
| I-5 | 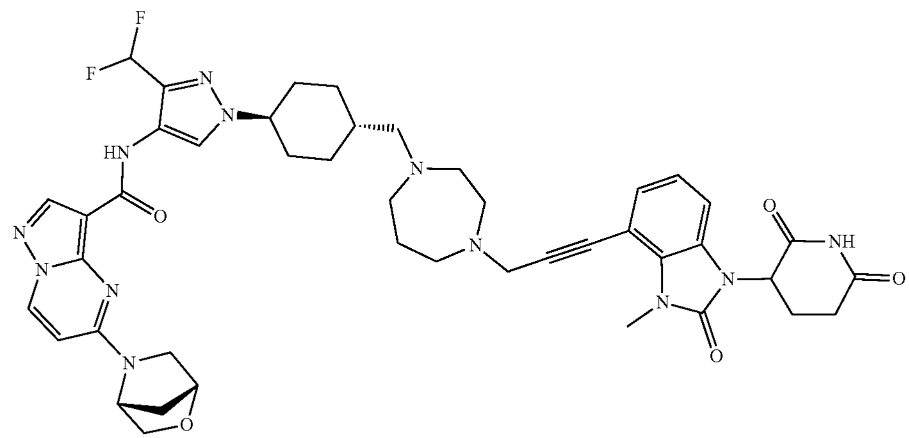 |
| I-6 | 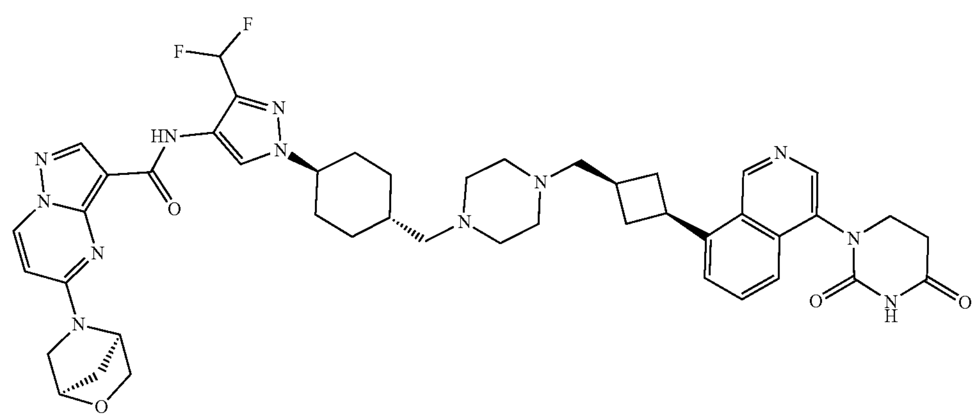 [SMILES: O=C1CCN(c2cncc3c2cccc3[C@H]2C[C@@H](CN3CCN(C[C@H]4CC[C@H](n5cc(NC(=O)c6cnn7ccc(N8C[C@H]9C[C@@H]8CO9)nc67)c(C(F)F)n5)CC4)CC3)C2)C(=O)N1] |

TABLE 1-continued
Exemplary Compounds
| I-# | Structure |
|---|---|
| I-7 | 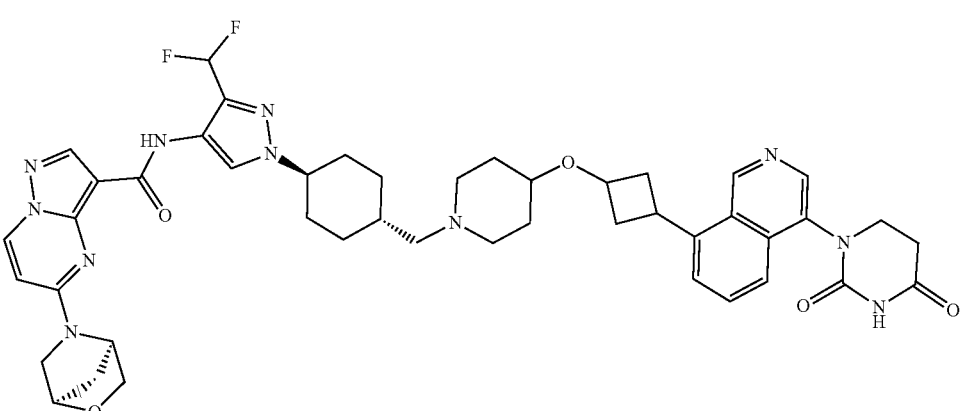 |
| I-8 | 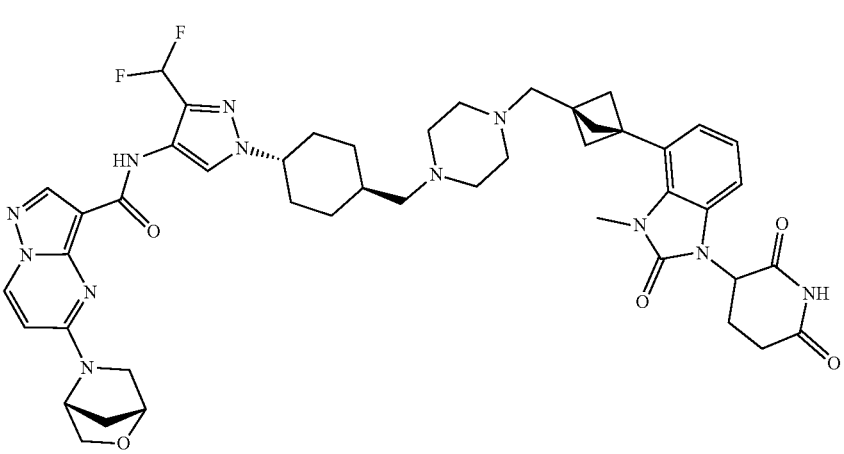 [SMILES: Cn1c(=O)n(C2CCC(=O)NC2=O)c2cccc([C@]34C[C@](CN5CCN(C[C@H]6CC[C@H](n7cc(NC(=O)c8cnn9ccc(N%10C[C@H]%11C[C@@H]%10CO%11)nc89)c(C(F)F)n7)CC6)CC5)(C3)C4)c21] |
| I-9 | 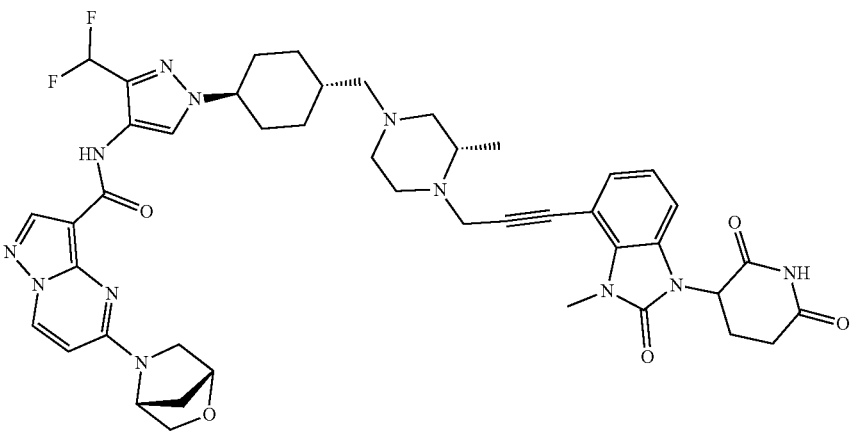 [SMILES: C[C@H]1CN(C[C@H]2CC[C@H](n3cc(NC(=O)c4cnn5ccc(N6C[C@H]7C[C@@H]6CO7)nc45)c(C(F)F)n3)CC2)CCN1CC#Cc1cccc2c1n(C)c(=O)n2C1CCC(=O)NC1=O] |

TABLE 1-continued
Exemplary Compounds
| I-# | Structure |
|---|---|
| I-10 | 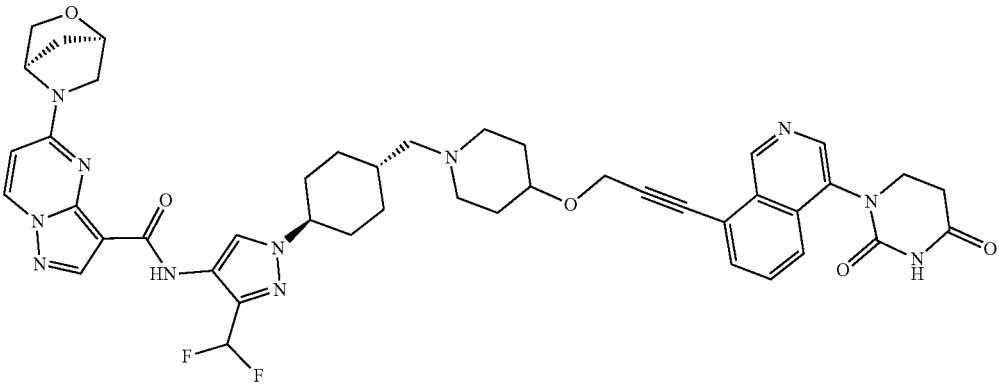 [SMILES: O=C1CCN(c2cncc3c(C#CCOC4CCN(C[C@H]5CC[C@H](n6cc(NC(=O)c7cnn8ccc(N9C[C@H]%10C[C@@H]9CO%10)nc78)c(C(F)F)n6)CC5)CC4)cccc23)C(=O)N1] |
| I-11 | 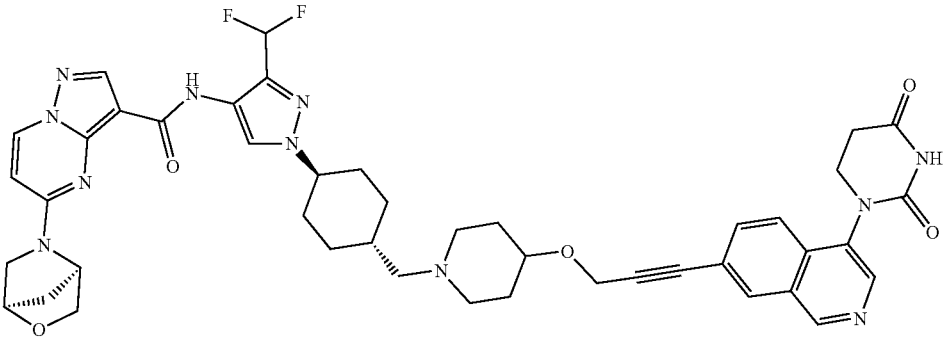 [SMILES: O=C1CCN(c2cncc3cc(C#CCOC4CCN(C[C@H]5CC[C@H](n6cc(NC(=O)c7cnn8ccc(N9C[C@H]%10C[C@@H]9CO%10)nc78)c(C(F)F)n6)CC5)CC4)ccc23)C(=O)N1] |
| I-12 | 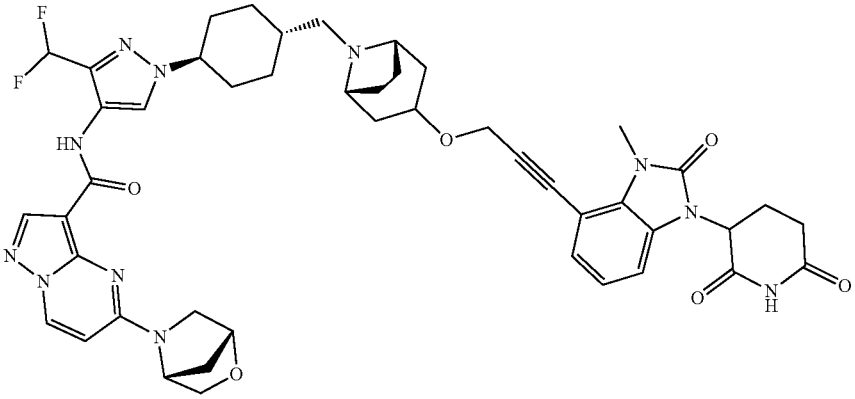 [SMILES: Cn1c(=O)n(C2CCC(=O)NC2=O)c2cccc(C#CCOC3C[C@H]4CC[C@@H](C3)N4C[C@H]3CC[C@H](n4cc(NC(=O)c5cnn6ccc(N7C[C@H]8C[C@@H]7CO8)nc56)c(C(F)F)n4)CC3)c21] |
| I-13 | 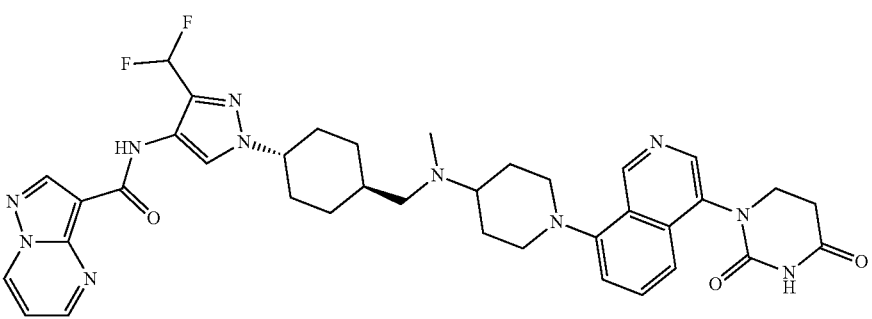 [SMILES: CN(C[C@H]1CC[C@H](n2cc(NC(=O)c3cnn4cccnc34)c(C(F)F)n2)CC1)C1CCN(c2cccc3c(N4CCC(=O)NC4=O)cncc23)CC1] |

TABLE 1-continued
Exemplary Compounds
I-# Structure
I-14 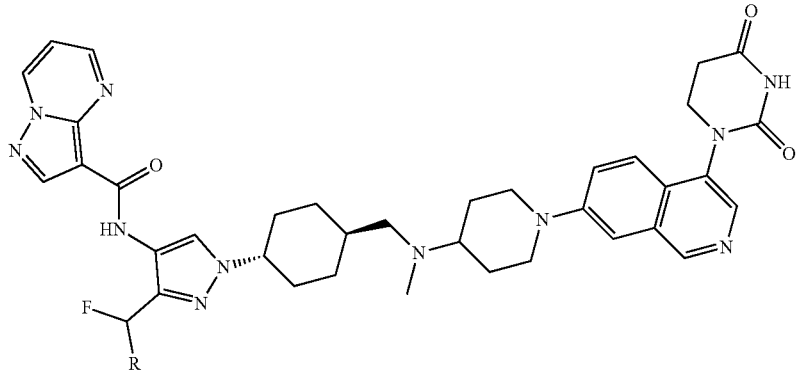
I-15 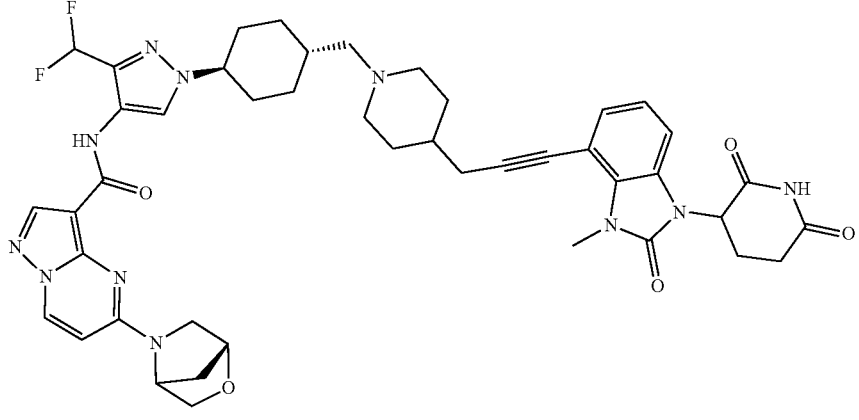 [SMILES: Cn1c(=O)n(C2CCC(=O)NC2=O)c2cccc(C#CCC3CCN(C[C@H]4CC[C@H](n5cc(NC(=O)c6cnn7ccc(N8C[C@H]9CC8CO9)nc67)c(C(F)F)n5)CC4)CC3)c21]
I-16 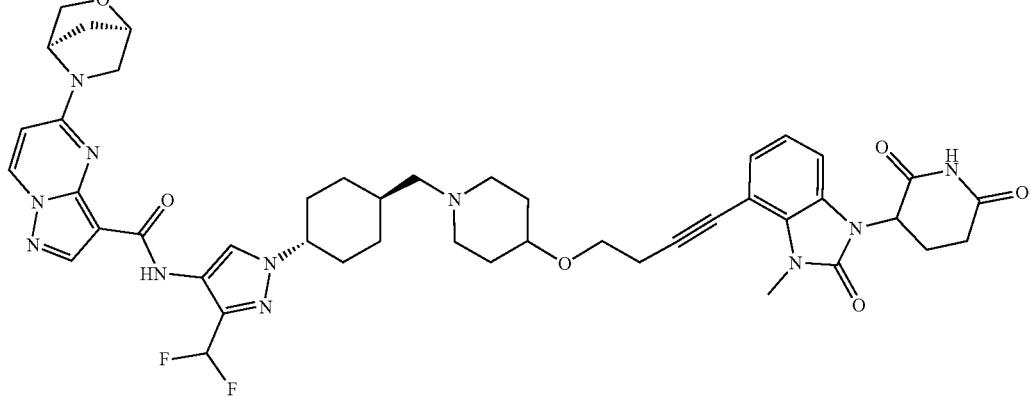

TABLE 1-continued

Exemplary Compounds

| I-# | Structure |
|---|---|
| I-17 | 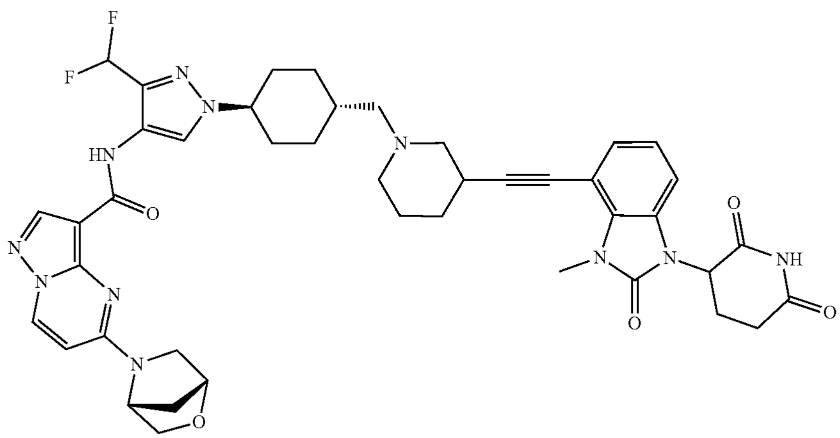 [SMILES: Cn1c(=O)n(C2CCC(=O)NC2=O)c2cccc(C#CC3CCCN(C[C@H]4CC[C@H](n5cc(NC(=O)c6cnn7ccc(N8C[C@H]9C[C@@H]8CO9)nc67)c(C(F)F)n5)CC4)C3)c21] |
| I-18 | 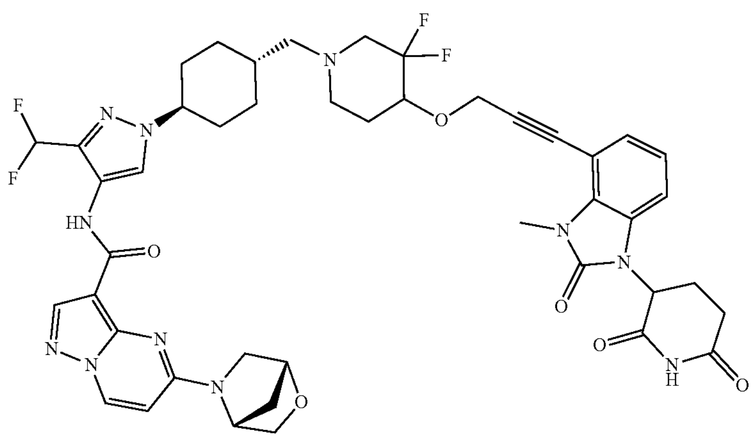 [SMILES: Cn1c(=O)n(C2CCC(=O)NC2=O)c2cccc(C#CCOC3CCN(C[C@H]4CC[C@H](n5cc(NC(=O)c6cnn7ccc(N8C[C@H]9C[C@@H]8CO9)nc67)c(C(F)F)n5)CC4)CC3(F)F)c21] |
| I-19 | 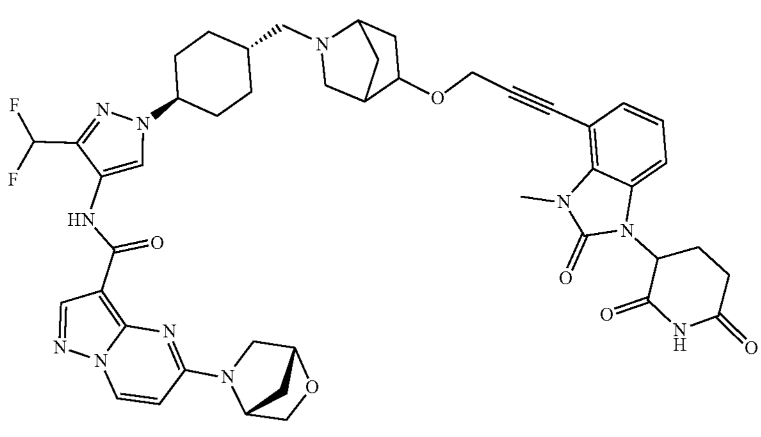 [SMILES: Cn1c(=O)n(C2CCC(=O)NC2=O)c2cccc(C#CCOC3CC4CC3CN4C[C@H]3CC[C@H](n4cc(NC(=O)c5cnn6ccc(N7C[C@H]8C[C@@H]7CO8)nc56)c(C(F)F)n4)CC3)c21] |

TABLE 1-continued

Exemplary Compounds

| I-# | Structure |
|---|---|
| I-20 | 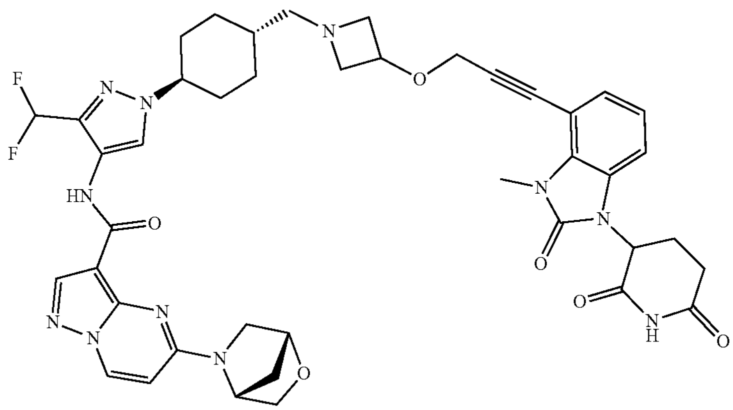 [SMILES: Cn1c(=O)n(C2CCC(=O)NC2=O)c2cccc(C#CCOC3CN(C[C@H]4CC[C@H](n5cc(NC(=O)c6cnn7ccc(N8C[C@H]9C[C@@H]8CO9)nc67)c(C(F)F)n5)CC4)C3)c21] |
| I-21 | 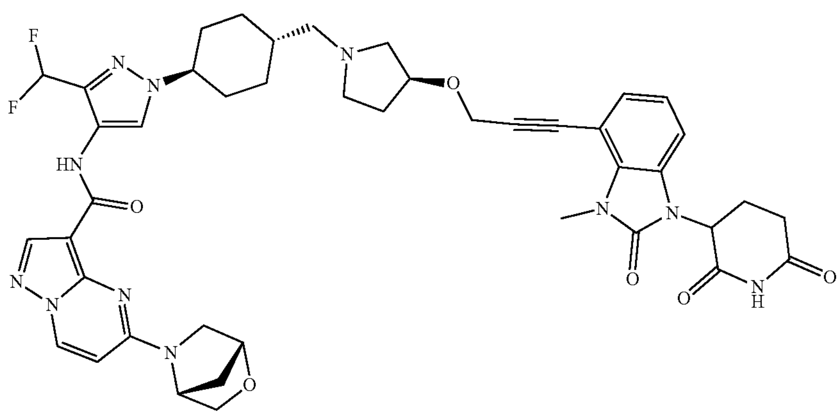 [SMILES: Cn1c(=O)n(C2CCC(=O)NC2=O)c2cccc(C#CCO[C@H]3CCN(C[C@H]4CC[C@H](n5cc(NC(=O)c6cnn7ccc(N8C[C@H]9C[C@@H]8CO9)nc67)c(C(F)F)n5)CC4)C3)c21] |
| I-22 | 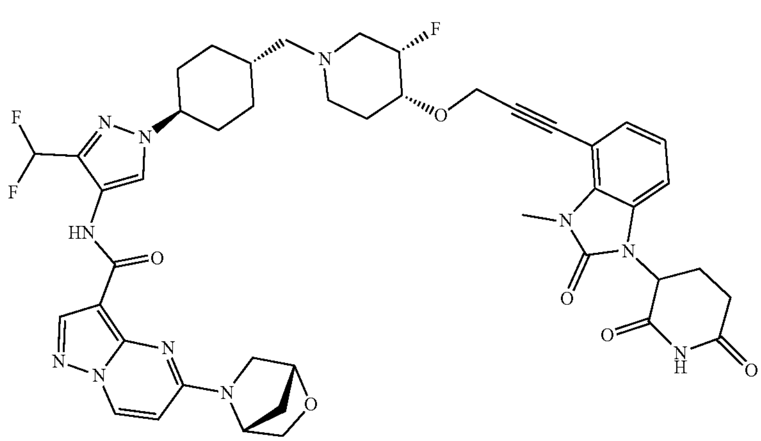 [SMILES: Cn1c(=O)n(C2CCC(=O)NC2=O)c2cccc(C#CCO[C@@H]3CCN(C[C@H]4CC[C@H](n5cc(NC(=O)c6cnn7ccc(N8C[C@H]9C[C@@H]8CO9)nc67)c(C(F)F)n5)CC4)C[C@@H]3F)c21] |

TABLE 1-continued

Exemplary Compounds

| I-# | Structure |
|-----|-----------|
| I-23 | 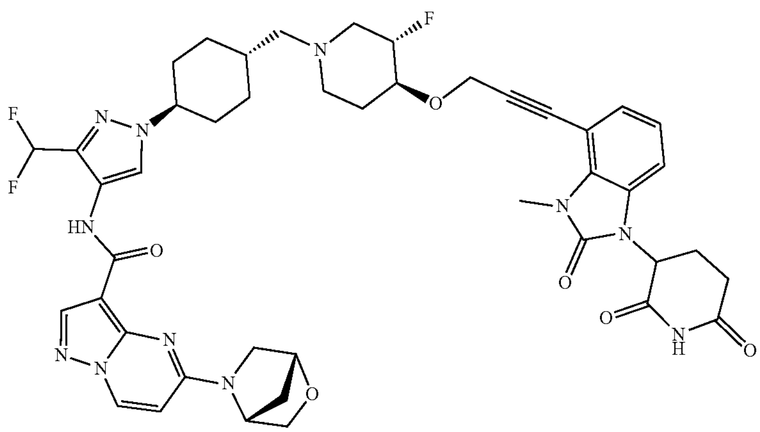 [SMILES: Cn1c(=O)n(C2CCC(=O)NC2=O)c2cccc(C#CCO[C@H]3CCN(C[C@H]4CC[C@H](n5cc(NC(=O)c6cnn7ccc(N8C[C@H]9C[C@@H]8CO9)nc67)c(C(F)F)n5)CC4)C[C@@H]3F)c21] |
| I-24 | 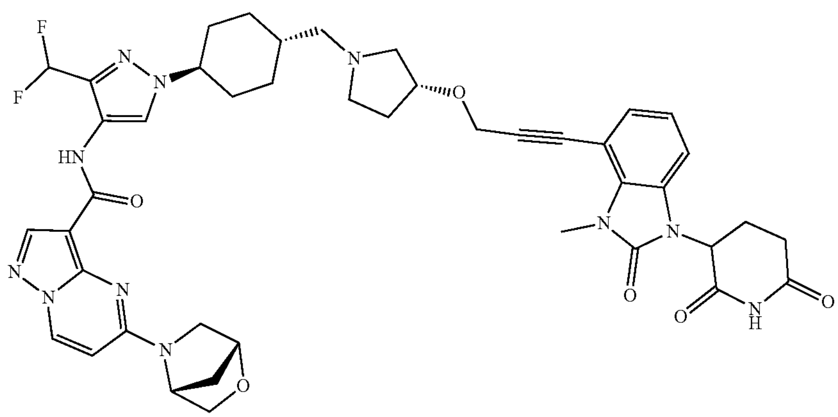 [SMILES: Cn1c(=O)n(C2CCC(=O)NC2=O)c2cccc(C#CCO[C@@H]3CCN(C[C@H]4CC[C@H](n5cc(NC(=O)c6cnn7ccc(N8C[C@H]9C[C@@H]8CO9)nc67)c(C(F)F)n5)CC4)C3)c21] |
| I-25 | 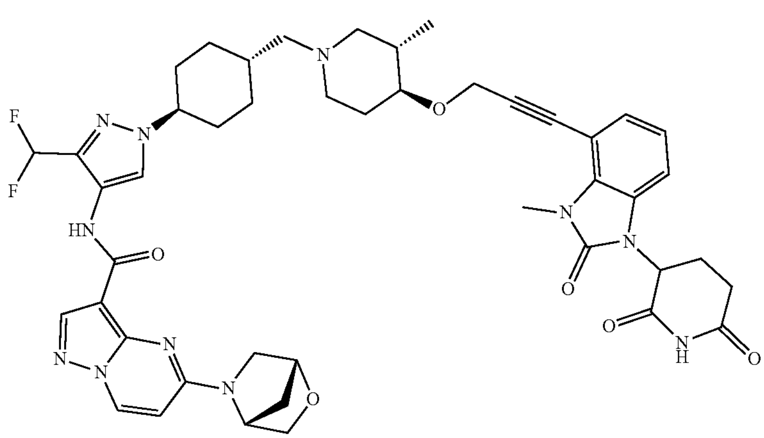 [SMILES: C[C@H]1CN(C[C@H]2CC[C@H](n3cc(NC(=O)c4cnn5ccc(N6C[C@H]7C[C@@H]6CO7)nc45)c(C(F)F)n3)CC2)CC[C@@H]1OCC#Cc1cccc2c1n(C)c(=O)n2C1CCC(=O)NC1=O] |

TABLE 1-continued
Exemplary Compounds
| I-# | Structure |
|---|---|
| I-26 | 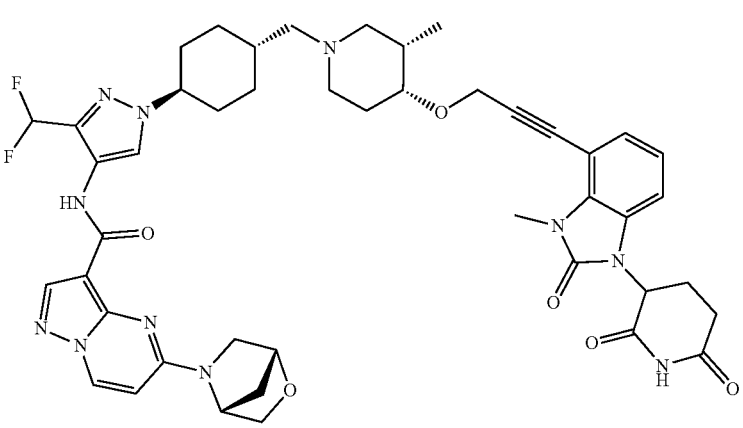 [SMILES: C[C@H]1CN(C[C@H]2CC[C@H](n3cc(NC(=O)c4cnn5ccc(N6C[C@H]7C[C@@H]6CO7)nc45)c(C(F)F)n3)CC2)CC[C@H]1OCC#Cc1cccc2c1n(C)c(=O)n2C1CCC(=O)NC1=O] |
| I-27 | 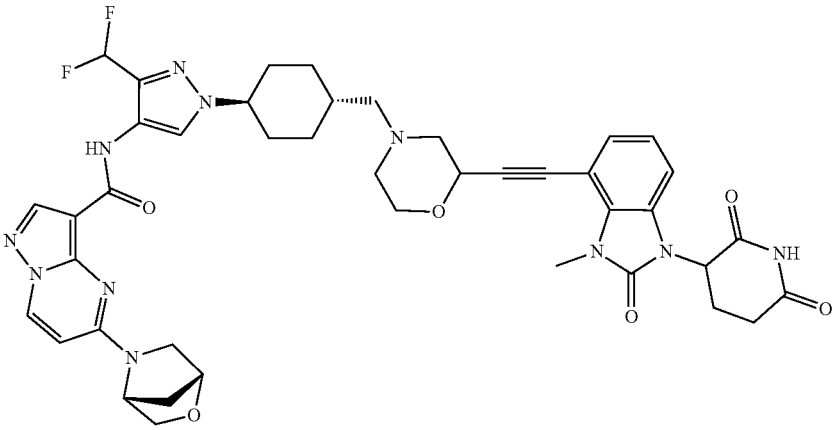 [SMILES: Cn1c(=O)n(C2CCC(=O)NC2=O)c2cccc(C#CC3CN(C[C@H]4CC[C@H](n5cc(NC(=O)c6cnn7ccc(N8C[C@H]9C[C@@H]8CO9)nc67)c(C(F)F)n5)CC4)CCO3)c21] |
| I-28 | 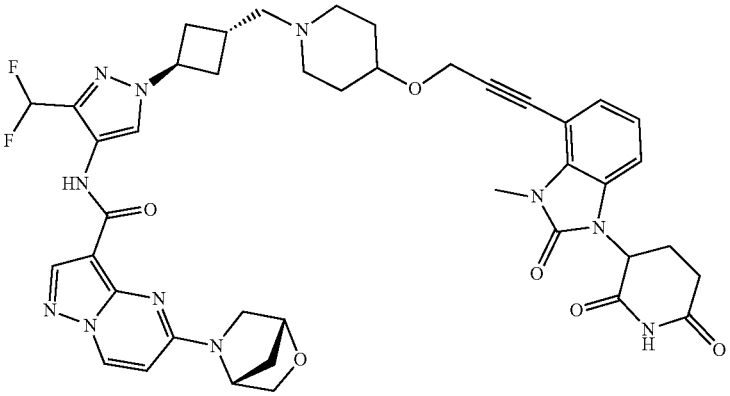 [SMILES: Cn1c(=O)n(C2CCC(=O)NC2=O)c2cccc(C#CCOC3CCN(C[C@H]4C[C@H](n5cc(NC(=O)c6cnn7ccc(N8C[C@H]9C[C@@H]8CO9)nc67)c(C(F)F)n5)C4)CC3)c21] |

TABLE 1-continued

Exemplary Compounds

| I-# | Structure |
|---|---|
| I-29 | 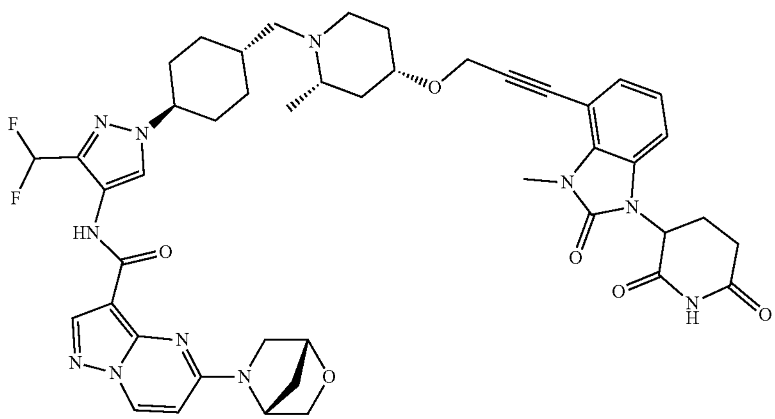 [SMILES: C[C@H]1C[C@@H](OCC#Cc2cccc3c2n(C)c(=O)n3C2CCC(=O)NC2=O)CCN1C[C@H]1CC[C@H](n2cc(NC(=O)c3cnn4ccc(N5C[C@H]6C[C@@H]5CO6)nc34)c(C(F)F)n2)CC1] |
| I-30 | 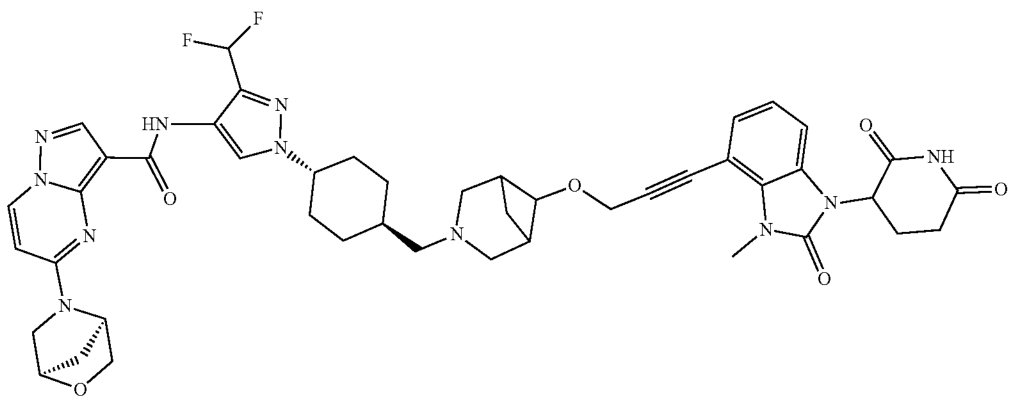 [SMILES: Cn1c(=O)n(C2CCC(=O)NC2=O)c2cccc(C#CCOC3C4CC3CN(C[C@H]3CC[C@H](n5cc(NC(=O)c6cnn7ccc(N8C[C@H]9C[C@@H]8CO9)nc67)c(C(F)F)n5)CC3)C4)c21] |
| I-31 | 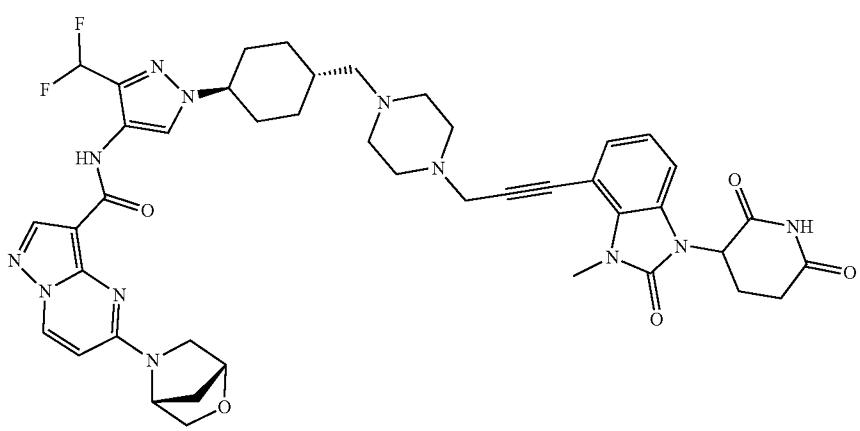 [SMILES: Cn1c(=O)n(C2CCC(=O)NC2=O)c2cccc(C#CCN3CCN(C[C@H]4CC[C@H](n5cc(NC(=O)c6cnn7ccc(N8C[C@H]9C[C@@H]8CO9)nc67)c(C(F)F)n5)CC4)CC3)c21] |

TABLE 1-continued

Exemplary Compounds

| I-# | Structure |
|---|---|
| I-32 | 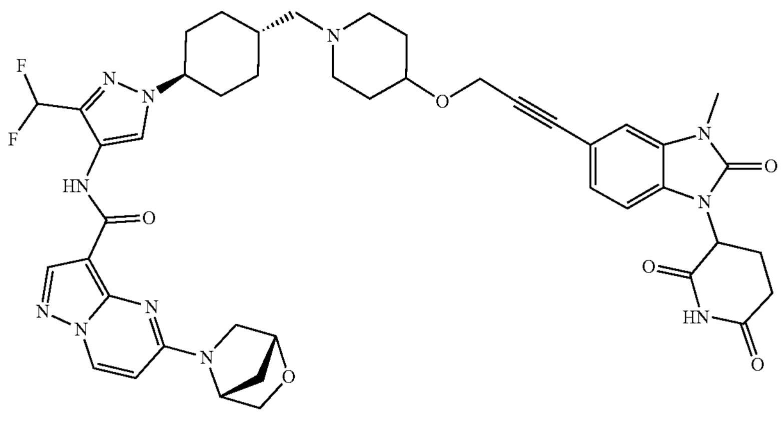 [SMILES: Cn1c(=O)n(C2CCC(=O)NC2=O)c2ccc(C#CCOC3CCN(C[C@H]4CC[C@H](n5cc(NC(=O)c6cnn7ccc(N8C[C@H]9C[C@@H]8CO9)nc67)c(C(F)F)n5)CC4)CC3)cc21] |
| I-33 | 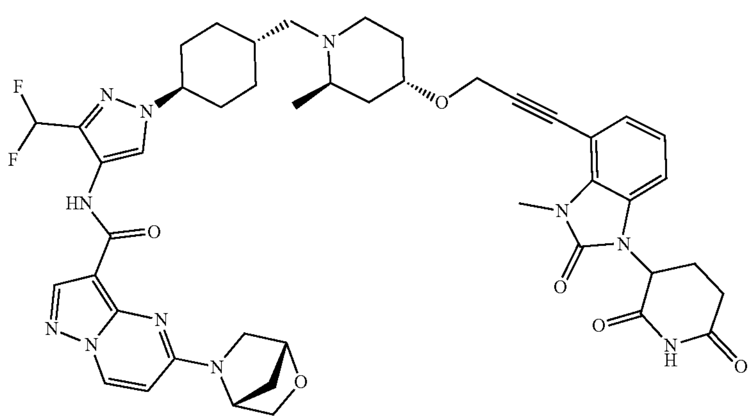 [SMILES: C[C@@H]1C[C@@H](OCC#Cc2cccc3c2n(C)c(=O)n3C2CCC(=O)NC2=O)CCN1C[C@H]1CC[C@H](n2cc(NC(=O)c3cnn4ccc(N5C[C@H]6C[C@@H]5CO6)nc34)c(C(F)F)n2)CC1] |
| I-34 | 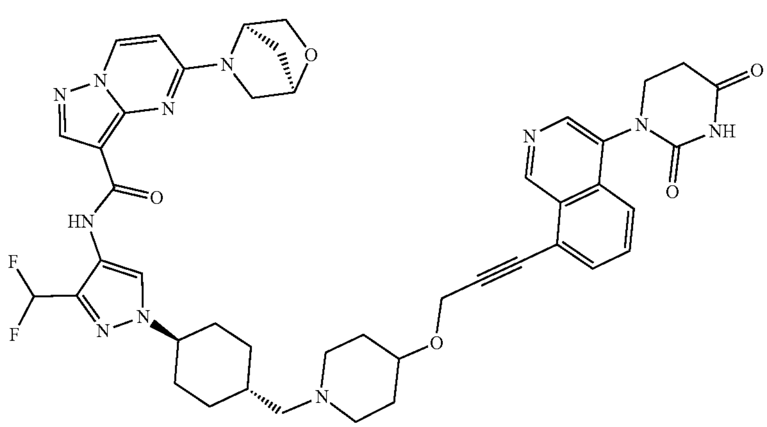 [SMILES: O=C1CCN(c2cncc3c(C#CCOC4CCN(C[C@H]5CC[C@H](n6cc(NC(=O)c7cnn8ccc(N9C[C@H]%10C[C@@H]9CO%10)nc78)c(C(F)F)n6)CC5)CC4)cccc23)C(=O)N1] |

TABLE 1-continued
Exemplary Compounds
| I-# | Structure |
|---|---|
| I-35 | 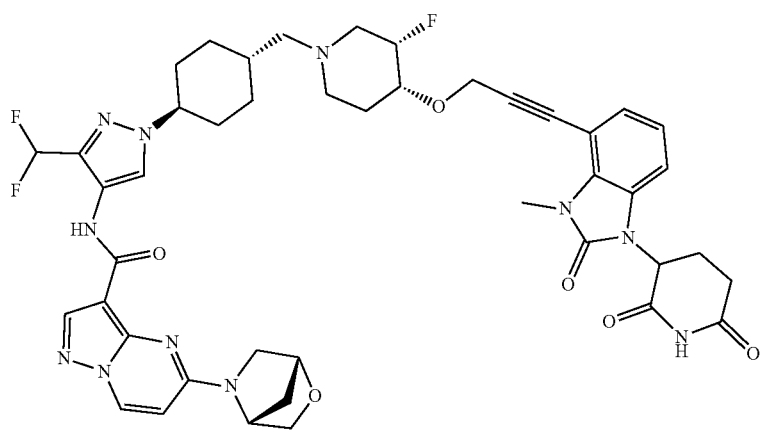 [SMILES: Cn1c(=O)n(C2CCC(=O)NC2=O)c2cccc(C#CCO[C@@H]3CCN(C[C@H]4CC[C@H](n5cc(NC(=O)c6cnn7ccc(N8C[C@H]9C[C@@H]8CO9)nc67)c(C(F)F)n5)CC4)C[C@@H]3F)c21] |
| I-36 | 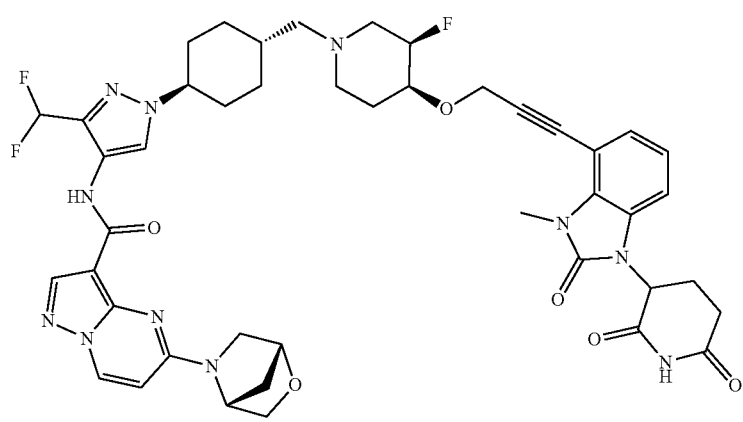 [SMILES: Cn1c(=O)n(C2CCC(=O)NC2=O)c2cccc(C#CCO[C@H]3CCN(C[C@H]4CC[C@H](n5cc(NC(=O)c6cnn7ccc(N8C[C@H]9C[C@@H]8CO9)nc67)c(C(F)F)n5)CC4)C[C@H]3F)c21] |
| I-37 | 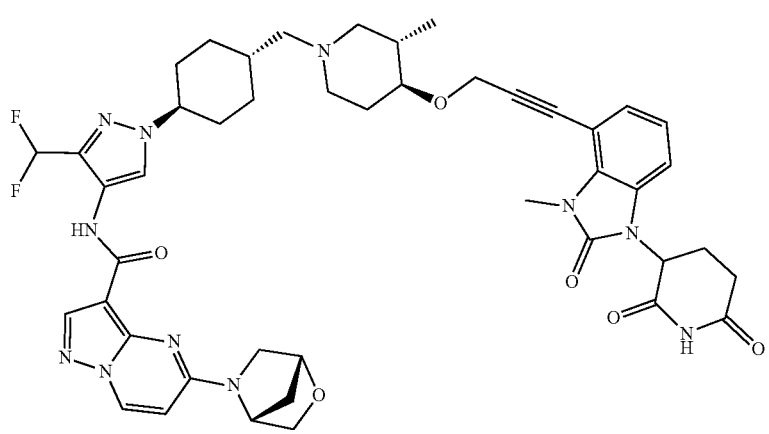 [SMILES: C[C@H]1CN(C[C@H]2CC[C@H](n3cc(NC(=O)c4cnn5ccc(N6C[C@H]7C[C@@H]6CO7)nc45)c(C(F)F)n3)CC2)CC[C@@H]1OCC#Cc1cccc2c1n(C)c(=O)n2C1CCC(=O)NC1=O] |

TABLE 1-continued

Exemplary Compounds

| I-# | Structure |
|---|---|
| I-38 | 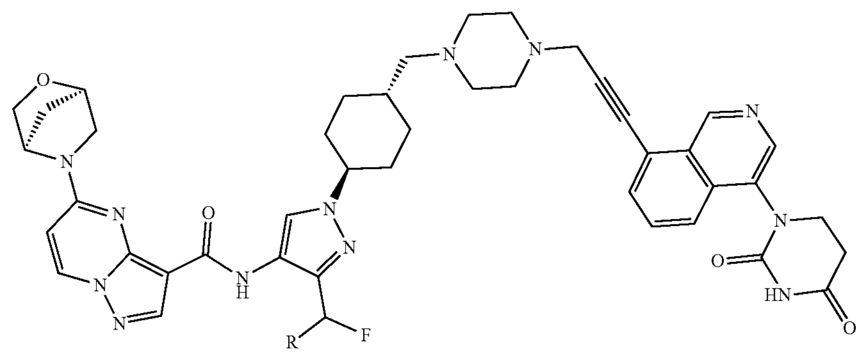 |
| I-39 | 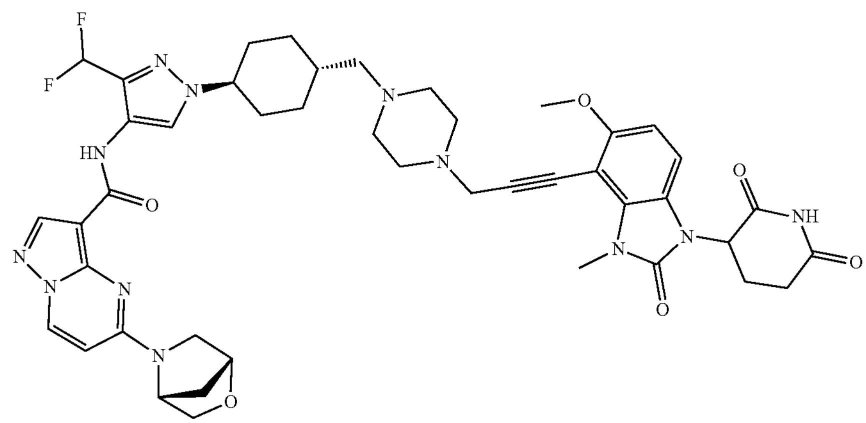 [SMILES: COc1ccc2c(c1C#CCN1CCN(C[C@H]3CC[C@H](n4cc(NC(=O)c5cnn6ccc(N7C[C@H]8C[C@@H]7CO8)nc56)c(C(F)F)n4)CC3)CC1)n(C)c(=O)n2C1CCC(=O)NC1=O] |
| I-40 | 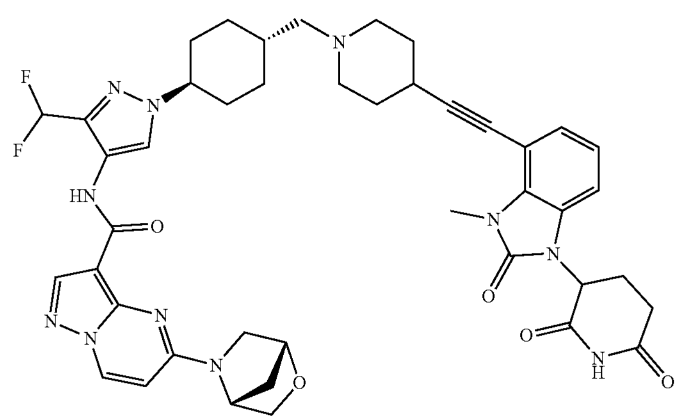 [SMILES: Cn1c(=O)n(C2CCC(=O)NC2=O)c2cccc(C#CC3CCN(C[C@H]4CC[C@H](n5cc(NC(=O)c6cnn7ccc(N8C[C@H]9C[C@@H]8CO9)nc67)c(C(F)F)n5)CC4)CC3)c21] |

TABLE 1-continued

Exemplary Compounds

| I-# | Structure |
|---|---|
| I-41 | 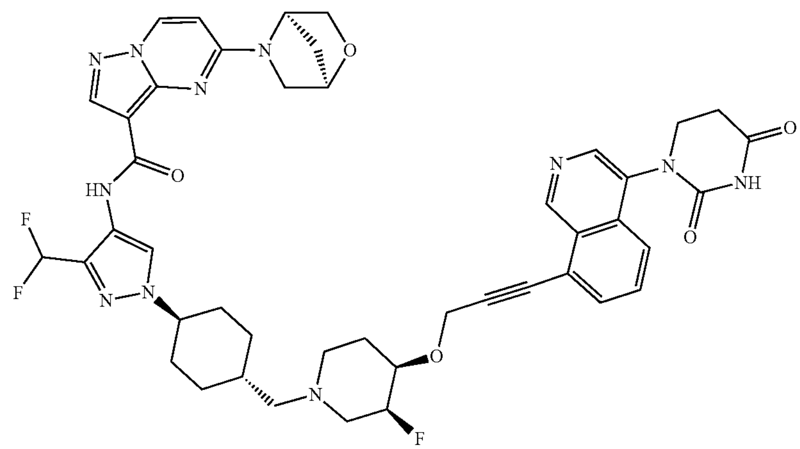 [SMILES: O=C1CCN(c2cncc3c(C#CCO[C@@H]4CCN(C[C@H]5CC[C@H](n6cc(NC(=O)c7cnn8ccc(N9C[C@H]%10C[C@@H]9CO%10)nc78)c(C(F)F)n6)CC5)C[C@@H]4F)cccc23)C(=O)N1] |
| I-42 | 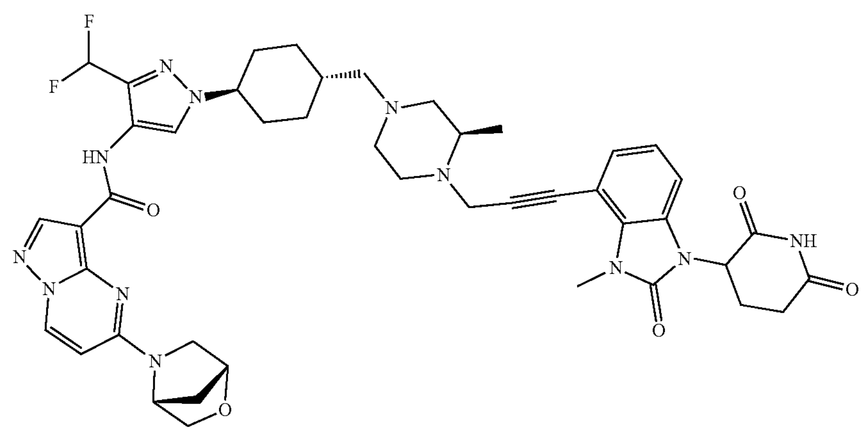 [SMILES: C[C@@H]1CN(C[C@H]2CC[C@H](n3cc(NC(=O)c4cnn5ccc(N6C[C@H]7C[C@@H]6CO7)nc45)c(C(F)F)n3)CC2)CCN1CC#Cc1cccc2c1n(C)c(=O)n2C1CCC(=O)NC1=O] |
| I-43 | 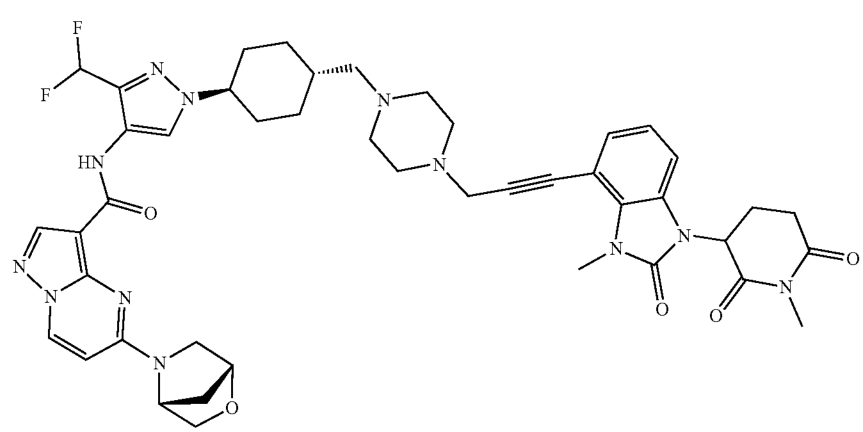 [SMILES: CN1C(=O)CCC(n2c(=O)n(C)c3c(C#CCN4CCN(C[C@H]5CC[C@H](n6cc(NC(=O)c7cnn8ccc(N9C[C@H]%10C[C@@H]9CO%10)nc78)c(C(F)F)n6)CC5)CC4)cccc32)C1=O] |

TABLE 1-continued

Exemplary Compounds

| I-# | Structure |
|---|---|
| I-44 | 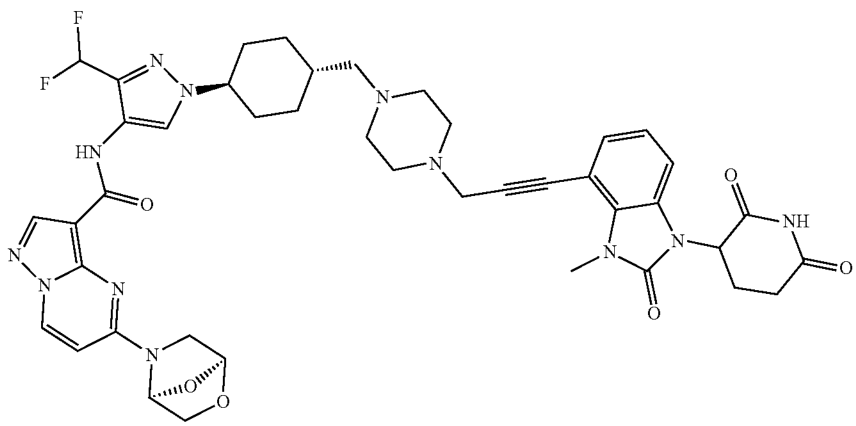 [SMILES: Cn1c(=O)n(C2CCC(=O)NC2=O)c2cccc(C#CCN3CCN(C[C@H]4CC[C@H](n5cc(NC(=O)c6cnn7ccc(N8C[C@H]9OC[C@@H]8O9)nc67)c(C(F)F)n5)CC4)CC3)c21] |
| I-45 | 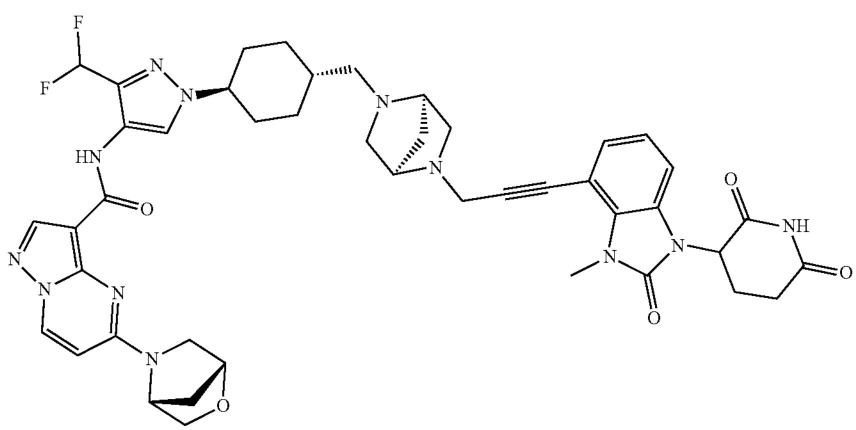 [SMILES: Cn1c(=O)n(C2CCC(=O)NC2=O)c2cccc(C#CCN3C[C@H]4C[C@@H]3CN4C[C@H]3CC[C@H](n4cc(NC(=O)c5cnn6ccc(N7C[C@H]8C[C@@H]7CO8)nc56)c(C(F)F)n4)CC3)c21] |
| I-46 | 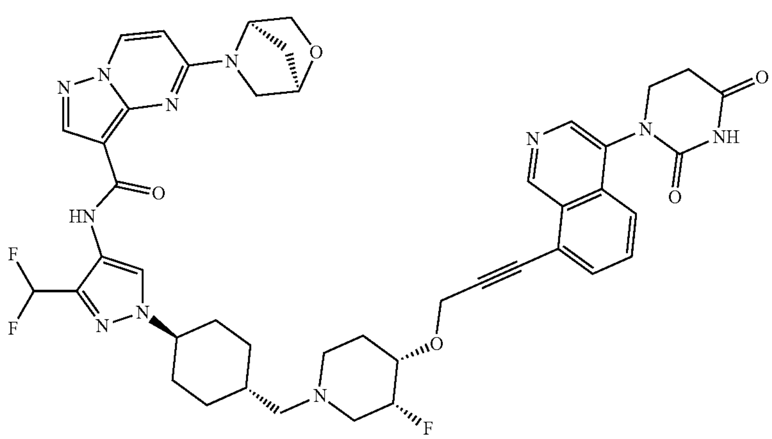 [SMILES: O=C1CCN(c2cncc3c(C#CCO[C@H]4CCN(C[C@H]5CC[C@H](n6cc(NC(=O)c7cnn8ccc(N9C[C@H]%10C[C@@H]9CO%10)nc78)c(C(F)F)n6)CC5)C[C@H]4F)cccc23)C(=O)N1] |

TABLE 1-continued

Exemplary Compounds

| I-# | Structure |
|-----|-----------|
| I-47 | 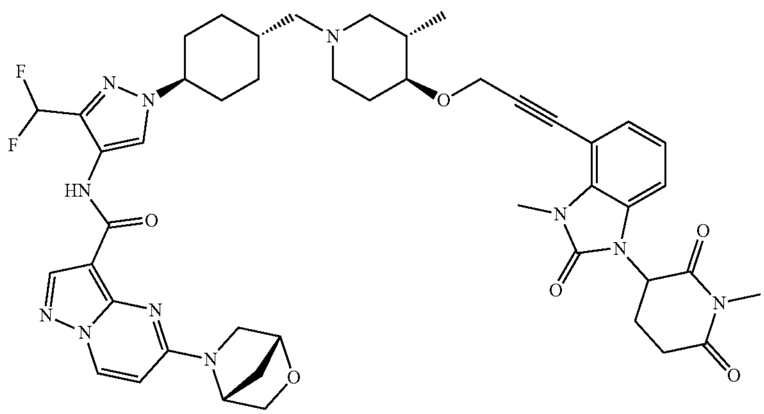 [SMILES: C[C@H]1CN(C[C@H]2CC[C@H](n3cc(NC(=O)c4cnn5ccc(N6C[C@H]7C[C@@H]6CO7)nc45)c(C(F)F)n3)CC2)CC[C@@H]1OCC#Cc1cccc2c1n(C)c(=O)n2C1CCC(=O)N(C)C1=O] |
| I-48 | 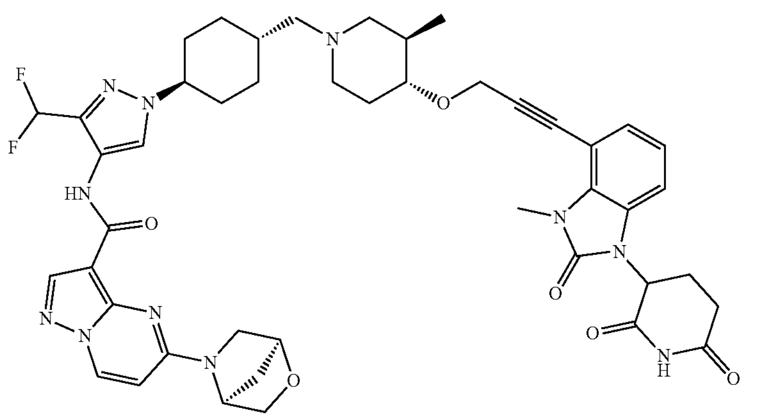 [SMILES: C[C@@H]1CN(C[C@H]2CC[C@H](n3cc(NC(=O)c4cnn5ccc(N6C[C@@H]7C[C@H]6CO7)nc45)c(C(F)F)n3)CC2)CC[C@H]1OCC#Cc1cccc2c1n(C)c(=O)n2C1CCC(=O)NC1=O] |
| I-49 | 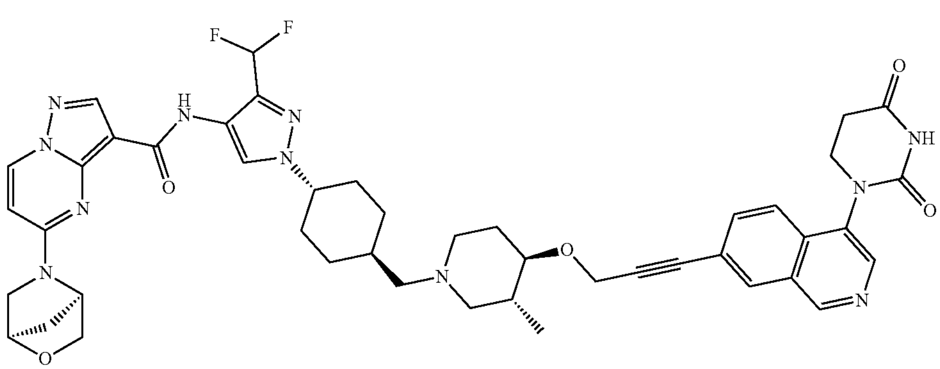 [SMILES: C[C@@H]1CN(C[C@H]2CC[C@H](n3cc(NC(=O)c4cnn5ccc(N6C[C@H]7C[C@@H]6CO7)nc45)c(C(F)F)n3)CC2)CC[C@H]1OCC#Cc1ccc2c(N3CCC(=O)NC3=O)cncc2c1] |

TABLE 1-continued

Exemplary Compounds

| I-# | Structure |
|---|---|
| I-50 | 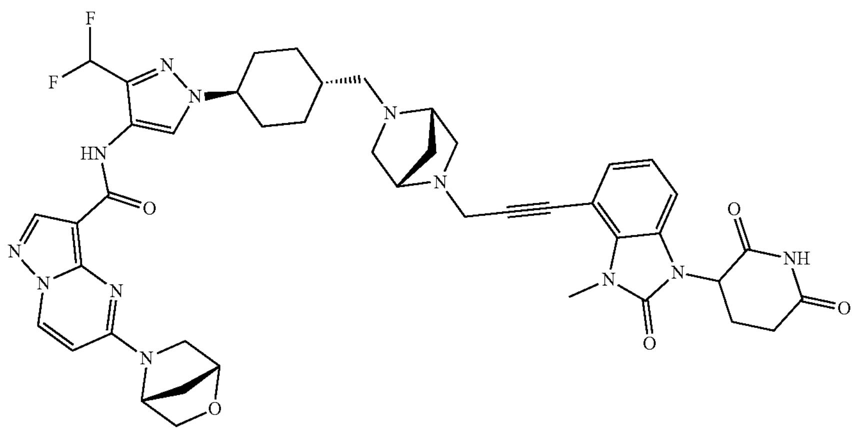 [SMILES: Cn1c(=O)n(C2CCC(=O)NC2=O)c2cccc(C#CCN3C[C@@H]4C[C@H]3CN4C[C@H]3CC[C@H](n4cc(NC(=O)c5cnn6ccc(N7C[C@H]8C[C@@H]7CO8)nc56)c(C(F)F)n4)CC3)c21] |
| I-51 | 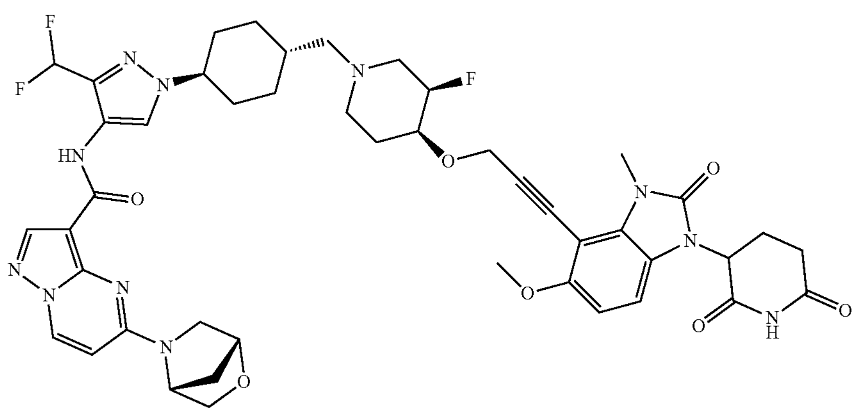 [SMILES: COc1ccc2c(c1C#CCO[C@H]1CCN(C[C@H]3CC[C@H](n4cc(NC(=O)c5cnn6ccc(N7C[C@H]8C[C@@H]7CO8)nc56)c(C(F)F)n4)CC3)C[C@H]1F)n(C)c(=O)n2C1CCC(=O)NC1=O] |
| I-52 | 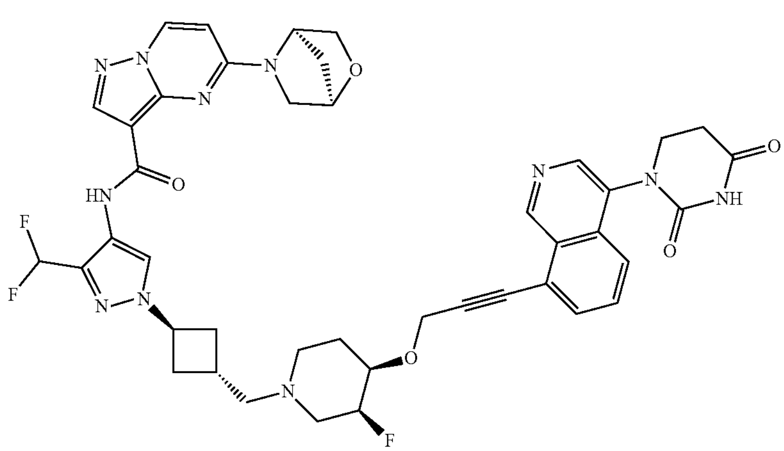 [SMILES: O=C1CCN(c2cncc3c(C#CCO[C@@H]4CCN(C[C@H]5C[C@H](n6cc(NC(=O)c7cnn8ccc(N9C[C@H]%10C[C@@H]9CO%10)nc78)c(C(F)F)n6)C5)C[C@@H]4F)cccc23)C(=O)N1] |

TABLE 1-continued

Exemplary Compounds

| I-# | Structure |
|---|---|
| I-53 | 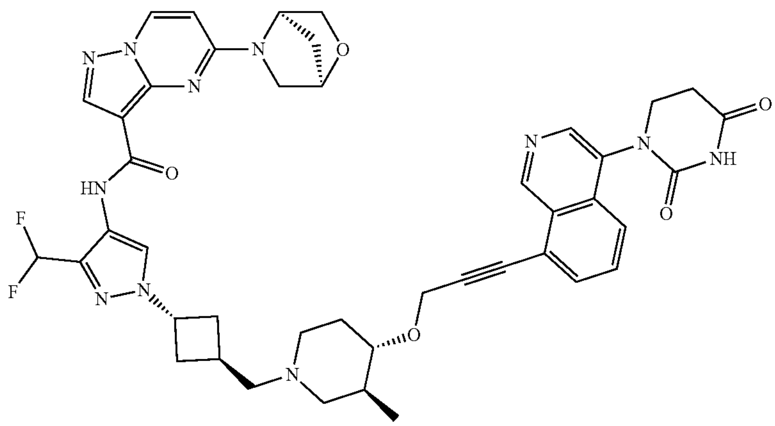 [SMILES: C[C@H]1CN(C[C@H]2C[C@H](n3cc(NC(=O)c4cnn5ccc(N6C[C@H]7C[C@@H]6CO7)nc45)c(C(F)F)n3)C2)CC[C@@H]1OCC#Cc1cccc2c(N3CCC(=O)NC3=O)cncc12] |
| I-54 | 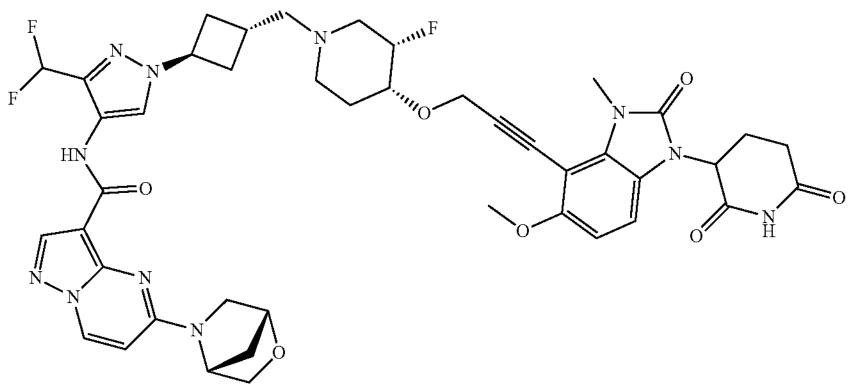 [SMILES: COc1ccc2c(c1C#CCO[C@@H]1CCN(C[C@H]3C[C@H](n4cc(NC(=O)c5cnn6ccc(N7C[C@H]8C[C@@H]7CO8)nc56)c(C(F)F)n4)C3)C[C@@H]1F)n(C)c(=O)n2C1CCC(=O)NC1=O] |
| I-55 | 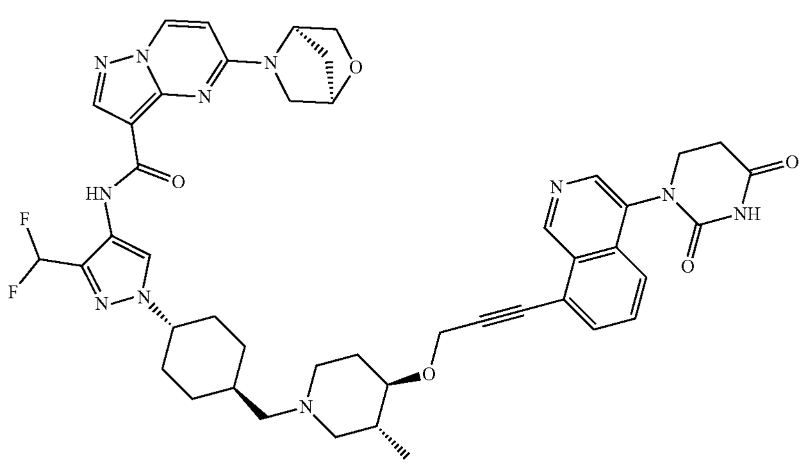 [SMILES: C[C@@H]1CN(C[C@H]2CC[C@H](n3cc(NC(=O)c4cnn5ccc(N6C[C@H]7C[C@@H]6CO7)nc45)c(C(F)F)n3)CC2)CC[C@H]1OCC#Cc1cccc2c(N3CCC(=O)NC3=O)cncc12] |

/ TABLE 1-continued
Exemplary Compounds
I-# Structure
I-56
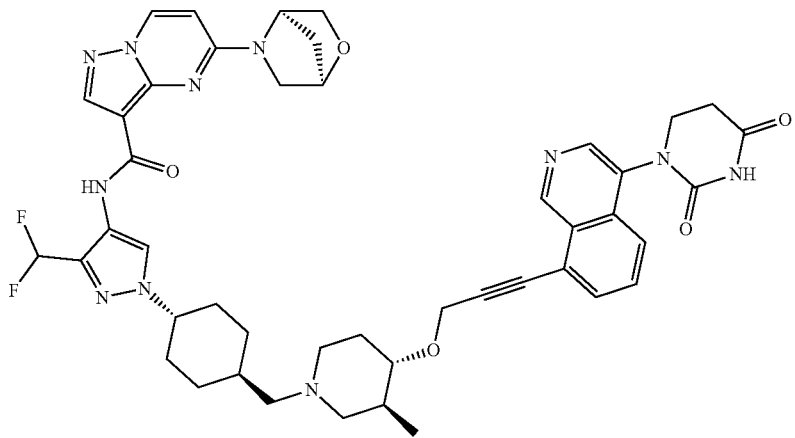 [SMILES: C[C@H]1CN(C[C@H]2CC[C@H](n3cc(NC(=O)c4cnn5ccc(N6C[C@H]7C[C@@H]6CO7)nc45)c(C(F)F)n3)CC2)CC[C@@H]1OCC#Cc1cccc2c(N3CCC(=O)NC3=O)cncc12]
I-57
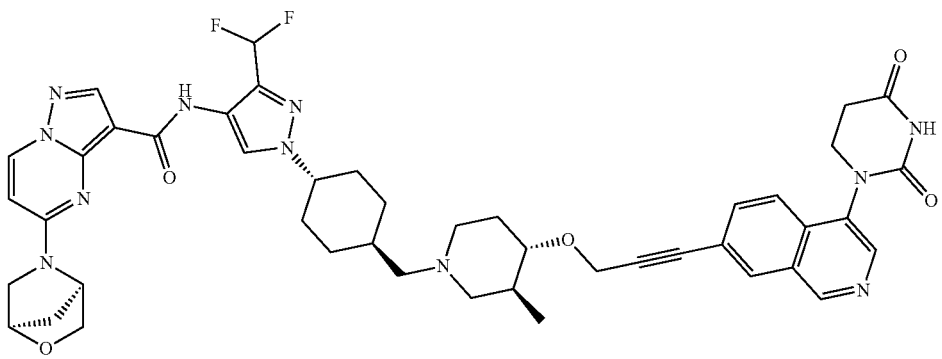 [SMILES: C[C@H]1CN(C[C@H]2CC[C@H](n3cc(NC(=O)c4cnn5ccc(N6C[C@H]7C[C@@H]6CO7)nc45)c(C(F)F)n3)CC2)CC[C@@H]1OCC#Cc1ccc2c(N3CCC(=O)NC3=O)cncc2c1]
I-58
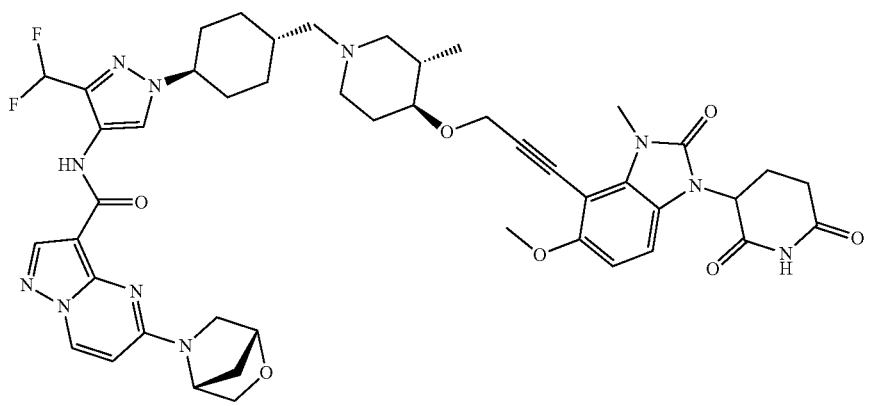 [SMILES: COc1ccc2c(c1C#CCO[C@H]1CCN(C[C@H]3CC[C@H](n4cc(NC(=O)c5cnn6ccc(N7C[C@H]8C[C@@H]7CO8)nc56)c(C(F)F)n4)CC3)C[C@@H]1C)n(C)c(=O)n2C1CCC(=O)NC1=O]

TABLE 1-continued

Exemplary Compounds

| I-# | Structure |
|---|---|
| I-59 | 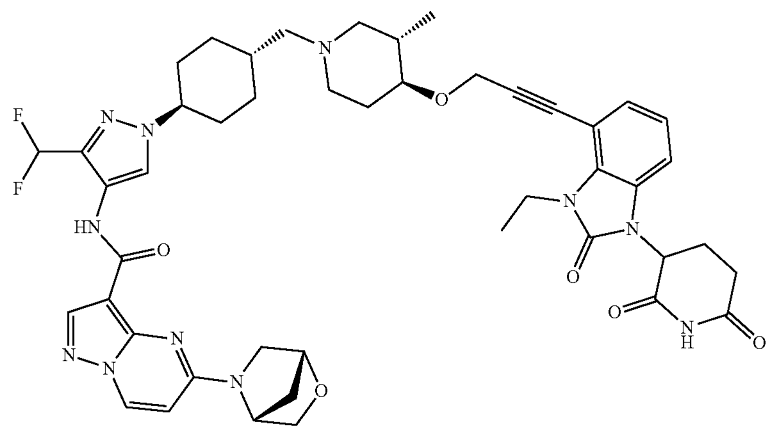 [SMILES: CCn1c(=O)n(C2CCC(=O)NC2=O)c2cccc(C#CCO[C@H]3CCN(C[C@H]4CC[C@H](n5cc(NC(=O)c6cnn7ccc(N8C[C@H]9C[C@@H]8CO9)nc67)c(C(F)F)n5)CC4)C[C@@H]3C)c21] |
| I-60 | 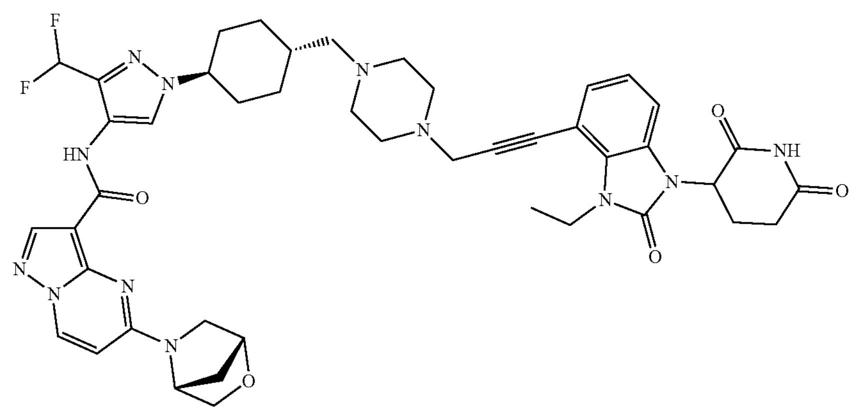 [SMILES: CCn1c(=O)n(C2CCC(=O)NC2=O)c2cccc(C#CCN3CCN(C[C@H]4CC[C@H](n5cc(NC(=O)c6cnn7ccc(N8C[C@H]9C[C@@H]8CO9)nc67)c(C(F)F)n5)CC4)CC3)c21] |
| I-61 | 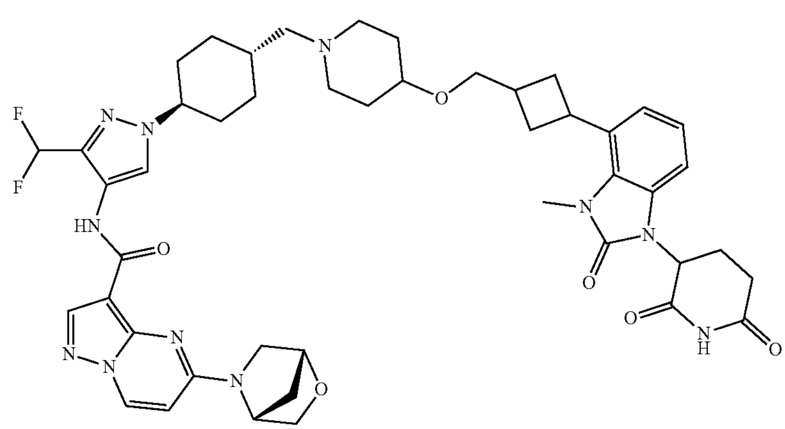 [SMILES: Cn1c(=O)n(C2CCC(=O)NC2=O)c2cccc(C3CC(COC4CCN(C[C@H]5CC[C@H](n6cc(NC(=O)c7cnn8ccc(N9C[C@H]%10C[C@@H]9CO%10)nc78)c(C(F)F)n6)CC5)CC4)C3)c21] |

TABLE 1-continued
Exemplary Compounds
| I-# | Structure |
|---|---|
| I-62 | 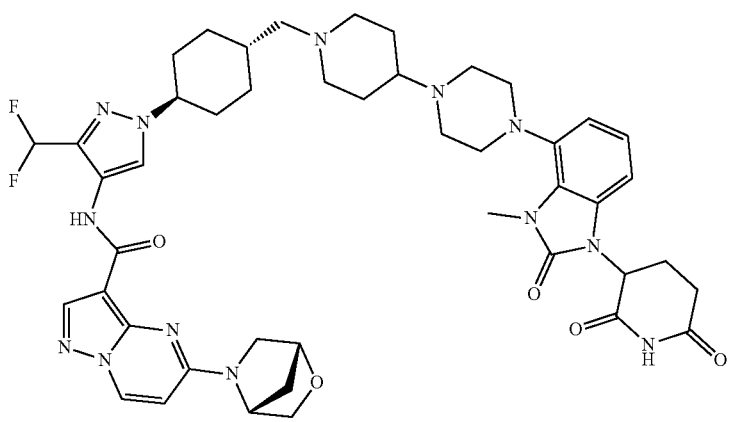 [SMILES: Cn1c(=O)n(C2CCC(=O)NC2=O)c2cccc(N3CCN(C4CCN(C[C@H]5CC[C@H](n6cc(NC(=O)c7cnn8ccc(N9C[C@H]%10C[C@@H]9CO%10)nc78)c(C(F)F)n6)CC5)CC4)CC3)c21] |
| I-63 | 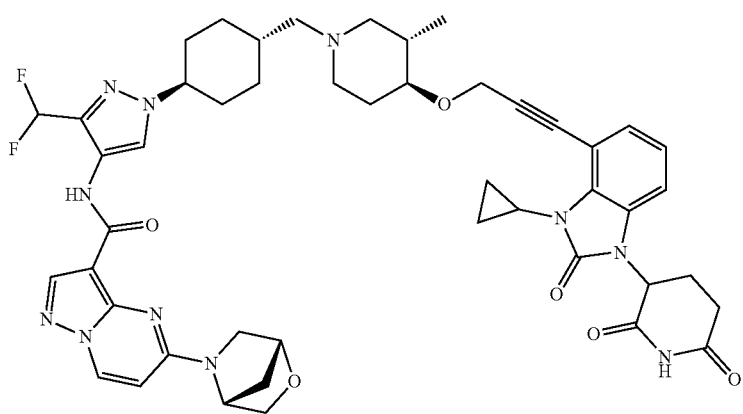 [SMILES: C[C@H]1CN(C[C@H]2CC[C@H](n3cc(NC(=O)c4cnn5ccc(N6C[C@H]7C[C@@H]6CO7)nc45)c(C(F)F)n3)CC2)CC[C@@H]1OCC#Cc1cccc2c1n(C1CC1)c(=O)n2C1CCC(=O)NC1=O] |
| I-64 | 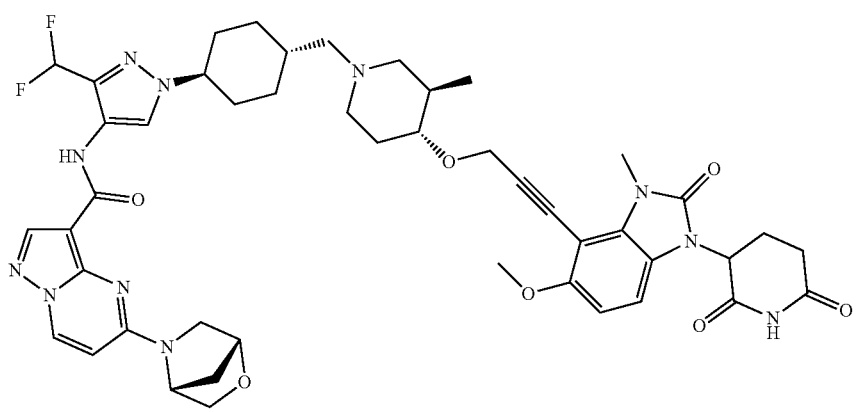 [SMILES: COc1ccc2c(c1C#CCO[C@@H]1CCN(C[C@H]3CC[C@H](n4cc(NC(=O)c5cnn6ccc(N7C[C@H]8C[C@@H]7CO8)nc56)c(C(F)F)n4)CC3)C[C@H]1C)n(C)c(=O)n2C1CCC(=O)NC1=O] |

TABLE 1-continued
Exemplary Compounds
| I-# | Structure |
|---|---|
| I-65 | 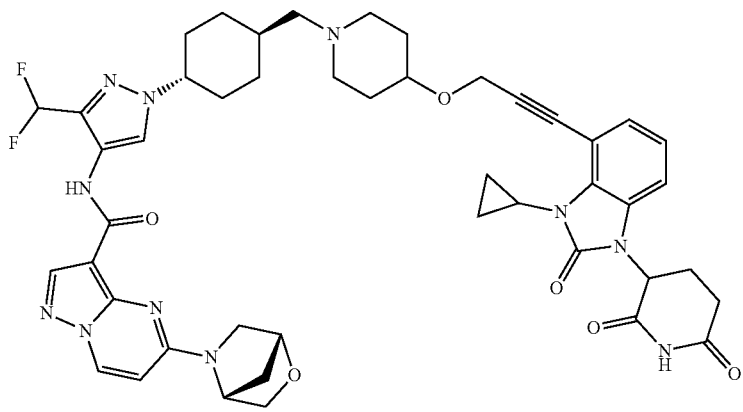 [SMILES: O=C1CCC(n2c(=O)n(C3CC3)c3c(C#CCOC4CCN(C[C@H]5CC[C@H](n6cc(NC(=O)c7cnn8ccc(N9C[C@H]%10C[C@@H]9CO%10)nc78)c(C(F)F)n6)CC5)CC4)cccc32)C(=O)N1] |
| I-66 | 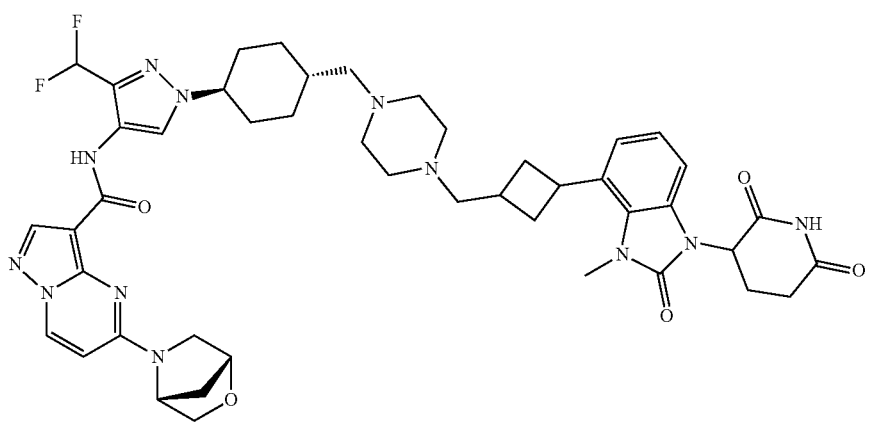 [SMILES: Cn1c(=O)n(C2CCC(=O)NC2=O)c2cccc(C3CC(CN4CCN(C[C@H]5CC[C@H](n6cc(NC(=O)c7cnn8ccc(N9C[C@H]%10C[C@@H]9CO%10)nc78)c(C(F)F)n6)CC5)CC4)C3)c21] |
| I-67 | 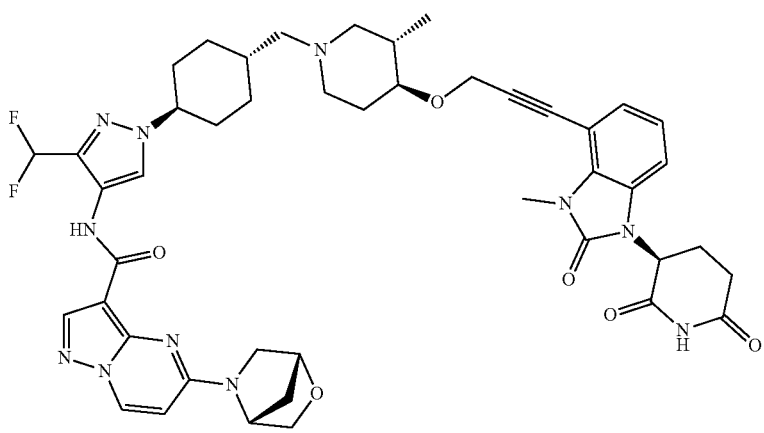 [SMILES: C[C@H]1CN(C[C@H]2CC[C@H](n3cc(NC(=O)c4cnn5ccc(N6C[C@H]7C[C@@H]6CO7)nc45)c(C(F)F)n3)CC2)CC[C@@H]1OCC#Cc1cccc2c1n(C)c(=O)n2[C@H]1CCC(=O)NC1=O] |

TABLE 1-continued

Exemplary Compounds

| I-# | Structure |
|---|---|
| I-68 | 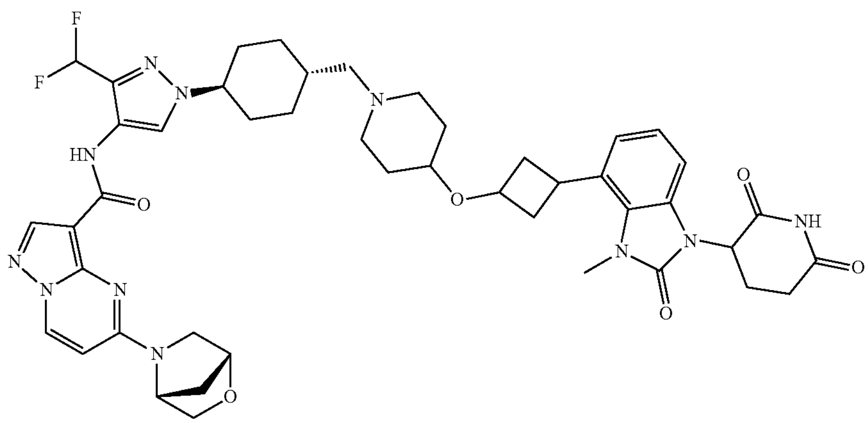 [SMILES: Cn1c(=O)n(C2CCC(=O)NC2=O)c2cccc(C3CC(OC4CCN(C[C@H]5CC[C@H](n6cc(NC(=O)c7cnn8ccc(N9C[C@H]%10C[C@@H]9CO%10)nc78)c(C(F)F)n6)CC5)CC4)C3)c21] |
| I-69 | 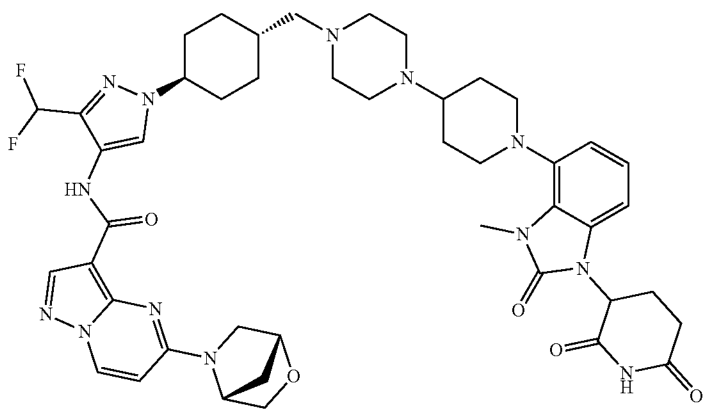 [SMILES: Cn1c(=O)n(C2CCC(=O)NC2=O)c2cccc(N3CCC(N4CCN(C[C@H]5CC[C@H](n6cc(NC(=O)c7cnn8ccc(N9C[C@H]%10C[C@@H]9CO%10)nc78)c(C(F)F)n6)CC5)CC4)CC3)c21] |
| I-70 | 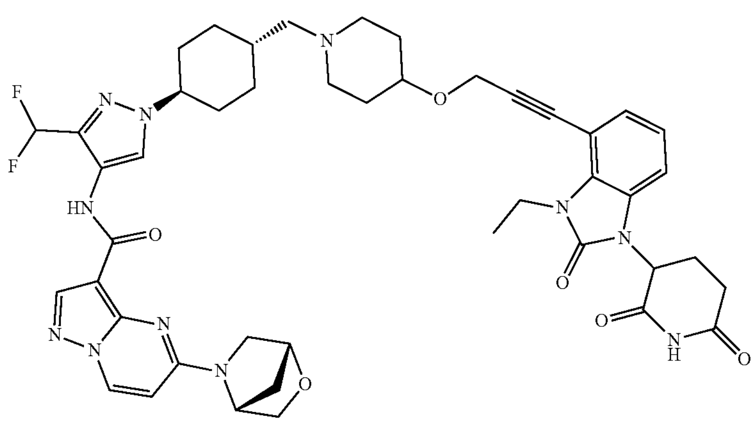 [SMILES: CCn1c(=O)n(C2CCC(=O)NC2=O)c2cccc(C#CCOC3CCN(C[C@H]4CC[C@H](n5cc(NC(=O)c6cnn7ccc(N8C[C@H]9C[C@@H]8CO9)nc67)c(C(F)F)n5)CC4)CC3)c21] |

TABLE 1-continued

Exemplary Compounds

| I-# | Structure |
| --- | --- |
| I-71 | 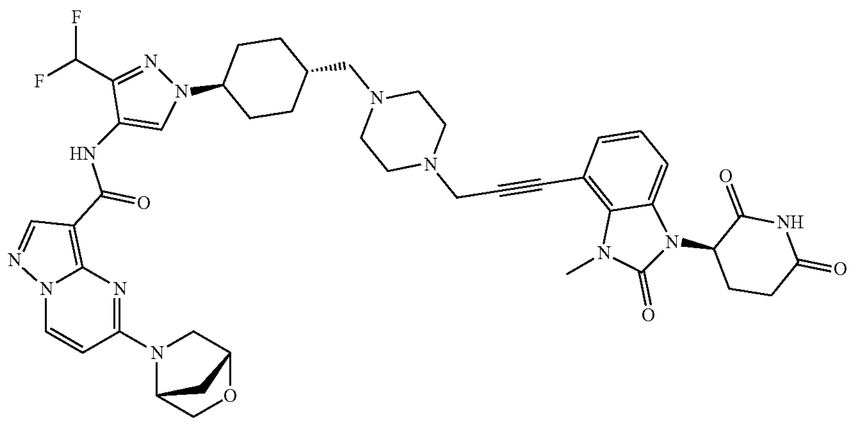 [SMILES: Cn1c(=O)n([C@@H]2CCC(=O)NC2=O)c2cccc(C#CCN3CCN(C[C@H]4CC[C@H](n5cc(NC(=O)c6cnn7ccc(N8C[C@H]9C[C@@H]8CO9)nc67)c(C(F)F)n5)CC4)CC3)c21] |
| I-72 | 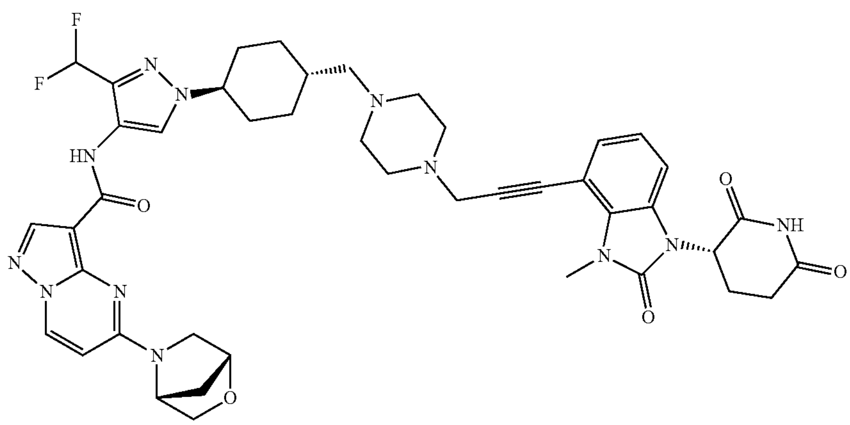 [SMILES: Cn1c(=O)n([C@H]2CCC(=O)NC2=O)c2cccc(C#CCN3CCN(C[C@H]4CC[C@H](n5cc(NC(=O)c6cnn7ccc(N8C[C@H]9C[C@@H]8CO9)nc67)c(C(F)F)n5)CC4)CC3)c21] |
| I-73 | 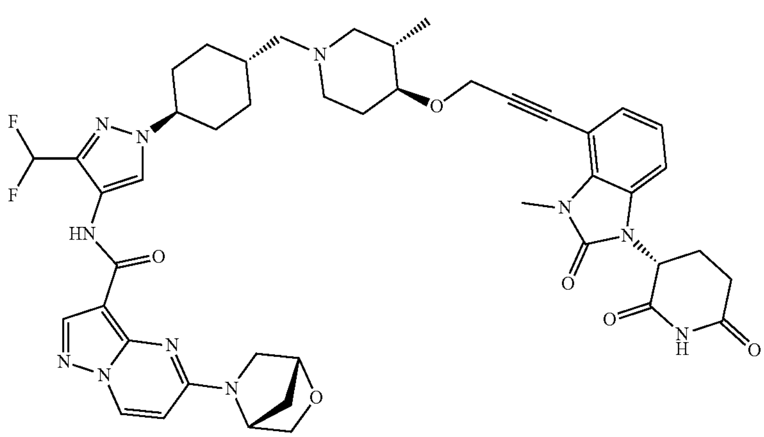 [SMILES: C[C@H]1CN(C[C@H]2CC[C@H](n3cc(NC(=O)c4cnn5ccc(N6C[C@H]7C[C@@H]6CO7)nc45)c(C(F)F)n3)CC2)CC[C@@H]1OCC#Cc1cccc2c1n(C)c(=O)n2[C@@H]1CCC(=O)NC1=O] |

TABLE 1-continued
Exemplary Compounds
| I-# | Structure |
|---|---|
| I-74 | 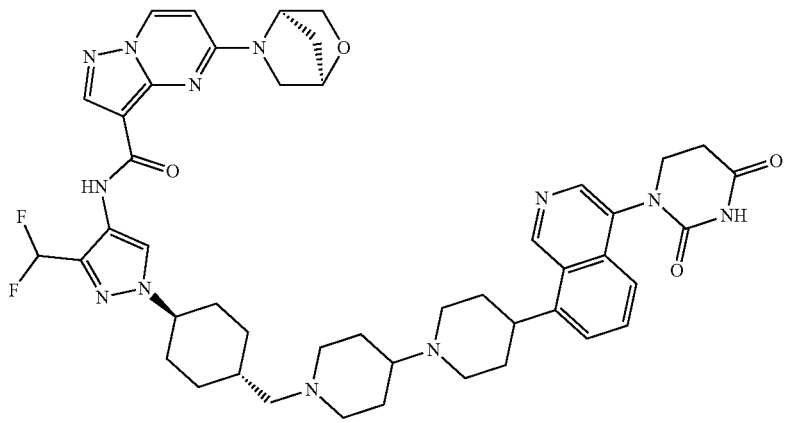 [SMILES: O=C1CCN(c2cncc3c(C4CCN(C5CCN(C[C@H]6CC[C@H](n7cc(NC(=O)c8cnn9ccc(N%10C[C@H]%11C[C@@H]%10CO%11)nc89)c(C(F)F)n7)CC6)CC5)CC4)cccc23)C(=O)N1] |
| I-75 | 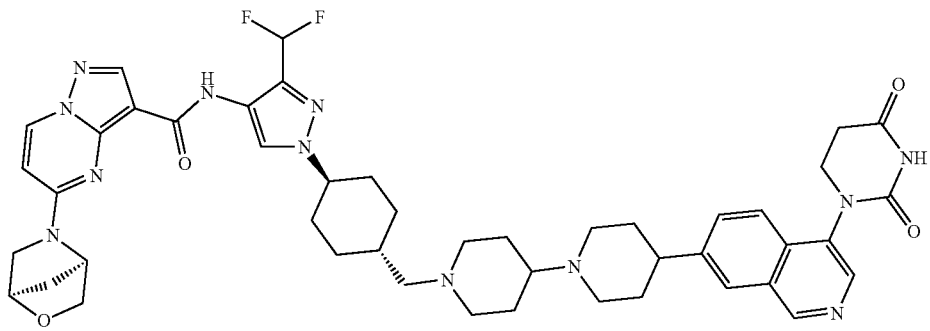 [SMILES: O=C1CCN(c2cncc3cc(C4CCN(C5CCN(C[C@H]6CC[C@H](n7cc(NC(=O)c8cnn9ccc(N%10C[C@H]%11C[C@@H]%10CO%11)nc89)c(C(F)F)n7)CC6)CC5)CC4)ccc23)C(=O)N1] |
| I-76 | 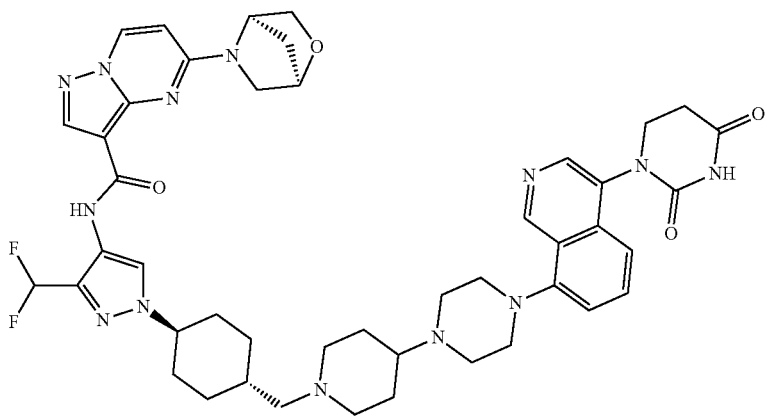 [SMILES: O=C1CCN(c2cncc3c(N4CCN(C5CCN(C[C@H]6CC[C@H](n7cc(NC(=O)c8cnn9ccc(N%10C[C@H]%11C[C@@H]%10CO%11)nc89)c(C(F)F)n7)CC6)CC5)CC4)cccc23)C(=O)N1] |
| I-77 | 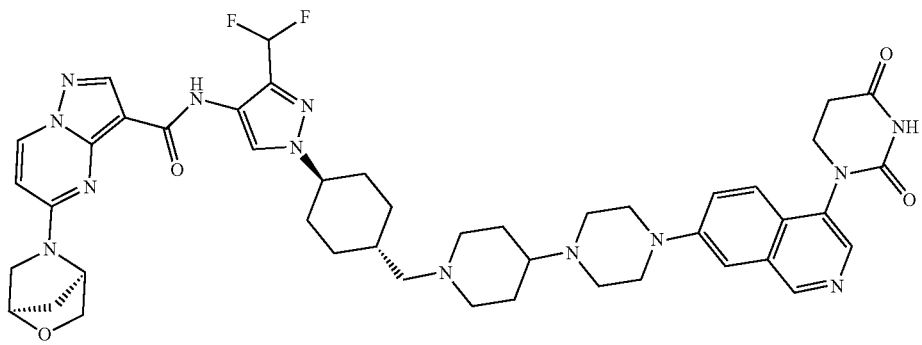 [SMILES: O=C1CCN(c2cncc3cc(N4CCN(C5CCN(C[C@H]6CC[C@H](n7cc(NC(=O)c8cnn9ccc(N%10C[C@H]%11C[C@@H]%10CO%11)nc89)c(C(F)F)n7)CC6)CC5)CC4)ccc23)C(=O)N1] |

TABLE 1-continued

Exemplary Compounds

| I-# | Structure |
|---|---|
| I-78 | 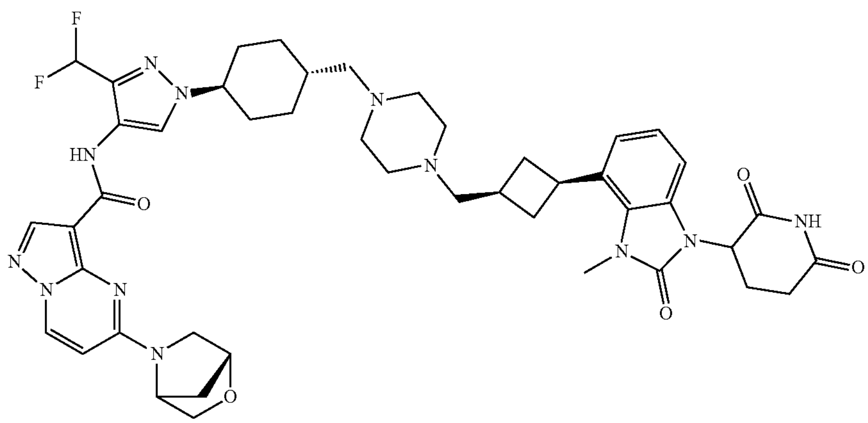 [SMILES: Cn1c(=O)n(C2CCC(=O)NC2=O)c2cccc([C@H]3C[C@@H](CN4CCN(C[C@H]5CC[C@H](n6cc(NC(=O)c7cnn8ccc(N9C[C@H]%10CC9CO%10)nc78)c(C(F)F)n6)CC5)CC4)C3)c21] |
| I-79 | 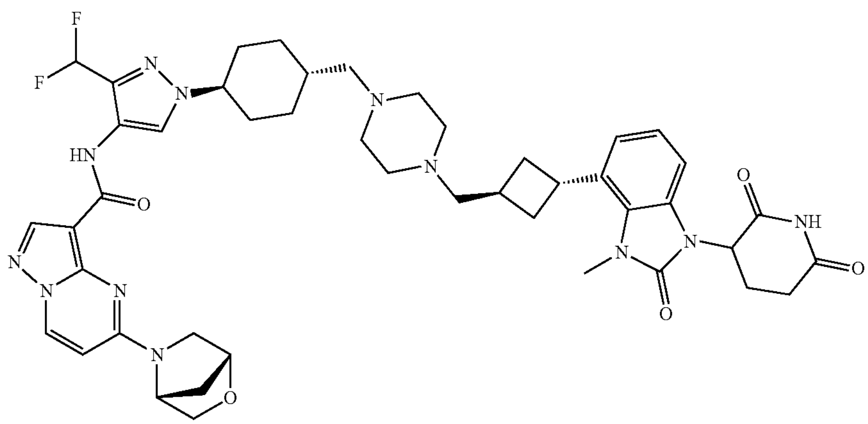 [SMILES: Cn1c(=O)n(C2CCC(=O)NC2=O)c2cccc([C@H]3C[C@H](CN4CCN(C[C@H]5CC[C@H](n6cc(NC(=O)c7cnn8ccc(N9C[C@H]%10C[C@@H]9CO%10)nc78)c(C(F)F)n6)CC5)CC4)C3)c21] |
| I-80 | 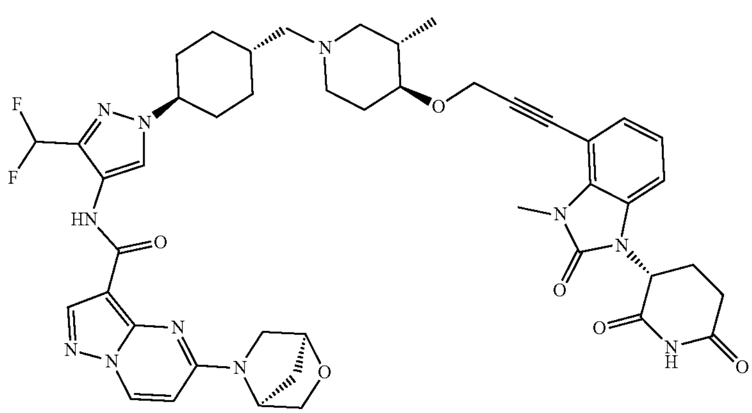 [SMILES: C[C@H]1CN(C[C@H]2CC[C@H](n3cc(NC(=O)c4cnn5ccc(N6C[C@@H]7C[C@H]6CO7)nc45)c(C(F)F)n3)CC2)CC[C@@H]1OCC#Cc1cccc2c1n(C)c(=O)n2[C@@H]1CCC(=O)NC1=O] |

TABLE 1-continued

Exemplary Compounds

| I-# | Structure |
|---|---|
| I-81 | *(structure)* |
| I-82 | *(structure)* |
| I-83 | *(structure)* |
| I-84 | *(structure)* |
| I-85 | *(structure)* |

TABLE 1-continued

Exemplary Compounds

| I-# | Structure |
|---|---|
| I-86 | 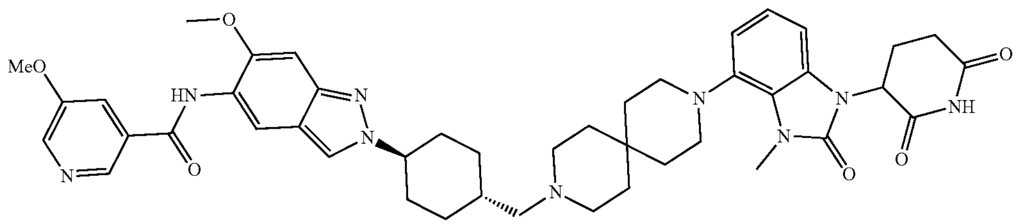 [SMILES: COc1cncc(C(=O)Nc2cc3cn([C@H]4CC[C@H](CN5CCC6(CC5)CCN(c5cccc7c5n(C)c(=O)n7C5CCC(=O)NC5=O)CC6)CC4)nc3cc2OC)c1] |
| I-87 | 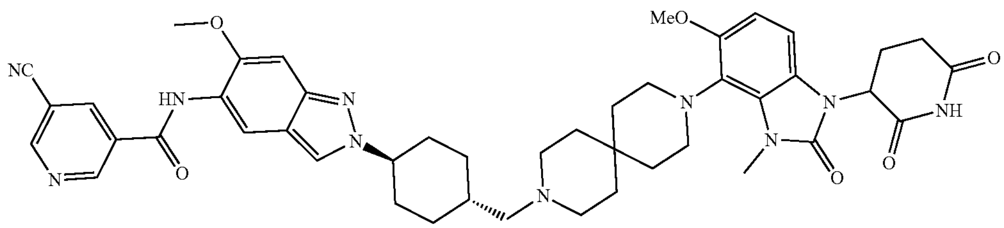 [SMILES: COc1cc2nn([C@H]3CC[C@H](CN4CCC5(CC4)CCN(c4c(OC)ccc6c4n(C)c(=O)n6C4CCC(=O)NC4=O)CC5)CC3)cc2cc1NC(=O)c1cncc(C#N)c1] |
| I-88 | 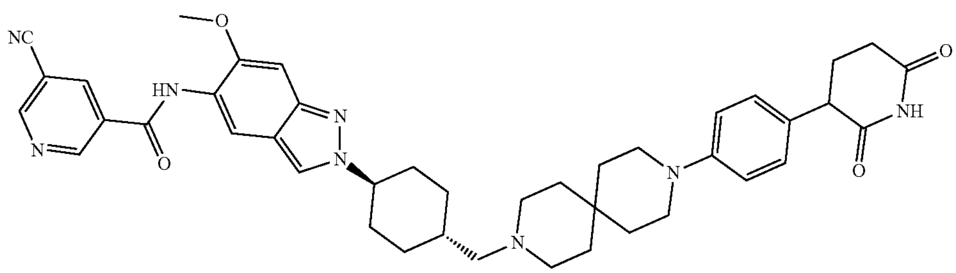 [SMILES: COc1cc2nn([C@H]3CC[C@H](CN4CCC5(CC4)CCN(c4ccc(C6CCC(=O)NC6=O)cc4)CC5)CC3)cc2cc1NC(=O)c1cncc(C#N)c1] |
| I-89 | 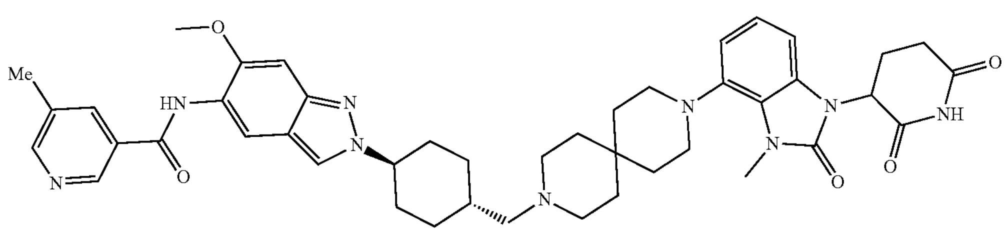 [SMILES: COc1cc2nn([C@H]3CC[C@H](CN4CCC5(CC4)CCN(c4cccc6c4n(C)c(=O)n6C4CCC(=O)NC4=O)CC5)CC3)cc2cc1NC(=O)c1cncc(C)c1] |
| I-90 | 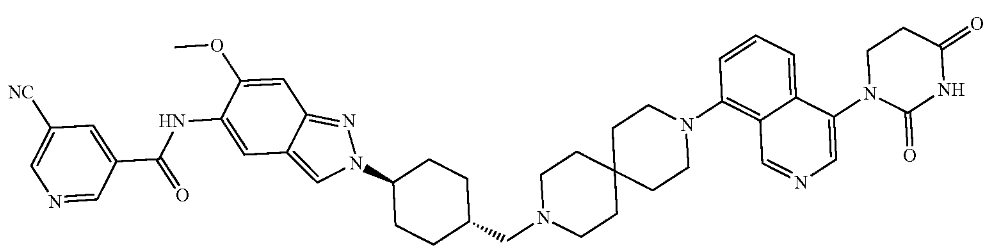 |
| I-91 | 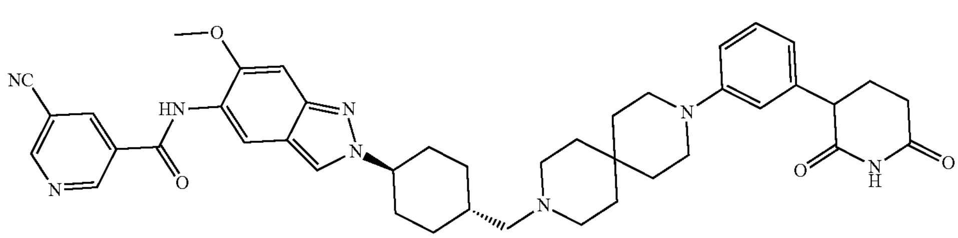 [SMILES: COc1cc2nn([C@H]3CC[C@H](CN4CCC5(CC4)CCN(c4cccc(C6CCC(=O)NC6=O)c4)CC5)CC3)cc2cc1NC(=O)c1cncc(C#N)c1] |

TABLE 1-continued

Exemplary Compounds

| I-# | Structure |
|---|---|
| I-92 | 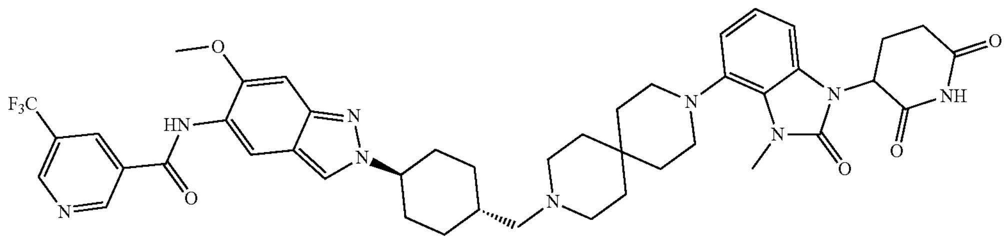 [SMILES: COc1cc2nn([C@H]3CC[C@H](CN4CCC5(CC4)CCN(c4cccc6c4n(C)c(=O)n6C4CCC(=O)NC4=O)CC5)CC3)cc2cc1NC(=O)c1cncc(C(F)(F)F)c1] |
| I-93 | 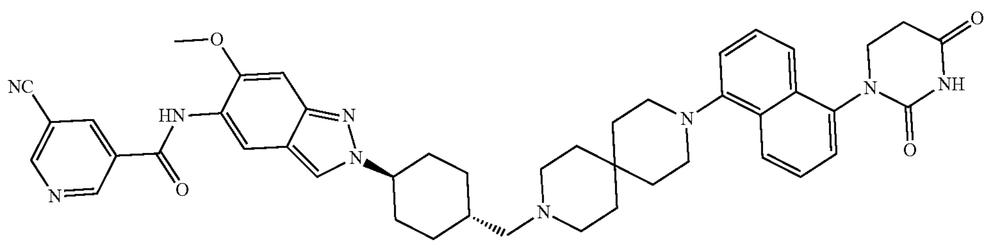 [SMILES: COc1cc2nn([C@H]3CC[C@H](CN4CCC5(CC4)CCN(c4cccc6c(N7CCC(=O)NC7=O)cccc46)CC5)CC3)cc2cc1NC(=O)c1cncc(C#N)c1] |
| I-94 | 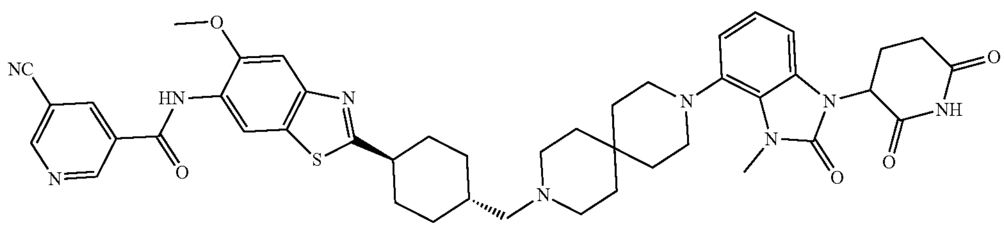 [SMILES: COc1cc2nc([C@H]3CC[C@H](CN4CCC5(CC4)CCN(c4cccc6c4n(C)c(=O)n6C4CCC(=O)NC4=O)CC5)CC3)sc2cc1NC(=O)c1cncc(C#N)c1] |
| I-95 | 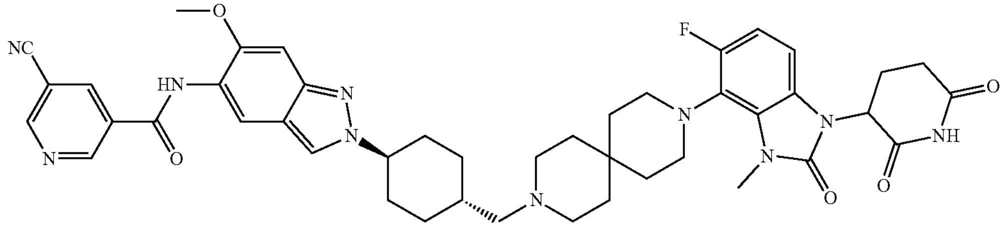 [SMILES: COc1cc2nn([C@H]3CC[C@H](CN4CCC5(CC4)CCN(c4c(F)ccc6c4n(C)c(=O)n6C4CCC(=O)NC4=O)CC5)CC3)cc2cc1NC(=O)c1cncc(C#N)c1] |
| I-96 | 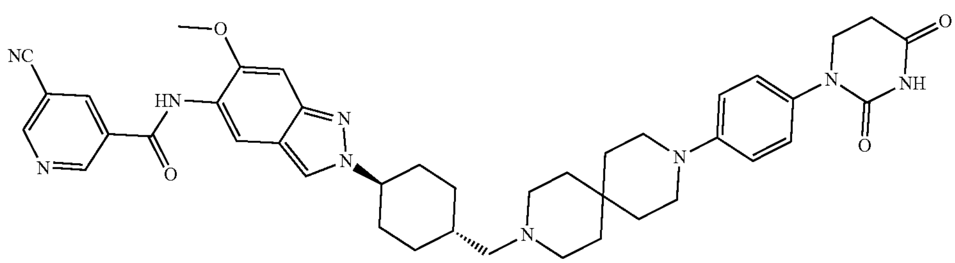 [SMILES: COc1cc2nn([C@H]3CC[C@H](CN4CCC5(CC4)CCN(c4ccc(N6CCC(=O)NC6=O)cc4)CC5)CC3)cc2cc1NC(=O)c1cncc(C#N)c1] |
| I-97 | 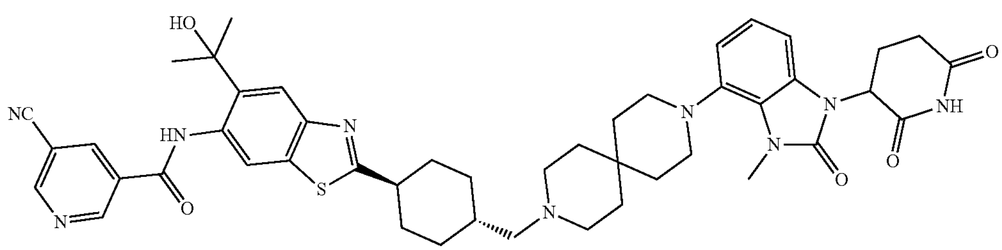 [SMILES: Cn1c(=O)n(C2CCC(=O)NC2=O)c2cccc(N3CCC4(CCN(C[C@H]5CC[C@H](c6nc7cc(C(C)(C)O)c(NC(=O)c8cncc(C#N)c8)cc7s6)CC5)CC4)CC3)c21] |

TABLE 1-continued

Exemplary Compounds

| I-# | Structure |
|---|---|
| I-98 | 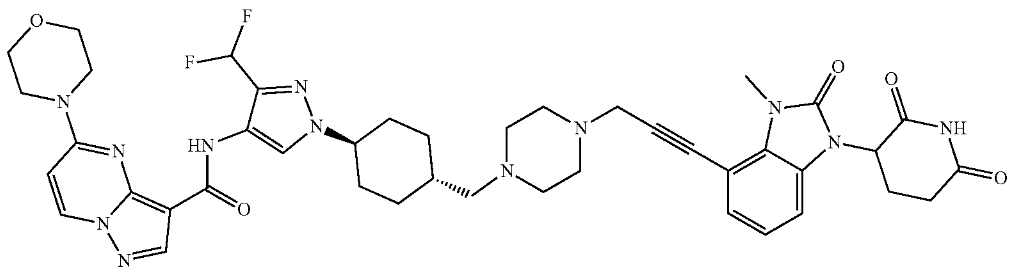 |
| I-99 | 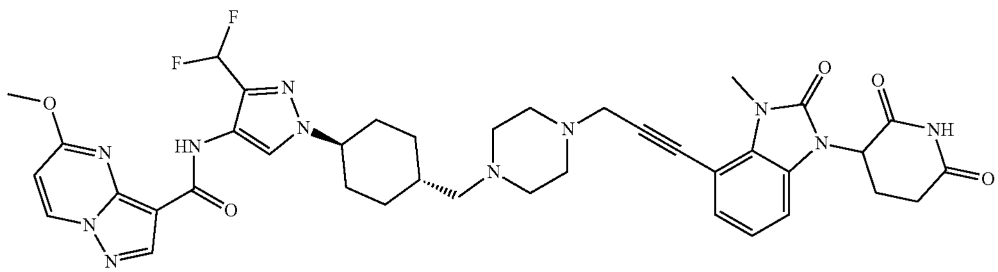 |
| I-100 | 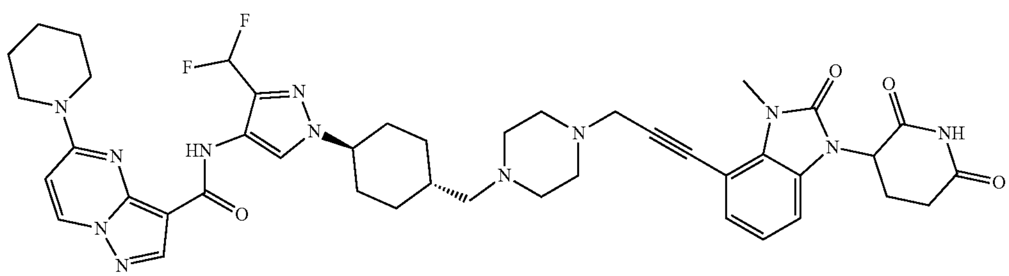 |
| I-101 | 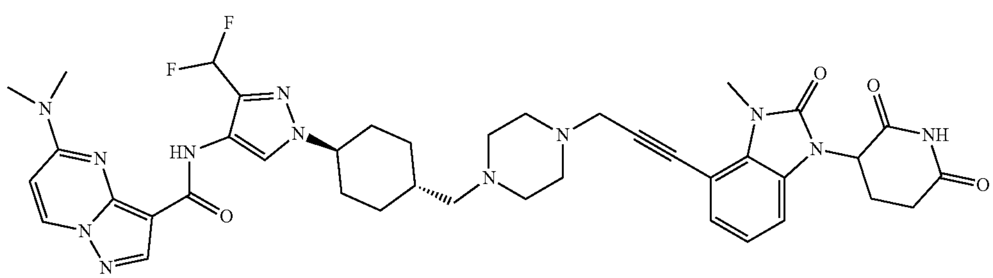 |
| I-102 | 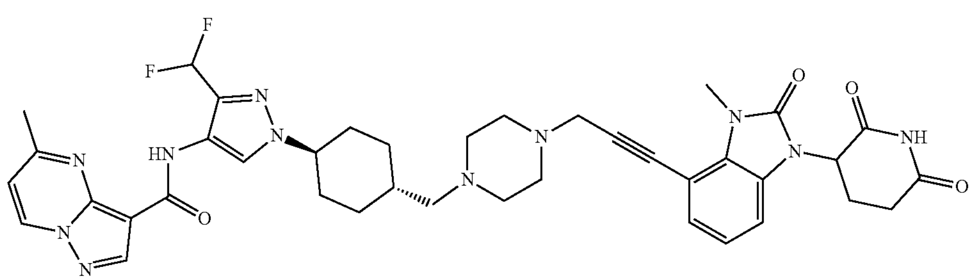 |

TABLE 1-continued

Exemplary Compounds

| I-# | Structure |
|---|---|
| I-103 | 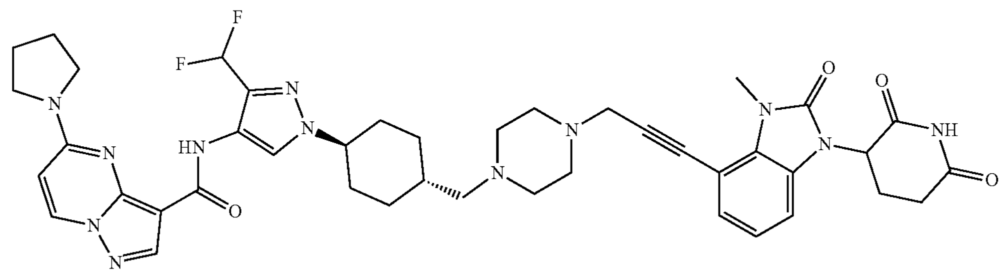 |
| I-104 | 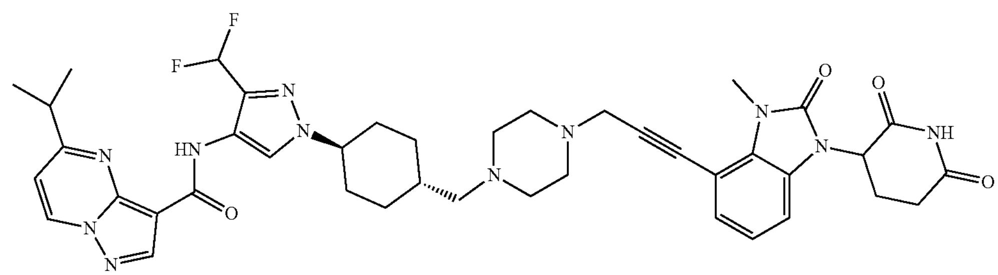 |
| I-105 | 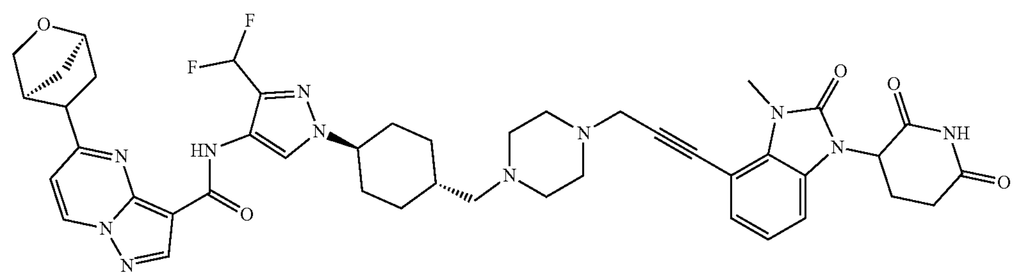 |
| I-106 | 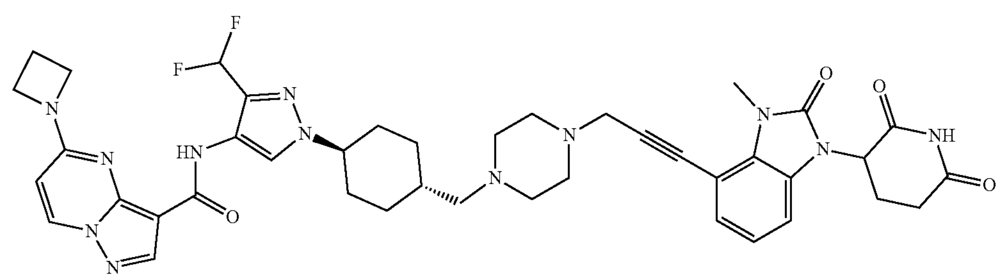 |
| I-107 | 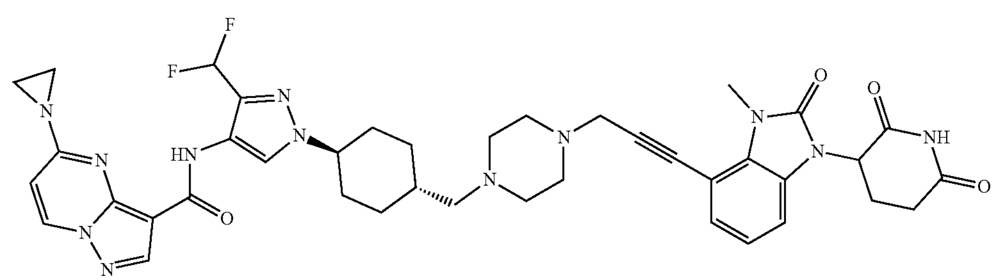 |

145

TABLE 1-continued

Exemplary Compounds

| I-# | Structure |
|---|---|
| I-108 | 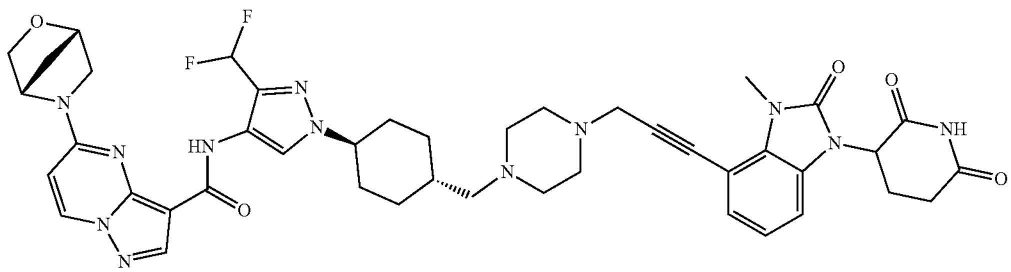 |
| I-109 | 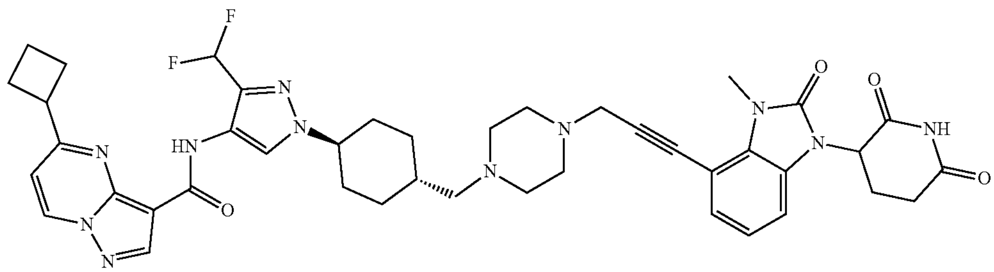 |
| I-110 | 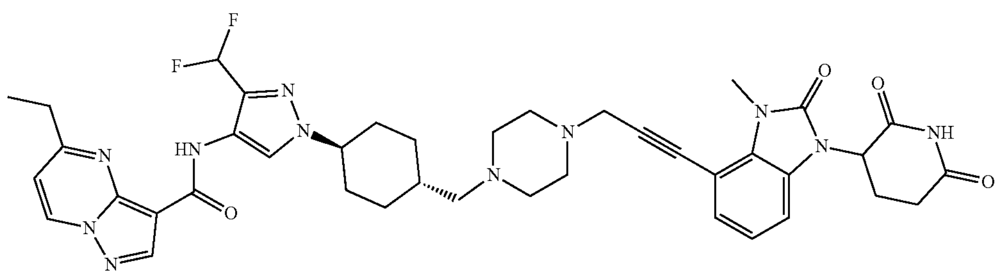 |
| I-111 | 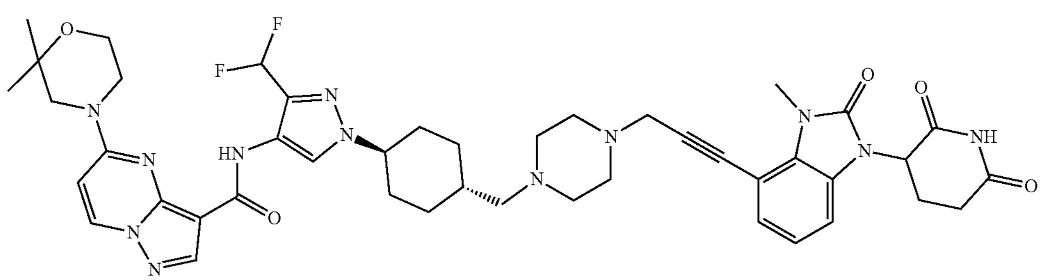 |
| I-112 | 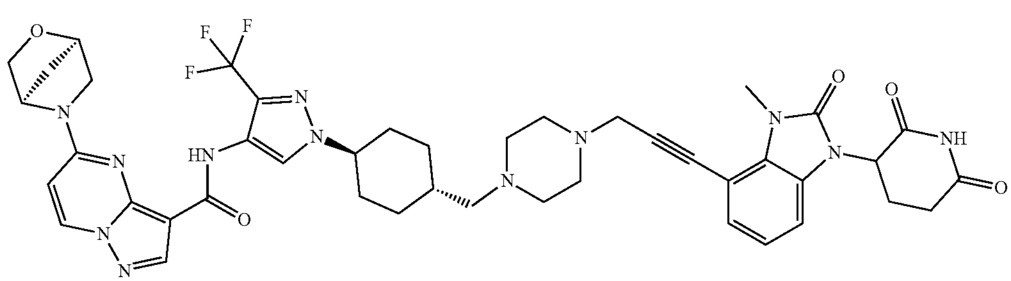 |

TABLE 1-continued
Exemplary Compounds
| I-# | Structure |
|---|---|
| I-113 | 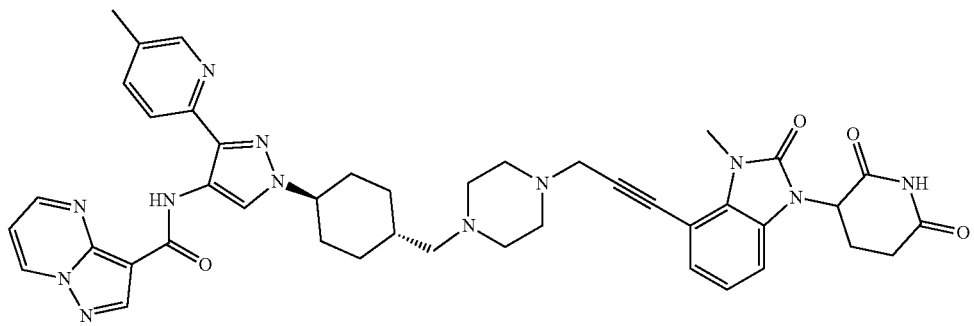 |
| I-114 | 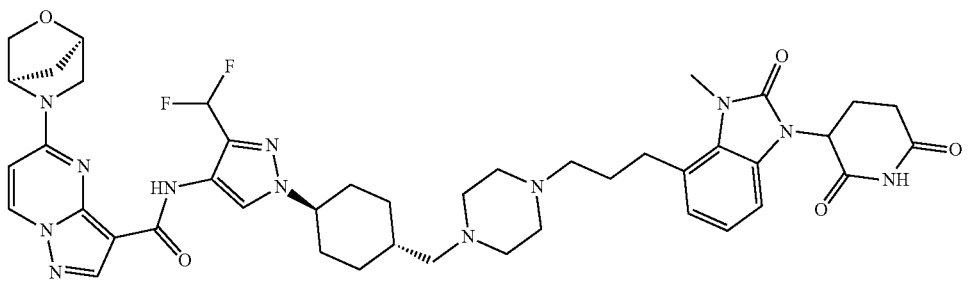 |
| I-115 | 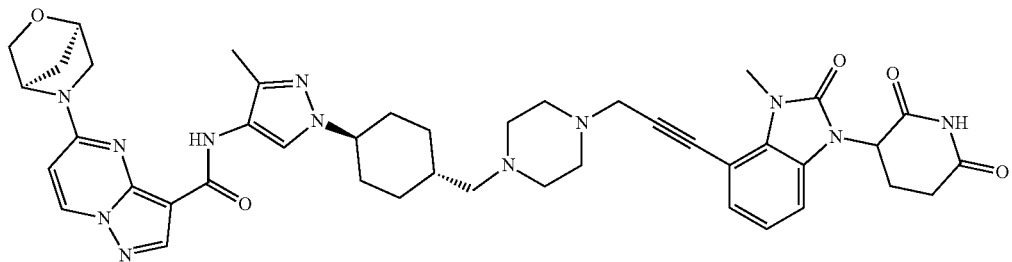 |
| I-116 | 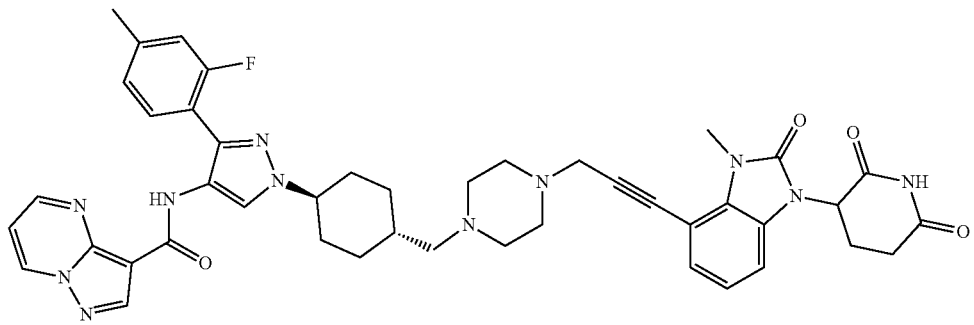 |
| I-117 | 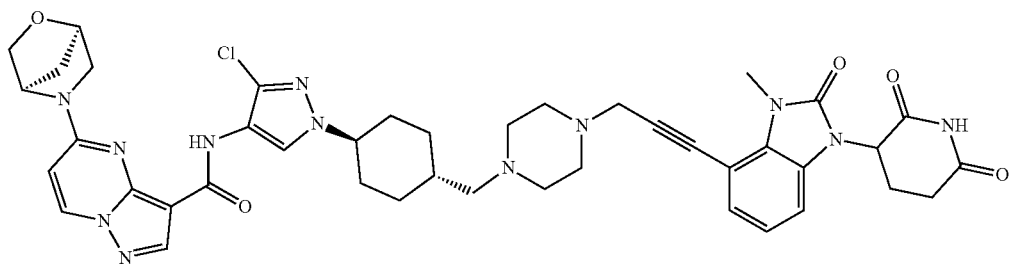 |

TABLE 1-continued

Exemplary Compounds

| I-# | Structure |
|---|---|
| I-118 | 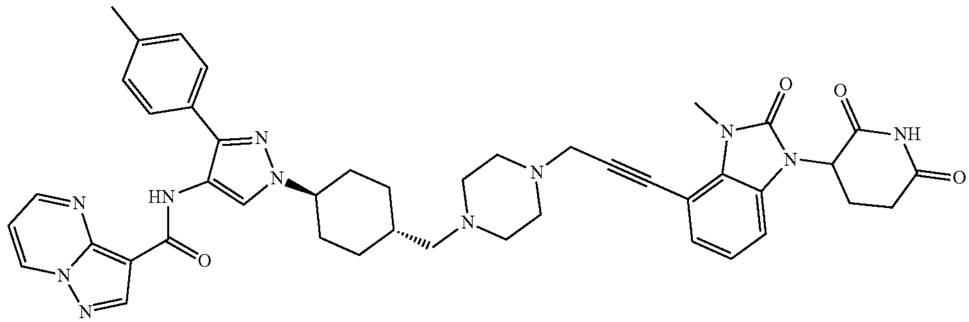 |
| I-119 | 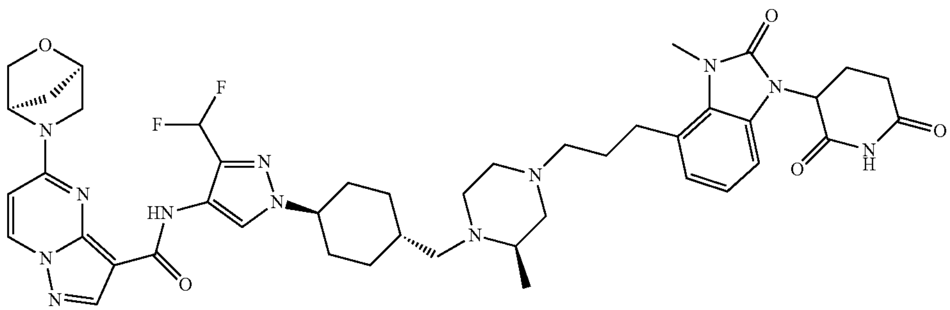 [SMILES: C[C@@H]1CN(CCCc2cccc3c2n(C)c(=O)n3C2CCC(=O)NC2=O)CCN1C[C@H]1CC[C@H](n2cc(NC(=O)c3cnn4ccc(N5C[C@H]6C[C@@H]5CO6)nc34)c(C(F)F)n2)CC1] |
| I-120 | 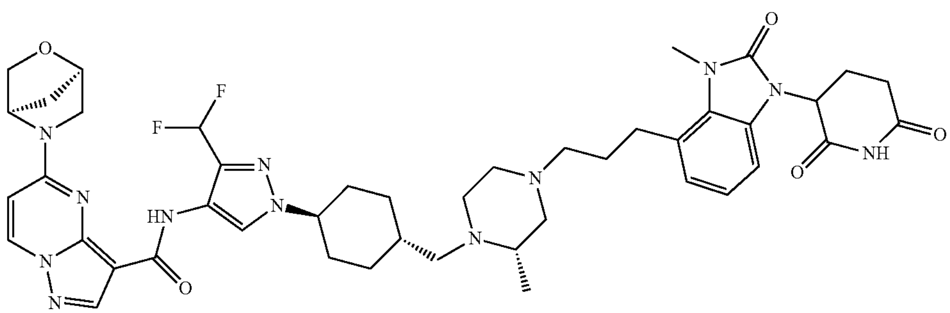 [SMILES: C[C@H]1CN(CCCc2cccc3c2n(C)c(=O)n3C2CCC(=O)NC2=O)CCN1C[C@H]1CC[C@H](n2cc(NC(=O)c3cnn4ccc(N5C[C@H]6C[C@@H]5CO6)nc34)c(C(F)F)n2)CC1] |
| I-121 | 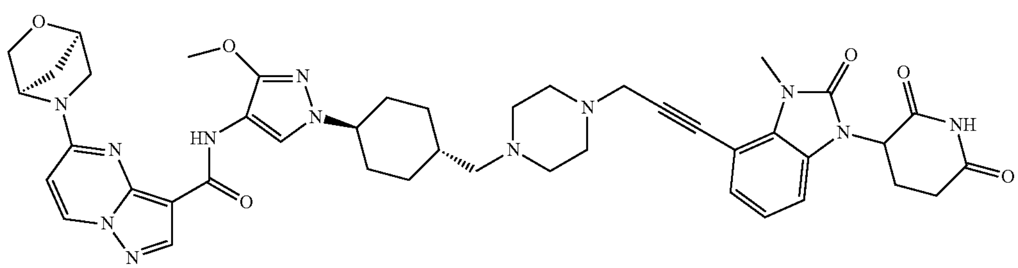 [SMILES: COc1nn([C@H]2CC[C@H](CN3CCN(CC#Cc4cccc5c4n(C)c(=O)n5C4CCC(=O)NC4=O)CC3)CC2)cc1NC(=O)c1cnn2ccc(N3C[C@H]4C[C@@H]3CO4)nc12] |
| I-122 | 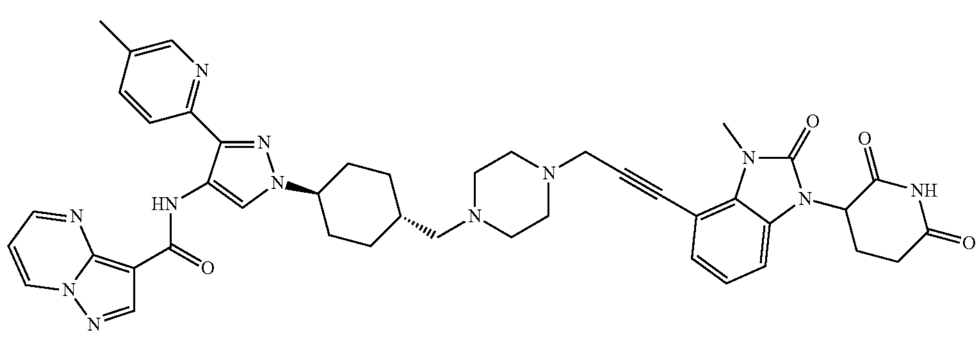 [SMILES: Cc1ccc(-c2nn([C@H]3CC[C@H](CN4CCN(CC#Cc5cccc6c5n(C)c(=O)n6C5CCC(=O)NC5=O)CC4)CC3)cc2NC(=O)c2cnn3cccnc23)nc1] |

TABLE 1-continued

Exemplary Compounds

| I-# | Structure |
|---|---|
| I-123 | 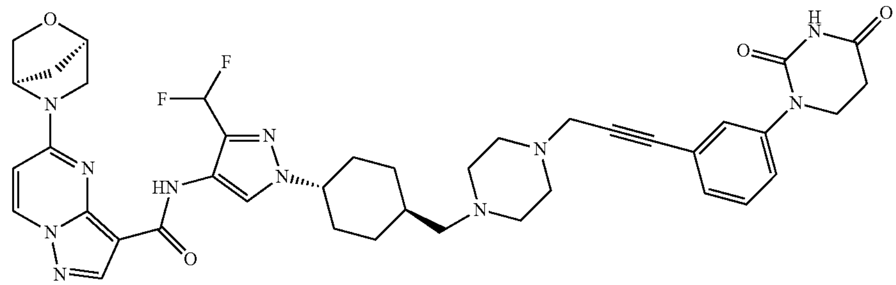 [SMILES: O=C1CCN(c2cccc(C#CCN3CCN(C[C@H]4CC[C@H](n5cc(NC(=O)c6cnn7ccc(N8C[C@H]9C[C@@H]8CO9)nc67)c(C(F)F)n5)CC4)CC3)c2)C(=O)N1] |
| I-124 | 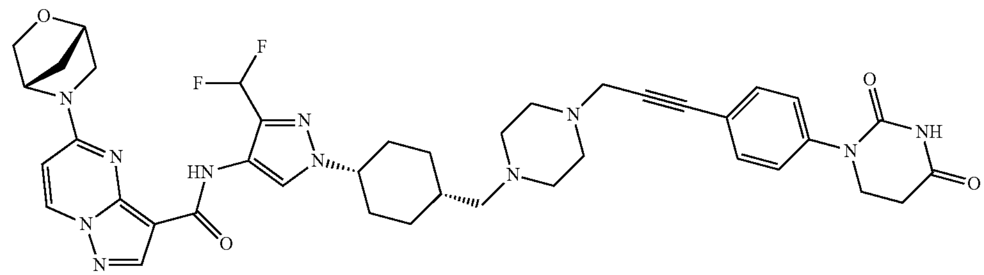 [SMILES: O=C1CCN(c2ccc(C#CCN3CCN(C[C@H]4CC[C@@H](n5cc(NC(=O)c6cnn7ccc(N8C[C@@H]9C[C@H]8CO9)nc67)c(C(F)F)n5)CC4)CC3)cc2)C(=O)N1] |
| I-125 | 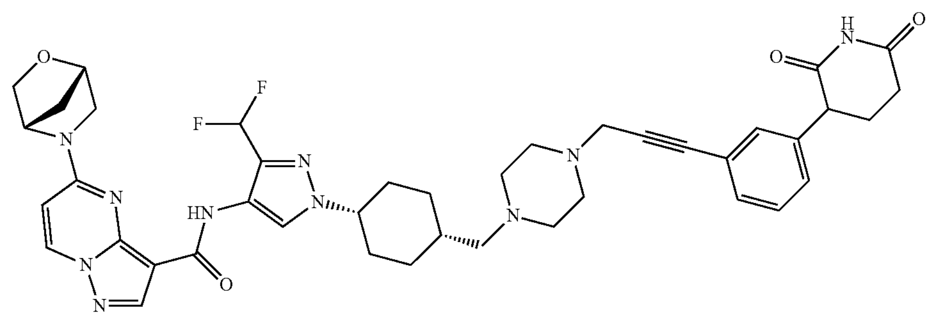 [SMILES: O=C1CCC(c2cccc(C#CCN3CCN(C[C@H]4CC[C@@H](n5cc(NC(=O)c6cnn7ccc(N8C[C@@H]9C[C@H]8CO9)nc67)c(C(F)F)n5)CC4)CC3)c2)C(=O)N1] |
| I-126 | 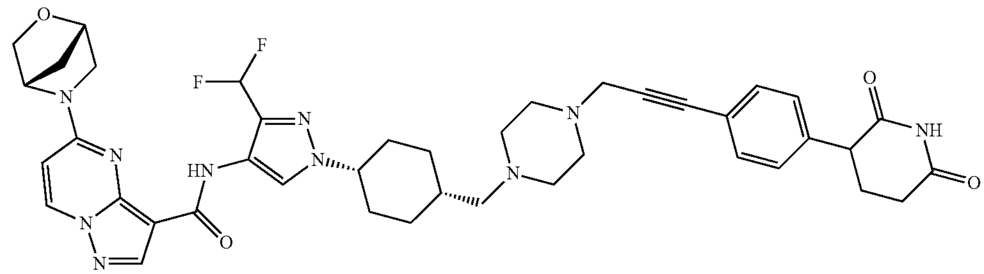 [SMILES: O=C1CCC(c2ccc(C#CCN3CCN(C[C@H]4CC[C@@H](n5cc(NC(=O)c6cnn7ccc(N8C[C@@H]9C[C@H]8CO9)nc67)c(C(F)F)n5)CC4)CC3)cc2)C(=O)N1] |

TABLE 1-continued
Exemplary Compounds
| I-# | Structure |
|---|---|
| I-127 | 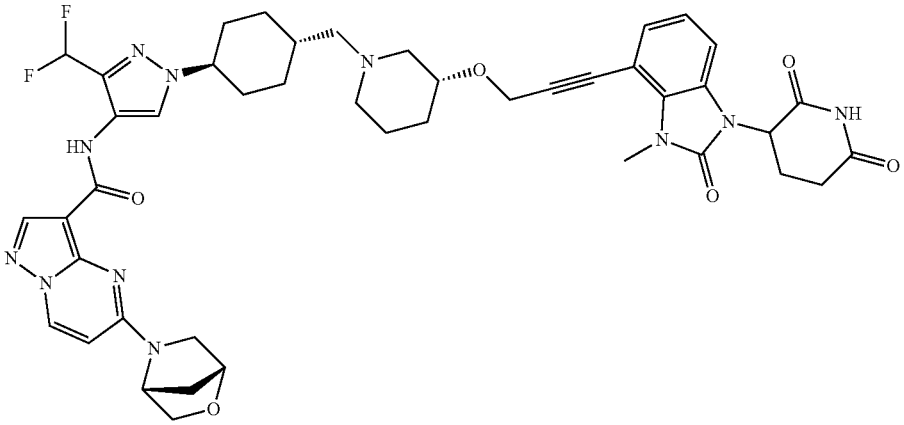 [SMILES: Cn1c(=O)n(C2CCC(=O)NC2=O)c2cccc(C#CCO[C@@H]3CCCN(C[C@H]4CC[C@H](n5cc(NC(=O)c6cnn7ccc(N8C[C@H]9C[C@@H]8CO9)nc67)c(C(F)F)n5)CC4)C3)c21] |
| I-128 | 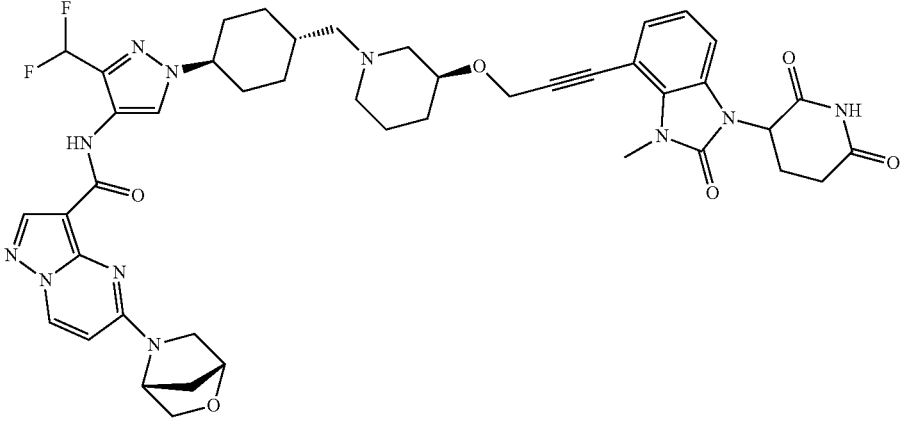 [SMILES: Cn1c(=O)n(C2CCC(=O)NC2=O)c2cccc(C#CCO[C@H]3CCCN(C[C@H]4CC[C@H](n5cc(NC(=O)c6cnn7ccc(N8C[C@H]9C[C@@H]8CO9)nc67)c(C(F)F)n5)CC4)C3)c21] |
| I-129 | 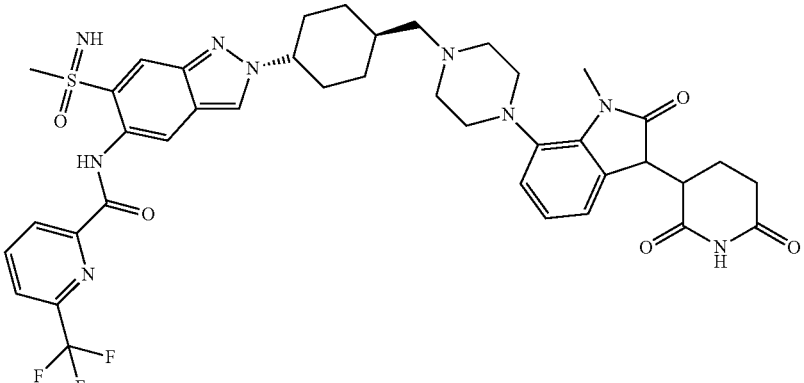 |

TABLE 1-continued
Exemplary Compounds
| I-# | Structure |
|---|---|
| I-130 | 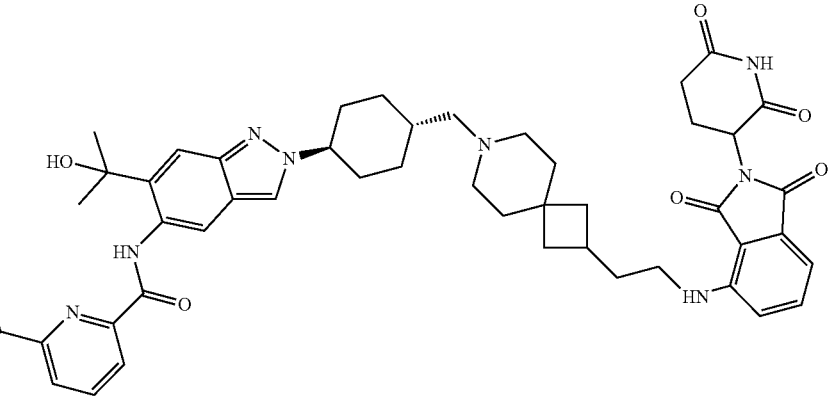 |
| I-131 | 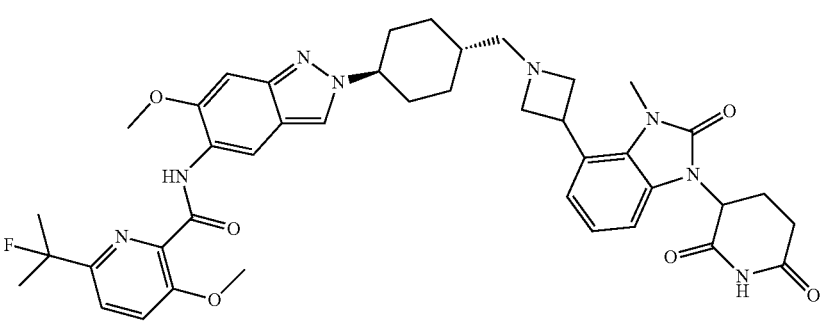 [SMILES: COc1cc2nn([C@H]3CC[C@H](CN4CC(c5cccc6c5n(C)c(=O)n6C5CCC(=O)NC5=O)C4)CC3)cc2cc1NC(=O)c1nc(C(C)(C)F)ccc1OC] |
| I-132 | 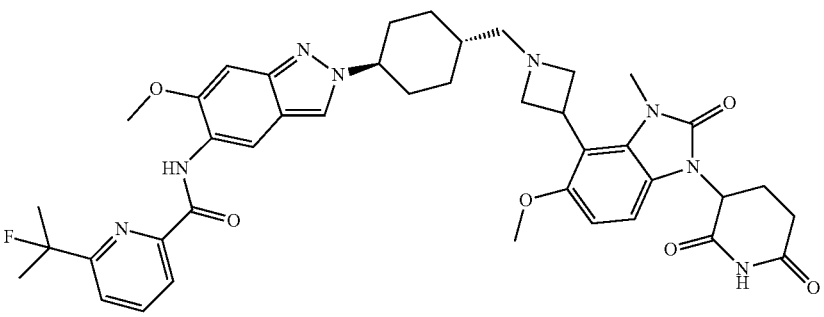 [SMILES: COc1cc2nn([C@H]3CC[C@H](CN4CC(c5c(OC)ccc6c5n(C)c(=O)n6C5CCC(=O)NC5=O)C4)CC3)cc2cc1NC(=O)c1cccc(C(C)(C)F)n1] |
| I-133 | 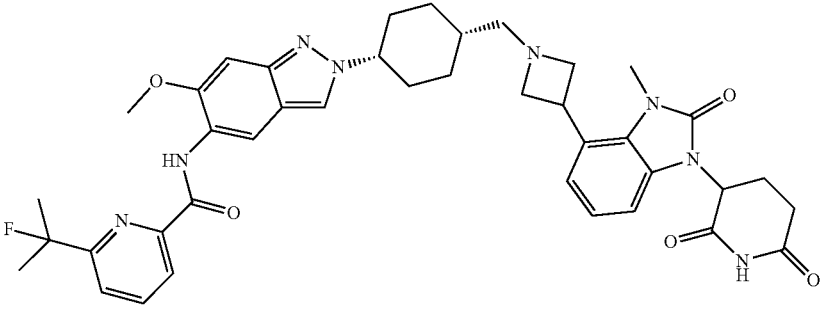 [SMILES: COc1cc2nn([C@H]3CC[C@@H](CN4CC(c5cccc6c5n(C)c(=O)n6C5CCC(=O)NC5=O)C4)CC3)cc2cc1NC(=O)c1cccc(C(C)(C)F)n1] |

TABLE 1-continued

Exemplary Compounds

| I-# | Structure |
|---|---|
| I-134 | 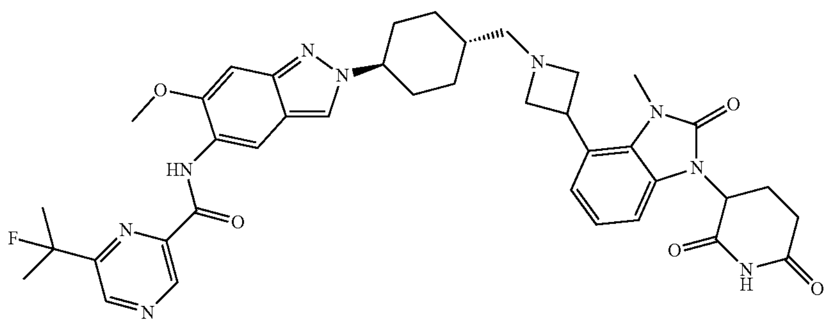 [SMILES: COc1cc2nn([C@H]3CC[C@H](CN4CC(c5cccc6c5n(C)c(=O)n6C5CCC(=O)NC5=O)C4)CC3)cc2cc1NC(=O)c1cncc(C(C)(C)F)n1] |
| I-135 | 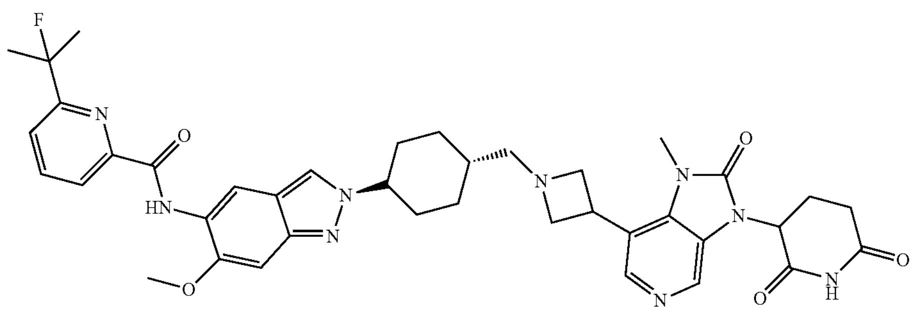 |
| I-136 | 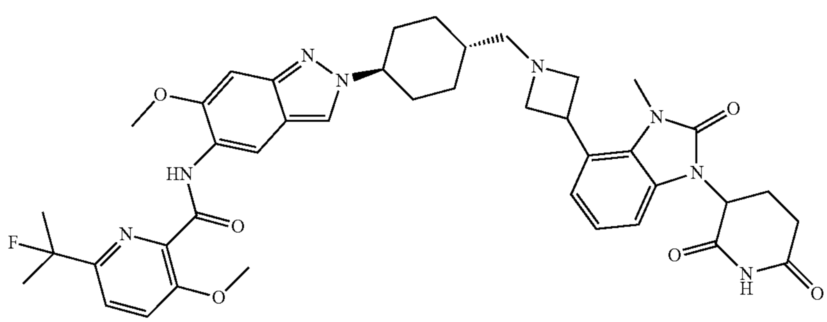 [SMILES: COc1cc2nn([C@H]3CC[C@H](CN4CC(c5cccc6c5n(C)c(=O)n6C5CCC(=O)NC5=O)C4)CC3)cc2cc1NC(=O)c1nc(C(C)(C)F)ccc1OC] |
| I-137 | 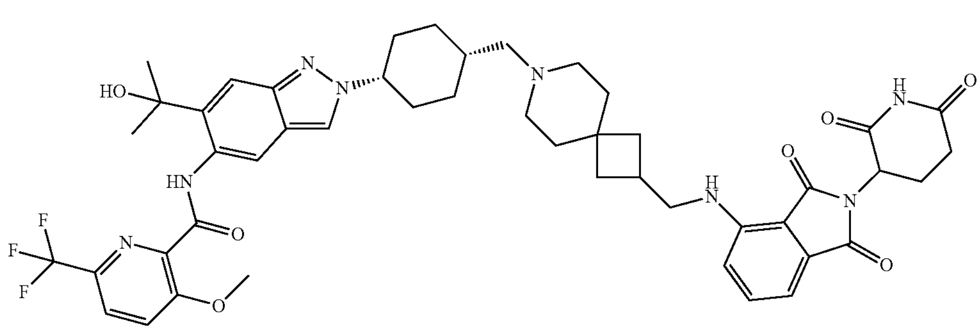 [SMILES: COc1ccc(C(F)(F)F)nc1C(=O)Nc1cc2cn([C@H]3CC[C@@H](CN4CCC5(CC4)CC(CNc4cccc6c4C(=O)N(C4CCC(=O)NC4=O)C6=O)C5)CC3)nc2cc1C(C)(C)O] |

TABLE 1-continued
Exemplary Compounds
| I-# | Structure |
|---|---|
| I-138 | 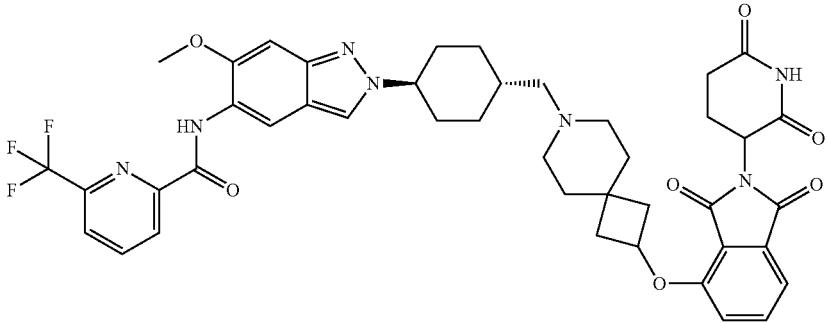 [SMILES: COc1cc2nn([C@H]3CC[C@H](CN4CCC5(CC4)CC(Oc4cccc6c4C(=O)N(C4CCC(=O)NC4=O)C6=O)C5)CC3)cc2cc1NC(=O)c1cccc(C(F)(F)F)n1] |
| I-139 | 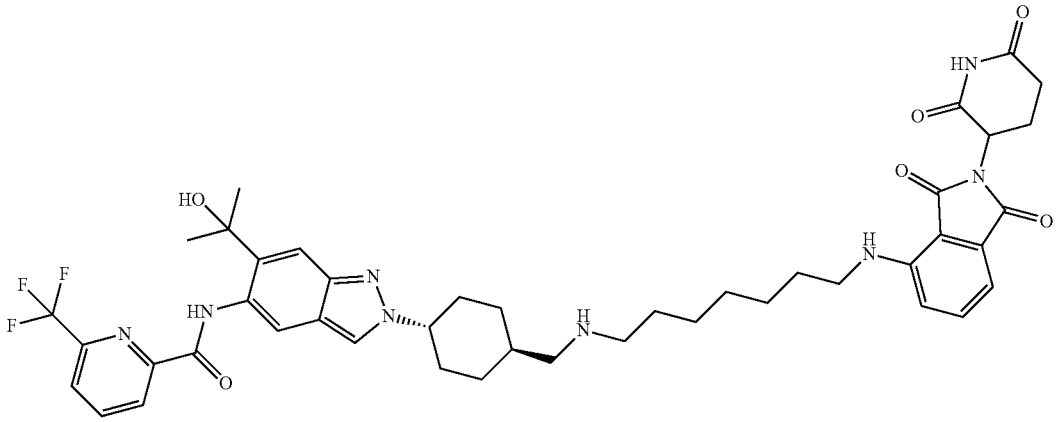 [SMILES: CC(C)(O)c1cc2nn([C@H]3CC[C@H](CNCCCCCCCNc4cccc5c4C(=O)N(C4CCC(=O)NC4=O)C5=O)CC3)cc2cc1NC(=O)c1cccc(C(F)(F)F)n1] |
| I-140 | 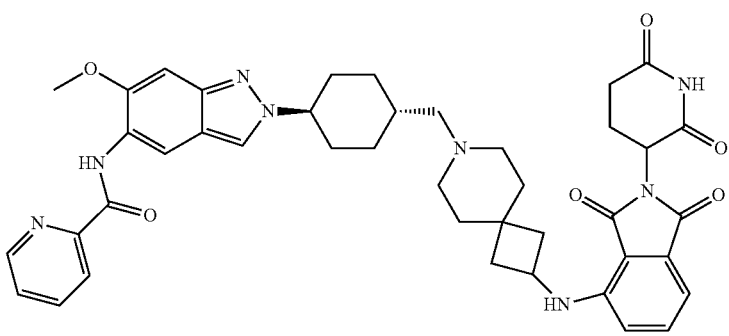 [SMILES: COc1cc2nn([C@H]3CC[C@H](CN4CCC5(CC4)CC(Nc4cccc6c4C(=O)N(C4CCC(=O)NC4=O)C6=O)C5)CC3)cc2cc1NC(=O)c1ccccn1] |
| I-141 | 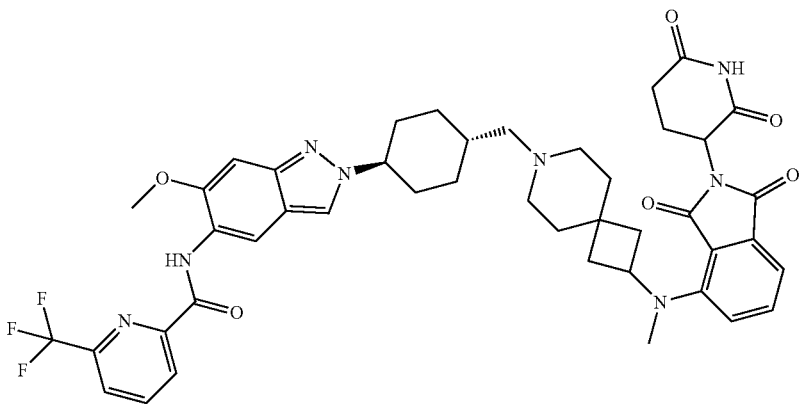 [SMILES: COc1cc2nn([C@H]3CC[C@H](CN4CCC5(CC4)CC(N(C)c4cccc6c4C(=O)N(C4CCC(=O)NC4=O)C6=O)C5)CC3)cc2cc1NC(=O)c1cccc(C(F)(F)F)n1] |

TABLE 1-continued

Exemplary Compounds

| I-# | Structure |
|---|---|
| I-142 | 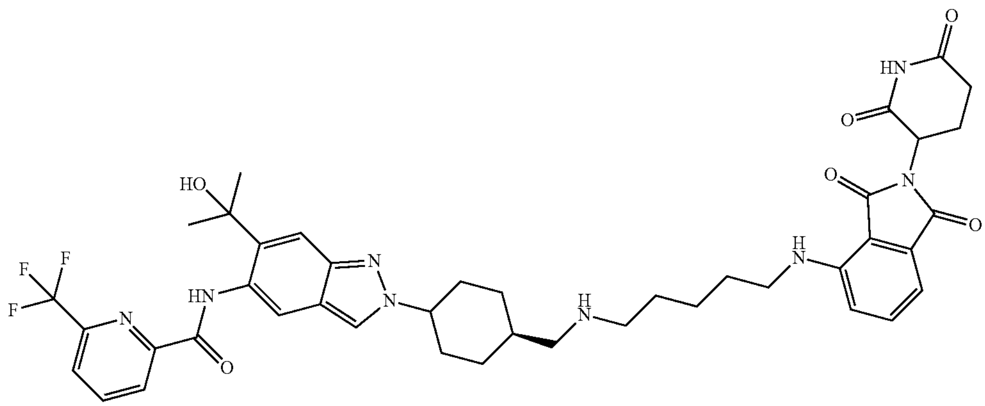 |
| I-143 | 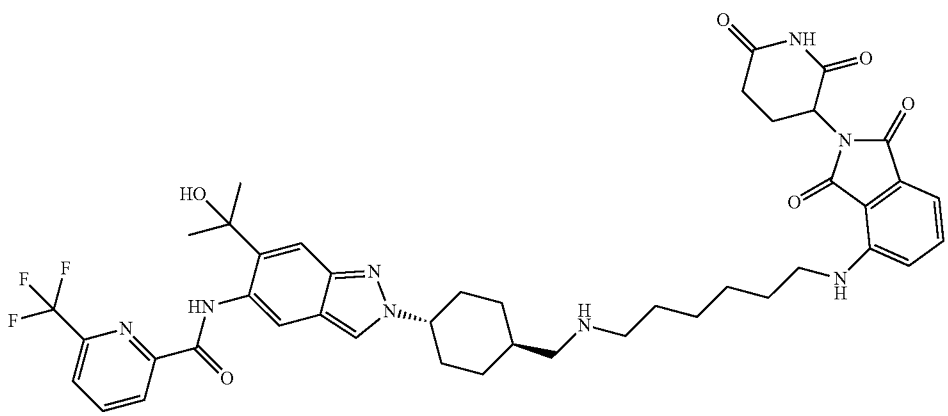 [SMILES: CC(C)(O)c1cc2nn([C@H]3CC[C@H](CNCCCCCCNc4cccc5c4C(=O)N(C4CCC(=O)NC4=O)C5=O)CC3)cc2cc1NC(=O)c1cccc(C(F)(F)F)n1] |
| I-144 | 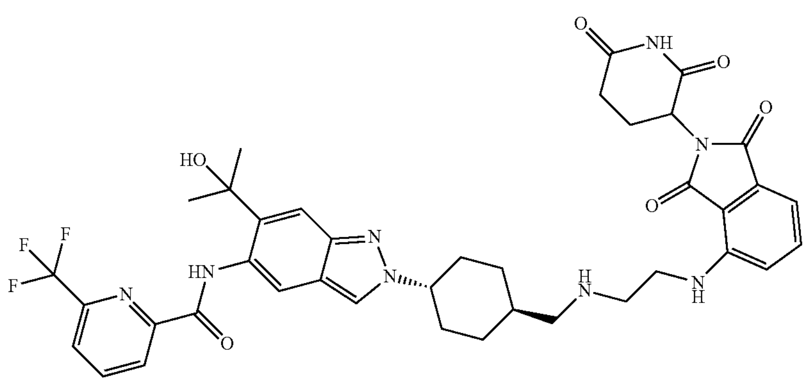 [SMILES: CC(C)(O)c1cc2nn([C@H]3CC[C@H](CNCCNc4cccc5c4C(=O)N(C4CCC(=O)NC4=O)C5=O)CC3)cc2cc1NC(=O)c1cccc(C(F)(F)F)n1] |
| I-145 | 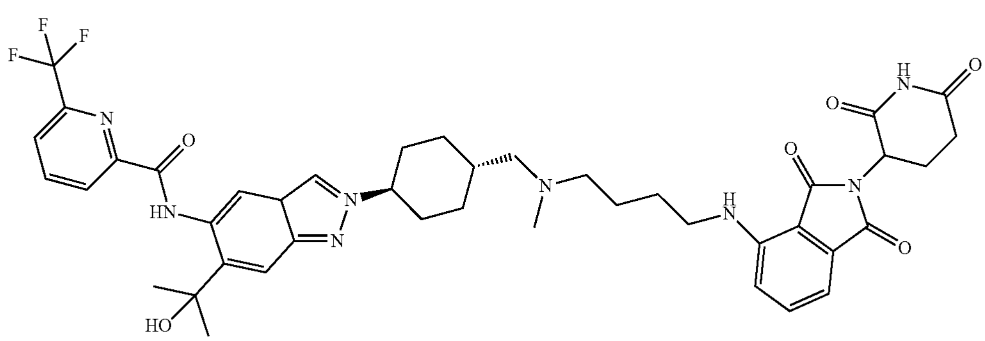 |

TABLE 1-continued

Exemplary Compounds

I-# Structure

I-146

I-147

I-148

I-149

TABLE 1-continued

Exemplary Compounds

| I-# | Structure |
|---|---|
| I-150 | 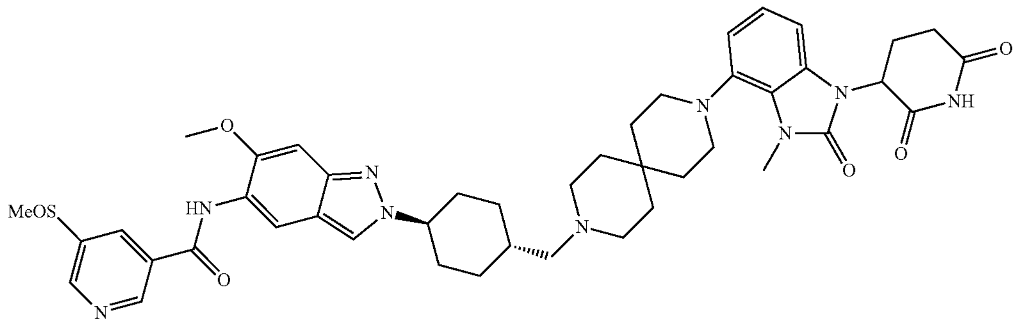 |
| I-151 | 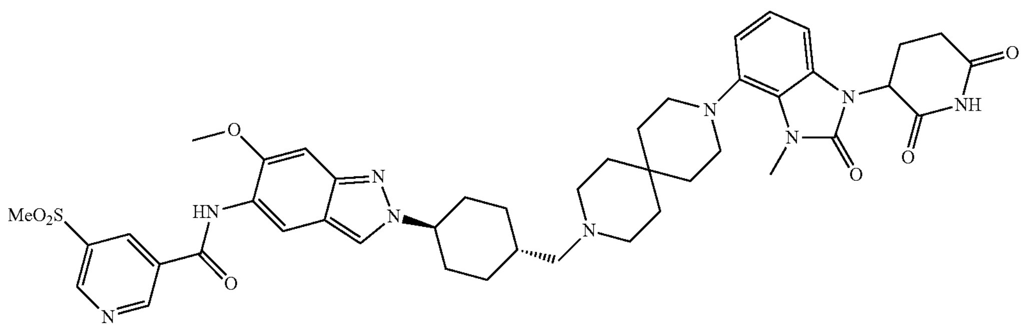 |
| I-152 | 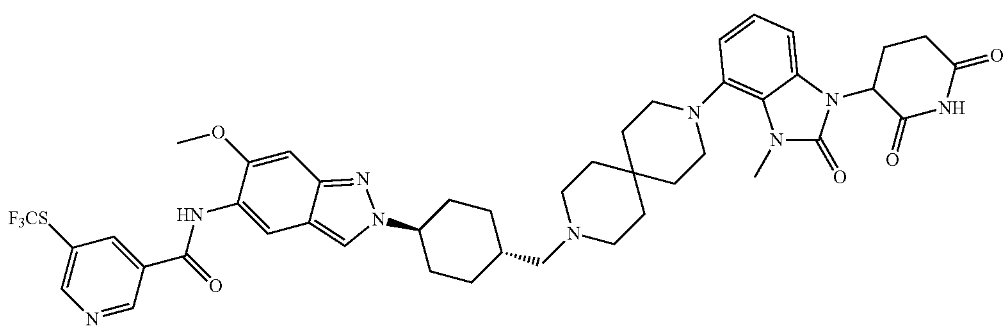 |
| I-153 | 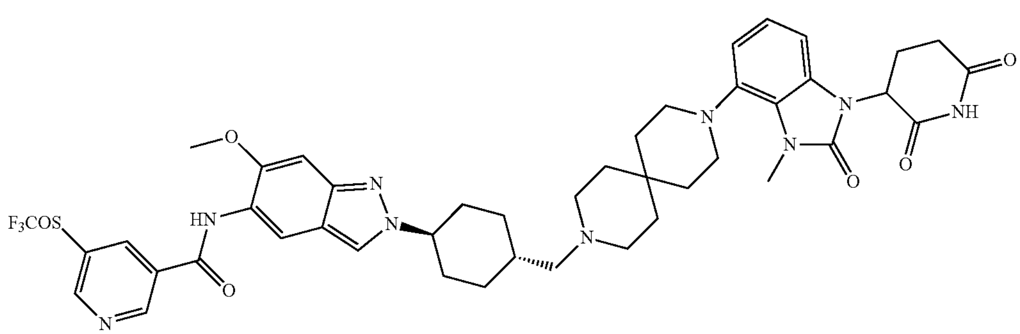 |

TABLE 1-continued

Exemplary Compounds

| I-# | Structure |
|---|---|
| I-154 | 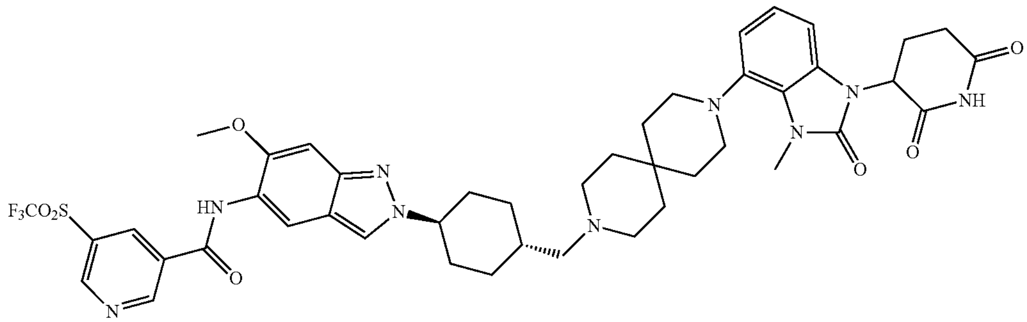 |
| I-155 | 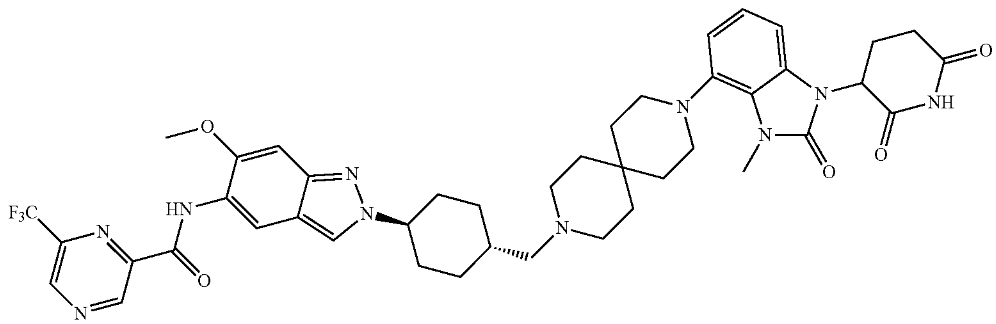 [SMILES: COc1cc2nn([C@H]3CC[C@H](CN4CCC5(CC4)CCN(c4cccc6c4n(C)c(=O)n6C4CCC(=O)NC4=O)CC5)CC3)cc2cc1NC(=O)c1cncc(C(F)(F)F)n1] |
| I-156 | 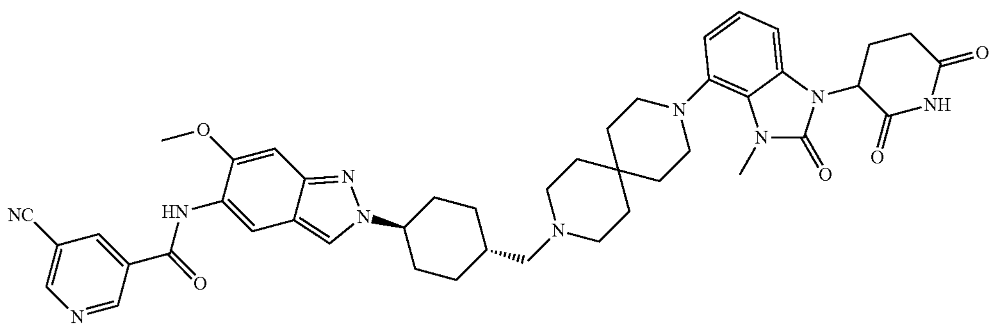 [SMILES: COc1cc2nn([C@H]3CC[C@H](CN4CCC5(CC4)CCN(c4cccc6c4n(C)c(=O)n6C4CCC(=O)NC4=O)CC5)CC3)cc2cc1NC(=O)c1cncc(C#N)c1] |
| I-157 | 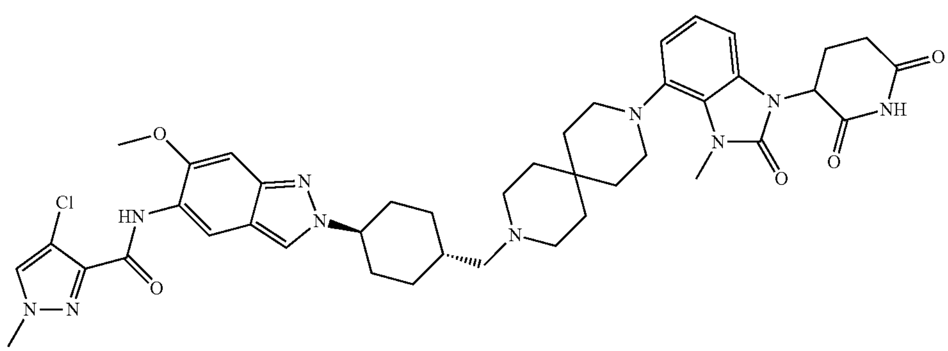 [SMILES: COc1cc2nn([C@H]3CC[C@H](CN4CCC5(CC4)CCN(c4cccc6c4n(C)c(=O)n6C4CCC(=O)NC4=O)CC5)CC3)cc2cc1NC(=O)c1nn(C)cc1Cl] |

TABLE 1-continued

Exemplary Compounds

| I-# | Structure |
|---|---|
| I-158 | 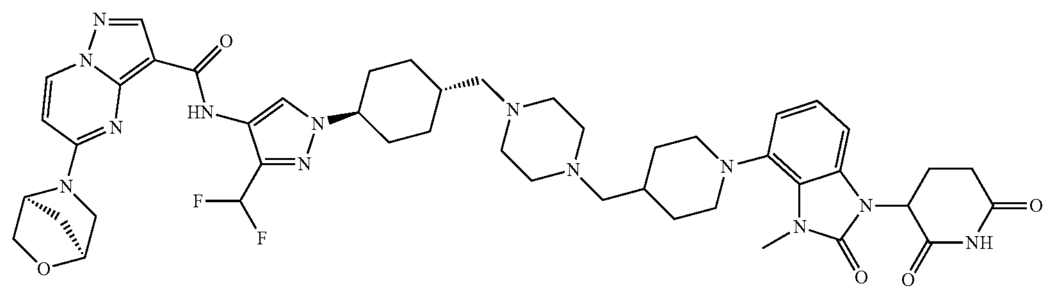 [SMILES: Cn1c(=O)n(C2CCC(=O)NC2=O)c2cccc(N3CCC(CN4CCN(C[C@H]5CC[C@H](n6cc(NC(=O)c7cnn8ccc(N9C[C@@H]%10C[C@H]9CO%10)nc78)c(C(F)F)n6)CC5)CC4)CC3)c21] |
| I-159 | 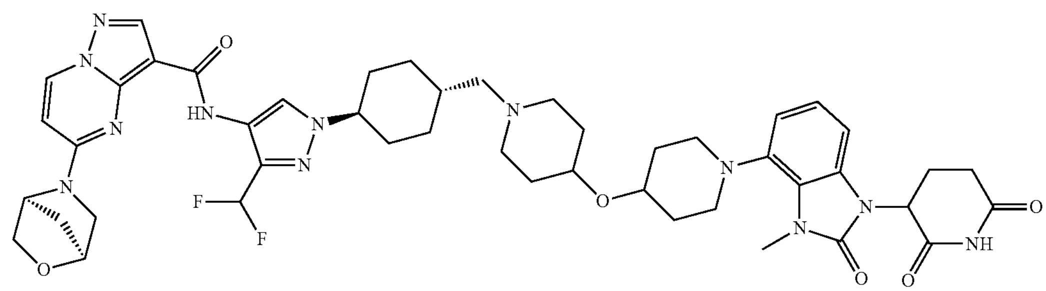 [SMILES: Cn1c(=O)n(C2CCC(=O)NC2=O)c2cccc(N3CCC(OC4CCN(C[C@H]5CC[C@H](n6cc(NC(=O)c7cnn8ccc(N9C[C@@H]%10C[C@H]9CO%10)nc78)c(C(F)F)n6)CC5)CC4)CC3)c21] |
| I-160 | 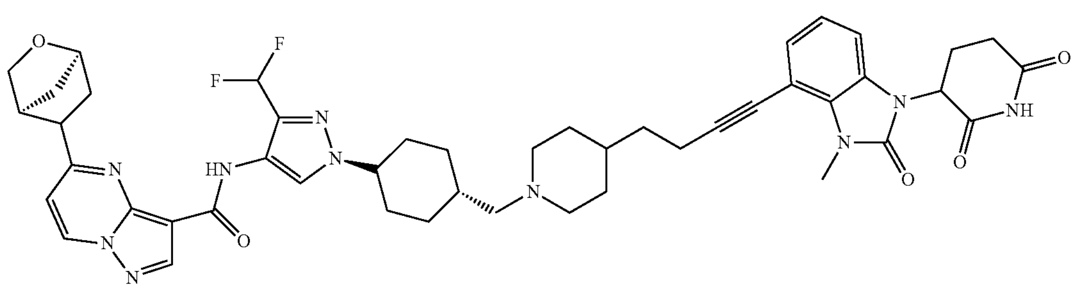 |
| I-161 | 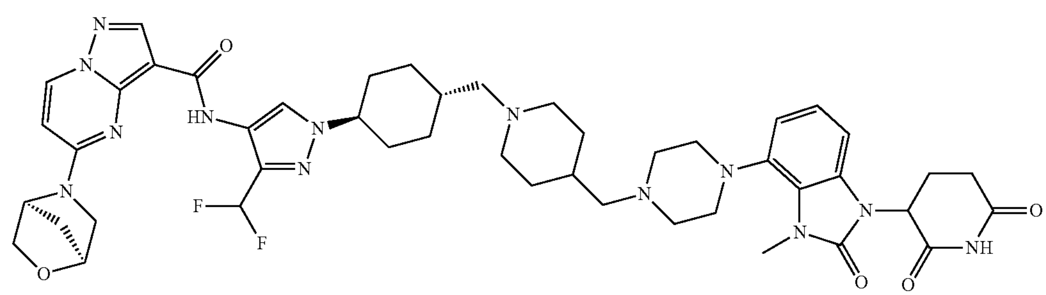 [SMILES: Cn1c(=O)n(C2CCC(=O)NC2=O)c2cccc(N3CCN(CC4CCN(C[C@H]5CC[C@H](n6cc(NC(=O)c7cnn8ccc(N9C[C@@H]%10C[C@H]9CO%10)nc78)c(C(F)F)n6)CC5)CC4)CC3)c21] |
| I-162 | 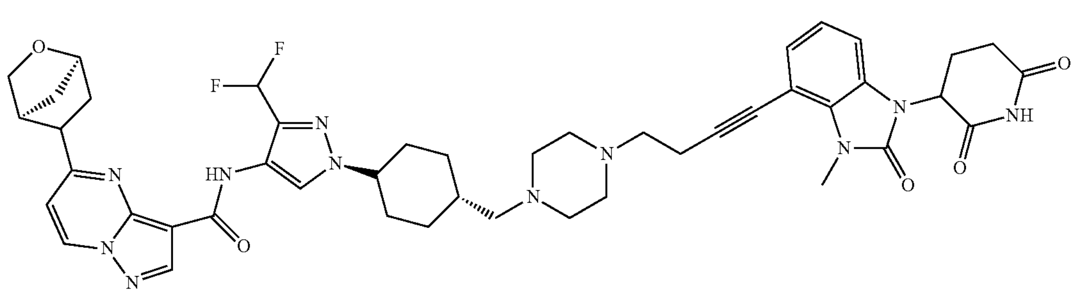 |

TABLE 1-continued

Exemplary Compounds

| I-# | Structure |
|---|---|
| I-163 | 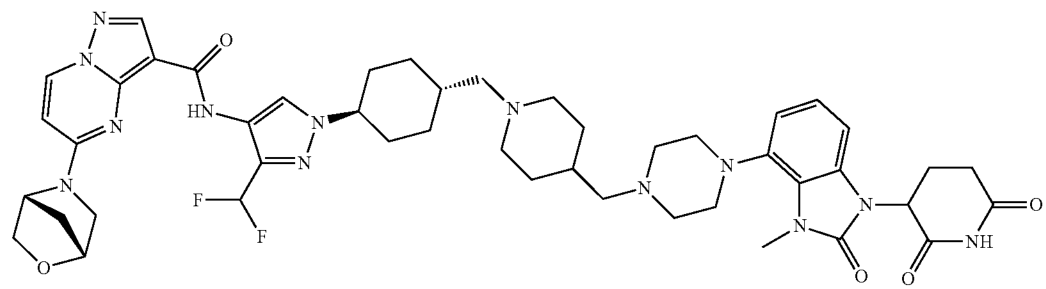 [SMILES: Cn1c(=O)n(C2CCC(=O)NC2=O)c2cccc(N3CCN(CC4CCN(C[C@H]5CC[C@H](n6cc(NC(=O)c7cnn8ccc(N9C[C@H]%10C[C@@H]9CO%10)nc78)c(C(F)F)n6)CC5)CC4)CC3)c21] |
| I-164 | 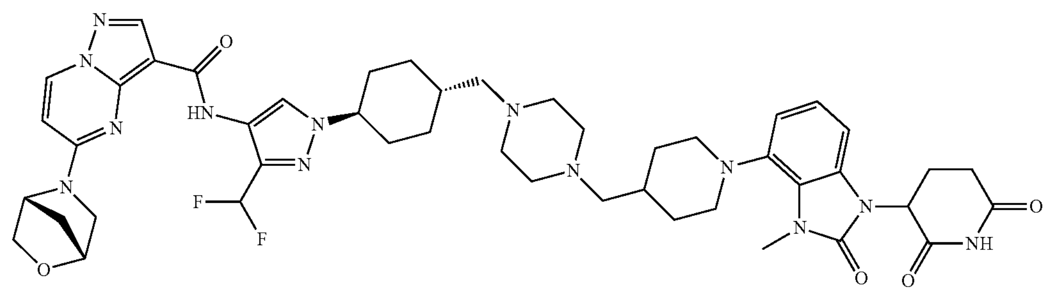 [SMILES: Cn1c(=O)n(C2CCC(=O)NC2=O)c2cccc(N3CCC(CN4CCN(C[C@H]5CC[C@H](n6cc(NC(=O)c7cnn8ccc(N9C[C@H]%10C[C@@H]9CO%10)nc78)c(C(F)F)n6)CC5)CC4)CC3)c21] |
| I-165 | 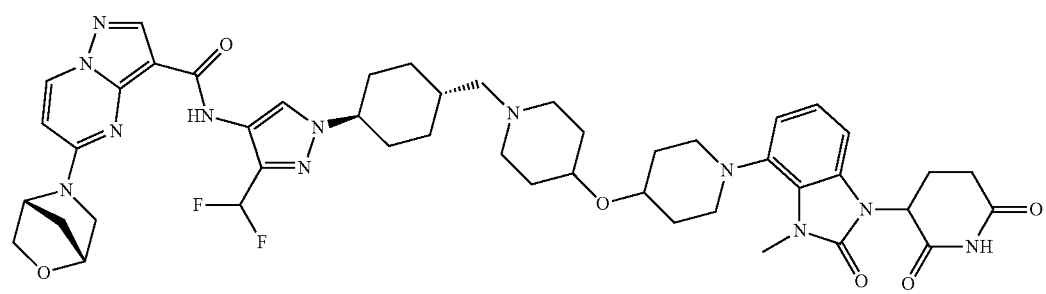 [SMILES: Cn1c(=O)n(C2CCC(=O)NC2=O)c2cccc(N3CCC(OC4CCN(C[C@H]5CC[C@H](n6cc(NC(=O)c7cnn8ccc(N9C[C@H]%10C[C@@H]9CO%10)nc78)c(C(F)F)n6)CC5)CC4)CC3)c21] |
| I-166 | 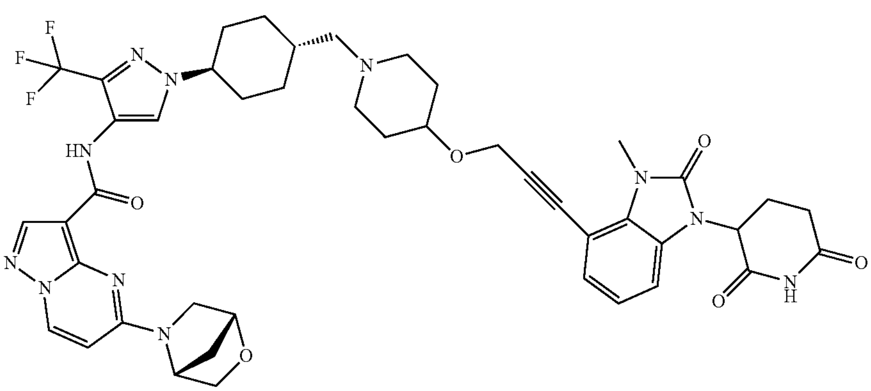 [SMILES: Cn1c(=O)n(C2CCC(=O)NC2=O)c2cccc(C#CCOC3CCN(C[C@H]4CC[C@H](n5cc(NC(=O)c6cnn7ccc(N8C[C@H]9C[C@@H]8CO9)nc67)c(C(F)(F)F)n5)CC4)CC3)c21] |

TABLE 1-continued

Exemplary Compounds

| I-# | Structure |
|---|---|
| I-167 | 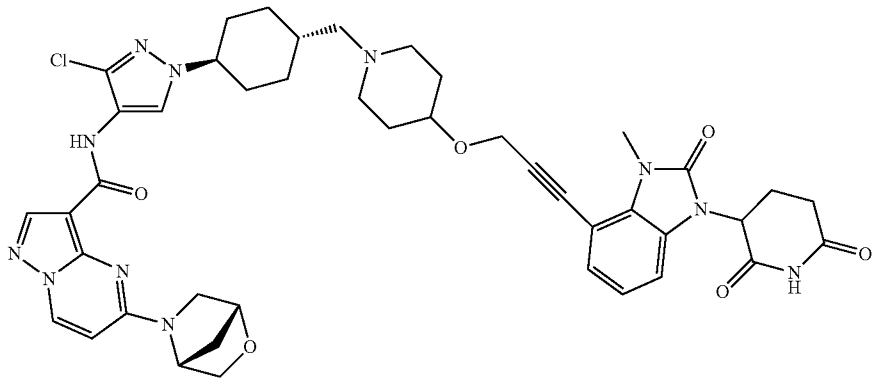 [SMILES: Cn1c(=O)n(C2CCC(=O)NC2=O)c2cccc(C#CCOC3CCN(C[C@H]4CC[C@H](n5cc(NC(=O)c6cnn7ccc(N8C[C@H]9C[C@@H]8CO9)nc67)c(Cl)n5)CC4)CC3)c21] |
| I-168 | 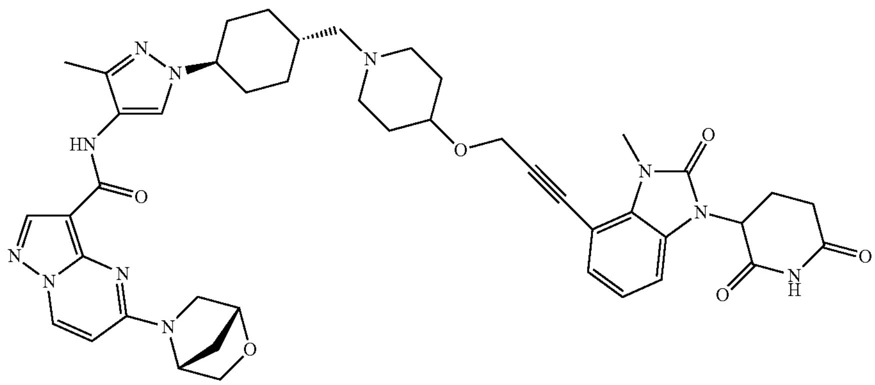 [SMILES: Cc1nn([C@H]2CC[C@H](CN3CCC(OCC#Cc4cccc5c4n(C)c(=O)n5C4CCC(=O)NC4=O)CC3)CC2)cc1NC(=O)c1cnn2ccc(N3C[C@H]4C[C@@H]3CO4)nc12] |
| I-169 | 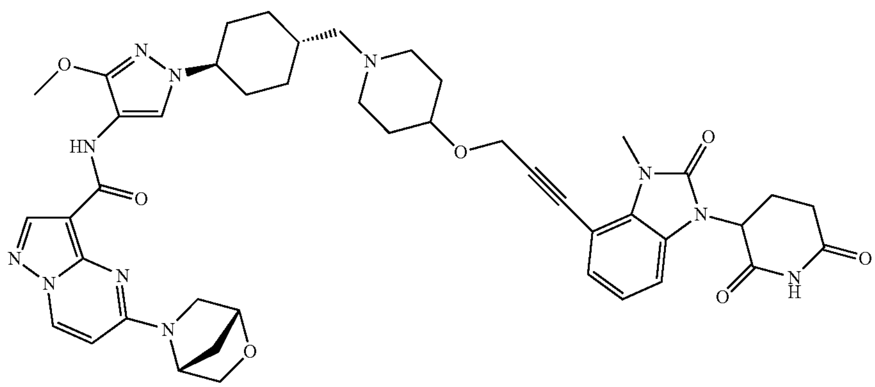 [SMILES: COc1nn([C@H]2CC[C@H](CN3CCC(OCC#Cc4cccc5c4n(C)c(=O)n5C4CCC(=O)NC4=O)CC3)CC2)cc1NC(=O)c1cnn2ccc(N3C[C@H]4C[C@@H]3CO4)nc12] |
| I-170 | 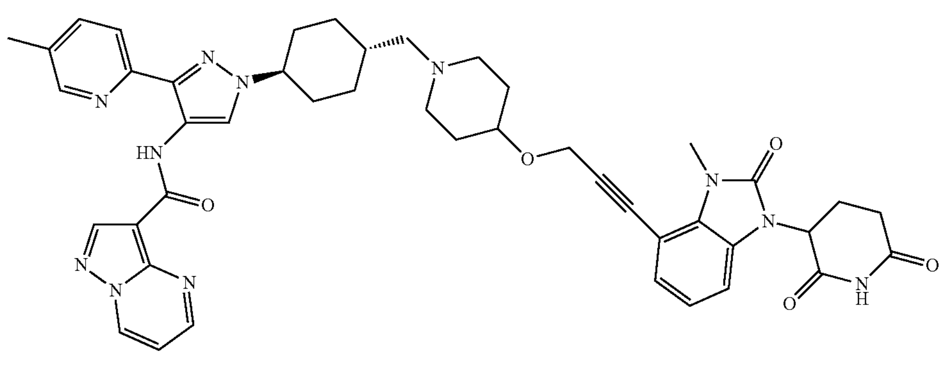 [SMILES: Cc1ccc(-c2nn([C@H]3CC[C@H](CN4CCC(OCC#Cc5cccc6c5n(C)c(=O)n6C5CCC(=O)NC5=O)CC4)CC3)cc2NC(=O)c2cnn3cccnc23)nc1] |

TABLE 1-continued

Exemplary Compounds

| I-# | Structure |
| --- | --- |
| I-171 | 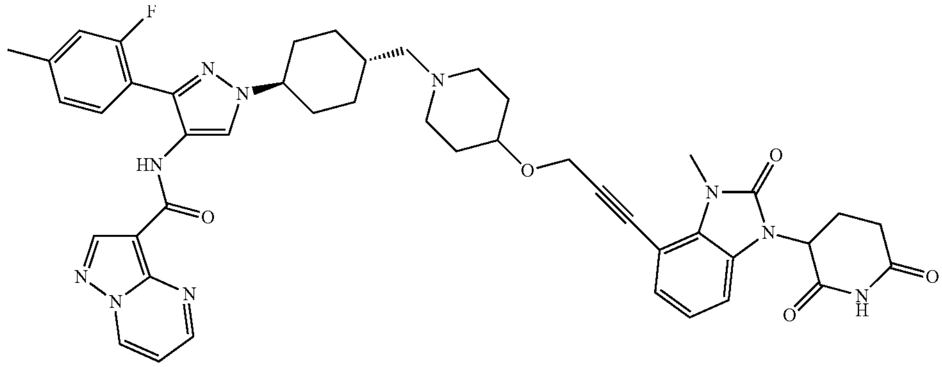 [SMILES: Cc1ccc(-c2nn([C@H]3CC[C@H](CN4CCC(OCC#Cc5cccc6c5n(C)c(=O)n6C5CCC(=O)NC5=O)CC4)CC3)cc2NC(=O)c2cnn3cccnc23)c(F)c1] |
| I-172 | 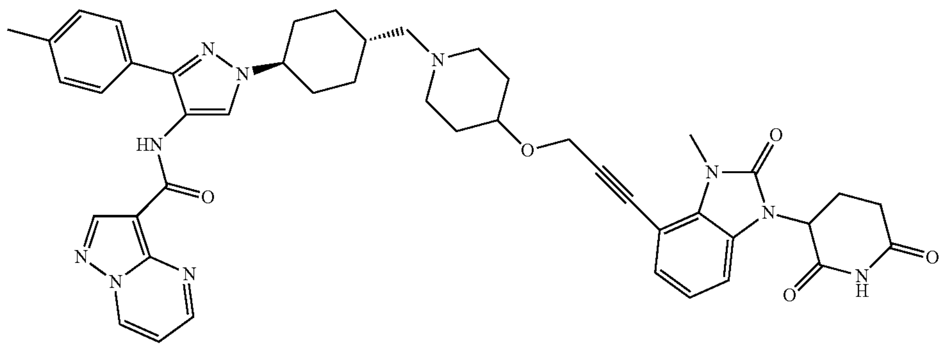 [SMILES: Cc1ccc(-c2nn([C@H]3CC[C@H](CN4CCC(OCC#Cc5cccc6c5n(C)c(=O)n6C5CCC(=O)NC5=O)CC4)CC3)cc2NC(=O)c2cnn3cccnc23)cc1] |
| I-173 | 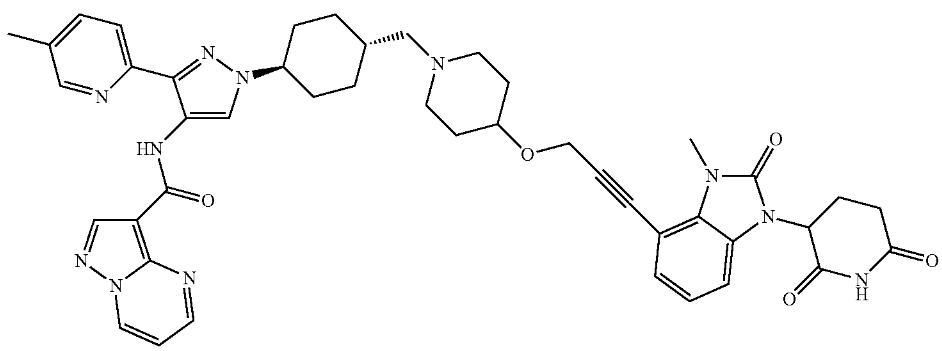 [SMILES: Cc1ccc(-c2nn([C@H]3CC[C@H](CN4CCC(OCC#Cc5cccc6c5n(C)c(=O)n6C5CCC(=O)NC5=O)CC4)CC3)cc2NC(=O)c2cnn3cccnc23)nc1] |
| I-174 | 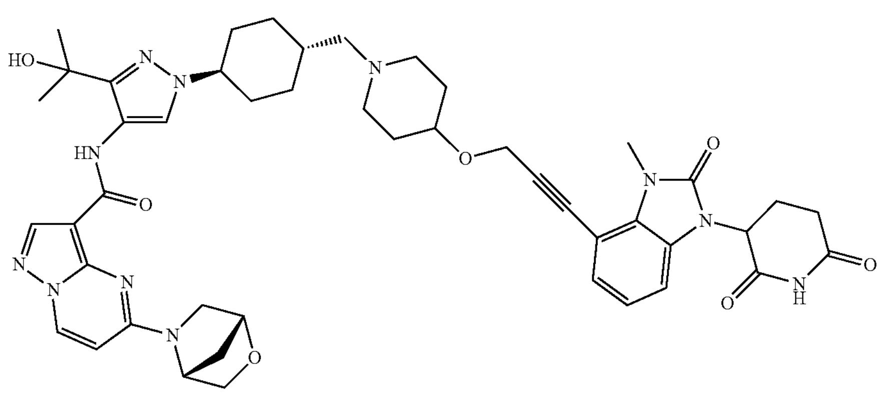 [SMILES: Cn1c(=O)n(C2CCC(=O)NC2=O)c2cccc(C#CCOC3CCN(C[C@H]4CC[C@H](n5cc(NC(=O)c6cnn7ccc(N8C[C@H]9C[C@@H]8CO9)nc67)c(C(C)(C)O)n5)CC4)CC3)c21] |

TABLE 1-continued

Exemplary Compounds

| I-# | Structure |
|---|---|
| I-175 | 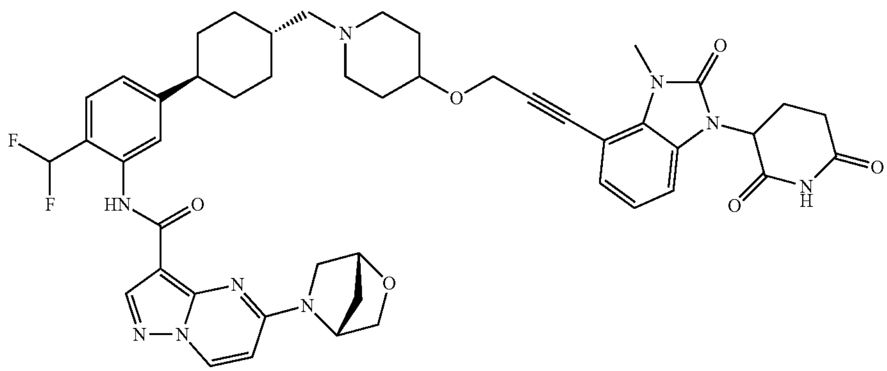 [SMILES: Cn1c(=O)n(C2CCC(=O)NC2=O)c2cccc(C#CCOC3CCN(C[C@H]4CC[C@H](c5ccc(C(F)F)c(NC(=O)c6cnn7ccc(N8C[C@H]9C[C@@H]8CO9)nc67)c5)CC4)CC3)c21] |
| I-176 | 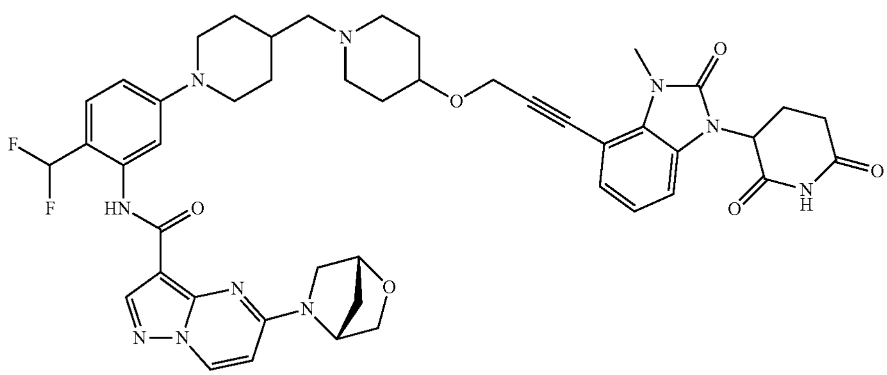 [SMILES: Cn1c(=O)n(C2CCC(=O)NC2=O)c2cccc(C#CCOC3CCN(CC4CCN(c5ccc(C(F)F)c(NC(=O)c6cnn7ccc(N8C[C@H]9C[C@@H]8CO9)nc67)c5)CC4)CC3)c21] |
| I-177 | 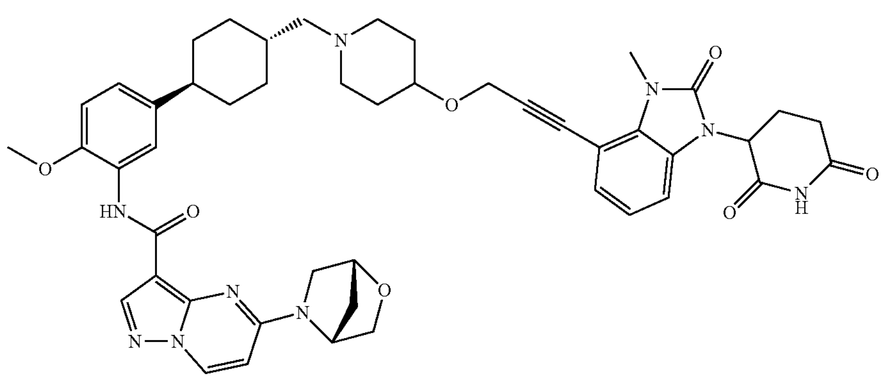 [SMILES: COc1ccc([C@H]2CC[C@H](CN3CCC(OCC#Cc4cccc5c4n(C)c(=O)n5C4CCC(=O)NC4=O)CC3)CC2)cc1NC(=O)c1cnn2ccc(N3C[C@H]4C[C@@H]3CO4)nc12] |
| I-178 | 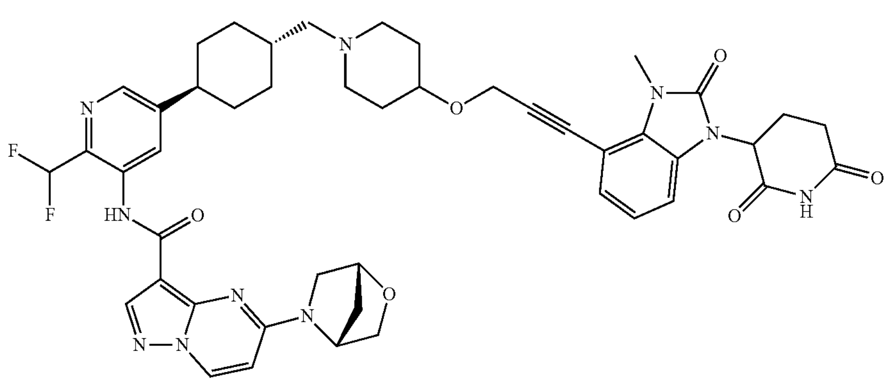 [SMILES: Cn1c(=O)n(C2CCC(=O)NC2=O)c2cccc(C#CCOC3CCN(C[C@H]4CC[C@H](c5cnc(C(F)F)c(NC(=O)c6cnn7ccc(N8C[C@H]9C[C@@H]8CO9)nc67)c5)CC4)CC3)c21] |

TABLE 1-continued

Exemplary Compounds

| I-# | Structure |
| --- | --- |
| I-179 | 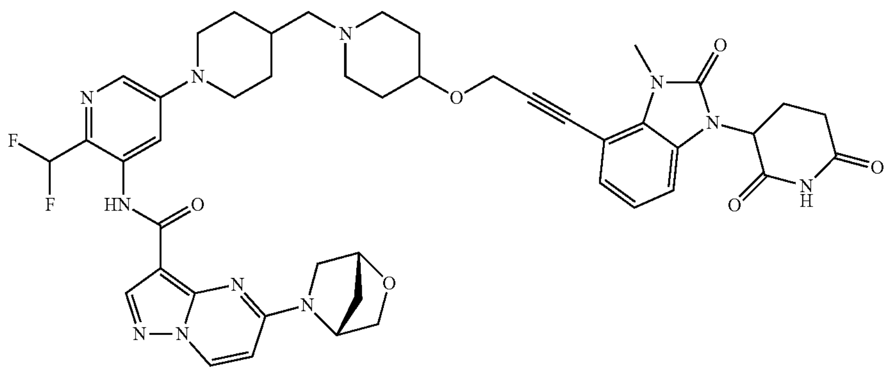 [SMILES: Cn1c(=O)n(C2CCC(=O)NC2=O)c2cccc(C#CCOC3CCN(CC4CCN(c5cnc(C(F)F)c(NC(=O)c6cnn7ccc(N8C[C@H]9C[C@@H]8CO9)nc67)c5)CC4)CC3)c21] |
| I-180 | 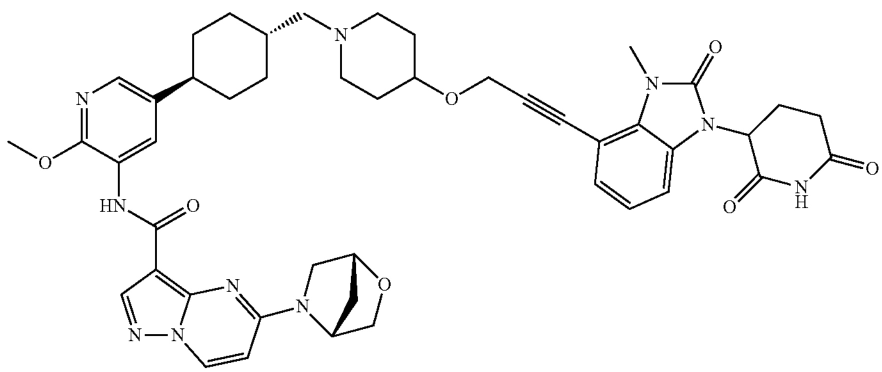 [SMILES: COc1ncc([C@H]2CC[C@H](CN3CCC(OCC#Cc4cccc5c4n(C)c(=O)n5C4CCC(=O)NC4=O)CC3)CC2)cc1NC(=O)c1cnn2ccc(N3C[C@H]4C[C@@H]3CO4)nc12] |
| I-181 | 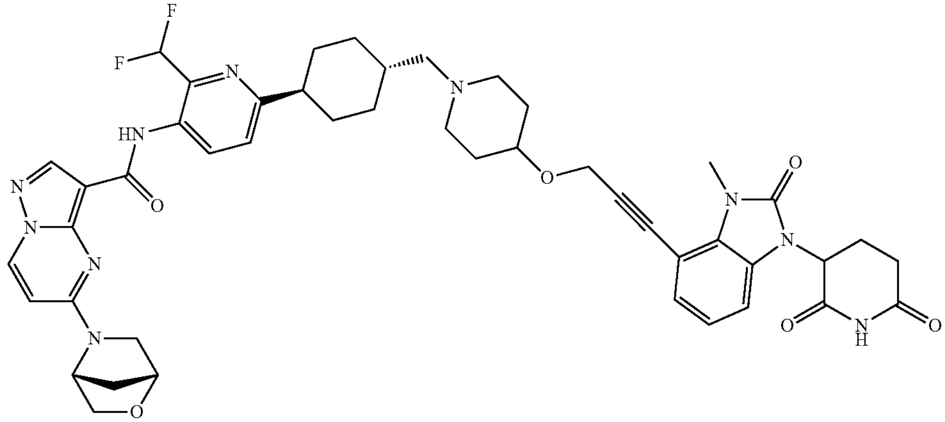 [SMILES: Cn1c(=O)n(C2CCC(=O)NC2=O)c2cccc(C#CCOC3CCN(C[C@H]4CC[C@H](c5ccc(NC(=O)c6cnn7ccc(N8C[C@H]9C[C@@H]8CO9)nc67)c(C(F)F)n5)CC4)CC3)c21] |

TABLE 1-continued

Exemplary Compounds

| I-# | Structure |
|---|---|
| I-182 | 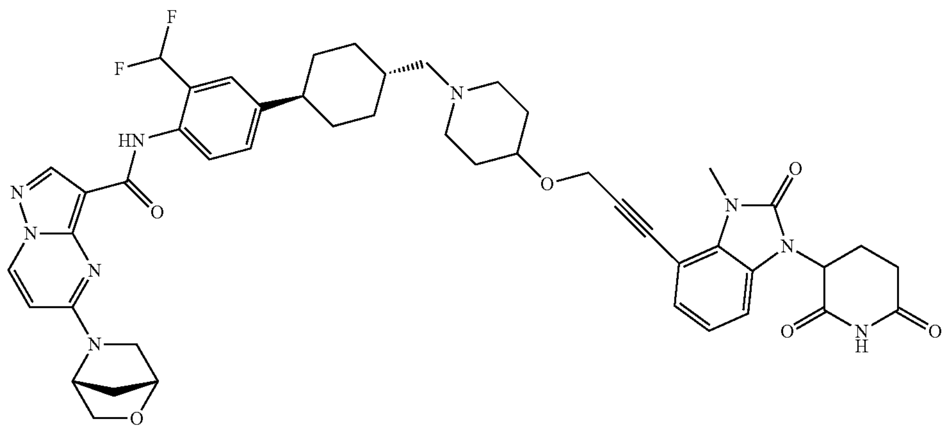 [SMILES: Cn1c(=O)n(C2CCC(=O)NC2=O)c2cccc(C#CCOC3CCN(C[C@H]4CC[C@H](c5ccc(NC(=O)c6cnn7ccc(N8C[C@H]9C[C@@H]8CO9)nc67)c(C(F)F)c5)CC4)CC3)c21] |
| I-183 | 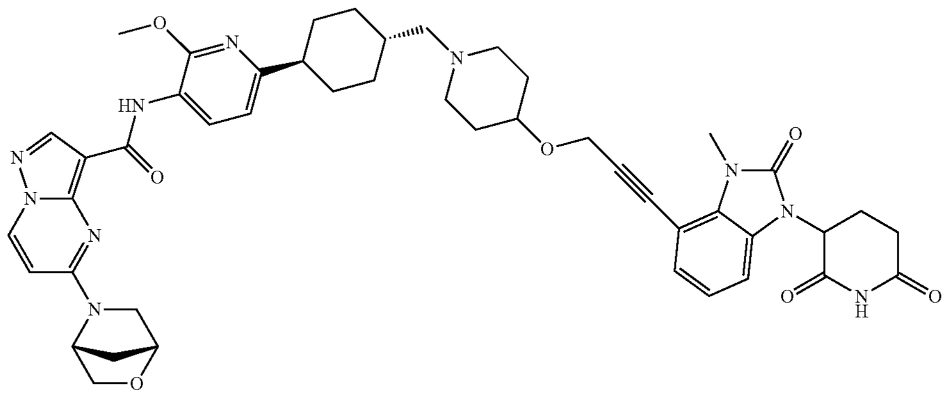 [SMILES: COc1nc([C@H]2CC[C@H](CN3CCC(OCC#Cc4cccc5c4n(C)c(=O)n5C4CCC(=O)NC4=O)CC3)CC2)ccc1NC(=O)c1cnn2ccc(N3C[C@H]4C[C@@H]3CO4)nc12] |
| I-184 | 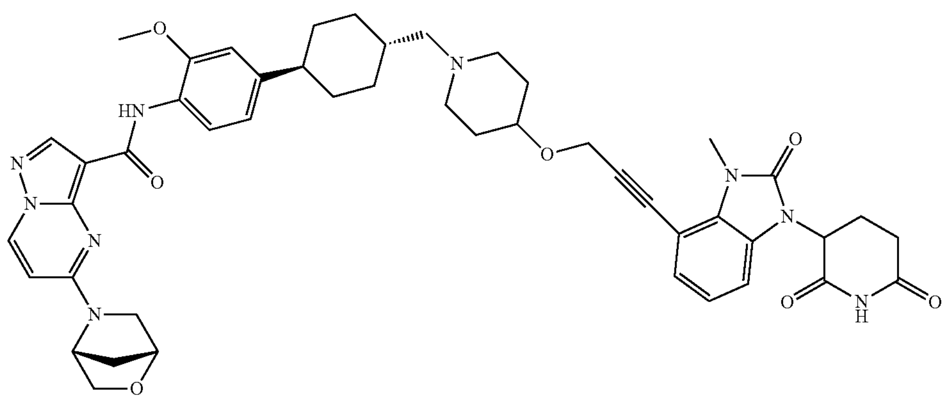 [SMILES: COc1cc([C@H]2CC[C@H](CN3CCC(OCC#Cc4cccc5c4n(C)c(=O)n5C4CCC(=O)NC4=O)CC3)CC2)ccc1NC(=O)c1cnn2ccc(N3C[C@H]4C[C@@H]3CO4)nc12] |
| I-185 | 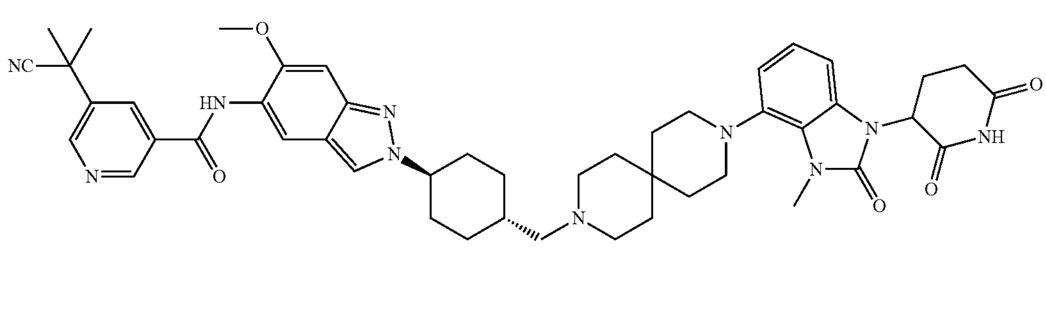 [SMILES: COc1cc2nn([C@H]3CC[C@H](CN4CCC5(CC4)CCN(c4cccc6c4n(C)c(=O)n6C4CCC(=O)NC4=O)CC5)CC3)cc2cc1NC(=O)c1cncc(C(C)(C)C#N)c1] |

TABLE 1-continued

Exemplary Compounds

| I-# | Structure |
|---|---|
| I-186 | 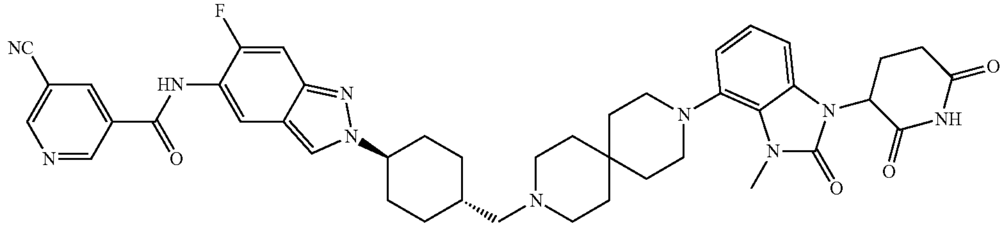 [SMILES: Cn1c(=O)n(C2CCC(=O)NC2=O)c2cccc(N3CCC4(CCN(C[C@H]5CC[C@H](n6cc7cc(NC(=O)c8cncc(C#N)c8)c(F)cc7n6)CC5)CC4)CC3)c21] |
| I-187 | 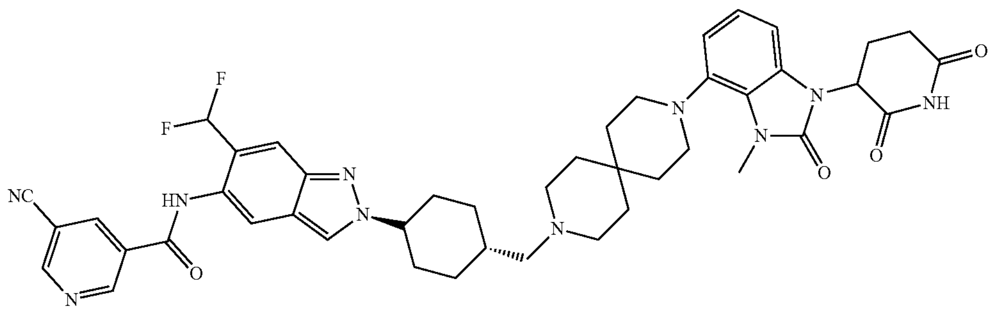 |
| I-188 | 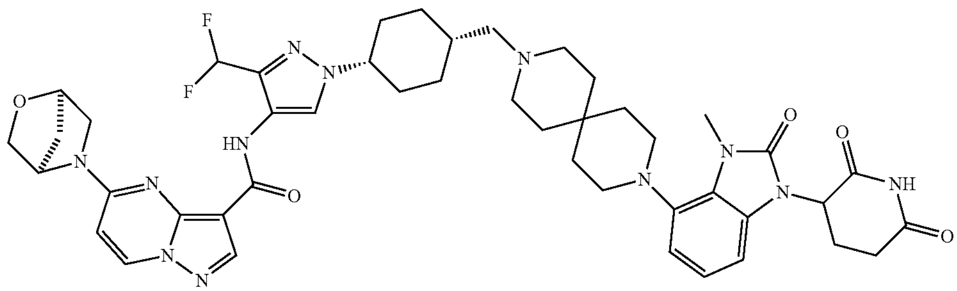 |
| I-189 | 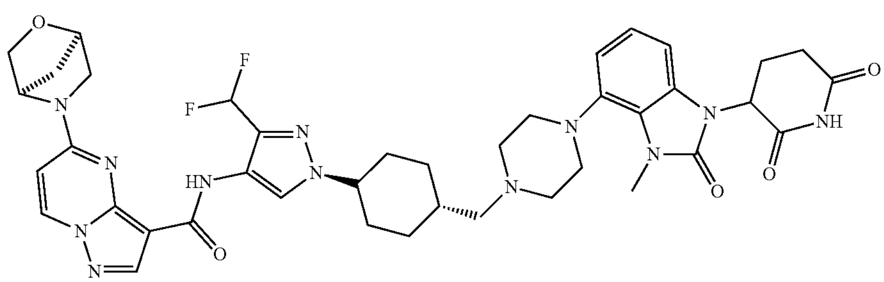 |
| I-190 | 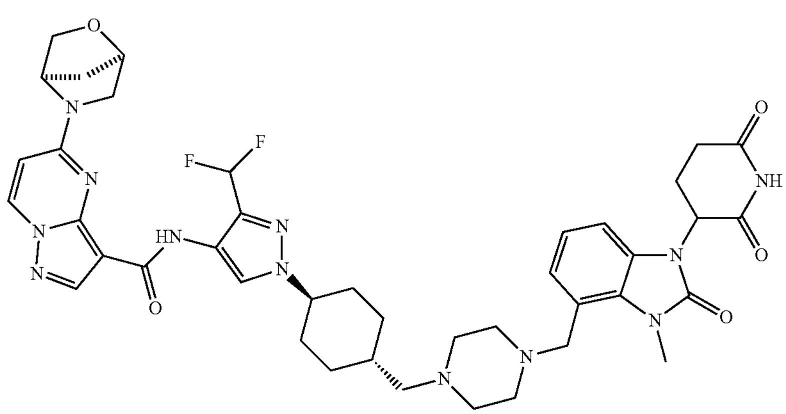 |

TABLE 1-continued
Exemplary Compounds
| I-# | Structure |
|---|---|
| I-191 | 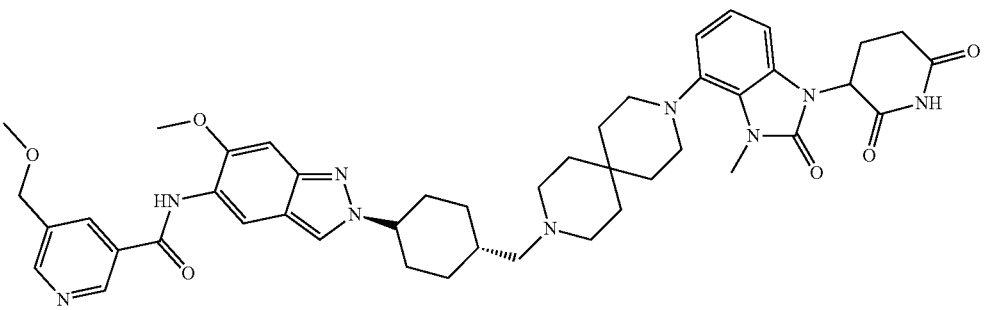 |
| I-192 | 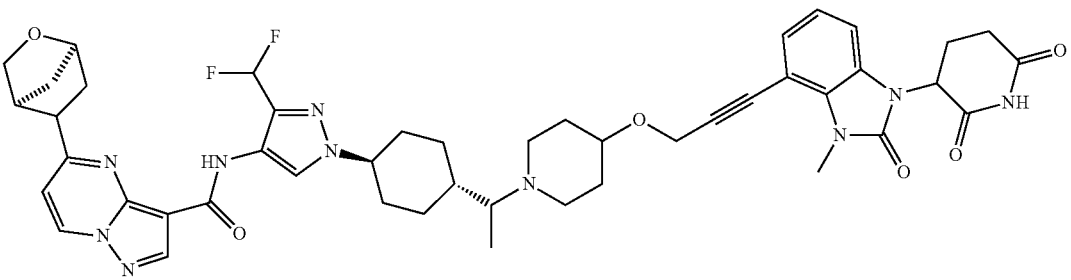 |
| I-193 | 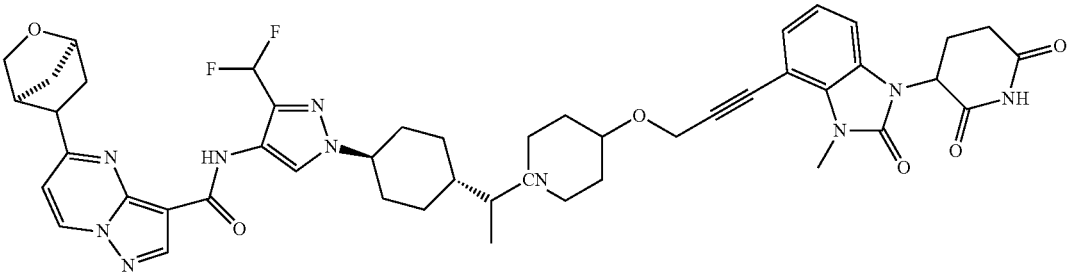 |
| I-194 | 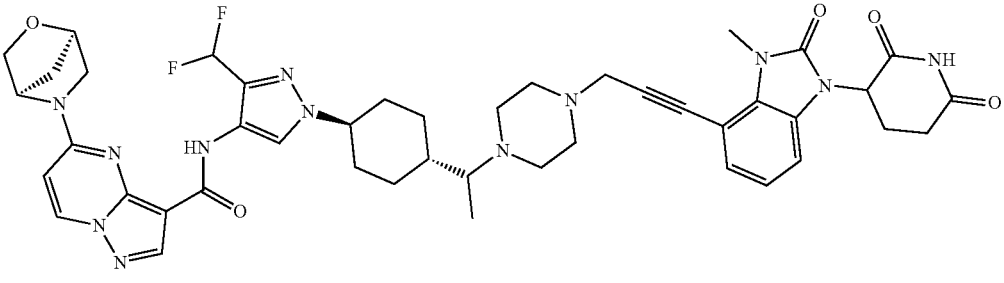 [SMILES: CC([C@H]1CC[C@H](n2cc(NC(=O)c3cnn4ccc(N5C[C@H]6C[C@@H]5CO6)nc34)c(C(F)F)n2)CC1)N1CCN(CC#Cc2cccc3c2n(C)c(=O)n3C2CCC(=O)NC2=O)CC1] |
| I-195 | 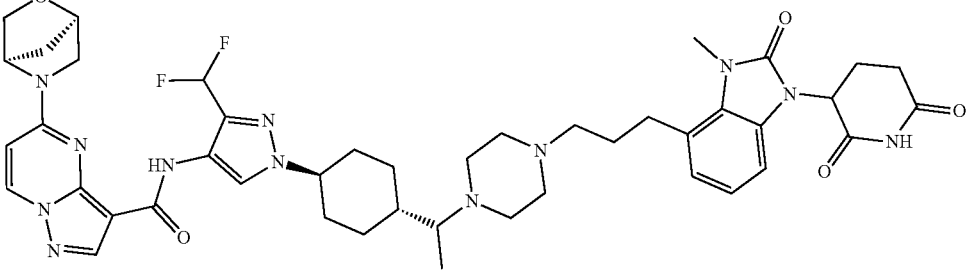 |

TABLE 1-continued

Exemplary Compounds

| I-# | Structure |
|---|---|
| I-196 | 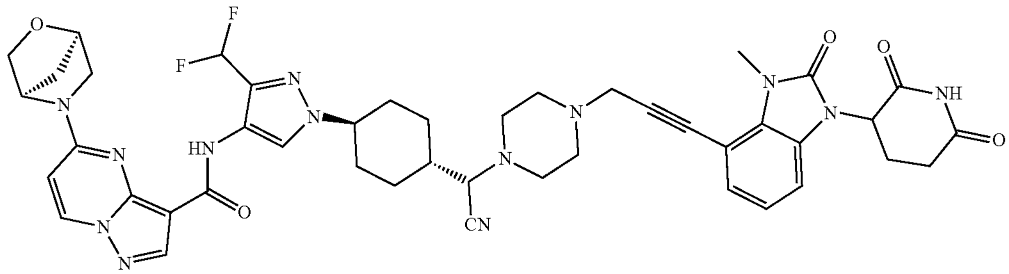 [SMILES: Cn1c(=O)n(C2CCC(=O)NC2=O)c2cccc(C#CCN3CCN(C(C#N)[C@H]4CC[C@H](n5cc(NC(=O)c6cnn7ccc(N8C[C@H]9C[C@@H]8CO9)nc67)c(C(F)F)n5)CC4)CC3)c21] |
| I-197 | 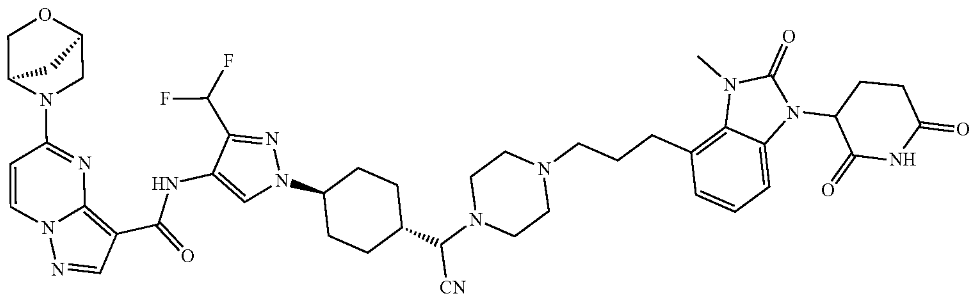 [SMILES: Cn1c(=O)n(C2CCC(=O)NC2=O)c2cccc(CCCN3CCN(C(C#N)[C@H]4CC[C@H](n5cc(NC(=O)c6cnn7ccc(N8C[C@H]9C[C@@H]8CO9)nc67)c(C(F)F)n5)CC4)CC3)c21] |
| I-198 | 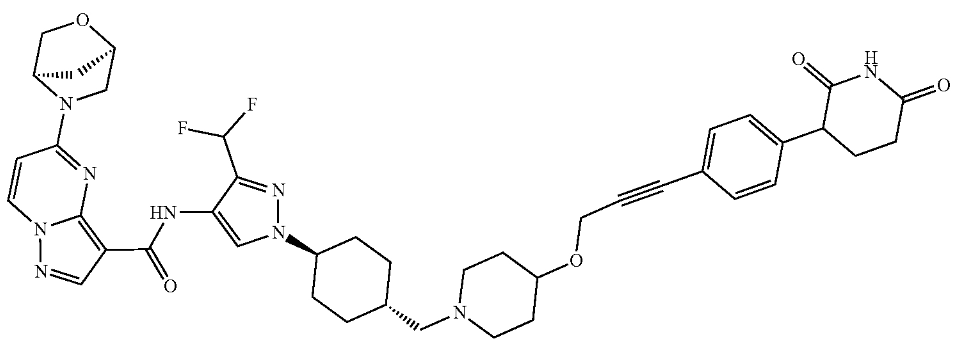 [SMILES: O=C1CCC(c2ccc(C#CCOC3CCN(C[C@H]4CC[C@H](n5cc(NC(=O)c6cnn7ccc(N8C[C@H]9C[C@@H]8CO9)nc67)c(C(F)F)n5)CC4)CC3)cc2)C(=O)N1] |
| I-199 | 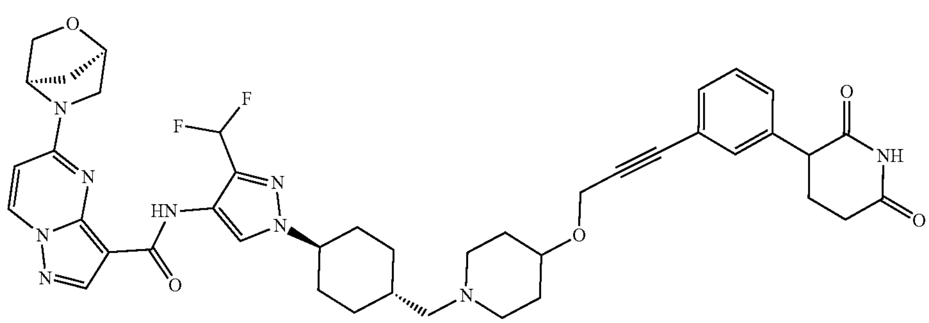 [SMILES: O=C1CCC(c2cccc(C#CCOC3CCN(C[C@H]4CC[C@H](n5cc(NC(=O)c6cnn7ccc(N8C[C@H]9C[C@@H]8CO9)nc67)c(C(F)F)n5)CC4)CC3)c2)C(=O)N1] |
| I-200 | 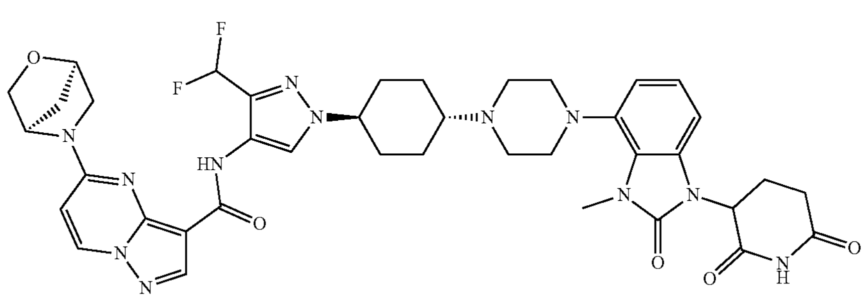 [SMILES: Cn1c(=O)n(C2CCC(=O)NC2=O)c2cccc(N3CCN([C@H]4CC[C@H](n5cc(NC(=O)c6cnn7ccc(N8C[C@H]9C[C@@H]8CO9)nc67)c(C(F)F)n5)CC4)CC3)c21] |

TABLE 1-continued

Exemplary Compounds

| I-# | Structure |
|---|---|
| I-201 | 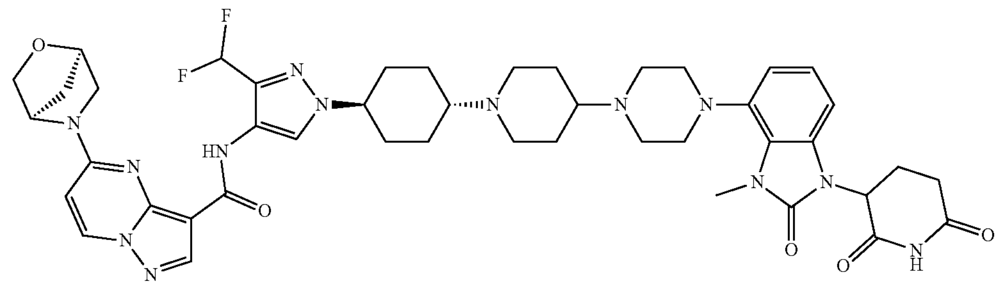 [SMILES: Cn1c(=O)n(C2CCC(=O)NC2=O)c2cccc(N3CCN(C4CCN([C@H]5CC[C@H](n6cc(NC(=O)c7cnn8ccc(N9C[C@H]%10C[C@@H]9CO%10)nc78)c(C(F)F)n6)CC5)CC4)CC3)c21] |
| I-202 | 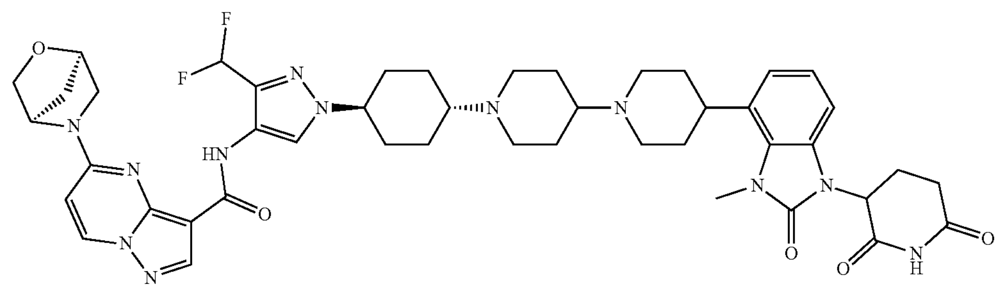 [SMILES: Cn1c(=O)n(C2CCC(=O)NC2=O)c2cccc(C3CCN(C4CCN([C@H]5CC[C@H](n6cc(NC(=O)c7cnn8ccc(N9C[C@H]%10C[C@@H]9CO%10)nc78)c(C(F)F)n6)CC5)CC4)CC3)c21] |
| I-203 | 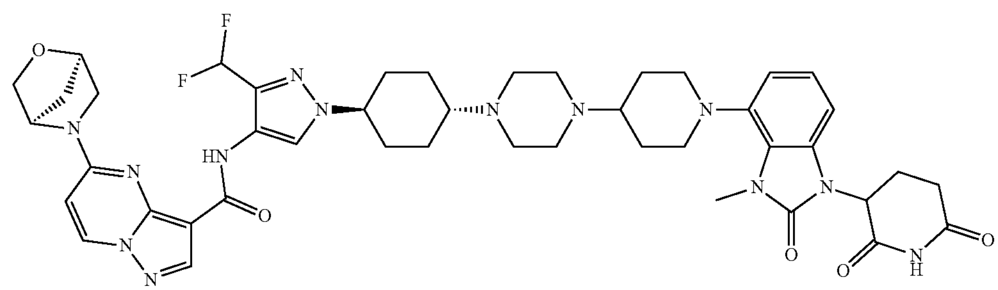 [SMILES: Cn1c(=O)n(C2CCC(=O)NC2=O)c2cccc(N3CCC(N4CCN([C@H]5CC[C@H](n6cc(NC(=O)c7cnn8ccc(N9C[C@H]%10C[C@@H]9CO%10)nc78)c(C(F)F)n6)CC5)CC4)CC3)c21] |
| I-204 | 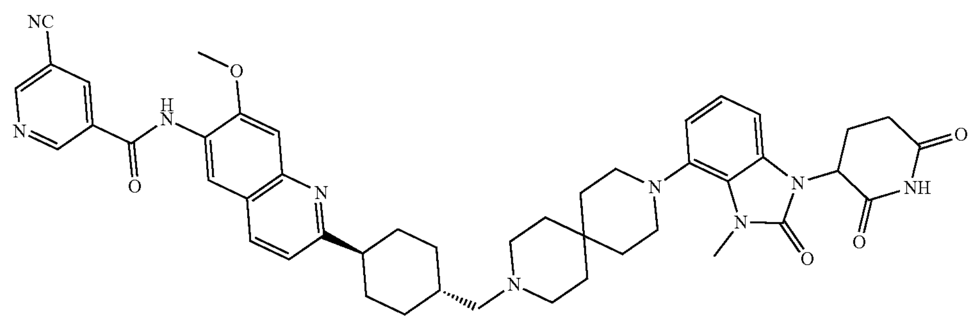 [SMILES: COc1cc2nc([C@H]3CC[C@H](CN4CCC5(CC4)CCN(c4cccc6c4n(C)c(=O)n6C4CCC(=O)NC4=O)CC5)CC3)ccc2cc1NC(=O)c1cncc(C#N)c1] |
| I-205 | 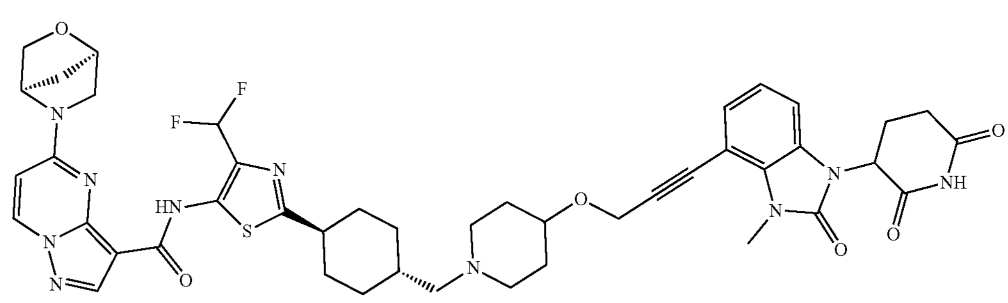 [SMILES: Cn1c(=O)n(C2CCC(=O)NC2=O)c2cccc(C#CCOC3CCN(C[C@H]4CC[C@H](c5nc(C(F)F)c(NC(=O)c6cnn7ccc(N8C[C@H]9C[C@@H]8CO9)nc67)s5)CC4)CC3)c21] |

TABLE 1-continued

Exemplary Compounds

| I-# | Structure |
|---|---|
| I-206 | 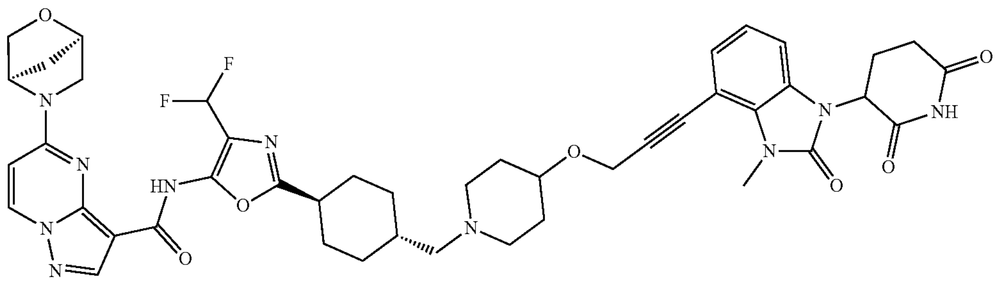 [SMILES: Cn1c(=O)n(C2CCC(=O)NC2=O)c2cccc(C#CCOC3CCN(C[C@H]4CC[C@H](c5nc(C(F)F)c(NC(=O)c6cnn7ccc(N8C[C@H]9C[C@@H]8CO9)nc67)o5)CC4)CC3)c21] |
| I-207 | 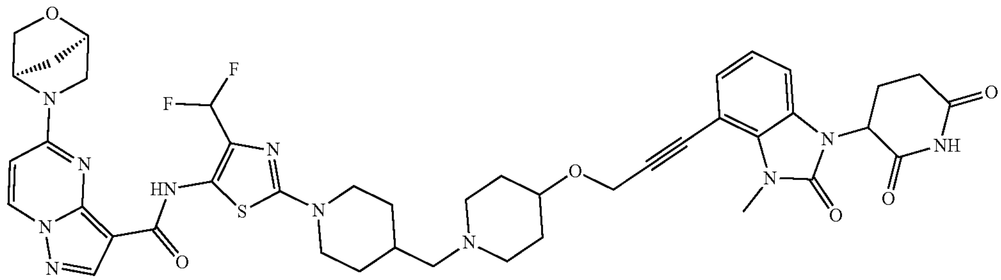 |
| I-208 | 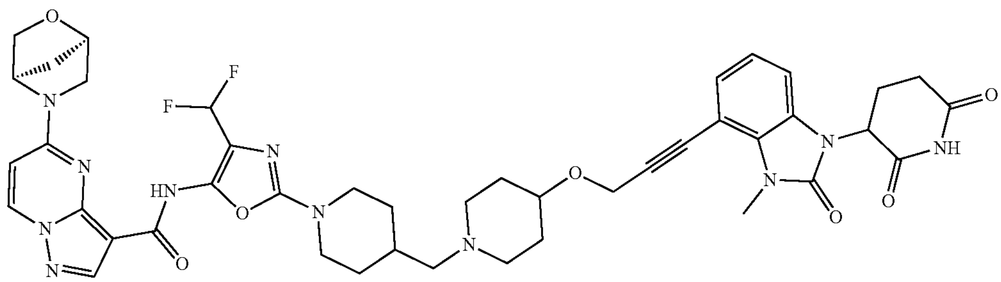 [SMILES: Cn1c(=O)n(C2CCC(=O)NC2=O)c2cccc(C#CCOC3CCN(CC4CCN(c5nc(C(F)F)c(NC(=O)c6cnn7ccc(N8C[C@H]9C[C@@H]8CO9)nc67)s5)CC4)CC3)c21] |
| I-209 | 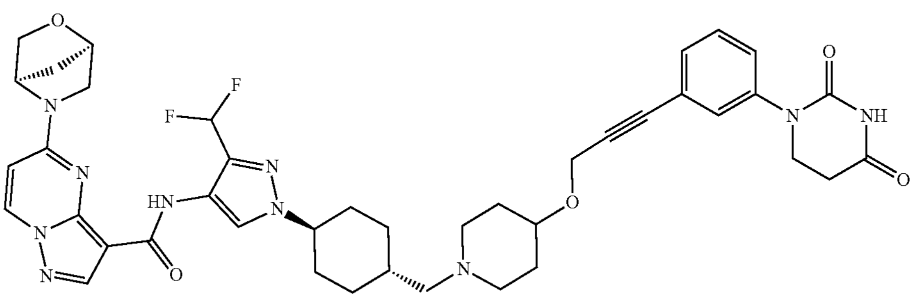 [SMILES: O=C1CCN(c2cccc(C#CCOC3CCN(C[C@H]4CC[C@H](n5cc(NC(=O)c6cnn7ccc(N8C[C@H]9C[C@@H]8CO9)nc67)c(C(F)F)n5)CC4)CC3)c2)C(=O)N1] |
| I-210 | 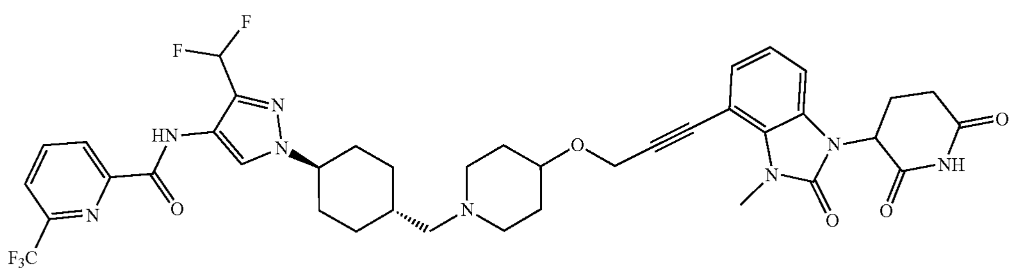 [SMILES: Cn1c(=O)n(C2CCC(=O)NC2=O)c2cccc(C#CCOC3CCN(C[C@H]4CC[C@H](n5cc(NC(=O)c6cccc(C(F)(F)F)n6)c(C(F)F)n5)CC4)CC3)c21] |

TABLE 1-continued

Exemplary Compounds

| I-# | Structure |
| --- | --- |
| I-211 | 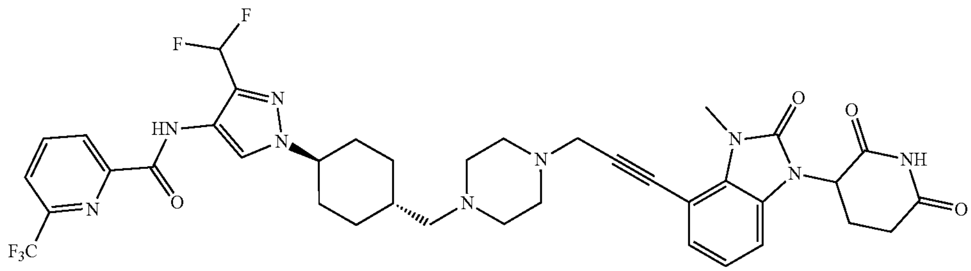 [SMILES: Cn1c(=O)n(C2CCC(=O)NC2=O)c2cccc(C#CCN3CCN(C[C@H]4CC[C@H](n5cc(NC(=O)c6cccc(C(F)(F)F)n6)c(C(F)F)n5)CC4)CC3)c21] |
| I-212 | 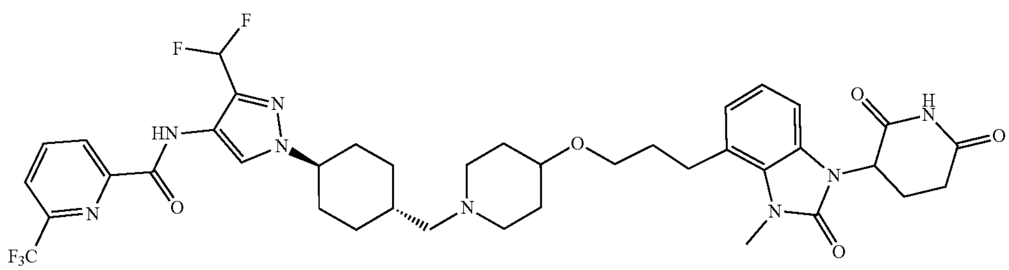 [SMILES: Cn1c(=O)n(C2CCC(=O)NC2=O)c2cccc(CCCOC3CCN(C[C@H]4CC[C@H](n5cc(NC(=O)c6cccc(C(F)(F)F)n6)c(C(F)F)n5)CC4)CC3)c21] |
| I-213 | 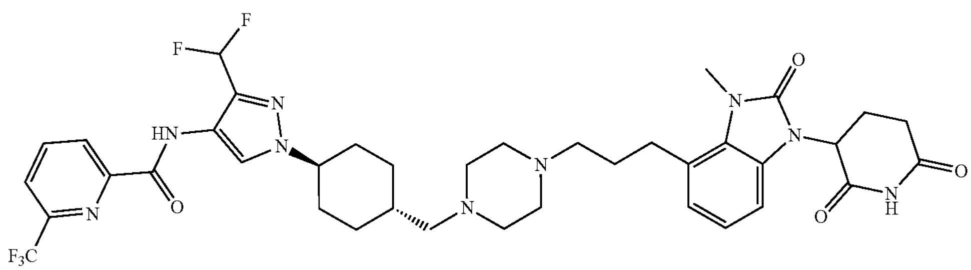 [SMILES: Cn1c(=O)n(C2CCC(=O)NC2=O)c2cccc(CCCN3CCN(C[C@H]4CC[C@H](n5cc(NC(=O)c6cccc(C(F)(F)F)n6)c(C(F)F)n5)CC4)CC3)c21] |
| I-214 | 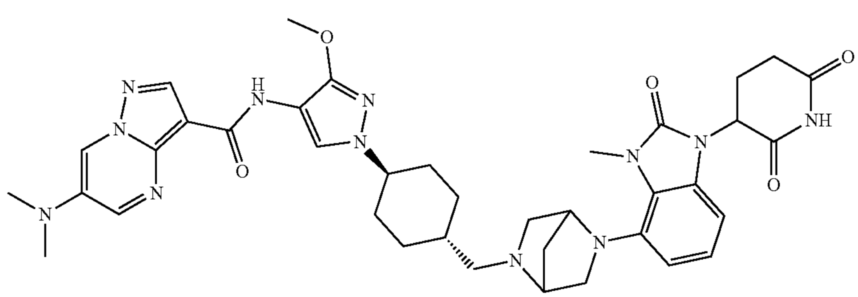 [SMILES: COc1nn([C@H]2CC[C@H](CN3CC4CC3CN4c3cccc4c3n(C)c(=O)n4C3CCC(=O)NC3=O)CC2)cc1NC(=O)c1cnn2cc(N(C)C)cnc12] |
| I-215 | 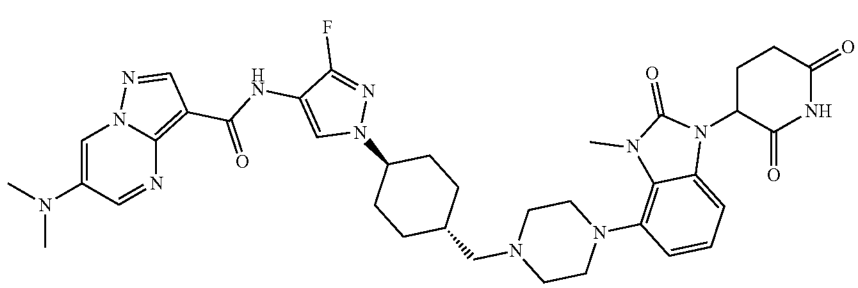 [SMILES: CN(C)c1cnc2c(C(=O)Nc3cn([C@H]4CC[C@H](CN5CCN(c6cccc7c6n(C)c(=O)n7C6CCC(=O)NC6=O)CC5)CC4)nc3F)cnn2c1] |

TABLE 1-continued

Exemplary Compounds

| I-# | Structure |
|---|---|
| I-216 | 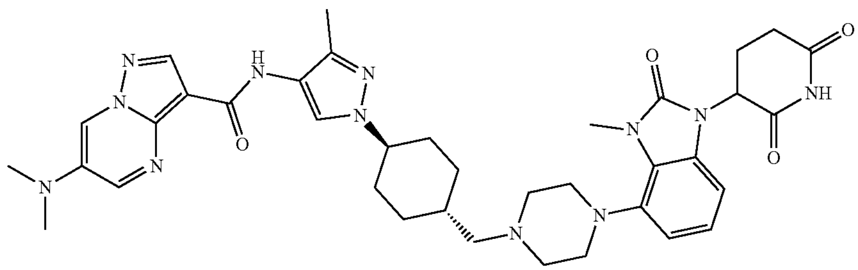 [SMILES: Cc1nn([C@H]2CC[C@H](CN3CCN(c4cccc5c4n(C)c(=O)n5C4CCC(=O)NC4=O)CC3)CC2)cc1NC(=O)c1cnn2cc(N(C)C)cnc12] |
| I-217 | 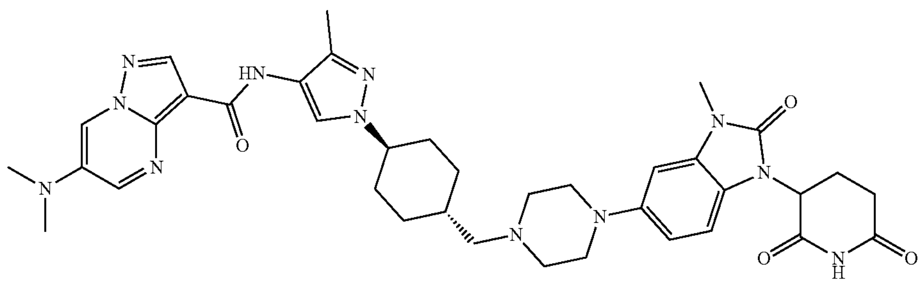 [SMILES: Cc1nn([C@H]2CC[C@H](CN3CCN(c4ccc5c(c4)n(C)c(=O)n5C4CCC(=O)NC4=O)CC3)CC2)cc1NC(=O)c1cnn2cc(N(C)C)cnc12] |
| I-218 | 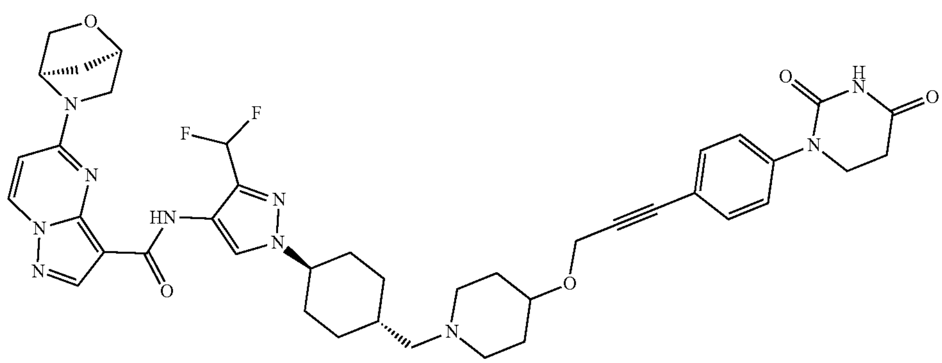 [SMILES: O=C1CCN(c2ccc(C#CCOC3CCN(C[C@H]4CC[C@H](n5cc(NC(=O)c6cnn7ccc(N8C[C@H]9C[C@@H]8CO9)nc67)c(C(F)F)n5)CC4)CC3)cc2)C(=O)N1] |
| I-219 | 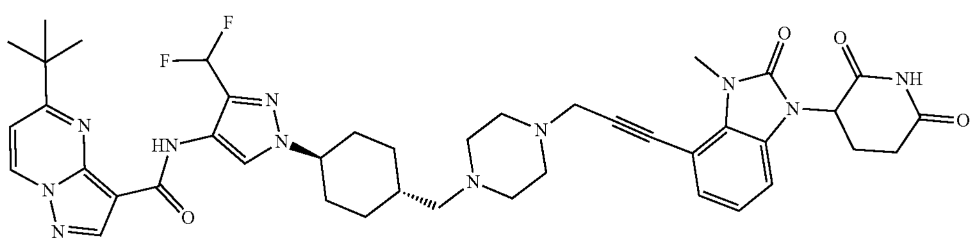 [SMILES: Cn1c(=O)n(C2CCC(=O)NC2=O)c2cccc(C#CCN3CCN(C[C@H]4CC[C@H](n5cc(NC(=O)c6cnn7ccc(C(C)(C)C)nc67)c(C(F)F)n5)CC4)CC3)c21] |
| I-220 | 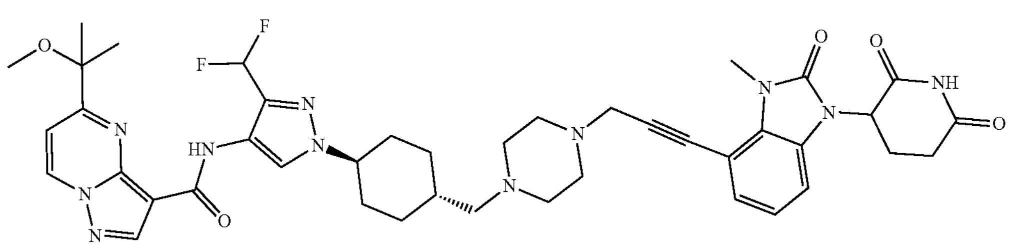 [SMILES: COC(C)(C)c1ccn2ncc(C(=O)Nc3cn([C@H]4CC[C@H](CN5CCN(CC#Cc6cccc7c6n(C)c(=O)n7C6CCC(=O)NC6=O)CC5)CC4)nc3C(F)F)c2n1] |

TABLE 1-continued

Exemplary Compounds

| I-# | Structure |
|---|---|
| I-221 | 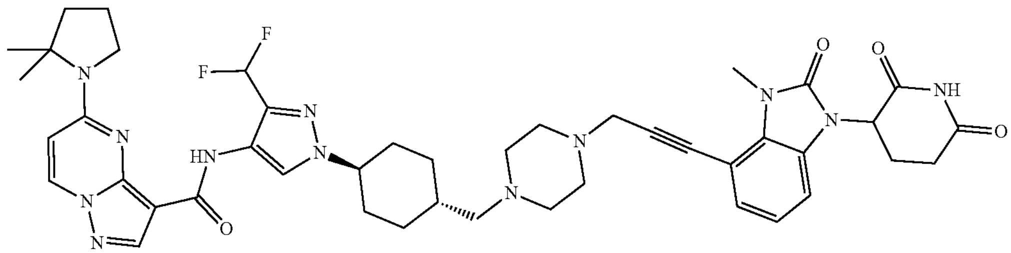 |
| I-222 | 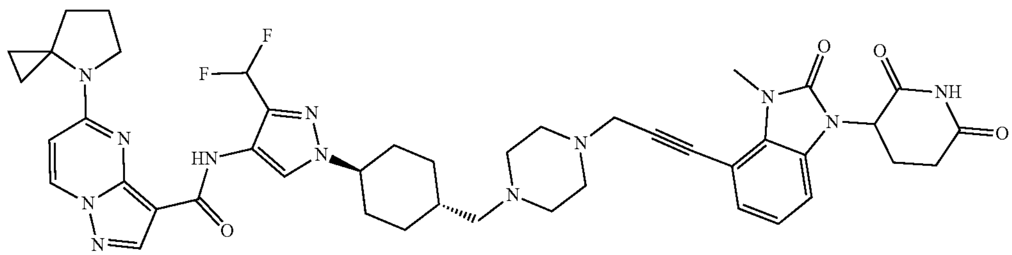 [SMILES: Cn1c(=O)n(C2CCC(=O)NC2=O)c2cccc(C#CCN3CCN(C[C@H]4CC[C@H](n5cc(NC(=O)c6cnn7ccc(N8CCCC89CC9)nc67)c(C(F)F)n5)CC4)CC3)c21] |
| I-223 | 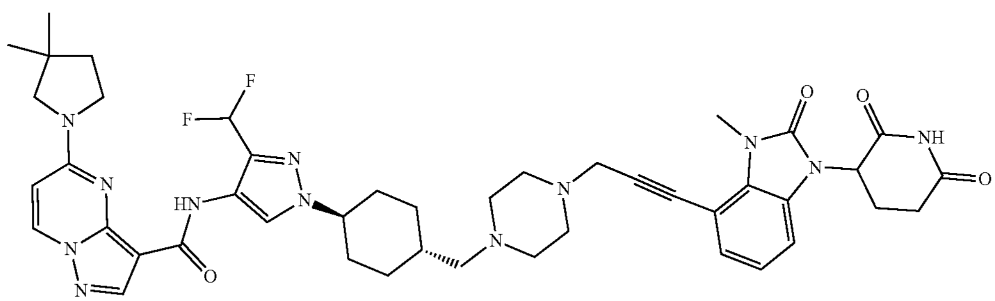 [SMILES: Cn1c(=O)n(C2CCC(=O)NC2=O)c2cccc(C#CCN3CCN(C[C@H]4CC[C@H](n5cc(NC(=O)c6cnn7ccc(N8CCC(C)(C)C8)nc67)c(C(F)F)n5)CC4)CC3)c21] |
| I-224 | 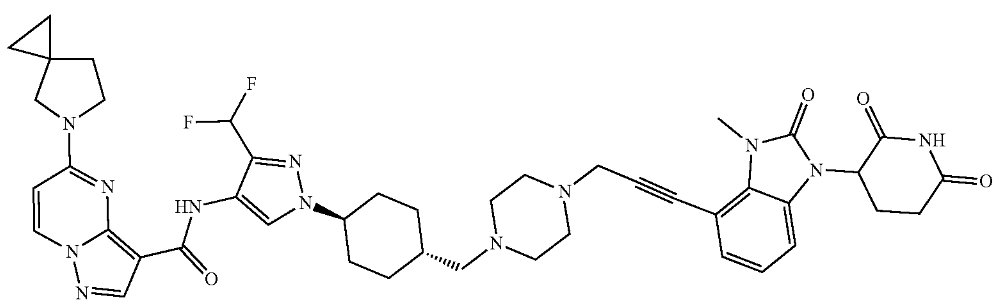 [SMILES: Cn1c(=O)n(C2CCC(=O)NC2=O)c2cccc(C#CCN3CCN(C[C@H]4CC[C@H](n5cc(NC(=O)c6cnn7ccc(N8CCC9(CC9)C8)nc67)c(C(F)F)n5)CC4)CC3)c21] |
| I-225 | 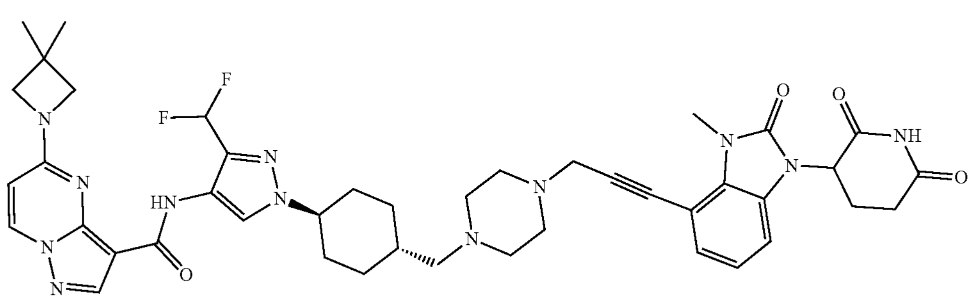 [SMILES: Cn1c(=O)n(C2CCC(=O)NC2=O)c2cccc(C#CCN3CCN(C[C@H]4CC[C@H](n5cc(NC(=O)c6cnn7ccc(N8CC(C)(C)C8)nc67)c(C(F)F)n5)CC4)CC3)c21] |

TABLE 1-continued

Exemplary Compounds

| I-# | Structure |
|---|---|
| I-226 | 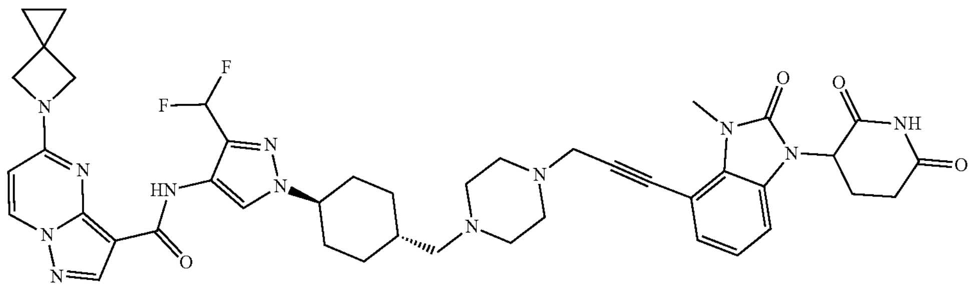 [SMILES: Cn1c(=O)n(C2CCC(=O)NC2=O)c2cccc(C#CCN3CCN(C[C@H]4CC[C@H](n5cc(NC(=O)c6cnn7ccc(N8CC9(CC9)C8)nc67)c(C(F)F)n5)CC4)CC3)c21] |
| I-227 | 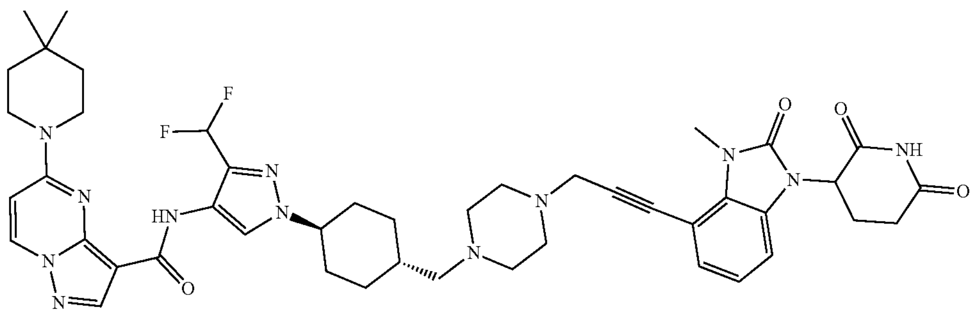 [SMILES: Cn1c(=O)n(C2CCC(=O)NC2=O)c2cccc(C#CCN3CCN(C[C@H]4CC[C@H](n5cc(NC(=O)c6cnn7ccc(N8CCC(C)(C)CC8)nc67)c(C(F)F)n5)CC4)CC3)c21] |
| I-228 | 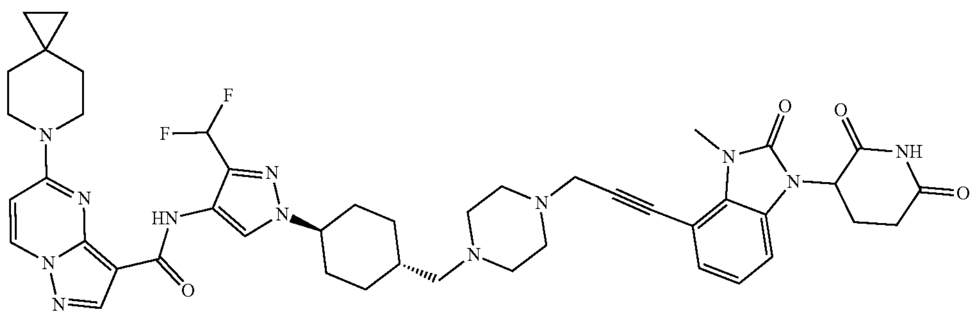 [SMILES: Cn1c(=O)n(C2CCC(=O)NC2=O)c2cccc(C#CCN3CCN(C[C@H]4CC[C@H](n5cc(NC(=O)c6cnn7ccc(N8CCC9(CC8)CC9)nc67)c(C(F)F)n5)CC4)CC3)c21] |
| I-229 | 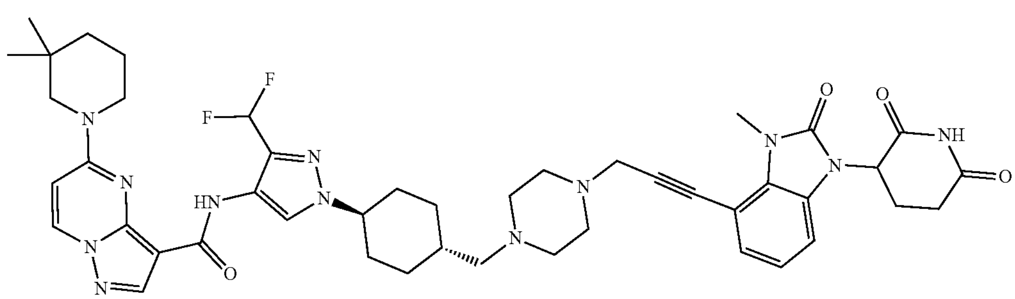 [SMILES: Cn1c(=O)n(C2CCC(=O)NC2=O)c2cccc(C#CCN3CCN(C[C@H]4CC[C@H](n5cc(NC(=O)c6cnn7ccc(N8CCCC(C)(C)C8)nc67)c(C(F)F)n5)CC4)CC3)c21] |
| I-230 | 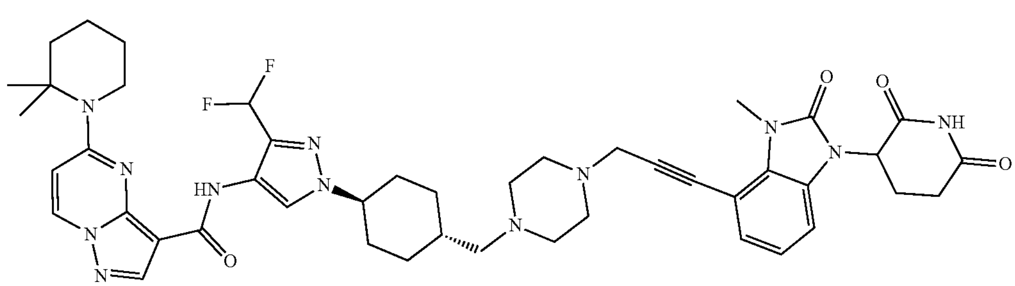 [SMILES: Cn1c(=O)n(C2CCC(=O)NC2=O)c2cccc(C#CCN3CCN(C[C@H]4CC[C@H](n5cc(NC(=O)c6cnn7ccc(N8CCCCC8(C)C)nc67)c(C(F)F)n5)CC4)CC3)c21] |

TABLE 1-continued
Exemplary Compounds
| I-# | Structure |
|---|---|
| I-231 | 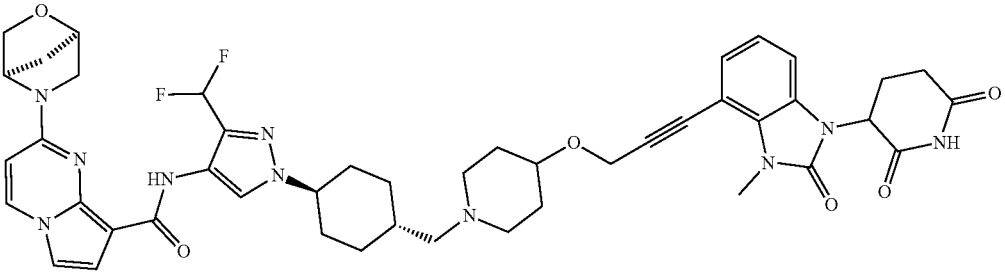 [SMILES: Cn1c(=O)n(C2CCC(=O)NC2=O)c2cccc(C#CCOC3CCN(C[C@H]4CC[C@H](n5cc(NC(=O)c6ccn7ccc(N8C[C@H]9C[C@@H]8CO9)nc67)c(C(F)F)n5)CC4)CC3)c21] |
| I-232 | 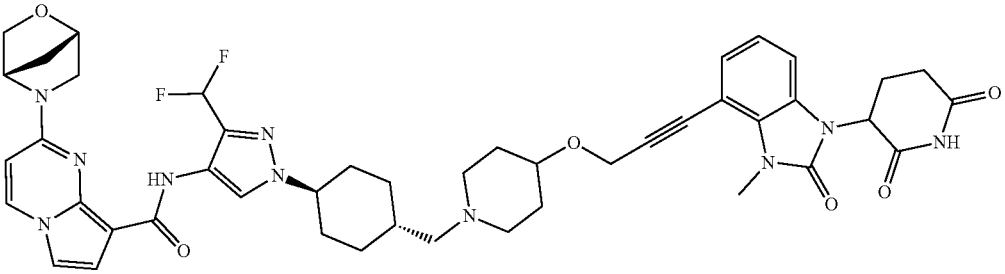 [SMILES: Cn1c(=O)n(C2CCC(=O)NC2=O)c2cccc(C#CCOC3CCN(C[C@H]4CC[C@H](n5cc(NC(=O)c6ccn7ccc(N8C[C@@H]9C[C@H]8CO9)nc67)c(C(F)F)n5)CC4)CC3)c21] |
| I-233 | 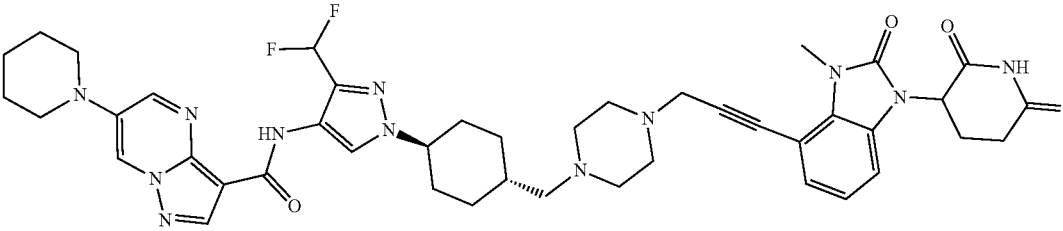 |
| I-234 | 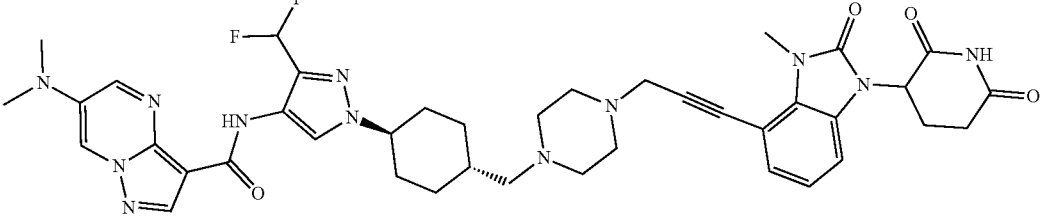 |
| I-235 | 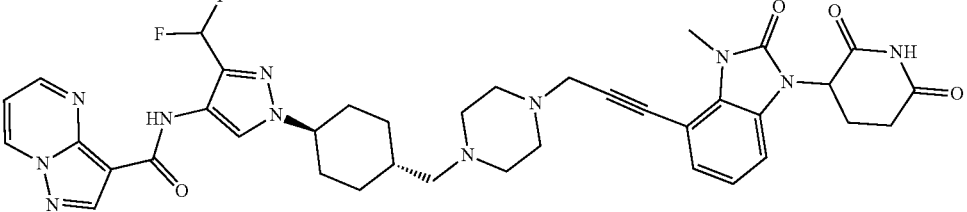 |

TABLE 1-continued

Exemplary Compounds

| I-# | Structure |
| --- | --- |
| I-236 | 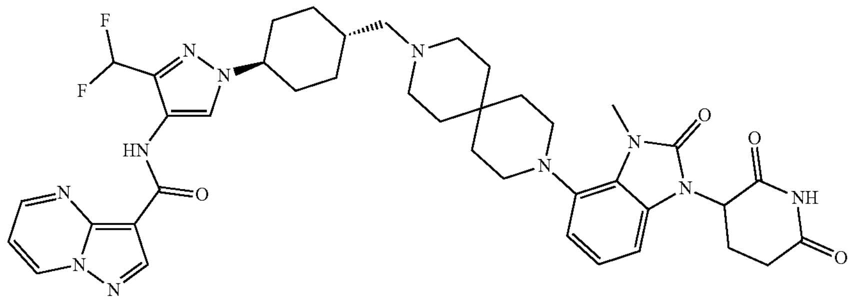 [SMILES: Cn1c(=O)n(C2CCC(=O)NC2=O)c2cccc(N3CCC4(CCN(C[C@H]5CC[C@H](n6cc(NC(=O)c7cnn8cccnc78)c(C(F)F)n6)CC5)CC4)CC3)c21] |
| I-237 | 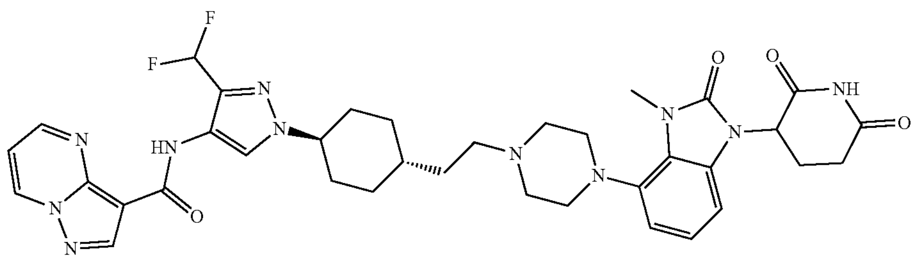 [SMILES: Cn1c(=O)n(C2CCC(=O)NC2=O)c2cccc(N3CCN(CC[C@H]4CC[C@H](n5cc(NC(=O)c6cnn7cccnc67)c(C(F)F)n5)CC4)CC3)c21] |
| I-238 | 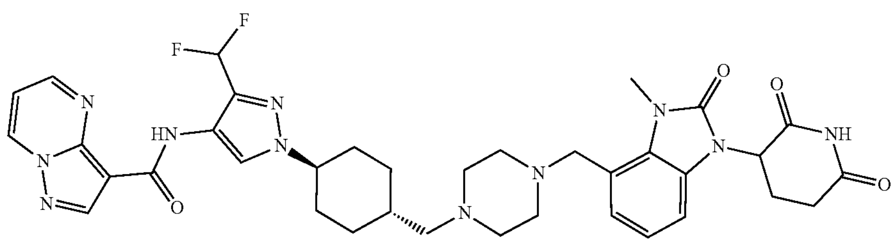 [SMILES: Cn1c(=O)n(C2CCC(=O)NC2=O)c2cccc(CN3CCN(C[C@H]4CC[C@H](n5cc(NC(=O)c6cnn7cccnc67)c(C(F)F)n5)CC4)CC3)c21] |
| I-239 | 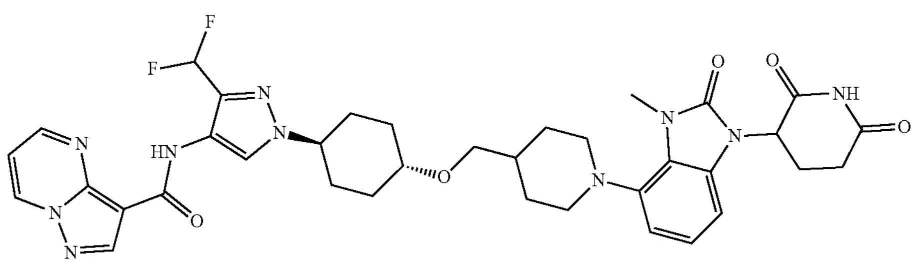 [SMILES: Cn1c(=O)n(C2CCC(=O)NC2=O)c2cccc(N3CCC(CO[C@H]4CC[C@H](n5cc(NC(=O)c6cnn7cccnc67)c(C(F)F)n5)CC4)CC3)c21] |
| I-240 | 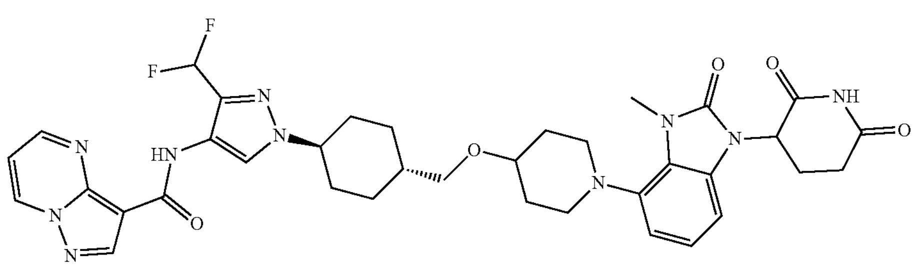 [SMILES: Cn1c(=O)n(C2CCC(=O)NC2=O)c2cccc(N3CCC(OC[C@H]4CC[C@H](n5cc(NC(=O)c6cnn7cccnc67)c(C(F)F)n5)CC4)CC3)c21] |

TABLE 1-continued

Exemplary Compounds

| I-# | Structure |
|---|---|
| I-241 | 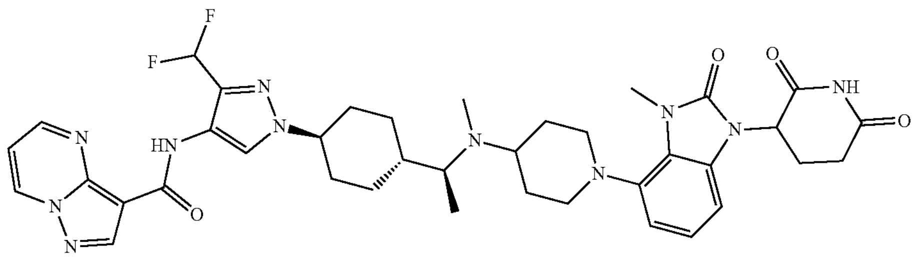 [SMILES: C[C@@H]([C@H]1CC[C@H](n2cc(NC(=O)c3cnn4cccnc34)c(C(F)F)n2)CC1)N(C)C1CCN(c2cccc3c2n(C)c(=O)n3C2CCC(=O)NC2=O)CC1] |
| I-242 | 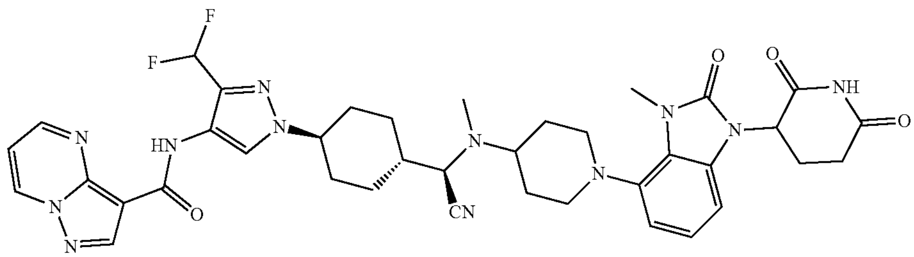 [SMILES: CN(C1CCN(c2cccc3c2n(C)c(=O)n3C2CCC(=O)NC2=O)CC1)[C@@H](C#N)[C@H]1CC[C@H](n2cc(NC(=O)c3cnn4cccnc34)c(C(F)F)n2)CC1] |
| I-243 | 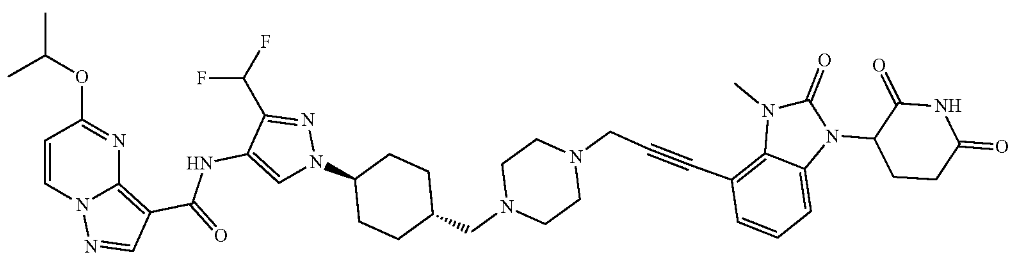 [SMILES: CC(C)Oc1ccn2ncc(C(=O)Nc3cn([C@H]4CC[C@H](CN5CCN(CC#Cc6cccc7c6n(C)c(=O)n7C6CCC(=O)NC6=O)CC5)CC4)nc3C(F)F)c2n1] |
| I-244 | 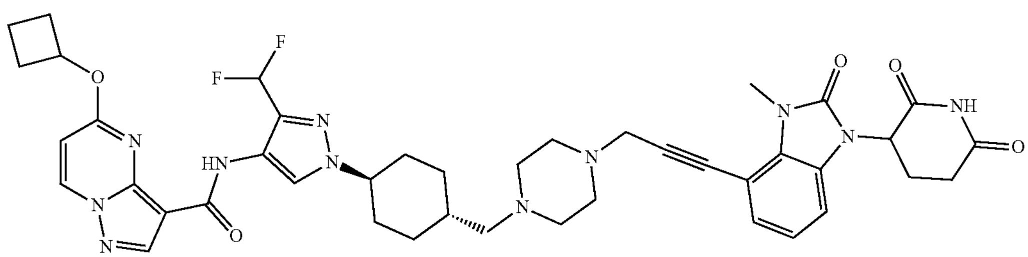 [SMILES: Cn1c(=O)n(C2CCC(=O)NC2=O)c2cccc(C#CCN3CCN(C[C@H]4CC[C@H](n5cc(NC(=O)c6cnn7ccc(OC8CCC8)nc67)c(C(F)F)n5)CC4)CC3)c21] |
| I-245 | 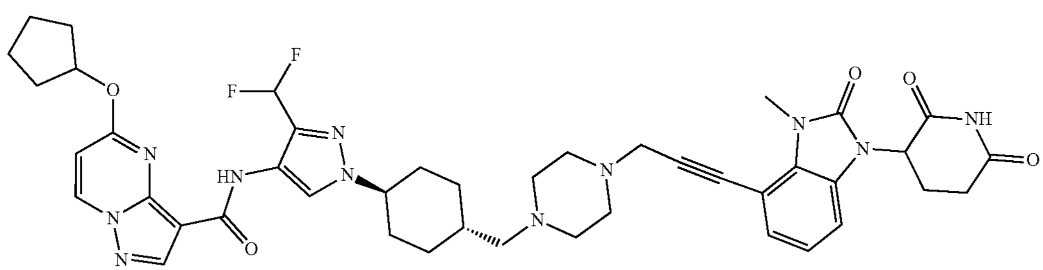 [SMILES: Cn1c(=O)n(C2CCC(=O)NC2=O)c2cccc(C#CCN3CCN(C[C@H]4CC[C@H](n5cc(NC(=O)c6cnn7ccc(OC8CCCC8)nc67)c(C(F)F)n5)CC4)CC3)c21] |

TABLE 1-continued

Exemplary Compounds

| I-# | Structure |
|---|---|
| I-246 | 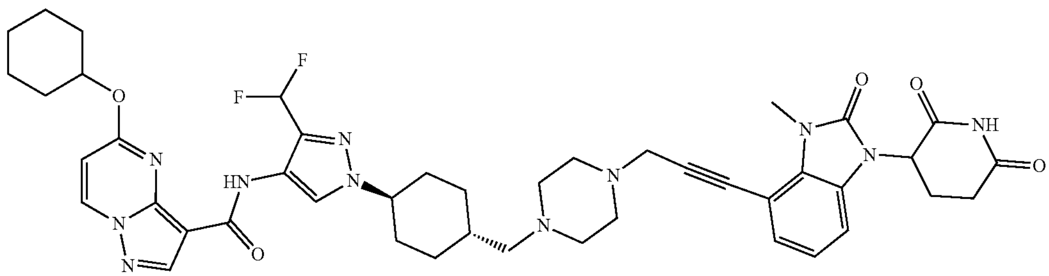 [SMILES: Cn1c(=O)n(C2CCC(=O)NC2=O)c2cccc(C#CCN3CCN(C[C@H]4CC[C@H](n5cc(NC(=O)c6cnn7ccc(OC8CCCCC8)nc67)c(C(F)F)n5)CC4)CC3)c21] |
| I-247 | 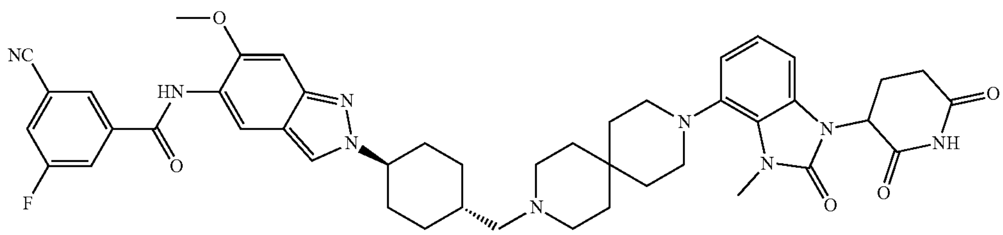 [SMILES: COc1cc2nn([C@H]3CC[C@H](CN4CCC5(CC4)CCN(c4cccc6c4n(C)c(=O)n6C4CCC(=O)NC4=O)CC5)CC3)cc2cc1NC(=O)c1cc(F)cc(C#N)c1] |
| I-248 | 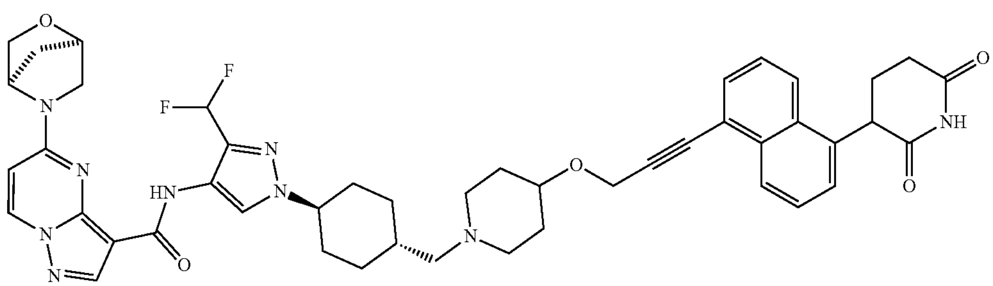 [SMILES: O=C1CCC(c2cccc3c(C#CCOC4CCN(C[C@H]5CC[C@H](n6cc(NC(=O)c7cnn8ccc(N9C[C@H]%10C[C@@H]9CO%10)nc78)c(C(F)F)n6)CC5)CC4)cccc23)C(=O)N1] |
| I-249 | 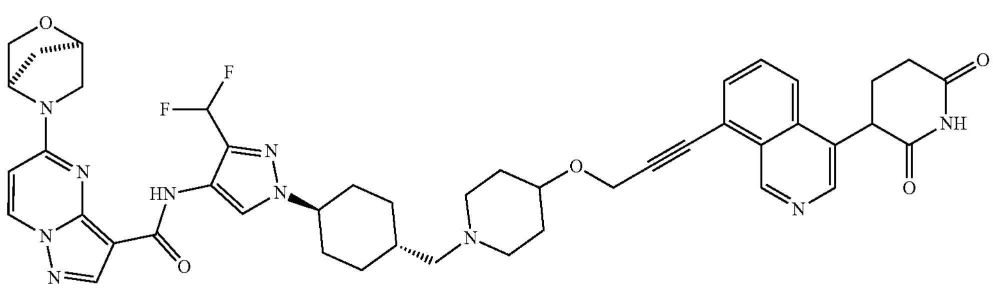 [SMILES: O=C1CCC(c2cncc3c(C#CCOC4CCN(C[C@H]5CC[C@H](n6cc(NC(=O)c7cnn8ccc(N9C[C@H]%10C[C@@H]9CO%10)nc78)c(C(F)F)n6)CC5)CC4)cccc23)C(=O)N1] |
| I-250 | 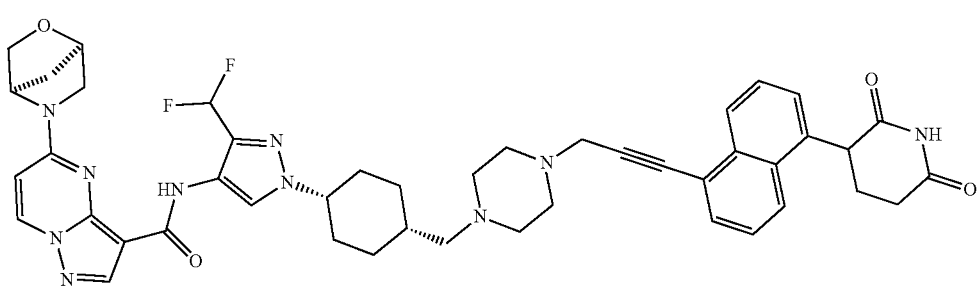 [SMILES: O=C1CCC(c2cccc3c(C#CCN4CCN(C[C@H]5CC[C@@H](n6cc(NC(=O)c7cnn8ccc(N9C[C@H]%10C[C@@H]9CO%10)nc78)c(C(F)F)n6)CC5)CC4)cccc23)C(=O)N1] |

TABLE 1-continued

Exemplary Compounds

| I-# | Structure |
| --- | --- |
| I-251 | 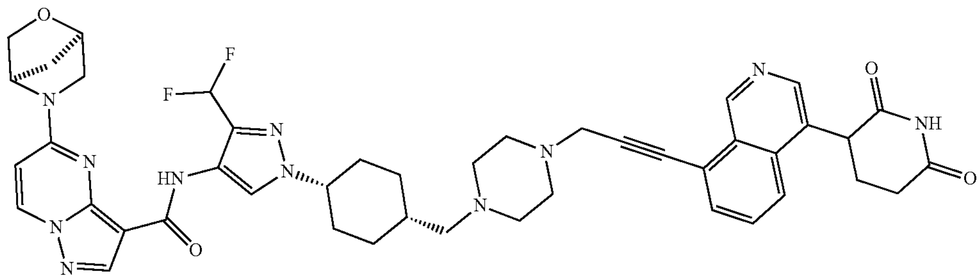 [SMILES: O=C1CCC(c2cncc3c(C#CCN4CCN(C[C@H]5CC[C@@H](n6cc(NC(=O)c7cnn8ccc(N9C[C@H]%10C[C@@H]9CO%10)nc78)c(C(F)F)n6)CC5)CC4)cccc23)C(=O)N1] |
| I-252 | 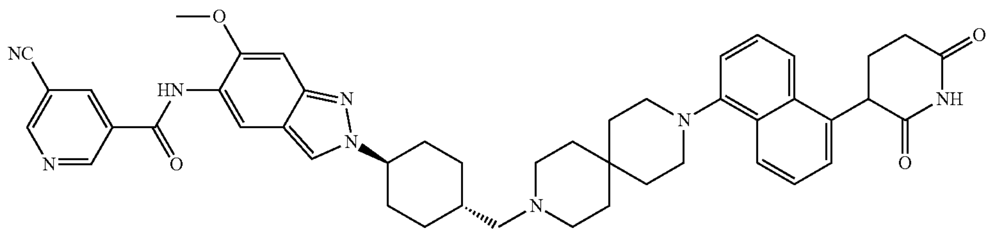 [SMILES: COc1cc2nn([C@H]3CC[C@H](CN4CCC5(CC4)CCN(c4cccc6c(C7CCC(=O)NC7=O)cccc46)CC5)CC3)cc2cc1NC(=O)c1cncc(C#N)c1] |
| I-253 | 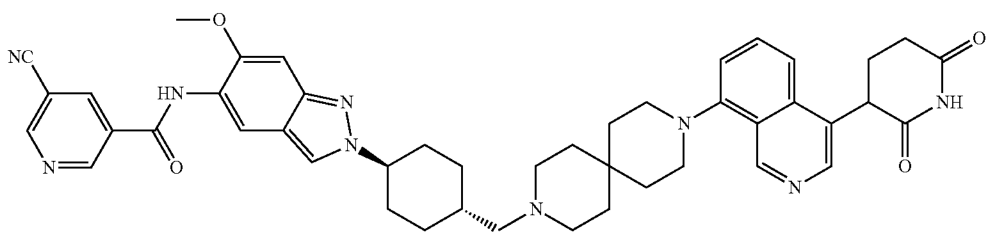 [SMILES: COc1cc2nn([C@H]3CC[C@H](CN4CCC5(CC4)CCN(c4cccc6c(C7CCC(=O)NC7=O)cncc46)CC5)CC3)cc2cc1NC(=O)c1cncc(C#N)c1] |
| I-254 | 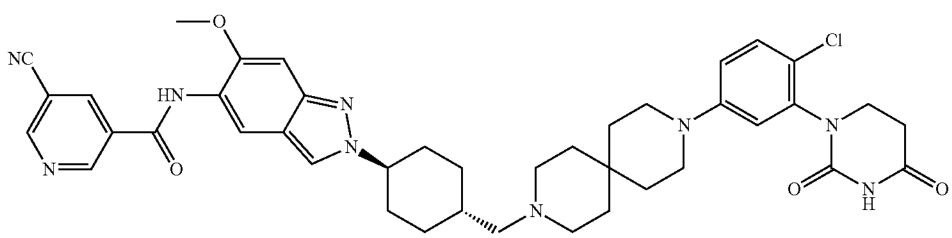 [SMILES: COc1cc2nn([C@H]3CC[C@H](CN4CCC5(CC4)CCN(c4ccc(Cl)c(N6CCC(=O)NC6=O)c4)CC5)CC3)cc2cc1NC(=O)c1cncc(C#N)c1] |
| I-255 | 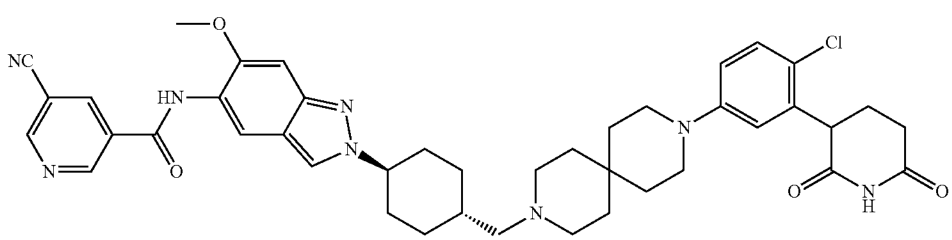 [SMILES: COc1cc2nn([C@H]3CC[C@H](CN4CCC5(CC4)CCN(c4ccc(Cl)c(C6CCC(=O)NC6=O)c4)CC5)CC3)cc2cc1NC(=O)c1cncc(C#N)c1] |
| I-256 | 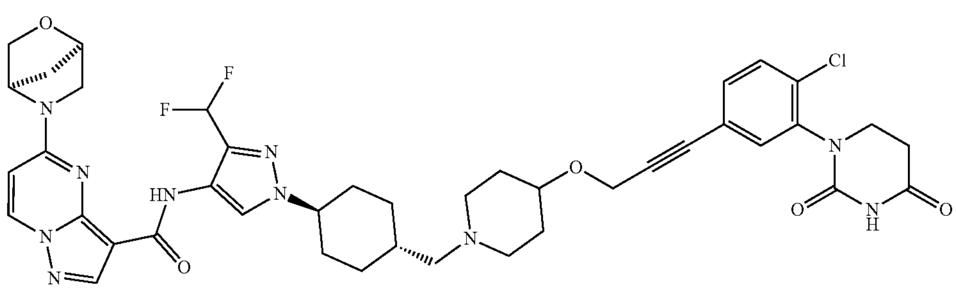 [SMILES: O=C1CCN(c2cc(C#CCOC3CCN(C[C@H]4CC[C@H](n5cc(NC(=O)c6cnn7ccc(N8C[C@H]9C[C@@H]8CO9)nc67)c(C(F)F)n5)CC4)CC3)ccc2Cl)C(=O)N1] |

TABLE 1-continued

Exemplary Compounds

| I-# | Structure |
|---|---|
| I-257 | 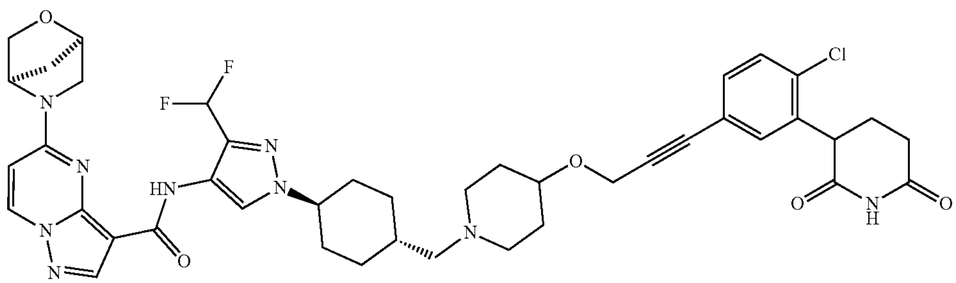 [SMILES: O=C1CCC(c2cc(C#CCOC3CCN(C[C@H]4CC[C@H](n5cc(NC(=O)c6cnn7ccc(N8C[C@H]9C[C@@H]8CO9)nc67)c(C(F)F)n5)CC4)CC3)ccc2Cl)C(=O)N1] |
| I-258 | 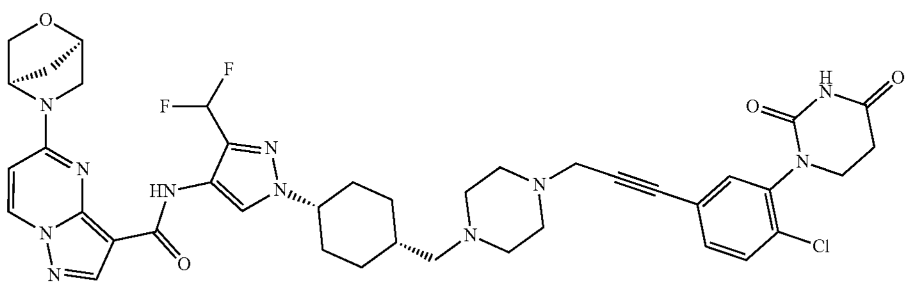 [SMILES: O=C1CCN(c2cc(C#CCN3CCN(C[C@H]4CC[C@@H](n5cc(NC(=O)c6cnn7ccc(N8C[C@H]9C[C@@H]8CO9)nc67)c(C(F)F)n5)CC4)CC3)ccc2Cl)C(=O)N1] |
| I-259 | 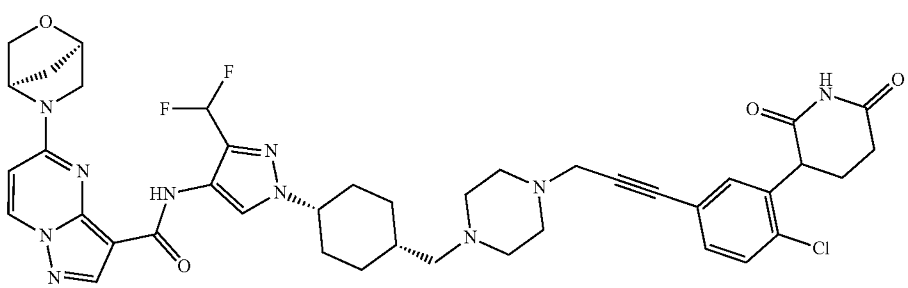 [SMILES: O=C1CCC(c2cc(C#CCN3CCN(C[C@H]4CC[C@@H](n5cc(NC(=O)c6cnn7ccc(N8C[C@H]9C[C@@H]8CO9)nc67)c(C(F)F)n5)CC4)CC3)ccc2Cl)C(=O)N1] |
| I-260 | 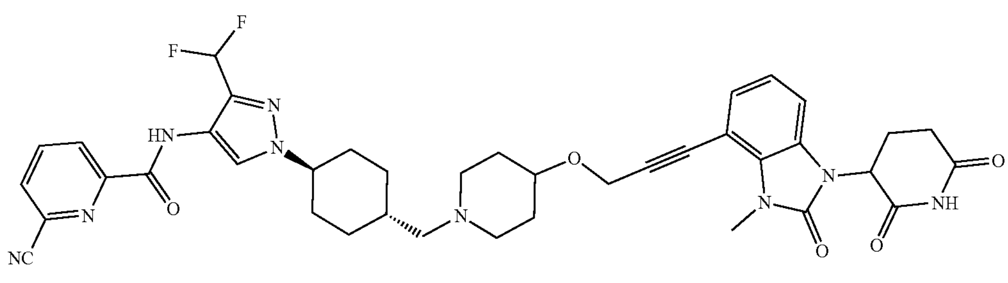 [SMILES: Cn1c(=O)n(C2CCC(=O)NC2=O)c2cccc(C#CCOC3CCN(C[C@H]4CC[C@H](n5cc(NC(=O)c6cccc(C#N)n6)c(C(F)F)n5)CC4)CC3)c21] |
| I-261 | 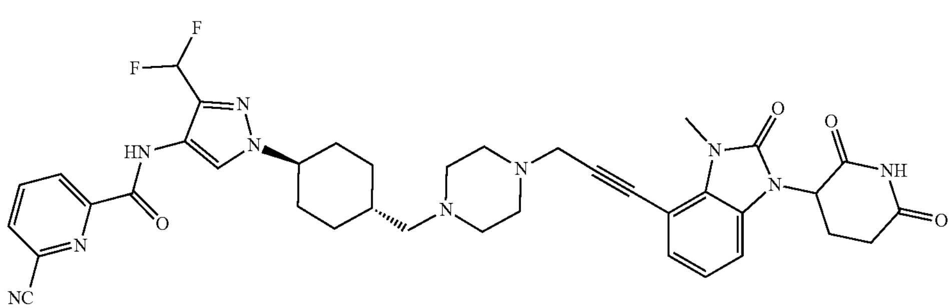 [SMILES: Cn1c(=O)n(C2CCC(=O)NC2=O)c2cccc(C#CCN3CCN(C[C@H]4CC[C@H](n5cc(NC(=O)c6cccc(C#N)n6)c(C(F)F)n5)CC4)CC3)c21] |

TABLE 1-continued

Exemplary Compounds

| I-# | Structure |
|---|---|
| I-262 | 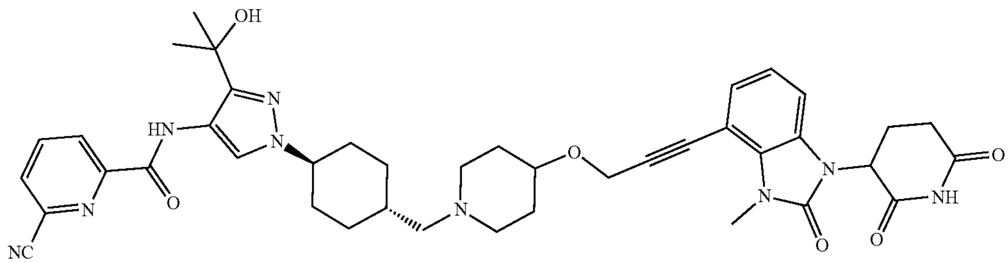 [SMILES: Cn1c(=O)n(C2CCC(=O)NC2=O)c2cccc(C#CCOC3CCN(C[C@H]4CC[C@H](n5cc(NC(=O)c6cccc(C#N)n6)c(C(C)(C)O)n5)CC4)CC3)c21] |
| I-263 | 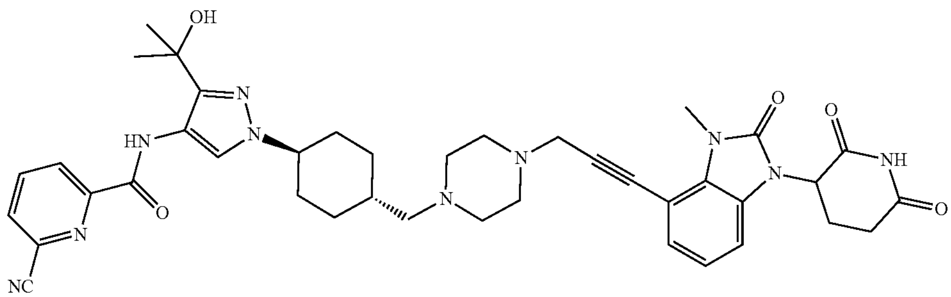 [SMILES: Cn1c(=O)n(C2CCC(=O)NC2=O)c2cccc(C#CCN3CCN(C[C@H]4CC[C@H](n5cc(NC(=O)c6cccc(C#N)n6)c(C(C)(C)O)n5)CC4)CC3)c21] |
| I-264 | 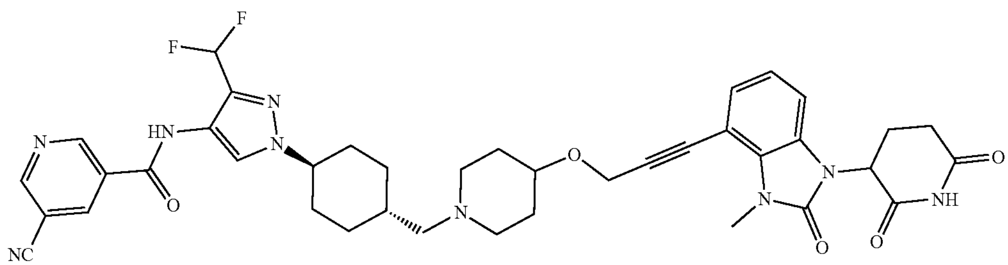 [SMILES: Cn1c(=O)n(C2CCC(=O)NC2=O)c2cccc(C#CCOC3CCN(C[C@H]4CC[C@H](n5cc(NC(=O)c6cncc(C#N)c6)c(C(F)F)n5)CC4)CC3)c21] |
| I-265 | 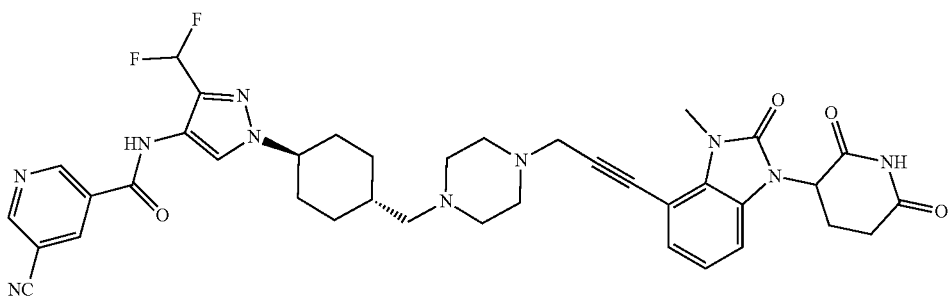 [SMILES: Cn1c(=O)n(C2CCC(=O)NC2=O)c2cccc(C#CCN3CCN(C[C@H]4CC[C@H](n5cc(NC(=O)c6cncc(C#N)c6)c(C(F)F)n5)CC4)CC3)c21] |
| I-266 | 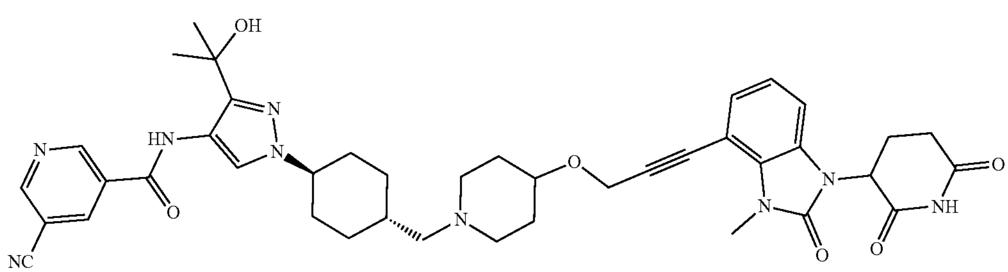 [SMILES: Cn1c(=O)n(C2CCC(=O)NC2=O)c2cccc(C#CCOC3CCN(C[C@H]4CC[C@H](n5cc(NC(=O)c6cncc(C#N)c6)c(C(C)(C)O)n5)CC4)CC3)c21] |

TABLE 1-continued
Exemplary Compounds
| I-# | Structure |
|---|---|
| I-267 | 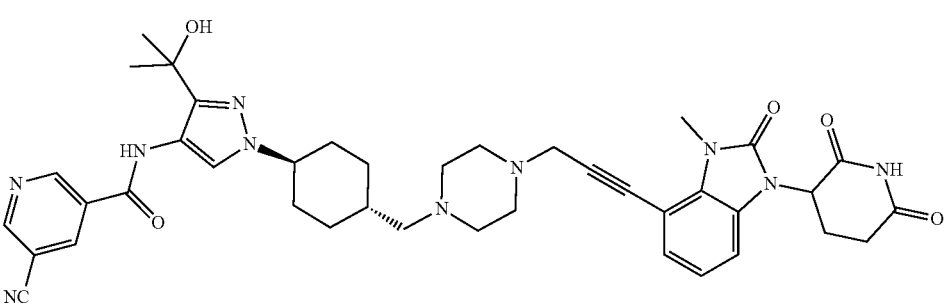 [SMILES: Cn1c(=O)n(C2CCC(=O)NC2=O)c2cccc(C#CCN3CCN(C[C@H]4CC[C@H](n5cc(NC(=O)c6cncc(C#N)c6)c(C(C)(C)O)n5)CC4)CC3)c21] |
| I-268 | 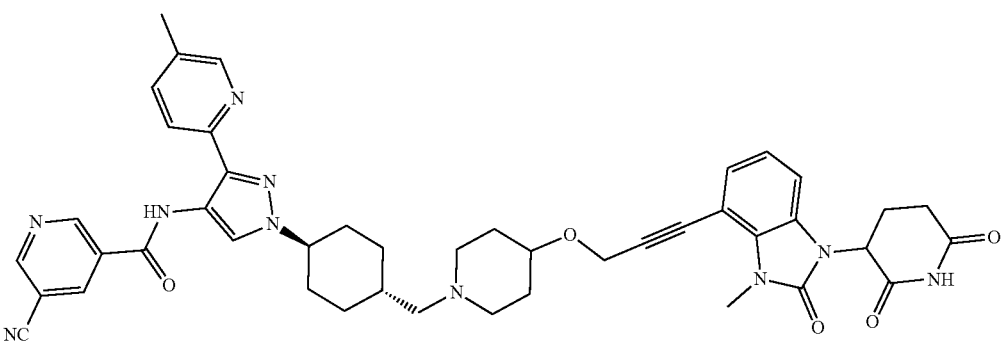 [SMILES: Cc1ccc(-c2nn([C@H]3CC[C@H](CN4CCC(OCC#Cc5cccc6c5n(C)c(=O)n6C5CCC(=O)NC5=O)CC4)CC3)cc2NC(=O)c2cncc(C#N)c2)nc1] |
| I-269 | 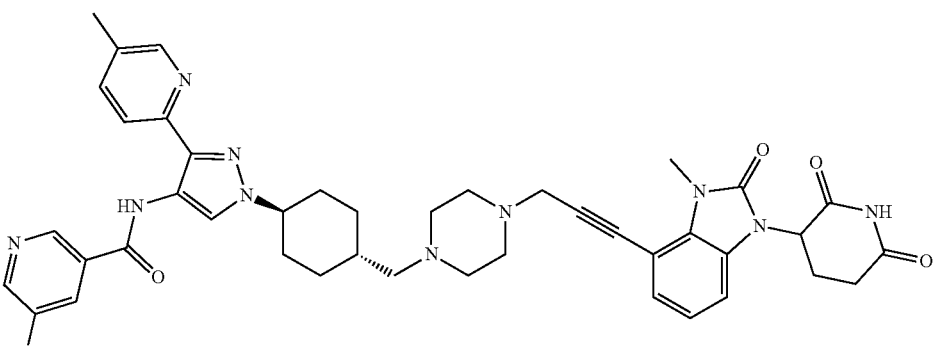 |
| I-270 | 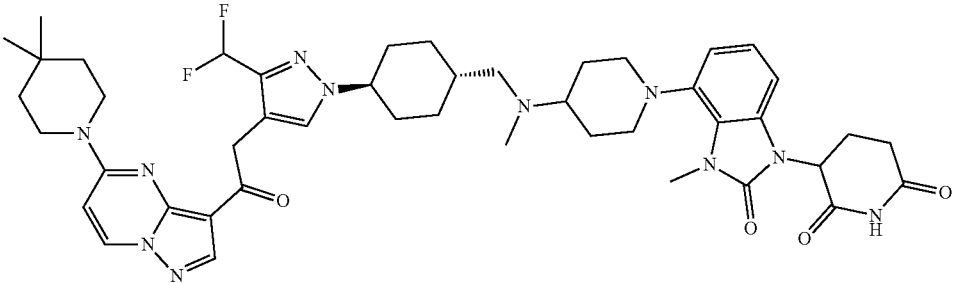 [SMILES: CN(C[C@H]1CC[C@H](n2cc(CC(=O)c3cnn4ccc(N5CCC(C)(C)CC5)nc34)c(C(F)F)n2)CC1)C1CCN(c2cccc3c2n(C)c(=O)n3C2CCC(=O)NC2=O)CC1] |

TABLE 1-continued

Exemplary Compounds

| I-# | Structure |
|---|---|
| I-271 | 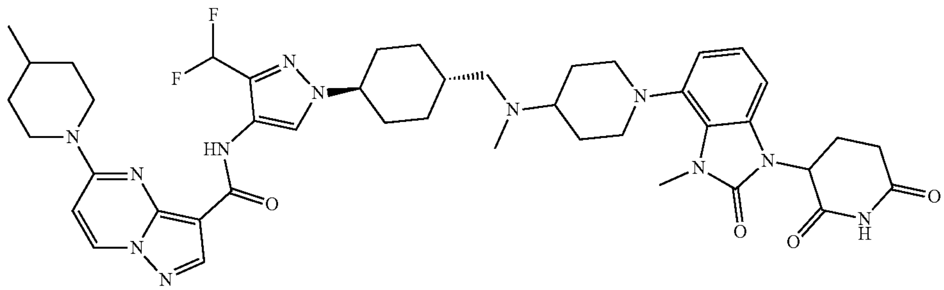 [SMILES: CC1CCN(c2ccn3ncc(C(=O)Nc4cn([C@H]5CC[C@H](CN(C)C6CCN(c7cccc8c7n(C)c(=O)n8C7CCC(=O)NC7=O)CC6)CC5)nc4C(F)F)c3n2)CC1] |
| I-272 | 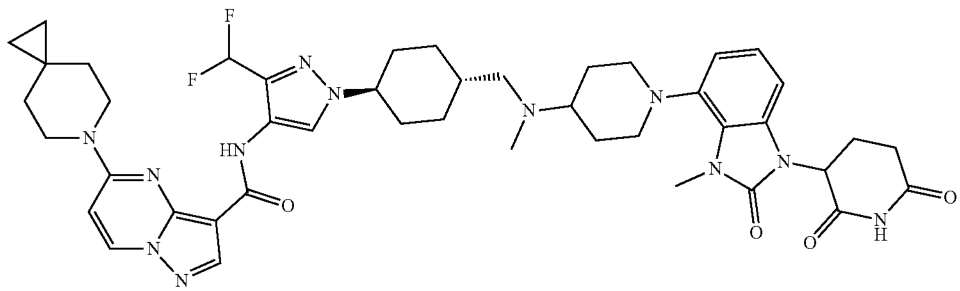 [SMILES: CN(C[C@H]1CC[C@H](n2cc(NC(=O)c3cnn4ccc(N5CCC6(CC5)CC6)nc34)c(C(F)F)n2)CC1)C1CCN(c2cccc3c2n(C)c(=O)n3C2CCC(=O)NC2=O)CC1] |
| I-273 | 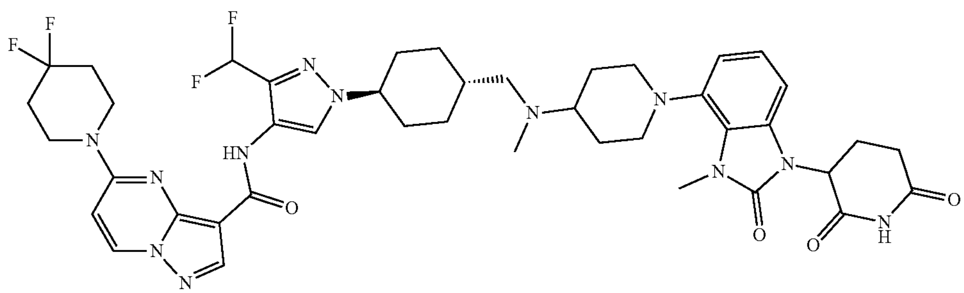 [SMILES: CN(C[C@H]1CC[C@H](n2cc(NC(=O)c3cnn4ccc(N5CCC(F)(F)CC5)nc34)c(C(F)F)n2)CC1)C1CCN(c2cccc3c2n(C)c(=O)n3C2CCC(=O)NC2=O)CC1] |
| I-274 | 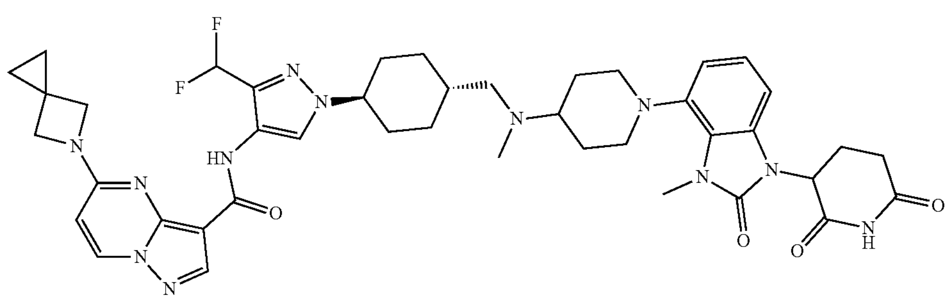 [SMILES: CN(C[C@H]1CC[C@H](n2cc(NC(=O)c3cnn4ccc(N5CC6(CC6)C5)nc34)c(C(F)F)n2)CC1)C1CCN(c2cccc3c2n(C)c(=O)n3C2CCC(=O)NC2=O)CC1] |
| I-275 | 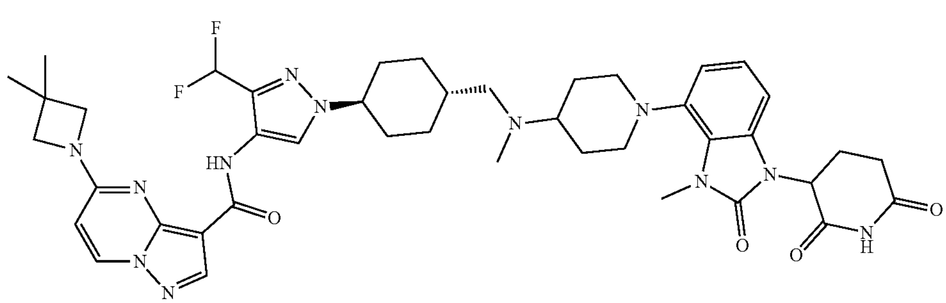 [SMILES: CN(C[C@H]1CC[C@H](n2cc(NC(=O)c3cnn4ccc(N5CC(C)(C)C5)nc34)c(C(F)F)n2)CC1)C1CCN(c2cccc3c2n(C)c(=O)n3C2CCC(=O)NC2=O)CC1] |

TABLE 1-continued

Exemplary Compounds

| I-# | Structure |
|---|---|
| I-276 | 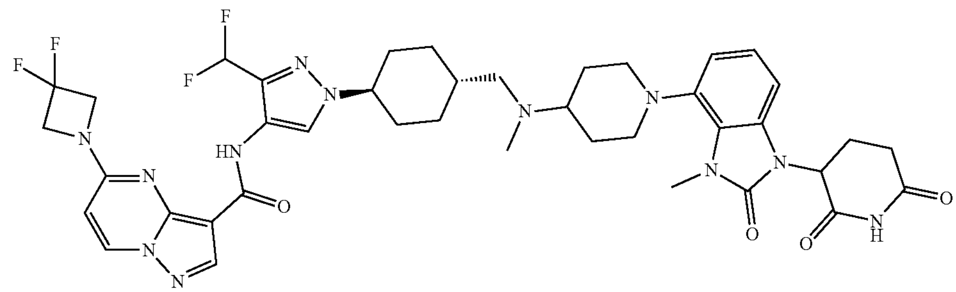 [SMILES: CN(C[C@H]1CC[C@H](n2cc(NC(=O)c3cnn4ccc(N5CC(F)(F)C5)nc34)c(C(F)F)n2)CC1)C1CCN(c2cccc3c2n(C)c(=O)n3C2CCC(=O)NC2=O)CC1] |
| I-277 | 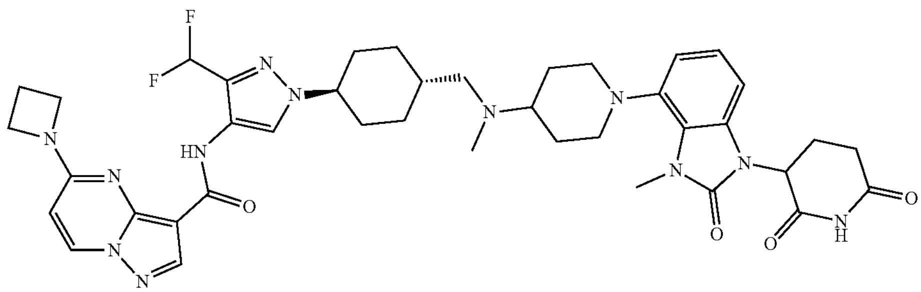 [SMILES: CN(C[C@H]1CC[C@H](n2cc(NC(=O)c3cnn4ccc(N5CCC5)nc34)c(C(F)F)n2)CC1)C1CCN(c2cccc3c2n(C)c(=O)n3C2CCC(=O)NC2=O)CC1] |
| I-278 | 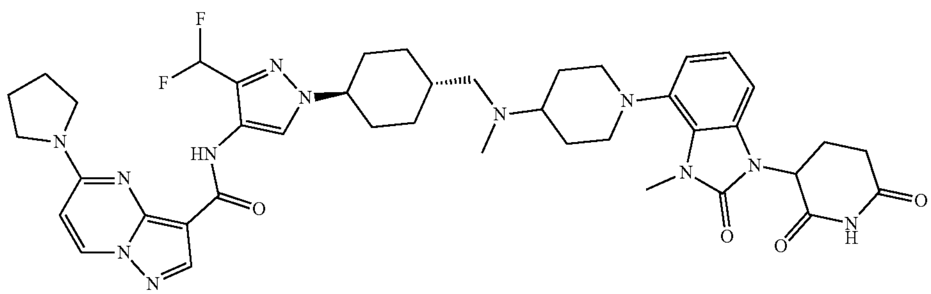 [SMILES: CN(C[C@H]1CC[C@H](n2cc(NC(=O)c3cnn4ccc(N5CCCC5)nc34)c(C(F)F)n2)CC1)C1CCN(c2cccc3c2n(C)c(=O)n3C2CCC(=O)NC2=O)CC1] |
| I-279 | 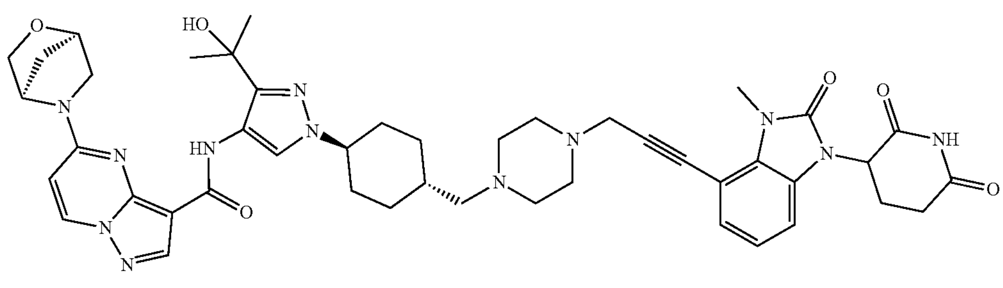 [SMILES: Cn1c(=O)n(C2CCC(=O)NC2=O)c2cccc(C#CCN3CCN(C[C@H]4CC[C@H](n5cc(NC(=O)c6cnn7ccc(N8C[C@H]9C[C@@H]8CO9)nc67)c(C(C)(C)O)n5)CC4)CC3)c21] |
| I-280 | 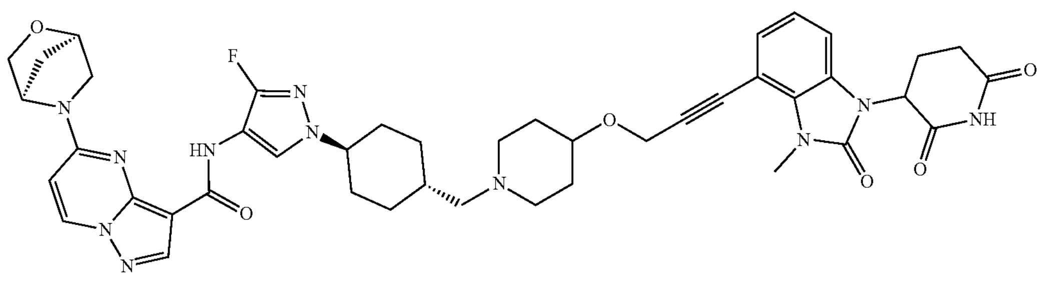 [SMILES: Cn1c(=O)n(C2CCC(=O)NC2=O)c2cccc(C#CCOC3CCN(C[C@H]4CC[C@H](n5cc(NC(=O)c6cnn7ccc(N8C[C@H]9C[C@@H]8CO9)nc67)c(F)n5)CC4)CC3)c21] |

TABLE 1-continued
Exemplary Compounds
| I-# | Structure |
|---|---|
| I-281 | 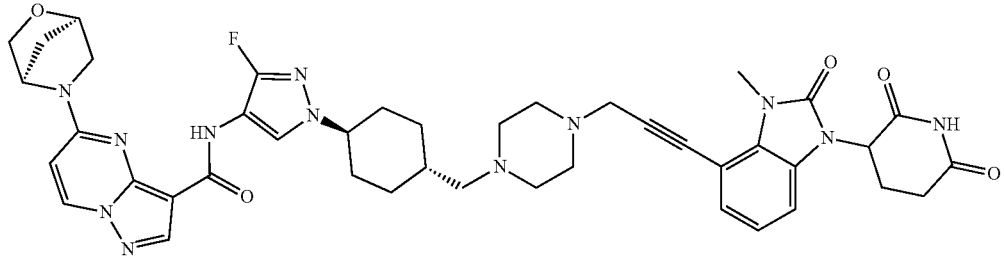 [SMILES: Cn1c(=O)n(C2CCC(=O)NC2=O)c2cccc(C#CCN3CCN(C[C@H]4CC[C@H](n5cc(NC(=O)c6cnn7ccc(N8C[C@H]9C[C@@H]8CO9)nc67)c(F)n5)CC4)CC3)c21] |
| I-282 | 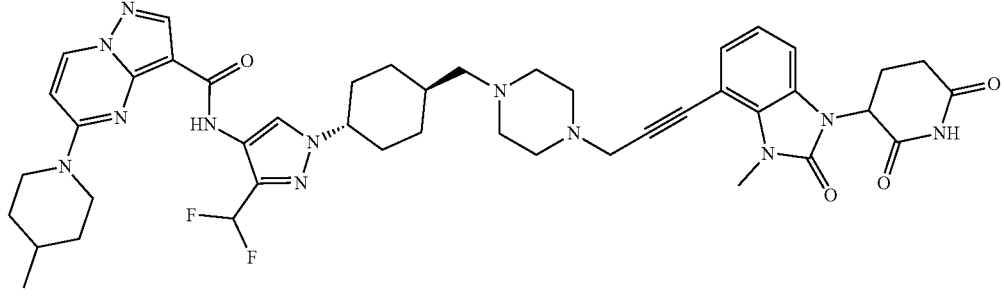 [SMILES: CC1CCN(c2ccn3ncc(C(=O)Nc4cn([C@H]5CC[C@H](CN6CCN(CC#Cc7cccc8c7n(C)c(=O)n8C7CCC(=O)NC7=O)CC6)CC5)nc4C(F)F)c3n2)CC1] |
| I-283 | 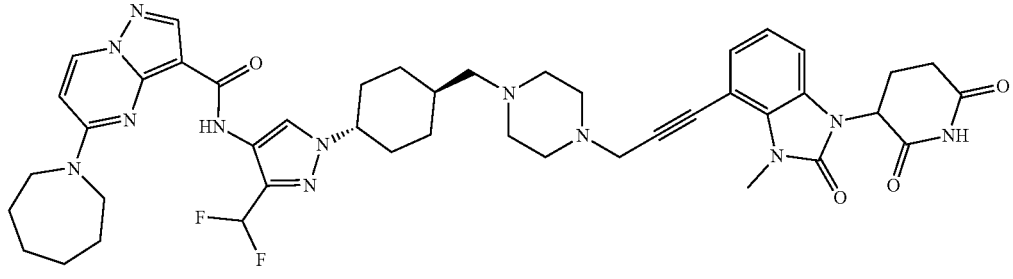 [SMILES: Cn1c(=O)n(C2CCC(=O)NC2=O)c2cccc(C#CCN3CCN(C[C@H]4CC[C@H](n5cc(NC(=O)c6cnn7ccc(N8CCCCCC8)nc67)c(C(F)F)n5)CC4)CC3)c21] |
| I-284 | 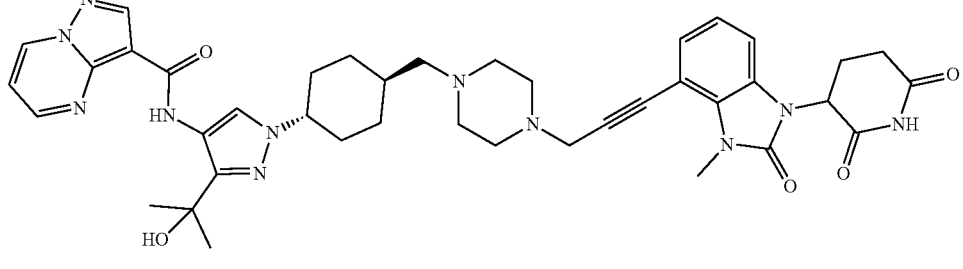 |
| I-285 | 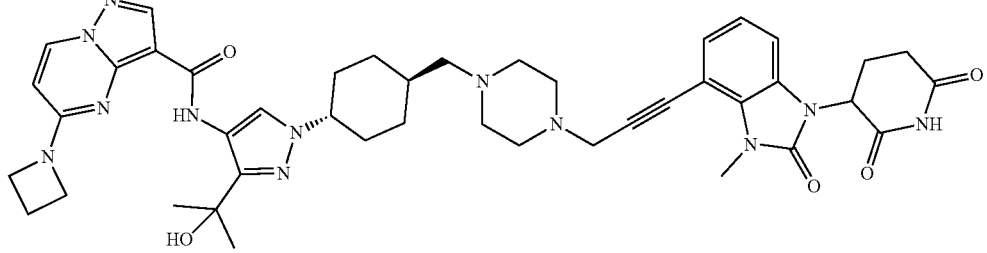 |

TABLE 1-continued

Exemplary Compounds

| I-# | Structure |
|---|---|
| I-286 | 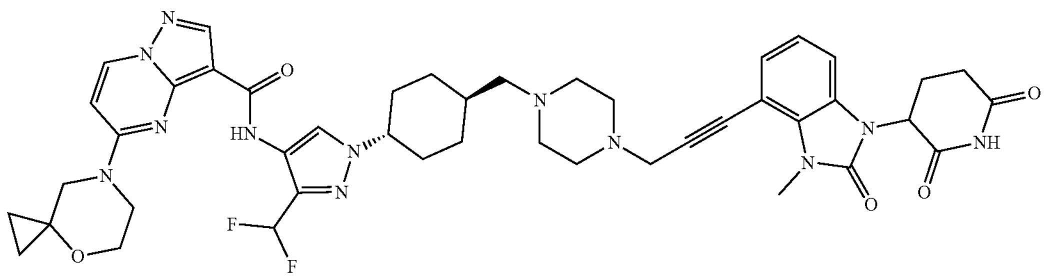 [SMILES: Cn1c(=O)n(C2CCC(=O)NC2=O)c2cccc(C#CCN3CCN(C[C@H]4CC[C@H](n5cc(NC(=O)c6cnn7ccc(N8CCOC9(CC9)C8)nc67)c(C(F)F)n5)CC4)CC3)c21] |
| I-287 | 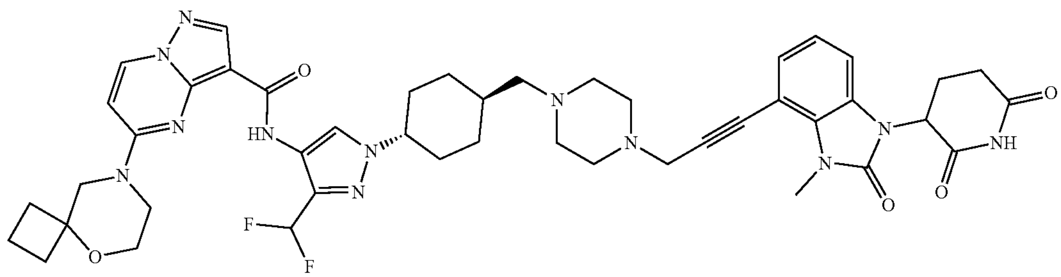 [SMILES: Cn1c(=O)n(C2CCC(=O)NC2=O)c2cccc(C#CCN3CCN(C[C@H]4CC[C@H](n5cc(NC(=O)c6cnn7ccc(N8CCOC9(CCC9)C8)nc67)c(C(F)F)n5)CC4)CC3)c21] |
| I-288 | 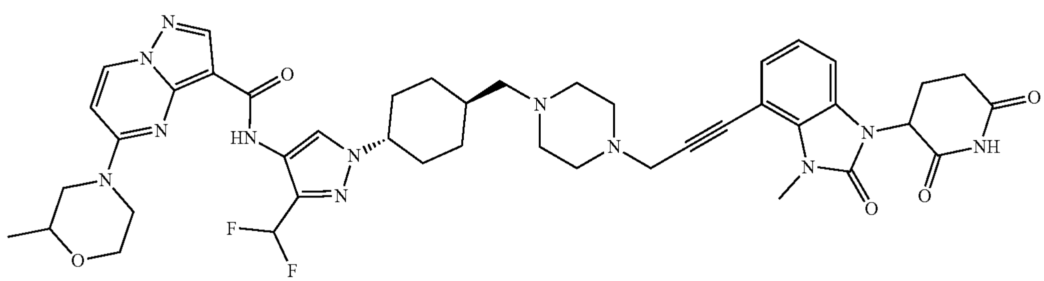 [SMILES: CC1CN(c2ccn3ncc(C(=O)Nc4cn([C@H]5CC[C@H](CN6CCN(CC#Cc7cccc8c7n(C)c(=O)n8C7CCC(=O)NC7=O)CC6)CC5)nc4C(F)F)c3n2)CCO1] |
| I-289 | 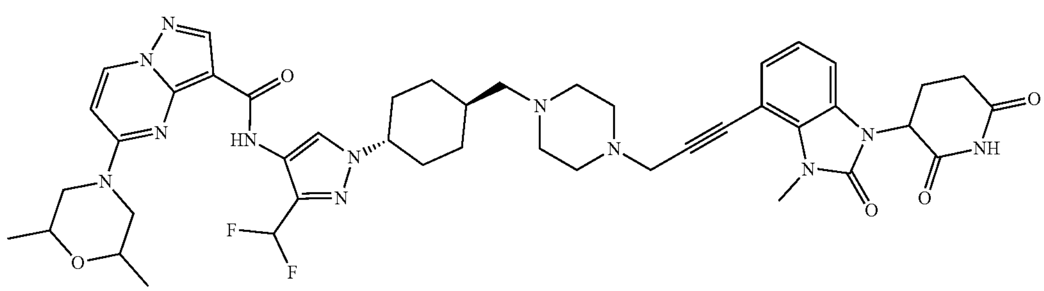 [SMILES: CC1CN(c2ccn3ncc(C(=O)Nc4cn([C@H]5CC[C@H](CN6CCN(CC#Cc7cccc8c7n(C)c(=O)n8C7CCC(=O)NC7=O)CC6)CC5)nc4C(F)F)c3n2)CC(C)O1] |
| I-290 | 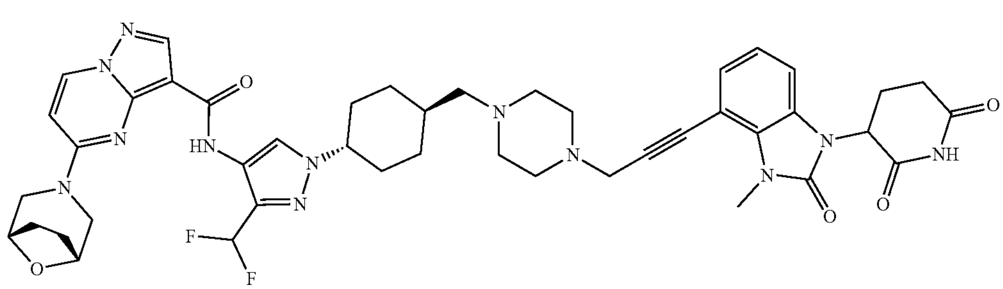 [SMILES: Cn1c(=O)n(C2CCC(=O)NC2=O)c2cccc(C#CCN3CCN(C[C@H]4CC[C@H](n5cc(NC(=O)c6cnn7ccc(N8C[C@H]9CC[C@@H](C8)O9)nc67)c(C(F)F)n5)CC4)CC3)c21] |

TABLE 1-continued

Exemplary Compounds

| I-# | Structure |
|---|---|
| I-291 | 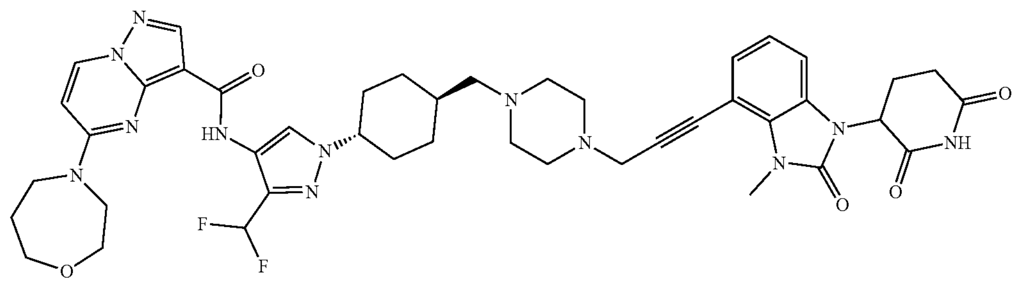 [SMILES: Cn1c(=O)n(C2CCC(=O)NC2=O)c2cccc(C#CCN3CCN(C[C@H]4CC[C@H](n5cc(NC(=O)c6cnn7ccc(N8CCCOCC8)nc67)c(C(F)F)n5)CC4)CC3)c21] |
| I-292 | 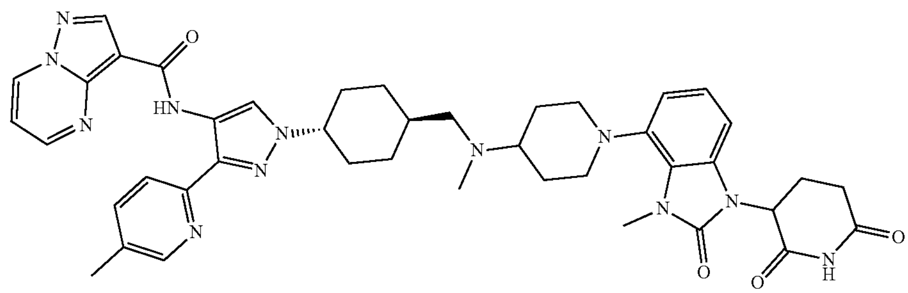 [SMILES: Cc1ccc(-c2nn([C@H]3CC[C@H](CN(C)C4CCN(c5cccc6c5n(C)c(=O)n6C5CCC(=O)NC5=O)CC4)CC3)cc2NC(=O)c2cnn3cccnc23)nc1] |
| I-293 | 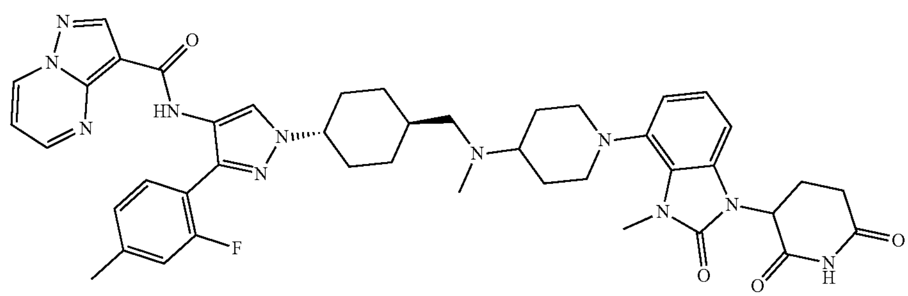 [SMILES: Cc1ccc(-c2nn([C@H]3CC[C@H](CN(C)C4CCN(c5cccc6c5n(C)c(=O)n6C5CCC(=O)NC5=O)CC4)CC3)cc2NC(=O)c2cnn3cccnc23)c(F)c1] |
| I-294 | 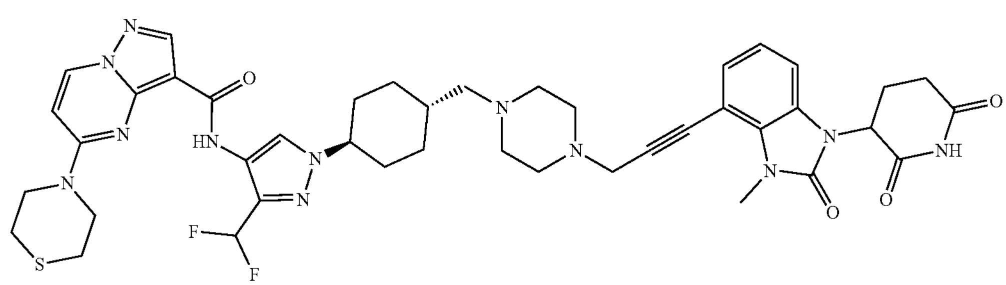 [SMILES: Cn1c(=O)n(C2CCC(=O)NC2=O)c2cccc(C#CCN3CCN(C[C@H]4CC[C@H](n5cc(NC(=O)c6cnn7ccc(N8CCSCC8)nc67)c(C(F)F)n5)CC4)CC3)c21] |
| I-295 | 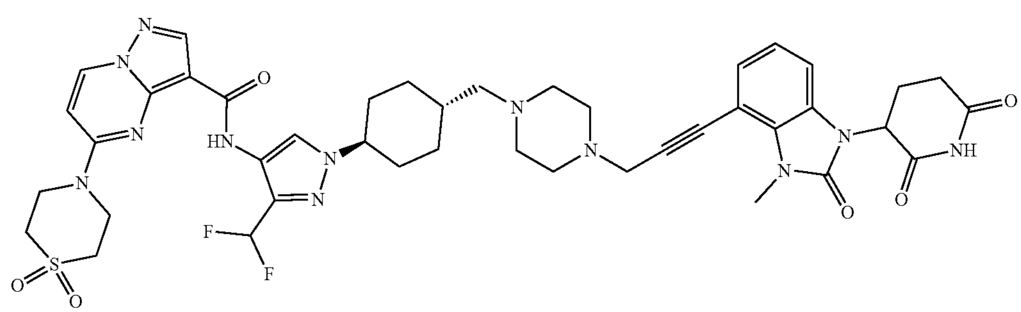 [SMILES: Cn1c(=O)n(C2CCC(=O)NC2=O)c2cccc(C#CCN3CCN(C[C@H]4CC[C@H](n5cc(NC(=O)c6cnn7ccc(N8CCS(=O)(=O)CC8)nc67)c(C(F)F)n5)CC4)CC3)c21] |

TABLE 1-continued

Exemplary Compounds

| I-# | Structure |
|---|---|
| I-296 | 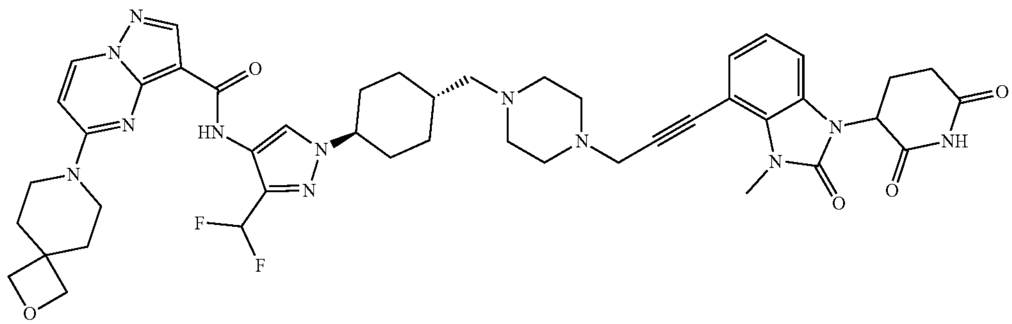 [SMILES: Cn1c(=O)n(C2CCC(=O)NC2=O)c2cccc(C#CCN3CCN(C[C@H]4CC[C@H](n5cc(NC(=O)c6cnn7ccc(N8CCC9(CC8)COC9)nc67)c(C(F)F)n5)CC4)CC3)c21] |
| I-297 | 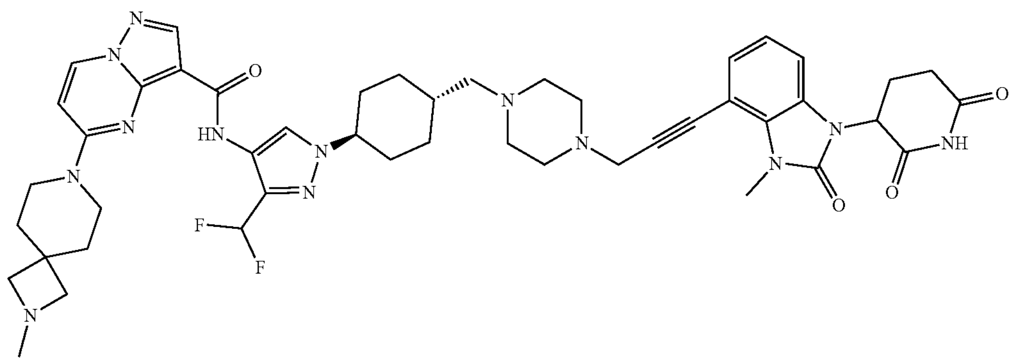 [SMILES: CN1CC2(CCN(c3ccn4ncc(C(=O)Nc5cn([C@H]6CC[C@H](CN7CCN(CC#Cc8cccc9c8n(C)c(=O)n9C8CCC(=O)NC8=O)CC7)CC6)nc5C(F)F)c4n3)CC2)C1] |
| I-298 | 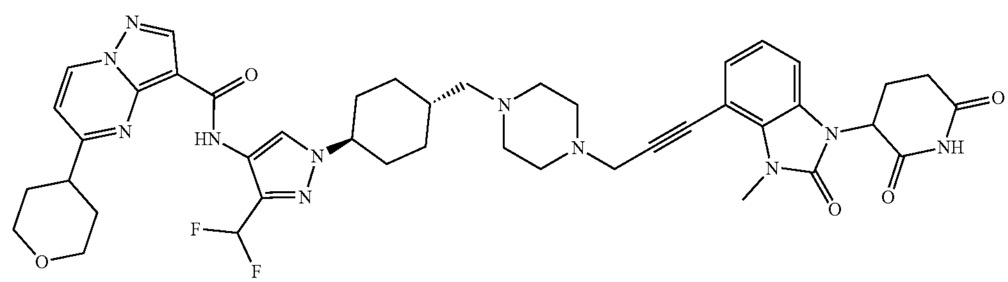 [SMILES: Cn1c(=O)n(C2CCC(=O)NC2=O)c2cccc(C#CCN3CCN(C[C@H]4CC[C@H](n5cc(NC(=O)c6cnn7ccc(C8CCOCC8)nc67)c(C(F)F)n5)CC4)CC3)c21] |
| I-299 | 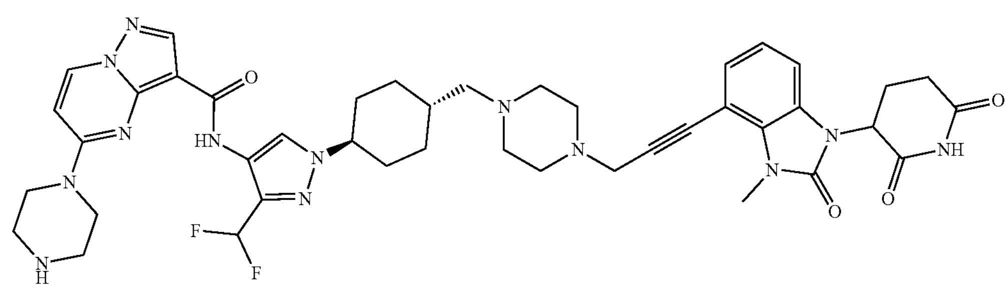 [SMILES: Cn1c(=O)n(C2CCC(=O)NC2=O)c2cccc(C#CCN3CCN(C[C@H]4CC[C@H](n5cc(NC(=O)c6cnn7ccc(N8CCNCC8)nc67)c(C(F)F)n5)CC4)CC3)c21] |
| I-300 | 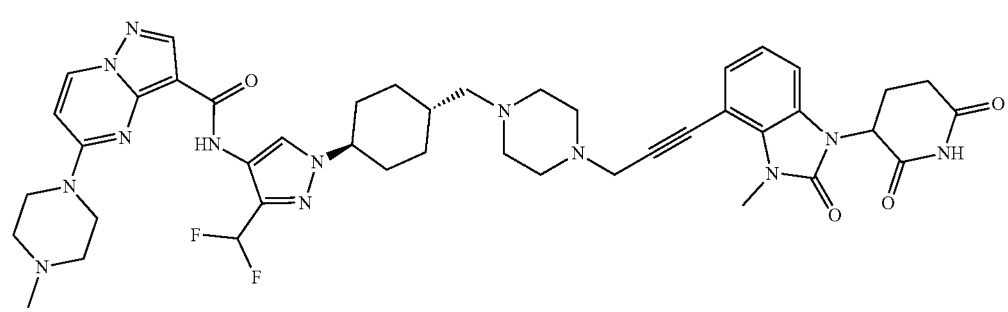 [SMILES: CN1CCN(c2ccn3ncc(C(=O)Nc4cn([C@H]5CC[C@H](CN6CCN(CC#Cc7cccc8c7n(C)c(=O)n8C7CCC(=O)NC7=O)CC6)CC5)nc4C(F)F)c3n2)CC1] |

TABLE 1-continued

Exemplary Compounds

| I-# | Structure |
|---|---|
| I-301 | 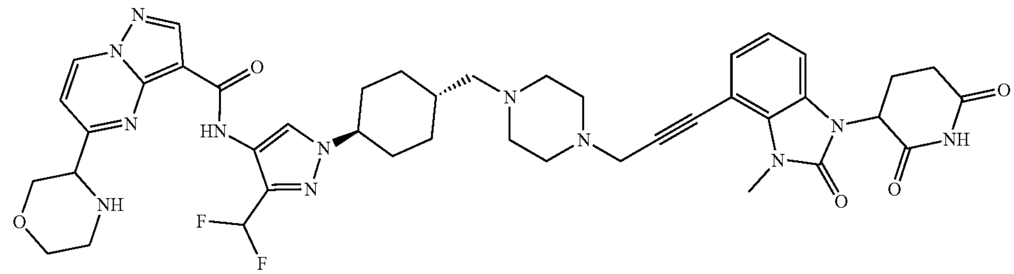 [SMILES: Cn1c(=O)n(C2CCC(=O)NC2=O)c2cccc(C#CCN3CCN(C[C@H]4CC[C@H](n5cc(NC(=O)c6cnn7ccc(C8COCCN8)nc67)c(C(F)F)n5)CC4)CC3)c21] |
| I-302 | 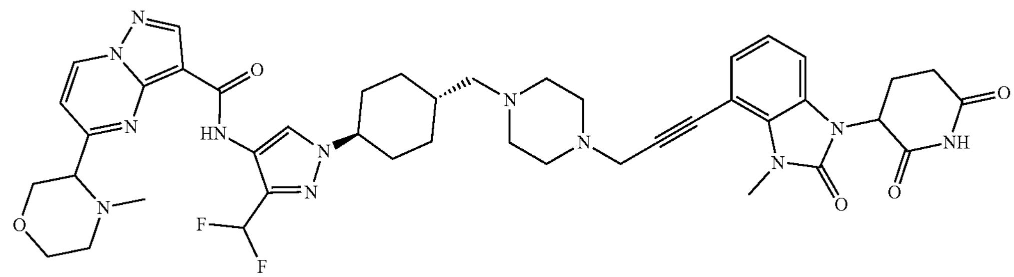 [SMILES: CN1CCOCC1c1ccn2ncc(C(=O)Nc3cn([C@H]4CC[C@H](CN5CCN(CC#Cc6cccc7c6n(C)c(=O)n7C6CCC(=O)NC6=O)CC5)CC4)nc3C(F)F)c2n1] |
| I-303 | 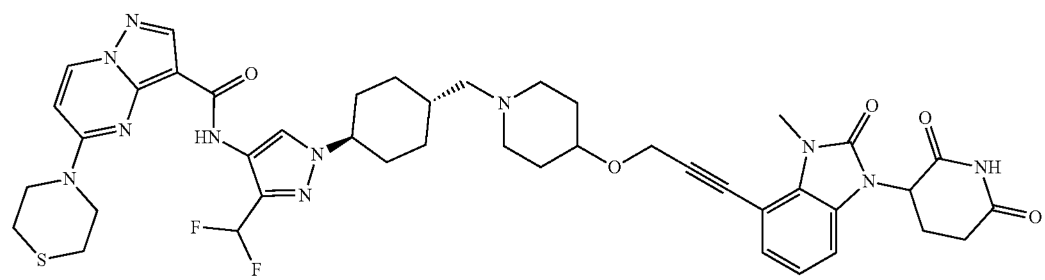 |
| I-304 | 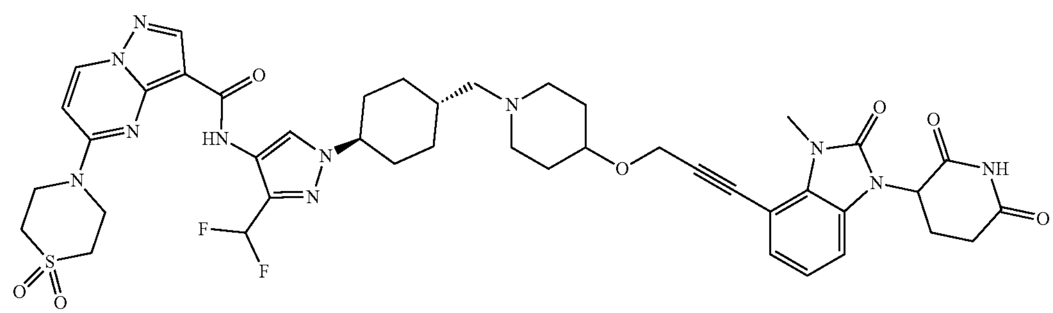 [SMILES: Cn1c(=O)n(C2CCC(=O)NC2=O)c2cccc(C#CCOC3CCN(C[C@H]4CC[C@H](n5cc(NC(=O)c6cnn7ccc(N8CCS(=O)(=O)CC8)nc67)c(C(F)F)n5)CC4)CC3)c21] |
| I-305 | 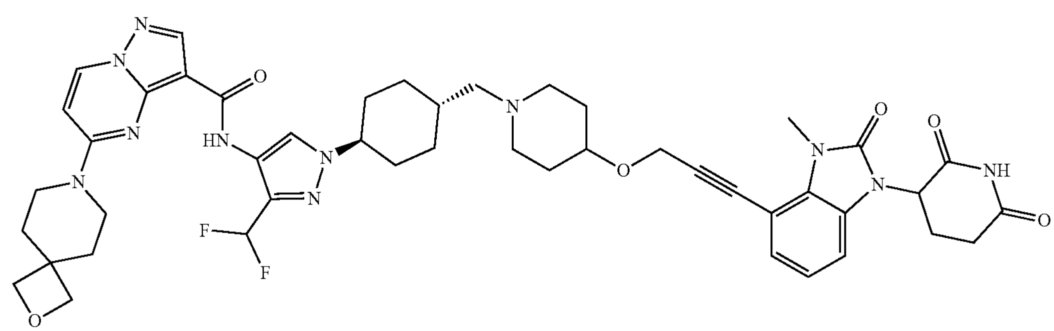 [SMILES: Cn1c(=O)n(C2CCC(=O)NC2=O)c2cccc(C#CCOC3CCN(C[C@H]4CC[C@H](n5cc(NC(=O)c6cnn7ccc(N8CCC9(CC8)COC9)nc67)c(C(F)F)n5)CC4)CC3)c21] |

TABLE 1-continued

Exemplary Compounds

| I-# | Structure |
|---|---|
| I-306 | 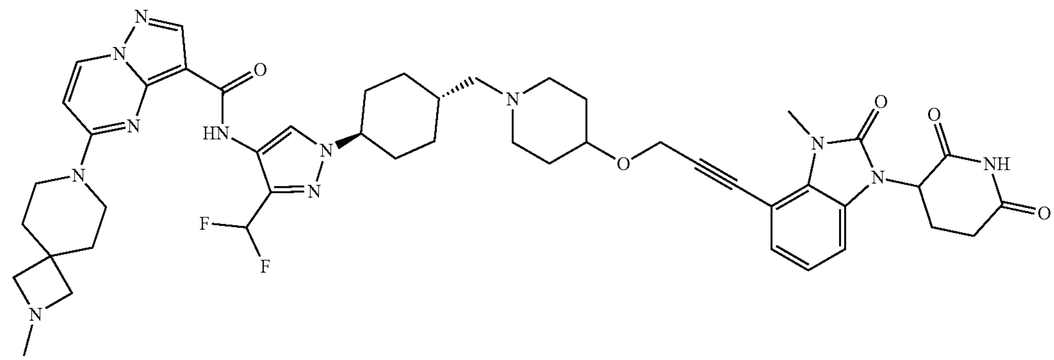 [SMILES: CN1CC2(CCN(c3ccn4ncc(C(=O)Nc5cn([C@H]6CC[C@H](CN7CCC(OCC#Cc8cccc9c8n(C)c(=O)n9C8CCC(=O)NC8=O)CC7)CC6)nc5C(F)F)c4n3)CC2)C1] |
| I-307 | 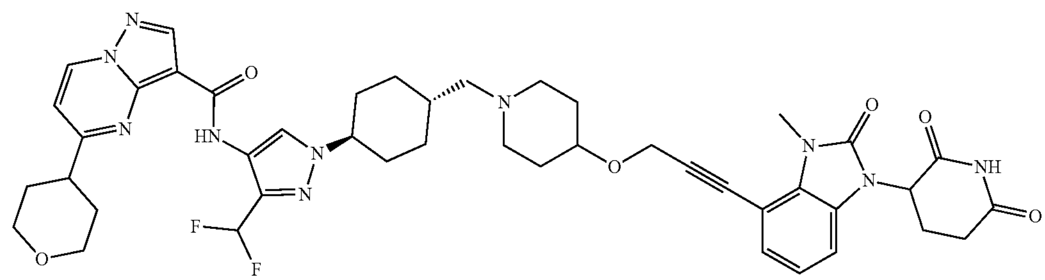 [SMILES: Cn1c(=O)n(C2CCC(=O)NC2=O)c2cccc(C#CCOC3CCN(C[C@H]4CC[C@H](n5cc(NC(=O)c6cnn7ccc(C8CCOCC8)nc67)c(C(F)F)n5)CC4)CC3)c21] |
| I-308 | 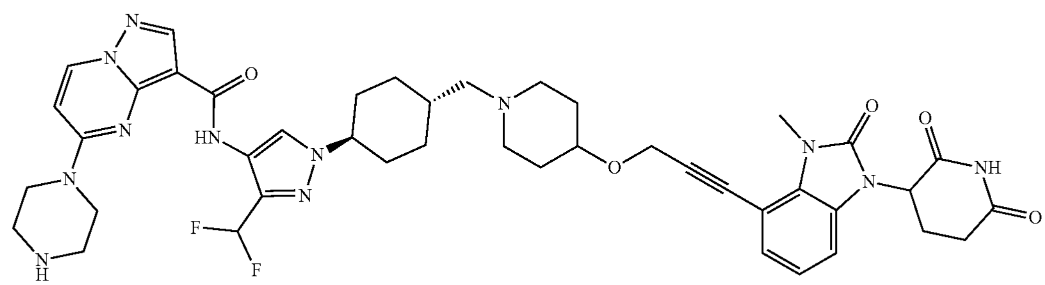 [SMILES: Cn1c(=O)n(C2CCC(=O)NC2=O)c2cccc(C#CCOC3CCN(C[C@H]4CC[C@H](n5cc(NC(=O)c6cnn7ccc(N8CCNCC8)nc67)c(C(F)F)n5)CC4)CC3)c21] |
| I-309 | 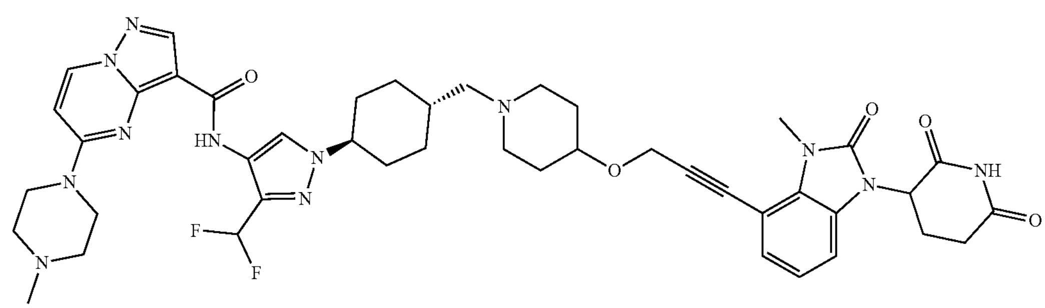 [SMILES: CN1CCN(c2ccn3ncc(C(=O)Nc4cn([C@H]5CC[C@H](CN6CCC(OCC#Cc7cccc8c7n(C)c(=O)n8C7CCC(=O)NC7=O)CC6)CC5)nc4C(F)F)c3n2)CC1] |
| I-310 | 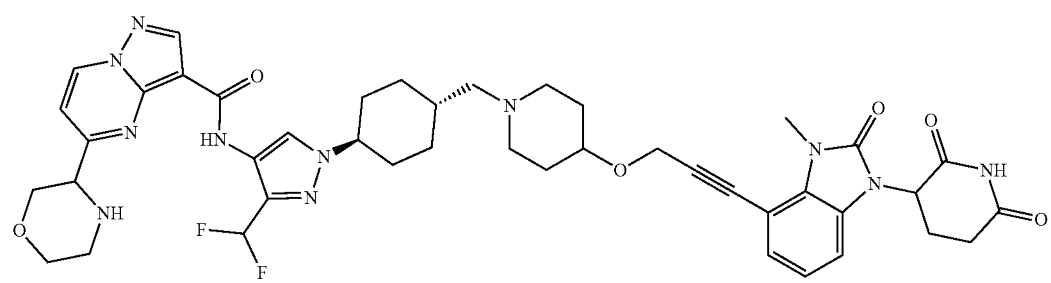 [SMILES: Cn1c(=O)n(C2CCC(=O)NC2=O)c2cccc(C#CCOC3CCN(C[C@H]4CC[C@H](n5cc(NC(=O)c6cnn7ccc(C8COCCN8)nc67)c(C(F)F)n5)CC4)CC3)c21] |

TABLE 1-continued

Exemplary Compounds

| I-# | Structure |
|---|---|
| I-311 | 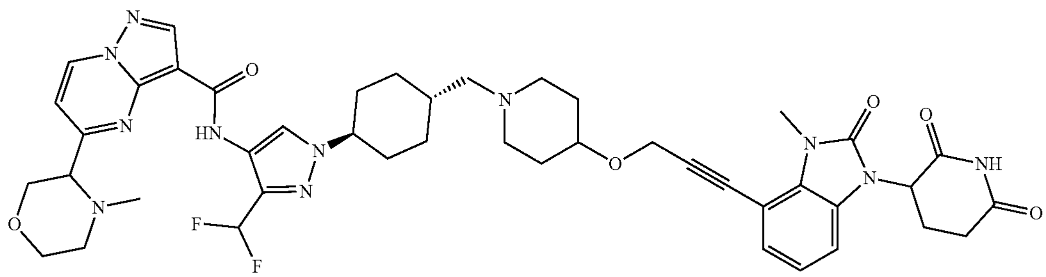 [SMILES: CN1CCOCC1c1ccn2ncc(C(=O)Nc3cn([C@H]4CC[C@H](CN5CCC(OCC#Cc6cccc7c6n(C)c(=O)n7C6CCC(=O)NC6=O)CC5)CC4)nc3C(F)F)c2n1] |
| I-312 | 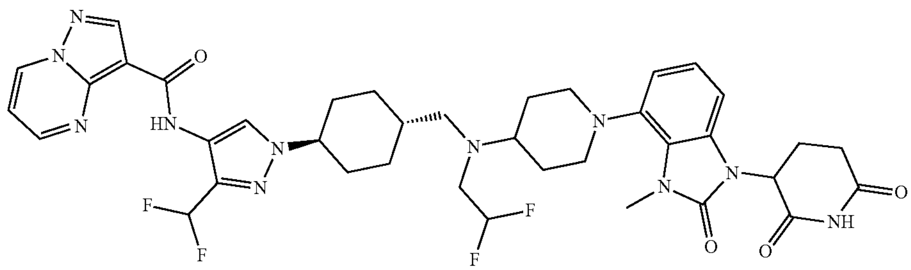 [SMILES: Cn1c(=O)n(C2CCC(=O)NC2=O)c2cccc(N3CCC(N(CC(F)F)C[C@H]4CC[C@H](n5cc(NC(=O)c6cnn7cccnc67)c(C(F)F)n5)CC4)CC3)c21] |
| I-313 | 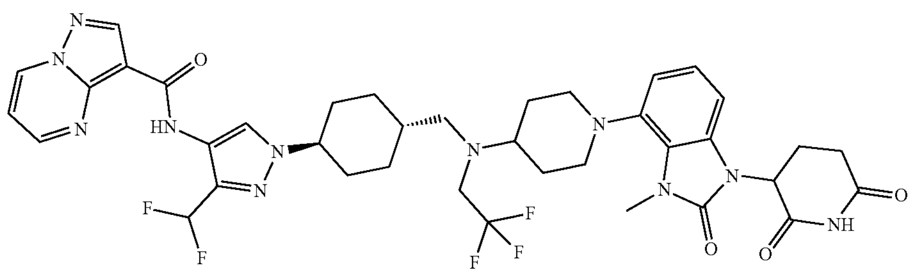 [SMILES: Cn1c(=O)n(C2CCC(=O)NC2=O)c2cccc(N3CCC(N(CC(F)(F)F)C[C@H]4CC[C@H](n5cc(NC(=O)c6cnn7cccnc67)c(C(F)F)n5)CC4)CC3)c21] |
| I-314 | 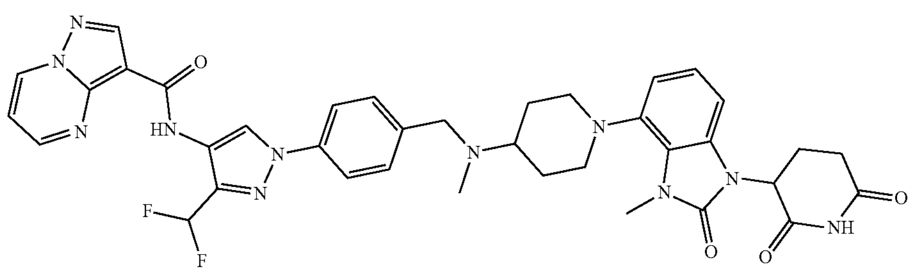 [SMILES: CN(Cc1ccc(-n2cc(NC(=O)c3cnn4cccnc34)c(C(F)F)n2)cc1)C1CCN(c2cccc3c2n(C)c(=O)n3C2CCC(=O)NC2=O)CC1] |
| I-315 | 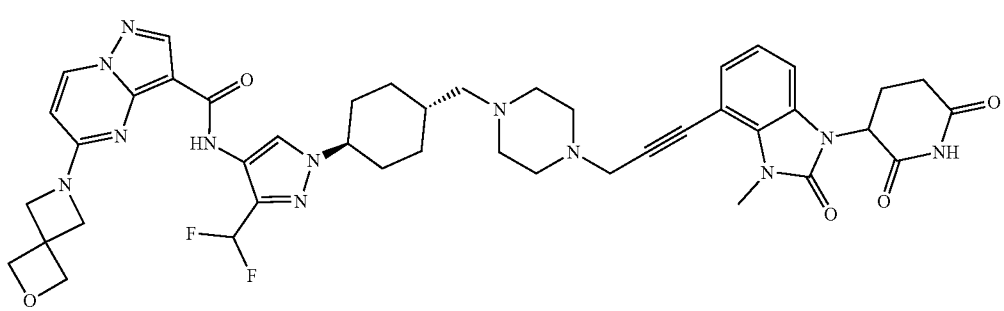 [SMILES: Cn1c(=O)n(C2CCC(=O)NC2=O)c2cccc(C#CCN3CCN(C[C@H]4CC[C@H](n5cc(NC(=O)c6cnn7ccc(N8CC9(COC9)C8)nc67)c(C(F)F)n5)CC4)CC3)c21] |

TABLE 1-continued
Exemplary Compounds
| I-# | Structure |
|---|---|
| I-316 | 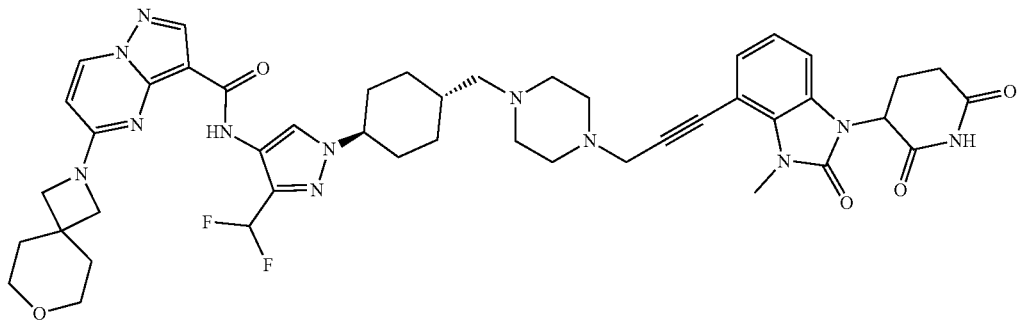 [SMILES: Cn1c(=O)n(C2CCC(=O)NC2=O)c2cccc(C#CCN3CCN(C[C@H]4CC[C@H](n5cc(NC(=O)c6cnn7ccc(N8CC9(CCOCC9)C8)nc67)c(C(F)F)n5)CC4)CC3)c21] |
| I-317 | 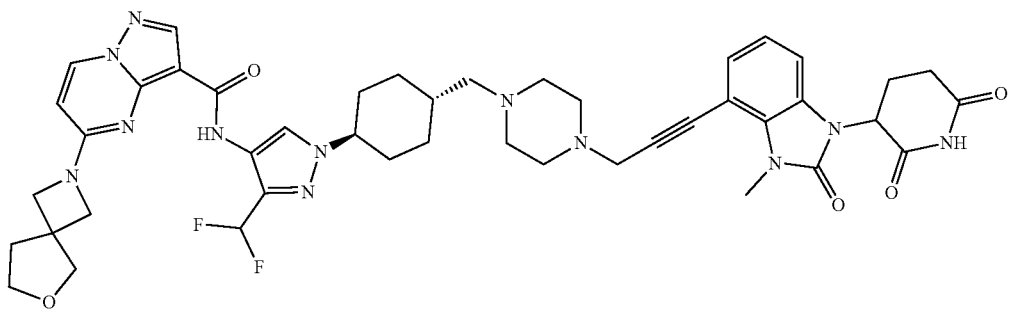 [SMILES: Cn1c(=O)n(C2CCC(=O)NC2=O)c2cccc(C#CCN3CCN(C[C@H]4CC[C@H](n5cc(NC(=O)c6cnn7ccc(N8CC9(CCOC9)C8)nc67)c(C(F)F)n5)CC4)CC3)c21] |
| I-318 | 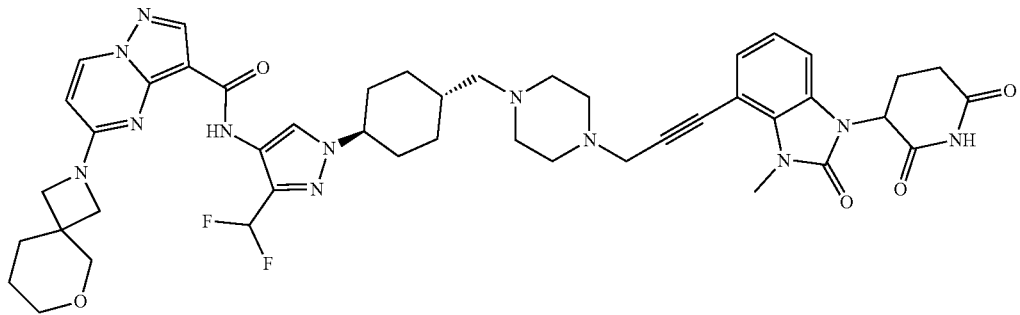 [SMILES: Cn1c(=O)n(C2CCC(=O)NC2=O)c2cccc(C#CCN3CCN(C[C@H]4CC[C@H](n5cc(NC(=O)c6cnn7ccc(N8CC9(CCCOC9)C8)nc67)c(C(F)F)n5)CC4)CC3)c21] |
| I-319 | 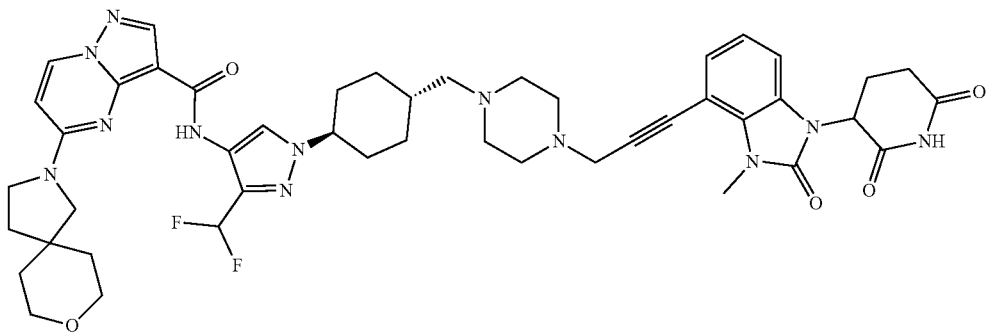 [SMILES: Cn1c(=O)n(C2CCC(=O)NC2=O)c2cccc(C#CCN3CCN(C[C@H]4CC[C@H](n5cc(NC(=O)c6cnn7ccc(N8CCC9(CCOCC9)C8)nc67)c(C(F)F)n5)CC4)CC3)c21] |

TABLE 1-continued

Exemplary Compounds

| I-# | Structure |
|---|---|
| I-320 | 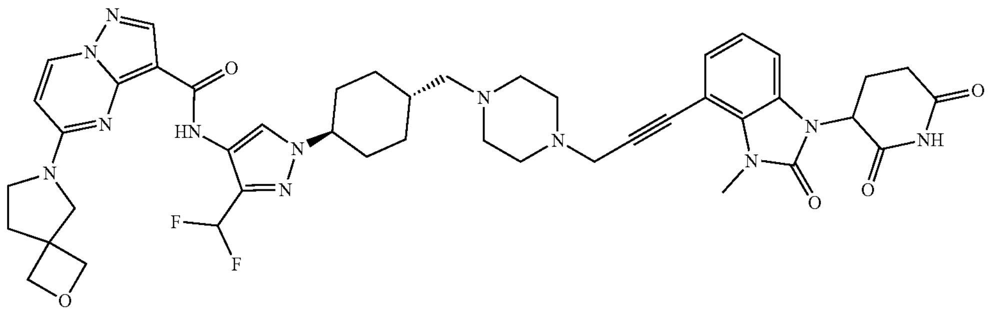 [SMILES: Cn1c(=O)n(C2CCC(=O)NC2=O)c2cccc(C#CCN3CCN(C[C@H]4CC[C@H](n5cc(NC(=O)c6cnn7ccc(N8CCC9(COC9)C8)nc67)c(C(F)F)n5)CC4)CC3)c21] |
| I-321 | 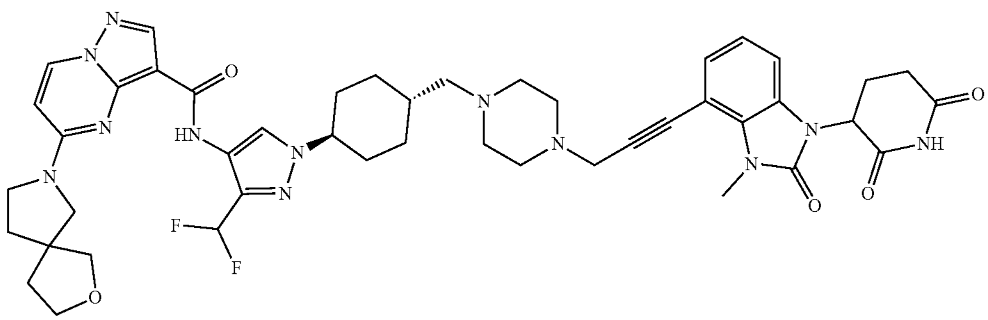 [SMILES: Cn1c(=O)n(C2CCC(=O)NC2=O)c2cccc(C#CCN3CCN(C[C@H]4CC[C@H](n5cc(NC(=O)c6cnn7ccc(N8CCC9(CCOC9)C8)nc67)c(C(F)F)n5)CC4)CC3)c21] |
| I-322 | 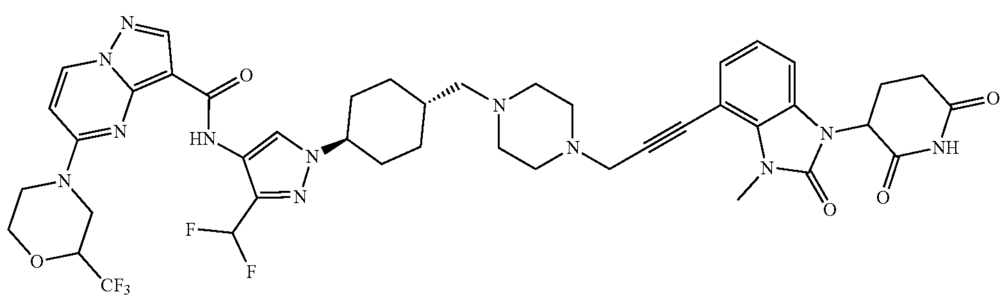 [SMILES: Cn1c(=O)n(C2CCC(=O)NC2=O)c2cccc(C#CCN3CCN(C[C@H]4CC[C@H](n5cc(NC(=O)c6cnn7ccc(N8CCOC(C(F)(F)F)C8)nc67)c(C(F)F)n5)CC4)CC3)c21] |
| I-323 | 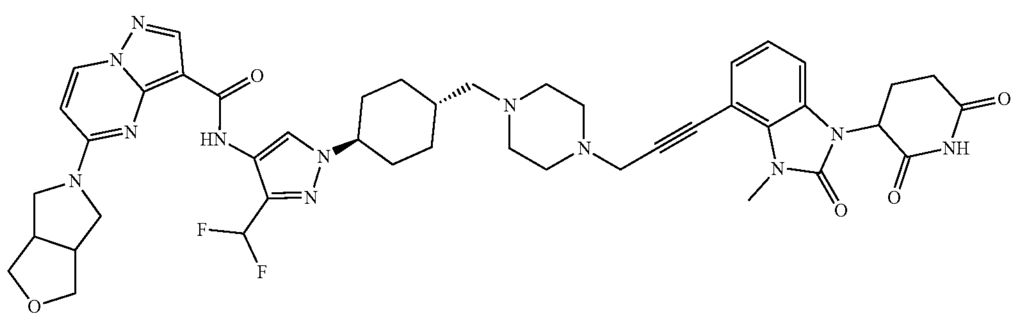 [SMILES: Cn1c(=O)n(C2CCC(=O)NC2=O)c2cccc(C#CCN3CCN(C[C@H]4CC[C@H](n5cc(NC(=O)c6cnn7ccc(N8CC9COCC9C8)nc67)c(C(F)F)n5)CC4)CC3)c21] |
| I-324 | 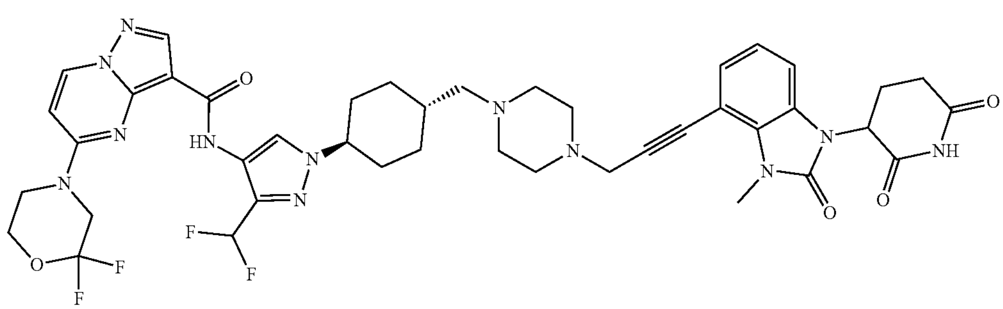 [SMILES: Cn1c(=O)n(C2CCC(=O)NC2=O)c2cccc(C#CCN3CCN(C[C@H]4CC[C@H](n5cc(NC(=O)c6cnn7ccc(N8CCOC(F)(F)C8)nc67)c(C(F)F)n5)CC4)CC3)c21] |

TABLE 1-continued
Exemplary Compounds
| I-# | Structure |
|---|---|
| I-325 | 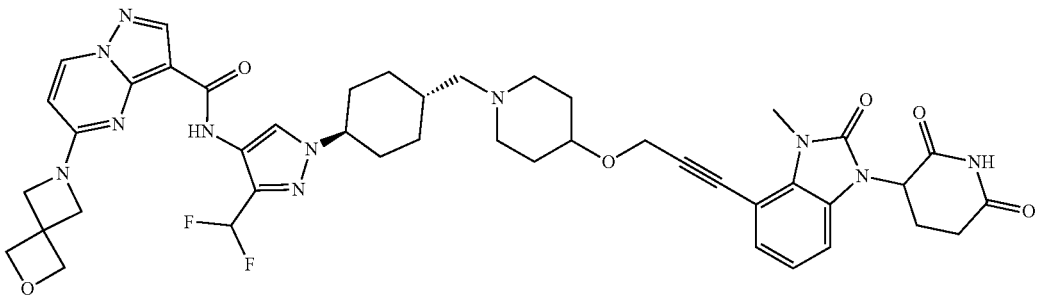 [SMILES: Cn1c(=O)n(C2CCC(=O)NC2=O)c2cccc(C#CCOC3CCN(C[C@H]4CC[C@H](n5cc(NC(=O)c6cnn7ccc(N8CC9(COC9)C8)nc67)c(C(F)F)n5)CC4)CC3)c21] |
| I-326 | 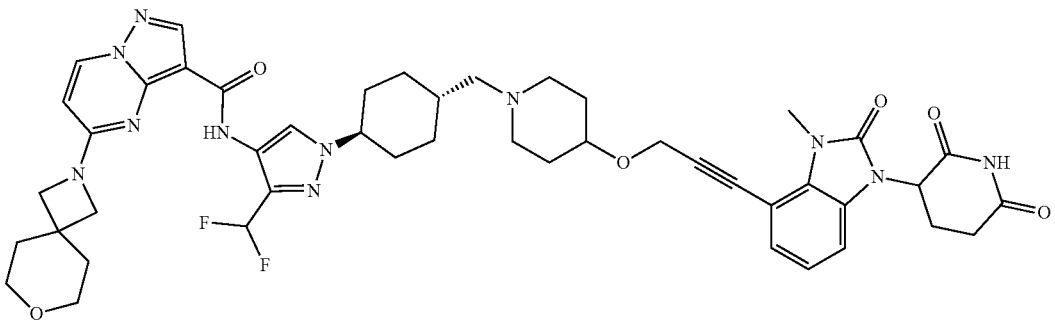 [SMILES: Cn1c(=O)n(C2CCC(=O)NC2=O)c2cccc(C#CCOC3CCN(C[C@H]4CC[C@H](n5cc(NC(=O)c6cnn7ccc(N8CC9(CCOCC9)C8)nc67)c(C(F)F)n5)CC4)CC3)c21] |
| I-327 | 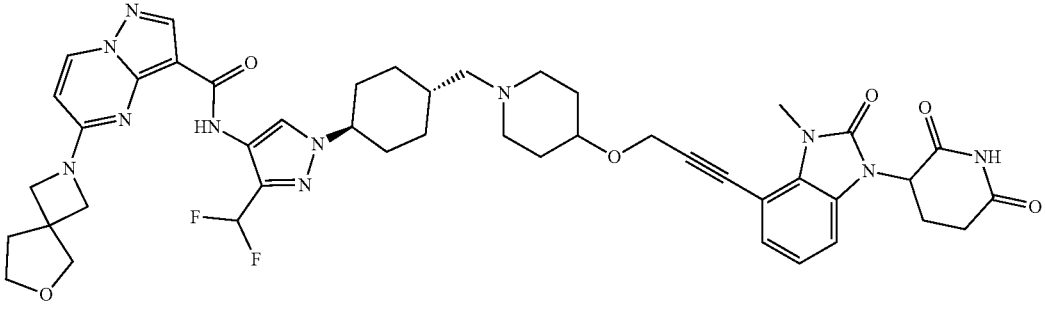 [SMILES: Cn1c(=O)n(C2CCC(=O)NC2=O)c2cccc(C#CCOC3CCN(C[C@H]4CC[C@H](n5cc(NC(=O)c6cnn7ccc(N8CC9(CCOC9)C8)nc67)c(C(F)F)n5)CC4)CC3)c21] |
| I-328 | 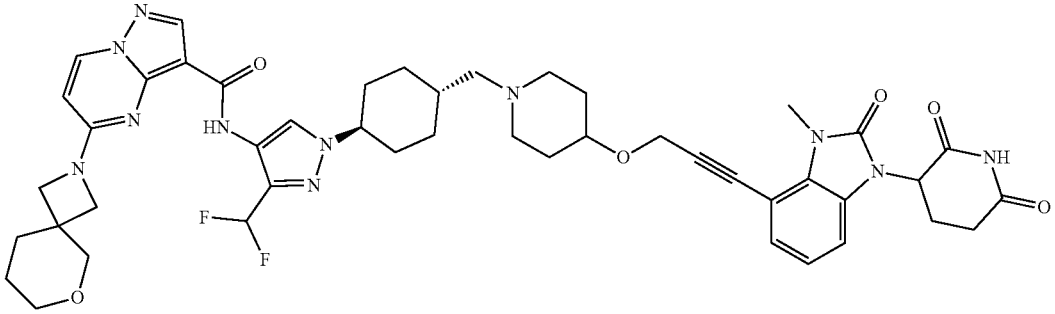 [SMILES: Cn1c(=O)n(C2CCC(=O)NC2=O)c2cccc(C#CCOC3CCN(C[C@H]4CC[C@H](n5cc(NC(=O)c6cnn7ccc(N8CC9(CCCOC9)C8)nc67)c(C(F)F)n5)CC4)CC3)c21] |

TABLE 1-continued

Exemplary Compounds

| I-# | Structure |
|---|---|
| I-329 | 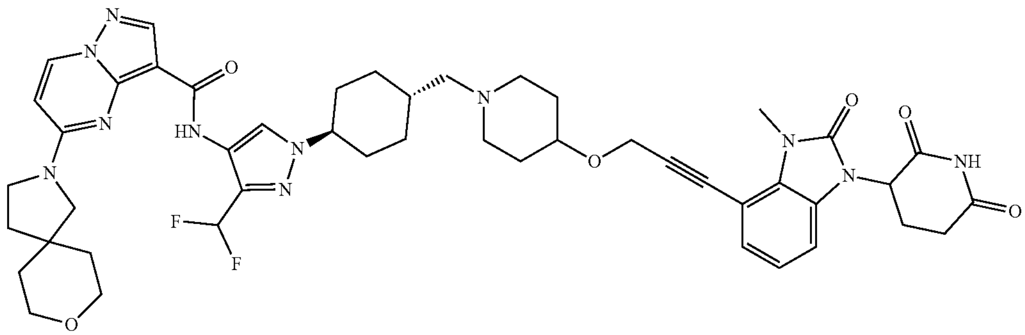 [SMILES: Cn1c(=O)n(C2CCC(=O)NC2=O)c2cccc(C#CCOC3CCN(C[C@H]4CC[C@H](n5cc(NC(=O)c6cnn7ccc(N8CCC9(CCOCC9)C8)nc67)c(C(F)F)n5)CC4)CC3)c21] |
| I-330 | 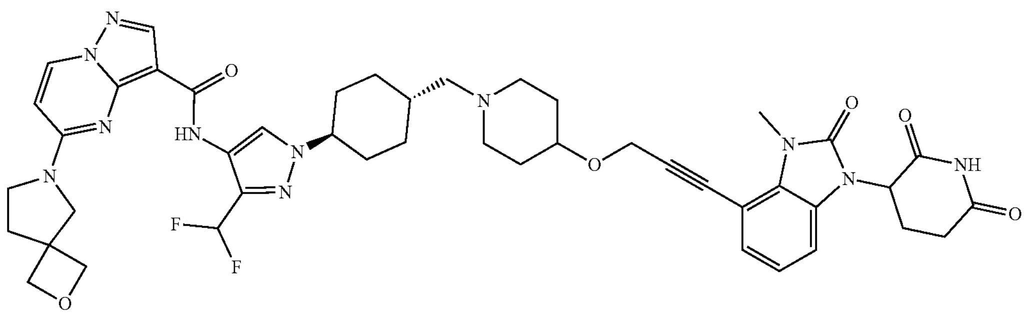 [SMILES: Cn1c(=O)n(C2CCC(=O)NC2=O)c2cccc(C#CCOC3CCN(C[C@H]4CC[C@H](n5cc(NC(=O)c6cnn7ccc(N8CCC9(COC9)C8)nc67)c(C(F)F)n5)CC4)CC3)c21] |
| I-331 | 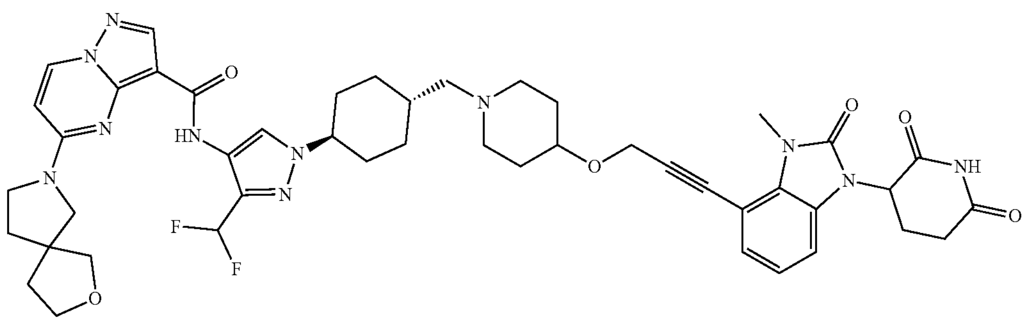 [SMILES: Cn1c(=O)n(C2CCC(=O)NC2=O)c2cccc(C#CCOC3CCN(C[C@H]4CC[C@H](n5cc(NC(=O)c6cnn7ccc(N8CCC9(CCOC9)C8)nc67)c(C(F)F)n5)CC4)CC3)c21] |
| I-332 | 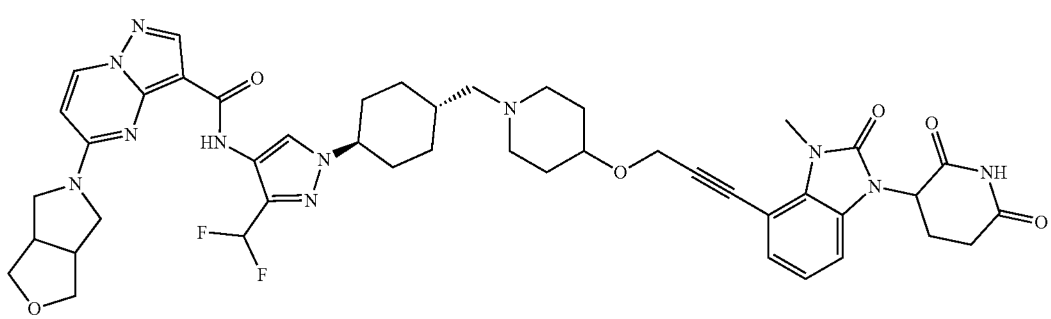 [SMILES: Cn1c(=O)n(C2CCC(=O)NC2=O)c2cccc(C#CCOC3CCN(C[C@H]4CC[C@H](n5cc(NC(=O)c6cnn7ccc(N8CC9COCC9C8)nc67)c(C(F)F)n5)CC4)CC3)c21] |
| I-333 | 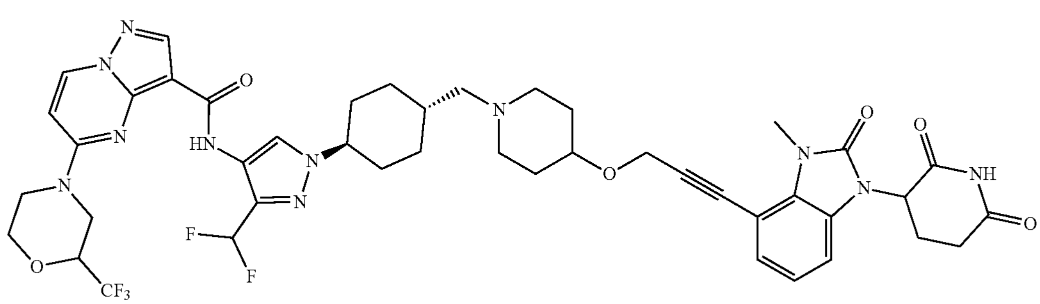 [SMILES: Cn1c(=O)n(C2CCC(=O)NC2=O)c2cccc(C#CCOC3CCN(C[C@H]4CC[C@H](n5cc(NC(=O)c6cnn7ccc(N8CCOC(C(F)(F)F)C8)nc67)c(C(F)F)n5)CC4)CC3)c21] |

TABLE 1-continued

Exemplary Compounds

| I-# | Structure |
|---|---|
| I-334 | 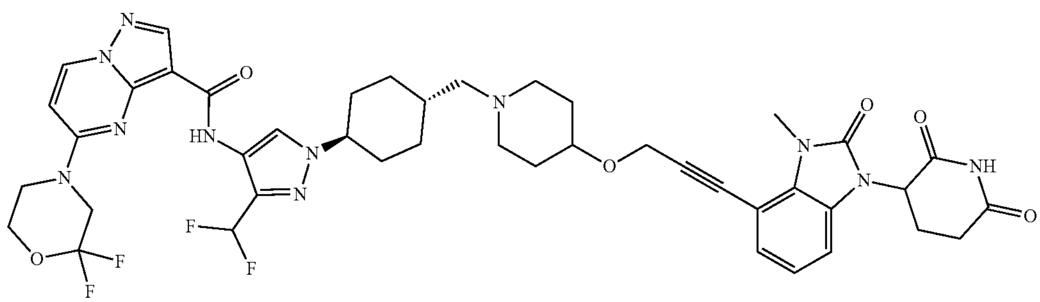 [SMILES: Cn1c(=O)n(C2CCC(=O)NC2=O)c2cccc(C#CCOC3CCN(C[C@H]4CC[C@H](n5cc(NC(=O)c6cnn7ccc(N8CCOC(F)(F)C8)nc67)c(C(F)F)n5)CC4)CC3)c21] |
| I-335 | 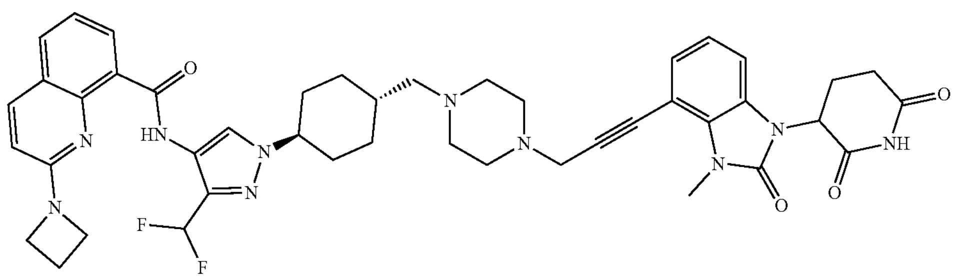 [SMILES: Cn1c(=O)n(C2CCC(=O)NC2=O)c2cccc(C#CCN3CCN(C[C@H]4CC[C@H](n5cc(NC(=O)c6cccc7ccc(N8CCC8)nc67)c(C(F)F)n5)CC4)CC3)c21] |
| I-336 | 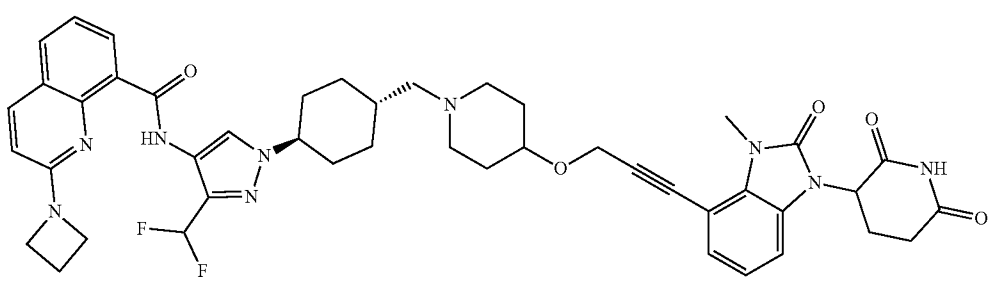 [SMILES: Cn1c(=O)n(C2CCC(=O)NC2=O)c2cccc(C#CCOC3CCN(C[C@H]4CC[C@H](n5cc(NC(=O)c6cccc7ccc(N8CCC8)nc67)c(C(F)F)n5)CC4)CC3)c21] |
| I-337 | 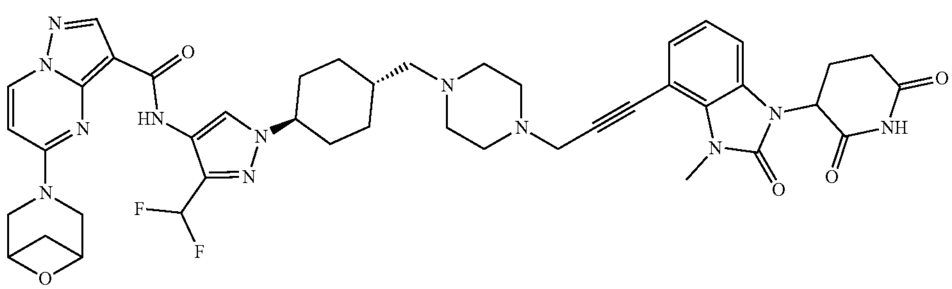 [SMILES: Cn1c(=O)n(C2CCC(=O)NC2=O)c2cccc(C#CCN3CCN(C[C@H]4CC[C@H](n5cc(NC(=O)c6cnn7ccc(N8CC9CC(C8)O9)nc67)c(C(F)F)n5)CC4)CC3)c21] |
| I-338 | 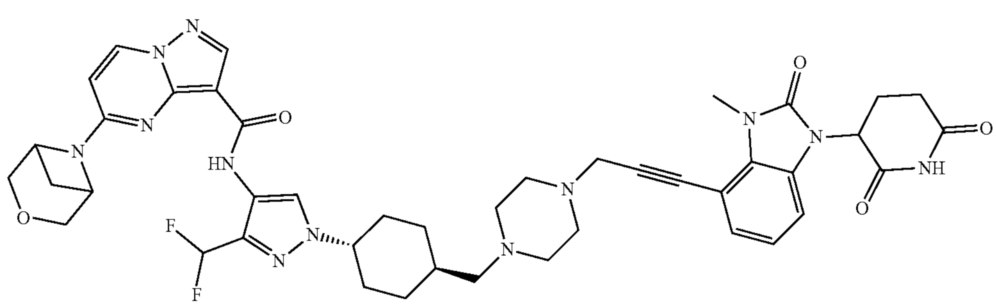 [SMILES: Cn1c(=O)n(C2CCC(=O)NC2=O)c2cccc(C#CCN3CCN(C[C@H]4CC[C@H](n5cc(NC(=O)c6cnn7ccc(N8C9COCC8C9)nc67)c(C(F)F)n5)CC4)CC3)c21] |

TABLE 1-continued

Exemplary Compounds

| I-# | Structure |
|---|---|
| I-339 | 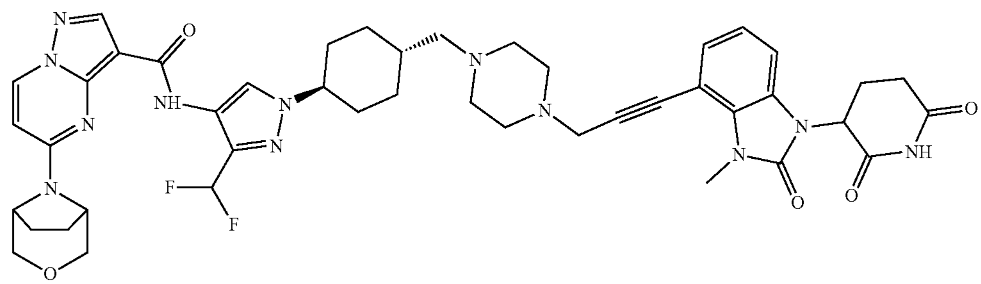 [SMILES: Cn1c(=O)n(C2CCC(=O)NC2=O)c2cccc(C#CCN3CCN(C[C@H]4CC[C@H](n5cc(NC(=O)c6cnn7ccc(N8C9CCC8COC9)nc67)c(C(F)F)n5)CC4)CC3)c21] |
| I-340 | 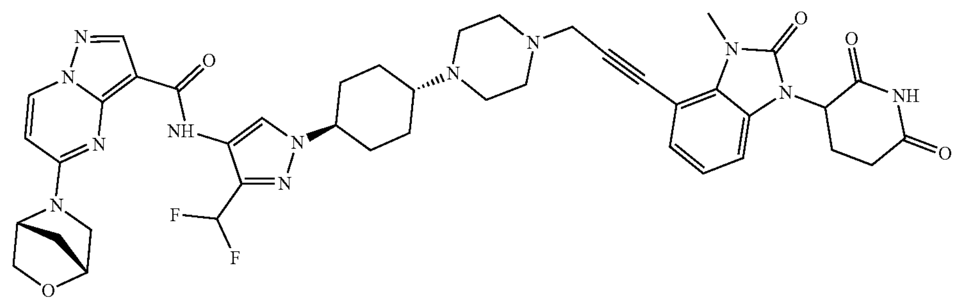 [SMILES: Cn1c(=O)n(C2CCC(=O)NC2=O)c2cccc(C#CCN3CCN([C@H]4CC[C@H](n5cc(NC(=O)c6cnn7ccc(N8C[C@H]9C[C@@H]8CO9)nc67)c(C(F)F)n5)CC4)CC3)c21] |
| I-341 | 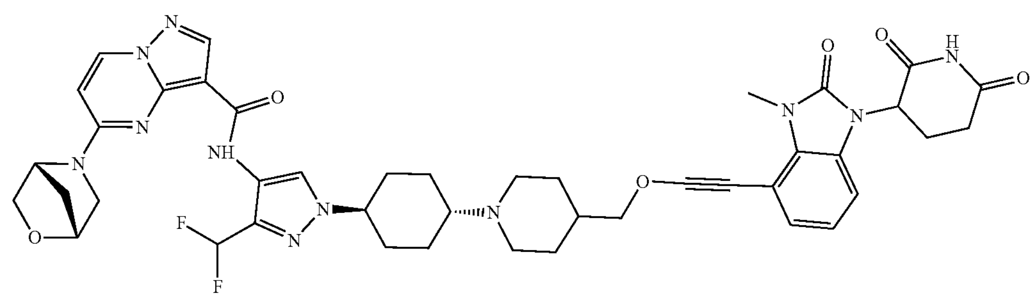 [SMILES: Cn1c(=O)n(C2CCC(=O)NC2=O)c2cccc(C#COCC3CCN([C@H]4CC[C@H](n5cc(NC(=O)c6cnn7ccc(N8C[C@H]9C[C@@H]8CO9)nc67)c(C(F)F)n5)CC4)CC3)c21] |
| I-342 | 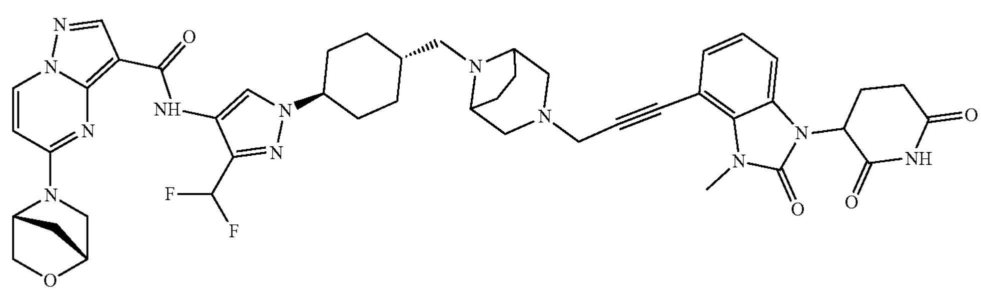 [SMILES: Cn1c(=O)n(C2CCC(=O)NC2=O)c2cccc(C#CCN3CC4CCC(C3)N4C[C@H]3CC[C@H](n4cc(NC(=O)c5cnn6ccc(N7C[C@H]8C[C@@H]7CO8)nc56)c(C(F)F)n4)CC3)c21] |
| I-343 | 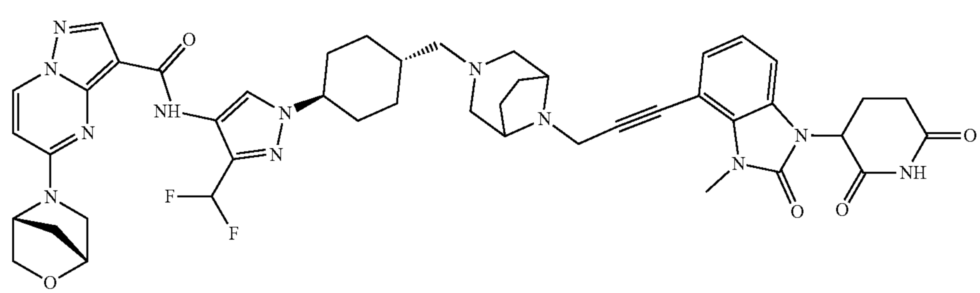 [SMILES: Cn1c(=O)n(C2CCC(=O)NC2=O)c2cccc(C#CCN3C4CCC3CN(C[C@H]3CC[C@H](n5cc(NC(=O)c6cnn7ccc(N8C[C@H]9C[C@@H]8CO9)nc67)c(C(F)F)n5)CC3)C4)c21] |

TABLE 1-continued

Exemplary Compounds

| I-# | Structure |
|---|---|
| I-344 | 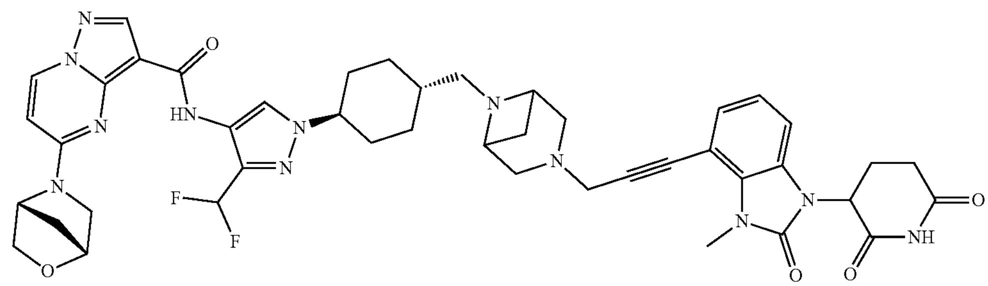 [SMILES: Cn1c(=O)n(C2CCC(=O)NC2=O)c2cccc(C#CCN3CC4CC(C3)N4C[C@H]3CC[C@H](n4cc(NC(=O)c5cnn6ccc(N7C[C@H]8C[C@@H]7CO8)nc56)c(C(F)F)n4)CC3)c21] |
| I-345 | 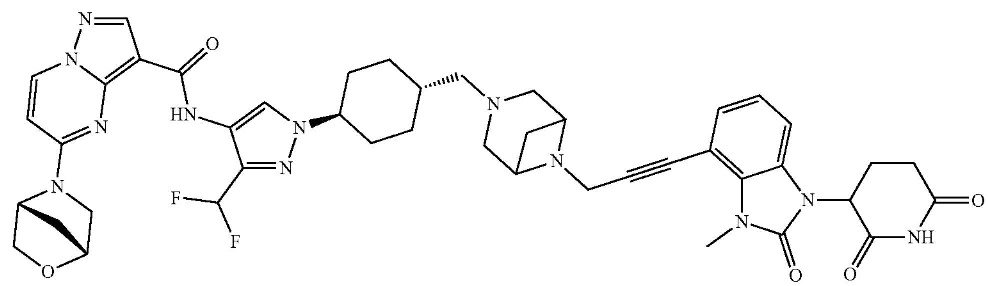 [SMILES: Cn1c(=O)n(C2CCC(=O)NC2=O)c2cccc(C#CCN3C4CC3CN(C[C@H]3CC[C@H](n5cc(NC(=O)c6cnn7ccc(N8C[C@H]9C[C@@H]8CO9)nc67)c(C(F)F)n5)CC3)C4)c21] |
| I-348 | 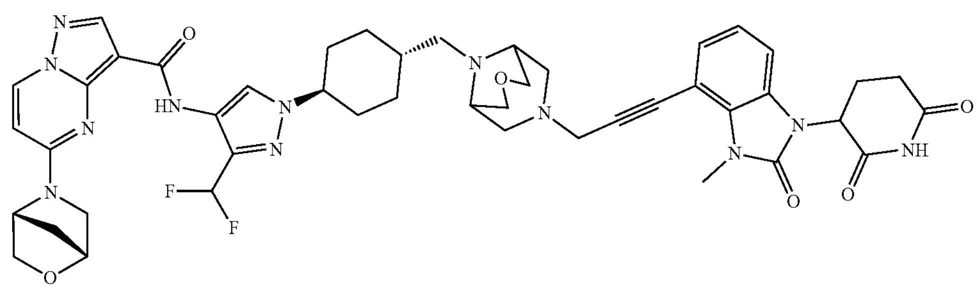 [SMILES: Cn1c(=O)n(C2CCC(=O)NC2=O)c2cccc(C#CCN3CC4COCC(C3)N4C[C@H]3CC[C@H](n4cc(NC(=O)c5cnn6ccc(N7C[C@H]8C[C@@H]7CO8)nc56)c(C(F)F)n4)CC3)c21] |
| I-349 | 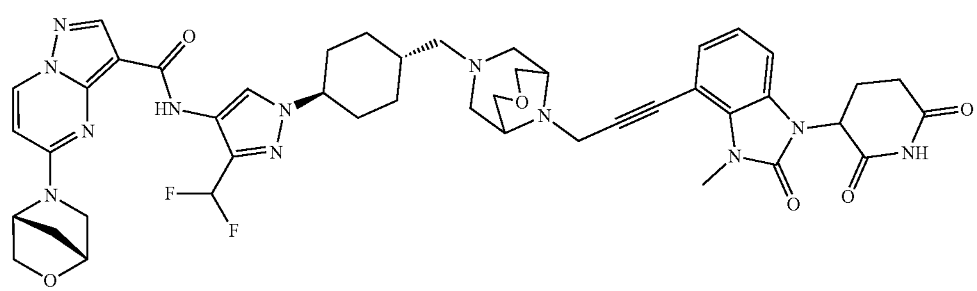 [SMILES: Cn1c(=O)n(C2CCC(=O)NC2=O)c2cccc(C#CCN3C4COCC3CN(C[C@H]3CC[C@H](n5cc(NC(=O)c6cnn7ccc(N8C[C@H]9C[C@@H]8CO9)nc67)c(C(F)F)n5)CC3)C4)c21] |
| I-351 | 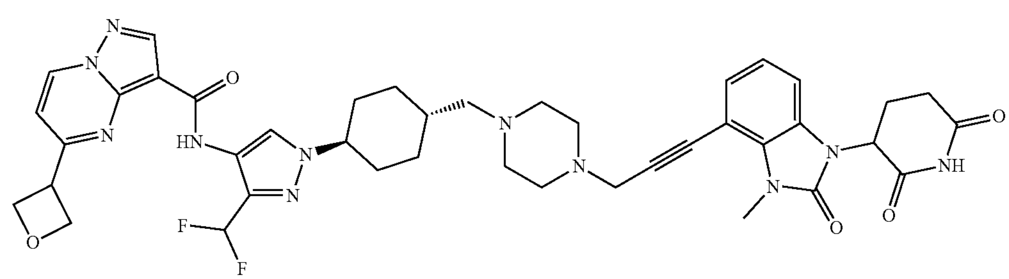 [SMILES: Cn1c(=O)n(C2CCC(=O)NC2=O)c2cccc(C#CCN3CCN(C[C@H]4CC[C@H](n5cc(NC(=O)c6cnn7ccc(C8COC8)nc67)c(C(F)F)n5)CC4)CC3)c21] |

TABLE 1-continued

Exemplary Compounds

| I-# | Structure |
|---|---|
| I-352 | 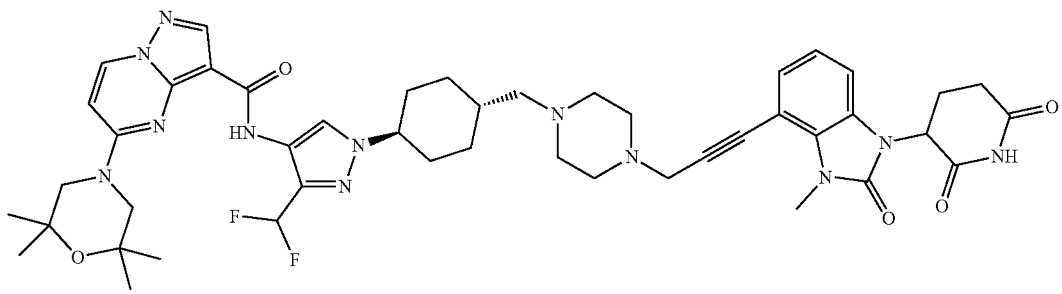 [SMILES: Cn1c(=O)n(C2CCC(=O)NC2=O)c2cccc(C#CCN3CCN(C[C@H]4CC[C@H](n5cc(NC(=O)c6cnn7ccc(N8CC(C)(C)OC(C)(C)C8)nc67)c(C(F)F)n5)CC4)CC3)c21] |
| I-353 | 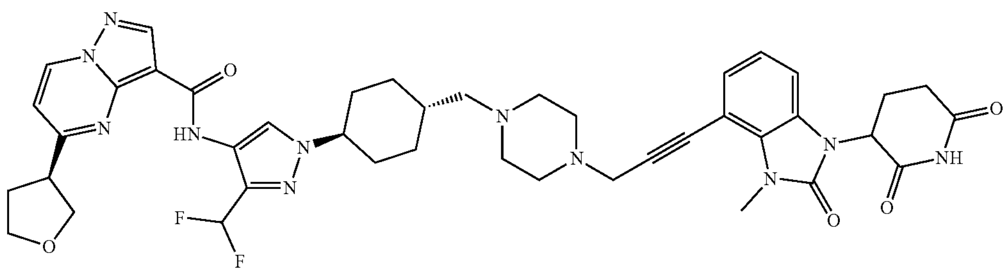 [SMILES: Cn1c(=O)n(C2CCC(=O)NC2=O)c2cccc(C#CCN3CCN(C[C@H]4CC[C@H](n5cc(NC(=O)c6cnn7ccc([C@@H]8CCOC8)nc67)c(C(F)F)n5)CC4)CC3)c21] |
| I-354 | 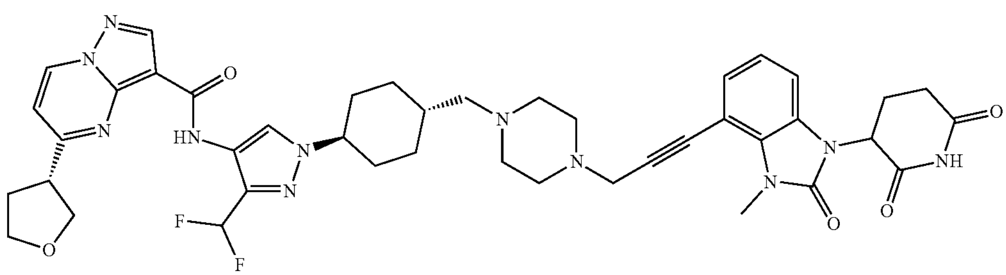 [SMILES: Cn1c(=O)n(C2CCC(=O)NC2=O)c2cccc(C#CCN3CCN(C[C@H]4CC[C@H](n5cc(NC(=O)c6cnn7ccc([C@H]8CCOC8)nc67)c(C(F)F)n5)CC4)CC3)c21] |
| I-355 | 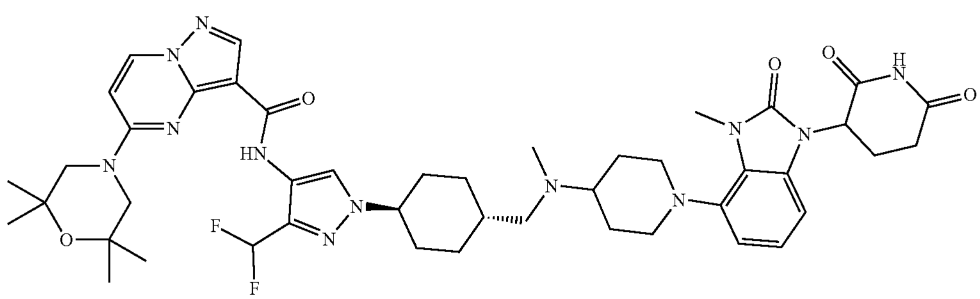 [SMILES: CN(C[C@H]1CC[C@H](n2cc(NC(=O)c3cnn4ccc(N5CC(C)(C)OC(C)(C)C5)nc34)c(C(F)F)n2)CC1)C1CCN(c2cccc3c2n(C)c(=O)n3C2CCC(=O)NC2=O)CC1] |
| I-356 | 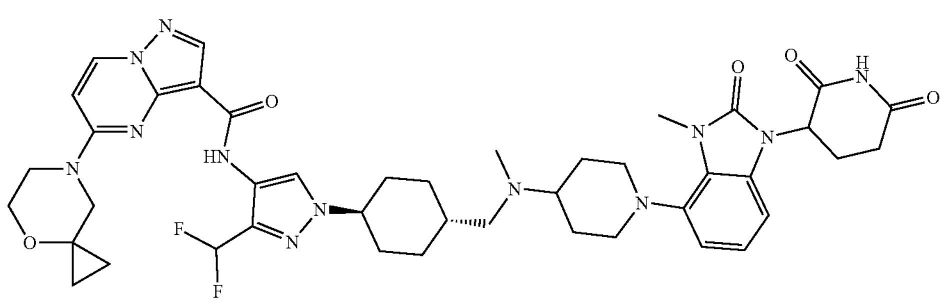 [SMILES: CN(C[C@H]1CC[C@H](n2cc(NC(=O)c3cnn4ccc(N5CCOC6(CC6)C5)nc34)c(C(F)F)n2)CC1)C1CCN(c2cccc3c2n(C)c(=O)n3C2CCC(=O)NC2=O)CC1] |

TABLE 1-continued

Exemplary Compounds

| I-# | Structure |
|---|---|
| I-357 | 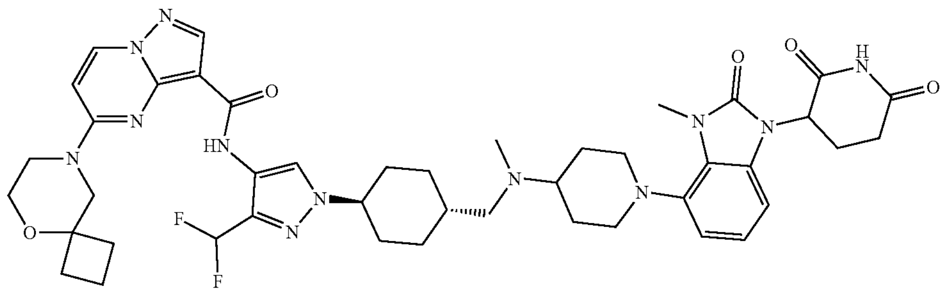 [SMILES: CN(C[C@H]1CC[C@H](n2cc(NC(=O)c3cnn4ccc(N5CCOC6(CCC6)C5)nc34)c(C(F)F)n2)CC1)C1CCN(c2cccc3c2n(C)c(=O)n3C2CCC(=O)NC2=O)CC1] |
| I-358 | 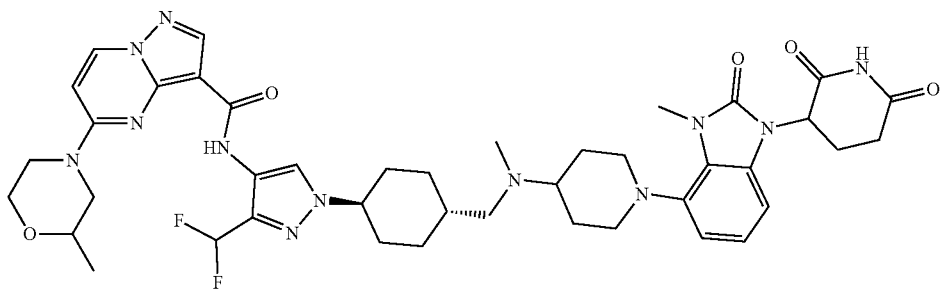 [SMILES: CC1CN(c2ccn3ncc(C(=O)Nc4cn([C@H]5CC[C@H](CN(C)C6CCN(c7cccc8c7n(C)c(=O)n8C7CCC(=O)NC7=O)CC6)CC5)nc4C(F)F)c3n2)CCO1] |
| I-359 | 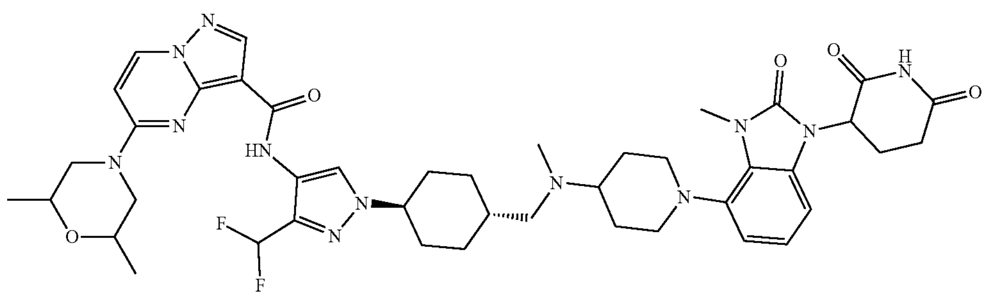 [SMILES: CC1CN(c2ccn3ncc(C(=O)Nc4cn([C@H]5CC[C@H](CN(C)C6CCN(c7cccc8c7n(C)c(=O)n8C7CCC(=O)NC7=O)CC6)CC5)nc4C(F)F)c3n2)CC(C)O1] |
| I-360 | 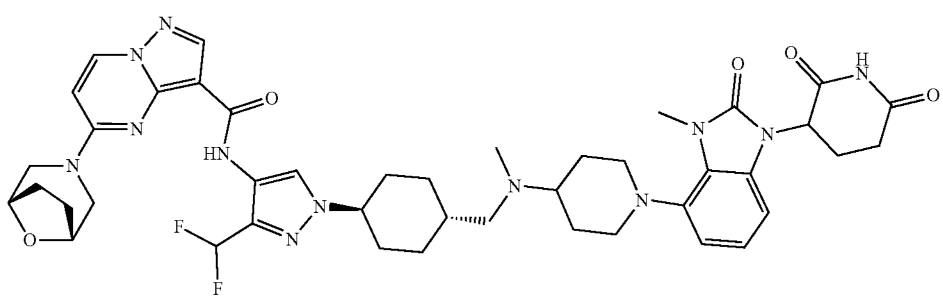 [SMILES: CN(C[C@H]1CC[C@H](n2cc(NC(=O)c3cnn4ccc(N5C[C@H]6CC[C@@H](C5)O6)nc34)c(C(F)F)n2)CC1)C1CCN(c2cccc3c2n(C)c(=O)n3C2CCC(=O)NC2=O)CC1] |
| I-361 | 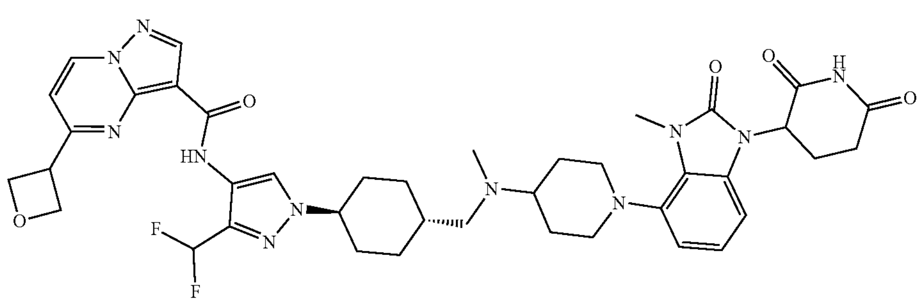 [SMILES: CN(C[C@H]1CC[C@H](n2cc(NC(=O)c3cnn4ccc(C5COC5)nc34)c(C(F)F)n2)CC1)C1CCN(c2cccc3c2n(C)c(=O)n3C2CCC(=O)NC2=O)CC1] |

TABLE 1-continued
Exemplary Compounds
| I-# | Structure |
|---|---|
| I-362 | 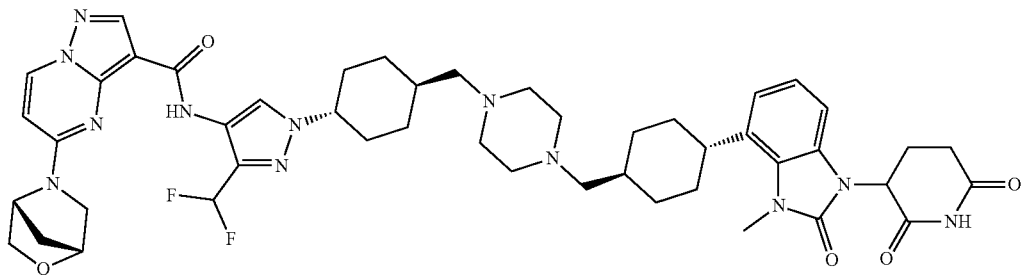 [SMILES: Cn1c(=O)n(C2CCC(=O)NC2=O)c2cccc([C@H]3CC[C@H](CN4CCN(C[C@H]5CC[C@H](n6cc(NC(=O)c7cnn8ccc(N9C[C@H]%10C[C@@H]9CO%10)nc78)c(C(F)F)n6)CC5)CC4)CC3)c21] |
| I-363 | 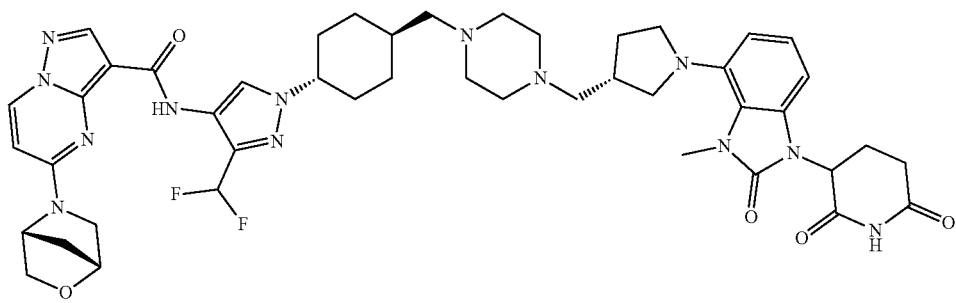 [SMILES: Cn1c(=O)n(C2CCC(=O)NC2=O)c2cccc(N3CC[C@@H](CN4CCN(C[C@H]5CC[C@H](n6cc(NC(=O)c7cnn8ccc(N9C[C@H]%10C[C@@H]9CO%10)nc78)c(C(F)F)n6)CC5)CC4)C3)c21] |
| I-364 | 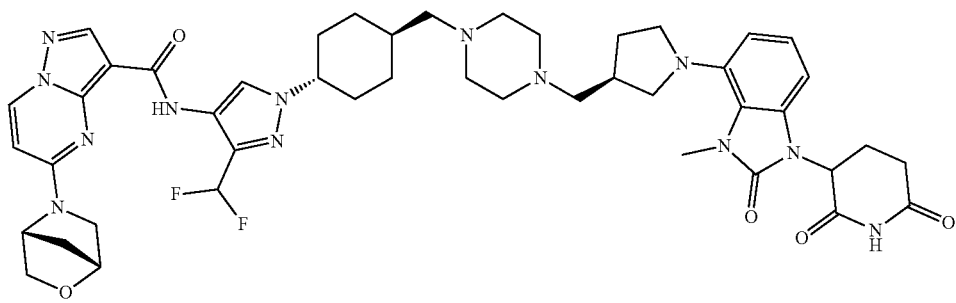 [SMILES: Cn1c(=O)n(C2CCC(=O)NC2=O)c2cccc(N3CC[C@H](CN4CCN(C[C@H]5CC[C@H](n6cc(NC(=O)c7cnn8ccc(N9C[C@H]%10C[C@@H]9CO%10)nc78)c(C(F)F)n6)CC5)CC4)C3)c21] |
| I-365 | 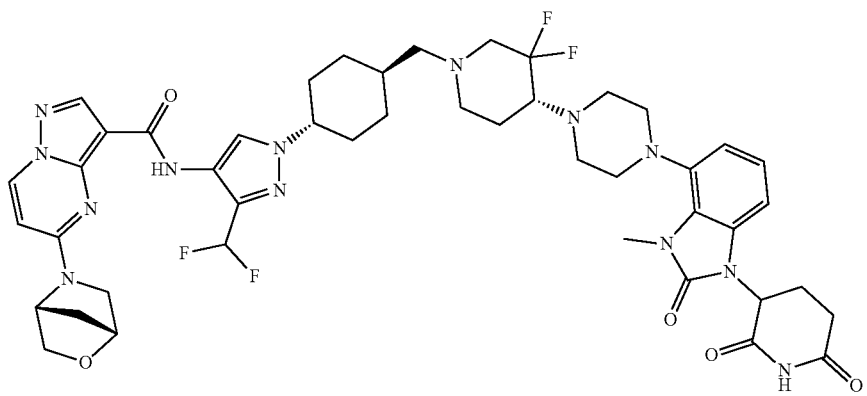 [SMILES: Cn1c(=O)n(C2CCC(=O)NC2=O)c2cccc(N3CCN([C@@H]4CCN(C[C@H]5CC[C@H](n6cc(NC(=O)c7cnn8ccc(N9C[C@H]%10C[C@@H]9CO%10)nc78)c(C(F)F)n6)CC5)CC4(F)F)CC3)c21] |

TABLE 1-continued
Exemplary Compounds
| I-# | Structure |
|---|---|
| I-366 | 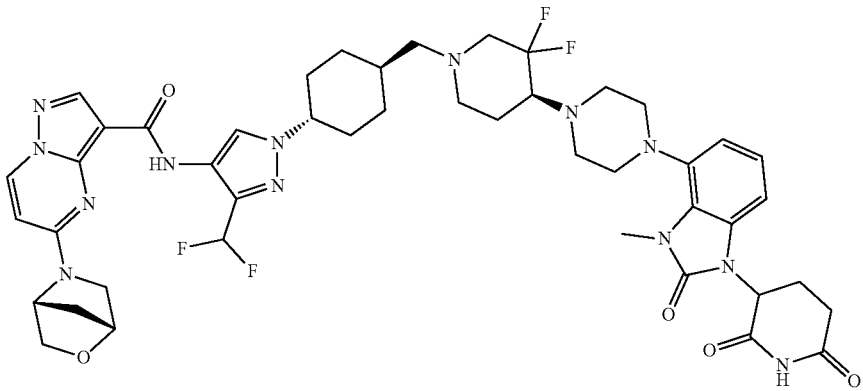 [SMILES: Cn1c(=O)n(C2CCC(=O)NC2=O)c2cccc(N3CCN([C@H]4CCN(C[C@H]5CC[C@H](n6cc(NC(=O)c7cnn8ccc(N9C[C@H]%10C[C@@H]9CO%10)nc78)c(C(F)F)n6)CC5)CC4(F)F)CC3)c21] |
| I-367 | 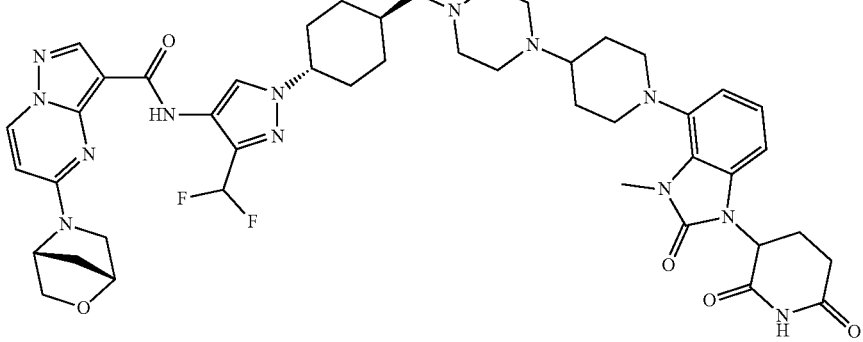 |
| I-368 | 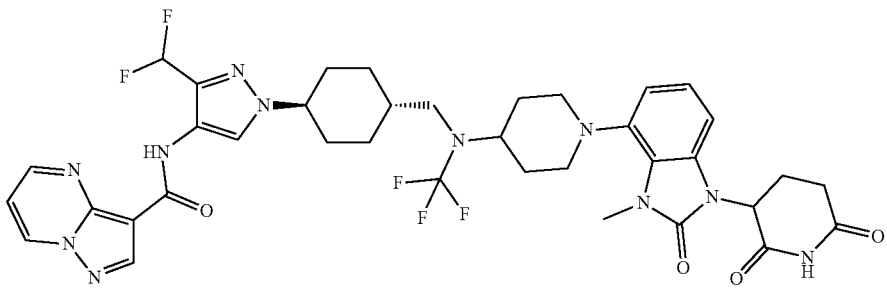 [SMILES: Cn1c(=O)n(C2CCC(=O)NC2=O)c2cccc(N3CCC(N(C[C@H]4CC[C@H](n5cc(NC(=O)c6cnn7cccnc67)c(C(F)F)n5)CC4)C(F)(F)F)CC3)c21] |
| I-369 | 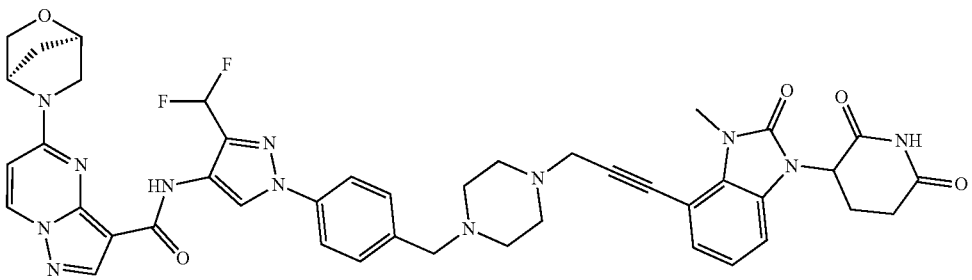 [SMILES: Cn1c(=O)n(C2CCC(=O)NC2=O)c2cccc(C#CCN3CCN(Cc4ccc(-n5cc(NC(=O)c6cnn7ccc(N8C[C@H]9C[C@@H]8CO9)nc67)c(C(F)F)n5)cc4)CC3)c21] |

TABLE 1-continued
Exemplary Compounds
| I-# | Structure |
|---|---|
| I-370 | 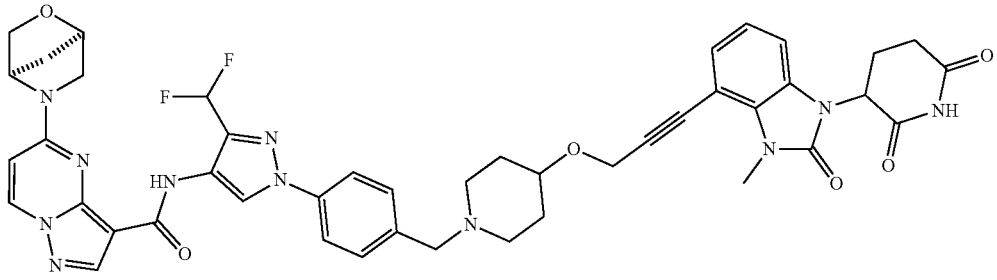 |
| I-371 | 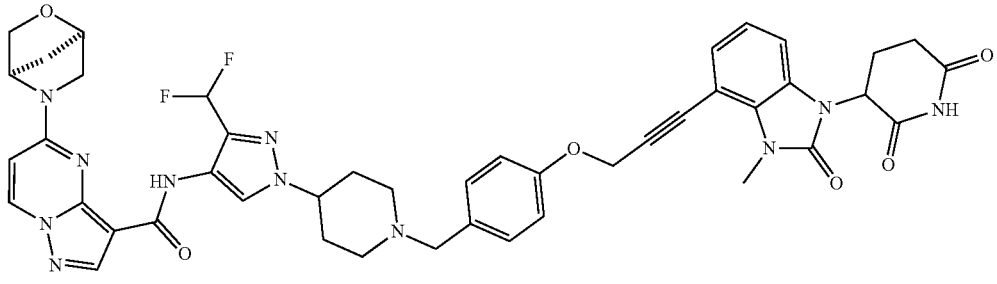 |
| I-372 | 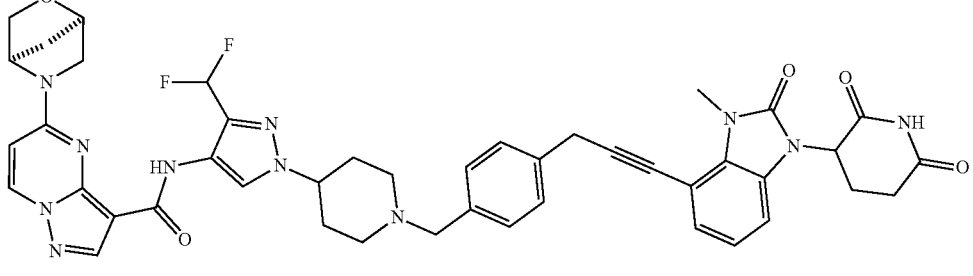 |
| I-373 | 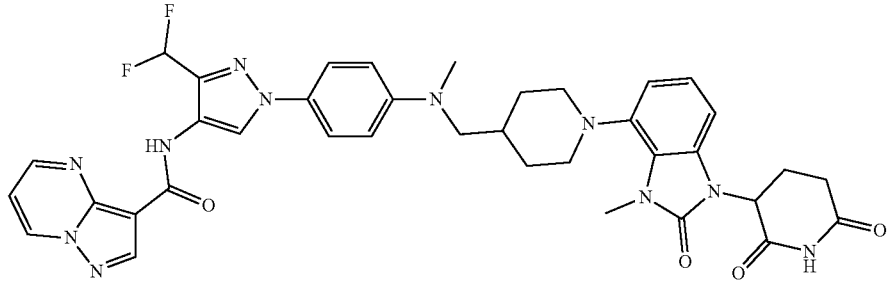 [SMILES: CN(CC1CCN(c2cccc3c2n(C)c(=O)n3C2CCC(=O)NC2=O)CC1)c1ccc(-n2cc(NC(=O)c3cnn4cccnc34)c(C(F)F)n2)cc1] |
| I-374 | 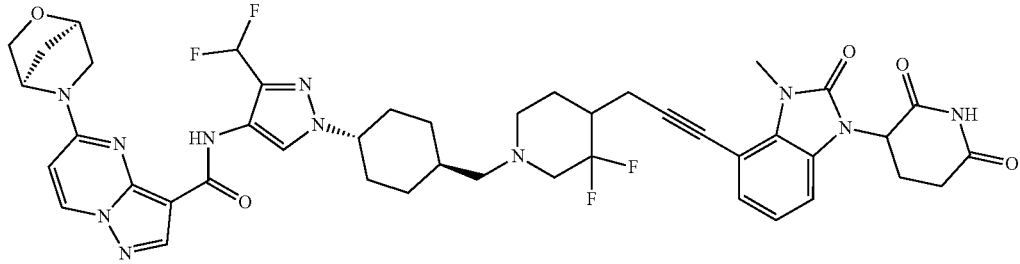 [SMILES: Cn1c(=O)n(C2CCC(=O)NC2=O)c2cccc(C#CCC3CCN(C[C@H]4CC[C@H](n5cc(NC(=O)c6cnn7ccc(N8C[C@H]9C[C@@H]8CO9)nc67)c(C(F)F)n5)CC4)CC3(F)F)c21] |

TABLE 1-continued

Exemplary Compounds

| I-# | Structure |
|---|---|
| I-375 | 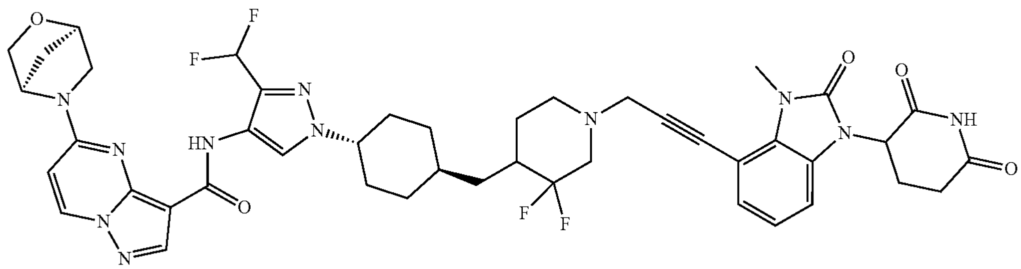 [SMILES: Cn1c(=O)n(C2CCC(=O)NC2=O)c2cccc(C#CCN3CCC(C[C@H]4CC[C@H](n5cc(NC(=O)c6cnn7ccc(N8C[C@H]9C[C@@H]8CO9)nc67)c(C(F)F)n5)CC4)C(F)(F)C3)c21] |
| I-376 | 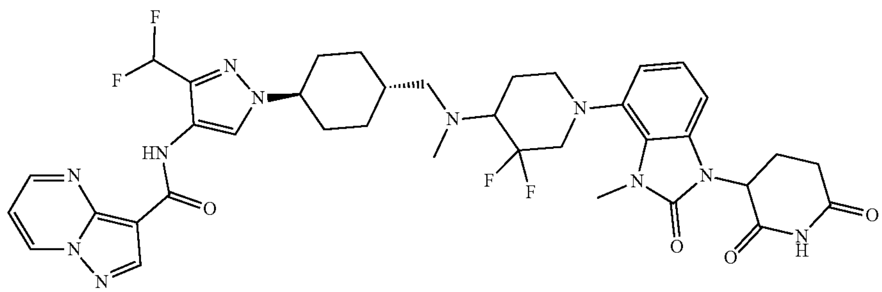 [SMILES: CN(C[C@H]1CC[C@H](n2cc(NC(=O)c3cnn4cccnc34)c(C(F)F)n2)CC1)C1CCN(c2cccc3c2n(C)c(=O)n3C2CCC(=O)NC2=O)CC1(F)F] |
| I-377 | 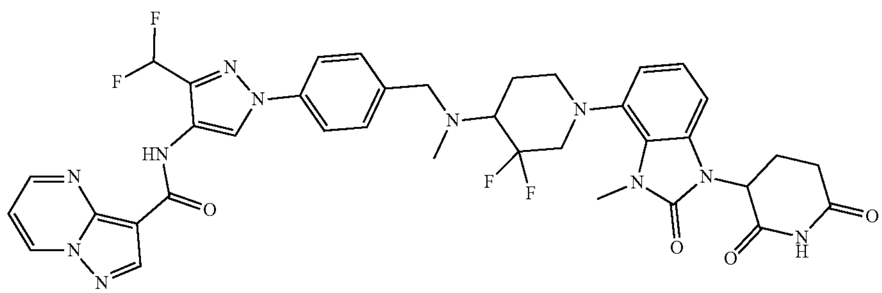 [SMILES: CN(Cc1ccc(-n2cc(NC(=O)c3cnn4cccnc34)c(C(F)F)n2)cc1)C1CCN(c2cccc3c2n(C)c(=O)n3C2CCC(=O)NC2=O)CC1(F)F] |
| I-378 | 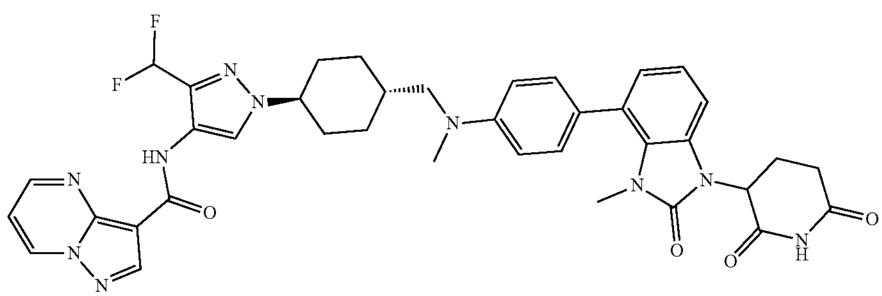 [SMILES: CN(C[C@H]1CC[C@H](n2cc(NC(=O)c3cnn4cccnc34)c(C(F)F)n2)CC1)c1ccc(-c2cccc3c2n(C)c(=O)n3C2CCC(=O)NC2=O)cc1] |
| I-379 | 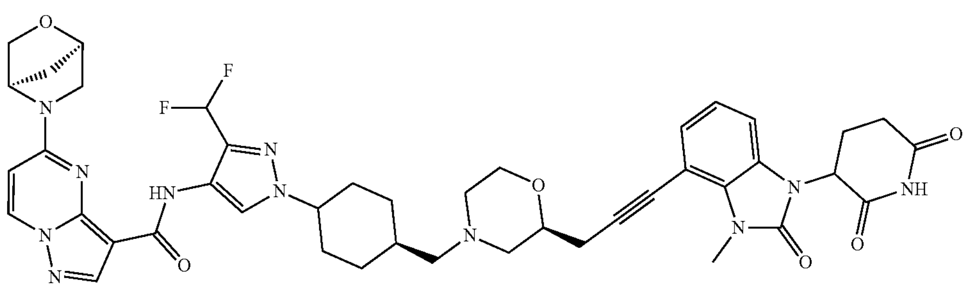 |

TABLE 1-continued

Exemplary Compounds

| I-# | Structure |
|---|---|
| I-380 | 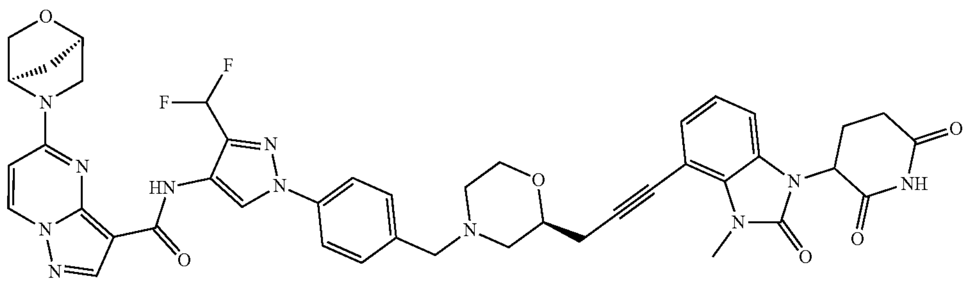 [SMILES: Cn1c(=O)n(C2CCC(=O)NC2=O)c2cccc(C#CC[C@H]3CN(Cc4ccc(-n5cc(NC(=O)c6cnn7ccc(N8C[C@H]9C[C@@H]8CO9)nc67)c(C(F)F)n5)cc4)CCO3)c21] |
| I-381 | 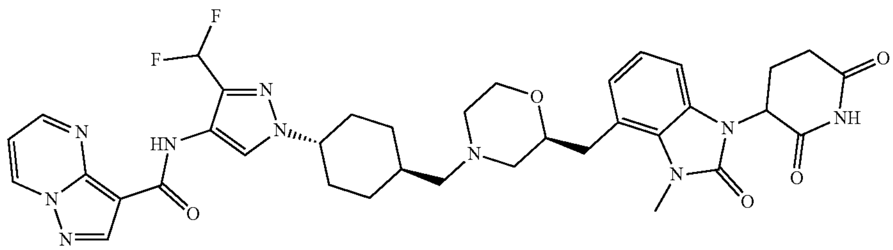 [SMILES: Cn1c(=O)n(C2CCC(=O)NC2=O)c2cccc(C[C@H]3CN(C[C@H]4CC[C@H](n5cc(NC(=O)c6cnn7cccnc67)c(C(F)F)n5)CC4)CCO3)c21] |
| I-382 | 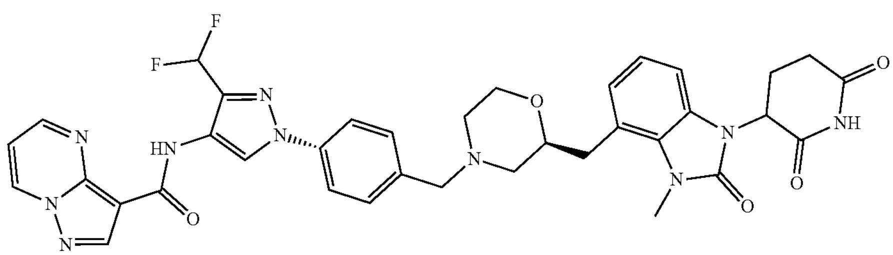 |
| I-383 | 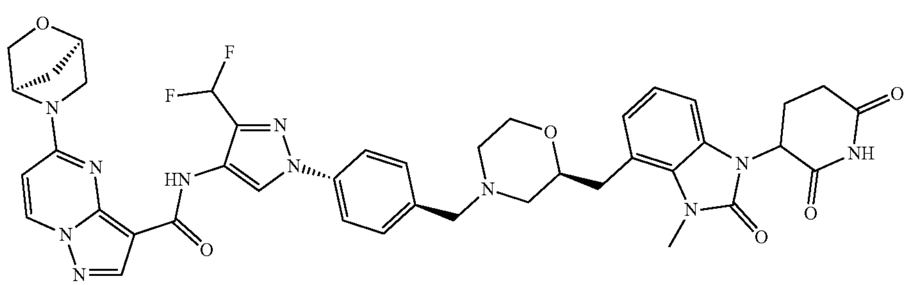 |
| I-384 | 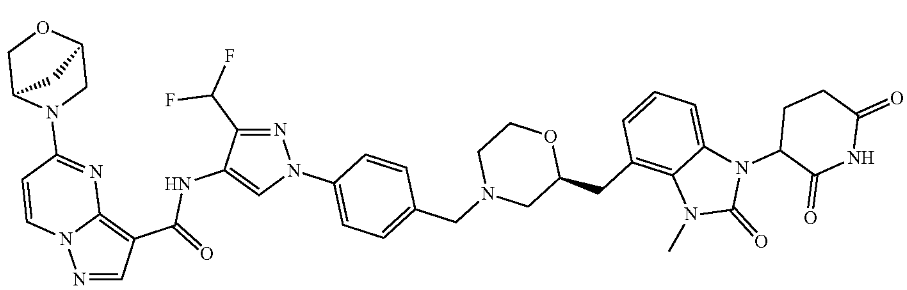 [SMILES: Cn1c(=O)n(C2CCC(=O)NC2=O)c2cccc(C[C@H]3CN(Cc4ccc(-n5cc(NC(=O)c6cnn7ccc(N8C[C@H]9C[C@@H]8CO9)nc67)c(C(F)F)n5)cc4)CCO3)c21] |

TABLE 1-continued
Exemplary Compounds
| I-# | Structure |
|---|---|
| I-385 | 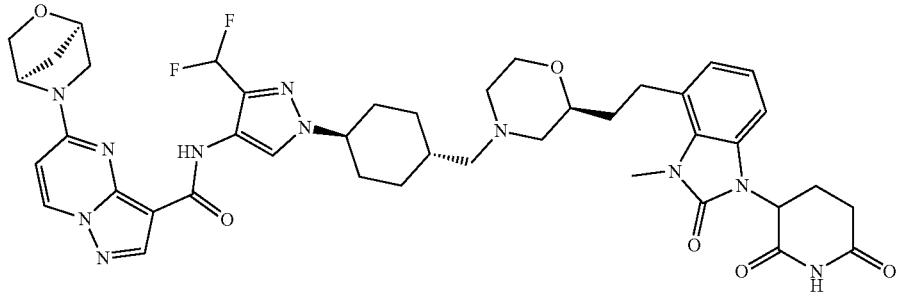 [SMILES: Cn1c(=O)n(C2CCC(=O)NC2=O)c2cccc(CC[C@H]3CN(C[C@H]4CC[C@H](n5cc(NC(=O)c6cnn7ccc(N8C[C@H]9C[C@@H]8CO9)nc67)c(C(F)F)n5)CC4)CCO3)c21] |
| I-386 | 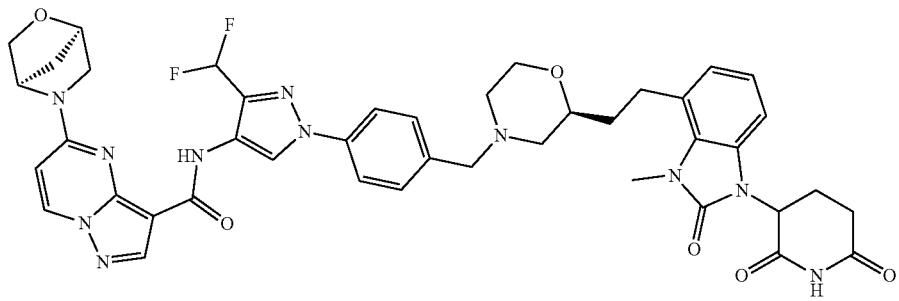 [SMILES: Cn1c(=O)n(C2CCC(=O)NC2=O)c2cccc(CC[C@H]3CN(Cc4ccc(-n5cc(NC(=O)c6cnn7ccc(N8C[C@H]9C[C@@H]8CO9)nc67)c(C(F)F)n5)cc4)CCO3)c21] |
| I-387 | 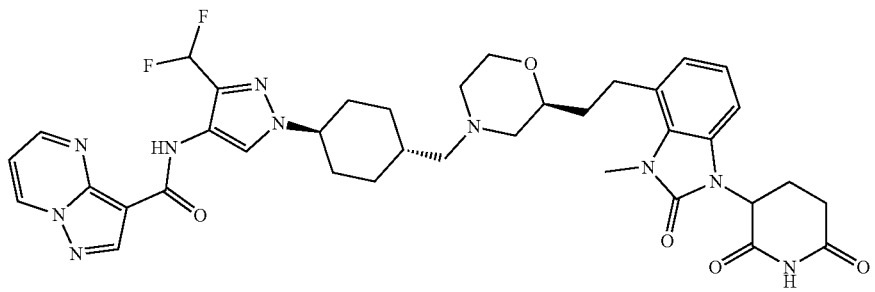 [SMILES: Cn1c(=O)n(C2CCC(=O)NC2=O)c2cccc(CC[C@H]3CN(C[C@H]4CC[C@H](n5cc(NC(=O)c6cnn7cccnc67)c(C(F)F)n5)CC4)CCO3)c21] |
| I-388 | 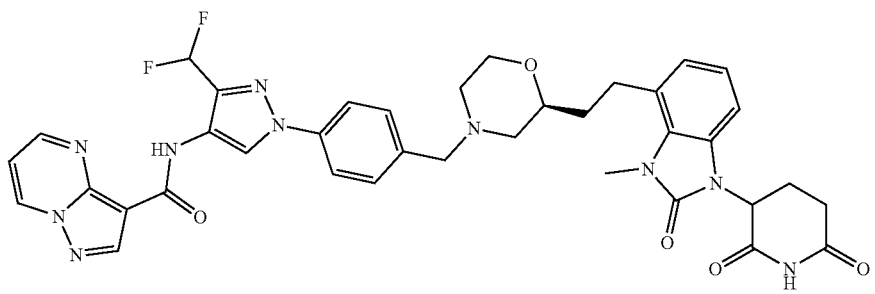 [SMILES: Cn1c(=O)n(C2CCC(=O)NC2=O)c2cccc(CC[C@H]3CN(Cc4ccc(-n5cc(NC(=O)c6cnn7cccnc67)c(C(F)F)n5)cc4)CCO3)c21] |
| I-389 | 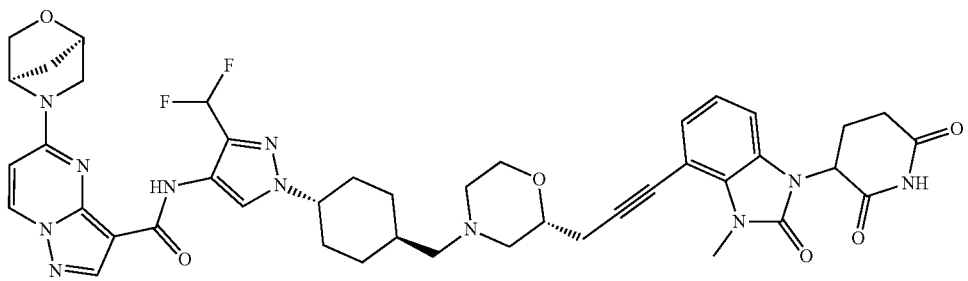 [SMILES: Cn1c(=O)n(C2CCC(=O)NC2=O)c2cccc(C#CC[C@@H]3CN(C[C@H]4CC[C@H](n5cc(NC(=O)c6cnn7ccc(N8C[C@H]9C[C@@H]8CO9)nc67)c(C(F)F)n5)CC4)CCO3)c21] |

TABLE 1-continued
Exemplary Compounds
| I-# | Structure |
|---|---|
| I-390 | 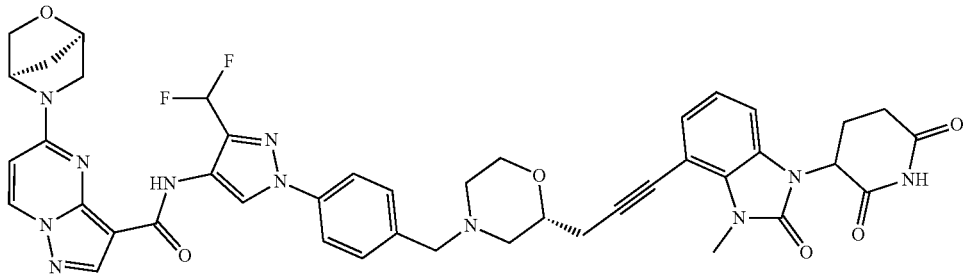 [SMILES: Cn1c(=O)n(C2CCC(=O)NC2=O)c2cccc(C#CC[C@@H]3CN(Cc4ccc(-n5cc(NC(=O)c6cnn7ccc(N8C[C@H]9C[C@@H]8CO9)nc67)c(C(F)F)n5)cc4)CCO3)c21] |
| I-391 | 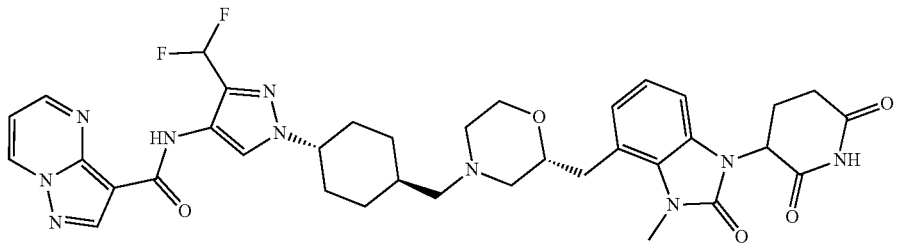 [SMILES: Cn1c(=O)n(C2CCC(=O)NC2=O)c2cccc(C[C@@H]3CN(C[C@H]4CC[C@H](n5cc(NC(=O)c6cnn7cccnc67)c(C(F)F)n5)CC4)CCO3)c21] |
| I-392 | 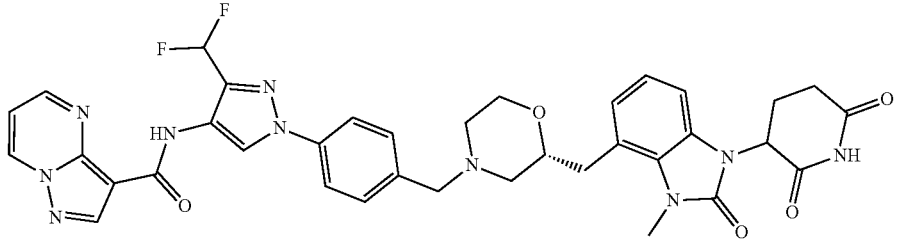 [SMILES: Cn1c(=O)n(C2CCC(=O)NC2=O)c2cccc(C[C@@H]3CN(Cc4ccc(-n5cc(NC(=O)c6cnn7cccnc67)c(C(F)F)n5)cc4)CCO3)c21] |
| I-393 | 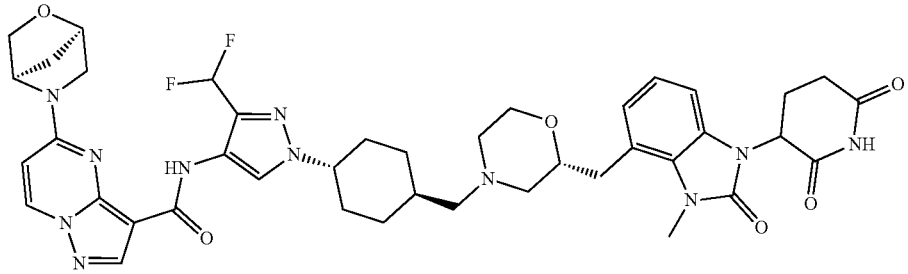 [SMILES: Cn1c(=O)n(C2CCC(=O)NC2=O)c2cccc(C[C@@H]3CN(C[C@H]4CC[C@H](n5cc(NC(=O)c6cnn7ccc(N8C[C@H]9C[C@@H]8CO9)nc67)c(C(F)F)n5)CC4)CCO3)c21] |
| I-394 | 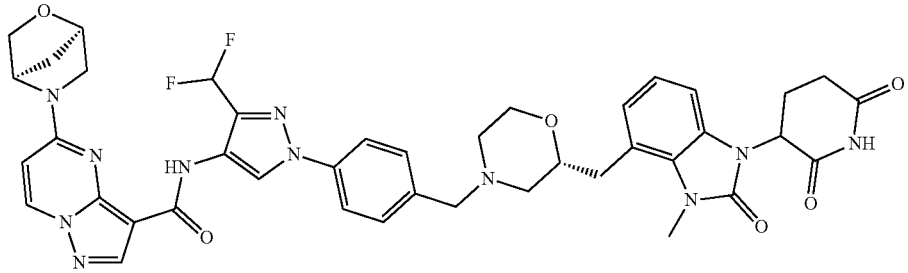 [SMILES: Cn1c(=O)n(C2CCC(=O)NC2=O)c2cccc(C[C@@H]3CN(Cc4ccc(-n5cc(NC(=O)c6cnn7ccc(N8C[C@H]9C[C@@H]8CO9)nc67)c(C(F)F)n5)cc4)CCO3)c21] |

TABLE 1-continued

Exemplary Compounds

| I-# | Structure |
|---|---|
| I-395 | 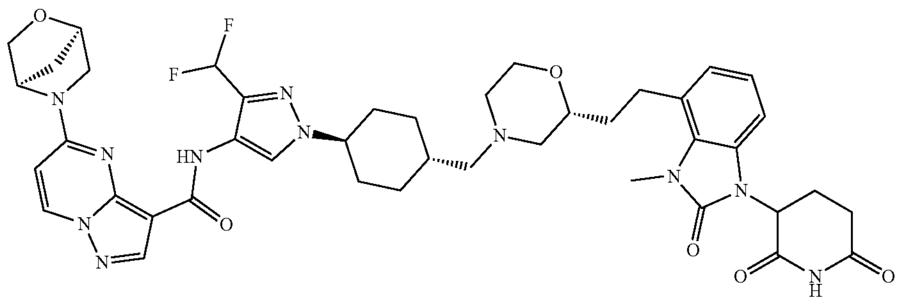 [SMILES: Cn1c(=O)n(C2CCC(=O)NC2=O)c2cccc(CC[C@@H]3CN(C[C@H]4CC[C@H](n5cc(NC(=O)c6cnn7ccc(N8C[C@H]9C[C@@H]8CO9)nc67)c(C(F)F)n5)CC4)CCO3)c21] |
| I-396 | 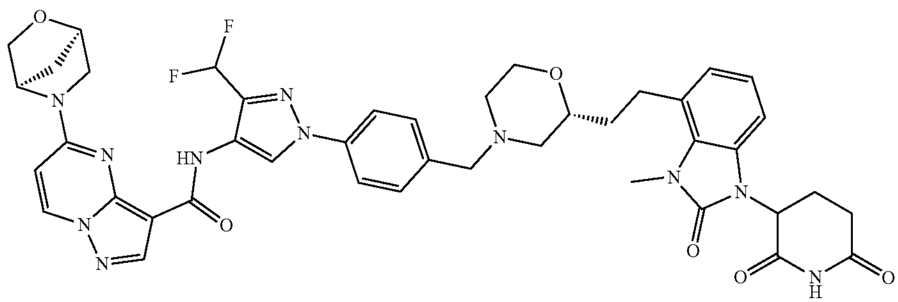 [SMILES: Cn1c(=O)n(C2CCC(=O)NC2=O)c2cccc(CC[C@@H]3CN(Cc4ccc(-n5cc(NC(=O)c6cnn7ccc(N8C[C@H]9C[C@@H]8CO9)nc67)c(C(F)F)n5)cc4)CCO3)c21] |
| I-397 | 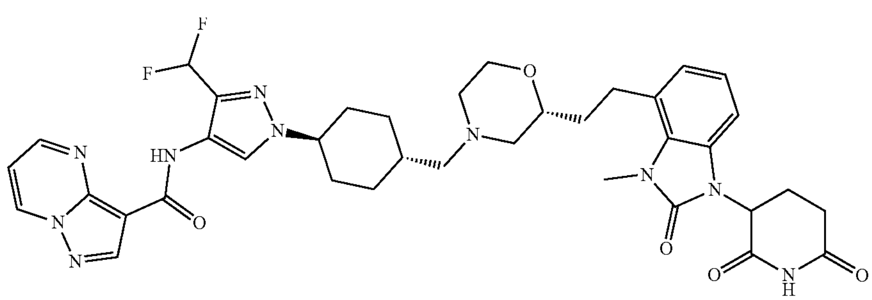 [SMILES: Cn1c(=O)n(C2CCC(=O)NC2=O)c2cccc(CC[C@@H]3CN(C[C@H]4CC[C@H](n5cc(NC(=O)c6cnn7cccnc67)c(C(F)F)n5)CC4)CCO3)c21] |
| I-398 | 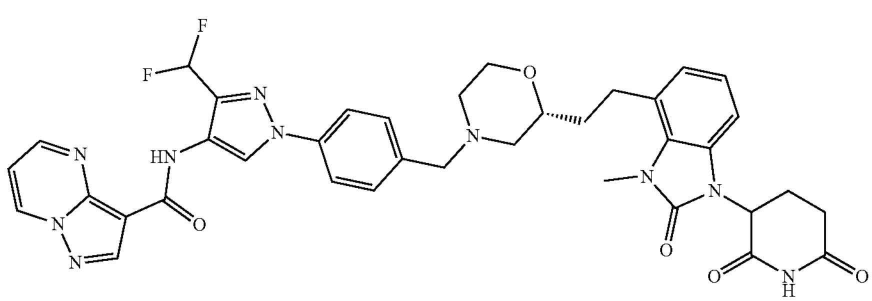 [SMILES: Cn1c(=O)n(C2CCC(=O)NC2=O)c2cccc(CC[C@@H]3CN(Cc4ccc(-n5cc(NC(=O)c6cnn7cccnc67)c(C(F)F)n5)cc4)CCO3)c21] |
| I-399 | 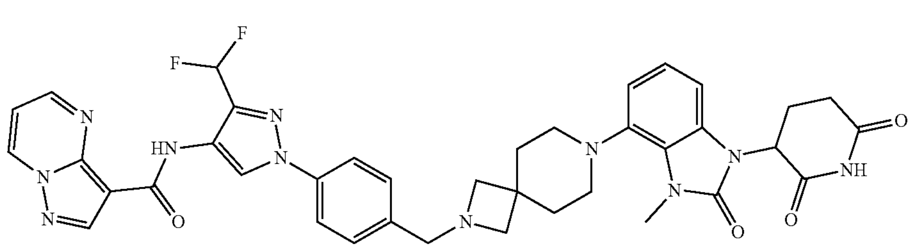 [SMILES: Cn1c(=O)n(C2CCC(=O)NC2=O)c2cccc(N3CCC4(CC3)CN(Cc3ccc(-n5cc(NC(=O)c6cnn7cccnc67)c(C(F)F)n5)cc3)C4)c21] |

US 12,091,411 B2
269 270
TABLE 1-continued
Exemplary Compounds
| I-# | Structure |
|---|---|
| I-400 | 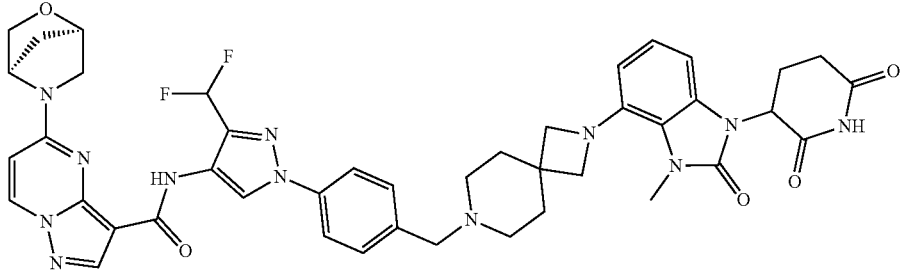 [SMILES: Cn1c(=O)n(C2CCC(=O)NC2=O)c2cccc(N3CC4(CCN(Cc5ccc(-n6cc(NC(=O)c7cnn8ccc(N9C[C@H]%10C[C@@H]9CO%10)nc78)c(C(F)F)n6)cc5)CC4)C3)c21] |
| I-401 | 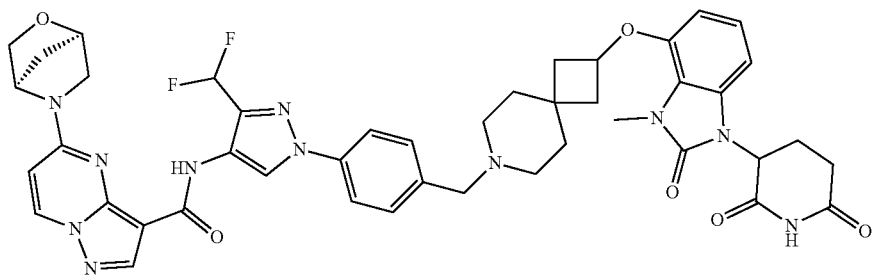 [SMILES: Cn1c(=O)n(C2CCC(=O)NC2=O)c2cccc(OC3CC4(CCN(Cc5ccc(-n6cc(NC(=O)c7cnn8ccc(N9C[C@H]%10C[C@@H]9CO%10)nc78)c(C(F)F)n6)cc5)CC4)C3)c21] |
| I-402 | 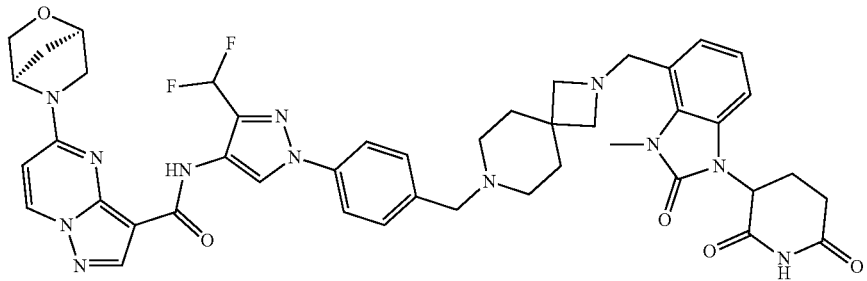 [SMILES: Cn1c(=O)n(C2CCC(=O)NC2=O)c2cccc(CN3CC4(CCN(Cc5ccc(-n6cc(NC(=O)c7cnn8ccc(N9C[C@H]%10C[C@@H]9CO%10)nc78)c(C(F)F)n6)cc5)CC4)C3)c21] |
| I-403 | 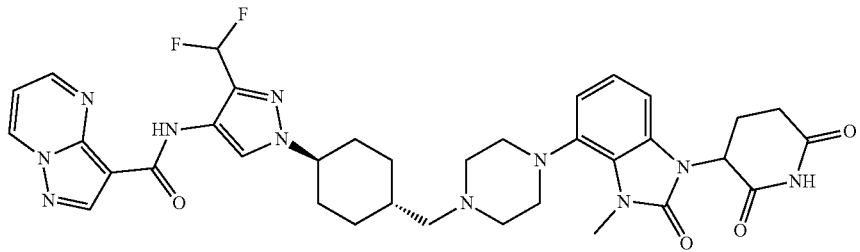 [SMILES: Cn1c(=O)n(C2CCC(=O)NC2=O)c2cccc(N3CCN(C[C@H]4CC[C@H](n5cc(NC(=O)c6cnn7cccnc67)c(C(F)F)n5)CC4)CC3)c21] |
| I-404 | 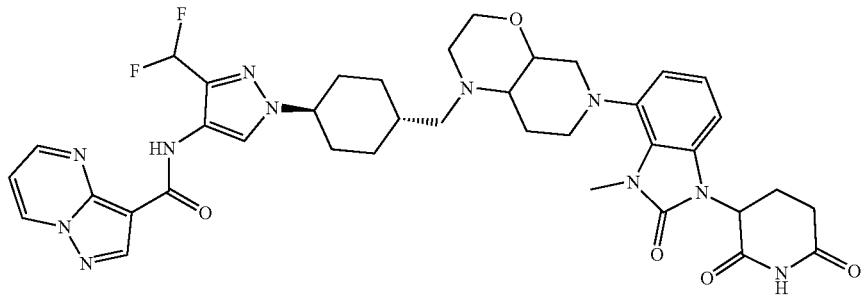 [SMILES: Cn1c(=O)n(C2CCC(=O)NC2=O)c2cccc(N3CCC4C(C3)OCCN4C[C@H]3CC[C@H](n4cc(NC(=O)c5cnn6cccnc56)c(C(F)F)n4)CC3)c21] |

TABLE 1-continued

Exemplary Compounds

| I-# | Structure |
|---|---|
| I-405 | 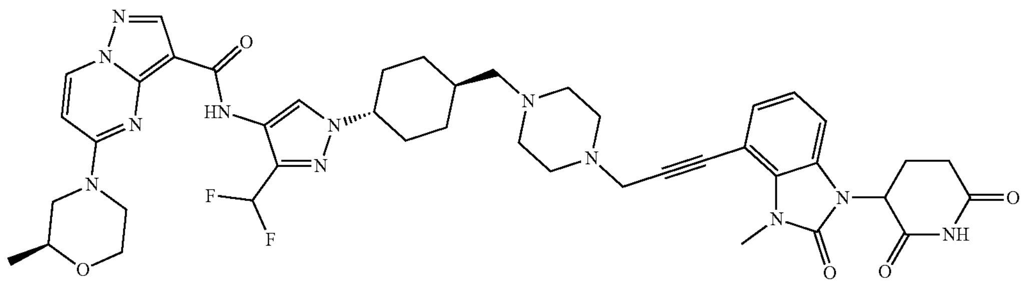 [SMILES: C[C@H]1CN(c2ccn3ncc(C(=O)Nc4cn([C@H]5CC[C@H](CN6CCN(CC#Cc7cccc8c7n(C)c(=O)n8C7CCC(=O)NC7=O)CC6)CC5)nc4C(F)F)c3n2)CCO1] |
| I-406 | 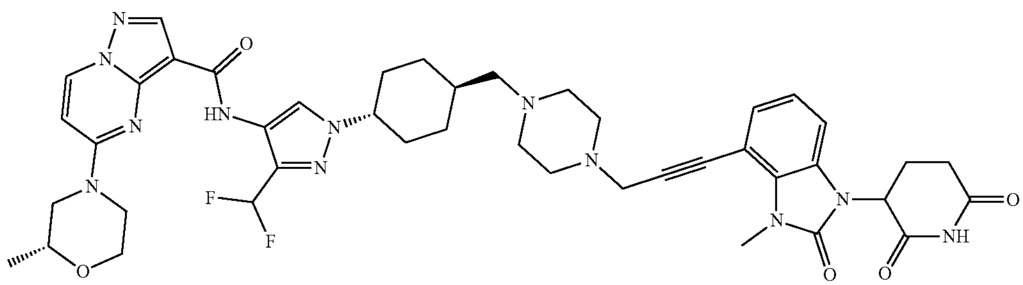 [SMILES: C[C@@H]1CN(c2ccn3ncc(C(=O)Nc4cn([C@H]5CC[C@H](CN6CCN(CC#Cc7cccc8c7n(C)c(=O)n8C7CCC(=O)NC7=O)CC6)CC5)nc4C(F)F)c3n2)CCO1] |
| I-407 | 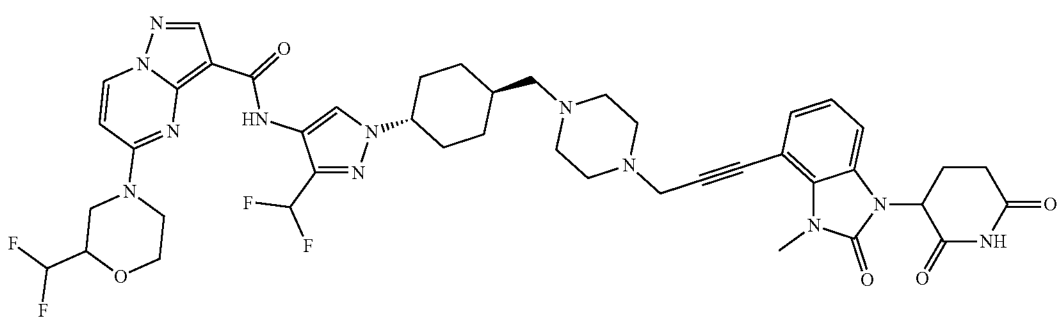 [SMILES: Cn1c(=O)n(C2CCC(=O)NC2=O)c2cccc(C#CCN3CCN(C[C@H]4CC[C@H](n5cc(NC(=O)c6cnn7ccc(N8CCOC(C(F)F)C8)nc67)c(C(F)F)n5)CC4)CC3)c21] |
| I-408 | 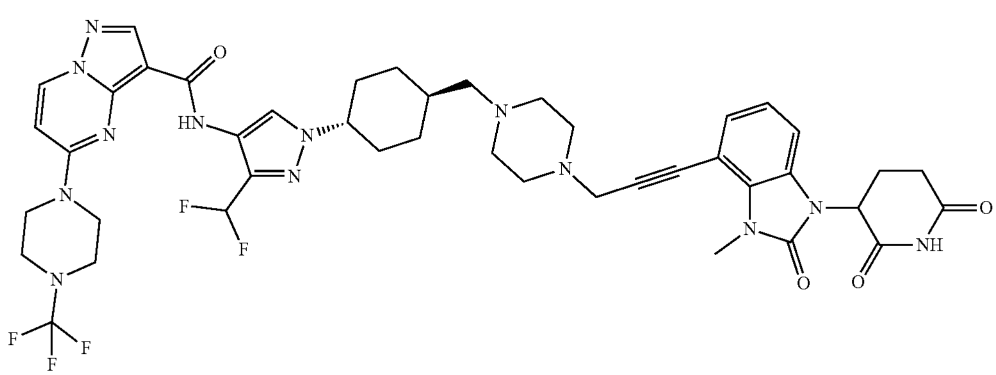 [SMILES: Cn1c(=O)n(C2CCC(=O)NC2=O)c2cccc(C#CCN3CCN(C[C@H]4CC[C@H](n5cc(NC(=O)c6cnn7ccc(N8CCN(C(F)(F)F)CC8)nc67)c(C(F)F)n5)CC4)CC3)c21] |

TABLE 1-continued

Exemplary Compounds

| I-# | Structure |
|---|---|
| I-409 | 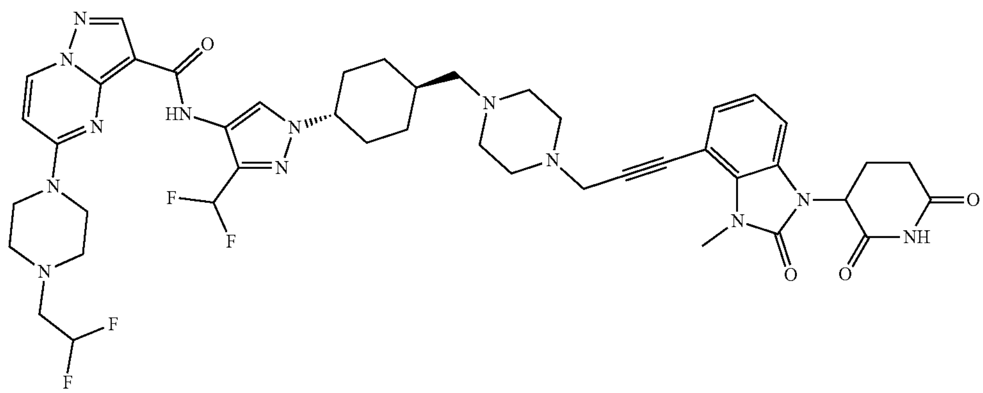 [SMILES: Cn1c(=O)n(C2CCC(=O)NC2=O)c2cccc(C#CCN3CCN(C[C@H]4CC[C@H](n5cc(NC(=O)c6cnn7ccc(N8CCN(CC(F)F)CC8)nc67)c(C(F)F)n5)CC4)CC3)c21] |
| I-410 | 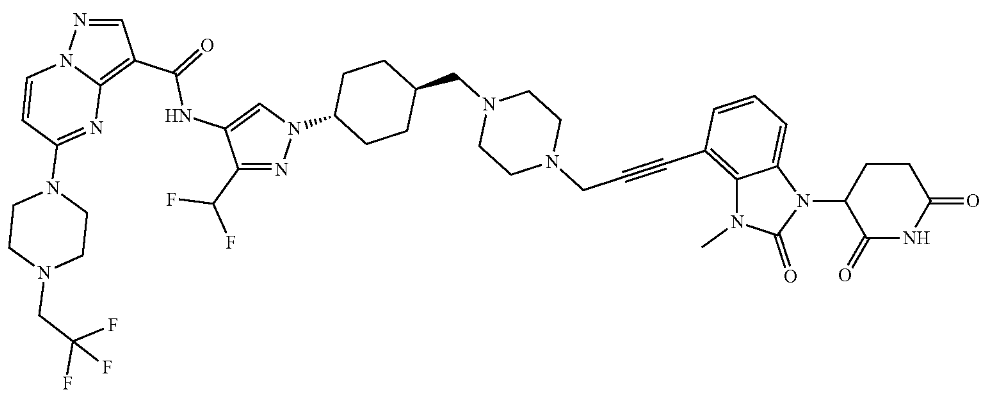 [SMILES: Cn1c(=O)n(C2CCC(=O)NC2=O)c2cccc(C#CCN3CCN(C[C@H]4CC[C@H](n5cc(NC(=O)c6cnn7ccc(N8CCN(CC(F)(F)F)CC8)nc67)c(C(F)F)n5)CC4)CC3)c21] |
| I-411 | 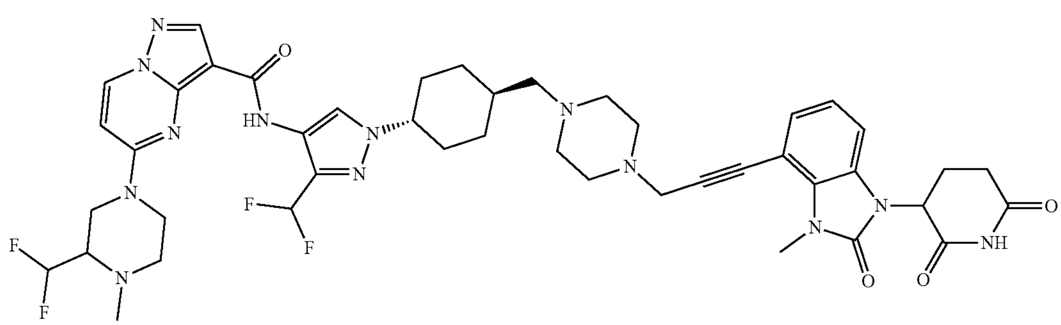 [SMILES: CN1CCN(c2ccn3ncc(C(=O)Nc4cn([C@H]5CC[C@H](CN6CCN(CC#Cc7cccc8c7n(C)c(=O)n8C7CCC(=O)NC7=O)CC6)CC5)nc4C(F)F)c3n2)CC1C(F)F] |
| I-412 | 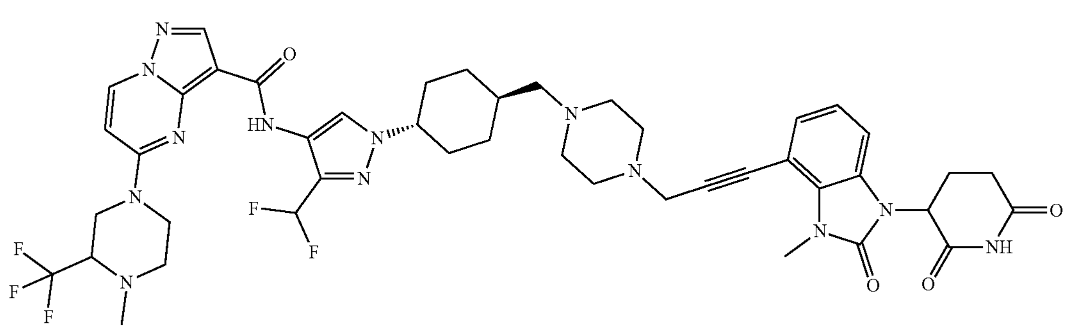 [SMILES: CN1CCN(c2ccn3ncc(C(=O)Nc4cn([C@H]5CC[C@H](CN6CCN(CC#Cc7cccc8c7n(C)c(=O)n8C7CCC(=O)NC7=O)CC6)CC5)nc4C(F)F)c3n2)CC1C(F)(F)F] |

275 276
TABLE 1-continued
Exemplary Compounds
| I-# | Structure |
|---|---|
| I-413 | 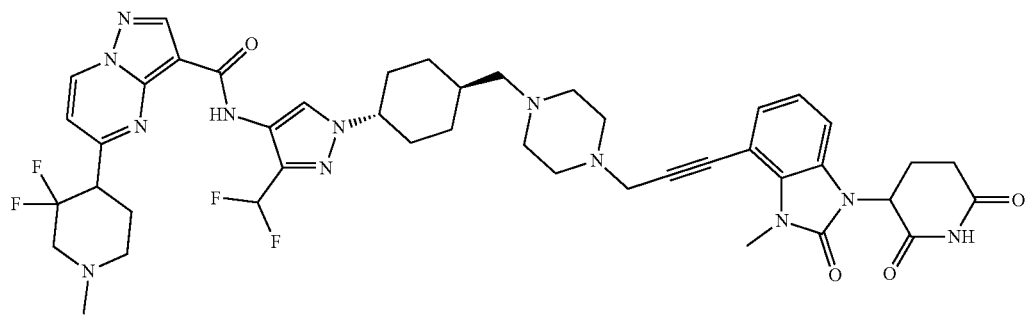 [SMILES: CN1CCC(c2ccn3ncc(C(=O)Nc4cn([C@H]5CC[C@H](CN6CCN(CC#Cc7cccc8c7n(C)c(=O)n8C7CCC(=O)NC7=O)CC6)CC5)nc4C(F)F)c3n2)C(F)(F)C1] |
| I-414 | 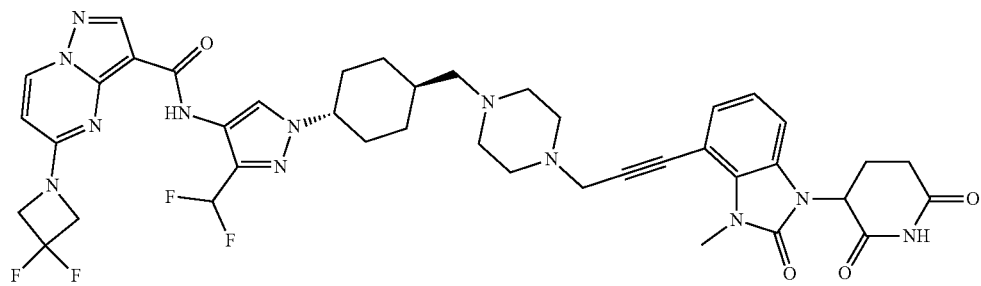 [SMILES: Cn1c(=O)n(C2CCC(=O)NC2=O)c2cccc(C#CCN3CCN(C[C@H]4CC[C@H](n5cc(NC(=O)c6cnn7ccc(N8CC(F)(F)C8)nc67)c(C(F)F)n5)CC4)CC3)c21] |
| I-415 | 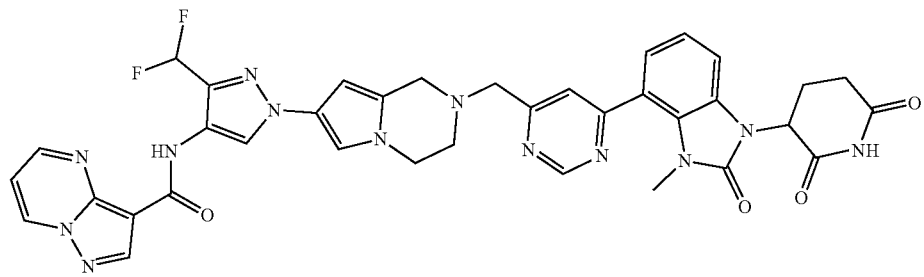 [SMILES: Cn1c(=O)n(C2CCC(=O)NC2=O)c2cccc(-c3cc(CN4CCn5cc(-n6cc(NC(=O)c7cnn8cccnc78)c(C(F)F)n6)cc5C4)ncn3)c21] |
| I-416 | 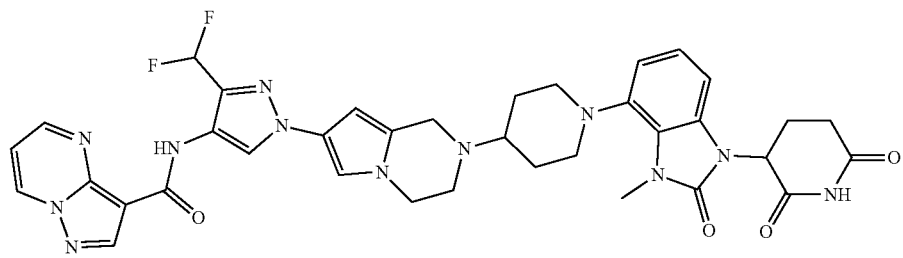 [SMILES: Cn1c(=O)n(C2CCC(=O)NC2=O)c2cccc(N3CCC(N4CCn5cc(-n6cc(NC(=O)c7cnn8cccnc78)c(C(F)F)n6)cc5C4)CC3)c21] |
| I-417 | 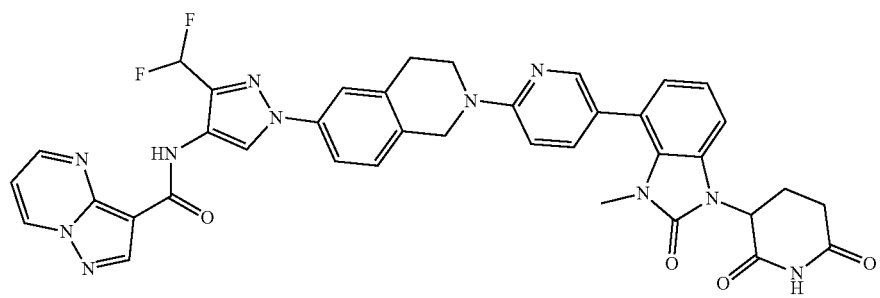 [SMILES: Cn1c(=O)n(C2CCC(=O)NC2=O)c2cccc(-c3ccc(N4CCc5cc(-n6cc(NC(=O)c7cnn8cccnc78)c(C(F)F)n6)ccc5C4)nc3)c21] |

TABLE 1-continued

Exemplary Compounds

| I-# | Structure |
|---|---|
| I-418 | 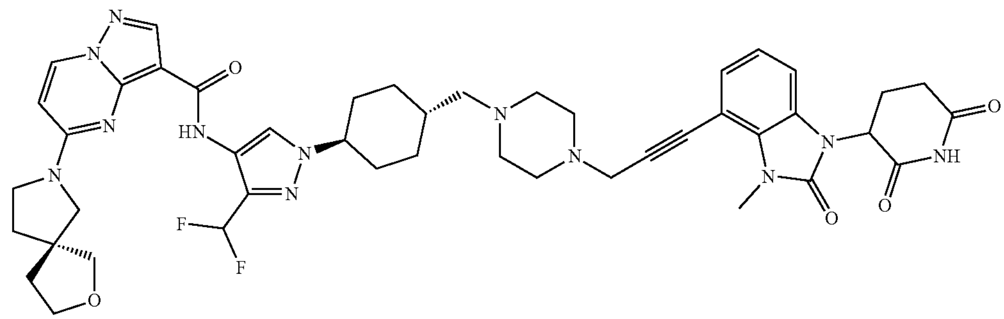 [SMILES: Cn1c(=O)n(C2CCC(=O)NC2=O)c2cccc(C#CCN3CCN(C[C@H]4CC[C@H](n5cc(NC(=O)c6cnn7ccc(N8CC[C@]9(CCOC9)C8)nc67)c(C(F)F)n5)CC4)CC3)c21] |
| I-419 | 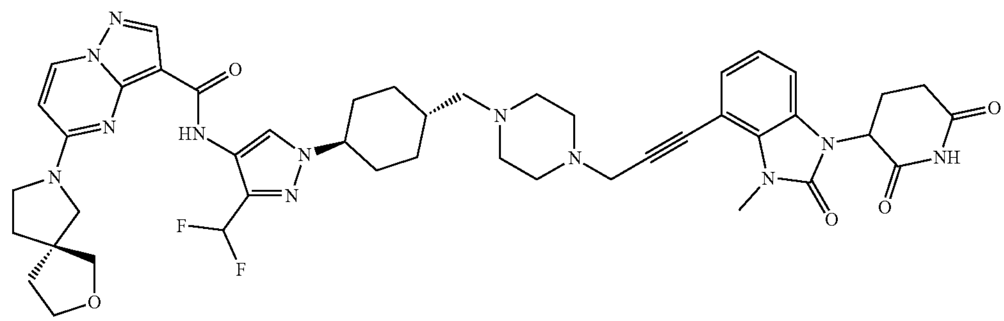 [SMILES: Cn1c(=O)n(C2CCC(=O)NC2=O)c2cccc(C#CCN3CCN(C[C@H]4CC[C@H](n5cc(NC(=O)c6cnn7ccc(N8CC[C@@]9(CCOC9)C8)nc67)c(C(F)F)n5)CC4)CC3)c21] |
| I-420 | 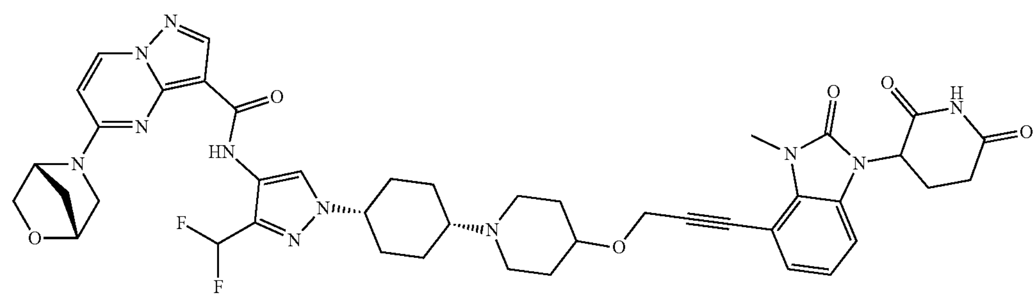 [SMILES: Cn1c(=O)n(C2CCC(=O)NC2=O)c2cccc(C#CCOC3CCN([C@H]4CC[C@@H](n5cc(NC(=O)c6cnn7ccc(N8C[C@H]9C[C@@H]8CO9)nc67)c(C(F)F)n5)CC4)CC3)c21] |
| I-421 | 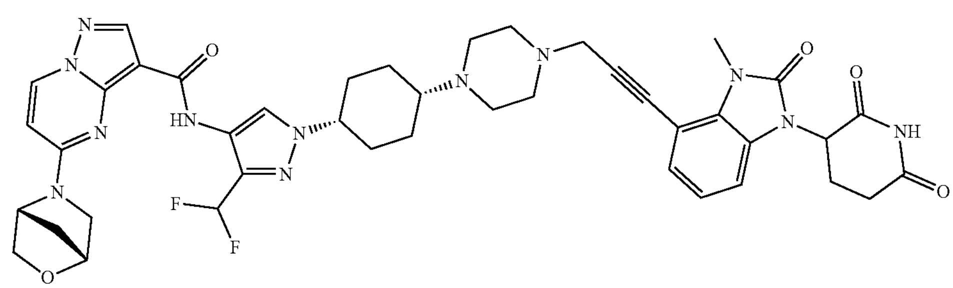 [SMILES: Cn1c(=O)n(C2CCC(=O)NC2=O)c2cccc(C#CCN3CCN([C@H]4CC[C@@H](n5cc(NC(=O)c6cnn7ccc(N8C[C@H]9C[C@@H]8CO9)nc67)c(C(F)F)n5)CC4)CC3)c21] |
| I-422 | 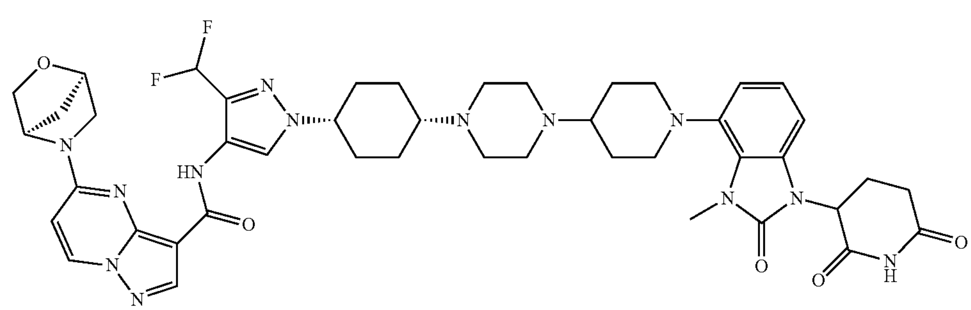 [SMILES: Cn1c(=O)n(C2CCC(=O)NC2=O)c2cccc(N3CCC(N4CCN([C@H]5CC[C@@H](n6cc(NC(=O)c7cnn8ccc(N9C[C@H]%10C[C@@H]9CO%10)nc78)c(C(F)F)n6)CC5)CC4)CC3)c21] |

TABLE 1-continued
Exemplary Compounds
| I-# | Structure |
| --- | --- |
| I-423 | 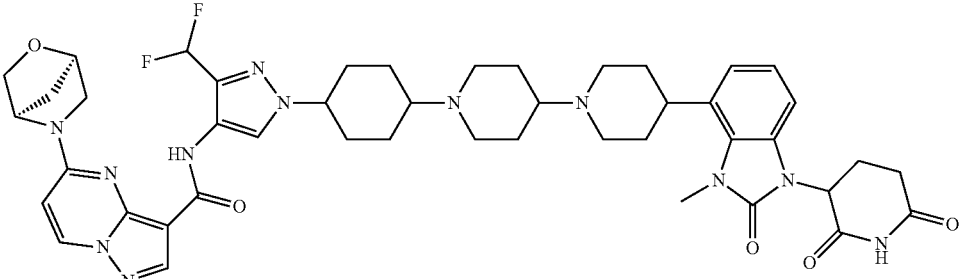 |
| I-424 | 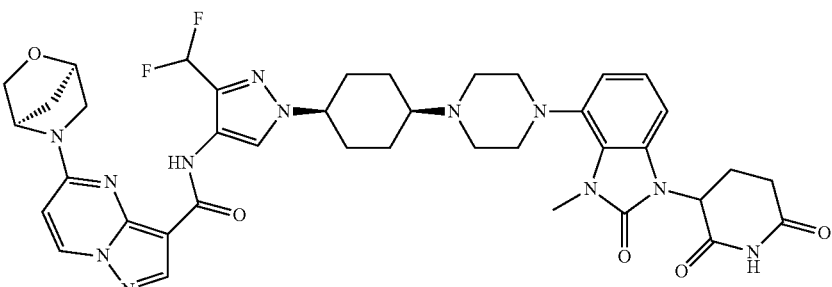 |
| I-425 | 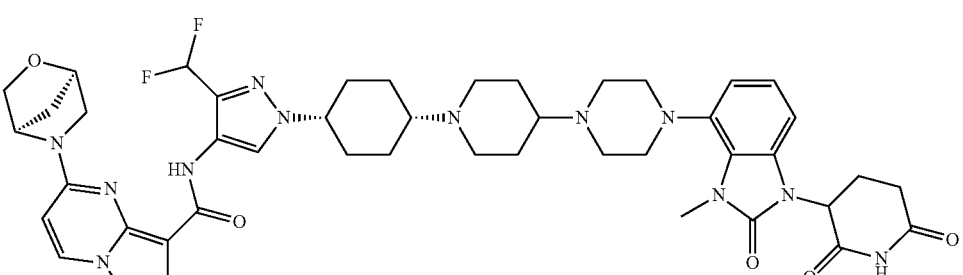 |
| I-426 | 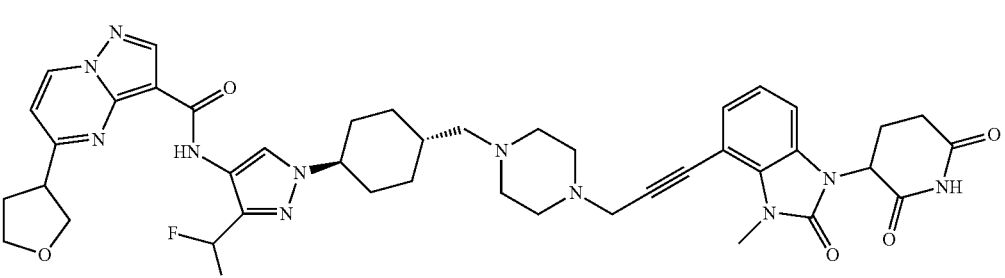 |
| I-427 | 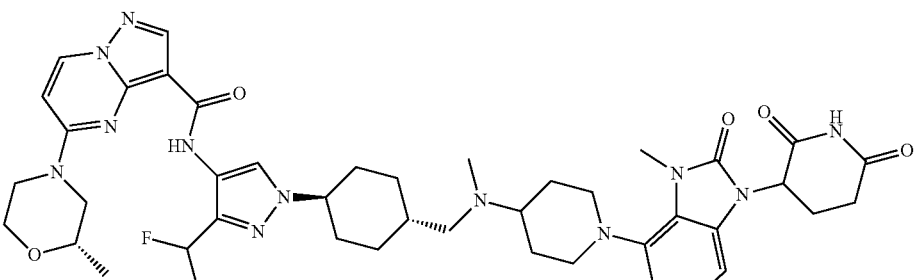 |

TABLE 1-continued

Exemplary Compounds

| I-# | Structure |
|---|---|
| I-428 | 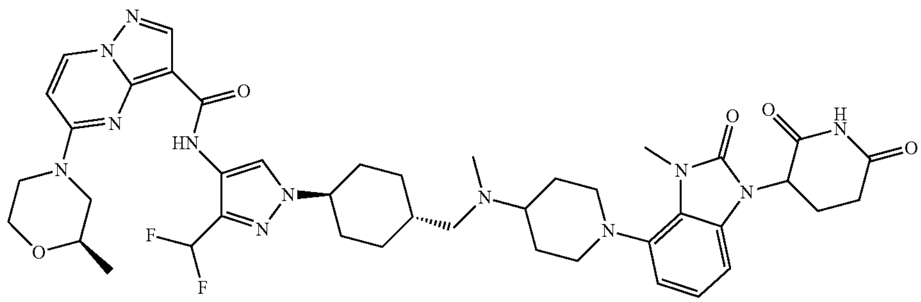 [SMILES: C[C@@H]1CN(c2ccn3ncc(C(=O)Nc4cn([C@H]5CC[C@H](CN(C)C6CCN(c7cccc8c7n(C)c(=O)n8C7CCC(=O)NC7=O)CC6)CC5)nc4C(F)F)c3n2)CCO1] |
| I-429 | 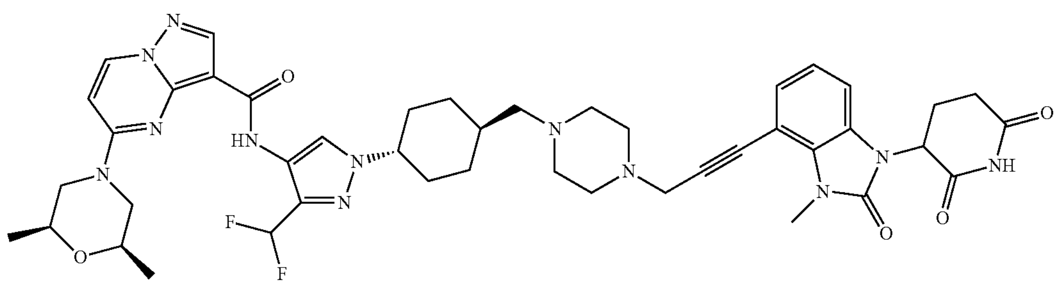 [SMILES: C[C@@H]1CN(c2ccn3ncc(C(=O)Nc4cn([C@H]5CC[C@H](CN6CCN(CC#Cc7cccc8c7n(C)c(=O)n8C7CCC(=O)NC7=O)CC6)CC5)nc4C(F)F)c3n2)C[C@H](C)O1] |
| I-430 | 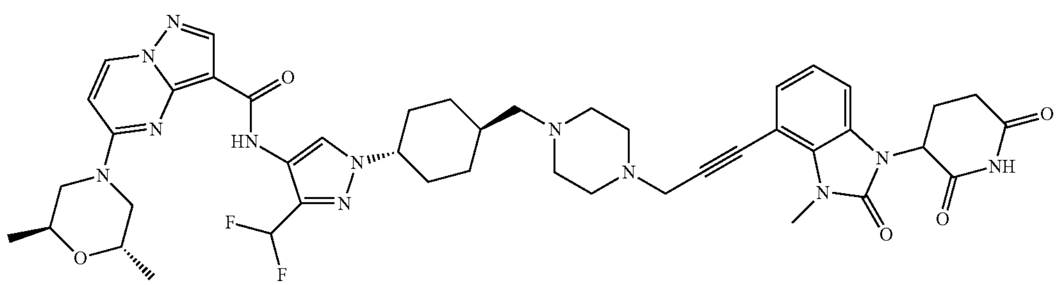 [SMILES: C[C@H]1CN(c2ccn3ncc(C(=O)Nc4cn([C@H]5CC[C@H](CN6CCN(CC#Cc7cccc8c7n(C)c(=O)n8C7CCC(=O)NC7=O)CC6)CC5)nc4C(F)F)c3n2)C[C@H](C)O1] |
| I-431 | 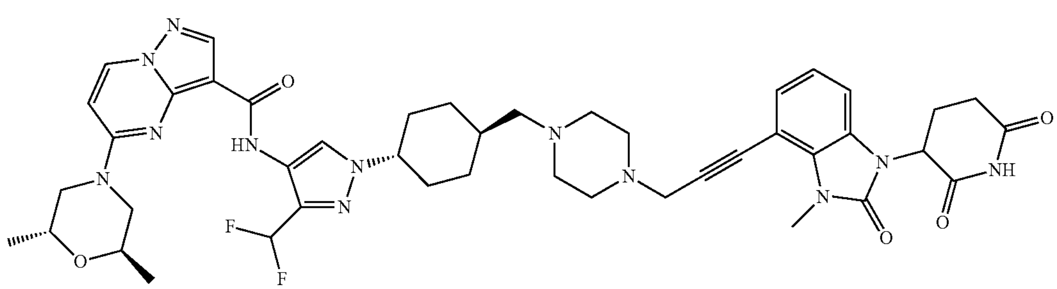 [SMILES: C[C@@H]1CN(c2ccn3ncc(C(=O)Nc4cn([C@H]5CC[C@H](CN6CCN(CC#Cc7cccc8c7n(C)c(=O)n8C7CCC(=O)NC7=O)CC6)CC5)nc4C(F)F)c3n2)C[C@@H](C)O1] |
| I-432 | 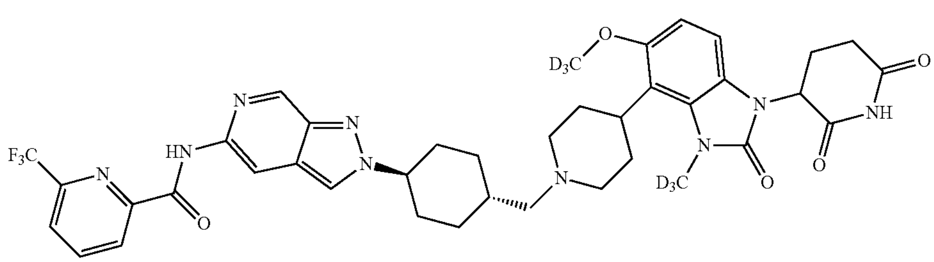 [SMILES: [2H]C([2H])([2H])Oc1ccc2c(c1C1CCN(C[C@H]3CC[C@H](n4cc5cc(NC(=O)c6cccc(C(F)(F)F)n6)ncc5n4)CC3)CC1)n(C([2H])([2H])[2H])c(=O)n2C1CCC(=O)NC1=O] |

TABLE 1-continued

Exemplary Compounds

| I-# | Structure |
|---|---|
| I-433 | 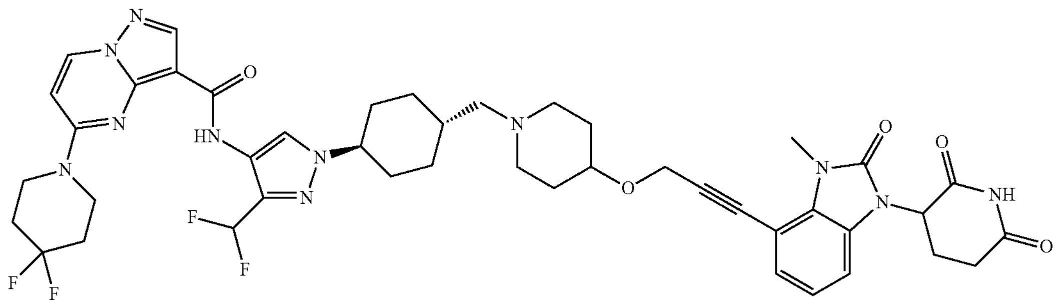 [SMILES: Cn1c(=O)n(C2CCC(=O)NC2=O)c2cccc(C#CCOC3CCN(C[C@H]4CC[C@H](n5cc(NC(=O)c6cnn7ccc(N8CCC(F)(F)CC8)nc67)c(C(F)F)n5)CC4)CC3)c21] |
| I-434 | 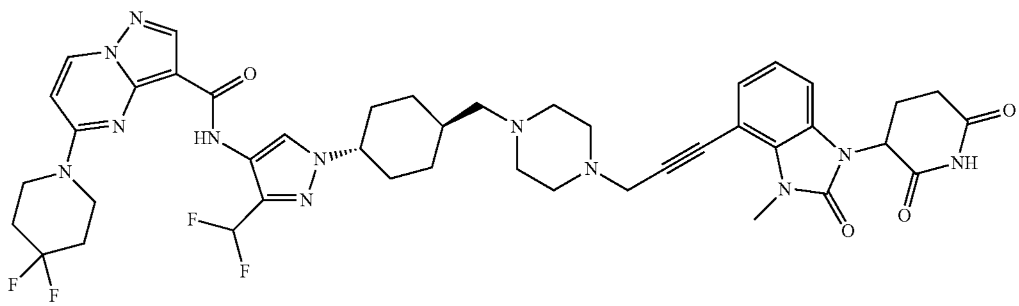 [SMILES: Cn1c(=O)n(C2CCC(=O)NC2=O)c2cccc(C#CCN3CCN(C[C@H]4CC[C@H](n5cc(NC(=O)c6cnn7ccc(N8CCC(F)(F)CC8)nc67)c(C(F)F)n5)CC4)CC3)c21] |
| I-435 | 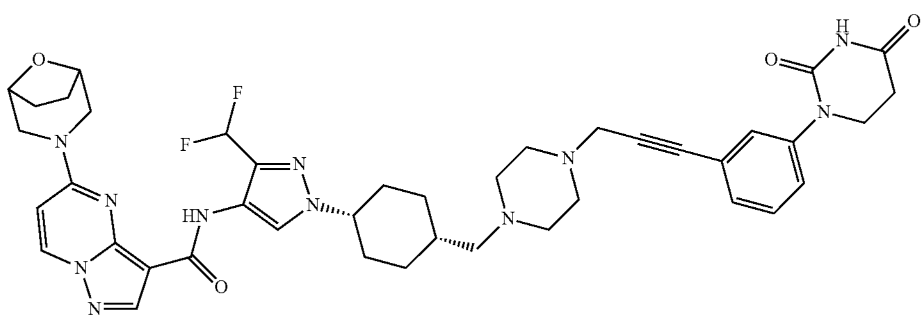 [SMILES: O=C1CCN(c2cccc(C#CCN3CCN(C[C@H]4CC[C@@H](n5cc(NC(=O)c6cnn7ccc(N8CC9CCC(C8)O9)nc67)c(C(F)F)n5)CC4)CC3)c2)C(=O)N1] |
| I-436 | 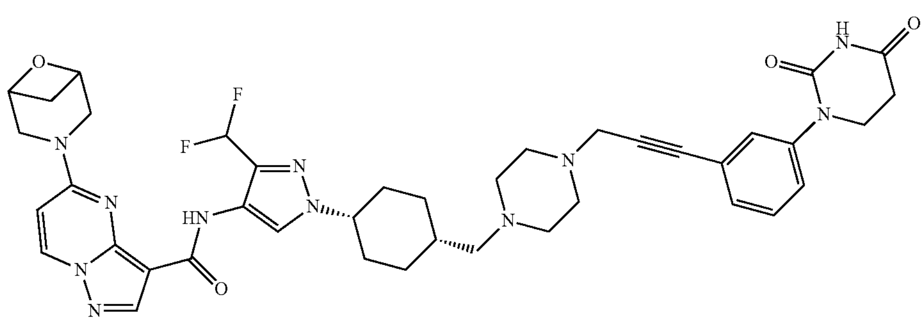 [SMILES: O=C1CCN(c2cccc(C#CCN3CCN(C[C@H]4CC[C@@H](n5cc(NC(=O)c6cnn7ccc(N8CC9CC(C8)O9)nc67)c(C(F)F)n5)CC4)CC3)c2)C(=O)N1] |
| I-437 | 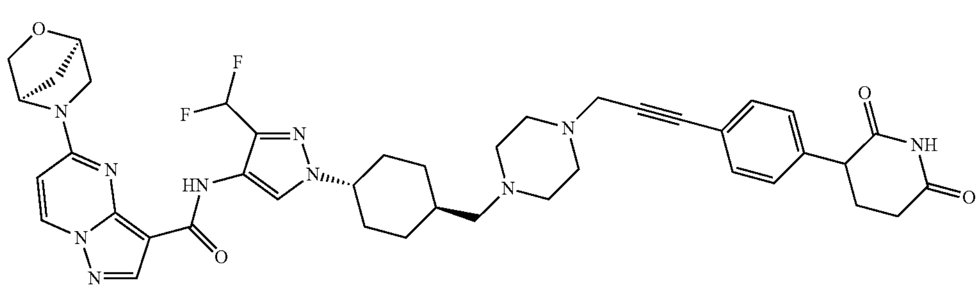 [SMILES: O=C1CCC(c2ccc(C#CCN3CCN(C[C@H]4CC[C@H](n5cc(NC(=O)c6cnn7ccc(N8C[C@H]9C[C@@H]8CO9)nc67)c(C(F)F)n5)CC4)CC3)cc2)C(=O)N1] |

TABLE 1-continued

Exemplary Compounds

| I-# | Structure |
|---|---|
| I-438 | 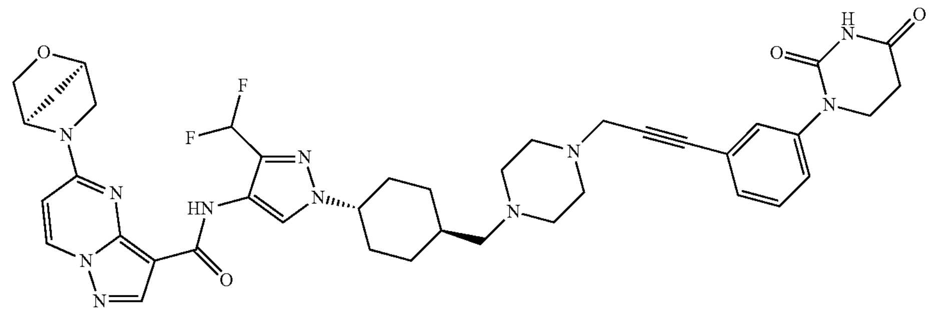 [SMILES: O=C1CCN(c2cccc(C#CCN3CCN(C[C@H]4CC[C@H](n5cc(NC(=O)c6cnn7ccc(N8C[C@H]9C[C@@H]8CO9)nc67)c(C(F)F)n5)CC4)CC3)c2)C(=O)N1] |
| I-439 | 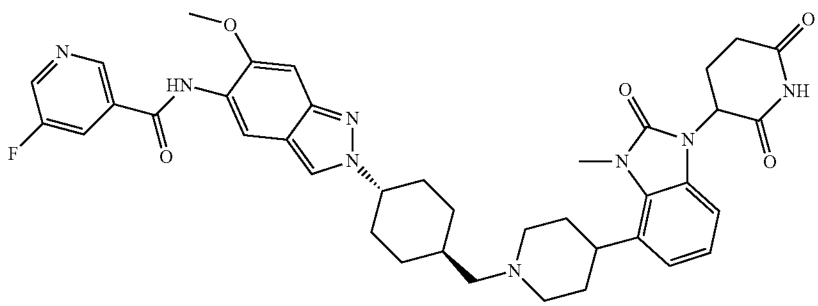 [SMILES: COc1cc2nn([C@H]3CC[C@H](CN4CCC(c5cccc6c5n(C)c(=O)n6C5CCC(=O)NC5=O)CC4)CC3)cc2cc1NC(=O)c1cncc(F)c1] |
| I-440 | 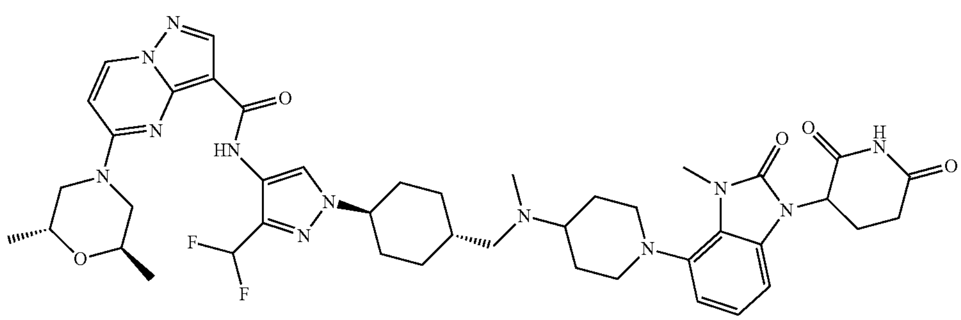 [SMILES: C[C@@H]1CN(c2ccn3ncc(C(=O)Nc4cn([C@H]5CC[C@H](CN(C)C6CCN(c7cccc8c7n(C)c(=O)n8C7CCC(=O)NC7=O)CC6)CC5)nc4C(F)F)c3n2)C[C@@H](C)O1] |
| I-441 | 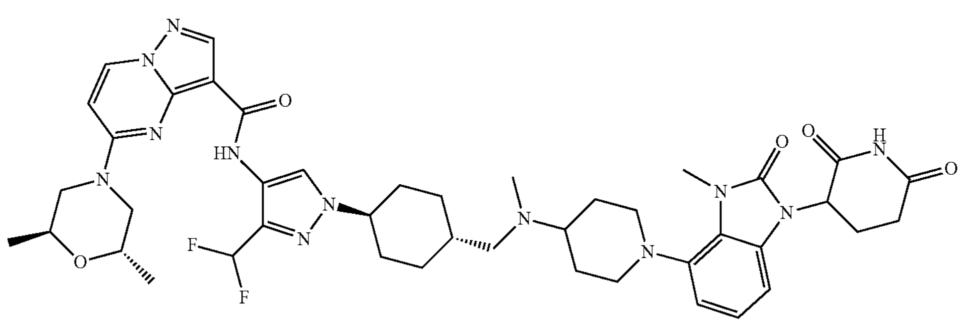 [SMILES: C[C@H]1CN(c2ccn3ncc(C(=O)Nc4cn([C@H]5CC[C@H](CN(C)C6CCN(c7cccc8c7n(C)c(=O)n8C7CCC(=O)NC7=O)CC6)CC5)nc4C(F)F)c3n2)C[C@H](C)O1] |
| I-442 | 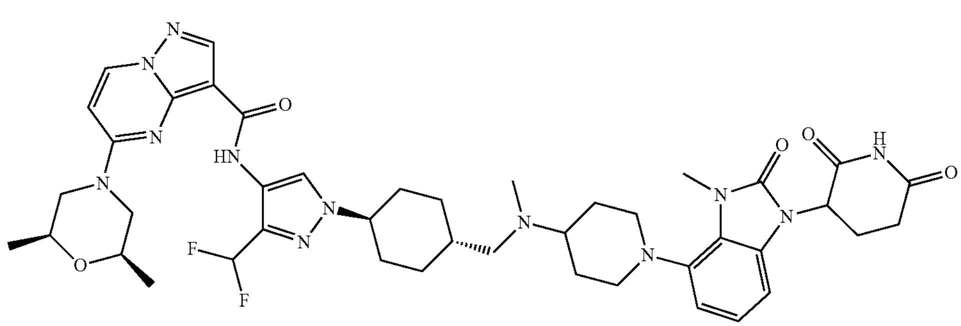 [SMILES: C[C@@H]1CN(c2ccn3ncc(C(=O)Nc4cn([C@H]5CC[C@H](CN(C)C6CCN(c7cccc8c7n(C)c(=O)n8C7CCC(=O)NC7=O)CC6)CC5)nc4C(F)F)c3n2)C[C@H](C)O1] |

TABLE 1-continued

Exemplary Compounds

| I-# | Structure |
|---|---|
| I-443 | 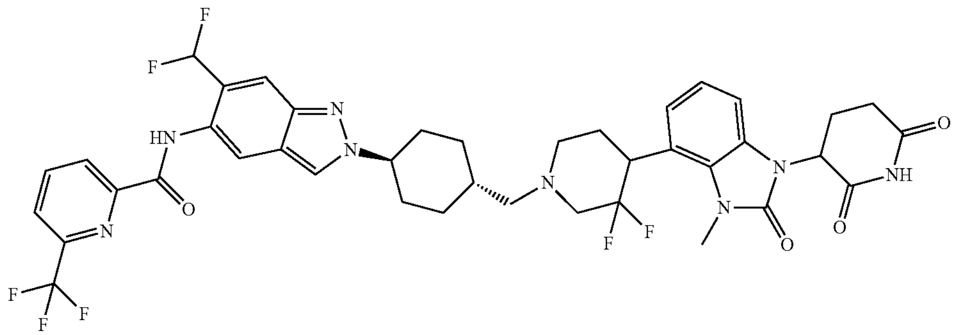 [SMILES: Cn1c(=O)n(C2CCC(=O)NC2=O)c2cccc(C3CCN(C[C@H]4CC[C@H](n5cc6cc(NC(=O)c7cccc(C(F)(F)F)n7)c(C(F)F)cc6n5)CC4)CC3(F)F)c21] |
| I-444 | 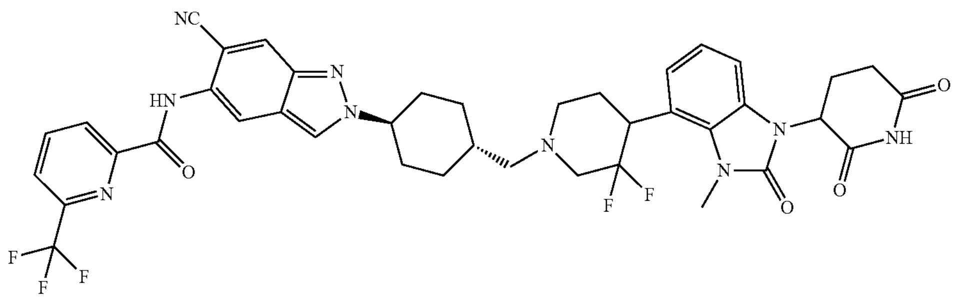 [SMILES: Cn1c(=O)n(C2CCC(=O)NC2=O)c2cccc(C3CCN(C[C@H]4CC[C@H](n5cc6cc(NC(=O)c7cccc(C(F)(F)F)n7)c(C#N)cc6n5)CC4)CC3(F)F)c21] |
| I-445 | 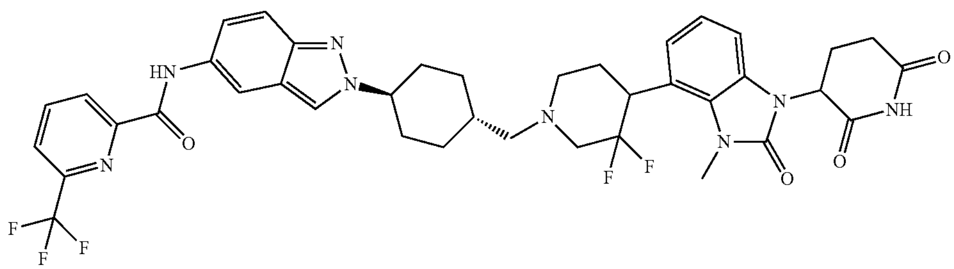 [SMILES: Cn1c(=O)n(C2CCC(=O)NC2=O)c2cccc(C3CCN(C[C@H]4CC[C@H](n5cc6cc(NC(=O)c7cccc(C(F)(F)F)n7)ccc6n5)CC4)CC3(F)F)c21] |
| I-446 | 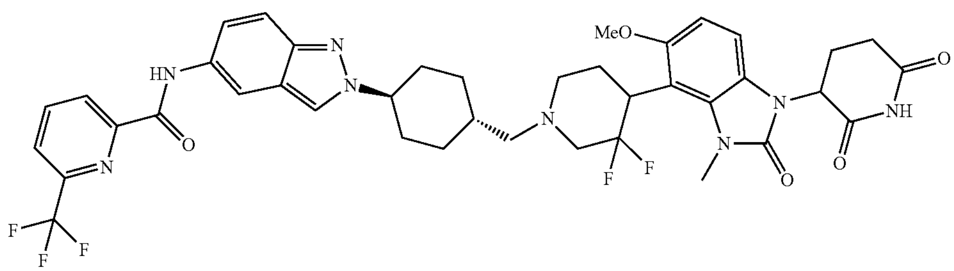 [SMILES: COc1ccc2c(c1C1CCN(C[C@H]3CC[C@H](n4cc5cc(NC(=O)c6cccc(C(F)(F)F)n6)ccc5n4)CC3)CC1(F)F)n(C)c(=O)n2C1CCC(=O)NC1=O] |
| I-447 | 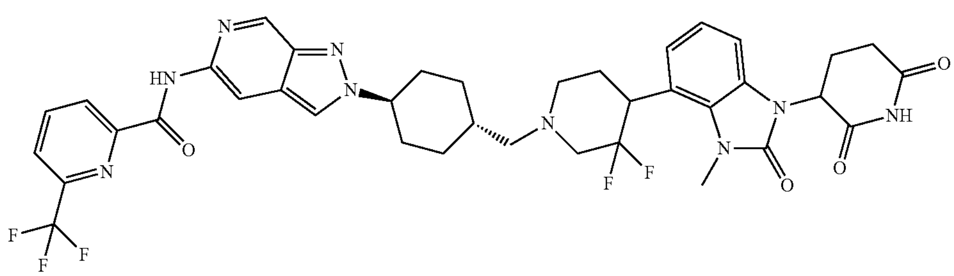 [SMILES: Cn1c(=O)n(C2CCC(=O)NC2=O)c2cccc(C3CCN(C[C@H]4CC[C@H](n5cc6cc(NC(=O)c7cccc(C(F)(F)F)n7)ncc6n5)CC4)CC3(F)F)c21] |

TABLE 1-continued

Exemplary Compounds

| I-# | Structure |
|---|---|
| I-448 | 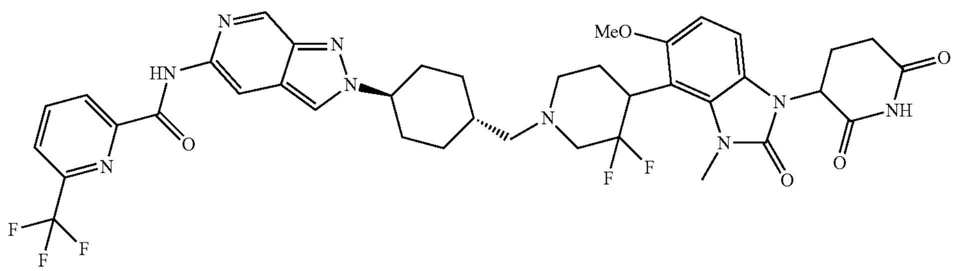 [SMILES: COc1ccc2c(c1C1CCN(C[C@H]3CC[C@H](n4cc5cc(NC(=O)c6cccc(C(F)(F)F)n6)ncc5n4)CC3)CC1(F)F)n(C)c(=O)n2C1CCC(=O)NC1=O] |
| I-449 | 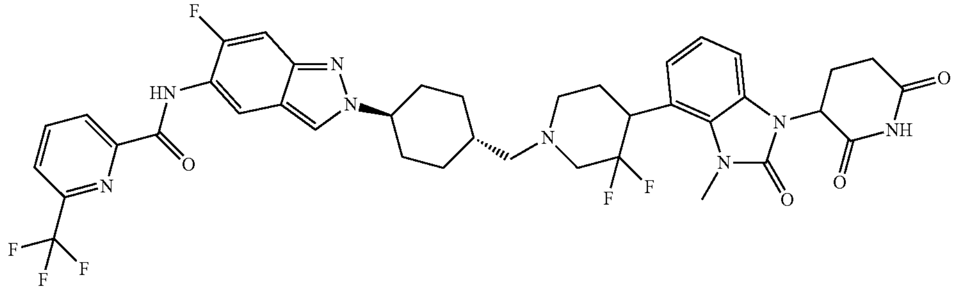 [SMILES: Cn1c(=O)n(C2CCC(=O)NC2=O)c2cccc(C3CCN(C[C@H]4CC[C@H](n5cc6cc(NC(=O)c7cccc(C(F)(F)F)n7)c(Cl)cc6n5)CC4)CC3(F)F)c21] |
| I-450 | 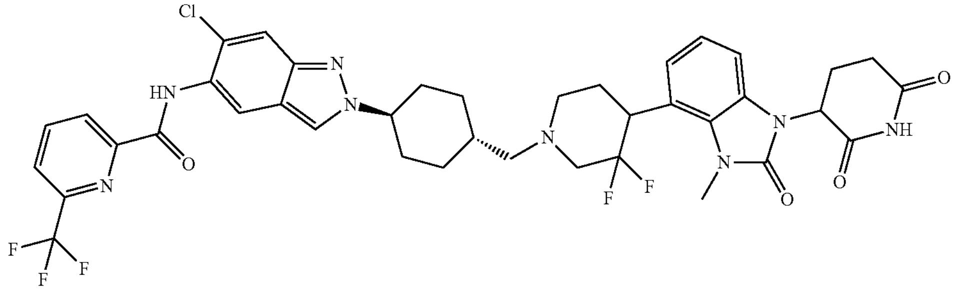 |
| I-451 | 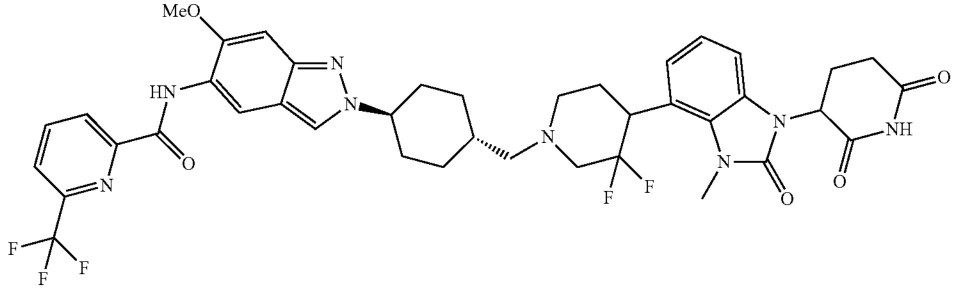 [SMILES: COc1cc2nn([C@H]3CC[C@H](CN4CCC(c5cccc6c5n(C)c(=O)n6C5CCC(=O)NC5=O)C(F)(F)C4)CC3)cc2cc1NC(=O)c1cccc(C(F)(F)F)n1] |
| I-452 | 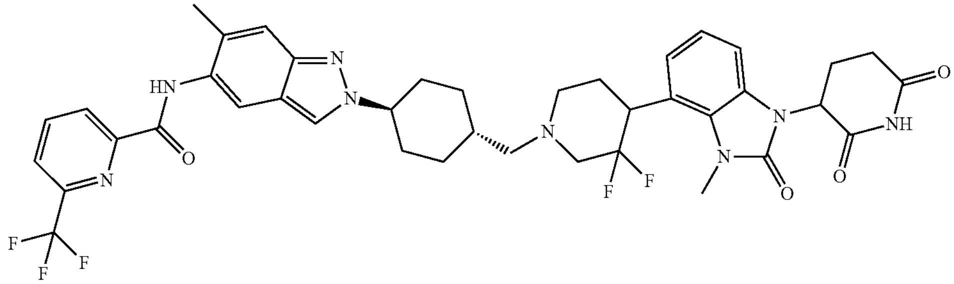 [SMILES: Cc1cc2nn([C@H]3CC[C@H](CN4CCC(c5cccc6c5n(C)c(=O)n6C5CCC(=O)NC5=O)C(F)(F)C4)CC3)cc2cc1NC(=O)c1cccc(C(F)(F)F)n1] |

TABLE 1-continued

Exemplary Compounds

| I-# | Structure |
|---|---|
| I-453 | 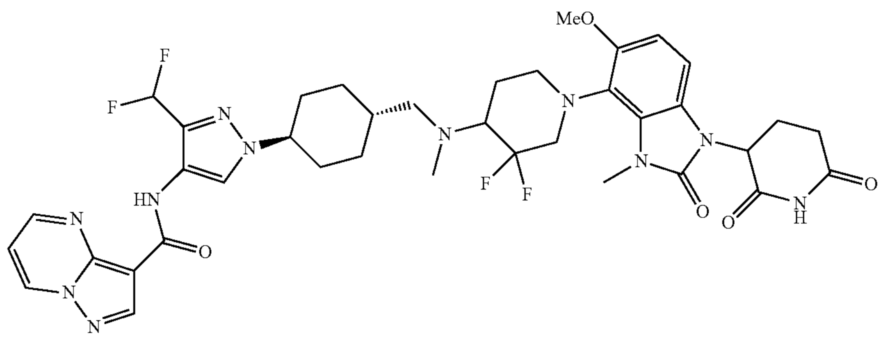 [SMILES: COc1ccc2c(c1N1CCC(N(C)C[C@H]3CC[C@H](n4cc(NC(=O)c5cnn6cccnc56)c(C(F)F)n4)CC3)C(F)(F)C1)n(C)c(=O)n2C1CCC(=O)NC1=O] |
| I-454 | 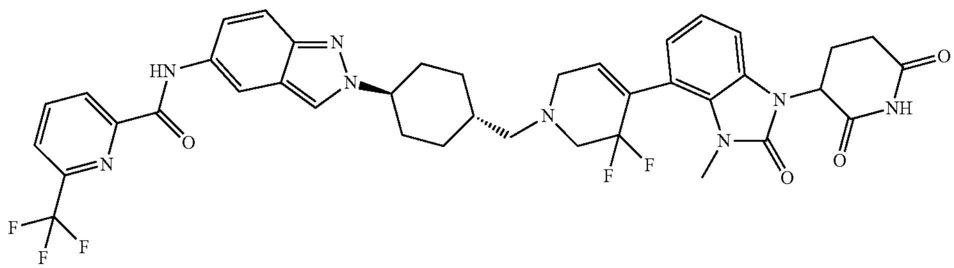 [SMILES: Cn1c(=O)n(C2CCC(=O)NC2=O)c2cccc(C3=CCN(C[C@H]4CC[C@H](n5cc6cc(NC(=O)c7cccc(C(F)(F)F)n7)ccc6n5)CC4)CC3(F)F)c21] |
| I-455 | 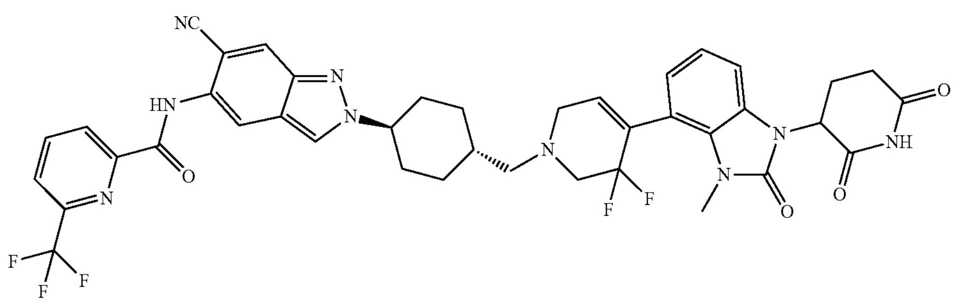 [SMILES: Cn1c(=O)n(C2CCC(=O)NC2=O)c2cccc(C3=CCN(C[C@H]4CC[C@H](n5cc6cc(NC(=O)c7cccc(C(F)(F)F)n7)c(C#N)cc6n5)CC4)CC3(F)F)c21] |
| I-456 | 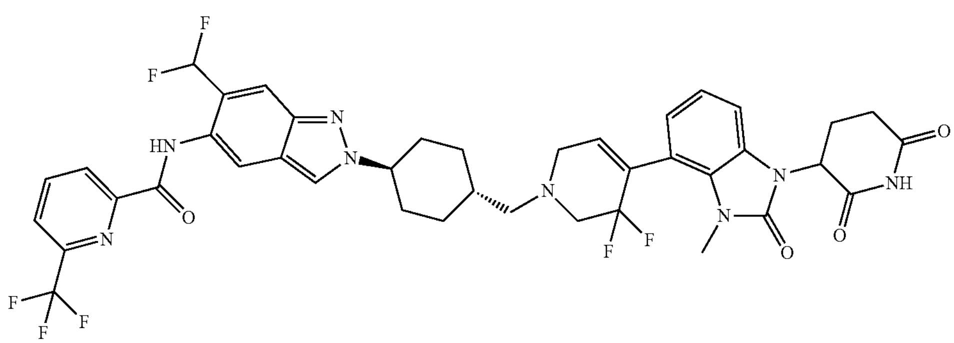 [SMILES: Cn1c(=O)n(C2CCC(=O)NC2=O)c2cccc(C3=CCN(C[C@H]4CC[C@H](n5cc6cc(NC(=O)c7cccc(C(F)(F)F)n7)c(C(F)F)cc6n5)CC4)CC3(F)F)c21] |
| I-457 | 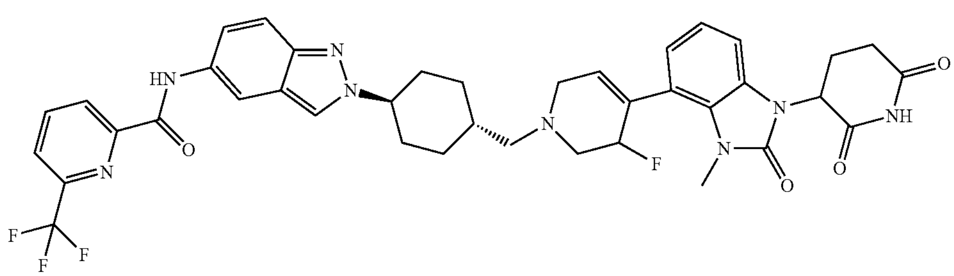 [SMILES: Cn1c(=O)n(C2CCC(=O)NC2=O)c2cccc(C3=CCN(C[C@H]4CC[C@H](n5cc6cc(NC(=O)c7cccc(C(F)(F)F)n7)ccc6n5)CC4)CC3F)c21] |

TABLE 1-continued

Exemplary Compounds

| I-# | Structure |
|---|---|
| I-458 | 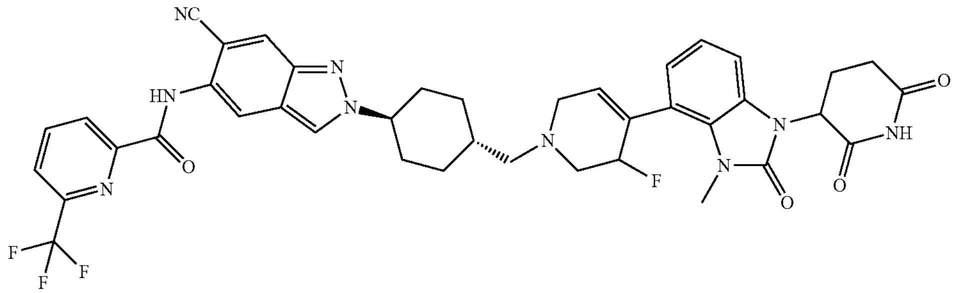 [SMILES: Cn1c(=O)n(C2CCC(=O)NC2=O)c2cccc(C3=CCN(C[C@H]4CC[C@H](n5cc6cc(NC(=O)c7cccc(C(F)(F)F)n7)c(C#N)cc6n5)CC4)CC3F)c21] |
| I-459 | 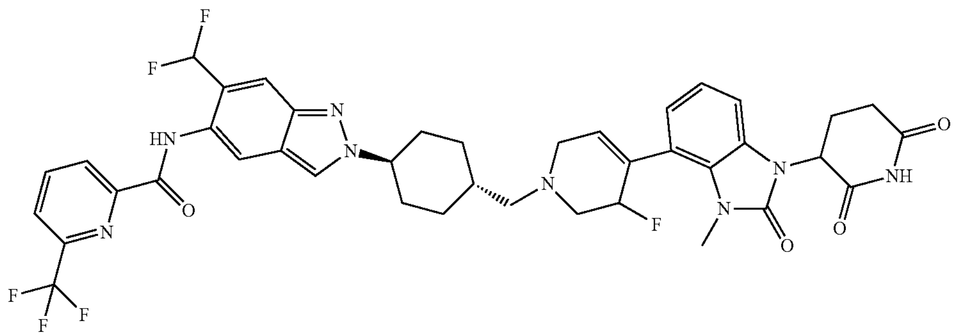 [SMILES: Cn1c(=O)n(C2CCC(=O)NC2=O)c2cccc(C3=CCN(C[C@H]4CC[C@H](n5cc6cc(NC(=O)c7cccc(C(F)(F)F)n7)c(C(F)F)cc6n5)CC4)CC3F)c21] |
| I-460 | 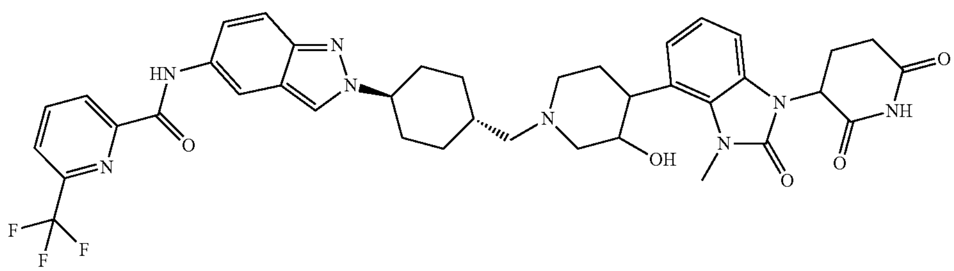 [SMILES: Cn1c(=O)n(C2CCC(=O)NC2=O)c2cccc(C3CCN(C[C@H]4CC[C@H](n5cc6cc(NC(=O)c7cccc(C(F)(F)F)n7)ccc6n5)CC4)CC3O)c21] |
| I-461 | 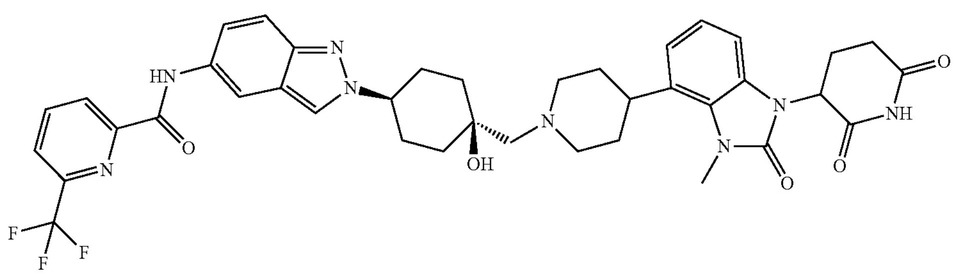 [SMILES: Cn1c(=O)n(C2CCC(=O)NC2=O)c2cccc(C3CCN(C[C@]4(O)CC[C@@H](n5cc6cc(NC(=O)c7cccc(C(F)(F)F)n7)ccc6n5)CC4)CC3)c21] |
| I-462 | 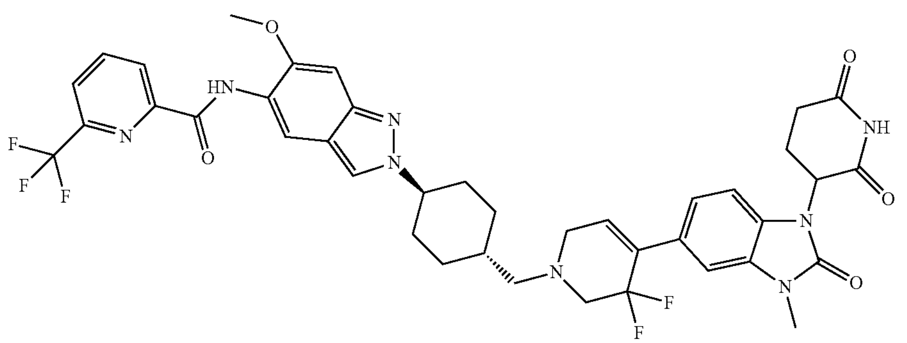 [SMILES: COc1cc2nn([C@H]3CC[C@H](CN4CC=C(c5ccc6c(c5)n(C)c(=O)n6C5CCC(=O)NC5=O)C(F)(F)C4)CC3)cc2cc1NC(=O)c1cccc(C(F)(F)F)n1] |

TABLE 1-continued

Exemplary Compounds

| I-# | Structure |
|---|---|
| I-463 | 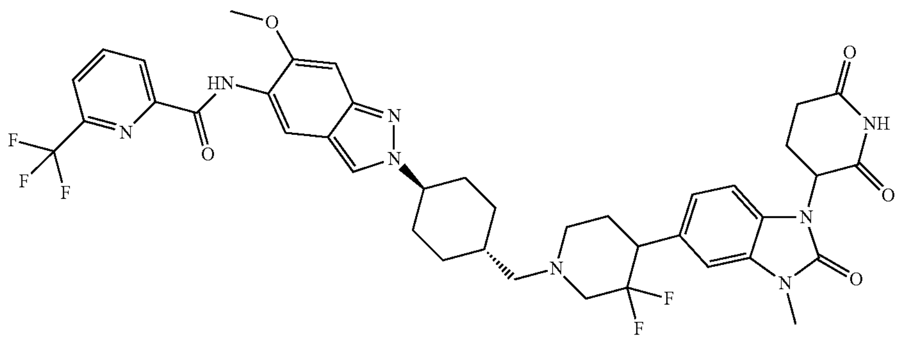 [SMILES: COc1cc2nn([C@H]3CC[C@H](CN4CCC(c5ccc6c(c5)n(C)c(=O)n6C5CCC(=O)NC5=O)C(F)(F)C4)CC3)cc2cc1NC(=O)c1cccc(C(F)(F)F)n1] |
| I-464 | 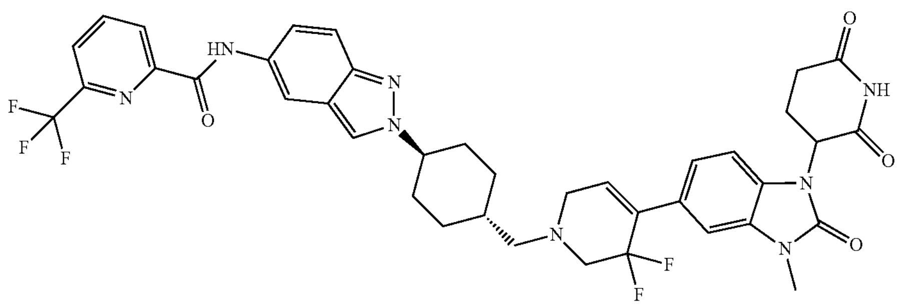 [SMILES: Cn1c(=O)n(C2CCC(=O)NC2=O)c2ccc(C3=CCN(C[C@H]4CC[C@H](n5cc6cc(NC(=O)c7cccc(C(F)(F)F)n7)ccc6n5)CC4)CC3(F)F)cc21] |
| I-465 | 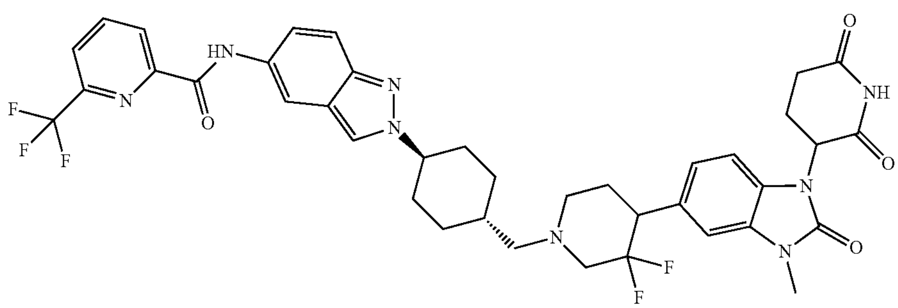 [SMILES: Cn1c(=O)n(C2CCC(=O)NC2=O)c2ccc(C3CCN(C[C@H]4CC[C@H](n5cc6cc(NC(=O)c7cccc(C(F)(F)F)n7)ccc6n5)CC4)CC3(F)F)cc21] |
| I-466 | 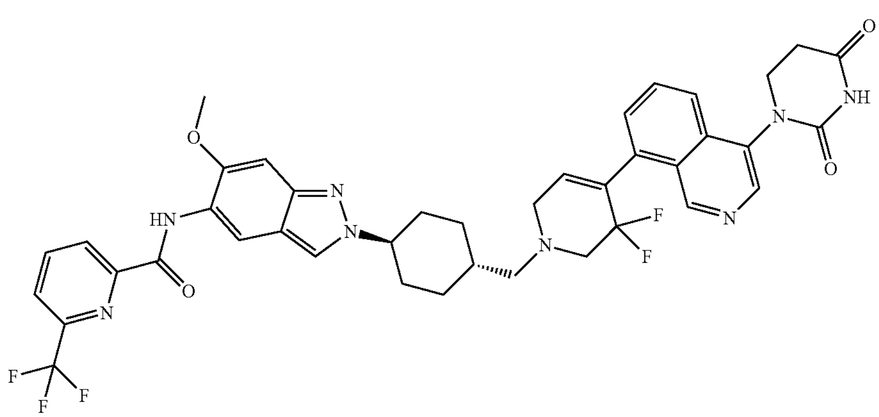 [SMILES: COc1cc2nn([C@H]3CC[C@H](CN4CC=C(c5cccc6c(N7CCC(=O)NC7=O)cncc56)C(F)(F)C4)CC3)cc2cc1NC(=O)c1cccc(C(F)(F)F)n1] |

TABLE 1-continued

Exemplary Compounds

| I-# | Structure |
|---|---|
| I-467 | 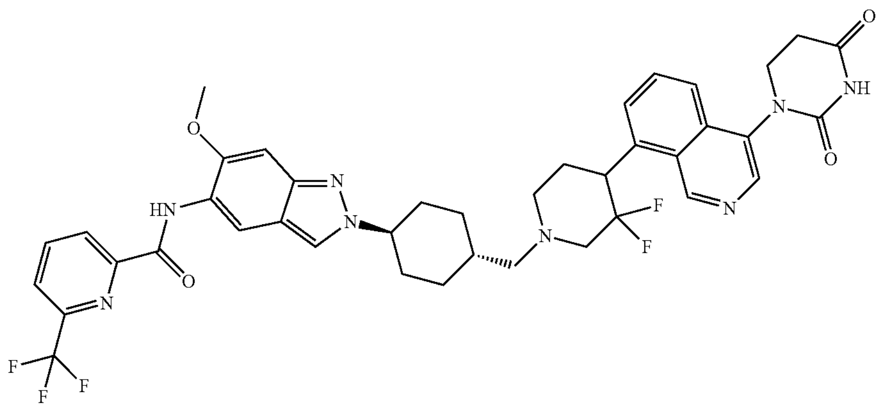 [SMILES: COc1cc2nn([C@H]3CC[C@H](CN4CCC(c5cccc6c(N7CCC(=O)NC7=O)cncc56)C(F)(F)C4)CC3)cc2cc1NC(=O)c1cccc(C(F)(F)F)n1] |
| I-468 | 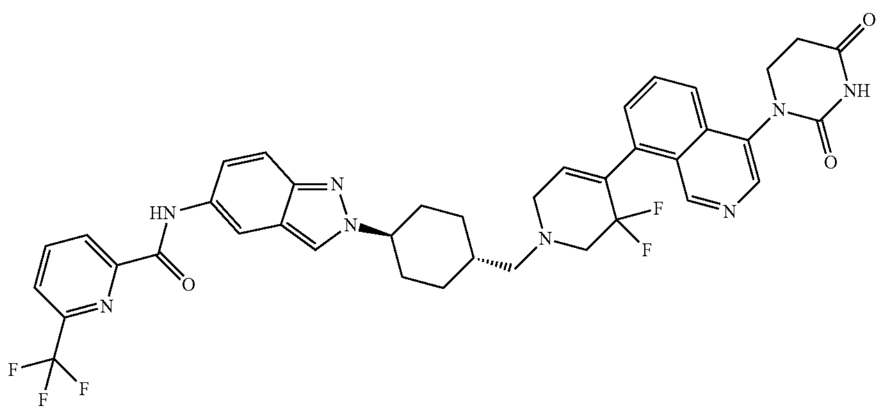 [SMILES: O=C1CCN(c2cncc3c(C4=CCN(C[C@H]5CC[C@H](n6cc7cc(NC(=O)c8cccc(C(F)(F)F)n8)ccc7n6)CC5)CC4(F)F)cccc23)C(=O)N1] |
| I-469 | 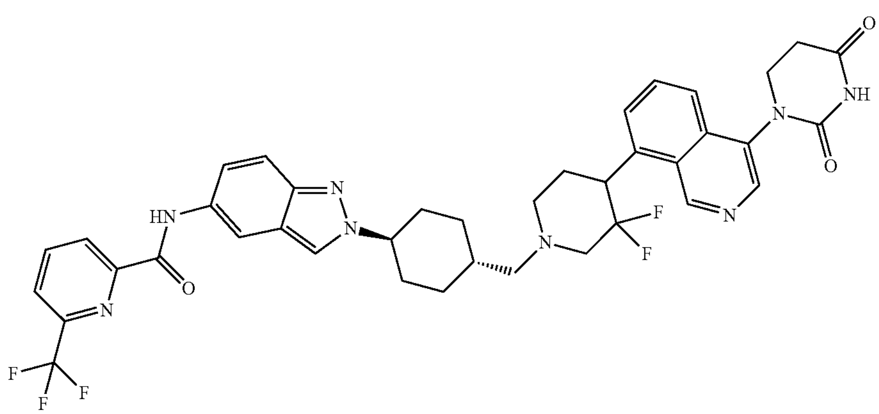 [SMILES: O=C1CCN(c2cncc3c(C4CCN(C[C@H]5CC[C@H](n6cc7cc(NC(=O)c8cccc(C(F)(F)F)n8)ccc7n6)CC5)CC4(F)F)cccc23)C(=O)N1] |
| I-470 | 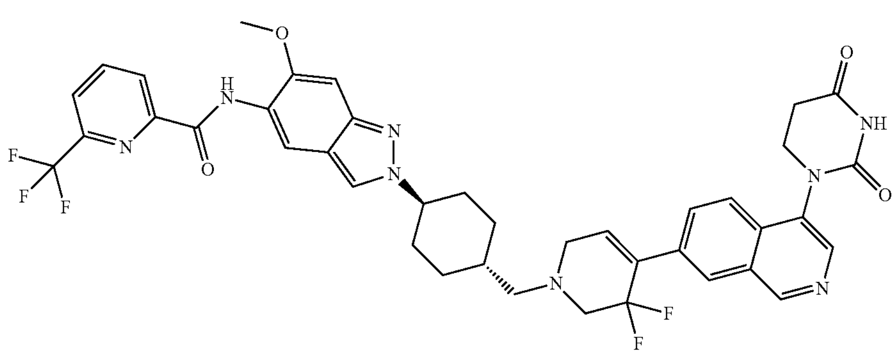 [SMILES: COc1cc2nn([C@H]3CC[C@H](CN4CC=C(c5ccc6c(N7CCC(=O)NC7=O)cncc6c5)C(F)(F)C4)CC3)cc2cc1NC(=O)c1cccc(C(F)(F)F)n1] |

TABLE 1-continued

Exemplary Compounds

| I-# | Structure |
|---|---|
| I-471 | 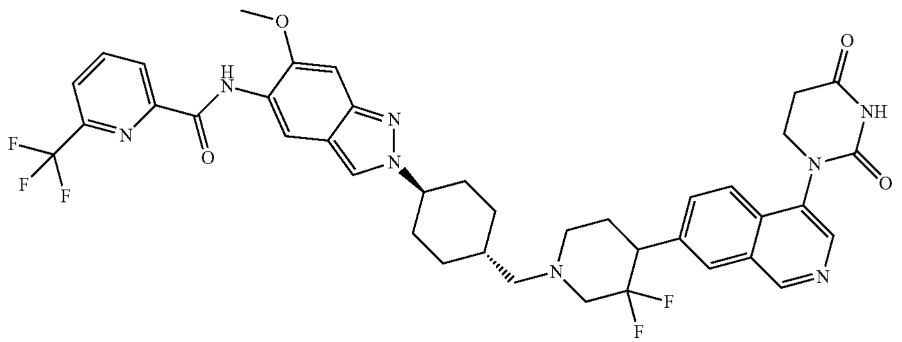 [SMILES: COc1cc2nn([C@H]3CC[C@H](CN4CCC(c5ccc6c(N7CCC(=O)NC7=O)cncc6c5)C(F)(F)C4)CC3)cc2cc1NC(=O)c1cccc(C(F)(F)F)n1] |
| I-472 | 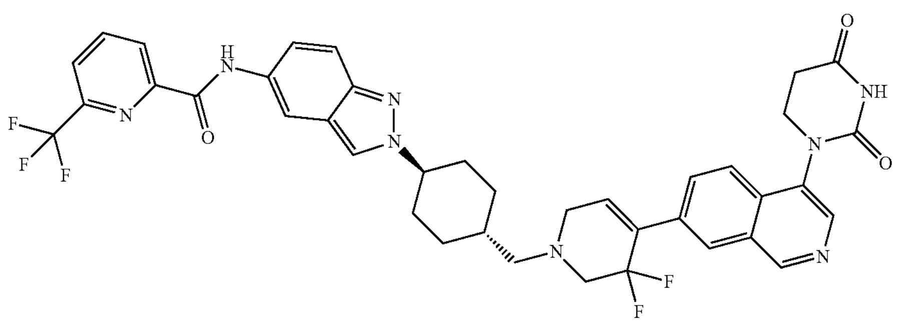 [SMILES: O=C1CCN(c2cncc3cc(C4=CCN(C[C@H]5CC[C@H](n6cc7cc(NC(=O)c8cccc(C(F)(F)F)n8)ccc7n6)CC5)CC4(F)F)ccc23)C(=O)N1] |
| I-473 | 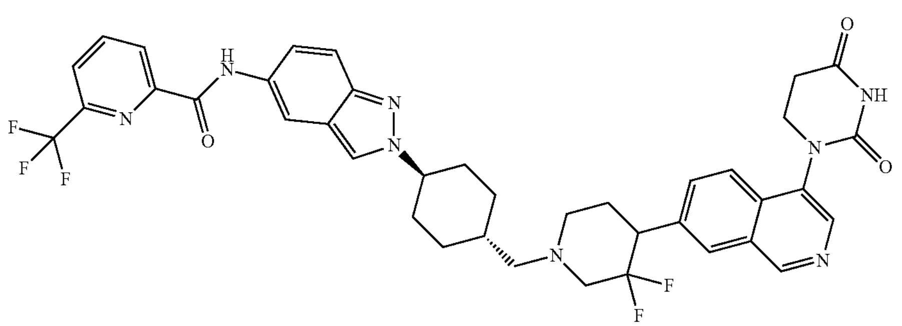 [SMILES: O=C1CCN(c2cncc3cc(C4CCN(C[C@H]5CC[C@H](n6cc7cc(NC(=O)c8cccc(C(F)(F)F)n8)ccc7n6)CC5)CC4(F)F)ccc23)C(=O)N1] |
| I-474 | 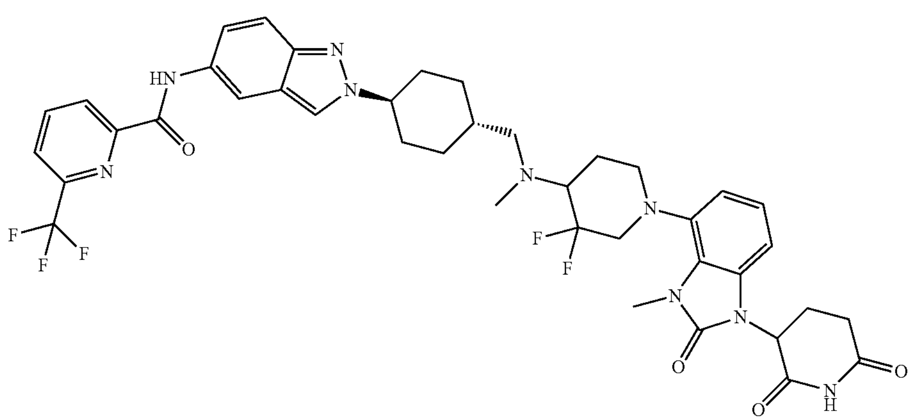 [SMILES: CN(C[C@H]1CC[C@H](n2cc3cc(NC(=O)c4cccc(C(F)(F)F)n4)ccc3n2)CC1)C1CCN(c2cccc3c2n(C)c(=O)n3C2CCC(=O)NC2=O)CC1(F)F] |

TABLE 1-continued

Exemplary Compounds

| I-# | Structure |
|---|---|
| I-475 | 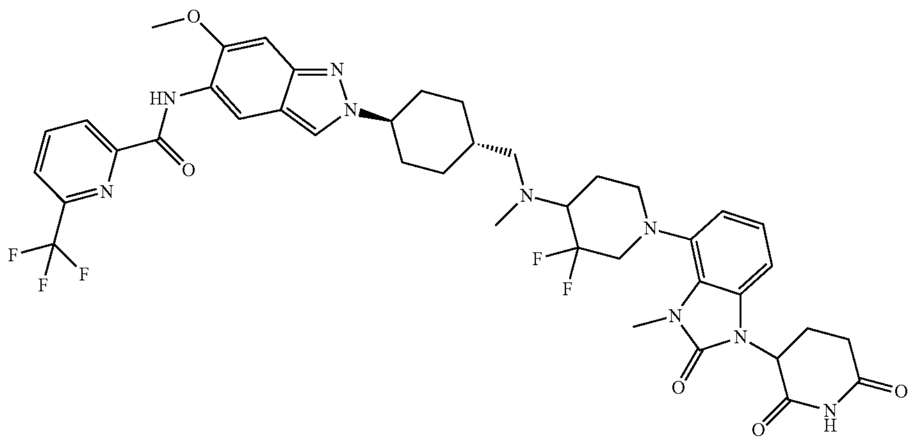 [SMILES: COc1cc2nn([C@H]3CC[C@H](CN(C)C4CCN(c5cccc6c5n(C)c(=O)n6C5CCC(=O)NC5=O)CC4(F)F)CC3)cc2cc1NC(=O)c1cccc(C(F)(F)F)n1] |
| I-476 | 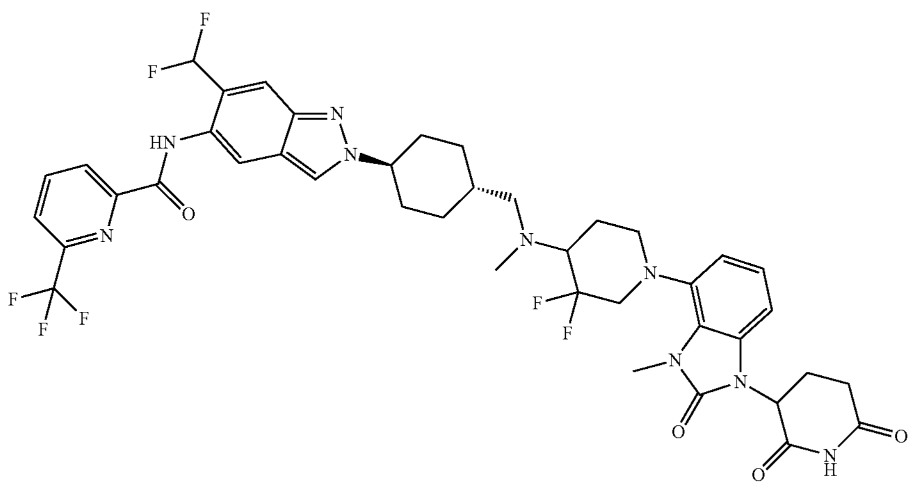 [SMILES: CN(C[C@H]1CC[C@H](n2cc3cc(NC(=O)c4cccc(C(F)(F)F)n4)c(C(F)F)cc3n2)CC1)C1CCN(c2cccc3c2n(C)c(=O)n3C2CCC(=O)NC2=O)CC1(F)F] |
| I-477 | 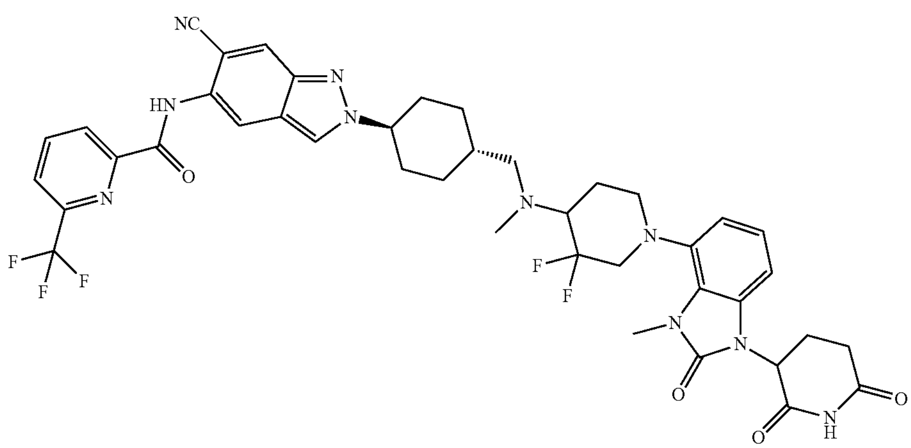 |

TABLE 1-continued

Exemplary Compounds

| I-# | Structure |
|---|---|
| I-478 | 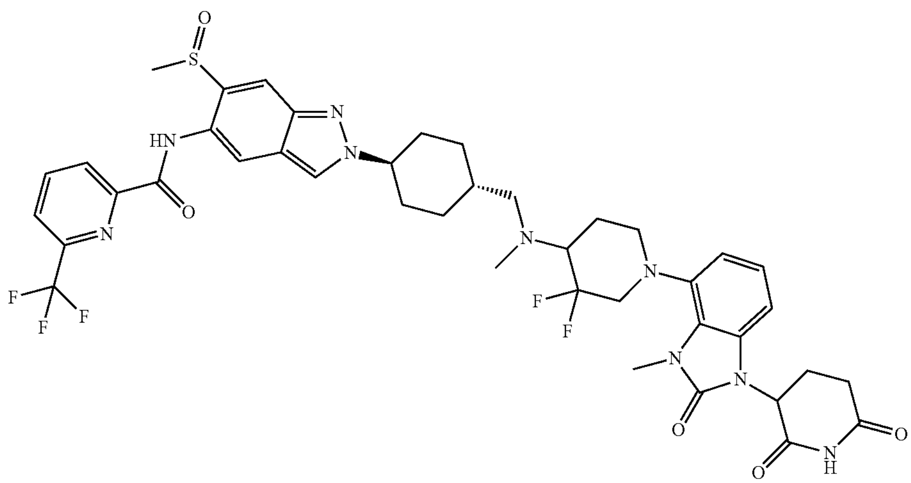 [SMILES: CN(C[C@H]1CC[C@H](n2cc3cc(NC(=O)c4cccc(C(F)(F)F)n4)c(S(C)=O)cc3n2)CC1)C1CCN(c2cccc3c2n(C)c(=O)n3C2CCC(=O)NC2=O)CC1(F)F] |
| I-479 | 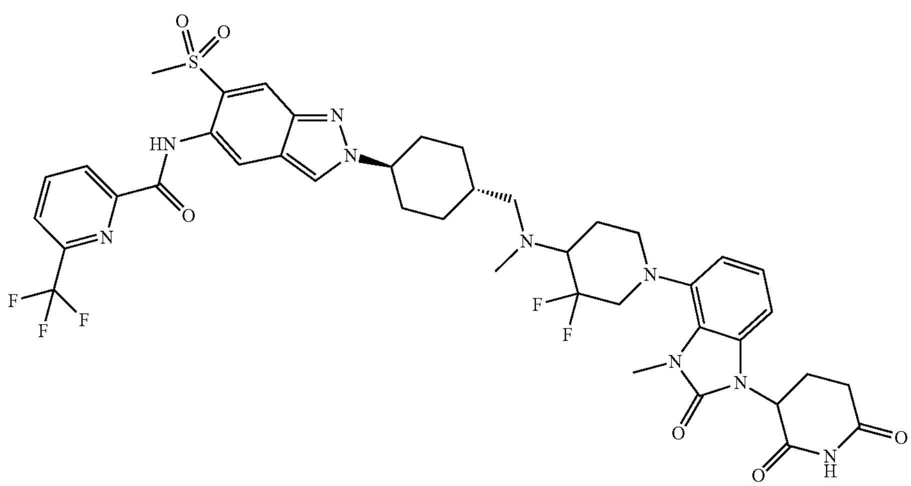 [SMILES: CN(C[C@H]1CC[C@H](n2cc3cc(NC(=O)c4cccc(C(F)(F)F)n4)c(S(C)(=O)=O)cc3n2)CC1)C1CCN(c2cccc3c2n(C)c(=O)n3C2CCC(=O)NC2=O)CC1(F)F] |
| I-480 | 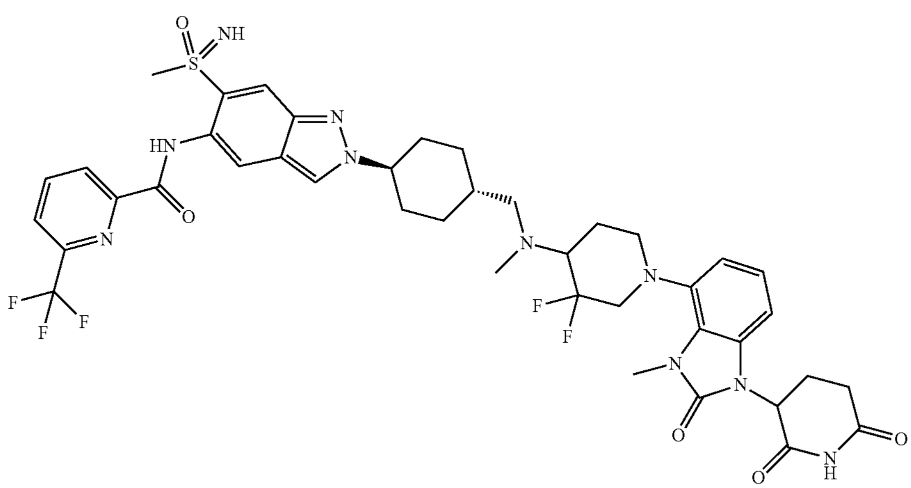 [SMILES: CN(C[C@H]1CC[C@H](n2cc3cc(NC(=O)c4cccc(C(F)(F)F)n4)c(S(C)(=N)=O)cc3n2)CC1)C1CCN(c2cccc3c2n(C)c(=O)n3C2CCC(=O)NC2=O)CC1(F)F] |

TABLE 1-continued

Exemplary Compounds

| I-# | Structure |
|---|---|
| I-481 | 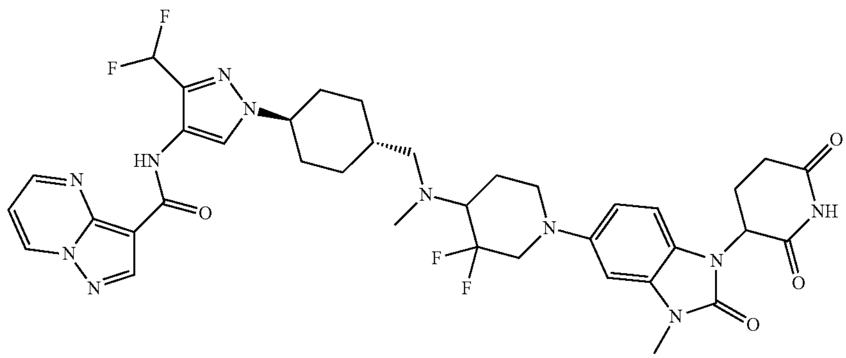 [SMILES: CN(C[C@H]1CC[C@H](n2cc(NC(=O)c3cnn4cccnc34)c(C(F)F)n2)CC1)C1CCN(c2ccc3c(c2)n(C)c(=O)n3C2CCC(=O)NC2=O)CC1(F)F] |
| I-482 | 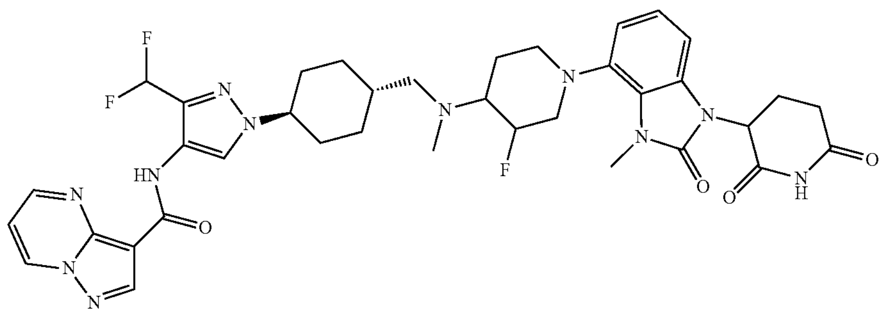 [SMILES: CN(C[C@H]1CC[C@H](n2cc(NC(=O)c3cnn4cccnc34)c(C(F)F)n2)CC1)C1CCN(c2cccc3c2n(C)c(=O)n3C2CCC(=O)NC2=O)CC1F] |
| I-483 | 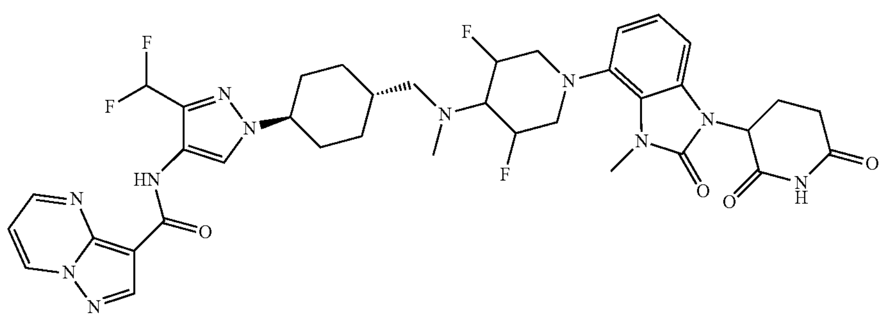 [SMILES: CN(C[C@H]1CC[C@H](n2cc(NC(=O)c3cnn4cccnc34)c(C(F)F)n2)CC1)C1C(F)CN(c2cccc3c2n(C)c(=O)n3C2CCC(=O)NC2=O)CC1F] |
| I-484 | 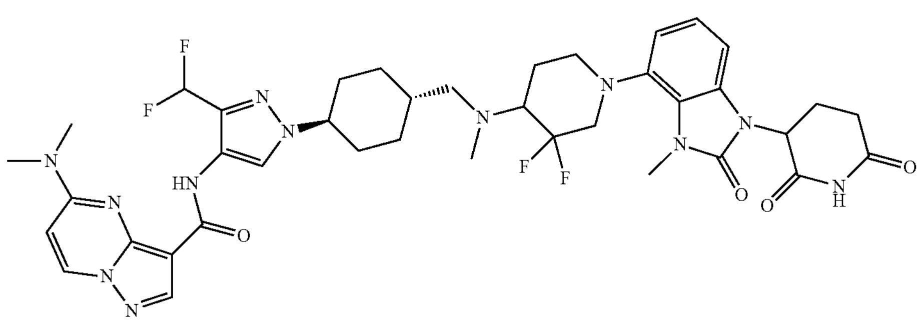 [SMILES: CN(C)c1ccn2ncc(C(=O)Nc3cn([C@H]4CC[C@H](CN(C)C5CCN(c6cccc7c6n(C)c(=O)n7C6CCC(=O)NC6=O)CC5(F)F)CC4)nc3C(F)F)c2n1] |

TABLE 1-continued

Exemplary Compounds

| I-# | Structure |
|---|---|
| I-485 | 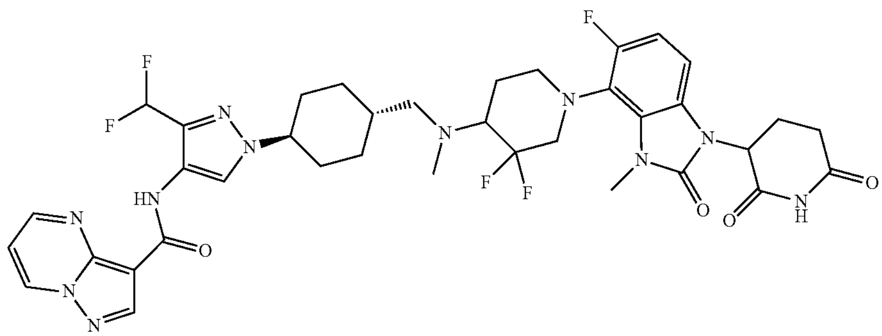 [SMILES: CN(C[C@H]1CC[C@H](n2cc(NC(=O)c3cnn4cccnc34)c(C(F)F)n2)CC1)C1CCN(c2c(F)ccc3c2n(C)c(=O)n3C2CCC(=O)NC2=O)CC1(F)F] |
| I-486 | 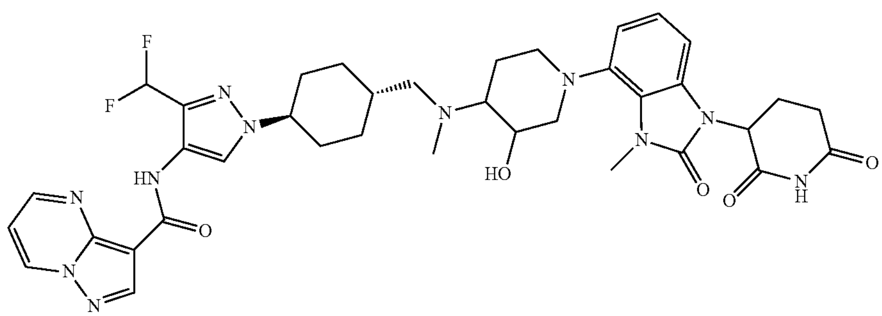 [SMILES: CN(C[C@H]1CC[C@H](n2cc(NC(=O)c3cnn4cccnc34)c(C(F)F)n2)CC1)C1CCN(c2cccc3c2n(C)c(=O)n3C2CCC(=O)NC2=O)CC1O] |
| I-487 | 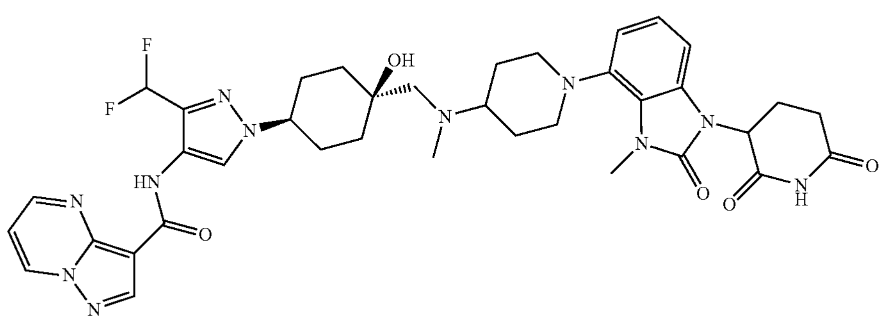 [SMILES: CN(C[C@]1(O)CC[C@@H](n2cc(NC(=O)c3cnn4cccnc34)c(C(F)F)n2)CC1)C1CCN(c2cccc3c2n(C)c(=O)n3C2CCC(=O)NC2=O)CC1] |
| I-488 | 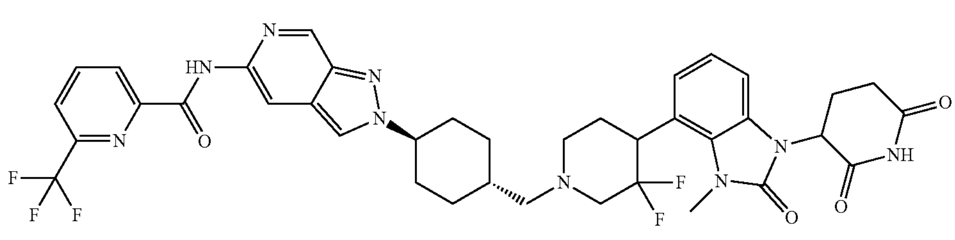 [SMILES: Cn1c(=O)n(C2CCC(=O)NC2=O)c2cccc(C3CCN(C[C@H]4CC[C@H](n5cc6cc(NC(=O)c7cccc(C(F)(F)F)n7)ncc6n5)CC4)CC3(F)F)c21] |
| I-489 | 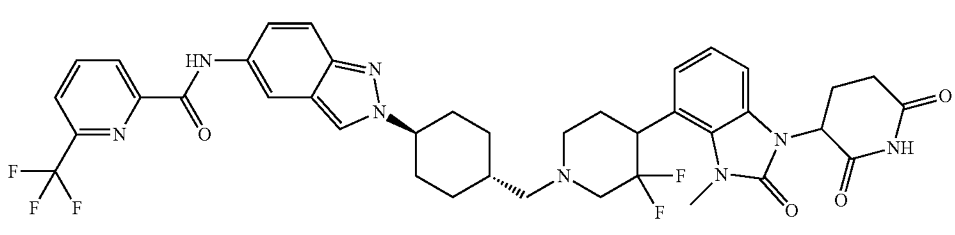 [SMILES: Cn1c(=O)n(C2CCC(=O)NC2=O)c2cccc(C3CCN(C[C@H]4CC[C@H](n5cc6cc(NC(=O)c7cccc(C(F)(F)F)n7)ccc6n5)CC4)CC3(F)F)c21] |

TABLE 1-continued
Exemplary Compounds
| I-# | Structure |
|---|---|
| I-490 | 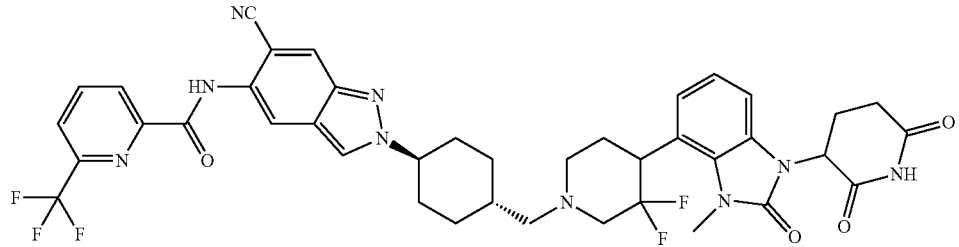 [SMILES: Cn1c(=O)n(C2CCC(=O)NC2=O)c2cccc(C3CCN(C[C@H]4CC[C@H](n5cc6cc(NC(=O)c7cccc(C(F)(F)F)n7)c(C#N)cc6n5)CC4)CC3(F)F)c21] |
| I-491 | 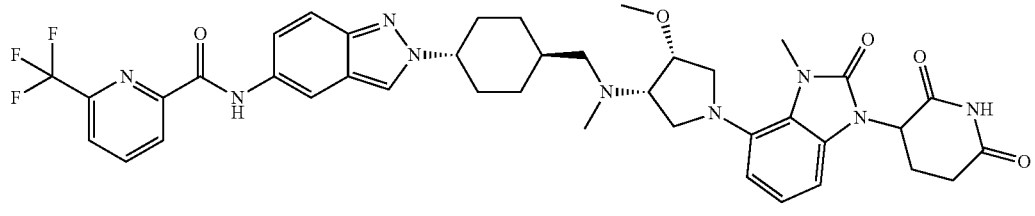 [SMILES: CO[C@@H]1CN(c2cccc3c2n(C)c(=O)n3C2CCC(=O)NC2=O)C[C@@H]1N(C)C[C@H]1CC[C@H](n2cc3cc(NC(=O)c4cccc(C(F)(F)F)n4)ccc3n2)CC1] |
| I-492 | 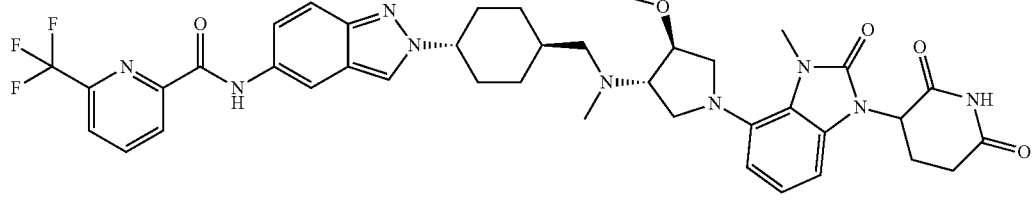 |
| I-493 | 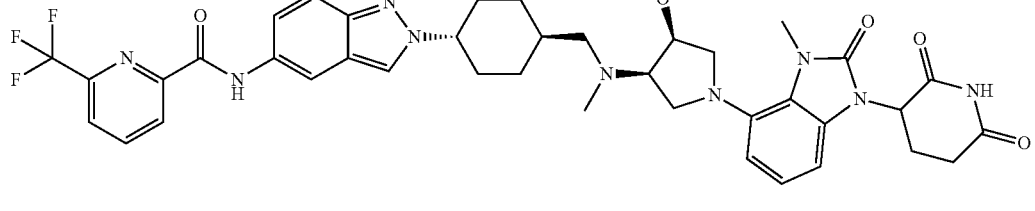 |
| I-494 | 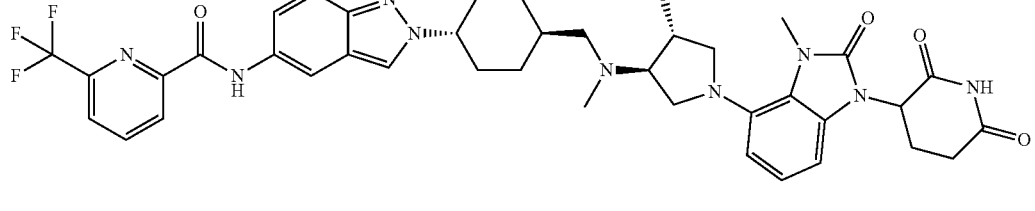 |
| I-495 | 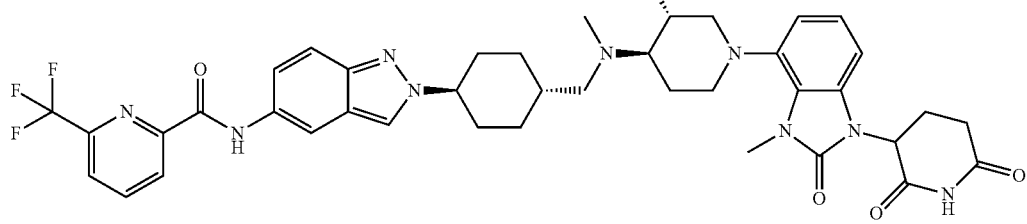 |

TABLE 1-continued
Exemplary Compounds
| I-# | Structure |
|---|---|
| I-496 | 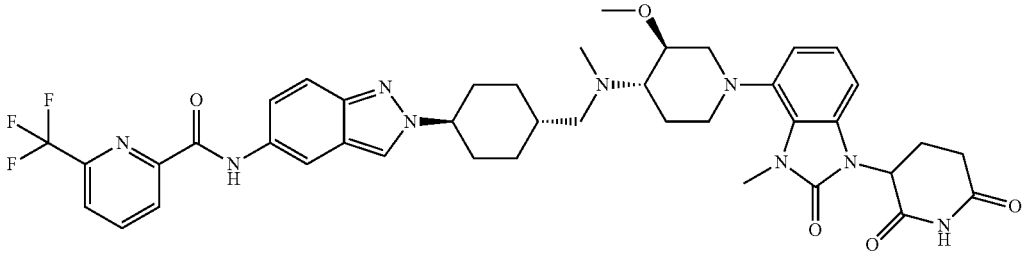 [SMILES: CO[C@H]1CN(c2cccc3c2n(C)c(=O)n3C2CCC(=O)NC2=O)CC[C@@H]1N(C)C[C@H]1CC[C@H](n2cc3cc(NC(=O)c4cccc(C(F)(F)F)n4)ccc3n2)CC1] |
| I-497 | 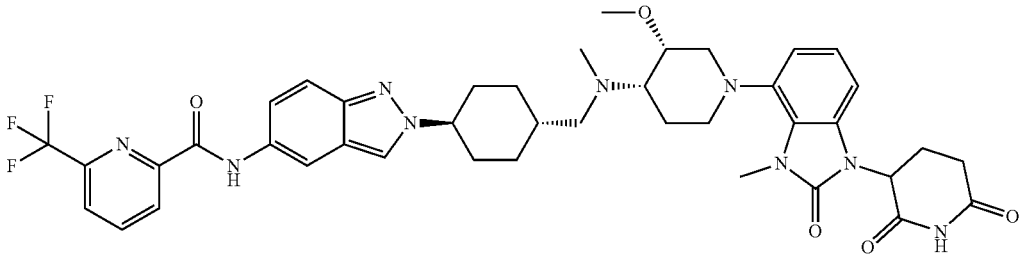 [SMILES: CO[C@@H]1CN(c2cccc3c2n(C)c(=O)n3C2CCC(=O)NC2=O)CC[C@@H]1N(C)C[C@H]1CC[C@H](n2cc3cc(NC(=O)c4cccc(C(F)(F)F)n4)ccc3n2)CC1] |
| I-498 | 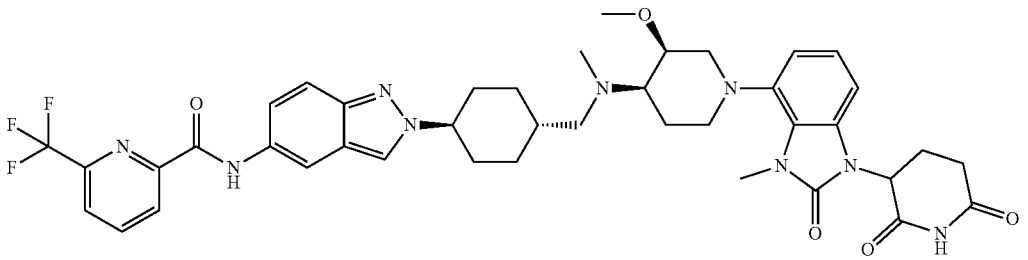 [SMILES: CO[C@H]1CN(c2cccc3c2n(C)c(=O)n3C2CCC(=O)NC2=O)CC[C@H]1N(C)C[C@H]1CC[C@H](n2cc3cc(NC(=O)c4cccc(C(F)(F)F)n4)ccc3n2)CC1] |
| I-499 | 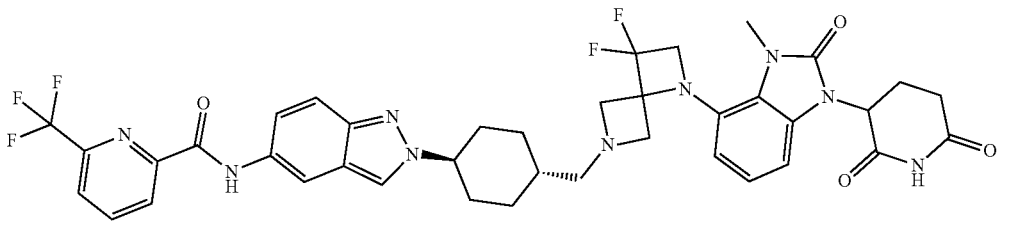 |
| I-500 | 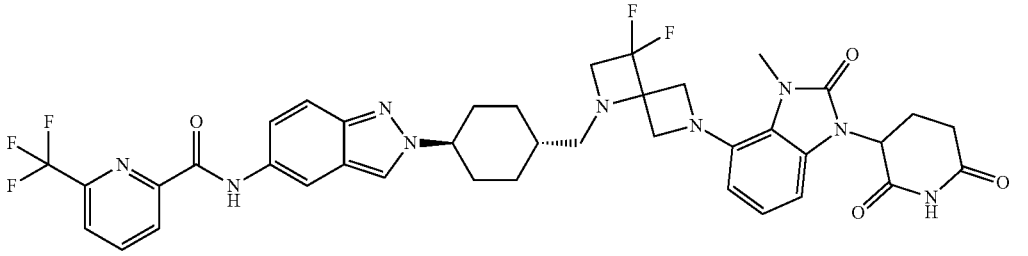 [SMILES: Cn1c(=O)n(C2CCC(=O)NC2=O)c2cccc(N3CC4(C3)N(C[C@H]3CC[C@H](n5cc6cc(NC(=O)c7cccc(C(F)(F)F)n7)ccc6n5)CC3)CC4(F)F)c21] |

TABLE 1-continued
Exemplary Compounds
| I-# | Structure |
|---|---|
| I-501 | 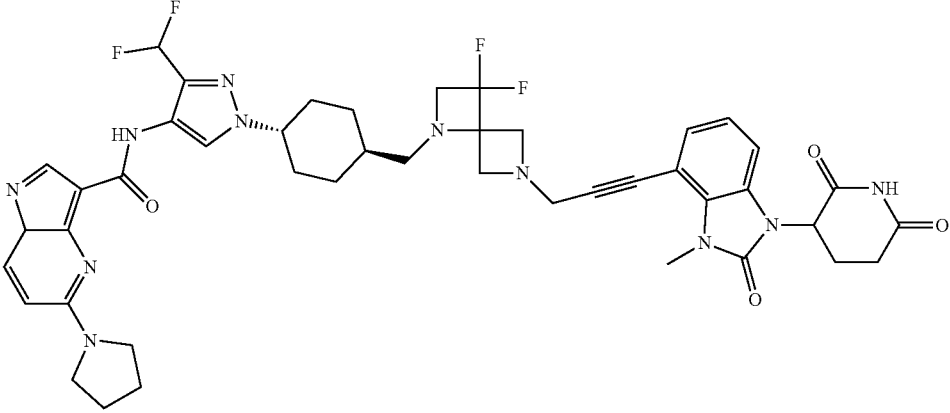 |
| I-502 | 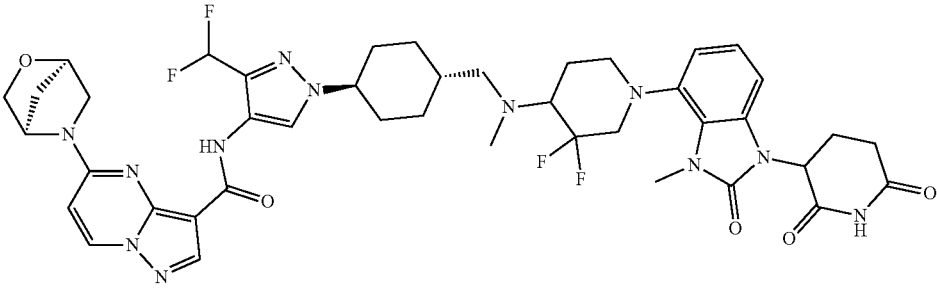 [SMILES: CN(C[C@H]1CC[C@H](n2cc(NC(=O)c3cnn4ccc(N5C[C@H]6C[C@@H]5CO6)nc34)c(C(F)F)n2)CC1)C1CCN(c2cccc3c2n(C)c(=O)n3C2CCC(=O)NC2=O)CC1(F)F] |
| I-503 | 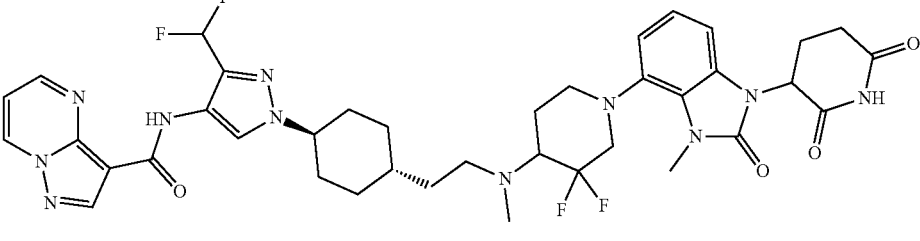 |
| I-504 | 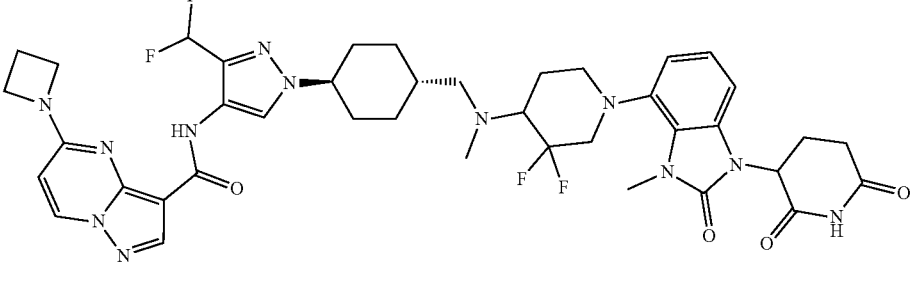 |
| I-505 | 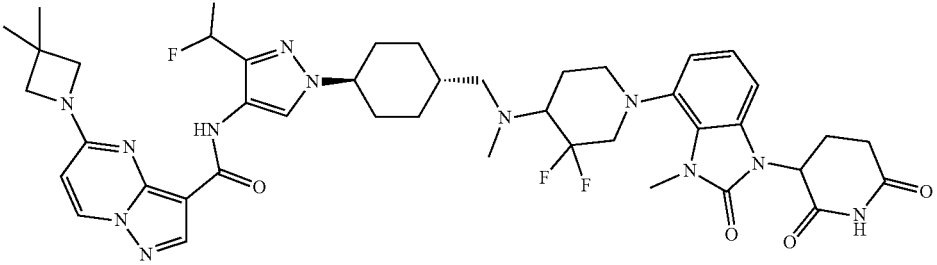 |

TABLE 1-continued

Exemplary Compounds

| I-# | Structure |
|---|---|
| I-506 | 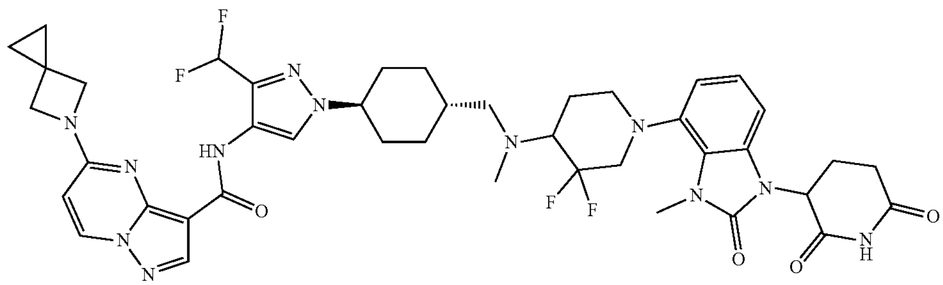 [SMILES: CN(C[C@H]1CC[C@H](n2cc(NC(=O)c3cnn4ccc(N5CC6(CC6)C5)nc34)c(C(F)F)n2)CC1)C1CCN(c2cccc3c2n(C)c(=O)n3C2CCC(=O)NC2=O)CC1(F)F] |
| I-507 | 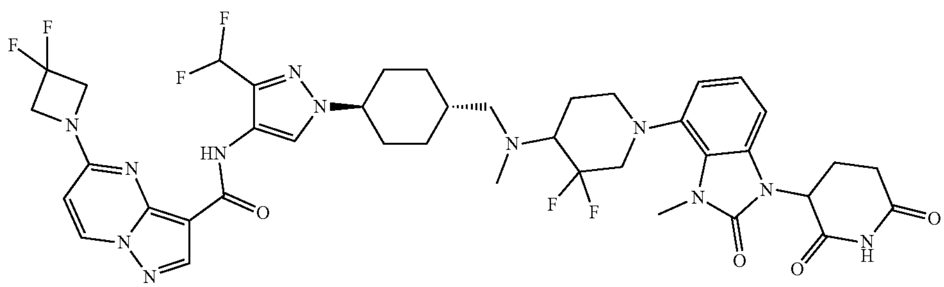 |
| I-508 | 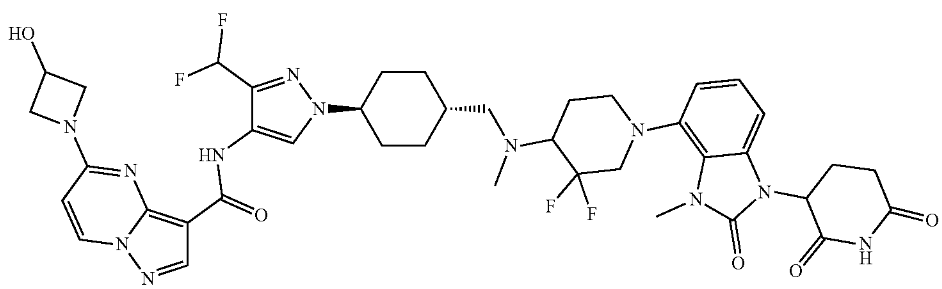 [SMILES: CN(C[C@H]1CC[C@H](n2cc(NC(=O)c3cnn4ccc(N5CC(O)C5)nc34)c(C(F)F)n2)CC1)C1CCN(c2cccc3c2n(C)c(=O)n3C2CCC(=O)NC2=O)CC1(F)F] |
| I-509 | 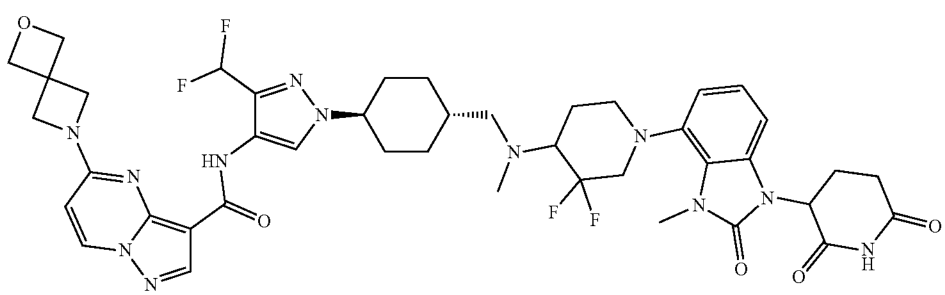 [SMILES: CN(C[C@H]1CC[C@H](n2cc(NC(=O)c3cnn4ccc(N5CC6(COC6)C5)nc34)c(C(F)F)n2)CC1)C1CCN(c2cccc3c2n(C)c(=O)n3C2CCC(=O)NC2=O)CC1(F)F] |
| I-510 | 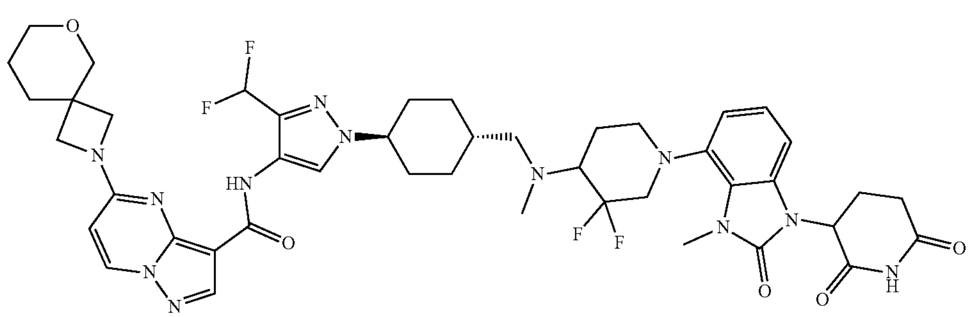 [SMILES: CN(C[C@H]1CC[C@H](n2cc(NC(=O)c3cnn4ccc(N5CC6(CCCOC6)C5)nc34)c(C(F)F)n2)CC1)C1CCN(c2cccc3c2n(C)c(=O)n3C2CCC(=O)NC2=O)CC1(F)F] |

TABLE 1-continued
Exemplary Compounds
| I-# | Structure |
|---|---|
| I-511 | 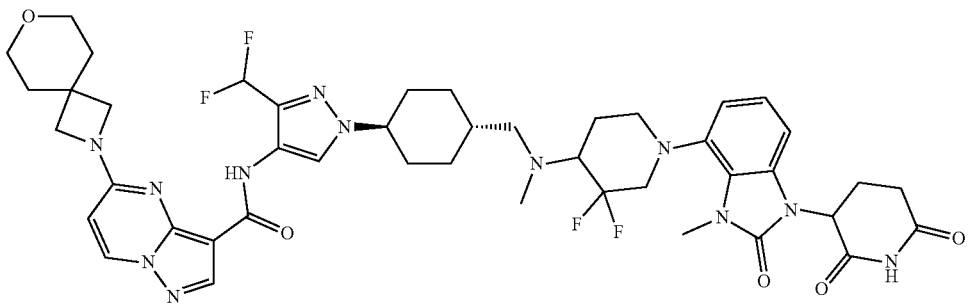 [SMILES: CN(C[C@H]1CC[C@H](n2cc(NC(=O)c3cnn4ccc(N5CC6(CCOCC6)C5)nc34)c(C(F)F)n2)CC1)C1CCN(c2cccc3c2n(C)c(=O)n3C2CCC(=O)NC2=O)CC1(F)F] |
| I-512 | 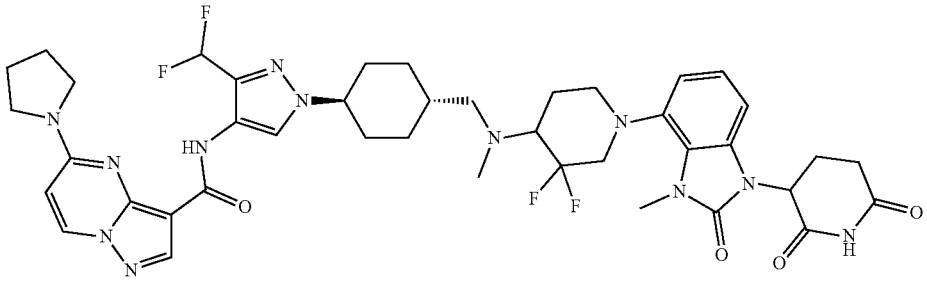 [SMILES: CN(C[C@H]1CC[C@H](n2cc(NC(=O)c3cnn4ccc(N5CCCC5)nc34)c(C(F)F)n2)CC1)C1CCN(c2cccc3c2n(C)c(=O)n3C2CCC(=O)NC2=O)CC1(F)F] |
| I-513 | 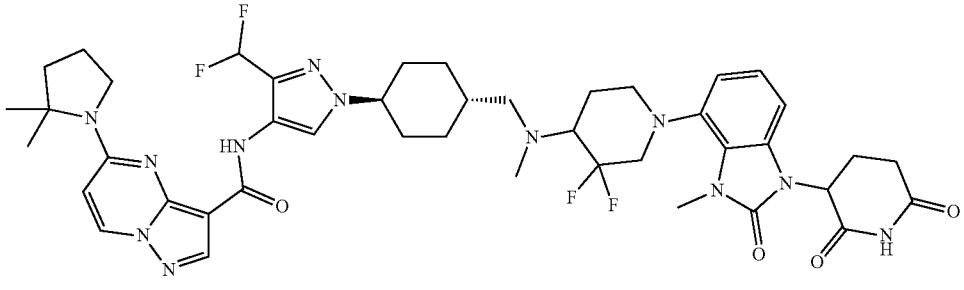 [SMILES: CN(C[C@H]1CC[C@H](n2cc(NC(=O)c3cnn4ccc(N5CCCC5(C)C)nc34)c(C(F)F)n2)CC1)C1CCN(c2cccc3c2n(C)c(=O)n3C2CCC(=O)NC2=O)CC1(F)F] |
| I-514 | 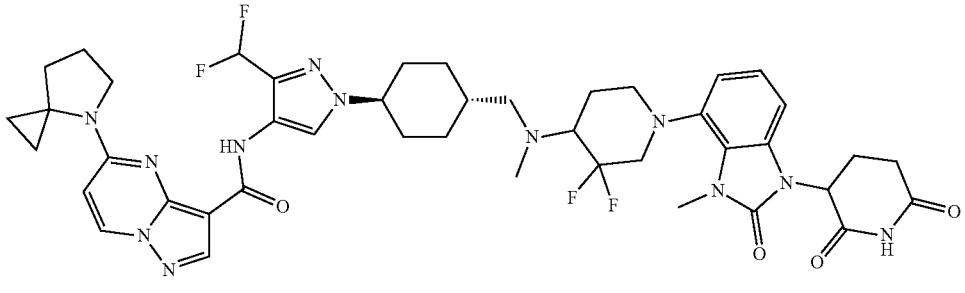 [SMILES: CN(C[C@H]1CC[C@H](n2cc(NC(=O)c3cnn4ccc(N5CCCC56CC6)nc34)c(C(F)F)n2)CC1)C1CCN(c2cccc3c2n(C)c(=O)n3C2CCC(=O)NC2=O)CC1(F)F] |
| I-515 | 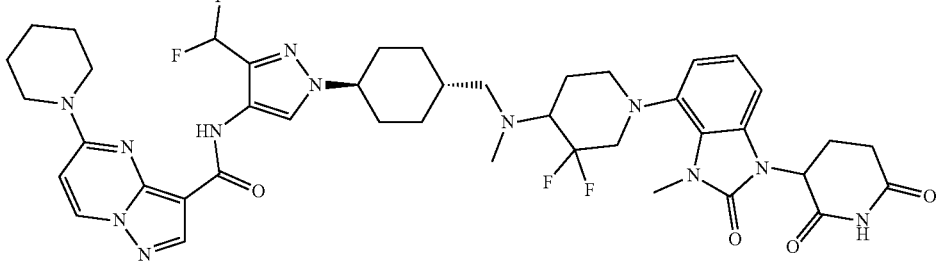 |

TABLE 1-continued

Exemplary Compounds

| I-# | Structure |
|---|---|
| I-516 | 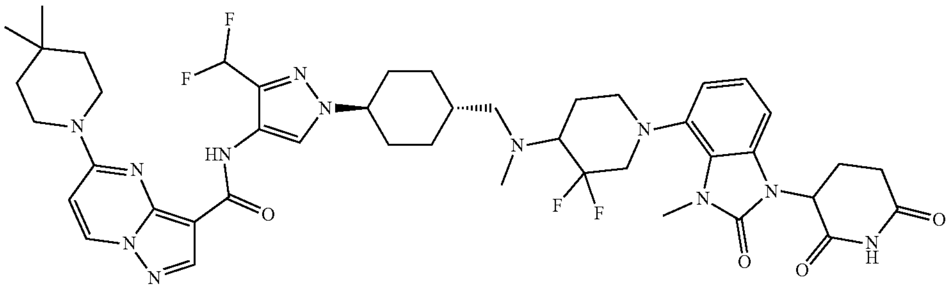 [SMILES: CN(C[C@H]1CC[C@H](n2cc(NC(=O)c3cnn4ccc(N5CCC(C)(C)CC5)nc34)c(C(F)F)n2)CC1)C1CCN(c2cccc3c2n(C)c(=O)n3C2CCC(=O)NC2=O)CC1(F)F] |
| I-517 | 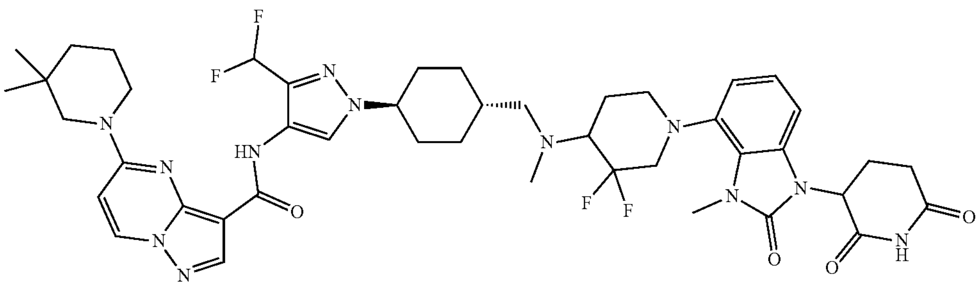 [SMILES: CN(C[C@H]1CC[C@H](n2cc(NC(=O)c3cnn4ccc(N5CCCC(C)(C)C5)nc34)c(C(F)F)n2)CC1)C1CCN(c2cccc3c2n(C)c(=O)n3C2CCC(=O)NC2=O)CC1(F)F] |
| I-518 | 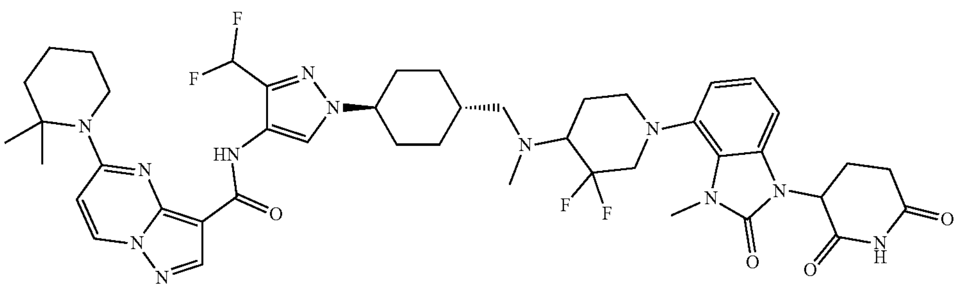 [SMILES: CN(C[C@H]1CC[C@H](n2cc(NC(=O)c3cnn4ccc(N5CCCCC5(C)C)nc34)c(C(F)F)n2)CC1)C1CCN(c2cccc3c2n(C)c(=O)n3C2CCC(=O)NC2=O)CC1(F)F] |
| I-519 | 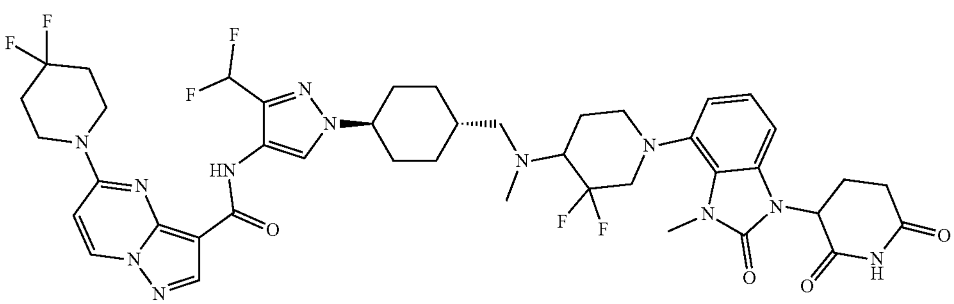 [SMILES: CN(C[C@H]1CC[C@H](n2cc(NC(=O)c3cnn4ccc(N5CCC(F)(F)CC5)nc34)c(C(F)F)n2)CC1)C1CCN(c2cccc3c2n(C)c(=O)n3C2CCC(=O)NC2=O)CC1(F)F] |
| I-520 | 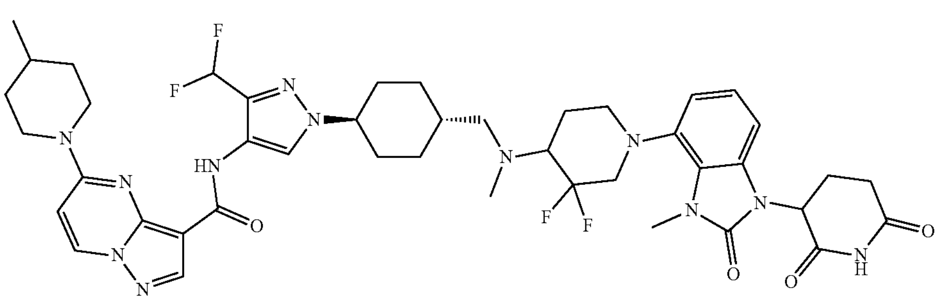 [SMILES: CC1CCN(c2ccn3ncc(C(=O)Nc4cn([C@H]5CC[C@H](CN(C)C6CCN(c7cccc8c7n(C)c(=O)n8C7CCC(=O)NC7=O)CC6(F)F)CC5)nc4C(F)F)c3n2)CC1] |

TABLE 1-continued
Exemplary Compounds
| I-# | Structure |
|---|---|
| I-521 | 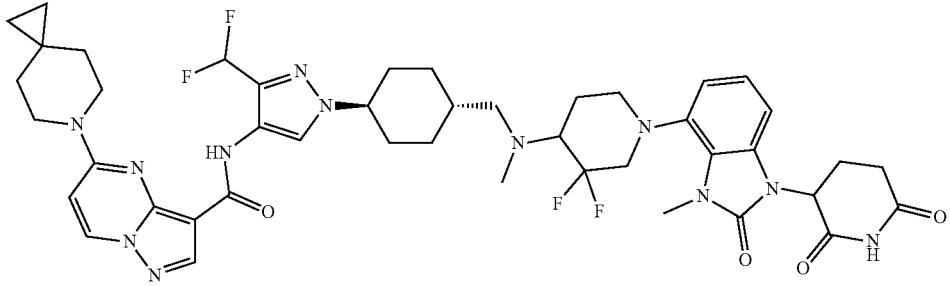 [SMILES: CN(C[C@H]1CC[C@H](n2cc(NC(=O)c3cnn4ccc(N5CCC6(CC5)CC6)nc34)c(C(F)F)n2)CC1)C1CCN(c2cccc3c2n(C)c(=O)n3C2CCC(=O)NC2=O)CC1(F)F] |
| I-522 | 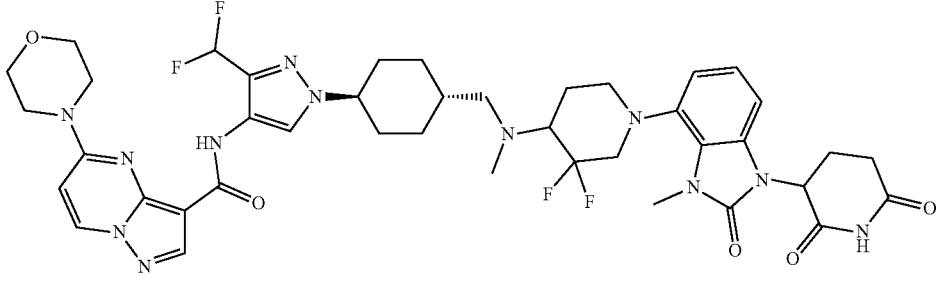 [SMILES: CN(C[C@H]1CC[C@H](n2cc(NC(=O)c3cnn4ccc(N5CCOCC5)nc34)c(C(F)F)n2)CC1)C1CCN(c2cccc3c2n(C)c(=O)n3C2CCC(=O)NC2=O)CC1(F)F] |
| I-523 | 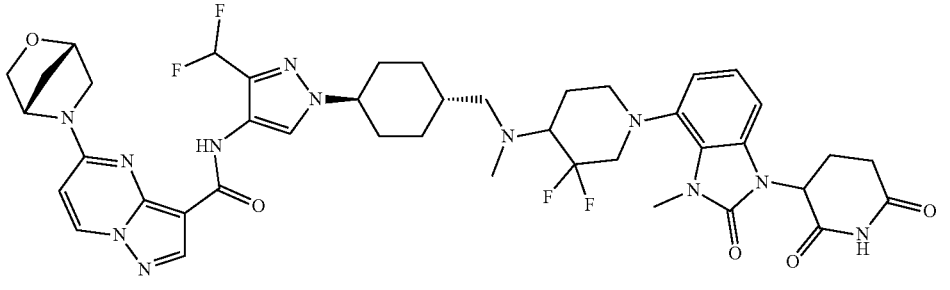 [SMILES: CN(C[C@H]1CC[C@H](n2cc(NC(=O)c3cnn4ccc(N5C[C@@H]6C[C@H]5CO6)nc34)c(C(F)F)n2)CC1)C1CCN(c2cccc3c2n(C)c(=O)n3C2CCC(=O)NC2=O)CC1(F)F] |
| I-524 | 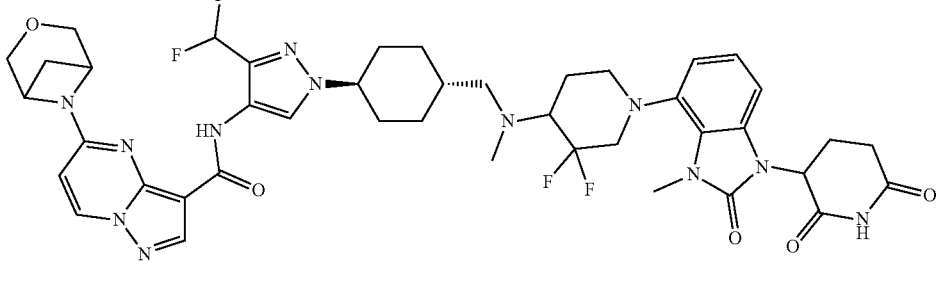 |
| I-525 | 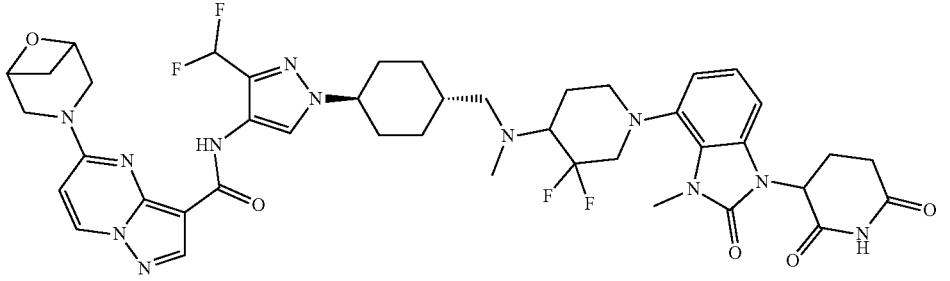 [SMILES: CN(C[C@H]1CC[C@H](n2cc(NC(=O)c3cnn4ccc(N5CC6CC(C5)O6)nc34)c(C(F)F)n2)CC1)C1CCN(c2cccc3c2n(C)c(=O)n3C2CCC(=O)NC2=O)CC1(F)F] |

TABLE 1-continued

Exemplary Compounds

| I-# | Structure |
|---|---|
| I-526 | 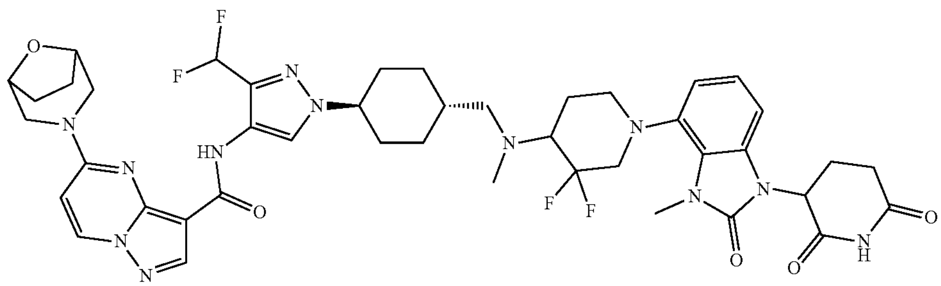 [SMILES: CN(C[C@H]1CC[C@H](n2cc(NC(=O)c3cnn4ccc(N5CC6CCC(C5)O6)nc34)c(C(F)F)n2)CC1)C1CCN(c2cccc3c2n(C)c(=O)n3C2CCC(=O)NC2=O)CC1(F)F] |
| I-527 | 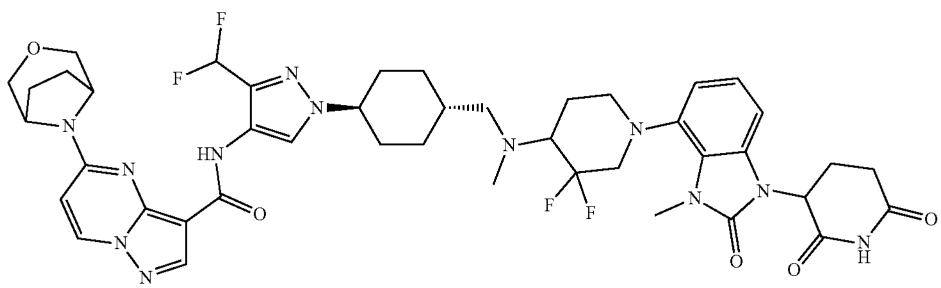 [SMILES: CN(C[C@H]1CC[C@H](n2cc(NC(=O)c3cnn4ccc(N5C6CCC5COC6)nc34)c(C(F)F)n2)CC1)C1CCN(c2cccc3c2n(C)c(=O)n3C2CCC(=O)NC2=O)CC1(F)F] |
| I-528 | 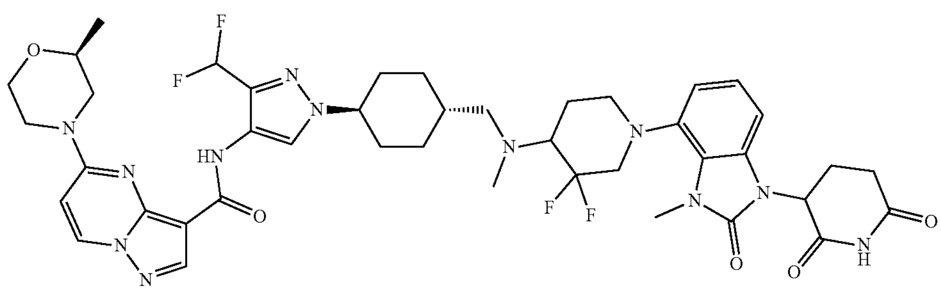 [SMILES: C[C@H]1CN(c2ccn3ncc(C(=O)Nc4cn([C@H]5CC[C@H](CN(C)C6CCN(c7cccc8c7n(C)c(=O)n8C7CCC(=O)NC7=O)CC6(F)F)CC5)nc4C(F)F)c3n2)CCO1] |
| I-529 | 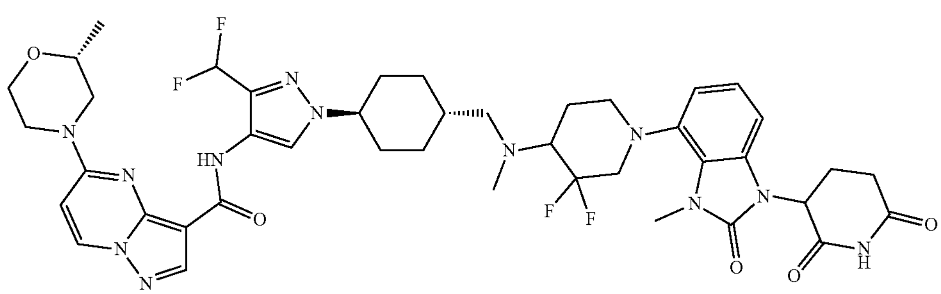 [SMILES: C[C@@H]1CN(c2ccn3ncc(C(=O)Nc4cn([C@H]5CC[C@H](CN(C)C6CCN(c7cccc8c7n(C)c(=O)n8C7CCC(=O)NC7=O)CC6(F)F)CC5)nc4C(F)F)c3n2)CCO1] |
| I-530 | 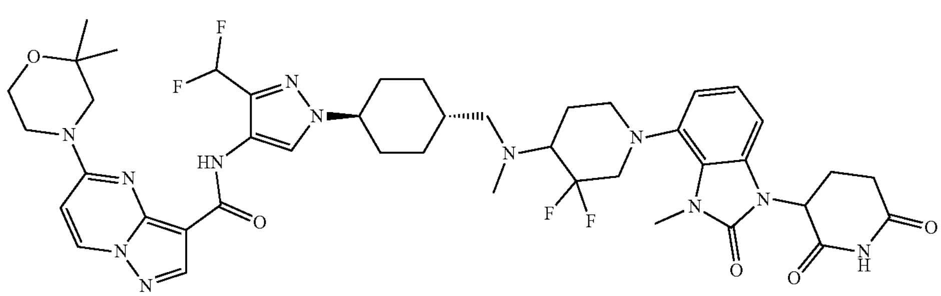 [SMILES: CN(C[C@H]1CC[C@H](n2cc(NC(=O)c3cnn4ccc(N5CCOC(C)(C)C5)nc34)c(C(F)F)n2)CC1)C1CCN(c2cccc3c2n(C)c(=O)n3C2CCC(=O)NC2=O)CC1(F)F] |

TABLE 1-continued

Exemplary Compounds

| I-# | Structure |
|---|---|
| I-531 | 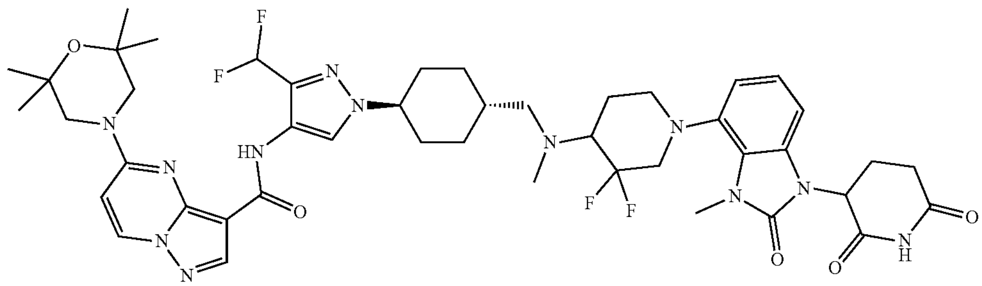 [SMILES: CN(C[C@H]1CC[C@H](n2cc(NC(=O)c3cnn4ccc(N5CC(C)(C)OC(C)(C)C5)nc34)c(C(F)F)n2)CC1)C1CCN(c2cccc3c2n(C)c(=O)n3C2CCC(=O)NC2=O)CC1(F)F] |
| I-532 | 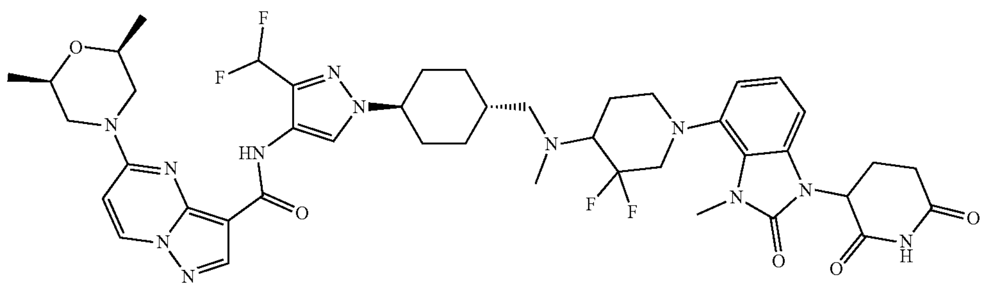 [SMILES: C[C@@H]1CN(c2ccn3ncc(C(=O)Nc4cn([C@H]5CC[C@H](CN(C)C6CCN(c7cccc8c7n(C)c(=O)n8C7CCC(=O)NC7=O)CC6(F)F)CC5)nc4C(F)F)c3n2)C[C@H](C)O1] |
| I-533 | 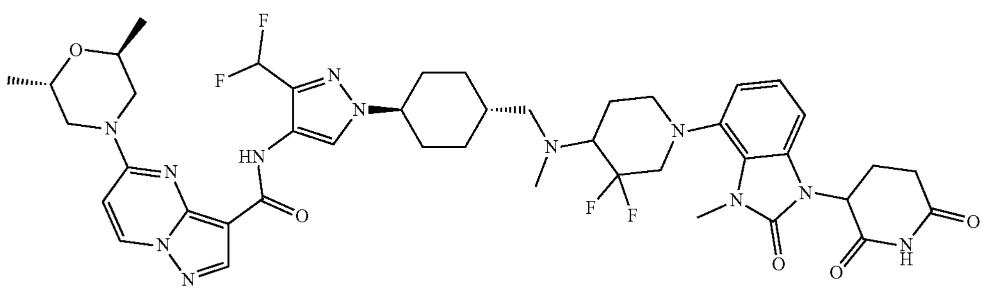 [SMILES: C[C@H]1CN(c2ccn3ncc(C(=O)Nc4cn([C@H]5CC[C@H](CN(C)C6CCN(c7cccc8c7n(C)c(=O)n8C7CCC(=O)NC7=O)CC6(F)F)CC5)nc4C(F)F)c3n2)C[C@H](C)O1] |
| I-534 | 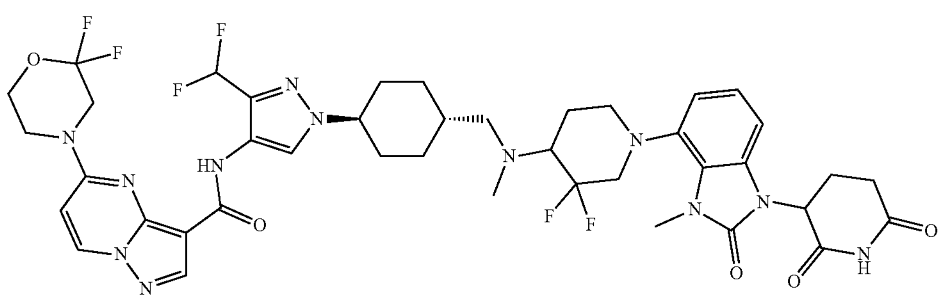 [SMILES: CN(C[C@H]1CC[C@H](n2cc(NC(=O)c3cnn4ccc(N5CCOC(F)(F)C5)nc34)c(C(F)F)n2)CC1)C1CCN(c2cccc3c2n(C)c(=O)n3C2CCC(=O)NC2=O)CC1(F)F] |
| I-535 | 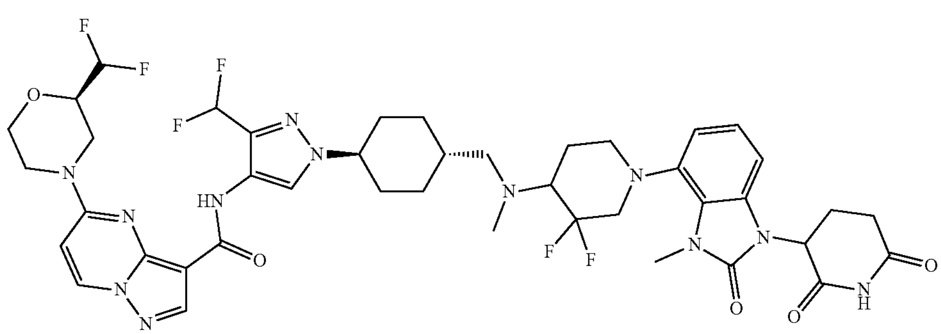 [SMILES: CN(C[C@H]1CC[C@H](n2cc(NC(=O)c3cnn4ccc(N5CCO[C@@H](C(F)F)C5)nc34)c(C(F)F)n2)CC1)C1CCN(c2cccc3c2n(C)c(=O)n3C2CCC(=O)NC2=O)CC1(F)F] |

TABLE 1-continued

Exemplary Compounds

| I-# | Structure |
|---|---|
| I-536 | 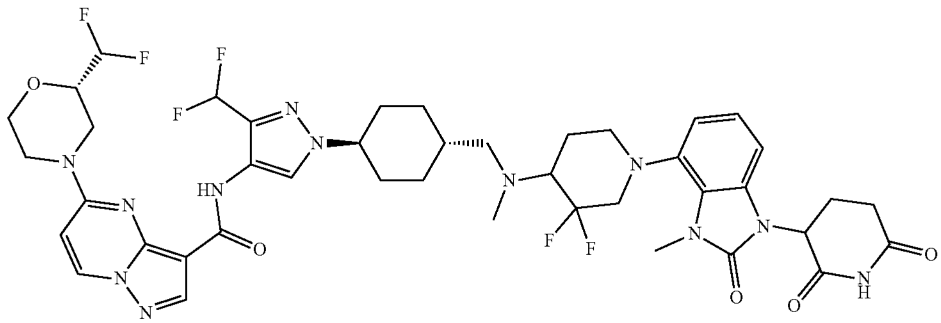 [SMILES: CN(C[C@H]1CC[C@H](n2cc(NC(=O)c3cnn4ccc(N5CCO[C@H](C(F)F)C5)nc34)c(C(F)F)n2)CC1)C1CCN(c2cccc3c2n(C)c(=O)n3C2CCC(=O)NC2=O)CC1(F)F] |
| I-537 | 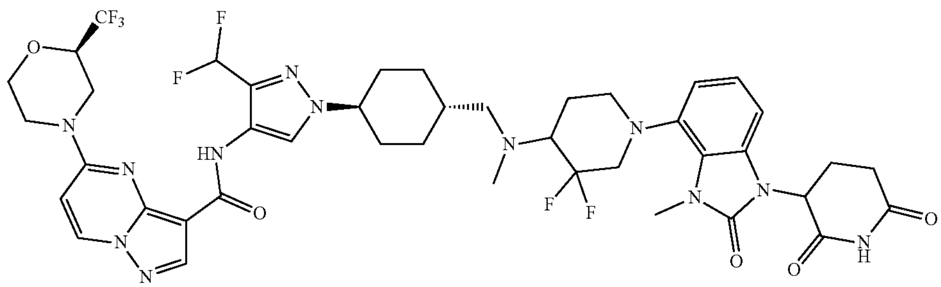 [SMILES: CN(C[C@H]1CC[C@H](n2cc(NC(=O)c3cnn4ccc(N5CCO[C@@H](C(F)(F)F)C5)nc34)c(C(F)F)n2)CC1)C1CCN(c2cccc3c2n(C)c(=O)n3C2CCC(=O)NC2=O)CC1(F)F] |
| I-538 | 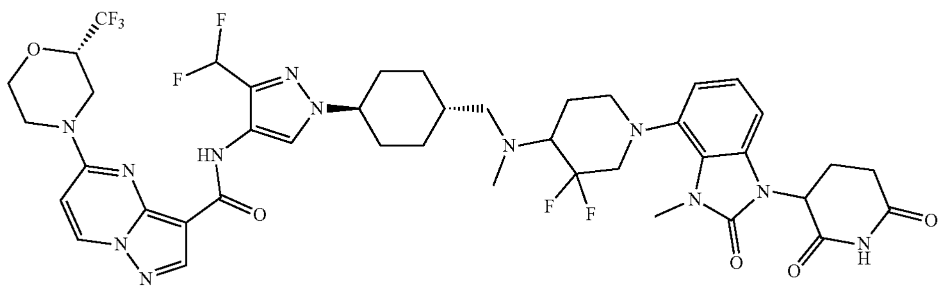 [SMILES: CN(C[C@H]1CC[C@H](n2cc(NC(=O)c3cnn4ccc(N5CCO[C@H](C(F)(F)F)C5)nc34)c(C(F)F)n2)CC1)C1CCN(c2cccc3c2n(C)c(=O)n3C2CCC(=O)NC2=O)CC1(F)F] |
| I-539 | 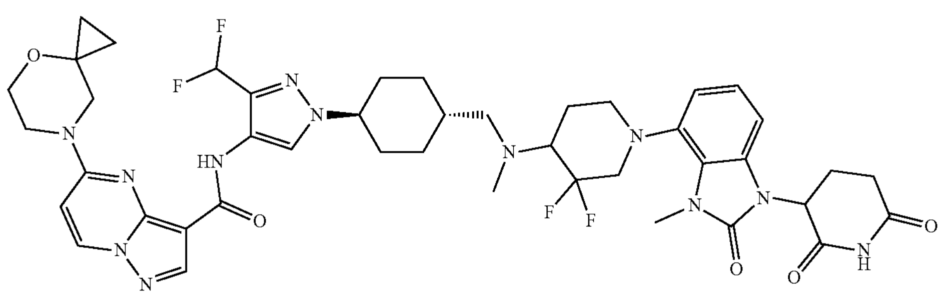 [SMILES: CN(C[C@H]1CC[C@H](n2cc(NC(=O)c3cnn4ccc(N5CCOC6(CC6)C5)nc34)c(C(F)F)n2)CC1)C1CCN(c2cccc3c2n(C)c(=O)n3C2CCC(=O)NC2=O)CC1(F)F] |
| I-540 | 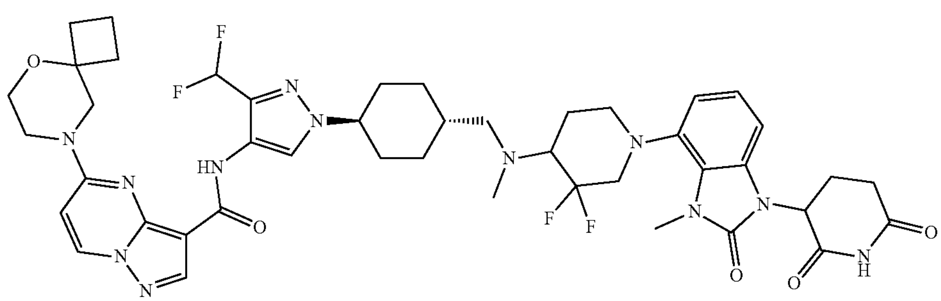 [SMILES: CN(C[C@H]1CC[C@H](n2cc(NC(=O)c3cnn4ccc(N5CCOC6(CCC6)C5)nc34)c(C(F)F)n2)CC1)C1CCN(c2cccc3c2n(C)c(=O)n3C2CCC(=O)NC2=O)CC1(F)F] |

TABLE 1-continued

Exemplary Compounds

| I-# | Structure |
| --- | --- |
| I-541 | 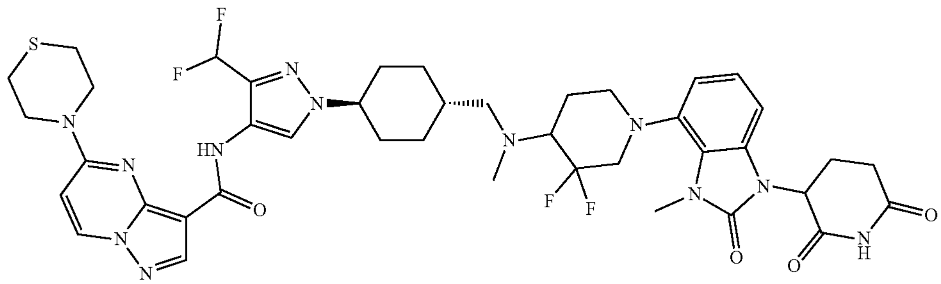 |
| I-542 | 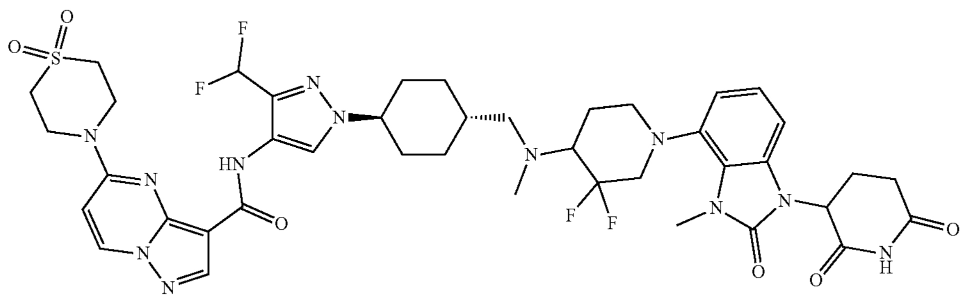 [SMILES: CN(C[C@H]1CC[C@H](n2cc(NC(=O)c3cnn4ccc(N5CCS(=O)(=O)CC5)nc34)c(C(F)F)n2)CC1)C1CCN(c2cccc3c2n(C)c(=O)n3C2CCC(=O)NC2=O)CC1(F)F] |
| I-543 | 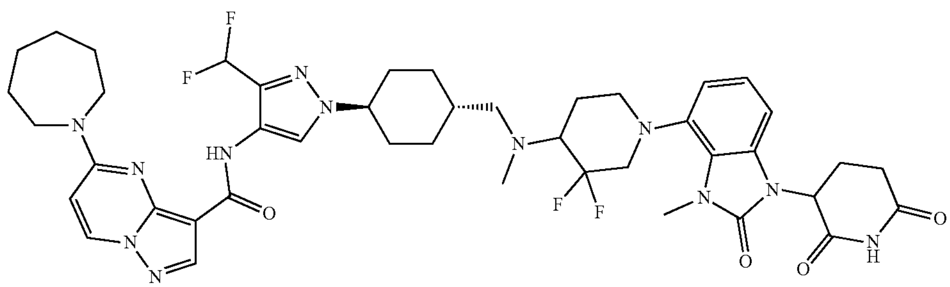 [SMILES: CN(C[C@H]1CC[C@H](n2cc(NC(=O)c3cnn4ccc(N5CCCCCC5)nc34)c(C(F)F)n2)CC1)C1CCN(c2cccc3c2n(C)c(=O)n3C2CCC(=O)NC2=O)CC1(F)F] |
| I-544 | 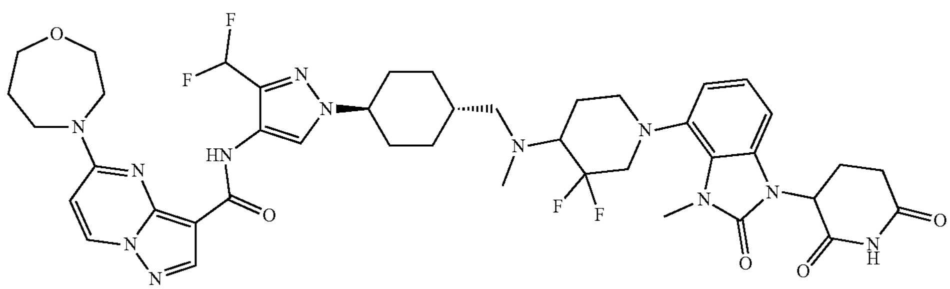 [SMILES: CN(C[C@H]1CC[C@H](n2cc(NC(=O)c3cnn4ccc(N5CCCOCC5)nc34)c(C(F)F)n2)CC1)C1CCN(c2cccc3c2n(C)c(=O)n3C2CCC(=O)NC2=O)CC1(F)F] |
| I-545 | 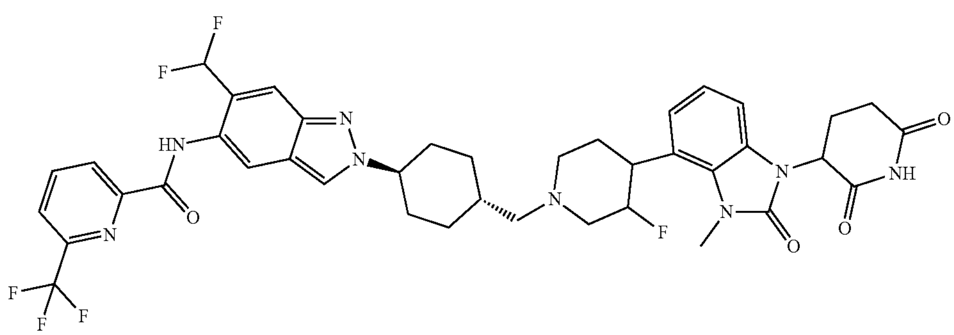 [SMILES: Cn1c(=O)n(C2CCC(=O)NC2=O)c2cccc(C3CCN(C[C@H]4CC[C@H](n5cc6cc(NC(=O)c7cccc(C(F)(F)F)n7)c(C(F)F)cc6n5)CC4)CC3F)c21] |

TABLE 1-continued
Exemplary Compounds
| I-# | Structure |
|---|---|
| I-546 | 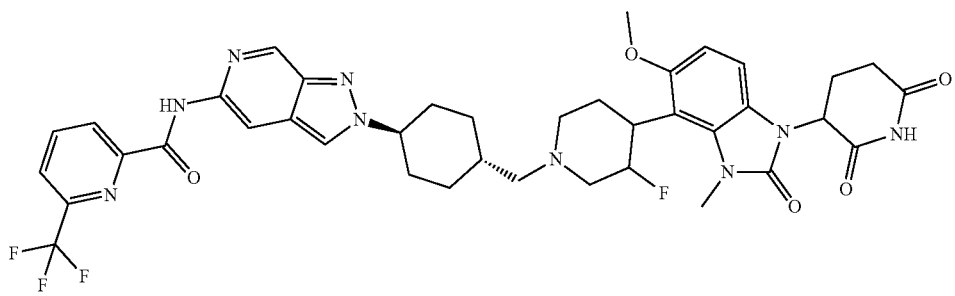 [SMILES: COc1ccc2c(c1C1CCN(C[C@H]3CC[C@H](n4cc5cc(NC(=O)c6cccc(C(F)(F)F)n6)ncc5n4)CC3)CC1F)n(C)c(=O)n2C1CCC(=O)NC1=O] |
| I-547 | 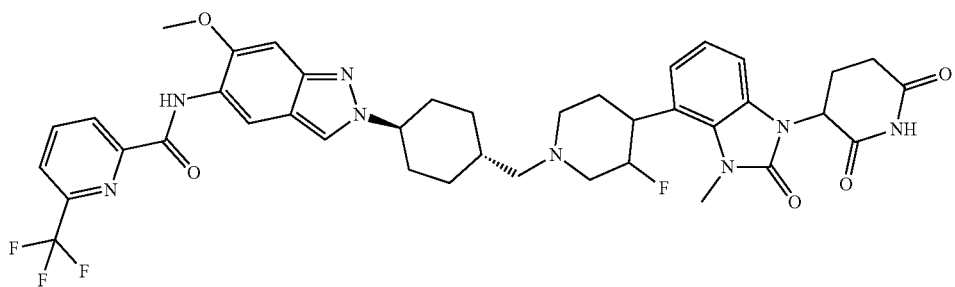 |
| I-548 | 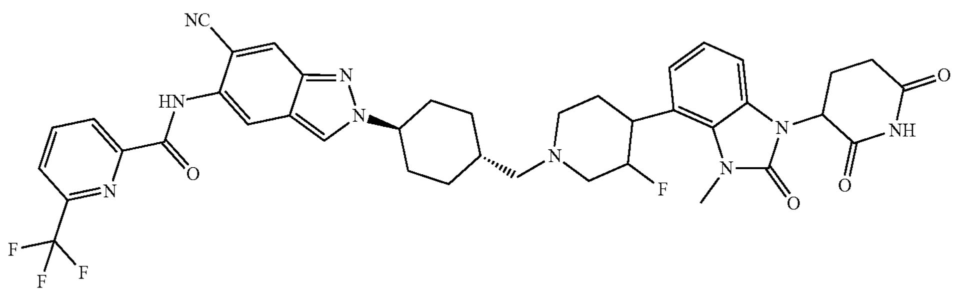 [SMILES: Cn1c(=O)n(C2CCC(=O)NC2=O)c2cccc(C3CCN(C[C@H]4CC[C@H](n5cc6cc(NC(=O)c7cccc(C(F)(F)F)n7)c(C#N)cc6n5)CC4)CC3F)c21] |
| I-549 | 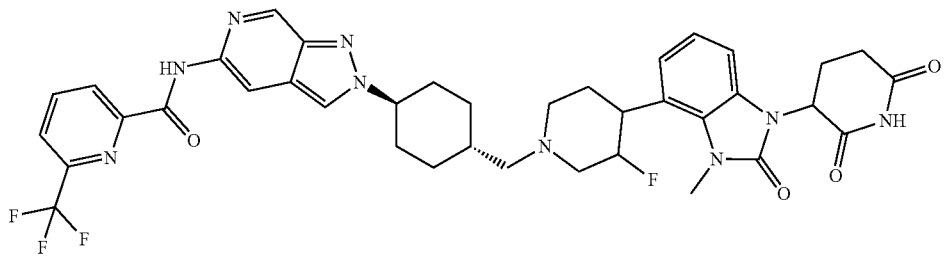 [SMILES: Cn1c(=O)n(C2CCC(=O)NC2=O)c2cccc(C3CCN(C[C@H]4CC[C@H](n5cc6cc(NC(=O)c7cccc(C(F)(F)F)n7)ncc6n5)CC4)CC3F)c21] |
| I-550 | 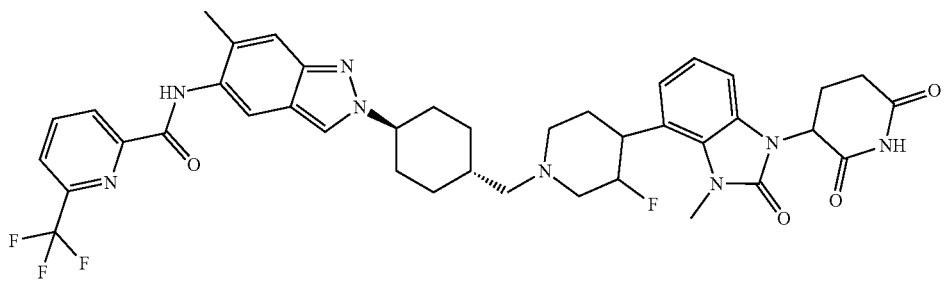 [SMILES: Cc1cc2nn([C@H]3CC[C@H](CN4CCC(c5cccc6c5n(C)c(=O)n6C5CCC(=O)NC5=O)C(F)C4)CC3)cc2cc1NC(=O)c1cccc(C(F)(F)F)n1] |

TABLE 1-continued
Exemplary Compounds
| I-# | Structure |
|---|---|
| I-551 | 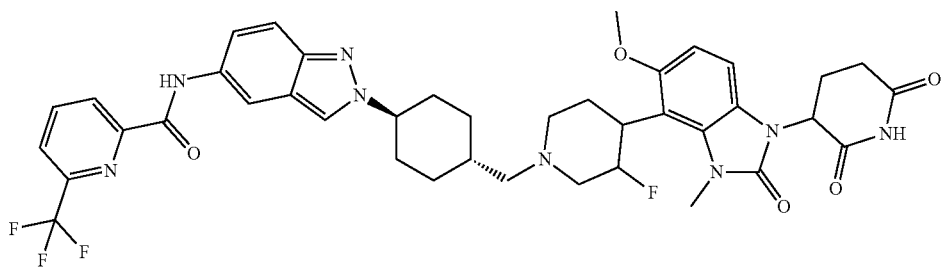 [SMILES: COc1ccc2c(c1C1CCN(C[C@H]3CC[C@H](n4cc5cc(NC(=O)c6cccc(C(F)(F)F)n6)ccc5n4)CC3)CC1F)n(C)c(=O)n2C1CCC(=O)NC1=O] |
| I-552 | 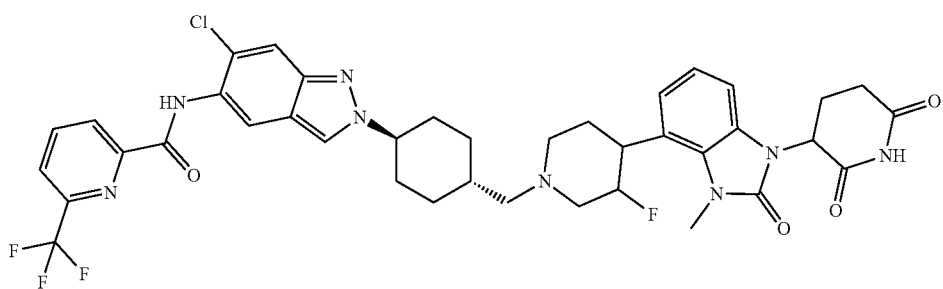 |
| I-553 | 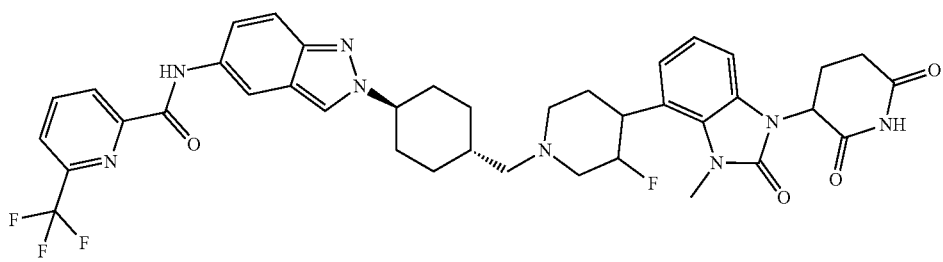 [SMILES: Cn1c(=O)n(C2CCC(=O)NC2=O)c2cccc(C3CCN(C[C@H]4CC[C@H](n5cc6cc(NC(=O)c7cccc(C(F)(F)F)n7)ccc6n5)CC4)CC3F)c21] |
| I-554 | 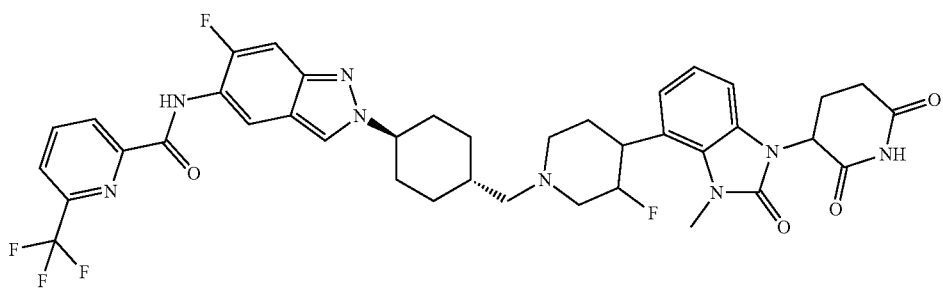 [SMILES: Cn1c(=O)n(C2CCC(=O)NC2=O)c2cccc(C3CCN(C[C@H]4CC[C@H](n5cc6cc(NC(=O)c7cccc(C(F)(F)F)n7)c(F)cc6n5)CC4)CC3F)c21] |
| I-555 | 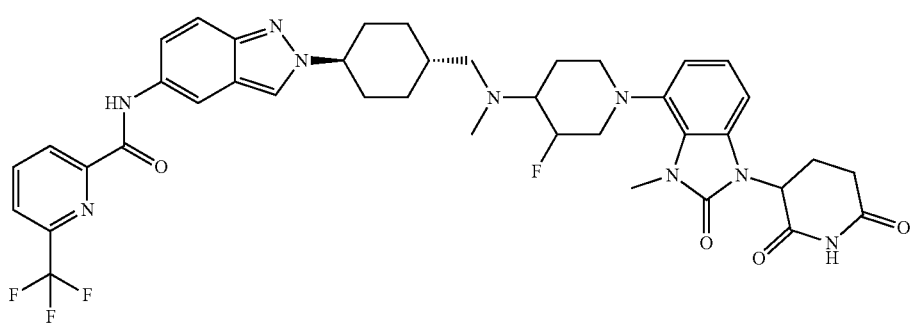 [SMILES: CN(C[C@H]1CC[C@H](n2cc3cc(NC(=O)c4cccc(C(F)(F)F)n4)ccc3n2)CC1)C1CCN(c2cccc3c2n(C)c(=O)n3C2CCC(=O)NC2=O)CC1F] |

TABLE 1-continued

Exemplary Compounds

| I-# | Structure |
|---|---|
| I-556 | 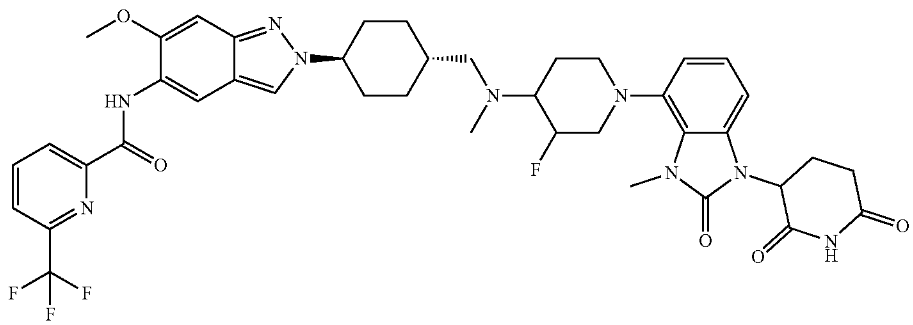 [SMILES: COc1cc2nn([C@H]3CC[C@H](CN(C)C4CCN(c5cccc6c5n(C)c(=O)n6C5CCC(=O)NC5=O)CC4F)CC3)cc2cc1NC(=O)c1cccc(C(F)(F)F)n1] |
| I-557 | 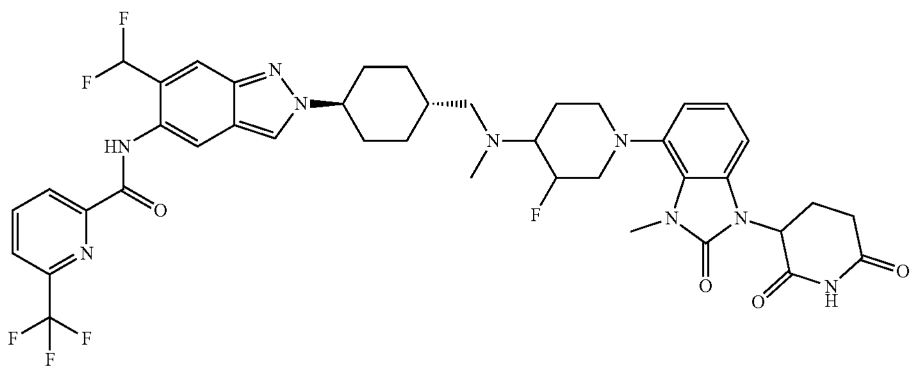 [SMILES: CN(C[C@H]1CC[C@H](n2cc3cc(NC(=O)c4cccc(C(F)(F)F)n4)c(C(F)F)cc3n2)CC1)C1CCN(c2cccc3c2n(C)c(=O)n3C2CCC(=O)NC2=O)CC1F] |
| I-558 | 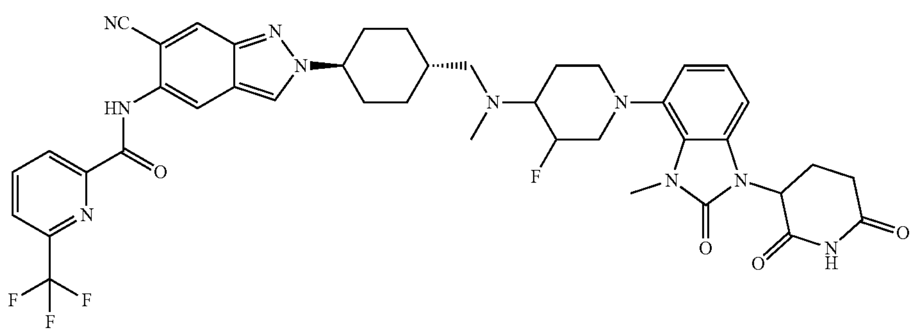 [SMILES: CN(C[C@H]1CC[C@H](n2cc3cc(NC(=O)c4cccc(C(F)(F)F)n4)c(C#N)cc3n2)CC1)C1CCN(c2cccc3c2n(C)c(=O)n3C2CCC(=O)NC2=O)CC1F] |
| I-559 | 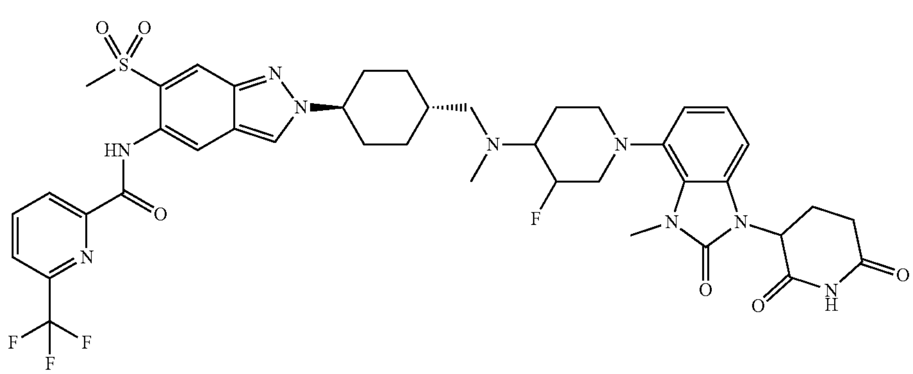 [SMILES: CN(C[C@H]1CC[C@H](n2cc3cc(NC(=O)c4cccc(C(F)(F)F)n4)c(S(C)(=O)=O)cc3n2)CC1)C1CCN(c2cccc3c2n(C)c(=O)n3C2CCC(=O)NC2=O)CC1F] |

TABLE 1-continued

Exemplary Compounds

| I-# | Structure |
|-----|-----------|
| I-560 | 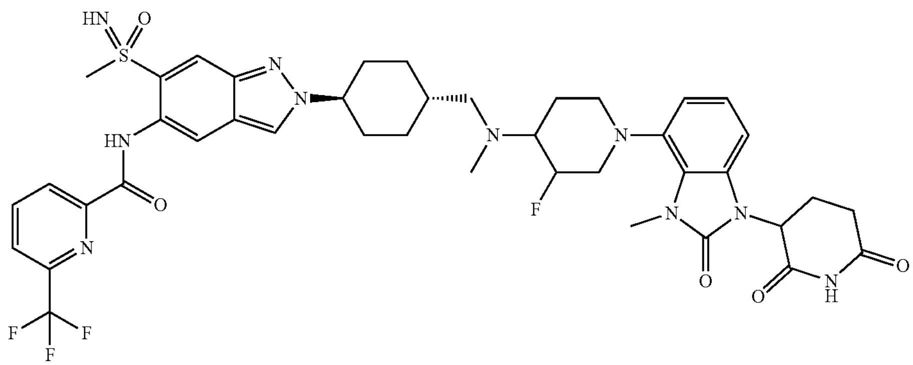 [SMILES: CN(C[C@H]1CC[C@H](n2cc3cc(NC(=O)c4cccc(C(F)(F)F)n4)c(S(C)(=N)=O)cc3n2)CC1)C1CCN(c2cccc3c2n(C)c(=O)n3C2CCC(=O)NC2=O)CC1F] |
| I-561 | 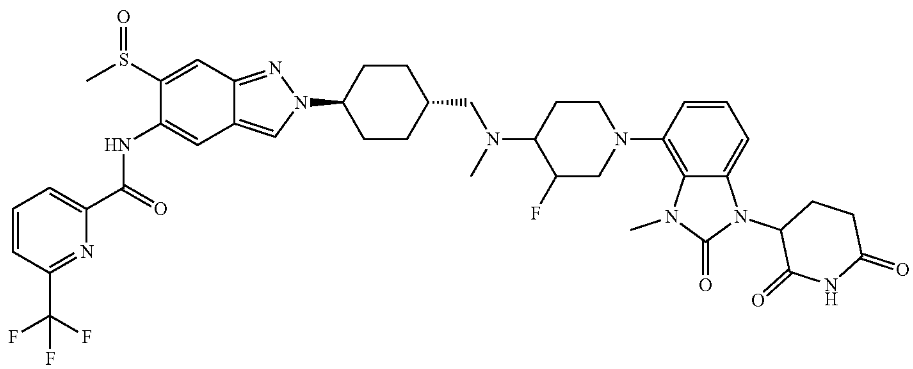 [SMILES: CN(C[C@H]1CC[C@H](n2cc3cc(NC(=O)c4cccc(C(F)(F)F)n4)c(S(C)=O)cc3n2)CC1)C1CCN(c2cccc3c2n(C)c(=O)n3C2CCC(=O)NC2=O)CC1F] |
| I-562 | 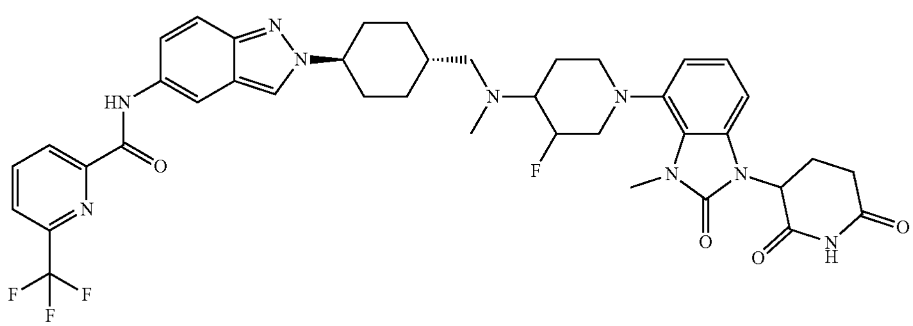 [SMILES: CN(C[C@H]1CC[C@H](n2cc3cc(NC(=O)c4cccc(C(F)(F)F)n4)ccc3n2)CC1)C1CCN(c2cccc3c2n(C)c(=O)n3C2CCC(=O)NC2=O)CC1F] |
| I-563 | 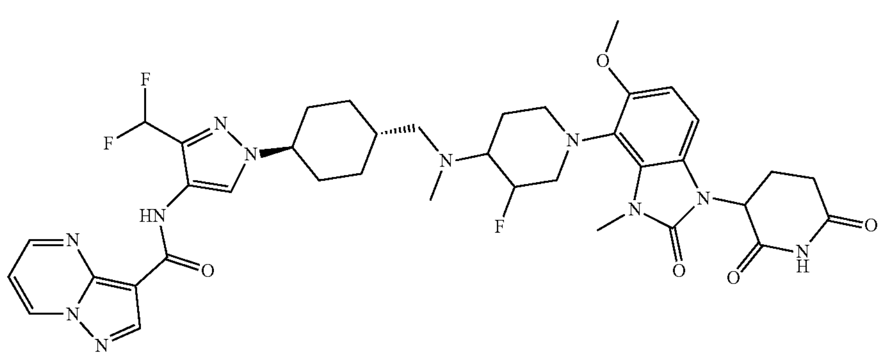 [SMILES: COc1ccc2c(c1N1CCC(N(C)C[C@H]3CC[C@H](n4cc(NC(=O)c5cnn6cccnc56)c(C(F)F)n4)CC3)C(F)C1)n(C)c(=O)n2C1CCC(=O)NC1=O] |

TABLE 1-continued

Exemplary Compounds

| I-# | Structure |
|---|---|
| I-564 | 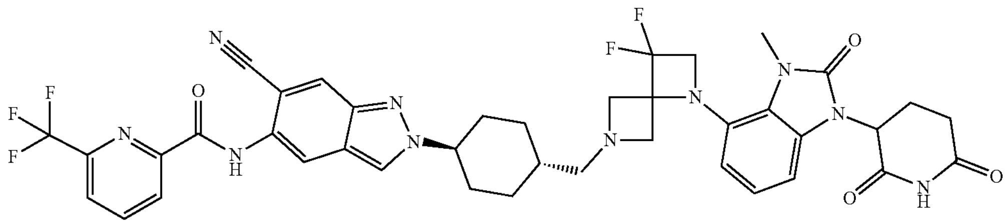 [SMILES: Cn1c(=O)n(C2CCC(=O)NC2=O)c2cccc(N3CC(F)(F)C34CN(C[C@H]3CC[C@H](n5cc6cc(NC(=O)c7cccc(C(F)(F)F)n7)c(C#N)cc6n5)CC3)C4)c21] |
| I-565 | 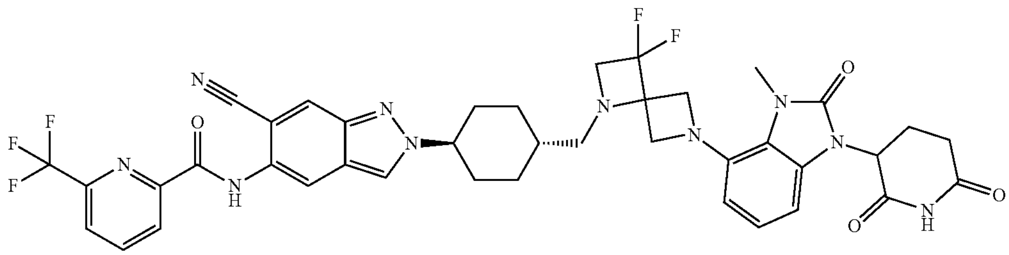 [SMILES: Cn1c(=O)n(C2CCC(=O)NC2=O)c2cccc(N3CC4(C3)N(C[C@H]3CC[C@H](n5cc6cc(NC(=O)c7cccc(C(F)(F)F)n7)c(C#N)cc6n5)CC3)CC4(F)F)c21] |
| I-566 | 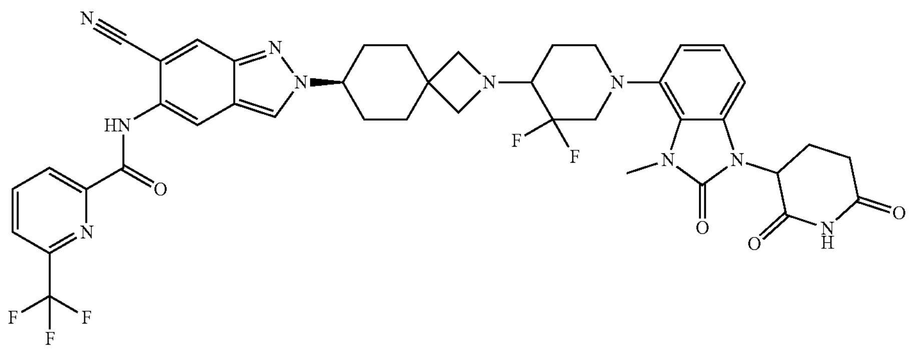 |
| I-567 | 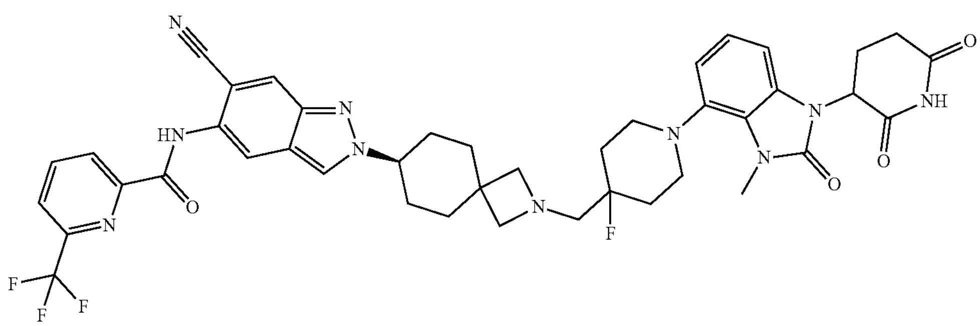 |
| I-568 | 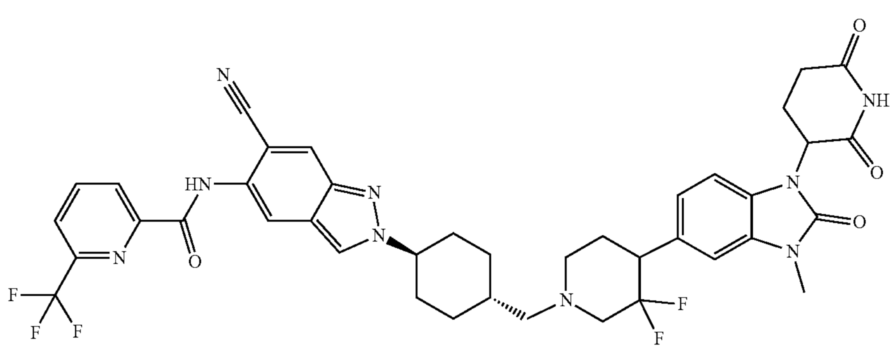 [SMILES: Cn1c(=O)n(C2CCC(=O)NC2=O)c2ccc(C3CCN(C[C@H]4CC[C@H](n5cc6cc(NC(=O)c7cccc(C(F)(F)F)n7)c(C#N)cc6n5)CC4)CC3(F)F)cc21] |

341 342
TABLE 1-continued
Exemplary Compounds
| I-# | Structure |
|---|---|
| I-569 | 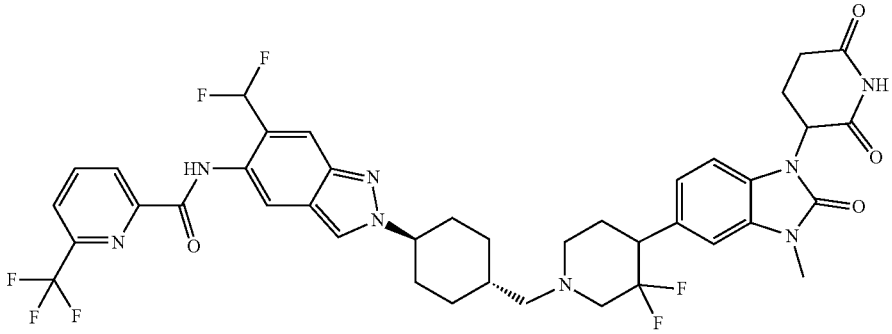 [SMILES: Cn1c(=O)n(C2CCC(=O)NC2=O)c2ccc(C3CCN(C[C@H]4CC[C@H](n5cc6cc(NC(=O)c7cccc(C(F)(F)F)n7)c(C(F)F)cc6n5)CC4)CC3(F)F)cc21] |
| I-570 | 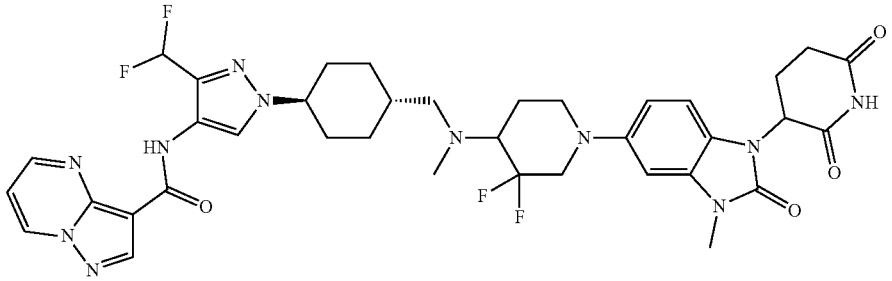 |
| I-571 | 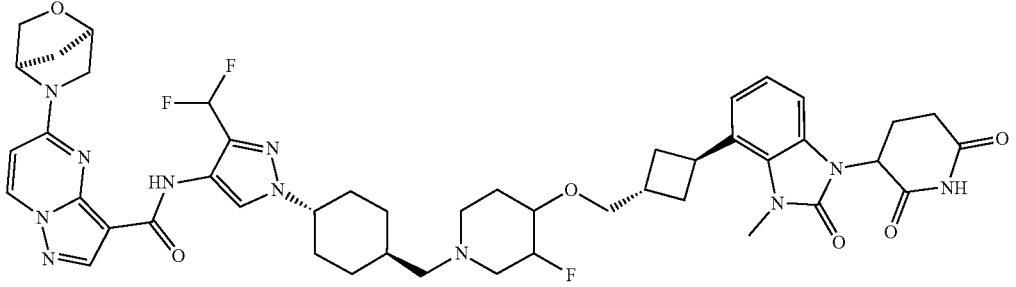 [SMILES: Cn1c(=O)n(C2CCC(=O)NC2=O)c2cccc([C@H]3C[C@H](COC4CCN(C[C@H]5CC[C@H](n6cc(NC(=O)c7cnn8ccc(N9C[C@H]%10C[C@@H]9CO%10)nc78)c(C(F)F)n6)CC5)CC4F)C3)c21] |
| I-572 | 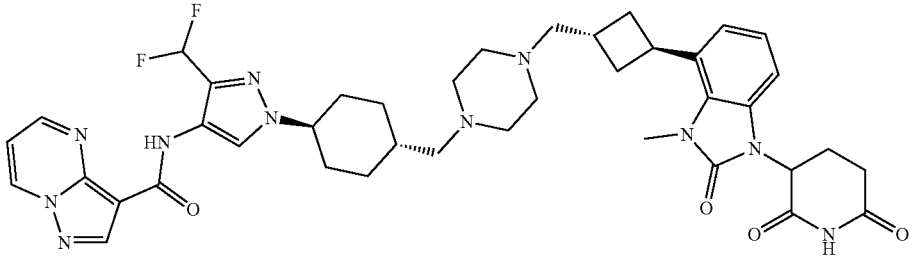 |
| I-573 | 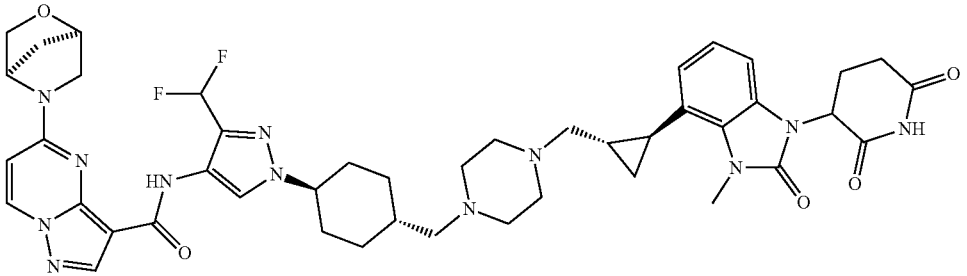 |

TABLE 1-continued
Exemplary Compounds
| I-# | Structure |
|---|---|
| I-574 | 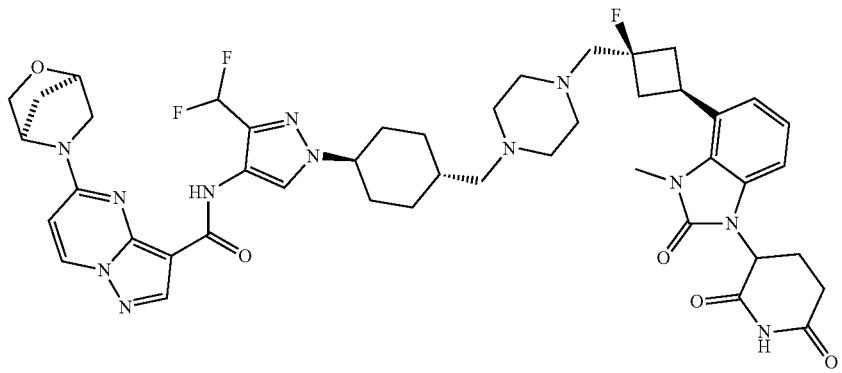 |
| I-575 | 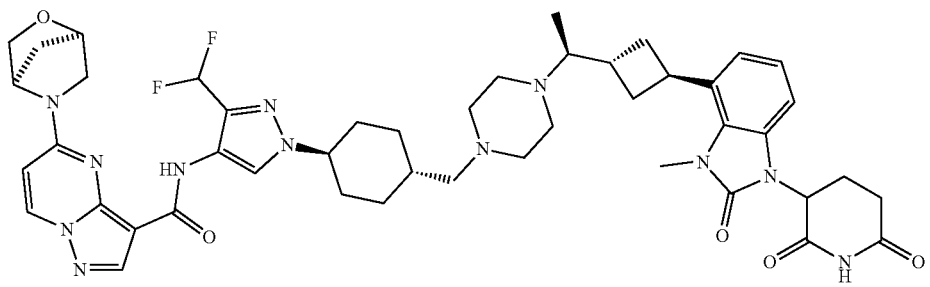 |
| I-576 | 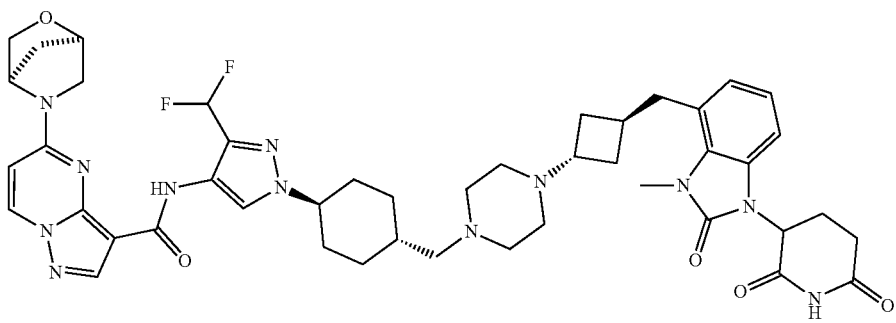 |
| I-577 | 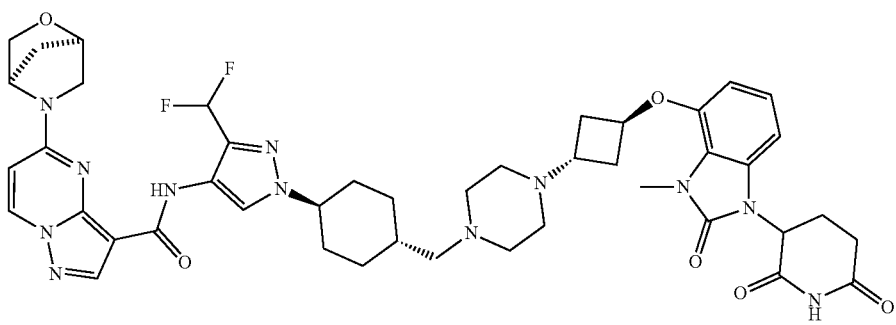 |

TABLE 1-continued

Exemplary Compounds

| I-# | Structure |
| --- | --- |
| I-578 | 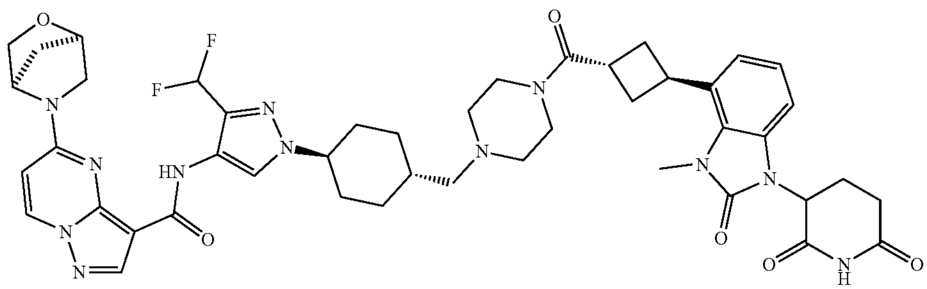 |
| I-579 | 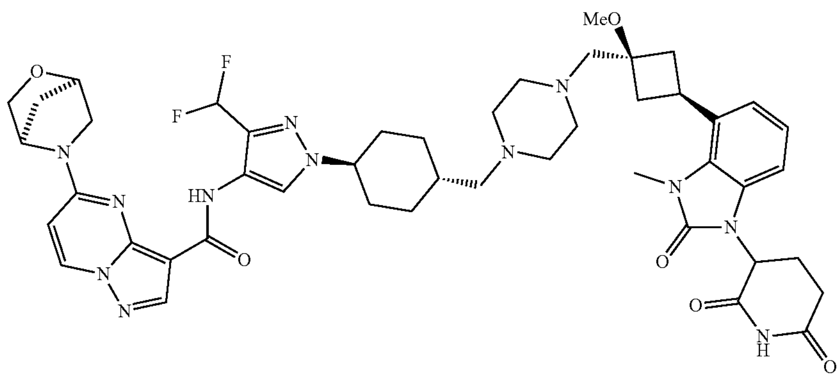 |
| I-580 | 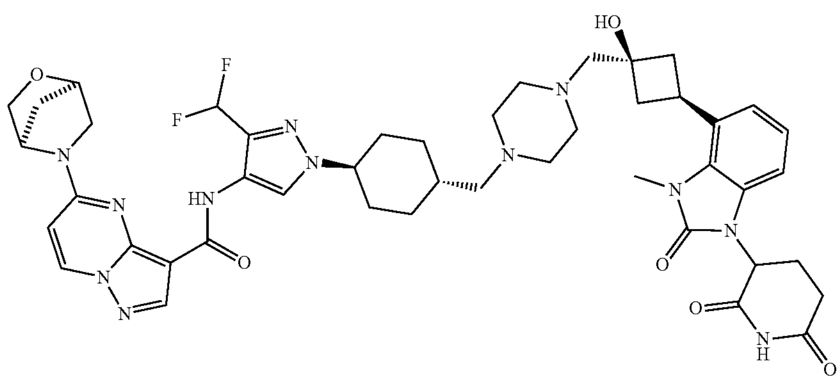 |
| I-581 | 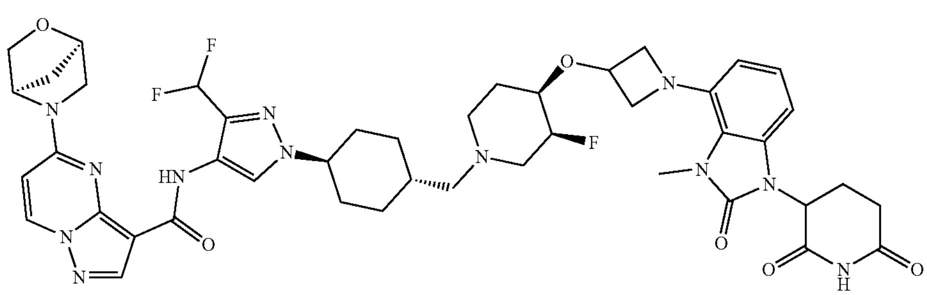 |

TABLE 1-continued

Exemplary Compounds

| I-# | Structure |
|---|---|
| I-582 | 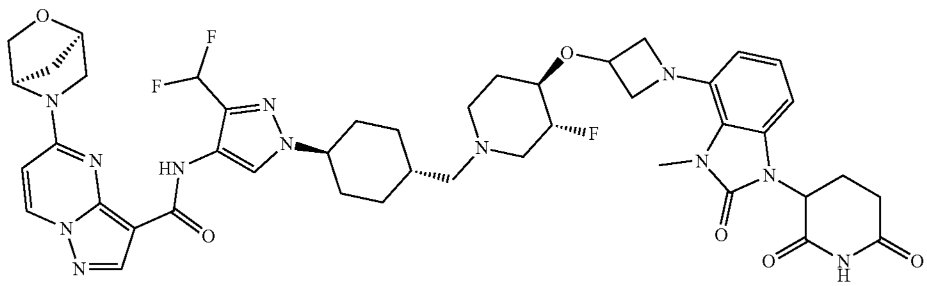 |
| I-583 | 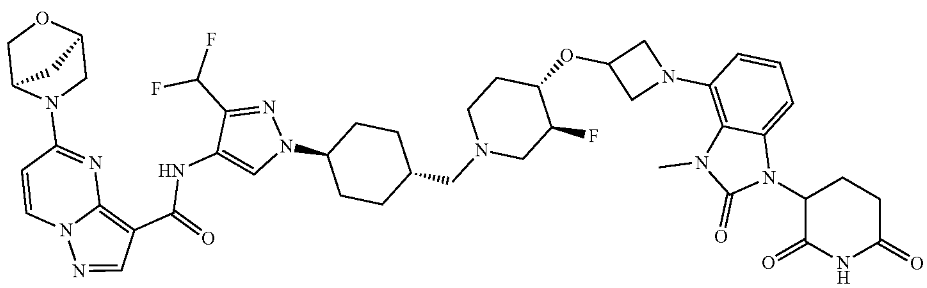 |
| I-584 | 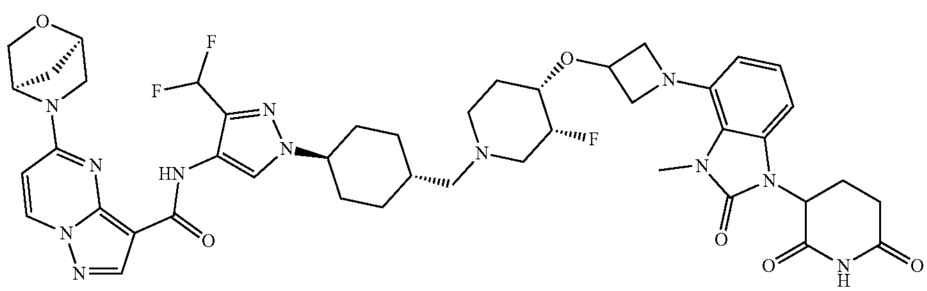 |
| I-585 | 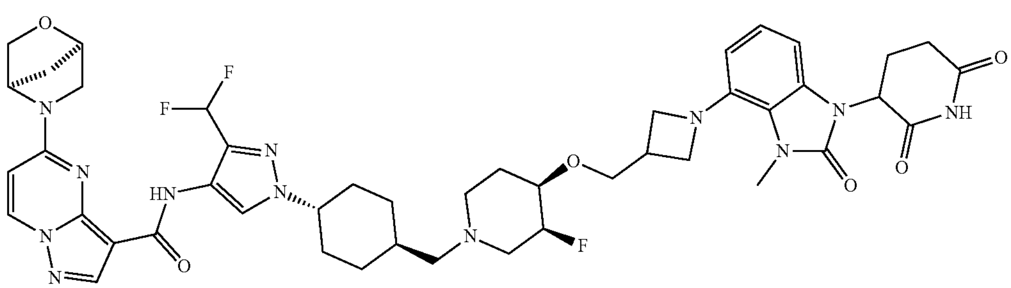 |
| I-586 | 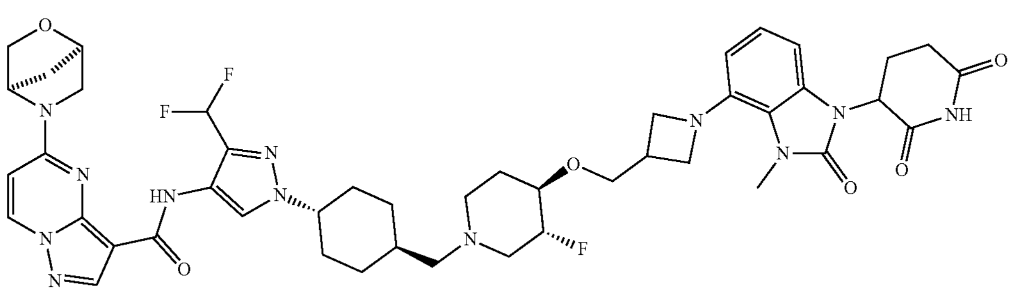 |

TABLE 1-continued

Exemplary Compounds

| I-# | Structure |
|---|---|
| I-587 | 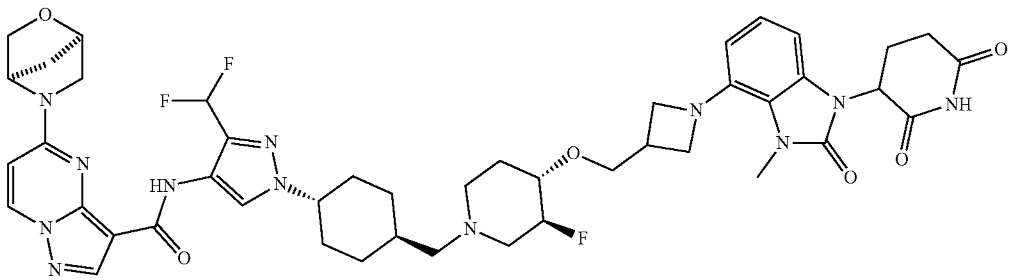 |
| I-588 | 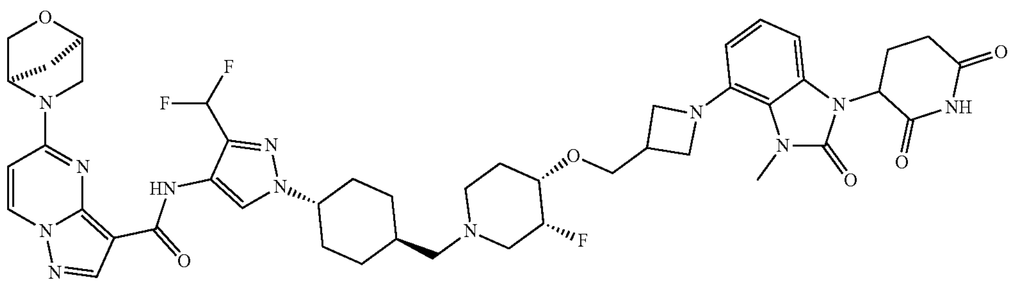 |
| I-589 | 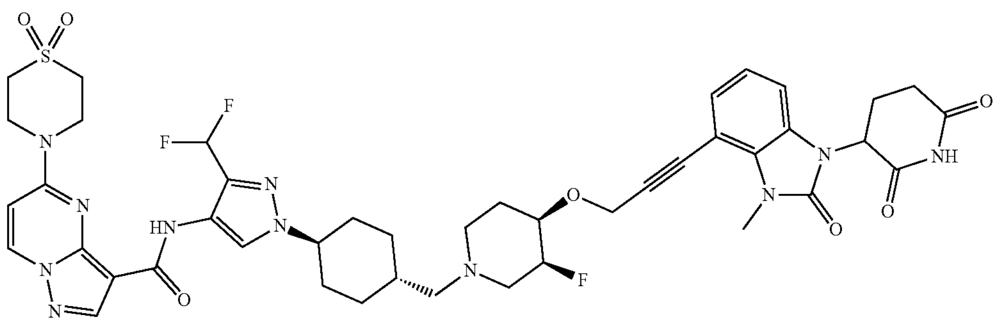 |
| I-590 | 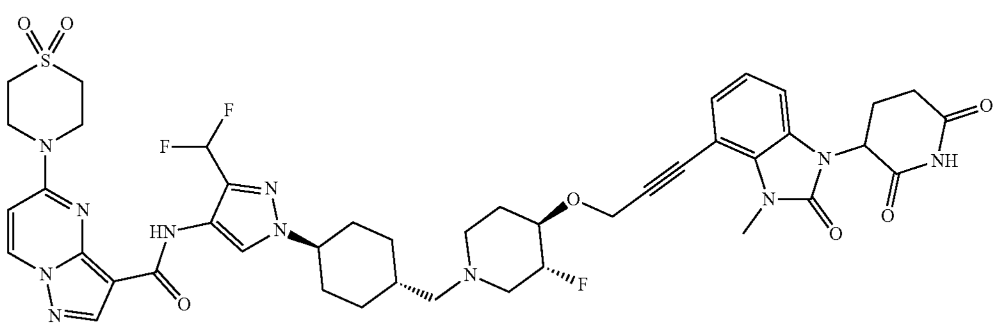 |
| I-591 | 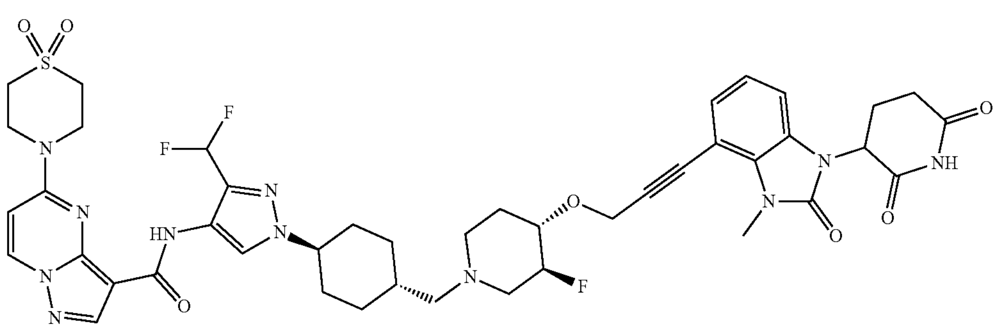 |

TABLE 1-continued

Exemplary Compounds

| I-# | Structure |
|---|---|
| I-592 | 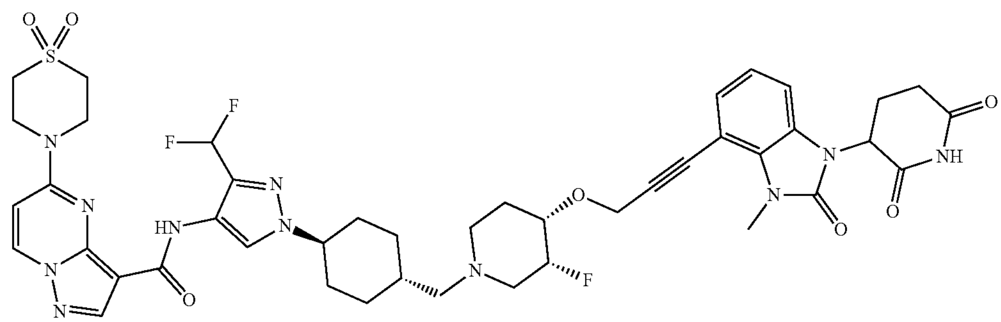 |
| I-593 | 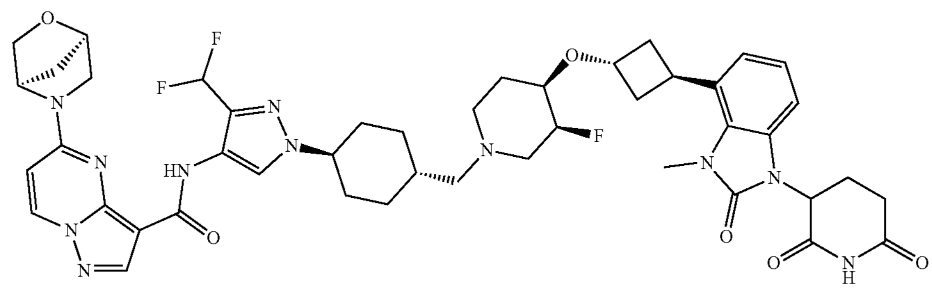 |
| I-594 | 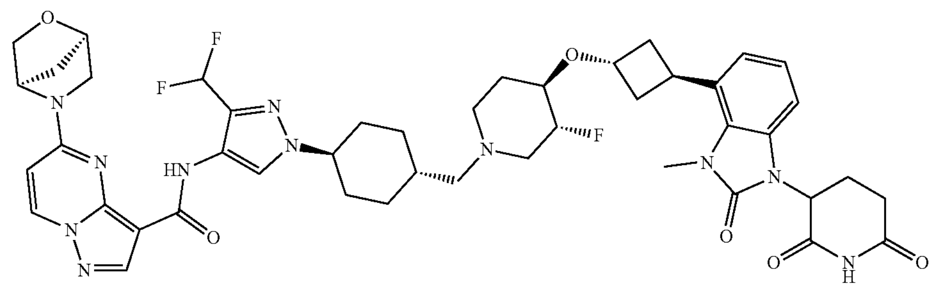 |
| I-595 | 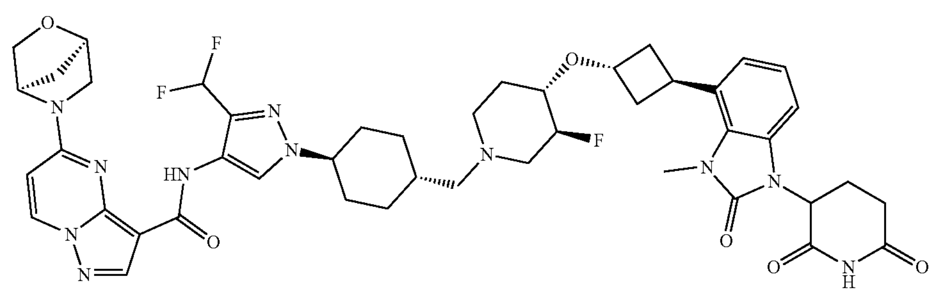 |
| I-596 | 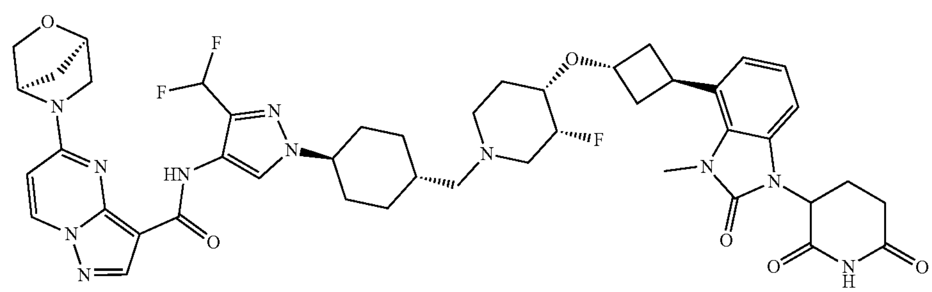 |

TABLE 1-continued
Exemplary Compounds
| I-# | Structure |
|---|---|
| I-597 | 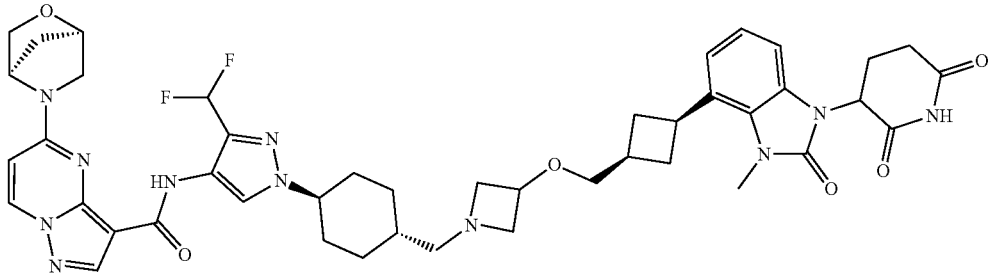 [SMILES: Cn1c(=O)n(C2CCC(=O)NC2=O)c2cccc([C@H]3C[C@@H](COC4CN(C[C@H]5CC[C@H](n6cc(NC(=O)c7cnn8ccc(N9C[C@H]%10C[C@@H]9CO%10)nc78)c(C(F)F)n6)CC5)C4)C3)c21] |
| I-598 | 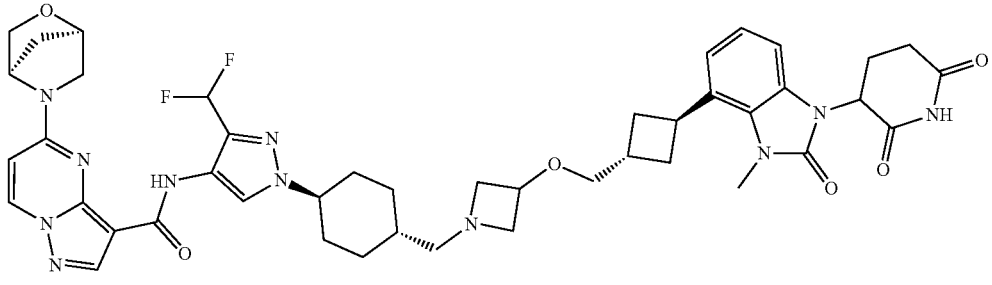 [SMILES: Cn1c(=O)n(C2CCC(=O)NC2=O)c2cccc([C@H]3C[C@H](COC4CN(C[C@H]5CC[C@H](n6cc(NC(=O)c7cnn8ccc(N9C[C@H]%10C[C@@H]9CO%10)nc78)c(C(F)F)n6)CC5)C4)C3)c21] |
| I-599 | 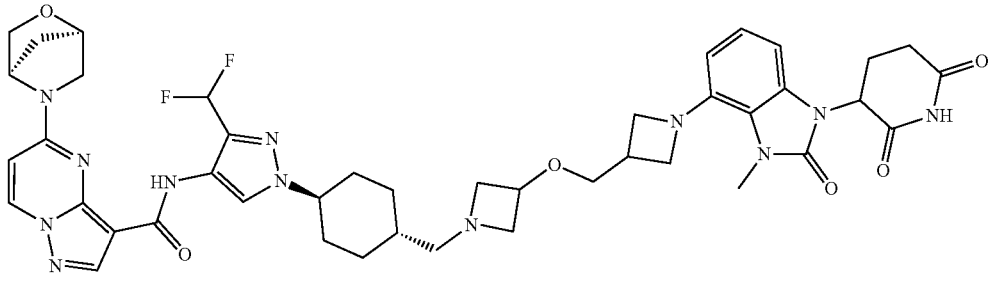 [SMILES: Cn1c(=O)n(C2CCC(=O)NC2=O)c2cccc(N3CC(COC4CN(C[C@H]5CC[C@H](n6cc(NC(=O)c7cnn8ccc(N9C[C@H]%10C[C@@H]9CO%10)nc78)c(C(F)F)n6)CC5)C4)C3)c21] |
| I-600 | 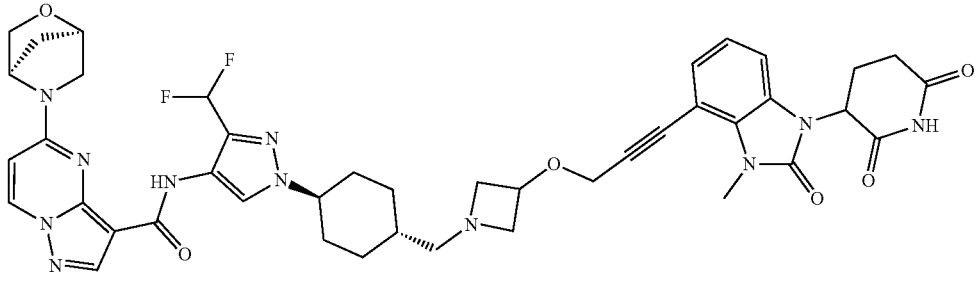 [SMILES: Cn1c(=O)n(C2CCC(=O)NC2=O)c2cccc(C#CCOC3CN(C[C@H]4CC[C@H](n5cc(NC(=O)c6cnn7ccc(N8C[C@H]9C[C@@H]8CO9)nc67)c(C(F)F)n5)CC4)C3)c21] |
| I-601 | 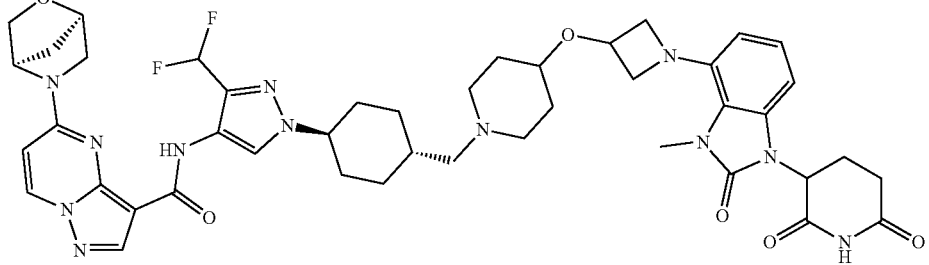 |

TABLE 1-continued

Exemplary Compounds

| I-# | Structure |
| --- | --- |
| I-602 | 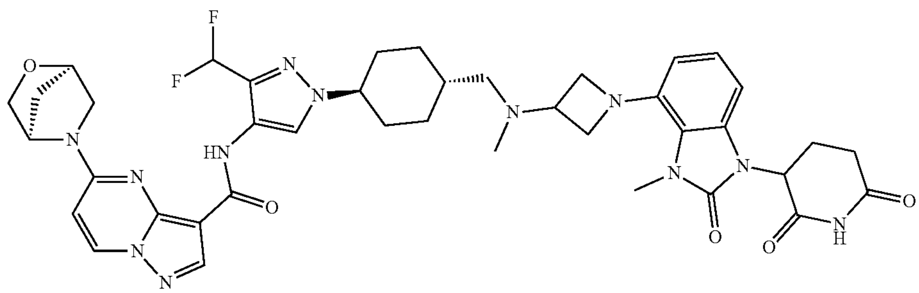 |
| I-603 | 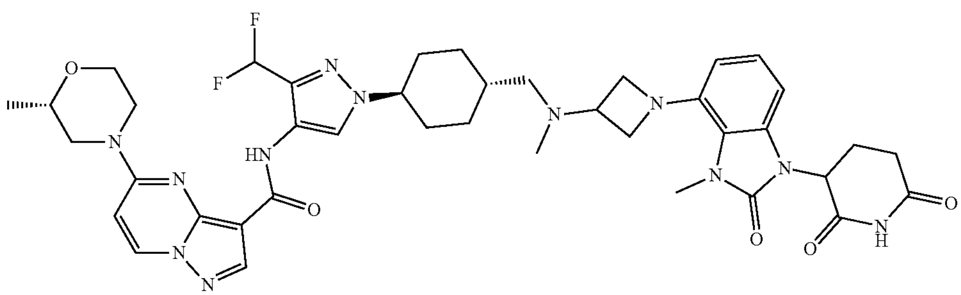 |
| I-604 | 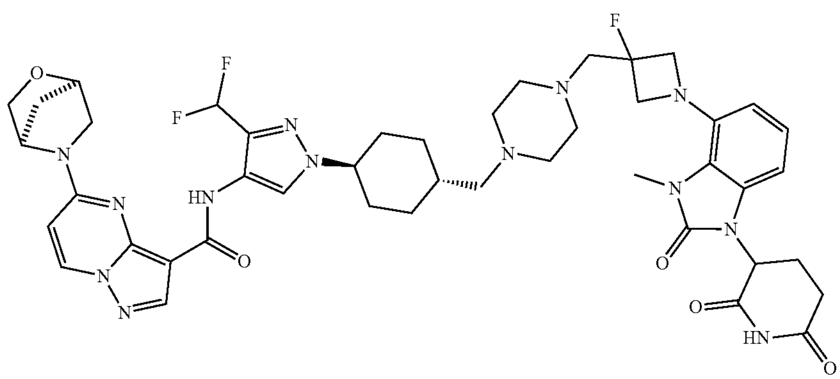 |
| I-605 | 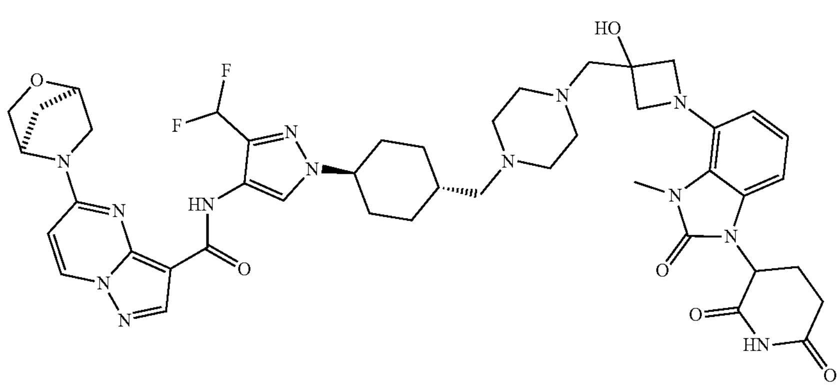 |

TABLE 1-continued

Exemplary Compounds

| I-# | Structure |
|---|---|
| I-606 | 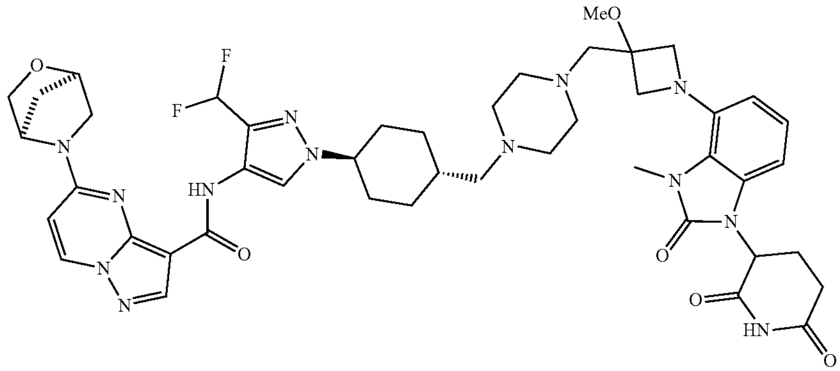 |
| I-607 | 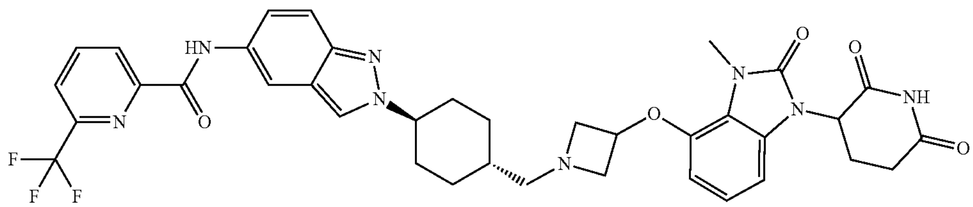 [SMILES: Cn1c(=O)n(C2CCC(=O)NC2=O)c2cccc(OC3CN(C[C@H]4CC[C@H](n5cc6cc(NC(=O)c7cccc(C(F)(F)F)n7)ccc6n5)CC4)C3)c21] |
| I-608 | 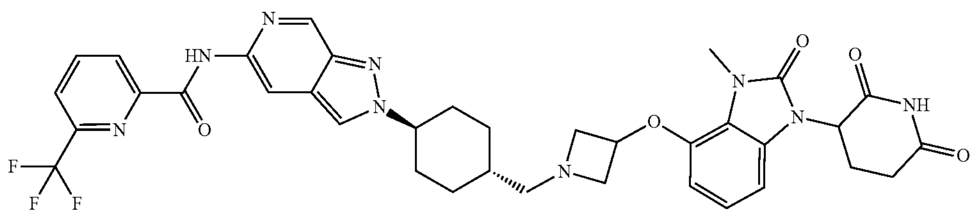 [SMILES: Cn1c(=O)n(C2CCC(=O)NC2=O)c2cccc(OC3CN(C[C@H]4CC[C@H](n5cc6cc(NC(=O)c7cccc(C(F)(F)F)n7)ncc6n5)CC4)C3)c21] |
| I-609 | 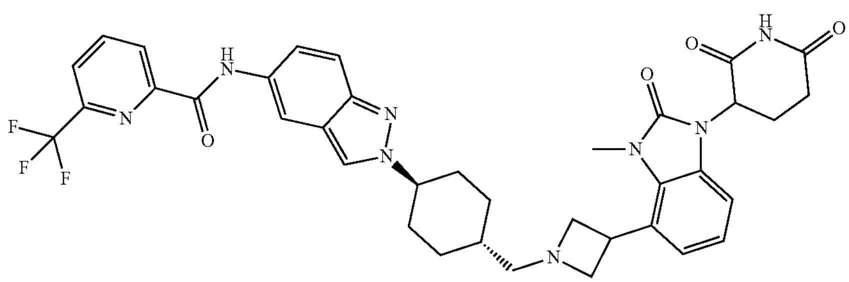 [SMILES: Cn1c(=O)n(C2CCC(=O)NC2=O)c2cccc(C3CN(C[C@H]4CC[C@H](n5cc6cc(NC(=O)c7cccc(C(F)(F)F)n7)ccc6n5)CC4)C3)c21] |
| I-610 | 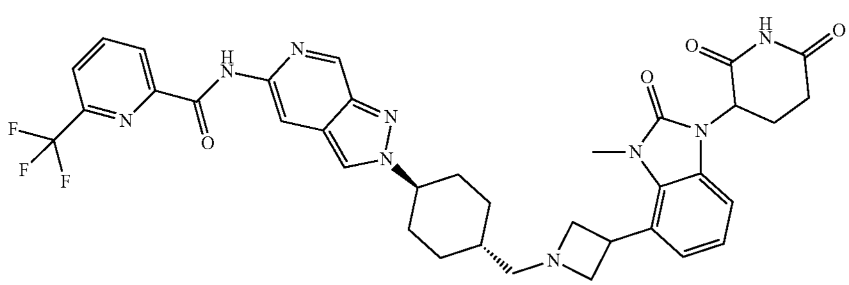 [SMILES: Cn1c(=O)n(C2CCC(=O)NC2=O)c2cccc(C3CN(C[C@H]4CC[C@H](n5cc6cc(NC(=O)c7cccc(C(F)(F)F)n7)ncc6n5)CC4)C3)c21] |

TABLE 1-continued

Exemplary Compounds

| I-# | Structure |
|---|---|
| I-611 | 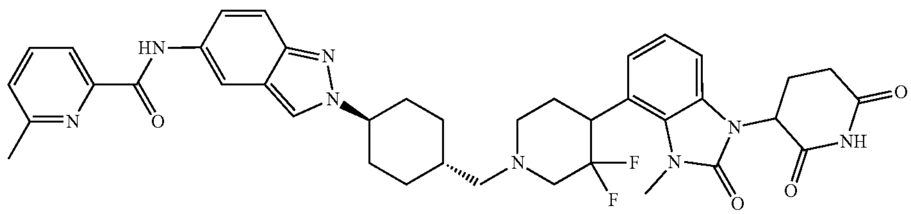 [SMILES: Cc1cccc(C(=O)Nc2ccc3nn([C@H]4CC[C@H](CN5CCC(c6cccc7c6n(C)c(=O)n7C6CCC(=O)NC6=O)C(F)(F)C5)CC4)cc3c2)n1] |
| I-612 | 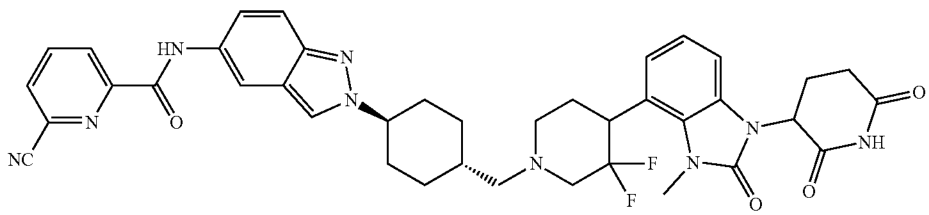 [SMILES: Cn1c(=O)n(C2CCC(=O)NC2=O)c2cccc(C3CCN(C[C@H]4CC[C@H](n5cc6cc(NC(=O)c7cccc(C#N)n7)ccc6n5)CC4)CC3(F)F)c21] |
| I-613 | 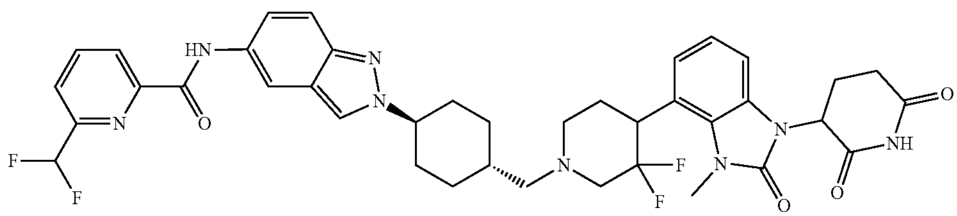 [SMILES: Cn1c(=O)n(C2CCC(=O)NC2=O)c2cccc(C3CCN(C[C@H]4CC[C@H](n5cc6cc(NC(=O)c7cccc(C(F)F)n7)ccc6n5)CC4)CC3(F)F)c21] |
| I-614 | 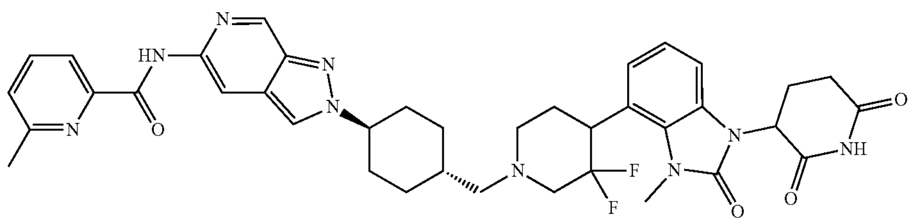 [SMILES: Cc1cccc(C(=O)Nc2cc3cn([C@H]4CC[C@H](CN5CCC(c6cccc7c6n(C)c(=O)n7C6CCC(=O)NC6=O)C(F)(F)C5)CC4)nc3cn2)n1] |
| I-615 | 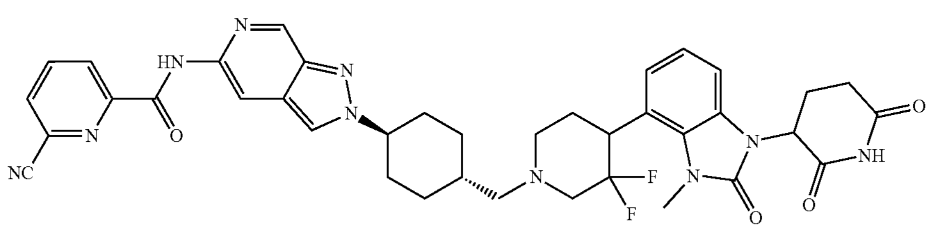 [SMILES: Cn1c(=O)n(C2CCC(=O)NC2=O)c2cccc(C3CCN(C[C@H]4CC[C@H](n5cc6cc(NC(=O)c7cccc(C#N)n7)ncc6n5)CC4)CC3(F)F)c21] |
| I-616 | 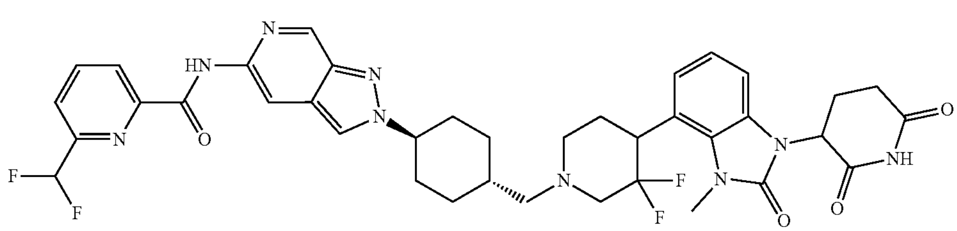 [SMILES: Cn1c(=O)n(C2CCC(=O)NC2=O)c2cccc(C3CCN(C[C@H]4CC[C@H](n5cc6cc(NC(=O)c7cccc(C(F)F)n7)ncc6n5)CC4)CC3(F)F)c21] |

TABLE 1-continued

Exemplary Compounds

| I-# | Structure |
|---|---|
| I-617 | 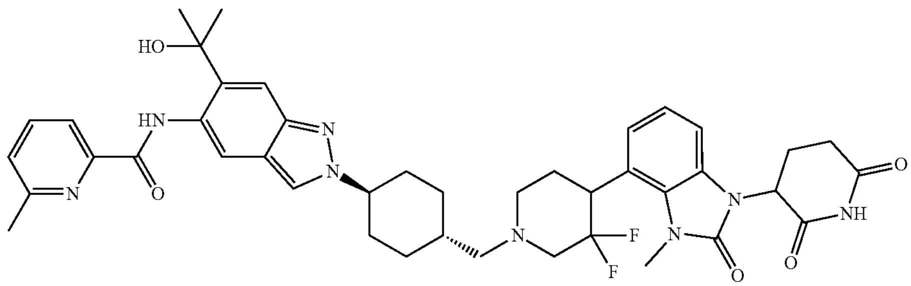 [SMILES: Cc1cccc(C(=O)Nc2cc3cn([C@H]4CC[C@H](CN5CCC(c6cccc7c6n(C)c(=O)n7C6CCC(=O)NC6=O)C(F)(F)C5)CC4)nc3cc2C(C)(C)O)n1] |
| I-618 | 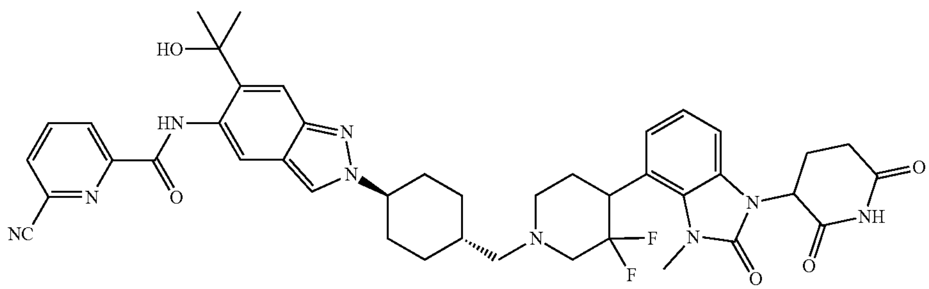 [SMILES: Cn1c(=O)n(C2CCC(=O)NC2=O)c2cccc(C3CCN(C[C@H]4CC[C@H](n5cc6cc(NC(=O)c7cccc(C#N)n7)c(C(C)(C)O)cc6n5)CC4)CC3(F)F)c21] |
| I-619 | 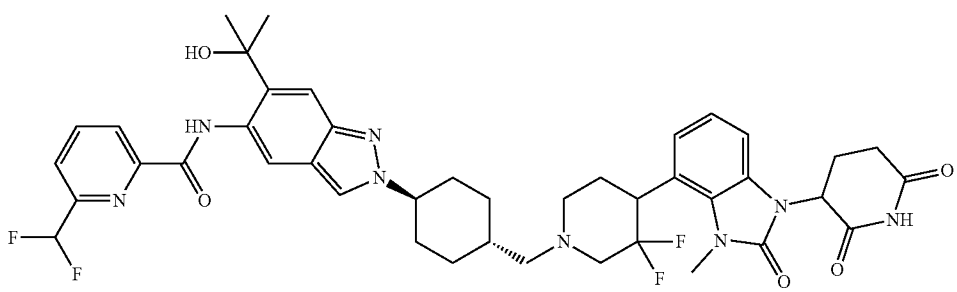 [SMILES: Cn1c(=O)n(C2CCC(=O)NC2=O)c2cccc(C3CCN(C[C@H]4CC[C@H](n5cc6cc(NC(=O)c7cccc(C(F)F)n7)c(C(C)(C)O)cc6n5)CC4)CC3(F)F)c21] |
| I-620 | 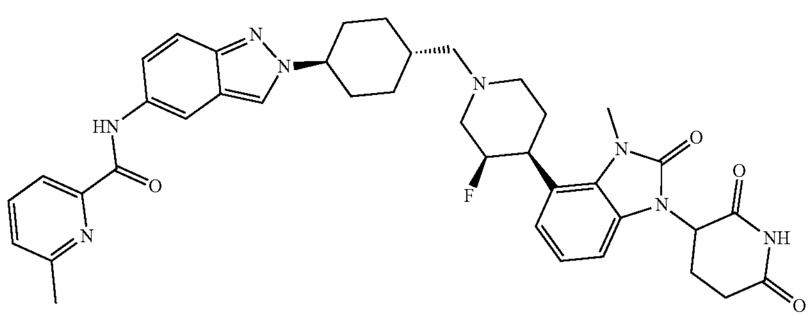 [SMILES: Cc1cccc(C(=O)Nc2ccc3nn([C@H]4CC[C@H](CN5CC[C@@H](c6cccc7c6n(C)c(=O)n7C6CCC(=O)NC6=O)[C@@H](F)C5)CC4)cc3c2)n1] |
| I-621 | 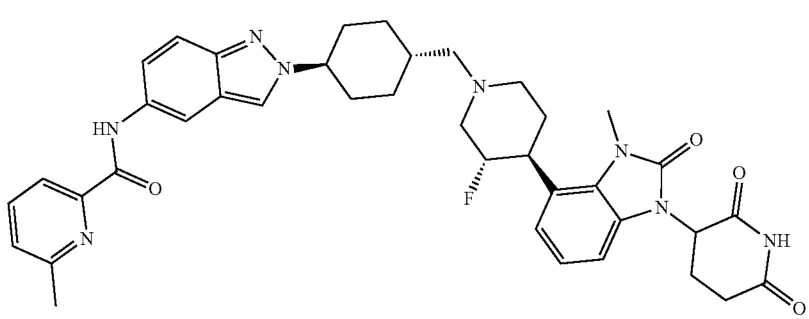 [SMILES: Cc1cccc(C(=O)Nc2ccc3nn([C@H]4CC[C@H](CN5CC[C@@H](c6cccc7c6n(C)c(=O)n7C6CCC(=O)NC6=O)[C@H](F)C5)CC4)cc3c2)n1] |

TABLE 1-continued

Exemplary Compounds

| I-# | Structure |
|---|---|
| I-622 | 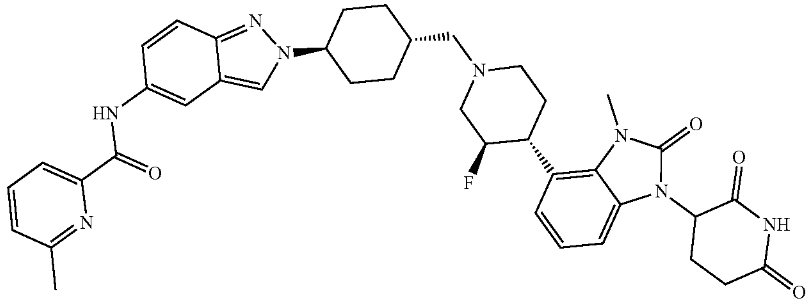 [SMILES: Cc1cccc(C(=O)Nc2ccc3nn([C@H]4CC[C@H](CN5CC[C@H](c6cccc7c6n(C)c(=O)n7C6CCC(=O)NC6=O)[C@@H](F)C5)CC4)cc3c2)n1] |
| I-623 | 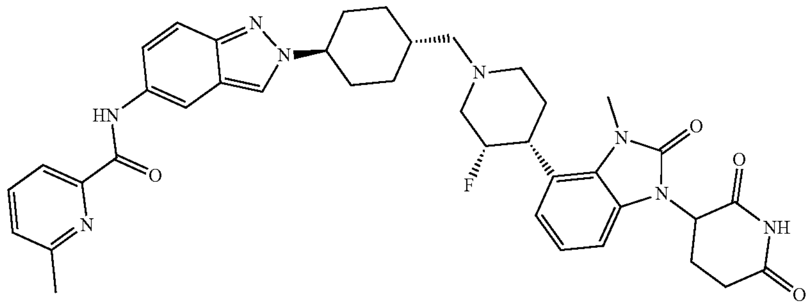 [SMILES: Cc1cccc(C(=O)Nc2ccc3nn([C@H]4CC[C@H](CN5CC[C@H](c6cccc7c6n(C)c(=O)n7C6CCC(=O)NC6=O)[C@H](F)C5)CC4)cc3c2)n1] |
| I-624 | 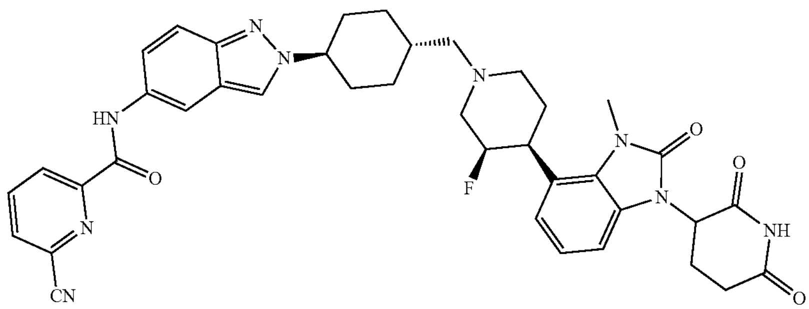 [SMILES: Cn1c(=O)n(C2CCC(=O)NC2=O)c2cccc([C@@H]3CCN(C[C@H]4CC[C@H](n5cc6cc(NC(=O)c7cccc(C#N)n7)ccc6n5)CC4)C[C@@H]3F)c21] |
| I-625 | 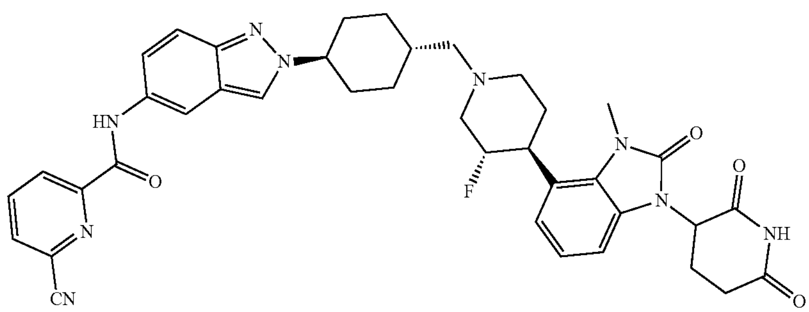 [SMILES: Cn1c(=O)n(C2CCC(=O)NC2=O)c2cccc([C@@H]3CCN(C[C@H]4CC[C@H](n5cc6cc(NC(=O)c7cccc(C#N)n7)ccc6n5)CC4)C[C@H]3F)c21] |
| I-626 | 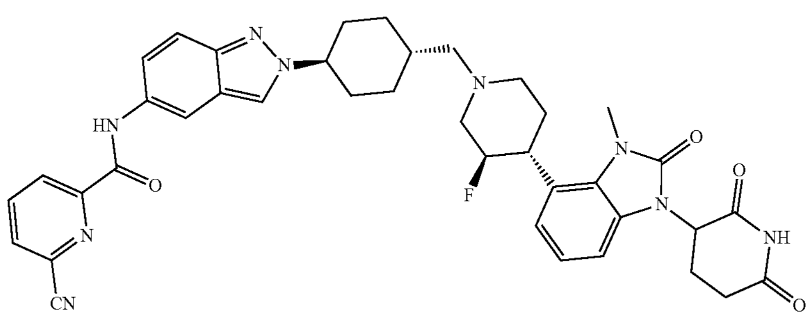 [SMILES: Cn1c(=O)n(C2CCC(=O)NC2=O)c2cccc([C@H]3CCN(C[C@H]4CC[C@H](n5cc6cc(NC(=O)c7cccc(C#N)n7)ccc6n5)CC4)C[C@@H]3F)c21] |

TABLE 1-continued
Exemplary Compounds
| I-# | Structure |
|---|---|
| I-627 | 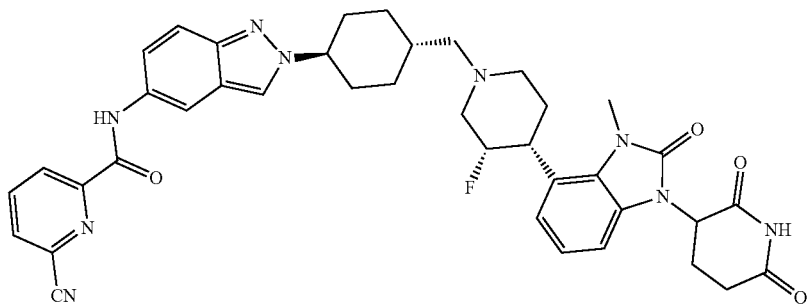 [SMILES: Cn1c(=O)n(C2CCC(=O)NC2=O)c2cccc([C@H]3CCN(C[C@H]4CC[C@H](n5cc6cc(NC(=O)c7cccc(C#N)n7)ccc6n5)CC4)C[C@H]3F)c21] |
| I-628 | 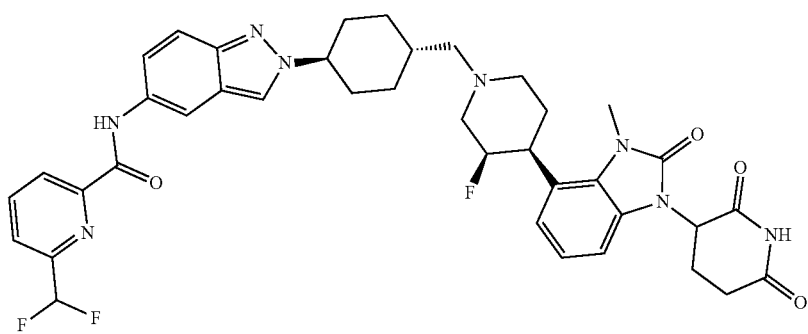 [SMILES: Cn1c(=O)n(C2CCC(=O)NC2=O)c2cccc([C@@H]3CCN(C[C@H]4CC[C@H](n5cc6cc(NC(=O)c7cccc(C(F)F)n7)ccc6n5)CC4)C[C@@H]3F)c21] |
| I-629 | 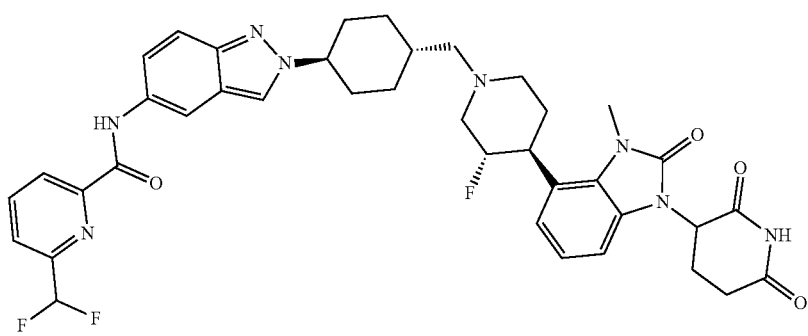 [SMILES: Cn1c(=O)n(C2CCC(=O)NC2=O)c2cccc([C@@H]3CCN(C[C@H]4CC[C@H](n5cc6cc(NC(=O)c7cccc(C(F)F)n7)ccc6n5)CC4)C[C@H]3F)c21] |
| I-630 | 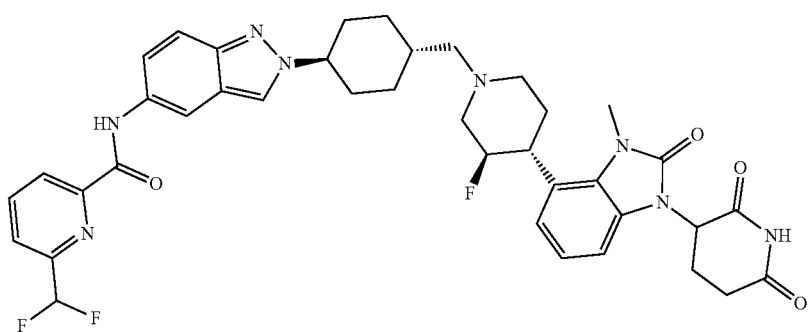 [SMILES: Cn1c(=O)n(C2CCC(=O)NC2=O)c2cccc([C@H]3CCN(C[C@H]4CC[C@H](n5cc6cc(NC(=O)c7cccc(C(F)F)n7)ccc6n5)CC4)C[C@@H]3F)c21] |

TABLE 1-continued

Exemplary Compounds

| I-# | Structure |
|---|---|
| I-631 | 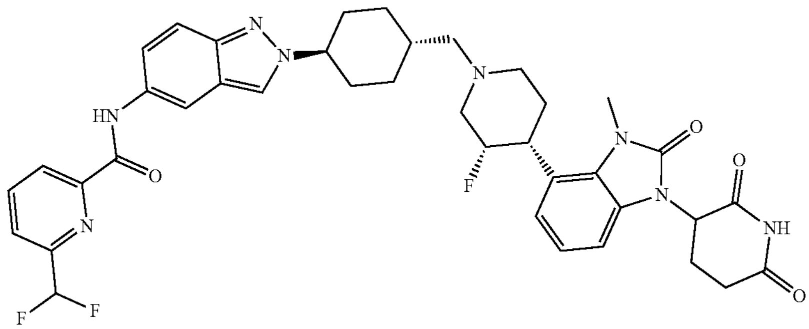 [SMILES: Cn1c(=O)n(C2CCC(=O)NC2=O)c2cccc([C@H]3CCN(C[C@H]4CC[C@H](n5cc6cc(NC(=O)c7cccc(C(F)F)n7)ccc6n5)CC4)C[C@H]3F)c21] |
| I-632 | 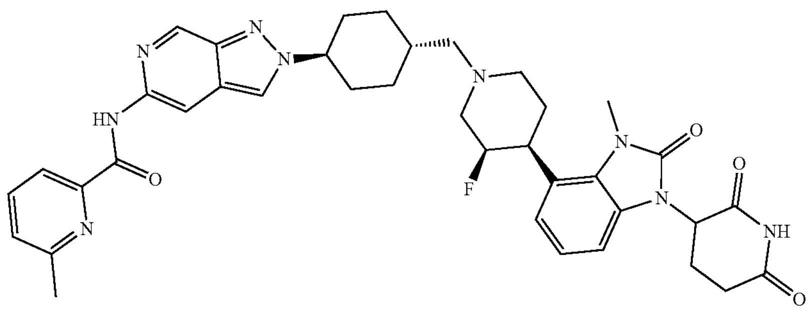 [SMILES: Cc1cccc(C(=O)Nc2cc3cn([C@H]4CC[C@H](CN5CC[C@@H](c6cccc7c6n(C)c(=O)n7C6CCC(=O)NC6=O)[C@@H](F)C5)CC4)nc3cn2)n1] |
| I-633 | 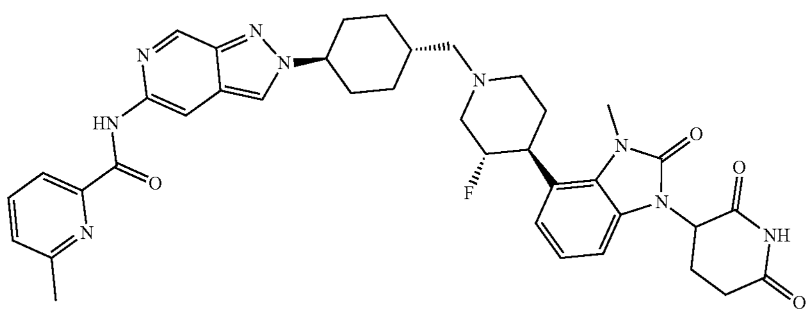 |
| I-634 | 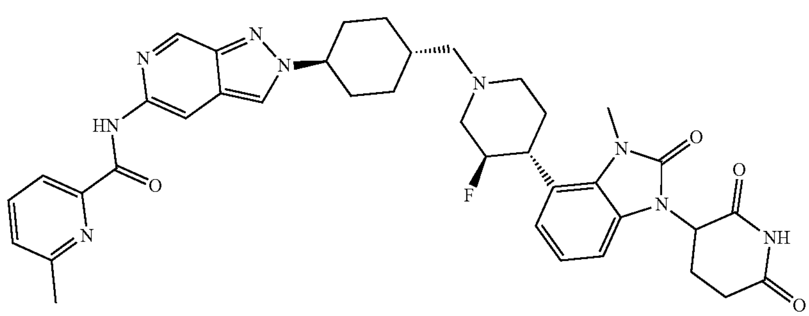 [SMILES: Cc1cccc(C(=O)Nc2cc3cn([C@H]4CC[C@H](CN5CC[C@H](c6cccc7c6n(C)c(=O)n7C6CCC(=O)NC6=O)[C@@H](F)C5)CC4)nc3cn2)n1] |

TABLE 1-continued
Exemplary Compounds
| I-# | Structure |
|---|---|
| I-635 | 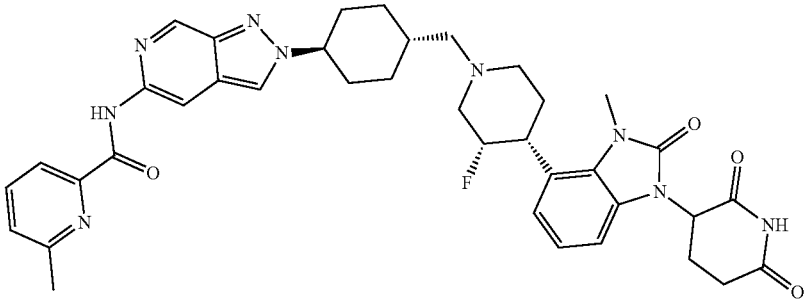 |
| I-636 | 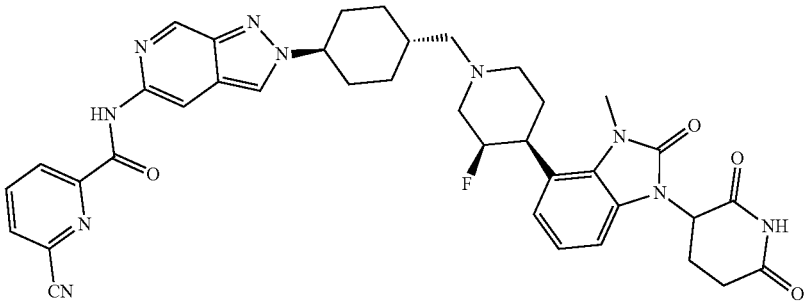 [SMILES: Cn1c(=O)n(C2CCC(=O)NC2=O)c2cccc([C@@H]3CCN(C[C@H]4CC[C@H](n5cc6cc(NC(=O)c7cccc(C#N)n7)ncc6n5)CC4)C[C@@H]3F)c21] |
| I-637 | 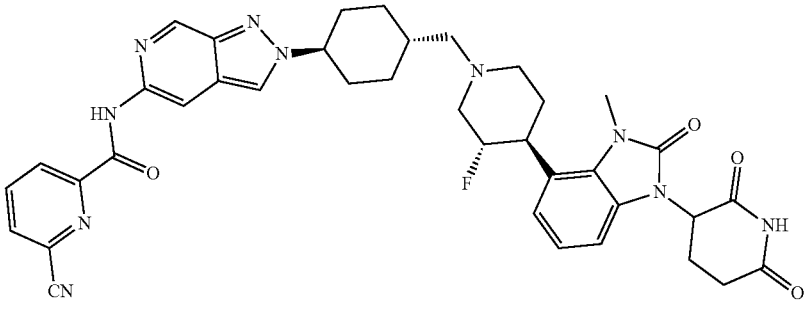 [SMILES: Cn1c(=O)n(C2CCC(=O)NC2=O)c2cccc([C@@H]3CCN(C[C@H]4CC[C@H](n5cc6cc(NC(=O)c7cccc(C#N)n7)ncc6n5)CC4)C[C@H]3F)c21] |
| I-638 | 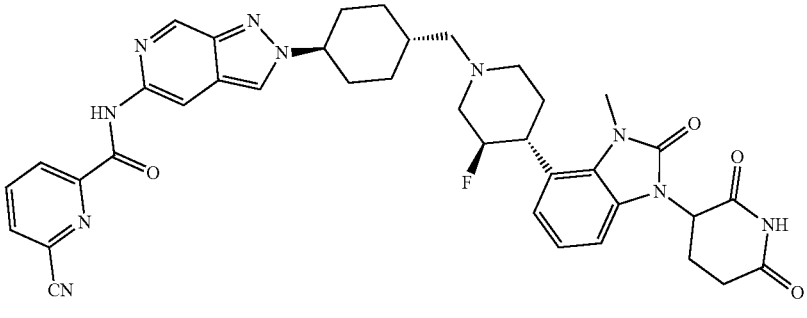 [SMILES: Cn1c(=O)n(C2CCC(=O)NC2=O)c2cccc([C@H]3CCN(C[C@H]4CC[C@H](n5cc6cc(NC(=O)c7cccc(C#N)n7)ncc6n5)CC4)C[C@@H]3F)c21] |
| I-639 | 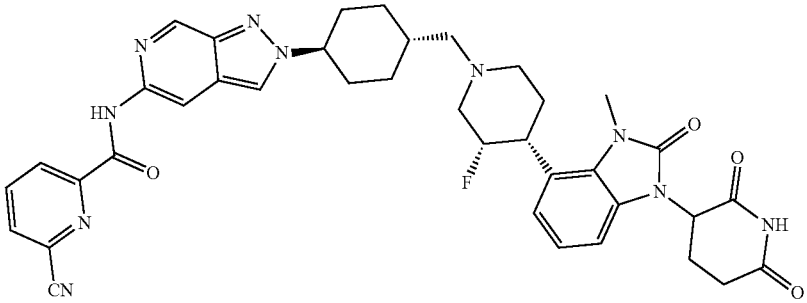 [SMILES: Cn1c(=O)n(C2CCC(=O)NC2=O)c2cccc([C@H]3CCN(C[C@H]4CC[C@H](n5cc6cc(NC(=O)c7cccc(C#N)n7)ncc6n5)CC4)C[C@H]3F)c21] |

TABLE 1-continued

Exemplary Compounds

| I-# | Structure |
|---|---|
| I-640 | 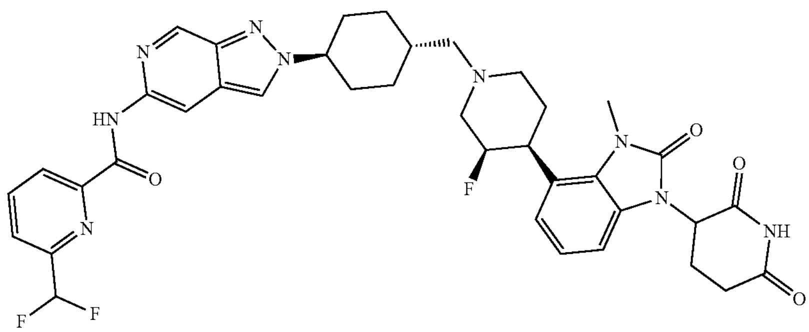 [SMILES: Cn1c(=O)n(C2CCC(=O)NC2=O)c2cccc([C@@H]3CCN(C[C@H]4CC[C@H](n5cc6cc(NC(=O)c7cccc(C(F)F)n7)ncc6n5)CC4)C[C@@H]3F)c21] |
| I-641 | 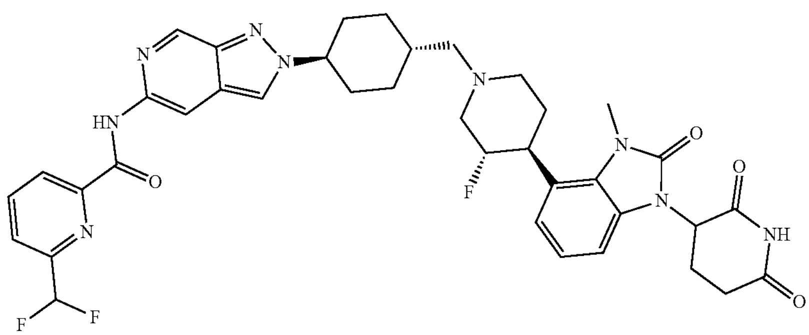 [SMILES: Cn1c(=O)n(C2CCC(=O)NC2=O)c2cccc([C@@H]3CCN(C[C@H]4CC[C@H](n5cc6cc(NC(=O)c7cccc(C(F)F)n7)ncc6n5)CC4)C[C@H]3F)c21] |
| I-642 | 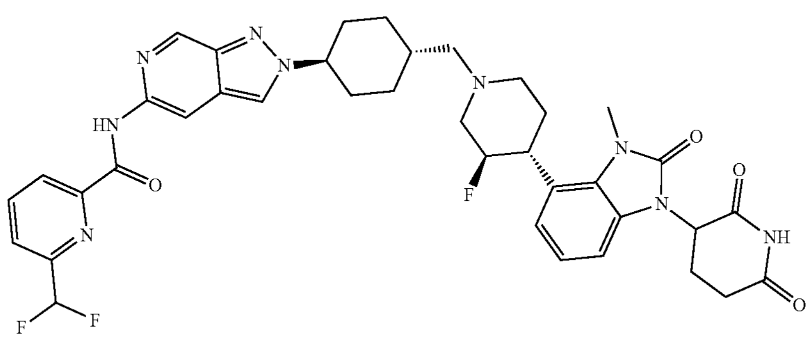 [SMILES: Cn1c(=O)n(C2CCC(=O)NC2=O)c2cccc([C@H]3CCN(C[C@H]4CC[C@H](n5cc6cc(NC(=O)c7cccc(C(F)F)n7)ncc6n5)CC4)C[C@@H]3F)c21] |
| I-643 | 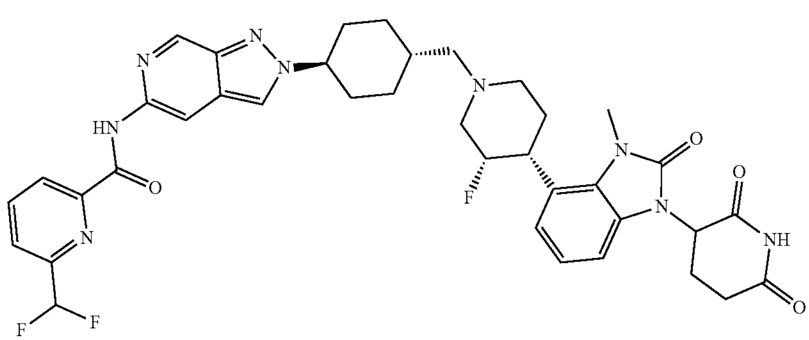 [SMILES: Cn1c(=O)n(C2CCC(=O)NC2=O)c2cccc([C@H]3CCN(C[C@H]4CC[C@H](n5cc6cc(NC(=O)c7cccc(C(F)F)n7)ncc6n5)CC4)C[C@H]3F)c21] |

TABLE 1-continued

Exemplary Compounds

| I-# | Structure |
|---|---|
| I-644 | 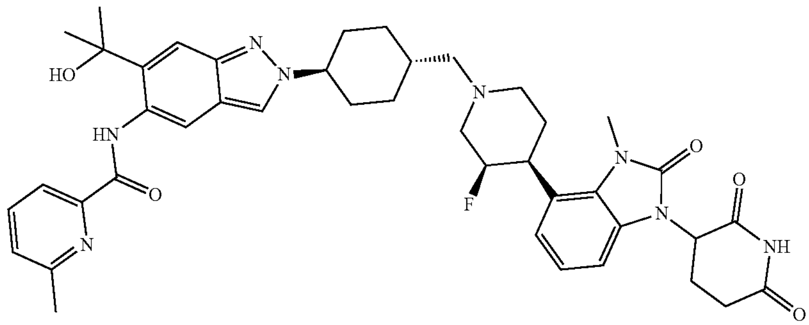 [SMILES: Cc1cccc(C(=O)Nc2cc3cn([C@H]4CC[C@H](CN5CC[C@@H](c6cccc7c6n(C)c(=O)n7C6CCC(=O)NC6=O)[C@@H](F)C5)CC4)nc3cc2C(C)(C)O)n1] |
| I-645 | 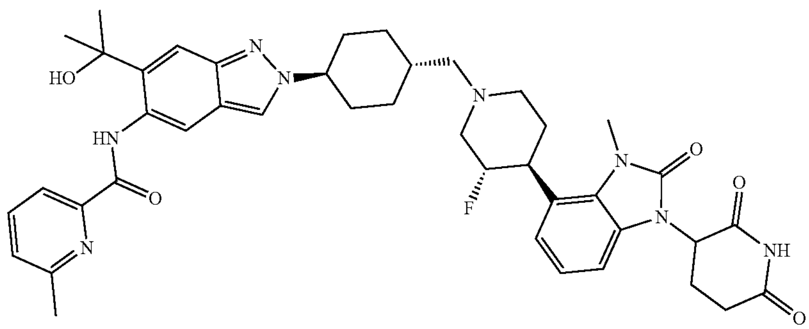 [SMILES: Cc1cccc(C(=O)Nc2cc3cn([C@H]4CC[C@H](CN5CC[C@@H](c6cccc7c6n(C)c(=O)n7C6CCC(=O)NC6=O)[C@H](F)C5)CC4)nc3cc2C(C)(C)O)n1] |
| I-646 | 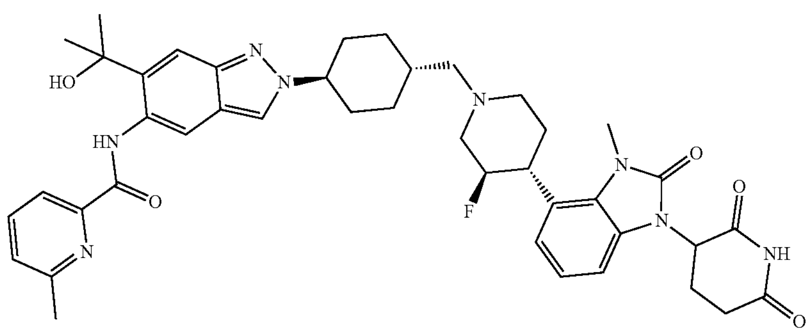 [SMILES: Cc1cccc(C(=O)Nc2cc3cn([C@H]4CC[C@H](CN5CC[C@H](c6cccc7c6n(C)c(=O)n7C6CCC(=O)NC6=O)[C@@H](F)C5)CC4)nc3cc2C(C)(C)O)n1] |
| I-647 | 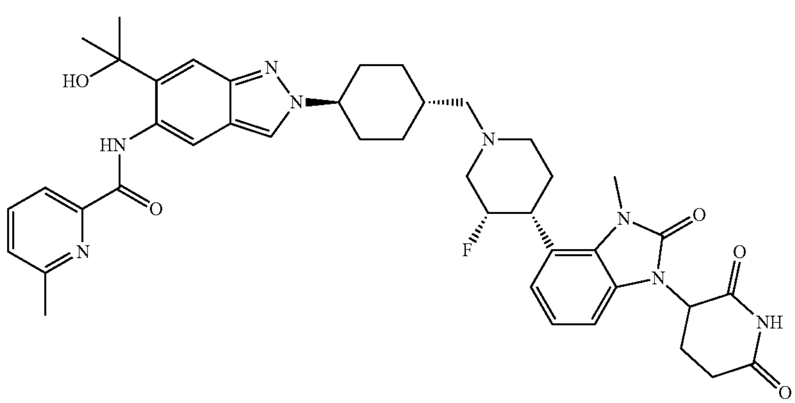 [SMILES: Cc1cccc(C(=O)Nc2cc3cn([C@H]4CC[C@H](CN5CC[C@H](c6cccc7c6n(C)c(=O)n7C6CCC(=O)NC6=O)[C@H](F)C5)CC4)nc3cc2C(C)(C)O)n1] |

TABLE 1-continued
Exemplary Compounds
| I-# | Structure |
|---|---|
| I-648 | 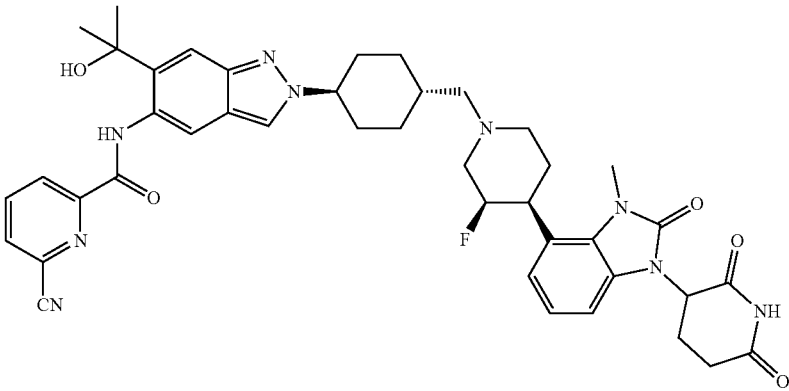 |
| I-649 | 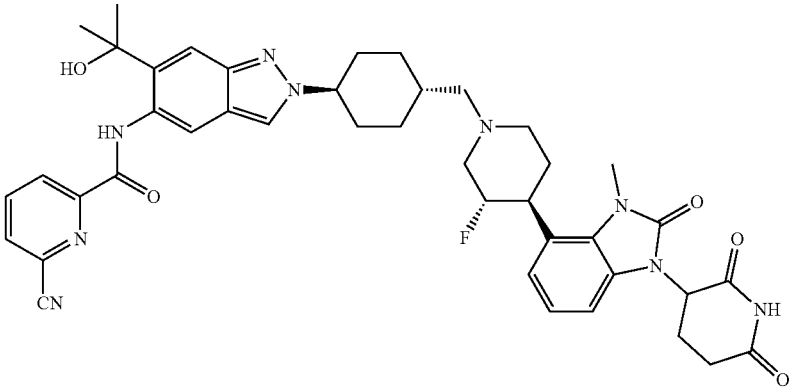 [SMILES: Cn1c(=O)n(C2CCC(=O)NC2=O)c2cccc([C@@H]3CCN(C[C@H]4CC[C@H](n5cc6cc(NC(=O)c7cccc(C#N)n7)c(C(C)(C)O)cc6n5)CC4)C[C@H]3F)c21] |
| I-650 | 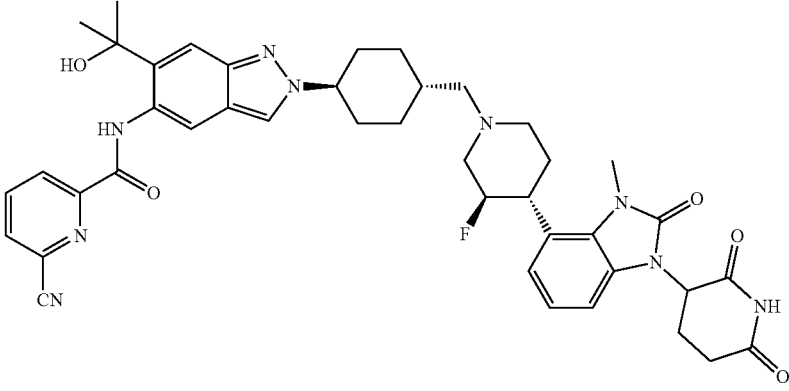 [SMILES: Cn1c(=O)n(C2CCC(=O)NC2=O)c2cccc([C@H]3CCN(C[C@H]4CC[C@H](n5cc6cc(NC(=O)c7cccc(C#N)n7)c(C(C)(C)O)cc6n5)CC4)C[C@@H]3F)c21] |
| I-651 | 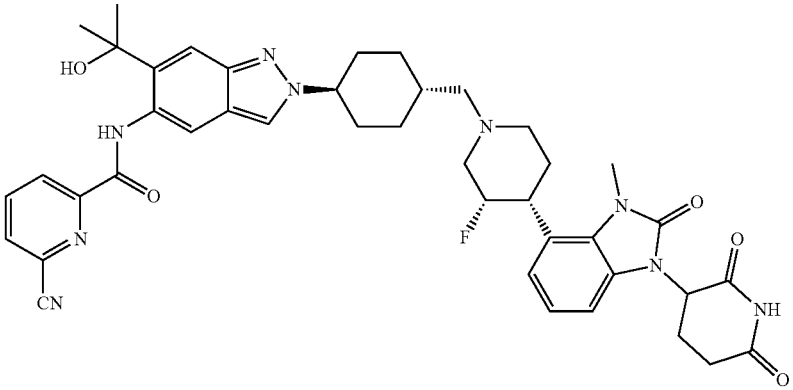 [SMILES: Cn1c(=O)n(C2CCC(=O)NC2=O)c2cccc([C@H]3CCN(C[C@H]4CC[C@H](n5cc6cc(NC(=O)c7cccc(C#N)n7)c(C(C)(C)O)cc6n5)CC4)C[C@H]3F)c21] |

TABLE 1-continued
Exemplary Compounds
| I-# | Structure |
|---|---|
| I-652 | 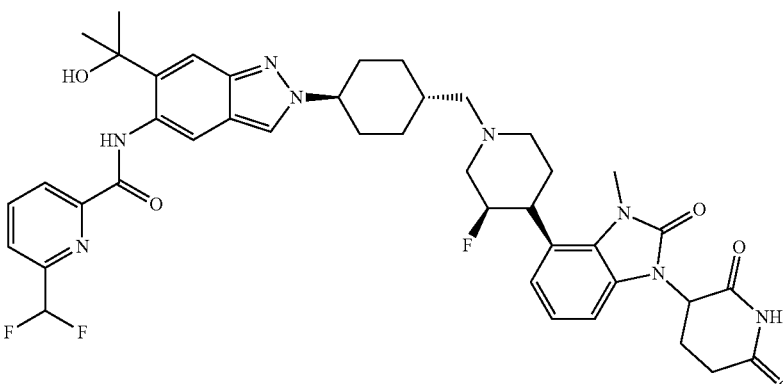 |
| I-653 | 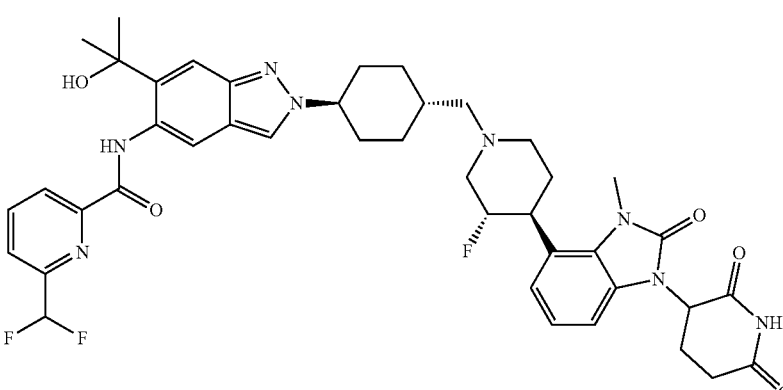 |
| I-654 | 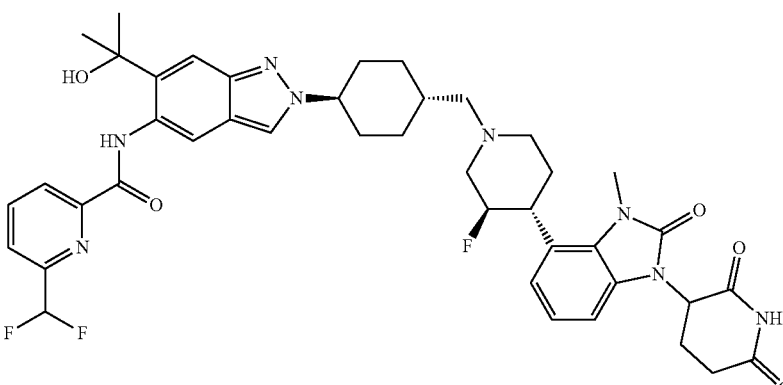 |

TABLE 1-continued
Exemplary Compounds
| I-# | Structure |
|---|---|
| I-655 | 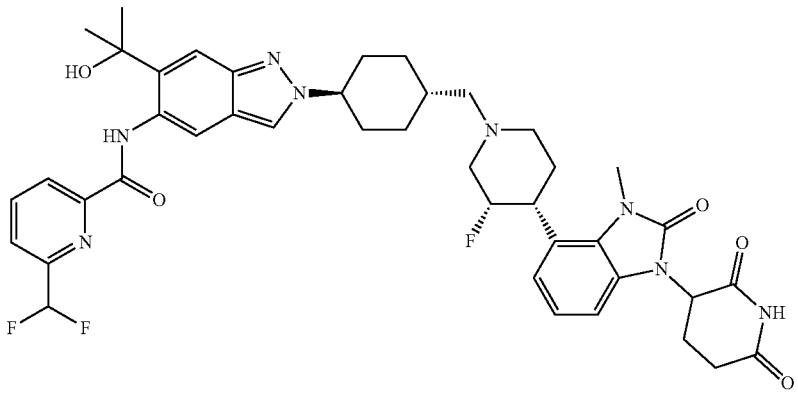 [SMILES: Cn1c(=O)n(C2CCC(=O)NC2=O)c2cccc([C@H]3CCN(C[C@H]4CC[C@H](n5cc6cc(NC(=O)c7cccc(C(F)F)n7)c(C(C)(C)O)cc6n5)CC4)C[C@H]3F)c21] |
| I-656 | 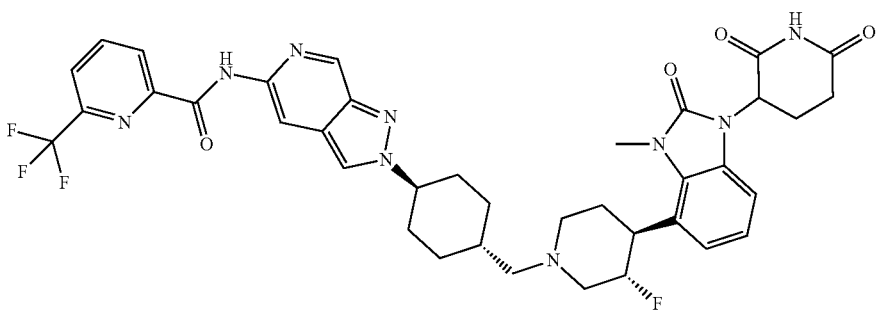 [SMILES: Cn1c(=O)n(C2CCC(=O)NC2=O)c2cccc([C@@H]3CCN(C[C@H]4CC[C@H](n5cc6cc(NC(=O)c7cccc(C(F)(F)F)n7)ncc6n5)CC4)C[C@H]3F)c21] |
| I-657 | 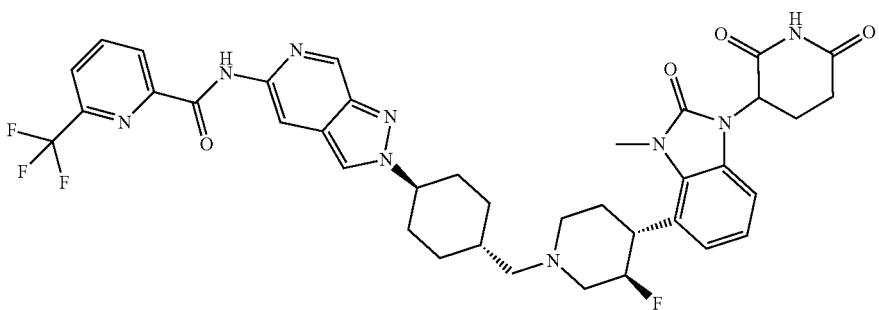 [SMILES: Cn1c(=O)n(C2CCC(=O)NC2=O)c2cccc([C@H]3CCN(C[C@H]4CC[C@H](n5cc6cc(NC(=O)c7cccc(C(F)(F)F)n7)ncc6n5)CC4)C[C@@H]3F)c21] |
| I-658 | 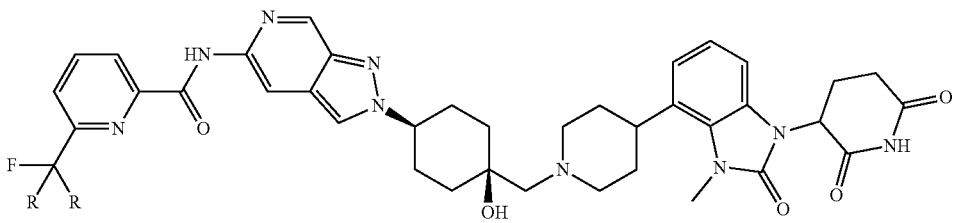 |
| I-659 | 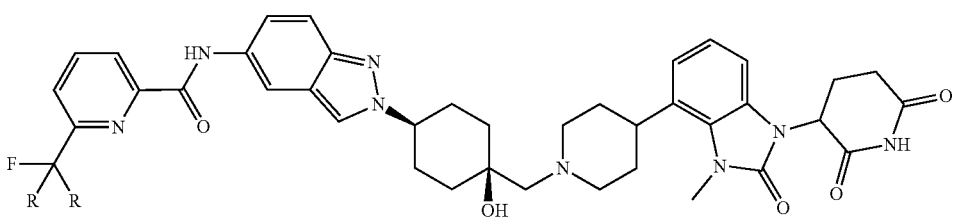 |

TABLE 1-continued

Exemplary Compounds

| I-# | Structure |
|---|---|
| I-660 | 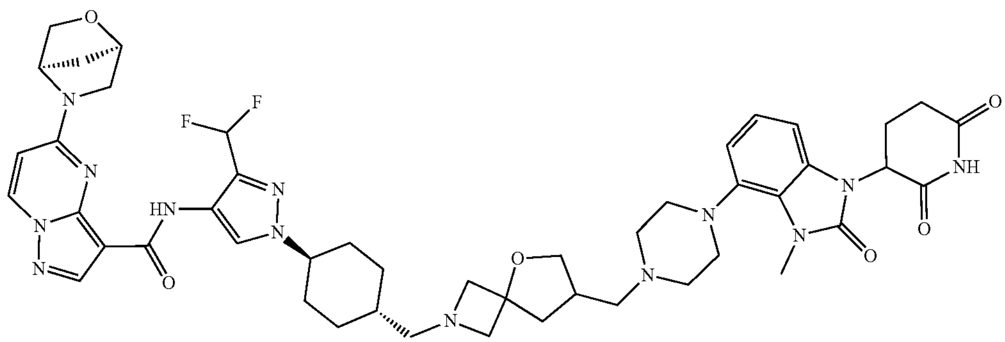 [SMILES: Cn1c(=O)n(C2CCC(=O)NC2=O)c2cccc(N3CCN(CC4COC5(C4)CN(C[C@H]4CC[C@H](n6cc(NC(=O)c7cnn8ccc(N9C[C@H]%10C[C@@H]9CO%10)nc78)c(C(F)F)n6)CC4)C5)CC3)c21] |
| I-661 | 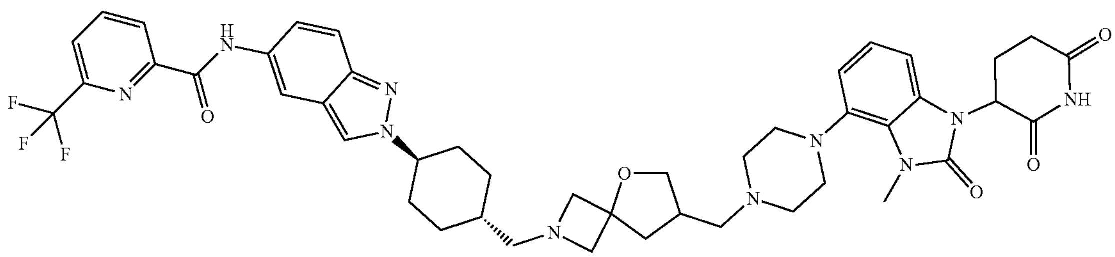 [SMILES: Cn1c(=O)n(C2CCC(=O)NC2=O)c2cccc(N3CCN(CC4COC5(C4)CN(C[C@H]4CC[C@H](n6cc7cc(NC(=O)c8cccc(C(F)(F)F)n8)ccc7n6)CC4)C5)CC3)c21] |
| I-662 | 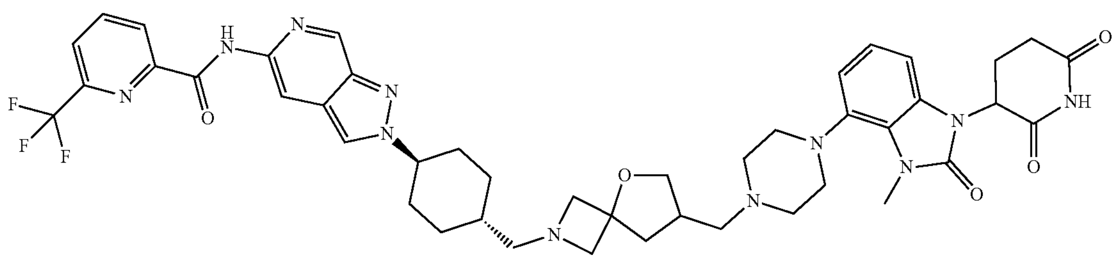 |
| I-663 | 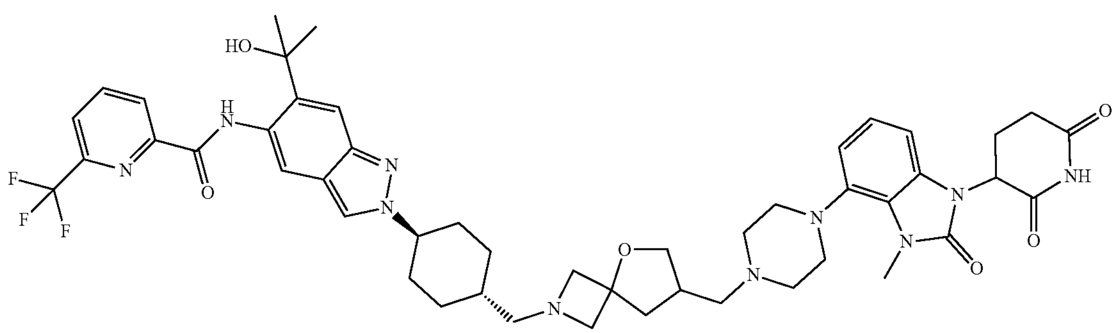 |
| I-664 | 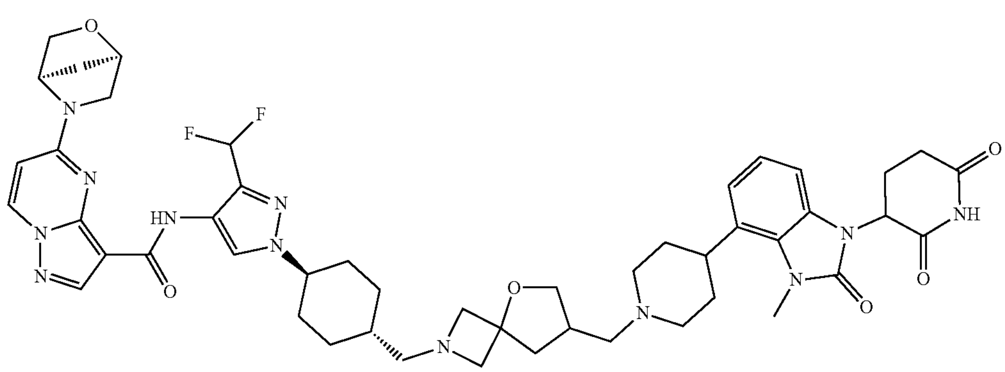 [SMILES: Cn1c(=O)n(C2CCC(=O)NC2=O)c2cccc(C3CCN(CC4COC5(C4)CN(C[C@H]4CC[C@H](n6cc(NC(=O)c7cnn8ccc(N9C[C@H]%10C[C@@H]9CO%10)nc78)c(C(F)F)n6)CC4)C5)CC3)c21] |

TABLE 1-continued

Exemplary Compounds

| I-# | Structure |
|---|---|
| I-665 | 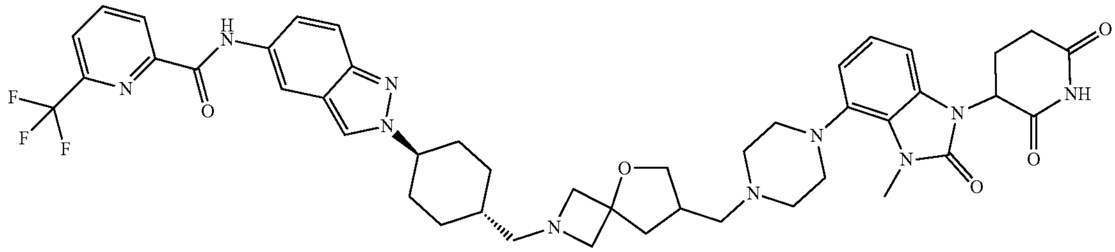 [SMILES: Cn1c(=O)n(C2CCC(=O)NC2=O)c2cccc(N3CCN(CC4COC5(C4)CN(C[C@H]4CC[C@H](n6cc7cc(NC(=O)c8cccc(C(F)(F)F)n8)ccc7n6)CC4)C5)CC3)c21] |
| I-666 | 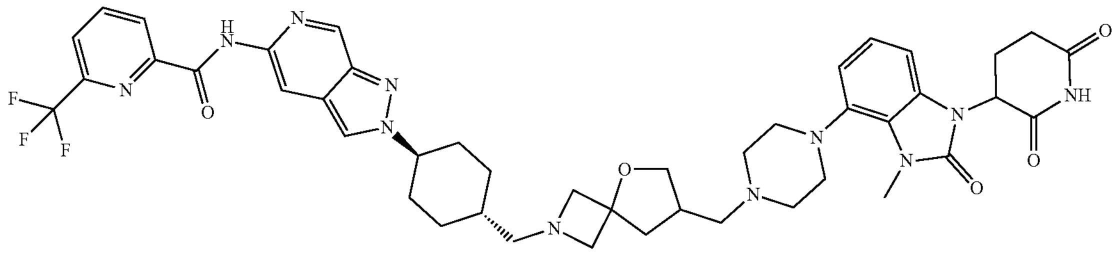 |
| I-667 | 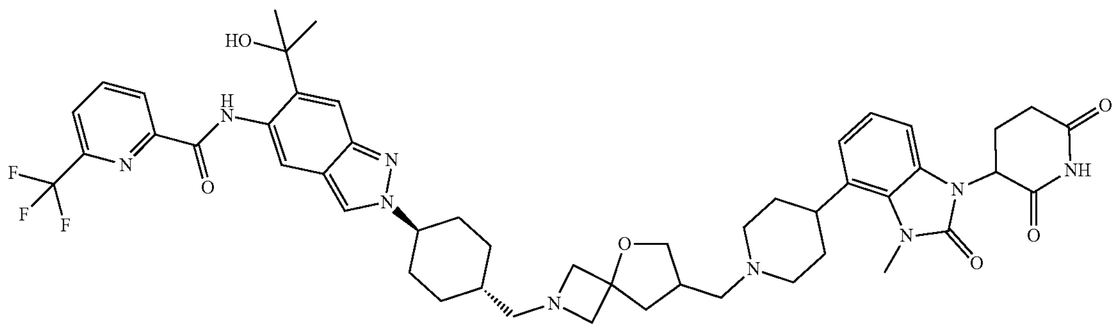 [SMILES: Cn1c(=O)n(C2CCC(=O)NC2=O)c2cccc(C3CCN(CC4COC5(C4)CN(C[C@H]4CC[C@H](n6cc7cc(NC(=O)c8cccc(C(F)(F)F)n8)c(C(C)(C)O)cc7n6)CC4)C5)CC3)c21] |
| I-668 | 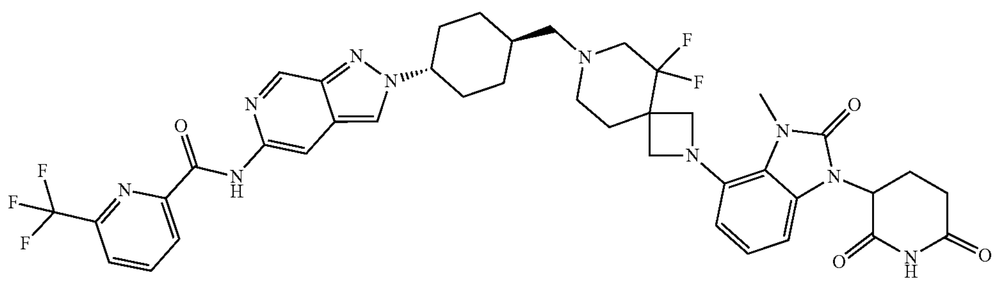 [SMILES: Cn1c(=O)n(C2CCC(=O)NC2=O)c2cccc(N3CC4(CCN(C[C@H]5CC[C@H](n6cc7cc(NC(=O)c8cccc(C(F)(F)F)n8)ncc7n6)CC5)CC4(F)F)C3)c21] |
| I-669 | 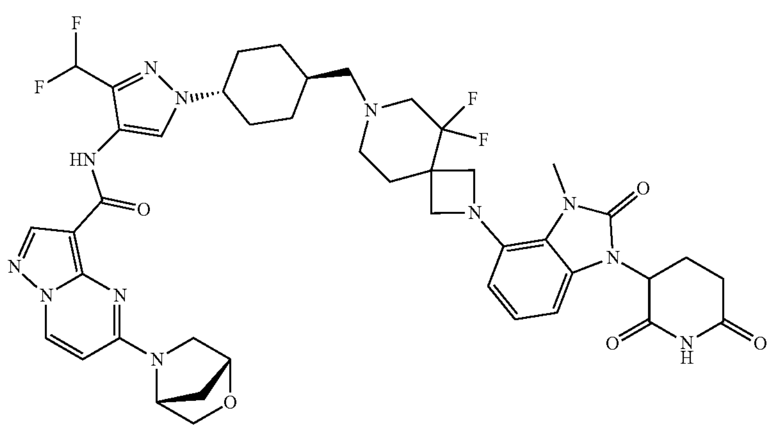 [SMILES: Cn1c(=O)n(C2CCC(=O)NC2=O)c2cccc(N3CC4(CCN(C[C@H]5CC[C@H](n6cc(NC(=O)c7cnn8ccc(N9C[C@H]%10C[C@@H]9CO%10)nc78)c(C(F)F)n6)CC5)CC4(F)F)C3)c21] |

TABLE 1-continued

Exemplary Compounds

| I-# | Structure |
|---|---|
| I-670 | 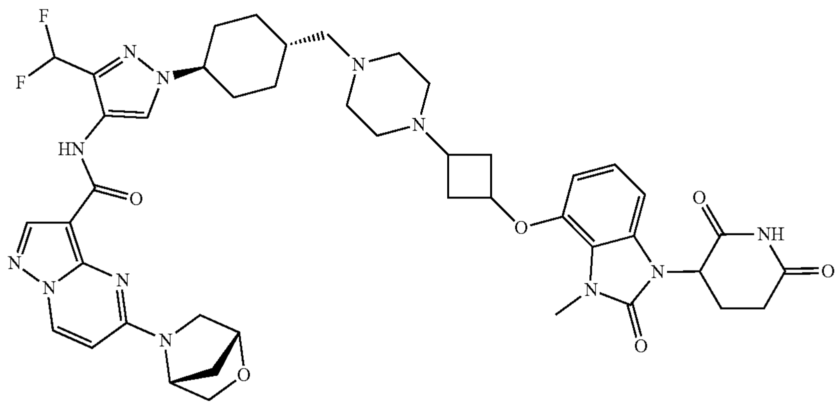 [SMILES: Cn1c(=O)n(C2CCC(=O)NC2=O)c2cccc(OC3CC(N4CCN(C[C@H]5CC[C@H](n6cc(NC(=O)c7cnn8ccc(N9C[C@H]%10C[C@@H]9CO%10)nc78)c(C(F)F)n6)CC5)CC4)C3)c21] |
| I-671 | 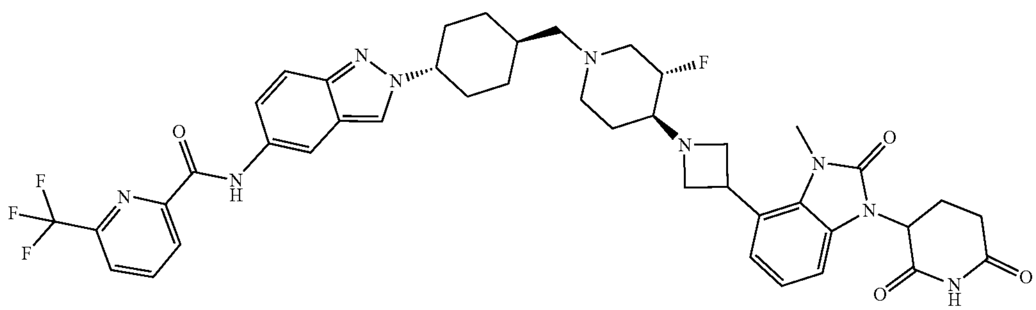 [SMILES: Cn1c(=O)n(C2CCC(=O)NC2=O)c2cccc(C3CN([C@H]4CCN(C[C@H]5CC[C@H](n6cc7cc(NC(=O)c8cccc(C(F)(F)F)n8)ccc7n6)CC5)C[C@@H]4F)C3)c21] |
| I-672 | 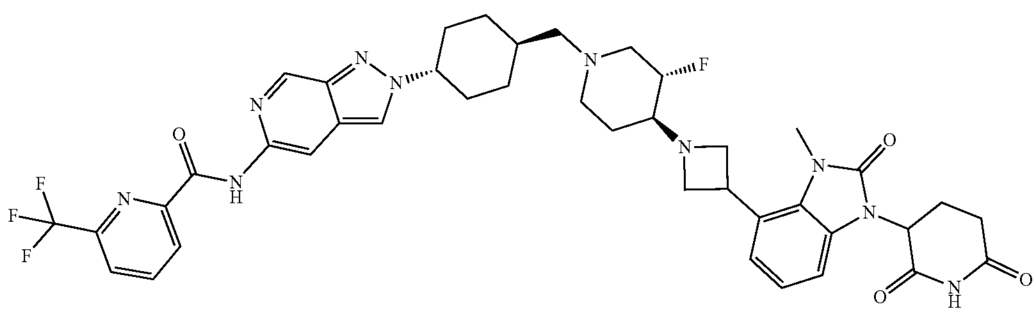 |
| I-673 | 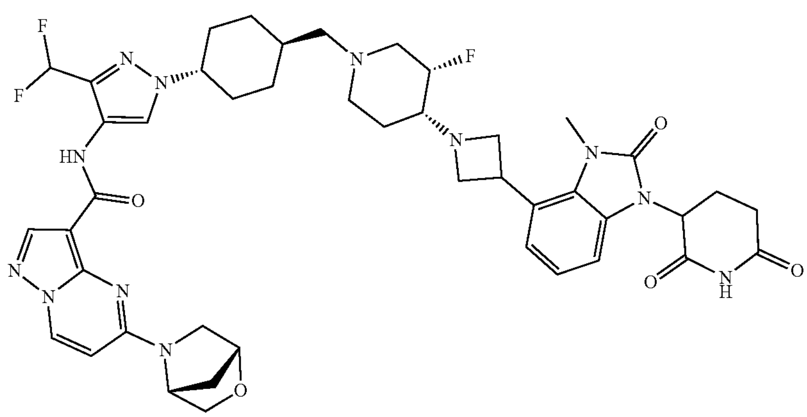 [SMILES: Cn1c(=O)n(C2CCC(=O)NC2=O)c2cccc(C3CN([C@@H]4CCN(C[C@H]5CC[C@H](n6cc(NC(=O)c7cnn8ccc(N9C[C@H]%10C[C@@H]9CO%10)nc78)c(C(F)F)n6)CC5)C[C@@H]4F)C3)c21] |

TABLE 1-continued

Exemplary Compounds

| I-# | Structure |
|---|---|
| I-674 | 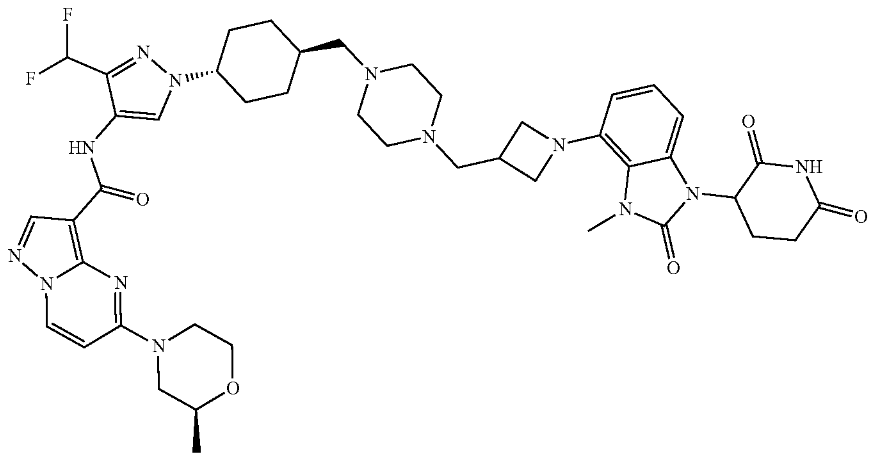 [SMILES: C[C@H]1CN(c2ccn3ncc(C(=O)Nc4cn([C@H]5CC[C@H](CN6CCN(CC7CN(c8cccc9c8n(C)c(=O)n9C8CCC(=O)NC8=O)C7)CC6)CC5)nc4C(F)F)c3n2)CCO1] |
| I-675 | 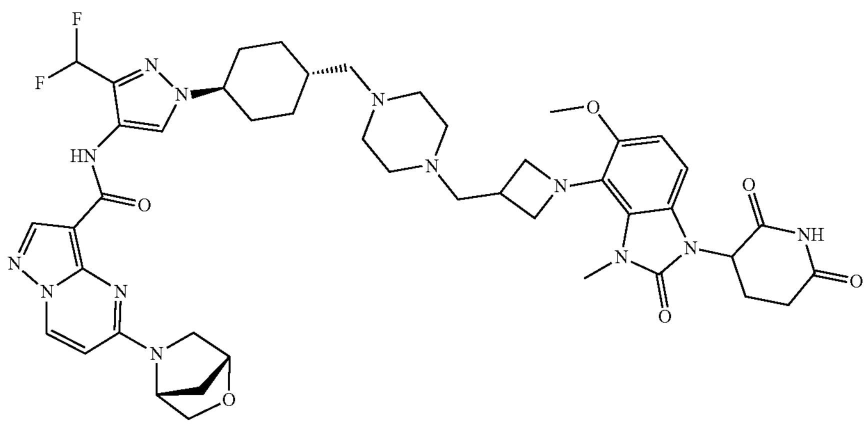 [SMILES: COc1ccc2c(c1N1CC(CN3CCN(C[C@H]4CC[C@H](n5cc(NC(=O)c6cnn7ccc(N8C[C@H]9C[C@@H]8CO9)nc67)c(C(F)F)n5)CC4)CC3)C1)n(C)c(=O)n2C1CCC(=O)NC1=O] |
| I-676 | 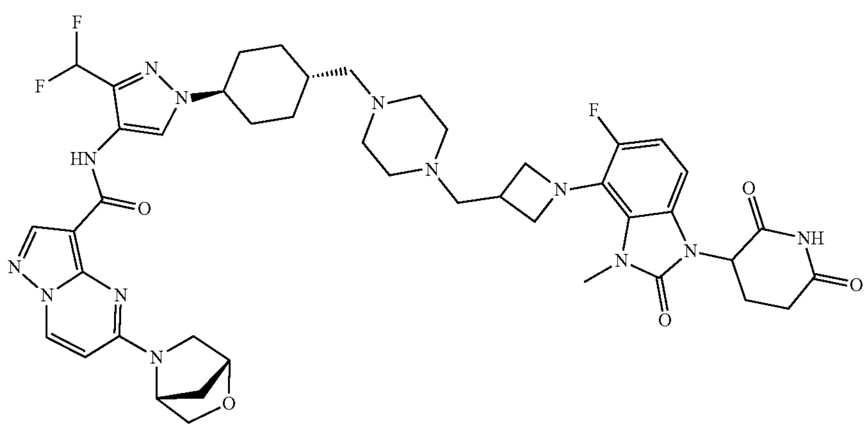 [SMILES: Cn1c(=O)n(C2CCC(=O)NC2=O)c2ccc(F)c(N3CC(CN4CCN(C[C@H]5CC[C@H](n6cc(NC(=O)c7cnn8ccc(N9C[C@H]%10C[C@@H]9CO%10)nc78)c(C(F)F)n6)CC5)CC4)C3)c21] |
| I-677 | 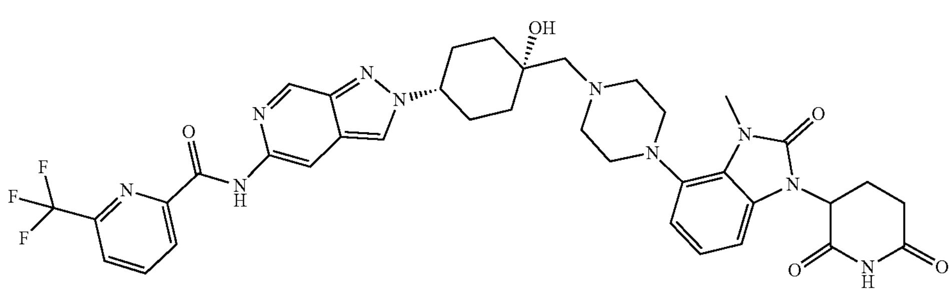 [SMILES: Cn1c(=O)n(C2CCC(=O)NC2=O)c2cccc(N3CCN(C[C@]4(O)CC[C@@H](n5cc6cc(NC(=O)c7cccc(C(F)(F)F)n7)ncc6n5)CC4)CC3)c21] |

TABLE 1-continued

Exemplary Compounds

| I-# | Structure |
|---|---|
| I-678 | 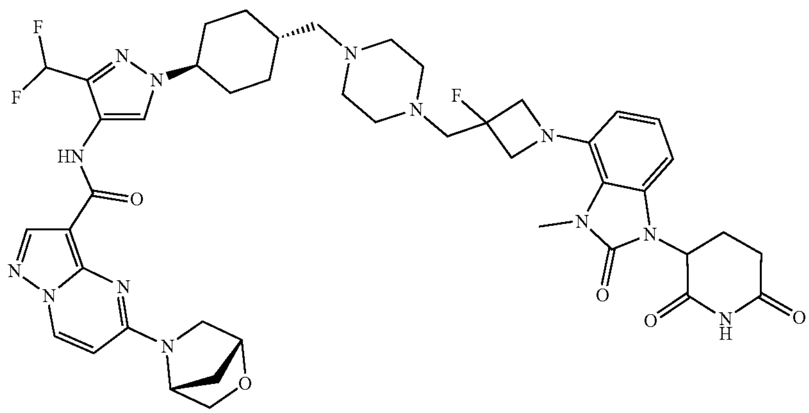 [SMILES: Cn1c(=O)n(C2CCC(=O)NC2=O)c2cccc(N3CC(F)(CN4CCN(C[C@H]5CC[C@H](n6cc(NC(=O)c7cnn8ccc(N9C[C@H]%10C[C@@H]9CO%10)nc78)c(C(F)F)n6)CC5)CC4)C3)c21] |
| I-679 | 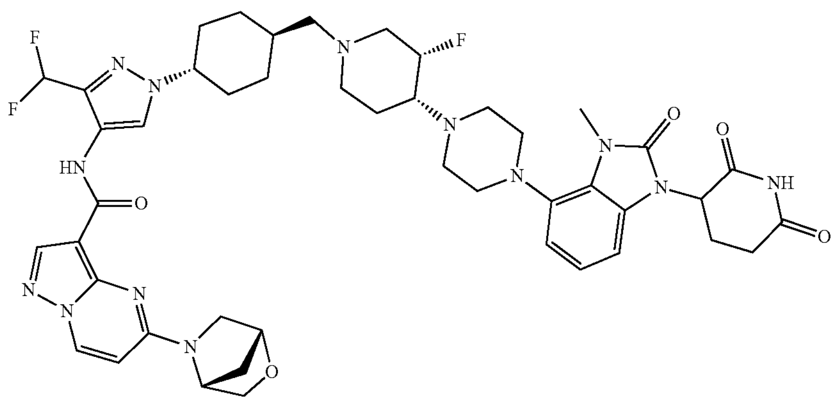 [SMILES: Cn1c(=O)n(C2CCC(=O)NC2=O)c2cccc(N3CCN([C@@H]4CCN(C[C@H]5CC[C@H](n6cc(NC(=O)c7cnn8ccc(N9C[C@H]%10C[C@@H]9CO%10)nc78)c(C(F)F)n6)CC5)C[C@@H]4F)CC3)c21] |
| I-680 | 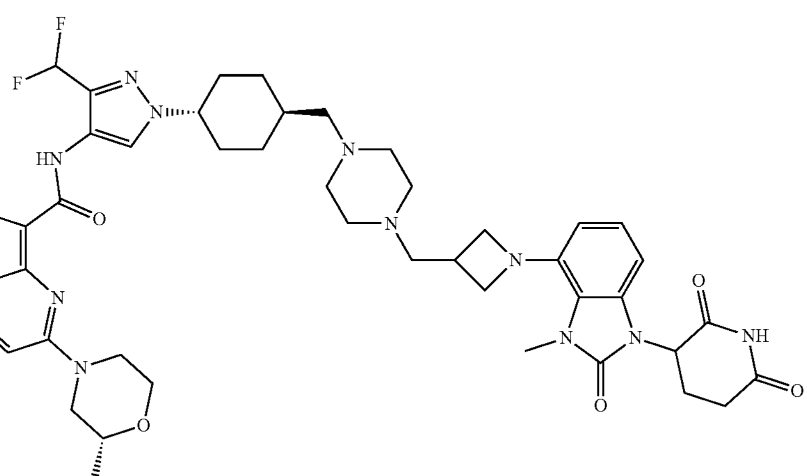 |

TABLE 1-continued

Exemplary Compounds

| I-# | Structure |
|---|---|
| I-681 | 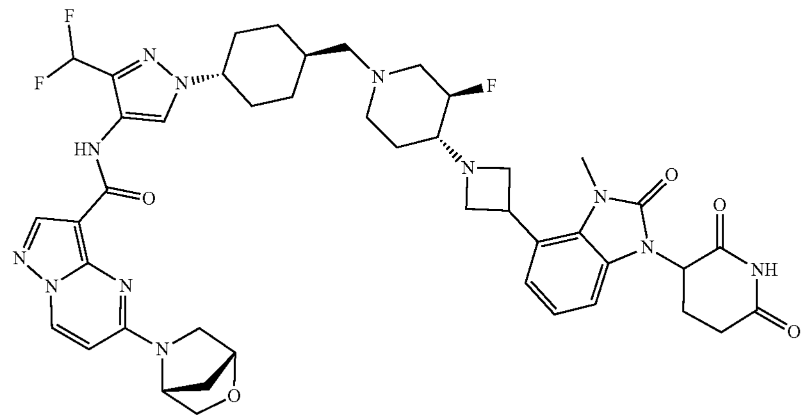 [SMILES: Cn1c(=O)n(C2CCC(=O)NC2=O)c2cccc(C3CN([C@@H]4CCN(C[C@H]5CC[C@H](n6cc(NC(=O)c7cnn8ccc(N9C[C@H]%10C[C@@H]9CO%10)nc78)c(C(F)F)n6)CC5)C[C@H]4F)C3)c21] |
| I-682 | 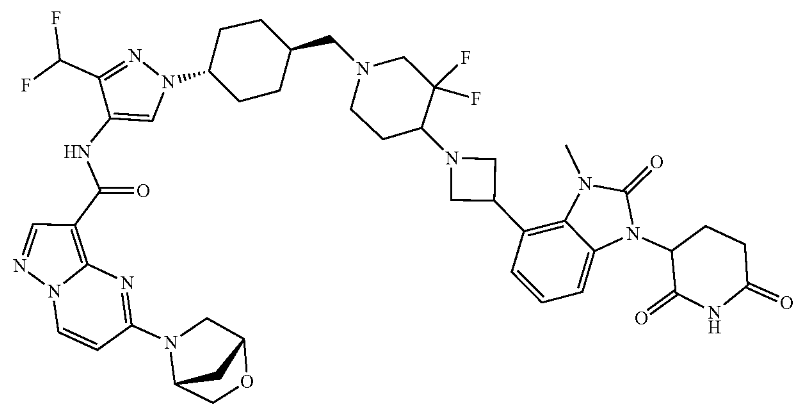 [SMILES: Cn1c(=O)n(C2CCC(=O)NC2=O)c2cccc(C3CN(C4CCN(C[C@H]5CC[C@H](n6cc(NC(=O)c7cnn8ccc(N9C[C@H]%10C[C@@H]9CO%10)nc78)c(C(F)F)n6)CC5)CC4(F)F)C3)c21] |
| I-683 | 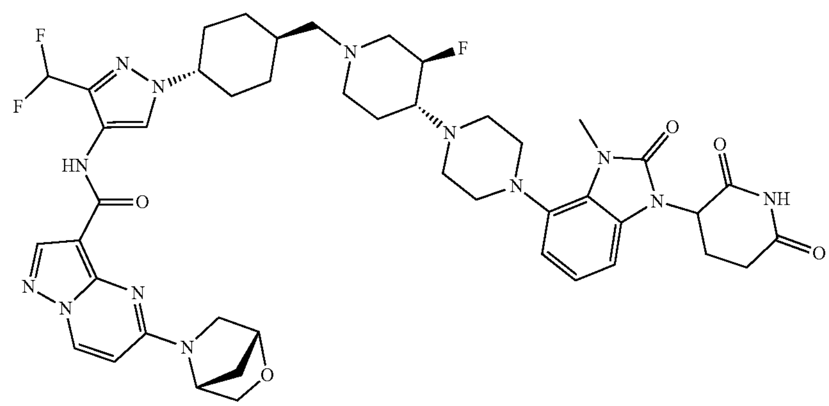 [SMILES: Cn1c(=O)n(C2CCC(=O)NC2=O)c2cccc(N3CCN([C@@H]4CCN(C[C@H]5CC[C@H](n6cc(NC(=O)c7cnn8ccc(N9C[C@H]%10C[C@@H]9CO%10)nc78)c(C(F)F)n6)CC5)C[C@H]4F)CC3)c21] |
| I-684 | 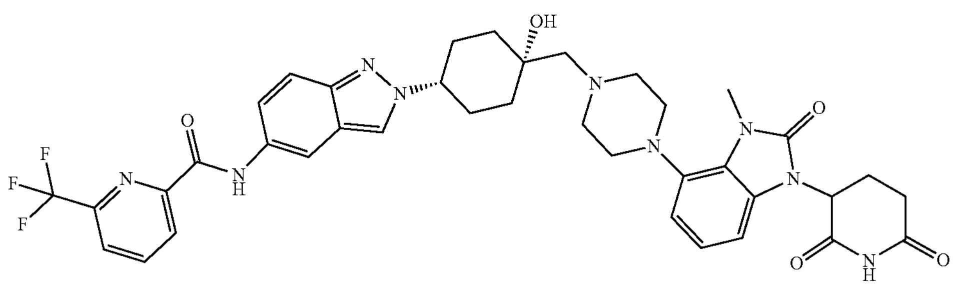 [SMILES: Cn1c(=O)n(C2CCC(=O)NC2=O)c2cccc(N3CCN(C[C@]4(O)CC[C@@H](n5cc6cc(NC(=O)c7cccc(C(F)(F)F)n7)ccc6n5)CC4)CC3)c21] |

TABLE 1-continued

Exemplary Compounds

| I-# | Structure |
|---|---|
| I-685 | 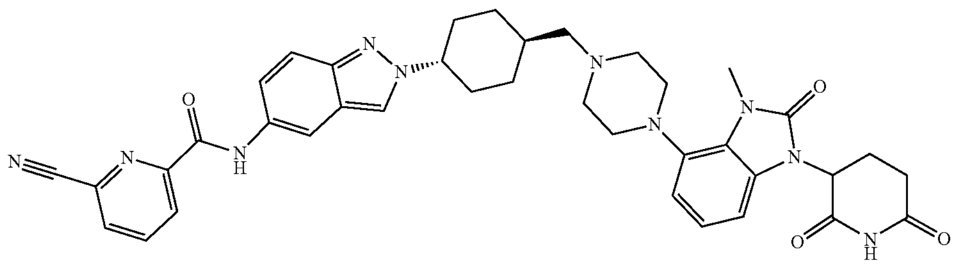 [SMILES: Cn1c(=O)n(C2CCC(=O)NC2=O)c2cccc(N3CCN(C[C@H]4CC[C@H](n5cc6cc(NC(=O)c7cccc(C#N)n7)ccc6n5)CC4)CC3)c21] |
| I-686 | 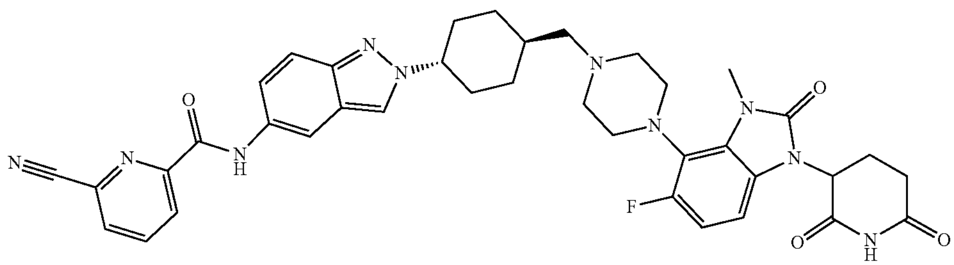 |
| I-687 | 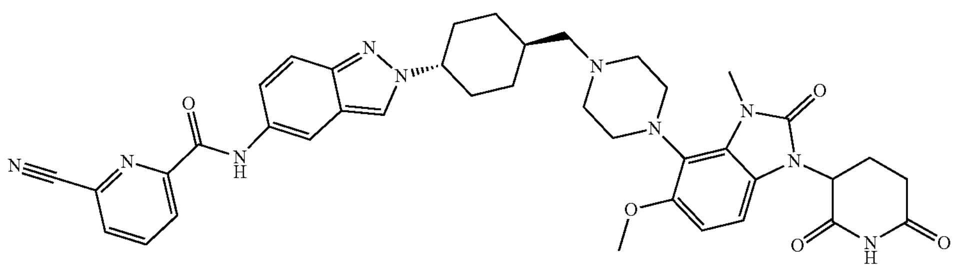 [SMILES: COc1ccc2c(c1N1CCN(C[C@H]3CC[C@H](n4cc5cc(NC(=O)c6cccc(C#N)n6)ccc5n4)CC3)CC1)n(C)c(=O)n2C1CCC(=O)NC1=O] |
| I-688 | 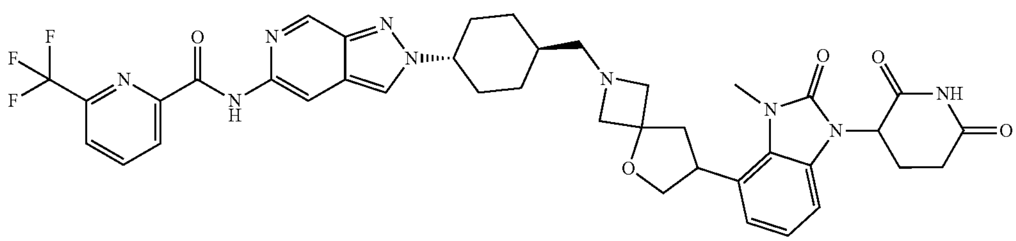 |
| I-689 | 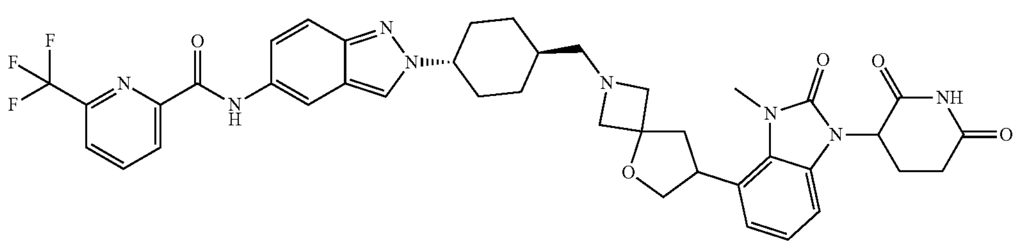 [SMILES: Cn1c(=O)n(C2CCC(=O)NC2=O)c2cccc(C3COC4(C3)CN(C[C@H]3CC[C@H](n5cc6cc(NC(=O)c7cccc(C(F)(F)F)n7)ccc6n5)CC3)C4)c21] |
| I-690 | 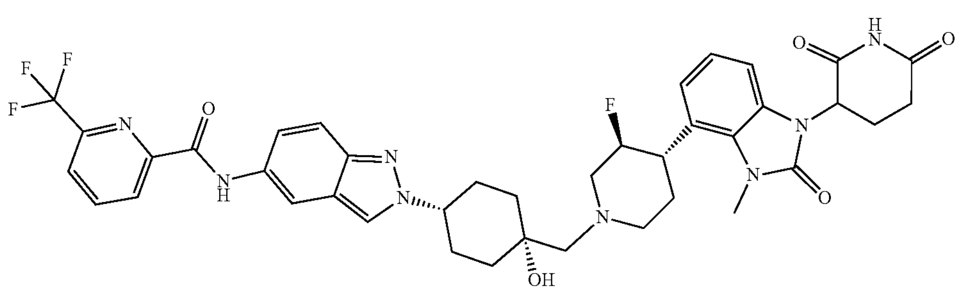 [SMILES: Cn1c(=O)n(C2CCC(=O)NC2=O)c2cccc([C@@H]3CCN(C[C@]4(O)CC[C@@H](n5cc6cc(NC(=O)c7cccc(C(F)(F)F)n7)ccc6n5)CC4)C[C@H]3F)c21] |

TABLE 1-continued

Exemplary Compounds

| I-# | Structure |
|---|---|
| I-691 | 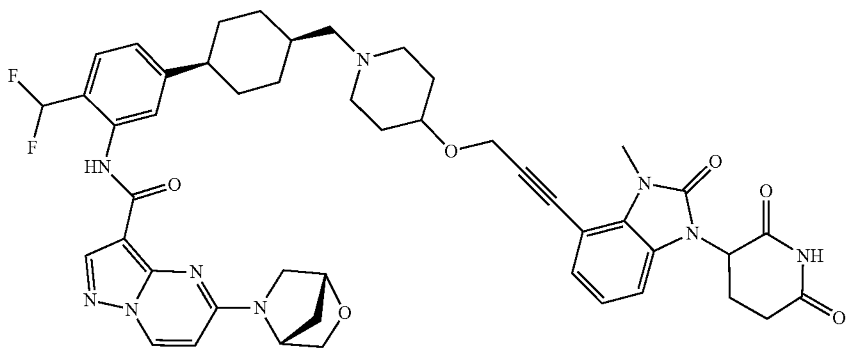 [SMILES: Cn1c(=O)n(C2CCC(=O)NC2=O)c2cccc(C#CCOC3CCN(C[C@H]4CC[C@@H](c5ccc(C(F)F)c(NC(=O)c6cnn7ccc(N8C[C@H]9C[C@@H]8CO9)nc67)c5)CC4)CC3)c21] |
| I-692 | 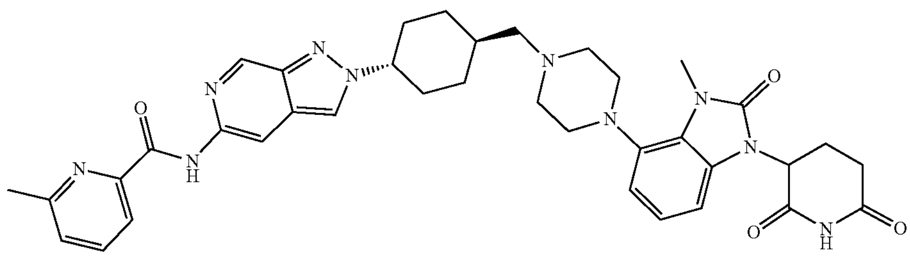 [SMILES: Cc1cccc(C(=O)Nc2cc3cn([C@H]4CC[C@H](CN5CCN(c6cccc7c6n(C)c(=O)n7C6CCC(=O)NC6=O)CC5)CC4)nc3cn2)n1] |
| I-693 | 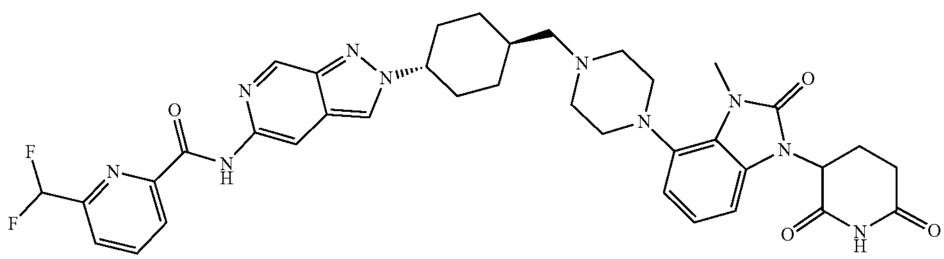 [SMILES: Cn1c(=O)n(C2CCC(=O)NC2=O)c2cccc(N3CCN(C[C@H]4CC[C@H](n5cc6cc(NC(=O)c7cccc(C(F)F)n7)ncc6n5)CC4)CC3)c21] |
| I-694 | 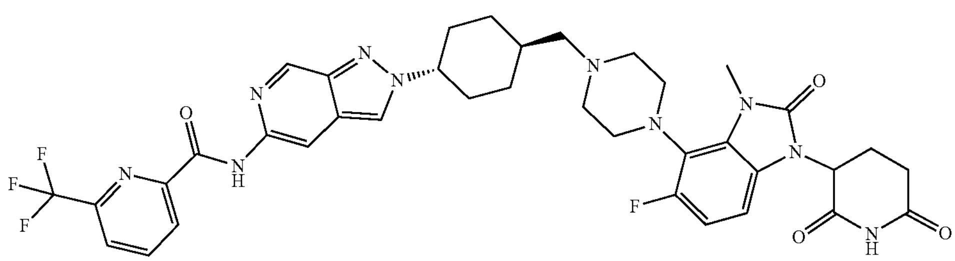 [SMILES: Cn1c(=O)n(C2CCC(=O)NC2=O)c2ccc(F)c(N3CCN(C[C@H]4CC[C@H](n5cc6cc(NC(=O)c7cccc(C(F)(F)F)n7)ncc6n5)CC4)CC3)c21] |
| I-695 | 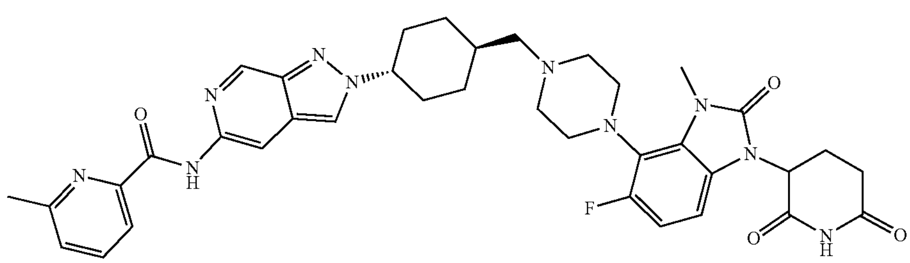 [SMILES: Cc1cccc(C(=O)Nc2cc3cn([C@H]4CC[C@H](CN5CCN(c6c(F)ccc7c6n(C)c(=O)n7C6CCC(=O)NC6=O)CC5)CC4)nc3cn2)n1] |

TABLE 1-continued

Exemplary Compounds

| I-# | Structure |
|---|---|
| I-696 | 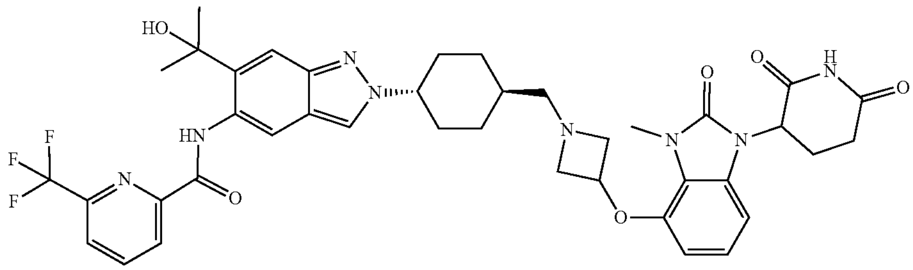 [SMILES: Cn1c(=O)n(C2CCC(=O)NC2=O)c2cccc(OC3CN(C[C@H]4CC[C@H](n5cc6cc(NC(=O)c7cccc(C(F)(F)F)n7)c(C(C)(C)O)cc6n5)CC4)C3)c21] |
| I-697 | 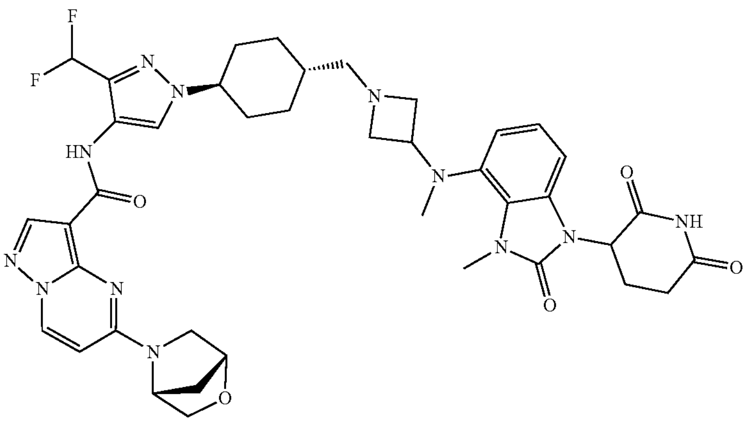 [SMILES: CN(c1cccc2c1n(C)c(=O)n2C1CCC(=O)NC1=O)C1CN(C[C@H]2CC[C@H](n3cc(NC(=O)c4cnn5ccc(N6C[C@H]7C[C@@H]6CO7)nc45)c(C(F)F)n3)CC2)C1] |
| I-698 | 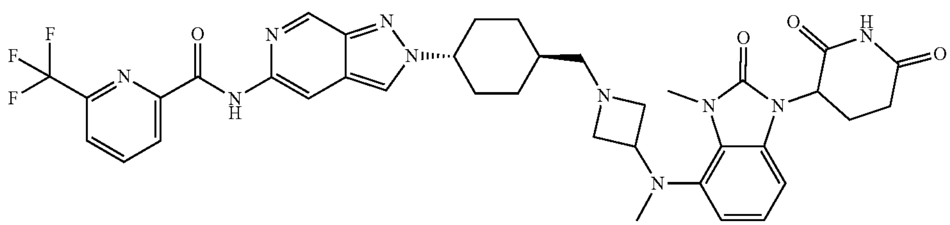 [SMILES: CN(c1cccc2c1n(C)c(=O)n2C1CCC(=O)NC1=O)C1CN(C[C@H]2CC[C@H](n3cc4cc(NC(=O)c5cccc(C(F)(F)F)n5)ncc4n3)CC2)C1] |
| I-699 | 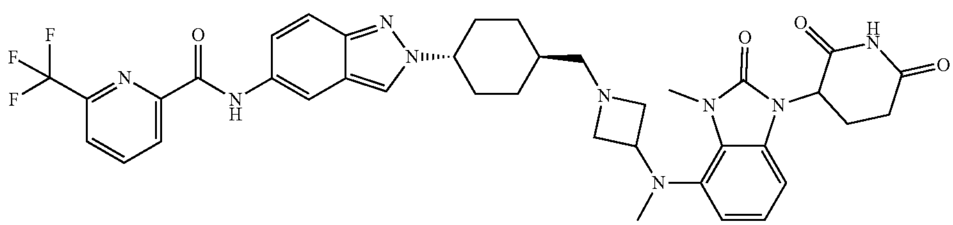 [SMILES: CN(c1cccc2c1n(C)c(=O)n2C1CCC(=O)NC1=O)C1CN(C[C@H]2CC[C@H](n3cc4cc(NC(=O)c5cccc(C(F)(F)F)n5)ccc4n3)CC2)C1] |
| I-700 | 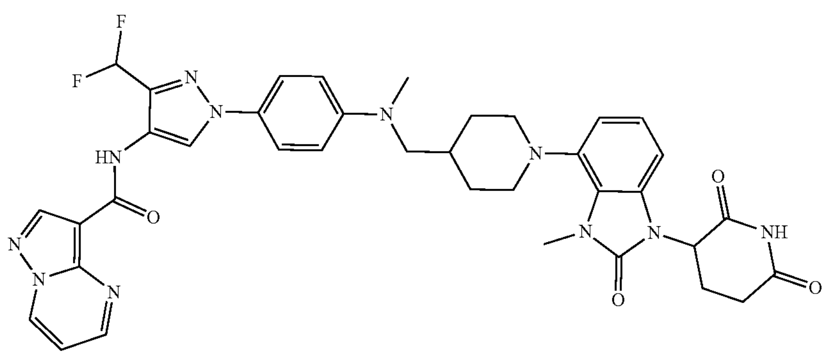 [SMILES: CN(CC1CCN(c2cccc3c2n(C)c(=O)n3C2CCC(=O)NC2=O)CC1)c1ccc(-n2cc(NC(=O)c3cnn4cccnc34)c(C(F)F)n2)cc1] |

TABLE 1-continued

Exemplary Compounds

| I-# | Structure |
|---|---|
| I-701 | 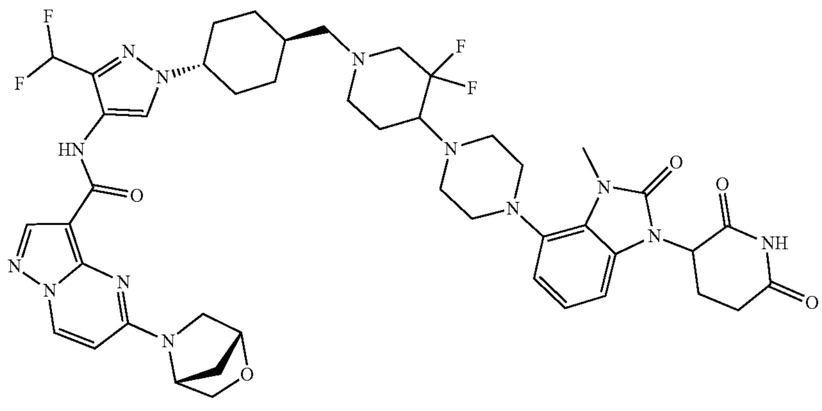 [SMILES: Cn1c(=O)n(C2CCC(=O)NC2=O)c2cccc(N3CCN(C4CCN(C[C@H]5CC[C@H](n6cc(NC(=O)c7cnn8ccc(N9C[C@H]%10C[C@@H]9CO%10)nc78)c(C(F)F)n6)CC5)CC4(F)F)CC3)c21] |
| I-702 | 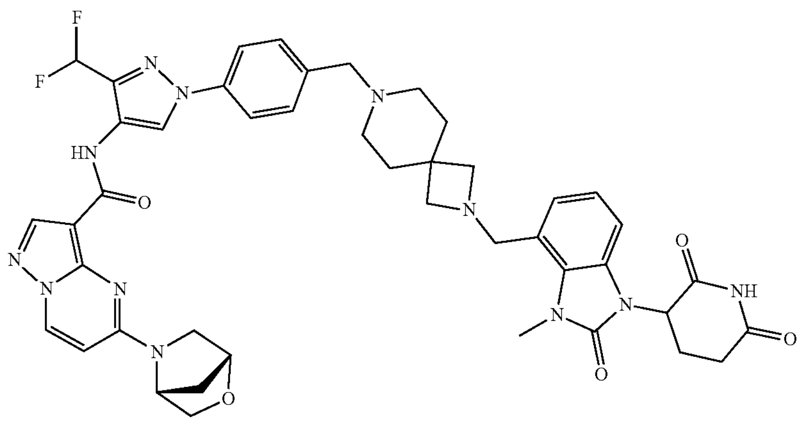 [SMILES: Cn1c(=O)n(C2CCC(=O)NC2=O)c2cccc(CN3CC4(CCN(Cc5ccc(-n6cc(NC(=O)c7cnn8ccc(N9C[C@H]%10C[C@@H]9CO%10)nc78)c(C(F)F)n6)cc5)CC4)C3)c21] |
| I-703 | 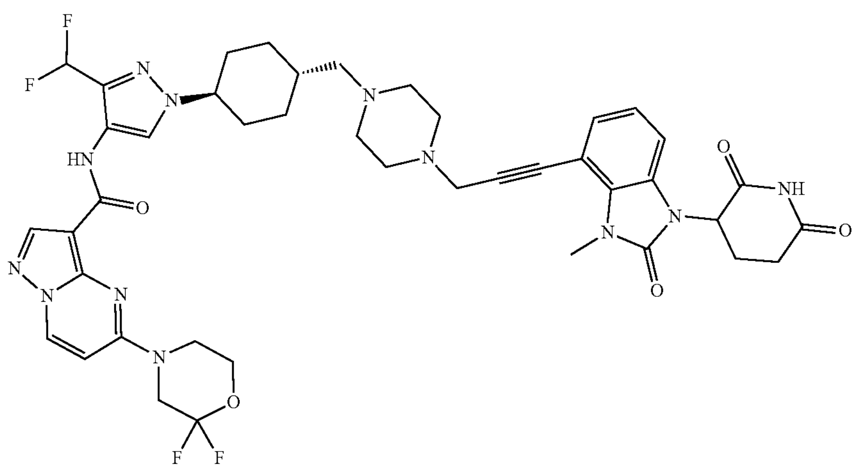 [SMILES: Cn1c(=O)n(C2CCC(=O)NC2=O)c2cccc(C#CCN3CCN(C[C@H]4CC[C@H](n5cc(NC(=O)c6cnn7ccc(N8CCOC(F)(F)C8)nc67)c(C(F)F)n5)CC4)CC3)c21] |
| I-704 | 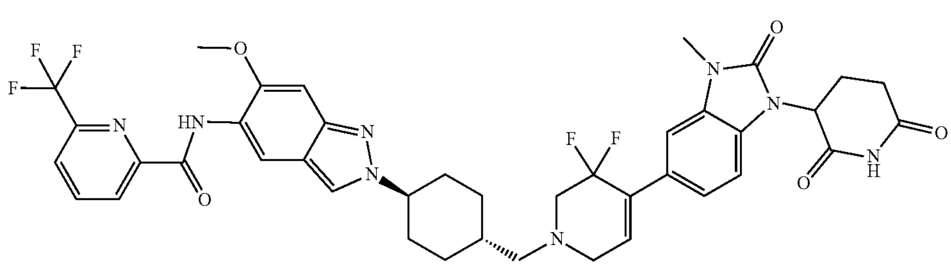 [SMILES: COc1cc2nn([C@H]3CC[C@H](CN4CC=C(c5ccc6c(c5)n(C)c(=O)n6C5CCC(=O)NC5=O)C(F)(F)C4)CC3)cc2cc1NC(=O)c1cccc(C(F)(F)F)n1] |

TABLE 1-continued

Exemplary Compounds

| I-# | Structure |
|---|---|
| I-705 | 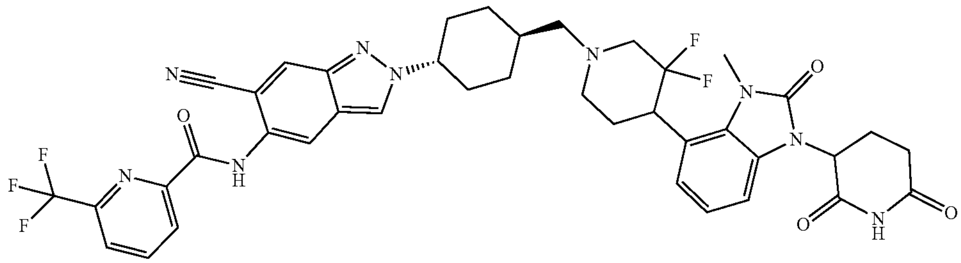 [SMILES: Cn1c(=O)n(C2CCC(=O)NC2=O)c2cccc(C3CCN(C[C@H]4CC[C@H](n5cc6cc(NC(=O)c7cccc(C(F)(F)F)n7)c(C#N)cc6n5)CC4)CC3(F)F)c21] |
| I-706 | 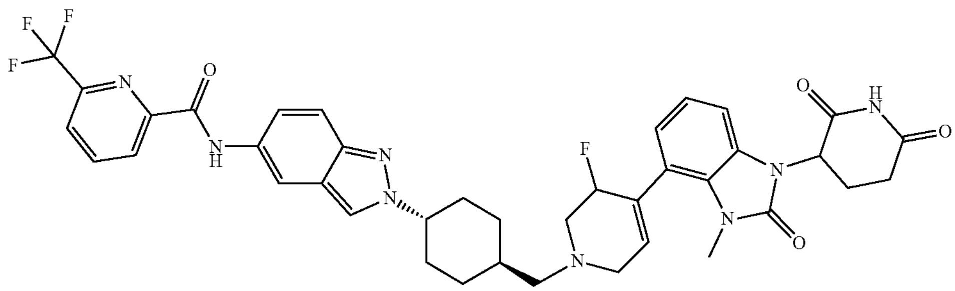 [SMILES: Cn1c(=O)n(C2CCC(=O)NC2=O)c2cccc(C3=CCN(C[C@H]4CC[C@H](n5cc6cc(NC(=O)c7cccc(C(F)(F)F)n7)ccc6n5)CC4)CC3F)c21] |
| I-707 | 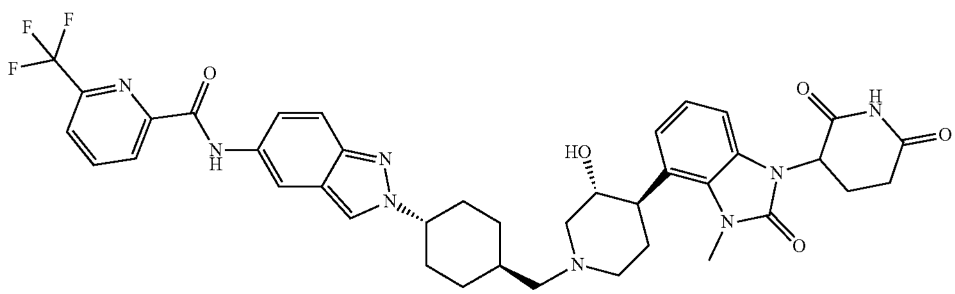 [SMILES: Cn1c(=O)n(C2CCC(=O)NC2=O)c2cccc([C@H]3CCN(C[C@H]4CC[C@H](n5cc6cc(NC(=O)c7cccc(C(F)(F)F)n7)ccc6n5)CC4)C[C@@H]3O)c21] |
| I-708 | 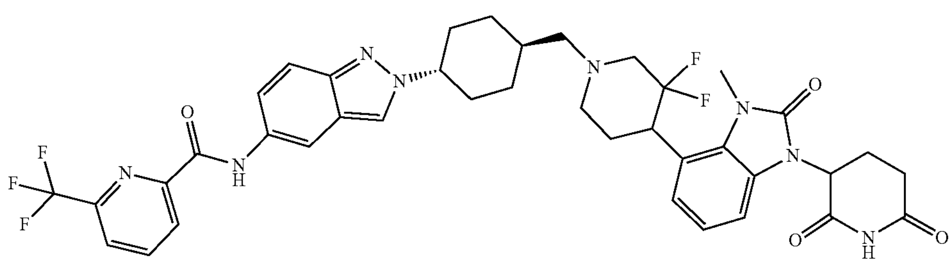 [SMILES: Cn1c(=O)n(C2CCC(=O)NC2=O)c2cccc(C3CCN(C[C@H]4CC[C@H](n5cc6cc(NC(=O)c7cccc(C(F)(F)F)n7)ccc6n5)CC4)CC3(F)F)c21] |
| I-709 | 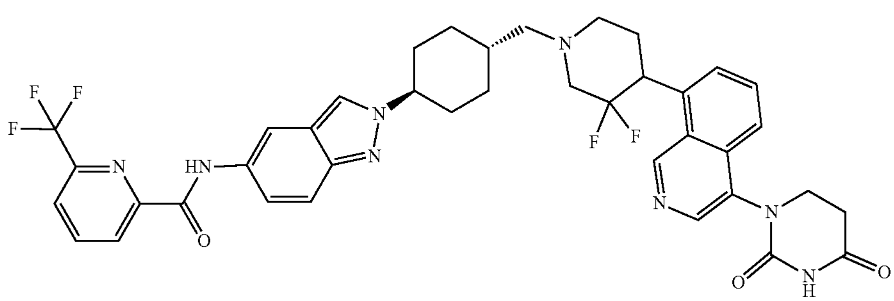 [SMILES: O=C1CCN(c2cncc3c(C4CCN(C[C@H]5CC[C@H](n6cc7cc(NC(=O)c8cccc(C(F)(F)F)n8)ccc7n6)CC5)CC4(F)F)cccc23)C(=O)N1] |

TABLE 1-continued

Exemplary Compounds

| I-# | Structure |
|---|---|
| I-710 | 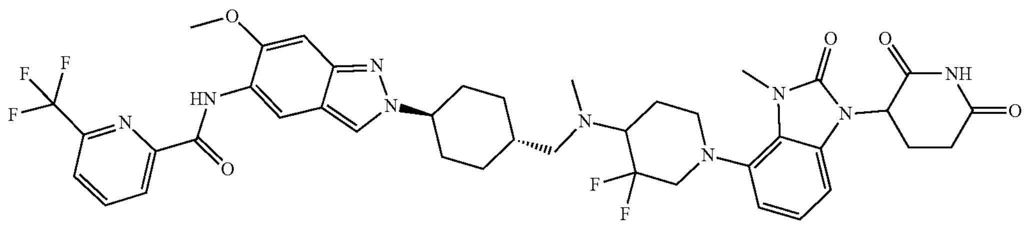 [SMILES: COc1cc2nn([C@H]3CC[C@H](CN(C)C4CCN(c5cccc6c5n(C)c(=O)n6C5CCC(=O)NC5=O)CC4(F)F)CC3)cc2cc1NC(=O)c1cccc(C(F)(F)F)n1] |
| I-711 | 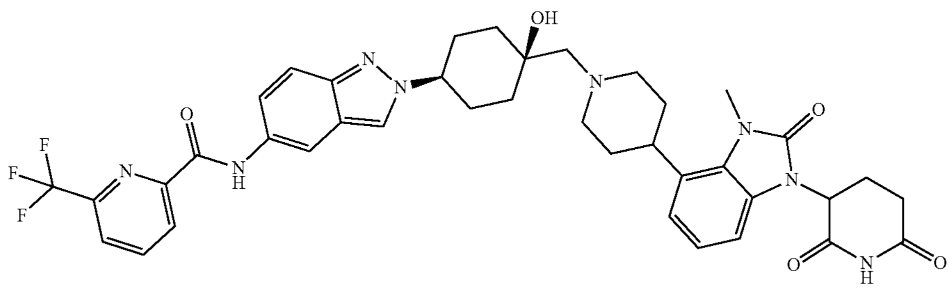 [SMILES: Cn1c(=O)n(C2CCC(=O)NC2=O)c2cccc(C3CCN(C[C@]4(O)CC[C@@H](n5cc6cc(NC(=O)c7cccc(C(F)(F)F)n7)ccc6n5)CC4)CC3)c21] |
| I-712 | 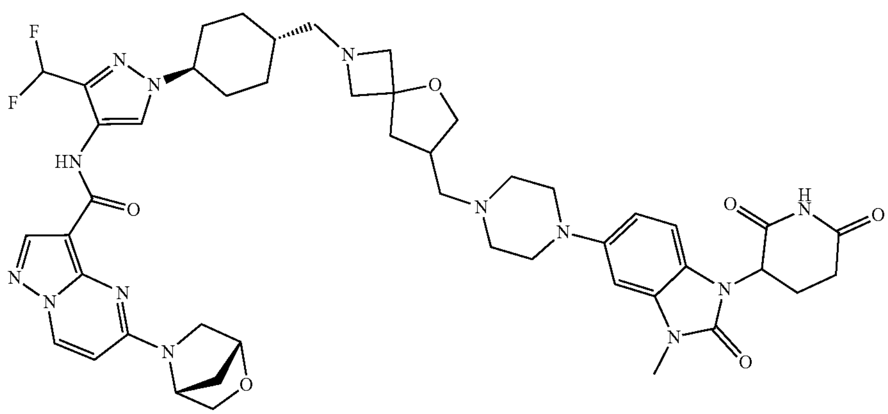 [SMILES: Cn1c(=O)n(C2CCC(=O)NC2=O)c2ccc(N3CCN(CC4COC5(C4)CN(C[C@H]4CC[C@H](n6cc(NC(=O)c7cnn8ccc(N9C[C@H]%10C[C@@H]9CO%10)nc78)c(C(F)F)n6)CC4)C5)CC3)cc21] |
| I-713 | 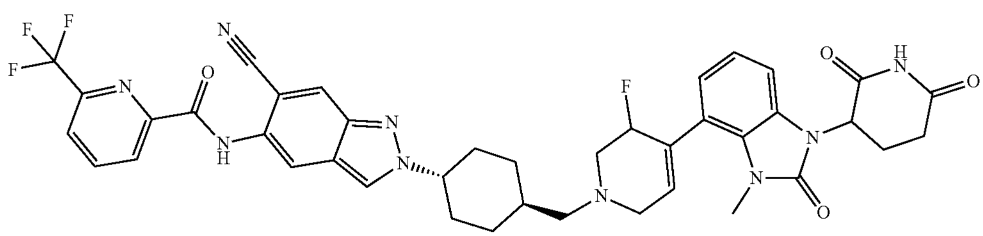 [SMILES: Cn1c(=O)n(C2CCC(=O)NC2=O)c2cccc(C3=CCN(C[C@H]4CC[C@H](n5cc6cc(NC(=O)c7cccc(C(F)(F)F)n7)c(C#N)cc6n5)CC4)CC3F)c21] |
| I-714 | 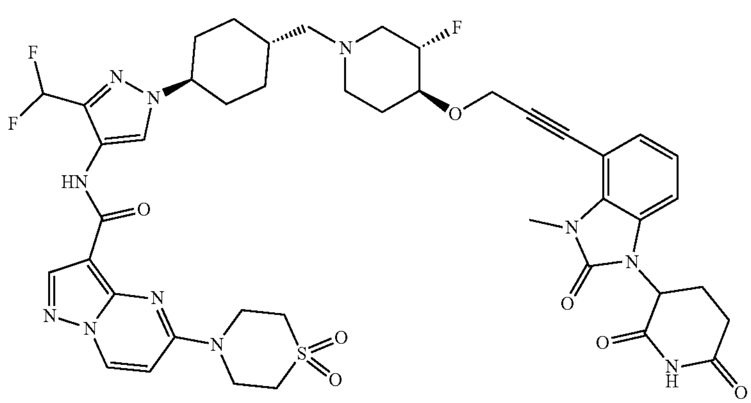 [SMILES: Cn1c(=O)n(C2CCC(=O)NC2=O)c2cccc(C#CCO[C@H]3CCN(C[C@H]4CC[C@H](n5cc(NC(=O)c6cnn7ccc(N8CCS(=O)(=O)CC8)nc67)c(C(F)F)n5)CC4)C[C@@H]3F)c21] |

TABLE 1-continued

Exemplary Compounds

| I-# | Structure |
|---|---|
| I-715 | 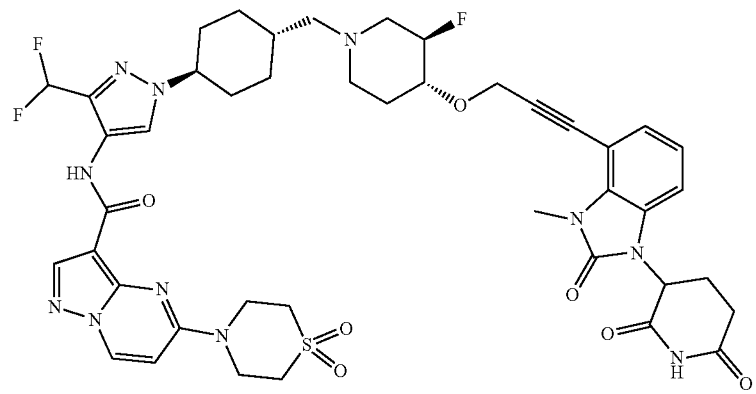 [SMILES: Cn1c(=O)n(C2CCC(=O)NC2=O)c2cccc(C#CCO[C@@H]3CCN(C[C@H]4CC[C@H](n5cc(NC(=O)c6cnn7ccc(N8CCS(=O)(=O)CC8)nc67)c(C(F)F)n5)CC4)C[C@H]3F)c21] |
| I-716 | 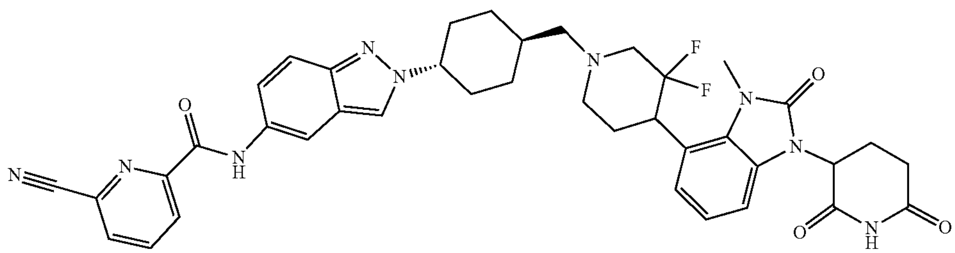 [SMILES: Cn1c(=O)n(C2CCC(=O)NC2=O)c2cccc(C3CCN(C[C@H]4CC[C@H](n5cc6cc(NC(=O)c7cccc(C#N)n7)ccc6n5)CC4)CC3(F)F)c21] |
| I-717 | 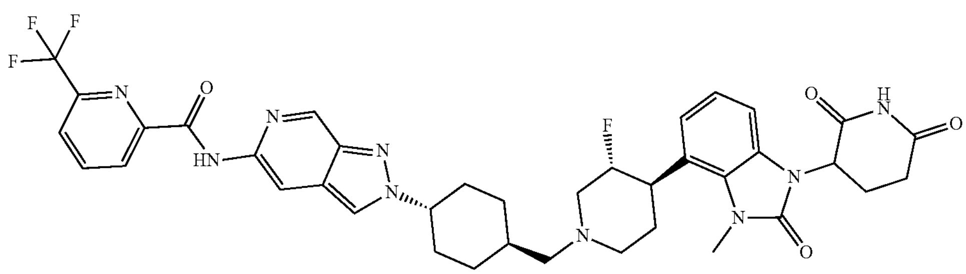 [SMILES: Cn1c(=O)n(C2CCC(=O)NC2=O)c2cccc([C@H]3CCN(C[C@H]4CC[C@H](n5cc6cc(NC(=O)c7cccc(C(F)(F)F)n7)ncc6n5)CC4)C[C@@H]3F)c21] |
| I-718 | 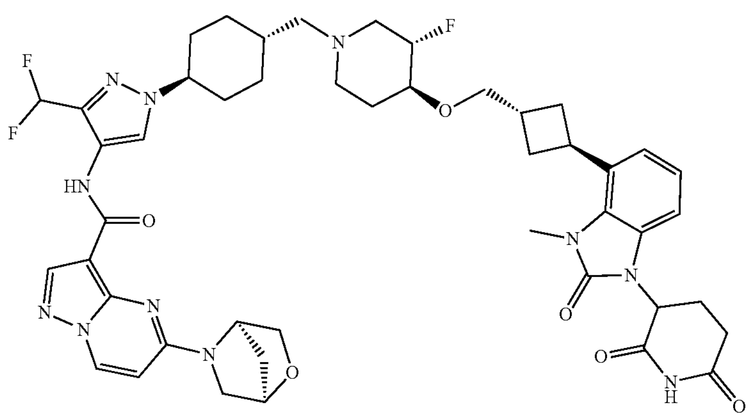 [SMILES: Cn1c(=O)n(C2CCC(=O)NC2=O)c2cccc([C@H]3C[C@H](CO[C@H]4CCN(C[C@H]5CC[C@H](n6cc(NC(=O)c7cnn8ccc(N9C[C@H]%10C[C@@H]9CO%10)nc78)c(C(F)F)n6)CC5)C[C@@H]4F)C3)c21] |

TABLE 1-continued
Exemplary Compounds
| I-# | Structure |
|---|---|
| I-719 | 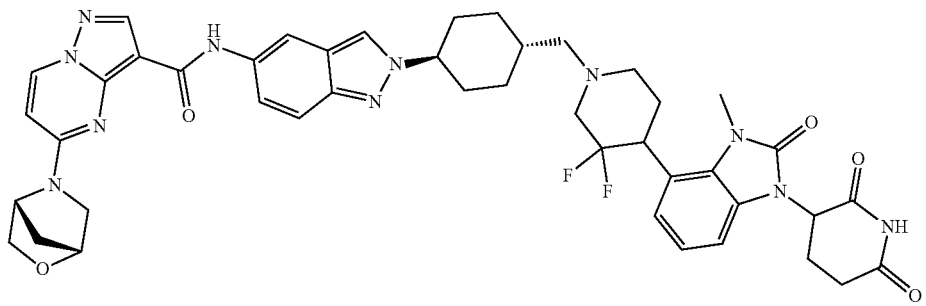 [SMILES: Cn1c(=O)n(C2CCC(=O)NC2=O)c2cccc(C3CCN(C[C@H]4CC[C@H](n5cc6cc(NC(=O)c7cnn8ccc(N9C[C@H]%10C[C@@H]9CO%10)nc78)ccc6n5)CC4)CC3(F)F)c21] |
| I-720 | 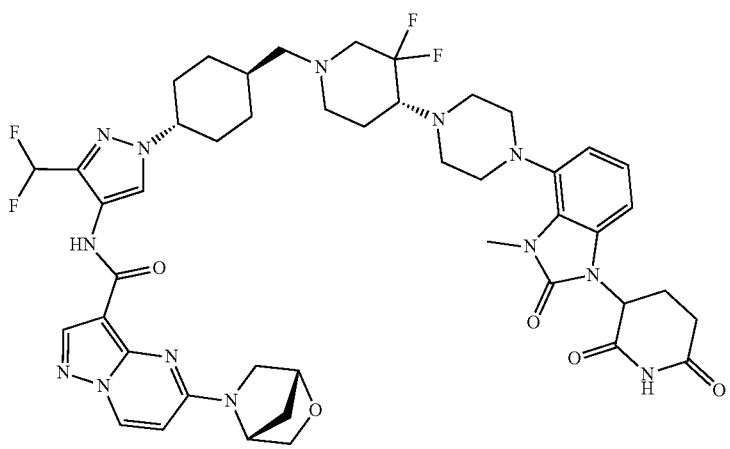 [SMILES: Cn1c(=O)n(C2CCC(=O)NC2=O)c2cccc(N3CCN([C@@H]4CCN(C[C@H]5CC[C@H](n6cc(NC(=O)c7cnn8ccc(N9C[C@H]%10C[C@@H]9CO%10)nc78)c(C(F)F)n6)CC5)CC4(F)F)CC3)c21] |
| I-721 | 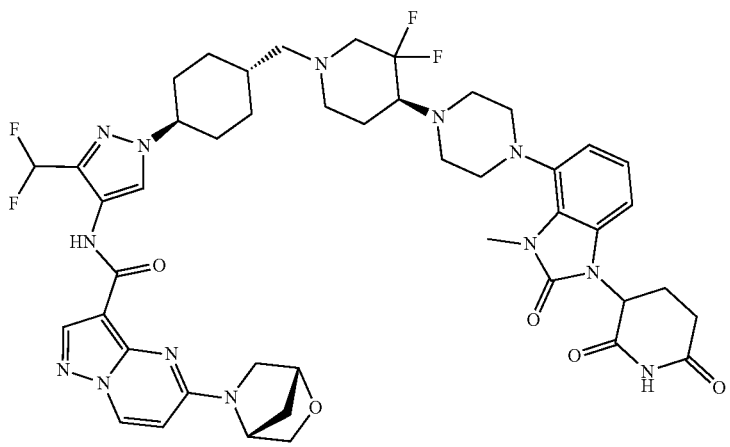 [SMILES: Cn1c(=O)n(C2CCC(=O)NC2=O)c2cccc(N3CCN([C@H]4CCN(C[C@H]5CC[C@H](n6cc(NC(=O)c7cnn8ccc(N9C[C@H]%10C[C@@H]9CO%10)nc78)c(C(F)F)n6)CC5)CC4(F)F)CC3)c21] |

TABLE 1-continued
Exemplary Compounds
| I-# | Structure |
|---|---|
| I-722 | 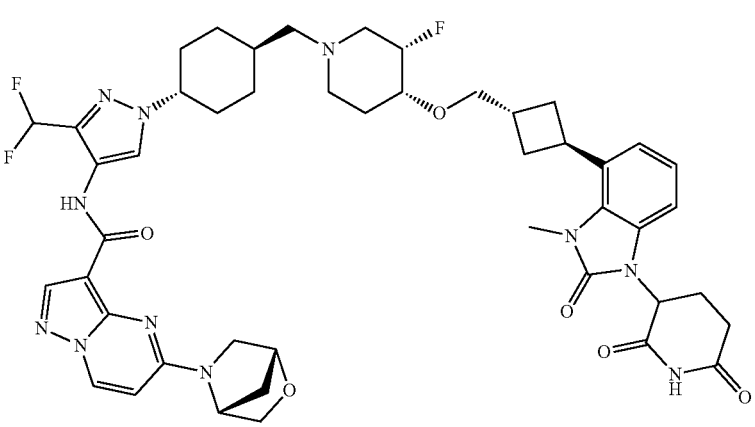 [SMILES: Cn1c(=O)n(C2CCC(=O)NC2=O)c2cccc([C@H]3C[C@H](CO[C@@H]4CCN(C[C@H]5CC[C@H](n6cc(NC(=O)c7cnn8ccc(N9C[C@H]%10C[C@@H]9CO%10)nc78)c(C(F)F)n6)CC5)C[C@@H]4F)C3)c21] |
| I-723 | 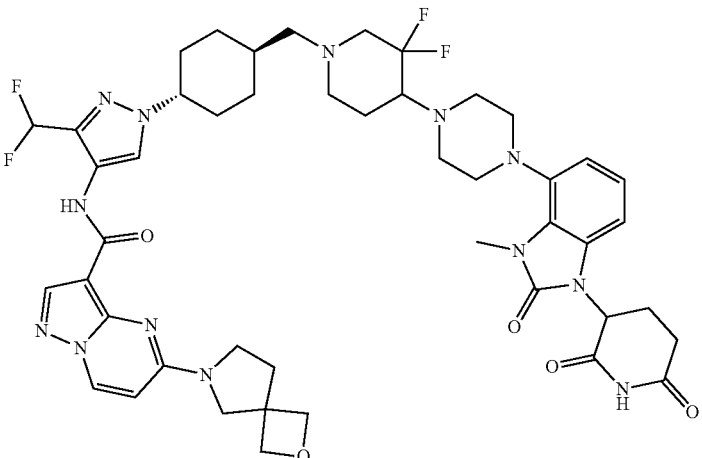 [SMILES: Cn1c(=O)n(C2CCC(=O)NC2=O)c2cccc(N3CCN(C4CCN(C[C@H]5CC[C@H](n6cc(NC(=O)c7cnn8ccc(N9CCC%10(COC%10)C9)nc78)c(C(F)F)n6)CC5)CC4(F)F)CC3)c21] |
| I-724 | 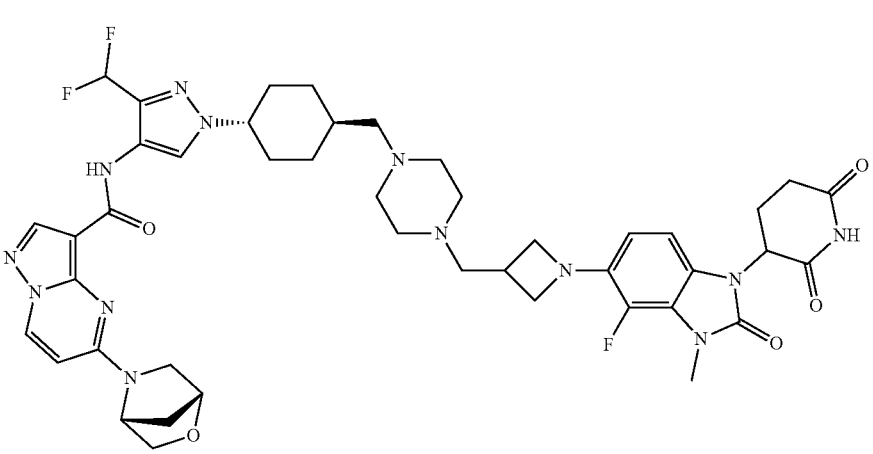 [SMILES: Cn1c(=O)n(C2CCC(=O)NC2=O)c2ccc(N3CC(CN4CCN(C[C@H]5CC[C@H](n6cc(NC(=O)c7cnn8ccc(N9C[C@H]%10C[C@@H]9CO%10)nc78)c(C(F)F)n6)CC5)CC4)C3)c(F)c21] |

TABLE 1-continued
Exemplary Compounds
| I-# | Structure |
|---|---|
| I-725 | 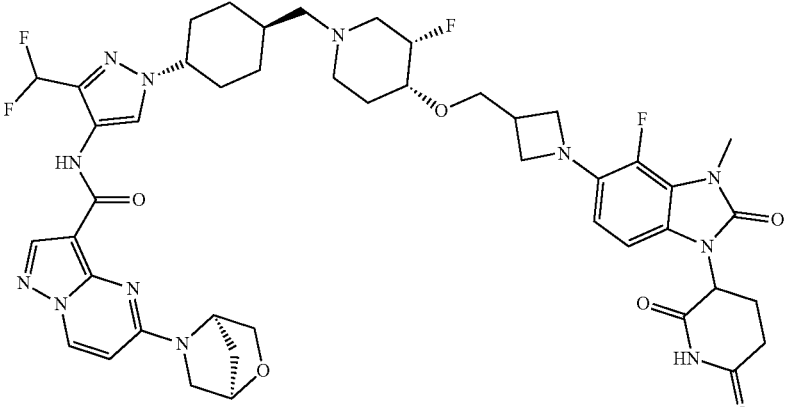 |
| I-726 | 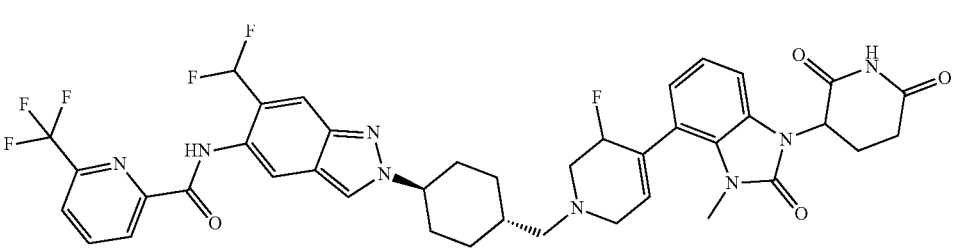 [SMILES: Cn1c(=O)n(C2CCC(=O)NC2=O)c2cccc(C3=CCN(C[C@H]4CC[C@H](n5cc6cc(NC(=O)c7cccc(C(F)(F)F)n7)c(C(F)F)cc6n5)CC4)CC3F)c21] |
| I-727 | 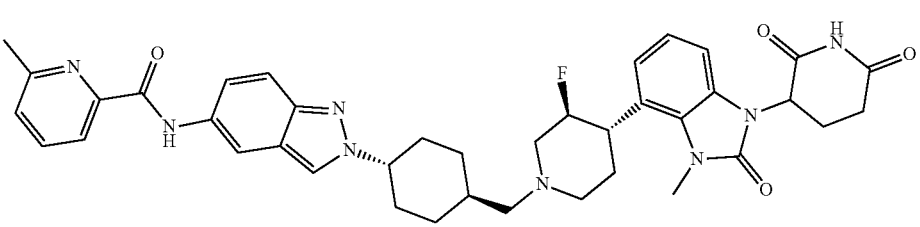 [SMILES: Cc1cccc(C(=O)Nc2ccc3nn([C@H]4CC[C@H](CN5CC[C@@H](c6cccc7c6n(C)c(=O)n7C6CCC(=O)NC6=O)[C@H](F)C5)CC4)cc3c2)n1] |
| I-728 | 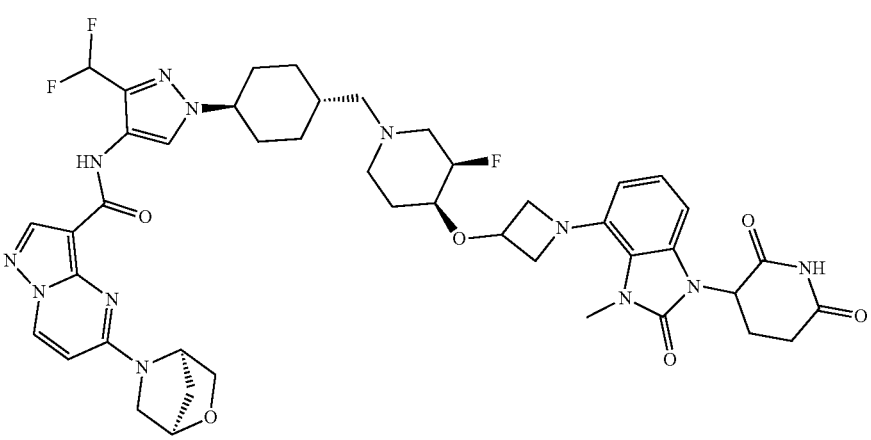 [SMILES: Cn1c(=O)n(C2CCC(=O)NC2=O)c2cccc(N3CC(O[C@H]4CCN(C[C@H]5CC[C@H](n6cc(NC(=O)c7cnn8ccc(N9C[C@H]%10C[C@@H]9CO%10)nc78)c(C(F)F)n6)CC5)C[C@H]4F)C3)c21] |

TABLE 1-continued
Exemplary Compounds
I-# Structure
I-729
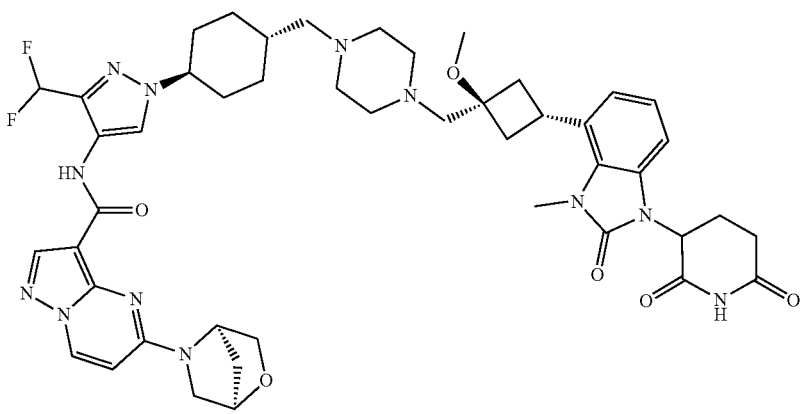 [SMILES: CO[C@]1(CN2CCN(C[C@H]3CC[C@H](n4cc(NC(=O)c5cnn6ccc(N7C[C@H]8C[C@@H]7CO8)nc56)c(C(F)F)n4)CC3)CC2)C[C@@H](c2cccc3c2n(C)c(=O)n3C2CCC(=O)NC2=O)C1]
I-730
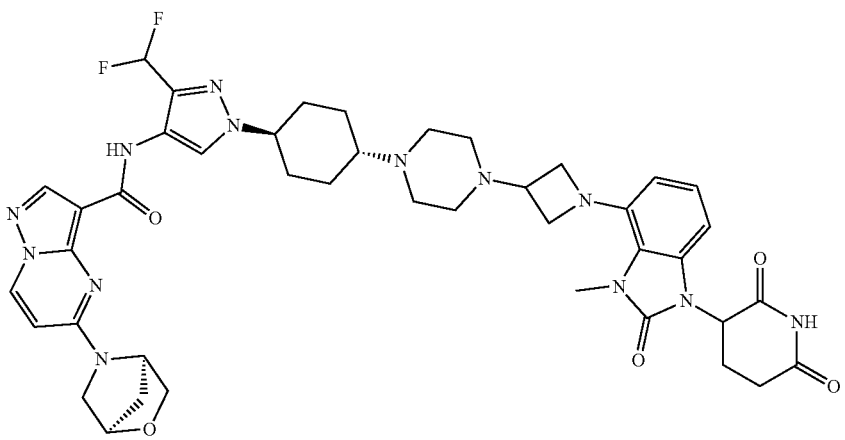 [SMILES: Cn1c(=O)n(C2CCC(=O)NC2=O)c2cccc(N3CC(N4CCN([C@H]5CC[C@H](n6cc(NC(=O)c7cnn8ccc(N9C[C@H]%10C[C@@H]9CO%10)nc78)c(C(F)F)n6)CC5)CC4)C3)c21]
I-731
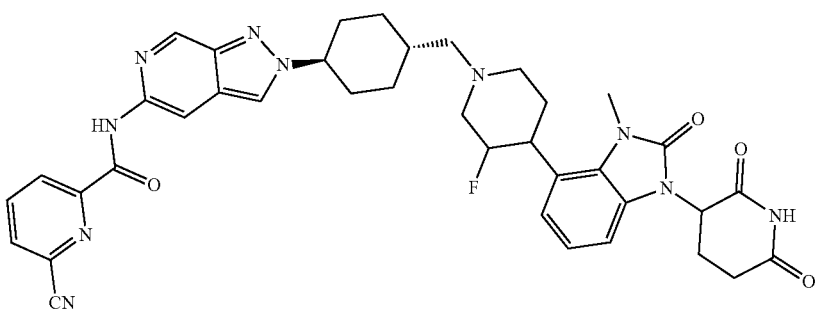
(R,R) and (S,S) mixture TABLE 1-continued Exemplary Compounds

| I-# | Structure |
|---|---|
| I-732 | 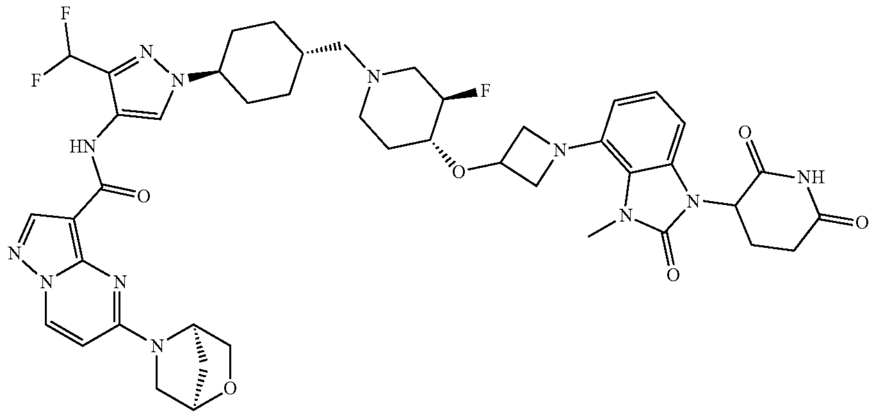 [SMILES: Cn1c(=O)n(C2CCC(=O)NC2=O)c2cccc(N3CC(O[C@@H]4CCN(C[C@H]5CC[C@H](n6cc(NC(=O)c7cnn8ccc(N9C[C@H]%10C[C@@H]9CO%10)nc78)c(C(F)F)n6)CC5)C[C@H]4F)C3)c21] |
| I-733 | 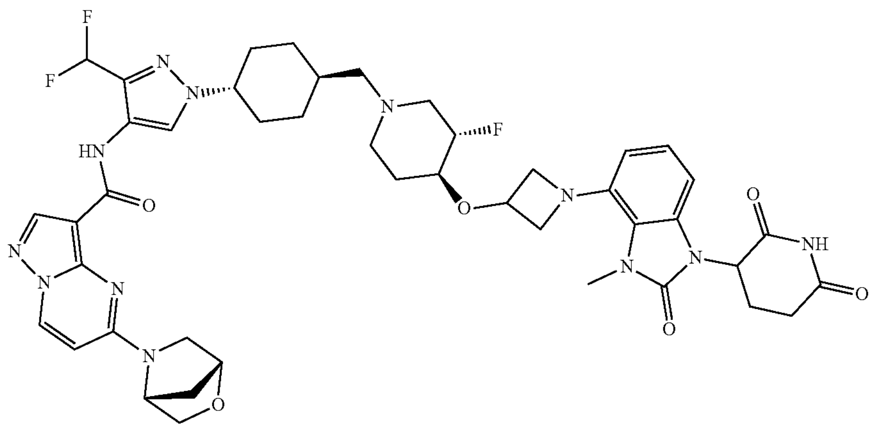 [SMILES: Cn1c(=O)n(C2CCC(=O)NC2=O)c2cccc(N3CC(O[C@H]4CCN(C[C@H]5CC[C@H](n6cc(NC(=O)c7cnn8ccc(N9C[C@H]%10C[C@@H]9CO%10)nc78)c(C(F)F)n6)CC5)C[C@@H]4F)C3)c21] |
| I-734 | 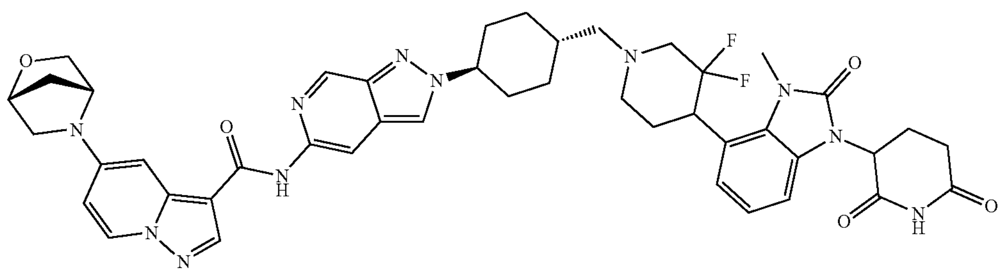 [SMILES: Cn1c(=O)n(C2CCC(=O)NC2=O)c2cccc(C3CCN(C[C@H]4CC[C@H](n5cc6cc(NC(=O)c7cnn8ccc(N9C[C@H]%10C[C@@H]9CO%10)cc78)ncc6n5)CC4)CC3(F)F)c21] |
| I-735 | 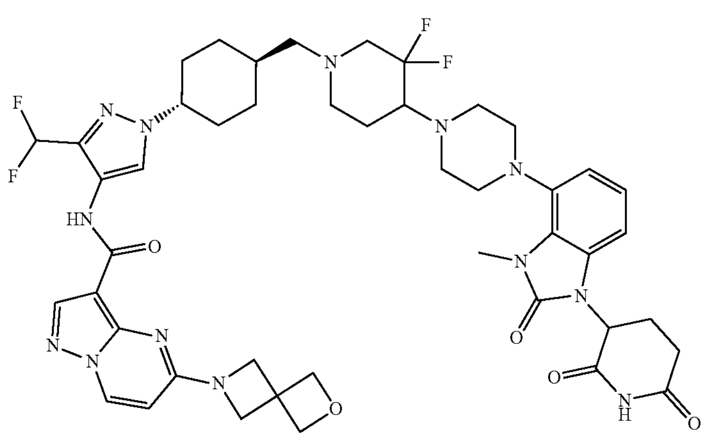 [SMILES: Cn1c(=O)n(C2CCC(=O)NC2=O)c2cccc(N3CCN(C4CCN(C[C@H]5CC[C@H](n6cc(NC(=O)c7cnn8ccc(N9CC%10(COC%10)C9)nc78)c(C(F)F)n6)CC5)CC4(F)F)CC3)c21] |

TABLE 1-continued
Exemplary Compounds
I-# Structure
I-736 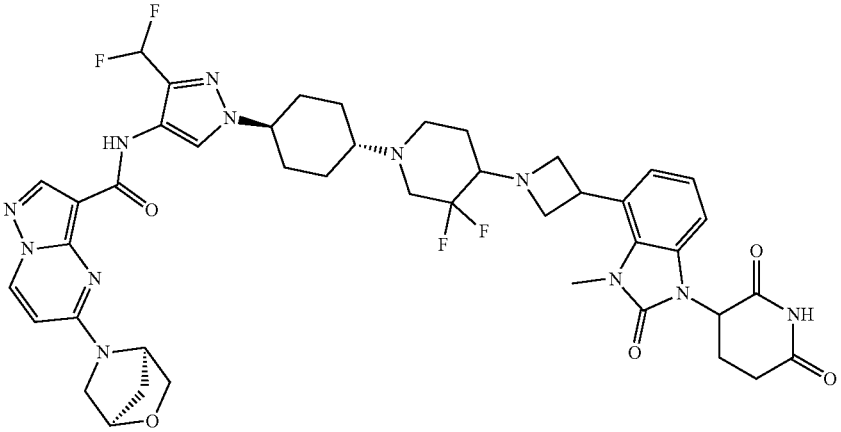 [SMILES: Cn1c(=O)n(C2CCC(=O)NC2=O)c2cccc(C3CN(C4CCN([C@H]5CC[C@H](n6cc(NC(=O)c7cnn8ccc(N9C[C@H]%10C[C@@H]9CO%10)nc78)c(C(F)F)n6)CC5)CC4(F)F)C3)c21]
I-737 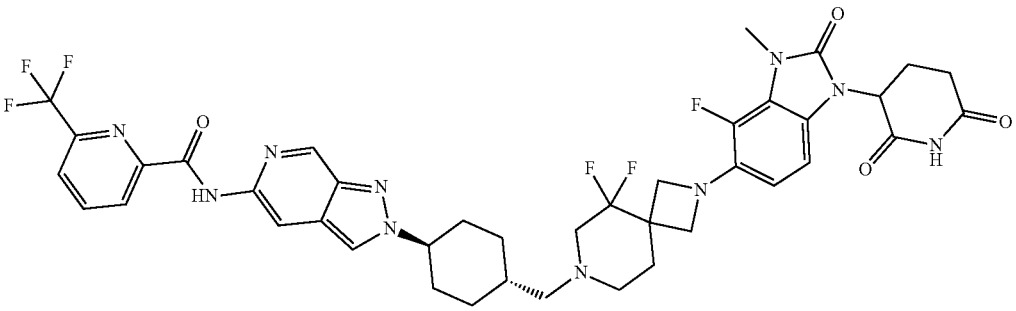 [SMILES: Cn1c(=O)n(C2CCC(=O)NC2=O)c2ccc(N3CC4(CCN(C[C@H]5CC[C@H](n6cc7cc(NC(=O)c8cccc(C(F)(F)F)n8)ncc7n6)CC5)CC4(F)F)C3)c(F)c21]
I-738 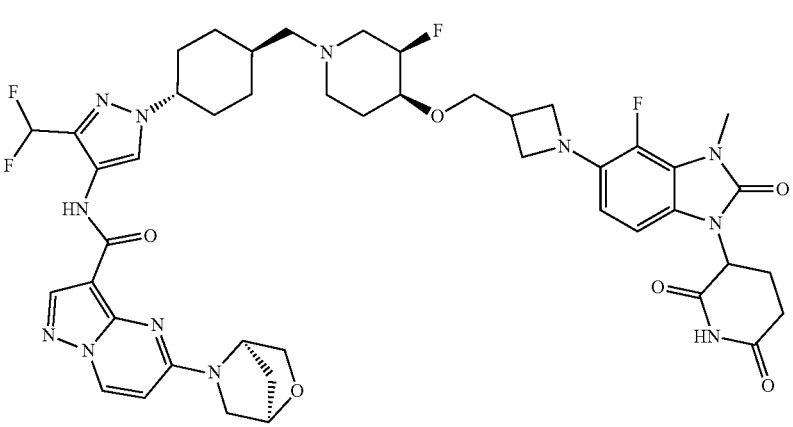 [SMILES: Cn1c(=O)n(C2CCC(=O)NC2=O)c2ccc(N3CC(CO[C@H]4CCN(C[C@H]5CC[C@H](n6cc(NC(=O)c7cnn8ccc(N9C[C@H]%10C[C@@H]9CO%10)nc78)c(C(F)F)n6)CC5)C[C@H]4F)C3)c(F)c21]

TABLE 1-continued

Exemplary Compounds

| I-# | Structure |
|---|---|
| I-739 | 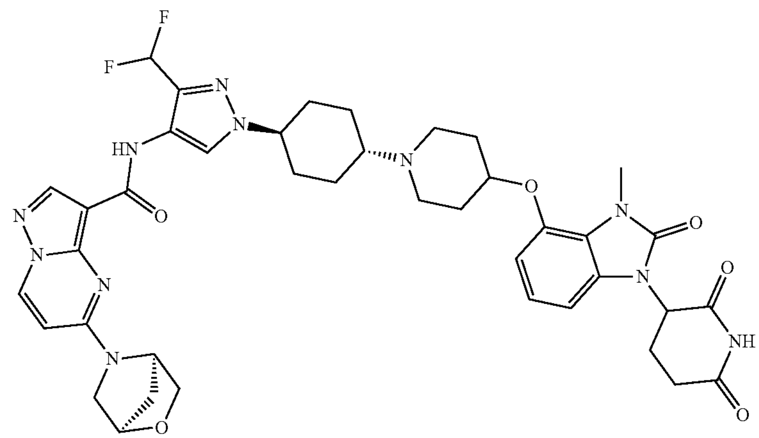 [SMILES: Cn1c(=O)n(C2CCC(=O)NC2=O)c2cccc(OC3CCN([C@H]4CC[C@H](n5cc(NC(=O)c6cnn7ccc(N8C[C@H]9C[C@@H]8CO9)nc67)c(C(F)F)n5)CC4)CC3)c21] |
| I-740 | 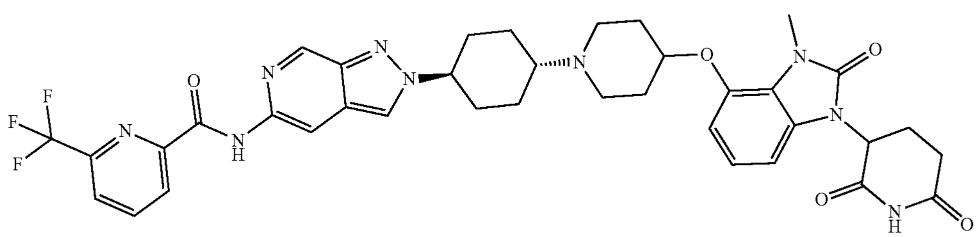 [SMILES: Cn1c(=O)n(C2CCC(=O)NC2=O)c2cccc(OC3CCN([C@H]4CC[C@H](n5cc6cc(NC(=O)c7cccc(C(F)(F)F)n7)ncc6n5)CC4)CC3)c21] |
| I-741 | 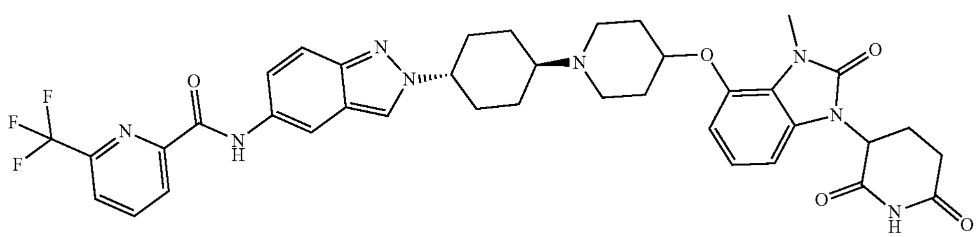 [SMILES: Cn1c(=O)n(C2CCC(=O)NC2=O)c2cccc(OC3CCN([C@H]4CC[C@H](n5cc6cc(NC(=O)c7cccc(C(F)(F)F)n7)ccc6n5)CC4)CC3)c21] |
| I-742 | 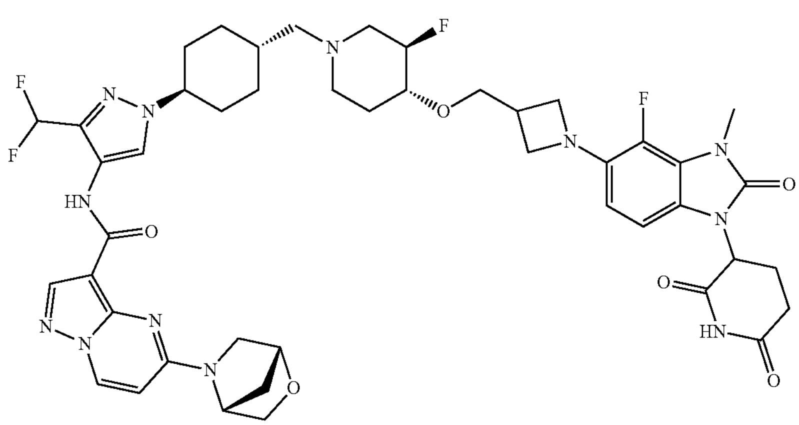 [SMILES: Cn1c(=O)n(C2CCC(=O)NC2=O)c2ccc(N3CC(CO[C@@H]4CCN(C[C@H]5CC[C@H](n6cc(NC(=O)c7cnn8ccc(N9C[C@H]%10C[C@@H]9CO%10)nc78)c(C(F)F)n6)CC5)C[C@H]4F)C3)c(F)c21] |

TABLE 1-continued

Exemplary Compounds

| I-# | Structure |
|---|---|
| I-743 | 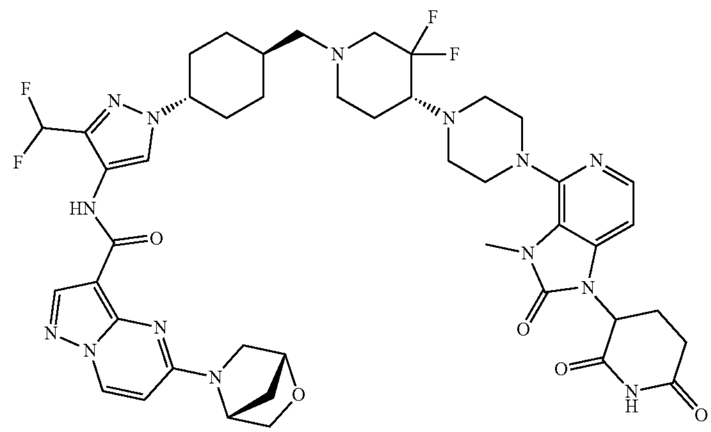 [SMILES: Cn1c(=O)n(C2CCC(=O)NC2=O)c2ccnc(N3CCN([C@@H]4CCN(C[C@H]5CC[C@H](n6cc(NC(=O)c7cnn8ccc(N9C[C@H]%10C[C@@H]9CO%10)nc78)c(C(F)F)n6)CC5)CC4(F)F)CC3)c21] |
| I-744 | 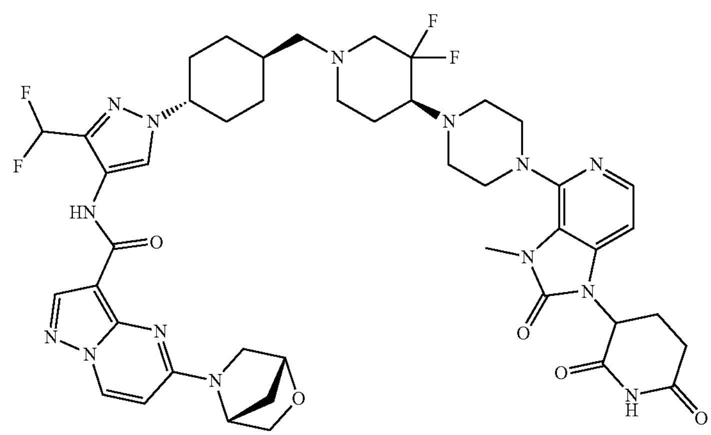 [SMILES: Cn1c(=O)n(C2CCC(=O)NC2=O)c2ccnc(N3CCN([C@H]4CCN(C[C@H]5CC[C@H](n6cc(NC(=O)c7cnn8ccc(N9C[C@H]%10C[C@@H]9CO%10)nc78)c(C(F)F)n6)CC5)CC4(F)F)CC3)c21] |
| I-745 | 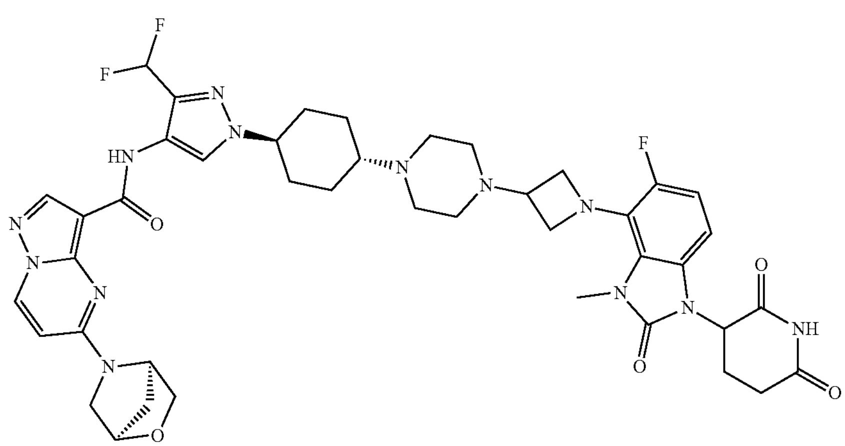 [SMILES: Cn1c(=O)n(C2CCC(=O)NC2=O)c2ccc(F)c(N3CC(N4CCN([C@H]5CC[C@H](n6cc(NC(=O)c7cnn8ccc(N9C[C@H]%10C[C@@H]9CO%10)nc78)c(C(F)F)n6)CC5)CC4)C3)c21] |

TABLE 1-continued
Exemplary Compounds
| I-# | Structure |
|---|---|
| I-746 | 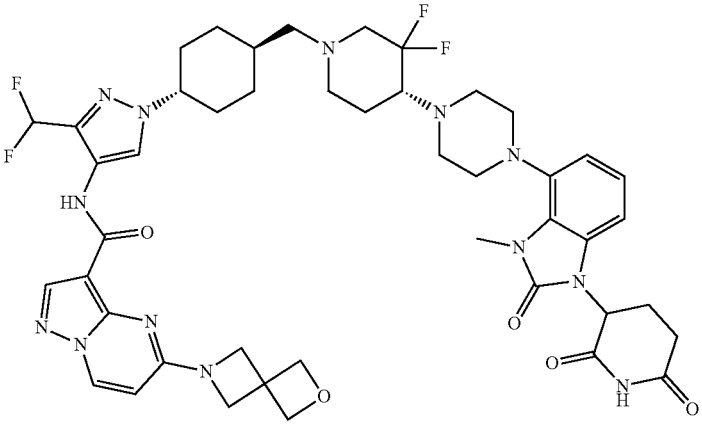 [SMILES: Cn1c(=O)n(C2CCC(=O)NC2=O)c2cccc(N3CCN([C@@H]4CCN(C[C@H]5CC[C@H](n6cc(NC(=O)c7cnn8ccc(N9CC%10(COC%10)C9)nc78)c(C(F)F)n6)CC5)CC4(F)F)CC3)c21] |
| I-747 | 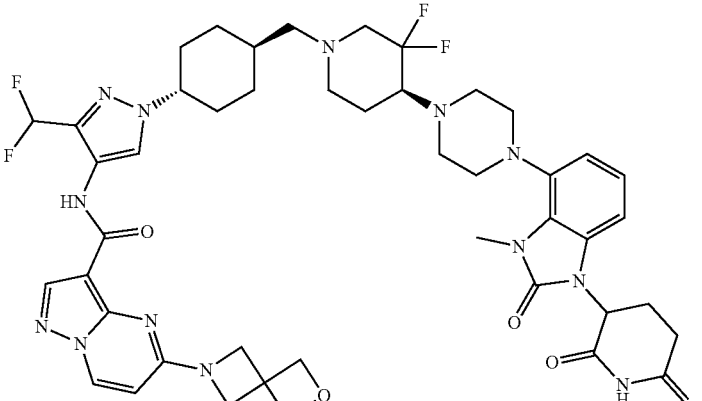 |
| I-748 | 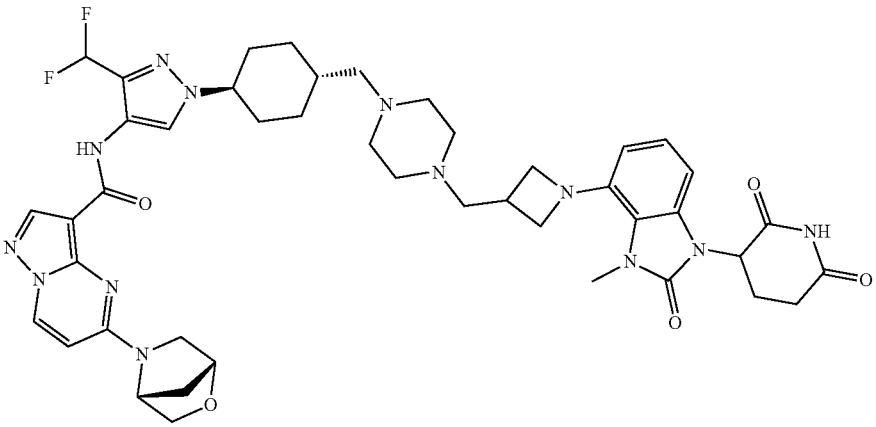 [SMILES: Cn1c(=O)n(C2CCC(=O)NC2=O)c2cccc(N3CC(CN4CCN(C[C@H]5CC[C@H](n6cc(NC(=O)c7cnn8ccc(N9C[C@H]%10C[C@@H]9CO%10)nc78)c(C(F)F)n6)CC5)CC4)C3)c21] |
| I-749 | 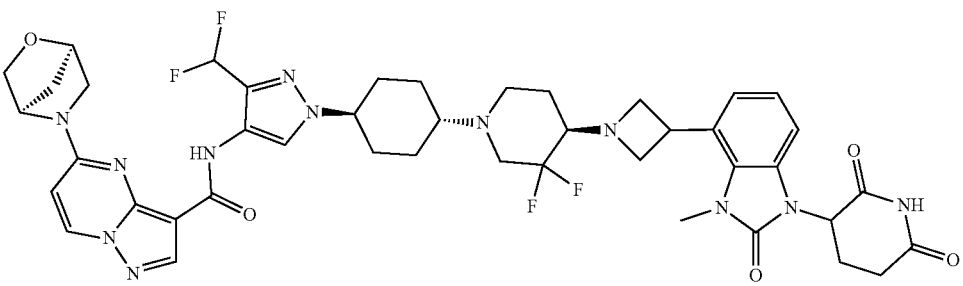 [SMILES: Cn1c(=O)n(C2CCC(=O)NC2=O)c2cccc(C3CN([C@@H]4CCN([C@H]5CC[C@H](n6cc(NC(=O)c7cnn8ccc(N9C[C@H]%10C[C@@H]9CO%10)nc78)c(C(F)F)n6)CC5)CC4(F)F)C3)c21] |

TABLE 1-continued
Exemplary Compounds
| I-# | Structure |
|---|---|
| I-750 | 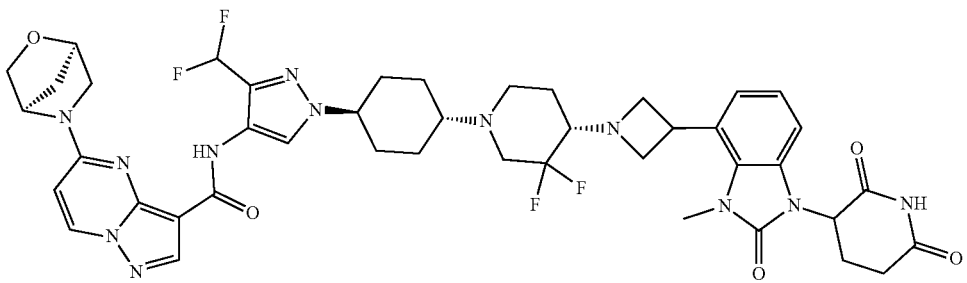 [SMILES: Cn1c(=O)n(C2CCC(=O)NC2=O)c2cccc(C3CN([C@H]4CCN([C@H]5CC[C@H](n6cc(NC(=O)c7cnn8ccc(N9C[C@H]%10C[C@@H]9CO%10)nc78)c(C(F)F)n6)CC5)CC4(F)F)C3)c21] |
| I-751 | 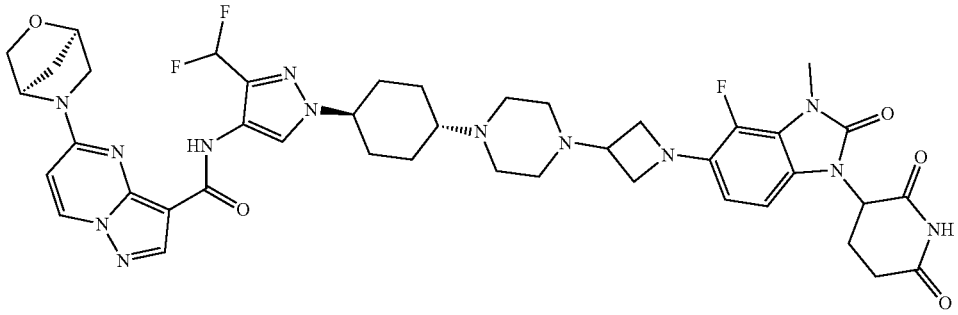 [SMILES: Cn1c(=O)n(C2CCC(=O)NC2=O)c2ccc(N3CC(N4CCN([C@H]5CC[C@H](n6cc(NC(=O)c7cnn8ccc(N9C[C@H]%10C[C@@H]9CO%10)nc78)c(C(F)F)n6)CC5)CC4)C3)c(F)c21] |
| I-752 | 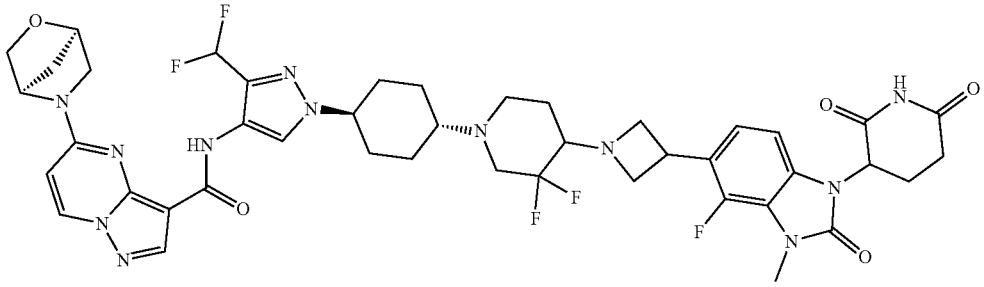 [SMILES: Cn1c(=O)n(C2CCC(=O)NC2=O)c2ccc(C3CN(C4CCN([C@H]5CC[C@H](n6cc(NC(=O)c7cnn8ccc(N9C[C@H]%10C[C@@H]9CO%10)nc78)c(C(F)F)n6)CC5)CC4(F)F)C3)c(F)c21] |
| I-753 | 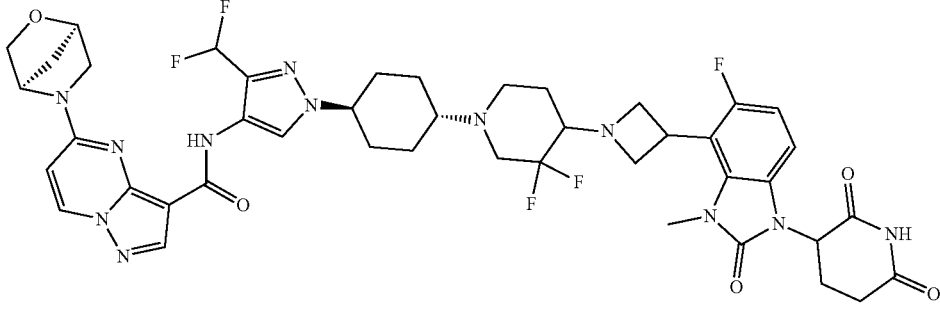 [SMILES: Cn1c(=O)n(C2CCC(=O)NC2=O)c2ccc(F)c(C3CN(C4CCN([C@H]5CC[C@H](n6cc(NC(=O)c7cnn8ccc(N9C[C@H]%10C[C@@H]9CO%10)nc78)c(C(F)F)n6)CC5)CC4(F)F)C3)c21] |
| I-754 | 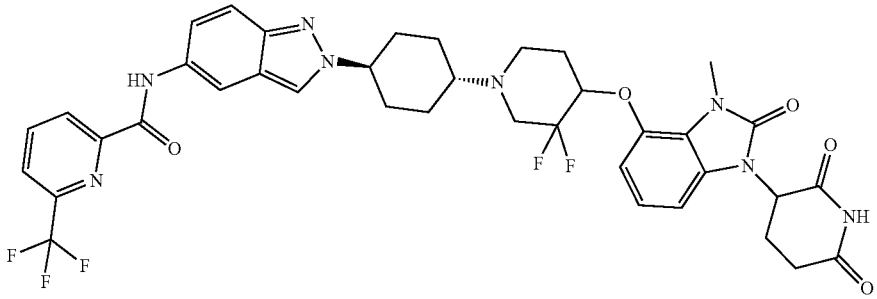 [SMILES: Cn1c(=O)n(C2CCC(=O)NC2=O)c2cccc(OC3CCN([C@H]4CC[C@H](n5cc6cc(NC(=O)c7cccc(C(F)(F)F)n7)ccc6n5)CC4)CC3(F)F)c21] |

TABLE 1-continued
Exemplary Compounds
| I-# | Structure |
|---|---|
| I-755 | 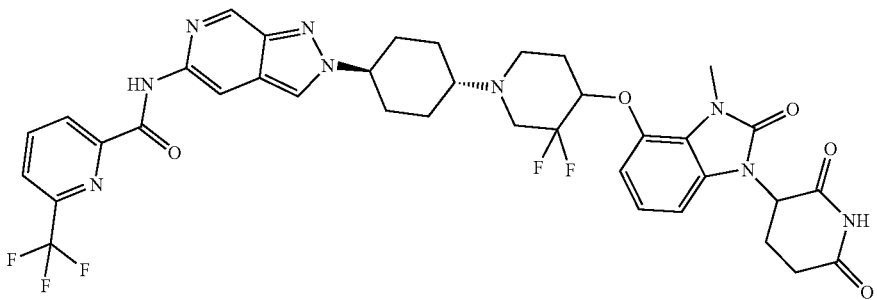 [SMILES: Cn1c(=O)n(C2CCC(=O)NC2=O)c2cccc(OC3CCN([C@H]4CC[C@H](n5cc6cc(NC(=O)c7cccc(C(F)(F)F)n7)ncc6n5)CC4)CC3(F)F)c21] |
| I-756 | 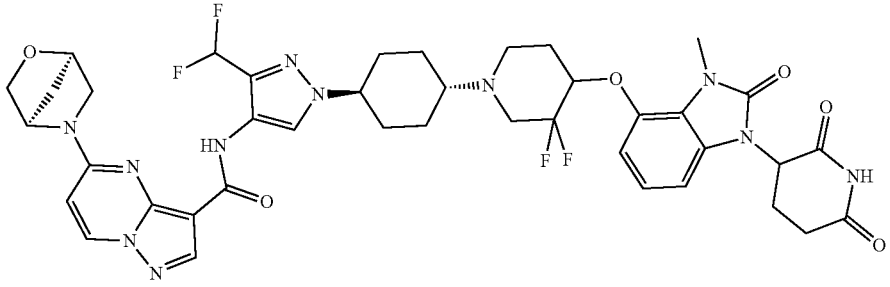 [SMILES: Cn1c(=O)n(C2CCC(=O)NC2=O)c2cccc(OC3CCN([C@H]4CC[C@H](n5cc(NC(=O)c6cnn7ccc(N8C[C@H]9C[C@@H]8CO9)nc67)c(C(F)F)n5)CC4)CC3(F)F)c21] |
| I-757 | 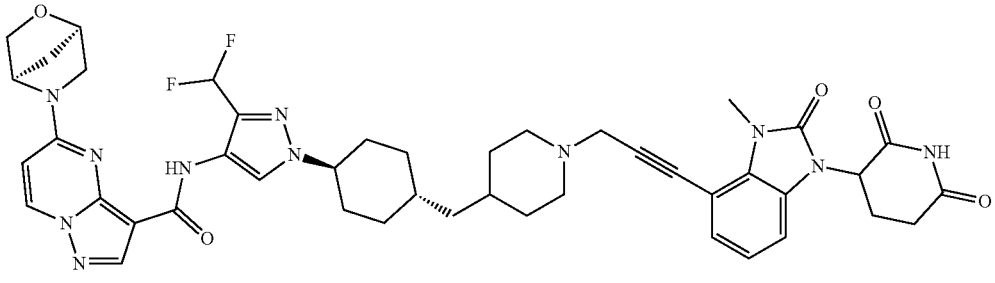 [SMILES: Cn1c(=O)n(C2CCC(=O)NC2=O)c2cccc(C#CCN3CCC(C[C@H]4CC[C@H](n5cc(NC(=O)c6cnn7ccc(N8C[C@H]9C[C@@H]8CO9)nc67)c(C(F)F)n5)CC4)CC3)c21] |
| I-758 | 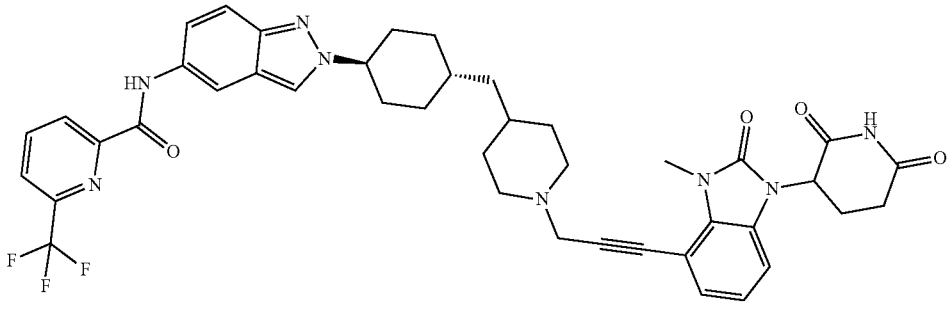 |
| I-759 | 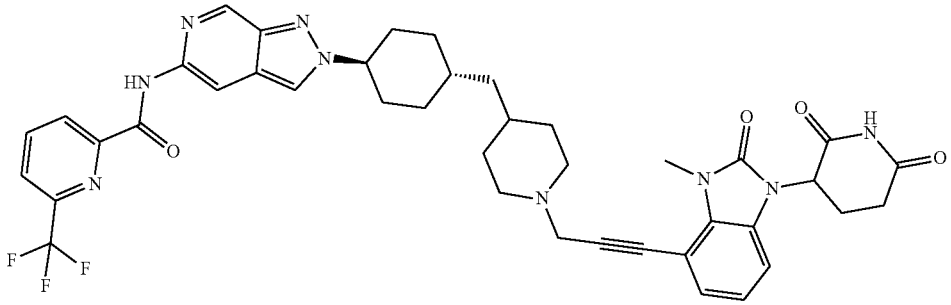 [SMILES: Cn1c(=O)n(C2CCC(=O)NC2=O)c2cccc(C#CCN3CCC(C[C@H]4CC[C@H](n5cc6cc(NC(=O)c7cccc(C(F)(F)F)n7)ccc6n5)CC4)CC3)c21] |

TABLE 1-continued

Exemplary Compounds

| I-# | Structure |
|---|---|
| I-760 | 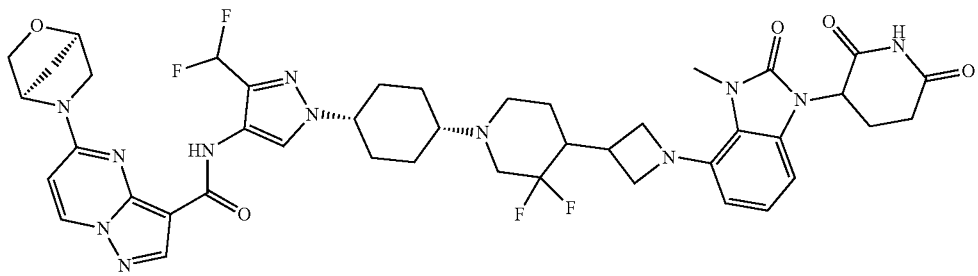 [SMILES: Cn1c(=O)n(C2CCC(=O)NC2=O)c2cccc(N3CC(C4CCN([C@H]5CC[C@@H](n6cc(NC(=O)c7cnn8ccc(N9C[C@H]%10C[C@@H]9CO%10)nc78)c(C(F)F)n6)CC5)CC4(F)F)C3)c21] |
| I-761 | 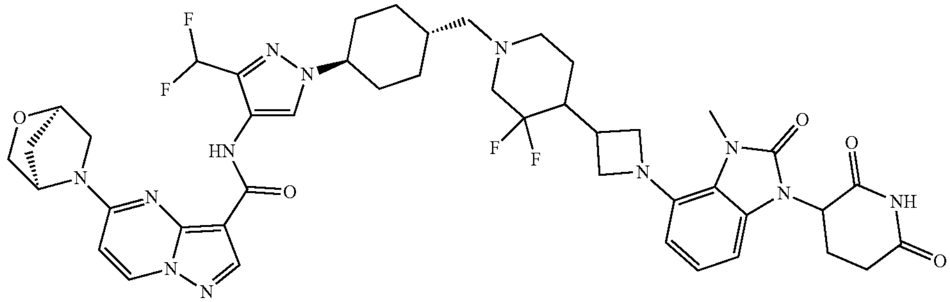 [SMILES: Cn1c(=O)n(C2CCC(=O)NC2=O)c2cccc(N3CC(C4CCN(C[C@H]5CC[C@H](n6cc(NC(=O)c7cnn8ccc(N9C[C@H]%10C[C@@H]9CO%10)nc78)c(C(F)F)n6)CC5)CC4(F)F)C3)c21] |
| I-762 | 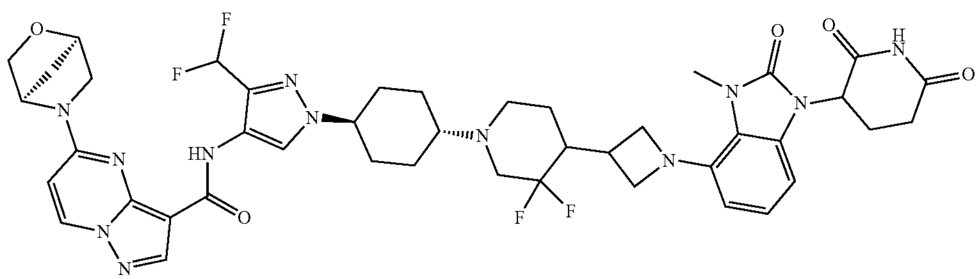 [SMILES: Cn1c(=O)n(C2CCC(=O)NC2=O)c2cccc(N3CC(C4CCN([C@H]5CC[C@H](n6cc(NC(=O)c7cnn8ccc(N9C[C@H]%10C[C@@H]9CO%10)nc78)c(C(F)F)n6)CC5)CC4(F)F)C3)c21] |
| I-763 | 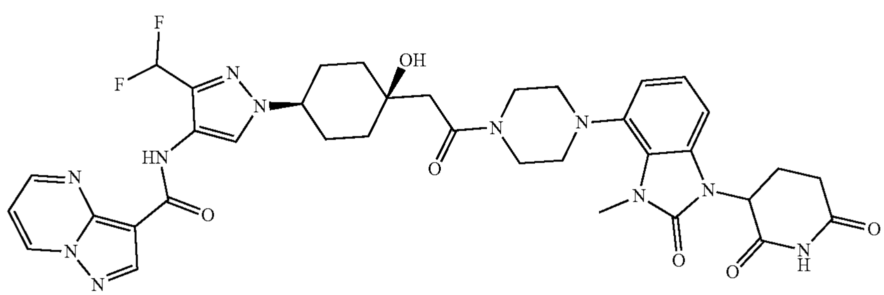 [SMILES: Cn1c(=O)n(C2CCC(=O)NC2=O)c2cccc(N3CCN(C(=O)C[C@]4(O)CC[C@@H](n5cc(NC(=O)c6cnn7cccnc67)c(C(F)F)n5)CC4)CC3)c21] |
| I-764 | 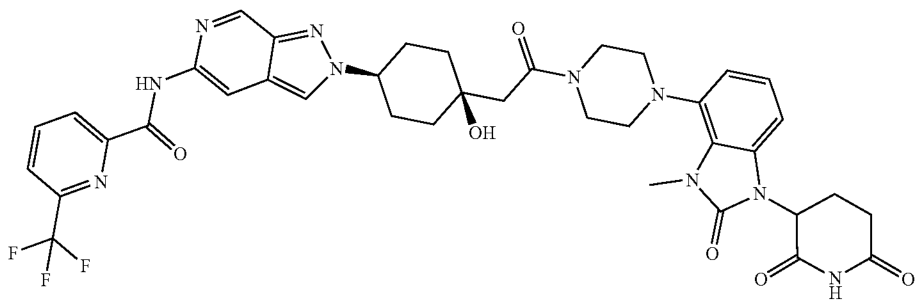 [SMILES: Cn1c(=O)n(C2CCC(=O)NC2=O)c2cccc(N3CCN(C(=O)C[C@]4(O)CC[C@@H](n5cc6cc(NC(=O)c7cccc(C(F)(F)F)n7)ncc6n5)CC4)CC3)c21] |

TABLE 1-continued

Exemplary Compounds

| I-# | Structure |
|---|---|
| I-765 | 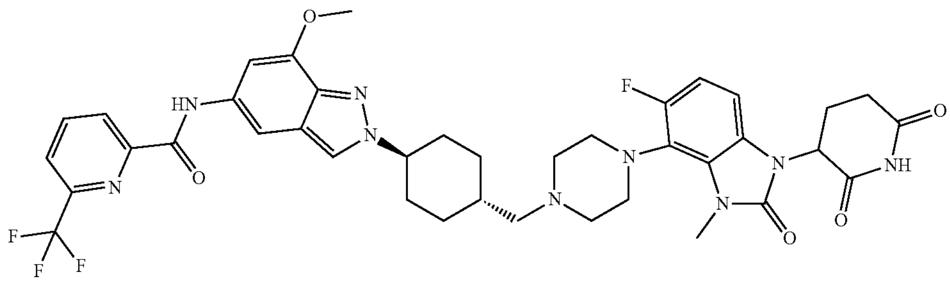 [SMILES: COc1cc(NC(=O)c2cccc(C(F)(F)F)n2)cc2cn([C@H]3CC[C@H](CN4CCN(c5c(F)ccc6c5n(C)c(=O)n6C5CCC(=O)NC5=O)CC4)CC3)nc12] |
| I-766 | 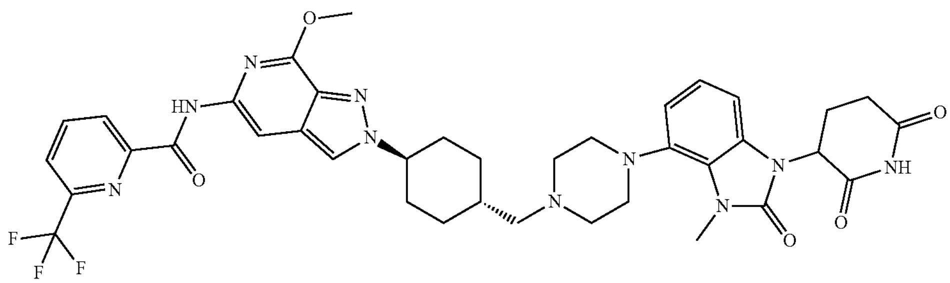 [SMILES: COc1nc(NC(=O)c2cccc(C(F)(F)F)n2)cc2cn([C@H]3CC[C@H](CN4CCN(c5cccc6c5n(C)c(=O)n6C5CCC(=O)NC5=O)CC4)CC3)nc12] |
| I-767 | 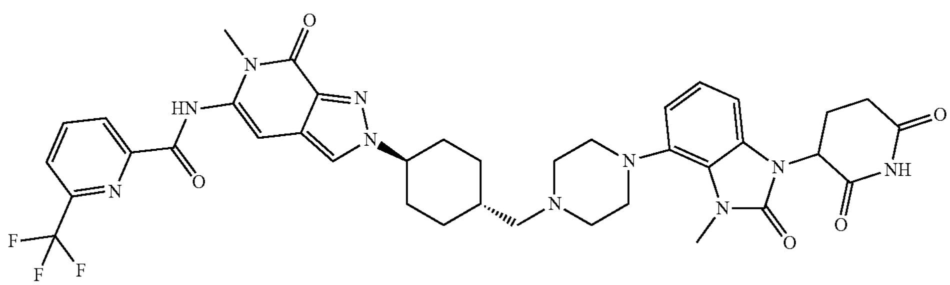 [SMILES: Cn1c(NC(=O)c2cccc(C(F)(F)F)n2)cc2cn([C@H]3CC[C@H](CN4CCN(c5cccc6c5n(C)c(=O)n6C5CCC(=O)NC5=O)CC4)CC3)nc2c1=O] |
| I-768 | 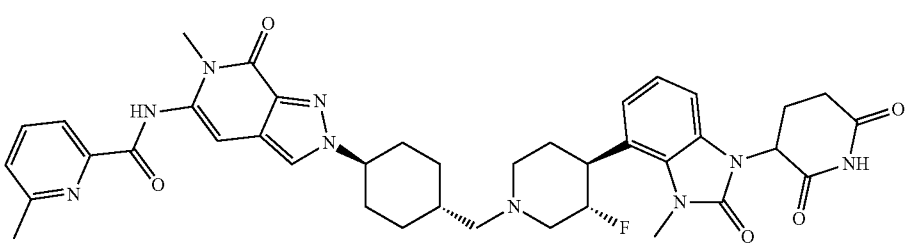 [SMILES: Cc1cccc(C(=O)Nc2cc3cn([C@H]4CC[C@H](CN5CC[C@@H](c6cccc7c6n(C)c(=O)n7C6CCC(=O)NC6=O)[C@H](F)C5)CC4)nc3c(=O)n2C)n1] |
| I-769 | 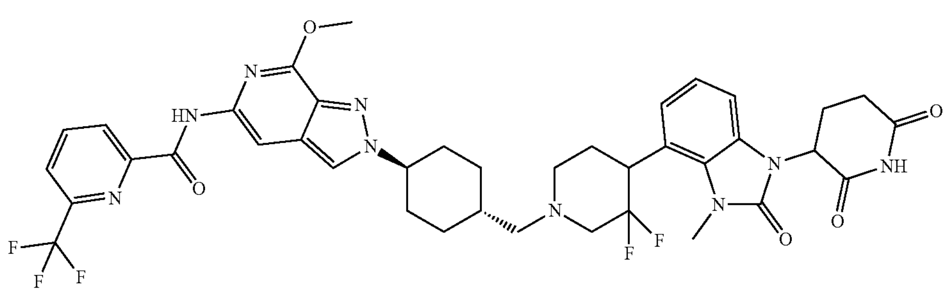 [SMILES: COc1nc(NC(=O)c2cccc(C(F)(F)F)n2)cc2cn([C@H]3CC[C@H](CN4CCC(c5cccc6c5n(C)c(=O)n6C5CCC(=O)NC5=O)C(F)(F)C4)CC3)nc12] |

TABLE 1-continued
Exemplary Compounds
| I-# | Structure |
|---|---|
| I-770 | 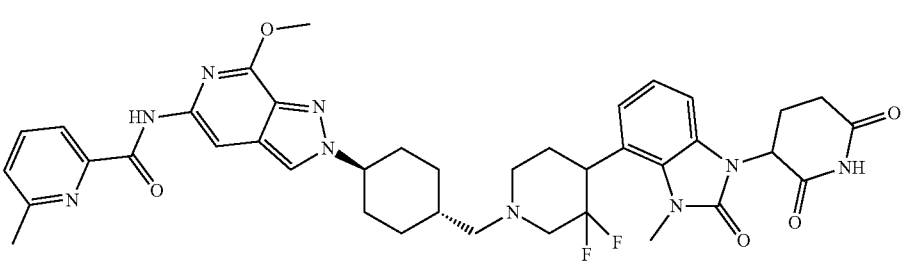 [SMILES: COc1nc(NC(=O)c2cccc(C)n2)cc2cn([C@H]3CC[C@H](CN4CCC(c5cccc6c5n(C)c(=O)n6C5CCC(=O)NC5=O)C(F)(F)C4)CC3)nc12] |
| I-771 | 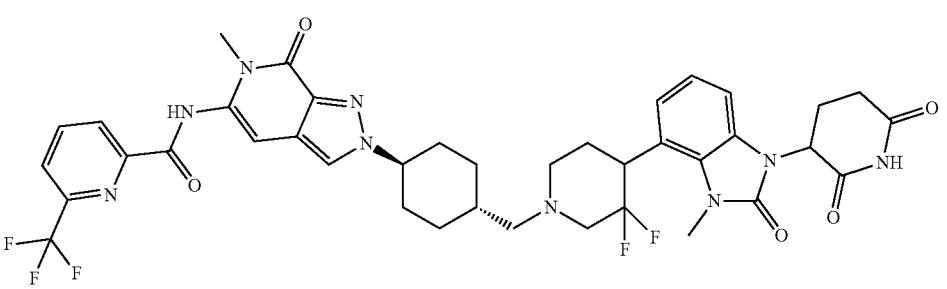 [SMILES: Cn1c(NC(=O)c2cccc(C(F)(F)F)n2)cc2cn([C@H]3CC[C@H](CN4CCC(c5cccc6c5n(C)c(=O)n6C5CCC(=O)NC5=O)C(F)(F)C4)CC3)nc2c1=O] |
| I-772 | 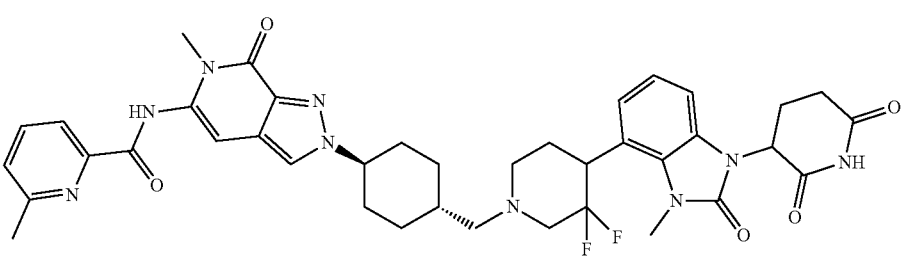 [SMILES: Cc1cccc(C(=O)Nc2cc3cn([C@H]4CC[C@H](CN5CCC(c6cccc7c6n(C)c(=O)n7C6CCC(=O)NC6=O)C(F)(F)C5)CC4)nc3c(=O)n2C)n1] |
| I-773 | 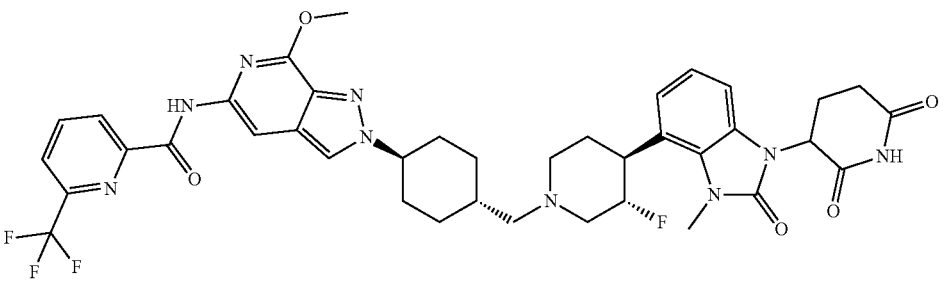 [SMILES: COc1nc(NC(=O)c2cccc(C(F)(F)F)n2)cc2cn([C@H]3CC[C@H](CN4CC[C@@H](c5cccc6c5n(C)c(=O)n6C5CCC(=O)NC5=O)[C@H](F)C4)CC3)nc12] |
| I-774 | 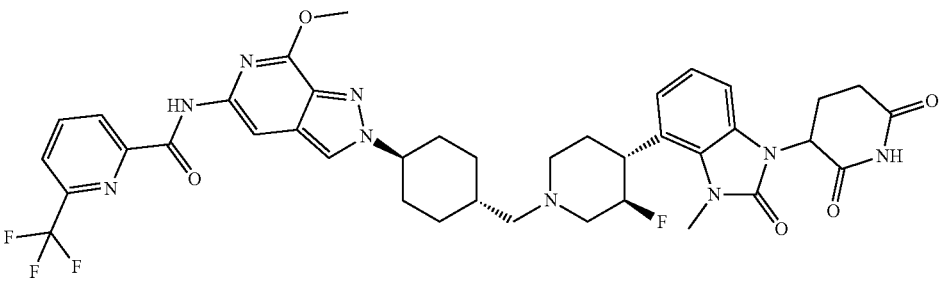 [SMILES: COc1nc(NC(=O)c2cccc(C(F)(F)F)n2)cc2cn([C@H]3CC[C@H](CN4CC[C@H](c5cccc6c5n(C)c(=O)n6C5CCC(=O)NC5=O)[C@@H](F)C4)CC3)nc12] |

TABLE 1-continued

Exemplary Compounds

| I-# | Structure |
|---|---|
| I-775 | 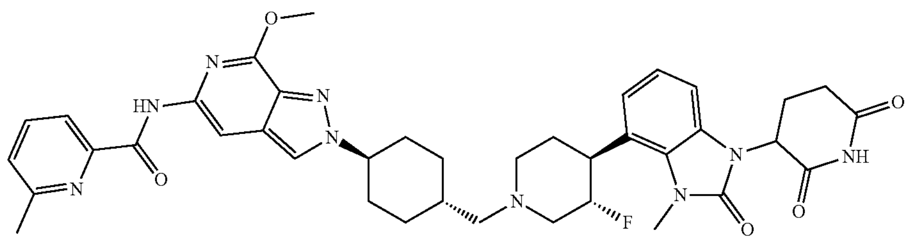 [SMILES: COc1nc(NC(=O)c2cccc(C)n2)cc2cn([C@H]3CC[C@H](CN4CC[C@@H](c5cccc6c5n(C)c(=O)n6C5CCC(=O)NC5=O)[C@H](F)C4)CC3)nc12] |
| I-776 | 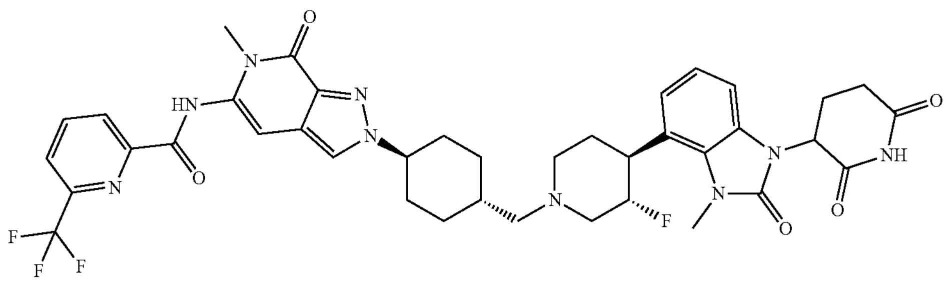 [SMILES: Cn1c(NC(=O)c2cccc(C(F)(F)F)n2)cc2cn([C@H]3CC[C@H](CN4CC[C@@H](c5cccc6c5n(C)c(=O)n6C5CCC(=O)NC5=O)[C@H](F)C4)CC3)nc2c1=O] |
| I-777 | 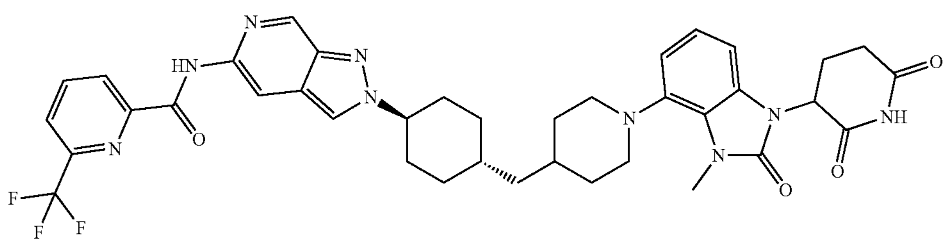 [SMILES: Cn1c(=O)n(C2CCC(=O)NC2=O)c2cccc(N3CCC(C[C@H]4CC[C@H](n5cc6cc(NC(=O)c7cccc(C(F)(F)F)n7)ncc6n5)CC4)CC3)c21] |
| I-778 | 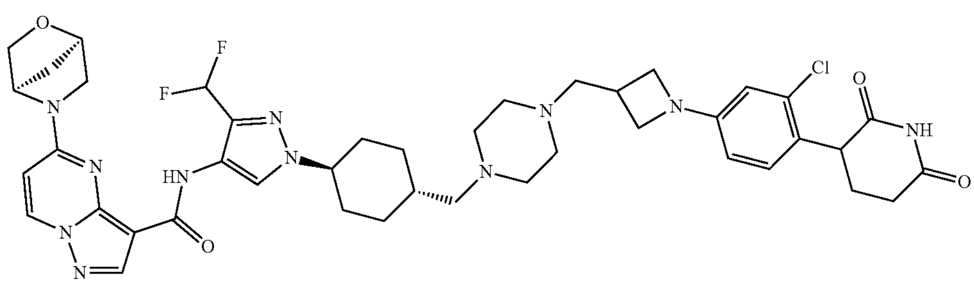 [SMILES: O=C1CCC(c2ccc(N3CC(CN4CCN(C[C@H]5CC[C@H](n6cc(NC(=O)c7cnn8ccc(N9C[C@H]%10C[C@@H]9CO%10)nc78)c(C(F)F)n6)CC5)CC4)C3)cc2Cl)C(=O)N1] |
| I-779 | 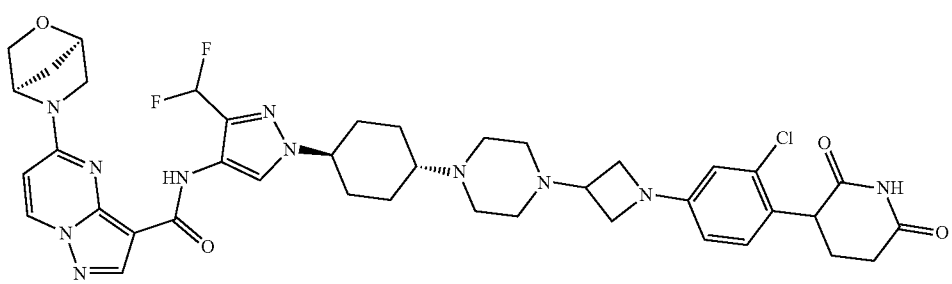 [SMILES: O=C1CCC(c2ccc(N3CC(N4CCN([C@H]5CC[C@H](n6cc(NC(=O)c7cnn8ccc(N9C[C@H]%10C[C@@H]9CO%10)nc78)c(C(F)F)n6)CC5)CC4)C3)cc2Cl)C(=O)N1] |

TABLE 1-continued

Exemplary Compounds

| I-# | Structure |
|---|---|
| I-780 | 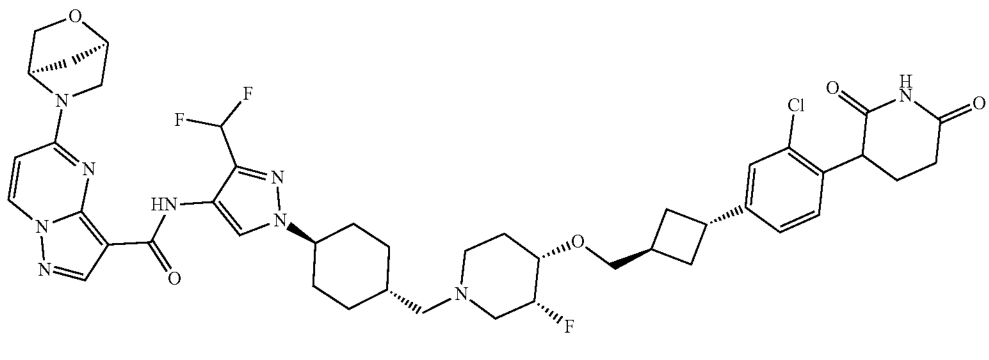 [SMILES: O=C1CCC(c2ccc([C@H]3C[C@H](CO[C@H]4CCN(C[C@H]5CC[C@H](n6cc(NC(=O)c7cnn8ccc(N9C[C@H]%10C[C@@H]9CO%10)nc78)c(C(F)F)n6)CC5)C[C@H]4F)C3)cc2Cl)C(=O)N1] |
| I-781 | 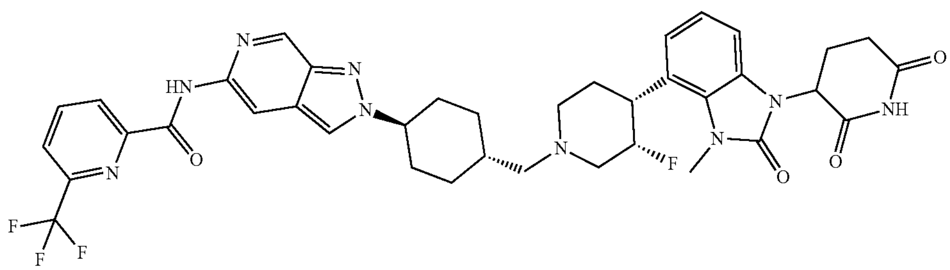 [SMILES: Cn1c(=O)n(C2CCC(=O)NC2=O)c2cccc([C@H]3CCN(C[C@H]4CC[C@H](n5cc6cc(NC(=O)c7cccc(C(F)(F)F)n7)ncc6n5)CC4)C[C@H]3F)c21] |
| I-782 | 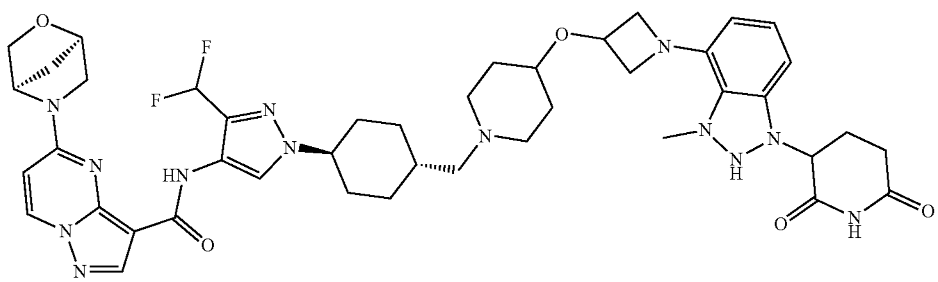 [SMILES: CN1NN(C2CCC(=O)NC2=O)c2cccc(N3CC(OC4CCN(C[C@H]5CC[C@H](n6cc(NC(=O)c7cnn8ccc(N9C[C@H]%10C[C@@H]9CO%10)nc78)c(C(F)F)n6)CC5)CC4)C3)c21] |
| I-783 | 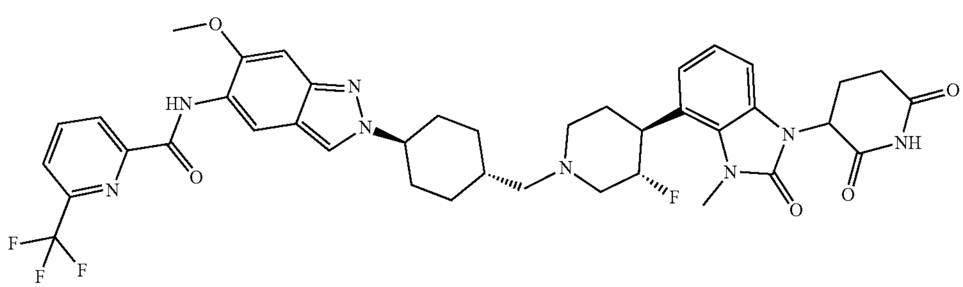 [SMILES: COc1cc2nn([C@H]3CC[C@H](CN4CC[C@@H](c5cccc6c5n(C)c(=O)n6C5CCC(=O)NC5=O)[C@H](F)C4)CC3)cc2cc1NC(=O)c1cccc(C(F)(F)F)n1] |
| I-784 | 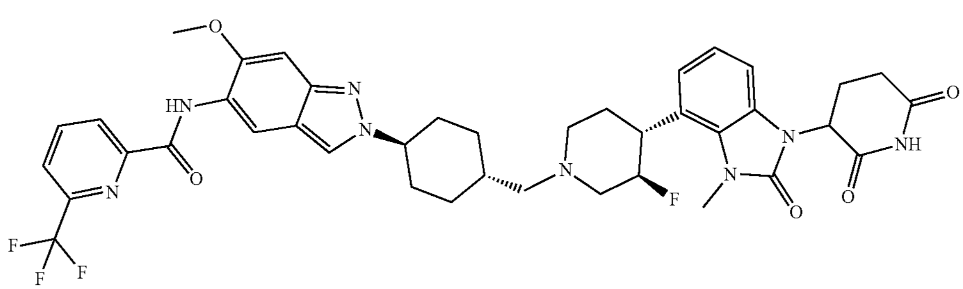 [SMILES: COc1cc2nn([C@H]3CC[C@H](CN4CC[C@H](c5cccc6c5n(C)c(=O)n6C5CCC(=O)NC5=O)[C@@H](F)C4)CC3)cc2cc1NC(=O)c1cccc(C(F)(F)F)n1] |

TABLE 1-continued

Exemplary Compounds

| I-# | Structure |
|---|---|
| I-785 | 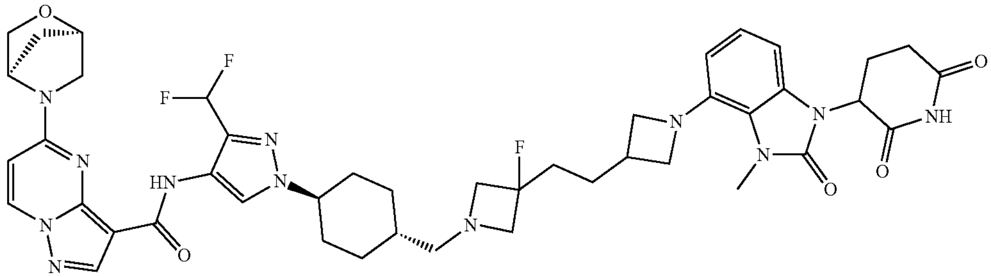 [SMILES: Cn1c(=O)n(C2CCC(=O)NC2=O)c2cccc(N3CC(CCC4(F)CN(C[C@H]5CC[C@H](n6cc(NC(=O)c7cnn8ccc(N9C[C@H]%10C[C@@H]9CO%10)nc78)c(C(F)F)n6)CC5)C4)C3)c21] |
| I-786 | 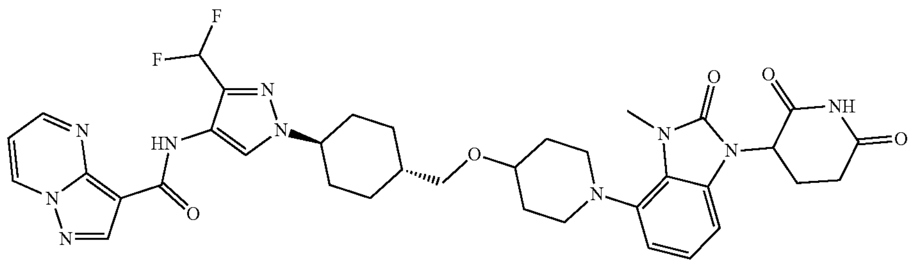 [SMILES: Cn1c(=O)n(C2CCC(=O)NC2=O)c2cccc(N3CCC(OC[C@H]4CC[C@H](n5cc(NC(=O)c6cnn7cccnc67)c(C(F)F)n5)CC4)CC3)c21] |
| I-787 | 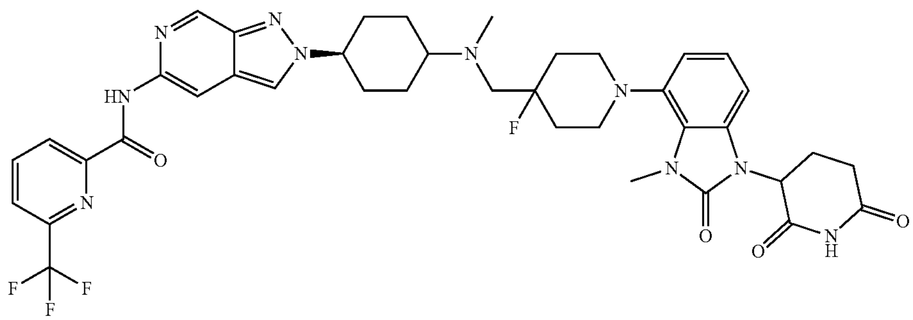 |
| I-788 | 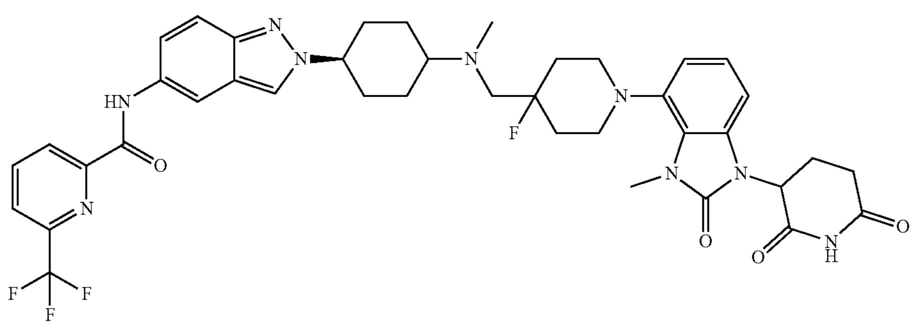 |
| I-789 | 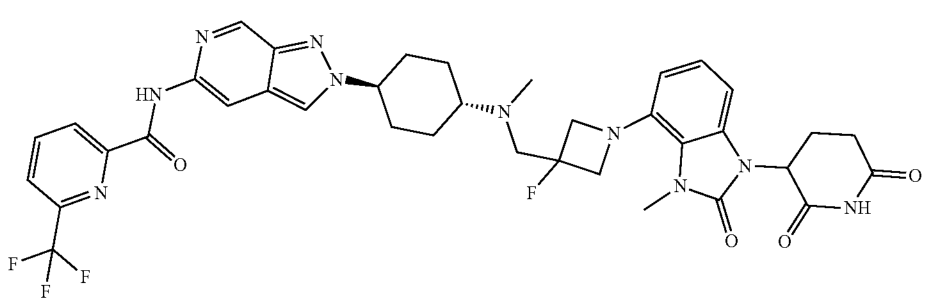 [SMILES: Cn1c(=O)n(C2CCC(=O)NC2=O)c2cccc(N3CC(F)(CN(C)[C@H]4CC[C@H](n5cc6cc(NC(=O)c7cccc(C(F)(F)F)n7)ncc6n5)CC4)C3)c21] |

TABLE 1-continued
Exemplary Compounds
| I-# | Structure |
|---|---|
| I-790 | 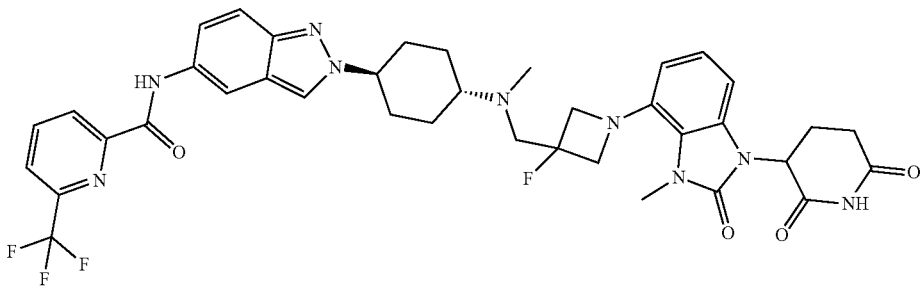 [SMILES: Cn1c(=O)n(C2CCC(=O)NC2=O)c2cccc(N3CC(F)(CN(C)[C@H]4CC[C@H](n5cc6cc(NC(=O)c7cccc(C(F)(F)F)n7)ccc6n5)CC4)C3)c21] |
| I-791 | 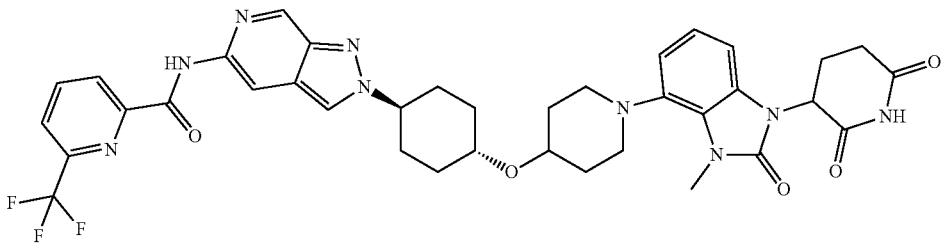 [SMILES: Cn1c(=O)n(C2CCC(=O)NC2=O)c2cccc(N3CCC(O[C@H]4CC[C@H](n5cc6cc(NC(=O)c7cccc(C(F)(F)F)n7)ncc6n5)CC4)CC3)c21] |
| I-792 | 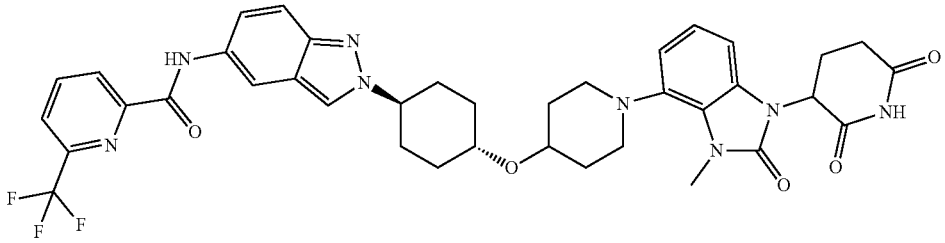 [SMILES: Cn1c(=O)n(C2CCC(=O)NC2=O)c2cccc(N3CCC(O[C@H]4CC[C@H](n5cc6cc(NC(=O)c7cccc(C(F)(F)F)n7)ccc6n5)CC4)CC3)c21] |
| I-793 | 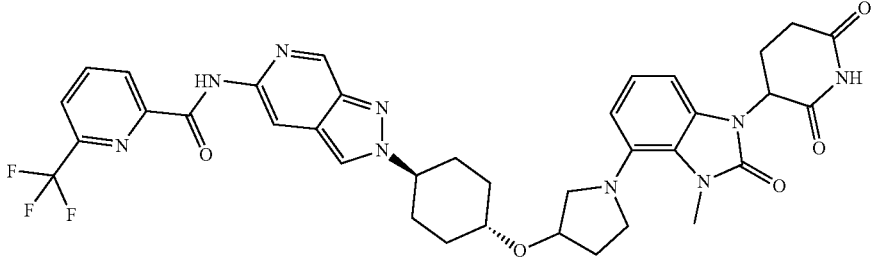 [SMILES: Cn1c(=O)n(C2CCC(=O)NC2=O)c2cccc(N3CCC(O[C@H]4CC[C@H](n5cc6cc(NC(=O)c7cccc(C(F)(F)F)n7)ncc6n5)CC4)C3)c21] |
| I-794 | 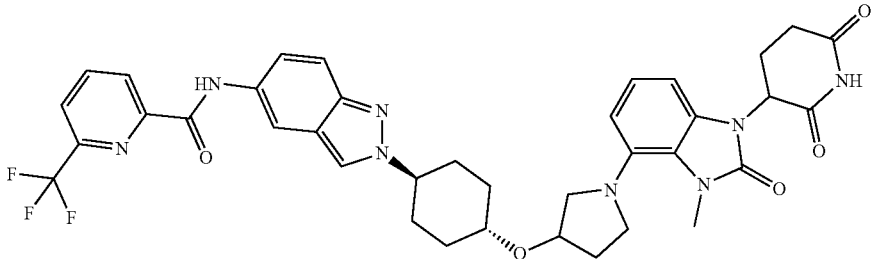 [SMILES: Cn1c(=O)n(C2CCC(=O)NC2=O)c2cccc(N3CCC(O[C@H]4CC[C@H](n5cc6cc(NC(=O)c7cccc(C(F)(F)F)n7)ccc6n5)CC4)C3)c21] |

TABLE 1-continued

Exemplary Compounds

| I-# | Structure |
|---|---|
| I-795 | 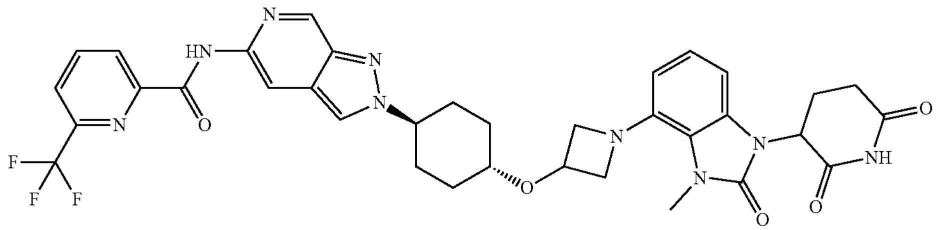 [SMILES: Cn1c(=O)n(C2CCC(=O)NC2=O)c2cccc(N3CC(O[C@H]4CC[C@H](n5cc6cc(NC(=O)c7cccc(C(F)(F)F)n7)ncc6n5)CC4)C3)c21] |
| I-796 | 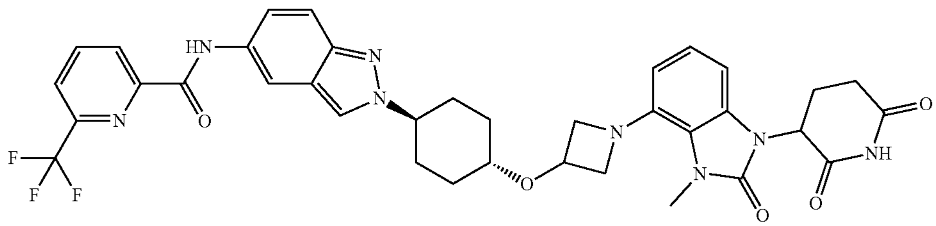 [SMILES: Cn1c(=O)n(C2CCC(=O)NC2=O)c2cccc(N3CC(O[C@H]4CC[C@H](n5cc6cc(NC(=O)c7cccc(C(F)(F)F)n7)ccc6n5)CC4)C3)c21] |

In some embodiments, the present invention provides a compound set forth in Table 1, above, or a pharmaceutically acceptable salt thereof.

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that it is effective to measurably degrade and/or inhibit an IRAK protein kinase, or a mutant thereof, in a biological sample or in a patient. In certain embodiments, the amount of compound in compositions of this invention is such that it is effective to measurably degrade and/or inhibit an IRAK protein kinase, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily or degratorily active metabolite or residue thereof.

As used herein, the term "inhibitorily active metabolite or residue thereof" means that a metabolite or residue thereof is also an inhibitor of an IRAK protein kinase, or a mutant thereof.

As used herein, the term "degratorily active metabolite or residue thereof" means that a metabolite or residue thereof is also a degrader of an IRAK protein kinase, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the degradation and/or inhibition of kinase activity of one or more enzymes.

Examples of kinases that are degraded and/or inhibited by the compounds and compositions described herein and against which the methods described herein are useful include those of the interleukin-1 receptor-associated kinase (IRAK) family of kinases, the members of which include IRAK-1, IRAK-2, and IRAK-4, or a mutant thereof. Li et al., "IRAK-4: A novel member of the IRAK family with the properties of an IRAK-kinase," *PNAS* 2002, 99(8), 5567-5572, Flannery et al., "The interleukin-1 receptor-associated kinases: Critical regulators of innate immune signaling" *Biochem Pharm* 2010, 80(12), 1981-1991 incorporated by reference in its entirety.

The activity of a compound utilized in this invention as a degrader and/or inhibitor of IRAK-1, IRAK-2, and/or IRAK-4, or a mutant thereof, may be assayed in vitro, in vivo or in a cell line. In vitro assays include assays that determine inhibition of either the phosphorylation activity and/or the subsequent functional consequences, or ATPase activity of activated IRAK-1, IRAK-2, and/or IRAK-4, or a mutant thereof. Alternate in vitro assays quantitate the ability of the inhibitor to bind to IRAK-1, IRAK-2 and/or IRAK-4. Inhibitor binding may be measured by radiolabeling the inhibitor prior to binding, isolating the inhibitor/IRAK-1, inhibitor/IRAK-2, or inhibitor/IRAK-4 complex and determining the amount of radiolabel bound. Alternatively, inhibitor binding may be determined by running a competition experiment where new inhibitors are incubated with IRAK-1, IRAK-2, and/or IRAK-4 bound to known radioligands. Representative in vitro and in vivo assays useful in assaying an IRAK-4 inhibitor include those described and disclosed in, e.g., Kim et al., "A critical role for IRAK4 kinase activity in Toll-like receptor-mediated innate immunity," *J. Exp. Med.* 2007 204(5), 1025-1036;

Lebakken et al., "A Fluorescence Lifetime Based Binding Assay to Characterize Kinase Inhibitors," *J. Biomol. Screen.* 2007, 12(6), 828-841; Maschera et al., "Overexpression of an enzymatically inactive interleukin-1-receptor-associated kinase activates nuclear factor-KB," *Biochem. J.* 1999, 339, 227-231; Song et al., "The kinase activities of interleukin-e receptor associated kinase (IRAK)-1 and 4 are redundant in the control of inflammatory cytokine expression in human cells," *Mol. Immunol.* 2009, 46, 1458-1466, the entirety of each of which is herein incorporated by reference. Detailed conditions for assaying a compound utilized in this invention as a degrader and/or inhibitor of IRAK-1, IRAK-2, and/or IRAK-4, or a mutant thereof, are set forth in the Examples below.

The best characterized member of the IRAK family is the serine/threonine kinase IRAK-4. IRAK-4 is implicated in signaling innate immune responses from Toll-like receptors (TLRs) and Toll/IL-1 receptors (TIRs).

Innate immunity detects pathogens through the recognition of pathogen-associated molecular patterns by TLRs, when then links to the adaptive immune response. TLRs recognize conserved structures of both microbes and endogenous molecules. TLRs which recognize bacterial and fungal components are located on the cell surface, whereas TLRs which recognize viral or microbial nucleic acids are localized to intracellular membranes such as endosomes and phagosomes. Cell surface TLRs can be targeted by small molecules and antibodies, whereas intracellular TLRs require targeting with oligonucleotides.

TLRs mediate the innate immune response by upregulating the expression of inflammatory genes in multiple target cells. See, e.g., Sen et al., "Transcriptional signaling by double-stranded RNA: role of TLR3," *Cytokine & Growth Factor Rev.* 2005, 16, 1-14, incorporated by reference in its entirety. While TLR-mediated inflammatory response is critical for innate immunity and host defense against infections, uncontrolled inflammation is detrimental to the host leading to sepsis and chronic inflammatory diseases, such as chronic arthritis, atherosclerosis, multiple sclerosis, cancers, autoimmune disorders such as rheumatoid arthritis, lupus, asthma, psoriasis, and inflammatory bowel diseases.

Upon binding of a ligand, most TLRs recruit the adaptor molecule MyD88 through the TIR domain, mediating the MyD88-dependent pathway. MyD88 then recruits IRAK-4, which engages with the nuclear factor-κB (NF-κB), mitogen-activated protein (MAP) kinase and interferon-regulatory factor cascades and leads to the induction of pro-inflammatory cytokines. The activation of NF-κB results in the induction of inflammatory cytokines and chemokines, such as TNF-α, IL-1 α, IL-6 and IL-8. The kinase activity of IRAK-4 has been shown to play a critical role in the TLR-mediated immune and inflammatory responses. IRAK4 is a key mediator of the innate immune response orchestrated by interleukin-1 receptor (IL-1R), interleukin-18 receptor (IL-18R), IL-33 receptor (IL-33R), and Toll-like receptors (TLRs). Inactivation of IRAK-1 and/or IRAK-4 activity has been shown to result in diminished production of cytokines and chemokines in response to stimulation of IL-1 and TLR ligands. See, e.g., Picard et al., "Clinical features and outcome of patients with IRAK-4 and MyD88 deficiency," Medicine (Baltimore), 2010, 89(6), 043-25; Li, "IRAK4 in TLR/IL-1R signaling: Possible clinical applications," *Eur J. Immunology* 2008, 38:614-618; Cohen et al., "Targeting protein kinases for the development of anti-inflammatory drugs," *Curr Opin. Cell Bio.* 2009, 21:317-324; Flannery et al., "The interleukin-1 receptor-associated kinases: Critical regulators of innate immune signalling," *Biochem. Pharm.* 2010, 80(12), 1981-1991; Gottipati et al., "IRAK1: A critical signaling mediator of innate immunity," *Cellular Signaling* 2008, 20, 269-276; Kim et al., "A critical role for IRAK4 kinase activity in Toll-like receptor-mediated innate immunity," *J. Exp. Med.* 2007 204(5), 1025-1036; Koziczak-Holbro et al., "IRAK-4 Kinase Activity Is Required for Interleukin-1 (IL-1) Receptor- and Toll-like Receptor 7-mediated Signaling and Gene Expression," *J. Biol. Chem.* 2007, 282(18), 13552-13560; Kubo-Murai et al., "IRAK-4-dependent Degradation of IRAK-1 is a Negative Feedback Signal for TLR-mediated NF-κB Activation," *J Biochem.* 2008, 143, 295-302; Maschera et al., "Overexpression of an enzymatically inactive interleukin-1-receptor-associated kinase activates nuclear factor-KB," *Biochem. J.* 1999, 339, 227-231; Lin et al., "Helical assembly in the MyD88-IRAK4-IRAK2 complex in TLR/IL-1R signalling," *Nature* 2010, 465(17), 885-891; Suzuki et al., "IRAK-4 as the central TIR signaling mediator in innate immunity," *TRENDS in Immunol.* 2002, 23(10), 503-506; Suzuki et al., "Severe impairment of interleukin-1 and Toll-like receptor signalling in mice lacking IRAK-4," *Nature* 2002, 416, 750-754; Swantek et al., "IL-1 Receptor-Associated Kinase Modulates Host Responsiveness to Endotoxin," *J. Immunol.* 2000, 164, 4301-4306; Hennessy, E., et al., "Targeting Toll-like receptors: emerging therapeutics?" *Nature Reviews*, vol. 9, pp: 293-307 (2010); Dinarello, C. "Interleukin-18 and the Pathogenesis of Inflammatory Diseases," *Seminars in Nephrology*, vol. 27, no. 1, pp: 98-114 (2007), the entirety of each of which is herein incorporated by reference. In fact, knockdown mice that express a catalytically inactive mutant IRAK-4 protein are completely resistant to septic shock and show impaired IL-1 activity. Moreover, these mice are resistant to joint and bone inflammation/destruction in an arthritis model, suggesting that IRAK-4 may be targeted to treat chronic inflammation. Further, while IRAK-4 appears to be vital for childhood immunity against some pyogenic bacteria, it has been shown to play a redundant role in protective immunity to most infections in adults, as demonstrated by one study in which patients older than 14 lacking IRAK-4 activity exhibited no invasive infections. Cohen et al., "Targeting protein kinases for the development of anti-inflammatory drugs," *Curr Opin. Cell Bio.* 2009, 21:317-324; Ku et al., "Selective predisposition to bacterial infections in IRAK-4-deficient children: IRAK-4-dependent TLRs are otherwise redundant in protective immunity," *J. Exp. Med.* 2007, 204(10), 2407-2422; Picard et al., "Inherited human IRAK-4 deficiency: an update," *Immunol. Res.* 2007, 38, 347-352; Song et al., "The kinase activities of interleukin-e receptor associated kinase (IRAK)-1 and 4 are redundant in the control of inflammatory cytokine expression in human cells," *Mol. Immunol.* 2009, 46, 1458-1466; Rokosz, L. et al., "Kinase inhibitors as drugs for chronic inflammatory and immunological diseases: progress and challenges," *Expert Opinions on Therapeutic Targets,* 12(7), pp: 883-903 (2008); Gearing, A. "Targeting toll-like receptors for drug development: a summary of commercial approaches," *Immunology and Cell Biology,* 85, pp: 490-494 (2007); Dinarello, C. "IL-1: Discoveries, controversies and future directions," *European Journal of Immunology,* 40, pp: 595-653 (2010), the entirety of each of which is herein incorporated by reference. Because TLR activation triggers IRAK-4 kinase activity, IRAK-4 inhibition presents an attractive target for treating the underlying causes of inflammation in countless diseases.

Representative IRAK-4 inhibitors include those described and disclosed in e.g., Buckley et al., *Bioorg. Med. Chem. Lett.* 2008, 18, 3211-3214; Buckley et al., *Bioorg. Med.*

Chem. Lett. 2008, 18, 3291-3295; Buckley et al., *Bioorg. Med. Chem. Lett.* 2008, 18, 3656-3660; Powers et al., "Discovery and initial SAR of inhibitors of interleukin-1 receptor-associated kinase-4," *Bioorg. Med. Chem. Lett.* 2006, 16, 2842-2845; Wng et al., "IRAK-4 Inhibitors for Inflammation," *Curr Topics in Med. Chem.* 2009, 9, 724-737, the entirety of each of which is herein incorporated by reference.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are degraders and/or inhibitors of one of more of IRAK-1, IRAK-2, and/or IRAK-4 and are therefore useful for treating one or more disorders associated with activity of one or more of IRAK-1, IRAK-2, and/or IRAK-4. Thus, in certain embodiments, the present invention provides a method for treating a IRAK-1-mediated, a IRAK-2-mediated, and/or a IRAK-4-mediated disorder comprising the step of administering to a patient in need thereof a compound of the present invention, or pharmaceutically acceptable composition thereof.

As used herein, the terms "IRAK-1-mediated", "IRAK-2-mediated", and/or "IRAK-4-mediated" disorders, diseases, and/or conditions as used herein means any disease or other deleterious condition in which one or more of IRAK-1, IRAK-2, and/or IRAK-4, or a mutant thereof, are known to play a role. Accordingly, another embodiment of the present invention relates to treating or lessening the severity of one or more diseases in which one or more of IRAK-1, IRAK-2, and/or IRAK-4, or a mutant thereof, are known to play a role.

In some embodiments, the present invention provides a method for treating one or more disorders, diseases, and/or conditions wherein the disorder, disease, or condition is a cancer, a neurodegenerative disorder, a viral disease, an autoimmune disease, an inflammatory disorder, a hereditary disorder, a hormone-related disease, a metabolic disorder, conditions associated with organ transplantation, immunodeficiency disorders, a destructive bone disorder, a proliferative disorder, an infectious disease, a condition associated with cell death, thrombin-induced platelet aggregation, liver disease, pathologic immune conditions involving T cell activation, a cardiovascular disorder, or a CNS disorder.

Diseases and conditions treatable according to the methods of this invention include, but are not limited to, cancer (see, e.g., Ngo, V. et al., "Oncogenically active MYD88 mutations in human lymphoma," *Nature*, vol. 000, pp: 1-7 (2010); Lust, J. et al., "Induction of a Chronic Disease State in patients With Smoldering of Indolent Multiple Myeloma by Targeting Interleukin 1ß-Induced Interleukin 6 Production and the Myeloma Proliferative Component," *Mayo Clinic Proceedings*, 84(2), pp: 114-122 (2009)), diabetes, cardiovascular disease, viral disease, autoimmune diseases such as lupus (see, e.g., Dinarello, C. "Interleukin-18 and the Pathogenesis of Inflammatory Diseases," *Seminars in Nephrology*, vol. 27, no. 1, pp: 98-114 (2007); Cohen et al., "Targeting protein kinases for the development of anti-inflammatory drugs," *Curr Opin. Cell Bio.* 2009, 21:317-324) and rheumatoid arthritis (see, e.g., Geyer, M. et al., "Actual status of antiinterleukin-1 therapies in rheumatic diseases," Current Opinion in Rheumatology, 22, pp: 246-251 (2010)), autoinflammatory syndromes (see, e.g., Hoffman, H. et al., "Efficacy and Safety of Rilonacept (Interleukin-1 Trap) in Patients with Cryopyrin-Associated Periodic Syndromes," *Arthritis & Rheumatism*, vol. 58, no. 8, pp: 2443-2452 (2008)), atherosclerosis, psoriasis, allergic disorders, inflammatory bowel disease (see, e.g., Cario, E. "Therapeutic Impact of Toll-like Receptors on Inflammatory Bowel Diseases: A Multiple-edged Sword," *Inflamm. Bowel Dis.*, 14, pp: 411-421 (2008)), inflammation (see, e.g., Dinarello, C. "Interleukin 1 and interleukin 18 as mediators of inflammation and the aging process," The American *Journal of Clinical Nutrition*, 83, pp: 447S-455S (2006)), acute and chronic gout and gouty arthritis (see, e.g., Terkeltaub, R. "Update on gout: new therapeutic strategies and options," *Nature*, vol. 6, pp: 30-38 (2010); Weaver, A. "Epidemiology of gout," *Cleveland Clinic Journal of Medicine*, vol. 75, suppl. 5, pp: S9-S12 (2008); Dalbeth, N. et al., "Hyperuricaemia and gout: state of the art and future perspectives," *Annals of Rheumatic Diseases*, 69, pp: 1738-1743 (2010); Martinon, F. et al., "Gout-associated uric acid crystals activate the NALP3 inflammasome," *Nature*, vol. 440, pp: 237-241 (2006); So, A. et al., "A pilot study of IL-1 inhibition by anakinra in acute gout," *Arthritis Research & Therapy*, vol. 9, no. 2, pp: 1-6 (2007); Terkeltaub, R. et al., "The interleukin 1 inhibitor rilonacept in treatment of chronic gouty arthritis: results of a placebo-controlled, monosequence crossover, non-randomised, single-blind pilot study," *Annals of Rheumatic Diseases*, 68, pp: 1613-1617 (2009); Torres, R. et al., "Hyperalgesia, synovitis and multiple biomarkers of inflammation are suppressed by interleukin 1 inhibition in a novel animal model of gouty arthritis," *Annals of Rheumatic Diseases*, 68, pp: 1602-1608 (2009)), neurological disorders, metabolic syndrome (see, e.g., Troseid, M. "The role of interleukin-18 in the metabolic syndrome," *Cardiovascular Diabetology*, 9:11, pp: 1-8 (2010)), immunodeficiency disorders such as AIDS and HIV (see, e.g., Iannello, A. et al., "Role of Interleukin-18 in the Development and Pathogenesis of AIDS," AIDS Reviews, 11, pp: 115-125 (2009)), destructive bone disorders (see, e.g., Hennessy, E., et al., "Targeting Toll-like receptors: emerging therapeutics?" *Nature Reviews*, vol. 9, pp: 293-307 (2010), osteoarthritis, proliferative disorders, Waldenström's Macroglobulinemia (see, e.g., Treon, et al., "Whole genome sequencing reveals a widely expressed mutation (MYD88 L265P) with oncogenic activity in Waldenström's Macroglobulinemia" 53rd ASH Annual Meeting; Xu, et al., "A somatic variant in MYD88 (L256P) revealed by whole genome sequencing differentiates lymphoplasmacytic lymphoma from marginal zone lymphomas" 53rd ASH Annual Meeting; Yang et al., "Disruption of MYD88 pathway signaling leads to loss of constitutive IRAK1, NK-kB and JAK/STAT signaling and induces apoptosis of cells expressing the MYD88 L265P mutation in Waldenström's Macroglobulinemia" 53rd ASH Annual Meeting; Iriyama et al., "Clinical significance of genetic mutations of CD79B, CARD11, MYD88, and EZH2 genes in diffuse large B-cell lymphoma patients" 53rd ASH Annual Meeting; infectious diseases, conditions associated with cell death, pathologic immune conditions involving T cell activation, and CNS disorders in a patient. In one embodiment, a human patient is treated with a compound of the current invention and a pharmaceutically acceptable carrier, adjuvant, or vehicle, wherein said compound is present in an amount to measurably degrade and/or inhibit IRAK-1 only, IRAK-2-only, IRAK-4-only and/or IRAK1 and IRAK4 kinase activity.

Compounds of the current invention are useful in the treatment of a proliferative disease selected from a benign or malignant tumor, solid tumor, carcinoma of the brain, kidney, liver, adrenal gland, bladder, breast, stomach, gastric tumors, ovaries, colon, rectum, prostate, pancreas, lung, vagina, cervix, testis, genitourinary tract, esophagus, larynx, skin, bone or thyroid, sarcoma, glioblastomas, neuroblastomas, multiple myeloma, gastrointestinal cancer, especially colon carcinoma or colorectal adenoma, a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, Hodgkins and Non-Hodgkins, a mammary carcinoma, follicular carcinoma, undifferentiated carcinoma, papillary carcinoma, seminoma, melanoma, an IL-1 driven disorder, an MyD88 driven disorder, Smoldering of indolent multiple myeloma, or hematological malignancies (including leukemia, diffuse large B-cell lymphoma (DLBCL), ABC DLBCL, chronic lymphocytic leukemia (CLL), chronic lymphocytic lymphoma, primary effusion lymphoma, Burkitt lymphoma/leukemia, acute lymphocytic leukemia, B-cell prolymphocytic leukemia, lymphoplasmacytic lymphoma, Waldenström's macroglobulinemia (WM), splenic marginal zone lymphoma, multiple myeloma, plasmacytoma, intravascular large B-cell lymphoma, AML, MDS).

In some embodiments the proliferative disease which can be treated according to the methods of this invention is an MyD88 driven disorder. In some embodiments, the MyD88 driven disorder which can be treated according to the methods of this invention is selected from ABC DLBCL, primary CNS lymphomas, primary extranodal lymphomas, Waldenström's macroglobulinemia, Hodgkin's lymphoma, primary cutaneous T-cell lymphoma and chronic lymphocytic leukemia.

In some embodiments the proliferative disease which can be treated according to the methods of this invention is an IL-1 driven disorder. In some embodiments the IL-1 driven disorder is Smoldering of indolent multiple myeloma.

Compounds according to the invention are useful in the treatment of inflammatory or obstructive airways diseases, resulting, for example, in reduction of tissue damage, airways inflammation, bronchial hyperreactivity, remodeling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics.

Compounds according to the invention are useful in the treatment of heteroimmune diseases. Examples of such heteroimmune diseases include, but are not limited to, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, such as therapy for or intended to restrict or abort symptomatic attack when it occurs, for example antiinflammatory or bronchodilatory. Prophylactic benefit in asthma may in particular be apparent in subjects prone to "morning dipping". "Morning dipping" is a recognized asthmatic syndrome, common to a substantial percentage of asthmatics and characterised by asthma attack, e.g. between the hours of about 4 to 6 am, i.e. at a time normally substantially distant form any previously administered symptomatic asthma therapy.

Compounds of the current invention can be used for other inflammatory or obstructive airways diseases and conditions to which the present invention is applicable and include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, but not limited to, acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

With regard to their anti-inflammatory activity, in particular in relation to inhibition of eosinophil activation, compounds of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma, eosinophilic asthma, eosinophilic COPD, and eosinophil-related disorders affecting the airways occasioned by drug-reaction.

Compounds of the invention are also useful in the treatment of inflammatory or allergic conditions of the skin, for example psoriasis, generalized pustular psoriasis (GPP), psoriasis vulgaris, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, systemic lupus erythematosus, *Pemphigus vulgaris, Pemphigus foliaceus*, paraneoplastic pemphigus, epidermolysis bullosa acquisita, acne vulgaris, hidradenitis suppurativa, Sweet syndrome, pyoderma gangrenosum, and other inflammatory or allergic conditions of the skin.

Compounds of the invention may also be used for the treatment of other diseases or conditions, such as diseases or conditions having an inflammatory component, for example, treatment of diseases and conditions of the eye such as ocular allergy, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca and vernal keratoconjunctivitis, interstitial lung fibrosis, psoriatic arthritis, systemic juvenile idiopathic arthritis, cryopyrin-associated periodic syndrome, nephritis, vasculitis, diverticulitis, interstitial cystitis, glomerulonephritis (with and without nephrotic syndrome, e.g. including idiopathic nephrotic syndrome or minal change nephropathy), chronic granulomatous disease, endometriosis, leptospiriosis renal disease, glaucoma, retinal disease, ageing, headache, pain, complex regional pain syndrome, cardiac hypertrophy, musclewasting, catabolic disorders, obesity, fetal growth retardation, hyperchlolesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, Type 1 diabetes, or Type 2 diabetes, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In some embodiments the inflammatory disease which can be treated according to the methods of this invention is an disease of the skin. In some embodiments, the inflammatory disease of the skin is selected from contact dermatitis, atopic dermatitis, alopecia areata, erythema multiforma, dermatitis herpetiformis, scleroderma, vitiligo, hypersensitivity angiitis, urticaria, bullous pemphigoid, pemphigus vulgaris, *Pemphigus foliaceus*, paraneoplastic pemphigus, epidermolysis bullosa acquisita, hidradenitis suppurativa, and other inflammatory or allergic conditions of the skin.

In some embodiments the inflammatory disease which can be treated according to the methods of this invention is selected from acute and chronic gout, chronic gouty arthritis, psoriasis, psoriatic arthritis, rheumatoid arthritis, juvenile rheumatoid arthritis, systemic juvenile idiopathic arthritis (SJIA), cryopyrin associated periodic syndrome (CAPS), adult onset Still's disease, macrophage activation syndrome (MAS), primary and secondary hemophagocytic lymphohistiocytosis (HLH), familial Mediterranean fever, NLRP12 autoinflammatory syndrome, and osteoarthritis.

In some embodiments the inflammatory disease which can be treated according to the methods of this invention is a TH17 mediated disease. In some embodiments the TH17 mediated disease is selected from Systemic lupus erythematosus, Multiple sclerosis, psoriasis vulgaris, hidradenitis suppurativa, and inflammatory bowel disease (including Crohn's disease or ulcerative colitis).

In some embodiments the inflammatory disease which can be treated according to the methods of this invention is selected from Sjogren's syndrome, allergic disorders, osteoarthritis, conditions of the eye such as ocular allergy, conjunctivitis, keratoconjunctivitis sicca and vernal conjunctivitis, and diseases affecting the nose such as allergic rhinitis or chronic rhinosinusitis with nasal polyps (CRSwNP).

In some embodiments, the present invention provides a method of treating hidradenitis suppurativa in a patient in need thereof, comprising administering a compound of the present invention, or a pharmaceutically acceptable salt thereof.

In some embodiments, the present invention provides a method of treating atopic dermatitis in a patient in need thereof, comprising administering a compound of the present invention, or a pharmaceutically acceptable salt thereof.

In some embodiments, the present invention provides a method of treating rheumatoid arthritis in a patient in need thereof, comprising administering a compound of the present invention, or a pharmaceutically acceptable salt thereof.

Cardiovascular diseases which can be treated according to the methods of this invention include, but are not limited to, restenosis, cardiomegaly, atherosclerosis, myocardial infarction, ischemic stroke, congestive heart failure, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, and deep venous thrombosis.

In some embodiments, the neurodegenerative disease which can be treated according to the methods of this invention include, but are not limited to, Alzheimer's disease, Parkinson's disease, amyotrophic lateral sclerosis, Huntington's disease, cerebral ischemia, and neurodegenerative disease caused by traumatic injury, glutamate neurotoxicity, hypoxia, epilepsy, treatment of diabetes, metabolic syndrome, obesity, organ transplantation and graft versus host disease.

The loss of IRAK4 function results in decreased $A\beta$ levels in an in vivo murine model of Alzheimer's disease and was associated with diminished microgliosis and astrogliosis in aged mice. Analysis of microglia isolated from the adult mouse brain revealed an altered pattern of gene expression associated with changes in microglial phenotype that were associated with expression of IRF transcription factors that govern microglial phenotype. Further, loss of IRAK4 function also promoted amyloid clearance mechanisms, including elevated expression of insulin-degrading enzyme. Finally, blocking IRAK function restored olfactory behavior (Cameron et al. "Loss of Interleukin Receptor-Associated Kinase 4 Signaling Suppresses Amyloid Pathology and Alters Microglial Phenotype in a Mouse Model of Alzheimer's Disease" Journal of Neuroscience (2012) 32(43), 15112-15123).

In some embodiments the invention provides a method of treating, preventing or lessening the severity of Alzheimer's disease comprising administering to a patient in need thereof a provided compound or a pharmaceutically acceptable salt or composition thereof.

In some embodiments the invention provides a method of treating a disease condition commonly occurring in connection with transplantation. In some embodiments, the disease or condition commonly occurring in connection with transplantation is selected from organ transplantation, organ transplant rejection, and graft versus host disease.

In some embodiments the invention provides a method of treating a metabolic disease. In some embodiments the metabolic disease is selected from Type 1 diabetes, Type 2 diabetes, metabolic syndrome, and obesity.

In some embodiments the invention provides a method of treating a viral disease. In some embodiments, the viral infection is HIV infection.

Furthermore, the invention provides the use of a compound according to the definitions herein, or a pharmaceutically acceptable salt, or a hydrate or solvate thereof for the preparation of a medicament for the treatment of a proliferative disease, an inflammatory disease, an obstructive respiratory disease, a cardiovascular disease, a metabolic disease, a neurological disease, a neurodegenerative disease, a viral disease, or a disorder commonly occurring in connection with transplantation.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

In some embodiments, the present invention provides a method of treating a disclosed disease or condition comprising administering to a patient in need thereof an effective amount of a compound disclosed herein or a pharmaceutically acceptable salt thereof and co-administering simultaneously or sequentially an effective amount of one or more additional therapeutic agents, such as those described herein. In some embodiments, the method includes co-administering one additional therapeutic agent. In some embodiments, the method includes co-administering two additional therapeutic agents. In some embodiments, the combination of the disclosed compound and the additional therapeutic agent or agents acts synergistically.

Examples of agents the combinations of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

One or more other therapeutic agent may be administered separately from a compound or composition of the invention, as part of a multiple dosage regimen. Alternatively, one or more other therapeutic agents may be part of a single dosage form, mixed together with a compound of this invention in a single composition. If administered as a multiple dosage regime, one or more other therapeutic agent and a compound or composition of the invention may be administered simultaneously, sequentially or within a period of time from one another, for example within 1, 2, 3, 4, 5, 6, 7, 8, 9, 10, 11, 12, 13, 14, 15, 16, 17, 18, 20, 21, 22, 23, or 24 hours from one another. In some embodiments, one or more other therapeutic agent and a compound or composition of the invention are administered as a multiple dosage regimen within greater than 24 hours a parts.

In one embodiment, the present invention provides a composition comprising a provided compound or a pharmaceutically acceptable salt thereof and one or more additional therapeutic agents. The therapeutic agent may be administered together with a provided compound or a pharmaceutically acceptable salt thereof, or may be administered prior to or following administration of a provided compound or a pharmaceutically acceptable salt thereof. Suitable therapeutic agents are described in further detail below. In certain embodiments, a provided compound or a pharmaceutically acceptable salt thereof may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a provided compound or a pharmaceutically acceptable salt thereof may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating an inflammatory disease, disorder or condition by administering to a patient in need thereof a provided compound or a pharmaceutically acceptable salt thereof and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-Bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiment, the present invention provides a method of treating gout comprising administering to a patient in need thereof a provided compound or a pharmaceutically acceptable salt thereof and one or more additional therapeutic agents selected from non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol and febuxostat (Uloric®).

In another embodiment, the present invention provides a method of treating rheumatoid arthritis comprising administering to a patient in need thereof a provided compound or a pharmaceutically acceptable salt thereof and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a provided compound or a pharmaceutically acceptable salt thereof and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating lupus comprising administering to a patient in need thereof a provided compound or a pharmaceutically acceptable salt thereof and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating inflammatory bowel disease comprising administering to a patient in need thereof a provided compound or a pharmaceutically acceptable salt thereof and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a provided compound or a pharmaceutically acceptable salt thereof and one or more additional therapeutic agents selected from anti-IL-33 antibodies such as REGN3500 (SAR440340) or CNTO 7160, Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, cromolyn sodium (Intal®), methylxanthines such as theophylline (Theo-Dur®, Theolair®, Slo-Bid®, Uniphyl®, Theo-24®) and aminophylline, and IgE antibodies such as omalizumab (Xolair®).

In some embodiments, the present invention provides a method of treating COPD comprising administering to a patient in need thereof a provided compound or a pharmaceutically acceptable salt thereof and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theolair®, Slo-Bid®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, In some embodiments, the present invention provides a method of treating eosinophilic COPD comprising administering to a patient in need thereof a provided compound or a pharmaceutically acceptable salt thereof and one or more additional therapeutic agents selected from an anti-IL-33 antibody such as REGN3500 (SAR440340) or CNTO 7160. In some embodiments, the present invention provides a method of treating eosinophilic asthma comprising administering to a patient in need thereof a provided compound or a pharmaceutically acceptable salt thereof and one or more additional therapeutic agents selected from an anti-IL-33 antibody such as REGN3500 (SAR440340) or CNTO 7160.

In some embodiments, the present invention provides a method of treating HIV comprising administering to a patient in need thereof a provided compound or a pharmaceutically acceptable salt thereof and one or more additional therapeutic agents selected from nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), and combinations thereof.

In another embodiment, the present invention provides a method of treating a hematological malignancy comprising administering to a patient in need thereof a provided compound or a pharmaceutically acceptable salt thereof and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a TYK2 inhibitor, a PI3K inhibitor, a SYK inhibitor, and combinations thereof.

In another embodiment, the present invention provides a method of treating a solid tumor comprising administering to a patient in need thereof a provided compound or a pharmaceutically acceptable salt thereof and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a TYK2 inhibitor, a PI3K inhibitor, a SYK inhibitor, and combinations thereof.

In another embodiment, the present invention provides a method of treating a hematological malignancy comprising administering to a patient in need thereof a provided compound or a pharmaceutically acceptable salt thereof and a Hedgehog (Hh) signaling pathway inhibitor. In some embodiments, the hematological malignancy is DLBCL (Ramirez et al "Defining causative factors contributing in the activation of hedgehog signaling in diffuse large B-cell lymphoma" Leuk. Res. (2012), published online July 17, and incorporated herein by reference in its entirety).

In another embodiment, the present invention provides a method of treating diffuse large B-cell lymphoma (DLBCL) comprising administering to a patient in need thereof a provided compound or a pharmaceutically acceptable salt thereof and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In some embodiments, the present invention provides a method of treating DLBCL comprising administering to a patient in need thereof a provided compound or a pharmaceutically acceptable salt thereof and a CHOP (cyclophosphamide, Hydrodaunorubicin®, Oncovin®, and prednisone or prednisolone) or R-CHOP (rituximab, cyclophosphamide, Hydrodaunorubicin®, Oncovin®, and prednisone or prednisolone) chemotherapy regimen.

In some embodiments, the present invention provides a method of treating DLBCL comprising administering to a patient in need thereof a provided compound or a pharmaceutically acceptable salt thereof and a rituximab/bendamustine chemotherapy regimen.

In some embodiments, the present invention provides a method of treating DLBCL comprising administering to a patient in need thereof a provided compound or a pharmaceutically acceptable salt thereof and a BTK inhibitor (e.g., ibrutinib).

In some embodiments, the present invention provides a method of treating DLBCL comprising administering to a patient in need thereof a provided compound or a pharmaceutically acceptable salt thereof and an anti-CD20 antibody (e.g., rituximab).

In some embodiments, the present invention provides a method of treating DLBCL comprising administering to a patient in need thereof a provided compound or a pharmaceutically acceptable salt thereof and an anti-CD79B ADC (e.g., polatuzumab).

In some embodiments, the present invention provides a method of treating DLBCL comprising administering to a patient in need thereof a provided compound or a pharmaceutically acceptable salt thereof and a BCL2 inhibitor (e.g., venetoclax).

In some embodiments, the present invention provides a method of treating DLBCL comprising administering to a patient in need thereof a provided compound or a pharmaceutically acceptable salt thereof and lenalidomide or pomalidomide In some embodiments, the present invention provides a method of treating DLBCL comprising administering to a patient in need thereof a provided compound or a pharmaceutically acceptable salt thereof and a PI3K inhibitor (e.g., umbralisib).

In some embodiments, the present invention provides a method of treating a T-cell disease or deficiency describing herein comprising administering to a patient in need thereof a provided compound or a pharmaceutically acceptable salt thereof and a PI3K inhibitor (e.g., umbralisib).

In some embodiments, the present invention provides a method of treating DLBCL comprising administering to a patient in need thereof a provided compound or a pharmaceutically acceptable salt thereof and a protesome inhibitor (e.g., bortezomib).

In some embodiments, the present invention provides a method of treating a T-cell disease or deficiency describing herein comprising administering to a patient in need thereof a provided compound or a pharmaceutically acceptable salt thereof and a protesome inhibitor (e.g., bortezomib).

In another embodiment, the present invention provides a method of treating multiple myeloma comprising administering to a patient in need thereof a provided compound or a pharmaceutically acceptable salt thereof and one or more additional therapeutic agents selected from bortezomib (Velcade®), and dexamethasone (Decadron®), a hedgehog signaling inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating Waldenström's macroglobulinemia comprising administering to a patient in need thereof a provided compound or a pharmaceutically acceptable salt thereof and one or more additional therapeutic agents selected from chlorambucil (Leukeran®), cyclophosphamide (Cytoxan®, Neosar®), fludarabine (Fludara®), cladribine (Leustatin®), rituximab (Rituxan®), a hedgehog signaling inhibitor, a BTK inhibitor, a JAK/pan-JAK inhibitor, a TYK2 inhibitor, a PI3K inhibitor, and a SYK inhibitor.

In some embodiments, one or more other therapeutic agent is an antagonist of the hedgehog pathway. Approved hedgehog pathway inhibitors which may be used in the present invention include sonidegib (Odomzo®, Sun Pharmaceuticals); and vismodegib (Erivedge®, Genentech), both for treatment of basal cell carcinoma.

In some embodiments, one or more other therapeutic agent is a Poly ADP ribose polymerase (PARP) inhibitor. In some embodiments, a PARP inhibitor is selected from olaparib (Lynparza®, AstraZeneca); rucaparib (Rubraca®, Clovis Oncology); niraparib (Zejula®, Tesaro); talazoparib (MDV3800/BMN 673/LT00673, Medivation/Pfizer/Biomarin); veliparib (ABT-888, AbbVie); and BGB-290 (BeiGene, Inc.).

In some embodiments, one or more other therapeutic agent is a histone deacetylase (HDAC) inhibitor. In some embodiments, an HDAC inhibitor is selected from vorinostat (Zolinza®, Merck); romidepsin (Istodax®, Celgene); panobinostat (Farydak®, Novartis); belinostat (Beleodaq®, Spectrum Pharmaceuticals); entinostat (SNDX-275, Syndax Pharmaceuticals) (NCT00866333); and chidamide (Epidaza®, HBI-8000, Chipscreen Biosciences, China).

In some embodiments, one or more other therapeutic agent is a CDK inhibitor, such as a CDK4/CDK6 inhibitor. In some embodiments, a CDK 4/6 inhibitor is selected from palbociclib (Ibrance®, Pfizer); ribociclib (Kisqali®, Novartis); abemaciclib (Ly2835219, Eli Lilly); and trilaciclib (G1T28, G1 Therapeutics).

In some embodiments, one or more other therapeutic agent is a folic acid inhibitor. Approved folic acid inhibitors useful in the present invention include pemetrexed (Alimta®, Eli Lilly).

In some embodiments, one or more other therapeutic agent is a CC chemokine receptor 4 (CCR4) inhibitor. CCR4 inhibitors being studied that may be useful in the present invention include mogamulizumab (Poteligeo®, Kyowa Hakko Kirin, Japan).

In some embodiments, one or more other therapeutic agent is an isocitrate dehydrogenase (IDH) inhibitor. IDH inhibitors being studied which may be used in the present invention include AG120 (Celgene; NCT02677922); AG221

(Celgene, NCT02677922; NCT02577406); BAY1436032 (Bayer, NCT02746081); IDH305 (Novartis, NCT02987010).

In some embodiments, one or more other therapeutic agent is an arginase inhibitor. Arginase inhibitors being studied which may be used in the present invention include AEB1102 (pegylated recombinant arginase, Aeglea Biotherapeutics), which is being studied in Phase 1 clinical trials for acute myeloid leukemia and myelodysplastic syndrome (NCT02732184) and solid tumors (NCT02561234); and CB-1158 (Calithera Biosciences).

In some embodiments, one or more other therapeutic agent is a glutaminase inhibitor. Glutaminase inhibitors being studied which may be used in the present invention include CB-839 (Calithera Biosciences).

In some embodiments, one or more other therapeutic agent is an antibody that binds to tumor antigens, that is, proteins expressed on the cell surface of tumor cells. Approved antibodies that bind to tumor antigens which may be used in the present invention include rituximab (Rituxan®, Genentech/BiogenIdec); ofatumumab (anti-CD20, Arzerra®, GlaxoSmithKline); obinutuzumab (anti-CD20, Gazyva®, Genentech), ibritumomab (anti-CD20 and Yttrium-90, Zevalin®, Spectrum Pharmaceuticals); daratumumab (anti-CD38, Darzalex®, Janssen Biotech), dinutuximab (anti-glycolipid GD2, Unituxin®, United Therapeutics); trastuzumab (anti-HER2, Herceptin®, Genentech); ado-trastuzumab emtansine (anti-HER2, fused to emtansine, Kadcyla®, Genentech); and pertuzumab (anti-HER2, Perjeta®, Genentech); and brentuximab vedotin (anti-CD30-drug conjugate, Adcetris®, Seattle Genetics).

In some embodiments, one or more other therapeutic agent is a topoisomerase inhibitor. Approved topoisomerase inhibitors useful in the present invention include irinotecan (Onivyde®, Merrimack Pharmaceuticals); topotecan (Hycamtin®, GlaxoSmithKline). Topoisomerase inhibitors being studied which may be used in the present invention include pixantrone (Pixuvri®, CTI Biopharma).

In some embodiments, one or more other therapeutic agent is an inhibitor of anti-apoptotic proteins, such as BCL-2. Approved anti-apoptotics which may be used in the present invention include venetoclax (Venclexta®, AbbVie/Genentech); and blinatumomab (Blincyto®, Amgen). Other therapeutic agents targeting apoptotic proteins which have undergone clinical testing and may be used in the present invention include navitoclax (ABT-263, Abbott), a BCL-2 inhibitor (NCT02079740).

In some embodiments, one or more other therapeutic agent is an androgen receptor inhibitor. Approved androgen receptor inhibitors useful in the present invention include enzalutamide (Xtandi®, Astellas/Medivation); approved inhibitors of androgen synthesis include abiraterone (Zytiga®, Centocor/Ortho); approved antagonist of gonadotropin-releasing hormone (GnRH) receptor (degaralix, Firmagon®, Ferring Pharmaceuticals).

In some embodiments, one or more other therapeutic agent is a selective estrogen receptor modulator (SERM), which interferes with the synthesis or activity of estrogens. Approved SERMs useful in the present invention include raloxifene (Evista®, Eli Lilly).

In some embodiments, one or more other therapeutic agent is an inhibitor of bone resorption. An approved therapeutic which inhibits bone resorption is Denosumab (Xgeva®, Amgen), an antibody that binds to RANKL, prevents binding to its receptor RANK, found on the surface of osteoclasts, their precursors, and osteoclast-like giant cells, which mediates bone pathology in solid tumors with osseous metastases. Other approved therapeutics that inhibit bone resorption include bisphosphonates, such as zoledronic acid (Zometa®, Novartis).

In some embodiments, one or more other therapeutic agent is an inhibitor of interaction between the two primary p53 suppressor proteins, MDMX and MDM2. Inhibitors of p53 suppression proteins being studied which may be used in the present invention include ALRN-6924 (Aileron), a stapled peptide that equipotently binds to and disrupts the interaction of MDMX and MDM2 with p53. ALRN-6924 is currently being evaluated in clinical trials for the treatment of AML, advanced myelodysplastic syndrome (MDS) and peripheral T-cell lymphoma (PTCL) (NCT02909972; NCT02264613).

In some embodiments, one or more other therapeutic agent is an inhibitor of transforming growth factor-beta (TGF-beta or TGFß). Inhibitors of TGF-beta proteins being studied which may be used in the present invention include NIS793 (Novartis), an anti-TGF-beta antibody being tested in the clinic for treatment of various cancers, including breast, lung, hepatocellular, colorectal, pancreatic, prostate and renal cancer (NCT 02947165). In some embodiments, the inhibitor of TGF-beta proteins is fresolimumab (GC1008; Sanofi-Genzyme), which is being studied for melanoma (NCT00923169); renal cell carcinoma (NCT00356460); and non-small cell lung cancer (NCT02581787). Additionally, in some embodiments, the additional therapeutic agent is a TGF-beta trap, such as described in Connolly et al. (2012) Int'l J. Biological Sciences 8:964-978. One therapeutic compound currently in clinical trials for treatment of solid tumors is M7824 (Merck KgaA—formerly MSB0011459X), which is a bispecific, anti-PD-L1/TGFß trap compound (NCT02699515); and (NCT02517398). M7824 is comprised of a fully human IgG1 antibody against PD-L1 fused to the extracellular domain of human TGF-beta receptor II, which functions as a TGFß "trap."

In some embodiments, one or more other therapeutic agent is selected from glembatumumab vedotin-monomethyl auristatin E (MMAE) (Celldex), an anti-glycoprotein NMB (gpNMB) antibody (CR011) linked to the cytotoxic MMAE. gpNMB is a protein overexpressed by multiple tumor types associated with cancer cells' ability to metastasize.

In some embodiments, one or more other therapeutic agent is an antiproliferative compound. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, $AZd_6244$ from AstraZeneca, PD181461 from Pfizer and leucovorin.

In some embodiments, the present invention provides a method of treating Alzheimer's disease comprising administering to a patient in need thereof a provided compound or a pharmaceutically acceptable salt thereof and one or more additional therapeutic agents selected from donepezil (Aricept®), rivastigmine (Excelon®), galantamine (Razadyne®), tacrine (Cognex®), and memantine (Namenda®).

In some embodiments, one or more other therapeutic agent is a taxane compound, which causes disruption of microtubules, which are essential for cell division. In some embodiments, a taxane compound is selected from paclitaxel (Taxol®, Bristol-Myers Squibb), docetaxel (Taxotere®, Sanofi-Aventis; Docefrez®, Sun Pharmaceutical), albumin-bound paclitaxel (Abraxane®; Abraxis/Celgene), cabazitaxel (Jevtana®, Sanofi-Aventis), and SID530 (SK Chemicals, Co.) (NCT00931008).

In some embodiments, one or more other therapeutic agent is a nucleoside inhibitor, or a therapeutic agent that interferes with normal DNA synthesis, protein synthesis, cell replication, or will otherwise inhibit rapidly proliferating cells.

In some embodiments, a nucleoside inhibitor is selected from trabectedin (guanidine alkylating agent, Yondelis®, Janssen Oncology), mechlorethamine (alkylating agent, Valchlor®, Aktelion Pharmaceuticals); vincristine (Oncovin®, Eli Lilly; Vincasar®, Teva Pharmaceuticals; Marqibo®, Talon Therapeutics); temozolomide (prodrug to alkylating agent 5-(3-methyltriazen-1-yl)-imidazole-4-carboxamide (MTIC) Temodar®, Merck); cytarabine injection (ara-C, antimetabolic cytidine analog, Pfizer); lomustine (alkylating agent, CeeNU®, Bristol-Myers Squibb; Gleostine®, NextSource Biotechnology); azacitidine (pyrimidine nucleoside analog of cytidine, Vidaza®, Celgene); omacetaxine mepesuccinate (cephalotaxine ester) (protein synthesis inhibitor, Synribo®; Teva Pharmaceuticals); asparaginase *Erwinia chrysanthemi* (enzyme for depletion of asparagine, Elspar®, Lundbeck; Erwinaze®, EUSA Pharma); eribulin mesylate (microtubule inhibitor, tubulin-based antimitotic, Halaven®, Eisai); cabazitaxel (microtubule inhibitor, tubulin-based antimitotic, Jevtana®, Sanofi-Aventis); capacetrine (thymidylate synthase inhibitor, Xeloda®, Genentech); bendamustine (bifunctional mechlorethamine derivative, believed to form interstrand DNA cross-links, Treanda®, Cephalon/Teva); ixabepilone (semi-synthetic analog of epothilone B, microtubule inhibitor, tubulin-based antimitotic, Ixempra®, Bristol-Myers Squibb); nelarabine (prodrug of deoxyguanosine analog, nucleoside metabolic inhibitor, Arranon®, Novartis); clorafabine (prodrug of ribonucleotide reductase inhibitor, competitive inhibitor of deoxycytidine, Clolar®, Sanofi-Aventis); and trifluridine and tipiracil (thymidine-based nucleoside analog and thymidine phosphorylase inhibitor, Lonsurf®, Taiho Oncology).

In some embodiments, one or more other therapeutic agent is a kinase inhibitor or VEGF-R antagonist. Approved VEGF inhibitors and kinase inhibitors useful in the present invention include: bevacizumab (Avastin®, Genentech/Roche) an anti-VEGF monoclonal antibody; ramucirumab (Cyramza®, Eli Lilly), an anti-VEGFR-2 antibody and ziv-aflibercept, also known as VEGF Trap (Zaltrap®; Regeneron/Sanofi). VEGFR inhibitors, such as regorafenib (Stivarga®, Bayer); vandetanib (Caprelsa®, AstraZeneca); axitinib (Inlyta®, Pfizer); and lenvatinib (Lenvima®, Eisai); Raf inhibitors, such as sorafenib (Nexavar®, Bayer AG and Onyx); dabrafenib (Tafinlar®, Novartis); and vemurafenib (Zelboraf®, Genentech/Roche); MEK inhibitors, such as cobimetanib (Cotellic®, Exelexis/Genentech/Roche); trametinib (Mekinist®, Novartis); Bcr-Abl tyrosine kinase inhibitors, such as imatinib (Gleevec®, Novartis); nilotinib (Tasigna®, Novartis); dasatinib (Sprycel®, BristolMyersSquibb); bosutinib (Bosulif®, Pfizer); and ponatinib (Inclusig®, Ariad Pharmaceuticals); Her2 and EGFR inhibitors, such as gefitinib (Iressa®, AstraZeneca); erlotinib (Tarceeva®, Genentech/Roche/Astellas); lapatinib (Tykerb®, Novartis); afatinib (Gilotrif®, Boehringer Ingelheim); osimertinib (targeting activated EGFR, Tagrisso®, AstraZeneca); and brigatinib (Alunbrig®, Ariad Pharmaceuticals); c-Met and VEGFR2 inhibitors, such as cabozanitib (Cometriq®, Exelexis); and multikinase inhibitors, such as sunitinib (Sutent®, Pfizer); pazopanib (Votrient®, Novartis); ALK inhibitors, such as crizotinib (Xalkori®, Pfizer); ceritinib (Zykadia®, Novartis); and alectinib (Alecenza®, Genentech/Roche); Bruton's tyrosine kinase inhibitors, such as ibrutinib (Imbruvica®, Pharmacyclics/Janssen); and Flt3 receptor inhibitors, such as midostaurin (Rydapt®, Novartis).

Other kinase inhibitors and VEGF-R antagonists that are in development and may be used in the present invention include tivozanib (Aveo Pharmaceuticals); vatalanib (Bayer/Novartis); lucitanib (Clovis Oncology); dovitinib (TK1258, Novartis); Chiauanib (Chipscreen Biosciences); CEP-11981 (Cephalon); linifanib (Abbott Laboratories); neratinib (HKI-272, Puma Biotechnology); radotinib (Supect®, IY5511, Il-Yang Pharmaceuticals, S. Korea); ruxolitinib (Jakafi®, Incyte Corporation); PTC299 (PTC Therapeutics); CP-547, 632 (Pfizer); foretinib (Exelexis, GlaxoSmithKline); quizartinib (Daiichi Sankyo) and motesanib (Amgen/Takeda).

In another embodiment, the present invention provides a method of treating organ transplant rejection or graft vs. host disease comprising administering to a patient in need thereof a provided compound or a pharmaceutically acceptable salt thereof and one or more additional therapeutic agents selected from a steroid, cyclosporin, FK506, rapamycin, a hedgehog signaling inhibitor, a BTK inhibitor, a JAK/pan-JAK inhibitor, a TYK2 inhibitor, a PI3K inhibitor, and a SYK inhibitor.

In another embodiment, the present invention provides a method of treating or lessening the severity of a disease comprising administering to a patient in need thereof a provided compound or a pharmaceutically acceptable salt thereof and a BTK inhibitor, wherein the disease is selected from inflammatory bowel disease, arthritis, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, *Pemphigus vulgaris*, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitis, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleroderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a provided compound or a pharmaceutically acceptable salt thereof and a PI3K inhibitor, wherein the disease is selected from a cancer, a neurodegenerative disorder, an angiogenic disorder, a viral disease, an autoimmune disease, an inflammatory disorder, a hormone-related disease, conditions associated with organ transplantation, immunodeficiency disorders, a destructive bone disorder, a proliferative disorder, an infectious disease, a condition associated with cell death, thrombin-induced platelet aggregation, chronic myelogenous leukemia (CML), chronic lymphocytic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a provided compound or a pharmaceutically acceptable salt thereof and a PI3K inhibitor, wherein the disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Dudos disease and Bannayan-Zonana syndrome, or diseases in which the PI3K/PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction, psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

In some embodiments, one or more other therapeutic agent is a phosphatidylinositol 3 kinase (PI3K) inhibitor. In some embodiments, a PI3K inhibitor is selected from idelalisib (Zydelig®, Gilead), alpelisib (BYL719, Novartis), taselisib (GDC-0032, Genentech/Roche); pictilisib (GDC-0941, Genentech/Roche); copanlisib (BAY806946, Bayer); duvelisib (formerly IPI-145, Infinity Pharmaceuticals); PQR309 (Piqur Therapeutics, Switzerland); and TGR1202 (formerly RP5230, TG Therapeutics).

In some embodiments, the present invention provides a method of treating AML comprising administering to a patient in need thereof a provided compound or a pharmaceutically acceptable salt thereof and one or more additional therapeutic agents selected from: FLT3 inhibitors; targeted agents such as IDH inhibitors, anti-CD33 ADCs (e.g. Mylotarg), BCL2 inhibitors, and Hedgehog inhibitors; and chemotherapy such as AraC, daunarubicin, etoposide, methotrexate, fludarabine, mitozantrone, azacytidine, and corticosteroids.

In some embodiments, the present invention provides a method of treating MDS comprising administering to a patient in need thereof a provided compound or a pharmaceutically acceptable salt thereof and one or more additional therapeutic agents selected from azacytidine, decitabine and revlimid.

In some embodiments, the present invention provides a method of treating inflammatory skin conditions such as hidradenitis suppurativa, comprising administering to a patient in need thereof a provided compound or a pharmaceutically acceptable salt thereof and one or more additional therapeutic agents selected from anti-TNF drugs.

In some embodiments, the present invention provides a method of treating inflammatory skin conditions such as atopic dermatitis, comprising administering to a patient in need thereof a provided compound or a pharmaceutically acceptable salt thereof and one or more additional therapeutic agents selected from IL-4/IL-13-targeted agents such as dupilumab.

In some embodiments, the present invention provides a method of treating inflammatory skin conditions such as psoriasis, comprising administering to a patient in need thereof a provided compound or a pharmaceutically acceptable salt thereof and one or more additional therapeutic agents selected from anti-IL-17 and anti-IL-23 antibodies.

The compounds and compositions, according to the method of the present invention, may be administered using any amount and any route of administration effective for treating or lessening the severity of a cancer, an autoimmune disorder, a proliferative disorder, an inflammatory disorder, a neurodegenerative or neurological disorder, schizophrenia, a bone-related disorder, liver disease, or a cardiac disorder. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting protein kinase activity or degrading a protein kinase in a biological sample comprising the step of contacting said biological sample with a compound of this invention, or a composition comprising said compound.

According to another embodiment, the invention relates to a method of inhibiting or degrading IRAK-1, IRAK-2, and/or IRAK-4, or a mutant thereof, activity in a biological sample comprising the step of contacting said biological sample with a compound of this invention, or a composition comprising said compound.

The term "biological sample", as used herein, includes, without limitation, cell cultures or extracts thereof, biopsied material obtained from a mammal or extracts thereof, and blood, saliva, urine, feces, semen, tears, or other body fluids or extracts thereof.

Inhibition and/or degradation of a protein kinase, or a protein kinase selected from IRAK-1, IRAK-2, and/or IRAK-4, or a mutant thereof, activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of degrading a protein kinase and/or inhibiting protein kinase activity in a patient comprising the step of administering to said patient a compound of the present invention, or a composition comprising said compound.

According to another embodiment, the invention relates to a method of degrading and/or inhibiting one or more of IRAK-1, IRAK-2, and/or IRAK-4, or a mutant thereof, activity in a patient comprising the step of administering to said patient a compound of the present invention, or a composition comprising said compound. In other embodiments, the present invention provides a method for treating a disorder mediated by one or more of IRAK-1, IRAK-2, and/or IRAK-4, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin.

The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™. Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

In some embodiments, one or more other therapeutic agent is an mTOR inhibitor, which inhibits cell proliferation, angiogenesis and glucose uptake. In some embodiments, an mTOR inhibitor is everolimus (Afinitor®, Novartis); temsirolimus (Torisel®, Pfizer); and sirolimus (Rapamune®, Pfizer).

In some embodiments, one or more other therapeutic agent is an aromatase inhibitor. In some embodiments, an aromatase inhibitor is selected from exemestane (Aromasin®, Pfizer); anastazole (Arimidex®, AstraZeneca) and letrozole (Femara®, Novartis).

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™ Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™) The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™ Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof, see WO 2008/118802, US 2010/0197686), navitoclax (and analogs thereof, see U.S. Pat. No. 7,390, 799), NH-1 (Shenayng Pharmaceutical University), obatoclax (and analogs thereof, see WO 2004/106328, US 2005/ 0014802), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-1 receptor, or antibodies that target the extracellular domain of IGF-1 receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/ pan-JAK, FAK, PDK1, PKB/Akt, Ras/MAPK, PI3K, SYK, TYK2, BTK and TEC family, and/or members of the cyclin-dependent kinase family (CDK) including staurosporne derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a PI3K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); l) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, Cl-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

Compounds which target, decrease or inhibit the activity of a protein or lipid phosphatase are e.g. inhibitors of phosphatase 1, phosphatase 2A, or CDC25, such as okadaic acid or a derivative thereof.

In some embodiments, one or more other therapeutic agent is a growth factor antagonist, such as an antagonist of platelet-derived growth factor (PDGF), or epidermal growth factor (EGF) or its receptor (EGFR). Approved PDGF antagonists which may be used in the present invention include olaratumab (Lartruvo®; Eli Lilly). Approved EGFR antagonists which may be used in the present invention include cetuximab (Erbitux®, Eli Lilly); necitumumab (Portrazza®, Eli Lilly), panitumumab (Vectibix®, Amgen); and osimertinib (targeting activated EGFR, Tagrisso®, AstraZeneca).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

Further examples of BTK inhibitory compounds, and conditions treatable by such compounds in combination with compounds of this invention can be found in WO 2008/039218, US 2008/0108636 and WO 2011/090760, US 2010/0249092, the entirety of each of which is herein incorporated by reference.

Further examples of SYK inhibitory compounds, and conditions treatable by such compounds in combination with compounds of this invention can be found in WO 2003/063794, US 2004/0029902, WO 2005/007623, US 2005/0075306, and WO 2006/078846, US 2006/0211657, the entirety of each of which is herein incorporated by reference.

Further examples of PI3K inhibitory compounds, and conditions treatable by such compounds in combination with compounds of this invention can be found in WO 2004/019973, US 2004/0106569, WO 2004/089925, US 2004/0242631, U.S. Pat. No. 8,138,347, WO 2002/088112, US 2004/0116421, WO 2007/084786, US 2010/0249126, WO 2007/129161, US 2008/0076768, WO 2006/122806, US 2008/0194579, WO 2005/113554, US 2008/0275067, and WO 2007/044729, US 2010/0087440, the entirety of each of which is herein incorporated by reference.

Further examples of JAK inhibitory compounds, and conditions treatable by such compounds in combination with compounds of this invention can be found in WO 2009/114512, US 2009/0233903, WO 2008/109943, US 2010/0197671, WO 2007/053452, US 2007/0191405, WO 2001/0142246, U.S. Ser. No. 2001/0053782, and WO 2007/070514, US 2007/0135461, the entirety of each of which is herein incorporated by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zaenestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™); carfilzomib (Kyprolis®, Amgen); and ixazomib (Ninlaro®, Takeda), and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino,17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl] phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgG1 antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate; non-steroidal glucocorticoid receptor agonists; LTB4 antagonists such LY293111, CGS025019C, CP-195543, SC-53228, BIIL 284, ONO 4057, SB 209247; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, and Takeda antagonists such as N-[[4-[[[6,7-dihydro-2-(4-methylphenyl)-5H-benzo-cyclohepten-8-yl]carbonyl]amino]phenyl]-methyl] tetrahydro-N,N-dimethyl-2H-pyran-4-aminium chloride (TAK-770).

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 µg/kg body weight/day of the additional therapeutic agent can be administered.

The amount of one or more other therapeutic agent present in the compositions of this invention may be no more than the amount that would normally be administered in a composition comprising that therapeutic agent as the only active agent. Preferably the amount of one or more other therapeutic agent in the presently disclosed compositions will range from about 50% to 100% of the amount normally present in a composition comprising that agent as the only therapeutically active agent. In some embodiments, one or more other therapeutic agent is administered at a dosage of about 50%, about 55%, about 60%, about 65%, about 70%, about 75%, about 80%, about 85%, about 90%, or about 95% of the amount normally administered for that agent. As used herein, the phrase "normally administered" means the amount an FDA approved therapeutic agent is approved for dosing per the FDA label insert.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

Exemplary Immuno-Oncology Agents

In some embodiments, one or more other therapeutic agent is an immuno-oncology agent. As used herein, the term "an immuno-oncology agent" refers to an agent which is effective to enhance, stimulate, and/or up-regulate immune responses in a subject. In some embodiments, the administration of an immuno-oncology agent with a compound of the invention has a synergic effect in treating a cancer.

An immuno-oncology agent can be, for example, a small molecule drug, an antibody, or a biologic or small molecule. Examples of biologic immuno-oncology agents include, but are not limited to, cancer vaccines, antibodies, and cytokines. In some embodiments, an antibody is a monoclonal antibody. In some embodiments, a monoclonal antibody is humanized or human.

In some embodiments, an immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses.

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTOR, Lymphotoxin α1β2, FAS, FASL, RELT, DR6, TROY, NGFR.

In some embodiments, an immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In some embodiments, a combination of a compound of the invention and an immuno-oncology agent can stimulate T cell responses. In some embodiments, an immuno-oncology agent is: (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4; or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

In some embodiments, an immuno-oncology agent is an antagonist of inhibitory receptors on NK cells or an agonists of activating receptors on NK cells. In some embodiments, an immuno-oncology agent is an antagonists of KIR, such as lirilumab.

In some embodiments, an immuno-oncology agent is an agent that inhibits or depletes macrophages or monocytes, including but not limited to CSF-1R antagonists such as CSF-1R antagonist antibodies including RG7155 (WO 2011/070024, US 2011/0165156, WO 2011/0107553, US 2012/0329997, WO 2011/131407, US 2013/0005949, WO 2013/087699, US 2014/0336363, WO 2013/119716, WO 2013/132044, US 2014/0079706) or FPA-008 (WO 2011/140249, US 2011/0274683; WO 2013/169264; WO 2014/036357, US 2014/0079699).

In some embodiments, an immuno-oncology agent is selected from agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell energy or exhaustion) and agents that trigger innate immune activation and/or inflammation at tumor sites.

In some embodiments, an immuno-oncology agent is a CTLA-4 antagonist. In some embodiments, a CTLA-4 antagonist is an antagonistic CTLA-4 antibody. In some embodiments, an antagonistic CTLA-4 antibody is YERVOY (ipilimumab) or tremelimumab.

In some embodiments, an immuno-oncology agent is a PD-1 antagonist. In some embodiments, a PD-1 antagonist is administered by infusion. In some embodiments, an immuno-oncology agent is an antibody or an antigen-binding portion thereof that binds specifically to a Programmed Death-1 (PD-1) receptor and inhibits PD-1 activity. In some embodiments, a PD-1 antagonist is an antagonistic PD-1 antibody. In some embodiments, an antagonistic PD-1 antibody is OPDIVO (nivolumab), KEYTRUDA (pembrolizumab), or MEDI-0680 (AMP-514; WO2012/145493). In some embodiments, an immuno-oncology agent may be pidilizumab (CT-011). In some embodiments, an immuno-oncology agent is a recombinant protein composed of the extracellular domain of PD-L2 (B7-DC) fused to the Fc portion of IgG1, called AMP-224.

In some embodiments, an immuno-oncology agent is a PD-L1 antagonist. In some embodiments, a PD-L1 antagonist is an antagonistic PD-L1 antibody. In some embodiments, a PD-L1 antibody is MPDL3280A (RG7446; WO 2010/077634, US 2010/0203056), durvalumab (MED14736), BMS-936559 (WO 2007/005874, US 2009/0055944), and MSB0010718C (WO 2013/079174, US 2014/0341917).

In some embodiments, an immuno-oncology agent is a LAG-3 antagonist. In some embodiments, a LAG-3 antagonist is an antagonistic LAG-3 antibody. In some embodiments, a LAG3 antibody is BMS-986016 (WO 2010/019570, US 2010/0150892, WO 2014/008218, US 2014/0093511), or IMP-731 or IMP-321 (WO 2008/132601, US 2010/0233183, WO 2009/044273, US 2011/0008331).

In some embodiments, an immuno-oncology agent is a CD137 (4-1BB) agonist. In some embodiments, a CD137 (4-1BB) agonist is an agonistic CD137 antibody. In some embodiments, a CD137 antibody is urelumab or PF-05082566 (WO12/32433).

In some embodiments, an immuno-oncology agent is a GITR agonist. In some embodiments, a GITR agonist is an agonistic GITR antibody. In some embodiments, a GITR antibody is BMS-986153, BMS-986156, TRX-518 (WO 2006/105021, US 2007/0098719, WO 2009/009116, US 2009/0136494), or MK-4166 (WO 2011/028683, US 2012/0189639).

In some embodiments, an immuno-oncology agent is an indoleamine (2,3)-dioxygenase (IDO) antagonist. In some embodiments, an IDO antagonist is selected from epacadostat (INCB024360, Incyte); indoximod (NLG-8189, NewLink Genetics Corporation); capmanitib (INC280, Novartis); GDC-0919 (Genentech/Roche); PF-06840003 (Pfizer); BMS.F001287 (Bristol-Myers Squibb); Phy906/KD108 (Phytoceutica); an enzyme that breaks down kynurenine (Kynase, Kyn Therapeutics); and NLG-919 (WO 2009/073620, US 2011/053941, WO 2009/132238, US 2011/136796, WO 2011/056652, US 2012/277217, WO 2012/142237, US 2014/066625).

In some embodiments, an immuno-oncology agent is an OX40 agonist. In some embodiments, an OX40 agonist is an agonistic OX40 antibody. In some embodiments, an OX40 antibody is MEDI-6383 or MEDI-6469.

In some embodiments, an immuno-oncology agent is an OX40L antagonist. In some embodiments, an OX40L antagonist is an antagonistic OX40 antibody. In some embodiments, an OX40L antagonist is RG-7888 (WO 2006/029879, U.S. Pat. No. 7,501,496).

In some embodiments, an immuno-oncology agent is a CD40 agonist. In some embodiments, a CD40 agonist is an agonistic CD40 antibody. In some embodiments, an immuno-oncology agent is a CD40 antagonist. In some embodiments, a CD40 antagonist is an antagonistic CD40 antibody. In some embodiments, a CD40 antibody is lucatumumab or dacetuzumab.

In some embodiments, an immuno-oncology agent is a CD27 agonist. In some embodiments, a CD27 agonist is an agonistic CD27 antibody. In some embodiments, a CD27 antibody is varlilumab.

In some embodiments, an immuno-oncology agent is MGA271 (to B7H3) (WO 2011/109400, US 2013/0149236).

In some embodiments, an immuno-oncology agent is abagovomab, adecatumumab, afutuzumab, alemtuzumab, anatumomab mafenatox, apolizumab, atezolimab, avelumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab.

In some embodiments, an immuno-oncology agent is an immunostimulatory agent. For example, antibodies blocking the PD-1 and PD-L1 inhibitory axis can unleash activated tumor-reactive T cells and have been shown in clinical trials to induce durable anti-tumor responses in increasing numbers of tumor histologies, including some tumor types that conventionally have not been considered immunotherapy sensitive. See, e.g., Okazaki, T. et al. (2013) Nat. Immunol. 14, 1212-1218; Zou et al. (2016) Sci. Transl. Med. 8. The anti-PD-1 antibody nivolumab (Opdivo®, Bristol-Myers Squibb, also known as ONO-4538, MDX1106 and BMS-936558), has shown potential to improve the overall survival in patients with RCC who had experienced disease progression during or after prior anti-angiogenic therapy.

In some embodiments, the immunomodulatory therapeutic specifically induces apoptosis of tumor cells. Approved immunomodulatory therapeutics which may be used in the present invention include pomalidomide (Pomalyst®, Celgene); lenalidomide (Revlimid®, Celgene); ingenol mebutate (Picato®, LEO Pharma).

In some embodiments, an immuno-oncology agent is a cancer vaccine. In some embodiments, the cancer vaccine is selected from sipuleucel-T (Provenge®, Dendreon/Valeant Pharmaceuticals), which has been approved for treatment of asymptomatic, or minimally symptomatic metastatic castrate-resistant (hormone-refractory) prostate cancer; and talimogene laherparepvec (Imlygic®, BioVex/Amgen, previously known as T-VEC), a genetically modified oncolytic viral therapy approved for treatment of unresectable cutaneous, subcutaneous and nodal lesions in melanoma. In some embodiments, an immuno-oncology agent is selected from an oncolytic viral therapy such as pexastimogene devacirepvec (PexaVec/JX-594, SillaJen/formerly Jennerex Biotherapeutics), a thymidine kinase- (TK-) deficient vaccinia virus engineered to express GM-CSF, for hepatocellular carcinoma (NCT02562755) and melanoma (NCT00429312); pelareorep (Reolysin®, Oncolytics Biotech), a variant of respiratory enteric orphan virus (reovirus) which does not replicate in cells that are not RAS-activated, in numerous cancers, including colorectal cancer (NCT01622543); prostate cancer (NCT01619813); head and neck squamous cell cancer (NCT01166542); pancreatic adenocarcinoma (NCT00998322); and non-small cell lung cancer (NSCLC) (NCT 00861627); enadenotucirev (NG-348, PsiOxus, formerly known as ColoAd1), an adenovirus engineered to express a full length CD80 and an antibody fragment specific for the T-cell receptor CD3 protein, in ovarian cancer (NCT02028117); metastatic or advanced epithelial tumors such as in colorectal cancer, bladder cancer, head and neck squamous cell carcinoma and salivary gland cancer (NCT02636036); ONCOS-102 (Targovax/formerly Oncos), an adenovirus engineered to express GM-CSF, in melanoma (NCT03003676); and peritoneal disease, colorectal cancer or ovarian cancer (NCT02963831); GL-ONC1 (GLV-1h68/GLV-1h153, Genelux GmbH), vaccinia viruses engineered to express beta-galactosidase (beta-gal)/beta-glucoronidase or beta-gal/human sodium iodide symporter (hNIS), respectively, were studied in peritoneal carcinomatosis (NCT01443260); fallopian tube cancer, ovarian cancer (NCT 02759588); or CG0070 (Cold Genesys), an adenovirus engineered to express GM-CSF, in bladder cancer (NCT02365818).

In some embodiments, an immuno-oncology agent is selected from JX-929 (SillaJen/formerly Jennerex Biotherapeutics), a TK- and vaccinia growth factor-deficient vaccinia virus engineered to express cytosine deaminase, which is able to convert the prodrug 5-fluorocytosine to the cytotoxic drug 5-fluorouracil; TG01 and TG02 (Targovax/formerly Oncos), peptide-based immunotherapy agents targeted for difficult-to-treat RAS mutations; and TILT-123 (TILT Biotherapeutics), an engineered adenovirus designated: Ad5/3-E2F-delta24-hTNFα-IRES-hIL20; and VSV-GP (ViraTherapeutics) a vesicular stomatitis virus (VSV) engineered to express the glycoprotein (GP) of lymphocytic choriomeningitis virus (LCMV), which can be further engineered to express antigens designed to raise an antigen-specific CD8+ T cell response.

In some embodiments, an immuno-oncology agent is a T-cell engineered to express a chimeric antigen receptor, or CAR. The T-cells engineered to express such chimeric antigen receptor are referred to as a CAR-T cells.

CARs have been constructed that consist of binding domains, which may be derived from natural ligands, single chain variable fragments (scFv) derived from monoclonal antibodies specific for cell-surface antigens, fused to endodomains that are the functional end of the T-cell receptor (TCR), such as the CD3-zeta signaling domain from TCRs, which is capable of generating an activation signal in T lymphocytes. Upon antigen binding, such CARs link to endogenous signaling pathways in the effector cell and generate activating signals similar to those initiated by the TCR complex.

For example, in some embodiments the CAR-T cell is one of those described in U.S. Pat. No. 8,906,682, the entirety of each of which is herein incorporated by reference, which discloses CAR-T cells engineered to comprise an extracellular domain having an antigen binding domain (such as a domain that binds to CD19), fused to an intracellular signaling domain of the T cell antigen receptor complex zeta chain (such as CD3 zeta). When expressed in the T cell, the CAR is able to redirect antigen recognition based on the antigen binding specificity. In the case of CD19, the antigen is expressed on malignant B cells. Over 200 clinical trials are currently in progress employing CAR-T in a wide range of indications. [https://clinicaltrials.gov/ct2/results?term=chimeric+antigen+receptors&pg=1].

In some embodiments, an immunostimulatory agent is an activator of retinoic acid receptor-related orphan receptor γ (RORγt). RORγt is a transcription factor with key roles in the differentiation and maintenance of Type 17 effector subsets of CD4+ (Th17) and CD8+ (Tc17) T cells, as well as the differentiation of IL-17 expressing innate immune cell subpopulations such as NK cells. In some embodiments, an activator of RORγt is LYC-55716 (Lycera), which is currently being evaluated in clinical trials for the treatment of solid tumors (NCT02929862).

In some embodiments, an immunostimulatory agent is an agonist or activator of a toll-like receptor (TLR). Suitable activators of TLRs include an agonist or activator of TLR9 such as SD-101 (Dynavax). SD-101 is an immunostimulatory CpG which is being studied for B-cell, follicular and other lymphomas (NCT02254772). Agonists or activators of TLR8 which may be used in the present invention include motolimod (VTX-2337, VentiRx Pharmaceuticals) which is being studied for squamous cell cancer of the head and neck (NCT02124850) and ovarian cancer (NCT02431559).

Other immuno-oncology agents that may be used in the present invention include urelumab (BMS-663513, Bristol-Myers Squibb), an anti-CD137 monoclonal antibody; varlilumab (CDX-1127, Celldex Therapeutics), an anti-CD27 monoclonal antibody; BMS-986178 (Bristol-Myers Squibb), an anti-OX40 monoclonal antibody; lirilumab (IPH2102/BMS-986015, Innate Pharma, Bristol-Myers Squibb), an anti-KIR monoclonal antibody; monalizumab (IPH2201, Innate Pharma, AstraZeneca) an anti-NKG2A monoclonal antibody; andecaliximab (GS-5745, Gilead Sciences), an anti-MMP9 antibody; MK-4166 (Merck & Co.), an anti-GITR monoclonal antibody.

In some embodiments, an immunostimulatory agent is selected from elotuzumab, mifamurtide, an agonist or activator of a toll-like receptor, and an activator of RORγt.

In some embodiments, an immunostimulatory therapeutic is recombinant human interleukin 15 (rhIL-15). rhIL-15 has been tested in the clinic as a therapy for melanoma and renal cell carcinoma (NCT01021059 and NCT01369888) and leukemias (NCT02689453). In some embodiments, an immunostimulatory agent is recombinant human interleukin 12 (rhIL-12). In some embodiments, an IL-15 based immunotherapeutic is heterodimeric IL-15 (hetIL-15, Novartis/Admune), a fusion complex composed of a synthetic form of endogenous IL-15 complexed to the soluble IL-15 binding protein IL-15 receptor alpha chain (IL15:sIL-15RA), which has been tested in Phase 1 clinical trials for melanoma, renal cell carcinoma, non-small cell lung cancer and head and neck squamous cell carcinoma (NCT02452268). In some embodiments, a recombinant human interleukin 12 (rhIL-12) is NM-IL-12 (Neumedicines, Inc.), NCT02544724, or NCT02542124.

In some embodiments, an immuno-oncology agent is selected from those descripted in Jerry L. Adams ET. AL., "Big opportunities for small molecules in immuno-oncology," Cancer Therapy 2015, Vol. 14, pages 603-622, the content of which is incorporated herein by reference in its entirety. In some embodiment, an immuno-oncology agent is selected from the examples described in Table 1 of Jerry L. Adams ET. AL. In some embodiments, an immuno-oncology agent is a small molecule targeting an immuno-oncology target selected from those listed in Table 2 of Jerry L. Adams ET. AL. In some embodiments, an immuno-oncology agent is a small molecule agent selected from those listed in Table 2 of Jerry L. Adams ET. AL.

In some embodiments, an immuno-oncology agent is selected from the small molecule immuno-oncology agents described in Peter L. Toogood, "Small molecule immuno-oncology therapeutic agents," Bioorganic & Medicinal Chemistry Letters 2018, Vol. 28, pages 319-329, the content of which is incorporated herein by reference in its entirety. In some embodiments, an immuno-oncology agent is an agent targeting the pathways as described in Peter L. Toogood.

In some embodiments, an immuno-oncology agent is selected from those described in Sandra L. Ross et al., "Bispecific T cell engager (BiTE®) antibody constructs can mediate bystander tumor cell killing", PLoS ONE 12(8): e0183390, the content of which is incorporated herein by reference in its entirety. In some embodiments, an immuno-oncology agent is a bispecific T cell engager (BiTE®) antibody construct. In some embodiments, a bispecific T cell engager (BiTE®) antibody construct is a CD19/CD3 bispecific antibody construct. In some embodiments, a bispecific T cell engager (BiTE®) antibody construct is an EGFR/CD3 bispecific antibody construct. In some embodiments, a bispecific T cell engager (BiTE®) antibody construct activates T cells. In some embodiments, a bispecific T cell engager (BiTE®) antibody construct activates T cells, which release cytokines inducing upregulation of intercellular adhesion molecule 1 (ICAM-1) and FAS on bystander cells. In some embodiments, a bispecific T cell engager (BiTE®) antibody construct activates T cells which result in induced bystander cell lysis. In some embodiments, the bystander cells are in solid tumors. In some embodiments, the bystander cells being lysed are in proximity to the BiTE®-activated T cells. In some embodiment, the bystander cells comprises tumor-associated antigen (TAA) negative cancer cells. In some embodiment, the bystander cells comprise EGFR-negative cancer cells. In some embodiments, an immuno-oncology agent is an antibody which blocks the PD-L1/PD1 axis and/or CTLA4. In some embodiments, an immuno-oncology agent is an ex-vivo expanded tumor-infiltrating T cell. In some embodiments, an immuno-oncology agent is a bispecific antibody construct or chimeric antigen receptors (CARs) that directly connect T cells with tumor-associated surface antigens (TAAs).

Exemplary Immune Checkpoint Inhibitors

In some embodiments, an immuno-oncology agent is an immune checkpoint inhibitor as described herein.

The term "checkpoint inhibitor" as used herein relates to agents useful in preventing cancer cells from avoiding the immune system of the patient. One of the major mechanisms of anti-tumor immunity subversion is known as "T-cell exhaustion," which results from chronic exposure to antigens that has led to up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulators. They act as molecular "gatekeepers" that allow extracellular information to dictate whether cell cycle progression and other intracellular signaling processes should proceed.

In some embodiments, an immune checkpoint inhibitor is an antibody to PD-1. PD-1 binds to the programmed cell death 1 receptor (PD-1) to prevent the receptor from binding to the inhibitory ligand PDL-1, thus overriding the ability of tumors to suppress the host anti-tumor immune response.

In one aspect, the checkpoint inhibitor is a biologic therapeutic or a small molecule. In another aspect, the checkpoint inhibitor is a monoclonal antibody, a humanized antibody, a fully human antibody, a fusion protein or a combination thereof. In a further aspect, the checkpoint inhibitor inhibits a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an additional aspect, the checkpoint inhibitor interacts with a ligand of a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an aspect, the checkpoint inhibitor is an immunostimulatory agent, a T cell growth factor, an interleukin, an antibody, a vaccine or a combination thereof. In a further aspect, the interleukin is IL-7 or IL-15. In a specific aspect, the interleukin is glycosylated IL-7. In an additional aspect, the vaccine is a dendritic cell (DC) vaccine.

Checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors or antibodies that bind to and block or inhibit immune checkpoint receptor ligands. Illustrative checkpoint molecules that may be targeted for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, γδ, and memory CD8$^+$ (αβ) T cells), CD160 (also referred to as BY55), CGEN-15049, CHK 1 and CHK2 kinases, A2aR, and various B-7 family ligands. B7 family ligands include, but are not limited to, B7-1, B7-2, B7-DC, B7-H1, B7-H2, B7-H3, B7-H4, B7-H5, B7-H6 and B7-H7. Checkpoint inhibitors include antibodies, or antigen binding fragments thereof, other binding proteins, biologic therapeutics, or small molecules, that bind to and block or inhibit the activity of one or more of CTLA-4, PDL1, PDL2, PD1, BTLA, HVEM, TIM3, GAL9, LAG3, VISTA, KIR, 2B4, CD 160 and CGEN-15049. Illustrative immune checkpoint inhibitors include Tremelimumab (CTLA-4 blocking antibody), anti-OX40, PD-L1 monoclonal Antibody (Anti-B7-H1; MED14736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody), and ipilimumab (anti-CTLA-4 checkpoint inhibitor). Checkpoint protein ligands include, but are not limited to PD-L1, PD-L2, B7-H3, B7-H4, CD28, CD86 and TIM-3.

In certain embodiments, the immune checkpoint inhibitor is selected from a PD-1 antagonist, a PD-L1 antagonist, and a CTLA-4 antagonist. In some embodiments, the checkpoint inhibitor is selected from the group consisting of nivolumab (Opdivo®), ipilimumab (Yervoy®), and pembrolizumab (Keytruda®). In some embodiments, the checkpoint inhibitor is selected from nivolumab (anti-PD-1 antibody, Opdivo®, Bristol-Myers Squibb); pembrolizumab (anti-PD-1 antibody, Keytruda®, Merck); ipilimumab (anti-CTLA-4 antibody, Yervoy®, Bristol-Myers Squibb); durvalumab (anti-PD-L1 antibody, Imfinzi®, AstraZeneca); and atezolizumab (anti-PD-L1 antibody, Tecentriq®, Genentech).

In some embodiments, the checkpoint inhibitor is selected from the group consisting of lambrolizumab (MK-3475), nivolumab (BMS-936558), pidilizumab (CT-011), AMP-224, MDX-1105, MED14736, MPDL3280A, BMS-936559, ipilimumab, lirlumab, IPH2101, pembrolizumab (Keytruda®), and tremelimumab.

In some embodiments, an immune checkpoint inhibitor is REGN2810 (Regeneron), an anti-PD-1 antibody tested in patients with basal cell carcinoma (NCT03132636); NSCLC (NCT03088540); cutaneous squamous cell carcinoma (NCT02760498); lymphoma (NCT02651662); and melanoma (NCT03002376); pidilizumab (CureTech), also known as CT-011, an antibody that binds to PD-1, in clinical trials for diffuse large B-cell lymphoma and multiple myeloma; avelumab (Bavencio®, Pfizer/Merck KGaA), also known as MSB0010718C), a fully human IgG1 anti-PD-L1 antibody, in clinical trials for non-small cell lung cancer, Merkel cell carcinoma, mesothelioma, solid tumors, renal cancer, ovarian cancer, bladder cancer, head and neck cancer, and gastric cancer; or PDR001 (Novartis), an inhibitory antibody that binds to PD-1, in clinical trials for non-small cell lung cancer, melanoma, triple negative breast cancer and advanced or metastatic solid tumors. Tremelimumab (CP-675,206; Astrazeneca) is a fully human monoclonal antibody against CTLA-4 that has been in studied in clinical trials for a number of indications, including: mesothelioma, colorectal cancer, kidney cancer, breast cancer, lung cancer and non-small cell lung cancer, pancreatic ductal adenocarcinoma, pancreatic cancer, germ cell cancer, squamous cell cancer of the head and neck, hepatocellular carcinoma, prostate cancer, endometrial cancer, metastatic cancer in the liver, liver cancer, large B-cell lymphoma, ovarian cancer, cervical cancer, metastatic anaplastic thyroid cancer, urothelial cancer, fallopian tube cancer, multiple myeloma, bladder cancer, soft tissue sarcoma, and melanoma. AGEN-1884 (Agenus) is an anti-CTLA4 antibody that is being studied in Phase 1 clinical trials for advanced solid tumors (NCT02694822).

In some embodiments, a checkpoint inhibitor is an inhibitor of T-cell immunoglobulin mucin containing protein-3 (TIM-3). TIM-3 inhibitors that may be used in the present invention include TSR-022, LY3321367 and MBG453. TSR-022 (Tesaro) is an anti-TIM-3 antibody which is being studied in solid tumors (NCT02817633). LY3321367 (Eli Lilly) is an anti-TIM-3 antibody which is being studied in solid tumors (NCT03099109). MBG453 (Novartis) is an anti-TIM-3 antibody which is being studied in advanced malignancies (NCT02608268).

In some embodiments, a checkpoint inhibitor is an inhibitor of T cell immunoreceptor with Ig and ITIM domains, or TIGIT, an immune receptor on certain T cells and NK cells. TIGIT inhibitors that may be used in the present invention include BMS-986207 (Bristol-Myers Squibb), an anti-TIGIT monoclonal antibody (NCT02913313); OMP-313M32 (Oncomed); and anti-TIGIT monoclonal antibody (NCT03119428).

In some embodiments, a checkpoint inhibitor is an inhibitor of Lymphocyte Activation Gene-3 (LAG-3). LAG-3 inhibitors that may be used in the present invention include BMS-986016 and REGN3767 and IMP321. BMS-986016 (Bristol-Myers Squibb), an anti-LAG-3 antibody, is being studied in glioblastoma and gliosarcoma (NCT02658981). REGN3767 (Regeneron), is also an anti-LAG-3 antibody, and is being studied in malignancies (NCT03005782). IMP321 (Immutep S.A.) is an LAG-3-Ig fusion protein, being studied in melanoma (NCT02676869); adenocarcinoma (NCT02614833); and metastatic breast cancer (NCT00349934).

Checkpoint inhibitors that may be used in the present invention include OX40 agonists. OX40 agonists that are being studied in clinical trials include PF-04518600/PF-8600 (Pfizer), an agonistic anti-OX40 antibody, in metastatic kidney cancer (NCT03092856) and advanced cancers and neoplasms (NCT02554812; NCT05082566); GSK3174998 (Merck), an agonistic anti-OX40 antibody, in Phase 1 cancer trials (NCT02528357); MED10562 (Medimmune/AstraZeneca), an agonistic anti-OX40 antibody, in advanced solid tumors (NCT02318394 and NCT02705482); MED16469, an agonistic anti-OX40 antibody (Medimmune/AstraZeneca), in patients with colorectal cancer (NCT02559024), breast cancer (NCT01862900), head and neck cancer (NCT02274155) and metastatic prostate cancer (NCT01303705); and BMS-986178 (Bristol-Myers Squibb) an agonistic anti-OX40 antibody, in advanced cancers (NCT02737475).

Checkpoint inhibitors that may be used in the present invention include CD137 (also called 4-1BB) agonists. CD137 agonists that are being studied in clinical trials include utomilumab (PF-05082566, Pfizer) an agonistic anti-CD137 antibody, in diffuse large B-cell lymphoma (NCT02951156) and in advanced cancers and neoplasms (NCT02554812 and NCT05082566); urelumab (BMS-663513, Bristol-Myers Squibb), an agonistic anti-CD137 antibody, in melanoma and skin cancer (NCT02652455) and glioblastoma and gliosarcoma (NCT02658981).

Checkpoint inhibitors that may be used in the present invention include CD27 agonists. CD27 agonists that are being studied in clinical trials include varlilumab (CDX-1127, Celldex Therapeutics) an agonistic anti-CD27 antibody, in squamous cell head and neck cancer, ovarian carcinoma, colorectal cancer, renal cell cancer, and glioblastoma (NCT02335918); lymphomas (NCT01460134); and glioma and astrocytoma (NCT02924038).

Checkpoint inhibitors that may be used in the present invention include glucocorticoid-induced tumor necrosis factor receptor (GITR) agonists. GITR agonists that are being studied in clinical trials include TRX518 (Leap Therapeutics), an agonistic anti-GITR antibody, in malignant melanoma and other malignant solid tumors (NCT01239134 and NCT02628574); GWN323 (Novartis), an agonistic anti-GITR antibody, in solid tumors and lymphoma (NCT 02740270); INCAGN01876 (Incyte/Agenus), an agonistic anti-GITR antibody, in advanced cancers (NCT02697591 and NCT03126110); MK-4166 (Merck), an agonistic anti-GITR antibody, in solid tumors (NCT02132754) and MEDI1873 (Medimmune/AstraZeneca), an agonistic hexameric GITR-ligand molecule with a human IgG1 Fc domain, in advanced solid tumors (NCT02583165).

Checkpoint inhibitors that may be used in the present invention include inducible T-cell co-stimulator (ICOS, also known as CD278) agonists. ICOS agonists that are being studied in clinical trials include MEDI-570 (Medimmune), an agonistic anti-ICOS antibody, in lymphomas (NCT02520791); GSK3359609 (Merck), an agonistic anti-ICOS antibody, in Phase 1 (NCT02723955); JTX-2011 (Jounce Therapeutics), an agonistic anti-ICOS antibody, in Phase 1 (NCT02904226).

Checkpoint inhibitors that may be used in the present invention include killer IgG-like receptor (KIR) inhibitors. KIR inhibitors that are being studied in clinical trials include lirilumab (IPH2102/BMS-986015, Innate Pharma/Bristol-Myers Squibb), an anti-KIR antibody, in leukemias (NCT01687387, NCT02399917, NCT02481297, NCT02599649), multiple myeloma (NCT02252263), and lymphoma (NCT01592370); IPH2101 (1-7F9, Innate Pharma) in myeloma (NCT01222286 and NCT01217203); and IPH4102 (Innate Pharma), an anti-KIR antibody that binds to three domains of the long cytoplasmic tail (KIR3DL2), in lymphoma (NCT02593045).

Checkpoint inhibitors that may be used in the present invention include CD47 inhibitors of interaction between CD47 and signal regulatory protein alpha (SIRPa). CD47/SIRPa inhibitors that are being studied in clinical trials include ALX-148 (Alexo Therapeutics), an antagonistic variant of (SIRPa) that binds to CD47 and prevents CD47/SIRPa-mediated signaling, in phase 1 (NCT03013218); TTI-621 (SIRPa-Fc, Trillium Therapeutics), a soluble recombinant fusion protein created by linking the N-terminal CD47-binding domain of SIRPa with the Fc domain of human IgG1, acts by binding human CD47, and preventing it from delivering its "do not eat" signal to macrophages, is in clinical trials in Phase 1 (NCT02890368 and NCT02663518); CC-90002 (Celgene), an anti-CD47 antibody, in leukemias (NCT02641002); and Hu5F9-G4 (Forty Seven, Inc.), in colorectal neoplasms and solid tumors (NCT02953782), acute myeloid leukemia (NCT02678338) and lymphoma (NCT02953509).

Checkpoint inhibitors that may be used in the present invention include CD73 inhibitors. CD73 inhibitors that are being studied in clinical trials include MEDI9447 (Medimmune), an anti-CD73 antibody, in solid tumors (NCT02503774); and BMS-986179 (Bristol-Myers Squibb), an anti-CD73 antibody, in solid tumors (NCT02754141).

Checkpoint inhibitors that may be used in the present invention include agonists of stimulator of interferon genes protein (STING, also known as transmembrane protein 173, or TMEM173). Agonists of STING that are being studied in clinical trials include MK-1454 (Merck), an agonistic synthetic cyclic dinucleotide, in lymphoma (NCT03010176); and ADU-S100 (MIW815, Aduro Biotech/Novartis), an agonistic synthetic cyclic dinucleotide, in Phase 1 (NCT02675439 and NCT03172936).

Checkpoint inhibitors that may be used in the present invention include CSF1R inhibitors. CSF1R inhibitors that are being studied in clinical trials include pexidartinib (PLX3397, Plexxikon), a CSF1R small molecule inhibitor, in colorectal cancer, pancreatic cancer, metastatic and advanced cancers (NCT02777710) and melanoma, non-small cell lung cancer, squamous cell head and neck cancer, gastrointestinal stromal tumor (GIST) and ovarian cancer (NCT02452424); and IMC-CS4 (LY3022855, Lilly), an anti-CSF-1R antibody, in pancreatic cancer (NCT03153410), melanoma (NCT03101254), and solid tumors (NCT02718911); and BLZ945 (4-[2((1R,2R)-2-hydroxycyclohexylamino)-benzothiazol-6-yloxyl]-pyridine-2-carboxylic acid methylamide, Novartis), an orally available inhibitor of CSF1R, in advanced solid tumors (NCT02829723).

Checkpoint inhibitors that may be used in the present invention include NKG2A receptor inhibitors. NKG2A receptor inhibitors that are being studied in clinical trials include monalizumab (IPH2201, Innate Pharma), an anti-NKG2A antibody, in head and neck neoplasms (NCT02643550) and chronic lymphocytic leukemia (NCT02557516).

In some embodiments, the immune checkpoint inhibitor is selected from nivolumab, pembrolizumab, ipilimumab, avelumab, durvalumab, atezolizumab, or pidilizumab.

EXEMPLIFICATION

Synthetic Methods

The following examples are intended to illustrate the invention and are not to be construed as being limitations thereon. Temperatures are given in degrees centigrade. If not mentioned otherwise, all evaporations were performed under reduced pressure, preferably between about 15 mm Hg and 100 mm Hg (=20-133 mbar). The structure of final products, intermediates and starting materials was confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention were either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

Intermediates (E)-4-ethoxy-1,1-difluorobut-3-en-2-one (Intermediate CJB)

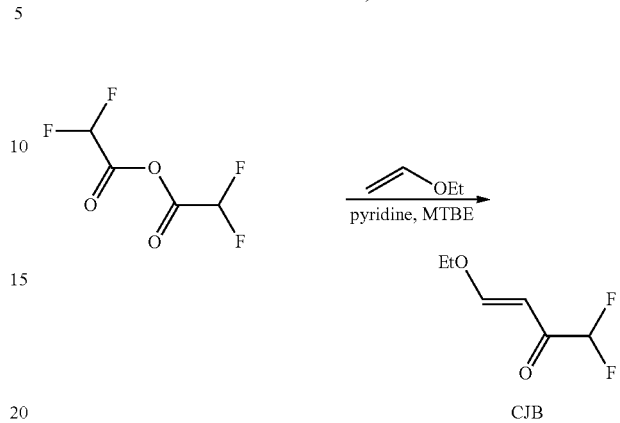

To a solution of (2,2-difluoroacetyl) 2,2-difluoroacetate (7.50 g, 43.0 mmol, CAS #401-67-2) was dissolved in MTBE (100 mL) at 0° C. Then a solution of vinyloxyethane (3.11 g, 43.0 mmol, CAS #109-92-2) in pyridine (3.75 g, 47.4 mmol) was added to the former mixture at 0° C. The resulting mixture was stirred at 20° C. for 12 hrs. On completion, the reaction mixture was diluted with water (100 mL) and extracted with EA (2×80 mL). The combined organic layer was washed with brine (80 mL) and dried over $Na_2SO_4$, filtered and the filtrate was concentrated in vacuo to give a residue. The residue was purified by column chromatography ($SiO_2$, Petroleum ether/Ethyl acetate=10:1 to 5:1) to give the title compound (3.00 g, 46% yield) as yellow liquid. $^1$H NMR (400 MHz, $CDCl_3$) δ 7.85 (d, J=12.0 Hz, 1H), 5.90 (d, J=4.0 Hz, 1H), 5.87-5.58 (m, 1H), 4.07 (q, J=8.0 Hz, 2H), 1.40 (t, J=8.0 Hz, 3H).

4-(4-Amino-3-(difluoromethyl)-1H-pyrazol-1-yl)cyclohexanol (Intermediate CJC)

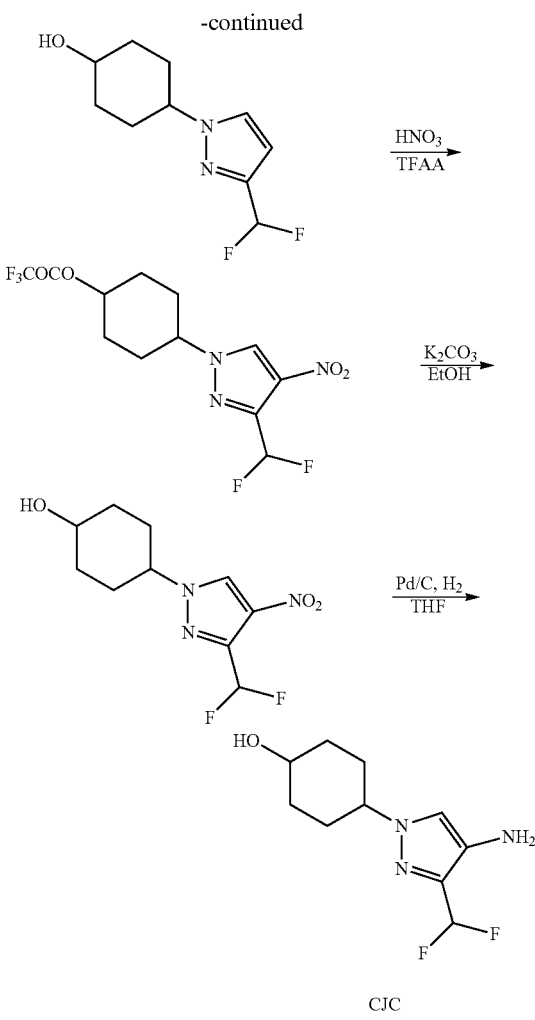

CJC

Step 1—Methyl 2-(4-(benzyloxy)cyclohexyl)hydrazinecarboxylate To a mixture of methyl N-aminocarbamate (2.48 g, 19.5 mmol, HCl, CAS #2987-06-6) in DCM (60 mL) was added TEA (3.96 g, 39.1 mmol) at 25° C. until the pH stabilized at 8. The mixture was stirred at 20° C. for 0.5 hr, then HOAc (2.35 g, 39.1 mmol) was added at 20° C. to solution until the pH stabilized at 5-6. The mixture was cooled to 0° C. Then 4-benzyloxycyclohexanone (4.00 g, 19.5 mmol, CAS #6294-89-9) was added and the mixture was stirred for 2 hrs. Next, NaBH(OAc)₃ (8.30 g, 39.1 mmol) was added in one portion. The resulting reaction mixture was stirred at 20° C. for 12 hrs. On completion, the reaction mixture was quenched with water (4 mL) and diluted with water (80 mL) and extracted with DCM (60 mL×2). The combined organic phase was washed with saturated sodium chloride solution (60 mL×2), dried over anhydrous sodium sulfate, filtered and concentrated to give a residue. The residue was purified by column chromatography (SiO₂, Petroleum ether/Ethyl acetate=1:1 to 1:2) to give the title compound (5.20 g, 95% yield) as colorless oil. ¹H NMR (400 MHz, DMSO-d₆) δ 8.62-8.39 (m, 1H), 7.38-7.35 (m, 1H), 7.32 (s, 2H), 7.29-7.23 (m, 1H), 4.48 (d, J=6.4 Hz, 1H), 4.46-4.43 (m, 2H), 3.55 (s, 3H), 3.51-3.45 (m, 1H), 3.40-3.21 (m, 1H), 2.86-2.71 (m, 1H), 1.83-1.74 (m, 2H), 1.49-1.40 (m, 6H).

Step 2—1-(4-(Benzyloxy)cyclohexyl)-3-(difluoromethyl)-1H-pyrazole. To a solution of methyl N-[(4-benzyloxycyclohexyl)amino]carbamate (4.50 g, 16.1 mmol) in toluene (50 mL) was added TFA (2.03 g, 17.7 mmol) at N₂. The mixture was stirred at 20° C. for 20 mins, then (E)-4-ethoxy-1,1-difluoro-but-3-en-2-one (2.91 g, 19.4 mmol, Intermediate CJB) was added in one portion. The mixture was then stirred at 20° C. for 12 hrs. On completion, the reaction mixture was diluted with water (100 mL) and extracted with EA (2×80 mL). The combined organic layer was washed with brine (100 mL) and dried over Na₂SO₄, filtered and the filtrate was concentrated in vacuo to give a residue. The residue was purified by column chromatography (SiO₂, Petroleum ether/Ethyl acetate=10:1 to 5:1) to give the title compound (4.00 g, 80% yield) as yellow oil. ¹H NMR (400 MHz, DMSO-d₆) δ 7.91-7.86 (m, 1H), 7.39-7.24 (m, 5H), 7.10-6.79 (m, 1H), 6.48 (d, J=0.8 Hz, 1H), 4.55-4.47 (m, 2H), 4.31-4.21 (m, J=4.0, 7.6, 11.2 Hz, 1H), 3.66 (d, J=2.8 Hz, 1H), 2.11-1.94 (m, 4H), 1.85-1.73 (m, 2H), 1.65-1.53 (m, 2H).

Step 3—4-(3-(Difluoromethyl)-1H-pyrazol-1-yl)cyclohexanol. To a solution of 1-(4-benzyloxycyclohexyl)-3-(difluoromethyl)pyrazole (4.00 g, 13.0 mmol) in THF (40 mL) was added H₂ (26.3 mg, 13.0 mmol) (15 psi) and Pd/C (1.20 g, 3.92 mmol). The mixture was stirred at 25° C. for 12 hrs. On completion, the reaction mixture was diluted with water (100 mL) and extracted with EA (100 mL×2). The combined organic phase was washed with saturated sodium chloride solution (100 mL×2), dried over anhydrous sodium sulfate, filtered and concentrated to give a residue. The residue was purified by column chromatography (SiO₂, Ethyl acetate/Petroleum ether=1:5 to 1:1) to give the title compound (1.98 g, 70% yield) as colorless oil. ¹H NMR (400 MHz, DMSO-d₆) δ 7.87 (d, J=2.0 Hz, 1H), 7.09-6.80 (m, 1H), 6.49-6.46 (m, 1H), 4.84-4.67 (m, 1H), 4.23-4.13 (m, J=4.0, 12.0 Hz, 1H), 3.54-3.42 (m, 1H), 2.02-1.86 (m, 5H), 1.83-1.69 (m, 3H), LC-MS (ESI+) m/z 217.0 (M+H)⁺.

Step 4—4-(3-(Difluoromethyl)-4-nitro-1H-pyrazol-1-yl)cyclohexyl 2,2,2-trifluoroacetate. To a solution of 4-[3-(difluoromethyl)pyrazol-1-yl]cyclohexanol (1.98 g, 9.16 mmol) in TFAA (15 mL) was added HNO₃ (1.41 g, 14.1 mmol) at 0° C. The mixture was then stirred at 25° C. for 12 hrs. On completion, the reaction mixture was poured into ice water (100 mL) and NaHCO₃ aqueous was added at 25° C. until pH stabilized at 7, then the mixture was extracted with EA 160 mL (2×80 mL). The organic layer was washed with saturated brine (2×80 mL). The organic layer was dried over anhydrous sodium sulfate and filtered. The filtrated was concentrated in vacuo. The residue was purified by column chromatography (SiO₂, Petroleum ether/Ethyl acetate=5:1 to 1:1) to give the title compound (2.80 g, 85% yield) as yellow solid. ¹H NMR (400 MHz, DMSO-d₆) δ 9.07 (s, 1H), 7.31 (t, J=5.6 Hz, 1H), 5.08-4.98 (m, J=4.0, 12.0 Hz, 1H), 4.50-4.40 (m, J=4.0, 12.0 Hz, 1H), 4.06-4.06 (m, 1H), 2.16 (d, J=12.0 Hz, 4H), 2.05-1.92 (m, 2H), 1.78-1.64 (m, 2H), LC-MS (ESI+) m/z 357.9 (M+H)⁺.

Step 5—4-(3-(Difluoromethyl)-4-nitro-1H-pyrazol-1-yl)cyclohexanol. To a solution of [4-[3-(difluoromethyl)-4-nitro-pyrazol-1-yl]cyclohexyl] 2,2,2-trifluoroacetate (2.80 g, 7.84 mmol) in EtOH (15 mL) as added K₂CO₃ (2.17 g, 15.6 mmol). The mixture was stirred at 25° C. for 1 hr. On completion, the reaction mixture was filtered and the filtrate was concentrated in vacuo to give the title compound (2.00 g, 97% yield) as yellow liquid. LC-MS (ESI⁺) m/z 261.9 (M+H)⁺.

Step 6—4-(4-Amino-3-(difluoromethyl)-1H-pyrazol-1-yl)cyclohexanol. To a solution of 4-[3-(difluoromethyl)-4-nitro-pyrazol-1-yl]cyclohexanol (2.00 g, 7.66 mmol) in THF (40 mL) was added H₂ (15.4 mg, 7.66 mmol) (15 psi) and Pd/C (600 mg, 2.30 mmol) The mixture was stirred at 25° C. for 12 hrs. On completion, the reaction mixture was diluted with water (60 mL) and extracted with EA (80 mL×2). The combined organic phase was washed with saturated sodium chloride solution (60 mL×2), dried over anhydrous sodium sulfate, filtered and concentrated to give a residue. The residue was purified by column chromatography (SiO$_2$, Ethyl acetate/Petroleum ether=1:5 to 1:1) to give the title compound (1.70 g, 99% yield) as colorless oil. LC-MS (ESI$^+$) m/z 232.0 (M+H)$^+$.

5-((1R,4R)-2-oxa-5-azabicyclo[2.2.1]heptan-5-yl)-N-(3-(difluoromethyl)-1-(4-oxocyclohexyl)-1H-pyrazol-4-yl)pyrazolo[1,5-a]pyrimidine-3-carboxamide (Intermediate CJD)

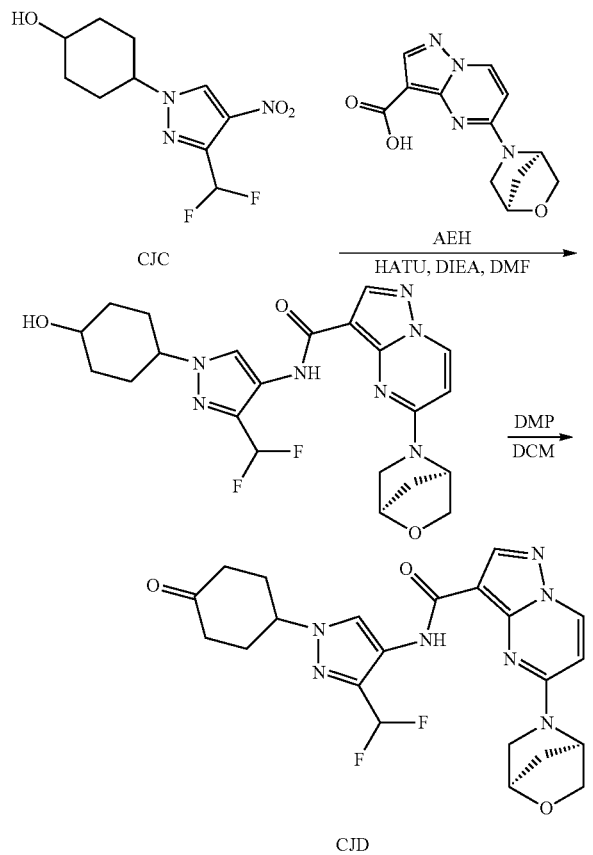

Step 1—5-((1R,4R)-2-oxa-5-azabicyclo[2.2.1]heptan-5-yl)-N-(3-(difluoromethyl)-1-(4-hydroxycyclohexyl)-1H-pyrazol-4-yl)pyrazolo[1,5-a]pyrimidine-3-carboxamide. To a solution of 5-[(1R,4R)-2-oxa-5-azabicyclo[2.2.1]heptan-5-yl]pyrazolo[1,5-a]pyrimidine-3-carboxylic acid (1.13 g, 4.32 mmol, Intermediate AEH) in DMF (12 mL) was added dropwise HATU (2.14 g, 5.62 mmol) and DIEA (1.68 g, 12.9 mmol) at 25° C. for 30 mins. Then 4-[4-amino-3-(difluoromethyl)pyrazol-1-yl]cyclohexanol (1.00 g, 4.32 mmol, Intermediate CJC) was added and the mixture was stirred at 60° C. for 12 hrs. On completion, the residue was diluted with water (60 mL) and extracted with EA (2×40 mL). The combined organic layer was washed with brine (40 mL) and dried over Na$_2$SO$_4$, filtered and the filtrate was concentrated in vacuo to give a residue. The residue was purified by column chromatography (SiO$_2$, Petroleum ether/Ethyl acetate=5:1 to 1:1) to give the title compound (1.80 g, 90% yield) as yellow oil. $^1$H NMR (400 MHz, DMSO-d$_6$) δ 9.54-9.46 (m, 1H), 8.78 (d, J=8.0 Hz, 1H), 8.38 (d, J=4.0 Hz, 1H), 8.25 (d, J=5.6 Hz, 1H), 7.30-6.93 (m, 1H), 6.88-6.42 (m, 1H), 4.77 (d, J=17.2 Hz, 1H), 4.69-4.47 (m, 1H), 4.27-4.15 (m, 1H), 3.87-3.77 (m, 2H), 3.76-3.61 (m, 1H), 3.54-3.42 (m, 1H), 3.17 (d, J=5.6 Hz, 2H), 2.04-1.88 (m, 4H), 1.79-1.69 (m, 3H), 1.63-1.52 (m, 1H), 1.31-1.21 (m, 2H), LC-MS (ESI$^+$) m/z 474.2 (M+H)$^+$.

Step 2—5-((1R,4R)-2-oxa-5-azabicyclo[2.2.1]heptan-5-yl)-N-(3-(difluoromethyl)-1-(4-oxocyclohexyl)-1H-pyrazol-4-yl)pyrazolo[1,5-a]pyrimidine-3-carboxamide. To a solution of N-[3-(difluoromethyl)-1-(4-hydroxycyclohexyl)pyrazol-4-yl]-5-[(1R,4R)-2-oxa-5-azabicyclo[2.2.1]heptan-5-yl]pyrazolo[1,5-a]pyrimidine-3-carboxamide (900 mg, 1.90 mmol) in DCM (10 mL) was added DMP (1.05 g, 2.47 mmol). The mixture was stirred at 40° C. for 3 hrs. On completion, the reaction mixture was quenched by Na$_2$S$_2$O$_3$ (20 mL) and NaHCO$_3$ (20 mL) at 25° C., and then extracted with DCM 50 mL (25 mL×2). The combined organic phase was washed with saturated sodium chloride solution (25 mL×2), dried over anhydrous sodium sulfate, filtered and concentrated to give the title compound (790 mg, 88% yield) as yellow solid. LC-MS (ESI$^+$) m/z 472.0 (M+H)$^+$.

[(5R)-5-(5-bromo-6-methoxy-indazol-2-yl)tetrahydropyran-2-yl]methanol (Intermediate CJG)

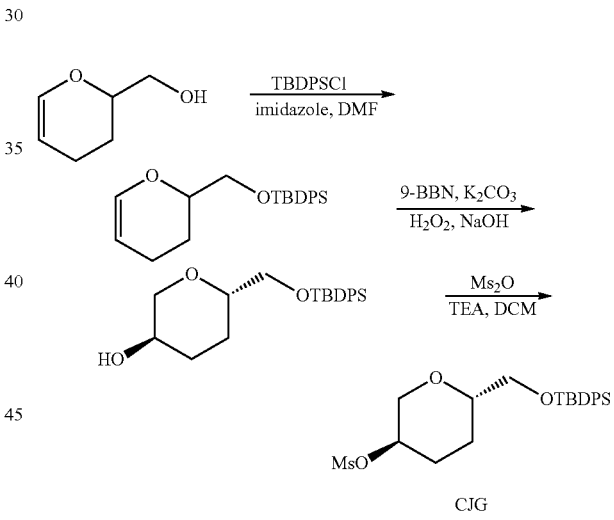

Step-1—Tert-butyl-(3,4-dihydro-2H-pyran-2-ylmethoxy)-diphenyl-silane. To a solution of 3,4-dihydro-2H-pyran-2-ylmethanol (10.0 g, 87.6 mmol, CAS #3749-36-8) in DMF (200 mL) was added imidazole (11.9 g, 175 mmol) and TBDPSCl (28.9 g, 105 mmol). The mixture was stirred at 25° C. for 2 hrs. On completion, the reaction mixture was diluted with EA (60 mL) and washed with water (3×10 mL). The organic layer was dried over Na$_2$SO$_4$, filtered and concentrated in vacuo. The reaction mixture was concentrated under reduced pressure to give a residue. Then the residue was purified by column chromatography (SiO$_2$, Petroleum ether/Ethyl acetate=20/1 to 1/1) to give the title compound (51 g, 83% yield) as colorless oil. $^1$H NMR (400 MHz, CDCl$_3$) δ 7.58 (t, J=1.6 Hz, 4H) 7.23-7.30 (m, 6H) 6.23 (d, J=6.0 Hz, 1H) 4.50-4.55 (m, 1H) 3.81 (t, J=2.0 Hz, 1H) 3.66-3.72 (m, 1H) 3.55-3.60 (m, 1H) 1.89-1.98 (m, 1H) 1.78-1.87 (m, 2H) 1.54-1.65 (m, 1H) 0.96 (s, 9H).

Step-2—6-[[Tert-butyl(diphenyl)silyl]oxymethyl]tetrahydropyran-3-ol. To a solution of tert-butyl-(3,4-dihydro-2H-pyran-2-ylmethoxy)-diphenyl-silane (10.0 g, 28.3 mmol) in THF (100 mL) was added 9-BBN (1 M, 141 mL) dropwise at 0° C. After addition, the mixture was brought to 25° C. and the reaction was continued at 25° C. for 14 hrs. The reaction mixture was then oxidized with NaOH (3 M, 56.7 mL) and $H_2O_2$ (259 mmol, 26.7 mL, 28% solution), and the reaction was keep at 55° C. for 1 hr. Next, $K_2CO_3$ (784 mg, 5.67 mmol) was added at 0° C. and the mixture was stirred for 1 hr. On completion, the reaction mixture was diluted with $H_2O$ (200 mL) and extracted with EA (3×50 mL). The combined organic layers were washed with brine (2×50 mL), dried over $Na_2SO_4$, filtered and concentrated under reduced pressure to give a residue. The aqueous phase was quenched by addition $Na_2S_2O_3$ (2000 mL). The residue was purified by column chromatography ($SiO_2$, Petroleum ether/Ethyl acetate=100/1 to 10/1) to give the title compound (10.1 g, 96% yield) as colorless oil. $^1$H NMR (400 MHz, $CDCl_3$) δ 7.72 (d, J=6.8 Hz, 4H) 7.39-7.46 (m, 6H) 4.16 (q, J=7.2 Hz, 1H) 4.01 (d, J=7.2 Hz, 1H) 3.77 (d, J=5.2 Hz, 1H) 3.68 (t, J=5.2 Hz, 1H) 3.57 (s, 1H) 3.37-3.44 (m, 1H) 3.12 (t, J=10.4 Hz, 1H) 2.34 (s, 1H) 2.09-2.18 (m, 1H) 1.82-1.90 (m, 1H) 1.36-1.48 (m, 2H) 1.11 (s, 9H). LC-MS ($ESI^+$) m/z 393.0 $(M+H)^+$.

Step 3—[6-[[Tert-butyl(diphenyl)silyl]oxymethyl]tetrahydropyran-3-yl] methanesulfonate. To a solution of 6-[[tert-butyl(diphenyl)silyl]oxymethyl]tetrahydropyran-3-ol (5.22 g, 14.0 mmol) in DCM (50 mL) was added TEA (2.85 g, 28.1 mmol) and methylsulfonyl methanesulfonate (3.68 g, 21.1 mmol). The mixture was stirred at 0° C. for 2 hrs. On completion, the residue was diluted with $H_2O$ (12 mL) and extracted with DCM (3×10 mL). The combined organic layers were dried over $Na_2SO_4$, filtered and concentrated under reduced pressure to give the title compound. LC-MS ($ESI^+$) m/z 466.2 $(M+H)^+$.

Step 4—[(5R)-5-(5-bromo-6-methoxy-indazol-2-yl)tetrahydropyran-2-yl]methanol. To a solution of [6-[[tert-butyl(diphenyl)silyl]oxymethyl]tetrahydropyran-3-yl] methanesulfonate (3.00 g, 6.69 mmol) in DMF (5 mL) was added 5-bromo-6-methoxy-2H-indazole (759 mg, 3.34 mmol, CAS #152626-78-3) and $Cs_2CO_3$ (2.18 g, 6.69 mmol). The mixture was stirred at 80° C. for 16 hrs. On completion, the residue was diluted with $H_2O$ (5 mL) and extracted with EA (3×10 mL). The combined organic layers were dried over $Na_2SO_4$, filtered and concentrated under reduced pressure to give a residue. The residue was purified by prep-HPLC (column: Phenomenex luna C18 150*25 mm*10 um; mobile phase: [water(FA)-ACN]; B %: 20%-50%, 10.5 min) to give the title compound (80 mg, 7% yield) as a yellow solid. $^1$H NMR (400 MHz, $CDCl_3$) δ 8.30 (s, 1H) 7.90 (s, 1H) 7.03 (s, 1H) 4.57-4.66 (m, 2H) 4.07 (d, J=2.4 Hz, 1H) 3.95 (s, 3H) 3.58-3.70 (m, 3H) 2.47-2.57 (m, 1H) 2.15-2.23 (m, 1H) 1.76-1.87 (m, 1H) 1.41-1.52 (m, 2H).

6-(1-Fluoro-1-methyl-ethyl)-N-[2-[(3R,6R)-6-formyltetrahydropyran-3-yl]-6-methoxy-indazol-5-yl]pyridine-2-carboxamide (Intermediate CJH)

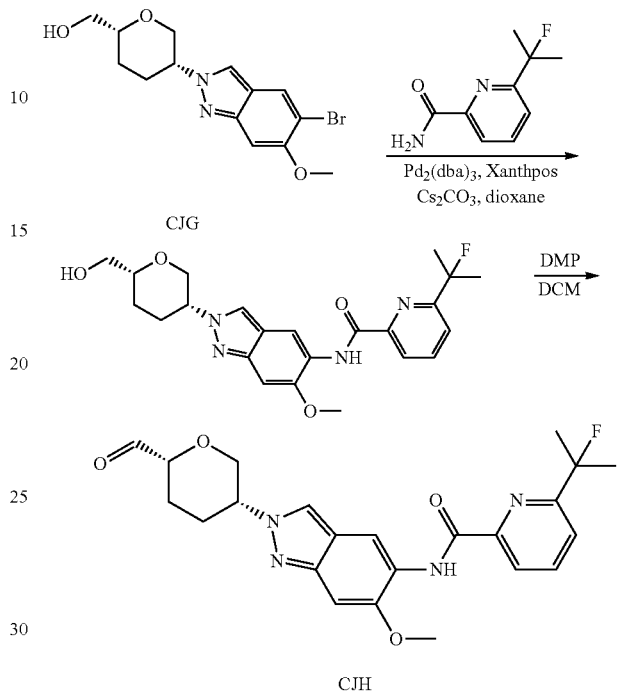

CJG

CJH

Step 1—6-(1-Fluoro-1-methyl-ethyl)-N-[(2S)-2-[6-(hydroxymethyl)tetrahydropyran-3-yl]-6-methoxy-indazol-5-yl]pyridine-2-carboxamide. A mixture of [(5R)-5-(5-bromo-6-methoxy-indazol-2-yl)tetrahydropyran-2-yl]methanol (80 mg, 230 umol, Intermediate CJG), 6-(1-fluoro-1-methyl-ethyl)pyridine-2-carboxamide (51.2 mg, 281 umol, CAS #152626-78-3), $Pd_2(dba)_3$ (21.4 mg, 23.4 umol), Xantphos (13.5 mg, 23.4 umol) and $Cs_2CO_3$ (152 mg, 468 umol) in dioxane (5 mL) was degassed and purged with $N_2$ three times. Then the mixture was stirred at 80° C. for 16 hrs under $N_2$ atmosphere. On completion the residue was diluted with $H_2O$ (5 mL) and extracted with EA (3×10 mL). The combined organic layers were washed with brine (2×9 mL), dried over $Na_2SO_4$, filtered and concentrated under reduced pressure to give a residue. The residue was purified by prep-HPLC (column: Phenomenex luna C18 150*25 mm*10 um; mobile phase: [water (FA)-ACN]; B %: 37%-67%, 10 min) to give the title compound (75 mg, 70% yield) as a white solid. $^1$H NMR (400 MHz, $CDCl_3$) δ 10.85 (s, 1H) 8.85 (s, 1H) 8.32 (s, 1H) 8.21 (d, J=7.6 Hz, 1H) 7.95 (t, J=7.6 Hz, 1H) 7.76 (d, J=7.6 Hz, 1H) 7.06 (s, 1H) 4.60-4.67 (m, 2H) 4.00-4.08 (m, 4H) 3.63-3.71 (m, 3H) 2.54 (d, J=14.0 Hz, 1H) 2.15-2.21 (m, 1H) 1.80-1.87 (m, 6H) 1.63 (s, 2H) 1.50 (s, 1H). LC-MS (ESI+) m/z 443.0 $(M+H)^+$.

Step 2—6-(1-Fluoro-1-methyl-ethyl)-N-[2-[(3R,6R)-6-formyltetrahydropyran-3-yl]-6-methoxy-indazol-5-yl]pyridine-2-carboxamide. To a solution of 6-(1-fluoro-1-methyl-ethyl)-N-[2-[(3R,6R)-6-(hydroxymethyl)tetrahydropyran-3-yl]-6-methoxy-indazol-5-yl]pyridine-2-carboxamide (75.0 mg, 169 umol) in DCM (1 mL) was added DMP (143 mg, 339 umol). The mixture was stirred at 25° C. for 2 hrs. On completion, the residue was diluted with $H_2O$ (5 mL) and extracted with DCM (3×5 mL). The combined organic layers were washed with brine (2×6 mL), dried over Na$_2$SO$_4$, filtered and concentrated under reduced pressure to give the title compound. LC-MS (ESI+) m/z 459.1 (M+H)$^+$.

5-Fluoro-N-[2-(4-formylcyclohexyl)-6-methoxy-indazol-5-yl]pyridine-3-carboxamide (Intermediate CJI)

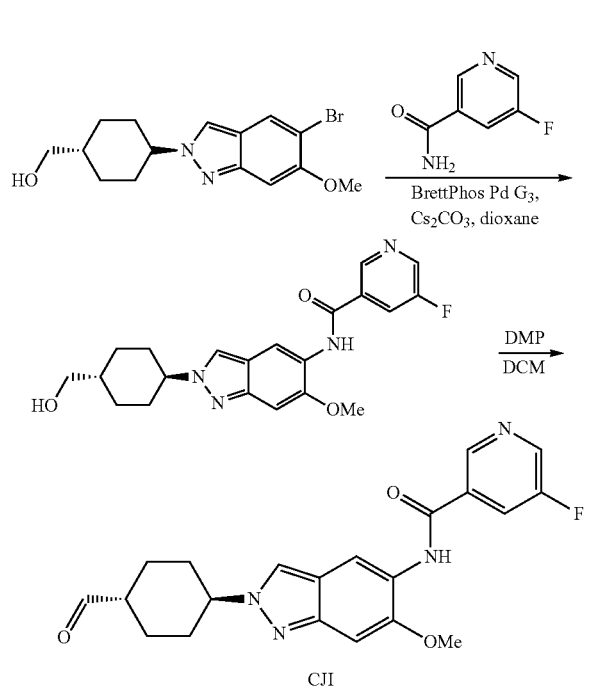

Step 1—5-Fluoro-N-[2-[4-(hydroxymethyl)cyclohexyl]-6-methoxy-indazol-5-yl]pyridine-3-carboxamide. A mixture of 5-fluoropyridine-3-carboxamide (107 mg, 766 umol, CAS #70-58-6), [4-(5-bromo-6-methoxy-indazol-2-yl)cyclohexyl]methanol (200 mg, 589 umol, synthesized via Steps 1-3 of Intermediate ATE), BrettPhos Pd G$_3$ (53 mg, 58 umol) and Cs$_2$CO$_3$ (576 mg, 1.77 mmol) in dioxane (3 mL) was degassed and purged with N$_2$ three times, and then the mixture was stirred at 90° C. for 16 hrs under N$_2$ atmosphere. On completion, the mixture was filtered and concentrated to give a residue. The residue was purified by column chromatography (SiO$_2$, Petroleum ether/Ethyl acetate=5/1 to 0/1) to give the title compound (164 mg, 62% yield) as a white solid. LC-MS (ESI$^+$) m/z 399.0 (M+H)$^+$.

Step 2—5-Fluoro-N-[2-(4-formylcyclohexyl)-6-methoxy-indazol-5-yl]pyridine-3-carboxamide. To a solution of 5-fluoro-N-[2-[4-(hydroxymethyl)cyclohexyl]-6-methoxy-indazol-5-yl]pyridine-3-carboxamide (104 mg, 261 umol) in DCM (1 mL) was added DMP (132 mg, 313 umol). The mixture was stirred at 25° C. for 1 hr. On completion, the reaction mixture was quenched with addition Na$_2$S$_2$O$_4$ (1 mL) and NaHCO$_3$ (1 mL). The reaction mixture was filtered and concentrated in vacuo. The residue was diluted with DCM (20 mL) and NaHCO$_3$ (20 mL). The mixture was filtered and concentrated to give a residue. The filtrate was concentrated and the mixture was extracted with DCM (10 mL×3). The organic layer was dried over Na2SO4, filtered, and concentrated in vacuo. Then the residue was purified by column chromatography (SiO$_2$, Petroleum ether/Ethyl acetate=5/1 to 0/1) to give the title compound (96 mg, 85% yield) as a brown solid. LC-MS (ESI$^+$) m/z 396.9 (M+H)$^+$.

5-(1-Piperidyl)pyrazolo[1,5-a]pyrimidine-3-carboxylic acid (Intermediate CJJ)

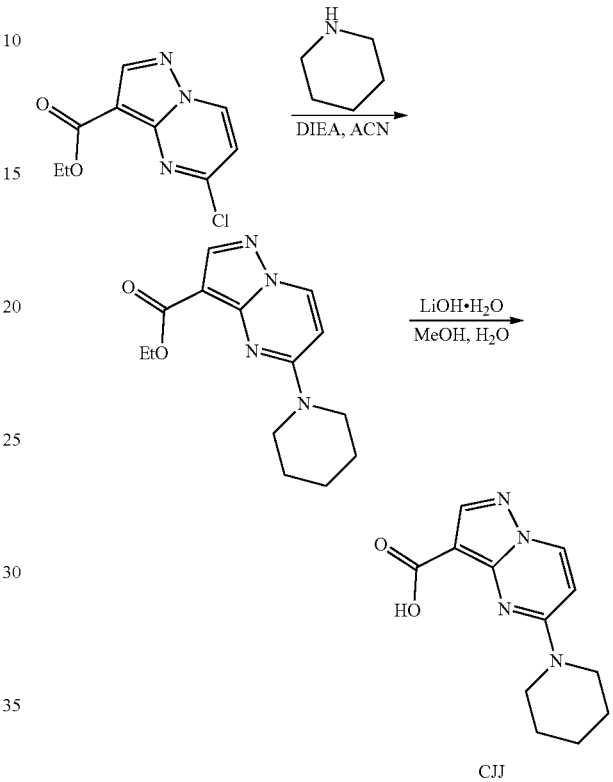

Step 1—Ethyl 5-(1-piperidyl)pyrazolo[1,5-a]pyrimidine-3-carboxylate. A mixture of ethyl 5-chloropyrazolo [1,5-a]pyrimidine-3-carboxylate (800 mg, 3.55 mmol, CAS #1224944-77-7), piperidine (603 mg, 7.09 mmol, CAS #110-89-4), DIEA (916 mg, 7.09 mmol) in ACN (12 mL) was degassed and purged with N$_2$ three times. Then the mixture was stirred at 60° C. for 2 hrs under N$_2$ atmosphere. On completion, the reaction mixture was concentrated in vacuo. Then the mixture was diluted with H$_2$O (30 mL) and extracted with EA (20 mL×3). The combined organic layers were washed with saturated NaCl (20 mL), dried over anhydrous Na$_2$SO$_4$, filtered and concentrated in vacuo to give the title compound (950 mg, 97% yield) as a yellow solid. $^1$H NMR (400 MHz, DMSO-d$_6$) δ 8.65 (d, J=8.0 Hz, 1H), 8.17 (s, 1H), 6.83 (d, J=8.0 Hz, 1H), 4.18-4.15 (m, 2H), 3.75-3.72 (m, 4H), 1.67-1.54 (m, 6H), 1.27 (t, J=7.2 Hz, 3H). LC-MS (ESI$^+$) m/z 275.1 (M+H)$^+$.

Step 2—5-(1-Piperidyl)pyrazolo[1,5-a]pyrimidine-3-carboxylic acid. To a solution of ethyl 5-(1-piperidyl) pyrazolo [1,5-a]pyrimidine-3-carboxylate (800 mg, 2.92 mmol) in MeOH (8 mL) and H$_2$O (2 mL) was added LiOH·H$_2$O (367 mg, 8.75 mmol). The mixture was stirred at 50° C. for 16 hrs. On completion, the reaction mixture was concentrated in vacuo. Then HCl (3M) was added to the mixture to adjust the pH=6, then the mixture was filtered to give the title compound (600 mg, 83% yield) as a white solid. $^1$H NMR (400 MHz, DMSO-d$_6$) δ 12.13-10.76 (m, 1H), 8.64 (d, J=8.0 Hz, 1H), 8.15 (s, 1H), 6.82 (d, J=8.0 Hz, 1H), 3.74-3.70 (m, 4H), 1.67-1.53 (m, 6H). LC-MS (ESI$^+$) m/z 247.0 (M+H)$^+$.

3-[4-[3-[4-[[4-[4-Amino-3-(difluoromethyl)pyrazol-1-yl]cyclohexyl]methyl]piperazin-1-yl]prop-1-ynyl]-3-methyl-2-oxo-benzimidazol-1-yl]piperidine-2,6-dione (Intermediate CJK)

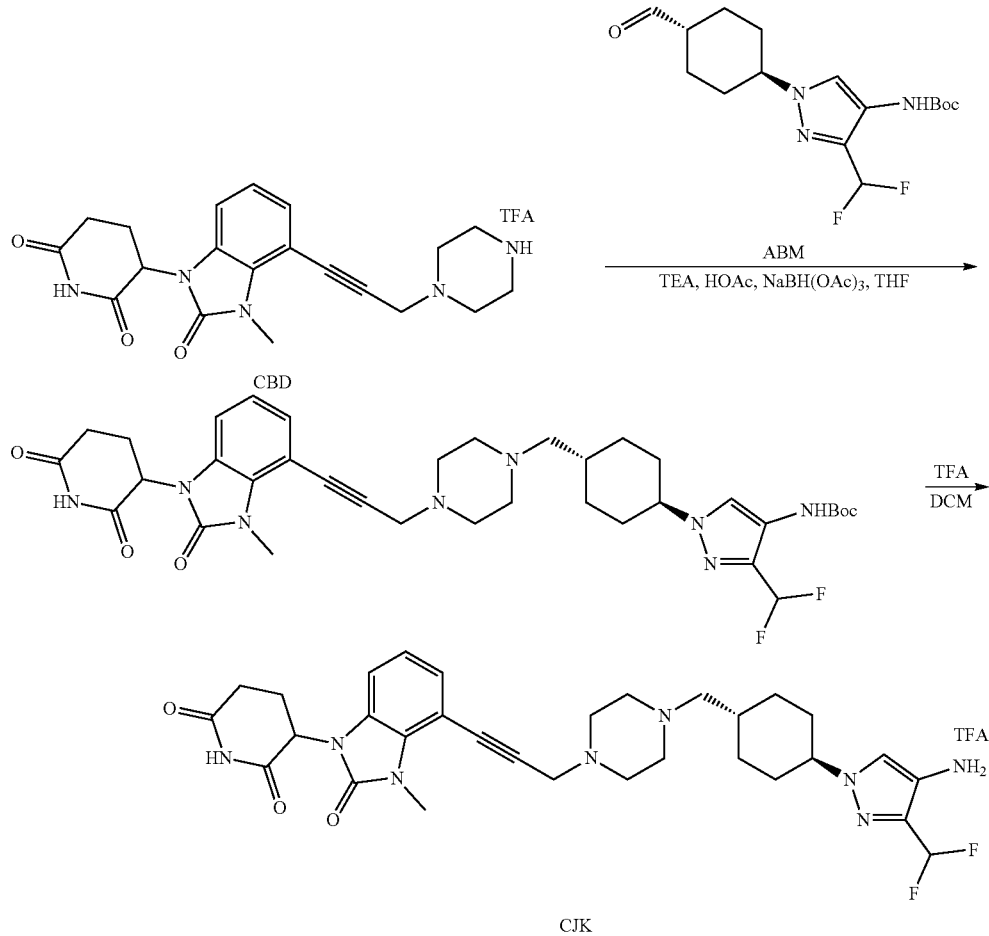

Step 1—Tert-butyl N-[3-(difluoromethyl)-1-[4-[[4-[3-[1-(2,6-dioxo-3-piperidyl)-3-methyl-2-oxo-benzimidazol-4-yl]prop-2-ynyl]piperazin-1-yl]methyl]cyclohexyl]pyrazol-4-yl]carbamate. A mixture of 3-[3-methyl-2-oxo-4-(3-piperazin-1-ylprop-1-ynyl) benzimidazol-1-yl] piperidine-2,6-dione (721 mg, 1.46 mmol, TFA, Intermediate CBD) in THF (10 mL) was added TEA (200 uL) to adjust pH=8, then the mixture was stirred at −20° C. for 0.5 hour. Then tert-butyl N-[3-(difluoromethyl)-1-(4-formylcyclohexyl) pyrazol-4-yl] carbamate (500 mg, 1.46 mmol, Intermediate ABM) and HOAc (80 uL) was added to adjust the pH=5, then the mixture was stirred at −20° C. for 1 hr. Finally, NaBH(OAc)$_3$ (339 mg, 1.60 mmol) was added and the mixture was stirred at −20° C. for 1 hr. On completion, the reaction mixture was quenched with water (0.5 mL) and concentrated in vacuo to give a residue. Then the residue was diluted with H$_2$O (100 mL) and extracted with EA (100 mL×3). The combined organic layers were washed with saturated NaCl (30 mL), dried over Na$_2$SO$_4$, filtered and concentrated in vacuo to give a residue. The residue was purified by column chromatography (SiO$_2$, DCM: MeOH=40:1 to 10:1) to give the title compound (700 mg, 68% yield) as yellow solid. $^1$H NMR (400 MHz, DMSO-d$_6$) δ 11.11 (s, 1H), 8.91 (s, 1H), 7.87 (s, 1H), 7.19-7.10 (m, 2H), 7.05-6.99 (m, 1H), 6.91-5.67 (m, 1H), 5.40 (dd, J=5.6, 12.4 Hz, 1H), 4.12 (t, J=10.4 Hz, 1H), 3.65 (s, 3H), 3.13-3.06 (m, 1H), 2.94-2.84 (m, 2H), 2.78-2.59 (m, 6H), 2.05-1.95 (m, 4H), 1.93-1.84 (m, 3H), 1.79-1.66 (m, 3H), 1.44 (s, 9H), 1.23 (s, 1H), 1.20-1.14 (m, 2H), 1.13-1.10 (m, 2H), 0.88-0.78 (m, 1H); LC-MS (ESI$^+$) m/z 709.3 (M+H)$^+$.

Step 2—3-[4-[3-[4-[[4-[4-Amino-3-(difluoromethyl) pyrazol-1-yl]cyclohexyl]methyl]piperazin-1-yl]prop-1-ynyl]-3-methyl-2-oxo-benzimidazol-1-yl]piperidine-2,6-dione. A mixture of tert-butyl N-[3-(difluoromethyl)-1-[4-[[4-[3-[1-(2,6-dioxo-3-piperidyl)-3-methyl-2-oxo-benzimidazol-4-yl]prop-2-ynyl]piperazin-1-yl]methyl]cyclohexyl]pyrazol-4-yl]carbamate (300 mg, 423 umol) in DCM (5 mL) was added TFA (2 mL), then the mixture was stirred at 20° C. for 1 hour. On completion, the reaction mixture was concentrated in vacuo to give the title compound (305 mg, 99% yield, TFA) as brown liquid. LC-MS (ESI$^+$) m/z 609.3 (M+H)$^+$.

505

5-Pyrrolidin-1-ylpyrazolo[1,5-a]pyrimidine-3-carboxylic acid (Intermediate CJL)

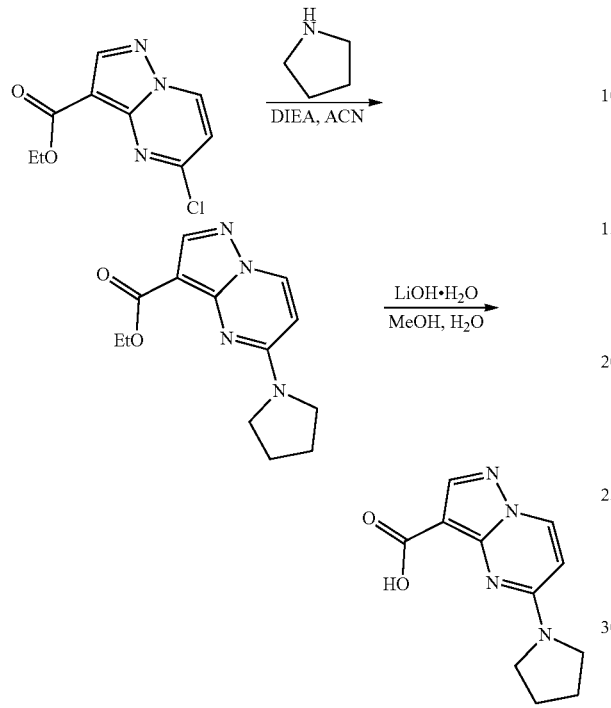

CJL

Step 1—Ethyl 5-pyrrolidin-1-ylpyrazolo [1,5-a]pyrimidine-3-carboxylate. A mixture of ethyl 5-chloropyrazolo[1,5-a]pyrimidine-3-carboxylate (1.20 g, 5.32 mmol, CAS #1224944-77-7), DIEA (1.85 mL) and pyrrolidine (756.50 mg, 10.6 mmol) in ACN (5 mL) was degassed and purged with $N_2$ three times. Then the mixture was stirred at 60° C. for 2 hrs under $N_2$ atmosphere. On completion, the reaction mixture was concentrated in vacuo to give a residue. The residue was diluted with $H_2O$ (50 mL) and extracted with DCM (100 mL×3). The combined organic layers were washed with saturated NaCl (20 mL), dried over $Na_2SO_4$, filtered and concentrated in vacuo to give a residue. The residue was purified by column chromatography ($SiO_2$, DCM:MeOH=50:1 to 20:1) to give the title compound (1.00 g, 72% yield) as white solid. $^1$H NMR (400 MHz, CDCl$_3$) δ 8.30-8.15 (m, 2H), 6.19 (d, J=7.6 Hz, 1H), 4.34 (q, J=7.2 Hz, 2H), 3.80 (s, 2H), 3.47 (s, 2H), 2.14-1.93 (m, 4H), 1.39 (t, J=7.2 Hz, 3H); LC-MS (ESI$^+$) m/z 261.2 (M+H)$^+$.

Step 2—5-Pyrrolidin-1-ylpyrazolo [1,5-a]pyrimidine-3-carboxylic acid. A mixture of ethyl 5-pyrrolidin-1-ylpyrazolo [1,5-a]pyrimidine-3-carboxylate (840 mg, 3.23 mmol) and LiOH·H$_2$O (406 mg, 9.68 mmol) in MeOH (10 mL) and H$_2$O (2 mL) was stirred at 60° C. for 2 hrs. On completion, the reaction mixture was filtered to give the title compound (700 mg, 93% yield) as white solid. $^1$H NMR (400 MHz, D$_2$O) δ 8.07 (d, J=8.0 Hz, 1H), 8.04 (s, 1H), 6.09 (d, J=8.0 Hz, 1H), 3.63-3.18 (m, 4H), 1.94 (s, 4H).

506

5-(Azetidin-1-yl)pyrazolo[1,5-a]pyrimidine-3-carboxylic acid (Intermediate CJM)

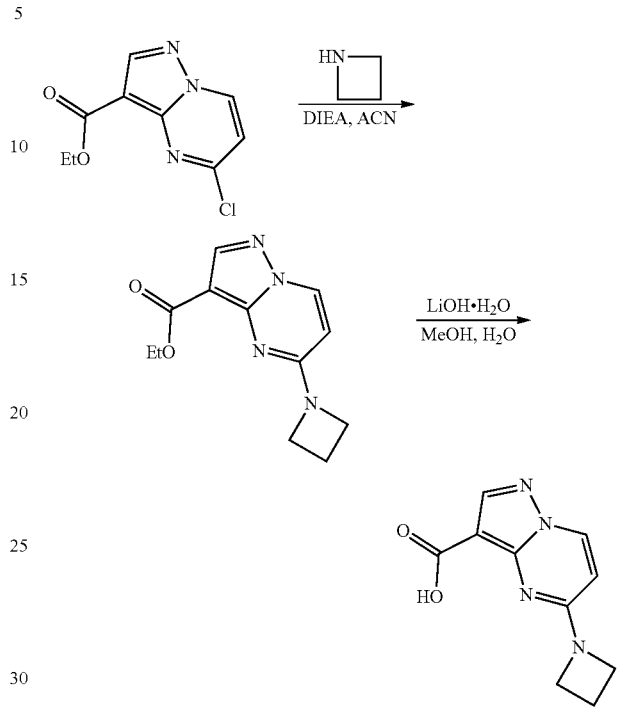

CJM

Step 1—Ethyl 5-(azetidin-1-yl)pyrazolo[1,5-a]pyrimidine-3-carboxylate. To a solution of ethyl 5-chloropyrazolo[1,5-a]pyrimidine-3-carboxylate (500 mg, 2.22 mmol) and azetidine (253 mg, 4.43 mmol) in ACN (10 mL) was added DIEA (572 mg, 4.43 mmol), then the mixture was stirred at 60° C. for 2 hrs. On completion, the reaction mixture was concentrated in vacuo to give a residue. The residue was diluted with water (20 mL) and extracted with EA (10 mL×3). The combined organic layer was dried over Na$_2$SO$_4$, filtered and concentrated in vacuo to give the title compound (400 mg, 73% yield) as white solid. $^1$H NMR (400 MHz, DMSO-d$_6$) δ 8.66 (d, J=7.6 Hz, 1H), 8.17 (s, 1H), 6.31 (d, J=7.6 Hz, 1H), 4.21-4.13 (m, 6H), 2.37 (t, J=7.6 Hz, 2H), 1.27 (t, J=7.2 Hz, 3H). LC-MS (ESI$^+$) m/z 246.7 (M+H)$^+$.

Step 2—5-(Azetidin-1-yl)pyrazolo[1,5-a]pyrimidine-3-carboxylic acid

To a solution of ethyl 5-(azetidin-1-yl)pyrazolo[1,5-a]pyrimidine-3-carboxylate (200 mg, 812 umol) in MeOH (2 mL) and H$_2$O (0.5 mL) was added LiOH·H$_2$O (68.1 mg, 1.62 mmol), then mixture was stirred at 60° C. for 2 hrs. On completion, the reaction mixture was concentrated in vacuo to remove MeOH, then acidified with hydrochloric acid (1 M) until the pH=5-6. Then the mixture was concentrated in vacuo to give the title compound (150 mg, 84% yield) as yellow oil. $^1$H NMR (400 MHz, DMSO-d$_6$) δ 8.61 (d, J=7.6 Hz, 1H), 8.04 (s, 1H), 6.21 (d, J=7.6 Hz, 1H), 4.19 (t, J=7.2 Hz, 4H), 2.34 (t, J=7.6 Hz, 2H).

4-Chloro-1-methyl-pyrazole-3-carboxylic acid (CAS #84547-85-3) (Intermediate CJN)

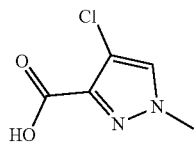

3-[4-[9-[[4-(5-Amino-6-methoxy-indazol-2-yl)cyclohexyl]methyl]-3,9-diazaspiro[5.5] undecan-3-yl]-3-methyl-2-oxo-benzimidazol-1-yl]piperidine-2,6-dione (Intermediate CJO)

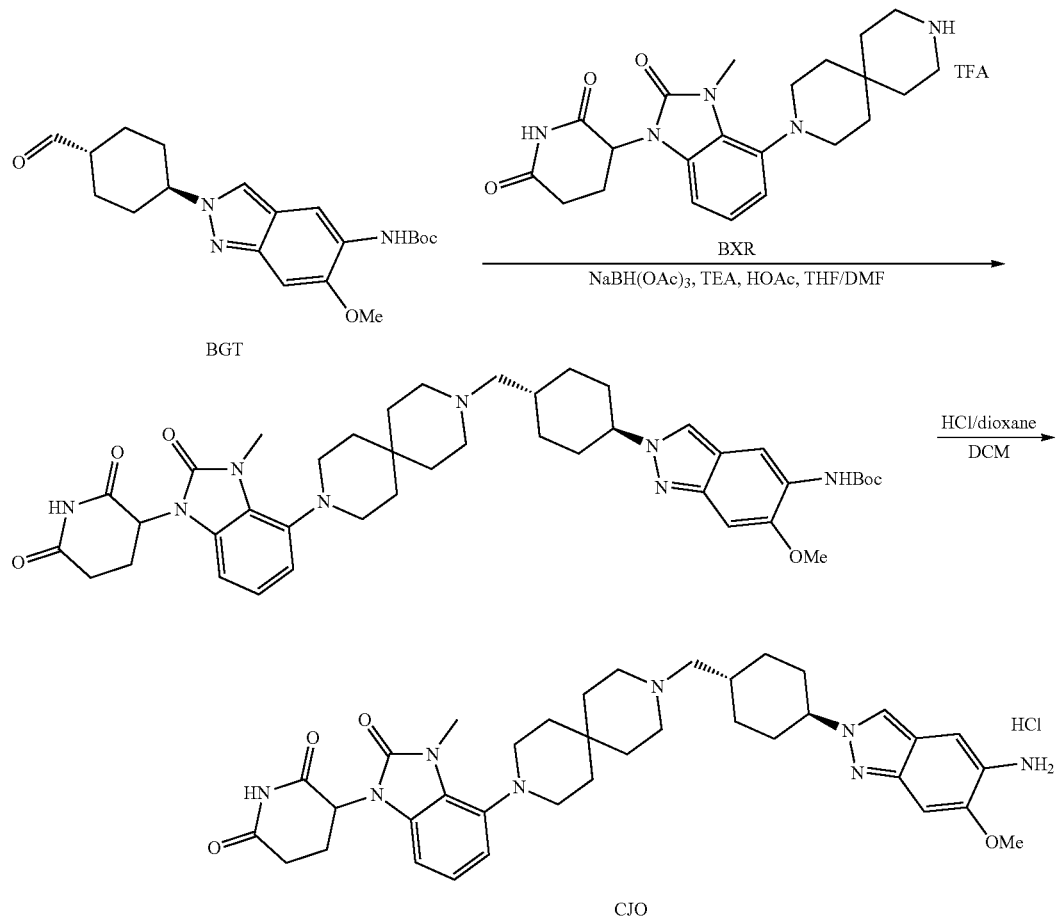

Step 1—Tert-butyl N-[2-[4-[[3-[1-(2,6-dioxo-3-piperidyl)-3-methyl-2-oxo-benzimidazol-4-yl]-3,9-diazaspiro[5.5]undecan-9-yl]methyl]cyclohexyl]-6-methoxy-indazol-5-yl]carbamate. To a solution of 3-[4-(3,9-diazaspiro[5.5]undecan-3-yl)-3-methyl-2-oxo-benzimidazol-1-yl]piperidine-2,6-dione (205 mg, 390 umol, TFA, Intermediate BXR) in DMF (2 mL) and THF (4 mL) was added TEA (39.4 mg, 390 umol, 54.3 uL), then the mixture was stirred at −10° C. for 10 mins. Next, tert-butyl N-[2-(4-formylcyclohexyl)-6-methoxy-indazol-5-yl]carbamate (145 mg, 390 umol, Intermediate BGT) and AcOH (46.8 mg, 780 umol, 44.6 uL) was added to the mixture, and the mixture was stirred at −10° C. for 20 mins. Next, NaBH(OAc)$_3$ (107 mg, 507 umol) was added to the mixture, and the mixture was stirred at −10° C. for 1 hr. On completion, the reaction mixture was quenched with H$_2$O (1 mL) and concentrated in vacuo to give a residue. The residue was purified by prep-HPLC (column: Phenomenex luna C18 150*25 mm*10 um; mobile phase: [water(FA)-ACN]; B %: 20%-50%, 15 min) to give the title compound (280 mg, 93% yield) as a white solid. $^1$H NMR (400 MHz, DMSO-d$_6$) δ 11.10 (s, 1H), 8.18 (s, 1H), 7.89 (s, 1H), 7.80 (s, 1H), 7.00-6.95 (m, 3H), 6.92-6.81 (m, 1H), 5.35 (dd, J=5.6, 12.8 Hz, 1H), 4.41-4.30 (m, 1H), 3.85 (s, 3H), 3.63 (s, 3H), 2.95-2.82 (m, 6H), 2.75-2.65 (m, 2H), 2.65-2.56 (m, 2H), 2.52-2.51 (m, 4H), 2.17-2.09 (m, 2H), 2.04-1.83 (m, 6H), 1.82-1.68 (m, 3H), 1.63-1.50 (m, 4H), 1.46 (s, 9H), 1.24-1.09 (m, 2H), LC-MS (ESI$^+$) m/z 769.5 (M+H)$^+$.

Step 2—3-[4-[9-[[4-(5-Amino-6-methoxy-indazol-2-yl)cyclohexyl]methyl]-3,9-diazaspiro[5.5] undecan-3-yl]-3-methyl-2-oxo-benzimidazol-1-yl]piperidine-2,6-dione. To a solution of tert-butyl N-[2-[4-[[3-[1-(2,6-dioxo-3-piperidyl)-3-methyl-2-oxo-benzimidazol-4-yl]-3,9-diazaspiro[5.5]undecan-9-yl]methyl]cyclohexyl]-6-methoxy-indazol-5-yl]carbamate (55.0 mg, 71.5 umol) in DCM (1 mL) was added HCl/dioxane (3 M, 2 mL). The mixture was stirred at 25° C. for 2 hrs. On completion, the reaction mixture was concentrated in vacuo to give the title compound (50.0 mg, 99% yield) as a yellow solid; LC-MS (ESI$^+$) m/z 669.4 (M+H)$^+$.

3-[3-Methyl-2-oxo-4-[4-(4-piperidyloxy)-1-piperidyl]benzimidazol-1-yl]piperidine-2,6-dione (Intermediate CJP)

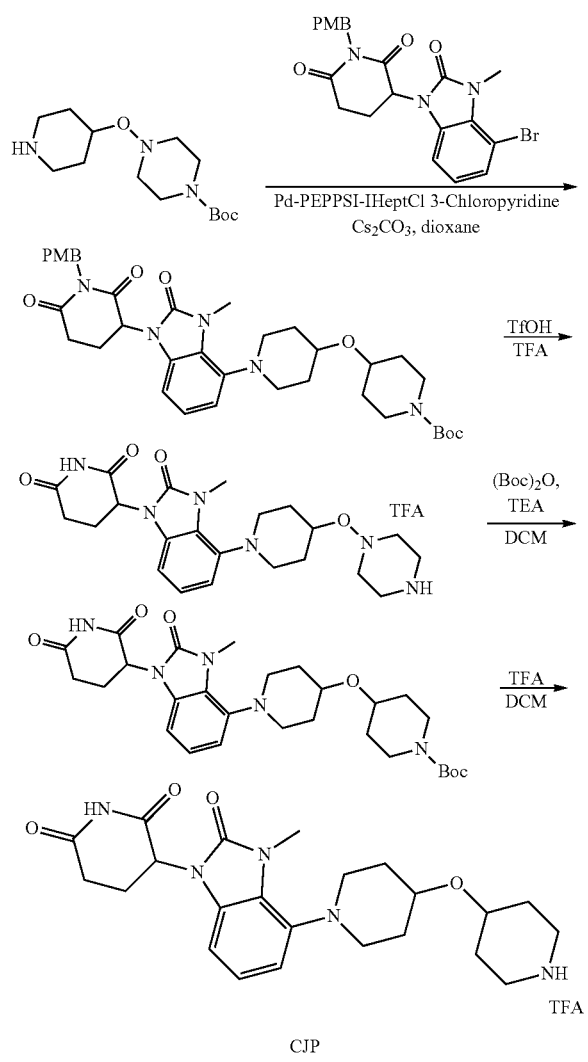

Step 1—Tert-butyl 4-[[1-[1-[1-[(4-methoxyphenyl)methyl]-2,6-dioxo-3-piperidyl]-3-methyl-2-oxo-benzimidazol-4-yl]-4-piperidyl]oxy]piperidine-1-carboxylate. A mixture of tert-butyl 4-(4-piperidyloxy)piperidine-1-carboxylate (500 mg, 1.76 mmol, CAS #845305-83-1), 3-(4-bromo-3-methyl-2-oxo-benzimidazol-1-yl)-1-[(4-methoxyphenyl)methyl] piperidine-2,6-dione (805 mg, 1.76 mmol, synthesized via Steps 1-4 of Intermediate HP), $Cs_2CO_3$ (1.72 g, 5.27 mmol), and 1,3-bis[2,6-bis(1-propylbutyl)phenyl]-4,5-dichloro-2H-imidazol-1-ium-2-ide; 3-chloropyridine; dichloropalladium (85.5 mg, 87.9 umol) in dioxane (12 mL) was degassed and purged with $N_2$ three times. Then the mixture was stirred at 100° C. for 16 hrs under $N_2$ atmosphere. On completion, the reaction mixture was concentrated in vacuo. The mixture was diluted with $H_2O$ (20 mL) and extracted with EA (20 mL×3). The combined organic layers were washed with saturated NaCl with $H_2O$ (10 mL), dried over anhydrous $Na_2SO_4$, filtered and concentrated in vacuo to give a residue. The residue was purified by column chromatography ($SiO_2$, PE:EA=50:1 to 1:1) to give the title compound (320 mg, 27% yield) as a yellow solid. $^1$H NMR (400 MHz, DMSO-$d_6$) δ 7.21 (d, J=8.4 Hz, 2H), 6.98-6.82 (m, 4H), 6.80-6.68 (m, 1H), 5.57-5.43 (m, 1H), 4.79-4.75 (m, 2H), 3.73 (s, 3H), 3.71-3.58 (m, 6H), 3.58-3.44 (m, 1H), 3.35 (s, 2H), 3.12-2.99 (m, 4H), 2.89-2.64 (m, 4H), 1.99 (s, 3H), 1.81-1.73 (m, 2H), 1.63-1.53 (m, 1H), 1.40 (s, 9H), 1.36-1.27 (m, 2H). LC-MS (ESI$^+$) m/z 662.2 (M+H)$^+$.

Step 2—3-[3-Methyl-2-oxo-4-[4-(4-piperidyloxy)-1-piperidyl]benzimidazol-1-yl]piperidine-2,6-dione. To a solution of tert-butyl 4-[[1-[1-[1-[(4-methoxyphenyl) methyl]-2,6-dioxo-3-piperidyl]-3-methyl-2-oxo-benzimidazol-4-yl]-4-piperidyl] oxy] piperidine-1-carboxylate (250 mg, 377 umol) in TFA (1 mL) was added TfOH (0.2 mL). The mixture was stirred at 70° C. for 2 hrs. On completion, the reaction mixture was concentrated in vacuo to give the title compound (205 mg, 97% yield, TFA) as a yellow oil. LC-MS (ESI$^+$) m/z 442.0 (M+H)$^+$.

Step 3—Tert-butyl 4-[[1-[1-(2,6-dioxo-3-piperidyl)-3-methyl-2-oxo-benzimidazol-4-yl]-4-piperidyl] oxy]piperidine-1-carboxylate. To a solution of 3-[3-methyl-2-oxo-4-[4-(4-piperidyloxy)-1-piperidyl]benzimidazol-1-yl] piperidine-2,6-dione (200 mg, 360 umol, TFA) in DCM (3 mL) was added (Boc)$_2$O (117 mg, 540 umol) and TEA (109 mg, 1.08 mmol). The mixture was stirred at 25° C. for 16 hrs. On completion, the reaction mixture was concentrated in vacuo. The mixture was diluted with $H_2O$ (5 mL) and extracted with EA (5 mL×3). The combined organic layers were washed with saturated NaCl with $H_2O$ (5 mL), dried over anhydrous $Na_2SO_4$, filtered and concentrated in vacuo to give a residue. The residue was purified by column chromatography ($SiO_2$, PE:EA=50:1 to 0:1) to give the title compound (190 mg, 97% yield) as a yellow solid. $^1$H NMR (400 MHz, DMSO-$d_6$) δ 11.08 (s, 1H), 7.00-6.93 (m, 1H), 6.92-6.82 (m, 2H), 5.34-5.30 (m, 1H), 4.03-3.98 (m, 1H), 3.69-3.64 (m, 2H), 3.62 (s, 3H), 3.56-3.47 (m, 1H), 3.14-3.06 (m, 4H), 3.05-2.96 (m, 2H), 2.77-2.57 (m, 4H), 2.00-1.98 (m, 1H), 1.98-1.95 (m, 1H), 1.81-1.73 (m, 2H), 1.68-1.51 (m, 2H), 1.44-1.38 (m, 9H), 1.36-1.27 (m, 2H). LC-MS (ESI$^+$) m/z 542.1 (M+H)$^+$.

Step 4—3-[3-Methyl-2-oxo-4-[4-(4-piperidyloxy)-1-piperidyl]benzimidazol-1-yl]piperidine-2,6-dione. To a solution of tert-butyl 4-[[1-[1-(2,6-dioxo-3-piperidyl)-3-methyl-2-oxo-benzimidazol-4-yl]-4-piperidyl]oxy]piperidine-1-carboxylate (100 mg, 184 umol) in DCM (1 mL) was added TFA (0.2 mL). The mixture was stirred at 25° C. for 1 hr. On completion, the reaction mixture was concentrated in vacuo to give the title compound (100 mg, 97% yield, TFA) as a yellow oil. LC-MS (ESI$^+$) m/z 442.0 (M+H)$^+$.

5-Methylsulfonylpyridine-3-carboxylic acid (Intermediate CJQ)

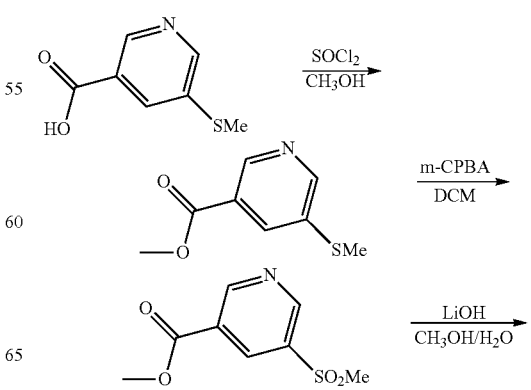

CJQ

Step 1—Methyl 5-methylsulfanylpyridine-3-carboxylate. To a solution of 5-methylsulfanylpyridine-3-carboxylic acid (300 mg, 1.77 mmol, CAS #74470-28-3) in CH₃OH (0.5 mL) was added thionyl chloride (421 mg, 3.55 mmol) at 0° C. The mixture was then stirred at 70° C. for 2 hrs. On completion, the mixture was concentrated to give a residue. The mixture was diluted with DCM (10 mL) quenched with NaHCO₃ (5 ml). The organic layer was dried over anhydrous sodium sulfate, filtered and concentrated in vacuo to give the title compound (300 mg, 92% yield) as a yellow oil. LC-MS (ESI⁺) m/z 184.2 (M+H)⁺.

Step 2—Methyl 5-methylsulfonylpyridine-3-carboxylate. To a solution of methyl 5-methylsulfanylpyridine-3-carboxylate (50 mg, 272 umol) in DCM (0.5 mL) was added m-CPBA (294 mg, 1.36 mmol, 80% solution). The mixture was stirred at 25° C. for 0.5 hr. On completion, the mixture was diluted with DCM (2 mL) and quenched with Na₂S₂O₃ (1 mL) and NaHCO₃ (1 mL). Then the organic organic layer was dried over anhydrous sodium sulfate, filtered and concentrated in vacuo to give a residue. The residue was purified by column chromatography (SiO₂, Petroleum ether/Ethyl acetate=5/1 to 0/1) to give the title compound (40 mg, 67% yield) as a white solid. LC-MS (ESI⁺) m/z 215.8 (M+H)⁺.

Step 3—5-Methylsulfonylpyridine-3-carboxylic acid. To a solution of methyl 5-methylsulfonylpyridine-3-carboxylate (40 mg, 185 umol) in MeOH (0.5 mL) and H₂O (0.1 mL) was added LiOH·H₂O (23.4 mg, 557 umol). The mixture was stirred at 25° C. for 1 hr. On completion, the mixture was concentrated to give a residue. Then to the mixture was added HCl (3 M) (0.5 mL) at 25° C. until the pH stabilized at 2-3. The mixture was filtered, and the filter cake was dried in vacuo to give the title compound (27 mg, 72% yield) as a white solid. LC-MS (ESI+) m/z 202.0 (M+H)⁺.

5-Methylsulfinylpyridine-3-carboxylic acid
(Intermediate CJR)

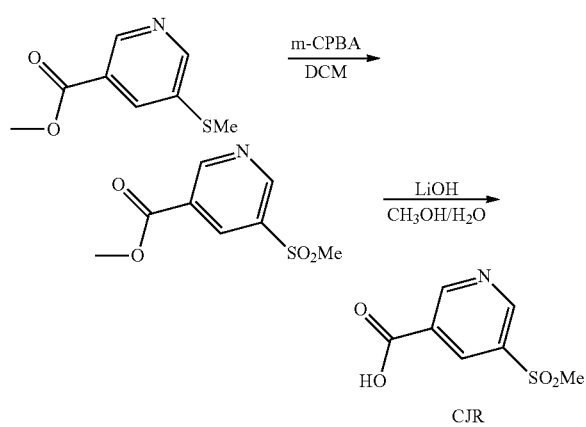

Step 1—Methyl 5-methylsulfinylpyridine-3-carboxylate. To a solution of methyl 5-methylsulfanylpyridine-3-carboxylate (100 mg, 545 umol, synthesized via Step 1 of Intermediate CJQ) in DCM (2 mL) was added m-CPBA (129 mg, 600 umol) at 0° C. The mixture was then stirred at 0° C. for 0.5 hrs. On completion, the mixture was quenched with saturated Na₂S₂O₃ (5 mL) and saturated NaHCO₃ (5 mL) at 25° C., and then stirred for 30 minutes. The mixture was then extracted with DCM (2×15 mL). Then the combined organic layers was washed with NaHCO₃ (2×15 mL) and washed with saturated salt solution (2×15 mL). The combined organic layer was dried over Na₂SO₄, filtered and the filtrate was concentrated in vacuo to give a residue. The residue by column chromatography (SiO2, PE:EA=5:1 to PE:EA=0:1, PE:EA=0:1, P1:Rf=0.14) to give the title compound (65 mg, 59.7% yield) as a white solid. ¹H NMR (400 MHz, DMSO-d6) δ 9.19 (d, J=2.0 Hz, 1H), 9.08 (d, J=2.0 Hz, 1H), 8.56 (t, J=2.0 Hz, 1H), 3.93 (s, 3H), 2.91 (s, 3H); LC-MS (ESI⁺) m/z 199.9 (M+H)⁺.

Step 2—5-Methylsulfinylpyridine-3-carboxylic acid. To a solution of methyl 5-methylsulfinylpyridine-3-carboxylate (65 mg, 326 umol) in H₂O (0.4 mL) and MeOH (2 mL) was added LiOH·H₂O (41.0 mg, 978 umol). The mixture was then stirred at 25° C. for 1 hr. On completion, the reaction mixture was adjusted to pH=3 and concentrated in vacuo to give the title compound (50 mg, 83% yield) as a yellow solid. LC-MS (ESI⁺) m/z 186.2 (M+H)⁺.

Tert-butyl 4-(4-piperidylmethyl)piperazine-1-carboxylate
(Intermediate CJS)

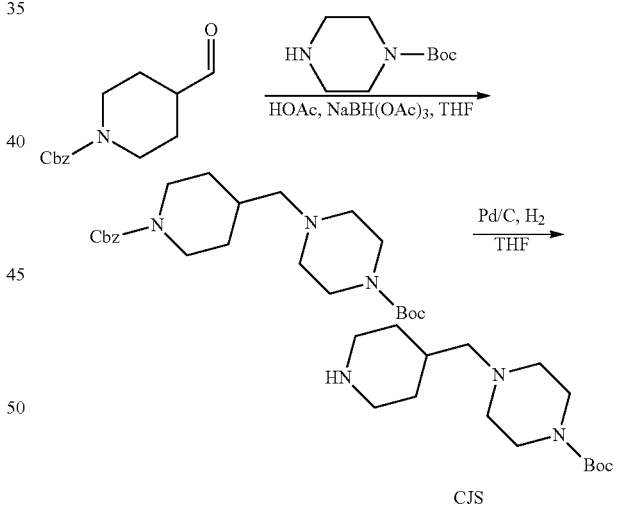

Step 1—Tert-butyl 4-[(1-benzyloxycarbonyl-4-piperidyl)methyl]piperazine-1-carboxylate. To a solution of benzyl 4-formylpiperidine-1-carboxylate (4.5 g, 18.2 mmol, CAS #138163-08-3), tert-butyl piperazine-1-carboxylate (4.07 g, 21.8 mmol, CAS #143238-38-4) in THF (80 mL) was added HOAc (1.09 g, 18.2 mmol), then the mixture was stirred at 0° C. for 30 mins. Next, NaBH(OAc)₃ (7.71 g, 36.4 mmol) was added and the mixture was stirred at 0° C. for 1.5 hrs. On completion, the reaction was diluted with water (80 mL), and extracted with EA (100 mL×3). The organic layers were combined, washed with brine (50 mL), dried over anhydrous Na₂SO₄, filtered and concentrated in vacuo to give a residue.

The residue was purified by column chromatography (SiO$_2$, PE/EA=2/1 to 1/1) to give the title compound (5.5 g, 72% yield) as colorless oil. $^1$H NMR (400 MHz, CDCl$_3$) δ 7.32-7.18 (m, 5H), 5.04 (s, 2H), 4.08 (d, J=11.2 Hz, 2H), 3.34 (s, 4H), 2.69 (t, J=11.2 Hz, 2H), 2.27 (s, 4H), 2.11 (s, 2H), 1.73-1.52 (m, 3H), 1.38 (s, 9H), 1.13-0.93 (m, 2H). LC-MS (ESI$^+$) m/z 418.5 (M+H)$^+$.

Step 2—Tert-butyl 4-(4-piperidylmethyl)piperazine-1-carboxylate. To a solution of tert-butyl 4-[(1-benzyloxycarbonyl-4-piperidyl)methyl]piperazine-1-carboxylate (1.5 g, 3.59 mmol) in THF (15 mL) was added Pd/C (500 mg, 10 wt %) under Ar. The suspension was degassed under vacuum and purged with H$_2$ three times, then stirred at 20° C. for 1 hr under H$_2$ atmosphere (15 psi). On completion, the reaction was filtered to give a filtrate, then concentrated in vacuo to give the title compound (1.0 g, 98% yield) as colorless oil. $^1$H NMR (400 MHz, CDCl$_3$) δ 3.45-3.36 (m, 3H), 3.11 (d, J=12.4 Hz, 2H), 2.74-2.43 (m, 4H), 2.40-2.25 (m, 4H), 2.17 (d, J=7.2 Hz, 2H), 1.76 (d, J=12.8 Hz, 2H), 1.63-1.60 (m, 1H), 1.50-1.41 (m, 9H), 1.32-1.03 (m, 2H).

3-[3-Methyl-2-oxo-4-[4-(piperazin-1-ylmethyl)-1-piperidyl]benzimidazol-1-yl]piperidine-2,6-dione (Intermediate CJT)

mmol), and 4 Å molecular sieves (1.3 g) in dioxane (10 mL) was degassed under vacuum and purged with N$_2$ three times. Then the mixture was stirred at 100° C. for 36 hrs under N$_2$ atmosphere. On completion, the reaction was cooled to rt, filtered to give a filtrate, then concentrated in vacuo to give a residue. The residue was purified by reverse phase (0.1% FA condition) to give the title compound (135 mg, 18% yield, FA) as off-white solid. $^1$H NMR (400 MHz, DMSO-d$_6$) δ 7.21 (d, J=8.8 Hz, 2H), 6.97-6.82 (m, 4H), 6.75 (d, J=5.2 Hz, 1H), 5.50 (d, J=5.6, 12.8 Hz, 1H), 4.88-4.70 (m, 2H), 3.72 (s, 3H), 3.62 (s, 3H), 3.32 (s, 3H), 3.19-2.94 (m, 3H), 2.85-2.61 (m, 4H), 2.34-2.27 (m, 4H), 2.20 (d, J=6.8 Hz, 2H), 2.09-1.97 (m, 1H), 1.81 (d, J=12.0 Hz, 2H), 1.64 (d, J=2.8 Hz, 1H), 1.49-1.21 (m, 12H). LC-MS (ESI$^+$) m/z 661.3 (M+H)$^+$.

Step 2—3-[3-Methyl-2-oxo-4-[4-(piperazin-1-ylmethyl)-1-piperidyl]benzimidazol-1-yl]piperidine-2,6-dione. A solution of tert-butyl 4-[[1-[1-[1-[(4-methoxyphenyl)methyl]-2,6-dioxo-3-piperidyl]-3-methyl-2-oxo-benzimidazol-4-yl]-4-piperidyl]methyl]piperazine-1-carboxylate (100 mg, 151 umol, FA) in TfOH (30 uL) and TFA (270 uL) was stirred at 70° C. for 2 hrs. On completion, the reaction was cooled to rt, then concentrated in vacuo to give the title compound (83 mg, 98% yield, TFA) as brown oil. LC-MS (ESI$^+$) m/z 441.1 (M+H)$^+$.

5-(3,3-Dimethylazetidin-1-yl)pyrazolo[1,5-a]pyrimidine-3-carboxylic acid (Intermediate CJU)

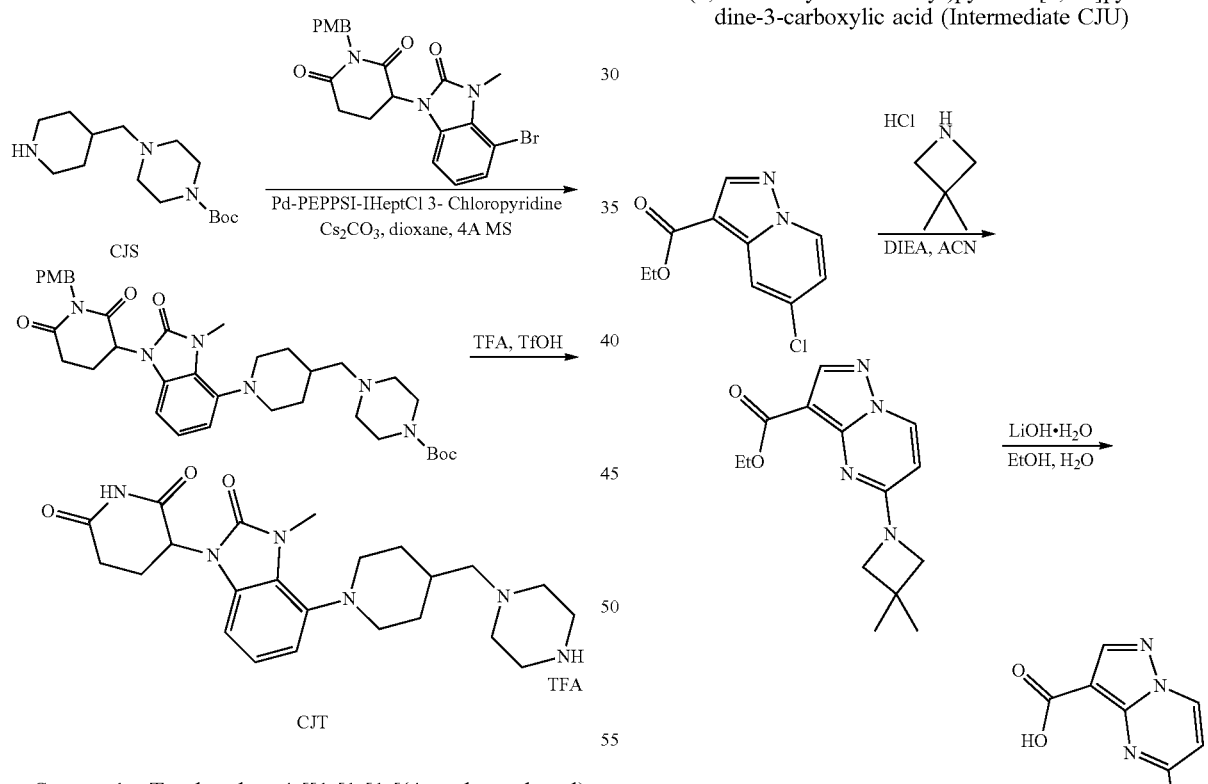

Step 1—Tert-butyl 4-[[1-[1-[1-[(4-methoxyphenyl)methyl]-2,6-dioxo-3-piperidyl]-3-methyl-2-oxo-benzimidazol-4-yl]-4-piperidyl]methyl]piperazine-1-carboxylate. A suspension of tert-butyl 4-(4-piperidylmethyl)piperazine-1-carboxylate (300 mg, 1.06 mmol, Intermediate CJS), 3-(4-bromo-3-methyl-2-oxo-benzimidazol-1-yl)-1-[(4-methoxyphenyl)methyl] piperidine-2,6-dione (485 mg, 1.06 mmol, synthesized via Steps 1-4 of Intermediate HP), 1,3-bis[2,6-bis(1-propylbutyl)phenyl]-4,5-dichloro-2H-imidazol-1-ium-2-ide; 3-chloropyridine; dichloropalladium (51.5 mg, 52.9 umol, CAS #1814936-54-3), Cs$_2$CO$_3$ (1.03 g, 3.18

Step 1—Ethyl 5-(3,3-dimethylazetidin-1-yl)pyrazolo[1,5-a]pyrimidine-3-carboxylate. To a solution of ethyl 5-chloropyrazolo[1,5-a]pyrimidine-3-carboxylate (500 mg, 2.22 mmol, CAS #1224944-77-7) and 3,3-dimethylazetidine (245 mg, 2.88 mmol, CAS #89381-03-3) in ACN (5 mL) was added DIEA (859 mg, 6.65 mmol), then the mixture was stirred at 65° C. for 4 hrs. On completion, the reaction mixture was concentrated in vacuo to give the residue. The residue was purified by column chromatography (SiO$_2$, PE/EA=20/1 to 1/1) to give the title compound (500 mg, 82% yield) as light yellow solid. $^1$H NMR (400 MHz, DMSO-d$_6$) δ 8.66 (d, J=7.6 Hz, 1H), 8.17 (s, 1H), 6.32 (d, J=7.6 Hz, 1H), 4.18 (q, J=7.2 Hz, 2H), 3.83 (s, 4H), 1.36-1.19 (m, 9H); LC-MS (ESI$^+$) m/z 274.8 (M+H)$^+$.

Step 2—5-(3, 3-Dimethylazetidin-1-yl) pyrazolo[1,5-a]pyrimidine-3-carboxylic acid. To a solution of ethyl 5-(3, 3-dimethylazetidin-1-yl)pyrazolo[1,5-a]pyrimidine-3-carboxylate (100 mg, 364 umol) in EtOH (2 mL) and H$_2$O (0.4 mL) was added LiOH·H$_2$O (61.1 mg, 1.46 mmol), then the mixture was stirred at 25° C. for 2 hrs. On completion, the reaction mixture was concentrated in vacuo to give the residue, and adjusted pH=6 using AcOH. Then the mixture was filtered and the filter cake was dried in vacuo to give the title compound (68.0 mg, 75% yield) as white solid $^1$H NMR (400 MHz, DMSO-d$_6$) δ 11.62 (s, 1H), 8.66 (d, J=7.6 Hz, 1H), 8.15 (s, 1H), 6.31 (d, J=7.6 Hz, 1H), 3.84 (s, 4H), 1.30 (s, 6H).

Ethyl 2-(trifluoromethylsulfonyloxy)pyrrolo[1,2-a]pyrimidine-8-carboxylate (Intermediate CJV)

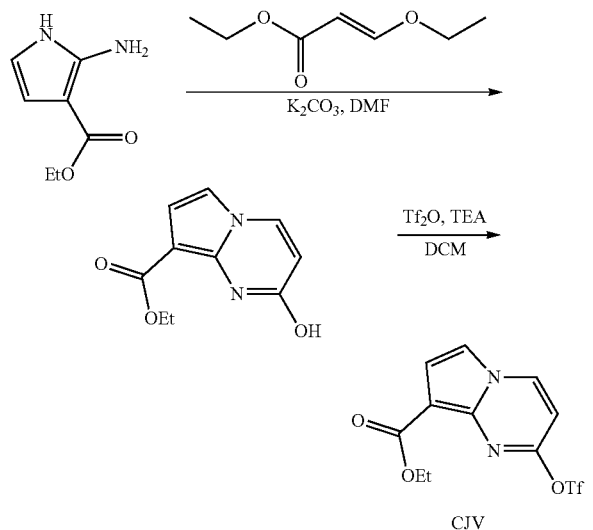

Step 1—Ethyl 2-hydroxypyrrolo[1,2-a]pyrimidine-8-carboxylate. To a solution of ethyl 2-amino-1H-pyrrole-3-carboxylate (4.00 g, 25.9 mmol, CAS #108290-86-4) in DMF (30 mL) was added K$_2$CO$_3$ (10.7 g, 77.8 mmol) and ethyl (E)-3-ethoxyprop-2-enoate (4.11 g, 28.5 mmol, CAS #1001-26-9). The mixture was then stirred at 80° C. for 12 hr. On completion, the reaction mixture was quenched with 3 M HCl at 25° C. until the pH=5, and then the mixture was filtered and the cake was dried to give a residue. The residue was purified by reversed phase (0.1% FA condition) to give the title compound (1.60 g, 29% yield) as purple solid. $^1$H NMR (400 MHz, DMSO-d$_6$) δ 10.51 (s, 1H), 8.31 (d, J=7.6 Hz, 1H), 7.00 (d, J=3.6 Hz, 1H), 6.63 (d, J=3.6 Hz, 1H), 6.03 (d, J=8.0 Hz, 1H), 4.25 (q, J=7.2 Hz, 2H), 1.27 (t, J=7.2 Hz, 3H); LC-MS (ESI$^+$) m/z 206.9 (M+H)$^+$.

Step 2—Ethyl 2-(trifluoromethylsulfonyloxy)pyrrolo[1,2-a]pyrimidine-8-carboxylate. To a solution of ethyl 2-hydroxypyrrolo[1,2-a]pyrimidine-8-carboxylate (700 mg, 3.39 mmol) in DCM (10 mL) was added Tf$_2$O (2.87 g, 10.1 mmol) and TEA (1.72 g, 16.9 mmol) at 0° C. Then the mixture was stirred at 20° C. for 2 hrs. On completion, the reaction mixture was diluted with DCM (10 mL) and washed with saturated sodium chloride solution (30 mL), dried over anhydrous sodium sulfate, filtered and concentrated to give a residue. The residue was purified by column chromatography (SiO$_2$, Petroleum ether/Ethyl acetate=10/1 to 3/1) to give the title compound (600 mg, 52% yield) as yellow solid. $^1$H NMR (400 MHz, DMSO-d$_6$) δ 9.14 (d, J=7.6 Hz, 1H), 7.70 (d, J=3.2 Hz, 1H), 7.40 (d, J=3.2 Hz, 1H), 7.19 (d, J=7.6 Hz, 1H), 4.26 (q, J=7.2 Hz, 2H), 1.30 (t, J=7.2 Hz, 3H); LC-MS (ESI$^+$) m/z 338.6 (M+H)$^+$.

5-2-[(1S,4S)-2-Oxa-5-azabicyclo[2.2.1]heptan-5-yl]pyrrolo[1,2-a]pyrimidine-8-carboxylic acid (Intermediate CJW)

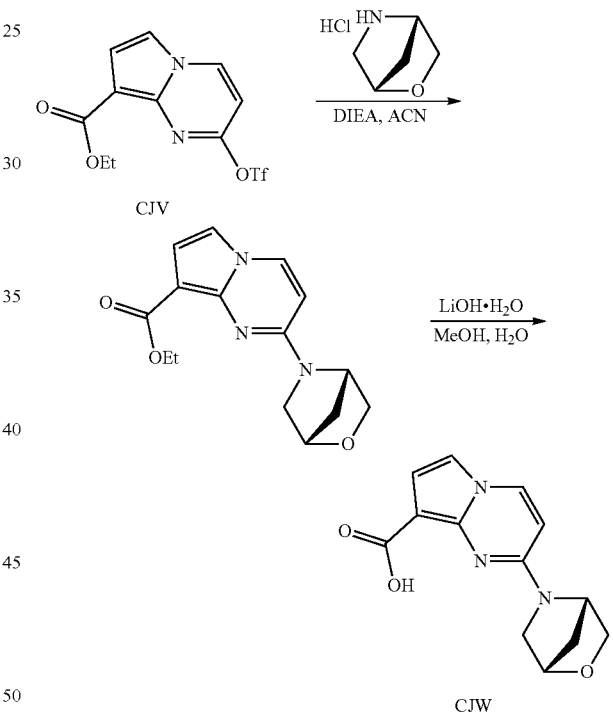

Step 1—Ethyl 2-[(1S,4S)-2-oxa-5-azabicyclo[2.2.1]heptan-5-yl]pyrrolo[1,2-a]pyrimidine-8-carboxylate. To a solution of ethyl 2-(trifluoromethylsulfonyloxy)pyrrolo[1,2-a]pyrimidine-8-carboxylate (600 mg, 1.77 mmol, Intermediate CJV) in ACN (8 mL) was added DIEA (1.15 g, 8.87 mmol) and (1S,4S)-2-oxa-5-azabicyclo[2.2.1]heptane (721 mg, 5.32 mmol, HCl, CAS #31560-06-2). The mixture was stirred at 60° C. for 12 hr. On completion, the reaction mixture was concentrated under reduced pressure to give a residue, and then diluted with H$_2$O (15 mL) and extracted with DCM (10 mL×2). The combined organic phase was washed with saturated sodium chloride solution (15 mL×2), dried over anhydrous sodium sulfate, filtered and concentrated to give the title compound (480 mg, 94% yield) as yellow solid. $^1$H NMR (400 MHz, DMSO-d$_6$) δ 8.43 (d, J=7.6 Hz, 1H), 6.99 (d, J=3.6 Hz, 1H), 6.84 (d, J=3.6 Hz, 1H), 6.57-6.31 (m, 1H), 5.02 (s, 1H), 4.71 (s, 1H), 4.18-4.09 (m, 2H), 3.81 (d, J=6.4 Hz, 1H), 3.69 (d, J=7.2 Hz, 1H), 3.54-3.48 (m, 1H), 3.43 (dd, J=4.0, 4.8 Hz, 1H), 1.98-1.83 (m, 2H), 1.26 (t, J=7.2 Hz, 3H); LC-MS (ESI$^+$) m/z 287.9 (M+H)$^+$.

Step 2—5-2-[(1S,4S)-2-Oxa-5-azabicyclo[2.2.1]heptan-5-yl]pyrrolo[1,2-a]pyrimidine-8-carboxylic acid. To a solution of ethyl 2-[(1S,4S)-2-oxa-5-azabicyclo[2.2.1]heptan-5-yl]pyrrolo[1,2-a]pyrimidine-8-carboxylate (480 mg, 1.67 mmol) in EtOH (5 mL) and H$_2$O (1 mL) was added LiOH·H$_2$O (210 mg, 5.01 mmol). The mixture was stirred at 60° C. for 36 hrs. On completion, the reaction mixture was quenched with 1 M HCl at 25° C. until the pH=7, and then filtered and the cake was dried under reduced pressure to give the title compound (300 mg, 69% yield) as yellow solid. LC-MS (ESI$^+$) m/z 260.0 (M+H)$^+$.

5-cyanopyridine-3-carboxylic acid (CAS #887579-62-6) (Intermediate CJX)

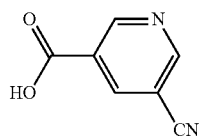

5-(4-Oxa-7-azaspiro[2.5]octan-7-yl)pyrazolo[1,5-a]pyrimidine-3-carboxylic acid (Intermediate CJY)

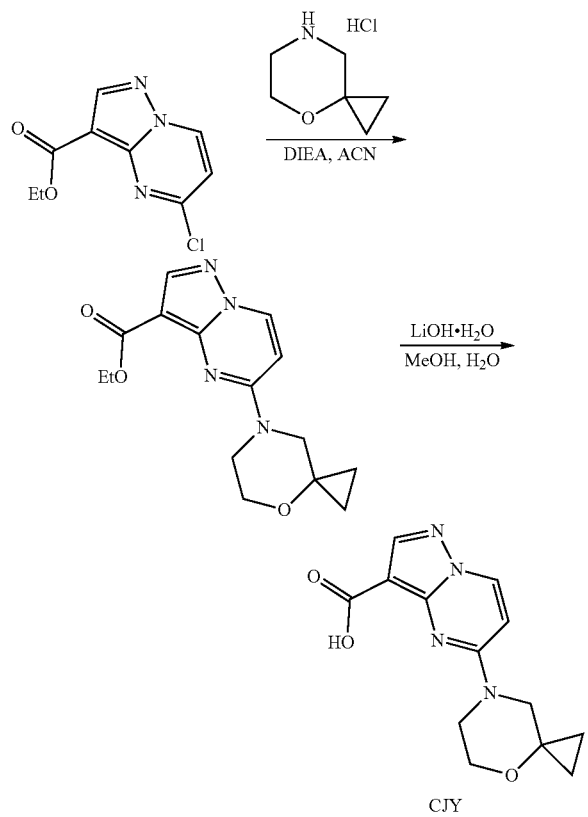

Step 1—Ethyl 5-(4-oxa-7-azaspiro[2.5]octan-7-yl)pyrazolo[1,5-a]pyrimidine-3-carboxylate. To a solution of ethyl 5-chloropyrazolo[1,5-a]pyrimidine-3-carboxylate (100 mg, 443 umol, CAS #1224944-77-7) in ACN (2 mL) was added DIEA (172 mg, 1.33 mmol, 232 uL) and 4-oxa-7-azaspiro [2.5]octane hydrochloride (66.3 mg, 443 umol, CAS #220291-92-9). The mixture was then stirred at 70° C. for 4 hrs. On completion, the mixture was poured into water (10 mL), separated the organic phase and the aqueous phase was extracted with EA (3×5 mL). The organic layers were combined and washed with brine (10 mL), dried over anhydrous Na$_2$SO$_4$ and concentrated to give the title compound (120 mg, 89.6% yield) as a white solid. $^1$H NMR (400 MHz, CDCl$_3$) δ 8.39-8.19 (m, 2H), 6.37 (d, J=8.0 Hz, 1H), 4.34 (q, J=7.2 Hz, 2H), 3.89 (s, 4H), 3.76 (s, 2H), 1.38 (t, J=7.2 Hz, 3H), 0.93-0.85 (m, 2H), 0.73-0.66 (m, 2H).

Step 2—5-(4-Oxa-7-azaspiro[2.5]octan-7-yl)pyrazolo[1,5-a]pyrimidine-3-carboxylic acid. To a solution of ethyl 5-(4-oxa-7-azaspiro[2.5]octan-7-yl)pyrazolo[1,5-a]pyrimidine-3-carboxylate (120 mg, 397 umol) in THF (2 mL) was added LiOH·H2O (83.3 mg, 1.98 mmol), MeOH (0.5 mL) and H$_2$O (0.5 mL). The mixture was then stirred at 70° C. for 10 hrs. On completion, the mixture was poured into water (10 mL) and adjusted to pH=3 with hydrochloric acid, then the organic phase was separated and the aqueous phase was extracted with EA (3×10 mL). The organic layers were combined and washed with brine (10 mL), dried over anhydrous Na$_2$SO$_4$ and concentrated to give a residue. The residue was triturated with PE to give the title compound (60.0 mg, 55% yield) as a white solid. $^1$H NMR (400 MHz, DMSO-d$_6$) δ 11.73 (s, 1H), 8.75 (d, J=8.0 Hz, 1H), 8.19 (s, 1H), 6.85 (d, J=8.0 Hz, 1H), 3.85 (d, J=3.2 Hz, 2H), 3.80-3.68 (m, 4H), 0.79-0.73 (m, 2H), 0.67-0.60 (m, 2H).

(S)-5-(2-methylmorpholino)pyrazolo[1,5-a]pyrimidine-3-carboxylic acid (Intermediate CJZ)

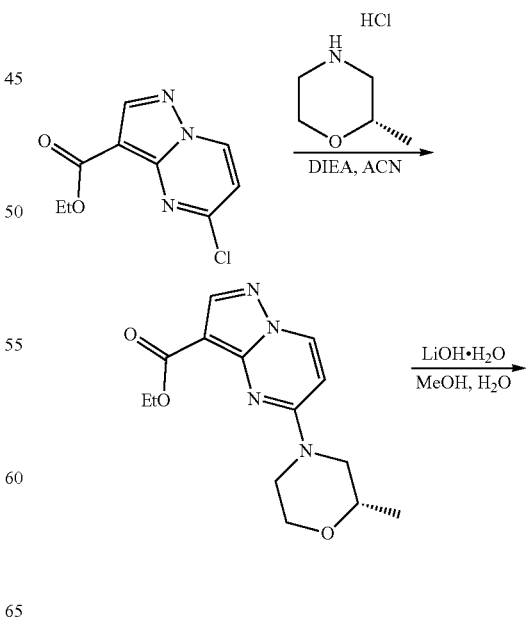

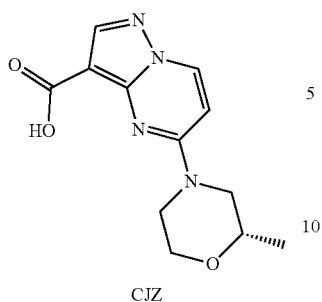

CJZ

Step 1—(S)-ethyl 5-(2-methylmorpholino)pyrazolo[1,5-a]pyrimidine-3-carboxylate. To a solution of ethyl 5-chloropyrazolo[1,5-a]pyrimidine-3-carboxylate (100 mg, 443 umol) were added DIEA (172 mg, 1.33 mmol) and (S)-2-methylmorpholine hydrochloride (61.0 mg, 443 umol, HCl, CAS #1147108-99-3). The mixture was then stirred at 70° C. for 4 hrs. On completion, the mixture was poured into water (10 mL), separated the organic phase and the aqueous phase was extracted with EA (3×5 mL). The organic layers were combined and washed with brine (10 mL), dried over anhydrous $Na_2SO_4$ and concentrated to give the title compound (120 mg, 93% yield) as a white solid. $^1$H NMR (400 MHz, $CDCl_3$) δ 8.35-8.29 (m, 2H), 6.43 (d, J=8.0 Hz, 1H), 4.48-4.22 (m, 4H), 4.06 (dd, J=3.2, 11.6 Hz, 1H), 3.75-3.63 (m, 2H), 3.22 (dt, J=3.2, 12.4 Hz, 1H), 2.92-2.81 (m, 1H), 1.42 (t, J=7.2 Hz, 3H), 1.31 (d, J=6.4 Hz, 3H).

Step 2—(S)-5-(2-methylmorpholino)pyrazolo[1,5-a]pyrimidine-3-carboxylic acid. To a solution of (S)-ethyl 5-(2-methylmorpholino)pyrazolo[1,5-a]pyrimidine-3-carboxylate (120 mg, 413 umol) in MeOH (0.5 mL) and $H_2O$ (0.5 mL) was added LiOH·$H_2O$ (86.7 mg, 2.07 mmol). The mixture was then stirred at 70° C. for 10 hrs. On completion, the mixture was poured into water (10 mL) and adjusted to pH=3 with hydrochloric acid, separated the organic phase and the aqueous phase was extracted with EA (3×10 mL). The organic layers were combined and washed with brine (10 mL), dried over anhydrous $Na_2SO_4$ and concentrated to give a residue. The crude product was triturated with EA (10 mL) at 20° C. for 30 mins, and the solid was collected to give the title compound (70.0 mg, 63% yield) as a white solid. $^1$H NMR (400 MHz, DMSO-$d_6$) δ 11.72 (s, 1H), 8.75 (d, J=8.0 Hz, 1H), 6.87 (d, J=8.0 Hz, 1H), 4.39 (d, J=7.2 Hz, 2H), 3.95 (dd, J=2.4, 11.6 Hz, 1H), 3.60-3.48 (m, 2H), 3.10-2.98 (m, 1H), 2.81-2.66 (m, 1H), 1.17 (d, J=6.0 Hz, 3H).

5-[(2R)-2-Methylmorpholin-4-yl]pyrazolo[1,5-a]pyrimidine-3-carboxylic acid (Intermediate CKA)

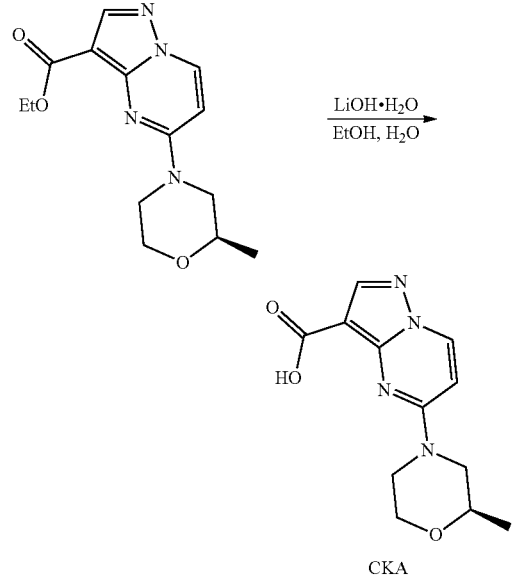

CKA

Step 1—Ethyl 5-[(2R)-2-methylmorpholin-4-yl]pyrazolo[1,5-a]pyrimidine-3-carboxylate. To a solution of ethyl 5-chloropyrazolo[1,5-a]pyrimidine-3-carboxylate (800 mg, 3.55 mmol) and (2R)-2-methylmorpholine (732 mg, 5.33 mmol, HCl salt, CAS #790184-33-7) in ACN (10 mL) was added DIEA (1.38 g, 10.6 mmol). The reaction mixture was then stirred at 70° C. for 16 hrs. On completion, the mixture was concentrated in vacuo. Then the residue was diluted with $H_2O$ (20 mL) and extracted with EA (2×30 mL). The combined organic layer was washed with brine (2×30 mL), dried over $Na_2SO_4$ and filtered. The filtrate was concentrated in vacuo to give the title compound (1.00 g, 97% yield) as a yellow solid. $^1$H NMR (400 MHz, DMSO-$d_6$) δ 8.74 (d, J=8.0 Hz, 1H), 8.21 (s, 1H), 6.86 (d, J=8.0 Hz, 1H), 4.57-4.28 (m, 2H), 4.19 (q, J=7.2 Hz, 2H), 3.93 (dd, J=2.4, 11.6 Hz, 1H), 3.66-3.46 (m, 2H), 3.05 (t, J=11.2 Hz, 1H), 2.73 (t, J=11.6 Hz, 1H), 1.28 (t, J=7.2 Hz, 3H), 1.16 (d, J=6.4 Hz, 3H); LCMS (ESI$^+$) m/z 290.8 (M+H)$^+$.

Step 2—5-[(2R)-2-Methylmorpholin-4-yl]pyrazolo[1,5-a]pyrimidine-3-carboxylic acid. To a solution of ethyl 5-[(2R)-2-methylmorpholin-4-yl]pyrazolo[1,5-a]pyrimidine-3-carboxylate (500 mg, 1.72 mmol) in EtOH (4.5 mL) and $H_2O$ (1.5 mL) was added LiOH·$H_2O$ (216 mg, 5.17 mmol). The mixture was then stirred at 60° C. for 3 hrs. On completion, the reaction mixture was adjusted to pH=3 and filtered. The filter cake was then dried in vacuo to give the title compound (318 mg, 70% yield) as a yellow solid. LC-MS (ESI$^+$) m/z 263.0 (M+H)$^+$.

5-[(2S,6S)-2,6-Dimethylmorpholin-4-yl]pyrazolo[1,5-a]pyrimidine-3-carboxylic acid (Intermediate CKB)

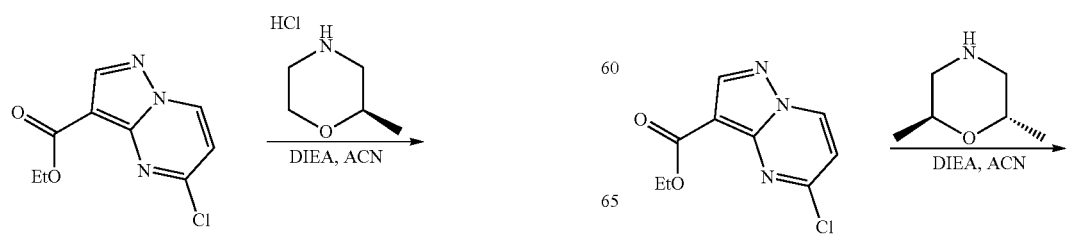

521

-continued

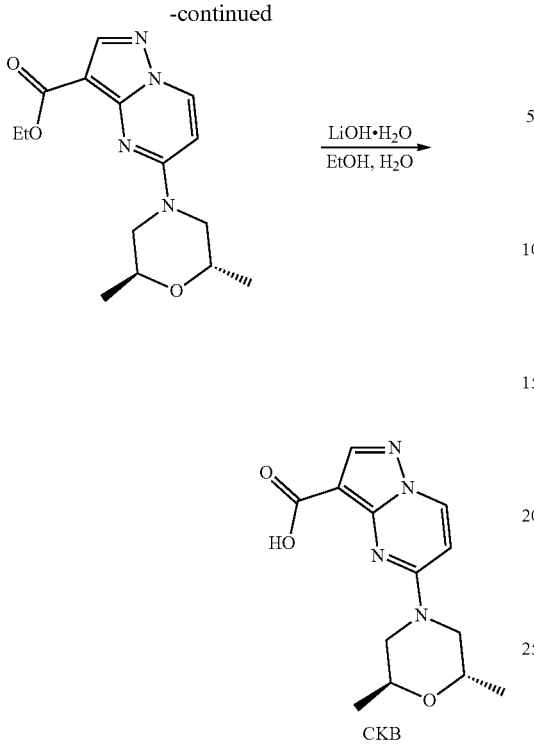

CKB

522

5-((2S,6R)-2,6-dimethylmorpholino)pyrazolo[1,5-a]pyrimidine-3-carboxylic acid (Intermediate CKC)

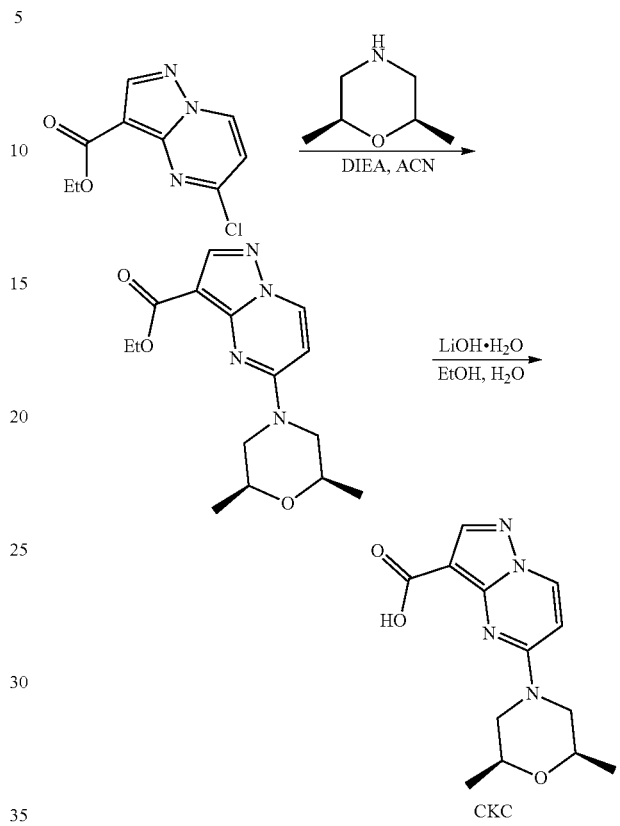

CKC

Step 1—Ethyl 5-[(2S,6S)-2,6-dimethylmorpholin-4-yl]pyrazolo[1,5-a]pyrimidine-3-carboxylate. To a solution of ethyl 5-chloropyrazolo[1,5-a]pyrimidine-3-carboxylate (400 mg, 1.77 mmol) in ACN (2 mL) was added DIEA (458 mg, 3.55 mmol) and (2S,6S)-2,6-dimethylmorpholine (403 mg, 3.50 mmol, CAS #276252-73-4). Then the mixture was stirred at 70° C. for 12 hrs. On completion, the reaction mixture was concentrated in vacuo. The mixture was quenched with water (2 mL) at 0° C. and extracted with EA (5 mL×3). The combined organic phase was dried over anhydrous sodium sulfate, filtered and concentrated to give a residue. The crude product was triturated with PE:EA=1:1 (10 mL) at 25° C. for 120 mins, then filtered and dried to give the compound (530 mg, 98% yield) as a yellow solid. $^1$H NMR (400 MHz, DMSO-d$_6$) δ 8.73 (d, J=8.0 Hz, 1H), 8.20 (s, 1H), 6.86 (d, J=8.0 Hz, 1H), 4.18 (q, J=6.8 Hz, 2H), 4.10-3.98 (m, 2H), 3.97-3.79 (m, 2H), 3.47 (dd, J=6.4, 13.2 Hz, 2H), 1.28 (t, J=7.2 Hz, 3H), 1.14 (d, J=6.4 Hz, 6H).

Step 2—5-[(2S,6S)-2,6-Dimethylmorpholin-4-yl]pyrazolo[1,5-a]pyrimidine-3-carboxylic acid. To a solution of ethyl 5-[(2S,6S)-2,6-dimethylmorpholin-4-yl]pyrazolo[1,5-a]pyrimidine-3-carboxylate (530 mg, 1.74 mmol) in EtOH (1 mL) and H$_2$O (0.3 mL) was added LiOH·H$_2$O (219 mg, 5.22 mmol) in H$_2$O (0.3 mL). The mixture was then stirred at 60° C. for 5 hrs. On completion, the reaction mixture concentrated in vacuo, and then dissolved in H$_2$O (5 mL), and 3N HCl was added to regulate the pH to 3. Then the mixture was filtered and filtrate was extracted with EA (10 mL×3). The combined organic phase was dried over anhydrous sodium sulfate, filtered and concentrated to give a residue to give the title compound (250 mg, 51% yield) as a yellow oil. $^1$H NMR (400 MHz, DMSO-d$_6$) δ 11.78-11.44 (m, 1H), 8.72 (d, J=8.0 Hz, 1H), 8.17 (s, 1H), 6.85 (d, J=8.0 Hz, 1H), 4.10-3.99 (m, 2H), 3.87 (d, J=10.8 Hz, 2H), 3.46 (dd, J=6.4, 13.2 Hz, 2H), 1.14 (d, J=6.4 Hz, 6H).

Step 1—Ethyl 5-[(2S,6R)-2,6-dimethylmorpholin-4-yl]pyrazolo[1,5-a]pyrimidine-3-carboxylate. To a solution ethyl 5-chloropyrazolo[1,5-a]pyrimidine-3-carboxylate (500 mg, 2.22 mmol, (2S,6R)-2,6-dimethylmorpholine (281 mg, 2.44 mmol, CAS #6485-55-8) in ACN (10 mL) was added DIEA (573 mg, 4.43 mmol), then the mixture was stirred at 80° C. for 18 hrs under N$_2$ atmosphere. On completion, the reaction was cooled to rt, concentrated in vacuo to give a residue. The residue was diluted with water (25 ml), then 1N HCl to adjust the pH=4, and extracted with EA (20 ml×3). The organic layers were combined, washed with brine (15 ml), dried over anhydrous Na$_2$SO$_4$, filtered and concentrated in vacuo to give the title compound (600 mg, 88% yield) as yellow solid. $^1$H NMR (400 MHz, DMSO-d$_6$) δ 8.74 (d, J=8.0 Hz, 1H), 8.20 (s, 1H), 6.87 (d, J=8.0 Hz, 1H), 4.78-4.24 (m, 2H), 4.18 (q, J=7.2 Hz, 2H), 3.65-3.53 (m, 2H), 2.63 (t, J=11.2 Hz, 2H), 1.28 (t, J=7.2 Hz, 3H), 1.16 (d, J=6.0 Hz, 6H). LC-MS (ESI$^+$) m/z 305.0 (M+H)$^+$.

Step 2—5-((2S,6R)-2,6-dimethylmorpholino)pyrazolo[1,5-a]pyrimidine-3-carboxylic acid. To a solution of ethyl 5-[(2S,6R)-2,6-dimethylmorpholin-4-yl]pyrazolo[1,5-a]pyrimidine-3-carboxylate (300 mg, 986 umol) in EtOH (3 mL) and H$_2$O (1 mL) was added LiOH·H$_2$O (82.7 mg, 1.97 mmol), then the mixture was stirred at 50° C. for 3 hrs. On completion, the reaction was cooled to rt and concentrated in vacuo to give a residue. The residue was diluted with water (15 ml), then 1N HCl to adjust the pH=3. The precipitate was filtered off, washed with water (5 ml), and dried in vacuo to give the title compound (210 mg, 77% yield) as off-white solid. ¹H NMR (400 MHz, DMSO-d₆) δ 11.69 (s, 1H), 8.74 (d, J=7.6 Hz, 1H), 8.18 (s, 1H), 6.87 (d, J=7.6 Hz, 1H), 4.43 (s, 2H), 3.67-3.52 (m, 2H), 2.62 (t, J=11.6 Hz, 2H), 1.16 (d, J=6.4 Hz, 6H).

5-(1,1-Dioxo-1,4-thiazinan-4-yl)pyrazolo[1,5-a]pyrimidine-3-carboxylic acid (Intermediate CKD)

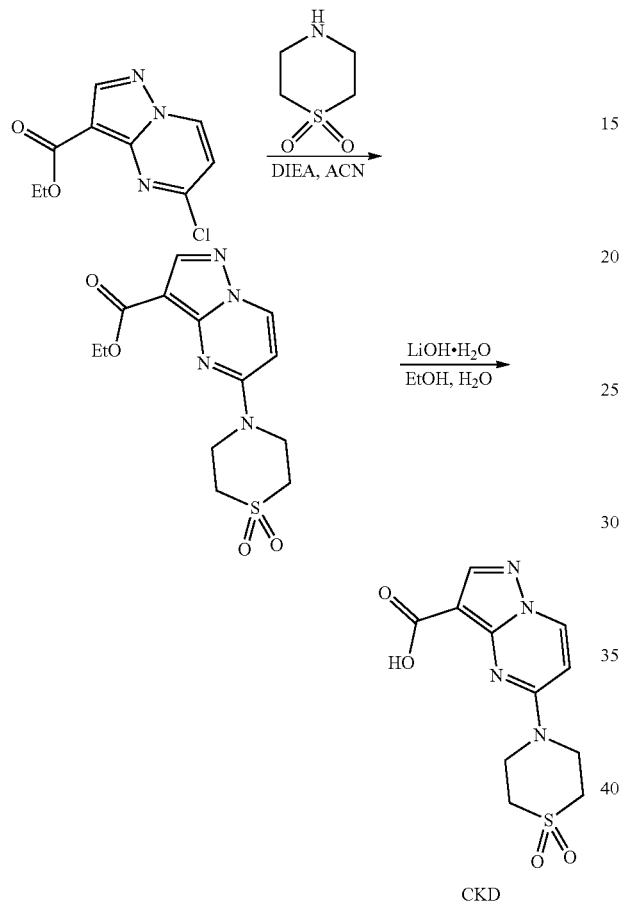

CKD

Step 1—Ethyl 5-(1,1-dioxo-1,4-thiazinan-4-yl)pyrazolo[1,5-a]pyrimidine-3-carboxylate. To a solution of ethyl 5-chloropyrazolo[1,5-a]pyrimidine-3-carboxylate (500 mg, 2.22 mmol) and 1,4-thiazinane 1,1-dioxide (599 mg, 4.43 mmol, CAS #39093-93-1) in ACN (10 mL) was added DIEA (572 mg, 4.43 mmol), then the mixture was stirred at 70° C. for 12 hrs. On completion, the reaction mixture was concentrated in vacuo to remove ACN, then the residue was diluted with water (20 mL) and extracted with EA (10 mL×3). The combined organic layer was dried over Na₂SO₄, filtered and concentrated in vacuo to give the title compound (600 mg, 83% yield) as a yellow solid. ¹H NMR (400 MHz, DMSO-d₆) δ 8.85 (d, J=7.6 Hz, 1H), 8.26 (s, 1H), 7.03 (d, J=7.6 Hz, 1H), 4.30-4.11 (m, 6H), 3.30-3.21 (m, 4H), 1.28 (t, J=7.2 Hz, 3H); LC-MS (ESI⁺) m/z 324.7 (M+H)⁺.

Step 2—5-(1,1-Dioxo-1,4-thiazinan-4-yl)pyrazolo[1,5-a]pyrimidine-3-carboxylic acid. To a solution of ethyl 5-(1,1-dioxo-1,4-thiazinan-4-yl)pyrazolo[1,5-a]pyrimidine-3-carboxylate (200 mg, 616 umol) in EtOH (3 mL) and H₂O (0.5 mL) was added LiOH·H₂O (51.7 mg, 1.23 mmol), then the mixture was stirred at 25° C. for 1 hrs. On completion, the reaction mixture was concentrated in vacuo to remove MeOH, then acidified with hydrochloric acid (1 M) until the pH=5-6. Then the mixture was concentrated in vacuo to give the title compound (150 mg, 82% yield) as a white solid. ¹H NMR (400 MHz, DMSO-d₆) δ 8.83 (d, J=7.6 Hz, 1H), 8.23 (s, 1H), 7.01 (d, J=7.6 Hz, 1H), 4.22 (s, 4H), 3.27-3.24 (m, 4H); LC-MS (ESI⁺) m/z 278.9 (M+H)⁺.

5-(6-Oxa-3-azabicyclo[3.1.1]heptan-3-yl)pyrazolo[1,5-a]pyrimidine-3-carboxylic acid (Intermediate CKE)

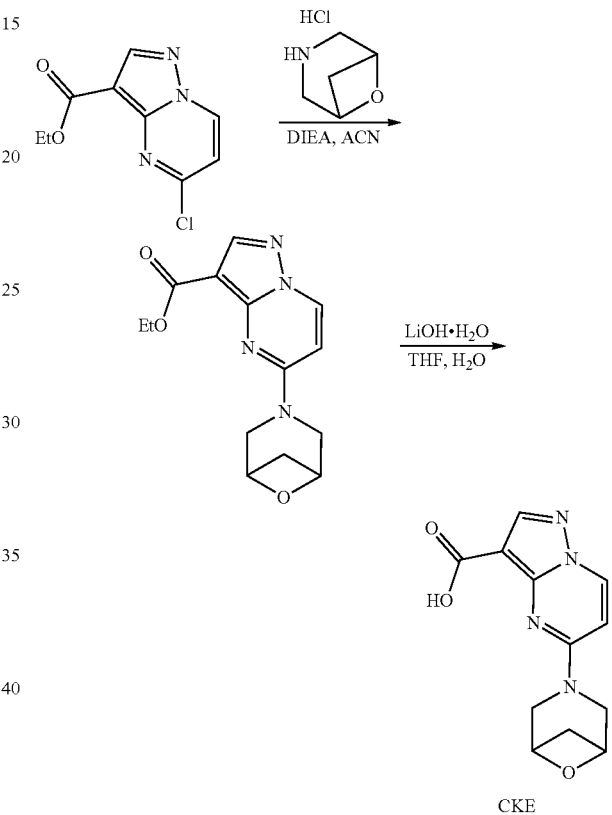

CKE

Step 1—Ethyl 5-(6-oxa-3-azabicyclo[3.1.1]heptan-3-yl)pyrazolo[1,5-a]pyrimidine-3-carboxylate. To a solution of ethyl 5-chloropyrazolo[1,5-a]pyrimidine-3-carboxylate (500 mg, 2.22 mmol) in ACN (5 mL) were added DIEA (572-mg, 4.43 mmol-) and 6-oxa-3-azabicyclo[3.1.1]heptane (360 mg, 2.66 mmol, HCl, CAS #1414958-33-0). The mixture was stirred at 60° C. for 12 hrs. On completion, the reaction mixture was concentrated in vacuo. The mixture was quenched with water (8 mL) at 0° C. and extracted with DCM (10 mL×3). The combined organic phase was dried over anhydrous sodium sulfate, filtered and concentrated to give a residue. The crude product was triturated with PE:EA=1:1 (10 mL) at 25° C. for 2 hrs to give the compound (450 mg, 63% yield) as a white solid. ¹H NMR (400 MHz, DMSO-d₆) δ 8.79 (d, J=8.0 Hz, 1H), 8.23 (s, 1H), 6.68 (d, J=8.0 Hz, 1H), 4.75 (s, 2H), 4.20 (q, J=7.2 Hz, 2H), 4.09-3.93 (m, 1H), 3.86-3.61 (m, 3H), 3.22-3.09 (m, 1H), 1.88 (d, J=9.2 Hz, 1H), 1.28 (t, J=7.2 Hz, 3H); LC-MS (ESI⁺) m/z 288.9 (M+H)⁺.

Step 2—5-(6-Oxa-3-azabicyclo[3.1.1]heptan-3-yl)pyrazolo[1,5-a]pyrimidine-3-carboxylic acid. To a solution of ethyl 5-(6-oxa-3-azabicyclo[3.1.1]heptan-3-yl)pyrazolo[1,5-a]pyrimidine-3-carboxylate (450 mg, 1.56 mmol) and NaOH (124 mg, 3.12 mmol) in H$_2$O (1 mL) and EtOH (3 mL) was added LiOH·H$_2$O (196 mg, 4.68 mmol) in H$_2$O (1 mL). The mixture was then stirred at 60° C. for 5 hrs. On completion, the reaction mixture concentrated in vacuo, and then dissolved in H$_2$O (8 mL) and 3N HCl was added to regulate the pH to 3, then the mixture was filtered and the filter cake was dried in vacuo to give a solid. The solid was then dissolved in EA (20 mL) and the filtrate was extracted with EA (15 mL×3). The combined organic phase was dried over anhydrous sodium sulfate, filtered and concentrated to give the title compound (250 mg, 61% yield) as a yellow solid. LC-MS (ESI$^+$) m/z 260.9 (M+H)$^+$.

N-[3-(difluoromethyl)-1-(4-formylcyclohexyl)pyrazol-4-yl]-5-(6-oxa-3-azabicyclo[3.1.1]heptan-3-yl)pyrazolo[1,5-a]pyrimidine-3-carboxamide (Intermediate CKF)

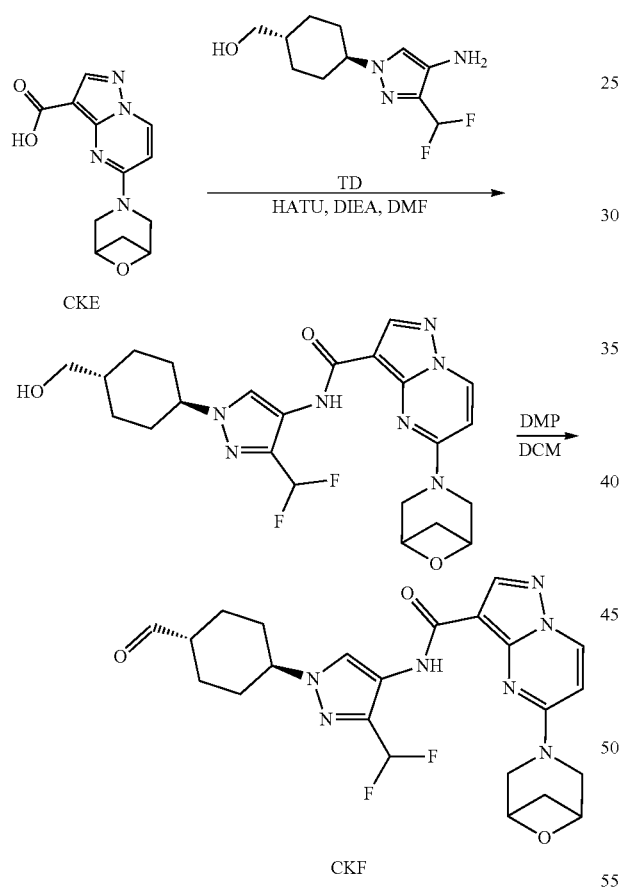

Step 1—N-[3-(difluoromethyl)-1-[4-(hydroxymethyl)cyclohexyl]pyrazol-4-yl]-5-(6-oxa-3-azabicyclo[3.1.1]heptan-3-yl)pyrazolo[1,5-a]pyrimidine-3-carboxamide. To a solution of 5-(6-oxa-3-azabicyclo[3.1.1]heptan-3-yl)pyrazolo[1,5-a]pyrimidine-3-carboxylic acid (200 mg, 768 umol, Intermediate CKE) in DMF (1.5 mL) was added [4-[4-amino-3-(difluoromethyl)pyrazol-1-yl]cyclohexyl]methanol (207 mg, 845 umol, Intermediate TD), DIEA (297 mg, 2.31 mmol) and HATU (292 mg, 768 umol) in DMF (0.5 mL). The mixture was then stirred at 25° C. for 1 hr. On completion, the mixture was quenched with water (3 mL) at 0° C. and extracted with EA (5 mL×3). The combined organic phase was dried over anhydrous sodium sulfate, filtered and concentrated to give a residue. The residue was purified by column chromatography (SiO$_2$, DCM/MeOH=15:1) to give the title compound (100 mg, 22% yield) as a yellow solid. $^1$H NMR (400 MHz, DMSO-d$_6$) δ 9.31 (s, 1H), 8.77 (d, J=8.0 Hz, 1H), 8.34 (s, 1H), 8.27 (s, 1H), 7.11 (t, J=54.0 Hz, 1H), 6.94 (d, J=8.0 Hz, 1H), 5.07 (d, J=3.6 Hz, 1H), 4.46 (d, J=2.4 Hz, 2H), 4.31 (dd, J=2.4, 4.4 Hz, 1H), 4.17 (tt, J=3.6, 11.6 Hz, 1H), 4.08-3.94 (m, 2H), 3.71 (dd, J=6.0, 13.6 Hz, 1H), 3.41-3.20 (m, 4H), 2.18-2.08 (m, 2H), 1.86 (d, J=11.6 Hz, 3H), 1.73 (dq, J=3.2, 12.4 Hz, 2H), 1.43 (d, J=2.8 Hz, 1H), 1.30-1.21 (m, 1H); LC-MS (ESI$^+$) m/z 488.0 (M+H)$^+$.

Step 2—N-[3-(difluoromethyl)-1-(4-formylcyclohexyl)pyrazol-4-yl]-5-(6-oxa-3-azabicyclo[3.1.1]heptan-3-yl)pyrazolo[1,5-a]pyrimidine-3-carboxamide. To a solution of N-[3-(difluoromethyl)-1-[4-(hydroxymethyl)cyclohexyl]pyrazol-4-yl]-5-(6-oxa-3-azabicyclo[3.1.1]heptan-3-yl)pyrazolo[1,5-a]pyrimidine-3-carboxamide (100 mg, 205 umol) in DCM (1 mL) was added DMP (95.7 mg, 225 umol). The mixture was then stirred at 25° C. for 1 hr. On completion, the mixture was quenched with saturated Na$_2$S$_2$O$_3$ (5 mL) and NaHCO$_3$ (5 mL) at 0° C. and extracted with DCM (10 mL×3). The combined organic phase was dried over anhydrous sodium sulfate, filtered and concentrated to give the title compound (100 mg, 97% yield) as a yellow solid. LC-MS (ESI$^+$) m/z 485.9 (M+H)$^+$.

5-(2-Oxa-6-azaspiro[3.3]heptan-6-yl)pyrazolo[1,5-a]pyrimidine-3-carboxylic acid (Intermediate CKG)

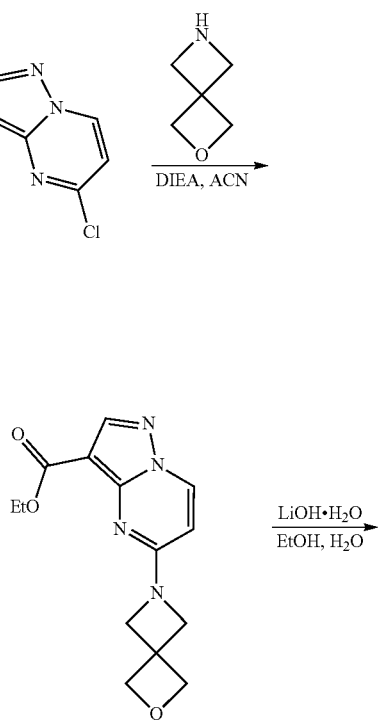

527

-continued

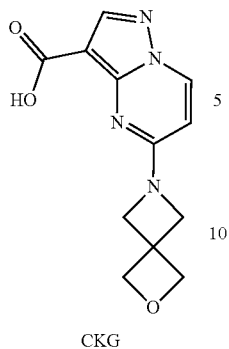

CKG

Step 1—Ethyl 5-(2-oxa-6-azaspiro[3.3]heptan-6-yl)pyrazolo[1,5-a]pyrimidine-3-carboxylate. To a mixture of ethyl 5-chloropyrazolo[1,5-a]pyrimidine-3-carboxylate (0.500 g, 2.22 mmol) and 2-oxa-6-azaspiro[3.3]heptane (439 mg, 4.43 mmol, CAS #174-78-7) in ACN (5 mL) was added DIEA (859 mg, 6.65 mmol). The reaction mixture was stirred at 80° C. for 12 hrs. On completion, the residue was diluted with water (10 mL), then the residue was extracted with EA (3×30 mL). The combined organic layer was dried over $Na_2SO_4$, filtered and filtrate was concentrated in vacuo to give the title compound (560 mg, 87% yield) as white solid. $^1$H NMR (400 MHz, DMSO-$d_6$) δ 8.68 (d, J=7.6 Hz, 1H), 8.18 (s, 1H), 6.34 (d, J=7.6 Hz, 1H), 4.74 (s, 4H), 4.35-4.29 (m, 4H), 4.19 (q, J=7.2 Hz, 2H), 1.28 (t, J=7.2 Hz, 3H). LC-MS (ESI$^+$) m/z 288.7 (M+H)$^+$.

Step 2—5-(2-Oxa-6-azaspiro[3.3]heptan-6-yl)pyrazolo[1,5-a]pyrimidine-3-carboxylic acid. To a solution of ethyl 5-(2-oxa-6-azaspiro[3.3]heptan-6-yl)pyrazolo[1,5-a]pyrimidine-3-carboxylate (300 mg, 1.04 mmol) in EtOH (5 mL) and H$_2$O (1 mL) was added LiOH·H$_2$O (130 mg, 3.12 mmol). The reaction mixture was stirred at 60° C. for 12 hrs. On completion, the mixture was acidified with 1N HCl until the pH=1-2, filtered and the filter cake was concentrated in vacuo to give the title compound (160 mg, 59% yield) as white solid. LC-MS (ESI$^+$) m/z 260.8 (M+H)$^+$.

1-(5-Bromo-2-chloro-phenyl)hexahydropyrimidine-2,4-dione (Intermediate CKH)

528

-continued

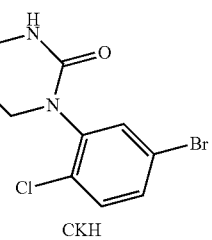

CKH

Step 1—3-(5-Bromo-2-chloro-anilino)propanoic acid. A mixture of 5-bromo-2-chloro-aniline (2.50 g, 12.1 mmol, CAS #60811-17-8) and acrylic acid (959 mg, 13.3 mmol) in AcOH (10 mL) and H$_2$O (40 mL) was stirred at 100° C. for 12 hrs. On completion, the reaction mixture was concentrated under reduced pressure to give the title compound (3.37 g, 100% yield) as a yellow solid. LC-MS (ESI$^+$) m/z 279.5 (M+H)$^+$.

Step 2—3-(5-Bromo-2-chloro-anilino)propenamide. To a mixture of 3-(5-bromo-2-chloro-anilino)propanoic acid (1.00 g, 3.59 mmol) in DMF (10 mL) was added NH$_3$·H$_2$O (5.03 g, 35.9 mmol, solution) until the pH=8. Then HATU (1.37 g, 3.59 mmol) was added and the mixture was stirred at 25° C. for 12 hrs. On completion, the reaction mixture was concentrated under reduced pressure to remove solvent. The residue was purified by reversed phase flash (0.1% FA condition) to give the title compound (610 mg, 61% yield) as a white solid. $^1$H NMR (400 MHz, DMSO-$d_6$) δ 7.42 (s, 1H), 7.19 (d, J=8.4 Hz, 1H), 6.91 (s, 1H), 6.87 (d, J=2.4 Hz, 1H), 6.72 (dd, J=2.4, 8.4 Hz, 1H), 5.66 (t, J=5.6 Hz, 1H), 3.38-3.32 (m, 2H), 2.36 (t, J=6.8 Hz, 2H); LC-MS (ESI$^+$) m/z 278.5 (M+H)$^+$.

Step 3—1-(5-Bromo-2-chloro-phenyl)hexahydropyrimidine-2,4-dione. To a mixture of 3-(5-bromo-2-chloro-anilino)propanamide (380 mg, 1.37 mmol) in ACN (5 mL) were added CDI (333 mg, 2.05 mmol), TEA (166 mg, 1.64 mmol) and DMAP (16.7 mg, 136 umol). The mixture was stirred 90° C. for 48 hrs. On completion, the reaction mixture was concentrated under reduced pressure to remove solvent. The mixture was quenched with water (10 mL) and extracted with ethyl acetate (15 mL×3). The combined organic phase was dried over anhydrous sodium sulfate, filtered and concentrated to give a residue. The residue was purified by reversed phase flash (0.1% FA condition) to give the title compound (310 mg, 74% yield) as a yellow solid. $^1$H NMR (400 MHz, DMSO-$d_6$) δ 10.52 (s, 1H), 7.81 (d, J=2.4 Hz, 1H), 7.62-7.53 (m, 2H), 3.80-3.68 (m, 1H), 3.65-3.56 (m, 1H), 2.77-2.69 (m, 2H); LC-MS (ESI$^+$) m/z 304.5 (M+H)$^+$.

1-[2-Chloro-5-(3-piperazin-1-ylprop-1-ynyl)phenyl]hexahydropyrimidine-2,4-dione (Intermediate CKI)

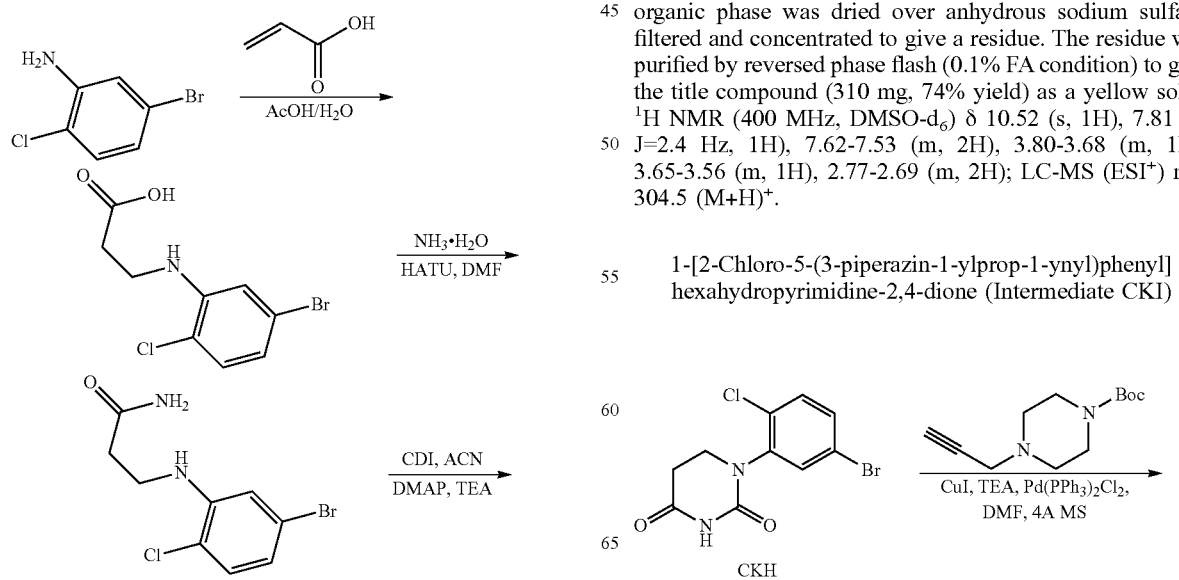

529

-continued

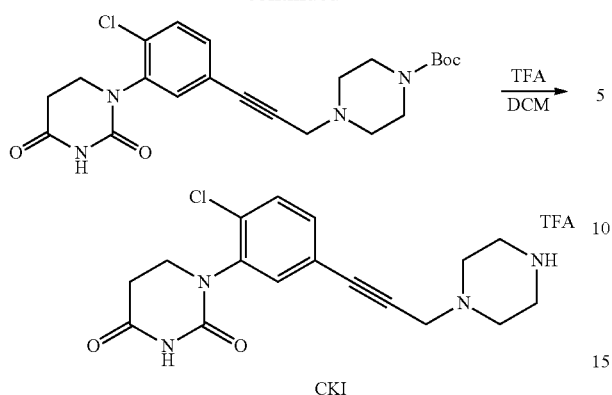

CKI

Step 1—Tert-butyl 4-[3-[4-chloro-3-(2,4-dioxohexahydropyrimidin-1-yl)phenyl]prop-2-ynyl] piperazine-1-carboxylate. To a solution of 1-(5-bromo-2-chloro-phenyl)hexahydropyrimidine-2,4-dione (92.0 mg, 303 umol, Intermediate CKH), tert-butyl 4-prop-2-ynylpiperazine-1-carboxylate (203 mg, 909 umol, CAS #199538-99-3) in DMF (4 mL) was added CuI (5.77 mg, 30.3 umol), TEA (153 mg, 1.52 mmol), 4 Å molecular sieves (303 umol) and Pd(PPh$_3$)$_2$Cl$_2$ (10.6 mg, 15.1 umol). The reaction mixture was stirred at 85° C. for 12 hrs under N$_2$. On completion, the mixture was filtered and concentrated to give a residue. The residue was purified by column chromatography (SiO$_2$, DCM/EA=1:0 to 1:3, R$_f$: 0.2, EA=65%) to give the title compound (80.0 mg, 59% yield) as a brown solid. $^1$H NMR (400 MHz, DMSO-d$_6$) δ 10.50 (s, 1H), 7.62 (d, J=2.0 Hz, 1H), 7.57 (d, J=8.4 Hz, 1H), 7.43 (dd, J=2.0, 8.4 Hz, 1H), 3.79-3.68 (m, 1H), 3.63-3.58 (m, 1H), 3.56 (s, 2H), 3.34 (d, J=5.2 Hz, 4H), 2.75-2.70 (m, 1H), 2.49-2.43 (m, 4H), 2.38 (t, J=5.2 Hz, 1H), 1.39 (s, 9H); LC-MS (ESI$^+$) m/z 446.9 (M+H)$^+$.

Step 2—1-[2-Chloro-5-(3-piperazin-1-ylprop-1-ynyl)phenyl]hexahydropyrimidine-2,4-dione. A mixture of tert-butyl 4-[3-[4-chloro-3-(2,4-dioxohexahydropyrimidin-1-yl)phenyl]prop-2-ynyl] piperazine-1-carboxylate (80.0 mg, 179 umol) in DCM (1 mL) and TFA (0.4 mL) was stirred at 25° C. for 1 hr. On completion, the reaction mixture was concentrated under reduced pressure to give the title compound (82.4 mg, 100% yield, TFA) as a brown oil. LC-MS (ESI$^+$) m/z 346.8 (M+H)$^+$.

5-(3-Oxa-8-azabicyclo[3.2.1]octan-8-yl)pyrazolo[1,5-a]pyrimidine-3-carboxylic acid (Intermediate CKJ)

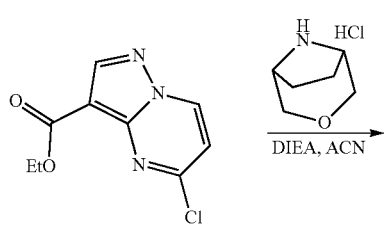

530

-continued

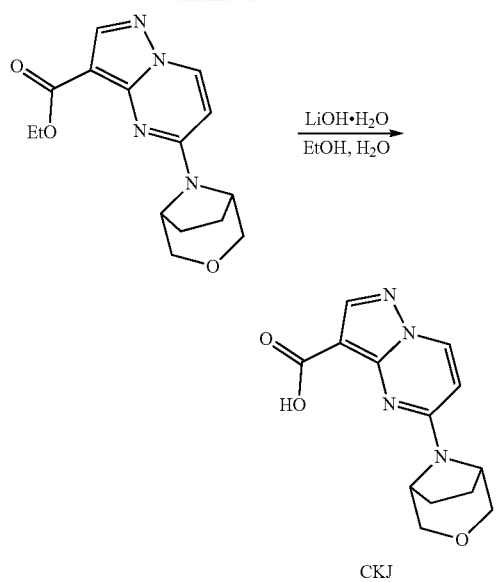

CKJ

Step 1—Ethyl 5-(3-oxa-8-azabicyclo[3.2.1]octan-8-yl)pyrazolo[1,5-a]pyrimidine-3-carboxylate. To a solution of ethyl 5-chloropyrazolo[1,5-a]pyrimidine-3-carboxylate (200 mg, 886 umol), 3-oxa-8-azabicyclo[3.2.1]octane (199 mg, 1.33 mmol, HCl, CAS #904316-92-3) and DIEA (229 mg, 1.77 mmol) in ACN (2 mL) was degassed and purged with N$_2$ three times. Then the mixture was stirred at 70° C. for 2 hrs under N$_2$ atmosphere. On completion, the reaction mixture was concentrated in vacuo to give a residue. The residue was diluted with water (20 mL), and extracted with EA (10 mL×3). The combined organic layers were dried over Na$_2$SO$_4$, filtered and concentrated in vacuo to give the title compound (222 mg, 82% yield) as white solid. $^1$H NMR (400 MHz, CDCl$_3$) δ 8.29 (s, 1H), 7.27 (s, 1H), 6.33-6.26 (m, 1H), 4.34 (q, J=7.2 Hz, 2H), 3.83 (d, J=11.2 Hz, 2H), 3.73-3.67 (m, 2H), 2.21-2.15 (m, 2H), 2.10-2.06 (m, 2H), 1.63 (s, 2H), 1.39 (t, J=7.2 Hz, 3H).

Step 2—5-(3-Oxa-8-azabicyclo[3.2.1]octan-8-yl)pyrazolo[1,5-a]pyrimidine-3-carboxylic acid. To a solution of ethyl 5-(3-oxa-8-azabicyclo[3.2.1]octan-8-yl)pyrazolo[1,5-a]pyrimidine-3-carboxylate (200 mg, 662 umol) and LiOH·H$_2$O (111 mg, 2.65 mmol) in a mixed solvent of H$_2$O (0.3 mL) and EtOH (1.2 mL) was degassed and purged with N$_2$ three times. Then the mixture was stirred at 70° C. for 12 hrs under N$_2$ atmosphere. On completion, the mixture was concentrated in vacuo to remove EtOH. Then, HCl (1N) was added until the pH=6, and the precipitate was collected and dried in vacuo to give the title compound (120 mg, 66% yield) as off-white solid. LC-MS (ESI$^+$) m/z 256.9 (M–17)$^+$.

Tert-butyl 7-prop-2-ynyl-3-oxa-7,9-diazabicyclo[3.3.1]nonane-9-carboxylate (Intermediate CKK)

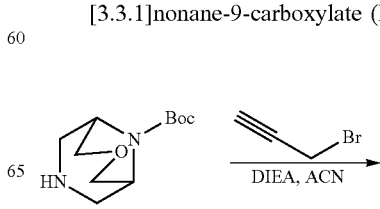

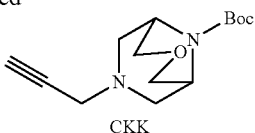

CKK

The solution of tert-butyl 3-oxa-7,9-diazabicyclo[3.3.1]nonane-9-carboxylate (900 mg, 3.94 mmol, CAS #1251010-45-3), 3-bromoprop-1-yne (645 mg, 4.34 mmol, 80% solution), and DIEA (1.53 g, 11.8 mmol) in ACN (20 mL) was degassed under vacuum and purged with N₂ three times. Then the mixture was stirred at 65° C. for 12 hrs under N₂ atmosphere. On completion, the reaction was cooled to rt and concentrated in vacuo to give a residue. The residue was diluted with water (50 mL) and extracted with EA (25 mL×3). The organic layers were combined, washed with brine (30 mL), dried over anhydrous Na₂SO₄, filtered and concentrated in vacuo to give the crude product. The crude product was purified by column chromatography (SiO₂, PE/EA=1/1 to 0/1) to give the title compound (940 mg, 89% yield) as brown oil. $^1$H NMR (400 MHz, CDCl₃) δ 4.07 (s, 1H), 4.01-3.88 (m, 3H), 3.88-3.75 (m, 2H), 3.43 (d, J=2.0 Hz, 2H), 2.96-2.73 (m, 4H), 2.29-2.19 (m, 1H), 1.49 (s, 9H).

3-[3-Methyl-4-[3-(3-oxa-7,9-diazabicyclo[3.3.1]nonan-7-yl)prop-1-ynyl]-2-oxo-benzimidazol-1-yl]piperidine-2,6-dione (Intermediate CKL)

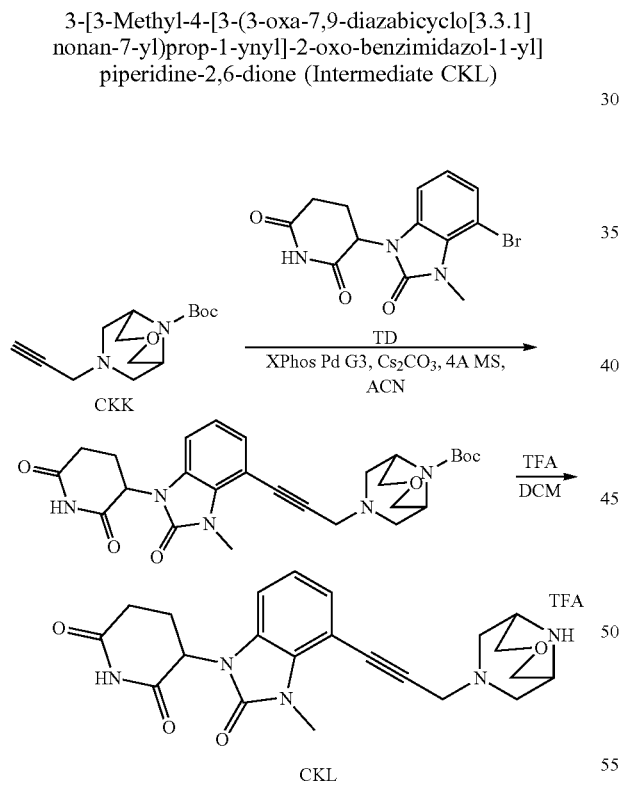

Step 1—Tert-butyl 7-[3-[1-(2,6-dioxo-3-piperidyl)-3-methyl-2-oxo-benzimidazol-4-yl]prop-2-ynyl]-3-oxa-7,9-diazabicyclo[3.3.1]nonane-9-carboxylate. A mixture of tert-butyl 7-prop-2-ynyl-3-oxa-7,9-diazabicyclo[3.3.1]nonane-9-carboxylate (420 mg, 1.58 mmol, Intermediate CKK), 3-(4-bromo-3-methyl-2-oxo-benzimidazol-1-yl)piperidine-2,6-dione (533 mg, 1.58 mmol, Intermediate HP), XPhos Pd G3 (133 mg, 158 umol), Cs₂CO₃ (1.54 g, 4.73 mmol), and 4 Å molecular sieves (500 mg) in ACN (10 mL) was degassed under vacuum and purged with N₂ three times. Then the mixture was stirred at 80° C. for 18 hrs under N₂ atmosphere. On completion, the reaction was cooled to rt, filtered to give a filtrate, concentrated in vacuo to give a residue. The residue was purified by reverse phase (0.1% FA condition) to give the title compound (75 mg, 4% yield, FA) as yellow solid. $^1$H NMR (400 MHz, DMSO-d₆) δ 11.12 (s, 1H), 7.56-6.86 (m, 3H), 5.41-5.36 (m, 1H), 3.99-3.69 (m, 4H), 3.67-3.47 (m, 6H), 3.20-2.81 (m, 4H), 2.81-2.55 (m, 4H), 2.06-1.96 (m, 1H), 1.46-1.30 (m, 9H). LC-MS (ESI+) m/z 524.2 (M+H)⁺.

Step 2—3-[3-Methyl-4-[3-(3-oxa-7,9-diazabicyclo[3.3.1]nonan-7-yl)prop-1-ynyl]-2-oxo-benzimidazol-1-yl]piperidine-2,6-dione. To a solution of tert-butyl 7-[3-[1-(2,6-dioxo-3-piperidyl)-3-methyl-2-oxo-benzimidazol-4-yl]prop-2-ynyl]-3-oxa-7,9-diazabicyclo[3.3.1]nonane-9-carboxylate (55 mg, 105 umol) in DCM (1 mL) was added TFA (154 mg, 1.35 mmol), then the mixture was stirred at 20° C. for 1 hr. On completion, the reaction was concentrated in vacuo to give the title compound (56 mg, 99% yield, TFA) as yellow oil. LC-MS (ESI+) m/z 423.9 (M+H)⁺.

5-(2-Oxa-7-azaspiro[3.5]nonan-7-yl)pyrazolo[1,5-a]pyrimidine-3-carboxylic acid (Intermediate CKM)

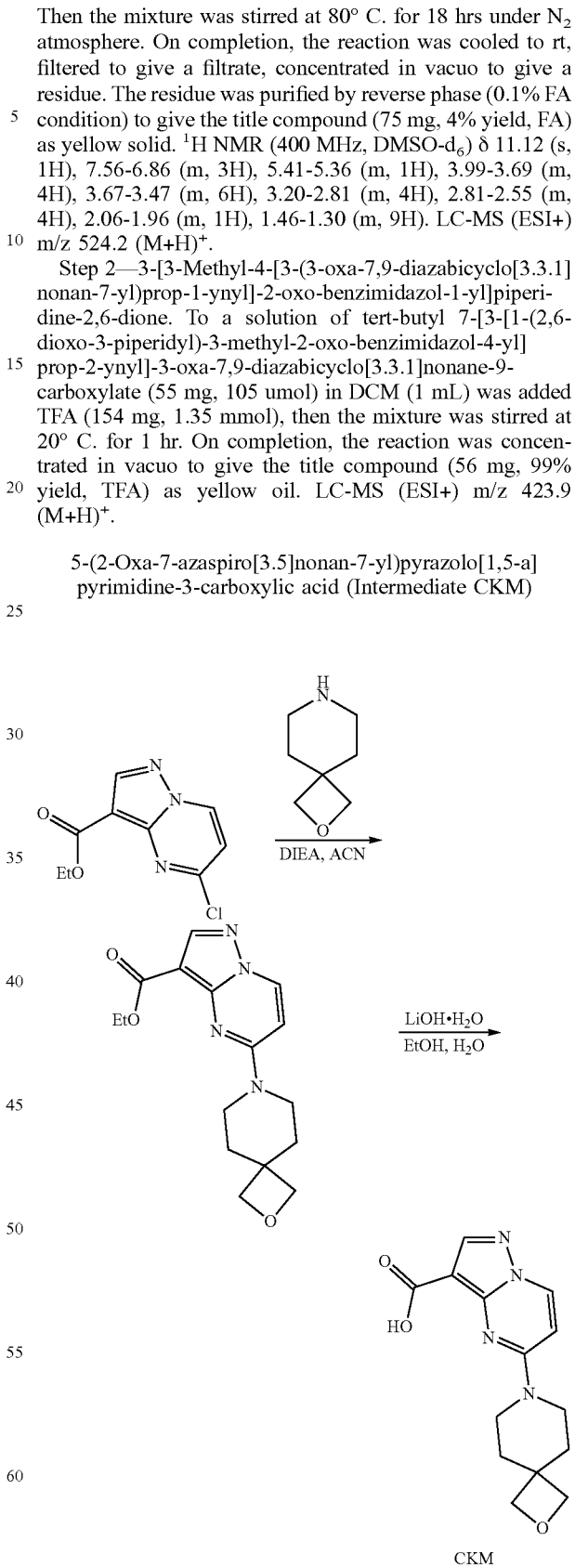

Step 1—Ethyl 5-(2-oxa-7-azaspiro[3.5]nonan-7-yl)pyrazolo[1,5-a]pyrimidine-3-carboxylate. To a solution of ethyl 5-chloropyrazolo[1,5-a]pyrimidine-3-carboxylate (300 mg, 1.33 mmol), 2-oxa-7-azaspiro[3.5]nonane (338 mg, 2.66 mmol), DIEA (343 mg, 2.66 mmol) in ACN (6 mL) was degassed and purged with $N_2$ three times, and then the mixture was stirred at 70° C. for 2 hrs under $N_2$ atmosphere. On completion, the reaction mixture was concentrated in vacuo to remove ACN, then the residue was diluted with water (20 mL) and extracted with EA (10 mL×3). The combined organic layer was dried over $Na_2SO_4$, filtered and concentrated in vacuo to give the title compound (310 mg, 73% yield) as a white solid. $^1$H NMR (400 MHz, DMSO-$d_6$) δ 8.68 (d, J=8.0 Hz, 1H), 8.18 (s, 1H), 6.88 (d, J=8.0 Hz, 1H), 4.37 (s, 4H), 4.19 (q, J=7.2 Hz, 2H), 3.71 (s, 4H), 1.89-1.82 (m, 4H), 1.28 (t, J=7.2 Hz, 3H); LC-MS (ESI$^+$) m/z 316.8 (M+H)$^+$.

Step 2—5-(2-Oxa-7-azaspiro[3.5]nonan-7-yl)pyrazolo[1,5-a]pyrimidine-3-carboxylic acid. To a solution of ethyl 5-(2-oxa-7-azaspiro [3.5]nonan-7-yl) pyrazolo[1,5-a]pyrimidine-3-carboxylate (155 mg, 489 umol), LiOH·$H_2O$ (61.6 mg, 1.47 mmol) in a mixed solvent of EtOH (1.2 mL) and $H_2O$ (0.3 mL) was stirred at 70° C. for 12 hrs. On completion, the mixture was concentrated in vacuo to remove EtOH and added HCl (1N) until the pH=6. The solid was precipitated. Then the mixture was filtered and filter cake was dried in vacuo to give the solid. The solid was dissolved in EA (15 mL) and then the organic phase dried over anhydrous sodium sulfate, filtered and concentrated to give the title compound (86 mg, 42% yield) as a pink solid. $^1$H NMR (400 MHz, DMSO-$d_6$) δ 8.74 (d, J=7.8 Hz, 1H), 8.18 (s, 1H), 6.78 (d, J=7.8 Hz, 1H), 3.63 (s, 5H), 2.08 (s, 1H); LC-MS (ESI$^+$) m/z 271.0 (M+H)$^+$.

5-(3,3-Difluoroazetidin-1-yl)pyrazolo[1,5-a]pyrimidine-3-carboxylic acid (Intermediate CKN)

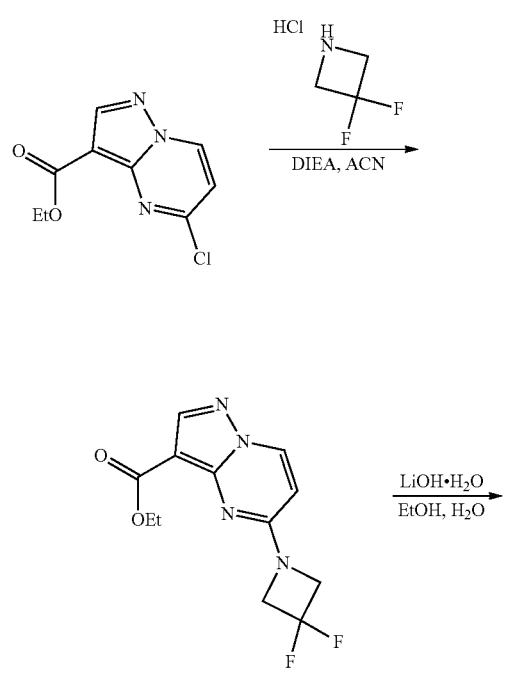

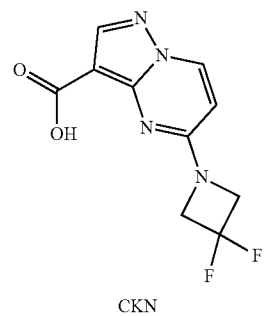

Step 1—Ethyl 5-(3,3-difluoroazetidin-1-yl)pyrazolo[1,5-a]pyrimidine-3-carboxylate. To a mixture of ethyl 5-chloropyrazolo[1,5-a]pyrimidine-3-carboxylate (1 g, 4.43 mmol) and 3,3-difluoroazetidine (1.15 g, 8.86 mmol, CAS #679431-52-8) in ACN (10 mL) was added DIEA (1.72 g, 13.3 mmol), then the reaction mixture was stirred at 90° C. for 12 hrs. On completion, the residue was diluted with water (20 mL), then the residue was extracted with EA (3×50 mL). The combined organic layer was dried over $Na_2SO_4$, filtered and concentrated in vacuo to give the title compound (1.20 g, 96% yield) as white solid. $^1$H NMR (400 MHz, DMSO-$d_6$) δ 8.85 (d, J=7.6 Hz, 1H), 8.26 (s, 1H), 6.52 (d, J=7.6 Hz, 1H), 4.61 (t, J=12.4 Hz, 4H), 4.22-4.17 (m, 2H), 1.28 (s, 3H); LC-MS (ESI$^+$) m/z 282.9 (M+H)$^+$.

Step 2—5-(3,3-Difluoroazetidin-1-yl)pyrazolo[1,5-a]pyrimidine-3-carboxylic acid. To a mixture of ethyl 5-(3,3-difluoroazetidin-1-yl)pyrazolo[1,5-a]pyrimidine-3-carboxylate (100 mg, 354 umol) in EtOH (2 mL) and $H_2O$ (1 mL) was added LiOH·$H_2O$ (44.6 mg, 1.06 mmol), then the reaction mixture was stirred at 60° C. for 12 hrs. On completion, the reaction mixture was acidized with HCl (1M) and filtered. The mixture was then concentrated in vacuo to give the title compound (70 mg, 78% yield) as white solid. LC-MS (ESI$^+$) m/z 236.7 (M−$H_2O$+H)$^+$.

2-Oxa-7-azaspiro[3.4]octane (Intermediate CKO)

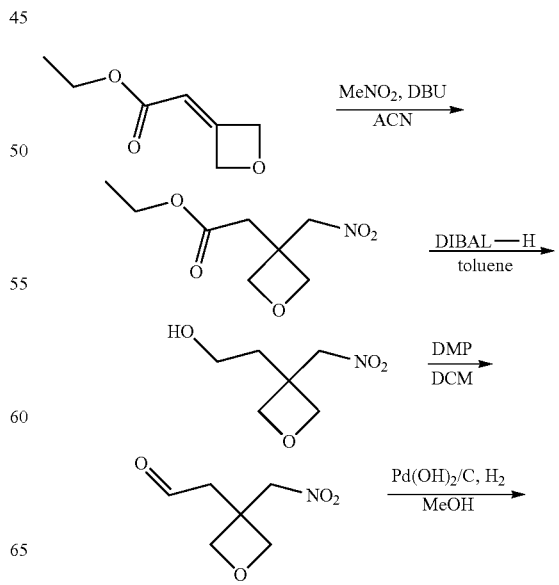

535

-continued

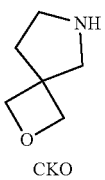

CKO

Step 1—Ethyl 2-[3-(nitromethyl)oxetan-3-yl]acetate. To a solution of ethyl 2-(oxetan-3-ylidene)acetate (4.00 g, 28.1 mmol, CAS #922500-91-2) in ACN (40 mL) was added nitromethane (8.59 g, 140 mmol) and DBU (856 mg, 5.63 mmol) at 0° C. The mixture was stirred at 25° C. for 4 hrs. On completion, the mixture was then concentrated to give a residue. Then the residue was diluted with H$_2$O (450 mL) and extracted with EA (80 mL×3). The organic phase was combined and dried over Na2SO4, filtered and concentrated to give a residue to give the title compound (5.00 g, 78% yield) as yellow oil. $^1$H NMR (400 MHz, CDCl$_3$-d$_6$) δ 4.96 (s, 2H), 4.70-4.51 (m, 4H), 4.17 (q, J=7.2 Hz, 2H), 2.97 (s, 2H), 1.28 (t, J=7.2 Hz, 3H).

Step 2—2-[3-(Nitromethyl)oxetan-3-yl]ethanol. To a solution of ethyl 2-[3-(nitromethyl)oxetan-3-yl]acetate (4.70 g, 23.1 mmol) in THF (50 mL) was added DIBAL-H (1 M, 57.8 mL). The mixture was stirred at 0° C. for 0.5 hr. On completion, the reaction mixture was quenched with H$_2$O (8 mL) and 10% NaOH (8 mL) at 0° C. Then the mixture was quenched with ice water (10 ml) and extracted with EA (5 ml×3). The combined organic phase was washed with H$_2$O (30 mL), dried over anhydrous sodium sulfate, filtered and concentrated to give a residue. The residue was purified by column chromatography (SiO$_2$, Petroleum ether/Ethyl acetate=5/1 to 1/1) to give the title compound (1.87 g, 50% yield) as white oil. $^1$H NMR (400 MHz, CDCl$_3$-d$_6$) δ 4.83 (s, 2H), 4.57-4.51 (m, 4H), 3.80-3.74 (m, 2H), 2.05 (t, J=6.0 Hz, 2H).

Step 3—2-[3-(Nitromethyl)oxetan-3-yl]acetaldehyde. To a solution of 2-[3-(nitromethyl)oxetan-3-yl]ethanol (1.87 g, 11.6 mmol) in DCM (20 mL) was added DMP (5.91 g, 13.9 mmol). The mixture was stirred at 25° C. for 1 hr. On completion, the reaction mixture was quenched with Na$_2$S$_2$O$_3$ (5 mL) and NaHCO$_3$ (5 mL). The reaction mixture was filtered and concentrated in vacuo to give the residue. The residue was diluted with DCM (15 mL) and washed with NaHCO$_3$ (10 mL×3). The organic layer was dried over Na$_2$SO$_4$, filtered and concentrated to give a residue. The residue was purified by column chromatography (SiO$_2$, Petroleum ether/Ethyl acetate=5/1 to 1/1) to give the title compound (0.950 g, 48% yield) as a yellow oil. $^1$H NMR (400 MHz, CDCl$_3$-d$_6$) δ 9.77 (s, 1H), 4.95 (s, 2H), 4.69-4.63 (m, 2H), 4.52 (d, J=7.2 Hz, 2H), 3.21 (s, 2H).

Step 4—2-Oxa-7-azaspiro[3.4]octane. To a solution of 2-[3-(nitromethyl)oxetan-3-yl]acetaldehyde (840 mg, 5.28 mmol) in MeOH (5 mL) was added Pd(OH)$_2$ (148 mg, 1.06 mmol) and H$_2$ (10.6 mg, 5.28 mmol) (15 psi). The mixture was stirred at 25° C. for 16 hrs. On completion, the mixture was filtered and concentrated to give the title compound (610 mg, 71% yield) as white oil. $^1$H NMR (400 MHz, CDCl$_3$-d$_6$) δ 4.60 (d, J=6.0 Hz, 2H), 4.58-4.55 (m, 2H), 3.22-3.16 (m, 2H), 2.96 (t, J=7.2 Hz, 2H), 2.02-1.94 (m, 2H).

536

5-(2-Oxa-7-azaspiro[3.4]octan-7-yl)pyrazolo[1,5-a]pyrimidine-3-carboxylic acid (Intermediate CKP)

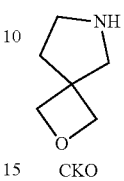

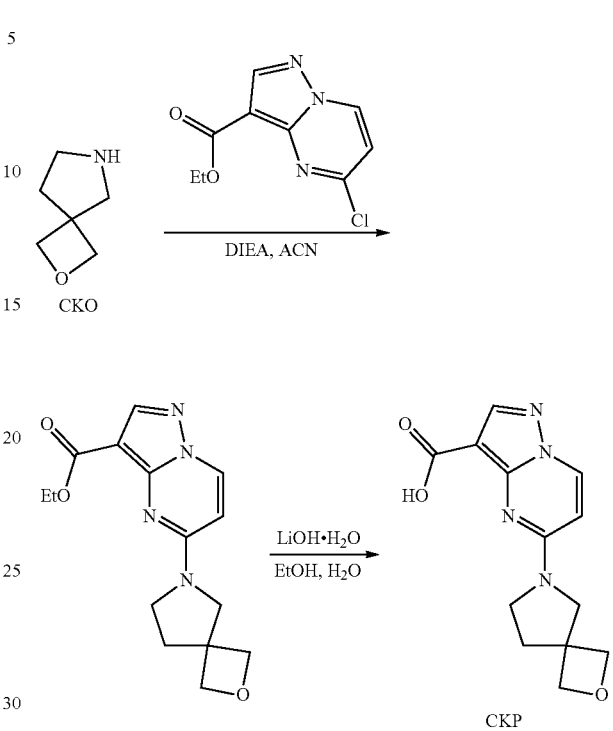

Step 1—Ethyl 5-(2-oxa-7-azaspiro[3.4]octan-7-yl)pyrazolo[1,5-a]pyrimidine-3-carboxylate. To a solution of 2-oxa-7-azaspiro[3.4]octane (610 mg, 5.39 mmol, Intermediate CKO) and ethyl 5-chloropyrazolo[1,5-a]pyrimidine-3-carboxylate (1.22 g, 5.39 mmol) in ACN (2 mL) was added DIEA (1.39 g, 10.7 mmol). The mixture was then stirred at 70° C. for 12 hrs. On completion, the mixture was concentrated in vacuo to remove the ACN. Then the mixture was diluted with EA (50 mL) and washed with H$_2$O (70 mL). The organic layer was dried over Na$_2$SO$_4$, filtered and concentrated to give a residue. The residue was purified by column chromatography (SiO$_2$, Petroleum ether/Ethyl acetate=2/1 to 1/2) to give the title compound (200 mg, 6% yield) as a white solid. $^1$H NMR (400 MHz, CDCl$_3$-d$_6$) δ 8.30-8.14 (m, 2H), 6.13 (d, J=7.6 Hz, 1H), 4.73-4.53 (m, 4H), 4.29 (q, J=7.2 Hz, 2H), 4.07-3.38 (m, 4H), 2.41-2.20 (m, 2H), 1.33 (t, J=7.2 Hz, 3H); LC-MS (ESI$^+$) m/z 303.5 (M+H)$^+$.

Step 2—5-(2-Oxa-7-azaspiro[3.4]octan-7-yl)pyrazolo[1,5-a]pyrimidine-3-carboxylic acid. To a solution of ethyl 5-(2-oxa-7-azaspiro[3.4]octan-7-yl)pyrazolo[1,5-a]pyrimidine-3-carboxylate (120 mg, 396 umol) in EtOH (2 mL) and H$_2$O (0.5 mL) was added LiOH·H$_2$O (49.9 mg, 1.19 mmol). The mixture was then stirred at 60° C. for 2 hrs. On completion, the mixture was concentrated to give a residue. To a mixture was added HCl (3 M) (0.5 mL) at 25° C. until the pH stabilized at 2-3. The mixture was filtered, and the filer cake was dried in vacuo to give the title compound (100 mg, 91% yield) as a white solid. LC-MS (ESI$^+$) m/z 275.3 (M+H)$^+$.

[4-[4-Amino-3-(difluoromethyl)pyrazol-1-yl]phenyl]
methanol (Intermediate CKQ)

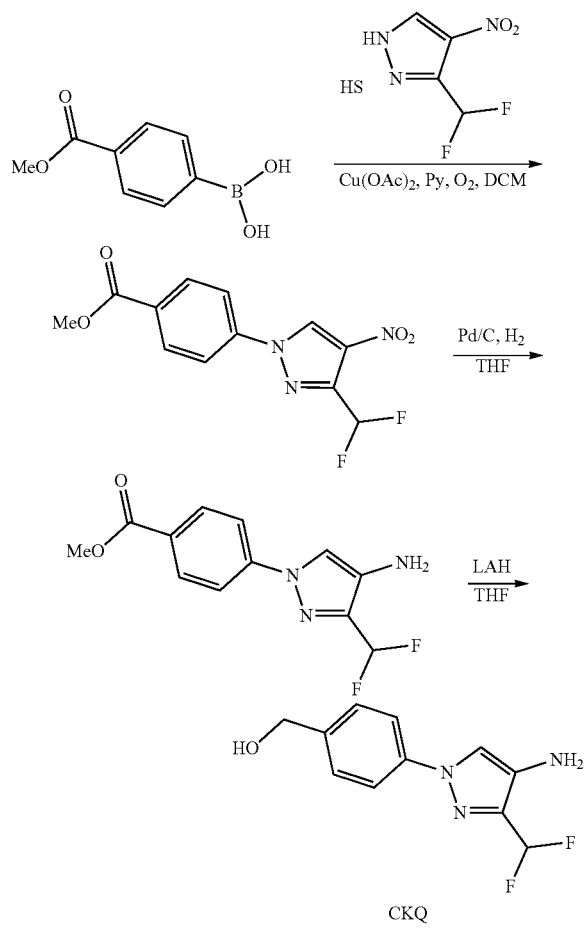

Step 1—Methyl 4-[3-(difluoromethyl)-4-nitro-pyrazol-1-yl]benzoate. To a solution of 3-(difluoromethyl)-4-nitro-1H-pyrazole (3 g, 18.4 mmol, Intermediate HS) and (4-methoxycarbonylphenyl)boronic acid (3.31 g, 18.4 mmol, CAS #99768-12-4) in DCM (30 mL) was added pyridine (4.37 g, 55.1 mmol, 4.45 mL), and Cu(OAc)$_2$ (5.01 g, 27.5 mmol). The mixture was stirred at 25° C. for 16 hrs under O$_2$. On completion, the reaction mixture was filtered and the filter cake was dried in vacuo to give a residue. The residue was triturated with (PE:DCM=5:1) and purified by column chromatography (SiO$_2$, PE:EA=30:1 to PE:EA=5:1, PE:EA=1:1, P1:Rf=0.4) to give the title compound (4 g, 73% yield) as a brown solid. LC-MS (ESI$^+$) m/z 297.6 (M+H)$^+$.

Step 2—Methyl 4-[4-amino-3-(difluoromethyl)pyrazol-1-yl]benzoate. To a solution of methyl 4-[3-(difluoromethyl)-4-nitro-pyrazol-1-yl]benzoate (2 g, 6.73 mmol) in THF (25 mL) was added Pd/C (500 mg, 6.73 mmol, 10 wt %). The mixture was stirred at 25° C. for 16 hrs under H$_2$. On completion, the reaction mixture was filtered and the filtrate was concentrated in vacuo to give the title compound (1.8 g, 100% yield) as a yellow solid, LC-MS (ESI$^+$) m/z 268.0 (M+H)$^+$.

Step 3—[4-[4-Amino-3-(difluoromethyl)pyrazol-1-yl]phenyl]methanol. To a solution of methyl 4-[4-amino-3-(difluoromethyl)pyrazol-1-yl]benzoate (1.8 g, 6.74 mmol) in THF (30 mL) was added LAH (281 mg, 7.41 mmol) at 0° C. The mixture was then stirred at 0° C. for 1 hr. On completion, the reaction mixture was quenched with water (0.3 mL), 15% NaOH (0.9 mL) and water (0.3 mL), dried over Na$_2$SO$_4$ filtered and the filtrate was concentrated in vacuo to give a residue. The residue was purified by column chromatography (SiO$_2$, PE:EA=1:0 to PE:EA=1:3, PE:EA=1:1, P1:Rf=0.5) to give the title compound (1.6 g, 99% yield) as a yellow solid. $^1$H NMR (400 MHz, DMSO-d$_6$) δ 7.77 (s, 1H), 7.67 (d, J=8.8 Hz, 2H), 7.40 (d, J=8.8 Hz, 2H), 7.20-6.88 (m, 1H), 5.24 (t, J=5.6 Hz, 1H), 4.51 (d, J=6.0 Hz, 2H), 4.38 (s, 2H). LCMS (ESI$^+$) m/z 239.7 (M+H)$^+$.

N-[3-(difluoromethyl)-1-(4-formylphenyl)pyrazol-4-yl]-5-[(1R,4R)-2-oxa-5-azabicyclo[2.2.1] heptan-5-yl]pyrazolo[1,5-a]pyrimidine-3-carboxamide (Intermediate CKR)

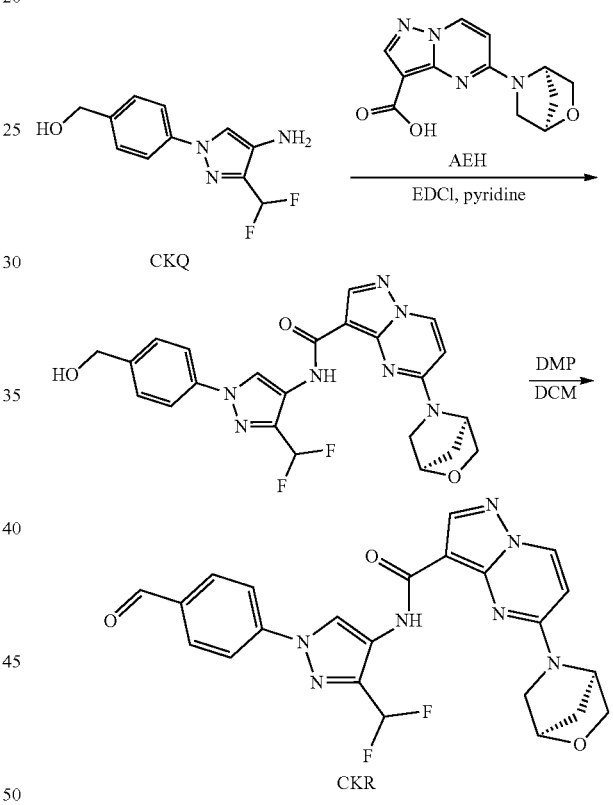

Step 1—N-[3-(difluoromethyl)-1-[4-(hydroxymethyl)phenyl]pyrazol-4-yl]-5-[(1R,4R)-2-oxa-5-azabicyclo[2.2.1]heptan-5-yl]pyrazolo[1,5-a]pyrimidine-3-carboxamide. To a solution of 5-[(1R,4R)-2-oxa-5-azabicyclo[2.2.1]heptan-5-yl]pyrazolo[1,5-a]pyrimidine-3-carboxylic acid (543 mg, 2.09 mmol, Intermediate AEH) and [4-[4-amino-3-(difluoromethyl) pyrazol-1-yl] phenyl]methanol (500 mg, 2.09 mmol, Intermediate CKQ) in pyridine (8 mL) was added EDCI (480 mg, 2.51 mmol) in 25° C. under N$_2$. The reaction mixture was then stirred at 25° C. for 2 hrs. On completion, the reaction mixture was concentrated in vacuo to give a residue. The residue was diluted with water (30 mL) and filtered and the filter cake was concentrated in vacuo to give the title compound (40.0 mg, 98% yield) as a brown solid. $^1$H NMR (400 MHz, DMSO-d$_6$) δ 9.60 (d, J=4.0 Hz, 1H), 8.97 (d, J=2.8 Hz, 1H), 8.80 (dd, J=2.0, 8.0 Hz, 1H), 8.30 (d, J=5.2 Hz, 1H), 7.79 (d, J=8.4 Hz, 2H), 7.47 (d, J=8.4 Hz, 2H), 7.43-7.13 (m, 1H), 6.92-6.43 (m, 1H), 5.35-4.76 (m, 3H), 4.55 (d, J=6.0 Hz, 2H), 3.86-3.42 (m, 4H), 2.07-1.92 (m, 2H), LCMS (ESI⁺) m/z 482.1 (M+H)⁺.

Step 2—N-[3-(difluoromethyl)-1-(4-formylphenyl)pyrazol-4-yl]-5-[(1R,4R)-2-oxa-5-azabicyclo[2.2.1] heptan-5-yl]pyrazolo[1,5-a]pyrimidine-3-carboxamide. To a solution N-[3-(difluoromethyl)-1-[4-(hydroxymethyl)phenyl]pyrazol-4-yl]-5-[(1R,4R)-2-oxa-5-azabicyclo[2.2.1]heptan-5-yl] pyrazolo[1,5-a]pyrimidine-3-carboxamide (100 mg, 207 umol) in DCM (5 mL) was added DMP (176 mg, 415 umol, 128 uL), then the reaction mixture was stirred at 25° C. for 1 hr. On completion, the reaction mixture was quenched with Na₂S₂O₃ (10 mL) and NaHCO₃ (10 mL) and extracted with DCM (2×15 mL). The combined organic phase was washed with NaHCO₃ (15 mL) and brine (15 mL), dried with anhydrous Na₂SO₄, filtered and the filtrate was concentrated in vacuo to give a residue. The residue was triturated with (PE:EA=0:1) to give the title compound (80 mg, 80% yield) as a brown solid. LCMS (ESI⁺) m/z 480.2 (M+H)⁺.

Tert-butyl (2R)-2-(bromomethyl)morpholine-4-carboxylate (Intermediate CKS)

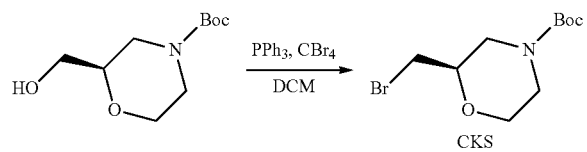

To a solution of tert-butyl (2R)-2-(hydroxymethyl)morpholine-4-carboxylate (1.00 g, 4.60 mmol, CAS #135065-69-6) in DCM (10 mL) was added PPh₃ (2.41 g, 9.21 mmol) and CBr₄ (3.05 g, 9.21 mmol) at 0° C. Then the reaction mixture was stirred at 25° C. for 1 hr. On completion, the mixture was filtered and the filtrate was concentrated in vacuo to give a residue. The residue was purified by column chromatography (SiO₂, PE/EA=12%, PE:EA=1:1, P1:Rf=0.3) to give the title compound (1.20 g, 93% yield) as a white solid. ¹H NMR (400 MHz, DMSO-d₆) δ 3.91 (d, J=12.0 Hz, 1H), 3.84 (dd, J=2.0, 11.6 Hz, 1H), 3.68 (d, J=13.2 Hz, 1H), 3.60-3.55 (m, 1H), 3.52-3.44 (m, 2H), 3.44-3.38 (m, 1H), 2.86 (s, 1H), 2.76-2.58 (m, 1H), 1.41 (s, 9H).

3-[3-Methyl-4-[[(2S)-morpholin-2-yl]methyl]-2-oxo-benzimidazol-1-yl]piperidine-2,6-dione (Intermediate CKT)

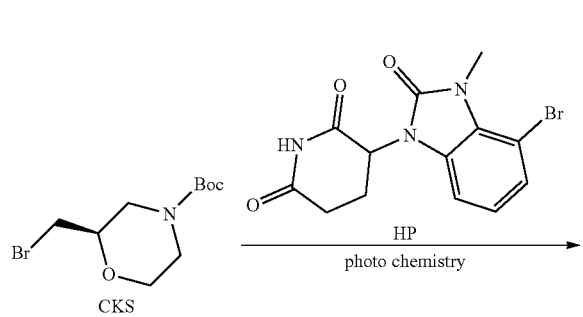

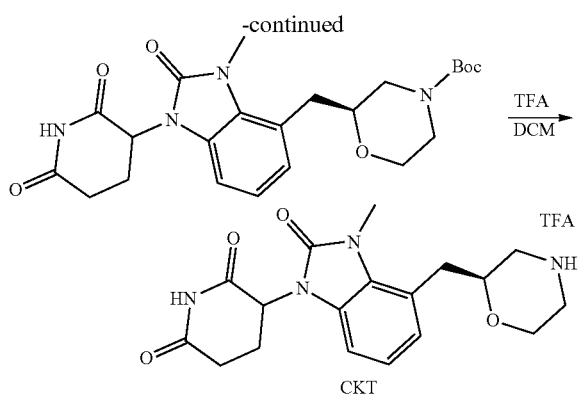

Step 1—Tert-butyl (2S)-2-[[1-(2,6-dioxo-3-piperidyl)-3-methyl-2-oxo-benzimidazol-4-yl]methyl] morpholine-4-carboxylate. To an 15 mL vial equipped with a stir bar was added tert-butyl (2R)-2-(bromomethyl)morpholine-4-carboxylate (1.00 g, 3.57 mmol, Intermediate CKS), 3-(4-bromo-3-methyl-2-oxo-benzimidazol-1-yl)piperidine-2,6-dione (928 mg, 2.75 mmol, Intermediate HP), Ir[dF(CF₃)ppy]₂(dtbpy)(PF₆) (61.6 mg, 54.9 umol), NiCl₂·dtbbpy (32.7 mg, 82.3 umol), TTMSS (682 mg, 2.75 mmol), and 2,6-lutidine (588 mg, 5.49 mmol) in DME (10 mL). The vial was sealed and placed under nitrogen was added. The reaction was stirred and irradiated with a 10 W blue LED lamp (3 cm away), with cooling water to keep the reaction temperature at 2 5° C. for 14 hrs. On completion, the mixture was filtered and filtrate was concentrated in vacuo to give a residue. The residue was purified by reverse phase (0.1% FA condition) to give the title compound (1.00 g, 79% yield) as a yellow solid. ¹H NMR (400 MHz, DMSO-d₆) δ 11.09 (s, 1H), 7.09-6.81 (m, 3H), 5.37 (dd, J=5.2, 12.4 Hz, 1H), 3.86 (d, J=12.8 Hz, 1H), 3.82-3.73 (m, 1H), 3.68 (d, J=12.8 Hz, 1H), 3.57 (s, 3H), 3.53 (s, 1H), 3.41-3.34 (m, 1H), 3.20-3.09 (m, 1H), 3.03-2.81 (m, 3H), 2.78-2.55 (m, 3H), 2.04-1.95 (m, 1H), 1.38 (s, 9H); LCMS (ESI⁺) m/z 359.0 (M+H−100)⁺.

Step 2—3-[3-Methyl-4-[[(2S)-morpholin-2-yl]methyl]-2-oxo-benzimidazol-1-yl]piperidine-2,6-dione. To a solution of tert-butyl (2S)-2-[[1-(2,6-dioxo-3-piperidyl)-3-methyl-2-oxo-benzimidazol-4-yl] methyl]morpholine-4-carboxylate (50.0 mg, 109 umol) in DCM (1 mL) was added TFA (462 mg, 4.05 mmol). The mixture was then stirred at 25° C. for 1 hr. On completion, the reaction mixture was concentrated in vacuo to give the title compound (50.0 mg, 97% yield, TFA) as yellow oil. LC-MS (ESI⁺) m/z 359.2 (M+H)⁺.

Tert-butyl (2S)-2-ethynylmorpholine-4-carboxylate (Intermediate CKU)

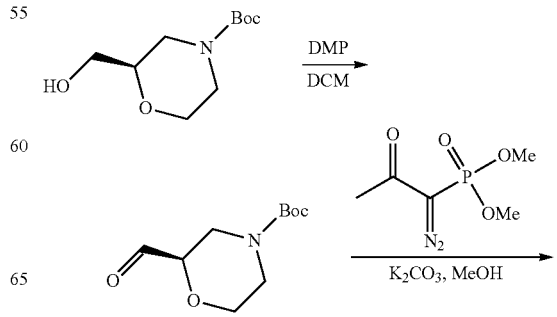

541

-continued

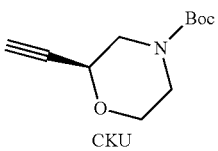

CKU

Step 1—Tert-butyl (2R)-2-formylmorpholine-4-carboxylate. To a solution of tert-butyl (2R)-2-(hydroxymethyl) morpholine-4-carboxylate (1.00 g, 4.60 mmol, CAS #135065-71-3) in DCM (30 mL) was added DMP (2.15 g, 5.06 mmol) at 0° C. The mixture was then warmed to 25° C. and stirred for 16 hrs. On completion, the reaction mixture was quenched with saturated $NaHCO_3$ (30 mL) and $Na_2S_2O_3$ (60 mL), then extracted with DCM (3×30 mL). The combined organic layers were washed with NaCl (30 mL×2), dried over $Na_2SO_4$, filtered and concentrated in vacuo to give the title compound (920 mg, 92% yield) as a yellow solid. $^1$H NMR (400 MHz, DMSO-$d_6$) δ 9.57 (s, 1H), 4.07 (dd, J=3.6, 8.8 Hz, 1H), 3.90-3.84 (m, 1H), 3.78 (d, J=12.4 Hz, 1H), 3.58-3.51 (m, 2H), 3.12-2.99 (m, 2H), 1.41 (s, 9H).

Step 2—Tert-butyl (2S)-2-ethynylmorpholine-4-carboxylate. To a solution of tert-butyl (2R)-2-formylmorpholine-4-carboxylate (920 mg, 4.27 mmol) and $K_2CO_3$ (1.18 g, 8.54 mmol) in MeOH (10 mL) was added 1-diazo-1-dimethoxyphosphoryl-propan-2-one (1.23 g, 6.40 mmol) dropwise at 0° C. The reaction mixture was stirred at 25° C. for 16 hrs. On completion, the mixture was filtered and concentrated to give a residue. The residue was purified by column chromatography (SiO$_2$, Petroleum ether/Ethyl acetate=1:0 to 5:1, EA=15%) to give the title compound (640 mg, 70% yield) as a yellow solid. $^1$H NMR (400 MHz, DMSO-$d_6$) δ 4.37-4.31 (m, 1H), 3.83-3.74 (m, 1H), 3.58-3.42 (m, 3H), 3.40-3.33 (m, 1H), 3.30-3.20 (m, 2H), 1.40 (s, 9H).

3-[3-Methyl-4-[2-[(2S)-morpholin-2-yl]ethyl]-2-oxo-benzimidazol-1-yl]piperidine-2,6-dione (Intermediate CKV)

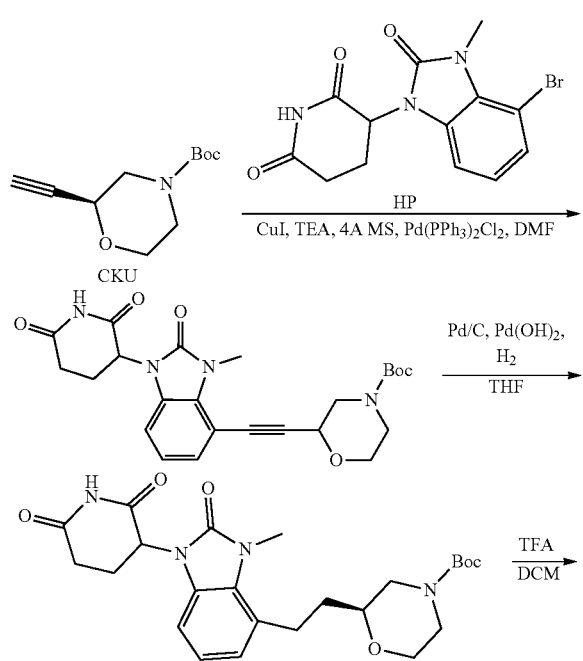

542

-continued

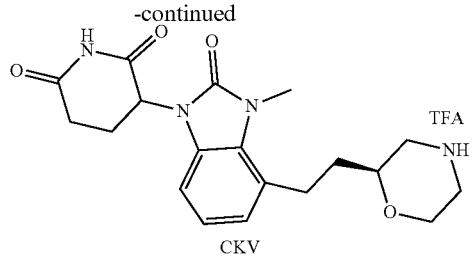

CKV

Step 1—Tert-butyl (2S)-2-[2-[1-(2,6-dioxo-3-piperidyl)-3-methyl-2-oxo-benzimidazol-4-yl]ethynyl] morpholine-4-carboxylate To a mixture of tert-butyl (2S)-2-ethynylmorpholine-4-carboxylate (200 mg, 946 umol, Intermediate CKU) in DMF (2 mL) were added 3-(4-bromo-3-methyl-2-oxo-benzimidazol-1-yl)piperidine-2,6-dione (160 mg, 473 umol, Intermediate HP), Pd(PPh$_3$)$_2$Cl$_2$ (66.4 mg, 94.6 umol), CuI (18.0 mg, 94.6 umol), Cs$_2$CO$_3$ (616 mg, 1.89 mmol), 4 Å molecular sieves (946 umol). The mixture was stirred at 80° C. for 3 hrs under N$_2$. On completion, the mixture was filtered and concentrated to give a residue. The residue was purified by column chromatography (SiO$_2$, Petroleum ether/Ethyl acetate=3:1 to 0:1), then triturated with PE:EA=1:1 (16 mL) at 25° C. for 120 mins to give the title compound (227 mg, 51% yield) as a yellow solid. $^1$H NMR (400 MHz, DMSO-$d_6$) δ 11.12 (s, 1H), 7.19 (d, J=7.6 Hz, 1H), 7.14-7.09 (m, 1H), 7.07-7.00 (m, 1H), 5.40 (dd, J=5.2, 12.4 Hz, 1H), 4.70 (dd, J=3.6, 6.0 Hz, 1H), 3.93-3.83 (m, 1H), 3.64 (d, J=3.2 Hz, 1H), 3.62 (s, 3H), 3.59-3.51 (m, 1H), 3.51-3.42 (m, 1H), 3.35 (d, J=10.0 Hz, 2H), 2.95-2.82 (m, 1H), 2.77-2.58 (m, 2H), 2.07-1.98 (m, 1H), 1.40 (s, 9H); LC-MS (ESI$^+$) m/z 491.1 (M+Na)$^+$.

Step 2—Tert-butyl (2S)-2-[2-[1-(2,6-dioxo-3-piperidyl)-3-methyl-2-oxo-benzimidazol-4-yl]ethyl] morpholine-4-carboxylate. To a mixture of Pd/C (80.0 mg, 10 wt %), Pd(OH)$_2$ (80.0 mg, 113 umol, 20 wt %) in THF (5 mL) was added tert-butyl (2S)-2-[2-[1-(2,6-dioxo-3-piperidyl)-3-methyl-2-oxo-benzimidazol-4-yl]ethynyl] morpholine-4-carboxylate (227 mg, 484 umol) at 25° C. The mixture was stirred at 25° C. for 16 hrs under H$_2$ (15 Psi). On completion, the reaction mixture was filtered and the filtrate was concentrated in vacuo to give the title compound (228 mg, 99% yield) as a white solid. $^1$H NMR (400 MHz, DMSO-$d_6$) δ 11.09 (s, 1H), 6.97-6.96 (m, 1H), 6.89-6.85 (m, 2H), 5.36 (dd, J=5.2, 12.4 Hz, 1H), 3.90-3.67 (m, 3H), 3.56 (s, 3H), 3.42-3.33 (m, 3H), 3.15-3.02 (m, 1H), 2.95-2.80 (m, 3H), 2.72-2.59 (m, 2H), 2.05-1.94 (m, 1H), 1.78-1.68 (m, 2H), 1.35 (s, 9H); LC-MS (ESI$^+$) m/z 372.9 (M−100+H)$^+$.

Step 3—3-[3-Methyl-4-[2-[(2S)-morpholin-2-yl]ethyl]-2-oxo-benzimidazol-1-yl]piperidine-2,6-dione. To a mixture of tert-butyl (2S)-2-[2-[1-(2,6-dioxo-3-piperidyl)-3-methyl-2-oxo-benzimidazol-4-yl] ethyl]morpholine-4-carboxylate (30.0 mg, 63.4 umol) in DCM (0.5 mL) was added TFA (0.3 mL). The mixture was stirred at 25° C. for 0.5 hr. On completion, the reaction mixture was concentrated under reduced pressure to give the title compound (30.8 mg, 100% yield, TFA) as a yellow oil. LC-MS (ESI$^+$) m/z 372.8 (M+H)$^+$.

3-[4-(2,7-Diazaspiro[3.5]nonan-2-yl)-3-methyl-2-oxo-benzimidazol-1-yl]piperidine-2,6-dione (Intermediate CKW)

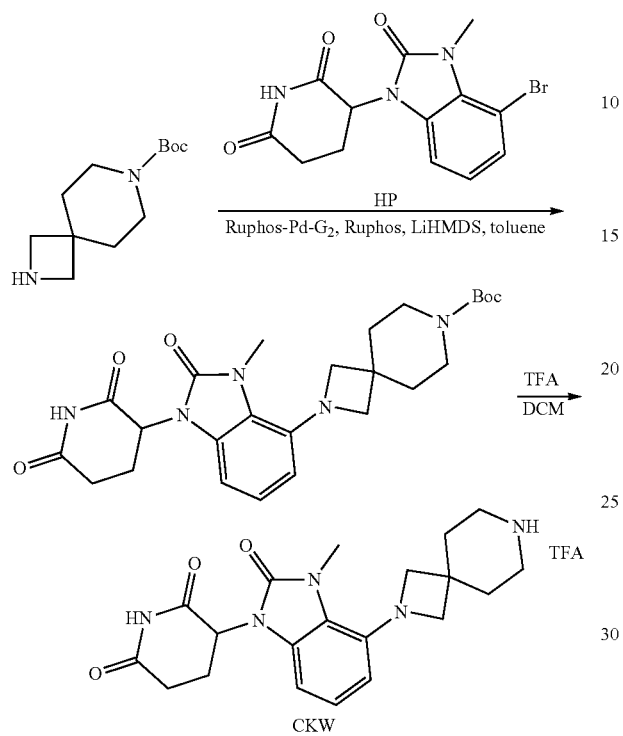

Step 1—Tert-butyl 2-[1-(2,6-dioxo-3-piperidyl)-3-methyl-2-oxo-benzimidazol-4-yl]-2,7-diazaspiro[3.5]nonane-7-carboxylate. To a solution of 3-(4-bromo-3-methyl-2-oxo-benzimidazol-1-yl)piperidine-2,6-dione (500 mg, 1.48 mmol, Intermediate HP), tert-butyl 2,7-diazaspiro[3.5]nonane-7-carboxylate (502 mg, 2.22 mmol, CAS #896464-16-7) and 4 Å molecular sieves (500 mg, 1.48 mmol) in toluene (10 mL) was added [2-(2-aminophenyl)phenyl]-chloro-palladium; dicyclohexyl-[2-(2,6-diisopropoxyphenyl)phenyl] phosphane (459 mg, 591 umol), RuPhos (276 mg, 591 umol) and LiHMDS (1 M, 7.39 mL) under N$_2$. The mixture was stirred at 80° C. for 12 hrs under N$_2$. On completion, the mixture was adjusted to pH=6 with FA. The mixture was filtered and concentrated in vacuo. The mixture was diluted with H$_2$O (30 mL), and extracted with EA (80 mL). The organic layers were washed with brine (30 mL), dried over anhydrous Na$_2$SO$_4$, filtered and concentrated in vacuo. The crude product was purified by prep-HPLC (column: Phenomenex luna C18 150*25 mm*10 um; mobile phase: [water(FA)-ACN]; B %: 50%-100%, 10 min) to give the title compound (157 mg, 22% yield) as black brown solid. $^1$H NMR (400 MHz, CDCl$_3$) δ 8.09 (s, 1H), 7.00 (t, J=8.0 Hz, 1H), 6.70 (d, J=8.0 Hz, 1H), 6.47 (d, J=8.0 Hz, 1H), 5.19 (dd, J=5.4, 12.4 Hz, 1H), 3.72 (s, 3H), 3.64 (s, 4H), 3.43-3.40 (d, 4H), 2.97-2.73 (m, 3H), 2.26-2.16 (m, 1H), 1.83-1.80 (m, 4H), 1.45 (s, 9H). LC-MS (ESI$^+$) m/z 483.9 (M+H)$^+$.

Step 2—3-[4-(2,7-Diazaspiro[3.5]nonan-2-yl)-3-methyl-2-oxo-benzimidazol-1-yl]piperidine-2,6-dione. To a solution of tert-butyl 2-[1-(2,6-dioxo-3-piperidyl)-3-methyl-2-oxo-benzimidazol-4-yl]-2,7-diazaspiro[3.5]nonane-7-carboxylate (80.0 mg, 165 umol) in DCM (3.00 mL) was added TFA (566 mg, 4.96 mmol, 367 uL). The mixture was stirred at 20° C. for 0.5 hr. On completion, the mixture was concentrated in vacuo to give the title compound (80.0 mg, 97% yield, TFA) as black brown oil. LC-MS (ESI$^+$) m/z 383.9 (M+H)$^+$.

Pyrazolo[1,5-a]pyrimidine-3-carboxylic acid (CAS #25940-35-6) (Intermediate CKX)

3-[3-Methyl-2-oxo-4-(4-oxo-1-piperidyl)benzimidazol-1-yl]piperidine-2,6-dione (Intermediate CKY)

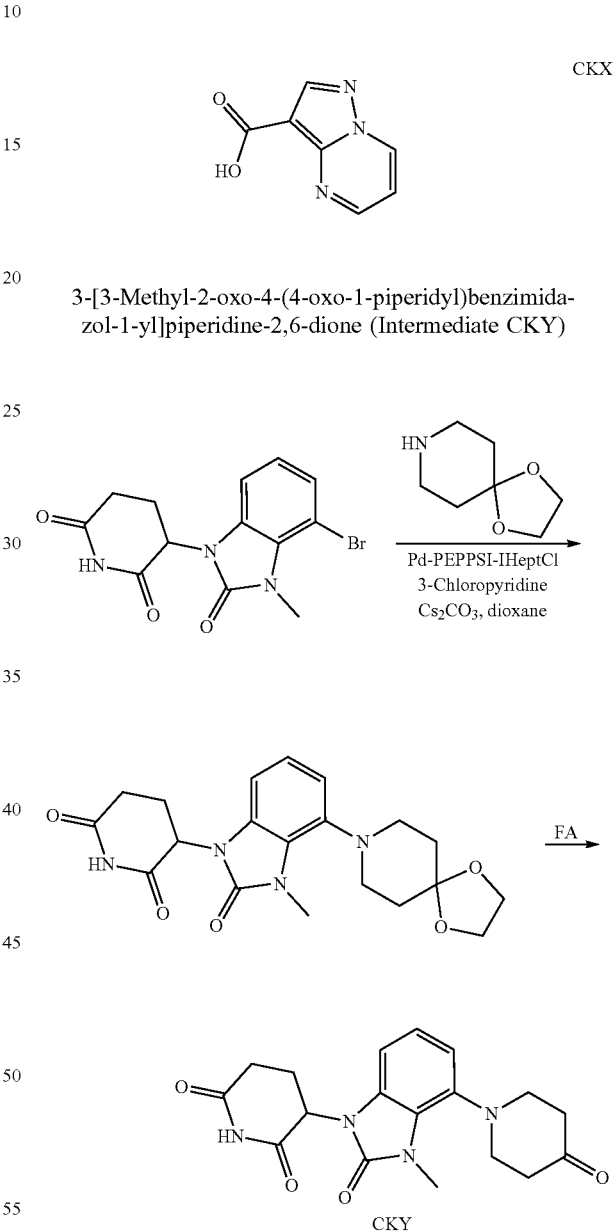

Step 1—3-[4-(1,4-Dioxa-8-azaspiro[4.5]decan-8-yl)-3-methyl-2-oxo-benzimidazol-1-yl]piperidine-2,6-dione. A mixture of 3-(4-bromo-3-methyl-2-oxo-benzimidazol-1-yl)piperidine-2,6-dione (2.00 g, 5.91 mmol, Intermediate HP), 1,4-dioxa-8-azaspiro[4.5]decane (1.27 g, 8.87 mmol, CAS #177-11-7), RuPhos Pd G$_3$ (989 mg, 1.18 mmol), and RuPhos (552 mg, 1.18 mmol) in toluene (20 mL) was degassed and purged with N$_2$ three times. Then LiHMDS (1 M, 29.57 mL) was added and the mixture was stirred at 100° C. for 2 hrs under N$_2$ atmosphere. On completion, FA was added to the mixture to adjust pH=6, then the reaction mixture was filtered to give the filtrate. The filtrated was concentrated and the residue was purified by column chromatography (SiO₂, PE/EA=1/1 to 0/1, P1/R$_f$=0.48) to give the title compound (2.10 g, 61.1% yield) as yellow solid. LC-MS (ESI⁺) m/z 400.9 (M+H)⁺.

Step 2—3-[3-Methyl-2-oxo-4-(4-oxo-1-piperidyl)benzimidazol-1-yl]piperidine-2,6-dione. To a solution of 3-[4-(1,4-dioxa-8-azaspiro[4.5]decan-8-yl)-3-methyl-2-oxo-benzimidazol-1-yl]piperidine-2,6-dione (1.10 g, 2.75 mmol) in HCOOH (3 mL) was stirred at 25° C. for 12 hrs. On completion, the reaction mixture concentrated under reduced pressure to give a residue. The crude product was triturated with PE:EA=10:1 (11 mL) at 25° C. for 60 mins then filtered to give the title compound (555 mg, 57% yield) as a yellow solid. ¹H NMR (400 MHz, DMSO-d₆) δ 11.17-11.03 (m, 1H), 7.04-6.87 (m, 3H), 5.37 (dd, J=5.2, 12.0 Hz, 1H), 3.72 (s, 3H), 3.18-3.04 (m, 2H), 2.96-2.79 (m, 3H), 2.75-2.57 (m, 5H), 2.35-2.29 (m, 1H), 2.05-1.95 (m, 1H). LC-MS (ESI⁺) m/z 356.9 (M+H)⁺.

Tert-butyl N-[1-[4-(1-aminoethyl)cyclohexyl]-3-(difluoromethyl)pyrazol-4-yl]carbamate (Intermediate CKZ)

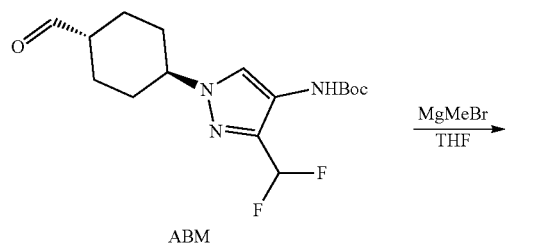

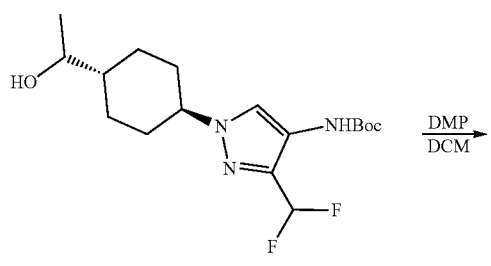

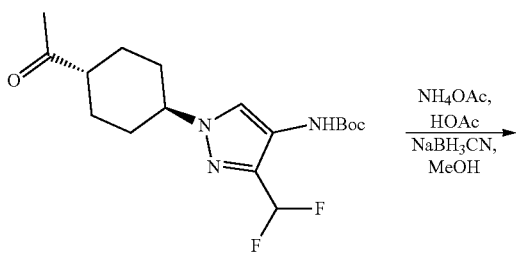

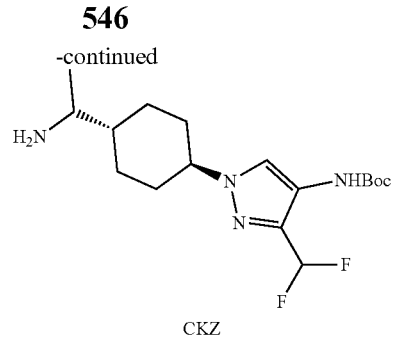

CKZ

Step 1—Tert-butyl N-[3-(difluoromethyl)-1-[4-(1-hydroxyethyl)cyclohexyl]pyrazol-4-yl]carbamate. To a solution of tert-butyl N-[3-(difluoromethyl)-1-(4-formylcyclohexyl)pyrazol-4-yl]carbamate (760 mg, 2.21 mmol, Intermediate ABM) in THF (6 mL) was added MeMgBr (3 M, 1.84 mL) at −15° C. The mixture was stirred at −15-0° C. for 3 hrs. On completion, the mixture was quenched with NH₄Cl (10 mL) at 0° C. and extracted with EA (15 mL×3). The combined organic phase was dried over anhydrous sodium sulfate, filtered and concentrated to give a residue. The residue was purified by column chromatography (SiO₂, PE/EA=2:1) to give the title compound (400 mg, 48% yield) as a yellow solid. ¹H NMR (400 MHz, CDCl₃-d) δ 7.92 (s, 1H), 6.88-6.56 (m, 2H), 4.00 (tt, J=4.0, 12.0 Hz, 1H), 3.63 (quin, J=6.4 Hz, 1H), 2.28-2.16 (m, 2H), 2.13-2.04 (m, 1H), 1.91-1.83 (m, 1H), 1.81-1.66 (m, 2H), 1.51 (s, 9H), 1.42-1.29 (m, 2H), 1.29-1.24 (m, 1H), 1.22 (d, J=6.4 Hz, 3H), 1.19-1.14 (m, 1H); LC-MS (ESI⁺) m/z 360.0 (M+H)⁺.

Step 2—Tert-butyl N-[1-(4-acetylcyclohexyl)-3-(difluoromethyl)pyrazol-4-yl]carbamate. To a solution of tert-butyl N-[3-(difluoromethyl)-1-[4-(1-hydroxyethyl)cyclohexyl]pyrazol-4-yl]carbamate (380 mg, 1.06 mmol) in DCM (4 mL) was added DMP (538 mg, 1.27 mmol). The mixture was stirred at 25° C. for 2 hrs. On completion, the mixture was quenched with saturated Na₂S₂O₃ (15 mL) and NaHCO₃ (15 mL) at 0° C. and extracted with DCM (25 mL×3). The combined organic phase was dried over anhydrous sodium sulfate, filtered and concentrated to give the title compound (365 mg, 91% yield) as a yellow solid. LC-MS (ESI⁺) m/z 358.3 (M+H)⁺.

Step 3—Tert-butyl N-[1-[4-(1-aminoethyl)cyclohexyl]-3-(difluoromethyl)pyrazol-4-yl]carbamate. To a mixture of tert-butyl N-[1-(4-acetylcyclohexyl)-3-(difluoromethyl)pyrazol-4-yl]carbamate (365 mg, 1.02 mmol) in MeOH (3.5 mL) was added NH₄OAc (314 mg, 4.08 mmol) and AcOH (0.05 mL). The mixture was stirred at 25° C. for 2 hrs. Then NaBH₃CN (76.9 mg, 1.22 mmol) was added and the mixture was stirred at 25° C. for 16 hrs. On completion, the mixture was quenched with 10% NaOH (5 mL) at 0° C. and extracted with DCM (15 mL×3). The combined organic phase was dried over anhydrous sodium sulfate, filtered and concentrated to give a residue. The crude product was triturated with PE/EA=2:1 (5 mL) at 0° C. for 30 min to give the title compound (250 mg, 61% yield) as a yellow solid. LC-MS (ESI⁺) m/z 359.2 (M+H)⁺.

3-[4-[4-[1-[4-[4-Amino-3-(difluoromethyl)pyrazol-1-yl]cyclohexyl]ethyl-methyl-amino]-1-piperidyl]-3-methyl-2-oxo-benzimidazol-1-yl]piperidine-2,6-dione (Intermediate CLA)

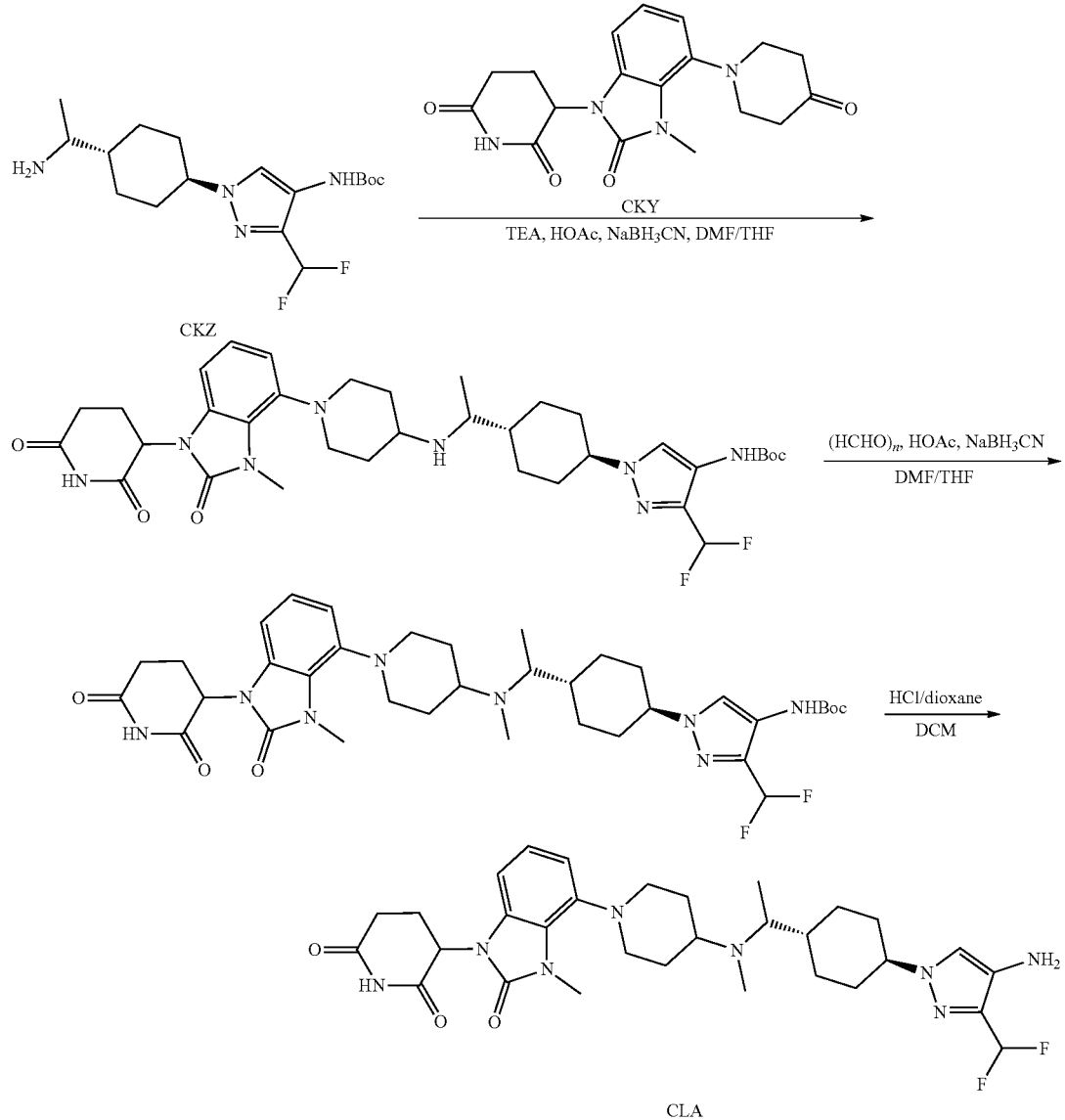

Step 1—Tert-butyl N-[3-(difluoromethyl)-1-[4-[1-[[1-[1-(2,6-dioxo-3-piperidyl)-3-methyl-2-oxo-benzimidazol-4-yl]-4-piperidyl]amino]ethyl]cyclohexyl]pyrazol-4-yl]carbamate. To a mixture of tert-butyl N-[1-[4-(1-aminoethyl)cyclohexyl]-3-(difluoromethyl)pyrazol-4-yl]carbamate (200 mg, 558 umol, Intermediate CKZ) in DMF (1 mL) was added AcOH (33.5 mg, 558 umol) until the pH stabilized at 5-6. Then 3-[3-methyl-2-oxo-4-(4-oxo-1-piperidyl)benzimidazol-1-yl]piperidine-2,6-dione (159 mg, 446 umol, Intermediate CKY) in THF (1 mL) was added and the mixture was stirred at 60° C. for 2 hrs. Next, NaBH$_3$CN (70.1 mg, 1.12 mmol) was added and the mixture was stirred at 60° C. for 12 hrs. On completion, the reaction mixture was concentrated in vacuo. The mixture was quenched with water (10 mL) at 0° C. and extracted with EA (15 mL×3). The combined organic phase was dried over anhydrous sodium sulfate, filtered and concentrated to give a residue. The residue was purified by column chromatography (SiO$_2$, DCM/MeOH=15:1) to give the title compound (240 mg, 59% yield) as a yellow solid. $^1$H NMR (400 MHz, DMSO-d$_6$) δ 11.09 (s, 1H), 8.94 (s, 1H), 7.90 (s, 1H), 7.03-6.97 (m, 1H), 6.94-6.87 (m, 2H), 5.75 (s, 1H), 5.36 (dd, J=5.6, 12.4 Hz, 1H), 4.20-4.08 (m, 1H), 3.71-3.60 (m, 3H), 3.22-3.12 (m, 2H), 2.91-2.76 (m, 3H), 2.74-2.58 (m, 3H), 2.15-1.95 (m, 6H), 1.88-1.68 (m, 7H), 1.45 (s, 9H), 1.36-1.22 (m, 3H), 1.21-1.11 (m, 3H); LC-MS (ESI$^+$) m/z 699.3 (M+H)$^+$.

Step 2—Tert-butyl N-[3-(difluoromethyl)-1-[4-[1-[[1-[1-(2,6-dioxo-3-piperidyl)-3-methyl-2-oxo-benzimidazol-4-yl]-4-piperidyl]-methyl-amino]ethyl]cyclohexyl]pyrazol-4-yl]carbamate. To a solution of tert-butyl N-[3-

(difluoromethyl)-1-[4-[1-[[1-[1-(2,6-dioxo-3-piperidyl)-3-methyl-2-oxo-benzimidazol-4-yl]-4-piperidyl]amino]ethyl]cyclohexyl]pyrazol-4-yl]carbamate (230 mg, 329 umol) in DMF (0.5 mL) and THF (0.5 mL) was added (HCHO)$_n$ (148.24 mg, 4.94 mmol) and AcOH (19.76 mg, 329 umol). The mixture was stirred at 25° C. for 30 mins. Then NaBH$_3$CN (24.8 mg, 394 umol) was added to the mixture and the mixture was stirred at 50° C. for 12 hrs. On completion, the reaction mixture was concentrated in vacuo. The mixture was quenched with water (10 mL) at 0° C. and extracted with EA (15 mL×3). The combined organic phase was dried over anhydrous sodium sulfate, filtered and concentrated to give a residue. The residue was purified by column chromatography (SiO$_2$, DCM/MeOH=25:1) to give the title compound (140 mg, 57% yield) as a yellow solid. $^1$H NMR (400 MHz, DMSO-d$_6$) δ 11.09 (d, J=1.6 Hz, 1H), 9.03-8.83 (m, 1H), 8.01-7.78 (m, 1H), 7.07-6.80 (m, 4H), 6.17 (t, J=7.2 Hz, 1H), 5.52-5.29 (m, 1H), 5.13-5.00 (m, 1H), 4.21-3.92 (m, 1H), 3.65 (d, J=8.0 Hz, 3H), 3.18-3.07 (m, 1H), 2.93-2.80 (m, 2H), 2.78-2.66 (m, 4H), 2.12-1.96 (m, 6H), 1.94-1.76 (m, 5H), 1.73-1.61 (m, 2H), 1.45 (s, 9H), 1.23 (s, 3H), 0.99-0.73 (m, 4H); LC-MS (ESI$^+$) m/z 743.1 (M+H)$^+$.

Step 3—3-[4-[4-[1-[4-[4-Amino-3-(difluoromethyl)pyrazol-1-yl]cyclohexyl]ethyl-methyl-amino]-1-piperidyl]-3-methyl-2-oxo-benzimidazol-1-yl]piperidine-2,6-dione. To a solution of tert-butyl N-[3-(difluoromethyl)-1-[4-[1-[[1-[1-(2,6-dioxo-3-piperidyl)-3-methyl-2-oxo-benzimidazol-4-yl]-4-piperidyl]-methyl-amino]ethyl]cyclohexyl]pyrazol-4-yl]carbamate (140 mg, 196 umol) in DCM (1 mL) was added HCl/dioxane (1 mL). The mixture was stirred at 25° C. for 1 hr. On completion, the reaction mixture was concentrated in vacuo to give the title compound (127 mg, 99% yield, HCl) as a yellow solid. LC-MS (ESI$^+$) m/z 613.4 (M+H)$^+$.

Tert-butyl (3,3-difluoropiperidin-4-yl)(methyl)carbamate (Intermediate CLB)

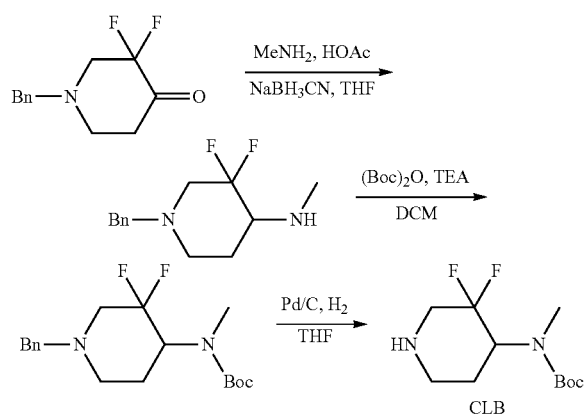

Step 1—1-Benzyl-3,3-difluoro-N-methyl-piperidin-4-amine. To a solution of 1-benzyl-3, 3-difluoro-piperidin-4-one (1 g, 4.44 mmol) in THF (5 mL) and AcOH (266 mg, 4.44 mmol) was added MeNH$_2$ (2 M, 35.5 mL) at N$_2$ atmosphere. The mixture was stirred at 40° C. for 2 hr. Then NaBH$_3$CN (279 mg, 4.44 mmol) was added and the mixture was stirred for 4 hrs. On completion, the mixture was added NaHCO$_3$ (10 ml), and the mixture was extracted with DCM (5 mL×3). The combined organic layer was dried over sodium sulfate, then concentrated in vacuo to give the title compound (1 g, 98% yield) as a white oil. $^1$H NMR (400 MHz, DMSO-d$_6$) δ 7.37-7.22 (m, 5H), 3.61-3.49 (m, 2H), 2.91-2.79 (m, 1H), 2.72-2.56 (m, 2H), 2.41-2.30 (m, 3H), 2.17 (t, J=10.4 Hz, 1H), 1.82 (t, J=8.8 Hz, 1H), 1.76-1.61 (m, 1H), 1.53-1.41 (m, 1H).

Step 2—Tert-butyl N-(1-benzyl-3,3-difluoro-4-piperidyl)-N-methyl-carbamate. To a solution of 1-benzyl-3,3-difluoro-N-methyl-piperidin-4-amine (1 g, 4.16 mmol) in DCM (10 mL) was added Boc$_2$O (999 mg, 4.58 mmol) and TEA (2.11 g, 20.8 mmol). The mixture was stirred at 25° C. for 2 hrs. On completion, water (10 ml) was added and the mixture was extracted with EA (10 ml) 3 times. The combined organic layer was dried over sodium sulfate, then concentrated in vacuo to give a residue. The residue was purified by column chromatography (SiO$_2$, Petroleum ether/Ethyl acetate=5/1) to give the title compound (1.2 g, 84% yield) as a white solid. $^1$H NMR (400 MHz, DMSO-d$_6$) 7.38-7.24 (m, 5H), 4.43-4.07 (m, 1H), 3.64-3.53 (m, 2H), 3.02 (t, J=10.0 Hz, 1H), 2.91 (d, J=10.0 Hz, 1H), 2.78 (s, 3H), 2.42-2.14 (m, 2H), 2.10-1.91 (m, 1H), 1.64 (s, 1H), 1.40 (s, 9H).

Step 3—Tert-butyl (3,3-difluoropiperidin-4-yl)(methyl)carbamate. To a solution of tert-butyl N-(1-benzyl-3, 3-difluoro-4-piperidyl)-N-methyl-carbamate (744 mg, 2.19 mmol) in MeOH (2 mL) was added Pd/C (730 mg, 10 wt %). The mixture was then stirred at 30° C. for 16 hrs under H$_2$ (50 psi). On completion, the mixture was filtered and concentrated in vacuo to give the title compound (350 mg, 63% yield) as a white oil. $^1$H NMR 4.69-4.21 (m, 1H), 3.29-3.15 (m, 2H), 2.90 (s, 3H), 2.83-2.69 (m, 2H), 1.98 (dd, J=2.8, 12.8 Hz, 1H), 1.84-1.74 (m, 1H), 1.68 (s, 3H), 1.48 (s, 9H).

3-[4-[3,3-Difluoro-4-(methylamino)-1-piperidyl]-3-methyl-2-oxo-benzimidazol-1-yl]piperidine-2,6-dione (Intermediate CLC)

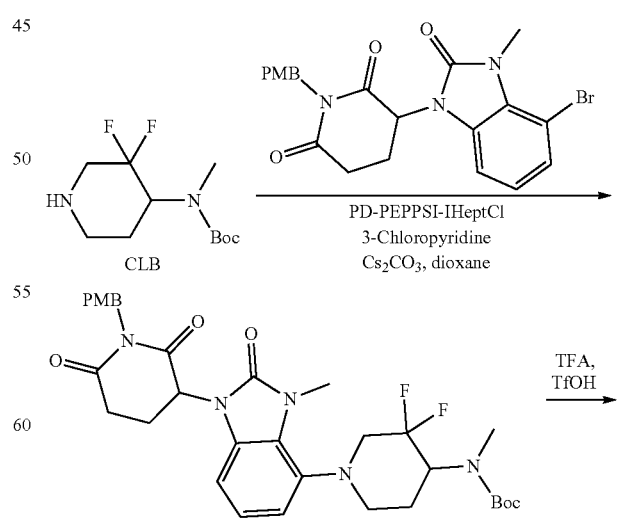

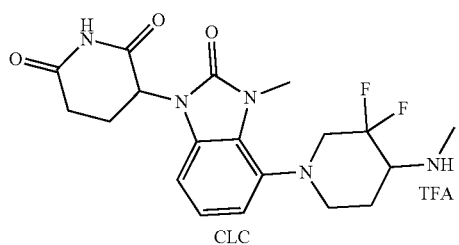

Step 1—Tert-butyl N-[3,3-difluoro-1-[1-[1-[(4-methoxyphenyl)methyl]-2,6-dioxo-3-piperidyl]-3-methyl-2-oxo-benzimidazol-4-yl]-4-piperidyl]-N-methyl-carbamate. A mixture of tert-butyl N-(3,3-difluoro-4-piperidyl)-N-methyl-carbamate (260 mg, 1.04 mmol, Intermediate CLB), 3-(4-bromo-3-methyl-2-oxo-benzimidazol-1-yl)-1-[(4-methoxyphenyl)methyl]piperidine-2,6-dione (476 mg, 1.04 mmol, synthesized via Steps 1-4 of Intermediate HP), 1,3-bis[2,6-bis(1-propylbutyl)phenyl]-4,5-dichloro-2H-imidazol-1-ium-2-ide; 3-chloropyridine; dichloropalladium (70.7 mg, 72.7 umol), and $Cs_2CO_3$ (1.02 g, 3.12 mmol) in dioxane (2 mL) was degassed and purged with $N_2$ three times. Then the mixture was stirred at 80° C. for 12 hrs under $N_2$ atmosphere. On completion, the mixture was extracted with EA (5 mL×3). The combined organic layer was dried over sodium sulfate, filtered then concentrated in vacuo to give a residue. The residue was purified by column chromatography ($SiO_2$, Petroleum ether/Ethyl acetate=5/1 to 2/1) give the title compound (250 mg, 38% yield) as a white solid. $^1$H NMR (400 MHz, DMSO-$d_6$) 7.23-7.17 (m, 2H), 7.12-7.04 (m, 1H), 7.02-6.93 (m, 1H), 6.85 (d, J=8.4 Hz, 2H), 5.75 (s, 1H), 5.58-5.47 (m, 1H), 4.79 (q, J=14.0 Hz, 3H), 3.72 (s, 3H), 3.62 (s, 3H), 3.22-2.89 (m, 6H), 2.14-1.64 (m, 5H), 1.42 (s, 9H), 0.99-0.65 (m, 2H).

Step 2—3-[4-[3,3-Difluoro-4-(methylamino)-1-piperidyl]-3-methyl-2-oxo-benzimidazol-1-yl] piperidine-2,6-dione. A mixture of tert-butyl N-[3,3-difluoro-1-[1-[1-[(4-methoxyphenyl)methyl]-2,6-dioxo-3-piperidyl]-3-methyl-2-oxo-benzimidazol-4-yl]-4-piperidyl]-N-methyl-carbamate (70 mg, 111 umol) in TFA (0.4 mL) and TfOH (0.1 mL) was stirred at 70° C. for 1 hr. On completion, the mixture was concentrated in vacuo to give the title compound (58 mg, 99% yield, TFA) as black brown solid. LC-MS (ESI$^+$) m/z 408.2 (M+H)$^+$.

3-[4-(2,7-Diazaspiro[3.5]nonan-2-ylmethyl)-3-methyl-2-oxo-benzimidazol-1-yl]piperidine-2,6-dione (Intermediate CLD)

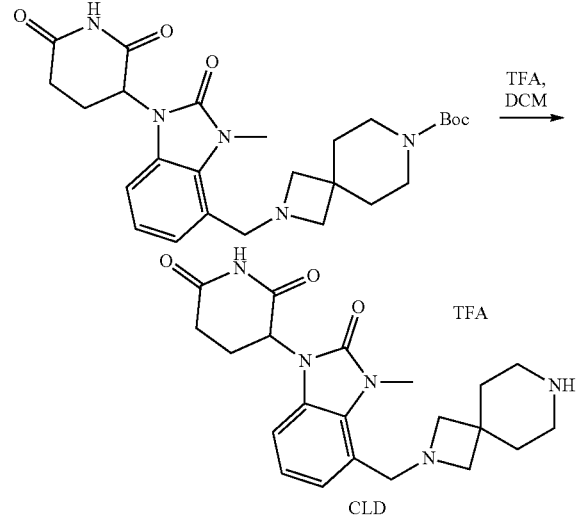

Step 1—Tert-butyl 2-[[1-(2,6-dioxo-3-piperidyl)-3-methyl-2-oxo-benzimidazol-4-yl]methyl]-2,7-diazaspiro[3.5]nonane-7-carboxylate. To a solution of tert-butyl 2,7-diazaspiro[3.5]nonane-7-carboxylate (236 mg, 1.04 mmol, CAS #896464-16-7) in THF (5 mL) was added HOAc (52.2 mg, 870 umol) and 1-(2,6-dioxo-3-piperidyl)-3-methyl-2-oxo-benzimidazole-4-carbaldehyde (250 mg, 870 umol, Intermediate WW) and the mixture was stirred 10° C. for 30 mins. Then $NaBH_3CN$ (54.6 mg, 870 umol) was added and the mixture was stirred at −10° C. for 2 hrs. On completion, the reaction mixture was concentrated in vacuo to give a residue. The residue was diluted with water (10 mL) and extracted with EA (20 mL×3). The combined organic layer was dried over $Na_2SO_4$, filtered and concentrated in vacuo to give the title compound (400 mg, 92% yield) as a yellow solid. LC-MS (ESI$^+$) m/z 498.2 (M+H)$^+$.

Step 2—3-[4-(2,7-Diazaspiro[3.5]nonan-2-ylmethyl)-3-methyl-2-oxo-benzimidazol-1-yl]piperidine-2,6-dione To a solution of tert-butyl 2-[[1-(2,6-dioxo-3-piperidyl)-3-methyl-2-oxo-benzimidazol-4-yl]methyl]-2,7-diazaspiro[3.5]nonane-7-carboxylate (100 mg, 200 umol) in DCM (2 mL) was added TFA (770 mg, 6.75 mmol). Then the mixture was stirred at 25° C. for 1 hr. On completion, the reaction mixture was concentrated in vacuo to give the title compound (100 mg, 97% yield) as a yellow oil. LC-MS (ESI$^+$) m/z 398.0 (M+H)$^+$.

2,2-Difluoromorpholine (Intermediate CLE)

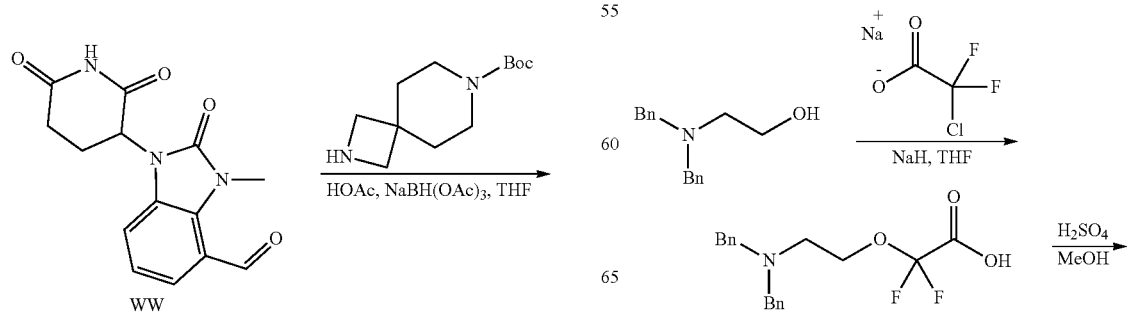

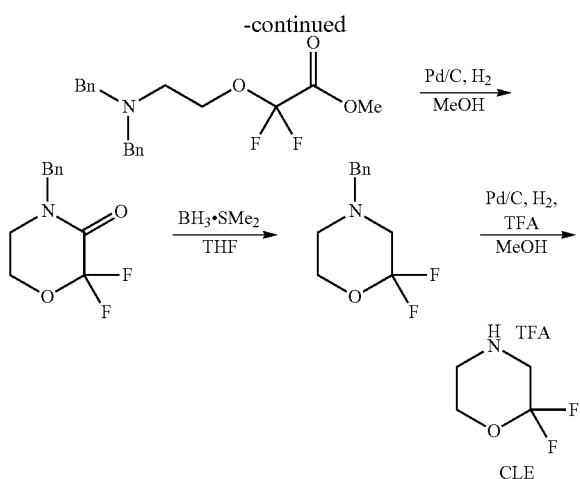

Step 1—2-[2-(Dibenzylamino)ethoxy]-2,2-difluoro-acetic acid. To a suspension of 2-(dibenzylamino)ethanol (10 g, 41.4 mmol, CAS #101-06-4), sodium 2-chloro-2,2-difluoro-acetate (8.21 g, 54 mmol, CAS #1895-39-2) in THF (80 mL) was added NaH (4.14 g, 104 mmol, 60% dispersion in mineral oil) at 0° C. Then the mixture was stirred at 65° C. for 18 hrs under $N_2$ atmosphere. On completion, the reaction was cooled to rt, quenched with saturated $NH_4Cl$ (20 mL), and concentrated in vacuo to give a residue. The residue was diluted with water (100 mL), and extracted with EA (50 mL×5). The organic layers were combined, washed with brine (50 mL), dried over anhydrous $Na_2SO_4$, filtered and concentrated in vacuo to give the crude product. The crude product was purified by column chromatography ($SiO_2$, DCM/MeOH=10/1) to give the title compound (6.4 g, 46% yield) as yellow oil. $^1$H NMR (400 MHz, DMSO-$d_6$) δ 7.45-7.30 (m, 8H), 7.29-7.21 (m, 2H), 3.86 (t, J=6.0 Hz, 2H), 3.71 (s, 4H), 2.71 (t, J=6.0 Hz, 2H). LC-MS (ESI+) m/z 336.1 (M+H)$^+$.

Step 2—Methyl 2-[2-(dibenzylamino)ethoxy]-2,2-difluoro-acetate. To a solution of 2-[2-(dibenzylamino)ethoxy]-2,2-difluoro-acetic acid (6.4 g, 19.1 mmol) in MeOH (80 mL) was added $H_2SO_4$ (936 mg, 9.54 mmol) dropwise, then the mixture was stirred at 65° C. for 48 hrs under $N_2$ atmosphere. On completion, the reaction was cooled to rt, and concentrated in vacuo to give a residue. The residue was purified by column chromatography ($SiO_2$, PE/EA=30/1) to give the title compound (1.5 g, 22% yield) as yellow oil. $^1$H NMR (400 MHz, DMSO-$d_6$) δ 7.42-7.27 (m, 8H), 7.27-7.19 (m, 2H), 4.01 (t, J=6.0 Hz, 2H), 3.87 (s, 3H), 3.62 (s, 4H), 2.68 (t, J=6.0 Hz, 2H). LC-MS (ESI+) m/z 350.3 (M+H)$^+$.

Step 3—4-Benzyl-2,2-difluoro-morpholin-3-one. To a solution of methyl 2-[2-(dibenzylamino)ethoxy]-2,2-difluoro-acetate (1.8 g, 5.15 mmol) in MeOH (10 mL) was added Pd/C (600 mg, 10 wt %) under Ar atmosphere. Then the mixture was degassed under vacuum, purged with $H_2$ three times, and stirred at 20° C. for 48 hrs under $H_2$ (15 psi) atmosphere. On completion, the reaction was filtered to give a filtrate, concentrated in vacuo to give the title compound (770 mg, 65% yield) as white solid. $^1$H NMR (400 MHz, DMSO-$d_6$) δ 7.45-7.21 (m, 5H), 4.60 (s, 2H), 4.33-4.22 (m, 2H), 3.51 (t, J=5.2 Hz, 2H). LC-MS (ESI+) m/z 350.3 (M+H)$^+$.

Step 4—4-Benzyl-2,2-difluoro-morpholine. To a solution of 4-benzyl-2,2-difluoro-morpholin-3-one (770 mg, 3.39 mmol) in THF (35 mL) was added $BH_3$ (1.59 mL, 10 M in $Me_2S$, 15.9 mmol) dropwise at 0° C. under $N_2$ atmosphere, then then the mixture was stirred at 60° C. for 16 hrs. On completion, the reaction was cooled to rt, quenched by 4N HCl (12 mL) at 0° C., then stirred at 60° C. for 2 hrs under $N_2$ atmosphere. Then, the reaction was concentrated in vacuo to give a residue. The residue was diluted with water (50 mL), basified by NaOH (10% aq) to adjust the pH=9, and extracted with EA (50 mL×3). The organic layers were combined, washed with brine (50 mL), dried over anhydrous $Na_2SO_4$, filtered and concentrated in vacuo to give the crude product. The crude product was purified by column chromatography ($SiO_2$, PE/EA=30/1) to give the title compound (390 mg, 53% yield) as light yellow oil. $^1$H NMR (400 MHz, DMSO-$d_6$) δ 7.43-7.17 (m, 5H), 4.00-3.98 (m, 2H), 3.60 (s, 2H), 2.74 (t, J=8.0 Hz, 2H), 2.54-2.50 (m, 2H). LC-MS (ESI+) m/z 214.1 (M+H)$^+$.

Step 5—2,2-Difluoromorpholine. To a solution of 4-benzyl-2,2-difluoro-morpholine (300 mg, 1.41 mmol) in MeOH (6 mL) and TFA (60 uL) was added Pd/C (150 mg, 10 wt %) under Ar atmosphere. Then the mixture was degassed under vacuum, purged with $H_2$ three times, and stirred at 25° C. for 24 hrs under $H_2$ (15 psi) atmosphere. On completion, the reaction was filtered to give a filtrate, concentrated in vacuo to give the title compound (250 mg, 74% yield, TFA) as white solid. $^1$H NMR (400 MHz, DMSO-$d_6$) δ 10.28-9.30 (m, 1H), 4.31-4.15 (m, 2H), 3.68 (t, J=8.0 Hz, 2H), 3.27 (t, J=5.2 Hz, 2H).

5-(2,2-Difluoromorpholin-4-yl)pyrazolo[1,5-a]pyrimidine-3-carboxylic acid (Intermediate CLF)

Step 1—Ethyl 5-(2,2-difluoromorpholin-4-yl)pyrazolo[1,5-a]pyrimidine-3-carboxylate. To a solution of ethyl 5-chloropyrazolo[1,5-a]pyrimidine-3-carboxylate (220 mg, 975 umol), 2,2-difluoromorpholine (277 mg, 1.17 mmol, TFA, Intermediate CLE) in ACN (5 mL) was added DIEA (504 mg, 3.90 mmol), then the mixture was stirred at 45° C. for 18 hrs under $N_2$ atmosphere. On completion, the reaction was cooled to rt and concentrated in vacuo to give a residue. The residue was diluted with citric acid (15 mL, 10% aq), and extracted with EA (15 mL×3). The organic layers were combined, washed with brine (10 mL), dried over anhydrous $Na_2SO_4$, filtered and concentrated in vacuo to give the crude product. The crude product was purified by column chromatography ($SiO_2$, PE/EA=3/1 to 1/1) to give the title compound (240 mg, 78% yield) as yellow solid. $^1$H NMR (400 MHz, DMSO-$d_6$) δ 8.88 (d, J=8.0 Hz, 1H), 8.28 (s, 1H), 6.98 (d, J=8.0 Hz, 1H), 4.29 (t, J=8.4 Hz, 2H), 4.25-4.16 (m, 4H), 3.92 (d, J=4.0 Hz, 2H), 1.29 (t, J=7.2 Hz, 3H).

Step 2—5-(2,2-Difluoromorpholin-4-yl)pyrazolo[1,5-a]pyrimidine-3-carboxylic acid. To a solution of ethyl 5-(2,2-difluoromorpholin-4-yl)pyrazolo[1,5-a]pyrimidine-3-carboxylate (210 mg, 672 umol) in EtOH (2.8 mL) and $H_2O$ (0.7 mL) was added LiOH·$H_2O$ (84.7 mg, 2.02 mmol), then the mixture was stirred at 45° C. for 8 hrs. On completion, the reaction was cooled to 25° C., concentrated in vacuo to give a residue. The residue was diluted with water (5 mL), acified by 3N HCl to adjust the pH=2, extracted with EA (5 mL×4). The organic layers were combined, washed with brine (5 mL), dried over anhydrous $Na_2SO_4$, filtered and concentrated in vacuo to give the title compound (165 mg, 86% yield) as off-white solid. $^1$H NMR (400 MHz, DMSO-$d_6$) δ 11.91 (s, 1H), 8.87 (d, J=7.6 Hz, 1H), 8.25 (s, 1H), 6.96 (d, J=7.6 Hz, 1H), 4.28 (t, J=8.4 Hz, 2H), 4.22 (t, J=5.2 Hz, 2H), 3.92 (d, J=4.4 Hz, 2H).

Tert-butyl 3,3-difluoro-4-(1,1,2,2,3,3,4,4,4-nonafluorobutylsulfonyloxy)-2,6-dihydropyridine-1-carboxylate (Intermediate CLG)

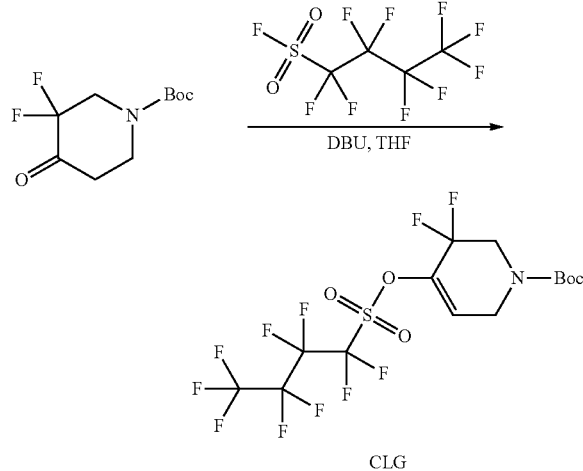

To a solution of tert-butyl 3,3-difluoro-4-oxo-piperidine-1-carboxylate (2.5 g, 10.6 mmol, CAS #346593-03-1) and DBU (4.85 g, 31.8 mmol) in THF (25 mL) was added 1,1,2,2,3,3,4,4,4-nonafluorobutane-1-sulfonyl fluoride (9.63 g, 31.8 mmol, CAS #375-72-4) in THF (25 mL). The mixture was then stirred at −20° C. for 2 hrs. On completion, the mixture was filtered and concentrated to give a residue. The residue was purified by column chromatography ($SiO_2$, Petroleum ether/Ethyl acetate=1/0 to 20/1) to give title compound (1.2 g, 21% yield) as a yellow oil. $^1$H NMR (400 MHz, $CDCl_3$-d) δ 6.31 (s, 1H), 4.26 (s, 2H), 3.98 (t, J=10.4 Hz, 2H), 1.50 (s, 9H).

3-[3-Methyl-2-oxo-5-(4,4,5,5-tetramethyl-1,3,2-dioxaborolan-2-yl)benzimidazol-1-yl]piperidine-2,6-dione (Intermediate CLH)

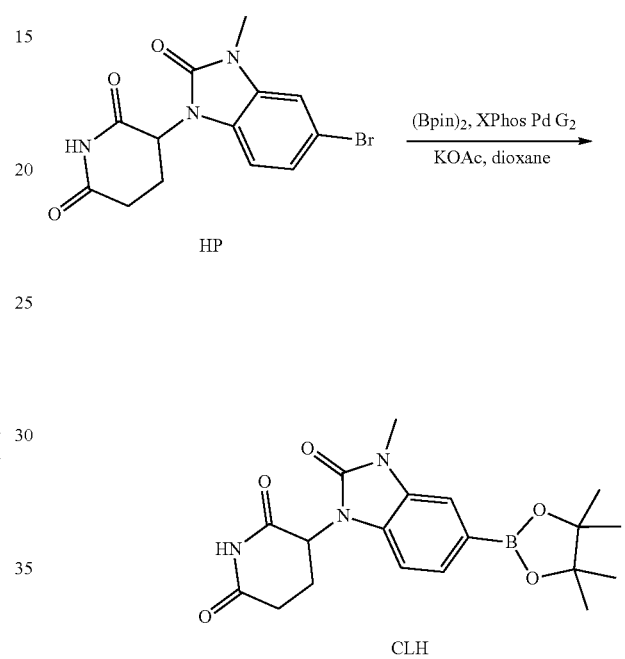

A mixture of 3-(5-bromo-3-methyl-2-oxo-benzimidazol-1-yl)piperidine-2,6-dione (1 g, 2.96 mmol, Intermediate HP), 4,4,5,5-tetramethyl-2-(4,4,5,5-tetramethyl-1,3,2-dioxaborolan-2-yl)-1,3,2-dioxaborolane (1.50 g, 5.91 mmol), [2-(2-aminophenyl)phenyl]-chloro-palladium; dicyclohexyl-[3-(2,4,6-triisopropylphenyl)phenyl]phosphane (232 mg, 295 umol) and KOAc (870 mg, 8.87 mmol) in dioxane (10 mL) was degassed and purged with $N_2$ three times. Then the mixture was stirred at 100° C. for 12 hrs under $N_2$ atmosphere. On completion, the mixture was filtered and concentrated in vacuo to give a residue. The mixture was quenched with water (10 mL) at 0° C. and extracted with EA (25 mL×3). The combined organic phase was dried over anhydrous sodium sulfate, filtered and concentrated to give a residue. The residue was purified by column chromatography ($SiO_2$, PE/EA=1:1 to DCM:EA=8:1-3:1). The crude product was triturated with PE/EA=3:1 (10 mL) at 25° C. for 12 hrs to give the title compound (1.19 g, 96% yield) as a gray solid. $^1$H NMR (400 MHz, DMSO-$d_6$) δ 11.11 (s, 1H), 7.43-7.37 (m, 2H), 7.15 (d, J=8.0 Hz, 1H), 5.40 (dd, J=5.4, 12.8 Hz, 1H), 3.37 (s, 3H), 2.96-2.83 (m, 1H), 2.78-2.58 (m, 2H), 2.06-1.98 (m, 1H), 1.30 (s, 12H); LC-MS (ESI$^+$) m/z 386.0 (M+H)$^+$.

3-[5-(3,3-Difluoro-2,6-dihydro-1H-pyridin-4-yl)-3-methyl-2-oxo-benzimidazol-1-yl]piperidine-2,6-dione (Intermediate CLI)

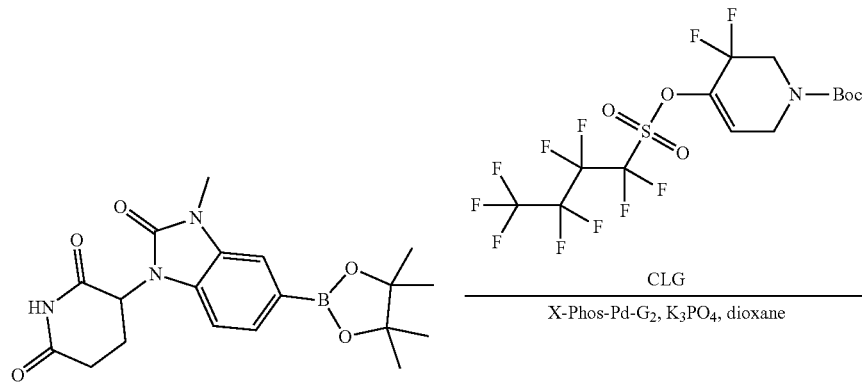

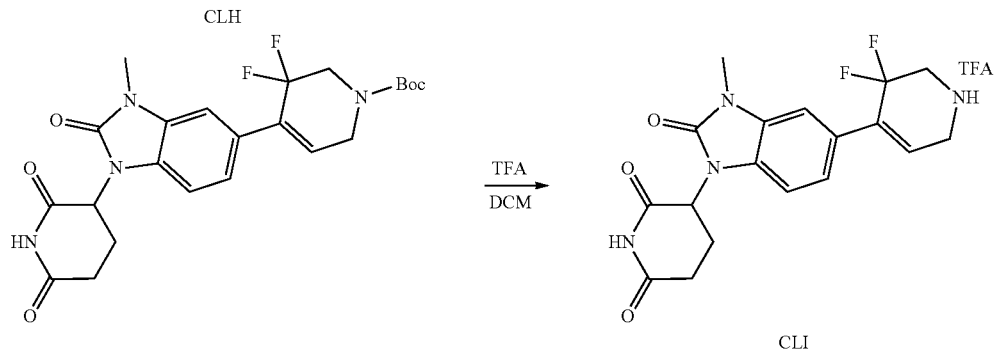

Step 1—Tert-butyl 4-[1-(2,6-dioxo-3-piperidyl)-3-methyl-2-oxo-benzimidazol-5-yl]-3,3-difluoro-2,6-dihydro-pyridine-1-carboxylate. A mixture of tert-butyl 3,3-difluoro-4-(1,1,2,2,3,3,4,4,4-nonafluorobutylsulfonyloxy)-2,6-dihydropyridine-1-carboxylate (1.07 g, 2.06 mmol, Intermediate CLG), 3-[3-methyl-2-oxo-5-(4,4,5,5-tetramethyl-1,3,2-dioxaborolan-2-yl)benzimidazol-1-yl]piperidine-2,6-dione (1.19 g, 3.09 mmol, Intermediate CLH), XPHOS-PD-G2 (162 mg, 205 umol), and K₃PO₄ (874 mg, 4.12 mmol) in dioxane (20 mL) was degassed and purged with N₂ three times. Then the mixture was stirred at 100° C. for 12 hrs under N₂ atmosphere. On completion, the mixture was filtered and concentrated in vacuo to give a residue. The residue was purified by reversed phase flash (0.1% FA condition) to give the title compound (150 mg, 14% yield) as a yellow solid. ¹H NMR (400 MHz, DMSO-d₆) δ 11.11 (s, 1H), 7.22 (s, 1H), 7.13 (s, 2H), 6.51 (s, 1H), 5.38 (dd, J=5.2, 12.6 Hz, 1H), 4.17 (s, 2H), 4.02-3.85 (m, 2H), 3.35 (s, 3H), 2.98-2.82 (m, 1H), 2.79-2.58 (m, 3H), 1.50-1.42 (m, 9H); LC-MS (ESI⁺) m/z 745.2 (M+H)⁺.

Step 2—3-[5-(3,3-Difluoro-2,6-dihydro-1H-pyridin-4-yl)-3-methyl-2-oxo-benzimidazol-1-yl]piperidine-2,6-dione. A mixture of tert-butyl 4-[1-(2,6-dioxo-3-piperidyl)-3-methyl-2-oxo-benzimidazol-5-yl]-3,3-difluoro-2,6-dihydropyridine-1-carboxylate (60 mg, 125.93 umol) in DCM (0.5 mL) and TFA (154.00 mg, 1.35 mmol, 0.1 mL) was stirred at 25° C. for 0.5 hr. On completion, the reaction mixture was concentrated in vacuo to give the title compound (60 mg, 97% yield, TFA) as a brown solid. LC-MS (ESI⁺) m/z 376.8 (M+H)⁺.

Tert-butyl 3-fluoro-4-(1,1,2,2,3,3,4,4,4-nonafluorobutylsulfonyloxy)-3,6-dihydro-2H-pyridine-1-carboxylate (Intermediate CLJ)

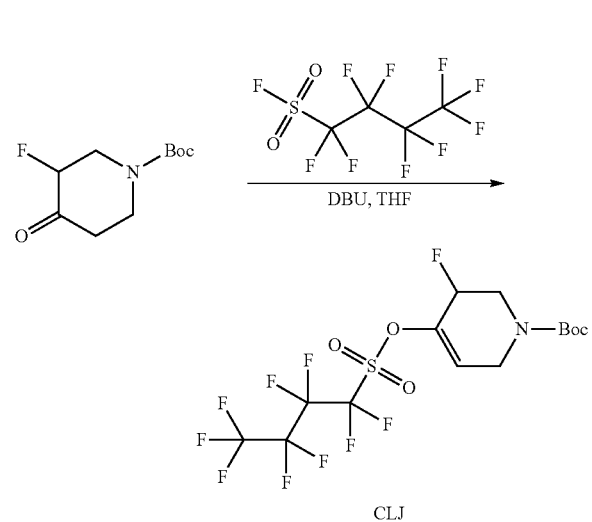

To a solution of tert-butyl 3-fluoro-4-oxo-piperidine-1-carboxylate (2.00 g, 9.21 mmol, CAS #211108-50-8) in THF (20 mL) was added DBU (4.20 g, 27.6 mmol) and 1,1,2,2,3,3,4,4,4-nonafluorobutane-1-sulfonyl fluoride (8.34 g, 27.6 mmol) at −10° C. Then the mixture was stirred at −10° C. for 1 hr. On completion, the reaction mixture was filtered and concentrated in vacuo to give a residue. The residue was purified by column chromatography (SiO₂, PE:EA=50:1 to PE:EA=30:1) to give the title compound (3.00 g, 65% yield) as a white solid. ¹H NMR (400 MHz, CDCl₃-d) δ 6.17 (s, 1H), 5.09-4.88 (m, 1H), 4.63-4.29 (m, 2H), 3.89-3.73 (m, 1H), 3.29 (dd, J=2.8, 14.8 Hz, 1H), 1.44 (s, 9H).

3-[3-Methyl-2-oxo-4-(4,4,5,5-tetramethyl-1,3,2-dioxaborolan-2-yl)benzimidazol-1-yl]piperidine-2,6-dione (Intermediate CLK)

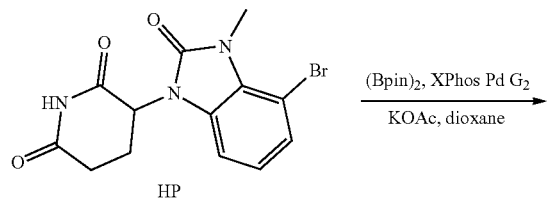

3-[4-(3-fluoro-1,2,3,6-tetrahydropyridin-4-yl)-3-methyl-2-oxo-benzimidazol-1-yl]piperidine-2,6-dione (Intermediate CLL)

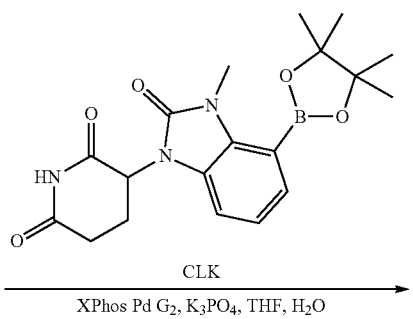

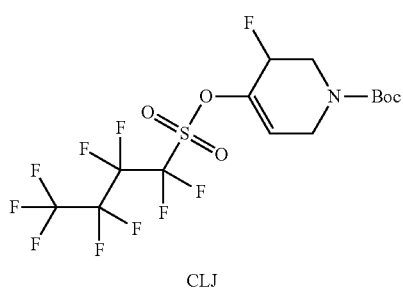

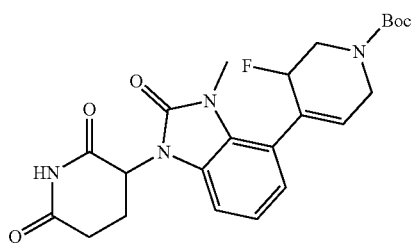

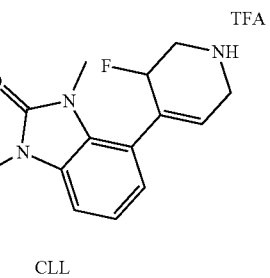

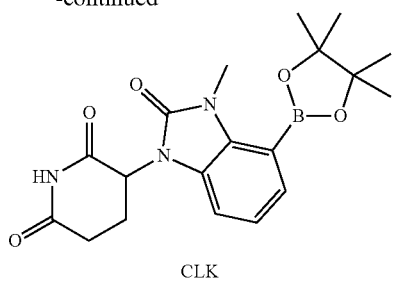

A mixture of 3-(4-bromo-3-methyl-2-oxo-benzimidazol-1-yl)piperidine-2,6-dione (3 g, 8.87 mmol, Intermediate HP), KOAc (2.61 g, 26.6 mmol), XPHOS-PD-G$_2$ (698 mg, 887 umol) and 4,4,5,5-tetramethyl-2-(4,4,5,5-tetramethyl-1,3,2-dioxaborolan-2-yl)-1,3,2-dioxaborolane (2.70 g, 10.6 mmol) in dioxane (30 mL) was degassed and purged with N$_2$ three times. Then the mixture was stirred at 65° C. for 16 hrs under N$_2$ atmosphere. On completion, the mixture was filtered and concentrated to give a residue. The residue was purified by column chromatography (SiO$_2$, Petroleum ether/Ethyl acetate=5/1 to 1/2) to give the title compound (1.7 g, 44% yield) as brown solid. LC-MS (ESI$^+$) m/z 385.7 (M+H)$^+$.

Step 1—Tert-butyl4-[1-(2,6-dioxo-3-piperidyl)-3-methyl-2-oxo-benzimidazol-4-yl]-3-fluoro-3,6-dihydro-2H-pyridine-1-carboxylate. A mixture of tert-butyl 3-fluoro-4-(1,1,2,2,3,3,4,4,4-nonafluorobutylsulfonyloxy)-3,6-dihydro-2H-pyridine-1-carboxylate (500 mg, 1.00 mmol, Intermediate CLJ), 3-[3-methyl-2-oxo-4-(4,4,5,5-tetramethyl-1,3,2-dioxaborolan-2-yl)benzimidazol-1-yl]piperidine-2,6-dione (463 mg, 1.20 mmol, Intermediate CLK), XPHOS-PD-G2 (157 mg, 200 umol), K$_3$PO$_4$ (637 mg, 3.00 mmol) in dioxane (5 mL) was degassed and purged with N$_2$ three times. Then the mixture was stirred at 80° C. for 12 hours under N$_2$ atmosphere. On completion, the reaction mixture was concentrated in vacuo to give a residue. Then the residue was purified by reverse phase (0.1% FA condition) to give the title compound (30.0 mg, 7% yield) as a brown solid. LC-MS (ESI$^+$) m/z 459.2 (M+H)$^+$.

Step 2—3-[4-(3-Fluoro-1,2,3,6-tetrahydropyridin-4-yl)-3-methyl-2-oxo-benzimidazol-1-yl]piperidine-2,6-dione. To a solution of tert-butyl 4-[1-(2,6-dioxo-3-piperidyl)-3-methyl-2-oxo-benzimidazol-4-yl]-3-fluoro-3,6-dihydro-2H-pyridine-1-carboxylate (30.0 mg, 65.4 umol) in DCM (1 mL) was added TFA (0.2 mL), then the mixture was stirred at 25° C. for 1 hr. On completion, the reaction mixture was concentrated in vacuo to give a residue to give the title compound (30.0 mg, 97% yield) as a yellow solid. LC-MS (ESI⁺) m/z 359.0 (M+H)⁺.

Tert-butyl (3R,4R)-3-hydroxy-4-(3-methyl-2-oxo-1H-benzimidazol-4-yl)piperidine-1-carboxylate (Intermediate CLM)

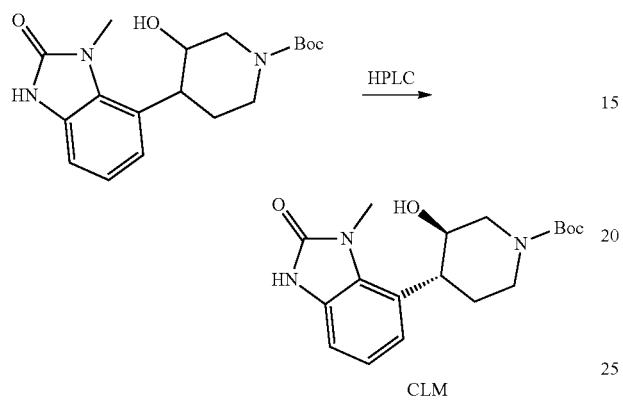

CLM

Tert-butyl 3-hydroxy-4-(3-methyl-2-oxo-1H-benzimidazol-4-yl)piperidine-1-carboxylate (500 mg, 1.44 mmol, synthesized via Steps 1-2 of Intermediate CON) was purified by prep-HPLC (column: Phenomenex luna C18 150*25 mm*10 um; mobile phase: [water(FA)-ACN]; B %: 19%-49%, 10 min) to give the title compound (360 mg, 72% yield) as white solid. ¹H NMR (400 MHz, DMSO-d₆) δ 10.82 (s, 1H), 6.94 (d, J=4.4 Hz, 2H), 6.84-6.78 (m, 1H), 4.98 (d, J=5.2 Hz, 1H), 4.23-4.08 (m, 1H), 4.05-3.90 (m, 1H), 3.55 (s, 3H), 3.52-3.44 (m, J=5.2, 10.0 Hz, 1H), 3.30-3.21 (m, 1H), 2.88-2.72 (m, 1H), 2.65-2.54 (m, 1H), 1.81-1.71 (m, 1H), 1.70-1.56 (m, J=3.6, 12.8 Hz, 1H), 1.42 (s, 9H); LC-MS (ESI⁺) m/z 370.0 (M+23)⁺.

3-[4-[(3R,4R)-3-Hydroxy-4-piperidyl]-3-methyl-2-oxo-benzimidazol-1-yl]piperidine-2,6-dione (Intermediate CLN)

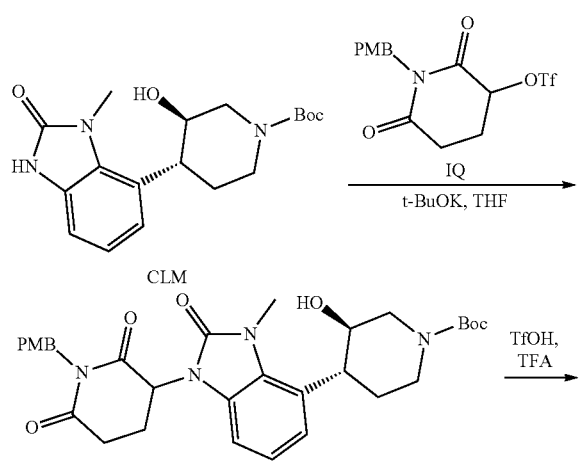

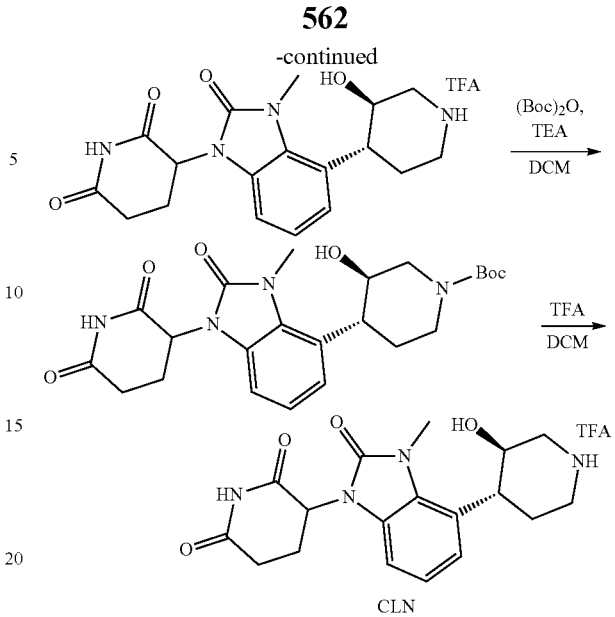

CLN

Step 1—Tert-butyl (3R,4R)-3-hydroxy-4-[1-[1-[(4-methoxyphenyl)methyl]-2,6-dioxo-3-piperidyl]-3-methyl-2-oxo-benzimidazol-4-yl]piperidine-1-carboxylate. To a solution of tert-butyl (3R,4R)-3-hydroxy-4-(3-methyl-2-oxo-1H-benzimidazol-4-yl) piperidine-1-carboxylate (200 mg, 575 umol, Intermediate CLM) in THF (5 mL) was added t-BuOK (193 mg, 1.73 mmol) and [1-[(4-methoxyphenyl)methyl]-2,6-dioxo-3-piperidyl] trifluoromethanesulfonate (439 mg, 1.15 mmol, Intermediate IQ) at −10° C. Then the mixture was stirred at −10° C. for 1 hr. On completion, the reaction mixture was quenched with H₂O (10 mL) at 25° C., and then extracted with EA (5 mL×2). The combined organic layers were washed with saturated sodium chloride solution (5 mL×2), dried over anhydrous sodium sulfate, filtered and concentrated to give a residue. The residue was purified by reversed phase (0.1% FA condition) to give the title compound (200 mg, 60% yield) as a blue solid. ¹H NMR (400 MHz, DMSO-d₆) δ 7.21 (d, J=8.4 Hz, 2H), 7.05-7.01 (m, 1H), 6.96 (t, J=7.6 Hz, 1H), 6.86 (d, J=8.4 Hz, 3H), 5.58-5.47 (m, J=5.2, 12.8 Hz, 1H), 5.04 (d, J=4.0 Hz, 1H), 4.86-4.72 (m, 2H), 4.24-4.10 (m, 1H), 4.07-3.92 (m, 1H), 3.72 (s, 3H), 3.71-3.69 (m, 1H), 3.62 (s, 3H), 3.54-3.47 (m, J=4.4, 9.6 Hz, 1H), 3.31-3.24 (m, 1H), 3.11-2.97 (m, 1H), 2.83-2.78 (m, 1H), 2.74-2.66 (m, 1H), 2.63-2.55 (m, 1H), 2.06-1.99 (m, 1H), 1.83-1.74 (m, 1H), 1.72-1.58 (m, 1H), 1.43 (s, 9H); LC-MS (ESI⁺) m/z 579.2 (M+H)⁺.

Step 2—3-[4-[(3R,4R)-3-Hydroxy-4-piperidyl]-3-methyl-2-oxo-benzimidazol-1-yl]piperidine-2,6-dione. Tert-butyl (3R,4R)-3-hydroxy-4-[1-[1-[(4-methoxyphenyl)methyl]-2,6-dioxo-3-piperidyl]-3-methyl-2-oxo-benzimidazol-4-yl]piperidine-1-carboxylate (200 mg, 345 umol) was dissolved in TFA (4 mL) and TfOH (0.5 mL). The mixture was stirred at 70° C. for 12 hrs. On completion, the reaction mixture was concentrated to give the title compound (163 mg, 99% yield, TFA) as a black brown oil. LC-MS (ESI⁺) m/z 359.2 (M+H)⁺.

Step 3—Tert-butyl 3,3-difluoro-4-(3-methyl-2-oxo-1H-benzimidazol-4-yl)piperidine-1-carboxylate. To a solution of 3-[4-[(3R,4R)-3-hydroxy-4-piperidyl]-3-methyl-2-oxo-benzimidazol-1-yl] piperidine-2,6-dione (163 mg, 345 umol, TFA) in DCM (4 mL) was added Boc₂O (112 mg, 517 umol) and TEA (104 mg, 1.04 mmol) at 0° C. Then the mixture was stirred at 25° C. for 3 hrs. On completion, the reaction mixture was diluted with H₂O (10 mL) and extracted with DCM (5 mL×2). The combined organic layers were washed with saturated sodium chloride solution (10 mL×2), dried over anhydrous sodium sulfate, filtered and concentrated to give a residue. The residue was purified by reversed phase (0.1% FA condition) to give the title compound (30.0 mg, 18% yield) as a white solid. ¹H NMR (400 MHz, DMSO-d₆) δ 11.09 (s, 1H), 7.06-6.92 (m, 3H), 5.44-5.30 (m, J=5.2, 12.4 Hz, 1H), 5.04 (d, J=4.8 Hz, 1H), 4.27-4.08 (m, 1H), 4.06-3.91 (m, 1H), 3.62 (s, 3H), 3.57-3.46 (m, 1H), 3.27 (d, J=3.6 Hz, 1H), 2.95-2.84 (m, 1H), 2.76-2.68 (m, 1H), 2.62 (d, J=17.6 Hz, 3H), 2.03-1.95 (m, 1H), 1.79 (d, J=10.8 Hz, 1H), 1.72-1.58 (m, 1H), 1.43 (s, 9H); LC-MS (ESI⁺) m/z 459.2 (M+H)⁺.

Step 4—3-[4-[(3R,4R)-3-Hydroxy-4-piperidyl]-3-methyl-2-oxo-benzimidazol-1-yl]piperidine-2,6-dione. Tert-butyl (3R, 4R)-4-[1-(2,6-dioxo-3-piperidyl)-3-methyl-2-oxo-benzimidazol-4-yl]-3-hydroxy-piperidine-1-carboxylate (25.0 mg, 54.5 umol) was dissolved in TFA (0.2 mL) and DCM (0.8 mL). The mixture was then stirred at 25° C. for 1 hr. On completion, the reaction mixture was concentrated under reduced pressure to give the title compound (25.0 mg, 97% yield, TFA) as an off-white solid. LC-MS (ESI⁺) m/z 359.1 (M+H)⁺.

3-[4-(3,3-difluoro-4-piperidyl)-3-methyl-2-oxo-benzimidazol-1-yl]piperidine-2,6-dione (Intermediate CLO)

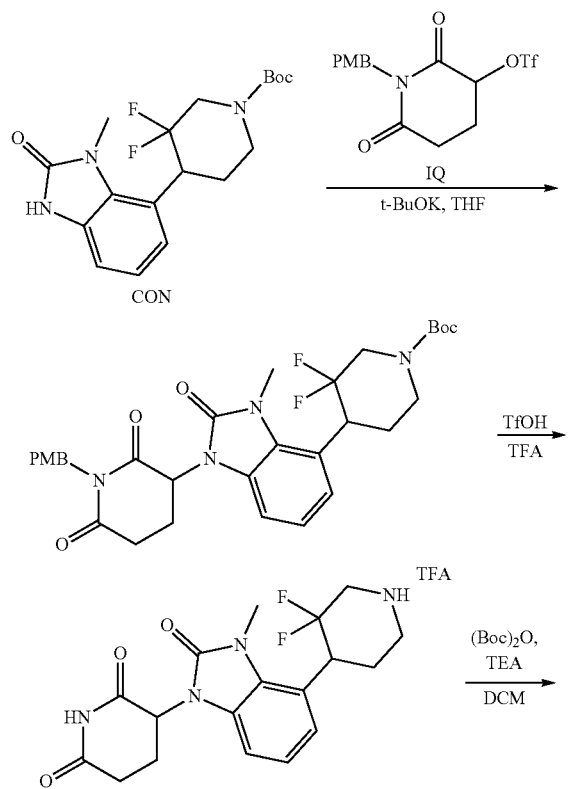

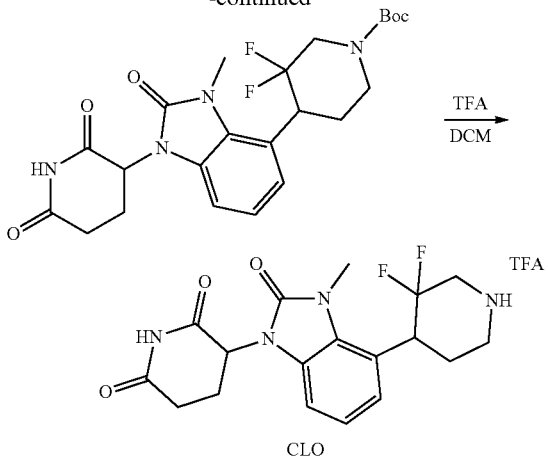

Step 1—Tert-butyl 3,3-difluoro-4-[1-[1-[(4-methoxyphenyl)methyl]-2,6-dioxo-3-piperidyl]-3-methyl-2-oxo-benzimidazol-4-yl]piperidine-1-carboxylate. To a solution of tert-butyl 3,3-difluoro-4-(3-methyl-2-oxo-1H-benzimidazol-4-yl)piperidine-1-carboxylate (70.0 mg, 190 umol, Intermediate CON) in THF (2 mL) was added t-BuOK (64.1 mg, 571 umol) and [1-[(4-methoxyphenyl)methyl]-2,6-dioxo-3-piperidyl] trifluoromethanesulfonate (145 mg, 381 umol, Intermediate IQ) at −10° C. The mixture was then stirred at −10° C. for 1 hr. On completion, the reaction mixture was quenched with H₂O (10 mL) at 20° C., and then extracted with EA (5 mL×2). The combined organic layers were washed with saturated sodium chloride solution (5 mL×2), dried over anhydrous sodium sulfate, filtered and concentrated to give a residue. The residue was purified by prep-TLC (SiO₂, DCM:MeOH=20:1) to give the title compound (110 mg, 96% yield) as an off-white solid. ¹H NMR (400 MHz, DMSO-d₆) δ 7.24-7.18 (m, 2H), 7.07 (s, 1H), 7.01 (s, 1H), 6.89-6.81 (m, 3H), 5.64-5.48 (m, J=4.8, 12.4 Hz, 1H), 4.88-4.70 (m, 3H), 4.31-4.18 (m, 1H), 4.17-3.98 (m, 2H), 3.72 (s, 3H), 3.71-3.70 (m, 1H), 3.57 (s, 3H), 3.05 (t, J=13.2 Hz, 1H), 2.82 (d, J=19.6 Hz, 1H), 2.75-2.69 (m, J=5.2, 9.6 Hz, 1H), 2.15-2.02 (m, 2H), 1.91 (d, J=12.4 Hz, 1H), 1.44 (s, 9H); LC-MS (ESI⁺) m/z 599.2 (M+H)⁺.

Step 2—3-[4-(3,3-Difluoro-4-piperidyl)-3-methyl-2-oxo-benzimidazol-1-yl]piperidine-2,6-dione. Tert-butyl 3,3-difluoro-4-[1-[1-[(4-methoxyphenyl)methyl]-2,6-dioxo-3-piperidyl]-3-methyl-2-oxo-benzimidazol-4-yl]piperidine-1-carboxylate (110 mg, 183 umol) was dissolved in TFA (1.5 mL) and TfOH (0.3 mL). The mixture was then stirred at 70° C. for 12 hrs. On completion, the reaction mixture was concentrated under reduced pressure to give the title compound (90.0 mg, 99% yield, TFA) as a black brown oil. LC-MS (ESI⁺) m/z 379.0 (M+H)⁺.

Step 3—Tert-butyl 4-[1-(2,6-dioxo-3-piperidyl)-3-methyl-2-oxo-benzimidazol-4-yl]-3,3-difluoro-piperidine-1-carboxylate. To a solution of 3-[4-(3,3-difluoro-4-piperidyl)-3-methyl-2-oxo-benzimidazol-1-yl]piperidine-2,6-dione (90.0 mg, 182 umol, TFA) in DCM (2 mL) was added Boc₂O (59.8 mg, 274 umol) and TEA (55.4 mg, 548 umol) at 0° C. The mixture was then stirred at 25° C. for 3 hrs. On completion, the reaction mixture was quenched with H₂O (10 mL) at 25° C., and then extracted with DCM (5 mL×2). The combined organic layers were washed with saturated sodium chloride solution (5 mL×2), dried over anhydrous sodium sulfate, filtered and concentrated to give the title compound (65.0 mg, 74% yield) as a brown solid. ¹H NMR (400 MHz, CDCl₃) δ 8.11 (s, 1H), 7.17 (d, J=8.0 Hz, 1H), 7.12-7.06 (m, 1H), 6.83-6.73 (m, 1H), 5.39-5.02 (m, 1H), 4.75-4.23 (m, 2H), 3.87-3.76 (m, 1H), 3.67 (d, J=6.0 Hz, 3H), 3.19-3.04 (m, 1H), 2.99-2.93 (m, 1H), 2.89-2.79 (m, 2H), 2.78-2.64 (m, 1H), 2.38-2.21 (m, 2H), 1.90 (d, J=13.6 Hz, 1H), 1.54 (s, 9H); LC-MS (ESI$^+$) m/z 479.1 (M+H)$^+$.

Step 4—3-[4-(3,3-Difluoro-4-piperidyl)-3-methyl-2-oxo-benzimidazol-1-yl]piperidine-2,6-dione. To a solution of tert-butyl 4-[1-(2,6-dioxo-3-piperidyl)-3-methyl-2-oxo-benzimidazol-4-yl]-3,3-difluoro-piperidine-1-carboxylate (25.0 mg, 52.5 umol) in DCM (0.5 mL) was added TFA (59.5 mg, 522 umol). The mixture was then stirred at 25° C. for 1 hr. On completion, the reaction mixture was concentrated under reduced pressure to give the title compound (25.0 mg, 97% yield, TFA) as a brown solid. LC-MS (ESI$^+$) m/z 379.2 (M+H)$^+$.

3-[(4-Methoxyphenyl)methyl]-1-[8-(4,4,5,5-tetramethyl-1,3,2-dioxaborolan-2-yl)-4-isoquinolyl]hexahydropyrimidine-2,4-dione (Intermediate CLP)

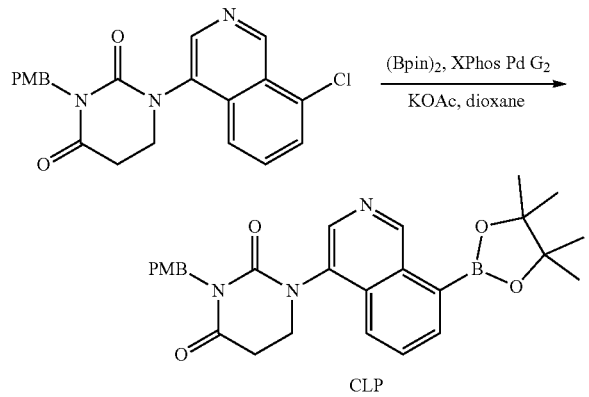

A mixture of 1-(8-chloro-4-isoquinolyl)-3-[(4-methoxyphenyl)methyl]hexahydropyrimidine-2,4-dione (2 g, 5.05 mmol, Steps 1-2 of Intermediate BSA), 4,4,5,5-tetramethyl-2-(4,4,5,5-tetramethyl-1,3, 2-dioxaborolan-2-yl)-1,3, 2-dioxaborolane (2.57 g, 10.1 mmol, CAS #73183-34-3), XPHOS-PD-G$_2$ (397 mg, 505 umol), and KOAc (1.49 g, 15.1 mmol) in dioxane (20 mL) was degassed and purged with N$_2$ three times. Then the mixture was stirred at 100° C. for 16 hrs under N$_2$ atmosphere. On completion, the reaction mixture was filtered and concentrated in vacuo. The residue was purified by reverse phase (FA condition) to give the title compound (1.2 g, 48% yield) as a black-brown solid. $^1$H NMR (400 MHz, DMSO-d$_6$) δ 8.70-8.50 (m, 1H), 7.85-7.78 (m, 1H), 7.26 (d, J=8.8 Hz, 1H), 7.17 (d, J=8.4 Hz, 2H), 6.84 (d, J=8.4 Hz, 3H), 4.84 (s, 1H), 4.71 (s, 2H), 3.73 (s, 2H), 3.71 (s, 3H), 3.21 (t, J=2.8, 6.8 Hz, 2H), 2.62 (t, J=6.8 Hz, 2H), 1.41 (s, 1H).

Tert-butyl 3,3-difluoro-4-(1,1,2,2,3,3,4,4,4-nonafluorobutylsulfonyloxy)-2,6-dihydropyridine-1-carboxylate (Intermediate CLQ)

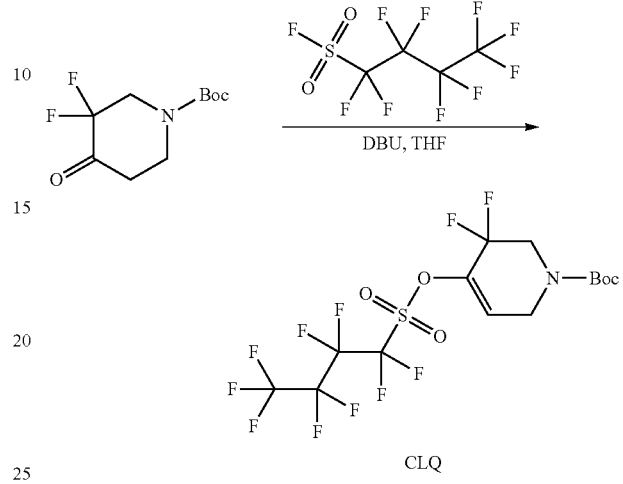

To a solution of tert-butyl 3,3-difluoro-4-oxo-piperidine-1-carboxylate (500 mg, 2.13 mmol, CAS #346593-03-1) and DBU (970 mg, 6.38 mmol) in THF (8 mL) was added a solution of 1,1,2,2,3,3,4,4,4-nonafluorobutane-1-sulfonyl fluoride (1.93 g, 6.38 mmol, CAS #375-72-4) in THF (5 mL). The mixture was stirred at −20° C. for 2 hrs. On completion, the reaction mixture was quenched with H$_2$O (3 mL) and diluted with water (15 mL) and extracted with EA (2×20 mL). The combined organic layers was washed with brine (2×15 mL) and dried over Na$_2$SO$_4$, filtered concentrated in vacuo to give a residue. The residue was purified by column chromatography (SiO$_2$, Petroleum ether/Ethyl acetate=1/0 to 20/1) to give the title compound (600 mg, 54% yield) as yellow oil. $^1$H NMR (400 MHz, CDCl$_3$) δ 6.32-6.04 (m, 1H), 4.18 (s, 2H), 3.90 (t, J=10.4 Hz, 2H), 1.44-1.37 (m, 9H).

Tert-butyl 3,3-difluoro-4-[4-[3-[(4-methoxyphenyl)methyl]-2,4-dioxo-hexahydropyrimidin-1-yl]-8-isoquinolyl]-2,6-dihydropyridine-1-carboxylate (Intermediate CLR)

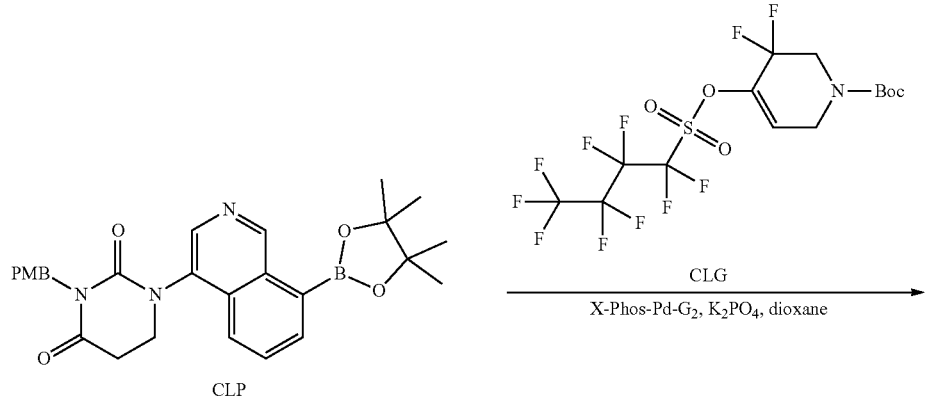

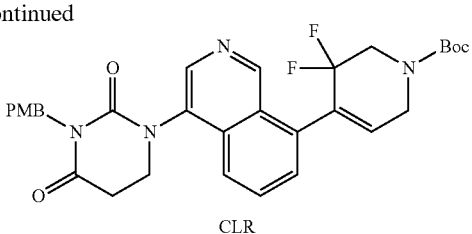

A mixture of 3-[(4-methoxyphenyl)methyl]-1-[8-(4,4,5,5-tetramethyl-1,3,2-dioxaborolan-2-yl)-4-isoquinolyl]hexahydropyrimidine-2,4-dione (700 mg, 1.44 mmol, Intermediate CLP), tert-butyl 3,3-difluoro-4-(1,1,2, 2,3,3,4,4,4-nonafluorobutylsulfonyloxy)-2,6-dihydropyridine-1-carboxylate (965 mg, 1.87 mmol, Intermediate CLQ), XPHOS-PD-$G_2$ (113 mg, 143 umol), and $K_3PO_4$ (914 mg, 4.31 mmol) in DMF (10 mL) was degassed and purged with $N_2$ three times. Then the mixture was stirred at 80° C. for 16 hrs under $N_2$ atmosphere. On completion, the reaction mixture was filtered and concentrated in vacuo to give a residue. The residue was purified by reverse phase (FA condition) to give the title compound (200 mg, 24% yield) as a brown solid. $^1$H NMR (400 MHz, DMSO-$d_6$) δ 9.31 (s, 1H), 8.61 (s, 1H), 7.99 (d, J=8.4 Hz, 1H), 7.83 (t, J=8.0 Hz, 1H), 7.57 (d, J=7.2 Hz, 1H), 7.26 (d, J=8.4 Hz, 2H), 6.88 (d, J=8.4 Hz, 2H), 6.47 (s, 1H), 4.84 (s, 2H), 4.28 (s, 2H), 4.19-4.07 (m, 2H), 4.00-3.90 (m, 1H), 3.83-3.76 (m, 1H), 3.73 (s, 3H), 3.20-3.11 (m, 1H), 3.03-2.93 (m, 1H), 1.48 (s, 9H). LC-MS (ESI$^+$) m/z 579.4 (M+H)$^+$.

1-[8-(3,3-Difluoro-4-piperidyl)-4-isoquinolyl]hexahydropyrimidine-2,4-dione (Intermediate CLS)

hexahydropyrimidin-1-yl]-8-isoquinolyl]-2,6-dihydropyridine-1-carboxylate (80 mg, 138 umol, Intermediate CLR) in THF (2 mL) was added Pd/C (138 umol, 10 wt %) under $N_2$. The suspension was degassed in vacuo and purged with $H_2$ several times. The mixture was stirred at 25° C. for 16 hours under $H_2$ (15 psi) atmosphere. On completion, the reaction mixture was filtered and concentrated in vacuo to give a residue. The residue was purified by reverse phase (0.1% FA condition) to give the title compound (40 mg, 49% yield) as a yellow solid. LC-MS (ESI+) m/z 581.2 (M+H)$^+$.

Step 2—1-[8-(3,3-Difluoro-4-piperidyl)-4-isoquinolyl]hexahydropyrimidine-2,4-dione. To a solution of tert-butyl 3,3-difluoro-4-[4-[3-[(4-methoxyphenyl)methyl]-2,4-dioxohexahydro pyrimidin-1-yl]-8-isoquinolyl]piperidine-1-carboxylate (30 mg, 51.6 umol, FA) in TfOH (0.2 mL) was added TFA (1 mL). The mixture was stirred at 70° C. for 2 hrs. On completion, the reaction mixture was concentrated in vacuo to give the title compound (24 mg, 97.8% yield, TFA) as a yellow oil. LC-MS (ESI+) m/z 361.1 (M+H)$^+$.

5-(Dimethylamino)pyrazolo[1,5-a]pyrimidine-3-carboxylic acid (Intermediate CLT)

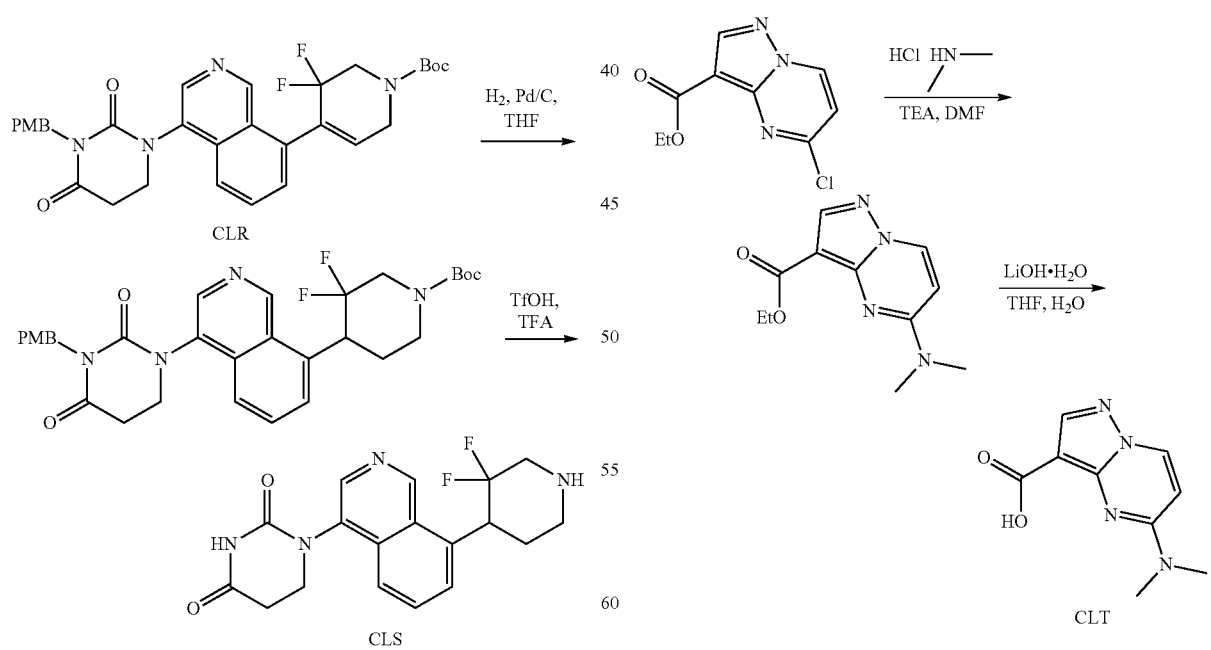

Step 1—Tert-butyl 3,3-difluoro-4-[4-[3-[(4-methoxyphenyl)methyl]-2,4-dioxohexahydropyrimidin-1-yl]-8-isoquinolyl]piperidine-1-carboxylate. To a solution of tert-butyl 3,3-difluoro-4-[4-[3-[(4-methoxyphenyl)methyl]-2,4-dioxo- Step 1—Ethyl 5-(dimethylamino)pyrazolo[1,5-a]pyrimidine-3-carboxylate. The solution of ethyl 5-chloropyrazolo[1,5-a]pyrimidine-3-carboxylate (2.1 g, 9.31 mmol), N-methylmethanamine (987 mg, 12.1 mmol, HCl), and TEA (2.83 g, 27.9 mmol) in DMF (25 mL) was degassed and purged with N₂ three times. Then the mixture was stirred at 65° C. for 4 hrs under N₂ atmosphere. On completion, the reaction was cooled to rt, diluted with water (150 ml), and extracted with EA (50 ml×4). The organic layers were combined, washed with brine (50 ml), dried over anhydrous Na₂SO₄, filtered and concentrated in vacuo to give the title compound (1.87 g, 85% yield) as yellow solid. $^1$H NMR (400 MHz, DMSO-d₆) δ 8.66 (d, J=8.0 Hz, 1H), 8.18 (s, 1H), 6.67 (d, J=8.0 Hz, 1H), 4.18 (q, J=7.2 Hz, 2H), 3.17 (s, 6H), 1.28 (t, J=7.2 Hz, 3H).

Step 2—5-(Dimethylamino)pyrazolo[1,5-a]pyrimidine-3-carboxylic acid. To a solution of ethyl 5-(dimethylamino)pyrazolo[1,5-a]pyrimidine-3-carboxylate (500 mg, 2.13 mmol) in THF (4 mL) and H₂O (1 mL) was added LiOH·H₂O (269 mg, 6.40 mmol) and the mixture was stirred at 20° C. for 1 hr. On completion, the reaction was concentrated in vacuo to give a residue. The residue was diluted with water (15 ml), acidified with 1N HCl to adjust the pH=5. The precipitate was filtered off, washed with water (5 ml), and dried in vacuo to give the title compound (350 mg, 79% yield) as off-white solid. $^1$H NMR (400 MHz, DMSO-d₆) δ 8.65 (d, J=8.0 Hz, 1H), 8.16 (s, 1H), 6.66 (d, J=8.0 Hz, 1H), 3.16 (s, 6H).

N-[3-(difluoromethyl)-1-(4-formylcyclohexyl)pyrazol-4-yl]-5-(dimethylamino)pyrazolo[1,5-a]pyrimidine-3-carboxamide (Intermediate CLU)

25° C. for 15 min. Then a solution of [4-[4-amino-3-(difluoromethyl)pyrazol-1-yl]cyclohexyl]methanol (118 mg, 484 umol, Intermediate TD) in DMF (0.5 mL) was added. The reaction mixture was then stirred at 60° C. for 2 hrs. On completion, the mixture was filtered and concentrated to give the title compound (160 mg, 68% yield) as white solid. LC-MS (ESI⁺) m/z 434.1 (M+H)⁺.

Step 2—N-[3-(difluoromethyl)-1-(4-formylcyclohexyl)pyrazol-4-yl]-5-(dimethylamino)pyrazolo[1,5-a]pyrimidine-3-carboxamide. To a solution of N-[3-(difluoromethyl)-1-[4-(hydroxymethyl)cyclohexyl]pyrazol-4-yl]-5-(dimethylamino)pyrazolo[1,5-a]pyrimidine-3-carboxamide (140 mg, 322 umol) in DCM (2 mL) was added DMP (164 mg, 387 umol). The mixture was stirred at 25° C. for 1 hr. On completion, the reaction mixture was quenched with Na₂S₂O₃ (8 mL) and NaHCO₃ (8 mL). The residue was diluted with DCM (50 mL) and NaHCO₃ (50 mL). The mixture was filtered and the filtrate was extracted with DCM. The organic layer was dried with Na₂SO₄, filtered and concentrated to give the title compound (150 mg, 96% yield) as a white solid. LC-MS (ESI⁺) m/z 432.2 (M+H)⁺.

N-[2-(4-formyl-4-hydroxy-cyclohexyl)indazol-5-yl]-6-(trifluoromethyl)pyridine-2-carboxamide (Intermediate CLV)

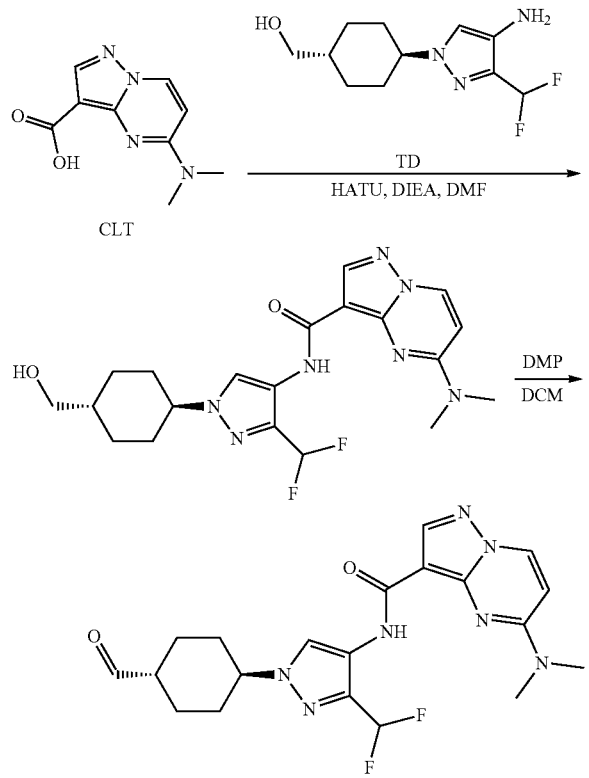

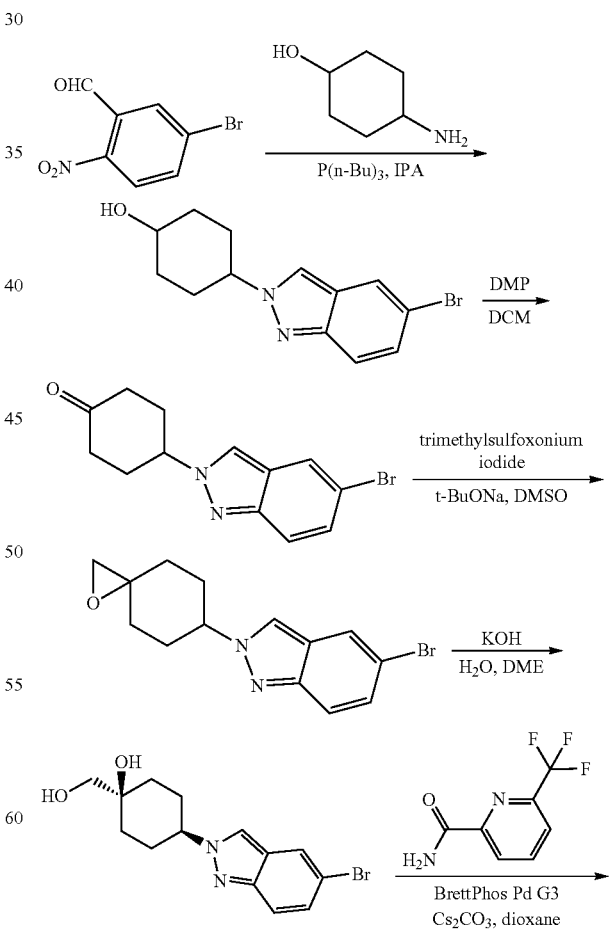

Step 1—N-[3-(difluoromethyl)-1-[4-(hydroxymethyl)cyclohexyl]pyrazol-4-yl]-5-(dimethylamino) pyrazolo[1,5-a]pyrimidine-3-carboxamide. A mixture of 5-(dimethylamino)pyrazolo[1,5-a]pyrimidine-3-carboxylic acid (100 mg, 484 umol, Intermediate CLT), DIEA (125 mg, 969 umol) and HATU (221 mg, 581 umol) in DMF (0.5 mL) was stirred at -continued

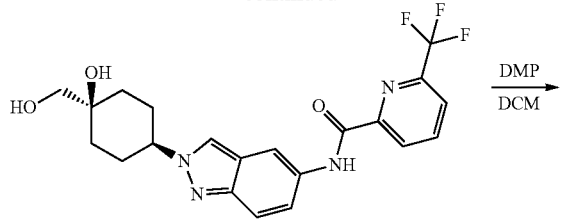

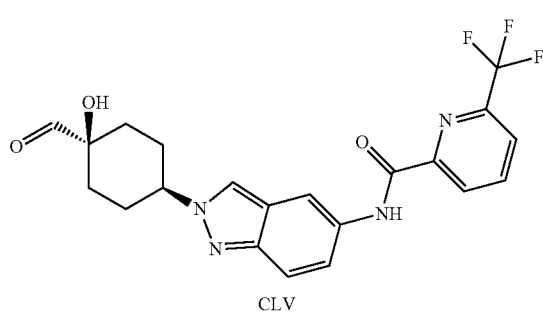

CLV

Step 1—4-(5-Bromoindazol-2-yl)cyclohexanol. To a solution of 5-bromo-2-nitro-benzaldehyde (4 g, 17.3 mmol, CAS #20357-20-4) in IPA (40 mL) was added 4-aminocyclohexanol (2.20 g, 19.1 mmol, CAS #6850-65-3). The mixture was stirred at 80° C. for 4 hrs. Then tributylphosphane (10.5 g, 52.1 mmol, 12.8 mL) was added at 25° C. The mixture was then stirred at 80° C. for 16 hrs under $N_2$. On completion, the reaction mixture was concentrated in vacuo to give a residue. The residue was purified by column chromatography ($SiO_2$, PE:EA=20:1 to PE:EA=2:1,PE:EA=0:1, P1:Rf=0.6) to give the title compound (2.2 g, 43% yield) as a brown oil. $^1$H NMR (400 MHz, DMSO-$d_6$) δ 8.45-8.30 (m, 1H), 7.93 (d, J=1.2 Hz, 1H), 7.68-7.53 (m, 1H), 7.29 (d, J=1.6, 9.2 Hz, 1H), 4.59-4.38 (m, 2H), 3.88-3.87 (m, 1H), 2.33-2.30 (m, 12.0 Hz, 2H), 1.91-1.72 (m, 4H), 1.69-1.55 (m, 2H), LC-MS (ESI$^+$) m/z 294.0 (M+H)$^+$.

Step 2—4-(5-Bromoindazol-2-yl)cyclohexanone. To a solution of 4-(5-bromoindazol-2-yl)cyclohexanol (2.8 g, 9.49 mmol) in DCM (80 mL) was added DMP (6.04 g, 14.2 mmol, 4.41 mL). The mixture was stirred at 25° C. for 4 hrs. On completion, the reaction mixture was quenched with $Na_2S_2O_3$ (200 mL) and $NaHCO_3$ (200 mL) and extracted with DCM (3×100 mL). The combined organic phase was washed with $NaHCO_3$ (100 mL) and brine (3×50 mL), dried with anhydrous $Na_2SO_4$, filtered and the filtrate was concentrated in vacuo to give residue. The residue was purified by column chromatography ($SiO_2$, PE:EA=20:1 to PE:EA=2:3,PE:EA=0:1, P1:Rf=0.6) to give the title compound (2.6 g, 94% yield) as a brown oil. $^1$H NMR (400 MHz, DMSO-$d_6$) δ 8.47 (s, 1H), 7.96 (d, J=1.2 Hz, 1H), 7.61 (d, J=9.2 Hz, 1H), 7.31 (dd, J=1.2, 9.2 Hz, 1H), 5.19-4.97 (m, 1H), 2.71-2.58 (m, 2H), 2.42-2.33 (m, 6H), LC-MS (ESI$^+$) m/z 292.0 (M+H)$^+$.

Step 3—5-Bromo-2-(1-oxaspiro[2.5]octan-6-yl)indazole. To a solution of t-BuONa (1.48 g, 15.3 mmol) in DMSO (50 mL) was added trimethylsulfoxonium iodide (3.38 g, 15.3 mmol). The mixture was then stirred at 65° C. for 2 hrs. Then 4-(5-bromoindazol-2-yl)cyclohexanone (1.5 g, 5.12 mmol) was added and the mixture was stirred at 25° C. for 2 hrs. On completion, the reaction mixture was quenched with water (30 mL) and filtered to give the title compound (1.5 g, 95% yield) as a white solid. $^1$H NMR (400 MHz, DMSO-$d_6$) δ 8.41 (s, 1H), 7.90 (d, J=1.3 Hz, 1H), 7.56 (d, J=9.8 Hz, 1H), 7.27-7.25 (m, 1H), 4.63-4.62 (m, 1H), 2.66 (s, 2H), 2.20-2.08 (m, 6H), 1.38-1.15 (m, 2H); LC-MS (ESI$^+$) m/z 306.0 (M+H)$^+$.

Step 4—4-(5-Bromoindazol-2-yl)-1-(hydroxymethyl)cyclohexanol. To a solution of 5-bromo-2-(1-oxaspiro[2.5]octan-6-yl)indazole (1.5 g, 4.88 mmol) in $H_2O$ (40 mL) and DME (10 mL) was added KOH (1.37 g, 24.4 mmol). The mixture was then stirred at 85° C. for 4 hrs. On completion, the reaction mixture was filtered. The residue was extracted with EA (2×50 mL). The combined organic layer was washed with brine (50 mL) and dried over $Na_2SO_4$, filtered and the filtrate was concentrated in vacuo to give a residue to give the title compound (750 mg, 47% yield) as a white solid. $^1$H NMR (400 MHz, DMSO-$d_6$) δ 8.38 (s, 1H), 7.99-7.86 (m, 1H), 7.58 (d, J=9.2 Hz, 1H), 7.29 (dd, J=1.2, 9.2 Hz, 1H), 4.63 (s, 1H), 4.50-4.32 (m, 1H), 4.22-4.11 (m, 1H), 3.29-3.13 (m, 2H), 2.34-2.08 (m, 2H), 1.97-1.80 (m, 2H), 1.66-1.49 (m, 4H); LC-MS (ESI$^+$) m/z 324.0 (M+H)$^+$.

Step 5—N-[2-[4-hydroxy-4-(hydroxymethyl)cyclohexyl]indazol-5-yl]-6-(trifluoromethyl)pyridine-2-carboxamide.

To a solution of 4-(5-bromoindazol-2-yl)-1-(hydroxymethyl)cyclohexanol (370 mg, 1.14 mmol) in dioxane (20 mL) was added 6-(trifluoromethyl)pyridine-2-carboxamide (259 mg, 1.37 mmol, CAS #22245-84-7), [2-(2-aminophenyl)phenyl]-chloro-palladium; dicyclohexyl-[2(2,6diisopropoxy phenyl)phenyl]phosphane (88.37 mg, 113 umol), $Cs_2CO_3$ (741 mg, 2.28 mmol) and 4 Å molecular sieves (5 mg). The mixture was then stirred at 100° C. for 4 hrs at $N_2$ atmosphere. On completion, the reaction mixture was filtered and the filtrate was concentrated, the residue was purified by reverse phase (0.1% FA condition) to give the title compound (150 mg, 55% yield) as a yellow solid. $^1$H NMR (400 MHz, DMSO-$d_6$) δ10.35 (s, 1H), 8.43-8.39 (m, 2H), 8.38-8.33 (m, 1H), 8.29 (d, J=1.2 Hz, 1H), 8.17 (dd, J=1.2, 7.6 Hz, 1H), 7.64-7.59 (m, 1H), 7.57-7.52 (m, 1H), 4.62 (s, 1H), 4.43-4.42 (m, 1H), 4.16 (s, 1H), 3.23 (d, J=5.6 Hz, 2H), 2.35-2.20 (m, 2H), 1.92 (br dd, J=2.4, 11.6 Hz, 2H), 1.66-1.58 (m, 4H); LC-MS (ESI$^+$) m/z 434.1 (M+H)$^+$.

Step 6—N-[2-(4-formyl-4-hydroxy-cyclohexyl)indazol-5-yl]-6-(trifluoromethyl)pyridine-2-carboxamide To a solution of N-[2-[4-hydroxy-4-(hydroxymethyl)cyclohexyl]indazol-5-yl]-6-(trifluoromethyl)pyridine-2-carboxamide (100 mg, 230.20 umol) in DCM (2 mL) was added DMP (146 mg, 345 umol, 106 uL). The mixture was stirred at 40° C. for 4 hrs. On completion, the reaction mixture was quenched with $Na_2S_2O_3$ (50 mL) and $NaHCO_3$ (50 mL) and extracted with DCM (3×30 mL). The combined organic phase was washed with $NaHCO_3$ (50 mL) and brine (3×50 mL), dried with anhydrous $Na_2SO_4$, filtered and the filtrate was concentrated in vacuo to give residue to give the title compound (99 mg, 99% yield) as a yellow solid. LC-MS (ESI$^+$) m/z 432.1 (M+H)$^+$.

Tert-butyl 3-fluoro-4-(3-methyl-2-oxo-1H-benzimidazol-4-yl)piperidine-1-carboxylate (Intermediate CLW)

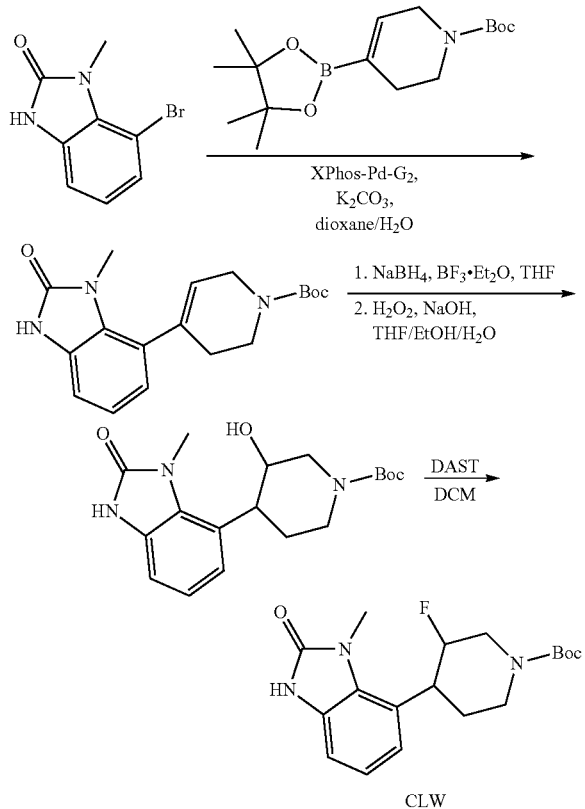

Step 1—Tert-butyl 4-(3-methyl-2-oxo-1H-benzimidazol-4-yl)-3,6-dihydro-2H-pyridine-1-carboxylate. To a mixture of 4-bromo-3-methyl-1H-benzimidazol-2-one (8.00 g, 35.2 mmol, synthesized via Steps 1-3 of Intermediate HP) and tert-butyl 4-(4,4,5,5-tetramethyl-1,3,2-dioxaborolan-2-yl)-3,6-dihydro-2H-pyridine-1-carboxylate (13.0 g, 42.2 mmol, CAS #286961-14-6) in dioxane (80 mL) H$_2$O (16 mL) was added K$_3$PO$_4$ (22.4 g, 105 mmol) and XPHOS-PD-G2 (1.39 g, 1.76 mmol), then the reaction mixture was stirred at 80° C. for 2 hrs. On completion, the residue was diluted with water (80 mL), then the residue was extracted with EA (3×100 mL). The combined organic layer was dried over Na$_2$SO$_4$, filtered and concentrated in vacuo to give a residue. The residue was purified by column chromatography (SiO$_2$, PE:EA=1:1, P1:Rf=0.3) to give the title compound (11.0 g, 94% yield) as white solid. $^1$H NMR (400 MHz, DMSO-d$_6$) δ 10.92 (s, 1H), 6.98-6.85 (m, 2H), 6.73 (dd, J=1.6, 7.2 Hz, 1H), 5.75 (s, 1H), 5.66 (s, 1H), 3.98 (s, 1H), 3.56 (t, J=5.2 Hz, 2H), 3.24 (s, 3H), 2.36 (d, J=1.6 Hz, 2H), 1.43 (s, 9H). LC-MS (ESI$^+$) m/z 330.0 (M+H)$^+$.

Step 2—Tert-butyl 3-hydroxy-4-(3-methyl-2-oxo-1H-benzimidazol-4-yl)piperidine-1-carboxylate. To a solution of BF$_3$·Et$_2$O (6.46 g, 45.5 mmol, 5.62 mL) in THF (50 mL) was added NaBH$_4$ (1.72 g, 45.5 mmol, 4.55 mL) at 0° C., then the mixture was allowed to warmed up to 25° C. over 1 hr. Next, the mixture was re-cooled to 0° C. and tert-butyl 4-(3-methyl-2-oxo-1H-benzimidazol-4-yl)-3,6-dihydro-2H-pyridine-1-carboxylate (5.00 g, 15.1 mmol) in THF (30 mL) was added. Then the mixture was allowed to warmed up to 25° C. and stirred for 2 hrs. The reaction mixture was cooled again to 0° C., then H$_2$O (15 mL), NaOH (10 M, 15.1 mL) and H$_2$O$_2$ (17.2 g, 151 mmol, 14.5 mL, 30% solution) were sequentially added. The resulting mixture was stirred at 65° C. for 13 hrs. On completion, the reaction mixture was quenched with Na$_2$SO$_3$ (25 mL) and NH$_4$Cl (25 mL), then the residue was extracted with EA (3×100 mL). The combined organic layer was dried over Na$_2$SO$_4$, filtered and concentrated in vacuo to give the title compound (7.00 g, quant. yield) as white solid. LC-MS (ESI$^+$) m/z 292.1 (M+H−56)$^+$.

Step 3—Tert-butyl 3-fluoro-4-(3-methyl-2-oxo-1H-benzimidazol-4-yl)piperidine-1-carboxylate. To a mixture of tert-butyl 3-hydroxy-4-(3-methyl-2-oxo-1H-benzimidazol-4-yl)piperidine-1-carboxylate (1.00 g, 2.88 mmol) in DCM (10 mL) was added DAST (1.39 g, 8.64 mmol, 1.14 mL) at 0° C., then the reaction mixture was stirred at 0° C. for 1 hr. On completion, the reaction mixture was quenched with MeOH (5 mL) and NaHCO$_3$ (10 mL), then the residue was extracted with DCM (3×100 mL). The residue was purified by prep-HPLC (column: Phenomenex luna C18 150*25 mm*10 um; mobile phase: [water(FA)-ACN]; B %: 39%-59%, 10 min) to give the title compound (200 mg, 20% yield) as white solid. LC-MS (ESI$^+$) m/z 699.3 (2M+H)$^+$.

3-[4-(3-Fluoro-4-piperidyl)-3-methyl-2-oxo-benzimidazol-1-yl]piperidine-2,6-dione (Intermediate CLX)

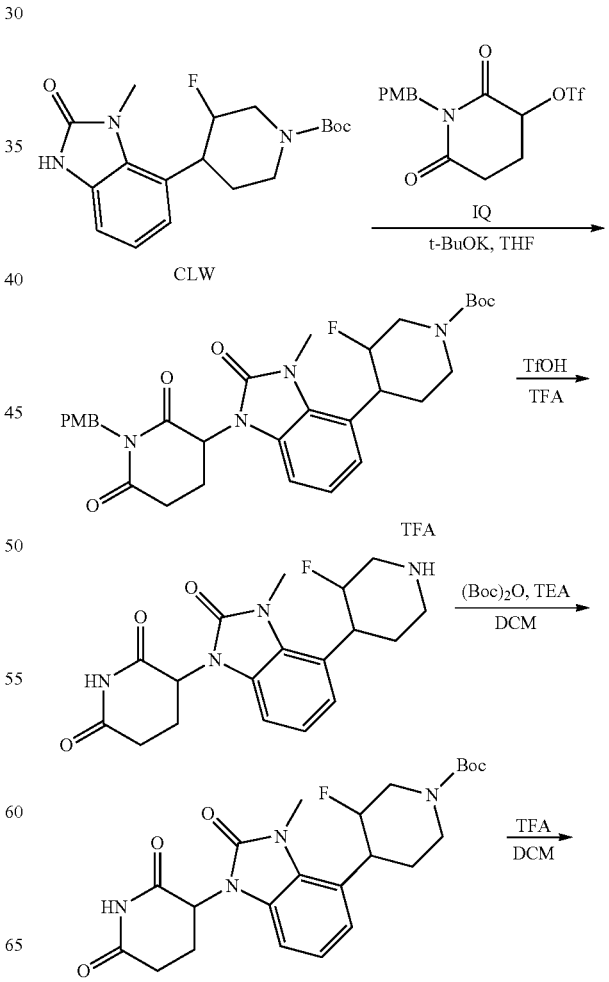

-continued

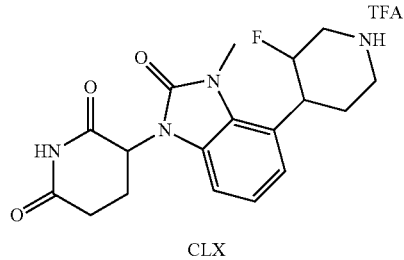

CLX

Step 1—Tert-butyl 3-fluoro-4-[1-[1-[(4-methoxyphenyl)methyl]-2,6-dioxo-3-piperidyl]-3-methyl-2-oxo-benzimidazol-4-yl]piperidine-1-carboxylate. To a solution of tert-butyl 3-fluoro-4-(3-methyl-2-oxo-1H-benzimidazol-4-yl)piperidine-1-carboxylate (200 mg, 572 umol, Intermediate CLW) in THF (5 mL) was added t-BuOK (128 mg, 1.14 mmol) and the mixture was stirred at 0° C. for 0.5 hr. Then [1-[(4-methoxyphenyl)methyl]-2,6-dioxo-3-piperidyl] trifluoromethanesulfonate (327 mg, 858 umol, Intermediate IQ) was added, and the reaction mixture was stirred at 0° C. for 1.5 hrs. On completion, the residue was diluted with water (50 mL), then the residue was extracted with EA (3×100 mL). The combined organic layer was dried over $Na_2SO_4$, filtered and concentrated in vacuo to give a residue. The residue was purified by column chromatography ($SiO_2$, PE:EA=2:1, P1:Rf=0.4) to give the title compound (300 mg, 90% yield) as white solid. LC-MS (ESI$^+$) m/z 581.2 (M+H)$^+$.

Step 2—3-[4-(3-Fluoro-4-piperidyl)-3-methyl-2-oxo-benzimidazol-1-yl]piperidine-2,6-dione. To a solution of tert-butyl 3-fluoro-4-[1-[1-[(4-methoxyphenyl)methyl]-2,6-dioxo-3-piperidyl]-3-methyl-2-oxo-benzimidazol-4-yl]piperidine-1-carboxylate (70.0 mg, 120 umol) in TFA (2.5 mL) was added TfOH (1.19 g, 7.93 mmol, 700 uL), then the reaction mixture was stirred at 70° C. for 2 hrs. On the completion, the reaction mixture was concentrated in vacuo to give the title compound (40.0 mg, 92% yield) as brown oil. LC-MS (ESI$^+$) m/z 361.1 (M+H)$^+$.

Step 3—Tert-butyl 4-[1-(2,6-dioxo-3-piperidyl)-3-methyl-2-oxo-benzimidazol-4-yl]-3-fluoro-piperidine-1-carboxylate. To a solution of 3-[4-(3-fluoro-4-piperidyl)-3-methyl-2-oxo-benzimidazol-1-yl]piperidine-2,6-dione (40.0 mg, 110 umol) in DCM (2 mL) was added TEA (11.2 mg, 110 umol, 15.4 uL) and Boc$_2$O (36.3 mg, 166 umol, 38.2 uL), then the reaction mixture was stirred at 25° C. for 1 hr. On the completion, the reaction mixture was concentrated in vacuo. The reaction mixture was triturated with PE:EA=6:1 and filtered to afford the title compound (50.0 mg, 98% yield) as a brown solid. LC-MS (ESI$^+$) m/z 461.1 (M+H)$^+$.

Step 4—3-[4-(3-Fluoro-4-piperidyl)-3-methyl-2-oxo-benzimidazol-1-yl]piperidine-2,6-dione. To a solution of tert-butyl 4-[1-(2,6-dioxo-3-piperidyl)-3-methyl-2-oxo-benzimidazol-4-yl]-3-fluoro-piperidine-1-carboxylate (50.0 mg, 108 umol) in DCM (2 mL) was added TFA (12.3 mg, 108 umol, 8.04 uL), the reaction mixture was then stirred at 25° C. for 1 hr. On the completion, the reaction mixture was concentrated in vacuo to give the title compound (50.0 mg, 97% yield, TFA) as brown oil. LC-MS (ESI$^+$) m/z 361.1 (M+H)$^+$.

Tert-butyl N-(3-fluoro-4-piperidyl)-N-methyl-carbamate (Intermediate CLY)

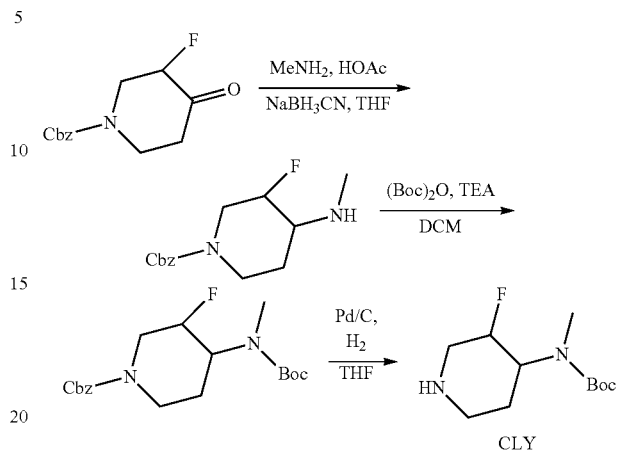

CLY

Step 1—Benzyl 3-fluoro-4-(methylamino)piperidine-1-carboxylate. To a solution of benzyl 3-fluoro-4-oxo-piperidine-1-carboxylate (1.00 g, 3.98 mmol, CAS #845256-59-9) and HOAc (526 mg, 8.76 mmol) in THF (10 mL) was added MeNH$_2$ (2 M, 6.2 mL), then the mixture was stirred at 25° C. for 1 hr. After that, NaBH$_3$CN (375 mg, 5.97 mmol) was added to the mixture and the reaction was stirred at 25° C. for 3 hrs. On completion, the reaction was quenched with saturated Na$_2$CO$_3$ (20 ml), concentrated in vacuo to give the aqueous phase, then extracted with EA (20 ml×4). The organic layers were combined, washed with brine (20 ml), dried over anhydrous Na$_2$SO$_4$, filtered and concentrated in vacuo to give the title compound (1.10 g, 71% yield) as yellow oil. LC-MS (ESI+) m/z 267.1 (M+H)$^+$.

Step 2—Benzyl 4-[tert-butoxycarbonyl(methyl)amino]-3-fluoro-piperidine-1-carboxylate. To a solution of benzyl 3-fluoro-4-(methylamino)piperidine-1-carboxylate (900 mg, 2.33 mmol), and TEA (706 mg, 6.98 mmol) in DCM (15 mL) was added tert-butoxycarbonyl tert-butyl carbonate (761 mg, 3.49 mmol), then the mixture was stirred at 25° C. for 16 hrs. On completion, the reaction was diluted with water (20 ml), and extracted with DCM (15 ml×3). The organic layers were combined, washed with brine (15 ml), dried over anhydrous Na$_2$SO$_4$, filtered and concentrated in vacuo to give a residue. The residue was purified by column chromatography (SiO$_2$, PE/EA=5/1) to give the title compound (800 mg, 93% yield) as yellow oil. $^1$H NMR (400 MHz, DMSO-d$_6$) δ 7.44-7.26 (m, 5H), 5.07 (s, 2H), 4.93-4.49 (m, 1H), 4.35-3.92 (m, 3H), 3.07-2.82 (m, 2H), 2.79-2.69 (m, 3H), 1.73-1.50 (m, 2H), 1.44-1.37 (m, 9H).

Step 3—Tert-butyl N-(3-fluoro-4-piperidyl)-N-methyl-carbamate. To a solution of benzyl 4-[tert-butoxycarbonyl(methyl)amino]-3-fluoro-piperidine-1-carboxylate (650 mg, 1.77 mmol) in THF (6 mL) was added Pd/C (300 mg, 10 wt %) under Ar atmosphere. Then the mixture was degassed under vacuum, purged with H$_2$ three times, stirred at 25° C. for 16 hrs under H$_2$ (15 psi) atmosphere. On completion, the reaction was filtered to give a filtrate, then concentrated in vacuo to give the title compound (410 mg, 99% yield) as brown oil. $^1$H NMR (400 MHz, CDCl$_3$) δ 5.04-4.37 (m, 1H), 4.33-3.80 (m, 1H), 3.47-2.98 (m, 2H), 2.97-2.77 (m, 3H), 2.77-2.59 (m, 1H), 2.08-1.73 (m, 1H), 1.69 (s, 2H), 1.67-1.54 (m, 1H), 1.51-1.41 (m, 9H).

3-[4-[3-Fluoro-4-(methylamino)-1-piperidyl]-5-methoxy-3-methyl-2-oxo-benzimidazol-1-yl]piperidine-2,6-dione (Intermediate CLZ)

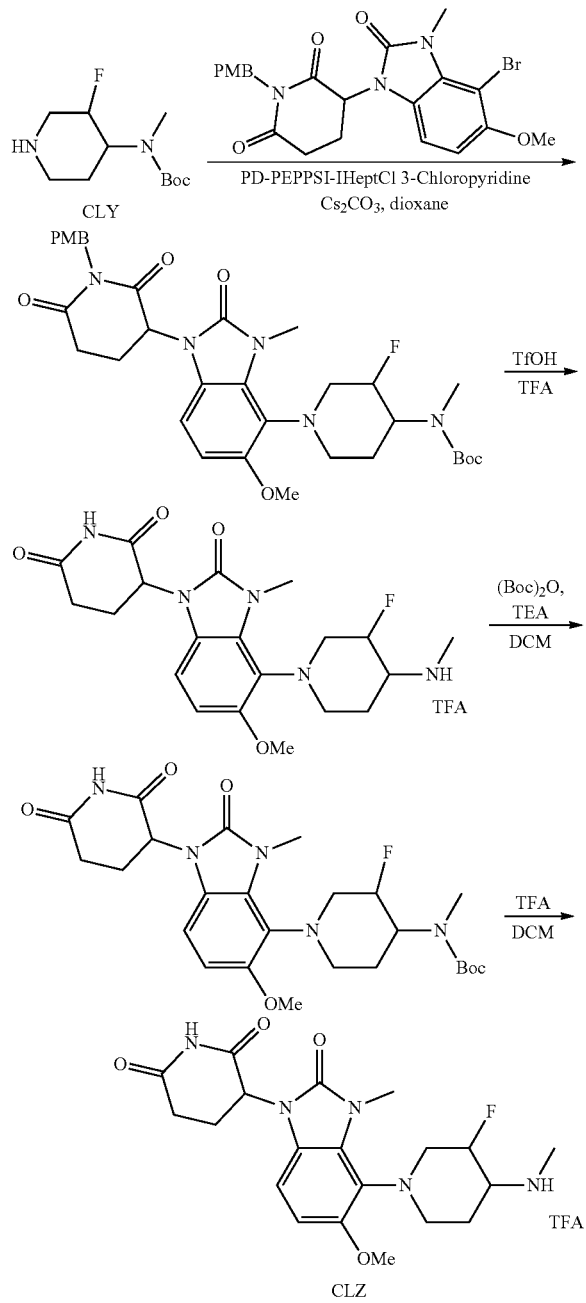

Step 1—Ethyl 2-[3-[3-[[tert-butoxycarbonyl(methyl)amino]methyl]azetidin-1-yl]isoxazol-5-yl]-3-methyl-butanoate. A mixture of tert-butyl N-(3-fluoro-4-piperidyl)-N-methyl-carbamate (100 mg, 430 umol, Intermediate CLY), 3-(4-bromo-5-methoxy-3-methyl-2-oxo-benzimidazol-1-yl)-1-[(4-methoxyphenyl) methyl]piperidine-2,6-dione (231 mg, 473 umol, synthesized via Steps 1-7 of Intermediate BRE), $Cs_2CO_3$ (701 mg, 2.15 mmol), and Pd-PEPPSI-IHeptCl (41.8 mg, 43.0 umol) in dioxane (5 mL) was degassed and purged with $N_2$ three times. Then the mixture was stirred at 100° C. for 16 hrs under $N_2$ atmosphere. On completion, the reaction mixture was filtered and concentrated in vacuo. The residue was purified by prep-HPLC (column: Phenomenex luna C18 150*25 mm*10 um; mobile phase: [water (FA)-ACN]; B %: 55%-85%, 10 min) to give the title compound (30 mg, 11% yield) as a white solid. $^1$H NMR (400 MHz, CDCl$_3$) δ 7.39-7.30 (m, 2H), 6.88-6.81 (m, 2H), 6.43 (dd, J=3.2, 8.4 Hz, 1H), 6.24 (t, J=8.0 Hz, 1H), 5.17 (d, J=5.2 Hz, 1H), 4.97 (s, 2H), 4.81-4.51 (m, 1H), 4.36-4.07 (m, 1H), 3.84-3.76 (m, 5H), 3.68 (s, 2H), 3.64-3.39 (m, 2H), 3.38-3.27 (m, 1H), 3.10-2.72 (m, 5H), 2.69-2.46 (m, 1H), 2.20-2.10 (m, 1H), 1.77 (d, J=3.6 Hz, 1H), 1.51 (s, 7H), 1.36-1.10 (m, 3H), 0.91-0.82 (m, 3H); LC-MS (ESI$^+$) m/z 640.4 (M+H)$^+$.

Step 2—3-[4-[3-fluoro-4-(methylamino)-1-piperidyl]-5-methoxy-3-methyl-2-oxo-benzimidazol-1-yl]piperidine-2,6-dione. To a solution of tert-butyl N-[3-fluoro-1-[5-methoxy-1-[1-[(4-methoxyphenyl)methyl]-2,6-dioxo-3-piperidyl]-3-methyl-2-oxo-benzimidazol-4-yl]-4-piperidyl]-N-methyl-carbamate (30 mg, 46.9 umol) in TfOH (0.06 mL) was added TFA (154 mg, 1.35 mmol), the reaction mixture was stirred at 70° C. for 2 hours. On completion, the reaction mixture was concentrated in vacuo to give the title compound (24 mg, 96% yield) as brown oil. LC-MS (ESI$^+$) m/z 420.2 (M+H)$^+$.

Step 3—Tert-butyl N-[1-[1-(2,6-dioxo-3-piperidyl)-5-methoxy-3-methyl-2-oxo-benzimidazol-4-yl]-3-fluoro-4-piperidyl]-N-methyl-carbamate. To a solution of 3-[4-[3-fluoro-4-(methylamino)-1-piperidyl]-5-methoxy-3-methyl-2-oxo-benzimidazol-1-yl]piperidine-2,6-dione (24 mg, 44.9 umol, TFA) in DCM (1 mL) was added TEA (13.6 mg, 135 umol) and (Boc)$_2$O (12.8 mg, 58.5 umol). The reaction mixture was stirred at 25° C. for 3 hrs. On completion, the reaction mixture was concentrated in vacuo to give the title compound (23 mg, 98% yield) as white solid. LC-MS (ESI$^+$) m/z 520.5 (M+H)$^+$.

Step 4—3-[4-[3-Fluoro-4-(methylamino)-1-piperidyl]-5-methoxy-3-methyl-2-oxo-benzimidazol-1-yl]piperidine-2,6-dione. To a solution of tert-butyl N-[1-[1-(2,6-dioxo-3-piperidyl)-5-methoxy-3-methyl-2-oxo-benzimidazol-4-yl]-3-fluoro-4-piperidyl]-N-methyl-carbamate (15 mg, 28.8 umol) in DCM (0.5 mL) was added TFA (231 mg, 2.03 mmol), then the reaction mixture was stirred at 25° C. for 2 hrs. On completion, the mixture was concentrated in vacuo to give the title compound (15 mg, 97% yield) as a white solid. $^1$H NMR (400 MHz, DMSO-d$_6$) δ 11.08 (s, 1H), 7.54 (d, J=8.0 Hz, 1H), 6.90 (d, J=8.4 Hz, 2H), 6.69 (d, J=8.4 Hz, 1H), 5.31 (dd, J=5.6, 12.8 Hz, 1H), 5.03-4.60 (m, 1H), 4.19-3.97 (m, 1H), 3.80 (s, 3H), 3.59-3.54 (m, 3H), 2.81 (s, 5H), 2.07-1.82 (m, 5H), 0.17--0.16 (m, 2H); LC-MS (ESI$^+$) m/z 420.3 (M+H)$^+$.

5-(2,2-Dimethylmorpholin-4-yl)pyrazolo[1,5-a]pyrimidine-3-carboxylic acid (Intermediate CMA)

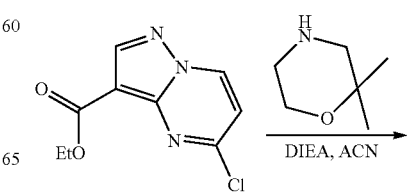

-continued

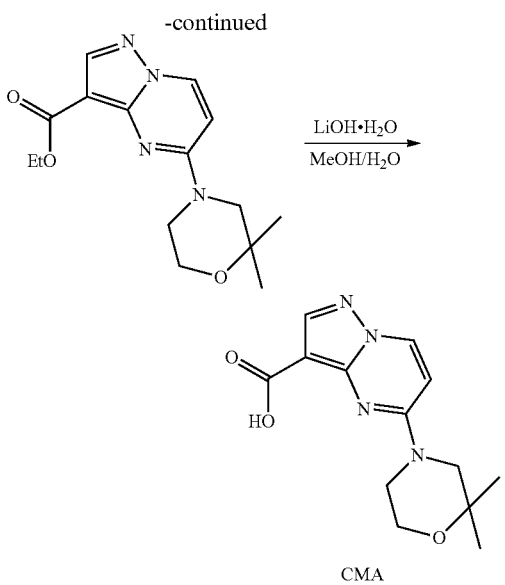

CMA

Step 1—Ethyl 5-(2,2-dimethylmorpholin-4-yl)pyrazolo[1,5-a]pyrimidine-3-carboxylate. A mixture of ethyl 5-chloropyrazolo[1,5-a]pyrimidine-3-carboxylate (1.00 g, 4.43 mmol), 2,2-dimethylmorpholine (1.02 g, 8.86 mmol, CAS #147688-58-2), and DIEA (1.15 g, 8.86 mmol) in ACN (12 mL) was degassed and purged with $N_2$ three times. Then the mixture was stirred at 60° C. for 2 hrs under $N_2$ atmosphere. On completion, the reaction mixture was concentrated under reduced pressure to remove solvent. The mixture was extracted with $H_2O$ (20 mL) and ethyl acetate (10 mL×3), the combined organic phase was dried over anhydrous sodium sulfate, filtered and concentrated to give the title compound (1.30 g, 96% yield) as a yellow oil. $^1H$ NMR (400 MHz, $CDCl_3$) δ 8.33-8.25 (m, 2H), 6.38 (d, J=8.0 Hz, 1H), 4.35 (q, J=7.2 Hz, 2H), 3.91-3.77 (m, 4H), 3.58 (s, 2H), 1.40 (t, J=7.2 Hz, 3H), 1.32-1.28 (m, 6H); LC-MS (ESI$^+$) m/z 305.1 (M+H)$^+$.

Step 2—5-(2,2-Dimethylmorpholin-4-yl)pyrazolo[1,5-a]pyrimidine-3-carboxylic acid. To a solution of ethyl 5-(2,2-dimethylmorpholin-4-yl)pyrazolo[1,5-a]pyrimidine-3-carboxylate (500 mg, 1.64 mmol) in MeOH (5 mL) and $H_2O$ (2 mL) was added LiOH·$H_2O$ (206 mg, 4.93 mmol), then mixture was stirred at 60° C. for 1 hr. On completion, the reaction mixture was concentrated under reduced pressure to remove solvent. Then the residue was acidified with 3N HCl until the pH=4-5, filtered and concentrated in vacuo to give the title compound (400 mg, 88% yield) as a white solid. $^1H$ NMR (400 MHz, DMSO-$d_6$) δ 8.70 (d, J=8.0 Hz, 1H), 8.14 (s, 1H), 6.83 (d, J=8.0 Hz, 1H), 3.73 (d, J=4.4 Hz, 4H), 3.57 (s, 2H), 1.17 (s, 6H); LC-MS (ESI$^+$) m/z 276.8 (M+H)$^+$.

3-[4-[4-[[4-[4-Amino-3-(difluoromethyl)pyrazol-1-yl]cyclohexyl]methyl-methyl-amino]-3,3-difluoro-1-piperidyl]-3-methyl-2-oxo-benzimidazol-1-yl]piperidine-2,6-dione (Intermediate CMB)

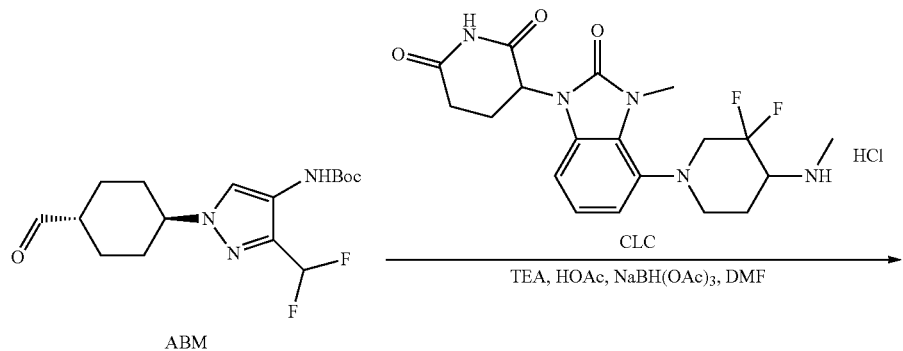

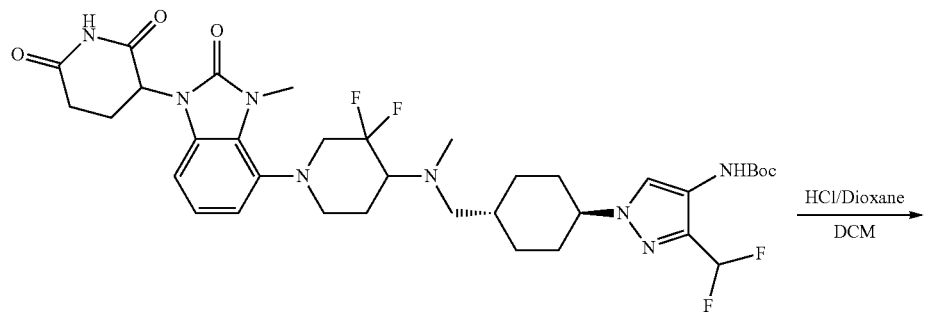

-continued

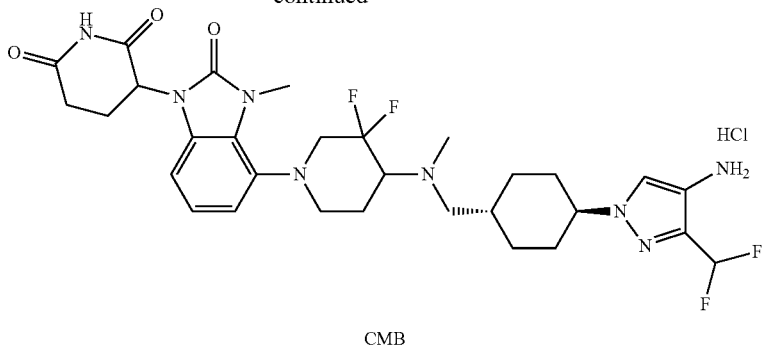

CMB

Step 1—Tert-butyl N-[3-(difluoromethyl)-1-[4-[[[1-[1-(2,6-dioxo-3-piperidyl)-3-methyl-2-oxo-benzimidazol-4-yl]-3,3-difluoro-4-piperidyl]-methyl-amino]methyl]cyclohexyl]pyrazol-4-yl]carbamate. To a solution of 3-[4-[3,3-difluoro-4-(methylamino)-1-piperidyl]-3-methyl-2-oxo-benzimidazol-1-yl]piperidine-2,6-dione (160 mg, 360 umol, HCl, Intermediate CLC) in DMF (5 mL) was added TEA (73.0 mg, 721 umol), then stirred at −10° C. for 15 mins. After that, HOAc (21.7 mg, 360 umol) and tert-butyl N-[3-(difluoromethyl)-1-(4-formylcyclohexyl)pyrazol-4-yl]carbamate (166 mg, 433 umol, Intermediate ABM) were added and the mixture was stirred at −10° C. for 45 mins. Next, NaBH(OAc)$_3$ (191 mg, 901 umol) was added to the mixture and the reaction was stirred at −10° C. for 1 hr. On completion, the reaction was diluted with water (40 ml), and extracted with EA (20 ml×3). The organic layers were combined, washed with brine (15 ml), dried over anhydrous Na$_2$SO$_4$, filtered and concentrated in vacuo to give a residue. The residue was purified by column chromatography (SiO$_2$, PE/EA=5/1 to 1/1) to give the title compound (120 mg, 38% yield) as yellow solid. $^1$H NMR (400 MHz, DMSO-d$_6$) δ 11.10 (s, 1H), 8.91 (s, 1H), 7.88 (s, 1H), 7.03-6.82 (m, 4H), 5.36 (dd, J=5.2, 12.8 Hz, 1H), 4.18-4.07 (m, 1H), 3.62 (s, 3H), 3.57 (s, 1H), 3.26-3.12 (m, 3H), 3.07-2.83 (m, 3H), 2.77-2.55 (m, 3H), 2.43 (s, 3H), 2.06-1.94 (m, 5H), 1.92-1.57 (m, 5H), 1.44 (s, 9H), 1.07-0.95 (m, 2H); LC-MS (ESI+) m/z 735.3 (M+H)$^+$.

Step 2—3-[4-[4-[[4-[4-Amino-3-(difluoromethyl)pyrazol-1-yl]cyclohexyl]methyl-methyl-amino]-3,3-difluoro-1-piperidyl]-3-methyl-2-oxo-benzimidazol-1-yl]piperidine-2,6-dione. The solution of tert-butyl N-[3-(difluoromethyl)-1-[4-[[[1-[1-(2,6-dioxo-3-piperidyl)-3-methyl-2-oxo-benzimidazol-4-yl]-3,3-difluoro-4-piperidyl]-methyl-amino]methyl]cyclohexyl]pyrazol-4-yl]carbamate (70 mg, 80.2 umol) in DCM (0.5 mL) and HCl/dioxane (2 mL) was stirred at 25° C. for 3 hrs. On completion, the reaction was concentrated in vacuo to give the title compound (55 mg, 89% yield, HCl) as yellow solid. LC-MS (ESI+) m/z 635.4 (M+H)$^+$.

3-[4-[4-(3,3-Difluoro-4-piperidyl)piperazin-1-yl]-3-methyl-2-oxo-benzimidazol-1yl] piperidine-2,6-dione (Intermediate CMC)

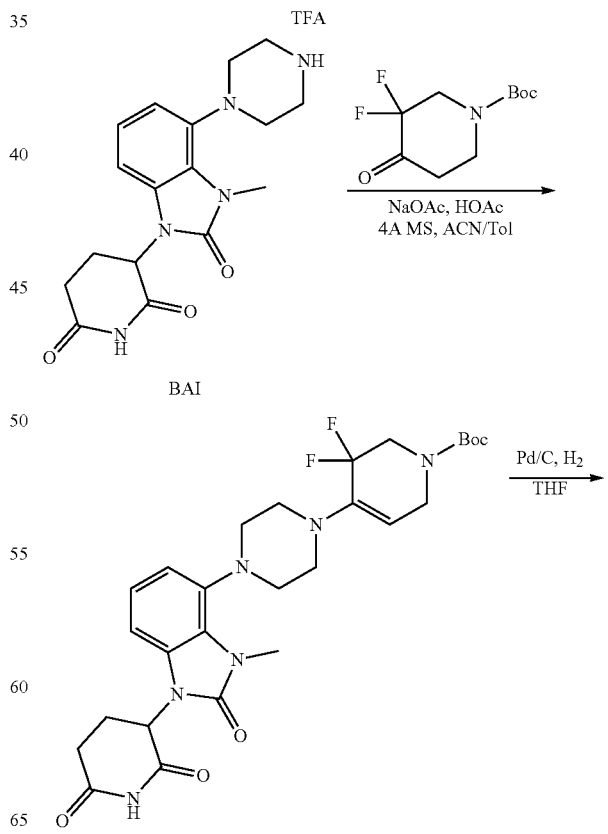

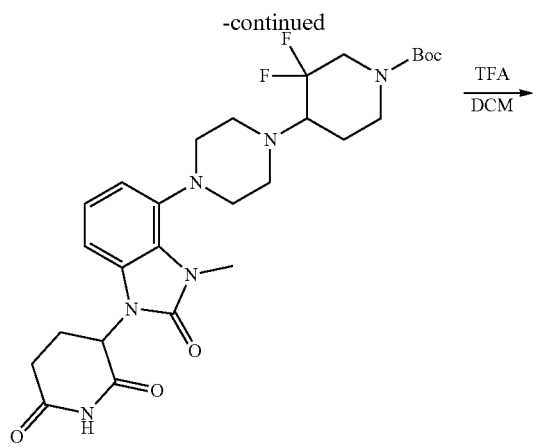

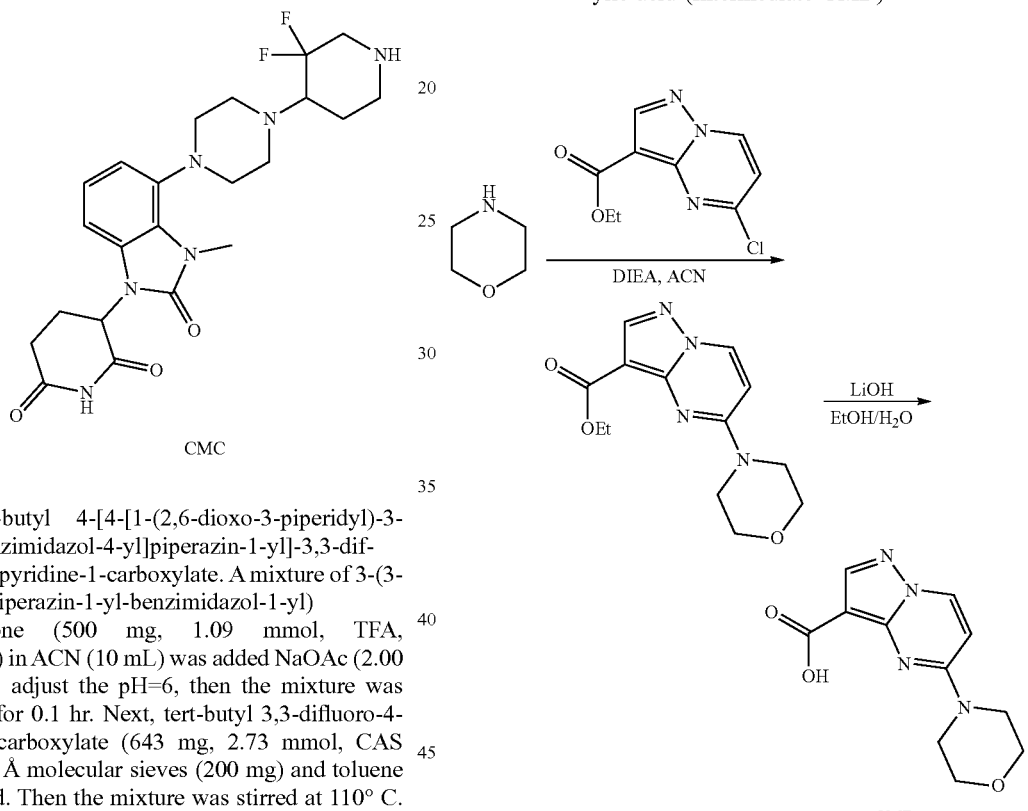

CMC

Step 1—Tert-butyl 4-[4-[1-(2,6-dioxo-3-piperidyl)-3-methyl-2-oxo-benzimidazol-4-yl]piperazin-1-yl]-3,3-difluoro-2,6-dihydropyridine-1-carboxylate. A mixture of 3-(3-methyl-2-oxo-4-piperazin-1-yl-benzimidazol-1-yl)piperidine-2,6-dione (500 mg, 1.09 mmol, TFA, Intermediate BAI) in ACN (10 mL) was added NaOAc (2.00 g, 24.4 mmol) to adjust the pH=6, then the mixture was stirred at 25° C. for 0.1 hr. Next, tert-butyl 3,3-difluoro-4-oxo-piperidine-1-carboxylate (643 mg, 2.73 mmol, CAS #346593-03-1), 4 Å molecular sieves (200 mg) and toluene (5 mL) was added. Then the mixture was stirred at 110° C. for 72 hrs. On completion, the reaction mixture was filtered and concentrated in vacuo to give a residue. Then the residue was purified by column chromatography (SiO₂, PE:EA=5:1 to 0:1) to give the title compound (230 mg, 38% yield) as yellow solid. LC-MS (ESI⁺) m/z 561.1 (M+H)⁺.

Step 2—Tert-butyl 4-[4-[1-(2,6-dioxo-3-piperidyl)-3-methyl-2-oxo-benzimidazol-4-yl]piperazin-1-yl]-3,3-difluoro-piperidine-1-carboxylate. To a solution of tert-butyl 4-[4-[1-(2,6-dioxo-3-piperidyl)-3-methyl-2-oxo-benzimidazol-4-yl]piperazin-1-yl]-3,3-difluoro-2,6-dihydropyridine-1-carboxylate (200 mg, 357 umol) in THF (5 mL) was added Pd/C (200 mg, 10 wt %) under N₂ atmosphere. The suspension was degassed and purged with H₂ three times. Then the mixture was stirred under H₂ (15 Ppsi) at 25° C. for 4 hrs. On completion, the reaction mixture was filtered and concentrated in vacuo to give the title compound (200 mg, 99% yield) as yellow liquid. $^1$H NMR (400 MHz, DMSO-$d_6$) δ 11.09 (s, 1H), 7.00-6.91 (m, 2H), 6.87 (s, 1H), 5.35 (dd, J=5.6, 12.4 Hz, 1H), 3.66-3.60 (m, 3H), 3.17-3.03 (m, 4H), 2.98-2.90 (m, 4H), 2.88-2.80 (m, 3H), 2.71-2.62 (m, 2H), 2.61-2.57 (m, 1H), 2.18 (s, 2H), 2.03-1.96 (m, 1H), 1.87-1.79 (m, 1H), 1.78-1.65 (m, 1H), 1.35 (s, 9H); LC-MS (ESI⁺) m/z 563.3 (M+H)⁺.

Step 3—3-[4-[4-(3,3-Difluoro-4-piperidyl)piperazin-1-yl]-3-methyl-2-oxo-benzimidazol-1yl] piperidine-2,6-dione. A mixture of tert-butyl 4-[4-[1-(2,6-dioxo-3-piperidyl)-3-methyl-2-oxo-benzimidazol-4-yl]piperazin-1-yl]-3,3-difluoro-piperidine-1-carboxylate (50.0 mg, 88.9 umol) in DCM (1 mL) was added TFA (0.2 mL), then the mixture was stirred at 25° C. for 1 hr. On completion, the reaction mixture was concentrated in vacuo to give the title compound (51.0 mg, 99% yield, TFA) as yellow liquid. LC-MS (ESI⁺) m/z 463.3 (M+H)⁺.

5-Morpholinopyrazolo[1,5-a]pyrimidine-3-carboxylic acid (Intermediate CMD)

CMD

Step 1—Ethyl 5-morpholinopyrazolo[1,5-a]pyrimidine-3-carboxylate. To a solution of morpholine (472 mg, 5.42 mmol) in ACN (10 mL) was added ethyl 5-chloropyrazolo[1,5-a]pyrimidine-3-carboxylate (815 mg, 3.61 mmol) and DIEA (1.40 g, 10.8 mmol). The mixture was then stirred at 60° C. for 12 hrs. On completion, the reaction mixture was extracted with ethyl acetate (20 mL×3), the combined organic phase was washed with H₂O (30 mL), dried over anhydrous sodium sulfate, filtered and concentrated to give a residue. The residue was purified by column chromatography (SiO₂, Petroleum ether/Ethyl acetate=1/1 to 1/3) to give the title compound (961 mg, 96% yield) as a light yellow solid. $^1$H NMR (400 MHz, DMSO-$d_6$): δ8.76 (d, J=8.0 Hz, 1H), 8.22 (s, 1H), 6.86 (d, J=8.0 Hz, 1H), 4.20 (m, J=7.2 Hz, 2H), 3.75 (m, J=4.4 Hz, 4H), 3.73-3.67 (m, 4H), 1.28 (t, J=7.2 Hz, 3H). LC-MS (ESI⁺) m/z 277.2 (M+H)⁺.

Step 2—5-Morpholinopyrazolo[1,5-a]pyrimidine-3-carboxylic acid. To a solution of ethyl 5-morpholinopyrazolo

[1,5-a]pyrimidine-3-carboxylate (50 mg, 180 umol) in EtOH (1 mL) was added LiOH·H$_2$O (22.7 mg, 542 umol) and H$_2$O (0.2 mL). The mixture was then stirred at 60° C. for 12 hrs. On completion, the mixture was filtered and concentrated to give the title compound (43 mg, 95.72% yield) as a white solid. LC-MS (ESI$^+$) m/z 249.0 (M+H)$^+$.

3-[3-methyl-5-[4-(5-oxa-2-azaspiro[3.4]octan-7-ylmethyl)piperazin-1-yl]-2-oxo-benzimidazol-1-yl]piperidine-2,6-dione (Intermediate CME)

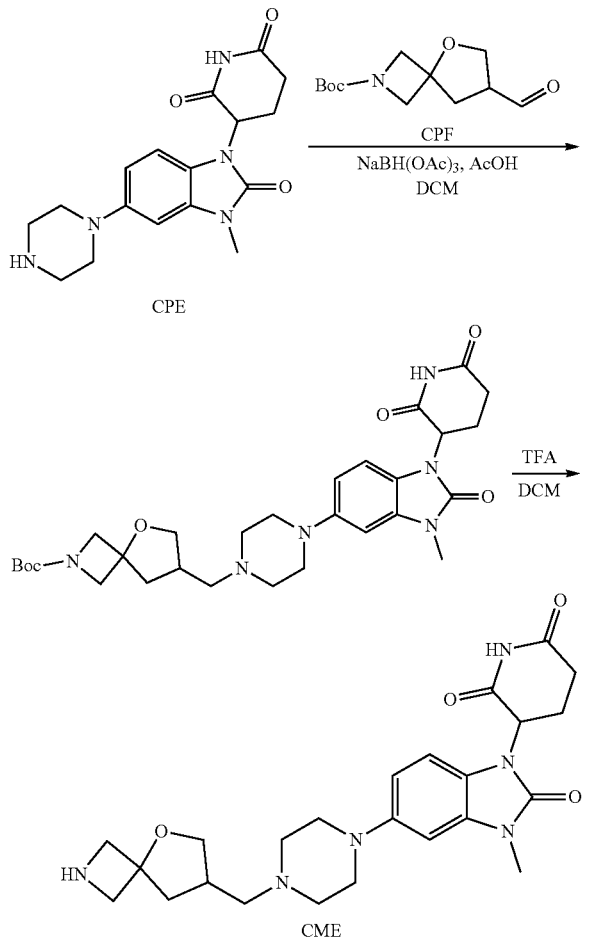

Step 1—Tert-butyl 7-((4-(1-(2,6-dioxopiperidin-3-yl)-3-methyl-2-oxo-2,3-dihydro-1H-benzo[d]imidazol-5-yl)piperazin-1-yl)methyl)-5-oxa-2-azaspiro[3.4]octane-2-carboxylate. To a solution of tert-butyl 7-formyl-5-oxa-2-azaspiro[3.4]octane-2-carboxylate (543 mg, 2.25 mmol, Intermediate CPF) and 3-(3-methyl-2-oxo-5-(piperazin-1-yl)-2,3-dihydro-1H-benzo[d]imidazol-1-yl)piperidine-2,6-dione (774 mg, 2.25 mmol, Intermediate CPE) in DCM (30 mL) was added AcOH (406 mg, 6.76 mmol) and NaBH(OAc)$_3$ (1.43 g, 6.76 mmol) at 20° C. under nitrogen flow. Then the reaction was stirred at 20° C. for 10 h under nitrogen atmosphere. On completion, the reaction was poured into NaHCO$_3$ (sat. aq. 40 mL) and extracted with DCM (50 mL×2). The combined organic phase is washed with brine (30 mL×2), dried over Na$_2$SO$_4$, filtered and concentrated to give a residue. The residue was purified by column chromatography on silica gel (eluted with dichloromethane:ethyl acetate=100:1 to 100:50) to give the title compound (947.62 mg, 55% yield) as a pink solid. LC-MS (ESI$^+$) m/z 569.3 (M+H)$^+$; $^1$H NMR (400 MHz, DMSO-d$_6$) δ=11.06 (s, 1H), 6.94 (d, J=8.8 Hz, 1H), 6.84 (d, J=2.0 Hz, 1H), 6.63 (dd, J=2.0, 8.8 Hz, 1H), 5.29 (dd, J=5.6, 12.8 Hz, 1H), 3.98-3.81 (m, 5H), 3.80-3.75 (m, 1H), 3.50 (dd, J=6.4, 8.4 Hz, 1H), 3.31 (s, 3H), 3.08 (br s, 4H), 3.00-2.82 (m, 2H), 2.77-2.55 (m, 5H), 2.36-2.28 (m, 2H), 2.23 (br dd, J=7.6, 12.8 Hz, 1H), 2.03-1.95 (m, 1H), 1.81 (dd, J=7.2, 12.8 Hz, 1H), 1.38 (s, 9H).

Step 2—3-(5-(4-(5-oxa-2-azaspiro[3.4]octan-7-ylmethyl)piperazin-1-yl)-3-methyl-2-oxo-2,3-dihydro-1H-benzo[d]imidazol-1-yl)piperidine-2,6-dione. To a solution of tert-butyl 7-((4-(1-(2,6-dioxopiperidin-3-yl)-3-methyl-2-oxo-2,3-dihydro-1H-benzo[d]imidazol-5-yl)piperazin-1-yl)methyl)-5-oxa-2-azaspiro[3.4]octane-2-carboxylate (200 mg, 351 umol) in DCM (5 mL) was added TFA (1.54 g, 13.51 mmol) at 20° C. under nitrogen flow. Then the reaction was stirred at 20° C. for 10 h under nitrogen atmosphere. On completion, the reaction was concentrated to give a residue. The residue was purified by prep-HPLC (EC978-453-P1A) column: Phenomenex Luna C18 150*25 mm*10 um; mobile phase: [water(FA)-ACN]; B %: 0%-12%, 10 min to give the title compound (56.1 mg, 33% yield) as yellow solid. LC-MS (ESI$^+$) m/z 469.4 (M+H)$^+$; $^1$H NMR (400 MHz, DMSO-d$_6$) δ=11.07 (s, 1H), 8.81 (br d, J=4.8 Hz, 2H), 6.98 (br d, J=8.8 Hz, 1H), 6.90 (br s, 1H), 6.68 (br d, J=8.0 Hz, 1H), 5.31 (dd, J=5.6, 12.8 Hz, 1H), 4.08-4.03 (m, 2H), 4.00-3.90 (m, 2H), 3.60-3.50 (m, 2H), 3.32 (br s, 3H), 3.18-2.97 (m, 4H), 2.96-2.84 (m, 2H), 2.77-2.59 (m, 4H), 2.54-2.52 (m, 5H), 2.04-1.96 (m, 1H), 1.92 (dd, J=7.6, 13.2 Hz, 1H).

5-[(1S,4S)-2-oxa-5-azabicyclo[2.2.1]heptan-5-yl]pyrazolo[1,5-a]pyrimidine-3-carboxylic acid (Intermediate CMG)

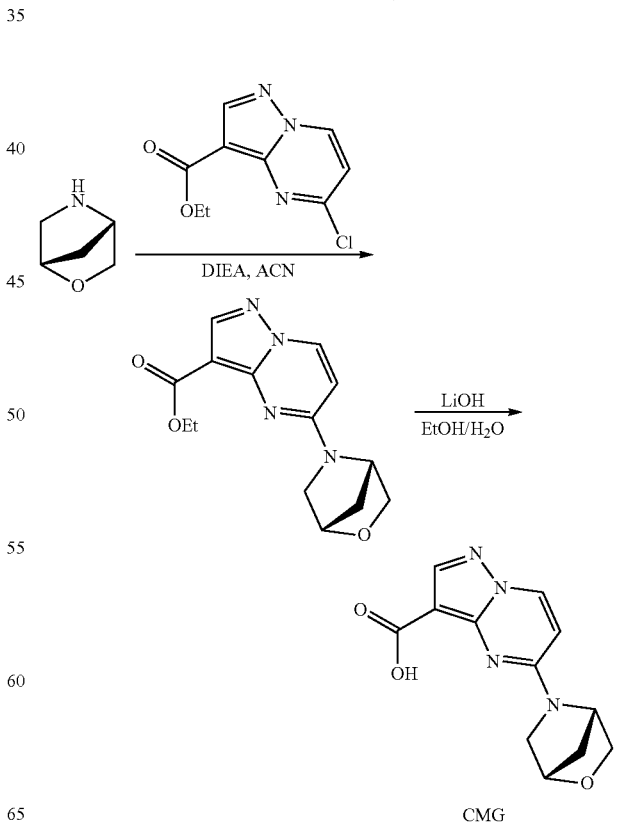

Step 1—Ethyl 5-[(1S,4S)-2-oxa-5-azabicyclo[2.2.1]heptan-5-yl]pyrazolo[1,5-a]pyrimidine-3-carboxylate. A mixture of (1S,4S)-2-oxa-5-azabicyclo[2.2.1]heptane (200 mg, 2.02 mmol, CAS #279-33-4), ethyl 5-chloropyrazolo[1,5-a]pyrimidine-3-carboxylate (455 mg, 2.02 mmol) and DIEA (782 mg, 6.05 mmol) in ACN (10 mL) was degassed and purged with N₂ three times. Then the mixture was stirred at 70° C. for 16 hrs. On completion, the reaction mixture was concentrated in vacuo. The residue was purified by column chromatography (SiO₂, Petroleum ether/Ethyl acetate=10/1 to 3/1) to give the title compound (410 mg, 70% yield) as a black solid. ¹H NMR (400 MHz, DMSO-d₆) δ 8.71 (d, J=7.6 Hz, 1H), 8.18 (s, 1H), 6.98-6.29 (m, 1H), 5.25-4.94 (m, 1H), 4.82-4.63 (m, 1H), 4.29-4.09 (m, 1H), 4.31-4.09 (m, 1H), 3.91-3.64 (m, 2H), 3.59-3.45 (m, 2H), 2.01-1.87 (m, 2H), 1.28 (t, J=7.2 Hz, 3H); LC-MS (ESI⁺) m/z 289.2 (M+H)⁺.

Step 2—5-[(1S,4S)-2-oxa-5-azabicyclo[2.2.1]heptan-5-yl]pyrazolo[1,5-a]pyrimidine-3-carboxylic acid. To a solution of ethyl 5-[(1S,4S)-2-oxa-5-azabicyclo[2.2.1]heptan-5-yl]pyrazolo[1,5-a]pyrimidine-3-carboxylate (100 mg, 347 umol) in H₂O (0.4 mL) and MeOH (2 mL) was added LiOH·H₂O (72.7 mg, 1.73 mmol). Then the reaction mixture was stirred at 50° C. for 2 hrs, then the reaction mixture was stirred at 70° C. for 2 hrs. On completion, the reaction mixture was concentrated in vacuo to give the title compound (24 mg, 96% yield) as a black solid. LC-MS (ESI⁺) m/z 261.2 (M+H)⁺.

5-(3-Oxa-6-azabicyclo[3.1.1]heptan-6-yl)pyrazolo[1,5-a]pyrimidine-3-carboxylic acid (Intermediate CMH)

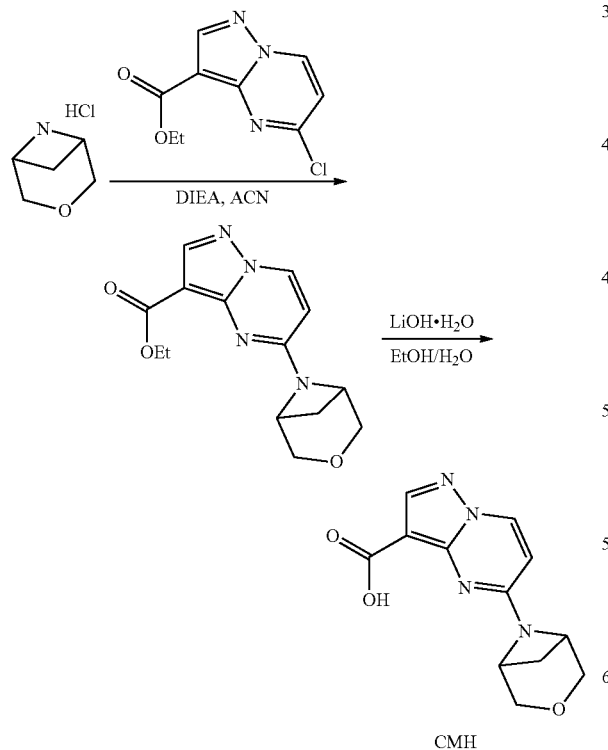

Step 1—Ethyl 5-(3-oxa-6-azabicyclo[3.1.1]heptan-6-yl)pyrazolo[1,5-a]pyrimidine-3-carboxylate. To a suspension of 3-oxa-6-azabicyclo[3.1.1]heptane (200 mg, 886 umol, CAS #286390-20-3), and ethyl 5-chloropyrazolo[1,5-a]pyrimidine-3-carboxylate (144 mg, 1.06 mmol) in ACN (10 mL) was added DIEA (286 mg, 2.22 mmol). Then the mixture was stirred at 80° C. for 2 hrs under N₂ atmosphere. On completion, the reaction was cooled to room temperature, concentrated in vacuo to give a residue. The residue was diluted with water (10 mL), and extracted with EA (15 mL×3). The organic layers were combined, washed with brine (15 mL), dried over anhydrous Na₂SO₄, filtered and concentrated in vacuo to give the title compound (180 mg, 67% yield) as yellow solid. ¹H NMR (400 MHz, DMSO-d₆) δ 8.78 (d, J=8.0 Hz, 1H), 8.23 (s, 1H), 6.60 (d, J=7.2 Hz, 1H), 4.56-4.51 (m, 2H), 4.20-4.15 (m, 2H), 3.81 (d, J=10.0 Hz, 2H), 3.26 (d, J=5.2 Hz, 3H), 2.77-2.67 (m, 1H), 1.87-1.85 (d, J=8.0 Hz, 1H), 1.25 (t, J=14.0 Hz, 3H); LC-MS (ESI⁺) m/z 289.0 (M+H)⁺.

Step 2—5-(3-Oxa-6-azabicyclo[3.1.1]heptan-6-yl)pyrazolo[1,5-a]pyrimidine-3-carboxylic acid. To a solution of ethyl 5-(3-oxa-6-azabicyclo[3.1.1]heptan-6-yl)pyrazolo[1,5-a]pyrimidine-3-carboxylate (180 mg, 624 umol) in EtOH (2.50 mL) and H₂O (0.50 mL) was added LiOH·H₂O (52.4 mg, 1.25 mmol). Then the mixture was stirred at 50° C. for 12 hrs. On completion, the reaction was cooled to rt, and concentrated in vacuo to give a residue. The residue was diluted with water (10 mL), acified by 3N HCl to adjust pH=5, then extracted with DCM (10 mL×5). The organic layers were combined, washed with brine (15 mL), dried over anhydrous Na₂SO₄ the reaction mixture was concentrated in vacuo to give the title compound (150 mg, 91% yield) as a gray solid. ¹H NMR (400 MHz, DMSO-d₆) δ 11.69 (s, 1H), 8.76 (d, J=8.0 Hz, 1H), 8.21 (s, 1H), 6.57 (d, J=4.0 Hz, 1H), 4.62 (s, 2H), 4.50-4.03 (m, J=3.2 Hz, 2H), 3.81-3.78 (m, J=12.0 Hz, 2H), 2.77-2.74 (m, 1H), 1.90-1.85 (d, J=10.8 Hz, 1H); LC-MS (ESI⁺) m/z 261.0 (M+H)⁺.

3-(4-(3-(((3S,4S)-3-fluoropiperidin-4-yl)oxy)prop-1-yn-1-yl)-3-methyl-2-oxo-2,3-dihydro-1H-benzo[d]imidazol-1-yl)piperidine-2,6-dione (Intermediate CMI)

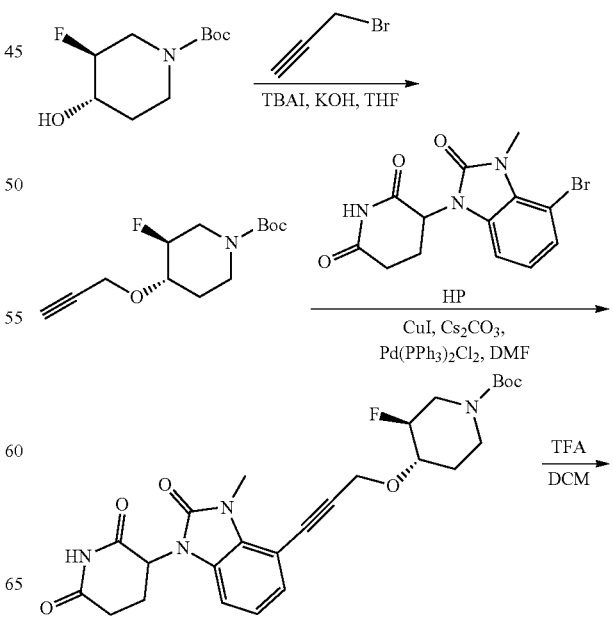

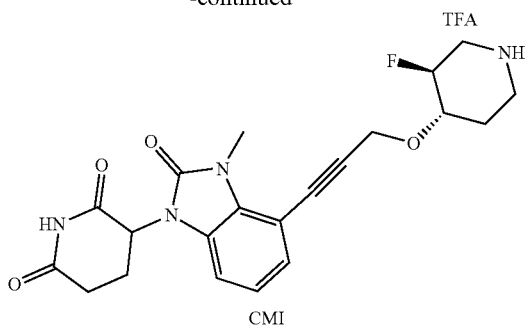

Step 1—Tert-butyl (3S,4S)-3-fluoro-4-(prop-2-yn-1-yloxy)piperidine-1-carboxylate. To a mixture of tert-butyl (3S,4S)-3-fluoro-4-hydroxy-piperidine-1-carboxylate (500 mg, 2.28 mmol, CAS #1174020-44-0) and 3-bromoprop-1-yne (509 mg, 3.42 mmol) in THF (8 mL) was added TBAI (85.0 mg, 228 umol) and KOH (192 mg, 3.42 mmol). The mixture was then stirred at 25° C. for 12 hrs. On completion, the reaction mixture was concentrated under reduced pressure to remove THF. The residue was diluted with water (50 mL) and extracted with EA (40 mL×3). The combined organic layers were washed with brine (50 mL), dried over anhydrous sodium sulfate, filtered and concentrated under reduced pressure to give a residue. The residue was purified by column chromatography (SiO$_2$, Petroleum ether/Ethyl acetate=1/0 to 10/1) to give the title compound (550 mg, 94% yield) as yellow oil. $^1$H NMR (400 MHz, CDCl$_3$) δ 4.55-4.37 (m, 1H), 4.31 (d, J=2.4 Hz, 2H), 3.97-3.83 (m, 1H), 3.82-3.71 (m, 1H), 3.69-3.59 (m, 1H), 3.42-3.27 (m, 1H), 3.26-3.09 (m, 1H), 2.46 (t, J=2.4 Hz, 1H), 2.08-1.95 (m, 1H), 1.61 (d, J=6.8 Hz, 1H), 1.47 (s, 9H).

Step 2—Tert-butyl (3S,4S)-4-((3-(1-(2,6-dioxopiperidin-3-yl)-3-methyl-2-oxo-2,3-dihydro-1H-benzo[d]imidazol-4-yl)prop-2-yn-1-yl)oxy)-3-fluoropiperidine-1-carboxylate. A mixture of tert-butyl (3S,4S)-3-fluoro-4-prop-2-ynoxy-piperidine-1-carboxylate (550 mg, 2.14 mmol), 3-(4-bromo-3-methyl-2-oxo-benzimidazol-1-yl)piperidine-2,6-dione (506 mg, 1.50 mmol, Intermediate HP), CuI (21.0 mg, 107 umol), Pd(PPh$_3$)$_2$Cl$_2$ (75.0 mg, 107 umol), 4 Å molecular sieves (500 mg, 2.14 mmol) and Cs$_2$CO$_3$ (2.09 g, 6.41 mmol) in DMF (10 mL) was degassed and purged with N$_2$ three times. Then the mixture was stirred at 80° C. for 4 hrs under N$_2$ atmosphere. On completion, the reaction mixture was filtered, and the filtrate diluted with water (50 mL) and extracted with EA (40 mL×3). The combined organic layers were washed with brine (50 mL), dried over Na$_2$SO$_4$, filtered and concentrated under reduced pressure to give a residue. The residue was purified by reversed-phase HPLC (0.1% FA condition, 0-60% ACN) to give the title compound (234 mg, 20% yield) as an off-white solid. $^1$H NMR (400 MHz, CDCl$_3$) δ 8.04 (s, 1H), 7.18 (d, J=8.0 Hz, 1H), 7.01 (t, J=8.0 Hz, 1H), 6.78 (d, J=8.0 Hz, 1H), 5.20 (dd, J=5.2, 12.8 Hz, 1H), 4.72-4.28 (m, 3H), 4.05-3.88 (m, 1H), 3.86-3.80 (m, 1H), 3.78 (s, 3H), 3.75-3.68 (m, 1H), 3.40-3.07 (m, 2H), 3.02-2.91 (m, 1H), 2.91-2.67 (m, 2H), 2.29-2.19 (m, 1H), 2.12-1.86 (m, 1H), 1.47 (s, 9H); LCMS (ESI$^+$) m/z 459.0 (M−56+H)$^+$.

Step 3—3-(4-(3-(((3S,4S)-3-fluoropiperidin-4-yl)oxy)prop-1-yn-1-yl)-3-methyl-2-oxo-2,3-dihydro-1H-benzo[d]imidazol-1-yl)piperidine-2,6-dione. To a solution of tert-butyl (3S,4S)-4-[3-[1-(2,6-dioxo-3-piperidyl)-3-methyl-2-oxo-benzimidazol-4-yl]prop-2-ynoxy]-3-fluoro-piperidine-1-carboxylate (200 mg, 389 umol) in DCM (3 mL) was added TFA (1.54 g, 13.51 mmol). The mixture was stirred at 25° C. for 0.5 hr. On completion, the reaction mixture was concentrated under reduced pressure to give the title compound (205 mg, 99% yield, TFA) as yellow oil. LCMS (ESI$^+$) m/z 415.0 (M+H)$^+$.

3-(4-(3-(((3S,4S)-1-(((1r,4S)-4-(4-amino-3-(difluoromethyl)-1H-pyrazol-1-yl)cyclohexyl) methyl)-3-fluoropiperidin-4-yl)oxy)prop-1-yn-1-yl)-3-methyl-2-oxo-2,3-dihydro-1H-benzo[d]imidazole-1-yl)piperidine-2,6-dione (Intermediate CMJ)

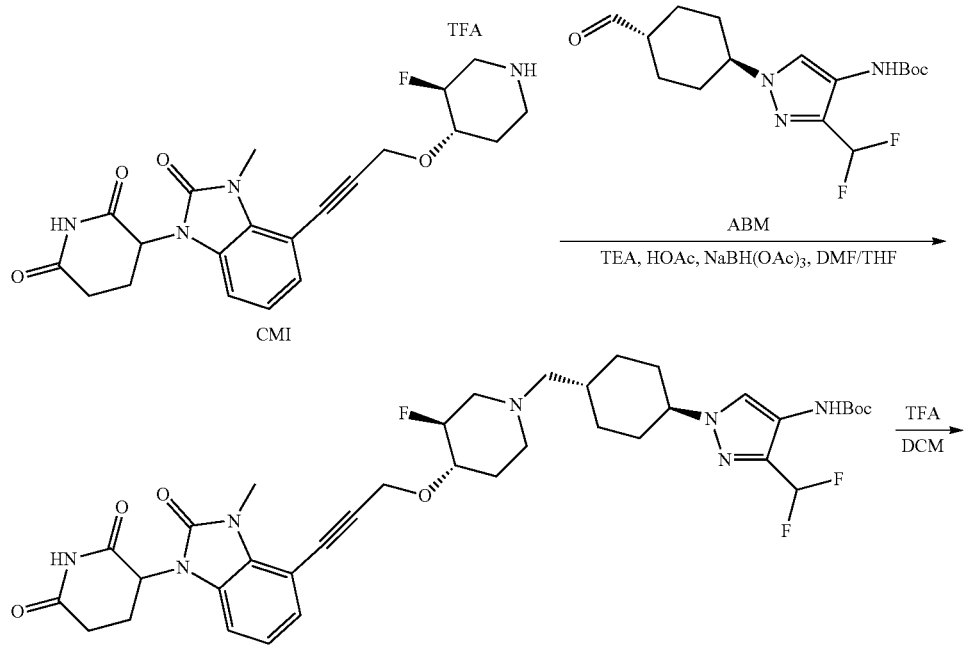

-continued

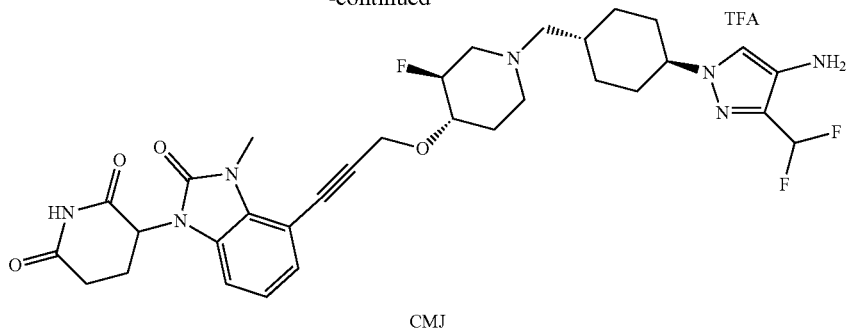

CMJ

Step 1—Tert-butyl (3-(difluoromethyl)-1-((1S,4r)-4-(((3S,4S)-4-((3-(1-(2,6-dioxopiperidin-3-yl)-3-methyl-2-oxo-2,3-dihydro-1H-benzo[d]imidazol-4-yl)prop-2-yn-1-yl)oxy)-3-fluoropiperidin-1-yl)methyl)cyclohexyl)-1H-pyrazol-4-yl)carbamate. To a solution of 3-[4-[3-[[(3S,4S)-3-fluoro-4-piperidyl]oxy]prop-1-ynyl]-3-methyl-2-oxo-benzimidazol-1-yl]piperidine-2,6-dione (239 mg, 452 umol, TFA salt, Intermediate CMI) in DMF (2 mL) and THF (2 mL) was added TEA (46.0 mg, 452 umol) and the mixture was stirred at −10° C. for 10 min. Then a solution of tert-butyl N-[3-(difluoromethyl)-1-(4-formylcyclohexyl)pyrazol-4-yl]carbamate (156 mg, 453 umol, Intermediate ABM) in DMF (2 mL) and AcOH (55.0 mg, 905 umol) was added and the mixture was stirred at −10° C. for 20 min. Next, NaBH(OAc)$_3$ (125 mg, 588 umol) was added and the mixture and stirred at −10° C. for 1 hr. On completion, the reaction mixture was quenched with water (20 mL) and extracted with EA (20 mL×3). The combined organic layers were washed with brine (20 mL), dried over Na$_2$SO$_4$, filtered and concentrated under reduced pressure to give a residue. The residue was purified by column chromatography (SiO$_2$, Petroleum ether/Ethyl acetate=1/0 to 0/1) to give the title compound (320 mg, 89% yield) as yellow oil. $^1$H NMR (400 MHz, CDCl$_3$) δ 8.26 (s, 1H), 8.02 (s, 1H), 7.92 (s, 1H), 7.20-7.12 (m, 1H), 7.00 (t, J=8.0 Hz, 1H), 6.57 (s, 3H), 5.21 (ddd, J=2.4, 5.2, 12.8 Hz, 1H), 4.59 (s, 2H), 4.06-3.97 (m, 1H), 3.79 (s, 3H), 3.69-3.60 (m, 1H), 3.06 (s, 1H), 2.95-2.92 (m, 1H), 2.87-2.80 (m, 1H), 2.79-2.70 (m, 2H), 2.27-2.13 (m, 6H), 1.97 (d, J=13.2 Hz, 2H), 1.78-1.62 (m, 6H), 1.51 (s, 9H), 1.11-0.99 (m, 2H); LCMS (ESI$^+$) m/z 742.3 (M+H)$^+$.

Step 2—3-(4-(3-(((3S,4S)-1-(((1r,4S)-4-(4-amino-3-(difluoromethyl)-1H-pyrazol-1-yl)cyclohexyl) methyl)-3-fluoropiperidin-4-yl)oxy)prop-1-yn-1-yl)-3-methyl-2-oxo-2,3-dihydro-1H-benzo[d]imidazole-1-yl)piperidine-2,6-dione. To a solution of tert-butyl N-[3-(difluoromethyl)-1-[4-[[(3S,4S)-4-[3-[1-(2,6-dioxo-3-piperidyl)-3-methyl-2-oxobenzimidazol-4-yl]prop-2-ynoxy]-3-fluoro-1-piperidyl]methyl]cyclohexyl]pyrazol-4-yl]carbamate (60.0 mg, 81 umol) in DCM (0.6 mL) was added TFA (308 mg, 2.70 mmol). The mixture was stirred at 25° C. for 15 min. On completion, the reaction mixture was concentrated under reduced pressure to give the title compound (60.0 mg, 99% yield, TFA) as yellow oil. LCMS (ESI$^+$) m/z 642.2 (M+H)$^+$.

3-[4-[3-[[(3R,4R)-3-fluoro-4-piperidyl]oxy]prop-1-ynyl]-3-methyl-2-oxo-benzimidazol-1-yl]piperidine-2,6-dione (Intermediate CMK)

Step 1—Tert-butyl (3R,4R)-3-fluoro-4-prop-2-ynoxy-piperidine-1-carboxylate. To a solution of tert-butyl(3R,4R)-3-fluoro-4-hydroxy-piperidine-1-carboxylate (500 mg, 2.28 mmol, CAS #1174020-43-9), 3-bromoprop-1-yne (406 mg, 3.42 mmol), KOH (191 mg, 3.42 mmol) in THF (5 mL) was added TBAI (84.2 mg, 228 umol). The mixture was then stirred at 25° C. for 16 hrs. On completion, the reaction mixture was concentrated in vacuo. The residue was diluted with H$_2$O (20 mL) and extracted with EA (30 mL×3). The combined organic layers were washed and dried over anhydrous Na$_2$SO$_4$, filtered and concentrated in vacuo to give the title compound (548 mg, 93% yield) as yellow solid. $^1$H NMR (400 MHz, DMSO-d$_6$) δ 4.56-4.37 (m, 1H), 4.27 (d, J=2.4 Hz, 2H), 3.77-3.70 (m, 1H), 3.69-3.58 (m, 1H), 3.46 (t, J=2.4 Hz, 1H), 3.39 (s, 2H), 3.23 (t, J=3.6, 8.4 Hz, 1H), 1.93-1.83 (m, 1H), 1.46 (d, J=3.6, 13.6 Hz, 1H), 1.39 (s, 9H)).

Step 2—Tert-butyl (3R,4R)-4-[3-[1-(2,6-dioxo-3-piperidyl)-3-methyl-2-oxo-benzimidazol-4-yl]prop-2-ynoxy]-3-fluoro-piperidine-1-carboxylate. A mixture of tert-butyl (3R,4R)-3-fluoro-4-prop-2-ynoxy-piperidine-1-carboxylate (448 mg, 1.74 mmol), 3-(4-bromo-3-methyl-2-oxo-benzimidazol-1-yl)piperidine-2,6-dione (392 mg, 1.16 mmol, Intermediate HP), CuI (22.1 mg, 116 umol), Pd(PPh$_3$)$_2$Cl$_2$ (81.4 mg, 116 umol) and Cs$_2$CO$_3$ (1.13 g, 3.48 mmol) in DMF (5 mL) was degassed and purged with N$_2$ three times. Then the mixture was stirred at 80° C. for 3 hrs under N$_2$ atmosphere. On completion, the reaction mixture was filtered and the filtrate was concentrated in vacuo to remove DMF, then the residue was diluted with water (50 mL) and extracted with EA (30 mL×3). The combined organic layer was dried over Na$_2$SO$_4$, filtered and concentrated in vacuo to give a residue. The residue was purified by reverse phase (0.1% FA condition) to give the title compound (290 mg, 48% yield) as a brown oil. $^1$H NMR (400 MHz, CDCl$_3$) δ 8.10 (s, 1H), 7.18 (d, J=7.6 Hz, 1H), 7.03-6.97 (m, 1H), 6.78 (d, J=7.6 Hz, 1H), 5.20 (d, J=5.2, 11.9 Hz, 1H), 4.56-4.38 (m, 1H), 4.05-3.87 (m, 1H), 3.86-3.79 (m, 1H), 3.74-3.69 (m, 1H), 3.40-3.11 (m, 2H), 3.05-2.91 (m, 1H), 2.90-2.56 (m, 2H), 2.32-2.14 (m, 1H), 2.12-1.97 (m, 1H), 1.58 (s, 6H), 1.47 (s, 9H). LC-MS (ESI$^+$) m/z 537.2 (M+Na)$^+$.

Step 3—3-[4-[3-[[(3R,4R)-3-fluoro-4-piperidyl]oxy]prop-1-ynyl]-3-methyl-2-oxo-benzimidazol-1-yl]piperidine-2,6-dione. A mixture of tert-butyl (3R,4R)-4-[3-[1-(2,6-dioxo-3-piperidyl)-3-methyl-2-oxo-benzimidazol-4-yl]prop-2-ynoxy]-3-fluoro-piperidine-1-carboxylate (180 mg, 349 umol) in TFA (0.3 mL) and DCM (1.5 mL) was degassed and purged with N$_2$ three times. Then the mixture was stirred at 25° C. for 1 hr under N$_2$ atmosphere. On completion, the reaction mixture was filtered and concentrated in vacuo to give the title compound (184 mg, 99% yield, TFA) as brown oil. LC-MS (ESI$^+$) m/z 415.1 (M+H)$^+$.

3-[4-[3-[[(3R,4R)-1-[[4-[4-amino-3-(difluoromethyl)pyrazol-1-yl]cyclohexyl]methyl]-3-fluoro-4-piperidyl]oxy]prop-1-ynyl]-3-methyl-2-oxo-benzimidazol-1-yl]piperidine-2,6-dione (Intermediate CML)

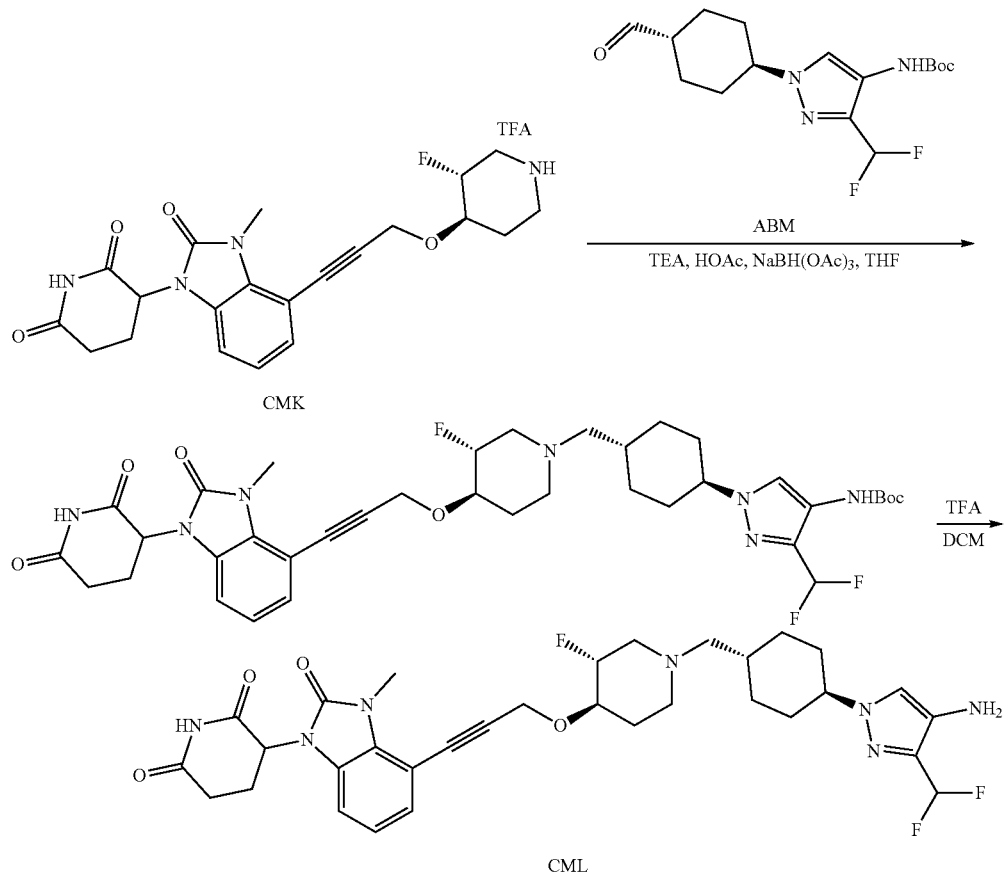

Step 1—Tert-butyl N-[3-(difluoromethyl)-1-[4-[[(3R,4R)-4-[3-[1-(2,6-dioxo-3-piperidyl)-3-methyl-2-oxo-benzimidazol-4-yl]prop-2-ynoxy]-3-fluoro-1-piperidyl]methyl]cyclohexyl]pyrazol-4-yl]carbamate. A mixture of 3-[4-[3-[[(3R,4R)-3-fluoro-4-piperidyl]oxy]prop-1-ynyl]-3-methyl-2-oxo-benzimidazol-1-yl]piperidine-2,6-dione (184 mg, 348 umol, TFA) in THF (1 mL) was added TEA (35.3 mg, 348 umol) at −10° C., then tert-butyl N-[3-(difluoromethyl)-1-(4-formylcyclohexyl)pyrazol-4-yl]carbamate (119 mg, 348 umol, Intermediate ABM) and HOAc (20.9 mg, 348 umol) was added and the mixture was stirred at −10° C. for 0.1 hr.

Then NaBH(OAc)₃ (110 mg, 522 umol) was added and the mixture was stirred at −10° C. for 1 hr. On completion, the reaction mixture was concentrated in vacuo to remove THF, then the residue was diluted with water (50 mL) and extracted with EA (30 mL×3). The combined organic layer was dried over Na₂SO₄, filtered and concentrated in vacuo to give the title compound (220 mg, 73% yield) as brown oil. LC-MS (ESI⁺) m/z 415.1 (M+H)⁺.

Step 2—3-[4-[3-[[(3R,4R)-1-[[4-[4-amino-3-(difluoromethyl)pyrazol-1-yl]cyclohexyl]methyl]-3-fluoro-4-piperidyl]oxy]prop-1-ynyl]-3-methyl-2-oxo-benzimidazol-1-yl]piperidine-2,6-dione. A mixture of tert-butyl N-[3-(difluoromethyl)-1-[4-[[(3R,4R)-4-[3-[1-(2,6-dioxo-3-piperidyl)-3-methyl-2-oxo-benzimidazol-4-yl]prop-2-ynoxy]-3-fluoro-1-piperidyl]methyl]cyclohexyl]pyrazol-4-yl]carbamate (112 mg, 130 umol) in TFA (0.5 mL) and DCM (1.5 mL) was degassed and purged with N₂ three times. Then the mixture was stirred at 25° C. for 1 hr. On completion, the reaction mixture was concentrated in vacuo to give the title compound (98 mg, 99% yield, TFA) as brown oil. LC-MS (ESI⁺) m/z 642.2 (M+H)⁺.

3-[4-[(3R,4R)-3-fluoro-4-piperidyl]-3-methyl-2-oxo-benzimidazol-1-yl]piperidine-2,6-dione (Intermediate CMM)

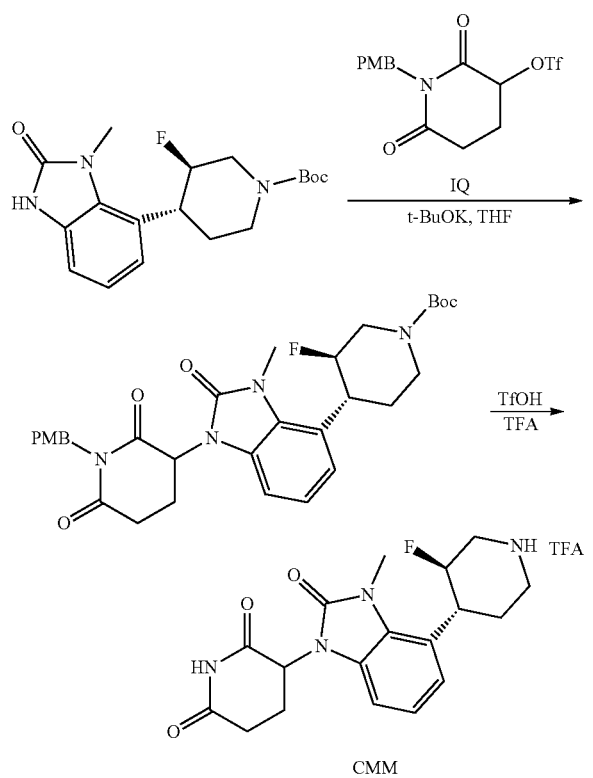

CMM

Step 1—Tert-butyl (3R,4R)-3-fluoro-4-[1-[1-[(4-methoxyphenyl)methyl]-2,6-dioxo-3-piperidyl]-3-methyl-2-oxo-benzimidazol-4-yl]piperidine-1-carboxylate. To a solution of tert-butyl (3R,4R)-3-fluoro-4-(3-methyl-2-oxo-1H-benzimidazol-4-yl)piperidine-1-carboxylate (300 mg, 858 umol, synthesized via SFC separation of Intermediate CLW) in THF (5 mL) was added t-BuOK (192 mg, 1.72 mmol) at stirred at 0° C. and the mixture was stirred for 0.5 hr. Then [1-[(4-methoxyphenyl)methyl]-2,6-dioxo-3-piperidyl] trifluoromethanesulfonate (491 mg, 1.29 mmol, Intermediate IQ) was added and the reaction mixture was stirred at 0° C. for 1.5 hrs. On completion, the residue was diluted with water (50 mL), then the residue was extracted with EA (3×50 mL). The combined organic layer was dried over Na₂SO₄, filtered and concentrated in vacuo to give a residue. The residue was purified by column chromatography (SiO₂, PE:EA=50:1 to PE:EA=3:1, PE:EA=2:1, P1:Rf=0.4) to give the title compound (400 mg, 80% yield). ¹H NMR (400 MHz, DMSO-d₆) δ 7.21 (d, J=8.4 Hz, 2H), 7.17 (d, J=8.0 Hz, 1H), 7.02-6.97 (m, 1H), 6.95-6.89 (m, 1H), 6.87-6.83 (m, 2H), 5.54 (dd, J=5.2, 12.8 Hz, 1H), 4.89-4.71 (m, 3H), 4.33 (d, J=3.2 Hz, 1H), 4.01-3.93 (m, 1H), 3.72 (s, 3H), 3.58 (s, 3H), 3.11-2.94 (m, 3H), 2.07 (s, 4H), 1.93-1.87 (m, 1H), 1.77-1.70 (m, 1H), 1.44 (s, 9H). LC-MS (ESI⁺) m/z 581.4 (M+H)⁺.

Step 2—3-[4-[(3R,4R)-3-fluoro-4-piperidyl]-3-methyl-2-oxo-benzimidazol-1-yl]piperidine-2,6-dione. To a solution of tert-butyl (3R,4R)-3-fluoro-4-[1-[1-[(4-methoxyphenyl)methyl]-2,6-dioxo-3-piperidyl]-3-methyl-2-oxo-benzimidazol-4-yl]piperidine-1-carboxylate (70.0 mg, 120 umol) in TFA (2.16 g, 18.9 mmol) was added TfOH (476 mg, 3.17 mmol), then the mixture was stirred at 80° C. for 1 hr. On completion, the reaction mixture was concentrated in vacuo to give the title compound (40.0 mg, 92% yield) as brown oil. LC-MS (ESI⁺) m/z 361.0 (M+H−56)⁺.

6-(Difluoromethyl)-N-[2-(4-formylcyclohexyl)indazol-5-yl]pyridine-2-carboxamide (Intermediate CMN)

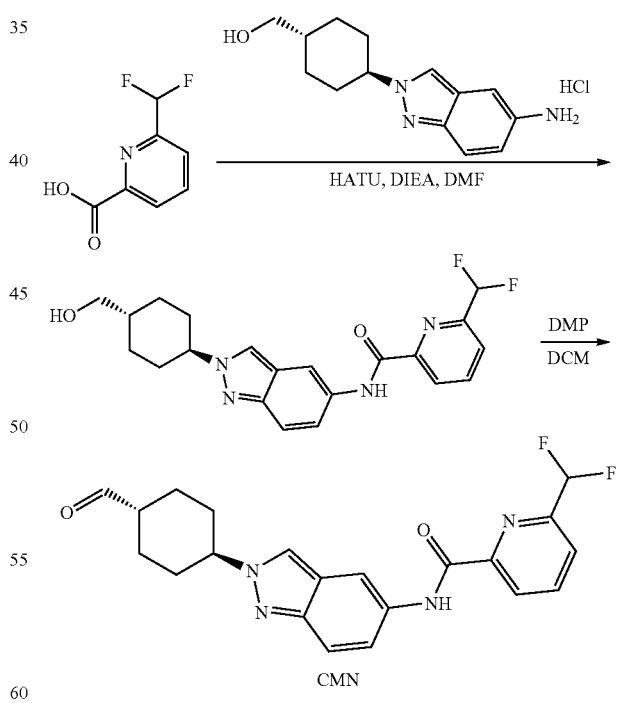

CMN

Step 1—6-(Difluoromethyl)-N-[2-[4-(hydroxymethyl)cyclohexyl]indazol-5-yl]pyridine-2-carboxamide. To a solution of 6-(difluoromethyl)pyridine-2-carboxylic acid (210 mg, 1.21 mmol, CAS #1256824-41-5) in DMF (1 mL) was added DIEA (470 mg, 3.64 mmol) and CMPI (371 mg, 1.46 mmol), then the mixture was stirred at 50° C. for 30 min.

Next, [4-(5-aminoindazol-2-yl)cyclohexyl]methanol (341 mg, 1.21 mmol, HCl, synthesized via Step 1 of Intermediate BUT) was added and the mixture was stirred at 50° C. for 4 hrs. On completion, the residue was diluted with water (20 mL) and extracted with EA (10 mL×3). The combined organic layer was dried over Na$_2$SO$_4$, filtered and concentrated in vacuo to give the title compound (400 mg, 82% yield) as brown solid. $^1$H NMR (400 MHz, DMSO-d$_6$) δ 10.48 (s, 1H), 8.40-8.27 (m, 3H), 7.29-7.27 (m, 1H), 7.97-7.62 (m, 2H), 7.60-6.94 (m, 1H), 4.51-4.38 (m, 1H), 3.01 (d, J=5.6 Hz, 2H), 2.12-1.91 (m, 2H), 1.90-1.86 (m, 1H), 1.17-1.13 (m, 3H); LC-MS (ESI$^+$) m/z 401.2 (M+H)$^+$.

Step 2—6-(Difluoromethyl)-N-[2-(4-formylcyclohexyl)indazol-5-yl]pyridine-2-carboxamide. To a solution of 6-(difluoromethyl)-N-[2-[4-(hydroxymethyl)cyclohexyl]indazol-5-yl]pyridine-2-carboxamide (100 mg, 249 umol) in DCM (3 mL) was added DMP (127 mg, 299 umol), then mixture was stirred at 25° C. for 1 hr. On completion, the reaction mixture was quenched with sat. Na$_2$S$_2$O$_3$ solution (10 mL) and NaHCO$_3$ solution (10 mL), the residue was diluted with water (10 mL) and extracted with DCM (10 mL×3). The combined organic layer was dried over Na$_2$SO$_4$, filtered and concentrated in vacuo to give the title compound (80 mg, 80% yield) as yellow solid. LC-MS (ESI$^+$) m/z 399.1 (M+H)$^+$.

3-[4-[(3S,4S)-3-fluoro-4-piperidyl]-3-methyl-2-oxo-benzimidazol-1-yl]piperidine-2,6-dione (Intermediate CMO)

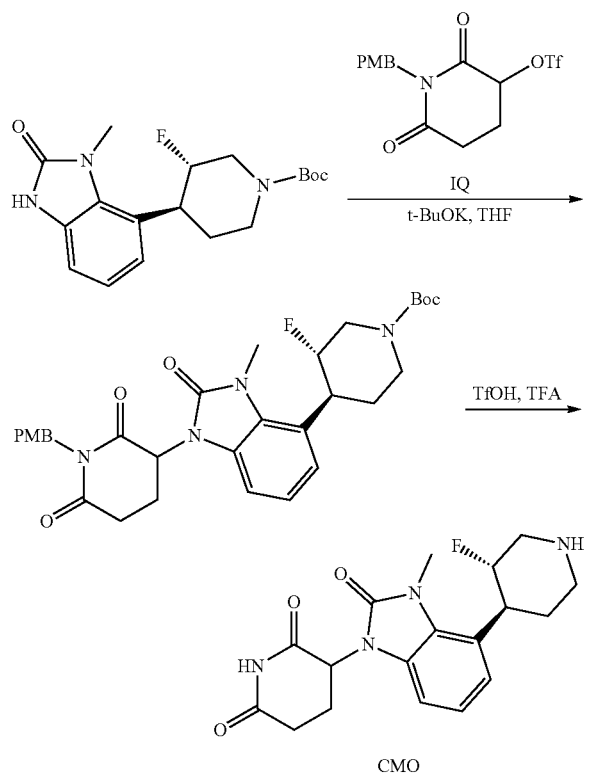

Step 1—Tert-butyl (3S,4S)-3-fluoro-4-[1-[1-[(4-methoxyphenyl)methyl]-2,6-dioxo-3-piperidyl]-3-methyl-2-oxo-benzimidazol-4-yl]piperidine-1-carboxylate. To a solution of tert-butyl (3S,4S)-3-fluoro-4-(3-methyl-2-oxo-1H-benzimidazol-4-yl) piperidine-1-carboxylate (130 mg, 372 umol, made via SFC separation of Intermediate CLW) in THF (13 mL) was added t-BuOK (41.7 mg, 372 umol), and the mixture was stirred at 0° C. for 0.5 hr. Then [1-[(4-methoxyphenyl)methyl]-2,6-dioxo-3-piperidyl] trifluoromethanesulfonate (212 mg, 558 umol, Intermediate IQ) was added and the reaction mixture was stirred at 0° C. for 1.5 hrs. On completion, the reaction mixture was diluted with water (5 mL), then the residue was extracted with EA (3×50 mL). The combined organic layer was dried over Na$_2$SO$_4$, filtered and concentrated in vacuo to give a residue. The residue was purified by column chromatography (SiO$_2$, PE:EA=1:1, P1:Rf=0.3) to give the title compound (200 mg, 92% yield) as white solid. $^1$H NMR (400 MHz, DMSO-d$_6$) δ 7.28-6.94 (m, 4H), 6.88-6.83 (m, 2H), 6.04 (dd, J=7.2, 10.4 Hz, 1H), 5.83 (d, J=5.2 Hz, 1H), 5.54 (dd, J=5.2, 12.8 Hz, 1H), 4.86-4.70 (m, 2H), 4.64-4.58 (m, 1H), 4.36-4.25 (m, 1H), 4.03 (q, J=7.2 Hz, 4H), 3.79 (s, 1H), 3.73-3.70 (m, 3H), 3.59 (s, 1H), 3.51 (s, 1H), 1.99 (s, 5H), 1.44 (s, 9H), 1.31-1.26 (m, 7H); LC-MS (ESI$^+$) m/z 581.3 (M+H)$^+$.

Step 2—3-[4-[(3S,4S)-3-fluoro-4-piperidyl]-3-methyl-2-oxo-benzimidazol-1-yl]piperidine-2,6-dione. To a solution of tert-butyl (3S,4S)-3-fluoro-4-[1-[1-[(4-methoxyphenyl)methyl]-2,6-dioxo-3-piperidyl]-3-methyl-2-oxo-benzimidazol-4-yl]piperidine-1-carboxylate (100 mg, 172 umol) in TFA (1 ml) and TfOH (340 mg, 2.27 mmol) stirred at 80° C. for 1 hr. On completion, the reaction mixture was concentrated in vacuo to give the title compound (61.0 mg, 74% yield, TFA) as red oil. LC-MS (ESI$^+$) m/z 361.1 (M+H)$^+$.

[4-(5-Aminopyrazolo[3,4-c]pyridin-2-yl)cyclohexyl]methanol (Intermediate CMP)

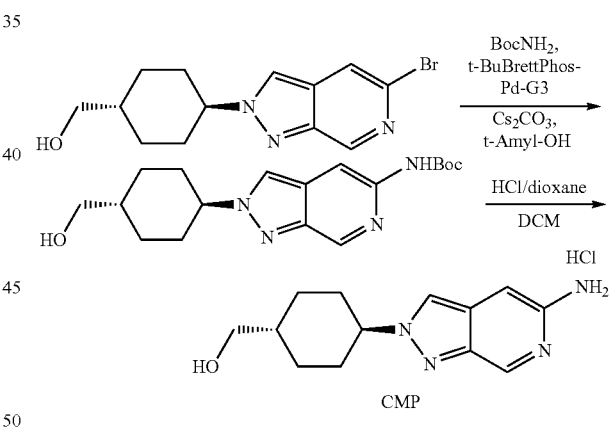

Step 1—Tert-butyl N-[2-[4-(hydroxymethyl)cyclohexyl]pyrazolo[3,4-c]pyridin-5-yl]carbamate. A mixture of [4-(5-bromopyrazolo[3,4-c]pyridin-2-yl)cyclohexyl]methanol (500 mg, 1.61 mmol, synthesized via Steps 1-3 of Intermediate BRR), Cs$_2$CO$_3$ (1.58 g, 4.84 mmol), 4 Å molecular sieves (30 mg), t-BuBrettPhos Pd G3 (138 mg, 161 umol) and tert-butyl carbamate (378 mg, 3.22 mmol) in t-Amyl-OH (6 mL) was degassed and purged with N$_2$ three times. Then the mixture was stirred at 100° C. for 48 hrs. On completion, the reaction mixture was filtered and concentrated in vacuo to give a residue. The residue was diluted with H$_2$O (100 mL), and extracted with EA (200 mL×3). The combined organic layers were washed with brine (50 mL), dried over anhydrous Na$_2$SO$_4$, filtered and concentrated in vacuo to give the crude product. The crude product was purified by column chromatography (SiO$_2$, PE:EA=5:1 to 1:3) first, then triturated with MeOH (5 mL) to give the title compound (200 mg, 36% yield) as white solid. $^1$H NMR (400 MHz, DMSO-$d_6$) δ 9.45-9.30 (m, 1H), 8.97-8.84 (m, 1H), 8.41 (s, 1H), 7.91-7.82 (m, 1H), 4.57-4.42 (m, 2H), 3.29 (t, J=5.6 Hz, 2H), 2.09-2.20 (m, 2H), 1.97-1.84 (m, 4H), 1.48 (s, 9H), 1.22-1.08 (m, 2H), 0.90 (t, J=7.2 Hz, 1H); LC-MS (ESI$^+$) m/z 347.3 (M+H)$^+$.

Step 2—[4-(5-Aminopyrazolo[3,4-c]pyridin-2-yl)cyclohexyl]methanol. A mixture of tert-butyl N-[2-[4-(hydroxymethyl)cyclohexyl]pyrazolo[3,4-c]pyridin-5-yl]carbamate (130 mg, 375 umol) in HCl/dioxane (4 M, 2 mL), then the mixture was stirred at 25° C. for 2 hrs. On completion, the mixture was concentrated in vacuo to give the title compound (106 mg, 100% yield, HCl) as yellow liquid. LC-MS (ESI$^+$) m/z 247.3 (M+H)$^+$.

N-[2-(4-formylcyclohexyl)pyrazolo[3,4-c]pyridin-5-yl]-6-methyl-pyridine-2-carboxamide (Intermediate CMQ)

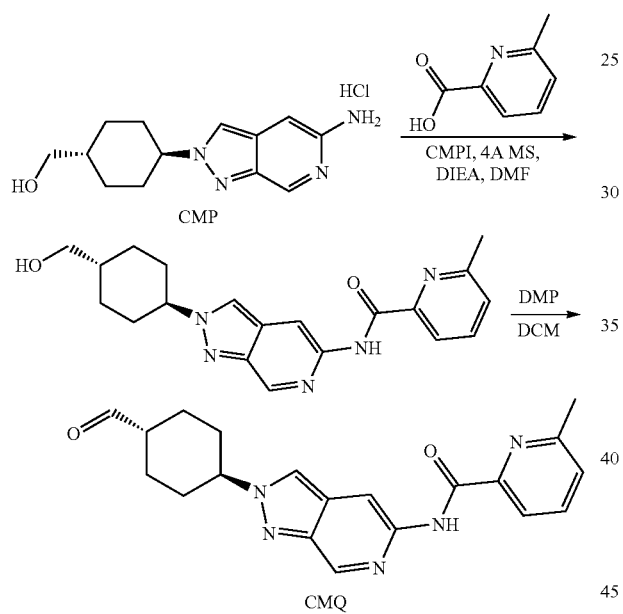

Step 1—N-[2-[4-(hydroxymethyl)cyclohexyl]pyrazolo[3,4-c]pyridin-5-yl]-6-methyl-pyridine-2-carboxamide. A mixture of 6-methylpyridine-2-carboxylic acid (77.1 mg, 562 umol, CAS #934-60-1), DIEA (145 mg, 1.12 mmol), 4 Å molecular sieves (50 mg) and CMPI (115 mg, 450 umol) in DMF (2 mL) was stirred at 60° C. for 2 hrs. Then [4-(5-aminopyrazolo[3,4-c]pyridin-2-yl)cyclohexyl]methanol (106 mg, 375 umol, HCl, Intermediate CMP) was added and the mixture was stirred at 60° C. for 14 hrs. On completion, the reaction mixture was filtered and concentrated in vacuo to give a residue. The residue was diluted with H$_2$O (30 mL), and extracted with EA (30 mL×3). The combined organic layers were washed with brine (20 mL), dried over anhydrous Na$_2$SO$_4$, filtered and concentrated in vacuo to give the crude product. The crude product was purified by column chromatography (SiO$_2$, PE:EA=1:1 to 1:4) to give the title compound (74.0 mg, 54% yield) as yellow solid. $^1$H NMR (400 MHz, DMSO-$d_6$) δ 10.41 (s, 1H), 9.09-9.00 (m, 1H), 8.59 (d, J=0.8 Hz, 1H), 8.48 (d, J=1.6 Hz, 1H), 8.05-7.94 (m, 2H), 7.57 (dd, J=1.2, 7.2 Hz, 1H), 4.61-4.47 (m, 1H), 3.29 (d, J=6.4 Hz, 3H), 2.63 (s, 3H), 2.22-2.14 (m, 2H), 1.99-1.87 (m, 4H), 1.57-1.44 (m, 1H), 1.24-1.11 (m, 2H); LC-MS (ESI$^+$) m/z 366.1 (M+H)$^+$.

Step 2—N-[2-(4-formylcyclohexyl)pyrazolo[3,4-c]pyridin-5-yl]-6-methyl-pyridine-2-carboxamide. A mixture of N-[2-[4-(hydroxymethyl)cyclohexyl]pyrazolo[3,4-c]pyridin-5-yl]-6-methyl-pyridine-2-carboxamide (60.0 mg, 164 umol) in DCM (1 mL) was added DMP (83.6 mg, 197 umol) at 0° C., then the mixture was stirred at 25° C. for 1 hr. On completion, the mixture was diluted with DCM (30 mL), quenched with saturated NaHCO$_3$ (5 mL) and saturated Na$_2$S$_2$O$_3$ (5 mL) at 25° C. for 0.5 hour. Then the organic layer was washed with saturated NaHCO$_3$ (30 mL×3) first, then washed again with brine (20 mL×3), dried over anhydrous Na$_2$SO$_4$, filtered and concentrated in vacuo to give the title compound (59.0 mg, 99% yield) as yellow solid. LC-MS (ESI$^+$) m/z 364.1 (M+H)$^+$.

6-(Difluoromethyl)pyridine-2-carboxamide (Intermediate CMR)

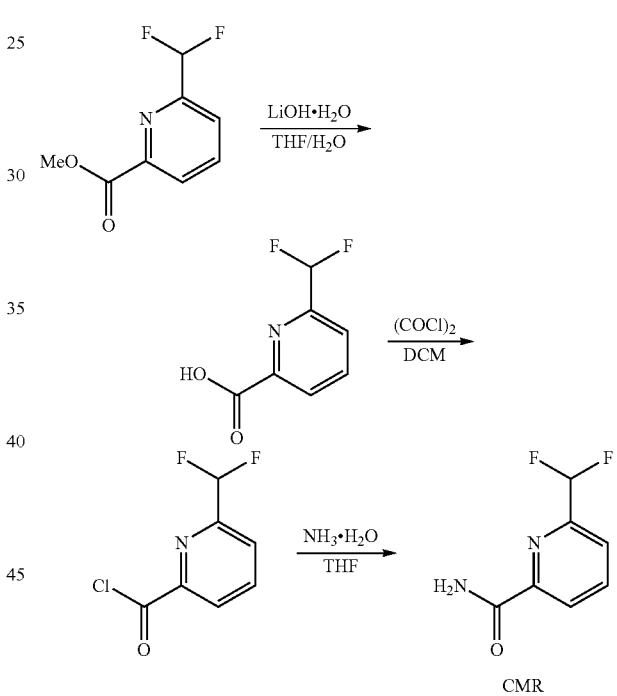

Step 1—6-(Difluoromethyl)pyridine-2-carboxylic acid. To a solution of methyl 6-(difluoromethyl)pyridine-2-carboxylate (6.91 g, 34.0 mmol, CAS #1379375-24-2) in THF (95 mL) was added LiOH·H$_2$O (3.56 g, 85.0 mmol) in H$_2$O (35 mL), then the mixture was stirred at 25° C. for 12 hrs. On completion, the reaction was concentrated in vacuo to give a residue. The residue was diluted with water (150 ml), extracted with DCM (75 ml×2), and separated to give an aqueous phase. The aqueous phase was acidified by HCl (3N) to adjust the pH=5-6, then the mixture was extracted with EA (100 ml×4). The organic layers were combined, dried over anhydrous Na$_2$SO$_4$, filtered and concentrated in vacuo to give the title compound (3.61 g, 61% yield) as off-white solid. $^1$H NMR (400 MHz, DMSO-$d_6$) δ 14.91-12.21 (m, 1H), 8.19 (d, J=4.8 Hz, 2H), 8.02-7.83 (m, 1H), 7.25-6.84 (m, 1H); LC-MS (ESI+) m/z 174.3 (M+H)$^+$.

Step 2—6-(Difluoromethyl)pyridine-2-carbonyl chloride. To a solution of 6-(difluoromethyl)pyridine-2-carboxylic acid (400 mg, 2.31 mmol) in DCM (3 mL) was added (COCl)$_2$ (587 mg, 4.62 mmol) at 0° C., then the mixture was stirred at 25° C. for 1 hr. On completion, the reaction was concentrated in vacuo to give the title compound (442 mg, 99% yield) as yellow oil.

Step 3—6-(Difluoromethyl)pyridine-2-carboxamide. A solution of 6-(difluoromethyl)pyridine-2-carbonyl chloride (442 mg, 2.31 mmol) in THF (5 mL) was added to NH$_3$·H$_2$O (5.38 g, 46.1 mmol, 30% solution) at 0° C., then the mixture was stirred at 25° C. for 1 hr. On completion, the reaction was diluted with water (20 ml), and extracted with EA (10 ml×3). The organic layers were combined, washed with brine (10 ml), dried over anhydrous Na$_2$SO$_4$, filtered and concentrated in vacuo to give the title compound (274 mg, 68% yield) as gray solid. $^1$H NMR (400 MHz, DMSO-d$_6$) δ 8.24-8.14 (m, 2H), 8.05 (s, 1H), 7.94-7.86 (m, 1H), 7.81 (s, 1H), 6.99 (t, J=54.8 Hz, 1H); LC-MS (ESI+) m/z 173.1 (M+H)$^+$.

6-(Difluoromethyl)-N-(2-((1r,4r)-4-formylcyclohexyl)-2H-pyrazolo[3,4-c]pyridin-5-yl)picolinamide (Intermediate CMS)

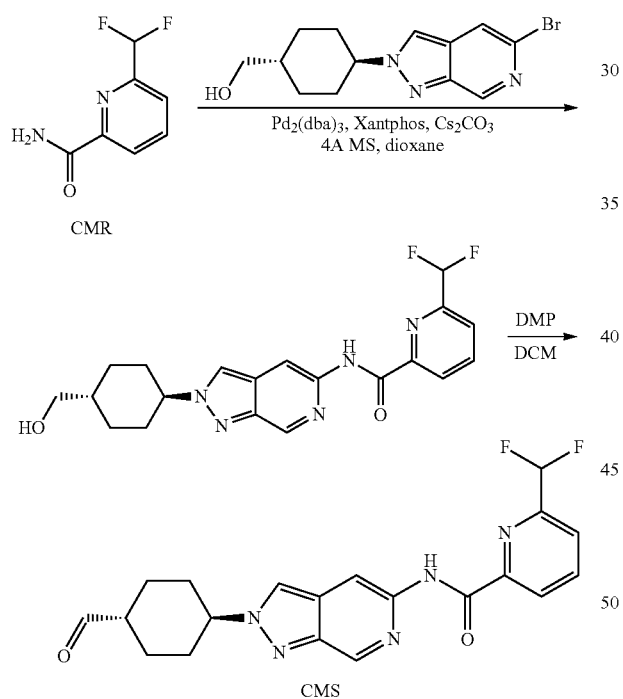

Step 1—6-(Difluoromethyl)-N-[2-[4-(hydroxymethyl)cyclohexyl]pyrazolo[3,4-c]pyridin-5-yl]pyridine-2-carboxamide. A mixture of [4-(5-bromopyrazolo[3,4-c]pyridin-2-yl)cyclohexyl]methanol (1 g, 3.22 mmol, synthesized via Steps 1-3 of Intermediate BRR), 6-(difluoromethyl)pyridine-2-carboxamide (555 mg, 3.22 mmol, Intermediate CMR), Pd$_2$(dba)$_3$ (295 mg, 322 umol), Xantphos (373 mg, 644 umol), Cs$_2$CO$_3$ (3.16 g, 9.68 mmol), and 4 Å molecular sieves (7 g) in dioxane (20 mL) was degassed under vacuum, and purged with N$_2$ three times. Then the mixture was stirred at 100° C. for 8 hrs under N$_2$ atmosphere. On completion, the reaction was cooled to rt, filtered to give a filtrate, concentrated in vacuo to give a residue. The residue was diluted with water (100 ml), and extracted with EA (50 ml×4). The organic layers were combined, washed with brine (50 ml), dried over anhydrous Na$_2$SO$_4$, filtered and concentrated in vacuo to give the crude product. The crude product was purified by column chromatography (SiO$_2$, PE/EA=10/1 to 1/1), then purified again by reverse phase (0.1% FA condition) to give the title compound (90 mg, 6% yield, FA) as yellow solid. $^1$H NMR (400 MHz, DMSO-d$_6$) δ 10.30 (s, 1H), 9.05 (s, 1H), 8.59 (s, 1H), 8.49 (s, 1H), 8.41-8.25 (m, 2H), 8.01 (d, J=7.6 Hz, 1H), 7.18 (t, J=54.8 Hz, 1H), 4.61-4.45 (m, 2H), 3.31-3.27 (m, 2H), 2.18 (d, J=9.6 Hz, 2H), 1.93 (d, J=10.4 Hz, 4H), 1.58-1.42 (m, 1H), 1.27-1.10 (m, 2H); LC-MS (ESI+) m/z 402.1 (M+H)$^+$.

Step 2—6-(Difluoromethyl)-N-[2-(4-formylcyclohexyl)pyrazolo[3,4-c]pyridin-5-yl]pyridine-2-carboxamide. To a solution of 6-(difluoromethyl)-N-[2-[4-(hydroxymethyl)cyclohexyl]pyrazolo[3,4-c]pyridin-5-yl] pyridine-2-carboxamide (60 mg, 134 umol, FA) in DCM (2 mL) was added DMP (73.9 mg, 174 umol) at 0° C., then the mixture was stirred at 25° C. for 2 hrs. On completion, the reaction was quenched by saturated NaHCO$_3$ (3 ml) and saturated Na$_2$S$_2$O$_3$ (3 ml) at 0° C., then extracted with DCM (3 ml×4). The organic layers were combined, dried over anhydrous Na$_2$SO$_4$, filtered and concentrated in vacuo to give the title compound (52 mg, 97% yield) as off-white solid. $^1$H NMR (400 MHz, DMSO-d$_6$) δ 10.30 (s, 1H), 9.65 (s, 1H), 9.06 (s, 1H), 8.60 (s, 1H), 8.50 (d, J=0.8 Hz, 1H), 8.41-8.26 (m, 2H), 8.01 (d, J=7.2 Hz, 1H), 7.35-7.00 (m, 1H), 4.68-4.51 (m, 1H), 2.47-2.40 (m, 1H), 2.25 (d, J=10.8 Hz, 2H), 2.13 (d, J=12.4 Hz, 2H), 2.08-1.94 (m, 2H), 1.52-1.42 (m, 2H); LC-MS (ESI+) m/z 400.0 (M+H)$^+$.

Step 3—6-(difluoromethyl)-N-(2-((1r,4r)-4-formylcyclohexyl)-2H-pyrazolo[3,4-c]pyridin-5-yl)picolinamide. To a solution of tert-butyl 4-[1-(2,6-dioxo-3-piperidyl)-3-methyl-2-oxo-benzimidazol-4-yl]piperazine-1-carboxylate (50 mg, 113 umol) in DCM (0.5 mL) was added TFA (154 mg, 1.35 mmol), then the mixture was stirred at 25° C. for 1 hr. On completion, the reaction was concentrated in vacuo to give the title compound (51 mg, 94% yield, TFA) as brown oil. LC-MS (ESI+) m/z 344.0 (M+H)$^+$.

3-(5-Fluoro-3-methyl-2-oxo-4-piperazin-1-yl-benzimidazol-1-yl)piperidine-2,6-dione (Intermediate CMT)

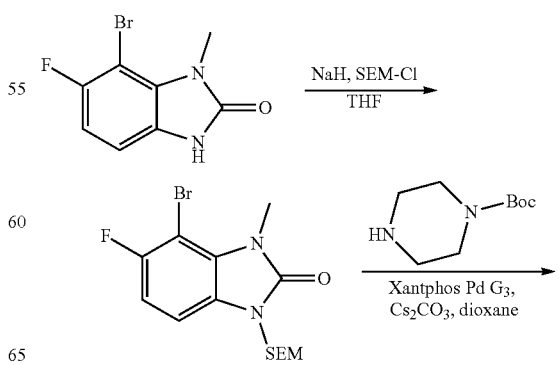

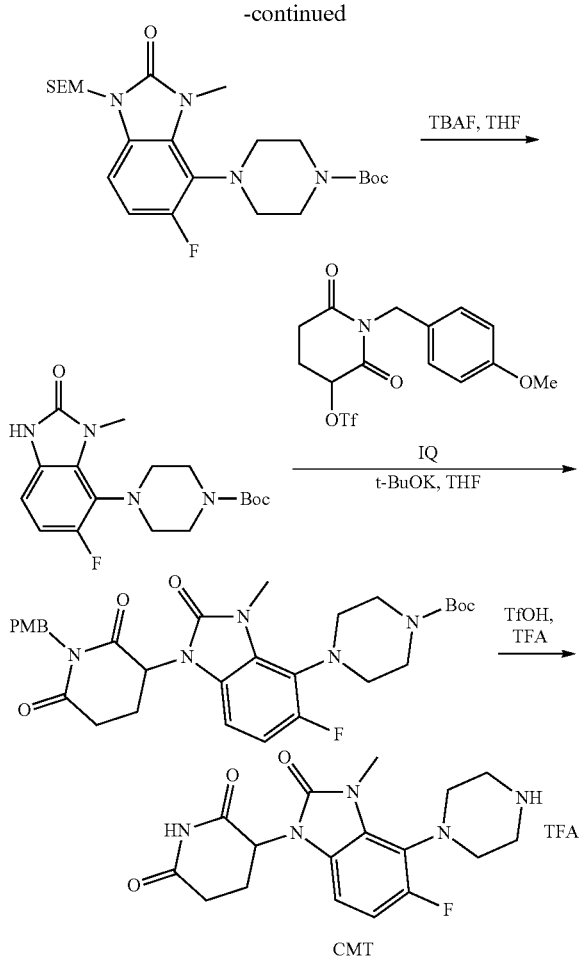

Step 1—4-Bromo-5-fluoro-3-methyl-1-(2-trimethylsilylethoxymethyl)benzimidazol-2-one. A mixture of 4-bromo-5-fluoro-3-methyl-1H-benzimidazol-2-one (8.00 g, 32.6 mmol, synthesized via Steps 1-3 of Intermediate BPW) in THF (150 mL) was degassed and purged with $N_2$ three times. Then the mixture was stirred at 0° C. for 30 min under $N_2$ atmosphere, and NaH (1.96 g, 48.9 mmol, 60% dispersion in mineral oil) was added and the mixture was degassed and purged with $N_2$ for three times. Then the mixture was stirred at 0° C. for 1 h under $N_2$ atmosphere. Next, SEM-Cl (8.16 g, 48.9 mmol) was added and the mixture was degassed and purged with $N_2$ three times. Then the mixture was stirred at 65° C. for 11 hrs under $N_2$ atmosphere. On completion, the reaction mixture was quenched with water (100 mL), then the reaction mixture was concentrated under reduced pressure to remove THF. The residue was diluted with water (100 mL) and extracted with ethyl acetate (200 mL×3). The combined organic layer was dried over $Na_2SO_4$, filtered and concentrated in vacuo to give a residue. The residue was purified by column chromatography ($SiO_2$, petroleum ether/ethyl acetate=10/0 to 2/1) to give the title compound (9.10 g, 72 yield) as a black brown oil. $^1$H NMR (400 MHz, $CDCl_3$) δ 7.04 (dd, J=4.4, 8.8 Hz, 1H), 6.95-6.86 (m, 1H), 5.30 (s, 2H), 3.78 (s, 3H), 3.62-3.56 (m, 2H), 0.94-0.88 (m, 2H), 0.01-0.05 (m, 9H). LC-MS (ESI$^+$) m/z 375.1 (M+H)$^+$.

Step 2—Tert-butyl 4-[5-fluoro-3-methyl-2-oxo-1-(2-trimethylsilylethoxymethyl)benzimidazol-4-yl]piperazine-1-carboxylate. A mixture of 4-bromo-5-fluoro-3-methyl-1-(2-trimethylsilylethoxymethyl)benzimidazol-2-one (1.00 g, 2.66 mmol)×4, tert-butyl piperazine-1-carboxylate (744 mg, 4.00 mmol, CAS #143238-38-4), XantPhos Pd $G_3$ (252 mg, 266 umol) and $Cs_2CO_3$ (2.60 g, 7.99 mmol) in dioxane (10 mL) was degassed and purged with $N_2$ three times. Then the mixture was stirred at 95° C. for 12 hrs under $N_2$ atmosphere. On completion, the reaction mixture was poured into water (100 mL), and extracted with ethyl acetate (100 mL×3). The combined organic layers were washed with brine (100 mL), dried over sodium sulfate and filtered. The filtrate was concentrated under reduced pressure to give a residue. The residue was purified by column chromatography ($SiO_2$, petroleum ether/ethyl acetate=1/0 to 1/1) to give the title compound (0.50 g, 39% yield) as a light yellow oil. $^1$H NMR (400 MHz, $CDCl_3$) δ 6.92 (dd, J=4.0, 8.8 Hz, 1H), 6.78 (dd, J=8.4, 12.8 Hz, 1H), 5.28 (s, 2H), 4.13-3.99 (m, 2H), 3.74 (s, 3H), 3.60 (dd, J=7.6, 8.8 Hz, 2H), 3.38-3.25 (m, 2H), 3.05 (s, 2H), 2.93 (d, J=11.2 Hz, 2H), 1.50 (s, 9H), 0.96-0.89 (m, 2H), −0.02 (s, 9H). LC-MS (ESI$^+$) m/z 481.1 (M+H)$^+$.

Step 3—Tert-butyl 4-(5-fluoro-3-methyl-2-oxo-1H-benzimidazol-4-yl)piperazine-1-carboxylate. To a solution of tert-butyl 4-[5-fluoro-3-methyl-2-oxo-1-(2-trimethylsilylethoxymethyl)benzimidazol-4-yl]piperazine-1-carboxylate (1.30 g, 2.70 mmol) in THF (10 mL) was added TBAF (1 M, 13.5 mL). The mixture was stirred at 60° C. for 12 hrs. On completion, the reaction mixture was poured into water (30 mL), and then extracted with ethyl acetate (30 mL×3). The combined organic layers were washed with brine (30 mL), dried over sodium sulfate and filtered. The filtrate was concentrated under reduced pressure to give a residue. The residue was purified by column chromatography ($SiO_2$, petroleum ether/ethyl acetate=1/0 to 0/1) to give the title compound (0.60 g, 62% yield) as a white solid. $^1$H NMR (400 MHz, DMSO-$d_6$) δ 10.89 (s, 1H), 6.78 (dd, J=0.8, 8.8 Hz, 2H), 3.90 (s, 2H), 3.55 (s, 3H), 3.09-2.93 (m, 6H), 1.42 (s, 9H). LC-MS (ESI$^+$) m/z 351.1 (M+H)$^+$.

Step 4—Tert-butyl 4-[5-fluoro-1-[1-[(4-methoxyphenyl)methyl]-2,6-dioxo-3-piperidyl]-3-methyl-2-oxo-benzimidazol-4-yl]piperazine-1-carboxylate. To a solution of tert-butyl 4-(5-fluoro-3-methyl-2-oxo-1H-benzimidazol-4-yl)piperazine-1-carboxylate (800 mg, 2.28 mmol) in THF (10 mL) was added t-BuOK (512 mg, 4.57 mmol) at −10° C. and the mixture was stirred −10° C. for 2.5 h. Next, [1-[(4-methoxyphenyl)methyl]-2,6-dioxo-3-piperidyl] trifluoromethanesulfonate (2.61 g, 6.85 mmol, Intermediate IQ) was added and the mixture was stirred at −10° C. for 2 h. On completion, the reaction mixture was quenched with saturated $NH_4Cl$ (30 ml) aqueous, and then extracted with ethyl acetate (30 mL×3). The combined organic layers were washed with brine (30 mL), dried over $Na_2SO_4$ and filtered. The filtrate was concentrated under reduced pressure to give a residue. The crude product was purified by reversed-phase (0.1% FA condition, $H_2O$/ACN=1:9) to give the title compound (670 mg, 49% yield) as a brown solid. $^1$H NMR (400 MHz, $CDCl_3$) δ 7.39-7.33 (m, 2H), 6.86-6.79 (m, 2H), 6.62 (dd, J=8.8, 12.8 Hz, 1H), 6.21 (dd, J=3.6, 8.4 Hz, 1H), 5.19 (dd, J=5.2, 13.2 Hz, 1H), 4.96 (s, 2H), 4.22-4.00 (m, 2H), 3.80 (s, 3H), 3.74 (s, 3H), 3.38-3.25 (m, 2H), 3.09-2.77 (m, 6H), 2.61-2.50 (m, 1H), 2.16 (m, J=2.6, 5.2, 13.2 Hz, 1H), 1.50 (s, 9H). LC-MS (ESI$^+$) m/z 582.2 (M+H)$^+$.

Step 5—3-(5-Fluoro-3-methyl-2-oxo-4-piperazin-1-yl-benzimidazol-1-yl)piperidine-2,6-dione. A solution of tert-butyl 4-[5-fluoro-1-[1-[(4-methoxyphenyl)methyl]-2,6-dioxo-3-piperidyl]-3-methyl-2-oxo-benzimidazol-4-yl]piperazine-1-carboxylate (50 mg, 85.96 umol) in TFA (1 mL) and TfOH (0.2 mL) was stirred at 70° C. for 1 hrs. On completion, the reaction mixture was concentrated under reduced pressure to give the title compound (60 mg TFA) as a black brown oil. LC-MS (ESI+) m/z 362.1 (M+H)+.

3-[3-Methyl-4-(5-oxa-2-azaspiro[3.4]octan-7-yl)-2-oxo-benzimidazol-1-yl]piperidine-2,6-dione (Intermediate CMU)

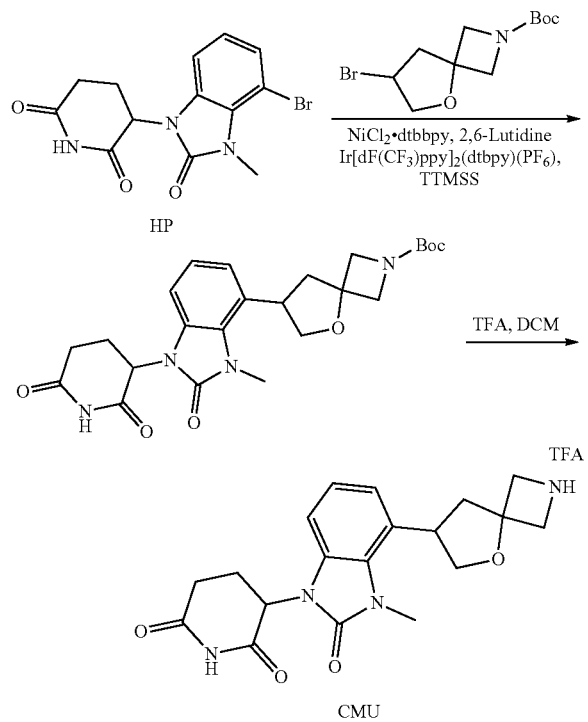

Step 1—Tert-butyl 7-[1-(2,6-dioxo-3-piperidyl)-3-methyl-2-oxo-benzimidazol-4-yl]-5-oxa-2-azaspiro[3.4]octane-2-carboxylate. To an 15 mL vial equipped with a stir bar was added 3-(4-bromo-3-methyl-2-oxo-benzimidazol-1-yl)piperidine-2,6-dione (222 mg, 658 umol, Intermediate HP), tert-butyl 7-bromo-5-oxa-2-azaspiro[3.4]octane-2-carboxylate (250 mg, 855 umol, CAS #1330765-30-4), Ir[dF(CF$_3$)ppy]$_2$(dtbpy)(PF$_6$) (14.7 mg, 13.1 umol), NiCl$_2$·dtbbpy (7.86 mg, 19.7 umol), TTMSS (163 mg, 658 umol), and 2,6-lutidine (141 mg, 1.32 mmol) in DME (50 mL). The vial was sealed and placed under nitrogen. The reaction was stirred and irradiated with a 10 W blue LED lamp (3 cm away), with cooling water to keep the reaction temperature at 25° C. for 14 hrs. On completion, the mixture was filtered and concentrated in vacuo to give a residue. The residue was purified by prep-HPLC (Phenomenex C18 250*50 mm*10 um; mobile phase: [water (NH4HCO3)-ACN]; B %: 22%-52%, 10 min). The crude product was triturated with MTBE (2 mL) at 25° C. for 120 mins to give the title compound (100 mg, 31% yield) as a white solid. $^1$H NMR (400 MHz, DMSO-d$_6$) δ 11.09 (s, 1H), 7.08-6.97 (m, 3H), 5.75 (s, 1H), 5.37 (dd, J=5.2, 12.6 Hz, 1H), 4.19-4.07 (m, 2H), 4.00-3.90 (m, 3H), 3.90-3.79 (m, 2H), 3.60 (s, 3H), 2.95-2.83 (m, 1H), 2.71-2.61 (m, 2H), 2.35-2.26 (m, 1H), 2.04-1.95 (m, 1H), 1.38 (s, 9H); LC-MS (ESI+) m/z 415.1 (M−56+H)+.

Step 2—3-[3-Methyl-4-(5-oxa-2-azaspiro[3.4]octan-7-yl)-2-oxo-benzimidazol-1-yl]piperidine-2,6-dione. To a solution of tert-butyl 7-[1-(2,6-dioxo-3-piperidyl)-3-methyl-2-oxo-benzimidazol-4-yl]-5-oxa-2-azaspiro[3.4]octane-2-carboxylate (40.0 mg, 85.01 umol) in DCM (1 mL) was added TFA (308 mg, 2.70 mmol). The mixture was stirred at 25° C. for 1 hr. On completion, the reaction mixture was concentrated in vacuo to give the compound (40.0 mg, 97% yield, TFA) as a yellow oil. LC-MS (ESI+) m/z 371.1 (M+H).

Benzyl 4-[(3-hydroxyazetidin-3-yl)methyl]piperazine-1-carboxylate (Intermediate CMV)

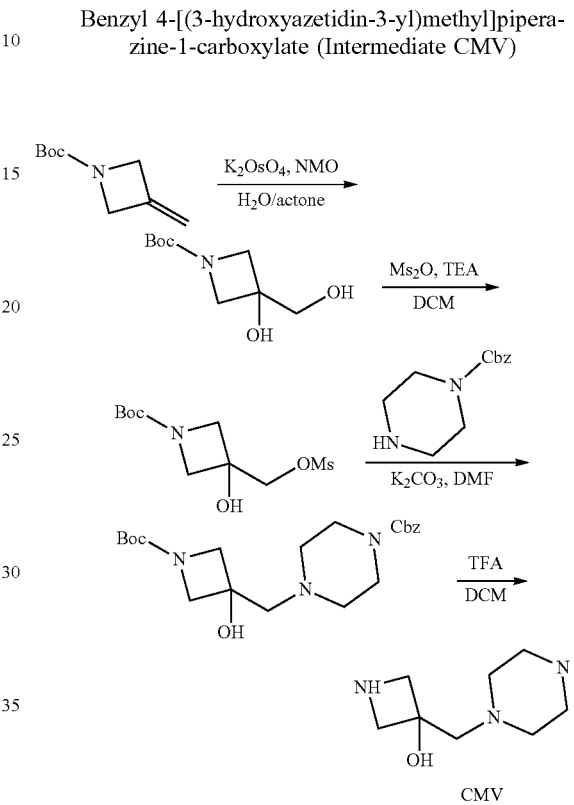

Step 1—Tert-butyl 3-hydroxy-3-(hydroxymethyl)azetidine-1-carboxylate. To a solution of tert-butyl 3-methyleneazetidine-1-carboxylate (4.50 g, 26.5 mmol, CAS #934664-41-2) in acetone (60 mL) and H$_2$O (35 mL) was added dipotassium dioxido(dioxo)osmium dihydrate (97.9 mg, 265 umol) and NMO (3.43 g, 29.2 mmol, 3.09 mL). The mixture was stirred at 25° C. for 16 hrs. On completion, the reaction mixture was quenched with Na$_2$SO$_3$ (50 mL) and extracted with EA (2×40 mL). The combined organic phase was washed with (20 mL) and brine (30 mL), dried with anhydrous Na$_2$SO$_4$, filtered and the filtrate was concentrated in vacuo to give residue. The residue was purified by column chromatography (SiO$_2$, DCM:EtOH=50:1 to DCM:EtOH=50:1, DCM:EtOH=10:1, P1:Rf=0.37) give the title compound (700 mg, 27% yield) as a white solid. $^1$H NMR (400 MHz, DMSO-d$_6$) δ 3.90-3.80 (m, 4H), 3.74 (s, 2H), 1.44 (s, 9H).

Step 2—Tert-butyl 3-hydroxy-3-(methylsulfonyloxymethyl)azetidine-1-carboxylate. To a solution of tert-butyl 3-hydroxy-3-(hydroxymethyl)azetidine-1-carboxylate (4.00 g, 19.6 mmol) in DCM (20 mL) was added TEA (1.99 g, 19.6 mmol, 2.74 mL) and methylsulfonyl methanesulfonate (6.86 g, 39.3 mmol) at 25° C., then the reaction mixture was stirred at 25° C. for 16 hrs. On completion, the reaction mixture was extracted with DCM (3×30 mL). The combined organic phase was washed with brine (25 mL), dried with anhydrous Na$_2$SO$_4$, filtered and the filtrate was concentrated in vacuo to give the title compound (950 mg, 17% yield) as a white solid. $^1$H NMR (400 MHz, DMSO-$d_6$) δ 4.37 (s, 2H), 3.98-3.85 (m, 4H), 3.10 (s, 3H), 1.46-1.41 (m, 9H).

Step 3—Benzyl 4-[(1-tert-butoxycarbonyl-3-hydroxy-azetidin-3-yl)methyl]piperazine-1-carboxylate. To a solution of benzyl piperazine-1-carboxylate (665 mg, 3.02 mmol, 583 ul, CAS #31166-44-6) and tert-butyl 3-hydroxy-3-(methylsulfonyloxymethyl)azetidine-1-carboxylate (850 mg, 3.02 mmol) in DMF (8 mL) was added $K_2CO_3$ (1.25 g, 9.06 mmol). Then the reaction mixture was stirred at 80° C. for 5 hrs. On completion, the residue was diluted with water (40 mL) and extracted with EA (2×20 mL). The combined organic layer was washed with brine (15 mL) and dried over $Na_2SO_4$, filtered and the filtrate was concentrated in vacuo to give a residue. The residue was purified by reverse phase (0.1% FA condition) to give the title compound (600 mg, 24% yield) as colorless oil. $^1$H NMR (400 MHz, DMSO-$d_6$) δ 7.41-7.30 (m, 5H), 5.14 (s, 2H), 3.97 (d, J=9.2 Hz, 2H), 3.81 (d, J=9.6 Hz, 2H), 3.57-3.50 (m, 4H), 2.72 (s, 2H), 2.50 (s, 4H), 1.44 (s, 9H); LCMS (ESI$^+$) m/z 350.1 (M+H−56)$^+$.

Step 4—Benzyl 4-[(3-hydroxyazetidin-3-yl)methyl]piperazine-1-carboxylate. To a solution of benzyl 4-[(1-tert-butoxycarbonyl-3-hydroxy-azetidin-3-yl)methyl]piperazine-1-carboxylate (200 mg, 493 umol) in DCM (4 mL) was added TFA (1.54 g, 13.5 mmol, 1 mL). The mixture was then stirred at 25° C. for 1 hr. On completion, the reaction mixture was concentrated in vacuo to give the title compound (205 mg, 99% yield, TFA) as colorless oil, LC-MS (ESI$^+$) m/z 306.1 (M+H)$^+$.

3-[4-[3-Hydroxy-3-(piperazin-1-ylmethyl)azetidin-1-yl]-3-methyl-2-oxo-benzimidazol-1-yl]piperidine-2,6-dione (Intermediate CMW)

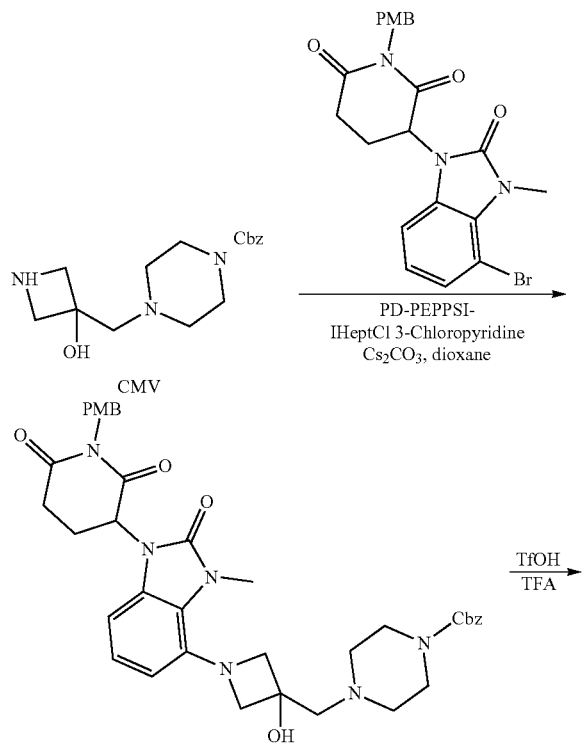

CMW

Step 1—Benzyl 4-[[3-hydroxy-1-[1-[1-[(4-methoxyphenyl)methyl]-2,6-dioxo-3-piperidyl]-3-methyl-2-oxo-benzimidazol-4-yl]azetidin-3-yl]methyl]piperazine-1-carboxylate. To a solution of benzyl 4-[(3-hydroxyazetidin-3-yl)methyl]piperazine-1-carboxylate (200 mg, 476 umol, TFA, Intermediate CMV) and 3-(4-bromo-3-methyl-2-oxo-benzimidazol-1-yl)-1-[(4-methoxyphenyl)methyl]piperidine-2,6-dione (218 mg, 476 umol, synthesized via Steps 1-4 of Intermediate HP) in dioxane (5 mL) was added 4 Å molecular sieves (200 mg), RuPhos Pd G$_3$ (39.8 mg, 47.6 umol) and $Cs_2CO_3$ (466 mg, 1.43 mmol). The mixture was stirred at 100° C. for 16 hrs. On completion, the reaction mixture was concentrated in vacuo to give a residue. The residue was purified by column chromatography (SiO$_2$, PE:EA=3:1 to DCM:MeOH=10:1, PE:EA=0:1, P1:Rf=0.18) and purified by prep-TLC (SiO$_2$, PE:EA=0:1, P1:Rf=0.18) to give the title compound (25.0 mg, 7% yield) as a white solid. LC-MS (ESI$^+$) m/z 683.8 (M+H)$^+$.

Step 2—3-[4-[3-Hydroxy-3-(piperazin-1-ylmethyl)azetidin-1-yl]-3-methyl-2-oxo-benzimidazol-1-yl]piperidine-2,6-dione. To a solution of benzyl 4-[[3-hydroxy-1-[1-[1-[(4-methoxyphenyl)methyl]-2,6-dioxo-3-piperidyl]-3-methyl-2-oxo-benzimidazol-4-yl]azetidin-3-yl]methyl]piperazine-1-carboxylate (22.0 mg, 32.2 umol) in TFA (1 mL) was added TfOH (340 mg, 2.27 mmol, 0.2 mL). The mixture was stirred at 70° C. for 2 hrs. On completion, the reaction mixture was concentrated in vacuo to give the title compound (16.0 mg, 91.5% yield, TFA) as black oil. LCMS (ESI$^+$) m/z 429.2 (M+H)$^+$.

6-Cyano-N-[2-(4-formylcyclohexyl)pyrazolo[3,4-c]pyridin-5-yl]pyridine-2-carboxamide (Intermediate CMX)

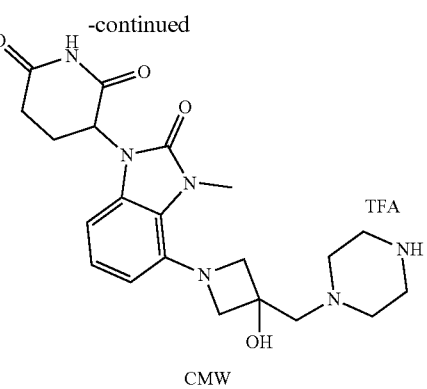

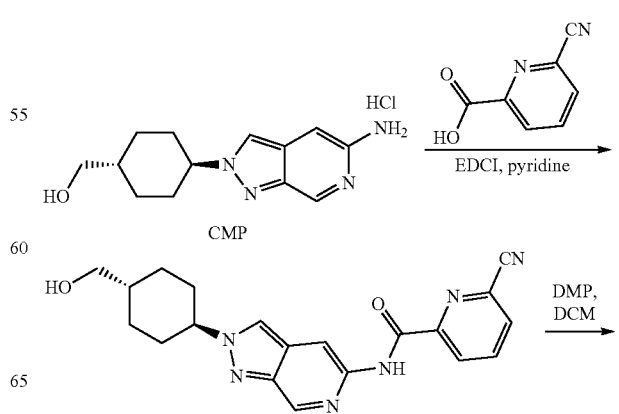

-continued

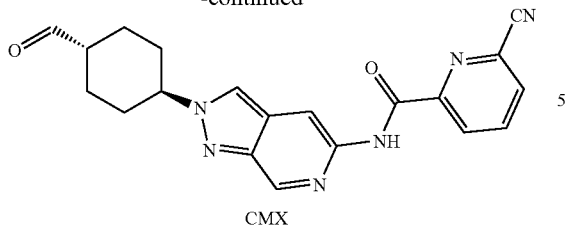

CMX

-continued

TFA, DCM →

Step 1—6-Cyano-N-[2-[4-(hydroxymethyl)cyclohexyl]pyrazolo[3,4-c]pyridin-5-yl]pyridine-2-carboxamide. To a solution of 6-cyanopyridine-2-carboxylic acid (72.1 mg, 487 umol, CAS #872602-74-9) and [4-(5-aminopyrazolo[3,4-c]pyridin-2-yl)cyclohexyl]methanol (80 mg, 324 umol, Intermediate CMP) in pyridine (2 mL) was added and EDCI (74.7 mg, 389 umol). The mixture was stirred 60° C. for 2 hrs. On completion, the reaction mixture was added drop by drop to water then filtered. Then the cake was dried in vacuo to give the title compound (90 mg, 73% yield) as a red solid. $^1$H NMR (400 MHz, DMSO-$d_6$) δ 12.44-12.05 (m, 1H), 10.24 (s, 1H), 9.06 (s, 1H), 8.65-8.54 (m, 1H), 8.45 (dt, J=2.0, 3.6 Hz, 1H), 8.39-8.21 (m, 2H), 4.55 (m, J=4.0, 8.0, 15.6 Hz, 2H), 3.29 (s, 1H), 2.26-2.12 (m, 2H), 2.02-1.85 (m, 4H), 1.58-1.40 (m, 1H), 1.27-1.08 (m, 2H); LC-MS (ESI$^+$) m/z 377.3 (M+H)$^+$.

Step 2—6-Cyano-N-[2-(4-formylcyclohexyl)pyrazolo[3,4-c]pyridin-5-yl]pyridine-2-carboxamide. To a solution of 6-cyano-N-[2-[4-(hydroxymethyl)cyclohexyl]pyrazolo[3,4-c]pyridin-5-yl]pyridine-2-carboxamide (80 mg, 212 umol) in DCM (3 mL) was added DMP (135 mg, 318 umol). The reaction mixture was stirred at 25° C. for 3 hrs. On completion, the reaction mixture was quenched with $Na_2S_2O_3$ (20 mL) and saturated $NaHCO_3$ (20 mL) at 25° C., and then stirred for 30 minutes. The mixture was extracted with DCM (2×30 mL). Then the combined organic layers was washed with $NaHCO_3$ (2×20 mL) and washed with saturated brine (2×20 mL). The combined organic layers was dried over $Na_2SO_4$, filtered and the filtrate was concentrated in vacuo to give the title compound (70 mg, 87% yield) as a white solid. $^1$H NMR (400 MHz, DMSO-$d_6$) δ 10.26 (s, 1H), 9.66 (s, 1H), 9.08 (s, 1H), 8.61 (s, 1H), 8.48-8.43 (m, 2H), 8.42-8.26 (m, 2H), 4.70-4.52 (m, 1H), 2.48-2.41 (m, 1H), 2.26 (dd, J=3.2, 12.4 Hz, 2H), 2.14 (d, J=11.2 Hz, 2H), 2.09-1.93 (m, 2H), 1.48 (m, J=3.2, 13.2 Hz, 2H); LC-MS (ESI$^+$) m/z 375.1 (M+H)$^+$.

3-[4-[1-(3,3-Difluoro-4-piperidyl)azetidin-3-yl]-3-methyl-2-oxo-benzimidazol-1-yl]piperidine-2,6-dione (Intermediate CMY)

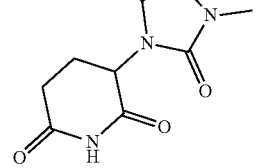

BRF

NaBH(OAc)$_3$,
TEA, HOAc, DMF
→

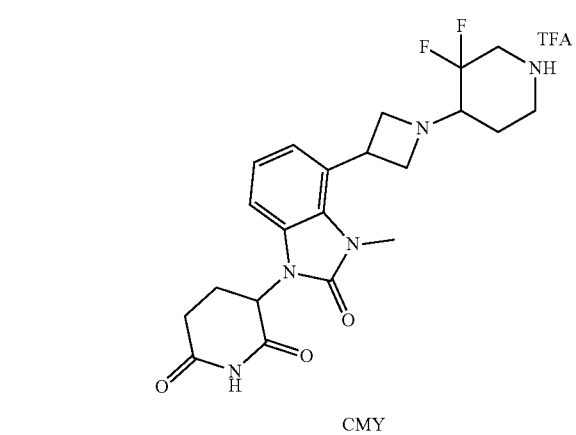

CMY

Step 1—Tert-butyl 4-[3-[1-(2,6-dioxo-3-piperidyl)-3-methyl-2-oxo-benzimidazol-4-yl]azetidin-1-yl]-3,3-difluoro-piperidine-1-carboxylate. To a solution of 3-[4-(azetidin-3-yl)-3-methyl-2-oxo-benzimidazol-1-yl]piperidine-2,6-dione (84 mg, 239 umol, TFA, Intermediate BRF) in DMF (1 mL) was added TEA (24.2 mg, 239 umol) and HOAc (14.3 mg, 239 umol) to adjust the pH=5. Then tert-butyl 3,3-difluoro-4-oxo-piperidine-1-carboxylate (84.4 mg, 359 umol) was added and the mixture was stirred at 100° C. for 13 hrs. Next, NaBH$_3$CN (18.0 mg, 287 umol) was added at 25° C. The mixture was then stirred at 100° C. for 3 hrs. On completion, the mixture was quenched with water (0.2 ml) and concentrated in vacuo to give a residue. The residue was purified by reverse phase (FA condition) to give the title compound (80 mg, 20% yield) as a white solid. LC-MS (ESI$^+$) m/z 534.4 (M+H)$^+$.

Step 2—3-[4-[1-(3,3-Difluoro-4-piperidyl)azetidin-3-yl]-3-methyl-2-oxo-benzimidazol-1-yl] piperidine-2,6-dione. A mixture of tert-butyl 4-[3-[1-(2, 6-dioxo-3-piperidyl)-3-methyl-2-oxo-benzimidazol-4-yl] azetidin-1-yl]-3,3-difluoro-piperidine-1-carboxylate (50 mg, 93.7 umol) and TFA (385 mg, 3.38 mmol) in DCM (1 mL) was stirred at 25° C. for 1 hr. On completion, the mixture was concentrated in vacuo to give the title compound (51.3 mg, 100% yield, TFA) as white solid. LC-MS (ESI$^+$) m/z 434.2 (M+H)$^+$.

Benzyl 3-[[3-(3-methyl-2-oxo-1H-benzimidazol-4-yl)cyclobutyl]methoxy]azetidine-1-carboxylate (Intermediate CMZ) and benzyl 3-[[3-(3-methyl-2-oxo-1H-benzimidazol-4-yl)cyclobutyl]methoxy]azetidine-1-carboxylate (Intermediate CNA)

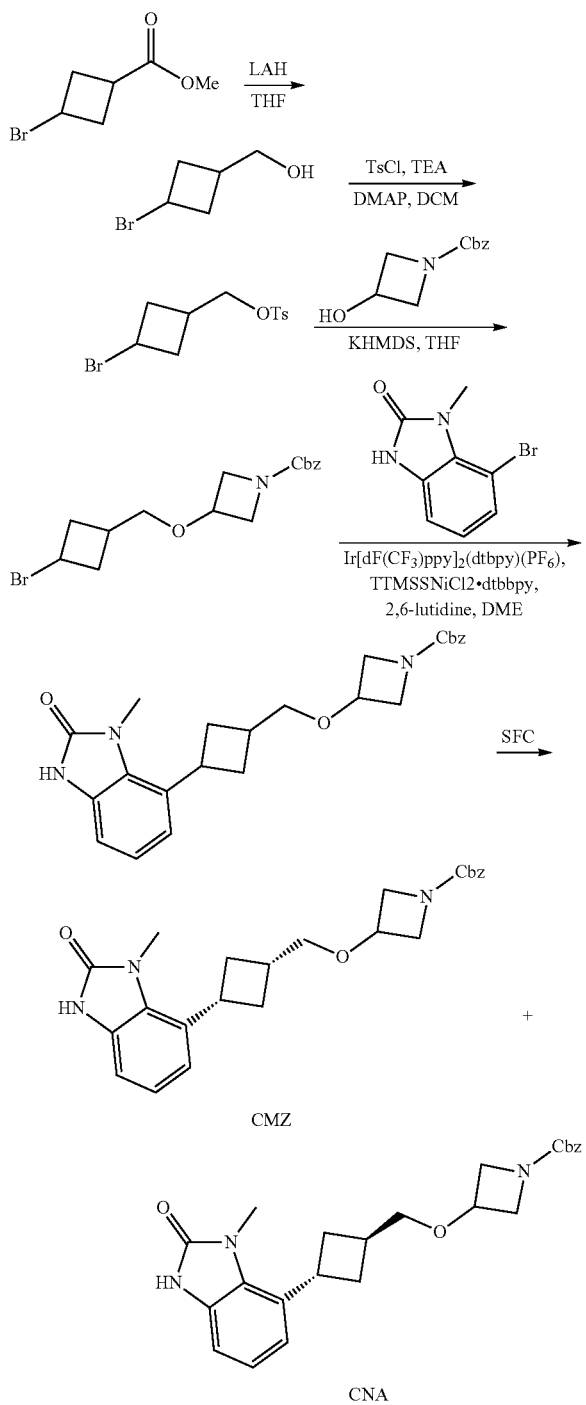

Step 1—(3-Bromocyclobutyl)methanol. To a solution of methyl 3-bromocyclobutanecarboxylate (10.0 g, 51.8 mmol, CAS #4935-00-6) in THF (150 mL) was added LiAlH$_4$ (2.36 g, 62.1 mmol) at 0° C. The mixture was then stirred at 25° C. for 1 hr. On completion, the mixture was quenched with H$_2$O (2.40 mL) and 15% NaOH aq. (2.40 mL) at 0° C. Then H$_2$O (7.20 mL) was added, then the mixture was dried with Na$_2$SO$_4$. The mixture was filtered and the organic layer was concentrated in vacuo to give the title compound (8.30 g, 97% yield) as a colorless oil. $^1$H NMR (400 MHz, CDCl$_3$) δ 4.65-4.50 (m, J=7.2 Hz, 1H), 3.66 (d, J=6.4 Hz, 2H), 2.83-2.70 (m, 1H), 2.64-2.49 (m, 4H)

Step 2—(3-Bromocyclobutyl)methyl 4-methylbenzenesulfonate. To a solution of (3-bromocyclobutyl)methanol (3.90 g, 22.7 mmol) in DCM (40 mL) was added 4-methylbenzenesulfonyl chloride (4.76 g, 24.9 mmol) with DMAP (554 mg, 4.54 mmol) and TEA (4.59 g, 45.3 mmol) at 0° C. Then the reaction mixture was stirred at 25° C. for 16 hrs. On completion, the mixture was diluted with H$_2$O (60 mL) and extracted with DCM (30 mL×3). The combined organic layers were washed with saturated NaCl (60 mL), dried over Na$_2$SO$_4$, filtered and concentrated in vacuo to give a residue. The residue was purified by column chromatography (SiO$_2$, PE:EA=10:1 to 3:1) to give the title compound (7.05 g, 92% yield) as a white solid. $^1$H NMR (400 MHz, CDCl$_3$-d) δ 7.79 (d, J=8.4 Hz, 2H), 7.36 (d, J=8.0 Hz, 2H), 4.50-4.30 (m, 1H), 4.03 (d, J=6.4 Hz, 2H), 2.96-2.85 (m, 1H), 2.59-2.48 (m, 4H), 2.46 (s, 3H).

Step 3—Benzyl 3-[(3-bromocyclobutyl)methoxy]azetidine-1-carboxylate. To a solution of benzyl 3-hydroxyazetidine-1-carboxylate (10.5 g, 50.5 mmol, CAS #128117-22-6) in THF (120 mL) was added KHMDS (1 M, 50.5 mL) at −10° C. The mixture was stirred at −10° C. for 0.5 h, then (3-bromocyclobutyl) methyl 4-methylbenzenesulfonate (12.4 g, 38.8 mmol) was added. The mixture was stirred at −10° C. for 1 hr. On completion, the mixture was diluted with H$_2$O (150 mL) and extracted with EA (150 mL×3). The combined organic layers were washed with saturated NaCl (100 mL), dried over Na$_2$SO$_4$, filtered and concentrated in vacuo to give a residue. The residue was purified by column chromatography (SiO$_2$, PE:EA=10:1 to 3:1) to give the title compound (2.80 g, 20% yield) as a yellow oil. $^1$H NMR (400 MHz, CDCl$_3$-d) δ 7.40-7.32 (m, 5H), 5.11 (s, 2H), 4.60-4.49 (m, 1H), 4.28-4.22 (m, 1H), 4.20-4.12 (m, 2H), 3.90 (dd, J=4.0, 10.0 Hz, 2H), 3.36 (d, J=6.0 Hz, 2H), 2.84-2.72 (m, 1H), 2.65-2.49 (m, 4H).

Step 4—Benzyl 3-[[3-(3-methyl-2-oxo-1H-benzimidazol-4-yl)cyclobutyl]methoxy]azetidine-1-carboxylate. To a mixture of 4-bromo-3-methyl-1H-benzimidazol-2-one (900 mg, 3.96 mmol, synthesized via Steps 1-3 of Intermediate HP), benzyl 3-[(3-bromocyclobutyl)methoxy]azetidine-1-carboxylate (1.83 g, 5.15 mmol), Ir[dF(CF$_3$)ppy]$_2$(dtbpy)(PF$_6$) (88.9 mg, 79.3 umol), NiCl$_2$·dtbbpy (47.3 mg, 119 umol), TTMSS (985 mg, 3.96 mmol) and 2,6-lutidine (849 mg, 7.93 mmol) in DME (90 mL). The vial was sealed and placed under nitrogen was added. The reaction was stirred and irradiated with a 10 W blue LED lamp (3 cm away), with cooling water to keep the reaction temperature at 25° C. for 14 hrs. On completion, the reaction mixture was filtered and concentrated in vacuo to give a residue. The residue was purified by column chromatography (SiO$_2$, PE:EA=5:1 to 0:1) to give the title compound (740 mg, 40% yield) as a light yellow oil. $^1$H NMR (400 MHz, DMSO-d$_6$) δ 10.83 (s, 1H), 7.41-7.28 (m, 5H), 7.08 (d, J=7.6 Hz, 1H), 6.98 (t, J=7.6 Hz, 1H), 6.86-6.81 (m, 1H), 5.06-5.02 (m, 2H), 4.38-4.30 (m, 1H), 4.19-4.12 (m, 2H), 3.83-3.72 (m, 2H), 3.62-3.59 (m, 1H), 3.54 (d, J=7.2 Hz, 2H), 3.45 (s, 3H), 2.35-2.25 (m, 2H), 2.19-2.09 (m, 2H), 1.79-1.75 (m, 1H). LC-MS (ESI$^+$) m/z 422.3 (M+H)$^+$.

Step 5—Benzyl 3-[[3-(3-methyl-2-oxo-1H-benzimidazol-4-yl)cyclobutyl]methoxy]azetidine-1-carboxylate and benzyl 3-[[3-(3-methyl-2-oxo-1H-benzimidazol-4-yl)cyclobutyl]methoxy] azetidine-1-carboxylate. Benzyl 3-[[3-(3-methyl-2-oxo-1H-benzimidazol-4-yl)cyclobutyl] methoxy]azetidine-1-carboxylate (740 mg, 1.76 mmol) was separated by SFC (column: DAICEL CHIRALCEL OJ (250 mm*30 mm, 10 um); mobile phase: [Neu-MeOH]) to give benzyl 3-[[3-(3-methyl-2-oxo-1H-benzimidazol-4-yl)cyclobutyl]methoxy]azetidine-1-carboxylate (240 mg, 32% yield, $t_R$=2.01) as a yellow oil ($^1$H NMR (400 MHz, DMSO-$d_6$) δ 10.82 (s, 1H), 7.40-7.27 (m, 5H), 7.03-6.92 (m, 2H), 6.82 (dd, J=1.2, 7.2 Hz, 1H), 5.03 (s, 2H), 4.31-4.24 (m, 1H), 4.17-4.07 (m, 2H), 3.99-3.88 (m, 1H), 3.80-3.67 (m, 2H), 3.49 (s, 3H), 3.35 (d, J=6.4 Hz, 2H), 2.56-2.52 (m, 1H), 2.40-2.31 (m, 2H), 1.98-1.88 (m, 2H); LC-MS (ESI$^+$) m/z 422.1 (M+H)$^+$ and benzyl 3-[[3-(3-methyl-2-oxo-1H-benzimidazol-4-yl)cyclobutyl]methoxy] azetidine-1-carboxylate (250 mg, 34% yield, $t_R$=2.21) as a yellow oil ($^1$H NMR (400 MHz, DMSO-$d_6$) δ 10.83 (s, 1H), 7.45-7.25 (m, 5H), 7.07 (d, J=8.0 Hz, 1H), 6.97 (t, J=7.6 Hz, 1H), 6.83 (d, J=7.6 Hz, 1H), 5.04 (s, 2H), 4.39-4.29 (m, 1H), 4.24-4.06 (m, 3H), 3.85-3.71 (m, 2H), 3.57-3.51 (m, 2H), 3.45 (s, 3H), 2.49-2.44 (m, 1H), 2.34-2.25 (m, 2H), 2.19-2.08 (m, 2H). LC-MS (ESI$^+$) m/z 422.3 (M+H)$^+$. The absolute stereochemistry of the diastereomers was assigned arbitrarily.

3-[4-[3-(Azetidin-3-yloxymethyl)cyclobutyl]-3-methyl-2-oxo-benzimidazol-1-yl]piperidine-2,6-dione (Intermediate CNB)

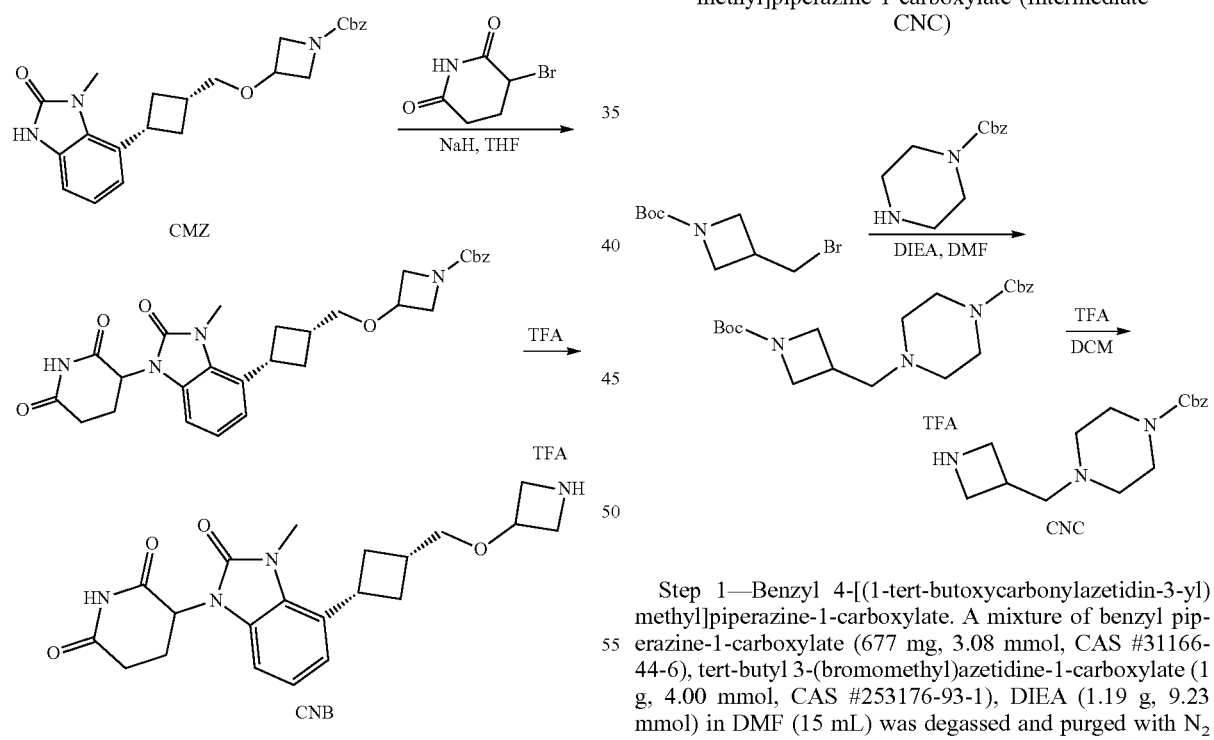

Step 1—Benzyl 3-[[3-[1-(2,6-dioxo-3-piperidyl)-3-methyl-2-oxo-benzimidazol-4-yl]cyclobutyl] methoxy]azetidine-1-carboxylate. A mixture of benzyl 3-[[3-(3-methyl-2-oxo-1H-benzimidazol-4-yl)cyclobutyl]methoxy] azetidine-1-carboxylate (30 mg, 71.2 μmol, Intermediate CMZ) in THF (1 mL) was added NaH (8.54 mg, 213 μmol, 60% dispersion in mineral oil) at 0° C., and the mixture was stirred at 25° C. for 1 hr. Then 3-bromopiperidine-2,6-dione (41.0 mg, 213 μmol, CAS #62595-74-8) was added and the mixture was stirred at 50° C. for 1 hr. On completion, the mixture was diluted with H$_2$O (10 mL), then quenched with saturated NH$_4$Cl (3 mL), and the mixture was stirred at 25° C. for 0.5 hr. Next the mixture was extracted with EA (20 mL×3). The combined organic layers were washed with saturated NaCl (10 mL), dried over Na$_2$SO$_4$, filtered and concentrated under reduced pressure to give a residue. The residue was separated by SFC (column: DAICEL CHIRALCEL OJ (250 mm*30 mm, 10 um); mobile phase: [0.1% NH$_3$H$_2$O IPA]) to give the title compound (10 mg, 40% yield) as a yellow oil. $^1$H NMR (400 MHz, CDCl$_3$-d) δ 8.20 (s, 1H), 7.41-7.29 (m, 5H), 7.14-7.02 (m, 2H), 6.68 (d, J=7.6 Hz, 1H), 5.21 (dd, J=5.2, 12.0 Hz, 1H), 5.11 (s, 2H), 4.31-4.12 (m, 3H), 3.98-3.85 (m, 3H), 3.68 (s, 3H), 3.37 (d, J=6.0 Hz, 2H), 2.99-2.68 (m, 3H), 2.63-2.53 (m, 1H), 2.50-2.39 (m, 2H), 2.25-2.18 (m, 1H), 2.09 (q, J=10.0 Hz, 2H). LC-MS (ESI$^+$) m/z 533.4 (M+H)$^+$.

Step 2—3-[4-[3-(Azetidin-3-yloxymethyl)cyclobutyl]-3-methyl-2-oxo-benzimidazol-1-yl]piperidine-2,6-dione. To a solution of benzyl 3-[[3-[1-(2,6-dioxo-3-piperidyl)-3-methyl-2-oxo-benzimidazol-4-yl]cyclobutyl] methoxy]azetidine-1-carboxylate (10 mg, 18.8 μmol) in TFA (100 μL) was stirred at 70° C. for 1 hr. On completion, the reaction mixture was concentrated in vacuo to give the title compound (8.0 mg, 79% yield, TFA) as brown oil. LC-MS (ESI$^+$) m/z 399.3 (M+H)$^+$.

Benzyl 4-[(1-tert-butoxycarbonylazetidin-3-yl)methyl]piperazine-1-carboxylate (Intermediate CNC)

Step 1—Benzyl 4-[(1-tert-butoxycarbonylazetidin-3-yl)methyl]piperazine-1-carboxylate. A mixture of benzyl piperazine-1-carboxylate (677 mg, 3.08 mmol, CAS #31166-44-6), tert-butyl 3-(bromomethyl)azetidine-1-carboxylate (1 g, 4.00 mmol, CAS #253176-93-1), DIEA (1.19 g, 9.23 mmol) in DMF (15 mL) was degassed and purged with N$_2$ three times. Then the mixture was stirred at 70° C. for 16 hrs under N$_2$ atmosphere. On completion, the reaction mixture was concentrated in vacuo to remove DMF. The residue was diluted with EA (100 mL), the organic layer was washed with brine (250 mL×3), dried over anhydrous Na$_2$SO$_4$, filtered and the filtrate was concentrated in vacuo to give a residue. The residue was purified by column chromatography (SiO$_2$, Petroleum ether/Ethyl acetate=5/1 to 0/1) to give the title compound (1.14 g, 95% yield) as yellow oil. $^1$H NMR (400 MHz, DMSO-d6) δ 7.41-7.24 (m, 6H), 7.20 (d, J=8.8 Hz, 2H), 6.91-6.79 (m, 3H), 6.63 (d, J=8.0 Hz, 1H), 5.47 (dd, J=5.2, 12.8 Hz, 1H), 5.12-5.00 (m, 2H), 4.86-4.70 (m, 2H), 3.92 (m, 2H), 3.72 (s, 2H), 3.56 (s, 2H), 3.51-3.46 (m, 2H), 3.32 (s, 6H), 2.74-2.74 (m, 1H), 2.88-2.74 (m, 2H), 2.68 (d, J=10.0 Hz, 1H), 2.62-2.58 (m, 2H), 2.35 (d, J=4.6 Hz, 4H), 2.06-1.97 (m, 1H); LC-MS (ESI+) m/z 390.2 (M+H)+.

Step 2—Benzyl 4-[(1-tert-butoxycarbonylazetidin-3-yl)methyl]piperazine-1-carboxylate. To a solution of benzyl 4-[(1-tert-butoxycarbonylazetidin-3-yl) methyl] piperazine-1-carboxylate (1.1 g, 2.82 mmol) in DCM (10 mL) was added TFA (2.75 mL, 37.1 mmol), then the reaction mixture was stirred at 25° C. for 3 hrs. On completion, the reaction mixture was concentrated in vacuo to give the title compound (1.1 g, 96% yield, TFA) as brown oil. LC-MS (ESI+) m/z 290.1 (M+H)+.

3-[3-methyl-2-oxo-4-[3-(piperazin-1-ylmethyl)azetidin-1-yl]benzimidazol-1-yl]piperidine-2,6-dione (Intermediate CND)

1H), 5.47 (dd, J=5.2, 12.8 Hz, 1H), 5.12-5.00 (m, 2H), 4.86-4.70 (m, 2H), 3.92 (m, 2H), 3.72 (s, 2H), 3.56 (s, 2H), 3.51-3.46 (m, 2H), 3.32 (s, 6H), 2.74-2.74 (m, 1H), 2.88-2.74 (m, 2H), 2.68 (d, J=10.0 Hz, 1H), 2.62-2.58 (m, 2H), 2.35 (d, J=4.8 Hz, 4H), 2.06-1.97 (m, 1H); LC-MS (ESI+) m/z 667.5 (M+H)+.

Step 2—3-[3-methyl-2-oxo-4-[3-(piperazin-1-ylmethyl)azetidin-1-yl]benzimidazol-1-yl]piperidine-2,6-dione. To a solution of benzyl 4-[[1-[1-[1-[(4-methoxyphenyl)methyl]-2,6-dioxo-3-piperidyl]-3-methyl-2-oxo-benzimidazol-4-yl]azetidin-3-yl]methyl]piperazine-1-carboxylate (50 mg, 74.9 umol) in TFA (0.3 mL) was added TfOH (0.3 mL, 3.40 mmol). The reaction mixture was stirred at 70° C. for 2 hrs. On completion, the reaction mixture was concentrated in vacuo to give the title compound (39 mg, 98% yield, TFA) as brown oil. LC-MS (ESI+) m/z 413.2 (M+H)+.

N-[3-(Difluoromethyl)-1-(4-formylcyclohexyl)pyrazol-4-yl]-5-[(2R)-2-methylmorpholin-4-yl]pyrazolo[1,5-a]pyrimidine-3-carboxamide (Intermediate CNE)

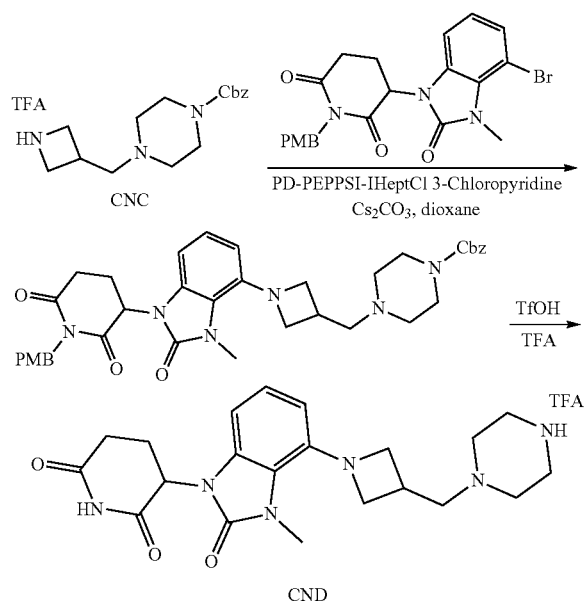

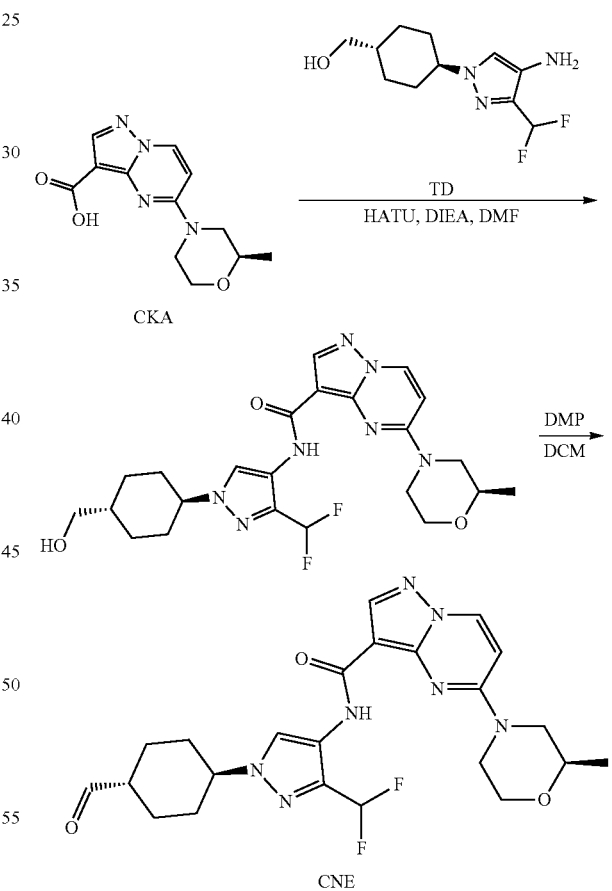

Step 1—Benzyl 4-[[1-[1-[1-[(4-methoxyphenyl)methyl]-2,6-dioxo-3-piperidyl]-3-methyl-2-oxo-benz imidazol-4-yl] azetidin-3-yl]methyl]piperazine-1-carboxylate. To a solution of benzyl 4-(azetidin-3-ylmethyl)piperazine-1-carboxylate (250 mg, 619 umol, TFA, Intermediate CNC) and 3-(4-bromo-3-methyl-2-oxo-benzimidazol-1-yl)-1-[(4-methoxyphenyl)methyl]piperidine-2,6-dione (189 mg, 413 umol, synthesized via Steps 1-4 of Intermediate HP) in dioxane (6 mL) was added Cs2CO3 (673 mg, 2.07 mmol) and Pd-PEPPSI-IHeptCl (40.2 mg, 41.3 umol). The reaction mixture was degassed under vacuum, purged with N2 three times, then the mixture was stirred at 100° C. for 5 hrs under N2 atmosphere. On completion, the mixture was cooled to rt, filtered to give a filtrate, and concentrated in vacuo to give a residue. The residue was purified by column chromatography (SiO2, Petroleum ether/Ethyl acetate=5/1 to 0/1) to give the title compound (220 mg, 79% yield) as a white solid. 1H NMR (400 MHz, DMSO-d6) δ 7.41-7.24 (m, 6H), 7.20 (d, J=8.8 Hz, 2H), 6.91-6.79 (m, 3H), 6.63 (d, J=8.0 Hz, Step 1—N-[3-(difluoromethyl)-1-[4-(hydroxymethyl)cyclohexyl]pyrazol-4-yl]-5-[(2R)-2-methylmorpholin-4-yl]pyrazolo[1,5-a]pyrimidine-3-carboxamide. To a solution of 5-[(2R)-2-methylmorpholin-4-yl]pyrazolo[1,5-a]pyrimidine-3-carboxylic acid (100 mg, 381 μmol, Intermediate CKA) in DMF (3 mL) was added HATU (173 mg, 457 μmol) and DIEA (246 mg, 1.91 mmol). The mixture was stirred at 25° C. for 30 mins. Then the mixture was added drop by drop to a solution of [4-[4-amino-3-(difluoromethyl)pyrazol-1-yl]cyclohexyl]methanol (93.5 mg, 381 μmol, Intermediate TD) in DMF (3 mL). The mixture was then stirred at 50° C. for 12 hrs. On completion, the reaction mixture was concentrated in vacuo to give the title compound (160 mg, 85% yield) as a white solid. LC-MS (ESI$^+$) m/z 490.3 (M+H)$^+$.

Step 2—N-[3-(Difluoromethyl)-1-(4-formylcyclohexyl)pyrazol-4-yl]-5-[(2R)-2-methylmorpholin-4-yl]pyrazolo[1,5-a]pyrimidine-3-carboxamide. To a solution of N-[3-(difluoromethyl)-1-[4-(hydroxymethyl)cyclohexyl]pyrazol-4-yl]-5-[(2R)-2-methylmorpholin-4-yl]pyrazolo[1,5-a]pyrimidine-3-carboxamide (150 mg, 306 μmol) in DCM (3 mL) was added DMP (194 mg, 459 μmol). The reaction mixture was stirred at 25° C. for 3 hrs. On completion, the reaction mixture was quenched by saturated Na$_2$S$_2$O$_3$ (20 mL) and saturated NaHCO$_3$ (20 mL) at 25° C., and then the mixture was stirred for 30 mins. The mixture was then extracted with DCM (2×15 mL). Then the combined organic layer was washed with NaHCO$_3$ (2×15 mL) and washed with saturated salt solution (2×15 mL). The combined organic layer was dried over Na$_2$SO$_4$, filtered and the filtrate was concentrated in vacuo to give the title compound (149 mg, 99% yield) as a yellow solid. $^1$H NMR (400 MHz, DMSO-d$_6$) δ 9.62 (s, 1H), 9.34 (s, 1H), 8.82 (d, J=8.0 Hz, 1H), 8.41 (s, 1H), 8.29 (s, 1H), 7.35-6.98 (m, 1H), 6.92 (d, J=8.0 Hz, 1H), 4.54-4.30 (m, 2H), 4.27-4.16 (m, 1H), 3.93 (dd, J=2.4, 11.6 Hz, 1H), 3.66-3.53 (m, 2H), 3.11 (t, J=11.2 Hz, 1H), 2.78 (t, J=11.6 Hz, 1H), 2.45-2.33 (m, 1H), 2.13-2.02 (m, 4H), 1.89-1.73 (m, 2H), 1.47-1.32 (m, 2H), 1.19 (d, J=6.4 Hz, 3H); LC-MS (ESI$^+$) m/z 488.2 (M+H)$^+$.

3-[4-[4-[(3S,4R)-3-fluoro-4-piperidyl]piperazin-1-yl]-3-methyl-2-oxo-benzimidazol-1-yl]piperidine-2,6-dione (Intermediate CNF)

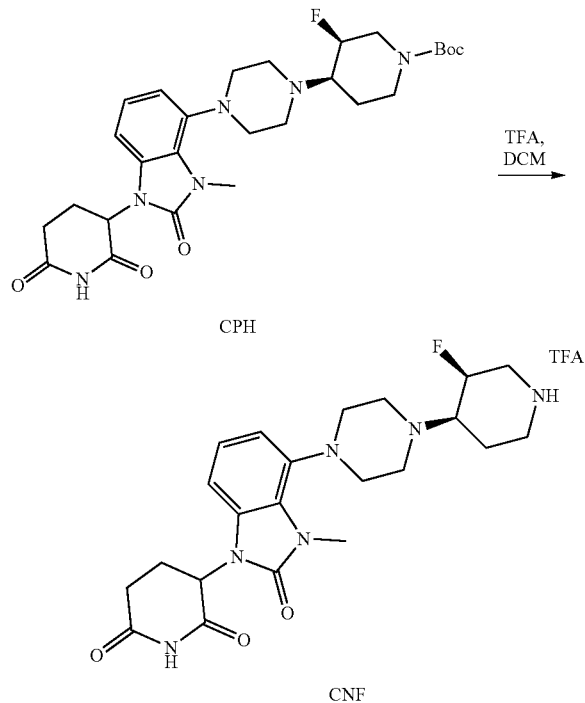

To a solution of tert-butyl (3S,4R)-4-[4-[1-(2,6-dioxo-3-piperidyl)-3-methyl-2-oxo-benzimidazol-4-yl]piperazin-1-yl]-3-fluoro-piperidine-1-carboxylate (40 mg, 73.4 μmol, from Intermediate CPH) in DCM (0.5 mL) and TFA (0.1 mL) and the mixture was stirred at 25° C. for 0.5 hr. On completion, the reaction mixture was concentrated in vacuo to give the title compound (40 mg, 97% yield, TFA) as yellow oil. LC-MS (ESI+) m/z 445.4 (M+H)$^+$.

Benzyl 4-[(3-fluoroazetidin-3-yl)methyl]piperazine-1-carboxylate (Intermediate CNG)

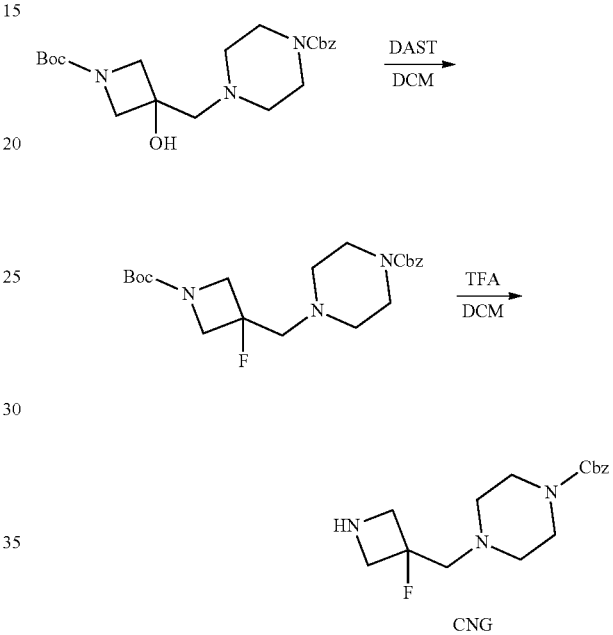

Step 1—Benzyl 4-[(1-tert-butoxycarbonyl-3-fluoro-azetidin-3-yl) methyl]piperazine-1-carboxylate. To a solution of benzyl 4-[(1-tert-butoxycarbonyl-3-hydroxy-azetidin-3-yl) methyl]piperazine-1-carboxylate (1.54 g, 3.80 mmol, synthesized via Steps 1-3 of Intermediate CMV) in DCM (15 mL) was added DAST (1.84 g, 11.3 mmol) at 0° C. under N$_2$. The reaction was then stirred at 25° C. for 1 hr under N$_2$. On completion, the reaction was quenched with NaHCO$_3$ solution (20 mL) at 0° C. and extracted with DCM (30 mL). The organic layer was washed with water (20 mL), dried over with Na$_2$SO$_4$ and concentrated in vacuo to give a residue. The residue was purified by column chromatography (SiO$_2$, PE/EA=75:25) to give the title compound (1.07 g, 69% yield) as colorless oil. $^1$H NMR (400 MHz, DMSO-d$_6$) δ 7.40-7.28 (m, 5H), 5.07 (s, 2H), 3.64 (s, 4H), 3.36 (d, J=6.0 Hz, 4H), 2.53-2.51 (m, 2H), 2.49-2.48 (m, 4H), 1.38 (s, 9H).

Step 2—Benzyl 4-[(3-fluoroazetidin-3-yl) methyl]piperazine-1-carboxylate. To a solution of benzyl 4-[(1-tert-butoxycarbonyl-3-fluoro-azetidin-3-yl) methyl] piperazine-1-carboxylate (445 mg, 1.09 mmol) in DCM (5 mL) was added TFA (2.61 g, 22.8 mmol) at 25° C. The reaction was stirred at 25° C. for 3 hrs. On completion, the reaction was concentrated in vacuo to give the title compound (460 mg, 99% yield, TFA) as yellow oil. LC-MS (ESI$^+$) m/z 308.2 (M+H)$^+$.

619

3-[4-[3-Fluoro-3-(piperazin-1-ylmethyl)azetidin-1-yl]-3-methyl-2-oxo-benzimidazol-1-yl]piperidine-2,6-dione (Intermediate CNH)

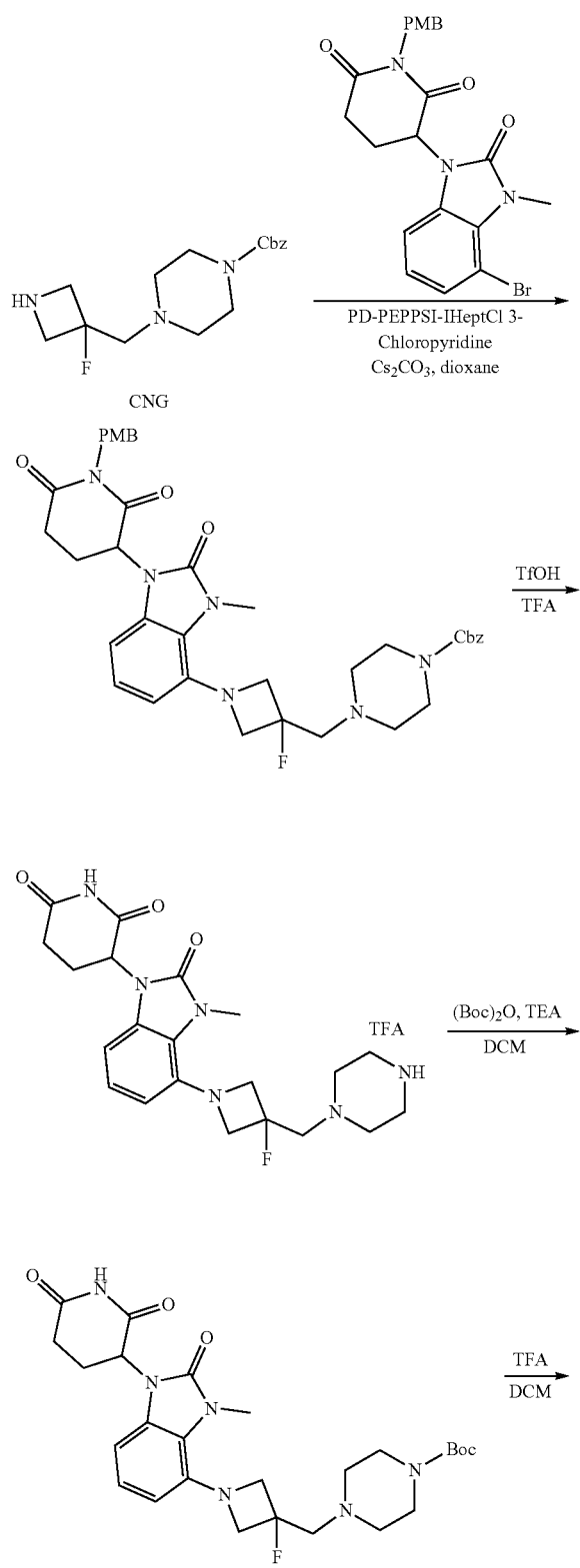

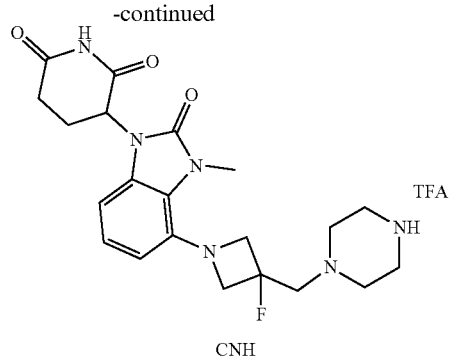

CNH

Step 1—Benzyl 4-[[3-fluoro-1-[1-[1-[(4-methoxyphenyl)methyl]-2,6-dioxo-3-piperidyl]-3-methyl-2-oxo-benzimidazol-4-yl]azetidin-3-yl]methyl]piperazine-1-carboxylate. To a solution of benzyl 4-[(3-fluoroazetidin-3-yl)methyl]piperazine-1-carboxylate (303 mg, 720 μmol, TFA, Intermediate CNG), 3-(4-bromo-3-methyl-2-oxo-benzimidazol-1-yl)-1-[(4-methoxyphenyl)methyl]piperidine-2,6-dione (300 mg, 654 μmol, synthesized via Steps 1-4 of Intermediate HP) and $Cs_2CO_3$ (853 mg, 2.62 mmol) in dioxane (6 mL) was added 1,3-bis[2,6-bis(1-propylbutyl)phenyl]-4,5-dichloro-2H-imidazol-1-ium-2-ide; 3-chloropyridine dichloropalladium (63 mg, 65 μmol) under $N_2$. The reaction was stirred at 110° C. for 4 hrs under $N_2$. On completion, the reaction was diluted with EA (30 mL). The organic layer was washed with water (30 mL), dried over with $Na_2SO_4$ and concentrated in vacuo. The residue was purified by column chromatography ($SiO_2$, PE/EA=59:41) to give the title compound (200 mg, 44% yield) as yellow solid. $^1$H NMR (400 MHz, DMSO-$d_6$) δ 7.38-7.31 (m, 5H), 7.20 (d, J=8.4 Hz, 2H), 6.95-6.89 (m, 1H), 6.87-6.83 (m, 2H), 6.72 (d, J=8.0 Hz, 1H), 6.70-6.59 (m, 1H), 5.75 (s, 1H), 5.52-5.44 (m, 1H), 5.09-5.07 (m, 2H), 4.96 (s, 1H), 4.83 (d, J=15.6 Hz, 2H), 4.79-4.71 (m, 1H), 3.72 (s, 3H), 3.68-3.63 (m, 2H), 3.56 (s, 3H), 3.37 (d, J=6.0 Hz, 4H), 3.30 (d, J=3.6 Hz, 1H), 3.09-2.99 (m, 1H), 2.85-2.77 (m, 1H), 2.64-2.76 (m, J=8.4, 13.2 Hz, 1H), 2.53 (s, 4H), 2.06-2.00 (m, 1H).

Step 2—3-[4-[3-Fluoro-3-(piperazin-1-ylmethyl)azetidin-1-yl]-3-methyl-2-oxo-benzimidazol-1-yl]piperidine-2,6-dione. To a solution of benzyl 4-[[3-fluoro-[1-[1-[(4-methoxyphenyl) methyl]-2,6-dioxo-3-piperidyl]-3-methyl-2-oxo-benzimidazol-4-yl]azetidin-3-yl]methyl]piperazine-1-carboxylate (200 mg, 292 μmol) in TFA (2 mL) was added TfOH (678 mg, 4.52 mmol). The reaction was then stirred at 70° C. for 2 hrs. On completion, the reaction was concentrated in vacuo to give the title compound (159 mg, 99% yield, TFA) as brown oil. LC-MS (ESI$^+$) m/z 431.2 (M+H)$^+$.

Step 3—Tert-butyl 4-[[1-[1-(2,6-dioxo-3-piperidyl)-3-methyl-2-oxo-benzimidazol-4-yl]-3-fluoro-azetidin-3-yl]methyl]piperazine-1-carboxylate. To a solution of 3-[4-[3-fluoro-3-(piperazin-1-ylmethyl) azetidin-1-yl]-3-methyl-2-oxo-benzimidazol-1-yl] piperidine-2,6-dione (159 mg, 292 μmol, TFA) and TEA (88.6 mg, 876 μmol) in DCM (1.5 mL) was added (Boc)$_2$O (95.6 mg, 438 μmol) at 0° C. Then the mixture was stirred at 25° C. for 1 hr. On completion, the reaction was diluted with DCM (10 mL). The organic layer was washed with water (10 mL×2), dried over with $Na_2SO_4$ and concentrated in vacuo. The residue was purified by reverse phase (0.1% FA condition) to give the title compound (154 mg, 99% yield) as yellow solid. LC-MS (ESI$^+$) m/z 475.1 (M+H−56)$^+$.

Step 4—3-[4-[3-Fluoro-3-(piperazin-1-ylmethyl)azetidin-1-yl]-3-methyl-2-oxo-benzimidazol-1-yl]piperidine-2,6-dione. To a solution of tert-butyl 4-[[1-[1-(2,6-dioxo-3-piperidyl)-3-methyl-2-oxo-benzimidazol-4-yl]-3-fluoro-azetidin-3-yl]methyl]piperazine-1-carboxylate (154 mg, 290 μmol) in DCM (1.5 mL) was added TFA (460 mg, 4.04 mmol). The reaction was then stirred at 25° C. for 1 hr. On completion, the reaction was concentrated in vacuo to give the title compound (124 mg, 99% yield) as brown oil. LC-MS (ESI+) m/z 431.2 (M+H)+.

Tert-butyl 4-(azetidin-3-ylmethyl)piperazine-1-carboxylate (Intermediate CNI)

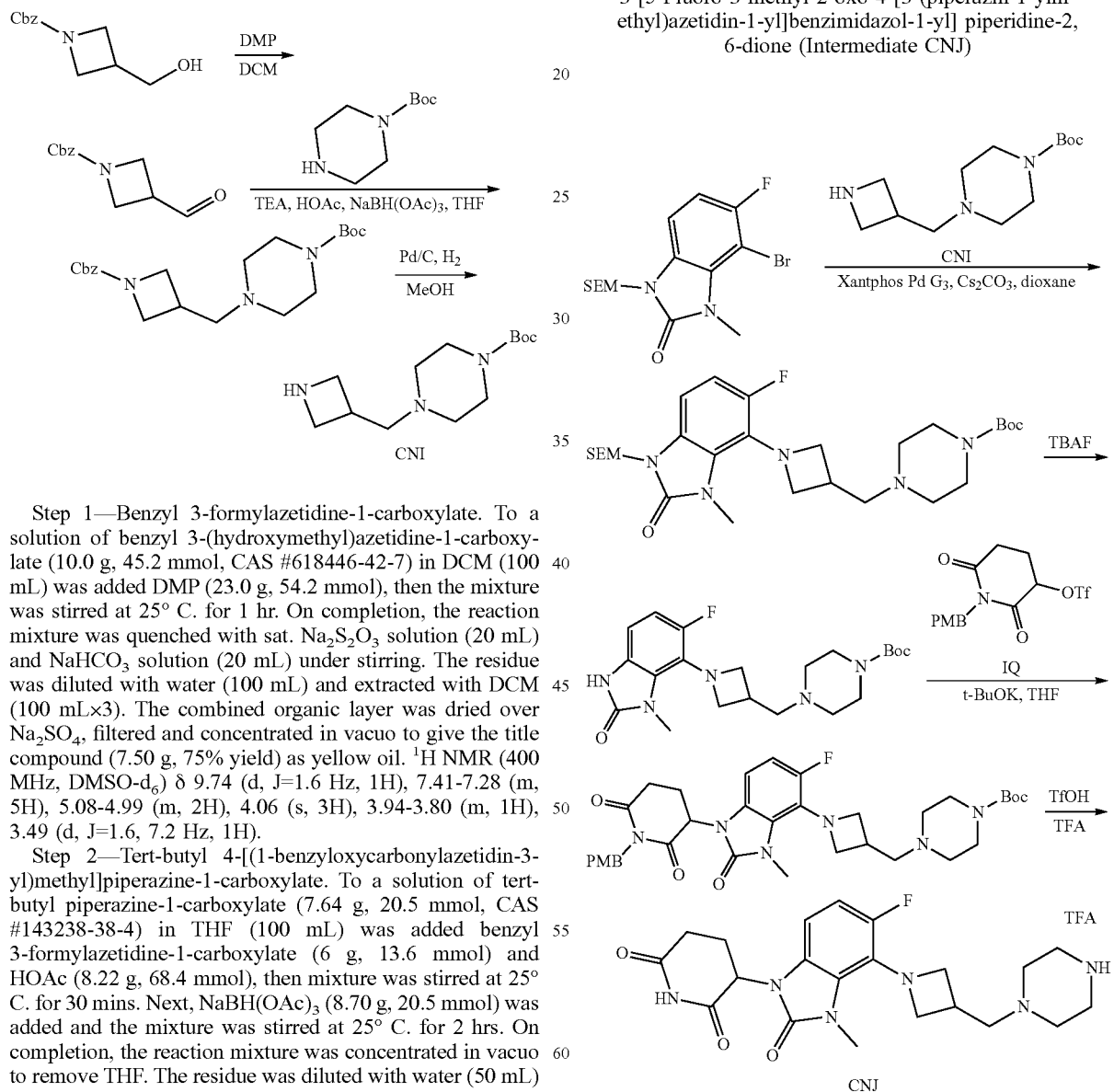

Step 1—Benzyl 3-formylazetidine-1-carboxylate. To a solution of benzyl 3-(hydroxymethyl)azetidine-1-carboxylate (10.0 g, 45.2 mmol, CAS #618446-42-7) in DCM (100 mL) was added DMP (23.0 g, 54.2 mmol), then the mixture was stirred at 25° C. for 1 hr. On completion, the reaction mixture was quenched with sat. $Na_2S_2O_3$ solution (20 mL) and $NaHCO_3$ solution (20 mL) under stirring. The residue was diluted with water (100 mL) and extracted with DCM (100 mL×3). The combined organic layer was dried over $Na_2SO_4$, filtered and concentrated in vacuo to give the title compound (7.50 g, 75% yield) as yellow oil. $^1$H NMR (400 MHz, DMSO-$d_6$) δ 9.74 (d, J=1.6 Hz, 1H), 7.41-7.28 (m, 5H), 5.08-4.99 (m, 2H), 4.06 (s, 3H), 3.94-3.80 (m, 1H), 3.49 (d, J=1.6, 7.2 Hz, 1H).

Step 2—Tert-butyl 4-[(1-benzyloxycarbonylazetidin-3-yl)methyl]piperazine-1-carboxylate. To a solution of tert-butyl piperazine-1-carboxylate (7.64 g, 20.5 mmol, CAS #143238-38-4) in THF (100 mL) was added benzyl 3-formylazetidine-1-carboxylate (6 g, 13.6 mmol) and HOAc (8.22 g, 68.4 mmol), then mixture was stirred at 25° C. for 30 mins. Next, NaBH(OAc)$_3$ (8.70 g, 20.5 mmol) was added and the mixture was stirred at 25° C. for 2 hrs. On completion, the reaction mixture was concentrated in vacuo to remove THF. The residue was diluted with water (50 mL) and extracted with EA (50 mL×3). The combined organic layer was dried over $Na_2SO_4$, filtered and concentrated in vacuo to give a residue. The residue was purified by column chromatography (SiO$_2$, PE:EA=50:1 to PE:EA=5:1) to give the title compound (8.00 g, 75% yield) as yellow solid. $^1$H NMR (400 MHz, DMSO-$d_6$) δ 7.40-7.28 (m, 5H), 5.01 (s, 2H), 4.06-3.97 (m, 2H), 3.63-3.48 (m, 2H), 3.29 (d, J=17.6 Hz, 4H), 2.82-2.71 (m, 1H), 2.50 (s, 2H), 2.27 (t, J=4.8 Hz, 4H), 1.38 (s, 9H); LC-MS (ESI+) m/z 390.3 (M+H)+.

Step 3—Tert-butyl 4-(azetidin-3-ylmethyl)piperazine-1-carboxylate. To a solution of tert-butyl 4-[(1-benzyloxycarbonylazetidin-3-yl)methyl]piperazine-1-carboxylate (8 g, 20.5 mmol) in MeOH (80 mL) was added Pd/C (8 g, 10 wt %) under N$_2$ atmosphere. The suspension was degassed and purged with H$_2$ three times. The mixture was then stirred under H$_2$ (50 Psi) at 50° C. for 12 hrs. On completion, the reaction mixture was filtered and concentrated in vacuo to give the title compound (4 g, 76% yield) as colorless oil. $^1$H NMR (400 MHz, DMSO-$d_6$) δ 3.89 (s, 2H), 3.60-3.47 (m, 7H), 3.07 (s, 1H), 2.79-2.72 (m, 4H), 2.57-2.51 (m, 2H), 1.63 (s, 9H).

3-[5-Fluoro-3-methyl-2-oxo-4-[3-(piperazin-1-ylmethyl)azetidin-1-yl]benzimidazol-1-yl] piperidine-2,6-dione (Intermediate CNJ)

Step 1—Tert-butyl 4-[[1-[5-fluoro-3-methyl-2-oxo-1-(2-trimethylsilylethoxymethyl)benzimidazol-4-yl]azetidin-3-yl]methyl]piperazine-1-carboxylate. A mixture of 4-bromo-5-fluoro-3-methyl-1-(2-trimethylsilylethoxymethyl)

benzimidazol-2-one (500 mg, 1.33 mmol, synthesized via Step 1 of Intermediate CMT), tert-butyl 4-(azetidin-3-ylmethyl)piperazine-1-carboxylate (442 mg, 1.73 mmol, Intermediate CNI), XantPhos Pd G₃ (126 mg, 133 µmol) and Cs₂CO₃ (1.30 g, 4.00 mmol) in dioxane (8 mL) was degassed and purged with N₂ three times. Then the mixture was stirred at 100° C. for 12 hrs under N₂ atmosphere. On completion, the reaction mixture was poured into water (20 mL), and then extracted with ethyl acetate (20 mL×3). The combined organic layers were washed with brine (20 mL), dried over sodium sulfate and filtered. The filtrate was concentrated under reduced pressure to give a residue. The residue was purified by column chromatography (SiO₂, petroleum ether/ethyl acetate=10/0 to 0/1) to give the title compound (580 mg, 73% yield) as a brown oil. ¹H NMR (400 MHz, CDCl₃) δ 6.89-6.84 (m, 1H), 6.83-6.76 (m, 1H), 5.26 (s, 2H), 4.11-4.02 (m, 2H), 3.79 (d, J=5.2 Hz, 2H), 3.73 (s, 3H), 3.61-3.56 (m, 2H), 3.45 (s, 4H), 3.00-2.88 (m, 1H), 2.75 (s, 2H), 2.42 (s, 4H), 1.47 (s, 9H), 0.95-0.88 (m, 2H), −0.03 (s, 9H); LC-MS (ESI+) m/z 550.2 (M+H)⁺.

Step 2—Tert-butyl 4-[[1-(5-fluoro-3-methyl-2-oxo-1H-benzimidazol-4-yl)azetidin-3-yl]methyl] piperazine-1-carboxylate. A solution of tert-butyl 4-[[1-[5-fluoro-3-methyl-2-oxo-1-(2-trimethylsilylethoxymethyl) benzimidazol-4-yl]azetidin-3-yl]methyl]piperazine-1-carboxylate (580 mg, 1.06 mmol) in TBAF (5 mL) was stirred at 60° C. for 12 hrs. On completion, the reaction mixture was concentrated under reduced pressure to give a residue. The residue was purified by column chromatography (SiO₂, petroleum ether/ethyl acetate=10/0 to 0/1) to give the title compound (288 mg, 63% yield) as a light yellow solid. ¹H NMR (400 MHz, CDCl₃) δ 6.93-6.69 (m, 2H), 5.38 (s, 1H), 4.09-4.00 (m, 2H), 3.80-3.74 (m, 2H), 3.72 (d, J=1.6 Hz, 3H), 3.44 (t, J=4.8 Hz, 4H), 2.97-2.87 (m, 1H), 2.74 (dd, J=2.8, 6.8 Hz, 2H), 2.40 (s, 4H), 1.47 (s, 9H); LC-MS (ESI+) m/z 420.1 (M+H)⁺.

Step 3—Tert-butyl 4-[[1-[5-fluoro-1-[1-[(4-methoxyphenyl)methyl]-2,6-dioxo-3-piperidyl]-3-methyl-2-oxo-benzimidazol-4-yl]azetidin-3-yl]methyl]piperazine-1-carboxylate. To a solution of tert-butyl 4-[[1-(5-fluoro-3-methyl-2-oxo-1H-benzimidazol-4-yl)azetidin-3-yl]methyl] piperazine-1-carboxylate (280 mg, 667 µmol) in THF (5 mL) was added t-BuOK (145 mg, 1.33 mmol) at −10° C. and the mixture was stirred at −10° C. for 0.5 hr. Then [1-[(4-methoxyphenyl)methyl]-2,6-dioxo-3-piperidyl] trifluoromethanesulfonate (381 mg, 1.00 mmol, Intermediate IQ) was added and the mixture was stirred at −10° C. for 1.5 hrs. On completion, the reaction mixture was poured into water (20 mL), and then extracted with ethyl acetate (20 mL×3). The combined organic layers were washed with brine (20 mL), dried over Na₂SO₄ and filtered. The filtrate was concentrated in vacuo to give a residue. The residue was purified by column chromatography (SiO₂, petroleum ether/ethyl acetate=10/0 to 0/1) and by reversed-phase (0.1% FA condition) to give the title compound (300 mg, 69% yield) as a white solid. ¹H NMR (400 MHz, CDCl₃) δ 7.35 (d, J=8.4 Hz, 2H), 6.82 (d, J=8.4 Hz, 2H), 6.63 (dd, J=8.4, 13.2 Hz, 1H), 6.15 (dd, J=3.6, 8.4 Hz, 1H), 5.17 (dd, J=5.6, 13.2 Hz, 1H), 4.95 (s, 2H), 4.05 (t, J=6.8 Hz, 2H), 3.80 (s, 3H), 3.78 (d, J=5.6 Hz, 2H), 3.74 (s, 3H), 3.53-3.45 (m, 4H), 3.04-2.94 (m, 2H), 2.85-2.76 (m, 3H), 2.61-2.53 (m, 1H), 2.48 (d, J=4.8 Hz, 4H), 2.19-2.09 (m, 1H), 1.47 (s, 9H). LC-MS (ESI+) m/z 651.3 (M+H)⁺.

Step 4—3-[5-Fluoro-3-methyl-2-oxo-4-[3-(piperazin-1-ylmethyl)azetidin-1-yl]benzimidazol-1-yl] piperidine-2,6-dione. A solution of tert-butyl 4-[[1-[5-fluoro-1-[1-[(4-methoxyphenyl)methyl]-2,6-dioxo-3-piperidyl]-3-methyl-2-oxo-benzimidazol-4-yl]azetidin-3-yl]methyl]piperazine-1-carboxylate (100 mg, 153 µmol) in TFA (1 mL) and TfOH (0.2 mL) and the mixture was stirred at 70° C. for 1 hr. On completion, the reaction mixture was concentrated in vacuo to give the title compound (83 mg, 99% yield, TFA) as a black brown oil. LC-MS (ESI+) m/z 431.2 (M+H)⁺.

3-[5-Methoxy-3-methyl-2-oxo-4-[3-(piperazin-1-ylmethyl)azetidin-1-yl]benzimidazol-1-yl]piperidine-2,6-dione (Intermediate CNK)

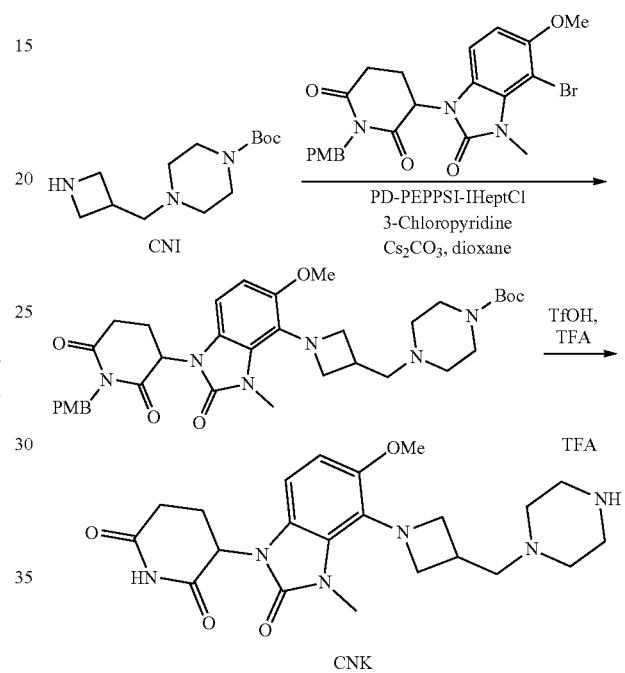

Step 1—Tert-butyl 4-[[1-[5-methoxy-1-[1-[(4-methoxyphenyl)methyl]-2,6-dioxo-3-piperidyl]-3-methyl-2-oxo-benzimidazol-4-yl]azetidin-3-yl]methyl]piperazine-1-carboxylate. A mixture of tert-butyl 4-(azetidin-3-ylmethyl) piperazine-1-carboxylate (400 mg, 1.57 mmol, Intermediate CNI), 3-(4-bromo-5-methoxy-3-methyl-2-oxo-benzimidazol-1-yl)-1-[(4-methoxyphenyl)methyl]piperidine-2,6-dione (764 mg, 1.57 mmol, synthesized via Step 1 of Intermediate BWM), 1,3-bis[2,6-bis(1-propylbutyl) phenyl]-4,5-dichloro-2H-imidazol-1-ium-2-ide; 3-chloropyridine; dichloropalladium (152 mg, 156 µmol), Cs₂CO₃ (1.53 g, 4.70 mmol) in dioxane (8 mL) was degassed and purged with N₂ three times. Then the mixture was stirred at 100° C. for 2 hrs under N₂ atmosphere. On completion, the mixture was quenched with water (0.2 ml) and concentrated in vacuo to give a residue. The residue was purified by reversed-phase (FA condition) to give the title compound (120 mg, 12% yield) as a yellow solid. ¹H NMR (400 MHz, CDCl₃) δ 7.40-7.35 (m, 2H), 6.88-6.77 (m, 2H), 6.45 (d, J=8.8 Hz, 1H), 6.19 (d, J=8.4 Hz, 1H), 5.17 (dd, J=5.6, 13.2 Hz, 1H), 4.01 (t, J=6.8 Hz, 2H), 3.88 (s, 3H), 3.80 (s, 3H), 3.75 (s, 2H), 3.46 (s, 4H), 3.04-2.94 (m, 1H), 2.88-2.72 (m, 3H), 2.58-2.55 (m, J=4.4, 13.2 Hz, 1H), 2.41 (s, 4H), 2.20-2.07 (m, 1H), 1.59 (s, 6H), 1.48 (s, 9H).

Step 2—3-[5-Methoxy-3-methyl-2-oxo-4-[3-(piperazin-1-ylmethyl)azetidin-1-yl]benzimidazol-1-yl]piperidine-2,6-dione. A mixture of tert-butyl 4-[[1-[5-methoxy-1-[1-[(4- methoxyphenyl)methyl]-2,6-dioxo-3-piperidyl]-3-methyl-2-oxo-benzimidazol-4-yl]azetidin-3-yl]methyl]piperazine-1-carboxylate (50 mg, 75.4 µmol) in TfOH (0.1 mL) and TFA (0.5 mL) was stirred at 70° C. for 1 hr. On completion, the mixture was concentrated in vacuo to give the title compound (41.9 mg, 100% yield, TFA) as black oil. LC-MS (ESI⁺) m/z 443.3 (M+H)⁺.

N-[3-(difluoromethyl)-1-(4-formylcyclohexyl)pyrazol-4-yl]-5-[(2S)-2-methylmorpholin-4-yl]pyrazolo[1,5-a]pyrimidine-3-carboxamide (Intermediate CNM)

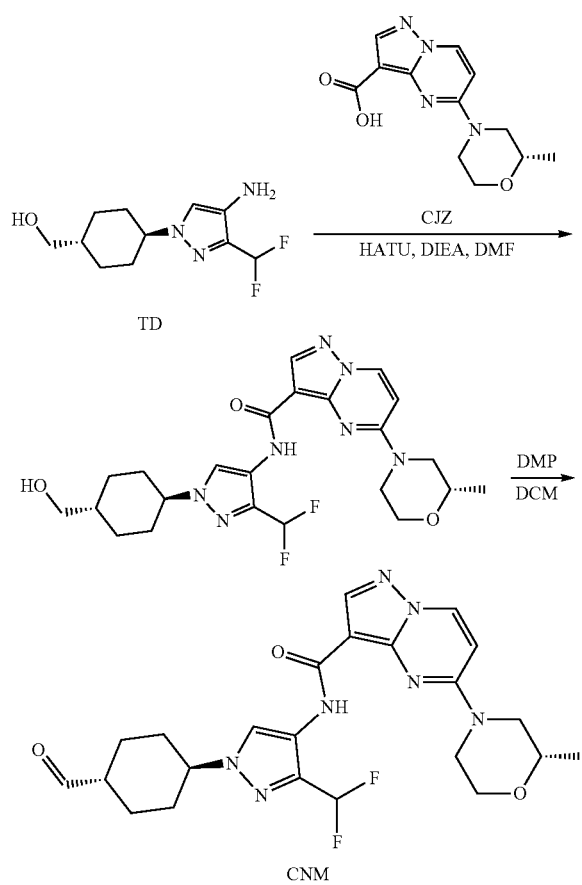

Step 1—N-[3-(difluoromethyl)-1-[4-(hydroxymethyl)cyclohexyl]pyrazol-4-yl]-5-[(2S)-2-methylmorpholin-4-yl]pyrazolo[1,5-a]pyrimidine-3-carboxamide. A mixture of 5-[(2S)-2-methylmorpholin-4-yl]pyrazolo[1,5-a]pyrimidine-3-carboxylic acid (192 mg, 733 umol, Intermediate CJZ), HATU (279 mg, 733 umol) and DIEA (237 mg, 1.83 mmol) in DMF (1 mL) was stirred at 25° C. for 30 mins. Then the mixture was added dropwise to a solution of [4-[4-amino-3-(difluoromethyl)pyrazol-1-yl]cyclohexyl]methanol (150 mg, 611 umol, Intermediate TD) and DIEA (237 mg, 1.83 mmol) in DMF (1 mL) at 25° C. The reaction mixture was stirred at 25° C. for 2 hrs. On completion, the mixture was quenched with water (10 mL) and extracted with ethyl acetate (5 mL×3). The combined organic phase was dried over anhydrous sodium sulfate, filtered and concentrated to give a residue. The residue was purified by column chromatography (SiO₂, Petroleum ether/Ethyl acetate=1:1 to 0:1, PE:EA=0:1, Rf=0.3) to give the title compound (290 mg, 96% yield) as a yellow solid. ¹H NMR (400 MHz, DMSO-d₆) δ 9.33 (s, 1H), 8.82 (d, J=8.0 Hz, 1H), 8.39 (s, 1H), 8.28 (s, 1H), 7.13 (t, J=53.6 Hz, 1H), 6.92 (d, J=8.0 Hz, 1H), 4.50-4.35 (m, 2H), 4.22-4.12 (m, 1H), 3.93 (dd, J=2.4, 11.6 Hz, 1H), 3.65-3.53 (m, 2H), 3.26 (d, J=6.0 Hz, 3H), 3.11 (dd, J=8.4, 12.4 Hz, 1H), 2.79 (t, J=11.6 Hz, 1H), 2.05 (d, J=9.6 Hz, 2H), 1.86 (d, J=11.2 Hz, 2H), 1.72 (dq, J=2.8, 12.4 Hz, 2H), 1.49-1.38 (m, 1H), 1.23-1.17 (m, 3H), 1.15-1.02 (m, 2H); LC-MS (ESI⁺) m/z 490.2 (M+H)⁺.

Step 2—N-[3-(difluoromethyl)-1-(4-formylcyclohexyl)pyrazol-4-yl]-5-[(2S)-2-methylmorpholin-4-yl]pyrazolo[1,5-a]pyrimidine-3-carboxamide. To a mixture of N-[3-(difluoromethyl)-1-[4-(hydroxymethyl)cyclohexyl]pyrazol-4-yl]-5-[(2S)-2-methylmorpholin-4-yl]pyrazolo[1,5-a]pyrimidine-3-carboxamide (140 mg, 286 umol) in DCM (5 mL) was added DMP (145 mg, 343 umol). The mixture was then stirred at 25° C. for 2 hrs. On completion, the reaction mixture was quenched with NaHCO₃ (20 mL) and Na₂S₂O₃ (20 mL), then extracted with DCM (3×15 mL). The combined organic layers were washed with NaCl (15 mL×2), dried over Na₂SO₄, filtered and concentrated in vacuo to give the title compound (130 mg, 93% yield) as a yellow solid. ¹H NMR (400 MHz, DMSO-d₆) δ 9.62 (s, 1H), 9.33 (s, 1H), 8.81 (d, J=8.0 Hz, 1H), 8.40 (s, 1H), 8.28 (s, 1H), 7.13 (t, J=53.6 Hz, 1H), 6.92 (d, J=8.0 Hz, 1H), 4.52-4.30 (m, 2H), 4.27-4.17 (m, 1H), 3.93 (dd, J=2.4, 11.6 Hz, 1H), 3.65-3.54 (m, 2H), 3.11 (t, J=11.2 Hz, 1H), 2.79 (t, J=11.6 Hz, 1H), 2.43-2.34 (m, 1H), 2.13-2.03 (m, 4H), 1.87-1.76 (m, 2H), 1.44-1.32 (m, 2H), 1.19 (d, J=6.4 Hz, 3H); LC-MS (ESI⁺) m/z 488.1 (M+H)⁺.

Tert-butyl (3S,4R)-4-(azetidin-3-yloxy)-3-fluoro-piperidine-1-carboxylate (Intermediate CNN)

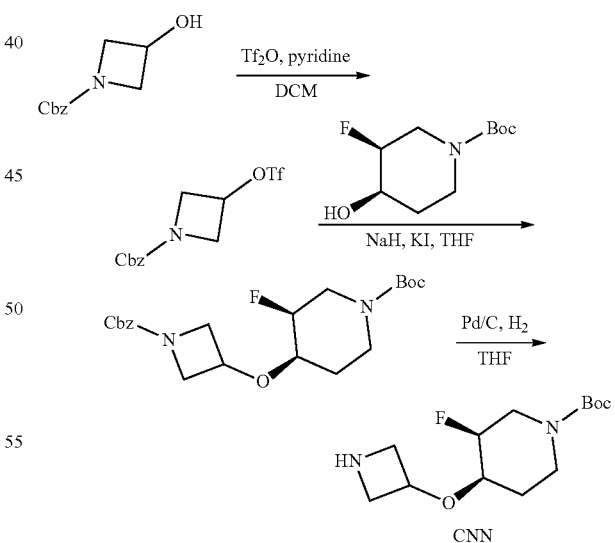

Step 1—Benzyl 3-(trifluoromethylsulfonyloxy)azetidine-1-carboxylate. To a stirring solution of benzyl 3-hydroxyazetidine-1-carboxylate (5.00 g, 24.1 mmol, CAS #128117-22-6), pyridine (3.82 g, 48.2 mmol), and DCM (50 mL) was added Tf₂O (8.17 g, 28.9 mmol) dropwise at 0° C. The mixture was stirred at 25° C. for 12 hrs. On completion, the mixture was diluted with H₂O (200 mL) and extracted with DCM (100 mL×3). The combined organic layers were washed with 1 M HCl (50 mL), the organic layer was separated and washed with saturated NaCl (100 mL), dried over Na$_2$SO$_4$, filtered and concentrated in vacuo to give the title compound (6.90 g, 84% yield) as a red oil. $^1$H NMR (400 MHz, CDCl$_3$-d) δ 7.46-7.31 (m, 5H), 5.49-5.42 (m, 1H), 5.13 (s, 2H), 4.47-4.39 (m, 2H), 4.30-4.22 (m, 2H).

Step 2—Tert-butyl (3S,4R)-4-(1-benzyloxycarbonylazetidin-3-yl)oxy-3-fluoro-piperidine-1-carboxylate. A mixture of tert-butyl (3S,4R)-3-fluoro-4-hydroxy-piperidine-1-carboxylate (2.90 g, 13.2 mmol, CAS #1174020-40-6) in THF (60 mL) was added NaH (1.18 g, 29.5 mmol, 60% dispersion in mineral oil) at 0° C., then the mixture was stirred at 50° C. for 1 hr. Next, benzyl 3-(trifluoromethylsulfonyloxy) azetidine-1-carboxylate (5.00 g, 14.7 mmol) and KI (489 mg, 2.94 mmol) was added, and the mixture was stirred at 50° C. for 4 hrs. On completion, the mixture was quenched with saturated NH$_4$Cl (5 mL) then stirred at 25° C. for 0.5 hr. Then, the mixture was diluted with H$_2$O (100 mL) and extracted with EA (100 mL×3). The combined organic layers were washed with saturated NaCl (50 mL), dried over Na$_2$SO$_4$, filtered and concentrated in vacuo to give a residue. The residue was purified by column chromatography (SiO$_2$, PE:EA=10:1 to 0:1) followed by reverse phase (0.1% FA condition) to give the title compound (1.55 g, 25% yield) as a colorless liquid. $^1$H NMR (400 MHz, DMSO-d$_6$) δ 7.42-7.27 (m, 5H), 5.03 (s, 2H), 4.85-4.65 (m, 1H), 4.51-4.44 (m, 1H), 4.20-4.09 (m, 2H), 4.03 (t, J=9.2 Hz, 1H), 3.88-3.71 (m, 3H), 3.65-3.51 (m, 1H), 3.15-2.74 (m, 2H), 1.70-1.53 (m, 2H), 1.38 (s, 9H). LC-MS (ESI$^+$) m/z 431.1 (M+Na)$^+$.

Step 3—Tert-butyl (3S,4R)-4-(azetidin-3-yloxy)-3-fluoro-piperidine-1-carboxylate. A mixture of tert-butyl (3S,4R)-4-(1-benzyloxycarbonylazetidin-3-yl)oxy-3-fluoro-piperidine-1-carboxylate (1.00 g, 2.45 mmol) in THF (10 mL) was added Pd/C (0.20 g, 10 wt %) under Ar atmosphere. The suspension was degassed and purged with H$_2$ three times. The mixture was stirred under H$_2$ (15 Psi) at 20° C. for 3 hrs. On completion, the reaction mixture was filtered and concentrated in vacuo to give the title compound (650 mg, 96% yield) as a colorless liquid. $^1$H NMR (400 MHz, DMSO-d$_6$) δ 4.78-4.58 (m, 1H), 4.41-4.29 (m, 1H), 4.04-3.96 (m, 1H), 3.89-3.73 (m, 1H), 3.55-3.34 (m, 5H), 3.16-2.77 (m, 3H), 1.65-1.52 (m, 2H), 1.38 (s, 9H).

3-[4-[3-[[(3S,4R)-3-Fluoro-4-piperidyl]oxy]azetidin-1-yl]-3-methyl-2-oxo-benzimidazol-1-yl]piperidine-2,6-dione (Intermediate CNO)

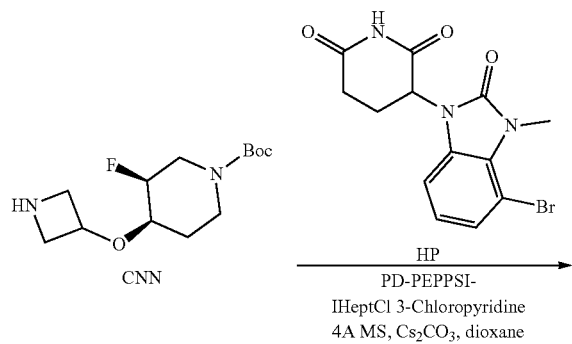

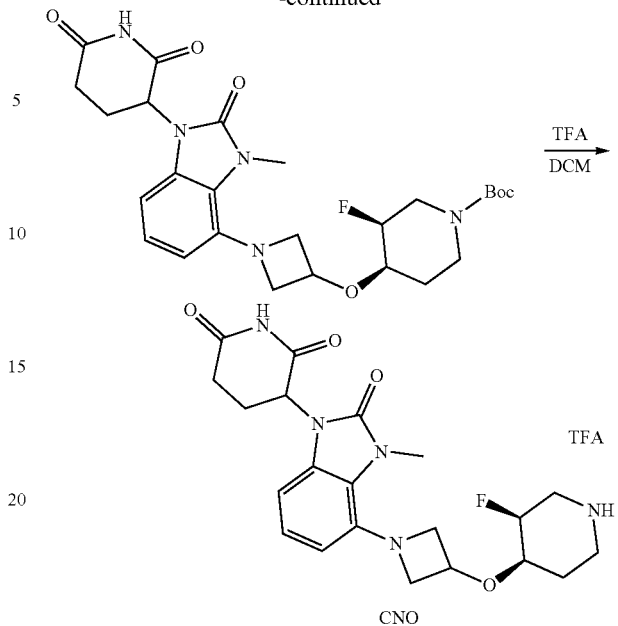

Step 1—Tert-butyl (3S,4R)-4-[1-[1-(2,6-dioxo-3-piperidyl)-3-methyl-2-oxo-benzimidazol-4-yl] azetidin-3-yl]oxy-3-fluoro-piperidine-1-carboxylate. A mixture of tert-butyl (3S,4R)-4-(azetidin-3-yloxy)-3-fluoro-piperidine-1-carboxylate (300 mg, 1.09 mmol, Intermediate CNN), 3-(4-bromo-3-methyl-2-oxo-benzimidazol-1-yl)piperidine-2,6-dione (333 mg, 984 μmol, Intermediate HP), 1,3-bis[2,6-bis(1-propylbutyl)phenyl]-4,5-dichloro-2H-imidazol-1-ium-2-ide 3-chloropyridine dichloropalladium (106 mg, 109 μmol), Cs$_2$CO$_3$ (1.07 g, 3.27 mmol) and 4 Å molecular sieves (300 mg) in dioxane (6 mL) was degassed and purged with N$_2$ three times. Then the mixture was stirred at 100° C. for 16 hrs under N$_2$ atmosphere. On completion, the reaction mixture was filtered to give the filtrate. Then, the mixture was diluted with H$_2$O (50 mL) and extracted with EA (50 mL×3). The combined organic layers were washed with saturated NaCl (50 mL), dried over Na$_2$SO$_4$, filtered and concentrated in vacuo to give a residue. The residue was purified by reverse phase (0.1% FA condition) to give the title compound (300 mg, 51% yield) as an off-white solid. $^1$H NMR (400 MHz, DMSO-d$_6$) δ 11.07 (s, 1H), 6.96 (t, J=8.0 Hz, 1H), 6.76 (d, J=7.6 Hz, 1H), 6.69 (d, J=8.0 Hz, 1H), 5.32 (dd, J=6.0, 12.8 Hz, 1H), 4.87-4.71 (m, 1H), 4.57-4.51 (m, 1H), 4.11-3.99 (m, 3H), 3.92-3.77 (m, 1H), 3.67-3.61 (m, 3H), 3.56 (s, 3H), 2.90-2.82 (m, 1H), 2.71-2.57 (m, 4H), 2.05-1.94 (m, 1H), 1.76-1.58 (m, 2H), 1.39 (s, 9H). LC-MS (ESI$^+$) m/z 532.2 (M+H)$^+$.

Step 2—3-[4-[3-[[(3S,4R)-3-Fluoro-4-piperidyl]oxy]azetidin-1-yl]-3-methyl-2-oxo-benzimidazol-1-yl]piperidine-2,6-dione. To a solution of tert-butyl (3S,4R)-4-[1-[1-(2,6-dioxo-3-piperidyl)-3-methyl-2-oxo-benzimidazol-4-yl] azetidin-3-yl]oxy-3-fluoro-piperidine-1-carboxylate (100 mg, 188 μmol) in DCM (1 mL) was added TFA (0.2 mL), then the mixture was stirred at 25° C. for 2 hrs. On completion, the reaction mixture was concentrated in vacuo to give the title compound (100 mg, 92% yield, TFA) as a brown oil. LC-MS (ESI$^+$) m/z 432.2 (M+H)$^+$.

Tert-butyl (3S,4R)-4-(azetidin-3-ylmethoxy)-3-fluoro-piperidine-1-carboxylate (Intermediate CNP)

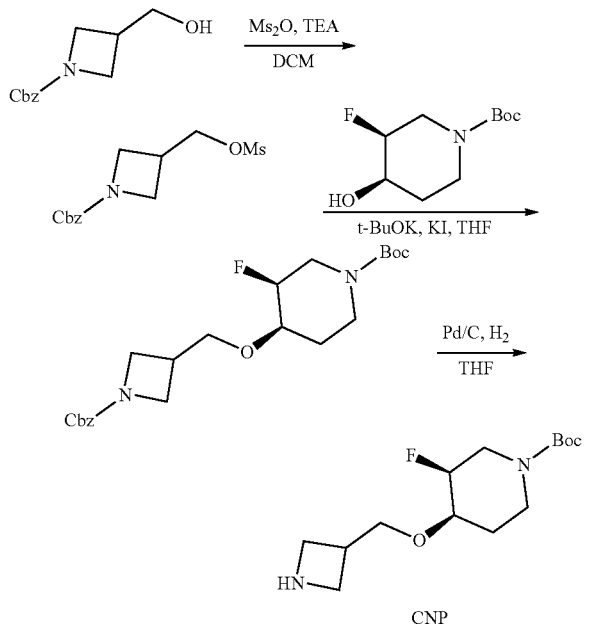

Step 1—Benzyl 3-(methylsulfonyloxymethyl)azetidine-1-carboxylate. To a solution of benzyl 3-(hydroxymethyl)azetidine-1-carboxylate (4.0 g, 18.1 mmol, CAS #618446-42-7) in DCM (40 mL) was added TEA (5.49 g, 54.2 mmol) and methylsulfonyl methanesulfonate (9.45 g, 54.2 mmol) at 0° C., then the mixture was stirred at 25° C. for 14 hrs. On completion, the reaction was washed with water (20 ml×3), then separated to give the organic phase. The organic phase was dried over anhydrous $Na_2SO_4$, filtered and concentrated in vacuo to give a residue. The residue was purified by column chromatography ($SiO_2$, PE/EA=1/1 to 3/2) to give the title compound (3.6 g, 66% yield) as yellow solid. $^1$H NMR (400 MHz, DMSO-$d_6$) δ 7.43-7.27 (m, 5H), 5.04 (s, 2H), 4.36 (d, J=6.4 Hz, 2H), 4.11-3.92 (m, 2H), 3.73 (s, 2H), 3.21 (s, 3H), 3.02-2.90 (m, 1H); LC-MS (ESI+) m/z 300.0 (M+H)$^+$.

Step 2—Tert-butyl (3S,4R)-4-[(1-benzyloxycarbonylazetidin-3-yl)methoxy]-3-fluoro-piperidine-1-carboxylate. To a solution of tert-butyl (3S,4R)-3-fluoro-4-hydroxy-piperidine-1-carboxylate (2.93 g, 13.4 mmol, CAS #1174020-40-6), and KI (222 mg, 1.34 mmol) in THF (80 mL) was added t-BuOK (1 M, 16.0 mL) at 0° C., then the mixture was stirred at 20° C. for 3 hrs. Next, benzyl 3-(methylsulfonyloxymethyl) azetidine-1-carboxylate (4 g, 13.4 mmol) was added to the mixture and the reaction was stirred at 20° C. for 12 hrs. On completion, the reaction was quenched by 1N HCl at 0° C. to adjust the pH=7, then concentrated in vacuo to give a residue. The residue was diluted with water (60 ml), and extracted with DCM (30 ml×3). The organic layers were combined, washed with brine (30 ml), dried over $Na_2SO_4$, filtered and concentrated in vacuo to give the crude product. The crude product was purified by column chromatography ($SiO_2$, PE/EA=10/1 to 7/2) to give the title compound (650 mg, 9% yield) as yellow oil. $^1$H NMR (400 MHz, DMSO-$d_6$) δ 7.41-7.27 (m, 5H), 5.02 (s, 2H), 4.91-4.71 (m, 1H), 4.02-3.91 (m, 3H), 3.84-3.72 (m, 1H), 3.69-3.50 (m, 5H), 3.19-3.01 (m, 1H), 2.99-2.71 (m, 2H), 1.72-1.52 (m, 2H), 1.38 (s, 9H); LC-MS (ESI+) m/z 445.2 (M+Na)$^+$.

Step 3—Tert-butyl (3S,4R)-4-(azetidin-3-ylmethoxy)-3-fluoro-piperidine-1-carboxylate. To a solution of tert-butyl (3S,4R)-4-[(1-benzyloxycarbonylazetidin-3-yl)methoxy]-3-fluoro-piperidine-1-carboxylate (325 mg, 598 μmol) in THF (3 mL) was added Pd/C (150 mg, 10 wt %) under Ar atmosphere. Then the mixture was degassed under vacuum, purged with $H_2$ three times, and stirred at 20° C. for 4 hrs under $H_2$ (15 psi) atmosphere. On completion, the reaction was filtered to give a filtrate, then concentrated in vacuo to give the title compound (345 mg, 97% yield) as brown oil. $^1$H NMR (400 MHz, DMSO-$d_6$) δ 4.93-4.69 (m, 1H), 4.03-3.96 (m, 1H), 3.86-3.72 (m, 1H), 3.66-3.55 (m, 3H), 3.50 (d, J=2.4 Hz, 3H), 3.27-2.99 (m, 3H), 2.98-2.68 (m, 2H), 1.73-1.64 (m, 1H), 1.63-1.52 (m, 1H), 1.38 (s, 9H); LC-MS (ESI+) m/z 289.0 (M+H)$^+$.

3-[4-[3-[[(3S,4R)-3-fluoro-4-piperidyl]oxymethyl]azetidin-1-yl]-3-methyl-2-oxo-benzimidazol-1-yl]piperidine-2,6-dione (Intermediate CNQ)

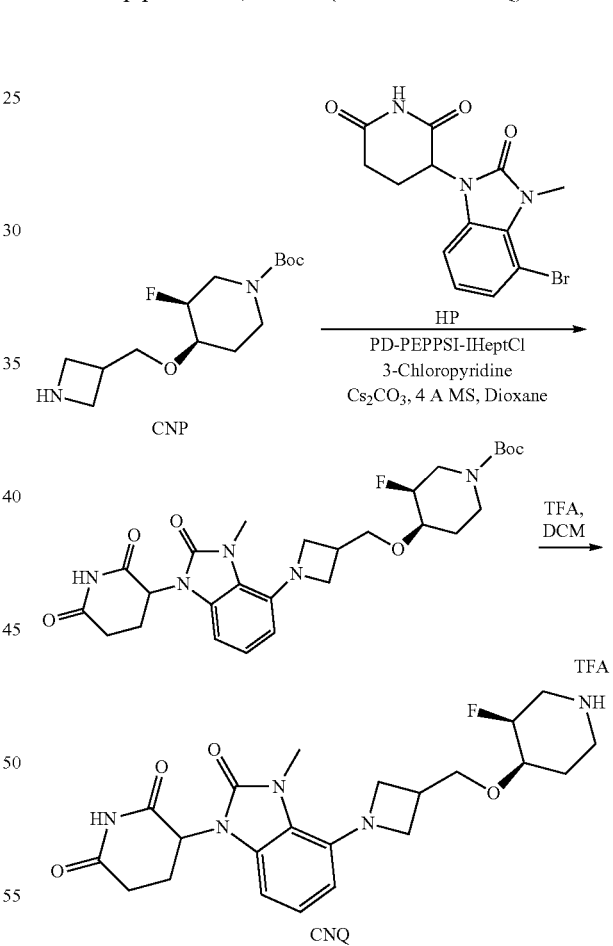

Step 1—Tert-butyl (3S,4R)-4-[[1-[1-(2,6-dioxo-3-piperidyl)-3-methyl-2-oxo-benzimidazol-4-yl]azetidin-3-yl]methoxy]-3-fluoro-piperidine-1-carboxylate. A mixture of 3-(4-bromo-3-methyl-2-oxo-benzimidazol-1-yl)piperidine-2,6-dione (330 mg, 975 μmol, Intermediate HP), tert-butyl (3S,4R)-4-(azetidin-3-ylmethoxy)-3-fluoro-piperidine-1-carboxylate (289.2 mg, 975 μmol, Intermediate CNP), 1,3-bis[2,6-bis(1-propylbutyl)phenyl]-4,5-dichloro-2H-imidazol-1-ium-2-ide 3-chloropyridine dichloropalladium (47.4 mg, 48.9 µmol), Cs$_2$CO$_3$ (265 mg, 813 µmol), and 4 Å molecular sieves (3 g) in dioxane (18 mL) was degassed under vacuum, purged with N$_2$ three times. Then the mixture was stirred at 100° C. for 12 hrs under N$_2$ atmosphere. On completion, the reaction was cooled to rt, filtered to give a filtrate, concentrated in vacuo to give a residue. The residue was purified by reverse phase (0.1% FA condition) to give the title compound (90 mg, 14% yield, 93.5% purity, FA) as white solid. $^1$H NMR (400 MHz, DMSO-d$_6$) δ 11.27-10.82 (m, 1H), 6.95 (t, J=8.0 Hz, 1H), 6.73 (d, J=7.6 Hz, 1H), 6.66 (d, J=8.4 Hz, 1H), 5.31 (dd, J=5.2, 12.4 Hz, 1H), 4.97-4.72 (m, 1H), 4.06-3.96 (m, 1H), 3.95-3.86 (m, 2H), 3.86-3.76 (m, 1H), 3.75-3.70 (m, 2H), 3.64-3.51 (m, 5H), 3.19-3.02 (m, 1H), 2.95-2.76 (m, 3H), 2.76-2.55 (m, 3H), 2.04-1.91 (m, 1H), 1.77-1.67 (m, 1H), 1.66-1.52 (m, 1H), 1.39 (s, 9H); LC-MS (ESI+) m/z 546.2 (M+H)$^+$.

Step 2—3-[4-[3-[[(3S,4R)-3-fluoro-4-piperidyl]oxymethyl]azetidin-1-yl]-3-methyl-2-oxo-benzimidazol-1-yl]piperidine-2,6-dione. To a solution of tert-butyl (3S,4R)-4-[[1-[1-(2,6-dioxo-3-piperidyl)-3-methyl-2-oxo-benzimidazol-4-yl] azetidin-3-yl]methoxy]-3-fluoro-piperidine-1-carboxylate (70 mg, 120 µmol, FA) in DCM (1.5 mL) was added TFA (230 mg, 2.02 mmol), then the mixture was stirred at 20° C. for 1 hr. On completion, the reaction was concentrated in vacuo to give the title compound (72 mg, 94% yield, TFA) as brown oil. LC-MS (ESI+) m/z 446.1 (M+H)$^+$.

Tert-butyl (3S,4S)-4-(azetidin-3-ylmethoxy)-3-fluoro-piperidine-1-carboxylate (Intermediate CNR)

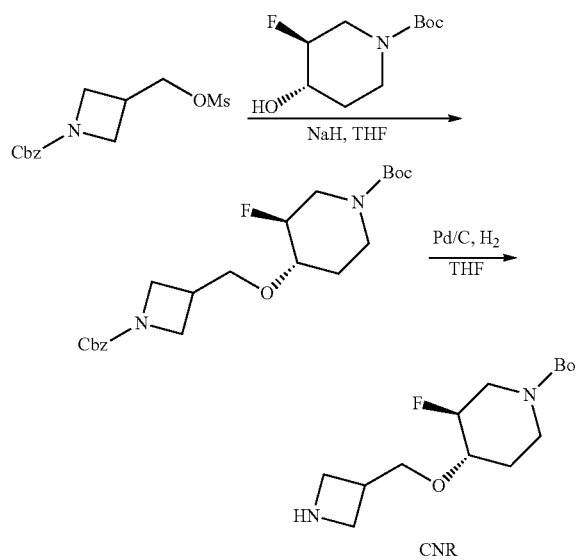

Step 1—Tert-butyl (3S,4S)-4-[(1-benzyloxycarbonylazetidin-3-yl)methoxy]-3-fluoro-piperidine-1-carboxylate. To a solution of tert-butyl (3S,4S)-3-fluoro-4-hydroxy-piperidine-1-carboxylate (4.76 g, 21.7 mmol, CAS #1174020-44-0) in THF (100 mL) was added NaH (1.34 g, 60% dispersion in mineral oil, 33.4 mmol) at 0° C., then the mixture was stirred at 50° C. for 1 hr. Next, benzyl 3-(methylsulfonyloxymethyl) azetidine-1-carboxylate (5.00 g, 16.7 mmol, synthesized via Step 1 of Intermediate CNP) was added to the mixture above and the reaction was stirred at 50° C. for 16 hrs. On completion, the mixture was diluted with H$_2$O (10 mL) and quenched with saturated NH$_4$Cl (3 mL), then the mixture was stirred at 25° C. for 0.5 hr. Then the mixture was concentrated in vacuo to give a residue. The residue was diluted with water (300 mL), and extracted with EA (200 mL×3). The organic layers were combined, washed with brine (100 mL), dried over anhydrous Na$_2$SO$_4$, filtered and concentrated in vacuo to give the crude product. The crude product was purified by column chromatography (SiO$_2$, PE/EA=10/1 to 7/1) and reverse phase (0.1% FA condition) to give the title compound (1.40 g, 20% yield, FA) as colorless liquid. $^1$H NMR (400 MHz, DMSO-d$_6$) δ 7.39-7.27 (m, 5H), 5.02 (s, 2H), 4.52-4.34 (m, 1H), 4.04-3.88 (m, 2H), 3.73-3.53 (m, 6H), 3.44-3.34 (m, 2H), 3.25-3.17 (m, 1H), 2.82-2.72 (m, 1H), 1.89-1.78 (m, 1H), 1.49-1.42 (m, 1H), 1.39 (s, 9H); LC-MS (ESI+) m/z 323.5 (M+H−100)$^+$.

Step 2—Tert-butyl (3S,4S)-4-(azetidin-3-ylmethoxy)-3-fluoro-piperidine-1-carboxylate. To a solution of tert-butyl (3S,4S)-4-[(1-benzyloxycarbonylazetidin-3-yl)methoxy]-3-fluoro-piperidine-1-carboxylate (1.00 g, 2.37 mmol) in THF (5 mL) was added Pd/C (1.00 g, 10 wt %) under Ar atmosphere, then the mixture was degassed under vacuum, and purged with H$_2$ three times. The mixture was then stirred at 20° C. for 4 hrs under H$_2$ (15 psi) atmosphere. On completion, the reaction was filtered to give a filtrate, then concentrated in vacuo to give the title compound (600 mg, 88% yield) as colorless oil. $^1$H NMR (400 MHz, DMSO-d$_6$) δ 4.53-4.31 (m, 1H), 3.71-3.51 (m, 4H), 3.50-3.34 (m, 4H), 3.26-3.12 (m, 4H), 2.82-2.70 (m, 1H), 1.91-1.79 (m, 1H), 1.52-1.43 (m, 1H), 1.39 (s, 9H).

3-[4-[3-[[(3S,4S)-3-fluoro-4-piperidyl]oxymethyl] azetidin-1-yl]-3-methyl-2-oxo-benzimidazol-1-yl] piperidine-2,6-dione (Intermediate CNS)

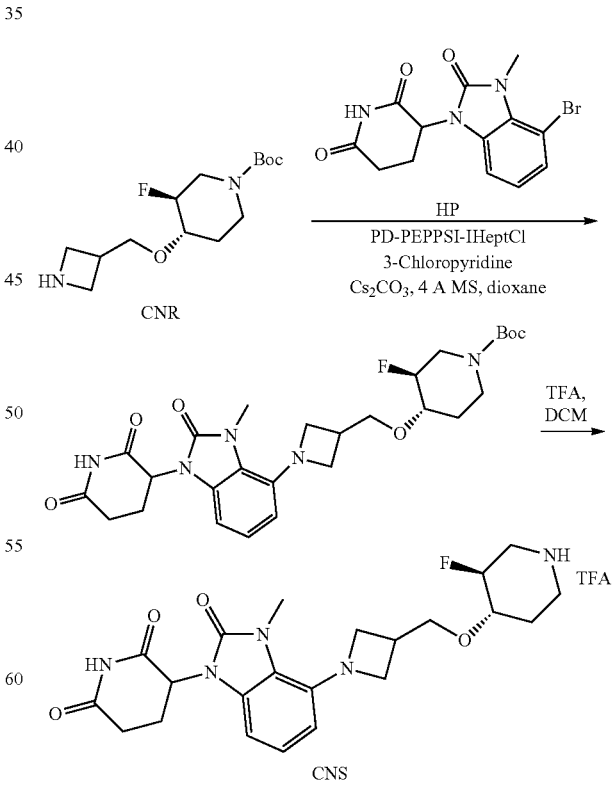

Step 1—Tert-butyl (3S,4S)-4-[[1-[1-(2,6-dioxo-3-piperidyl)-3-methyl-2-oxo-benzimidazol-4-yl]azetidin-3-yl]

methoxy]-3-fluoro-piperidine-1-carboxylate. The mixture of 3-(4-bromo-3-methyl-2-oxo-benzimidazol-1-yl)piperidine-2,6-dione (116 mg, 343 µmol, Intermediate HP), tert-butyl (3S,4S)-4-(azetidin-3-ylmethoxy)-3-fluoro-piperidine-1-carboxylate (90.0 mg, 312 µmol, Intermediate CNR), 1,3-bis[2,6-bis(1-propylbutyl)phenyl]-4,5-dichloro-2H-imidazol-1-ium-2-ide 3-chloropyridine dichloropalladium (30.4 mg, 31.2 µmol), Cs$_2$CO$_3$ (305 mg, 936 µmol), and 4 Å molecular sieves (100 mg) in dioxane (5 mL) was degassed and purged with N$_2$ three times. Then the mixture was stirred at 100° C. for 16 hrs under N$_2$ atmosphere. On completion, the reaction was cooled to rt, filtered to give a filtrate, concentrated in vacuo to give a residue. The residue was diluted with water (50 mL), extracted with EA (100 mL×3). The organic layers were combined, washed with brine (50 mL), dried over anhydrous Na$_2$SO$_4$, filtered and concentrated in vacuo to give the crude product. The crude product was purified by reverse phase (0.1% FA condition) to give the title compound (50.0 mg, 29% yield, FA) as white solid. $^1$H NMR (400 MHz, DMSO-d$_6$) δ 11.08 (s, 1H), 6.99-6.92 (m, 1H), 6.77-6.64 (m, 2H), 5.32 (dd, J=5.2, 12.8 Hz, 1H), 4.56-4.38 (m, 1H), 3.90 (t, J=7.2 Hz, 2H), 3.82-3.72 (m, 3H), 3.61-3.58 (m, 2H), 3.57 (s, 3H), 3.26-3.19 (m, 1H), 2.94-2.77 (m, 3H), 2.74-2.68 (m, 1H), 2.65-2.57 (m, 2H), 2.02-1.95 (m, 1H), 1.92-1.84 (m, 1H), 1.53-1.43 (m, 2H), 1.40 (s, 9H); LC-MS (ESI+) m/z 546.2 (M+H)$^+$.

Step 2—3-[4-[3-[[(3S,4S)-3-fluoro-4-piperidyl]oxymethyl]azetidin-1-yl]-3-methyl-2-oxo-benzimidazol-1-yl]piperidine-2,6-dione. To a solution of tert-butyl (3S,4S)-4-[[1-[1-(2,6-dioxo-3-piperidyl)-3-methyl-2-oxo-benzimidazol-4-yl] azetidin-3-yl]methoxy]-3-fluoro-piperidine-1-carboxylate (50.0 mg, 91.6 µmol, FA) in DCM (1 mL) was added TFA (768 mg, 6.73 mmol). Then the mixture was stirred at 20° C. for 1 hr. On completion, the reaction was concentrated in vacuo to give the title compound (50.0 mg, 98% yield, TFA) as light yellow oil. LC-MS (ESI+) m/z 446.1 (M+H)$^+$.

Tert-butyl (3R,4S)-4-(azetidin-3-ylmethoxy)-3-fluoro-piperidine-1-carboxylate (Intermediate CNT)

Step 1—Tert-butyl (3R,4S)-4-[(1-benzyloxycarbonylazetidin-3-yl)methoxy]-3-fluoro-piperidine-1-carboxylate. To a solution of tert-butyl (3R,4S)-3-fluoro-4-hydroxy-piperidine-1-carboxylate (5.13 g, 23.3 mmol, CAS #1174020-42-8) in THF (100 mL) was added t-BuOK (1 M, 28.0 mL) at 0° C., then the reaction mixture was stirred at 0° C. for 1 hr. Next, benzyl 3-(methylsulfonyloxymethyl)azetidine-1-carboxylate (7.00 g, 23.3 mmol, synthesized via Step 1 of Intermediate CNP) and KI (388 mg, 2.34 mmol) was added, and the reaction mixture was stirred at 25° C. for 16 hrs. On completion, the residue was diluted with water (30 mL) and extracted with EA (2×40 mL). The combined organic layer was washed with brine (40 mL) and dried over Na$_2$SO$_4$, filtered and the filtrate was concentrated in vacuo to give a residue. The residue was purified by column chromatography (SiO$_2$, PE:EA=10:1 to PE:EA=2:1, PE:EA=1:1, P1:Rf=0.29) to give the title compound (2.50 g, 25% yield) as a yellow solid. $^1$H NMR (400 MHz, DMSO-d$_6$) δ 7.49-7.20 (m, 5H), 5.06 (d, J=5.2 Hz, 1H), 5.02 (s, 2H), 4.90-4.73 (m, 1H), 4.64-4.48 (m, 1H), 3.95-3.92 (m, 1H), 3.57-3.48 (m, 1H), 3.22-3.02 (m, 2H), 2.99-2.83 (m, 2H), 2.79-2.71 (m, 1H), 1.99 (s, 1H), 1.71-1.65 (m, 1H), 1.63-1.52 (m, 3H), 1.38 (s, 9H), LC-MS (ESI$^+$) m/z 445.1 (M+Na)$^+$.

Step 2—Tert-butyl (3R,4S)-4-(azetidin-3-ylmethoxy)-3-fluoro-piperidine-1-carboxylate. To a solution of tert-butyl (3R,4S)-4-[(1-benzyloxycarbonylazetidin-3-yl)methoxy]-3-fluoro-piperidine-1-carboxylate (1.00 g, 2.37 mmol) in THF (10 mL) was added Pd/C (500 mg, 10 wt %). The mixture was stirred at 25° C. for 16 hrs. On completion, the reaction mixture was filtered and the filtrate was concentrated in vacuo to give the title compound (677 mg, 99% yield) as brown oil. LCMS (ESI$^+$) m/z 289.1 (M+H)$^+$.

3-[4-[3-[[(3R,4S)-3-fluoro-4-piperidyl]oxymethyl] azetidin-1-yl]-3-methyl-2-oxo-benzimidazol-1-yl] piperidine-2,6-dione (Intermediate CNU)

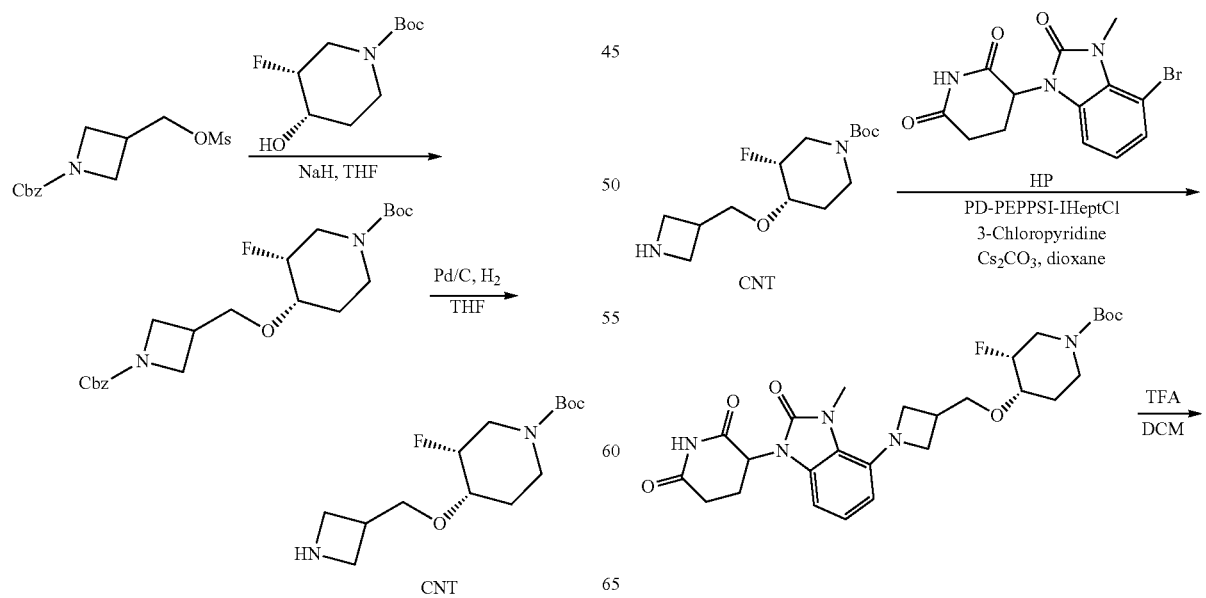

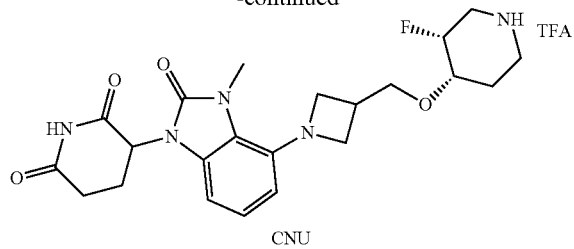

CNU

Step 1—Tert-butyl (3R,4S)-4-[[1-[1-(2,6-dioxo-3-piperidyl)-3-methyl-2-oxo-benzimidazol-4-yl]azetidin-3-yl]methoxy]-3-fluoro-piperidine-1-carboxylate. To a solution of tert-butyl (3R,4S)-4-(azetidin-3-ylmethoxy)-3-fluoro-piperidine-1-carboxylate (260 mg, 901 μmol, Intermediate CNT) and 3-(4-bromo-3-methyl-2-oxo-benzimidazol-1-yl)piperidine-2,6-dione (304 mg, 901 μmol, Intermediate HP) in dioxane (8 mL) was added 1,3-bis[2,6-bis(1-propylbutyl)phenyl]-4,5-dichloro-2H-imidazol-1-ium-2-ide; 3-chloropyridine dichloropalladium (87.7 mg, 90.1 μmol), Cs$_2$CO$_3$ (881 mg, 2.70 mmol) and 4 Å molecular sieves (50 mg). The mixture was stirred at 100° C. for 16 hrs. On completion, the reaction mixture was concentrated in vacuo to give a residue. The residue was purified by reverse phase (0.1% FA condition) to give the title compound (75.0 mg, 15% yield) as a brown solid. $^1$H NMR (400 MHz, DMSO-d$_6$) δ 11.07 (s, 1H), 7.01-6.89 (m, 1H), 6.78-6.61 (m, 2H), 5.31 (dd, J=5.2, 12.8 Hz, 1H), 4.93-4.74 (m, 1H), 4.05-3.95 (m, 2H), 3.93-3.75 (t, J=7.6 Hz, 2H), 3.74-3.70 (m, 2H), 3.56 (s, 3H), 2.93-2.75 (m, 4H), 2.73-2.66 (m, 2H), 2.64-2.55 (m, 3H), 1.74-1.68 (m, 1H), 1.64-1.53 (m, 2H), 1.38 (s, 9H), LCMS (ESI$^+$) m/z 546.2 (M+H)$^+$.

Step 2—3-[4-[3-[[(3R,4S)-3-fluoro-4-piperidyl]oxymethyl]azetidin-1-yl]-3-methyl-2-oxo-benzimidazol-1-yl]piperidine-2,6-dione. To a solution of tert-butyl (3R,4S)-4-[[1-[1-(2,6-dioxo-3-piperidyl)-3-methyl-2-oxo-benzimidazol-4-yl]azetidin-3-yl]methoxy]-3-fluoro-piperidine-1-carboxylate (72.0 mg, 131 μmol) in DCM (1.5 mL) was added TFA (767 mg, 6.73 mmol). The mixture was stirred at 25° C. for 1 hr. On completion, the reaction mixture was concentrated in vacuo to give the title compound (72.0 mg, 97% yield, TFA) as a brown solid. LCMS (ESI$^+$) m/z 446.2 (M+H)$^+$.

Benzyl 5,5-difluoro-2,7-diazaspiro[3.5]nonane-7-carboxylate (Intermediate CNV)

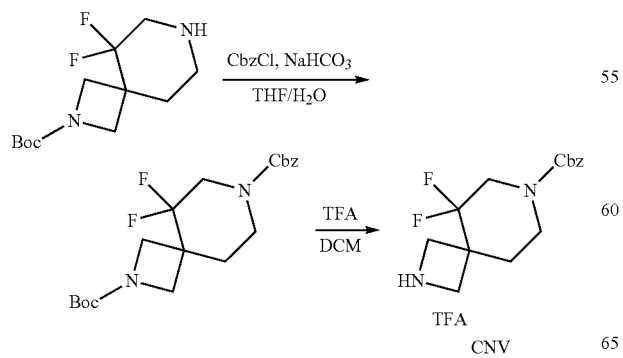

Step 1—07-benzyl 02-tert-butyl 5,5-difluoro-2,7-diazaspiro[3.5]nonane-2,7-dicarboxylate. To a solution of tert-butyl 5,5-difluoro-2,7-diazaspiro[3.5]nonane-2-carboxylate (900 mg, 3.43 mmol, CAS #2007920-32-1) in THF (9 mL) as added CbzCl (643 mg, 3.77 mmol) and TEA (364 mg, 3.60 mmol). The mixture was stirred at 25° C. for 16 hrs. On completion, the mixture was filtered and concentrated to give the title compound (1.30 g, 96% yield) as yellow oil. $^1$H NMR (400 MHz, CDCl$_3$) δ 7.35-7.22 (m, 5H), 5.07 (s, 2H), 4.01 (d, J=8.8 Hz, 2H), 3.54 (d, J=8.8 Hz, 2H), 3.42 (d, J=2.0 Hz, 2H), 1.93 (s, 2H), 1.52 (s, 2H), 1.37 (s, 9H).

Step 2—Benzyl 5,5-difluoro-2,7-diazaspiro[3.5]nonane-7-carboxylate. To a solution of 07-benzyl 02-tert-butyl 5,5-difluoro-2,7-diazaspiro[3.5]nonane-2,7-dicarboxylate (1.30 g, 3.28 mmol) in DCM (1 mL) was added TFA (0.3 mL). The mixture was stirred at 25° C. for 2 hrs. On completion, the mixture was concentrated to give the title compound (1.30 g, 96% yield, TFA) as a yellow oil. LC-MS (ESI$^+$) m/z 297.0 (M+H)$^+$.

3-[4-(5,5-Difluoro-2,7-diazaspiro[3.5]nonan-2-yl)-3-methyl-2-oxo-benzimidazol-1-yl] piperidine-2,6-dione (Intermediate CNW)

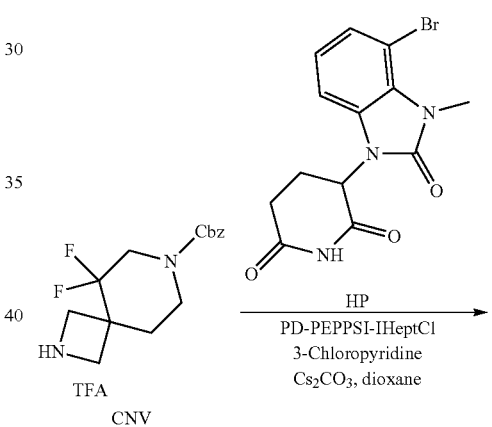

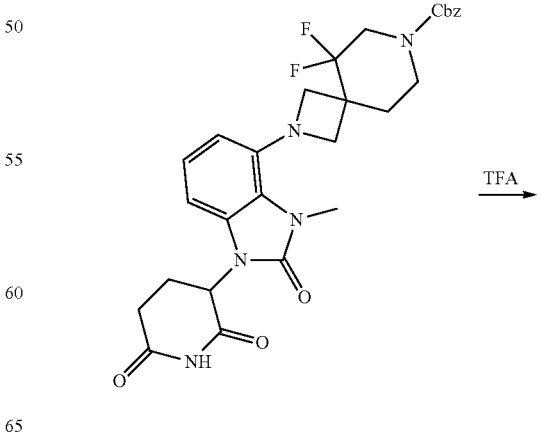

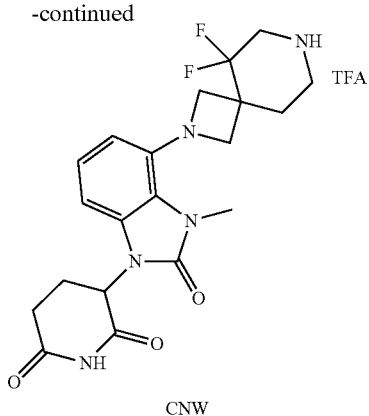

CNW

Step 1—Benzyl 2-[1-(2,6-dioxo-3-piperidyl)-3-methyl-2-oxo-benzimidazol-4-yl]-5,5-difluoro-2,7-diazaspiro[3.5]nonane-7-carboxylate. A mixture of benzyl 5,5-difluoro-2,7-diazaspiro[3.5]nonane-7-carboxylate (1.30 g, 3.17 mmol, TFA, Intermediate CNV), 3-(4-bromo-3-methyl-2-oxo-benzimidazol-1-yl)piperidine-2,6-dione (714 mg, 2.11 mmol, Intermediate HP), 1,3-bis[2,6-bis(1-propylbutyl)phenyl]-4,5-dichloro-2H-imidazol-1-ium-2-ide; 3-chloropyridine dichloropalladium (205 mg, 211 μmol), Cs$_2$CO$_3$ (2.06 g, 6.34 mmol) and 4 Å molecular sieves (20 mg, 2.11 mmol) in dioxane (15 mL) was degassed and purged with N$_2$ three times. Then the mixture was stirred at 100° C. for 16 hrs under N$_2$ atmosphere. On completion, the mixture was filtered and concentrated to give a residue. The residue was purified by reversed phase flash (0.1% FA condition) to give the title compound (540 mg, 43% yield) as black solid. $^1$H NMR (400 MHz, DMSO-d$_6$) δ 11.08 (s, 1H), 7.51-7.26 (m, 5H), 7.10-6.86 (m, 1H), 6.76 (dd, J=8.0, 11.2 Hz, 2H), 5.75 (s, 1H), 5.33 (dd, J=5.2, 12.4 Hz, 1H), 5.12 (s, 2H), 4.05-3.91 (m, 2H), 3.76 (d, J=1.6 Hz, 2H), 3.71 (d, J=7.6 Hz, 2H), 3.57 (s, 3H), 2.97-2.80 (m, 1H), 2.74-2.54 (m, 3H), 2.14-1.93 (m, 3H); LC-MS (ESI$^+$) m/z 554.0 (M+H)$^+$.

Step 2—3-[4-(5,5-Difluoro-2,7-diazaspiro[3.5]nonan-2-yl)-3-methyl-2-oxo-benzimidazol-1-yl] piperidine-2,6-dione. To a solution of benzyl 2-[1-(2,6-dioxo-3-piperidyl)-3-methyl-2-oxo-benzimidazol-4-yl]-5,5-difluoro-2,7-diazaspiro[3.5]nonane-7-carboxylate (80.0 mg, 144 μmol) was added TFA (0.4 mL). The mixture was then stirred at 25° C. for 1 hr. On completion, the mixture was filtered and concentrated to give the title compound (70.0 mg, 90% yield, TFA) as a black oil. LC-MS (ESI$^+$) m/z 420.1 (M+H)$^+$.

(3-Bromocyclobutyl)methoxy-tert-butyl-dimethyl-silane (Intermediate CNX)

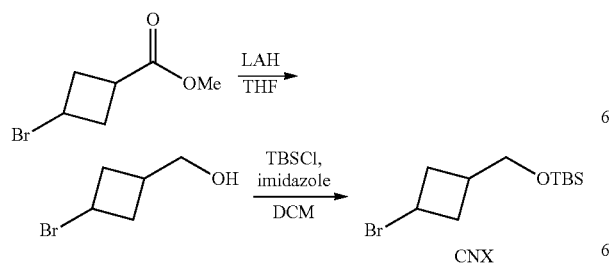

Step 1—(3-Bromocyclobutyl)methanol. To a solution of methyl 3-bromocyclobutanecarboxylate (10.0 g, 51.8 mmol, CAS #4935-00-6) in THF (150 mL) was added LiAlH$_4$ (2.36 g, 62.1 mmol) at 0° C. The mixture was stirred at 25° C. for 1 hr. On completion, the mixture was quenched with H$_2$O (2.40 mL) and 15% NaOH aq. (2.40 mL) at 0° C., then additional H$_2$O (7.20 mL) was added. After that, the mixture was dried with Na$_2$SO$_4$, then the mixture was filtered and the organic layer was concentrated in vacuo to give the title compound (8.30 g, 97% yield) as a colorless oil. $^1$H NMR (400 MHz, CDCl$_3$) δ 4.65-4.50 (m, J=7.2 Hz, 1H), 3.66 (d, J=6.4 Hz, 2H), 2.83-2.70 (m, 1H), 2.64-2.49 (m, 4H).

Step 2—(3-Bromocyclobutyl)methoxy-tert-butyl-dimethyl-silane. To a solution of (3-bromocyclobutyl)methanol (8.30 g, 50.2 mmol) in DCM (100 mL) was added TBSCl (11.3 g, 75.4 mmol) and imidazole (6.85 g, 100 mmol). The mixture was stirred at 25° C. for 1 hr. On completion, the reaction mixture was diluted with H$_2$O (400 mL) and extracted with DCM 400 mL (200 mL×2). The combined organic layers were washed with saturated sodium chloride solution (200 mL×2), dried over anhydrous sodium sulfate, filtered and concentrated to give the title compound (14.0 g, 99% yield) as a colorless oil. $^1$H NMR (400 MHz, CDCl$_3$) δ 4.64-4.50 (m, 1H), 3.60 (d, J=5.2 Hz, 2H), 2.79-2.66 (m, 1H), 2.65-2.53 (m, 4H), 0.94-0.90 (m, 9H), 0.10-0.04 (m, 6H).

7-((1R,3r)-3-(((tert-butyldimethylsilyl)oxy)methyl)cyclobutyl)-1-methyl-1,3-dihydro-2H-benzo[d]imidazol-2-one (Intermediate CNY) and 7-((1s,3s)-3-(((tert-butyldimethylsilyl)oxy)methyl)cyclobutyl)-1-methyl-1,3-dihydro-2H-benzo[d]imidazol-2-one (Intermediate CNZ)

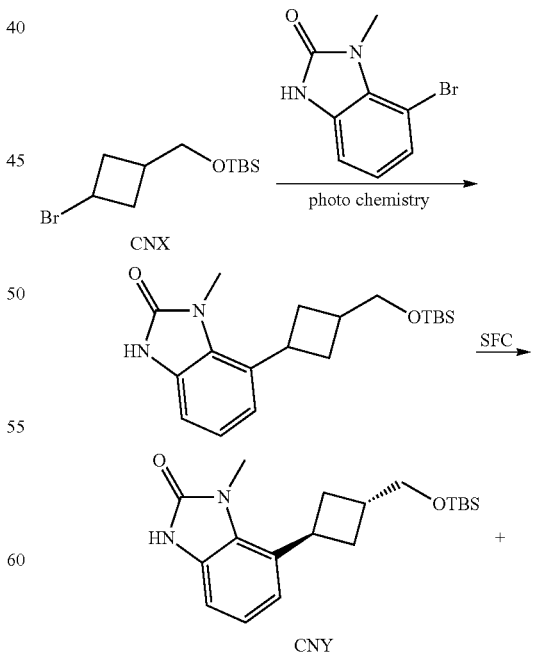

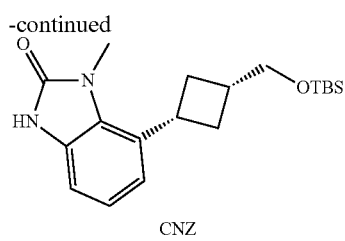

CNZ

Step 1—4-[3-[[Tert-butyl(dimethyl)silyl]oxymethyl]cyclobutyl]-3-methyl-1H-benzimidazol-2-one. To an 15 mL vial equipped with a stir bar was added 4-bromo-3-methyl-1H-benzimidazol-2-one (4.30 g, 18.9 mmol, synthesized via Steps 1-3 of Intermediate HP), (3-bromocyclobutyl) methoxy-tert-butyl-dimethyl-silane (6.88 g, 24.6 mmol, Intermediate CNX), Ir[dF(CF$_3$)ppy]$_2$(dtbpy)(PF$_6$) (212 mg, 189 µmol), NiCl$_2$·dtbbpy (376 mg, 946 µmol), TTMSS (4.71 g, 18.9 mmol, 5.84 mL), and 2,6-lutidine (4.06 g, 37.8 mmol) in DME (50 mL). The vial was sealed and placed under nitrogen. The reaction was stirred and irradiated with a blue 10 W LED lamp (3 cm away), with cooling water to keep the reaction temperature at 25° C. for 14 hrs. On completion, the reaction mixture was filtered and concentrated to give a residue. The residue was diluted with H$_2$O (500 mL) and extracted with EA (300 mL×2). The combined organic layers were washed with saturated sodium chloride solution (600 mL×2), dried over anhydrous sodium sulfate, filtered and concentrated to give a residue. The residue was purified by column chromatography (SiO$_2$, DCM/MeOH=100/1 to 20/1) and reversed phase (0.1% FA condition) to give the title compound (5.00 g, 38% yield) as an off-white solid. LC-MS (ESI$^+$) m/z 347.1 (M+H)$^+$.

Step 2—7-((1R,3r)-3-(((tert-butyldimethylsilyl)oxy) methyl)cyclobutyl)-1-methyl-1,3-dihydro-2H-benzo[d]imidazol-2-one and 7-((1s,3s)-3-(((tert-butyldimethylsilyl)oxy) methyl)cyclobutyl)-1-methyl-1,3-dihydro-2H-benzo[d] imidazol-2-one. 7-(3-(((Tert-butyldimethylsilyl)oxy) methyl)cyclobutyl)-1-methyl-1,3-dihydro-2H-benzo[d] imidazol-2-one-3-[tert-butyl(dimethyl)silyl] oxy-piperidine-1-carboxylate was purified by SFC (column: DAICEL CHIRALPAK AD (250 mm*50 mm, 10 um); mobile phase: [CO$_2$-MeOH (0.1% NH$_3$H$_2$O)]; B %: 20%-20%, B2.7; 90 min) to give 7-((1s,3s)-3-(((tert-butyldimethylsilyl)oxy)methyl)cyclobutyl)-1-methyl-1,3-dihydro-2H-benzo[d]imidazol-2-one (1.50 g, 30% yield, t$_R$=1.029) as a yellow solid ($^1$H NMR (400 MHz, DMSO-d$_6$) δ 10.82 (s, 1H), 7.04-6.90 (m, 2H), 6.81 (dd, J=1.2, 7.6 Hz, 1H), 3.98-3.83 (m, 1H), 3.55 (d, J=5.2 Hz, 2H), 3.49 (s, 3H), 2.48-2.37 (m, 1H), 2.33-2.20 (m, 2H), 2.07-1.91 (m, 2H), 0.87 (s, 9H), 0.12--0.04 (m, 6H)) and 7-((1r,3r)-3-(((tert-butyldimethylsilyl)oxy)methyl)cyclobutyl)-1-methyl-1,3-dihydro-2H-benzo[d]imidazol-2-one (3.00 g, 60% yield, t$_R$=1.241) as a yellow solid ($^1$H NMR (400 MHz, DMSO-d$_6$) δ 10.82 (s, 1H), 7.07 (d, J=8.0 Hz, 1H), 6.97 (t, J=7.6 Hz, 1H), 6.83 (dd, J=0.8, 7.6 Hz, 1H), 4.18-4.06 (m, J=8.0 Hz, 1H), 3.74 (d, J=6.4 Hz, 2H), 3.44 (s, 3H), 2.48-2.35 (m, 1H), 2.33-2.20 (m, 2H), 2.19-2.09 (m, 2H), 0.94-0.87 (m, 9H), 0.11-0.04 (m, 6H)). The absolute stereochemistry of the diastereomers was assigned arbitrarily.

3-[4-[3-[[(3S,4S)-3-fluoro-4-piperidyl]oxymethyl] cyclobutyl]-3-methyl-2-oxo-benzimidazol-1-yl]piperidine-2,6-dione (Intermediate COA)

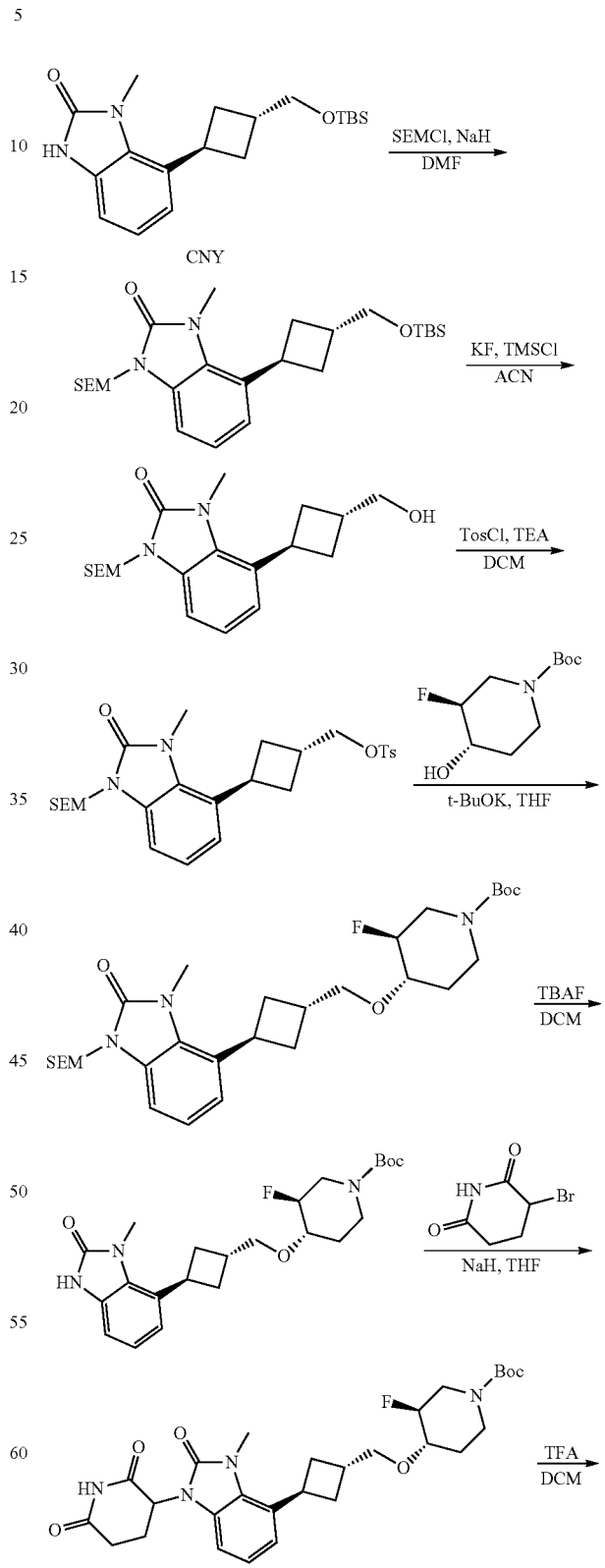

-continued

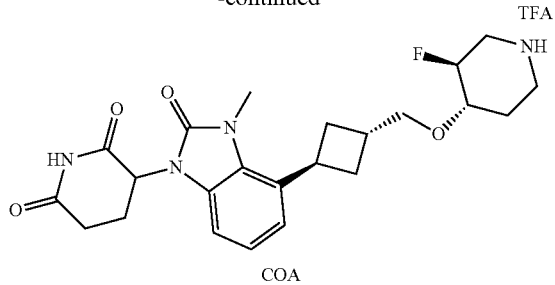

Step 1—4-[3-[[Tert-butyl(dimethyl)silyl]oxymethyl]cyclobutyl]-3-methyl-1-(2-trimethylsilylethoxy methyl)benzimidazol-2-one. To a solution of 4-[3-[[tert-butyl(dimethyl)silyl]oxymethyl]cyclobutyl]-3-methyl-1H-benzimidazol-2-one (3.00 g, 8.66 mmol, Intermediate CNY) in THF (30 mL) was added NaH (519 mg, 12.9 mmol, 60% dispersion in mineral oil) and the mixture was stirred at 0° C. for 0.5 hr. Next, SEM-Cl (1.88 g, 11.2 mmol) was added and the reaction mixture was stirred at 25° C. for 13.5 hrs. On completion, the reaction mixture was quenched with NH$_4$Cl (150 mL) at 20° C., and then extracted with EA (100 mL×3). The combined organic layers were washed with saturated sodium chloride solution (100 mL×3), dried over anhydrous sodium sulfate, filtered and concentrated to give a residue. The residue was purified by column chromatography (SiO$_2$, Petroleum ether/Ethyl acetate=50/1 to 10/1) to give the title compound (2.20 g, 53% yield) as a yellow oil. $^1$H NMR (400 MHz, DMSO-d$_6$) δ 7.23-7.14 (m, 1H), 7.12-7.04 (m, 2H), 5.22 (s, 2H), 4.21-4.05 (m, 1H), 3.74 (d, J=6.4 Hz, 2H), 3.53 (dd, J=2.8, 8.0 Hz, 2H), 3.51 (s, 3H), 2.47-2.38 (m, 1H), 2.33-2.22 (m, 2H), 2.20-2.11 (m, 2H), 0.90 (s, 9H), 0.87-0.84 (m, 2H), 0.10-0.04 (m, 6H), 0.04-0.01 (m, 9H).

Step 2—4-[3-(Hydroxymethyl)cyclobutyl]-3-methyl-1-(2-trimethylsilylethoxymethyl)benzimidazol-2-one. To a solution of 4-[3-[[tert-butyl(dimethyl)silyl]oxymethyl]cyclobutyl]-3-methyl-1-(2-trimethylsilylethoxymethyl)benzimidazol-2-one (2.00 g, 4.19 mmol) in ACN (5 mL) was added KF (268 mg, 4.61 mmol) and TMSCl (455 mg, 4.19 mmol). The mixture was then stirred at 25° C. for 0.5 hr. On completion, the reaction mixture was diluted with H$_2$O (80 mL) and extracted with EA (40 mL×2). The combined organic layers were washed with saturated sodium chloride solution (40 mL×2), dried over anhydrous sodium sulfate, filtered and concentrated to give the title compound (1.50 g, 98% yield) as a yellow oil. LC-MS (ESI$^+$) m/z 363.1 (M+H)$^+$.

Step 3—[3-[3-Methyl-2-oxo-1-(2-trimethylsilylethoxymethyl)benzimidazol-4-yl]cyclobutyl]methyl 4-methylbenzenesulfonate. To a solution of 4-[3-(hydroxymethyl)cyclobutyl]-3-methyl-1-(2-trimethylsilylethoxymethyl) benzimidazol-2-one (1.10 g, 3.03 mmol) in DCM (15 mL) was added 4-methylbenzenesulfonyl chloride (867 mg, 4.55 mmol) and TEA (1.23 g, 12.1 mmol) at 0° C. The mixture was then stirred at 25° C. for 12 hrs. On completion, the reaction mixture was diluted with H$_2$O (40 mL) and extracted with DCM (30 mL×2). The combined organic layers were washed with saturated sodium chloride solution (30 mL×2), dried over anhydrous sodium sulfate, filtered and concentrated to give a residue. The residue was purified by column chromatography (SiO$_2$, Petroleum ether/Ethyl acetate=5/1 to 3/1) to give the title compound (960 mg, 61% yield) as a yellow solid. $^1$H NMR (400 MHz, DMSO-d$_6$) δ 7.84 (d, J=8.4 Hz, 2H), 7.51 (d, J=8.0 Hz, 2H), 7.22-6.98 (m, 3H), 5.21 (s, 2H), 4.24 (d, J=7.2 Hz, 2H), 4.15-4.06 (m, J=8.0 Hz, 1H), 3.55-3.48 (m, 2H), 3.42 (s, 3H), 2.60-2.53 (m, 1H), 2.44 (s, 3H), 2.33-2.22 (m, 2H), 2.12-2.02 (m, 2H), 0.87-0.77 (m, 2H), 0.00--0.16 (m, 9H); LC-MS (ESI$^+$) m/z 517.2 (M+H)$^+$.

Step 4—Tert-butyl (3S,4S)-3-fluoro-4-[[3-[3-methyl-2-oxo-1-(2-trimethylsilylethoxymethyl)benzimidazol-4-yl]cyclobutyl]methoxy]piperidine-1-carboxylate. To a solution of tert-butyl (3S,4S)-3-fluoro-4-hydroxy-piperidine-1-carboxylate (330 mg, 1.51 mmol, CAS #1174020-44-0) in THF (8 mL) was added NaH (69.6 mg, 1.74 mmol, 60% dispersion in mineral oil) at 0° C. and the mixture was stirred at 0° C. for 1 hr. Next, [3-[3-methyl-2-oxo-1-(2-trimethylsilylethoxymethyl) benzimidazol-4-yl]cyclobutyl]methyl 4-methylbenzenesulfonate (600 mg, 1.16 mmol) was added and the mixture was stirred at 80° C. for 13 hrs. On completion, the reaction mixture was quenched by addition NH$_4$Cl (30 mL) at 20° C., and then extracted with EA (20 mL×2). The combined organic layers were washed with saturated sodium chloride solution (20 mL×2), dried over anhydrous sodium sulfate, filtered and concentrated to give a residue. The residue was purified by column chromatography (SiO$_2$, Petroleum ether/Ethyl acetate=5/1 to 3/2) to give the title compound (400 mg, 61% yield) as a yellow solid. $^1$H NMR (400 MHz, DMSO-d$_6$) δ 7.23-7.15 (m, 1H), 7.07 (d, J=4.4 Hz, 2H), 5.28 (d, J=4.4 Hz, 1H), 5.22 (s, 2H), 4.58-4.40 (m, 1H), 4.21-4.16 (m, 1H), 3.72-3.67 (m, 2H), 3.66-3.60 (m, 2H), 3.51 (s, 3H), 3.41 (d, J=4.4 Hz, 2H), 3.25-3.16 (m, 2H), 2.37-2.25 (m, 2H), 2.21-2.10 (m, 2H), 1.93-1.83 (m, 1H), 1.81-1.69 (m, 1H), 1.56-1.47 (m, 1H), 1.40 (s, 9H), 0.86-0.80 (m, 2H), −0.07 (s, 9H); LC-MS (ESI$^+$) m/z 564.2 (M+H)$^+$.

Step 5—Tert-butyl (3S,4S)-3-fluoro-4-[[3-(3-methyl-2-oxo-1H-benzimidazol-4-yl)cyclobutyl]methoxy] piperidine-1-carboxylate. To a solution of tert-butyl (3S,4S)-3-fluoro-4-[[3-[3-methyl-2-oxo-1-(2-trimethylsilylethoxymethyl) benzimidazol-4-yl]cyclobutyl]methoxy]piperidine-1-carboxylate (400 mg, 709 μmol) in dioxane (8 mL) was added TBAF (1 M, 7.10 mL). The mixture was stirred at 80° C. for 12 hrs. On completion, the reaction mixture was diluted with H$_2$O (20 mL) and extracted with EA (15 mL×3). The combined organic layers were washed with saturated sodium chloride solution (20 mL×3), dried over anhydrous sodium sulfate, filtered and concentrated to give a residue. The residue was purified by column chromatography (SiO$_2$, Petroleum ether/Ethyl acetate=2/1 to 1/2) to give the title compound (200 mg, 65% yield) as a white solid. $^1$H NMR (400 MHz, DMSO-d$_6$) δ 10.83 (s, 1H), 7.08 (d, J=8.0 Hz, 1H), 6.97 (t, J=7.6 Hz, 1H), 6.83 (d, J=7.2 Hz, 1H), 4.60-4.39 (m, 1H), 4.21-4.10 (m, J=8.0 Hz, 1H), 3.75-3.66 (m, 2H), 3.66-3.55 (m, 2H), 3.52-3.36 (m, 5H), 3.29-3.20 (m, 1H), 2.49-2.48 (m, 1H), 2.37-2.23 (m, 2H), 2.21-2.08 (m, 2H), 1.94-1.82 (m, 1H), 1.59-1.46 (m, 1H), 1.39 (s, 9H); LC-MS (ESI$^+$) m/z 456.1 (M+23)$^+$.

Step 6—Tert-butyl (3S,4S)-4-[[3-[1-(2,6-dioxo-3-piperidyl)-3-methyl-2-oxo-benzimidazol-4-yl] cyclobutyl]methoxy]-3-fluoro-piperidine-1-carboxylate. To a solution of tert-butyl (3S,4S)-3-fluoro-4-[[3-(3-methyl-2-oxo-1H-benzimidazol-4-yl)cyclobutyl] methoxy]piperidine-1-carboxylate (100 mg, 230 μmol) in THF (2 mL) was added NaH (27.6 mg, 692 μmol, 60% dispersion in mineral oil) at 0° C. and the mixture was stirred at 0° C. for 1 hr. Then 3-bromopiperidine-2,6-dione (132 mg, 692 μmol, CAS #62595-74-8) was added at 0° C. then the mixture was stirred at 60° C. for 3 hrs. On completion, the reaction mixture was quenched with FA at 20° C. until the pH=5, and then diluted with H₂O (6 mL) and extracted with EA (3 mL×2). The combined organic layers were washed with saturated sodium chloride solution (3 mL×2), dried over anhydrous sodium sulfate, filtered and concentrated to give a residue. The residue was purified by prep-HPLC purification (column: Phenomenex luna C18 150*25 mm*10 um; mobile phase: [water(FA)-ACN]; gradient: 50%-70% B over 15 min) to give the title compound (30.0 g, 23% yield) as a white solid. ¹H NMR (400 MHz, DMSO-d₆) δ 11.08 (s, 1H), 7.17 (d, J=7.6 Hz, 1H), 7.05 (t, J=7.6 Hz, 1H), 7.01-6.96 (m, 1H), 5.44-5.30 (m, 1H), 4.59-4.39 (m, 1H), 4.26-4.12 (m, 1H), 3.78-3.69 (m, 2H), 3.67 (d, J=9.6 Hz, 1H), 3.65-3.59 (m, 2H), 3.52 (s, 3H), 3.45-3.42 (m, 1H), 2.94-2.83 (m, 1H), 2.72-2.63 (m, 2H), 2.59 (d, J=0.4 Hz, 1H), 2.40-2.28 (m, 3H), 2.20-2.12 (m, 2H), 2.04-1.94 (m, 1H), 1.93-1.82 (m, 1H), 1.55-1.48 (m, 1H), 1.40 (s, 9H); LC-MS (ESI⁺) m/z 489.1 (M−56+H)⁺.

Step 7—3-[4-[3-[[(3S,4S)-3-fluoro-4-piperidyl]oxymethyl]cyclobutyl]-3-methyl-2-oxo-benzimidazol-1-yl]piperidine-2,6-dione. Tert-butyl (3S,4S)-4-[[3-[1-(2,6-dioxo-3-piperidyl)-3-methyl-2-oxo-benzimidazol-4-yl]cyclobutyl]methoxy]-3-fluoro-piperidine-1-carboxylate (25.0 mg, 45.9 μmol) was dissolved in DCM (1 mL) and TFA (0.3 mL), then the mixture was stirred at 25° C. for 0.5 hr. On completion, the reaction mixture was concentrated under reduced pressure to give the title compound (25.0 mg, 97% yield, TFA) as an off-white solid. LC-MS (ESI⁺) m/z 445.1 (M+H)⁺.

5-[(1R,4R)-2-oxa-5-azabicyclo[2.2.1]heptan-5-yl]pyrazolo[1,5-a]pyrimidine-3-carboxamide (Intermediate COB)

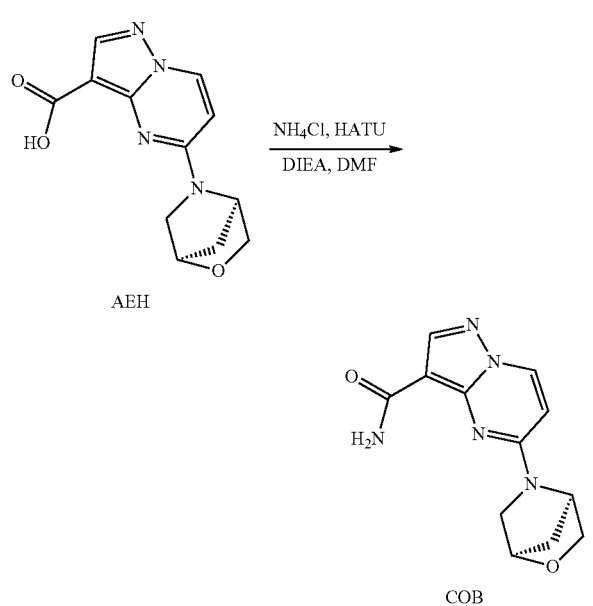

To a solution of 5-[(1R,4R)-2-oxa-5-azabicyclo[2.2.1]heptan-5-yl]pyrazolo[1,5-a]pyrimidine-3-carboxylic acid (3.50 g, 13.4 mmol, Intermediate AEH) and HATU (6.14 g, 16.1 mmol) in DMF (20 mL) was added DIEA (5.21 g, 40.3 mmol) and the mixture was stirred at 25° C. for 30 mins. Then NH₄Cl (1.08 g, 20.1 mmol) was added and the mixture was stirred at 25° C. for 1 hr. On completion, the reaction mixture was concentrated in vacuo to give a residue. The residue was purified by reverse phase (0.1% FA condition) to give the title compound (3.40 g, 98% yield) as a white solid. ¹H NMR (400 MHz, DMSO-d₆) δ 8.72 (d, J=7.6 Hz, 1H), 8.12 (s, 1H), 7.32 (s, 1H), 7.14 (s, 1H), 6.89-6.20 (m, 1H), 5.29-4.97 (m, 1H), 4.73 (d, J=10.4 Hz, 1H), 3.87-3.68 (m, 2H), 3.57 (d, J=10.8 Hz, 1H), 3.42 (s, 1H), 2.04-1.87 (m, 2H). LC-MS (ESI⁺) m/z 260.1 (M+H)⁺.

N-[2-(4-formylcyclohexyl)indazol-5-yl]-5-[(1R,4R)-2-oxa-5-azabicyclo[2.2.1]heptan-5-yl] pyrazolo[1,5-a]pyrimidine-3-carboxamide (Intermediate COC)

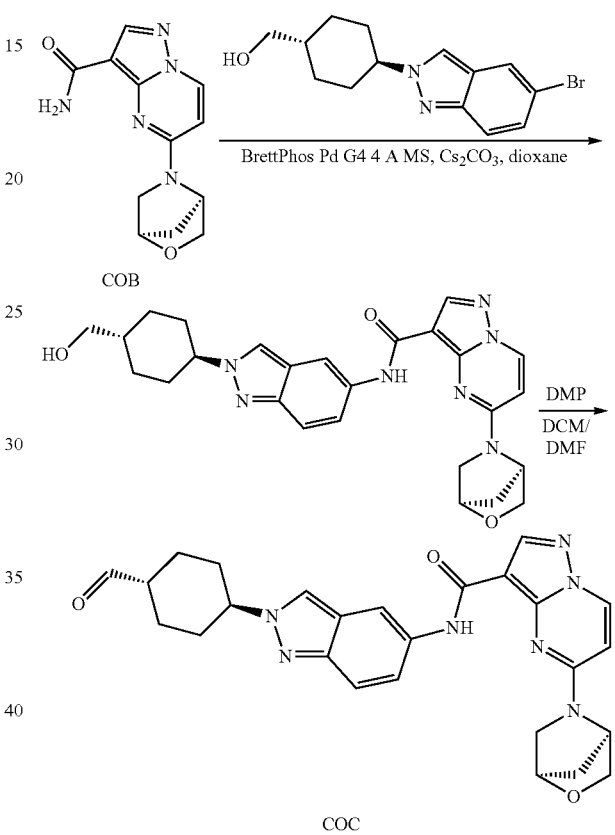

Step 1—N-[2-[4-(hydroxymethyl)cyclohexyl]indazol-5-yl]-5-[(1R,4R)-2-oxa-5-azabicyclo[2.2.1] heptan-5-yl]pyrazolo[1,5-a]pyrimidine-3-carboxamide. A mixture of 5-[(1R,4R)-2-oxa-5-azabicyclo[2.2.1]heptan-5-yl]pyrazolo[1,5-a]pyrimidine-3-carboxamide (830 mg, 3.20 mmol, Intermediate COB), [4-(5-bromoindazol-2-yl)cyclohexyl]methanol (890 mg, 2.88 mmol, synthesized via Step 1 of Intermediate BTW), 4 Å molecular sieves (50 mg), Cs₂CO₃ (2.09 g, 6.40 mmol) and BrettPhos Pd G4 (294 mg, 320 μmol) in dioxane (10 mL) was degassed and purged with N₂ three times. Then the mixture was stirred at 100° C. for 16 hrs under N₂ atmosphere. On completion, the reaction mixture was filtered to give the filtrate. Then, the filtrate was concentrated in vacuo to give a residue. The residue was triturated with H₂O (10 mL), then, triturated with PE:EA=1:1 to give the title compound (1.20 g, 76% yield) as a yellow solid. ¹H NMR (400 MHz, DMSO-d₆) δ 10.05-9.78 (m, 1H), 8.81 (d, J=7.6 Hz, 1H), 8.39-8.17 (m, 3H), 7.60 (d, J=9.2 Hz, 1H), 7.21 (d, J=8.8 Hz, 1H), 6.92-6.44 (m, 1H), 5.26-4.77 (m, 2H), 4.50 (t, J=4.8 Hz, 1H), 4.44-4.33 (m, 1H), 4.01-3.86 (m, 1H), 3.87-3.73 (m, 2H), 3.68 (d, J=10.8 Hz, 1H), 2.18-2.11 (m, 2H), 2.08-2.00 (m, 2H), 1.96-1.87 (m, 4H), 1.53-1.44 (m, 1H), 1.21-1.10 (m, 2H). LC-MS (ESI$^+$) m/z 488.1 (M+H)$^+$.

Step 2—N-[2-(4-formylcyclohexyl)indazol-5-yl]-5-[(1R, 4R)-2-oxa-5-azabicyclo[2.2.1]heptan-5-yl] pyrazolo[1,5-a]pyrimidine-3-carboxamide. To a solution of N-[2-[4-(hydroxymethyl)cyclohexyl]indazol-5-yl]-5-[(1R,4R)-2-oxa-5-azabicyclo [2.2.1]heptan-5-yl]pyrazolo[1,5-a]pyrimidine-3-carboxamide (120 mg, 246 µmol) in DCM (1 mL) and DMF (1 mL) was added DMP (208 mg, 492 µmol), then the mixture was stirred at 25° C. for 5 hrs. On completion, the mixture quenched with saturated NaHCO$_3$ (5 mL) and saturated Na$_2$S$_2$O$_3$ (5 mL) and stirred at 25° C. for 0.5 hr. After that, the mixture was extracted with DCM/MeOH=10/1 (50 mL×3), then the combined organic layers were washed with saturated NaCl (50 mL), the organic layers were dried over Na$_2$SO$_4$, filtered and concentrated in vacuo to give the title compound (80.0 mg, 66% yield) as a brown solid. $^1$H NMR (400 MHz, DMSO-d$_6$) δ 10.04-9.81 (m, 1H), 9.73-9.61 (m, 1H), 8.81 (d, J=7.6 Hz, 1H), 8.37-7.94 (m, 3H), 7.65-7.57 (m, 1H), 7.24-7.19 (m, 1H), 6.92-6.46 (m, 1H), 5.29-4.74 (m, 2H), 4.52-4.35 (m, 1H), 3.99-3.73 (m, 3H), 3.68 (d, J=10.4 Hz, 1H), 3.51-3.39 (m, 1H), 2.26-2.17 (m, 2H), 2.15-2.07 (m, 2H), 2.06-1.95 (m, 4H), 1.50-1.39 (m, 2H). LC-MS (ESI$^+$) m/z 486.2 (M+H)$^+$.

3-Methyl-4-piperazin-1-yl-1-(2-trimethylsilylethoxymethyl)benzimidazol-2-one (Intermediate COD)

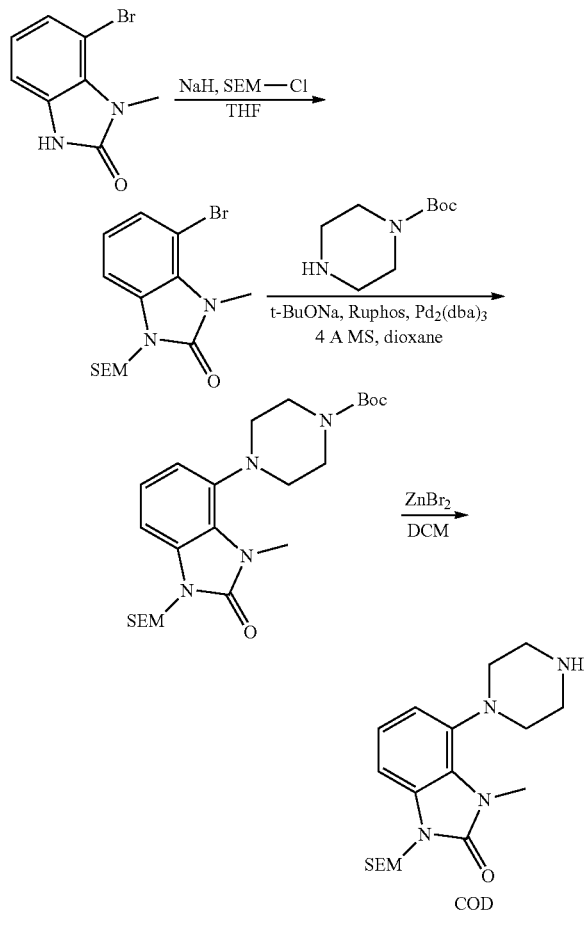

Step 1—4-Bromo-3-methyl-1-(2-trimethylsilylethoxymethyl)benzimidazol-2-one. To a solution of 4-bromo-3-methyl-1H-benzimidazol-2-one (19.3 g, 85.0 mmol, synthesized via Steps 1-3 of Intermediate HP) in THF (200 mL) was added NaH (5.10 g, 127 mmol, 60% dispersion in mineral oil) at 0° C., then the mixture was stirred at 20° C. for 3 hrs. Next, SEM-Cl (25.0 g, 128 mmol, 85% solution) was added to the mixture above dropwise at 0° C., then the reaction was stirred at 20° C. for 15 hrs. On completion, the reaction was quenched with saturated NH$_4$Cl at 0° C. to adjust the pH=7, concentrated in vacuo to remove THF, then extracted with EA (200 ml×3). The organic layers were combined, dried over anhydrous Na$_2$SO$_4$, filtered and concentrated in vacuo to give a residue. The residue was purified by column chromatography (SiO$_2$, PE/EA=10/1 to 4/1) to give the title compound (55.7 g, 91% yield) as white solid. $^1$H NMR (400 MHz, DMSO-d$_6$) δ 7.23 (dd, J=2.8, 8.0 Hz, 2H), 7.03-6.96 (m, 1H), 5.25 (s, 2H), 3.61 (s, 3H), 3.53 (t, J=8.0 Hz, 2H), 0.83 (t, J=8.0 Hz, 2H), −0.07 (s, 9H); LC-MS (ESI$^+$) m/z 379.0 (M+Na)$^+$.

Step 2—Tert-butyl 4-[3-methyl-2-oxo-1-(2-trimethylsilylethoxymethyl)benzimidazol-4-yl]piperazine-1-carboxylate. A mixture of 4-bromo-3-methyl-1-(2-trimethylsilylethoxymethyl)benzimidazol-2-one (10.0 g, 28.0 mmol), tert-butyl piperazine-1-carboxylate (7.82 g, 42.0 mmol, CAS #143238-38-4), Pd$_2$(dba)$_3$ (2.56 g, 2.80 mmol), RuPhos (1.31 g, 2.80 mmol), 4 Å molecular sieves (500 mg) and t-BuONa (8.07 g, 84.0 mmol) in dioxane (100 mL) was degassed and purged with N$_2$ three times. Then the mixture was stirred at 100° C. for 16 hrs under N$_2$ atmosphere. On completion, the reaction mixture was filtered and concentrated in vacuo to give a residue. The residue was diluted with H$_2$O (100 mL) and extracted with EA (200 mL×3). The combined organic layers were washed with brine (100 mL), dried over Na$_2$SO$_4$, filtered and concentrated in vacuo to give the crude product. The crude product was purified by column chromatography (SiO$_2$, PE:EA=10:1 to 5:1) to give the title compound (22.5 g, 87% yield) as a brown oil. $^1$H NMR (400 MHz, CDCl$_3$) δ 7.08-7.02 (m, 1H), 7.00-6.96 (m, 1H), 6.91 (dd, J=1.2, 8.0 Hz, 1H), 5.31 (d, J=1.2 Hz, 2H), 4.27-4.02 (m, 2H), 3.75 (s, 3H), 3.65-3.58 (m, 2H), 3.18-2.98 (m, 4H), 2.92-2.78 (m, 2H), 1.50 (s, 9H), 0.98-0.89 (m, 2H), 0.01-−0.06 (m, 9H); LC-MS (ESI$^+$) m/z 463.2 (M+H)$^+$.

Step 3—3-Methyl-4-piperazin-1-yl-1-(2-trimethylsilylethoxymethyl)benzimidazol-2-one. To a mixture of tert-butyl 4-[3-methyl-2-oxo-1-(2-trimethylsilylethoxymethyl) benzimidazol-4-yl] piperazine-1-carboxylate (2.50 g, 5.40 mmol) in DCM (100 mL) was added ZnBr$_2$ (6.08 g, 27.0 mmol), then the mixture was stirred at 20° C. for 16 hrs. On completion, the reaction mixture was concentrated in vacuo to give a residue. The residue was diluted with brine (200 mL) and extracted with EA (200 mL×3). The combined organic layers were concentrated in vacuo to give a residue. Then the residue was diluted with DCM (50 mL) and MeOH (50 mL), dried over Na$_2$SO$_4$, filtered and concentrated in vacuo to give the title compound (1.96 g, 100% yield) as a yellow solid. $^1$H NMR (400 MHz, DMSO-d$_6$) δ 7.05-6.96 (m, 2H), 6.89 (dd, J=1.2, 7.6 Hz, 1H), 5.21 (s, 2H), 3.61 (s, 3H), 3.56-3.50 (m, 2H), 3.06-2.83 (m, 8H), 0.86-0.80 (m, 2H), −0.07 (s, 9H); LC-MS (ESI$^+$) m/z 363.3 (M+H)$^+$.

647

Tert-butyl (4R)-3,3-difluoro-4-[4-[3-methyl-2-oxo-1-(2-trimethylsilylethoxymethyl) benzimidazol-4-yl]piperazin-1-yl]piperidine-1-carboxylate (Intermediate COE) and Tert-butyl (4S)-3,3-difluoro-4-[4-[3-methyl-2-oxo-1-(2-trimethylsilylethoxymethyl) benzimidazol-4-yl]piperazin-1-yl]piperidine-1-carboxylate (Intermediate COF)

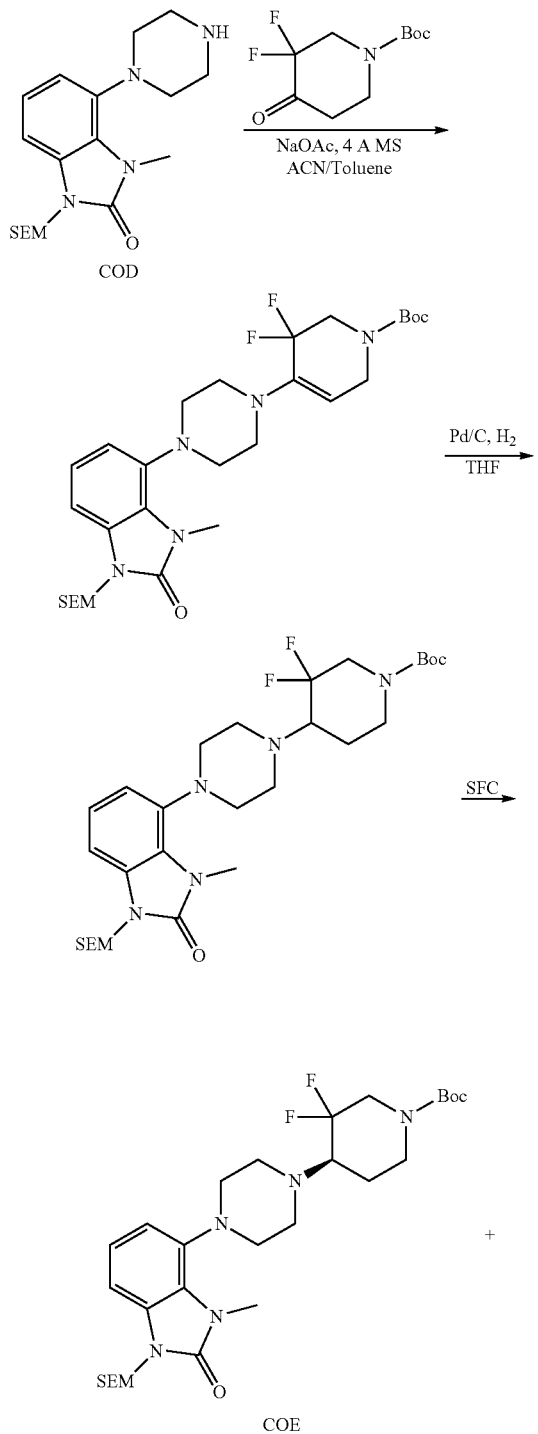

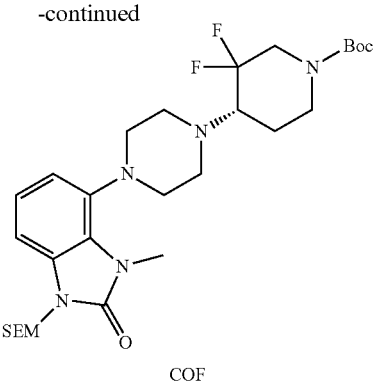

COF

Step 1—Tert-butyl 3,3-difluoro-4-[4-[3-methyl-2-oxo-1-(2-trimethylsilylethoxymethyl)benzimidazol-4-yl]piperazin-1-yl]-2,6-dihydropyridine-1-carboxylate. To a mixture of 3-methyl-4-piperazin-1-yl-1-(2-trimethylsilylethoxymethyl)benzimidazol-2-one (1.96 g, 5.41 mmol, Intermediate COD) and tert-butyl 3,3-difluoro-4-oxo-piperidine-1-carboxylate (1.91 g, 8.11 mmol, CAS #1215071-17-2) in ACN (15 mL) and toluene (15 mL) was added 4 Å molecular sieves (500 mg) and NaOAc (2.22 g, 27.0 mmol), then the mixture was stirred at 110° C. for 60 hrs. On completion, the reaction mixture was filtered and concentrated in vacuo to give a residue. Then the residue was diluted with $H_2O$ (200 mL) and extracted with EA (200 mL×3). The combined organic layers were washed with saturated NaCl (100 mL), dried over $Na_2SO_4$, filtered and concentrated in vacuo to a residue. The residue was purified by column chromatography ($SiO_2$, PE:EA=10:1 to 3:1) to give the title compound (2.00 g, 64% yield) as a yellow liquid. $^1$H NMR (400 MHz, DMSO-$d_6$) δ 7.06-6.95 (m, 3H), 5.22 (s, 2H), 3.75 (t, J=6.0 Hz, 1H), 3.62 (s, 3H), 3.56-3.51 (m, 2H), 3.40-3.34 (m, 3H), 3.12-2.83 (m, 5H), 2.81-2.72 (m, 1H), 1.63-1.71 (m, 3H), 1.42 (s, 9H), 0.87-0.81 (m, 2H), −0.07 (s, 9H); LC-MS (ESI$^+$) m/z 580.7 (M+H)$^+$.

Step 2—Tert-butyl 3,3-difluoro-4-[4-[3-methyl-2-oxo-1-(2-trimethylsilylethoxymethyl)benzimidazol-4-yl]piperazin-1-yl]piperidine-1-carboxylate. To a solution of tert-butyl 3,3-difluoro-4-[4-[3-methyl-2-oxo-1-(2-trimethylsilylethoxymethyl)benzimidazol-4-yl]piperazin-1-yl]-2,6-dihydropyridine-1-carboxylate (2.00 g, 3.45 mmol) in THF (10 mL) was added Pd/C (2.00 g, 1.88 mmol, 10 wt %) under Ar atmosphere. The suspension was degassed and purged with $H_2$ three times. The mixture was then stirred under $H_2$ (15 Psi) at 20° C. for 16 hrs. On completion, the reaction mixture was filtered and concentrated in vacuo to give a residue. Then the residue purified by reverse phase (0.1% FA condition) to give the title compound (1.00 g, 50% yield) as a light yellow liquid. $^1$H NMR (400 MHz, DMSO-$d_6$) δ 7.05-6.90 (m, 3H), 5.21 (s, 2H), 4.17-4.05 (m, 1H), 3.61 (s, 3H), 3.53 (t, J=8.0 Hz, 2H), 3.17-3.03 (m, 2H), 3.00-2.71 (m, 10H), 1.86-1.79 (m, 1H), 1.78-1.66 (m, 1H), 1.40 (s, 9H), 0.83 (t, J=8.0 Hz, 2H), −0.07 (s, 9H); LC-MS (ESI$^+$) m/z 582.7 (M+H)$^+$.

Step 3—Tert-butyl (4R)-3,3-difluoro-4-[4-[3-methyl-2-oxo-1-(2-trimethylsilylethoxymethyl) benzimidazol-4-yl]piperazin-1-yl]piperidine-1-carboxylate and tert-butyl (4S)-3,3-difluoro-4-[4-[3-methyl-2-oxo-1-(2-trimethylsilylethoxymethyl)benzimidazol-4-yl]piperazin-1-yl]piperidine-1-carboxylate. A mixture of tert-butyl 3,3-difluoro-4-[4-[3-methyl-2-oxo-1-(2-trimethylsilylethoxymethyl)benzimidazol-4-yl]piperazin-1- yl]piperidine-1-carboxylate (2.00 g, 3.44 mmol) was separated by Charil SFC (column: DAICEL CHIRALPAK IG (250 mm×30 mm, 10 um); mobile phase: [PE-IPA]; 40% B isocratic elution mode) to give tert-butyl (4R)-3,3-difluoro-4-[4-[3-methyl-2-oxo-1-(2-trimethylsilylethoxymethyl) benzimidazol-4-yl]piperazin-1-yl]piperidine-1-carboxylate (1.00 g, 50% yield, 100% ee, $t_R$=1.63) ($^1$H NMR (400 MHz, DMSO-$d_6$) δ 7.03-6.91 (m, 3H), 5.21 (s, 2H), 4.17-4.06 (m, 1H), 3.61 (s, 3H), 3.53 (t, J=8.0 Hz, 2H), 3.16-3.03 (m, 2H), 3.02-2.68 (m, 10H), 1.86-1.79 (m, 1H), 1.77-1.65 (m, 1H), 1.40 (s, 9H), 0.83 (t, J=8.0 Hz, 2H), −0.07 (s, 9H); LC-MS (ESI$^+$) m/z 582.3 (M+H)$^+$ and tert-butyl (4S)-3,3-difluoro-4-[4-[3-methyl-2-oxo-1-(2-trimethylsilylethoxymethyl)benzimidazol-4-yl]piperazin-1-yl]piperidine-1-carboxylate (800 mg, 40% yield, 97.2% ee, $t_R$=1.95) ($^1$H NMR (400 MHz, DMSO-$d_6$) δ 7.03-6.92 (m, 3H), 5.21 (s, 2H), 4.18-4.06 (m, 1H), 3.61 (s, 3H), 3.56-3.49 (m, 2H), 3.16-3.03 (m, 2H), 3.02-2.71 (m, 10H), 1.86-1.80 (m, 1H), 1.77-1.65 (m, 1H), 1.40 (s, 9H), 0.86-0.81 (m, 2H), −0.07 (s, 9H); LC-MS (ESI$^+$) m/z 582.3 (M+H)$^+$). The absolute stereochemistry of the enantiomers was assigned arbitrarily.

3-[4-[4-[(4S)-3,3-difluoro-4-piperidyl]piperazin-1-yl]-3-methyl-2-oxo-benzimidazol-1-yl]piperidine-2,6-dione (Intermediate COG)

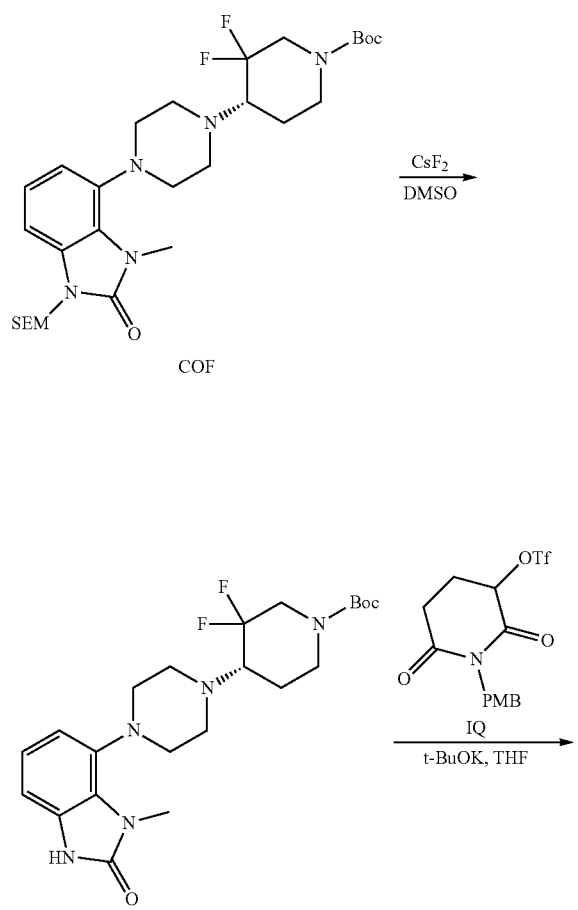

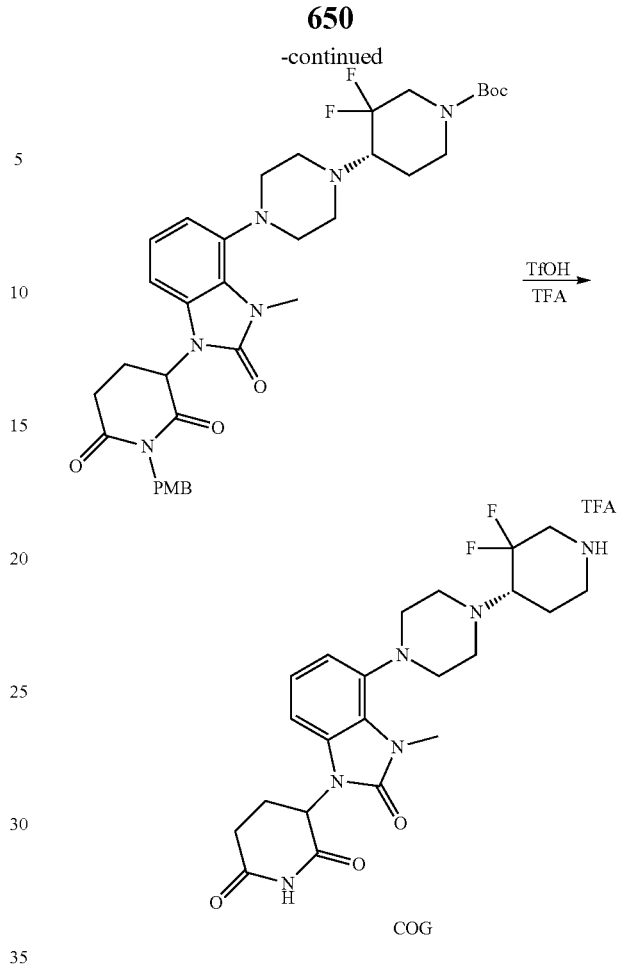

Step 1—Tert-butyl (4S)-3,3-difluoro-4-[4-(3-methyl-2-oxo-1H-benzimidazol-4-yl)piperazin-1-yl]piperidine-1-carboxylate. A mixture of tert-butyl (4S)-3,3-difluoro-4-[4-[3-methyl-2-oxo-1-(2-trimethylsilylethoxymethyl) benzimidazol-4-yl]piperazin-1-yl]piperidine-1-carboxylate (800 mg, 1.38 mmol, Intermediate COF) in DMSO (4 mL) was added CsF (3.13 g, 20.6 mmol), then the mixture was stirred at 120° C. for 5 hrs. On completion, the reaction mixture was diluted with H$_2$O (100 mL) and extracted with EA (100 mL×3). The combined organic layers were dried over Na$_2$SO$_4$, filtered and concentrated in vacuo to a residue. The residue was purified by column chromatography (SiO$_2$, PE:EA=3:1 to 2:3) to give the title compound (350 mg, 56% yield) as yellow solid. $^1$H NMR (400 MHz, DMSO-$d_6$) δ 10.80 (s, 1H), 6.95-6.69 (m, 3H), 4.16-4.06 (m, 1H), 3.55 (s, 3H), 3.16-3.02 (m, 2H), 3.00-2.72 (m, 10H), 1.86-1.79 (m, 1H), 1.77-1.65 (m, 1H), 1.40 (s, 9H); LC-MS (ESI$^+$) m/z 452.1 (M+H)$^+$.

Step 2—Tert-butyl (4S)-3,3-difluoro-4-[4-[1-[1-[(4-methoxyphenyl)methyl]-2,6-dioxo-3-piperidyl]-3-methyl-2-oxo-benzimidazol-4-yl]piperazin-1-yl]piperidine-1-carboxylate. A mixture of tert-butyl(4S)-3,3-difluoro-4-[4-(3-methyl-2-oxo-1H-benzimidazol-4-yl)piperazin-1-yl] piperidine-1-carboxylate (350 mg, 775 μmol) in THF (2 mL) was added t-BuOK (217 mg, 1.94 mmol), the mixture was stirred at −20° C. for 1 hr. Then [1-[(4-methoxyphenyl) methyl]-2,6-dioxo-3-piperidyl] trifluoromethanesulfonate (591 mg, 1.55 mmol, Intermediate IQ) was added at −20° C., and the mixture was stirred at −20° C. for 0.5 hr. On completion, the reaction mixture was quenched with water (0.5 mL) and concentrated in vacuo to give a residue. Then the residue was diluted with H₂O (50 mL) and extracted with EA (50 mL×3). The combined organic layers were washed with saturated NaCl (30 mL), dried over Na₂SO₄, filtered and concentrated in vacuo to a residue. The residue was purified by column chromatography (SiO₂, PE:EA=5:1 to 2:3) to give the title compound (320 mg, 60% yield) as yellow solid. $^1$H NMR (400 MHz, DMSO-d₆) δ 7.21 (d, J=8.8 Hz, 2H), 6.95-6.89 (m, 2H), 6.85 (d, J=8.8 Hz, 2H), 6.81-6.73 (m, 1H), 5.50 (dd, J=5.2, 13.2 Hz, 1H), 4.85-4.72 (m, 2H), 4.16-4.06 (m, 1H), 3.72 (s, 3H), 3.62 (s, 3H), 3.18-3.05 (m, 2H), 3.05-2.81 (m, 10H), 2.80-2.64 (m, 3H), 2.07-2.00 (m, 1H), 1.87-1.80 (m, 1H), 1.78-1.65 (m, 1H), 1.40 (s, 9H); LC-MS (ESI⁺) m/z 683.3 (M+H)⁺.

Step 3—3-[4-[4-[(4S)-3,3-difluoro-4-piperidyl]piperazin-1-yl]-3-methyl-2-oxo-benzimidazol-1-yl]piperidine-2,6-dione. A mixture of tert-butyl (4S)-3,3-difluoro-4-[4-[1-[1-[(4-methoxyphenyl)methyl]-2,6-dioxo-3-piperidyl]-3-methyl-2-oxo-benzimidazol-4-yl]piperazin-1-yl]piperidine-1-carboxylate (150 mg, 220 μmol) in TFA (2 mL) was added TfOH (0.5 mL), then the mixture was stirred at 80° C. for 1 hr. On completion, the reaction mixture was concentrated in vacuo to give the title compound (126 mg, 100% yield, TFA) as black brown liquid. LC-MS (ESI⁺) m/z 463.2 (M+H)⁺.

3-[4-[4-[(4R)-3,3-difluoro-4-piperidyl]piperazin-1-yl]-3-methyl-2-oxo-benzimidazol-1-yl] piperidine-2,6-dione (Intermediate COH)

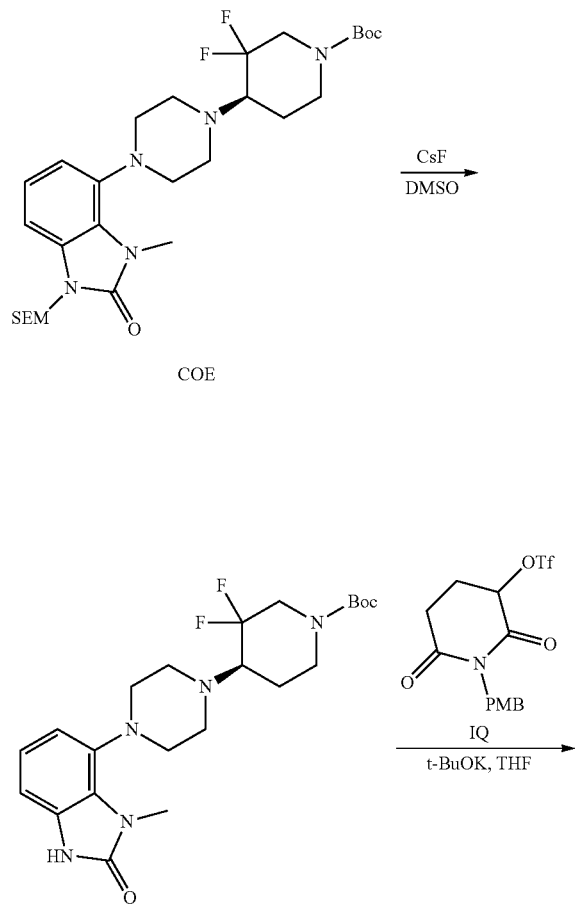

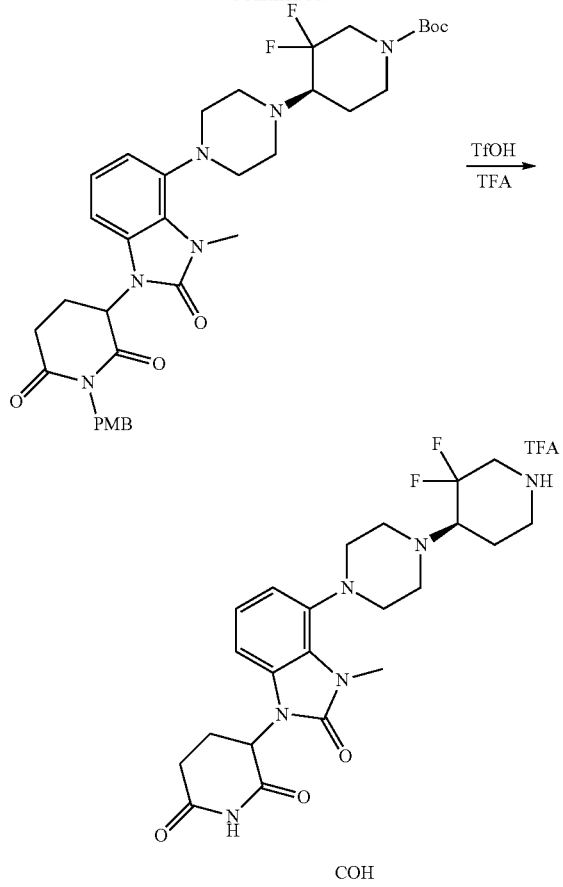

COH

Step 1—Tert-butyl (4R)-3,3-difluoro-4-[4-(3-methyl-2-oxo-1H-benzimidazol-4-yl)piperazin-1-yl]piperidine-1-carboxylate. To a solution of tert-butyl (4R)-3,3-difluoro-4-[4-[3-methyl-2-oxo-1-(2-trimethylsilylethoxymethyl)benzimidazol-4-yl]piperazin-1-yl]piperidine-1-carboxylate (850 mg, 1.46 mmol, Intermediate COE) in DMSO (4 mL) was added CsF (6.66 g, 43.8 mmol), the mixture was then stirred at 110° C. for 5 hrs. On completion, the mixture was diluted with H₂O (20 mL) and extracted with EA (50 mL×3). The combined organic layers were washed with saturated NaCl (30 mL), dried over Na₂SO₄, filtered and concentrated in vacuo to give the title compound (1.25 g, 94% yield) as a light yellow solid. $^1$H NMR (400 MHz, DMSO-d₆) δ10.81 (s, 1H), 6.96-6.69 (m, 3H), 4.17-4.05 (m, 1H), 3.65-3.52 (m, 3H), 3.35-3.29 (m, 2H), 3.15-3.01 (m, 2H), 2.96-2.79 (m, 8H), 1.87-1.78 (m, 1H), 1.77-1.65 (m, 1H), 1.40 (s, 9H). LC-MS (ESI⁺) m/z 452.0 (M+H)⁺.

Step 2—Tert-butyl (4R)-3,3-difluoro-4-[4-[1-[1-[(4-methoxyphenyl)methyl]-2,6-dioxo-3-piperidyl]-3-methyl-2-oxo-benzimidazol-4-yl]piperazin-1-yl]piperidine-1-carboxylate. To a solution of tert-butyl (4R)-3,3-difluoro-4-[4-(3-methyl-2-oxo-1H-benzimidazol-4-yl)piperazin-1-yl] piperidine-1-carboxylate (1.1 g, 2.44 mmol) in THF (15 mL) was added tBuOK (683 mg, 6.09 mmol) and the mixture was stirred at −10° C. for 0.5 hr. Then [1-[(4-methoxyphenyl)methyl]-2,6-dioxo-3-piperidyl] trifluoromethanesulfonate (1.86 g, 4.87 mmol, Intermediate IQ) was added and the mixture was stirred at −10° C. for 0.5 hr. On completion, the mixture was diluted with H₂O (50 mL) and extracted with EA (50 mL×3). The combined organic layers were washed with saturated NaCl (50 mL), dried over Na₂SO₄, filtered and concentrated in vacuo to give a residue. The residue was purified by column chromatography (SiO$_2$, PE:EA=5:1 to 1:1) to give the title compound (1.00 g, 60% yield) as a light yellow solid. $^1$H NMR (400 MHz, DMSO-d$_6$) δ 7.21 (d, J=8.4 Hz, 2H), 6.92 (d, J=4.0 Hz, 2H), 6.88-6.82 (m, 2H), 6.81-6.73 (m, 1H), 5.50 (dd, J=5.2, 12.8 Hz, 1H), 4.87-4.72 (m, 2H), 4.13-4.05 (m, 1H), 3.72 (s, 3H), 3.65-3.60 (m, 3H), 3.18-3.10 (m, 1H), 3.09-3.01 (m, 2H), 3.01-2.76 (m, 10H), 2.76-2.62 (m, 2H), 2.08-2.00 (m, 1H), 1.88-1.79 (m, 1H), 1.78-1.66 (m, 1H), 1.40 (s, 9H). LC-MS (ESI$^+$) m/z 683.5. (M+H)$^+$.

Step 3—3-[4-[4-[(4R)-3,3-difluoro-4-piperidyl]piperazin-1-yl]-3-methyl-2-oxo-benzimidazol-1-yl] piperidine-2,6-dione. A solution of tert-butyl (4R)-3,3-difluoro-4-[4-[1-[1-[(4-methoxyphenyl)methyl]-2,6-dioxo-3-piperidyl]-3-methyl-2-oxo-benzimidazol-4-yl]piperazin-1-yl]piperidine-1-carboxylate (800 mg, 1.17 mmol) in TFA (4 mL) and TfOH (0.8 mL) was stirred at 70° C. for 3 hrs. On completion, the reaction mixture was concentrated in vacuo to give the title compound (650 mg, 86% yield) as a black brown oil. LC-MS (ESI$^+$) m/z 463.1 (M+H)$^+$.

3-[4-[3-[[(3S,4R)-3-Fluoro-4-piperidyl]oxymethyl] cyclobutyl]-3-methyl-2-oxo-benzimidazol-1-yl]piperidine-2,6-dione (Intermediate COI)

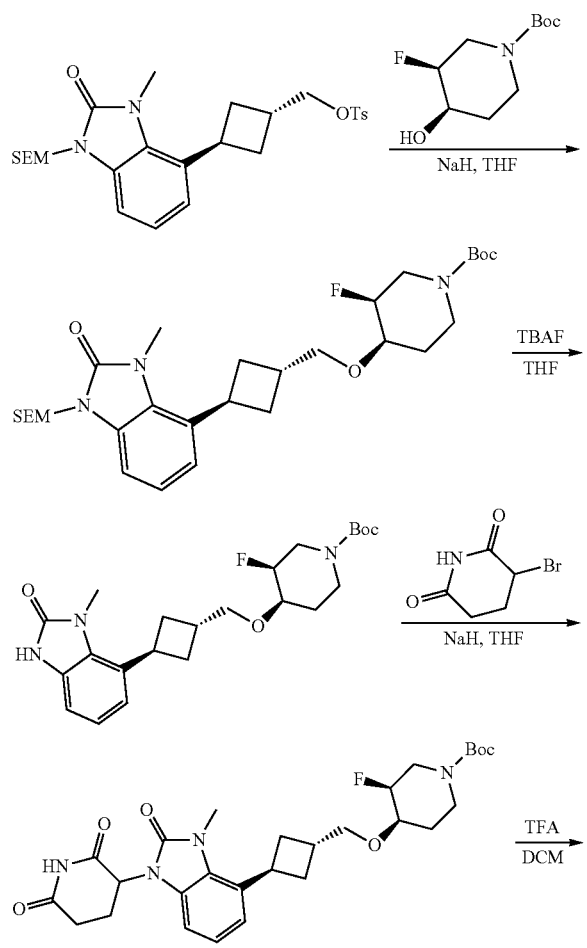

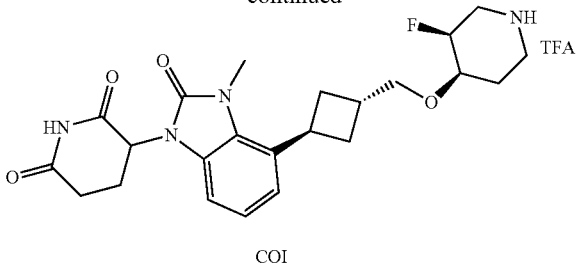

COI

Step 1—Tert-butyl (3S,4R)-3-fluoro-4-[[3-[3-methyl-2-oxo-1-(2-trimethylsilylethoxymethyl) benzimidazol-4-yl] cyclobutyl]methoxy]piperidine-1-carboxylate. A mixture of tert-butyl (3S,4R)-3-fluoro-4-hydroxy-piperidine-1-carboxylate (342 mg, 1.56 mmol, CAS #1174020-40-6) in DMF (6 mL) was added NaH (71.9 mg, 1.80 mmol, 60% dispersion in mineral oil), then the mixture was stirred at 0° C. for 13 hrs. Next, [3-[3-methyl-2-oxo-1-(2-trimethylsilylethoxymethyl)benzimidazol-4-yl]cyclobutyl]methyl4-methylbenzenesulfonate (620 mg, 1.20 mmol, synthesized via Steps 1-3 of Intermediate COA) was added and the mixture was stirred at 80° C. for 3 hrs. On completion, the reaction mixture was quenched with H$_2$O (1 mL) and extracted with ethyl acetate (5 mL×3). The combined organic phase was dried over anhydrous sodium sulfate, filtered and concentrated to give a residue. The residue was purified by column chromatography (SiO$_2$, PE/EA=10:1 to 3:1) to give the compound (480 mg, 63% yield) as a yellow oil. $^1$H NMR (400 MHz, DMSO-d$_6$) δ 7.21-7.16 (m, 1H), 7.08 (d, J=4.4 Hz, 2H), 5.22 (s, 2H), 5.06 (d, J=5.2 Hz, 1H), 4.66-4.49 (m, 2H), 4.09-4.00 (m, 1H), 3.93 (dddd, J=1.6, 4.8, 9.2, 14.0 Hz, 2H), 3.72-3.61 (m, 4H), 3.51 (s, 3H), 2.35-2.26 (m, 2H), 2.21-2.12 (m, 2H), 1.77-1.69 (m, 1H), 1.59-1.53 (m, 3H), 1.38 (s, 9H), 0.83 (t, J=8.0 Hz, 2H), 0.07 (s, 9H); LC-MS (ESI$^+$) m/z 390.0 (M−56+H)$^+$.

Step 2—Tert-butyl (3S,4R)-3-fluoro-4-[[3-(3-methyl-2-oxo-1H-benzimidazol-4-yl)cyclobutyl] methoxy]piperidine-1-carboxylate. To a solution of tert-butyl (3S,4R)-3-fluoro-4-[[3-[3-methyl-2-oxo-1-(2-trimethylsilylethoxymethyl) benzimidazol-4-yl]cyclobutyl] methoxy]piperidine-1-carboxylate (480 mg, 851 μmol) in dioxane (1 mL) was added TBAF (1 M, 8.51 mL). The mixture was stirred at 80° C. for 12 hrs. On completion, the reaction mixture was concentrated in vacuo. The mixture was diluted with water (5 mL) at 0° C. and extracted with EA (15 mL×3). The combined organic phase was dried over anhydrous sodium sulfate, filtered and concentrated to give a residue. The residue was purified by column chromatography (SiO$_2$, PE/EA=8:1 to 1:1) to give the compound (160 mg, 39% yield) as a white solid. $^1$H NMR (400 MHz, DMSO-d$_6$) δ 10.83 (s, 1H), 7.08 (d, J=8.0 Hz, 1H), 6.97 (t, J=7.6 Hz, 1H), 6.83 (dd, J=0.8, 7.6 Hz, 1H), 4.95-4.76 (m, 1H), 4.21-4.10 (m, 1H), 4.08-3.98 (m, 1H), 3.81 (td, J=2.4, 4.8 Hz, 1H), 3.72-3.57 (m, 3H), 3.57-3.51 (m, 1H), 3.45 (s, 3H), 3.21-3.02 (m, 1H), 3.01-2.82 (m, 1H), 2.36-2.24 (m, 2H), 2.19-2.09 (m, 2H), 1.77-1.68 (m, 1H), 1.66-1.57 (m, 1H), 1.39 (s, 9H); LC-MS (ESI$^+$) m/z 378.1 (M−56+H)$^+$.

Step 3—Tert-butyl (3S,4R)-4-[[3-[1-(2,6-dioxo-3-piperidyl)-3-methyl-2-oxo-benzimidazol-4-yl] cyclobutyl] methoxy]-3-fluoro-piperidine-1-carboxylate. A mixture of 3-bromopiperidine-2,6-dione (199 mg, 1.04 mmol, CAS #62595-74-8) in DMF (2 mL) was added NaH (41.5 mg, 1.04 mmol, 60% dispersion in mineral oil), then the mixture was stirred at 0° C. for 1 hr. Next, tert-butyl (3S,4R)-3- fluoro-4-[[3-(3-methyl-2-oxo-1H-benzimidazol-4-yl)cy-clobutyl]methoxy]piperidine-1-carboxylate (150 mg, 346 μmol) was added and stirred at 60° C. for 3 hrs. On completion, the reaction mixture was added FA at 25° C. until the pH stabilized at 5-6. Then the reaction mixture was diluted with EA (5 mL), and extracted with ethyl acetate (10 mL×3). The combined organic phase was dried over anhydrous sodium sulfate, filtered and concentrated to give a residue. The residue was purified by prep-HPLC (Phenomenex luna C18 150*25 mm*10 um; mobile phase: [water (FA)-ACN]; gradient: 38%-68% B) to give the compound (16.0 mg, 7% yield) as a yellow solid. LC-MS (ESI$^+$) m/z 489.2 (M−56+H)$^+$.

Step 4—3-[4-[3-[[(3S,4R)-3-Fluoro-4-piperidyl]oxymethyl]cyclobutyl]-3-methyl-2-oxo-benzimidazol-1-yl]piperidine-2,6-dione. To a solution of tert-butyl (3S,4R)-4-[[3-[1-(2,6-dioxo-3-piperidyl)-3-methyl-2-oxo-benzimidazol-4-yl] cyclobutyl]methoxy]-3-fluoro-piperidine-1-carboxylate (16.0 mg, 29.3 μmol) in DCM (0.5 mL) was added TFA (153 mg, 1.35 mmol). The mixture was then stirred at 25° C. for 1 hr. On completion, the reaction mixture was concentrated in vacuo to give the compound (16.0 mg, 97% yield, TFA) as a yellow oil. LC-MS (ESI$^+$) m/z 445.2 (M+H)$^+$.

3-[4-[4-[1-[[4-[4-Amino-3-(difluoromethyl)pyrazol-1-yl]cyclohexyl]methyl]-3,3-difluoro-4-piperidyl] piperazin-1-yl]-3-methyl-2-oxo-benzimidazol-1-yl] piperidine-2,6-dione (Intermediate COJ)

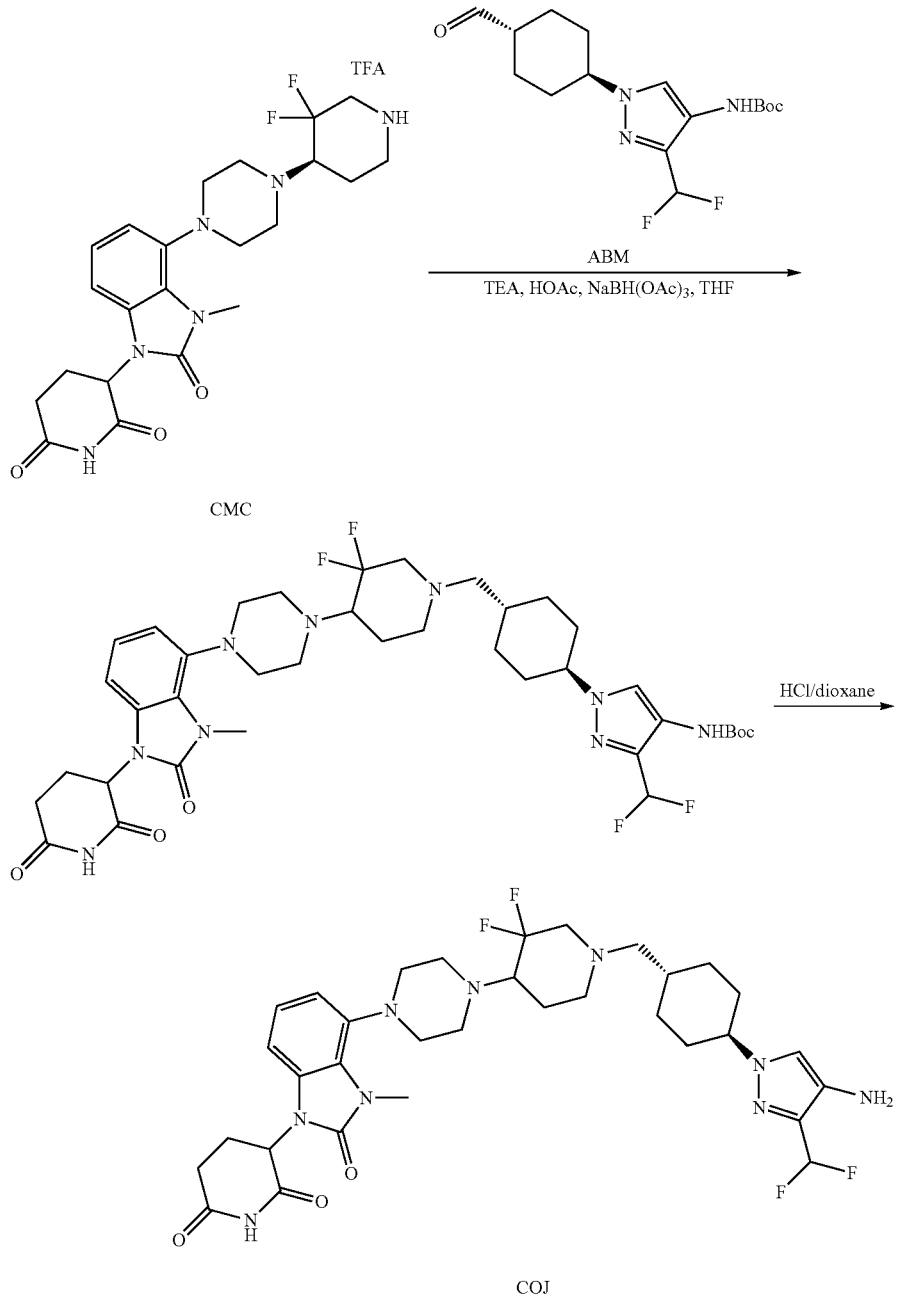

Step 1—Tert-butyl N-[3-(difluoromethyl)-1-[4-[[4-[4-[1-(2,6-dioxo-3-piperidyl)-3-methyl-2-oxo-benzimidazol-4-yl]piperazin-1-yl]-3,3-difluoro-1-piperidyl]methyl]cyclohexyl]pyrazol-4-yl]carbamate. To a mixture of 3-[4-[4-(3,3-difluoro-4-piperidyl)piperazin-1-yl]-3-methyl-2-oxo-benzimidazol-1-yl] piperidine-2,6-dione (600 mg, 1.04 mmol, TFA, Intermediate CMC) in DMF (2 mL) was added TEA (210 mg, 2.08 mmol) at 25° C. until the pH stabilized at 8. The mixture was then stirred at 25° C. for 0.25 hr, then HOAc (125 mg, 2.08 mmol) was added at 25° C. until pH stabilized at 5-6. The mixture was then cooled to −15° C. Subsequently, tert-butyl N-[3-(difluoromethyl)-1-(4-formyl-cyclohexyl)pyrazol-4-yl]carbamate (321 mg, 936 µmol, Intermediate ABM) in DMF (6 mL) was added and the mixture was stirred for 0.5 hr. Finally, NaBH(OAc)$_3$ (441 mg, 2.08 mmol) was added in one portion and the resulting reaction mixture was stirred at −15° C. for 2 hrs. On completion, the mixture was filtered and concentrated to give a residue. The residue was purified with reversed phase flash (0.1% FA condition) to give the title compound (360 mg, 39% yield) as white solid. $^1$H NMR (400 MHz, DMSO-d$_6$) δ 11.08 (s, 1H), 9.01-8.76 (m, 1H), 7.87 (s, 1H), 7.04-6.85 (m, 4H), 5.35 (dd, J=5.6, 12.4 Hz, 1H), 4.19-4.06 (m, 2H), 3.63 (s, 3H), 2.99-2.84 (m, 10H), 2.68-2.58 (m, 2H), 2.37-2.01 (m, 8H), 1.91-1.62 (m, 9H), 1.45 (s, 9H); LC-MS (ESI$^+$) m/z 790.3 (M+H)$^+$.

Step 2—3-[4-[4-[1-[[4-[4-Amino-3-(difluoromethyl)pyrazol-1-yl]cyclohexyl]methyl]-3,3-difluoro-4-piperidyl]piperazin-1-yl]-3-methyl-2-oxo-benzimidazol-1-yl]piperidine-2,6-dione. To a solution of tert-butyl N-[3-(difluoromethyl)-1-[4-[[4-[4-[1-(2,6-dioxo-3-piperidyl)-3-methyl-2-oxo-benzimidazol-4-yl]piperazin-1-yl]-3,3-difluoro-1-piperidyl]methyl]cyclohexyl]pyrazol-4-yl]carbamate (70.0 mg, 88.6 µmol) in DCM (1 mL) was added HCl/dioxane (2 mL). The mixture was then stirred at 25° C. for 0.5 hr. On completion, the mixture was filtered and concentrated to give the title compound (64.0 mg, 99% yield, HCl) as a white solid. LC-MS (ESI$^+$) m/z 690.2 (M+H)$^+$.

3-(5-Bromo-4-fluoro-3-methyl-2-oxo-benzimidazol-1-yl)-1-[(4-methoxyphenyl)methyl] piperidine-2,6-dione (Intermediate COK)

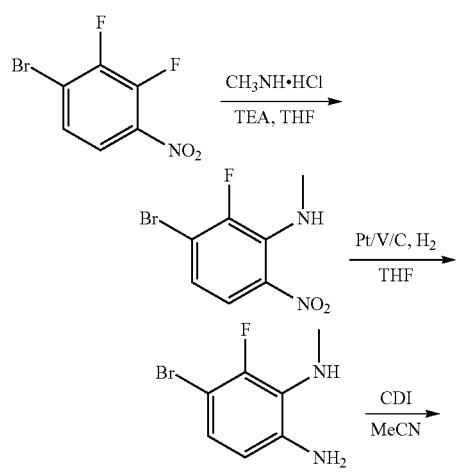

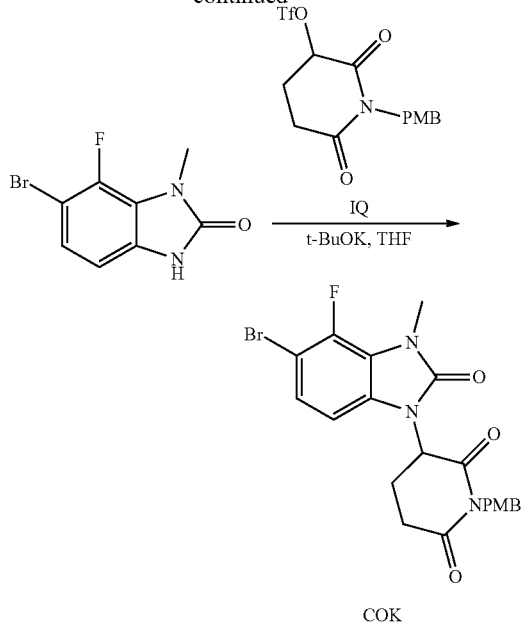

Step 1—3-Bromo-2-fluoro-N-methyl-6-nitroaniline. To a solution of methanamine hydrochloride (7.09 g, 105 mmol) in THF (150 mL) was added TEA (12.7 g, 126 mmol, 17.5 mL) at 0° C. and the mixture was stirred for 10 mins. Next, 1-bromo-2,3-difluoro-4-nitrobenzene (5 g, 21.01 mmol, CAS #1003708-24-4) was added and the reaction was stirred for 4 hrs at 25° C. On completion, the reaction mixture was quenched with H$_2$O (50 mL) under stirring. The residue was diluted with water (500 mL) and extracted with EA (50 mL×3). The combined organic layer was dried over Na$_2$SO$_4$, filtered and concentrated in vacuo to give the title compound (5 g, 95% yield) as yellow solid. LC-MS (ESI$^+$) m/z 249.1 (M+H)$^+$.

Step 2—5-Bromo-6-fluoro-N1-methylbenzene-1,2-diamine. To 3-bromo-2-fluoro-N-methyl-6-nitro-aniline (200 mg, 803 umol) in THF (10 mL) was added Pt/V/C (41.93 mg, 160 umol) under N$_2$ atmosphere. The suspension was degassed and purged with H$_2$ three times. The mixture was stirred under H$_2$ (15 Psi) at 25° C. for 0.5 hr. On completion, the reaction mixture was filtered and concentrated in vacuo to give the title compound (170 mg, 97% yield) as a black brown oil. LC-MS (ESI$^+$) m/z 218.8 (M+H)$^+$.

Step 3—6-Bromo-7-fluoro-1-methyl-1,3-dihydro-2H-benzo[d]imidazol-2-one. To a solution of 4-bromo-3-fluoro-N2-methyl-benzene-1,2-diamine (170 mg, 776 umol) in MeCN (10 mL) was added CDI (188 mg, 1.16 mmol) at 25° C. Then the reaction mixture was stirred at 85° C. for 12 hrs. On completion, the reaction mixture was concentrated in vacuo then poured into ice water (3 mL) to give the title compound (160 mg, 39% yield) as brown solid. LC-MS (ESI$^+$) m/z 249.1 (M+H)$^+$.

Step 4—3-(5-Bromo-4-fluoro-3-methyl-2-oxo-2,3-dihydro-1H-benzo[d]imidazol-1-yl)-1-(4-methoxybenzyl)piperidine-2,6-dione. To a solution of 5-bromo-4-fluoro-3-methyl-1H-benzimidazol-2-one (160 mg, 652 umol) in THF (15 mL) was added t-BuOK (109 mg, 979 umol). The mixture was stirred at −10° C. for 30 mins. Then a solution of [1-[(4-methoxyphenyl) methyl]-2,6-dioxo-3-piperidyl] trifluoromethanesulfonate (298 mg, 783 umol, Intermediate IQ) in THF (15 mL) was added dropwise to the mixture, and the reaction mixture was stirred at −10° C. for 30 mins. On completion, the reaction mixture was quenched with H₂O (0.2 mL) under stirring, then the reaction mixture was diluted with H₂O (10 mL), and extracted with DCM (10×3 mL). The combined organic layers was washed with brine (2×10 mL), dried over Na$_2$SO$_4$, filtered and concentrated in vacuo to give the title compound (200 mg, 64% yield) as a yellow solid. $^1$H NMR (400 MHz, DMSO-d$_6$) δ 7.30 (dd, J=6.4, 8.4 Hz, 1H), 7.21 (d, J=8.4 Hz, 2H), 6.93 (br d, J=8.1 Hz, 1H), 6.86 (d, J=8.8 Hz, 2H), 5.57 (dd, J=5.6, 13.2 Hz, 1H), 4.87-4.70 (m, 2H), 3.73 (s, 3H), 3.50 (d, J=1.8 Hz, 3H), 3.08-3.01 (m, 1H), 2.85 (br d, J=2.4 Hz, 1H), 2.81-2.65 (m, 2H); LC-MS (ESI$^+$) m/z 476.1 (M+H)$^+$.

3-[4-Fluoro-3-methyl-2-oxo-5-[3-(piperazin-1-ylmethyl)azetidin-1-yl]benzimidazol-1-yl]piperidine-2,6-dione (Intermediate COL)

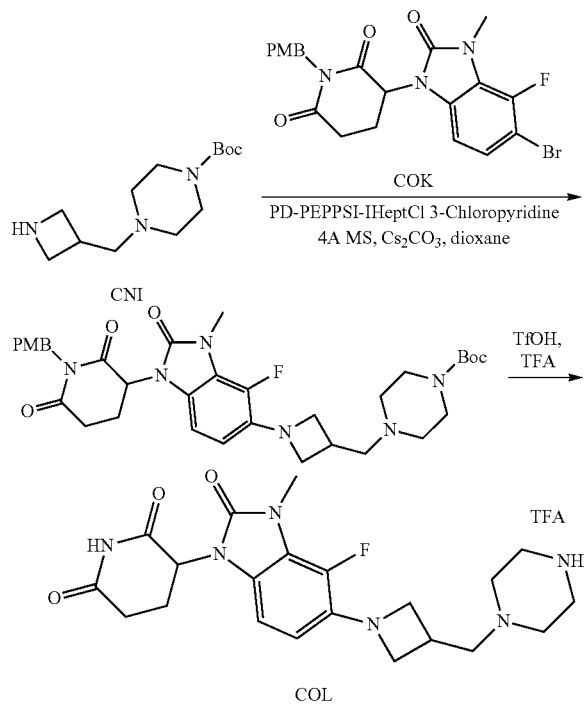

Step 1—Tert-butyl 4-[[1-[4-fluoro-1-[1-[(4-methoxyphenyl)methyl]-2,6-dioxo-3-piperidyl]-3-methyl-2-oxo-benzimidazol-5-yl]azetidin-3-yl]methyl]piperazine-1-carboxylate. A mixture of tert-butyl 4-(azetidin-3-ylmethyl)piperazine-1-carboxylate (409 mg, 1.60 mmol, Intermediate CNI), 3-(5-bromo-4-fluoro-3-methyl-2-oxo-benzimidazol-1-yl)-1-[(4-methoxyphenyl)methyl] piperidine-2,6-dione (509 mg, 1.07 mmol, Intermediate COK), Cs$_2$CO$_3$ (1.04 g, 3.20 mmol) and 4 Å molecular sieves (200 mg) in dioxane (10 mL) was added 1,3-bis[2,6-bis(1-propylbutyl)phenyl]-4,5-dichloro-2H-imidazol-1-ium-2-ide 3-chloropyridine dichloropalladium (104 mg, 107 μmol), then the mixture was degassed and purged with N$_2$ three times. Then the mixture was stirred at 100° C. for 48 hrs under N$_2$ atmosphere. On completion, the reaction was cooled to rt, filtered to give a filtrate, and concentrated in vacuo to give a residue. The residue was diluted with water (50 mL), and extracted with EA (50 mL×3). The organic layers were combined, washed with brine (50 mL), dried over anhydrous Na$_2$SO$_4$, filtered and concentrated in vacuo to give the crude product.

The crude product was purified by reverse phase (0.1% FA condition) to give the title compound (180 mg, 26% yield, FA) as yellow solid. $^1$H NMR (400 MHz, DMSO-d$_6$) δ 7.19 (d, J=8.8 Hz, 2H), 6.85 (d, J=8.8 Hz, 2H), 6.66 (d, J=8.8 Hz, 1H), 6.15 (t, J=8.4 Hz, 1H), 5.44 (dd, J=5.2, 13.2 Hz, 1H), 4.84-4.71 (m, 2H), 3.97 (t, J=6.8 Hz, 2H), 3.72 (s, 3H), 3.50 (t, J=6.0 Hz, 2H), 3.45-3.42 (m, 3H), 3.31-3.26 (m, 4H), 3.09-2.99 (m, 1H), 2.93-2.85 (m, 1H), 2.83-2.76 (m, 1H), 2.74-2.65 (m, 1H), 2.57 (d, J=7.2 Hz, 2H), 2.33-2.29 (m, 4H), 2.05-1.99 (m, 1H), 1.39 (s, 9H); LC-MS (ESI+) m/z 651.1 (M+H)$^+$.

Step 2—3-[4-Fluoro-3-methyl-2-oxo-5-[3-(piperazin-1-ylmethyl)azetidin-1-yl]benzimidazol-1-yl]piperidine-2,6-dione. A mixture of tert-butyl 4-[[1-[4-fluoro-1-[1-[(4-methoxyphenyl)methyl]-2,6-dioxo-3-piperidyl]-3-methyl-2-oxo-benzimidazol-5-yl]azetidin-3-yl]methyl]piperazine-1-carboxylate (150 mg, 231 μmol, FA) in TFA (2 mL) was added TfOH (1 mL), then the mixture was stirred at 80° C. for 1 hr. On completion, the reaction was concentrated in vacuo to give the title compound (125 mg, 99% yield, TFA) as black brown liquid. LC-MS (ESI+) m/z 431.0 (M+H)$^+$.

3-[4-Fluoro-5-[3-[[(3S,4R)-3-fluoro-4-piperidyl]oxymethyl]azetidin-1-yl]-3-methyl-2-oxo-benzimidazol-1-yl]piperidine-2,6-dione (Intermediate COM)

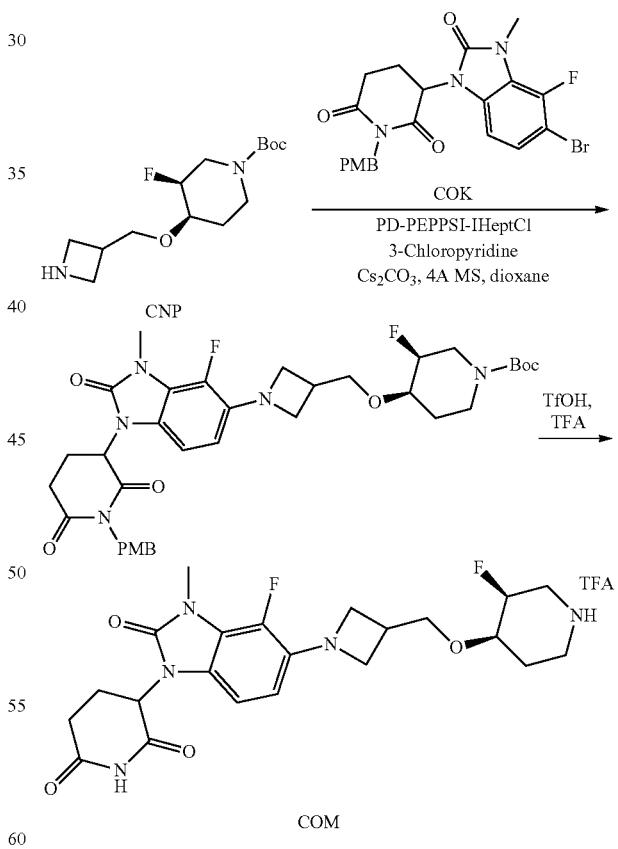

Step 1—Tert-butyl (3S,4R)-3-fluoro-4-[[1-[4-fluoro-1-[1-[(4-methoxyphenyl)methyl]-2,6-dioxo-3-piperidyl]-3-methyl-2-oxo-benzimidazol-5-yl]azetidin-3-yl]methoxy]piperidine-1-carboxylate. A mixture of tert-butyl (3S,4R)-4-(azetidin-3-ylmethoxy)-3-fluoro-piperidine-1-carboxylate (500 mg, 1.73 mmol, Intermediate CNP), 3-(5-bromo-4- fluoro-3-methyl-2-oxo-benzimidazol-1-yl)-1-[(4-methoxyphenyl)methyl]piperidine-2,6-dione (743 mg, 1.56 mmol, Intermediate COK), 1,3-bis[2,6-bis(1-propylbutyl)phenyl]-4,5-dichloro-2H-imidazol-1-ium-2-ide 3-chloropyridine dichloropalladium (168 mg, 173 μmol), $Cs_2CO_3$ (1.69 g, 5.20 mmol) and 4 Å molecular sieves (500 mg) in dioxane (10 mL) was degassed and purged with $N_2$ three times. Then the mixture was stirred at 100° C. for 16 hrs under $N_2$ atmosphere. On completion, the reaction mixture was filtered and concentrated in vacuo to give a residue. The residue was purified by column chromatography ($SiO_2$, PE:EA=5:1 to 0:1) to give the title compound (370 mg, 31% yield) as a brown solid. $^1$H NMR (400 MHz, $CDCl_3$-d) δ 7.36 (d, J=8.4 Hz, 2H), 6.83 (d, J=8.8 Hz, 2H), 6.14-6.00 (m, 2H), 5.13 (dd, J=5.2, 13.2 Hz, 1H), 5.00-4.92 (m, 2H), 4.75-4.60 (m, 1H), 4.00 (t, J=7.6 Hz, 2H), 3.96-3.89 (m, 1H), 3.85-3.74 (m, 6H), 3.71-3.65 (m, 3H), 3.58 (d, J=1.6 Hz, 3H), 3.46-3.33 (m, 1H), 3.24-3.14 (m, 1H), 3.04-2.92 (m, 2H), 2.86-2.76 (m, 1H), 2.62-2.50 (m, 1H), 2.19-2.11 (m, 1H), 1.95-1.86 (m, 1H), 1.74-1.68 (m, 1H), 1.47 (s, 9H). LC-MS (ESI$^+$) m/z 684.3 (M+H)$^+$.

Step 2—3-[4-Fluoro-5-[3-[[(3S,4R)-3-fluoro-4-piperidyl]oxymethyl]azetidin-1-yl]-3-methyl-2-oxo-benzimidazol-1-yl]piperidine-2,6-dione. A solution of tert-butyl (3S,4R)-3-fluoro-4-[[1-[4-fluoro-1-[1-[(4-methoxyphenyl)methyl]-2,6-dioxo-3-piperidyl]-3-methyl-2-oxo-benzimidazol-5-yl]azetidin-3-yl]methoxy]piperidine-1-carboxylate (370 mg, 541 μmol) in TfOH (0.5 mL) and TFA (2.5 mL) was stirred at 70° C. for 2 hrs. On completion, the reaction mixture was concentrated in vacuo to give the title compound (300 mg, 86% yield) as a brown oil. LC-MS (ESI$^+$) m/z 464.1 (M+H)$^+$.

Tert-butyl 3,3-difluoro-4-(3-methyl-2-oxo-1H-benzimidazol-4-yl)piperidine-1-carboxylate (Intermediate CON)

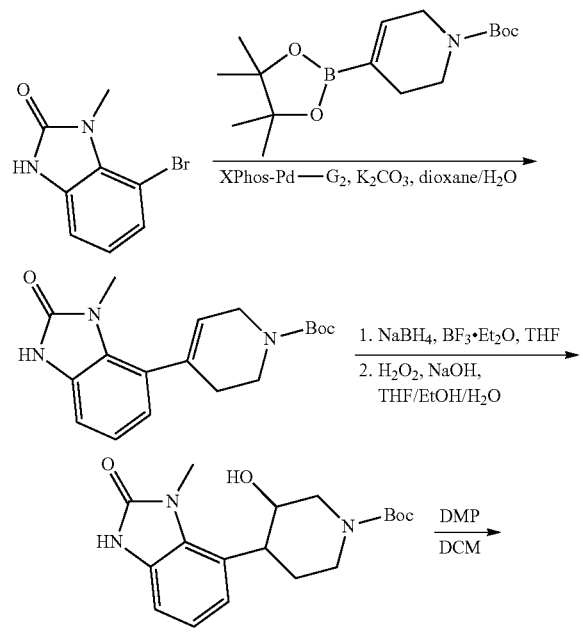

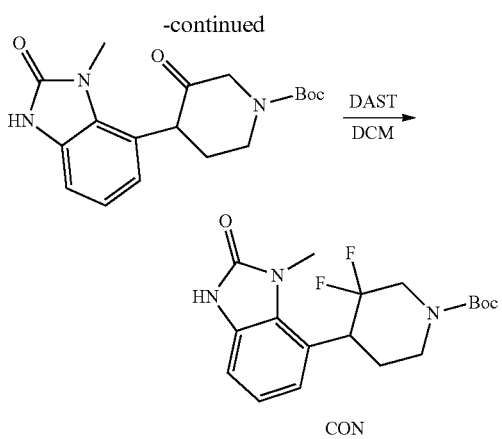

Step 1—Tert-butyl 4-(3-methyl-2-oxo-1H-benzimidazol-4-yl)-3,6-dihydro-2H-pyridine-1-carboxylate. A mixture of 4-bromo-3-methyl-1H-benzimidazol-2-one (500 mg, 2.20 mmol, synthesized via Steps 1-3 of Intermediate HP), tert-butyl 4-(4,4,5,5-tetramethyl-1,3,2-dioxaborolan-2-yl)-3,6-dihydro-2H-pyridine-1-carboxylate (817 mg, 2.64 mmol, CAS #286961-14-6), XPHOS-PD-$G_2$ (173 mg, 220 umol), and $K_3PO_4$ (1.40 g, 6.61 mmol) in dioxane (5 mL) and $H_2O$ (1 mL) was degassed and purged with $N_2$ three times. Then the mixture was stirred at 80° C. for 3 hrs under $N_2$ atmosphere. On completion, the reaction mixture was filtered and concentrated under reduced pressure to give a residue. The residue was purified by column chromatography ($SiO_2$, Petroleum ether/Ethyl acetate=2/1 to 1/1) to give the title compound (700 mg, 96% yield) as a white solid. $^1$H NMR (400 MHz, DMSO-$d_6$) δ 10.92 (s, 1H), 7.00-6.83 (m, 2H), 6.79-6.68 (m, J=1.2, 7.6 Hz, 1H), 5.66 (s, 1H), 3.98 (s, 2H), 3.56 (t, J=5.2 Hz, 2H), 3.24 (s, 3H), 2.37 (s, 2H), 1.43 (s, 9H); LC-MS (ESI$^+$) m/z 329.8 (M+H)$^+$.

Step 2—Tert-butyl 3-hydroxy-4-(3-methyl-2-oxo-1H-benzimidazol-4-yl)piperidine-1-carboxylate. To a solution of $BF_3·Et_2O$ (646 mg, 4.55 mmol) in THF (5 mL) was added $NaBH_4$ (172 mg, 4.55 mmol) at 0° C., then the mixture was allowed to warmed up to 25° C. over 1 hr. Next, the mixture was re-cooled to 0° C. and a solution of tert-butyl 4-(3-methyl-2-oxo-1H-benzimidazol-4-yl)-3,6-dihydro-2H-pyridine-1-carboxylate (500 mg, 1.52 mmol) in THF (5 mL) was added. Then the mixture was allowed to warmed up to 25° C. and stirred for 2 hrs. The reaction mixture was cooled again to 0° C., then, $H_2O$ (1.5 mL), NaOH (10 M, 1.52 mL) and $H_2O_2$ (1.72 g, 15.1 mmol, 30% solution) were sequentially added. The resulting mixture was stirred at 65° C. for 12 hrs. On completion, the reaction mixture was quenched by $Na_2SO_3$ (20 mL) and $NH_4Cl$ (20 mL) at 0° C., and then extracted with EA (20 mL×3). The combined organic phase was washed with saturated sodium chloride solution (20 mL×3), dried over anhydrous sodium sulfate, filtered and concentrated to give a residue. The residue was purified by column chromatography ($SiO_2$, Petroleum ether/Ethyl acetate=1/1 to 0/1) to give the title compound (380 mg, 72% yield) as a white solid. $^1$H NMR (400 MHz, DMSO-$d_6$) δ 10.82 (s, 1H), 6.94 (d, J=4.4 Hz, 2H), 6.84-6.80 (m, 1H), 4.98 (d, J=5.2 Hz, 1H), 4.20-4.09 (m, 1H), 4.00-3.90 (m, 1H), 3.55 (s, 3H), 3.48 (td, J=4.8, 10.0 Hz, 1H), 3.28-3.18 (m, 2H), 2.88-2.74 (m, 1H), 1.96-1.85 (m, 1H), 1.69-1.59 (m, 1H), 1.43 (s, 9H); LC-MS (ESI$^+$) m/z 369.8 (M+23)$^+$.

Step 3—Tert-butyl 4-(3-methyl-2-oxo-1H-benzimidazol-4-yl)-3-oxo-piperidine-1-carboxylate. To a solution of tert-butyl 3-hydroxy-4-(3-methyl-2-oxo-1H-benzimidazol-4-yl)

piperidine-1-carboxylate (330 mg, 949 umol) in DCM (6 mL) was added DMP (523 mg, 1.23 mmol). The mixture was then stirred at 25° C. for 1 hr. On completion, the reaction mixture was quenched with $Na_2S_2O_3$ (10 mL) and $NaHCO_3$ (10 mL) at 2 5° C., and then extracted with DCM (10 mL×2). The combined organic phase was washed with saturated sodium chloride solution (10 mL×2), dried over anhydrous sodium sulfate, filtered and concentrated to give the title compound (320 mg, 97% yield) as a purplish red solid. LC-MS (ESI$^+$) m/z 367.7 (M+23)$^+$.

Step 4—Tert-butyl 3,3-difluoro-4-(3-methyl-2-oxo-1H-benzimidazol-4-yl)piperidine-1-carboxylate. To a solution of tert-butyl 4-(3-methyl-2-oxo-1H-benzimidazol-4-yl)-3-oxo-piperidine-1-carboxylate (270 mg, 781 umol) in DCM (5 mL) was added DAST (504 mg, 3.13 mmol) at 0° C. The mixture was then stirred at 25° C. for 2 hrs. On completion, the reaction mixture was quenched with $NaHCO_3$ (10 mL) at 25° C., and then extracted with DCM (5 mL×2). The combined organic phase was washed with saturated sodium chloride solution (5 mL×2), dried over anhydrous sodium sulfate, filtered and concentrated to give a residue. The residue was purified by column chromatography ($SiO_2$, Petroleum ether/Ethyl acetate=1/1 to 1/2) to give the title compound (120 mg, 41% yield) as a yellow solid. $^1$H NMR (400 MHz, DMSO-$d_6$) δ 10.97 (s, 1H), 7.04-6.88 (m, 3H), 4.35-4.17 (m, 1H), 4.16-4.06 (m, 1H), 4.05-3.93 (m, 1H), 3.59-3.45 (m, 4H), 3.16-3.04 (m, 1H), 2.19-2.04 (m, 1H), 1.88 (d, J=13.2 Hz, 1H), 1.43 (s, 9H); LC-MS (ESI$^+$) m/z 367.8 (M+H)$^+$.

Tert-butyl 8-prop-2-ynyl-3,8-diazabicyclo[3.2.1]octane-3-carboxylate (Intermediate COO)

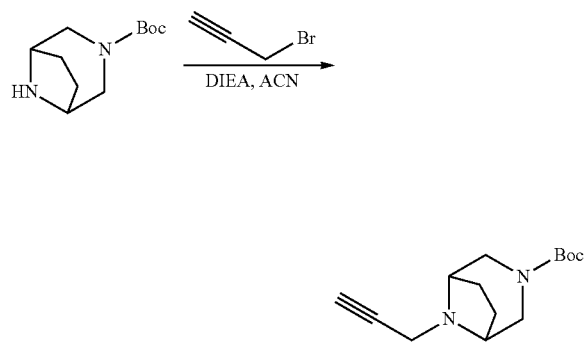

To a solution of tert-butyl 3,8-diazabicyclo[3.2.1]octane-3-carboxylate (500 mg, 2.36 mmol, CAS #201162-53-0) in ACN (8 mL) was added DIEA (608 mg, 4.71 mmol) and 3-bromoprop-1-yne (350 mg, 2.36 mmol, 80% solution, CAS #103-96-7). The mixture was then stirred at 25° C. for 3 hrs. On completion, the reaction mixture was diluted with $H_2O$ (20 mL) and extracted with EA (10 mL×2). The combined organic layers were washed with saturated sodium chloride solution (15 mL×2), dried over anhydrous sodium sulfate, filtered and concentrated to give a residue. The residue was purified by column chromatography ($SiO_2$, Petroleum ether/Ethyl acetate=5/1 to 3/1) to give the title compound (510 mg, 86% yield) as a yellow solid. $^1$H NMR (400 MHz, CDCl$_3$) δ 3.79 (d, J=12.0 Hz, 1H), 3.65 (d, J=12.0 Hz, 1H), 3.40-3.26 (m, 2H), 3.15 (d, J=2.4 Hz, 2H), 3.13-2.98 (m, 2H), 2.23 (t, J=2.4 Hz, 1H), 1.95-1.84 (m, 2H), 1.71-1.60 (m, 2H), 1.45 (s, 9H).

3-[4-[3-(3,8-Diazabicyclo[3.2.1]octan-8-yl)prop-1-ynyl]-3-methyl-2-oxo-benzimidazol-1-yl] piperidine-2,6-dione (Intermediate COP)

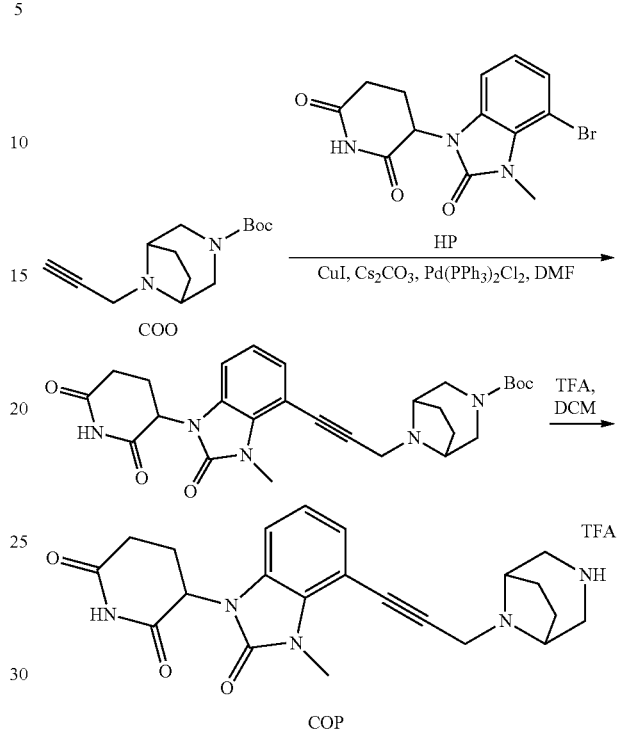

Step 1—Tert-butyl 8-[3-[1-(2,6-dioxo-3-piperidyl)-3-methyl-2-oxo-benzimidazol-4-yl]prop-2-ynyl]-3,8-diazabicyclo[3.2.1]octane-3-carboxylate. A mixture of tert-butyl 8-prop-2-ynyl-3,8-diazabicyclo[3.2.1]octane-3-carboxylate (166 mg, 665 umol, Intermediate COO), 3-(4-bromo-3-methyl-2-oxo-benzimidazol-1-yl)piperidine-2,6-dione (150 mg, 443 umol, Intermediate HP), CuI (4.22 mg, 22.1 umol), Pd(PPh$_3$)$_2$Cl$_2$ (15.5 mg, 22.1 umol), 4 Å molecular sieves (100 mg, 443 umol) and Cs$_2$CO$_3$ (433 mg, 1.33 mmol) in DMF (2 mL) was degassed and purged with N$_2$ three times. Then the mixture was stirred at 85° C. for 6 hrs under N$_2$ atmosphere. On completion, the reaction mixture was filtered, then diluted with H$_2$O (15 mL) and extracted with EA (10 mL×2). The combined organic layers were washed with saturated sodium chloride solution (15 mL×2), dried over anhydrous sodium sulfate, filtered and concentrated to give a residue. The residue was purified by prep-TLC (SiO$_2$, DCM:MeOH=10:1) to give the title compound (80.0 mg, 35% yield) as a brown solid. $^1$H NMR (400 MHz, DMSO-d$_6$) δ 11.12 (s, 1H), 7.18-7.08 (m, 2H), 7.04-6.99 (m, 1H), 5.44-5.35 (dd, J=5.6, 12.4 Hz, 1H), 3.67 (s, 1H), 3.65 (s, 3H), 3.60 (s, 1H), 3.57 (s, 1H), 3.42 (s, 2H), 3.34 (s, 1H), 3.02-2.95 (m, 1H), 2.94-2.83 (m, 2H), 2.77-2.68 (m, 1H), 2.66-2.59 (m, 1H), 2.08-1.98 (m, 1H), 1.94-1.86 (dd, J=4.0, 6.8 Hz, 2H), 1.48 (q, J=7.2 Hz, 2H), 1.39 (s, 9H); LC-MS (ESI$^+$) m/z 508.2 (M+H)$^+$.

Step 2—3-[4-[3-(3,8-Diazabicyclo[3.2.1]octan-8-yl)prop-1-ynyl]-3-methyl-2-oxo-benzimidazol-1-yl] piperidine-2,6-dione. To a solution of tert-butyl 8-[3-[1-(2,6-dioxo-3-piperidyl)-3-methyl-2-oxo-benzimidazol-4-yl] prop-2-ynyl]-3,8-diazabicyclo[3.2.1]octane-3-carboxylate (70.0 mg, 137 umol) in DCM (1 mL) was added TFA (157 mg, 1.38 mmol). The mixture was then stirred at 25° C. for 1 hr. On completion, the reaction mixture was concentrated under reduced pressure to give the title compound (70.0 mg, 97% yield, TFA) as a brown solid. LC-MS (ESI⁺) m/z 408.0 (M+H)⁺.

Tert-butyl 9-prop-2-ynyl-3-oxa-7,9-diazabicyclo [3.3.1]nonane-7-carboxylate (Intermediate COQ)

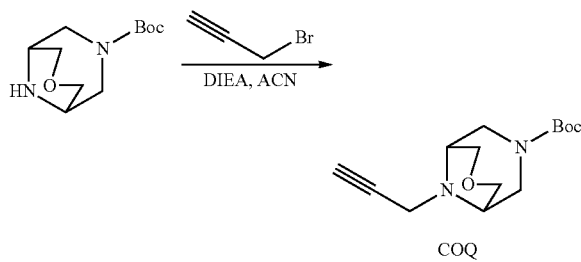

A mixture of tert-butyl 3-oxa-7,9-diazabicyclo[3.3.1] nonane-7-carboxylate (800 mg, 3.50 mmol, CAS #864448-41-9), 3-bromoprop-1-yne (573 mg, 3.85 mmol, 80% solution), and DIEA (1.36 g, 10.5 mmol) in ACN (10 mL) was stirred at 60° C. for 2 hrs. On completion, the mixture was diluted with H₂O (20 mL) and extracted with DCM (20 ml×3). The combined organic layer was dried over Na₂SO₄, filtered and the filtrate was concentrated in vacuo to give the title compound (800 mg, 85% yield) as a yellow oil. ¹H NMR (400 MHz, DMSO-d₆) δ 3.83 (d, J=13.2 Hz, 1H), 3.80-3.74 (m, 3H), 3.72-3.65 (m, 2H), 3.59 (d, J=2.4 Hz, 2H), 3.34 (s, 1H), 3.21-3.15 (m, 1H), 2.71 (d, J=12.0 Hz, 2H), 1.38 (s, 9H).

3-[3-Methyl-4-[3-(3-oxa-7,9-diazabicyclo[3.3.1] nonan-9-yl)prop-1-ynyl]-2-oxo-benzimidazol-1-yl] piperidine-2,6-dione (Intermediate COR)

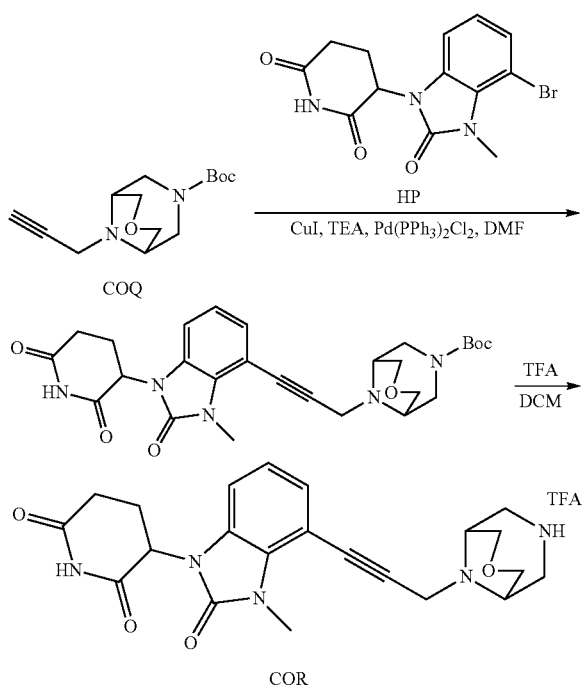

Step 1—Tert-butyl 9-[3-[1-(2,6-dioxo-3-piperidyl)-3-methyl-2-oxo-benzimidazol-4-yl]prop-2-ynyl]-3-oxa-7,9-diazabicyclo[3.3.1]nonane-7-carboxylate. A mixture of tert-butyl 9-prop-2-ynyl-3-oxa-7,9-diazabicyclo[3.3.1]nonane-7-carboxylate (481 mg, 1.81 mmol, Intermediate COQ), 3-(4-bromo-3-methyl-2-oxo-benzimidazol-1-yl)piperidine-2,6-dione (470 mg, 1.39 mmol, Intermediate HP), CuI (13.2 mg, 69.4 umol), Pd(PPh₃)₂Cl₂ (48.7 mg, 69.4 umol) and TEA (562 mg, 5.56 mmol) in DMF (2 mL) was degassed and purged with N₂ three times. Then the mixture was stirred at 85° C. for 16 hrs under N₂ atmosphere. On completion, the mixture was concentrated in vacuo to remove DMF, then the mixture was diluted with water (10 mL×3). The combined organic layers were washed with NaCl (5 mL), dried over Na₂SO₄, filtered and concentrated in vacuo to give a residue. The residue was purified by column chromatography (SiO₂, Petroleum ether/Ethyl acetate=0/1) to give the title compound (330 mg, 45% yield) as a brown solid. ¹H NMR (400 MHz, DMSO-d₆) δ 11.12 (s, 1H), 7.15 (d, J=7.6 Hz, 1H), 7.12-7.08 (m, 1H), 7.04-6.98 (m, 1H), 5.39 (dd, J=5.2, 12.8 Hz, 1H), 3.90-3.76 (m, 5H), 3.72 (dd, J=5.2, 10.8 Hz, 2H), 3.62 (s, 3H), 3.40 (d, J=13.2 Hz, 2H), 3.25 (d, J=13.2 Hz, 1H), 2.81 (d, J=12.0 Hz, 2H), 2.75-2.59 (m, 3H), 2.05-1.99 (m, 1H), 1.39 (s, 9H); LC-MS (ESI⁺) m/z 524.3 (M+H)⁺.

Step 2—3-[3-Methyl-4-[3-(3-oxa-7,9-diazabicyclo[3.3.1] nonan-9-yl)prop-1-ynyl]-2-oxo-benzimidazol-1-yl]piperidine-2,6-dione. A mixture of tert-butyl 9-[3-[1-(2,6-dioxo-3-piperidyl)-3-methyl-2-oxo-benzimidazol-4-yl]prop-2-ynyl]-3-oxa-7,9-diazabicyclo[3.3.1]nonane-7-carboxylate (100 mg, 190 umol) in DCM (1 mL) and TFA (0.2 mL) was stirred at 25° C. for 2 hrs. On completion, the mixture was concentrated in vacuo to give the title compound (102 mg, 100% yield, TFA) as brown oil. LC-MS (ESI⁺) m/z 424.1 (M+H)⁺.

Tert-butyl 3,3-difluoro-4-prop-2-ynyl-piperidine-1-carboxylate (Intermediate COS)

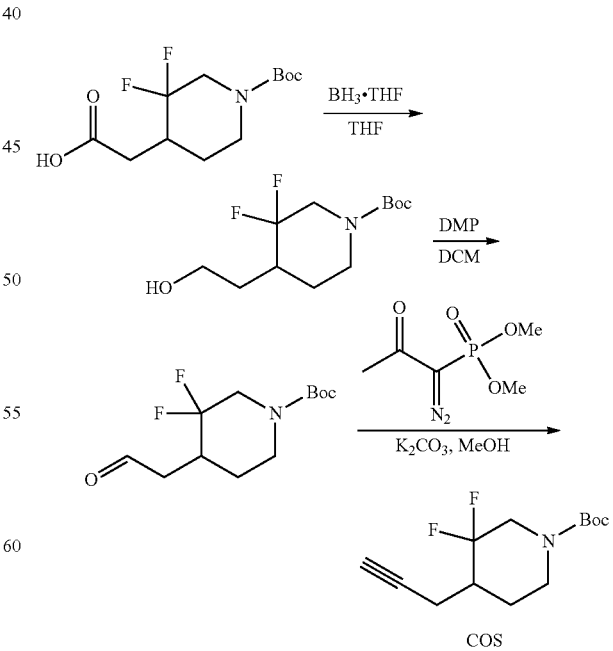

Step 1—Tert-butyl 3,3-difluoro-4-(2-hydroxyethyl)piperidine-1-carboxylate. To a solution of 2-(1-tert-butoxycarbonyl-3,3-difluoro-4-piperidyl)acetic acid (1.40 g, 5.01 mmol, CAS #1373503-54-8) in THF (3 mL) was added BH₃·THF (1 M, 15.0 mL) at 0° C. The mixture was then stirred at 25° C. for 12 hrs. On completion, the reaction mixture was quenched with MeOH (10 mL) at 0° C., and then diluted with H₂O (30 mL) and extracted with EA (20 mL×2). The combined organic layers were washed with saturated sodium chloride solution (20 mL×2), dried over anhydrous sodium sulfate, filtered and concentrated to give a residue. The residue was purified by column chromatography (SiO₂, Petroleum ether/Ethyl acetate=3/1 to 2/1) to give the title compound (1.03 g, 77% yield) as a colorless oil. ¹H NMR (400 MHz, DMSO-d₆) δ 4.53 (t, J=5.2 Hz, 1H), 4.13-3.98 (m, 1H), 3.88 (d, J=8.0 Hz, 1H), 3.52-3.40 (m, 2H), 3.29-3.03 (m, 1H), 2.97-2.74 (m, 1H), 2.17-2.00 (m, 1H), 1.88-1.75 (m, 2H), 1.39 (s, 9H), 1.35-1.21 (m, 2H).

Step 2—Tert-butyl 3,3-difluoro-4-(2-oxoethyl)piperidine-1-carboxylate. To a solution of tert-butyl 3,3-difluoro-4-(2-hydroxyethyl)piperidine-1-carboxylate (1.03 g, 3.88 mmol) in DCM (15 mL) was added DMP (1.98 g, 4.66 mmol). The mixture was then stirred at 25° C. for 2 hrs. On completion, the reaction mixture was quenched with Na₂S₂O₃ (15 mL) and NaHCO₃ (15 mL) at 25° C., and then extracted with DCM (10 mL×2). The combined organic phase was washed with saturated sodium chloride solution (10 mL×2), dried over anhydrous sodium sulfate, filtered and concentrated to give the title compound (900 mg, 88% yield) as a colorless oil. ¹H NMR (400 MHz, DMSO-d₆) δ 9.66 (s, 1H), 4.21-3.98 (m, 1H), 3.88 (s, 1H), 3.31-3.09 (m, 1H), 3.04-2.82 (m, 1H), 2.80-2.71 (m, J=1.2, 4.8, 17.6 Hz, 1H), 2.67-2.54 (m, 1H), 2.49-2.40 (m, 1H), 1.82-1.72 (m, 1H), 1.41-1.38 (m, 9H), 1.36-1.25 (m, 1H).

Step 3—Tert-butyl 3,3-difluoro-4-prop-2-ynyl-piperidine-1-carboxylate. To a solution of tert-butyl 3,3-difluoro-4-(2-oxoethyl)piperidine-1-carboxylate (900 mg, 3.42 mmol) in MeOH (10 mL) was added K₂CO₃ (944 mg, 6.84 mmol) and 1-diazo-1-dimethoxyphosphoryl-propan-2-one (722 mg, 3.76 mmol, CAS #90965-06-3) at 0° C. Then the mixture was stirred at 25° C. for 12 hrs. On completion, the reaction mixture was quenched by addition H₂O (5 mL) at 20° C., and then extracted with EA (5 mL×2). The combined organic layers were washed with saturated sodium chloride solution (5 mL×2), dried over anhydrous sodium sulfate, filtered and concentrated to give a residue. The residue was purified by column chromatography (SiO₂, Petroleum ether/Ethyl acetate=20/1 to 10/1) to give the title compound (630 mg, 71% yield) as a colorless oil. ¹H NMR (400 MHz, DMSO-d₆) δ 4.16-3.99 (m, 1H), 3.96-3.86 (m, 1H), 3.26-3.05 (m, 1H), 3.03-2.82 (m, 2H), 2.54 (d, J=2.4 Hz, 1H), 2.28-2.11 (m, 2H), 1.97-1.88 (m, 1H), 1.40-1.38 (m, 9H), 1.37-1.29 (m, 1H).

3-[4-[3-(3,3-Difluoro-4-piperidyl)prop-1-ynyl]-3-methyl-2-oxo-benzimidazol-1-yl]piperidine-2,6-dione (Intermediate COT)

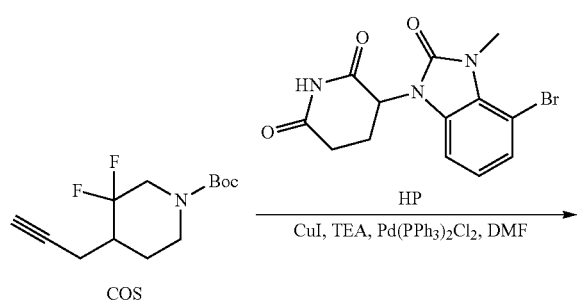

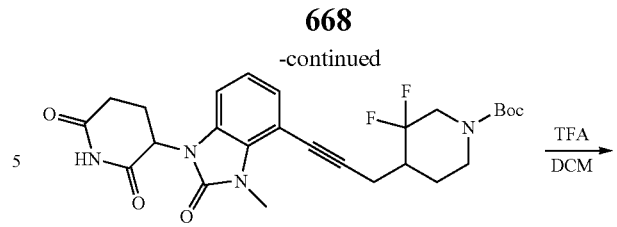

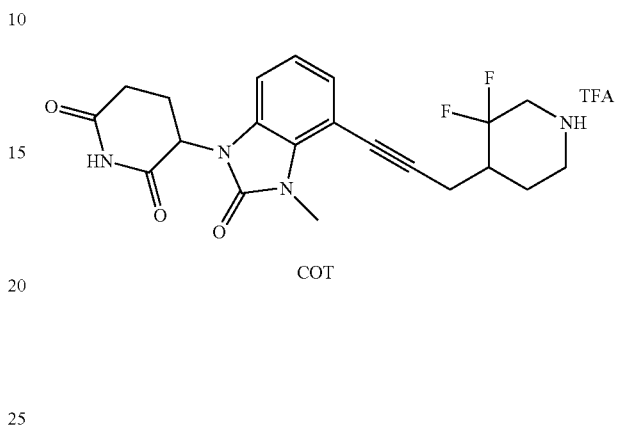

COT

Step 1—Tert-butyl 4-[3-[1-(2,6-dioxo-3-piperidyl)-3-methyl-2-oxo-benzimidazol-4-yl]prop-2-ynyl]-3,3-difluoro-piperidine-1-carboxylate. A mixture of tert-butyl 3,3-difluoro-4-prop-2-ynyl-piperidine-1-carboxylate (575 mg, 2.22 mmol, Intermediate COS), 3-(4-bromo-3-methyl-2-oxo-benzimidazol-1-yl)piperidine-2,6-dione (500 mg, 1.48 mmol, Intermediate HP), CuI (14.0 mg, 73.9 umol), Pd(PPh₃)₂Cl₂ (51.8 mg, 73.9 umol), 4 Å molecular sieves (200 mg) and Cs₂CO₃ (1.45 g, 4.44 mmol) in DMF (10 mL) was degassed and purged with N₂ three times, and then the mixture was stirred at 85° C. for 12 hrs under N₂ atmosphere. On completion, the reaction mixture was filtered and the filtrate was concentrated to give a residue. The residue was diluted with H₂O (30 mL) and extracted with EA (20 mL×2). The combined organic layers were washed with saturated sodium chloride solution (20 mL×2), dried over anhydrous sodium sulfate, filtered and concentrated to give a residue. The residue was purified by column chromatography (SiO₂, Petroleum ether/Ethyl acetate=2/1 to 2/3) to give the title compound (360 mg, 47% yield) as a brown solid. ¹H NMR (400 MHz, DMSO-d₆) δ 11.11 (s, 1H), 7.15-6.95 (m, 3H), 5.46-5.30 (m, J=5.2, 12.4 Hz, 1H), 4.22-4.03 (m, 1H), 4.01-3.88 (m, 1H), 3.62 (s, 3H), 3.28-3.07 (m, 1H), 2.99-2.81 (m, 3H), 2.76-2.67 (m, 1H), 2.67-2.59 (m, 1H), 2.56 (t, J=8.4 Hz, 1H), 2.44-2.30 (m, 1H), 2.06-1.96 (m, 2H), 1.46 (d, J=13.6 Hz, 1H), 1.40 (s, 9H); LC-MS (ESI⁺) m/z 460.9 (M+H−56)⁺.

Step 2—3-[4-[3-(3,3-Difluoro-4-piperidyl)prop-1-ynyl]-3-methyl-2-oxo-benzimidazol-1-yl]piperidine-2,6-dione. To a solution of tert-butyl 4-[3-[1-(2,6-dioxo-3-piperidyl)-3-methyl-2-oxo-benzimidazol-4-yl] prop-2-ynyl]-3,3-difluoro-piperidine-1-carboxylate (50.0 mg, 96.8 umol) in DCM (1 mL) was added TFA (220 mg, 1.94 mmol). The mixture was then stirred at 25° C. for 1 hr. On completion, the reaction mixture was concentrated under reduced pressure to give the title compound (50.0 mg, 97% yield, TFA) as a brown solid. LC-MS (ESI⁺) m/z 416.8 (M+H)⁺.

Ethyl 5-[(5R)-2-oxa-7-azaspiro[4.4]nonan-7-yl]pyrazolo[1,5-a]pyrimidine-3-carboxylate (Intermediate COU) and 5-[(5S)-2-oxa-7-azaspiro[4.4]nonan-7-yl]pyrazolo[1,5-a]pyrimidine-3-carboxylate (Intermediate COV)

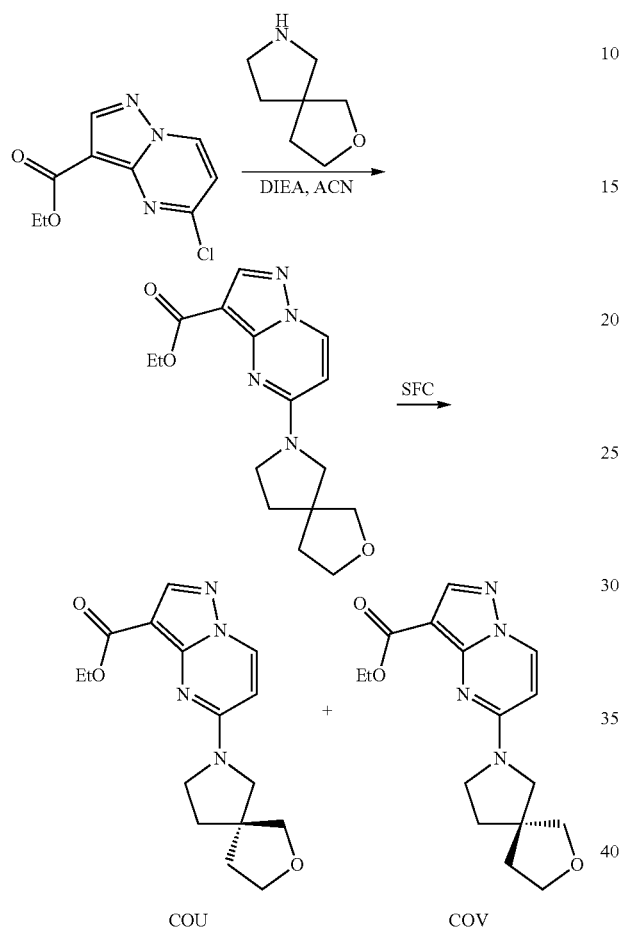

Step 1—Ethyl 5-(2-oxa-7-azaspiro[4.4]nonan-7-yl)pyrazolo[1,5-a]pyrimidine-3-carboxylate. To a solution of ethyl 5-chloropyrazolo[1,5-a]pyrimidine-3-carboxylate (200 mg, 886 mmol) and 2-oxa-7-azaspiro[4.4]nonane (225 mg, 1.77 mmol, CAS #175-97-3) MACN (2 mL) was added DIEA (344 mg, 2.66 mmol), then the mixture was stirred at 70° C. for 1 hr. On completion, the reaction mixture was concentrated in vacuo to remove ACN. The residue was diluted with water (10 mL) and extracted with EA (10 mL×3). The combined organic layer was dried over $Na_2SO_4$, filtered and concentrated in vacuo to give the title compound (260 mg, 92% yield) as a yellow solid. $^1$H NMR (400 MHz, DMSO-$d_6$) δ 8.67 (d, J=7.6 Hz, 1H), 8.17 (s, 1H), 6.50 (d, J=7.2 Hz, 1H), 4.02 (q, J=7.2 Hz, 2H), 3.82 (t, J=7.2 Hz, 2H), 3.67 (s, 1H), 3.60 (q, J=8.4 Hz, 4H), 3.50 (d, J=5.2 Hz, 2H), 2.02 (d, J=9.6 Hz, 1H), 1.97-1.85 (m, 3H), 1.21-1.15 (m, 3H). LC-MS (ESI$^+$) m/z 316.8 (M+H)$^+$.

Step 2—Ethyl 5-[(5R)-2-oxa-7-azaspiro[4.4]nonan-7-yl]pyrazolo[1,5-a]pyrimidine-3-carboxylate and 5-[(5S)-2-oxa-7-azaspiro[4.4]nonan-7-yl]pyrazolo[1,5-a]pyrimidine-3-carboxylate. Ethyl 5-(2-oxa-7-azaspiro[4.4] nonan-7-yl) pyrazolo[1,5-a]pyrimidine-3-carboxylate (550 mg, 1.74 mmol) was separated by SFC (column: DAICEL CHIRAL-PAK IG (250 mm*30 mm, 10 um); mobile phase: [0.1% $NH_3H_2O$ EtOH]) to give ethyl 5-[(5R)-2-oxa-7-azaspiro[4.4]nonan-7-yl]pyrazolo[1,5-a]pyrimidine-3-carboxylate ((200 mg, 36% yield, $t_R$=1.194) as a white solid And ethyl 5-[(5S)-2-oxa-7-azaspiro[4.4] nonan-7-yl]pyrazolo[1,5-a]pyrimidine-3-carboxylate ((200 mg, 632 umol, 36% yield), $t_R$=1.666) as a white solid. The absolute stereochemistry of the enantiomers was assigned arbitrarily.

Tert-butyl 5-(4-azaspiro[2.4]heptan-4-yl)pyrazolo[1,5-a]pyrimidine-3-carboxylic acid (Intermediate COW)

To a solution of ethyl 5-[(5S)-2-oxa-7-azaspiro[4.4]nonan-7-yl]pyrazolo[1,5-a]pyrimidine-3-carboxylate (100 mg, 316 umol, Intermediate COV) in $H_2O$ (0.5 mL) and EtOH (2.0 mL) was added LiOH·$H_2O$ (26.5 mg, 632 umol), then the mixture was stirred at 50° C. for 12 hours. On completion, the reaction mixture was concentrated in vacuo to remove EtOH, then acidified with hydrochloric acid (1 M) until the pH=5-6. Next the reaction mixture was filtered to give the title compound (70.0 mg, 76% yield) as a white solid. LC-MS (ESI$^+$) m/z 270.8 (M−18+H)$^+$.

Tert-butyl N-(3-fluoro-4-piperidyl)-N-methyl-carbamate (Intermediate COX)

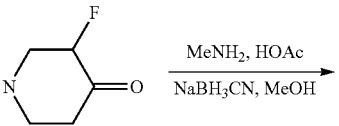

671

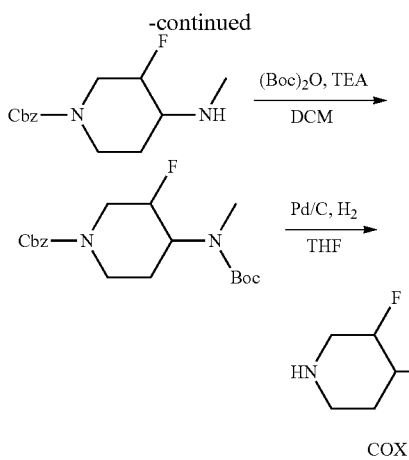

COX

Step 1—Benzyl 3-fluoro-4-(methylamino)piperidine-1-carboxylate. To a solution of methanamine hydrochloride (13.4 g, 199 mmol) in MeOH (200 mL) was added TEA (3.02 g, 29.8 mmol) at 25° C., then the mixture was stirred at 25° C. for 10 mins. Next, benzyl 3-fluoro-4-oxo-piperidine-1-carboxylate (5 g, 19.9 mmol, CAS #845256-59-9) was added to the mixture followed by AcOH (1.20 g, 19.9 mmol), then the mixture was stirred at 45° C. for 0.5 hr. Finally, the mixture was cooled to 25° C. and NaBH$_3$CN (1.88 g, 29.8 mmol) was added slowly, then the reaction was stirred for 2 hrs at 45° C. On completion, the reaction mixture was quenched with H$_2$O (50 mL) under stirring. The residue was diluted with water (10 mL) and extracted with EA (50 mL×3). The combined organic layer was dried over Na$_2$SO$_4$, filtered and concentrated in vacuo to give the title compound (2 g, 80% yield) as light yellow oil. LC-MS (ESI$^+$) m/z 267.1 (M+H)$^+$.

Step 2—4-(Cyclopentylamino)-2-methylsulfanyl-pyrimidine-5-carbaldehyde. To a solution of benzyl 3-fluoro-4-(methylamino)piperidine-1-carboxylate (5 g, 18.7 mmol) in DCM (80 mL) was added TEA (5.7 g, 56.3 mmol) at 25° C., then the mixture was stirred at 25° C. for 10 mins. Next, (Boc)$_2$O (6.15 g, 28.1 mmol) was added to the mixture. then the mixture was stirred at 25° C. for 2 hr. On completion, the reaction mixture was quenched with H$_2$O (40 mL) under stirring. The residue was diluted with water (20 mL) and extracted with DCM (50 mL×3). The combined organic layer was dried over Na$_2$SO$_4$, filtered and concentrated in vacuo to give a residue. The residue was purified by flash silica gel chromatography (SiO$_2$, Petroleum ether/Ethyl acetate=1/1, P1:Rf=0.4) to give the title compound (5 g, 73% yield) as light yellow solid, LC-MS (ESI$^+$) m/z 389.1. (M+Na)$^+$.

Step 3—Tert-butyl N-(3-fluoro-4-piperidyl)-N-methyl-carbamate. To a solution of benzyl 4-[tert-butoxycarbonyl (methyl)amino]-3-fluoro-piperidine-1-carboxylate (2 g, 5.46 mmol) in THF (20 mL) was added Pd/C (0.2 g, 10 wt %) under N$_2$ atmosphere. The suspension was degassed and purged with H$_2$ three times. The mixture was then stirred under H$_2$ (15 psi) at 25° C. for 6 hrs. On completion, the reaction mixture was filtered and concentrated in vacuo to give the title compound (1.2 g, 95% yield) as a brown oil. $^1$H NMR (400 MHz, DMSO-d$_6$) δ 4.82-4.27 (m, 1H), 4.26-3.69 (m, 1H), 3.27-3.15 (m, 2H), 3.12-2.98 (m, 1H), 2.96-2.80 (m, 1H), 2.73 (s, 1H), 2.69 (m, 1H), 2.66-2.53 (m, 1H), 2.43-2.27 (m, 2H), 2.11-1.72 (m, 1H), 1.64-1.48 (m, 1H), 1.44-1.36 (m, 9H).

672

3-[4-[3-Fluoro-4-(methylamino)-1-piperidyl]-3-methyl-2-oxo-benzimidazol-1-yl]piperidine-2,6-dione (Intermediate COY)

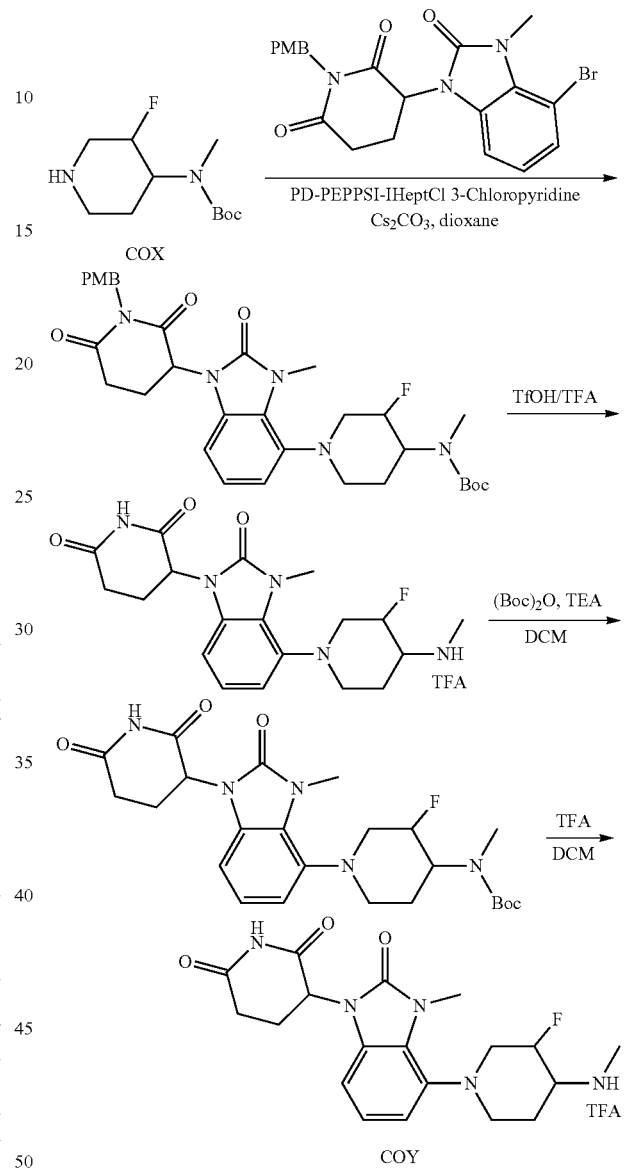

Step 1—Tert-butyl N-[3-fluoro-1-[1-[1-[(4-methoxyphenyl)methyl]-2,6-dioxo-3-piperidyl]-3-methyl-2-oxo-benzimidazol-4-yl]-4-piperidyl]-N-methyl-carbamate. A mixture of tert-butyl N-(3-fluoro-4-piperidyl)-N-methyl-carbamate (500 mg, 2.15 mmol, Intermediate COX), 3-(4-bromo-3-methyl-2-oxo-benzimidazol-1-yl)-1-[(4-methoxyphenyl) methyl]piperidine-2,6-dione (986 mg, 2.15 mmol, synthesized via Steps 1-4 of Intermediate HP) in dioxane (25 mL) was added 1,3-bis[2,6-bis(1-propylbutyl)phenyl]-4,5-dichloro-2H-imidazol-1-ium-2-ide 3-chloropyridine dichloropalladium (209 mg, 215 umol), and Cs$_2$CO$_3$ (1.40 g, 4.30 mmol). The mixture was stirred at 100° C. for 30 hrs under N$_2$. On completion, the residue was diluted with water (20 mL) and extracted with EA (20 mL×3). The combined organic layer was dried over Na$_2$SO$_4$, filtered and concentrated in vacuo to give a residue. The residue was purified by column chromatography (SiO$_2$, PE:EA=99:1 to PE:EA=1:100, PE:EA=3:1, P1:Rf=0.13) to give the title compound (620 mg, 47% yield) as light yellow oil. LC-MS (ESI$^+$) m/z 610.1 (M+H)$^+$.

Step 2—3-[4-[3-Fluoro-4-(methylamino)-1-piperidyl]-3-methyl-2-oxo-benzimidazol-1-yl]piperidine-2,6-dione. To a solution of tert-butyl N-[3-fluoro-1-[1-[1-[(4-methoxyphenyl)methyl]-2,6-dioxo-3-piperidyl]-3-methyl-2-oxo-benzimidazol-4-yl]-4-piperidyl]-N-methyl-carbamate (615 mg, 1.01 mmol) in TFA (0.6 mL) was added TfOH (41.8 g, 278 mmol) dropwise at 25° C. Then the reaction mixture was stirred at 70° C. for 1 hr. On completion, the reaction mixture was concentrated in vacuo to give the title compound (357 mg, 90% yield) as light yellow solid. m/z 390.1 (M+H)$^+$.

Step 3—Tert-butylN-[1-[1-(2,6-dioxo-3-piperidyl)-3-methyl-2-oxo-benzimidazol-4-yl]-3-fluoro-4-piperidyl]-N-methyl-carbamate. To a solution of 3-[4-[3-fluoro-4-(methylamino)-1-piperidyl]-3-methyl-2-oxo-benzimidazol-1-yl]piperidine-2,6-dione (350 mg, 898 umol) in DCM (10 mL) was added TEA (272 mg, 2.70 mmol) at 25° C., then the mixture was stirred at 25° C. for 10 mins. Next, (Boc)$_2$O (294 mg, 1.35 mmol) was added to the mixture, and the mixture was stirred at 25° C. for 2 hrs. On completion, the reaction mixture was quenched H$_2$O (50 mL) under stirring. The residue was diluted with water (10 mL) and extracted with EA (20 mL×3). The combined organic layer was dried over Na$_2$SO$_4$, filtered and concentrated in vacuo to give a residue. The residue was purified by flash silica gel chromatography (SiO$_2$, Petroleum ether/Ethyl acetate=1/1, P1:Rf=0.46) to give the title compound (357 mg, 81.14% yield) as light yellow solid. 1H NMR (400 MHz, DMSO-d6) δ 11.10 (s, 1H), 7.05-6.98 (m, 2H), 6.93 (dd, J=2.4, 6.4 Hz, 1H), 5.41-5.32 (m, 1H), 5.00-4.77 (m, 1H), 4.19-4.08 (m, 1H), 3.97-3.82 (m, 1H), 3.61 (s, 2H), 3.51-3.40 (m, 1H), 3.09 (d, J=10.8 Hz, 1H), 3.01-2.87 (m, 2H), 2.86-2.82 (m, 3H), 2.80-2.61 (m, 3H), 2.05-1.96 (m, 3H), 1.81-1.62 (m, 1H), 1.45-1.40 (m, 9H). LC-MS (ESI$^+$) m/z 490.1 (M+H)$^+$.

Step 4—3-[4-[3-Fluoro-4-(methylamino)-1-piperidyl]-3-methyl-2-oxo-benzimidazol-1-yl]piperidine-2,6-dione. To a solution of tert-butyl N-[1-[1-(2,6-dioxo-3-piperidyl)-3-methyl-2-oxo-benzimidazol-4-yl]-3-fluoro-4-piperidyl]-N-methyl-carbamate (50 mg, 102 umol) in DCM (0.5 mL) was added TFA (0.1 mL) dropwise at 0° C., then the reaction mixture was stirred at 25° C. for 1 hr. On completion, (31 mg, 97% yield) as light yellow solid. LC-MS (ESI$^+$) m/z 390.2 (M+H)$^+$.

Tert-butyl 4-((1s,3r)-3-((3-methyl-2-oxo-2,3-di-hydro-1H-benzo[d]imidazol-4-yl)methyl)cyclobutyl)piperazine-1-carboxylate (Intermediate CPA)

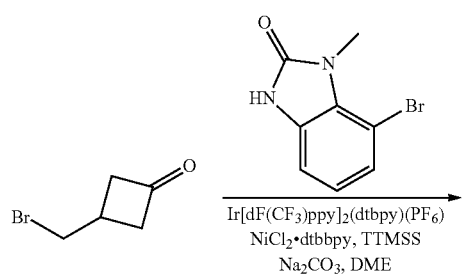

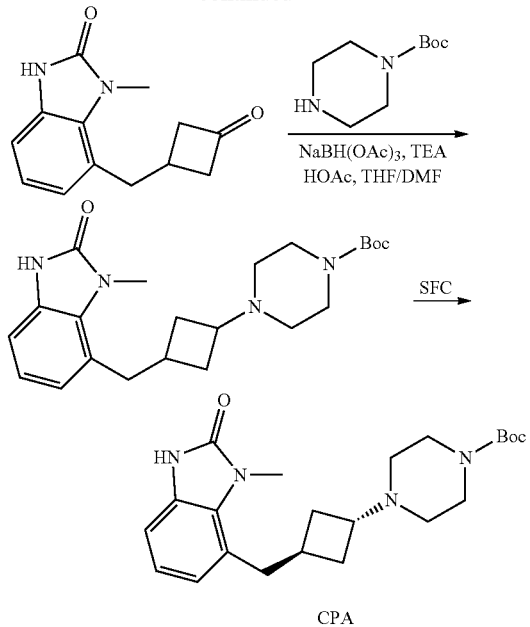

Step 1—3-Methyl-4-[(3-oxocyclobutyl)methyl]-1H-benzimidazol-2-one. To an 15 mL vial equipped with a stir bar was added 4-bromo-3-methyl-1H-benzimidazol-2-one (1 g, 4.40 mmol, synthesized via Steps 1-3 of Intermediate HP), 3-(bromomethyl)cyclobutanone (933 mg, 5.73 mmol, CAS #463961-43-5), Ir[dF(CF$_3$)ppy]$_2$(dtbpy)(PF$_6$) (49.4 mg, 44.0 umol), NiCl$_2$·dtbbpy (26.3 mg, 66.1 umol), TTMSS (1.10 g, 4.40 mmol, 1.36 mL), and Na$_2$CO$_3$ (933 mg, 8.81 mmol) in DME (20 mL). The vial was sealed and placed under nitrogen. Then the reaction was stirred and irradiated with a 10 W blue LED lamp (3 cm away), with cooling water to keep the reaction temperature at 25° C. for 14 hrs. On completion, the reaction mixture was filtered and concentrated in vacuo to give a residue. The residue was triturated with PE/EA=5/1. Then the residue was filtered and concentrated in vacuo to give the title compound (600 mg, 59% yield) as a yellow solid. $^1$H NMR (400 MHz, CDCl$_3$) δ 10.34 (s, 1H), 7.15-7.05 (m, 1H), 7.03-7.01 (m, 1H), 6.84 (dd, J=1.2, 7.2 Hz, 1H), 3.70 (s, 3H), 3.25 (d, J=7.6 Hz, 2H), 3.22-3.14 (m, 2H), 2.91-2.86 (m, 1H), 2.86-2.82 (m, 1H), 2.79-2.74 (m, 1H); LC-MS (ESI$^+$) m/z 231.2 (M+H)$^+$.

Step 2—Tert-butyl 4-[3-[(3-methyl-2-oxo-1H-benzimidazol-4-yl)methyl]cyclobutyl]piperazine-1-carboxylate. A mixture of 3-methyl-4-[(3-oxocyclobutyl)methyl]-1H-benzimidazol-2-one (2.5 g, 10.8 mmol), tert-butyl piperazine-1-carboxylate (2.02 g, 10.9 mmol, CAS #143238-38-4) in THF (10 mL) and added HOAc (1 mL) to adjust the pH=5 and the mixture was stirred at −10° C. for 0.5 hr. Then NaBH(OAc)$_3$ (4.60 g, 21.7 mmol) was added and the mixture was stirred at −10° C. for 1.5 hr. On completion, the reaction mixture was quenched with water (0.1 mL), and then diluted with water (30 mL) and extracted with EA (20 mL×5). The combined organic layers were washed with brine (30 mL), dried over Na$_2$SO$_4$, filtered and concentrated under reduced pressure to give a residue. The crude product was purified by reverse phase (FA condition) to give the title compound (2.2 g, 50% yield) as a yellow solid. $^1$H NMR (400 MHz, CDCl$_3$) δ 10.21 (d, J=12.0 Hz, 1H), 7.00-6.92 (m, 2H), 6.84-6.77 (m, 1H), 3.68-3.61 (m, 3H), 3.44 (s, 4H), 3.04 (d, J=6.0 Hz, 1H), 2.58-2.48 (m, 1H), 2.32-2.20 (m, 7H), 2.14-2.05 (m, 1H), 2.00-1.88 (m, 1H), 1.66-1.60 (m, 1H), 1.47-1.44 (s, 9H); LC-MS (ESI⁺) m/z 401.2 (M+H)⁺.

Step 3—Tert-butyl 4-((1s,3r)-3-((3-methyl-2-oxo-2,3-dihydro-1H-benzo[d]imidazol-4-yl)methyl)cyclobutyl)piperazine-1-carboxylate. Tert-butyl 4-[3-[(3-methyl-2-oxo-1H-benzimidazol-4-yl) methyl]cyclobutyl]piperazine-1-carboxylate (1 g, 2.50 mmol) was purified by prep-HPLC (column: DAICEL CHIRALPAK AD (250 mm×30 mm, 10 um); mobile phase: [0.1% NH₃H₂O MeOH]) to give the title compound (200 mg, 20% yield) as a white solid. ¹H NMR (400 MHz, DMSO-d₆) δ 10.81 (s, 1H), 6.92-6.70 (m, 3H), 4.39-4.04 (m, 1H), 3.46 (s, 3H), 3.27 (s, 4H), 3.17 (d, J=2.0 Hz, 1H), 2.96 (d, J=6.8 Hz, 2H), 2.48-2.41 (m, 1H), 2.22-2.17 (m, 1H), 2.16-2.11 (m, 4H), 2.10 (s, 1H), 1.48 (d, J=9.6 Hz, 2H), 1.38 (s, 9H); LC-MS (ESI⁺) m/z 401.2 (M+H)⁺.

3-[3-Methyl-2-oxo-4-[(3-piperazin-1-ylcyclobutyl) methyl]benzimidazol-1-yl]piperidine-2,6-dione (Intermediate CPB)

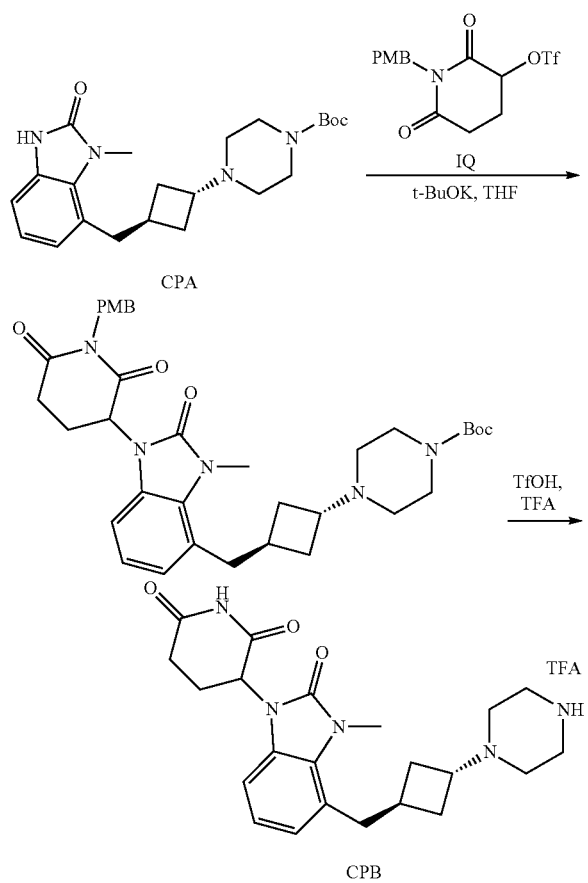

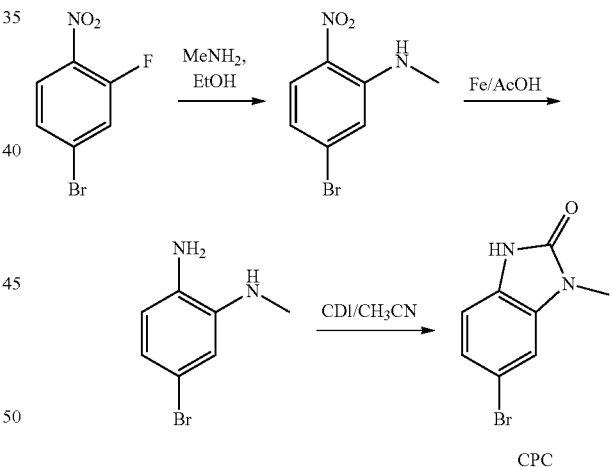

Step 1—Tert-butyl 4-[3-[[1-[1-[(4-methoxyphenyl) methyl]-2,6-dioxo-3-piperidyl]-3-methyl-2-oxo-benzimidazol-4-yl]methyl]cyclobutyl]piperazine-1-carboxylate. To a solution of tert-butyl 4-[3-[(3-methyl-2-oxo-1H-benzimidazol-4-yl)methyl]cyclobutyl]piperazine-1-carboxylate (140 mg, 349.5 umol, Intermediate CPA) in THF (10 mL) was added tBuOK (39.2 mg, 349 umol) and the mixture was stirred at 0° C. for 0.5 hr. Then [1-[(4-methoxyphenyl) methyl]-2,6-dioxo-3-piperidyl] trifluoromethanesulfonate (266 mg, 699 umol, Intermediate IQ) was added and the mixture was stirred at 0° C. for 1 hr. On completion, the reaction mixture was quenched with water (1 mL) and concentrated under reduced pressure to remove THF. Then the mixture was diluted with water (10 mL) and extracted with EA (10 mL×3). The combined organic layers were washed with brine (10 mL), dried over Na₂SO₄, filtered and concentrated under reduced pressure to give a residue. The crude product was purified by reversed phase (FA condition) to give the title compound (150 mg, 69% yield) as a white solid. ¹H NMR (400 MHz, CDCl₃) δ 7.40-7.34 (m, 2H), 7.34-7.31 (m, 1H), 6.89-6.85 (m, 1H), 6.84-6.83 (m, 1H), 6.82-6.81 (m, 1H), 6.40 (d, J=7.6 Hz, 1H), 5.20 (dd, J=5.6, 12.8 Hz, 1H), 4.97 (d, J=6.4 Hz, 1H), 4.89 (s, 1H), 3.80-3.77 (m, 4H), 3.66 (s, 2H), 3.49 (d, J=4.0 Hz, 3H), 3.12 (d, J=8.0 Hz, 1H), 3.04-2.97 (m, 1H), 2.96-2.91 (m, 1H), 2.89-2.81 (m, 1H), 2.66-2.60 (m, 1H), 2.59-2.53 (m, 1H), 2.36-2.30 (m, 4H), 2.18-2.12 (m, 3H), 1.99-1.90 (m, 4H), 1.46 (s, 9H); LC-MS (ESI⁺) m/z 632.4 (M+H)⁺.

Step 2—3-[3-Methyl-2-oxo-4-[(3-piperazin-1-ylcyclobutyl)methyl]benzimidazol-1-yl]piperidine-2,6-dione. A solution of tert-butyl 4-[3-[[1-[1-[(4-methoxyphenyl) methyl]-2,6-dioxo-3-piperidyl]-3-methyl-2-oxo-benzimidazol-4-yl]methyl]cyclobutyl]piperazine-1-carboxylate (90 mg, 142 umol) in TfOH (0.1 mL) and TFA (0.5 mL) was stirred at 70° C. for 2 hr. On completion, the reaction mixture was concentrated under reduced pressure to give the title compound (74 mg, 98% yield) as a brown solid. LC-MS (ESI⁺) m/z 412.1 (M+H)⁺.

5-Bromo-3-methyl-1H-benzimidazol-2-one (Intermediate CPC)

Step 1—5-Bromo-N-methyl-2-nitro-aniline. 4-bromo-2-fluoro-1-nitro-benzene (230 g, 1.05 mol, CAS #321-23-3) was added to a solution of methylamine in tetrahydrofuran (2 M, 1.51 L). The mixture was stirred at 15° C. for 10 minutes. On completion, the mixture was diluted with H₂O (250 mL) and extracted with EtOAc (3×300 mL). The combined organic layers were washed with brine (300 mL), dried over Na₂SO₄, filtered and concentrated in vacuo to give the title compound (200 g, 83% yield) as a yellow solid. ¹H NMR (400 MHz, DMSO-d₆) δ 8.22 (s, 1H), 7.98 (d, J=9.2 Hz, 1H), 7.16 (d, J=1.6 Hz, 1H), 6.82 (dd, J=8.4, 1.6 Hz, 1H), 2.95 (d, J=4.8 Hz, 3H).

Step 2—4-Bromo-N2-methyl-benzene-1,2-diamine. To a mixture of 5-bromo-N-methyl-2-nitro-aniline (200 g, 865 mmol) in EtOAc (1 L) and H₂O (500 mL) was added AcOH (1.00 L). The mixture was warmed to 50° C., and then Fe (174 g, 3.11 mol) was added to the reaction mixture. After that, the reaction mixture was stirred at 80° C. for 6 hours. On completion, the mixture was filtered through celite. The filtrate was concentrated in vacuo and the residue was diluted with H₂O (250 mL) and extracted with EtOAc (3×300 mL). The combined organic layers were washed with aq. NaHCO₃ and brine (300 mL), dried over Na₂SO₄, filtered and concentrated in vacuo. The residue was purified by flash silica gel chromatography to give the title compound (130 g, 75% yield) as black oil. ¹H NMR (400 MHz, DMSO-d₆) δ 6.55-6.52 (m, 1H), 6.48-6.45 (m, 1H), 6.43-6.42 (m, 1H), 4.89-4.88 (m, 1H), 4.61 (s, 2H), 2.70 (d, J=4.0 Hz, 3H).

Step 3—5-Bromo-3-methyl-1H-benzimidazol-2-one. To a solution of 4-bromo-N2-methyl-benzene-1,2-diamine (110 g, 547 mmol) in CH₃CN (1.3 L) was added CDI (177 g, 1.09 mol). The mixture was stirred at 80° C. for 6 hours under N₂. On completion, the mixture was concentrated in vacuo. The mixture was diluted with H₂O (1.0 L) and filtered. The filter cake was washed with water (3×200 mL) and dried in vacuo to give the title compound (106 g, 85% yield) as a white solid. ¹H NMR (400 MHz, DMSO-d₆) δ 11.00 (s, 1H), 7.33 (s, 1H), 7.13 (d, J=8.0 Hz, 1H), 6.92 (d, J=8.0 Hz, 1H), 3.27 (s, 3H).

3-(5-bromo-3-methyl-2-oxo-benzimidazol-1-yl)piperidine-2,6-dione (3-(5-bromo-3-methyl-2-oxo-2,3-dihydro-1H-1,3-benzodiazol-1-yl)piperidine-2,6-dione (Intermediate CPD)

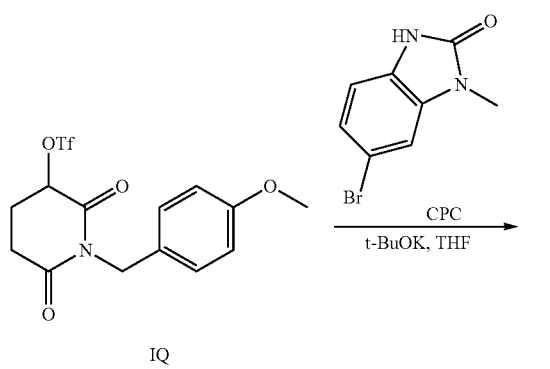

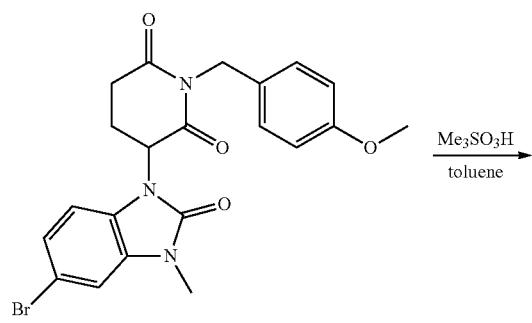

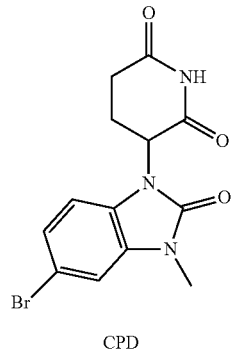

CPD

Step 1—3-(5-Bromo-3-methyl-2-oxo-benzimidazol-1-yl)-1-[(4-methoxyphenyl)methyl]piperidine-2,6-dione. To a solution of 5-bromo-3-methyl-1H-benzimidazol-2-one (4.90 g, 21.6 mmol, Intermediate CPC) in THF (300 mL) was added t-BuOK (3.63 g, 32.3 mmol) at 0° C. The mixture was stirred at 0-10° C. for 1 hour under N₂. Then a solution of [1-[(4-methoxyphenyl) methyl]-2, 6-dioxo-3-piperidyl] trifluoromethanesulfonate (9.87 g, 25.9 mmol, Intermediate IQ) in THF (100 mL) was added to the reaction mixture at 0-10° C. during 30 minutes. The mixture was stirred at 0-10° C. for 30 minutes under N₂. An additional solution of [1-[(4-methoxyphenyl) methyl]-2, 6-dioxo-3-piperidyl] trifluoromethanesulfonate (2.47 g, 6.47 mmol) in THF (20 mL) was added to the reaction mixture at 0-10° C. dropwise. The mixture was then stirred at 0-10° C. for another 30 minutes under N₂. On completion, the reaction was quenched water (400 mL) and extracted with EA (3×200 mL). The combined organic layer was concentrated in vacuo. The residue was triturated with EA (80 mL) and filtered. The filter cake was collected and dried in vacuo to give the title compound (6.70 g, 67% yield) as light yellow solid. The filtrate was also concentrated in vacuo and the residue was purified by column chromatography to give another batch title compound (1.80 g, 18% yield) as light yellow solid. ¹H NMR (400 MHz, DMSO-d₆) δ 7.47 (d, J=1.6 Hz, 1H), 7.21-7.16 (m, 3H), 7.01 (d, J=8.0 Hz, 1H), 6.85 (d, J=8.8 Hz, 2H), 5.55-5.51 (m, 1H), 4.84-4.73 (m, 2H), 3.72 (s, 3H), 3.33 (s, 3H), 3.04-3.00 (m, 1H), 2.83-2.67 (m, 2H), 2.07-2.05 (m, 1H).

Step 2—3-(5-Bromo-3-methyl-2-oxo-benzimidazol-1-yl) piperidine-2,6-dione. To a mixture of 3-(5-bromo-3-methyl-2-oxo-benzimidazol-1-yl)-1-[(4-methoxyphenyl)methyl] piperidine-2,6-dione (8.50 g, 18.6 mmol) in toluene (50 mL) was added methanesulfonic acid (33.8 g, 351 mmol, 25 mL) at room temperature (15° C.). The mixture was stirred at 120° C. for 2 hours. On completion, the reaction mixture was cooled to room temperature and concentrated in vacuo. The residue was poured into ice/water (200 mL), and extracted with EA (3×100 mL). The combined organic layer was washed with brine (50 mL), dried over Na₂SO₄, filtered and concentrated in vacuo. The residue was triturated with EA (80 mL) and filtered. The filtrate cake was collected and dried in vacuo to give the title compound (4.20 g, 67% yield) as off-white solid. ¹H NMR (400 MHz, DMSO-d₆) δ 11.12 (s, 1H), 7.47 (d, J=2.0 Hz, 1H), 7.22 (d, J=8.4 Hz, 1H), 7.10 (d, J=8.4 Hz, 1H), 5.40-5.35 (m, 1H), 2.34 (s, 3H), 2.92-2.88 (m, 1H), 2.71-2.60 (m, 2H), 2.03-1.99 (m, 1H).

3-(3-methyl-2-oxo-5-(piperazin-1-yl)-2,3-dihydro-1H-benzo[d]imidazol-1-yl)piperidine-2,6-dione (Intermediate CPE)

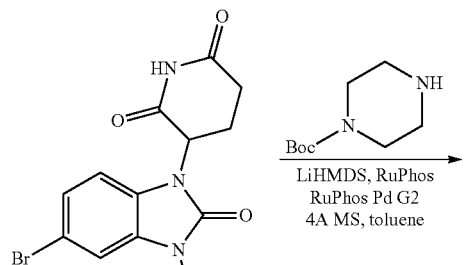

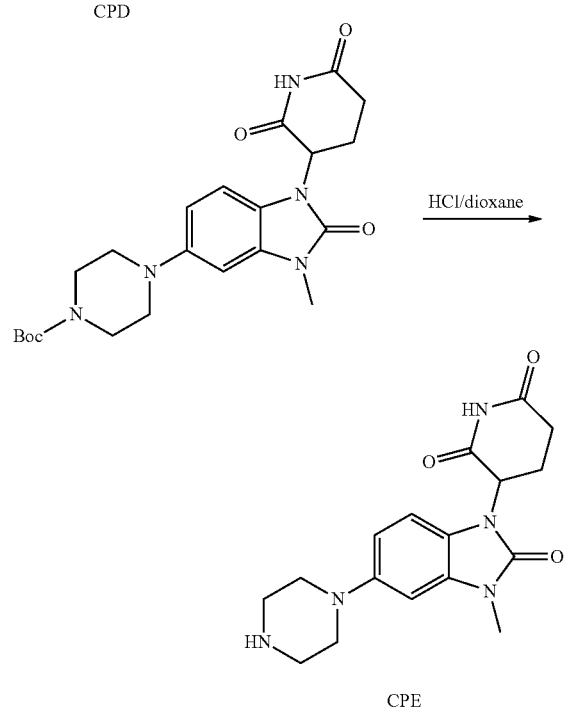

Step 1—Tert-butyl 4-(1-(2,6-dioxopiperidin-3-yl)-3-methyl-2-oxo-2,3-dihydro-1H-benzo[d]imidazol-5-yl)piperazine-1-carboxylate. To a solution of 3-(5-bromo-3-methyl-2-oxo-2,3-dihydro-1H-benzo[d]imidazol-1-yl) piperidine-2,6-dione (20 g, 59.1 mmol, Intermediate CPD) and tert-butyl piperazine-1-carboxylate (13.2 g, 70.9 mmol, CAS #143238-38-4) in toluene (400 mL) was added RuPhos (1.38 g, 2.96 mmol), RuPhos Pd G3 (2.47 g, 2.96 mmol), 4 Å molecular sieves (20 g, 200 mmol) and LiHMDS (1 M, 295.72 mL) at 20° C. under nitrogen flow. Then the reaction was stirred at 100° C. for 10 h under nitrogen atmosphere. On completion, the reaction was poured into water (500 mL) and extracted with ethyl acetate (500 mL×2). The combined organic phase is washed with brine (300 mL×2), dried over sodium sulfate, then filtered to give the filtrate and concentrated to give a residue. The residue was triturated with PE:EtOAc=30:1 (20 mL) at 25° C., then filtered to give the title compound (9 g, 21% yield) as brown solid. LC-MS (ESI$^+$) m/z 444.2 (M+H)$^+$.

Step 2—3-(3-Methyl-2-oxo-5-(piperazin-1-yl)-2,3-dihydro-1H-benzo[d]imidazol-1-yl)piperidine-2,6-dione. To a solution of tert-butyl 4-(1-(2,6-dioxopiperidin-3-yl)-3-methyl-2-oxo-2,3-dihydro-1H-benzo[d]imidazol-5-yl)piperazine-1-carboxylate (1 g, 2.25 mmol) in HCl/dioxane (4 M, 20 mL) at 20° C. under nitrogen flow and the reaction was stirred at 20° C. for 2 h under nitrogen atmosphere. On completion, the reaction was concentrated to give the title compound (1.1 g) as a brown solid. $^1$H NMR (400 MHz, DMSO-d$_6$) δ=9.27 (br d, J=0.8 Hz, 2H), 7.01 (d, J=8.8 Hz, 1H), 6.93 (d, J=2.0 Hz, 1H), 6.71 (dd, J=2.0, 8.8 Hz, 1H), 5.32 (dd, J=5.2, 12.8 Hz, 1H), 3.37-3.29 (m, 7H), 3.24 (br d, J=4.0 Hz, 4H), 2.96-2.83 (m, 1H), 2.76-2.58 (m, 2H), 2.05-1.94 (m, 1H).

Tert-butyl 7-formyl-5-oxa-2-azaspiro[3.4]octane-2-carboxylate (Intermediate CPF)

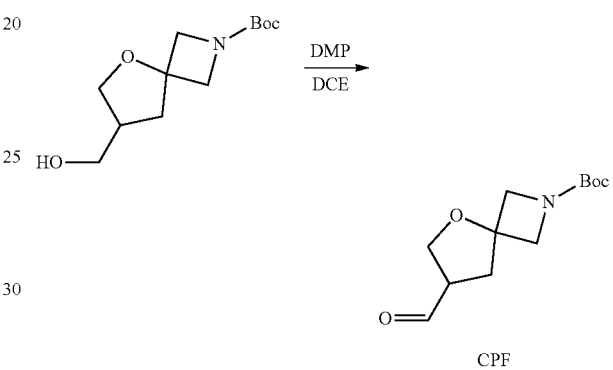

To a solution of tert-butyl 7-(hydroxymethyl)-5-oxa-2-azaspiro[3.4]octane-2-carboxylate (5.5 g, 22.6 mmol, CAS #1330764-06-1) in DCM (110 mL) was added DMP (14.3 g, 33.9 mmol) at 20° C. under nitrogen flow. Then the reaction was stirred at 20° C. for 10 h under nitrogen atmosphere. On completion, the reaction was poured into NaHCO$_3$ (sat. aq, 200 mL) and extracted with DCM (100 mL×2). The combined organic phase is washed with brine (70 mL×2), dried over Na$_2$SO$_4$, filtered and concentrated to give the title compound (9 g) as a yellow gum. $^1$H NMR (400 MHz, DMSO-d$_6$) δ=9.59 (d, J=1.6 Hz, 1H), 4.06 (dd, J=4.4, 9.2 Hz, 1H), 3.91-3.82 (m, 3H), 3.79-3.67 (m, 2H), 3.26-3.15 (m, 1H), 2.40-2.32 (m, 1H), 2.23 (br d, J=9.2 Hz, 1H), 1.37 (s, 9H).

3-[3-Methyl-4-[4-(5-oxa-2-azaspiro[3.4]octan-7-ylmethyl)piperazin-1-yl]-2-oxo-benzimidazol-1-yl]piperidine-2,6-dione (Intermediate CPG)

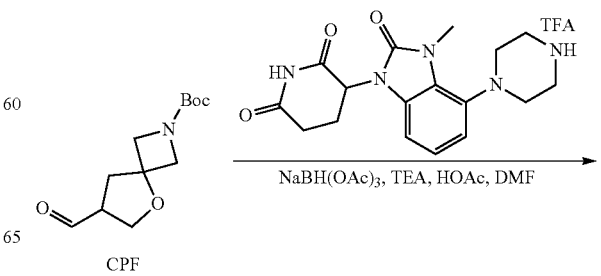

-continued

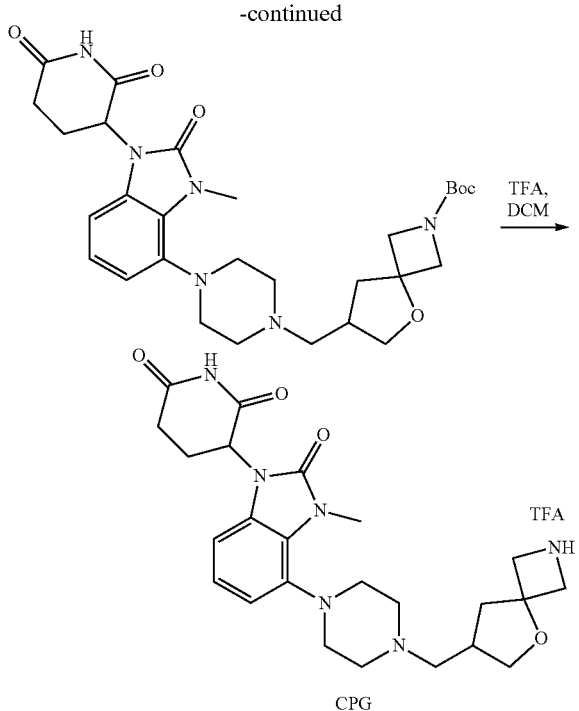

CPG

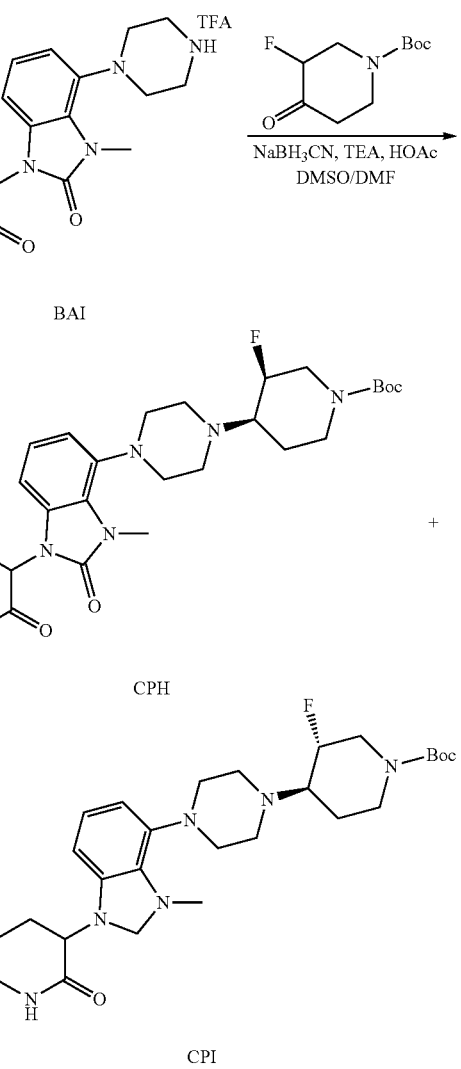

Step 1—Tert-butyl 7-[[4-[1-(2,6-dioxo-3-piperidyl)-3-methyl-2-oxo-benzimidazol-4-yl]piperazin-1-yl]methyl]-5-oxa-2-azaspiro[3.4]octane-2-carboxylate. To a solution of 3-(3-methyl-2-oxo-4-piperazin-1-yl-benzimidazol-1-yl)piperidine-2,6-dione (60 mg, 131 umol, TFA, Intermediate BAI) in THF (1 mL) was added TEA (13.3 mg, 131 umol) under stirring for 10 min. Then tert-butyl 7-formyl-5-oxa-2-azaspiro[3.4]octane-2-carboxylate (31.6 mg, 131 umol, Intermediate CPF) and HOAc (7.88 mg, 131 umol) was added until the pH=6-7 at 25° C. and the mixture was stirred at 25° C. for 30 mins. Next, NaBH(OAc)₃ (41.7 mg, 196 umol) was added and the mixture was stirred at 25° C. for 2 hrs. On completion, the reaction mixture was quenched with water (0.05 mL) to give the residue. The residue was diluted with water (2 mL) and extracted with EA (1 mL×3). The combined organic layer was dried over Na₂SO₄, filtered and concentrated in vacuo to give the title compound (70 mg, 88% yield) as a white solid. LCMS (ESI⁺) m/z 569.3 (M+H)⁺.

Step 2—3-[3-Methyl-4-[4-(5-oxa-2-azaspiro[3.4]octan-7-ylmethyl)piperazin-1-yl]-2-oxo-benzimidazol-1-yl]piperidine-2,6-dione. To a solution of tert-butyl 7-[[4-[1-(2,6-dioxo-3-piperidyl)-3-methyl-2-oxo-benzimidazol-4-yl]piperazin-1-yl]methyl]-5-oxa-2-azaspiro[3.4]octane-2-carboxylate (70 mg, 123 umol) in DCM (1 mL) was added TFA (14.0 mg, 123 umol), then the mixture was stirred at 25° C. for 1 hr. On completion, the reaction mixture was concentrated in vacuo to the title compound (70 mg, 98% yield) as a brown oil. LC-MS (ESI⁺) m/z 469.1 (M+H)⁺.

Tert-butyl (3S,4R)-4-(4-(1-(2,6-dioxopiperidin-3-yl)-3-methyl-2-oxo-2,3-dihydro-1H-benzo[d]imidazol-4-yl)piperazin-1-yl)-3-fluoropiperidine-1-carboxylate (Intermediate CPH) and tert-butyl (3R,4R)-4-(4-(1-(2,6-dioxopiperidin-3-yl)-3-methyl-2-oxo-2,3-dihydro-1H-benzo[d]imidazol-4-yl)piperazin-1-yl)-3-fluoropiperidine-1-carboxylate (Intermediate CPI)

To a solution of 3-(3-methyl-2-oxo-4-piperazin-1-yl-benzimidazol-1-yl)piperidine-2,6-dione (400 mg, 874 μmol, TFA, Intermediate BAI) in DMF (4 mL) and DMSO (0.5 mL) was added TEA (88.4 mg, 874 μmol) at 25° C. until the pH stabilized at 8. The mixture was stirred at 25° C. for 0.5 hrs, then AcOH (52.5 mg, 874 μmol) was added at 25° C. to solution until the pH stabilized at 5-6. Subsequently, tert-butyl 3-fluoro-4-oxo-piperidine-1-carboxylate (227 mg, 1.05 mmol, CAS #211108-50-8) was added and the mixture was stirred for 1 hr at 60° C. Finally, NaBH₃CN (82.4 mg, 1.31 mmol) was added in one portion and the resulting reaction mixture was stirred at 50° C. for 2 hrs. On completion, the mixture was quenched with water (20 mL) and extracted with ethyl acetate (10 mL×3). The combined organic phase was dried over anhydrous sodium sulfate, filtered and concentrated to give a residue. The residue was purified by prep-HPLC (column: Waters xbridge 150*25 mm 10 um; mobile phase: [water(NH₄HCO₃)-ACN]; B %: 30%-60%, 14 min) to give tert-butyl (3S,4R)-4-(4-(1-(2,6-dioxopiperidin-3-yl)-3-methyl-2-oxo-2,3-dihydro-1H-benzo[d]imidazol-4-yl)piperazin-1-yl)-3-fluoropiperidine-1-carboxylate (3, 60 mg, 11% yield, FA) as a white solid (¹H NMR (400 MHz, DMSO-d₆) δ 11.08 (s, 1H), 7.03-6.81 (m, 3H), 5.35 (dd, J=5.2, 12.8 Hz, 1H), 5.11-4.93 (m, 1H), 4.28-3.98 (m, 2H), 3.62 (s, 3H), 3.11-2.76 (m, 9H), 2.75-2.66 (m, 2H), 2.66-2.55 (m, 3H), 2.04-1.93 (m, 1H), 1.75-1.63 (m, 2H), 1.39 (s, 9H); LC-MS (ESI⁺) m/z 545.3 (M+H)⁺ and tert-butyl (3R,4R)-4-(4-(1-(2,6-dioxopiperidin-3-yl)-3-methyl-2-oxo-2,3-dihydro-1H-benzo[d]imidazol-4-yl)piperazin-1-yl)-3-fluoropiperidine-1-carboxylate (4, 20 mg, 3% yield, FA) as a white solid (¹H NMR (400 MHz, CHLOROFORM-d) δ 8.18 (s, 1H), 7.06-6.88 (m, 2H), 6.59 (d, J=7.6 Hz, 1H), 5.21 (dd, J=5.2, 12.4 Hz, 1H), 5.09-4.86 (m, 1H), 4.63-4.16 (m, 2H), 3.76 (s, 3H), 3.06 (s, 4H), 2.88-2.68 (m, 5H), 2.31-2.13 (m, 1H), 2.06-1.96 (m, 1H), 1.79-1.60 (m, 6H), 1.48 (s, 9H); LC-MS (ESI⁺) m/z 545.3 (M+H)⁺. The cis/trans confirmation was confirmed by 2D NMR.

3-[4-[4-[(3R,4R)-3-fluoro-4-piperidyl]piperazin-1-yl]-3-methyl-2-oxo-benzimidazol-1-yl]piperidine-2,6-dione (Intermediate CPJ)

Tert-butyl (3S,4R)-4-[3-[1-(2,6-dioxo-3-piperidyl)-3-methyl-2-oxo-benzimidazol-4-yl]azetidin-1-yl]-3-fluoro-piperidine-1-carboxylate (Intermediate CPK) and tert-butyl(3R,4R)-4-[3-[1-(2,6-dioxo-3-piperidyl)-3-methyl-2-oxo-benzimidazol-4-yl]azetidin-1-yl]-3-fluoro-piperidine-1-carboxylate (Intermediate CPL)

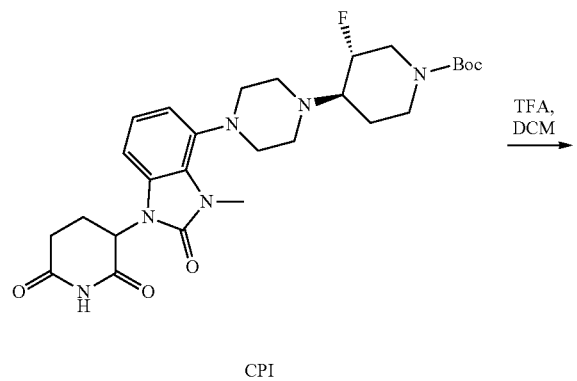

CPI

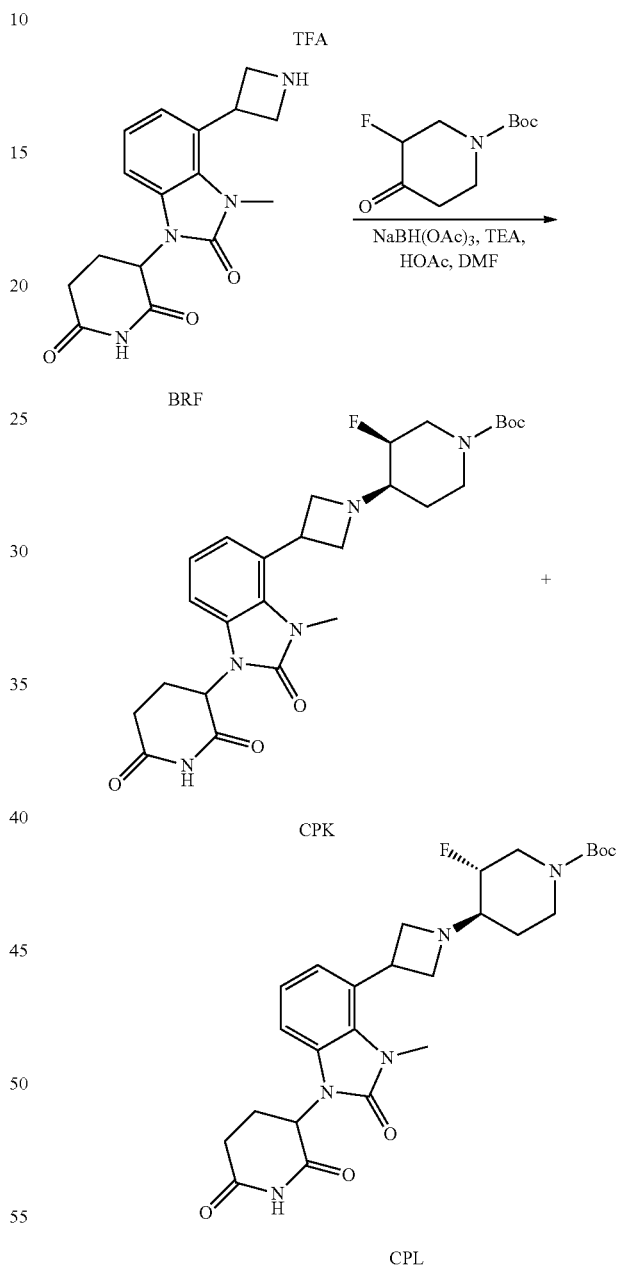

CPJ

A solution of tert-butyl (3R,4R)-4-[4-[1-(2,6-dioxo-3-piperidyl)-3-methyl-2-oxo-benzimidazol-4-yl]piperazin-1-yl]-3-fluoro-piperidine-1-carboxylate (30 mg, 55 μmol, Intermediate CPI) in DCM (0.5 mL) and TFA (0.1 mL) was stirred at 25° C. for 0.5 hrs. On completion, the reaction mixture was concentrated in vacuo to give the title compound (30 mg, 97% yield, TFA) as yellow oil. LC-MS (ESI+) m/z 445.4 (M+H)⁺.

To a solution of 3-[4-(azetidin-3-yl)-3-methyl-2-oxo-benzimidazol-1-yl]piperidine-2,6-dione (530 mg, 1.24 mmol, TFA, Intermediate BRF) in DMF (5 mL) and TEA (125 mg, 1.24 mmol) was stirred for 10 mins. Then, tert-butyl 3-fluoro-4-oxo-piperidine-1-carboxylate (268 mg, CAS #211108-50-8) and HOAc (74.3 mg, 1.24 mmol) was added until the pH=6-7, and the mixture was stirred at −10° C. for 30 min. Then NaBH(OAc)₃ (656 mg, 3.09 mmol) was added at 25° C. for 10 hrs. On completion, the reaction mixture was quenched with water (0.05 mL) to give a residue. The residue was purified by prep-HPLC (column: Phenomenex luna C18 150*25 mm*10 um; mobile phase: [water (FA)-ACN]) to give tert-butyl (3S,4R)-4-[3-[1-(2,6-dioxo-3-piperidyl)-3-methyl-2-oxo-benzimidazol-4-yl] azetidin-1-yl]-3-fluoro-piperidine-1-carboxylate (80.0 mg, 12.5% yield, t_R=0.284) as a white solid ($^1$H NMR (400 MHz, DMSO-d$_6$) δ 11.09 (s, 1H), 7.18 (d, J=7.6 Hz, 1H), 7.09-7.00 (m, 2H), 5.36 (d, J=5.2, 12.4 Hz, 1H), 4.76-4.58 (m, 1H), 4.24 (quin, J=7.2 Hz, 1H), 4.08-3.97 (m, 1H), 3.87-3.76 (m, 1H), 3.69-3.63 (m, 2H), 3.52 (s, 3H), 3.28 (s, 1H), 3.17-3.00 (m, 2H), 2.95-2.82 (m, 2H), 2.76-2.57 (m, 3H), 2.44-2.30 (m, 1H), 2.03-1.95 (m, 1H), 1.57-1.51 (m, 1H), 1.39 (s, 9H); LC-MS (ESI$^+$) m/z 516.2 (M+H)$^+$) and is tert-butyl (3R,4R)-4-[3-[1-(2,6-dioxo-3-piperidyl)-3-methyl-2-oxo-benzimidazol-4-yl]azetidin-1-yl]-3-fluoro-piperidine-1-carboxylate (80.0 mg, 12.5% yield, t_R=0.302) as a white solid ($^1$H NMR (400 MHz, DMSO-d6) δ 11.09 (s, 1H), 7.20 (d, J=7.6 Hz, 1H), 7.08-7.00 (m, 2H), 5.36 (dd, J=5.2, 12.4 Hz, 1H), 4.46-4.30 (m, 1H), 4.25-4.19 (m, 1H), 3.73-3.60 (m, 3H), 3.60-3.54 (m, 1H), 3.51 (s, 3H), 3.47 (s, 1H), 3.24 (dd, J=4.0, 7.6 Hz, 3H), 2.91-2.83 (m, 1H), 2.73-2.55 (m, 3H), 2.04-1.94 (m, 1H), 1.76-1.66 (m, 1H), 1.39 (s, 9H), 1.32-1.23 (m, 1H); LC-MS (ESI$^+$) m/z 516.2 (M+H)$^+$). The cis/trans configurations were assigned arbitrarily.

3-[4-[1-[(3S,4R)-3-Fluoro-4-piperidyl]azetidin-3-yl]-3-methyl-2-oxo-benzimidazol-1-yl] piperidine-2,6-dione (Intermediate CPM)

To a solution of tert-butyl (3S,4R)-4-[3-[1-(2,6-dioxo-3-piperidyl)-3-methyl-2-oxo-benzimidazol-4-yl]azetidin-1-yl]-3-fluoro-piperidine-1-carboxylate (50.0 mg, 97.0 μmol, Intermediate CPK) in DCM (3 mL) was added TFA (921 mg, 8.08 mmol), then the mixture was stirred for 2 hrs at 25° C. On completion, the mixture was concentrated in vacuo to give a residue to give the title compound (50.0 mg, 97.4% yield) as brown oil. LC-MS (ESI$^+$) m/z 416.1 (M+H)$^+$.

3-[4-[1-[(3R,4R)-3-Fluoro-4-piperidyl]azetidin-3-yl]-3-methyl-2-oxo-benzimidazol-1-yl] piperidine-2,6-dione (Intermediate CPN)

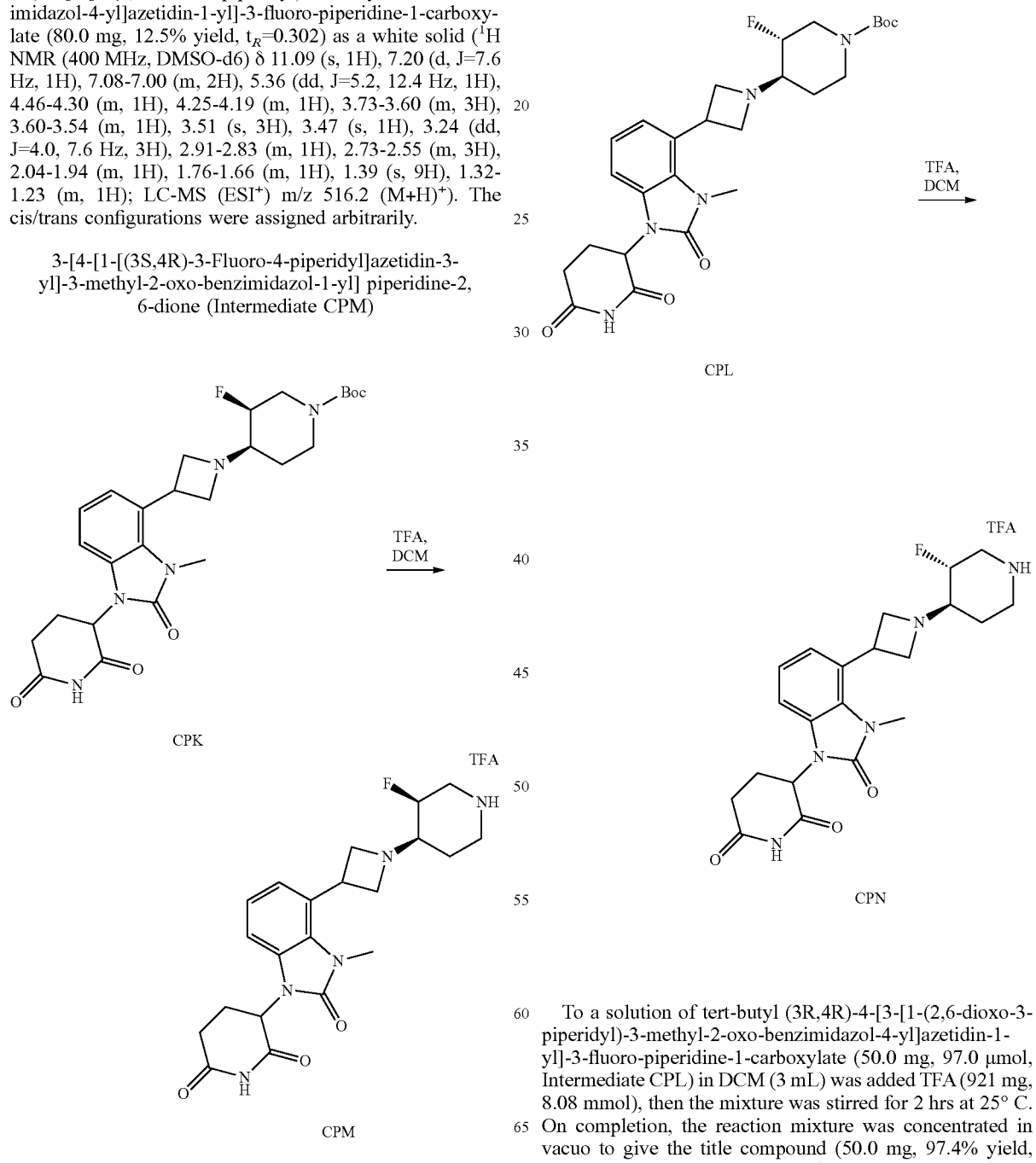

To a solution of tert-butyl (3R,4R)-4-[3-[1-(2,6-dioxo-3-piperidyl)-3-methyl-2-oxo-benzimidazol-4-yl]azetidin-1-yl]-3-fluoro-piperidine-1-carboxylate (50.0 mg, 97.0 μmol, Intermediate CPL) in DCM (3 mL) was added TFA (921 mg, 8.08 mmol), then the mixture was stirred for 2 hrs at 25° C. On completion, the reaction mixture was concentrated in vacuo to give the title compound (50.0 mg, 97.4% yield, TFA) as brown oil. LC-MS (ESI$^+$) m/z 416.1 (M+H)$^+$.

4-(5-Bromopyrazolo[3,4-c]pyridin-2-yl)-1-(hydroxymethyl)cyclohexanol (Intermediate CPO)

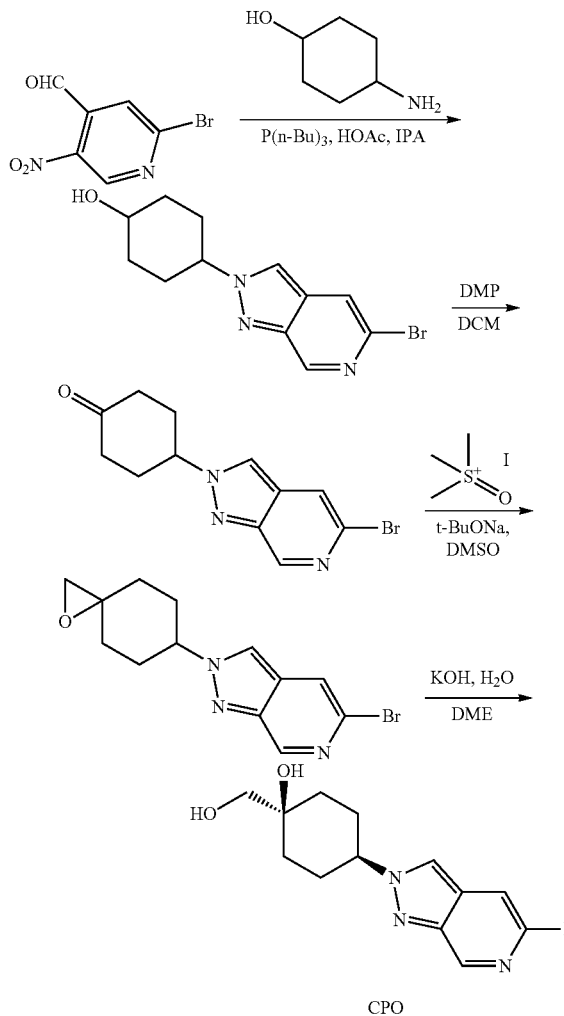

Step 1—4-(5-Bromopyrazolo[3,4-c]pyridin-2-yl)cyclohexanol. A mixture of 2-bromo-5-nitro-pyridine-4-carbaldehyde (5 g, 21.6 mmol, synthesized via Steps 1-2 of Intermediate BRR) and 4-aminocyclohexanol (4.99 g, 43.2 mmol, CAS #247489-62-9) in HOAc (0.05 mL) and i-PrOH (50 mL) was stirred at 80° C. for 1 hr under $N_2$. Next, the mixture was cooled to 25° C., then the tributylphosphane (13.1 g, 64.9 mmol) was added to the mixture under $N_2$. The mixture was then stirred at 80° C. for 4 hrs. On completion, the reaction mixture was concentrated in vacuo to give a residue. The residue was purified by column chromatography (SiO$_2$, PE:EA=5:1 to PE:EA=0:1, PE:EA=0:1, P1:Rf=0.45) then re-purified by reverse phase (0.1% FA condition). Next, the residue was triturated with EA:PE=1:10 (11 mL) to give the title compound (800 mg, 12% yield) as a yellow solid. $^1$H NMR (400 MHz, DMSO-d$_6$) δ 9.00 (d, J=5.2 Hz, 1H), 8.55 (d, J=3.6 Hz, 1H), 7.94 (dd, J=1.2, 3.6 Hz, 1H), 4.78-4.49 (m, 2H), 3.89 (d, J=2.8 Hz, 1H), 2.31 (m, J=3.6, 12.0 Hz, 1H), 2.10 (d, J=9.6 Hz, 1H), 1.98 (d, J=10.4 Hz, 1H), 1.91-1.84 (m, 1H), 1.79 (dd, J=3.2, 13.2 Hz, 1H), 1.72-1.58 (m, 1H), 1.49-1.33 (m, 1H); LC-MS (ESI$^+$) m/z 297.9 (M+H)$^+$.

Step 2—4-(5-Bromopyrazolo[3,4-c]pyridin-2-yl)cyclohexanone. To a solution of 4-(5-bromopyrazolo[3,4-c]pyridin-2-yl)cyclohexanol (700 mg, 2.36 mmol) in DCM (5 mL) was added DMP (1.20 g, 2.84 mmol). The reaction mixture was stirred at 25° C. for 3 hrs. On completion, the reaction mixture was quenched with saturated $Na_2S_2O_3$ (30 mL) and saturated NaHCO$_3$ (30 mL) at 25° C., and then the mixture was stirred for 30 minutes. The mixture was next extracted with DCM (2×30 mL). The combined organic layer was washed with NaHCO$_3$ (2×30 mL) and washed with saturated salt solution (2×30 mL). The combined organic layer was dried over Na$_2$SO$_4$, filtered and the filtrate was concentrated in vacuo to give the title compound (690 mg, 99% yield) as a white solid. $^1$H NMR (400 MHz, DMSO-d$_6$) δ 9.03 (s, 1H), 8.64 (s, 1H), 7.98 (d, J=1.2 Hz, 1H), 5.27-5.09 (m, 1H), 2.75-2.60 (m, 2H), 2.45-2.34 (m, 6H); LC-MS (ESI$^+$) m/z 295.9 (M+H)$^+$.

Step 3—5-Bromo-2-(1-oxaspiro[2.5]octan-6-yl)pyrazolo[3,4-c]pyridine. To a solution of t-BuONa (539 mg, 5.61 mmol) in DMSO (6 mL) was added (dimethyl(oxo)-16-sulfaneyl)methane iodide (1.23 g, 5.61 mmol, CAS #1774-47-6). The mixture was stirred at 65° C. for 2 hrs. Next, 4-(5-bromopyrazolo[3,4-c]pyridin-2-yl)cyclohexanone (550 mg, 1.87 mmol) was added and the mixture was stirred at 25° C. for 3 hrs. On completion, the reaction mixture was diluted with H$_2$O (20 mL) and extracted with EA (8 mL×3). The combined organic layers were washed with saturated NaCl (10 mL), dried over Na$_2$SO$_4$, filtered and concentrated in vacuo to give the title compound (450 mg, 78% yield) as a white solid. LC-MS (ESI$^+$) m/z 307.9 (M+H)$^+$.

Step 4—4-(5-Bromopyrazolo[3,4-c]pyridin-2-yl)-1-(hydroxymethyl)cyclohexanol. To a solution of 5-bromo-2-(1-oxaspiro[2.5]octan-6-yl)pyrazolo[3,4-c]pyridine (380 mg, 1.23 mmol) in DME (1 mL) and H$_2$O (4 mL) was added KOH (345 mg, 6.17 mmol). The mixture was stirred at 85° C. for 2 hrs. On completion, the reaction mixture was diluted with H$_2$O (10 mL) and filtered. The cake was dried in vacuo then purified by reverse phase (0.1% FA condition) to give the title compound (220 mg, 53% yield) as a white solid. $^1$H NMR (400 MHz, DMSO-d$_6$) δ 9.00 (t, J=1.2 Hz, 1H), 8.55 (d, J=0.8 Hz, 1H), 7.94 (d, J=1.2 Hz, 1H), 4.63 (t, J=6.0 Hz, 1H), 4.60-4.52 (m, 1H), 4.19 (s, 1H), 3.22 (d, J=6.0 Hz, 2H), 2.35-2.22 (m, 2H), 1.92 (dd, J=2.0, 11.6 Hz, 2H), 1.66-1.56 (m, 4H); LC-MS (ESI$^+$) m/z 326.0 (M+H)$^+$.

N-[2-(4-formyl-4-hydroxy-cyclohexyl)pyrazolo[3,4-c]pyridin-5-yl]-6-(trifluoromethyl) pyridine-2-carboxamide (Intermediate CPP)

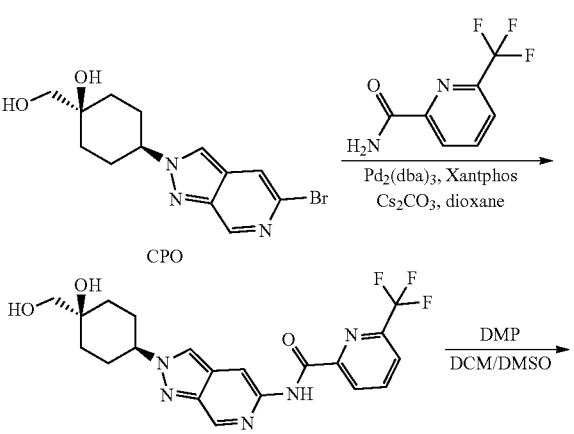

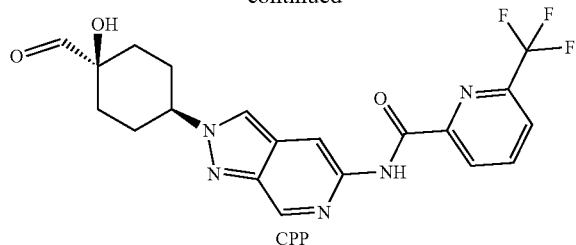

Step 1—N-[2-[4-hydroxy-4-(hydroxymethyl)cyclohexyl]pyrazolo[3,4-c]pyridin-5-yl]-6-(trifluoromethyl)pyridine-2-carboxamide. To a mixture of 4-(5-bromopyrazolo[3,4-c]pyridin-2-yl)-1-(hydroxymethyl)cyclohexanol (200 mg, 613 µmol, Intermediate CPO) and 6-(trifluoromethyl)pyridine-2-carboxamide (128 mg, 674 µmol, CAS #22245-84-7) in dioxane (2 mL) was added 4 Å molecular sieves (5 mg), Cs$_2$CO$_3$ (399 mg, 1.23 mmol), [2-(2-aminophenyl)phenyl]-methylsulfonyloxy-palladium dicyclohexyl-[3,6-dimethoxy-2-(2,4,6-triisopropylphenyl)phenyl] phosphane (55.5 mg, 61.3 µmol). The reaction mixture was then stirred at 100° C. for 16 hrs. On completion, the reaction mixture was filtered and the filtrate was concentrated in vacuo to give a residue. The residue was purified by column chromatography (SiO$_2$, PE:EA=5:1 to PE:EA=0:1,PE:EA=0:1, P1:Rf=0.15) and reverse phase (0.1% FA condition) to give the title compound (110 mg, 41% yield) as a white solid. $^1$H NMR (400 MHz, DMSO-d$_6$) δ 10.19 (s, 1H), 9.06 (s, 1H), 8.60 (s, 1H), 8.50-8.45 (m, 2H), 8.45-8.37 (m, 1H), 8.23 (d, J=7.6 Hz, 1H), 4.63 (t, J=5.4 Hz, 1H), 4.53 (tt, J=3.6, 12.0 Hz, 1H), 4.18 (s, 1H), 3.24 (d, J=5.2 Hz, 2H), 2.37-2.22 (m, 2H), 2.02-1.90 (m, 2H), 1.68-1.58 (m, 4H); LC-MS (ESI$^+$) m/z 436.2 (M+H)$^+$.

Step 2—N-[2-(4-formyl-4-hydroxy-cyclohexyl)pyrazolo[3,4-c]pyridin-5-yl]-6-(trifluoromethyl) pyridine-2-carboxamide. To a solution of N-[2-[4-hydroxy-4-(hydroxymethyl)cyclohexyl]pyrazolo[3,4-c]pyridin-5-yl]-6-(trifluoromethyl)pyridine-2-carboxamide (95 mg, 218 µmol) in DMSO (1 mL) and DCM (1 mL) was added DMP (185 mg, 436 µmol). The reaction mixture was stirred at 25° C. for 3 hrs. On completion, the reaction mixture was quenched with saturated Na$_2$S$_2$O$_3$ (20 mL) and saturated NaHCO$_3$ (20 mL) at 25° C., and then stirred for 30 mins. The mixture was extracted with EA (2×10 mL). Then the combined organic layer was washed with NaHCO$_3$ (2×15 mL) and washed with saturated salt solution (2×15 mL). The combined organic layer was dried over Na$_2$SO$_4$, filtered and the filtrate was concentrated in vacuo to give the title compound (94 mg, 99% yield) as a yellow solid. LC-MS (ESI$^+$) m/z 434.2 (M+H)$^+$.

(3-Bromocyclobutoxy)methylbenzene (Intermediate CPQ)

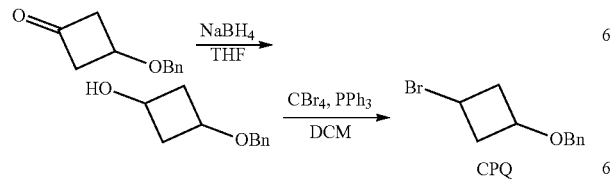

Step 1—3-Benzyloxycyclobutanol. To a solution of 3-benzyloxycyclobutanone (50.0 g, 283 mmol, CAS #30830-27-4) in THF (800 mL) was added NaBH$_4$ (12.9 g, 343 mmol) and the mixture was degassed and purged with N$_2$ for three times. Then the mixture was stirred at −10° C. for 2 hrs under N$_2$ atmosphere. On completion, the reaction mixture was quenched with saturated NH$_4$Cl (300 mL) aqueous, and then extracted with ethyl acetate (300 mL×3). The combined organic layer was dried over Na$_2$SO$_4$, filtered and concentrated in vacuo to give the title compound (49 g, 98% yield) as a colorless oil. $^1$H NMR (400 MHz, CDCl$_3$) δ 7.39-7.28 (m, 5H), 4.43 (s, 2H), 3.93 (t, J=6.8 Hz, 1H), 3.64 (t, J=6.8 Hz, 1H), 2.73 (m, J=3.2, 6.4, 9.6 Hz, 2H), 2.01-1.86 (m, 2H).

Step 2—(3-Bromocyclobutoxy)methylbenzene. To a solution of 3-benzyloxycyclobutanol (23.5 g, 131 mmol) in DCM (800 mL) was added CBr$_4$ (56.8 g, 171 mmol) and PPh$_3$ (69.1 g, 263 mmol). Then the mixture was degassed and purged with N$_2$ three times, and then the mixture was stirred at 20° C. for 16 hrs under N$_2$ atmosphere. On completion, the reaction liquid was filtered. The filtrate was concentrated in vacuo to give a residue. The residue was purified by column chromatography (SiO$_2$, petroleum ether/ethyl acetate=1/0 to 10/1) to give the title compound (14 g, 17% yield, 80% purity) as a colorless oil. $^1$H NMR (400 MHz, CDCl$_3$) δ 7.39-7.30 (m, 5H), 4.60-4.47 (m, 2H), 4.43 (s, 2H), 2.86-2.57 (m, 4H).

3-Methyl-4-(1-oxaspiro[2.3]hexan-5-yl)-1-(2-trimethylsilylethoxymethyl)benzimidazol-2-one (Intermediate CPR)

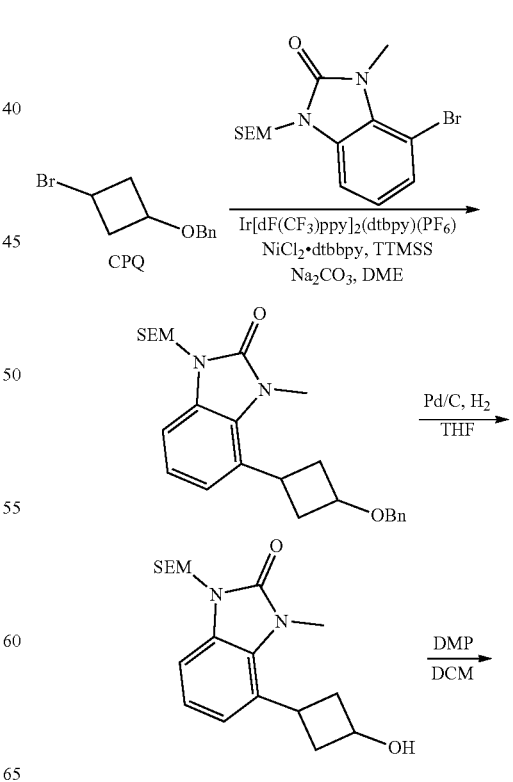

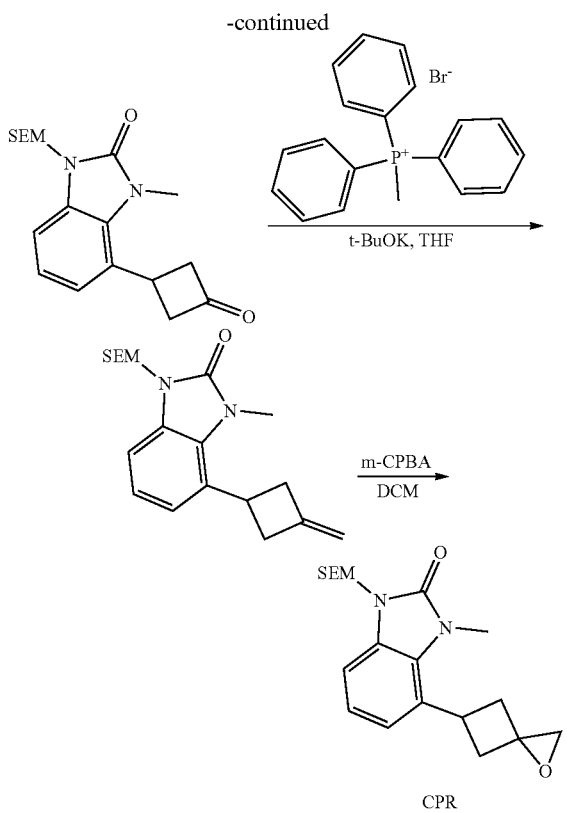

CPR

Step 1—4-(3-Benzyloxycyclobutyl)-3-methyl-1-(2-trimethylsilylethoxymethyl)benzimidazol-2-one. To an 15 mL vial equipped with a stir bar was added 4-bromo-3-methyl-1-(2-trimethylsilylethoxymethyl)benzimidazol-2-one (15.9 g, 44.6 mmol, synthesized via Step 1 of Intermediate COD), (3-bromocyclobutoxy)methylbenzene (14 g, 58.0 mmol, Intermediate CPQ) bis[3,5-difluoro-2-[5-(trifluoromethyl)-2-pyridyl]phenyl]iridium(1+); 4-tert-butyl-2-(4-tert-butyl-2-pyridyl) pyridine hexafluorophosphate (501 mg, 446 µmol), NiCl$_2$·dtbbpy (266 mg, 669 µmol), TTMSS (11.1 g, 44.6 mmol) and Na$_2$CO$_3$ (9.47 g, 89.3 mmol) in DME (400 mL). The vial was sealed and placed under nitrogen and the reaction was stirred and irradiated with a 10 W blue LED lamp (3 cm away), with cooling water to keep the reaction temperature at 25° C. for 14 hrs. On completion, the reaction mixture was poured into water (150 mL), and then extracted with ethyl acetate (150 mL×3). The combined organic layers were washed with brine (100 mL), dried over sodium sulfate and filtered. The filtrate was concentrated in vacuo to give a residue. The residue was purified by column chromatography (SiO$_2$, petroleum ether/ethyl acetate=10/1 to 0/1) to give the title compound (8.50 g, 43% yield) as a brown oil. $^1$H NMR (400 MHz, CDCl$_3$) δ 7.41-7.29 (m, 5H), 7.16-7.06 (m, 3H), 5.31 (s, 2H), 4.51 (s, 2H), 4.10 (s, 1H), 3.67-3.62 (m, 3H), 3.62-3.58 (m, 2H), 2.74-2.60 (m, 2H), 2.59-2.49 (m, 1H), 2.34-2.21 (m, 2H), 0.96-0.89 (m, 2H), 0.00-0.06 (m, 9H); LC-MS (ESI$^+$) m/z 461.2 (M+Na)$^+$.

Step 2—4-(3-Hydroxycyclobutyl)-3-methyl-1-(2-trimethylsilylethoxymethyl)benzimidazol-2-one. To a solution of 4-(3-benzyloxycyclobutyl)-3-methyl-1-(2-trimethylsilylethoxymethyl)benzimidazol-2-one (6.70 g, 15.2 mmol) in THF (100 mL) was added Pd/C (10 wt %, 6.70 g) under N$_2$ atmosphere. The suspension was degassed and purged with H$_2$ three times. The mixture was stirred under H$_2$ (50 Psi) at 20° C. for 12 hrs. On completion, the reaction liquid was filtered. The filtrate was concentrated in vacuo to give a residue. The residue was purified by column chromatography (SiO$_2$, petroleum ether/ethyl acetate=10/1 to 0/1) to give the title compound (3.6 g, 65% yield) as a light yellow oil. $^1$H NMR (400 MHz, CDCl$_3$) δ 7.10 (dd, J=6.8, 14.4 Hz, 3H), 5.31 (s, 2H), 4.64-4.30 (m, 1H), 4.21-4.04 (m, 1H), 3.64 (d, J=13.6 Hz, 3H), 3.63-3.56 (m, 2H), 3.56-3.43 (m, 1H), 2.83-2.58 (m, 2H), 2.48-2.17 (m, 2H), 0.92 (t, J=8.0 Hz, 2H), 0.03 (s, 9H); LC-MS (ESI$^+$) m/z 371.1 (M+Na)$^+$.

Step 3—3-Methyl-4-(3-oxocyclobutyl)-1-(2-trimethylsilylethoxymethyl)benzimidazol-2-one. To a solution of 4-(3-hydroxycyclobutyl)-3-methyl-1-(2-trimethylsilylethoxymethyl)benzimidazol-2-one (3.50 g, 10.0 mmol) in DCM (50 mL) was added DMP (5.54 g, 13.0 mmol). The mixture was then stirred at 25° C. for 2 hrs. On completion, the reaction mixture was quenched with saturated NaHCO$_3$ (50 mL) aqueous and saturated Na$_2$S$_2$O$_3$ (50 mL) aqueous, and then extracted with DCM (80 mL×3). The combined organic layers were washed with brine (50 mL), dried over Na$_2$SO$_4$ and filtered. The filtrate was concentrated in vacuo to give a residue. The residue was purified by column chromatography (SiO$_2$, petroleum ether/ethyl acetate=10/1 to 0/1) to give the title compound (3.2 g, 89% yield) as an off-white solid. $^1$H NMR (400 MHz, CDCl$_3$) δ 7.20-7.03 (m, 3H), 5.32 (s, 2H), 4.36-4.22 (m, 1H), 3.70 (s, 3H), 3.65-3.58 (m, 2H), 3.57-3.47 (m, 2H), 3.44-3.34 (m, 2H), 0.99-0.86 (m, 2H), 0.03 (s, 9H); LC-MS (ESI$^+$) m/z 369.1 (M+Na)$^+$.

Step 4—3-Methyl-4-(3-methylenecyclobutyl)-1-(2-trimethylsilylethoxymethyl)benzimidazol-2-one. To a solution of methyl(triphenyl)phosphonium; bromide (1.34 g, 3.75 mmol, CAS #1779-49-3) in THF (15 mL) was added n-BuLi (2.5 M, 1.73 mL) and the mixture was stirred at 0° C. for 0.5 hr. Next, 3-methyl-4-(3-oxocyclobutyl)-1-(2-trimethylsilylethoxymethyl)benzimidazol-2-one (1 g, 2.89 mmol) was added dropwise at 0° C. After addition, the mixture was stirred at 25° C. for 14.5 hrs. On completion, the reaction mixture was quenched with saturated NH$_4$Cl (50 mL) aqueous, and then extracted with ethyl acetate (50 mL×3). The combined organic layers were washed with brine (50 mL), dried over Na$_2$SO$_4$ and filtered. The filtrate was concentrated in vacuo to give a residue. The residue was purified by column chromatography (SiO$_2$, petroleum ether/ethyl acetate=1/0 to 2/1) to give the title compound (580 mg, 54% yield) as a colorless oil. $^1$H NMR (400 MHz, CDCl$_3$) δ 7.20 (dd, J=1.2, 7.6 Hz, 1H), 7.14-7.05 (m, 2H), 5.32 (s, 2H), 4.94-4.85 (m, 2H), 4.12 (t, J=8.4 Hz, 1H), 3.66 (s, 3H), 3.61 (dd, J=7.6, 8.8 Hz, 2H), 3.16-3.07 (m, 2H), 3.07-2.97 (m, 2H), 0.96-0.90 (m, 2H), 0.03--0.08 (m, 9H); LC-MS (ESI$^+$) m/z 367.1 (M+Na)$^+$.

Step 5—3-Methyl-4-(1-oxaspiro[2.3]hexan-5-yl)-1-(2-trimethylsilylethoxymethyl)benzimidazol-2-one. To a solution of 3-methyl-4-(3-methylenecyclobutyl)-1-(2-trimethylsilylethoxymethyl)benzimidazol-2-one (660 mg, 1.92 mmol) in DCM (5 mL) was added m-CPBA (583 mg, 2.87 mmol, 85% solution). The mixture was stirred at 25° C. for 6 hrs. On completion, the reaction mixture was quenched with saturated NaHCO$_3$ (20 mL) and saturated Na$_2$S$_2$O$_3$ (20 mL) aqueous, and then extracted with DCM (30 mL×3). The combined organic layers were washed with brine (30 mL), dried over Na$_2$SO$_4$ and filtered. The filtrate was concentrated in vacuo to give a residue. The residue was purified by column chromatography (SiO$_2$, petroleum ether/ethyl acetate=1/0 to 1/1) to give the title compound (600 mg, 83% yield) as a light yellow oil. $^1$H NMR (400 MHz, CDCl$_3$) δ 7.25-7.20 (m, 1H), 7.18-7.07 (m, 2H), 5.32 (s, 2H), 4.30-3.94 (m, 1H), 3.71-3.65 (m, 3H), 3.62 (t, J=8.4 Hz, 2H), 3.02-2.83 (m, 3H), 2.82 (s, 1H), 2.75-2.64 (m, 2H), 0.96-0.90 (m, 2H), 0.02 (s, 9H); LC-MS (ESI+) m/z 383.1 (M+Na)+.

Tert-butyl 4-[[1-hydroxy-3-[3-methyl-2-oxo-1-(2-trimethylsilylethoxymethyl)benzimidazol-4-yl]cyclobutyl]methyl]piperazine-1-carboxylate (Intermediate CPS) and Tert-butyl 4-[[1-hydroxy-3-[3-methyl-2-oxo-1-(2-trimethylsilylethoxymethyl)benzimidazol-4-yl]cyclobutyl]methyl]piperazine-1-carboxylate (Intermediate CPT)

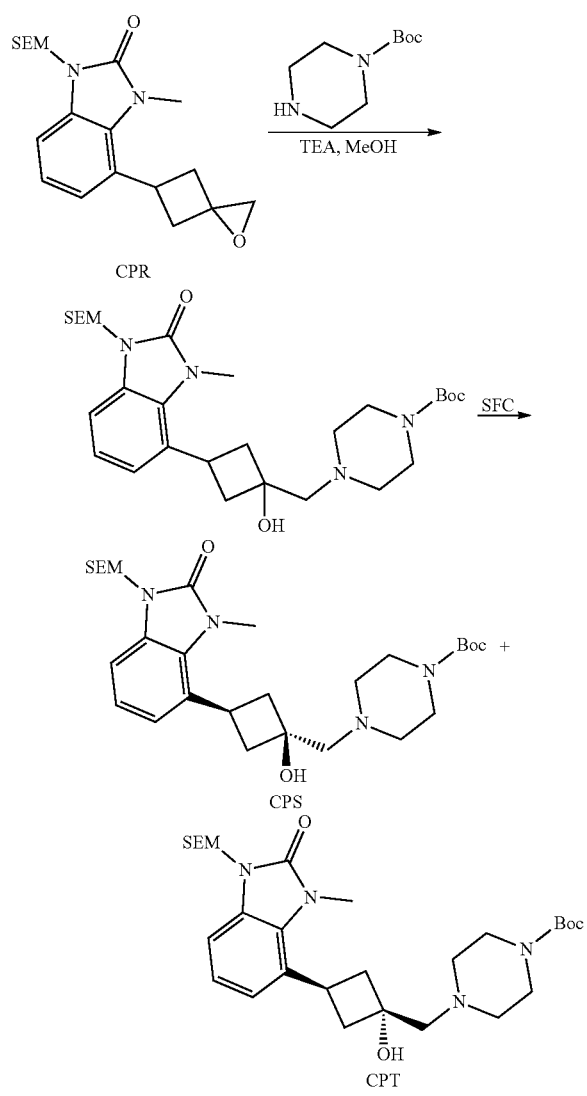

Step 1—Tert-butyl 4-[[1-hydroxy-3-[3-methyl-2-oxo-1-(2-trimethylsilylethoxymethyl)benzimidazol-4-yl]cyclobutyl]methyl]piperazine-1-carboxylate. To a solution of 3-methyl-4-(1-oxaspiro[2.3]hexan-5-yl)-1-(2-trimethylsilylethoxymethyl)benzimidazol-2-one (600 mg, 1.66 mmol, Intermediate CPR) in MeOH (10 mL) was added TEA (336 mg, 3.33 mmol) and tert-butyl piperazine-1-carboxylate (464 mg, 2.50 mmol, CAS #143238-38-4). The mixture was then stirred at 65° C. for 3 hrs. On completion, the reaction mixture was poured into water (20 mL), and then extracted with ethyl acetate (20 mL×3). The combined organic layers were washed with brine (20 mL), dried over sodium sulfate and filtered. The filtrate was concentrated in vacuo to give a residue. The residue was purified by column chromatography (SiO2, petroleum ether/ethyl acetate=1/0 to 0/1). to give the title compound (750 mg, 74% yield) as a light yellow oil. 1H NMR (400 MHz, CDCl3) δ 7.21-7.01 (m, 3H), 5.31 (s, 2H), 4.37 (t, J=8.8 Hz, 1H), 3.73-3.64 (m, 3H), 3.64-3.55 (m, 3H), 3.48 (d, J=4.0 Hz, 4H), 2.64-2.43 (m, 8H), 2.41-2.27 (m, 2H), 1.51-1.44 (m, 9H), 0.97-0.88 (m, 2H), 0.03 (s, 9H); LC-MS (ESI+) m/z 547.2 (M+H)+.

Step 2—Tert-butyl 4-[[1-hydroxy-3-[3-methyl-2-oxo-1-(2-trimethylsilylethoxymethyl)benzimidazol-4-yl]cyclobutyl]methyl]piperazine-1-carboxylate and Tert-butyl 4-[[1-hydroxy-3-[3-methyl-2-oxo-1-(2-trimethylsilylethoxymethyl)benzimidazol-4-yl]cyclobutyl]methyl]piperazine-1-carboxylate. Tert-butyl4-[[1-hydroxy-3-[3-methyl-2-oxo-1-(2-trimethylsilylethoxymethyl)benzimidazol-4-yl] cyclobutyl]methyl]piperazine-1-carboxylate (750 mg, 1.37 mmol) was separated by SFC (column: DAICEL CHIRALCEL OX (250 mm×30 mm, 10 um); mobile phase: [CO2-MeOH (0.1% NH3H2O)]) to give tert-butyl 4-[[1-hydroxy-3-[3-methyl-2-oxo-1-(2-trimethylsilylethoxymethyl)benzimidazol-4-yl]cyclobutyl]methyl] piperazine-1-carboxylate (180 mg 24% yield, tR=0.968) as a light yellow oil (1H NMR (400 MHz, CDCl3) δ 7.21 (d, J=7.2 Hz, 1H), 7.15-7.04 (m, 2H), 5.31 (s, 2H), 3.64 (s, 3H), 3.63-3.58 (m, 3H), 3.51 (s, 4H), 2.80 (s, 2H), 2.70-2.45 (m, 8H), 1.50-1.47 (m, 9H), 1.39-1.22 (m, 1H), 0.97-0.88 (m, 2H), 0.03 (s, 9H); LC-MS (ESI+) m/z 547.3 (M+H)+) and tert-butyl 4-[[1-hydroxy-3-[3-methyl-2-oxo-1-(2-trimethylsilylethoxymethyl)benzimidazol-4-yl]cyclobutyl]methyl] piperazine-1-carboxylate (300 mg, 37% yield, tR=1.237) as a light yellow oil (1H NMR (400 MHz, CDCl3) δ 7.15-7.00 (m, 3H), 5.31 (s, 2H), 4.38 (t, J=8.8 Hz, 1H), 3.68 (s, 3H), 3.64-3.58 (m, 2H), 3.50 (s, 2H), 3.49-3.41 (m, 3H), 2.65-2.47 (m, 8H), 2.39-2.29 (m, 2H), 1.47 (s, 9H), 0.97-0.89 (m, 2H), 0.03 (s, 9H); LC-MS (ESI+) m/z 547.3 (M+H)+). The cis/trans confirmation was confirmed by 2D NMR.

3-[4-[3-Hydroxy-3-(piperazin-1-ylmethyl)cyclobutyl]-3-methyl-2-oxo-benzimidazol-1-yl]piperidine-2,6-dione (Intermediate CPU)

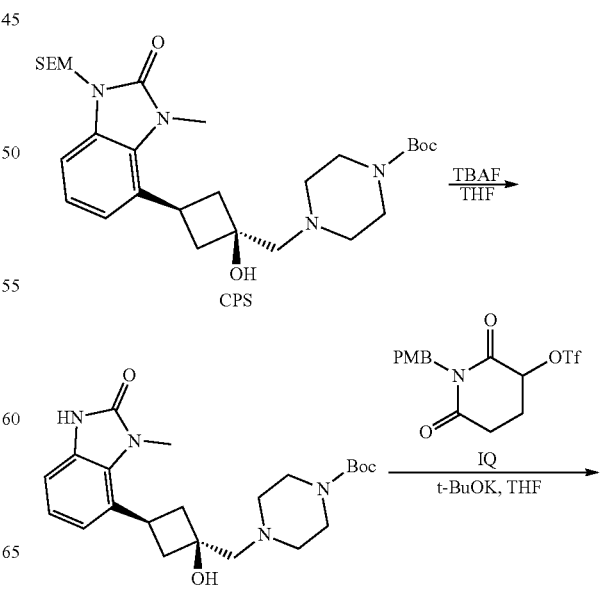

-continued

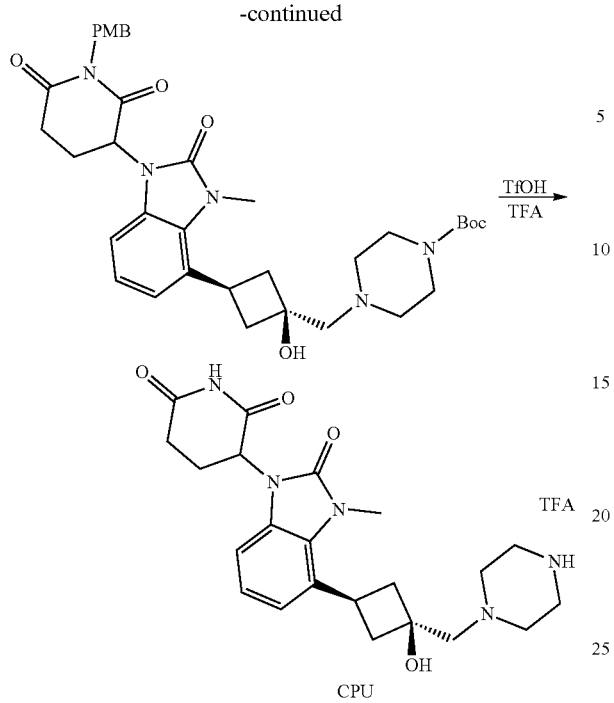

Step 1—Tert-butyl 4-[[1-hydroxy-3-[3-methyl-2-oxo-1-(2-trimethylsilylethoxymethyl)benzimidazol-4-yl]cyclobutyl]methyl]piperazine-1-carboxylate. To a solution of tert-butyl 4-[[1-hydroxy-3-[3-methyl-2-oxo-1-(2-trimethylsilylethoxymethyl) benzimidazol-4-yl]cyclobutyl]methyl]piperazine-1-carboxylate (180 mg, 329 μmol, Intermediate CPS) in TBAF (3 mL) was stirred at 65° C. for 5 hrs. On completion, the reaction mixture was poured into water (5 mL), and then extracted with ethyl acetate (5 mL×3). The combined organic layers were washed with brine (5 mL), dried over sodium sulfate and filtered. The filtrate was concentrated in vacuo to give a residue. The crude product was purified by reversed-phase (0.1% FA condition) and by prep-TLC (ethyl acetate:methanol=5:1) to give the title compound (70.0 mg, 48% yield) as a white solid. $^1$H NMR (400 MHz, CDCl$_3$) δ 8.28 (s, 1H), 7.20-7.15 (m, 1H), 7.08 (t, J=7.6 Hz, 1H), 6.93 (d, J=7.6 Hz, 1H), 3.63 (s, 3H), 3.62-3.57 (m, 1H), 3.51 (s, 4H), 2.81 (s, 2H), 2.62 (d, J=14.0 Hz, 4H), 2.57-2.46 (m, 4H), 1.48 (s, 9H); LC-MS (ESI$^+$) m/z 417.1 (M+H)$^+$.

Step 2—Tert-butyl 4-[[1-hydroxy-3-[1-[1-[(4-methoxyphenyl)methyl]-2,6-dioxo-3-piperidyl]-3-methyl-2-oxo-benzimidazol-4-yl]cyclobutyl]methyl]piperazine-1-carboxylate. To a solution of tert-butyl 4-[[1-hydroxy-3-(3-methyl-2-oxo-1H-benzimidazol-4-yl)cyclobutyl]methyl]piperazine-1-carboxylate (70.0 mg, 168 μmol) in THF (1 mL) was added t-BuOK (37.7 mg, 336 μmol) at −10° C. and stirred for −10° C. for 0.5 h. Next, [1-[(4-methoxyphenyl)methyl]-2,6-dioxo-3-piperidyl] trifluoromethanesulfonate (192 mg, 504 μmol, Intermediate IQ) was added and the mixture was stirred at −10° C. for 1.5 hrs. On completion, the reaction mixture was poured into water (5 mL), and then extracted with ethyl acetate (5 mL×3). The combined organic layers were washed with brine (5 mL), dried over sodium sulfate and filtered. The filtrate was concentrated in vacuo to give a residue. The crude product was purified by reversed-phase (FA condition) to give the title compound (45 mg, 35% yield) as a white solid. $^1$H NMR (400 MHz, CDCl$_3$) δ 7.41-7.35 (m, 2H), 7.18 (d, J=8.0 Hz, 1H), 6.97 (t, J=8.0 Hz, 1H), 6.83 (d, J=8.4 Hz, 2H), 6.39 (d, J=7.6 Hz, 1H), 5.20 (dd, J=5.6, 12.8 Hz, 1H), 5.03-4.92 (m, 2H), 3.80 (s, 3H), 3.66 (s, 3H), 3.52 (s, 3H), 3.09-2.96 (m, 1H), 2.91-2.74 (m, 3H), 2.71-2.59 (m, 5H), 2.58-2.46 (m, 4H), 2.20-2.11 (m, 1H), 1.94-1.88 (m, 1H), 1.48 (s, 9H), 1.27 (d, J=4.0 Hz, 1H); LC-MS (ESI$^+$) m/z 648.3 (M+H)$^+$.

Step 3—3-[4-[3-Hydroxy-3-(piperazin-1-ylmethyl)cyclobutyl]-3-methyl-2-oxo-benzimidazol-1-yl]piperidine-2,6-dione. To a solution of tert-butyl 4-[[1-hydroxy-3-[1-[1-[(4-methoxyphenyl)methyl]-2,6-dioxo-3-piperidyl]-3-methyl-2-oxo-benzimidazol-4-yl]cyclobutyl]methyl]piperazine-1-carboxylate (40.0 mg, 61.7 μmol) in TFA (0.5 mL) and TfOH (0.1 mL) was stirred at 70° C. for 0.5 hrs. On completion, the reaction mixture was concentrated in vacuo to give the title compound (33.0 mg, 98% yield, TFA) as a black brown oil. LC-MS (ESI$^+$) m/z 428.2 (M+H)$^+$.

4-(Azetidin-3-yl)-3-methyl-1H-benzimidazol-2-one (Intermediate CPV)

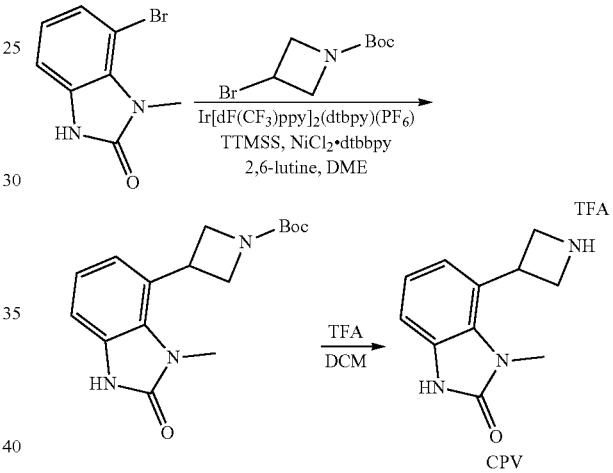

Step 1—Tert-butyl 3-(3-methyl-2-oxo-1H-benzimidazol-4-yl)azetidine-1-carboxylate. To an 15 mL vial equipped with a stir bar was added 4-bromo-3-methyl-1H-benzimidazol-2-one (5.50 g, 13.21 mmol, synthesized via Steps 1-3 of Intermediate HP), tert-butyl 3-bromoazetidine-1-carboxylate (11.4 g, 26.4 mmol, CAS #1064194-10-0), Ir[dF(CF$_3$)ppy]$_2$(dtbpy)(PF$_6$) (272 mg, 132 μmol), NiCl$_2$·dtbbpy (145 mg, 198 μmol), TTMSS (6.03 g, 13.2 mmol) and 2,6-lutidine (5.19 g, 26.4 mmol) in DME (72 mL). Then the vial was sealed and placed under nitrogen and the reaction was stirred and irradiated with a blue 10 W LED lamp (3 cm away), with cooling water to keep the reaction temperature at 25° C. for 14 hrs. On completion, the reaction mixture filtered and concentrated in vacuo to give a residue. The residue was triturated with 20 mL solution PE/EA=5/1. Then the residue was filtered and concentrated in vacuo to give the title compound (4.80 g, 70% yield) as a yellow solid. $^1$H NMR (400 MHz, DMSO-d$_6$) δ 10.90 (s, 1H), 7.14 (d, J=8.0 Hz, 1H), 7.03 (t, J=8.0 Hz, 1H), 6.89 (d, J=7.2 Hz, 1H), 4.48-4.36 (m, 1H), 4.26 (t, J=8.4 Hz, 2H), 3.94 (t, J=7.2 Hz, 2H), 3.43 (s, 3H), 1.40 (s, 9H); LC-MS (ESI$^+$) m/z 248.2 (M−56+H)$^+$.

Step 2—4-(Azetidin-3-yl)-3-methyl-1H-benzimidazol-2-one. To a solution of tert-butyl 3-(3-methyl-2-oxo-1H-benzimidazol-4-yl)azetidine-1-carboxylate (4.50 g, 8.24 mmol)

in DCM (50 mL) was added TFA (1.70 g, 44.9 mmol), then the mixture was stirred at 25° C. for 2 hrs. On completion, the reaction mixture was concentrated in vacuo to give the title compound (4.5 g, 96% yield) as brown oil. LC-MS (ESI$^+$) m/z 204.1 (M+H)$^+$.

Tert-butyl (3S,4R)-3-fluoro-4-[3-(3-methyl-2-oxo-1H-benzimidazol-4-yl)azetidin-1-yl]piperidine-1-carboxylate (Intermediate CPW) and tert-butyl (3S,4S)-3-fluoro-4-[3-(3-methyl-2-oxo-1H-benzimidazol-4-yl)azetidin-1-yl]piperidine-1-carboxylate (Intermediate CPX)

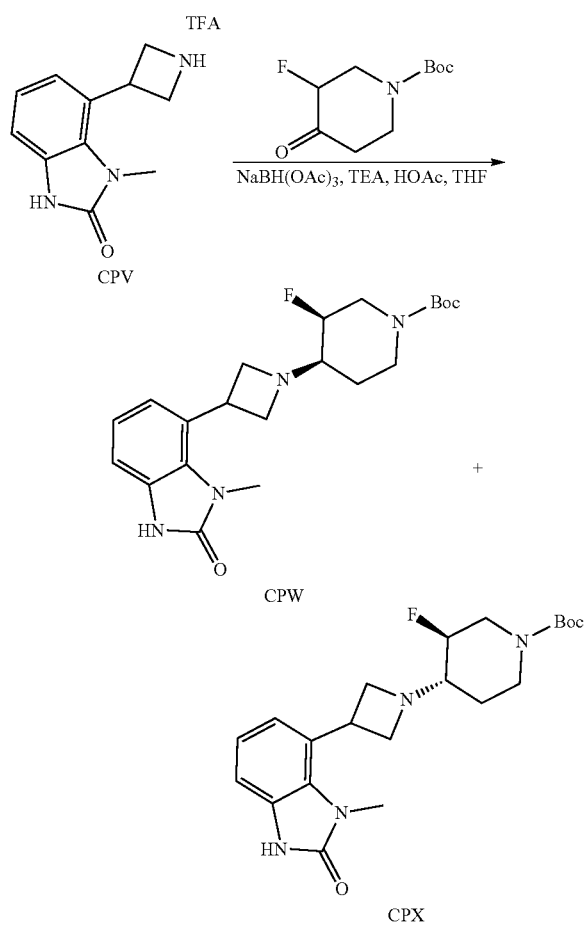

To a solution of 4-(azetidin-3-yl)-3-methyl-1H-benzimidazol-2-one (4.00 g, 12.6 mmol, TFA, Intermediate CPV) in THF (50 mL) and TEA (638 mg, 6.30 mmol) was stirred for 10 mins at −10° C. Then tert-butyl 3-fluoro-4-oxo-piperidine-1-carboxylate (3.01 g, 13.87 mmol), and HOAc (379 mg, 6.30 mmol) was added until the pH=6-7, and the mixture was stirred at −10° C. for 30 min. Then NaBH(OAc)$_3$ (6.68 g, 31.5 mmol) was added and the mixture was stirred at −10° C. for 2 hrs. On completion, the reaction mixture was quenched with water (2 mL) to give a residue. The residue was purified by prep-HPLC (column: Phenomenex luna C18 (250*70 mm, 15 um); mobile phase: [water (FA)-ACN]) to give tert-butyl (3S,4R)-3-fluoro-4-[3-(3-methyl-2-oxo-1H-benzimidazol-4-yl) azetidin-1-yl] piperidine-1-carboxylate (1.40 g, 27% yield, t$_R$=0.241) as a yellow solid ($^1$H NMR (400 MHz, CHLOROFORM-d) δ 10.44 (s, 1H), 7.03-6.94 (m, 3H), 4.98-4.81 (m, 1H), 4.68-4.59 (m, 1H), 4.41-4.23 (m, 3H), 4.03-3.83 (m, 2H), 3.48 (s, 3H), 3.20-2.75 (m, 4H), 1.98-1.73 (m, 2H), 1.45 (s, 9H); LC-MS (ESI$^+$) m/z 405.3 (M+H)$^+$) and tert-butyl (3S,4S)-3-fluoro-4-[3-(3-methyl-2-oxo-1H-benzimidazol-4-yl)azetidin-1-yl]piperidine-1-carboxylate (1.20 g, 23.5% yield, t$_R$=0.275) as a yellow solid ($^1$H NMR (400 MHz, CHLOROFORM-d) δ 9.72-9.56 (m, 1H), 7.12-7.00 (m, 3H), 5.10-4.86 (m, 2H), 4.84-4.50 (m, 4H), 4.25 (s, 2H), 4.07-3.94 (m, 1H), 3.15 (d, J=8.4 Hz, 1H), 2.73 (d, J=10.0 Hz, 2H), 2.07-1.88 (m, 2H), 1.74 (dd, J=4.8, 12.4 Hz, 2H), 1.48 (s, 9H); LC-MS (ESI$^+$) m/z 405.3 (M+H)$^+$). The cis/trans confirmation was confirmed by 2D NMR.

3-[4-[1-[(3S,4S)-3-Fluoro-4-piperidyl]azetidin-3-yl]-3-methyl-2-oxo-benzimidazol-1-yl]piperidine-2,6-dione (Intermediate CPY)

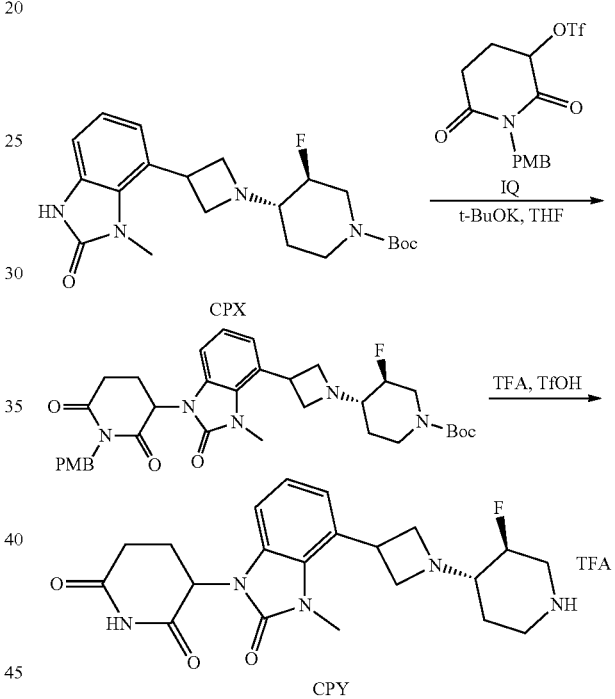

Step 1—Tert-butyl (3S,4S)-3-fluoro-4-[3-[1-[1-[(4-methoxyphenyl)methyl]-2,6-dioxo-3-piperidyl]-3-methyl-2-oxo-benzimidazol-4-yl]azetidin-1-yl]piperidine-1-carboxylate. To a solution of tert-butyl (3S,4S)-3-fluoro-4-[3-(3-methyl-2-oxo-1H-benzimidazol-4-yl)azetidin-1-yl] piperidine-1-carboxylate (500 mg, 1.24 mmol, Intermediate CPX) in THF (5 mL) was added t-BuOK (277 mg, 2.47 mmol) at −10° C. and the mixture was stirred for 30 min. Then [1-[(4-methoxyphenyl)methyl]-2,6-dioxo-3-piperidyl] trifluoromethanesulfonate (943 mg, 2.47 mmol, Intermediate IQ) was added and the reaction mixture was stirred at −10° C. for 1.5 hrs. On completion, the residue was diluted with water (200 mL) and extracted with EA (100 mL×3). The combined organic layer was dried over Na$_2$SO$_4$, filtered and concentrated in vacuo to give a residue. Then the residue was purified by reverse phase (0.1% FA condition) to give the title compound (100 mg, 13% yield) as yellow oil. LC-MS (ESI$^+$) m/z 636.3 (M+H)$^+$.

Step 2—3-[4-[1-[(3S,4S)-3-Fluoro-4-piperidyl]azetidin-3-yl]-3-methyl-2-oxo-benzimidazol-1-yl]piperidine-2,6-dione. To a solution of tert-butyl (3S,4S)-3-fluoro-4-[3-[1-[1-[(4-methoxyphenyl)methyl]-2,6-dioxo-3-piperidyl]-3-methyl-2-oxo-benzimidazol-4-yl]azetidin-1-yl]piperidine-1-carboxylate (100 mg, 157 μmol) in TFA (1.40 g, 12.2 mmol) was added TfOH (0.20 mL), then the mixture was stirred at 70° C. for 2 hrs. On completion, the reaction mixture was concentrated in vacuo to give the title compound (60.0 mg, 72% yield) as brown oil. $^1$H NMR (400 MHz, DMSO-d6) δ 7.41-7.28 (m, 5H), 5.03 (s, 2H), 4.52-4.33 (m, 2H), 4.13 (s, 2H), 3.77 (s, 3H), 3.61-3.49 (m, 2H), 3.31 (s, 1H), 3.07 (d, J=3.6, 9.2, 13.2 Hz, 2H), 1.85 (dd, J=4.0, 8.4 Hz, 1.2H), 1.39 (s, 9H); LC-MS (ESI$^+$) m/z 416.1 (M+H)$^+$.

N-[2-(4-formylcyclohexyl)indazol-5-yl]-6-methyl-pyridine-2-carboxamide (Intermediate CPZ)

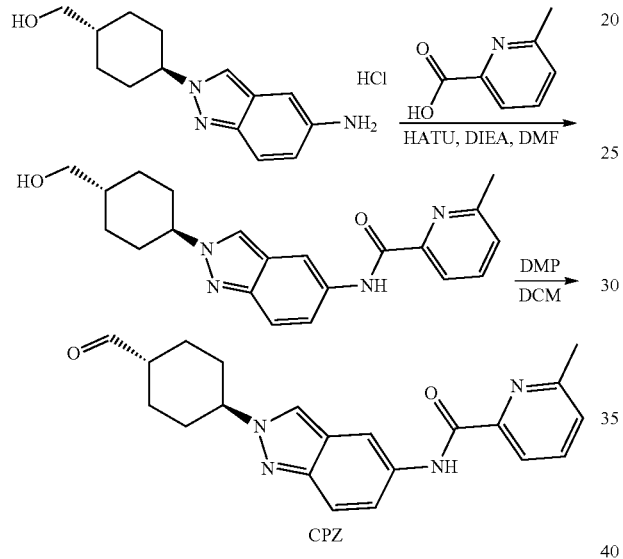

Step 1—N-[2-[4-(hydroxymethyl)cyclohexyl]indazol-5-yl]-6-methyl-pyridine-2-carboxamide. To a solution of 6-methylpyridine-2-carboxylic acid (73.0 mg, 532 umol, CAS #934-60-1) in DMF (3 mL) was added DIEA (275 mg, 2.13 mmol, 370 uL) and CMPI (149 mg, 585 umol) and the mixture was stirred at 25° C. for 30 mins. Then [4-(5-aminoindazol-2-yl)cyclohexyl]methanol (150 mg, 532 umol, HCl, synthesized via Step 1 of Intermediate BUT) in THF (3 mL) was added and the mixture was stirred at 25° C. for 2 hrs. On completion, the reaction mixture was added into ice water (50 mL), and the precipitate was collected by filtration to give the title compound (180 mg, 79% yield) as yellow solid. $^1$H NMR (400 MHz, DMSO-d$_6$) δ 10.37 (s, 1H), 8.38 (s, 1H), 8.34 (s, 1H), 7.98-7.89 (m, 2H), 7.63-7.55 (m, 2H), 7.53 (dt, J=1.6, 6.6 Hz, 1H), 4.50 (t, J=5.2 Hz, 1H), 4.46-4.36 (m, 1H), 3.29 (t, J=5.6 Hz, 2H), 2.63 (s, 3H), 2.14 (d, J=9.2 Hz, 2H), 1.95-1.87 (m, 4H), 1.53-1.43 (m, 1H), 1.15-1.08 (m, 2H); m/z 365.1 (M+H).

Step 2—N-[2-(4-formylcyclohexyl)indazol-5-yl]-6-methyl-pyridine-2-carboxamide. To a solution of N-[2-[4-(hydroxymethyl)cyclohexyl]indazol-5-yl]-6-methyl-pyridine-2-carboxamide (100 mg, 274 umol) in DMSO (0.1 mL) and DCM (1 mL) was added DMP (139 mg, 329 umol, 101 uL). The mixture was stirred at 25° C. for 2 hrs. On completion, the mixture was quenched with saturated Na$_2$S$_2$O$_3$ (100 mL) and NaHCO$_3$ (100 mL) at 0° C. and extracted with DCM (200 mL×3). The combined organic phase was dried over anhydrous sodium sulfate, filtered and concentrated to give a residue to give the title compound (87.0 mg, 77% yield) as red solid. $^1$H NMR (400 MHz, DMSO-d$_6$) δ 10.38 (s, 1H), 9.65 (s, 1H), 8.39 (s, 1H), 8.34 (d, J=1.2 Hz, 1H), 7.95 (s, 1H), 7.94 (d, J=3.2 Hz, 1H), 7.62-7.59 (m, 1H), 7.58-7.51 (m, 2H), 4.46 (tt, J=3.6, 11.6 Hz, 1H), 2.64 (s, 3H), 2.46-2.37 (m, 1H), 2.22 (dd, J=2.8, 12.8 Hz, 2H), 2.16-2.07 (m, 2H), 2.02-1.93 (m, 2H), 1.45 (dq, J=3.2, 12.9 Hz, 2H); LC-MS (ESI$^+$) m/z 363.1 (M+H).

3-(3-Methyl-2-oxo-1H-benzimidazol-4-yl)cyclobutanecarboxylic acid (Intermediate CQA)

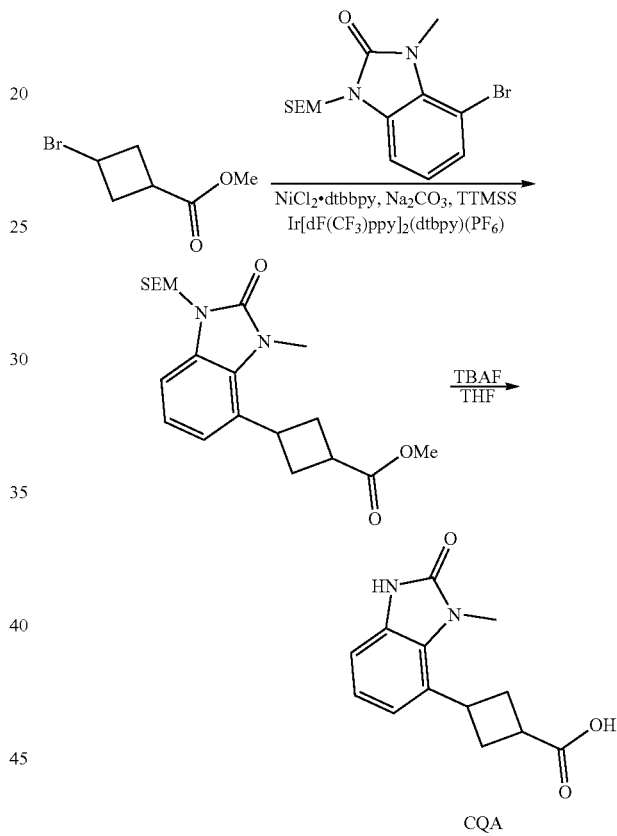

Step 1—Methyl 3-(3-methyl-2-oxo-1-((2-(trimethylsilyl)ethoxy)methyl)-2,3-dihydro-1H-benzo[d]imidazol-4-yl)cyclobutane-1-carboxylate. To an 40 mL vial equipped with a stir bar was added 4-bromo-3-methyl-1-(2-trimethylsilylethoxymethyl)benzimidazol-2-one (28.9 g, 80.9 mmol, synthesized via Step 1 of Intermediate COD), methyl 3-bromo-cyclobutanecarboxylate (20.3 g, 105 mmol, CAS #4935-00-6), Ir[dF(CF$_3$)ppy]$_2$(dtbpy)(PF$_6$) (908 mg, 809 μmol), NiCl$_2$·dtbbpy (483 mg, 1.21 mmol), TTMSS (20.1 g, 80.0 mmol), and Na$_2$CO$_3$ (17.1 g, 161 mmol) in DME (408 mL). The vial was sealed and placed under nitrogen and the reaction was stirred and irradiated with a 4×50 W [455 nm] blue LED lamp (3 cm away), with cooling water to keep the reaction temperature at 25° C. for 14 hrs. On completion, the mixture was filtered gave filtrate and concentrated in vacuo to give a residue. The mixture was diluted with water (40 mL) at 0° C. and extracted with ethyl acetate (40 mL×3). The combined organic phase was dried over anhydrous sodium sulfate, filtered and concentrated to give a residue. The residue was purified by column chromatography (SiO$_2$, PE/EA=20:1 to 15:1) to give the compound (5.00 g, 15% yield) as a yellow oil. $^1$H NMR (400 MHz, DMSO-d$_6$) δ 7.20 (dd, J=2.8, 6.0 Hz, 1H), 7.12-7.05 (m, 3H), 5.22 (s, 2H), 4.33-4.18 (m, 1H), 4.13-3.97 (m, 1H), 3.67 (s, 1H), 3.62 (s, 2H), 3.57-3.54 (m, 2H), 3.52 (s, 1H), 3.50 (s, 2H), 3.25-3.13 (m, 1H), 2.64-2.53 (m, 2H), 2.42-2.28 (m, 2H), 0.83 (t, J=8.0 Hz, 2H), −0.07 (s, 9H); LC-MS (ESI$^+$) m/z 360.1 (M−28+H)$^+$.

Step 2—3-(3-Methyl-2-oxo-1H-benzimidazol-4-yl)cyclobutanecarboxylic acid. To a solution of methyl 3-[3-methyl-2-oxo-1-(2-trimethylsilylethoxymethyl)benzimidazol-4-yl] cyclobutanecarboxylate (650 mg, 1.66 mmol) in THF (1.5 mL) was added TBAF (1 M, 8.32 mL). The mixture was then stirred at 80° C. for 12 hrs. On completion, the mixture was extracted with ethyl acetate (15 mL×3), the combined organic phase was washed with H$_2$O (30 mL), dried over anhydrous sodium sulfate, filtered and concentrated to give the title compound (260 mg, 63% yield) as a yellow solid. $^1$H NMR (400 MHz, DMSO-d$_6$) δ 12.27 (m, 1H), 10.94 (s, 1H), 7.16 (d, J=7.6 Hz, 1H), 7.08-7.03 (m, 1H), 6.96-6.88 (m, 1H), 4.36-4.01 (m, 1H), 3.57 (s, 1H), 3.59 (m, 1H), 3.52 (s, 1H), 3.24-3.08 (m, 1H), 2.66-2.60 (m, 2H), 2.55-2.35 (m, 2H). LC-MS (ESI$^+$) m/z 242.3 (M+H)$^+$.

Tert-butyl 4-((1r,3r)-3-(3-methyl-2-oxo-2,3-dihydro-1H-benzo[d]imidazol-4-yl)cyclobutane-1-carbonyl)piperazine-1-carboxylate (Intermediate CQB) and tert-butyl 4-((1s,3s)-3-(3-methyl-2-oxo-2,3-dihydro-1H-benzo[d]imidazol-4-yl)cyclobutane-1-carbonyl)piperazine-1-carboxylate (Intermediate CQC)

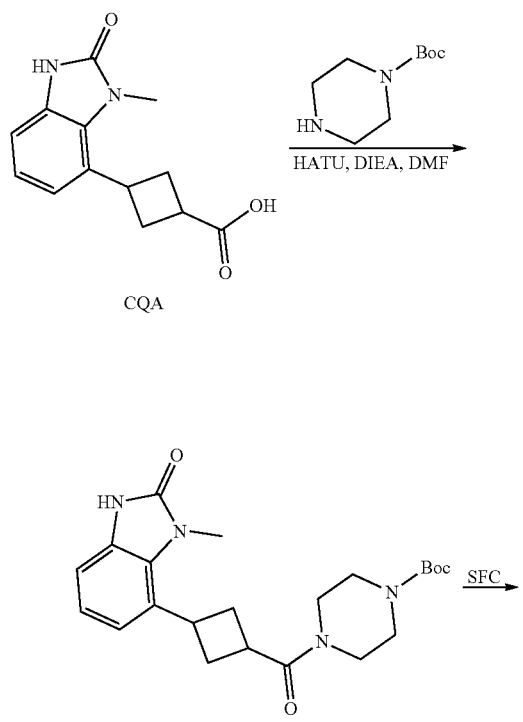

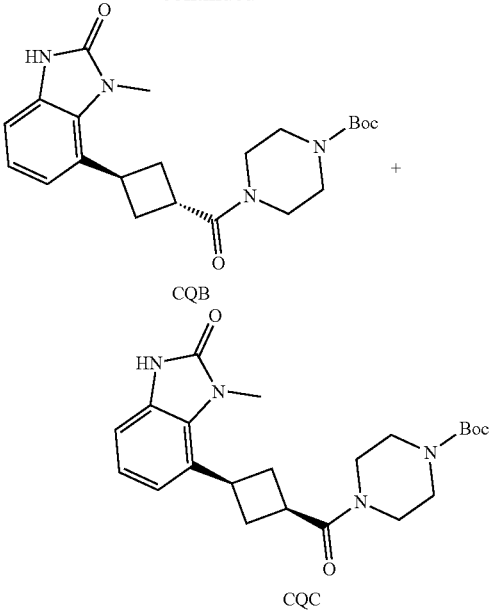

Step 1—Tert-butyl 4-[3-(3-methyl-2-oxo-1H-benzimidazol-4-yl)cyclobutanecarbonyl]piperazine-1-carboxylate. To a mixture of 3-(3-methyl-2-oxo-1H-benzimidazol-4-yl)cyclobutanecarboxylic acid (170 mg, 690 umol, Intermediate CQA) in DMF (0.5 mL) was added DIEA (267 mg, 2.07 mmol) at 25° C. until the pH stabilized at 8, then DIEA (133 mg, 1.04 mmol) was added. The mixture was stirred at 25° C. for 0.5 hr, then to a solution of tert-butyl piperazine-1-carboxylate (153 mg, 690 umol, HCl) in DMF (0.5 mL) was added HATU (288 mg, 759 umol) at 25° C. until the pH stabilized at 8. After that, the former mixture was added to the later mixture. The mixture was stirred at 60° C. for 12 hrs. On completion, the reaction mixture was quenched with H$_2$O (0.1 mL) at 25° C., and then the mixture was extracted with ethyl acetate (10 mL×3). The combined organic phase was washed with H$_2$O (20 mL), dried over anhydrous sodium sulfate, filtered and concentrated to give a residue. The residue was purified by column chromatography (SiO$_2$, dichloromethane/Methanol=30/1 to 10/1), and then the residue was purified by reversed phase flash (0.1% FA condition), then by SFC (column: DAICEL CHIRALCEL OJ (250 mm*30 mm, 10 um); mobile phase: [Neu-MeOH]; B %: 25%-25%, C9; 151 min) to give the title compound (250 mg, 87% yield) as a yellow solid. $^1$H NMR (400 MHz, DMSO-d$_6$) δ 10.91 (s, 1H), 7.20 (d, J=8.0 Hz, 1H), 7.06 (t, J=8.0 Hz, 1H), 6.96-6.86 (m, 1H), 4.19-4.03 (m, 1H), 3.57-3.50 (m, 3H), 3.49 (s, 3H), 3.37 (s, 6H), 2.77-2.62 (m, 2H), 2.52-2.40 (m, 2H), 1.47 (s, 9H).

Step 2—Tert-butyl 4-((1r,3r)-3-(3-methyl-2-oxo-2,3-dihydro-1H-benzo[d]imidazol-4-yl)cyclobutane-1-carbonyl)piperazine-1-carboxylate and tert-butyl 4-((1s,3s)-3-(3-methyl-2-oxo-2,3-dihydro-1H-benzo[d]imidazol-4-yl)cyclobutane-1-carbonyl)piperazine-1-carboxylate. Tert-butyl 4-[3-(3-methyl-2-oxo-1H-benzimidazol-4-yl)cyclobutanecarbonyl]piperazine-1-carboxy late (400 mg, 965 umol) was detected by SFC (column: DAICEL CHIRALCEL OJ (250 mm*30 mm, 10 um); mobile phase: [Neu-MeOH]; B %: 25%-25%, C9; 151 min) to give tert-butyl 4-((1r,3r)-3-(3-methyl-2-oxo-2,3-dihydro-1H-benzo[d]imidazol-4-yl)cyclobutane-1-carbonyl)piperazine-1-carboxylate (7, 121 mg, 30% yield) as a white solid ($^1$H NMR (400 MHz, DMSO-$d_6$) δ 10.91 (s, 1H), 7.20 (d, J=8.0 Hz, 1H), 7.06 (t, J=8.0 Hz, 1H), 6.96-6.86 (m, 1H), 4.19-4.03 (m, 1H), 3.57-3.50 (m, 3H), 3.49 (s, 3H), 3.37 (s, 6H), 2.77-2.62 (m, 2H), 2.52-2.40 (m, 2H), 1.47 (s, 9H)) and tert-butyl 4-((1s,3s)-3-(3-methyl-2-oxo-2,3-dihydro-1H-benzo[d]imidazol-4-yl)cyclobutane-1-carbonyl)piperazine-1-carboxylate to give the second fraction (7a, 129 mg, 32% yield) as a white solid ($^1$H NMR (400 MHz, DMSO-$d_6$) δ 10.85 (s, 1H), 7.04-6.94 (m, 2H), 6.91-6.78 (m, 1H), 5.76 (s, 1H), 4.08-3.92 (m, 1H), 3.52 (s, 3H), 3.43 (m, J=6.0 Hz, 6H), 3.30 (m, J=3.2 Hz, 3H), 2.49-2.44 (m, 1H), 2.41-2.30 (m, 2H), 1.41 (s, 9H)).

3-[3-Methyl-2-oxo-4-[3-(piperazine-1-carbonyl) cyclobutyl]benzimidazol-1-yl]piperid me-2,6-dione (Intermediate CQD)

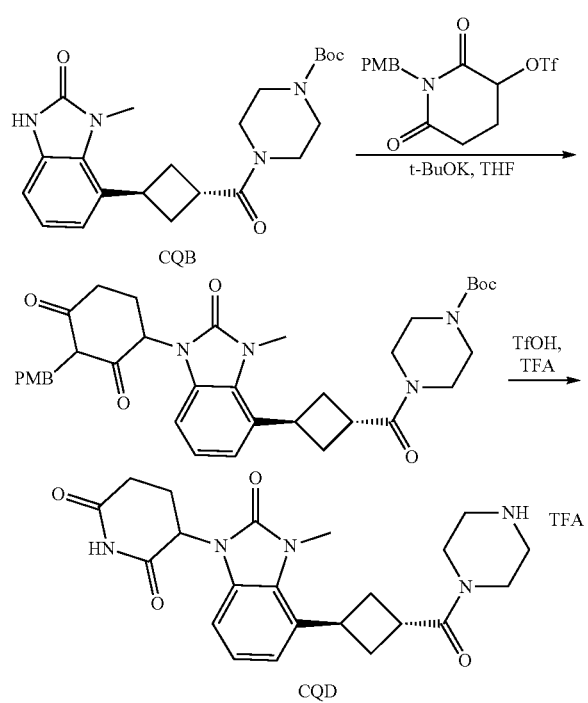

Step 1—Tert-butyl 4-[3-[1-[1-[(4-methoxyphenyl)methyl]-2,6-dioxo-3-piperidyl]-3-methyl-2-oxo-benzimidazol-4-yl]cyclobutanecarbonyl]piperazine-1-carboxylate. To a solution of tert-butyl 4-[3-(3-methyl-2-oxo-1H-benzimidazol-4-yl)cyclobutanecarbonyl] piperazine-1-carboxylate (100 mg, 241 umol, Intermediate CQB) in THF (2 mL) was added dropwise t-BuOK (40.6 mg, 361 umol) at −10° C. for 30 mins. Then [1-[(4-methoxyphenyl)methyl]-2,6-dioxo-3-piperidyl] trifluoromethanesulfonate (183 mg, 482 umol, Intermediate IQ) was added dropwise at −10° C. The resulting mixture was stirred at −10° C. for 30 mins. On completion, the reaction mixture was quenched with H$_2$O (0.1 mL) at 25° C., and then the mixture was extracted with ethyl acetate (10 mL×3). The combined organic phase was washed with H$_2$O (20 mL), dried over anhydrous sodium sulfate, filtered and concentrated to give a residue. The residue was purified by reversed phase flash (0.1% FA condition), to give the title compound (130 mg, 83% yield) as a brown oil. $^1$H NMR (400 MHz, DMSO-$d_6$) δ 7.29-7.15 (m, 3H), 7.02 (m, J=7.6 Hz, 1H), 6.93-6.81 (m, 3H), 5.76 (s, 2H), 5.52 (m, J=5.2, 12.4 Hz, 1H), 4.89-4.71 (m, 2H), 4.18-4.02 (m, 1H), 3.73 (s, 4H), 3.51 (s, 3H), 3.48 (m, 2H), 3.19-2.99 (m, 2H), 2.88-2.78 (m, 1H), 2.77-2.69 (m, 1H), 2.69-2.54 (m, 3H), 2.47-2.30 (m, 3H), 2.12-1.97 (m, 1H), 1.41 (s, 9H), 1.29-1.11 (m, 1H). LC-MS (ESI$^+$) m/z 646.5 (M+H)$^+$.

Step 2—3-[3-Methyl-2-oxo-4-[3-(piperazine-1-carbonyl) cyclobutyl]benzimidazol-1-yl]piperidine-2,6-dione. To a solution of tert-butyl 4-[3-[1-[1-[(4-methoxyphenyl)methyl]-2,6-dioxo-3-piperidyl]-3-methyl-2-oxo-benzimidazol-4-yl]cyclobutanecarbonyl]piperazine-1-carboxylate (90.0 mg, 139 umol) in TFA (1 mL) was added TfOH (10.8 mg, 72.0 mmol). The mixture was stirred at 70° C. for 2 hrs. On completion, the mixture was filtered and concentrated to give the title compound (70.0 mg, 93% yield, TFA, salt) as a brown solid. $^1$H NMR (400 MHz, DMSO-$d_6$) δ 7.29-7.15 (m, 3H), 7.02 (m, J=7.6 Hz, 1H), 6.93-6.81 (m, 3H), 5.76 (s, 2H), 5.52 (m, J=5.2, 12.4 Hz, 1H), 4.89-4.71 (m, 2H), 4.18-4.02 (m, 1H), 3.73 (s, 4H), 3.51 (s, 3H), 3.48 (m, 2H), 3.19-2.99 (m, 2H), 2.88-2.78 (m, 1H), 2.77-2.69 (m, 1H), 2.69-2.54 (m, 3H), 2.47-2.30 (m, 3H), 2.12-1.97 (m, 1H), 1.41 (s, 9H), 1.29-1.11 (m, 1H). LC-MS (ESI$^+$) m/z 426.2 (M+H)$^+$.

Tert-butyl 4-(3-methylsulfonyloxycyclobutyl)piperazine-1-carboxylate (Intermediate CQE)

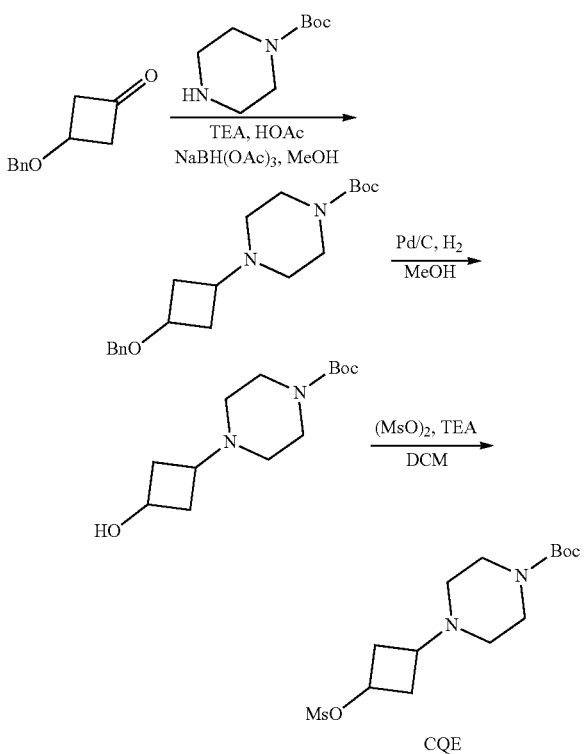

Step 1—Tert-butyl 4-(3-benzyloxycyclobutyl)piperazine-1-carboxylate. To a solution of 3-benzyloxycyclobutanone (5 g, 28.3 mmol, CAS #30830-27-4) in MeOH (30 mL) was added TEA (6.38 g, 63.0 mmol) at 25° C. until pH stabilized at 8. The mixture was stirred at 25° C. for 0.5 hrs. Then HOAc (3.79 g, 63.0 mmol) was added at 25° C. to the solution until pH stabilized at 5-6. Subsequently, tert-butyl piperazine-1-carboxylate (5.87 g, 31.5 mmol, CAS #57260-

71-6) was added and stirred for 0.5 hrs at −15° C. After that, NaBH(OAc)$_3$ (13.3 g, 63.0 mmol) was added in one portion and the resulting reaction mixture was stirred at −15° C. for 2 hrs. On completion, the reaction mixture was quenched with H$_2$O (0.1 mL) at 25° C., and then the mixture was extracted with ethyl acetate (200 mL×3), the combined organic phase was washed with H$_2$O (500 mL), dried over anhydrous sodium sulfate, filtered and concentrated to give a residue. The residue was purified by column chromatography (SiO$_2$, Petroleum ether/Ethyl acetate=1/0 to 4/5) to give the title compound (4 g, 36% yield) as a white solid. $^1$H NMR (400 MHz, CDCl$_3$) δ 7.28-7.17 (m, 5H), 4.35 (s, 2H), 3.72 (m, J=7.2 Hz, 1H), 3.41-3.33 (m, 4H), 2.42-2.31 (m, 2H), 2.30-2.25 (m, 1H), 2.23 (m, J=4.4 Hz, 4H), 1.89-1.75 (m, 2H), 1.38 (s, 9H).

Step 2—Tert-butyl 4-(3-hydroxycyclobutyl)piperazine-1-carboxylate. To a solution of Pd/C (10 wt %) in MeOH (10 mL) was added tert-butyl 4-(3-benzyloxycyclobutyl)piperazine-1-carboxylate (2.5 g, 7.22 mmol) in MeOH (50 mL) at 25° C. The mixture was stirred at 50° C. for 12 hrs under H$_2$ (50 Psi). On completion, the reaction mixture was filtered and the filtrate was concentrated under reduced pressure to give the title compound (1.8 g, 97% yield) as a white solid. $^1$H NMR (400 MHz, CDCl$_3$) δ 4.10-3.90 (m, 1H), 3.43-3.30 (m, 4H), 3.04 (m, 1H), 2.48 (m, J=2.8, 6.8, 9.2 Hz, 1H), 2.28-2.19 (m, 4H), 2.01-1.95 (m, 1H), 1.79-1.72 (m, 1H), 1.39 (s, 8H).

Step 3—Tert-butyl 4-(3-methylsulfonyloxycyclobutyl)piperazine-1-carboxylate. To a solution of tert-butyl 4-(3-hydroxycyclobutyl)piperazine-1-carboxylate (1.5 g, 5.9 mmol) in DCM (15 mL) was added TEA (1.78 g, 17.5 mmol) and methylsulfonyl methanesulfonate (1.53 g, 8.78 mmol) at 0° C. The reaction mixture was then stirred at 25° C. for 16 hrs. On completion, the reaction mixture was diluted with H$_2$O (30 mL), and extracted with DCM (2×30 mL). The combined organic layer was washed with brine (2×30 mL), dried over Na$_2$SO$_4$ and filtered. The filtrate was concentrated in vacuo to give a residue. The residue was purified by column chromatography (SiO$_2$, DCM:MeOH=40:1, DCM:MeOH=15:1, P1:Rf=0.64) to give the title compound (1.7 g, 86% yield) as a yellow oil. $^1$H NMR (400 MHz, DMSO-d$_6$) δ 3.35-3.24 (m, 7H), 3.15 (s, 1H), 2.62-2.54 (m, 2H), 2.43-2.34 (m, 1H), 2.25-2.15 (m, 4H), 2.05-1.92 (m, 2H), 1.39 (s, 9H).

3-(4-Hydroxy-3-methyl-2-oxo-benzimidazol-1-yl)-1-[(4-methoxyphenyl)methyl]piperidine-2,6-dione (Intermediate CQF)

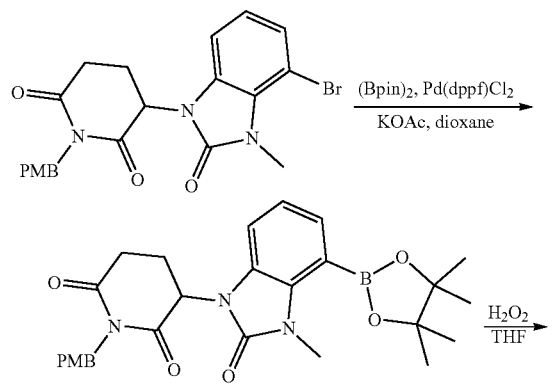

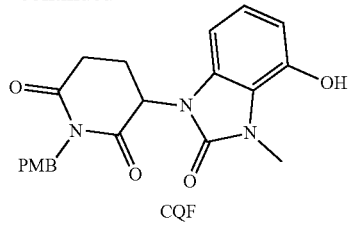

Step 1—3-Methyl-4-(4,4,5,5-tetramethyl-1,3,2-dioxaborolan-2-yl)-1-(2-trimethylsilylethoxymethyl)benzimidazol-2-one. A mixture of 3-(4-bromo-3-methyl-2-oxo-benzimidazol-1-yl)-1-[(4-methoxyphenyl) methyl] piperidine-2,6-dione (5 g, 10.9 mmol, synthesized via Steps 1-4 of Intermediate HP), KOAc (3.21 g, 32.7 mmol), Pd(dppf)Cl$_2$ (399 mg, 545 μmol) and Pin$_2$B$_2$ (3.60 g, 14.1 mmol) in dioxane (50 mL) was degassed and purged with N$_2$ three times. Then the mixture was stirred at 70° C. for 12 hrs under N$_2$ atmosphere. On completion, the reaction mixture was filtered and concentrated to give a residue. The residue was purified by reversed phase flash (0.1% FA condition) to give the title compound (1.5 g, 27% yield) as a white solid. $^1$H NMR (400 MHz, DMSO-d$_6$) δ 7.43-7.28 (m, 1H), 7.21 (dd, J=2.0, 8.8 Hz, 2H), 7.10-7.01 (m, 1H), 7.00-6.93 (m, 1H), 6.86 (d, J=8.8 Hz, 2H), 5.55 (td, J=6.4, 12.8 Hz, 1H), 4.89-4.72 (m, 2H), 3.73 (s, 3H), 3.49 (s, 2H), 3.37 (s, 3H), 3.13-2.99 (m, 1H), 2.86-2.69 (m, 2H), 2.11-1.99 (m, 1H), 1.35 (s, 6H).

Step 2—3-(4-Hydroxy-3-methyl-2-oxo-benzimidazol-1-yl)-1-[(4-methoxyphenyl)methyl]piperidine-2,6-dione. To a solution of 1-[(4-methoxyphenyl)methyl]-3-[3-methyl-2-oxo-4-(4,4,5,5-tetramethyl-1,3,2-dioxaborolan-2-yl)benzimidazol-1-yl]piperidine-2,6-dione (3 g, 5.94 mmol) in THF (30 mL) was added H$_2$O$_2$ (6.89 g, 60.7 mmol) at 0° C. The mixture was then stirred at 0° C. for 6 hrs under N$_2$. On completion, the reaction mixture was quenched with Na$_2$SO$_3$ (300 mL) at 0° C., and then extracted with EA (100 mL×2). The combined organic phase was washed with saturated sodium chloride solution (150 mL×2), dried over anhydrous sodium sulfate, filtered and concentrated to give a residue. The crude product was triturated with PE at 25° C. for 2 hrs, then filtered and dried to give the title compound (2.2 g, 79% yield) as a white solid. $^1$H NMR (400 MHz, DMSO-d$_6$) δ 9.81 (s, 1H), 7.30-7.16 (m, 2H), 6.89-6.83 (m, 2H), 6.81-6.74 (m, 1H), 6.55 (d, J=8.0 Hz, 1H), 6.49 (d, J=7.6 Hz, 1H), 5.45 (dd, J=5.2, 12.8 Hz, 1H), 4.89-4.70 (m, 2H), 3.73 (s, 3H), 3.53 (s, 3H), 3.13-2.98 (m, 1H), 2.83 (d, J=2.4 Hz, 1H), 2.80-2.75 (m, 1H), 2.74-2.63 (m, 1H).

3-[3-Methyl-2-oxo-4-(3-piperazin-1-ylcyclobutoxy)benzimidazol-1-yl]piperidine-2,6-dione (Intermediate CQG)

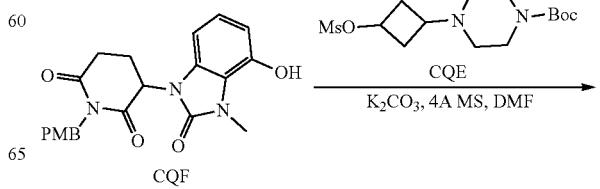

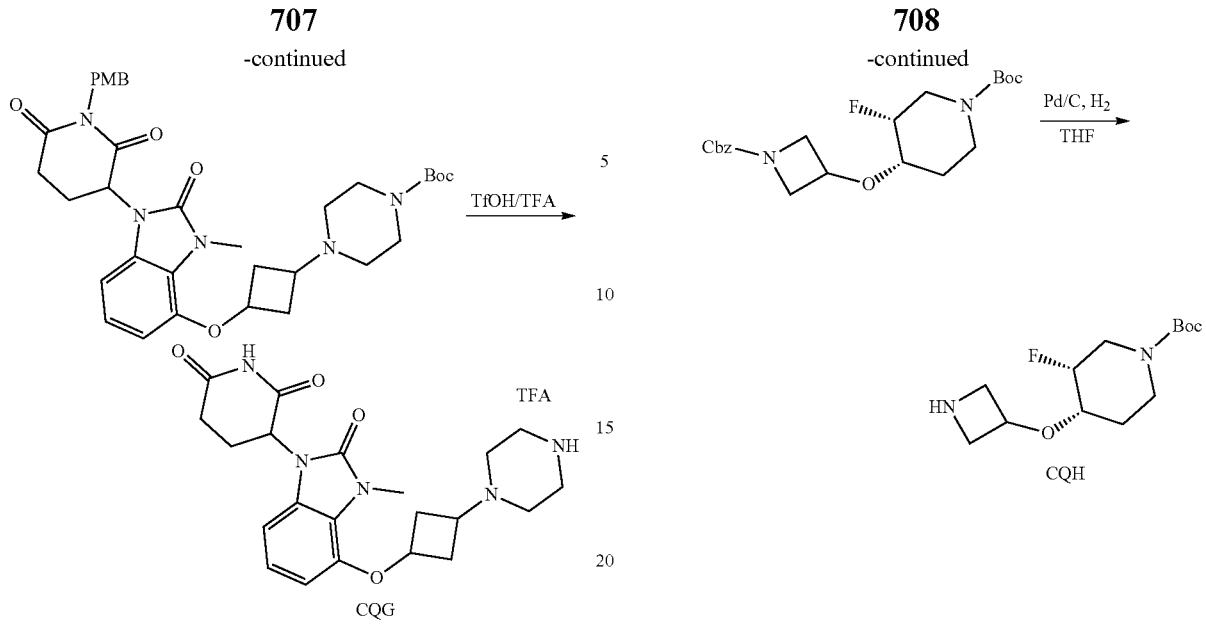

Step 1—Tert-butyl 4-[3-[1-[1-[(4-methoxyphenyl)methyl]-2,6-dioxo-3-piperidyl]-3-methyl-2-oxo-benzimidazol-4-yl]oxycyclobutyl]piperazine-1-carboxylate. To a solution of 3-(4-hydroxy-3-methyl-2-oxo-benzimidazol-1-yl)-1-[(4-methoxyphenyl) methyl]piperidine-2,6-dione (394 mg, 996 μmol, Intermediate CQF) and tert-butyl 4-(3-methylsulfonyloxycyclobutyl)piperazine-1-carboxylate (500 mg, 1.50 mmol, Intermediate CQE) in DMF (5 mL) was added K$_2$CO$_3$ (275 mg, 1.99 mmol) and KI (33.0 mg, 199 μmol). Then the mixture was stirred at 85° C. for 12 hrs. On completion, the reaction mixture was quenched with H$_2$O (50 mL), then extracted with EA (15 mL×2). The combined organic phase was washed with brine (20 mL×2), dried over anhydrous sodium sulfate, filtered and concentrated to give a residue. The residue was purified by prep-TLC (DCM:EA=1:3, P1:Rf=0.55) and reverse phase (0.1% FA condition) to give the title compound (80 mg, 12% yield) as colorless oil. LC-MS (ESI+) m/z 634.4 (M+H)$^+$.

Step 2—3-[3-Methyl-2-oxo-4-(3-piperazin-1-ylcyclobutoxy)benzimidazol-1-yl]piperidine-2,6-dione. To a solution of tert-butyl 4-[3-[1-[1-[(4-methoxyphenyl)methyl]-2,6-dioxo-3-piperidyl]-3-methyl-2-oxo-benzimidazol-4-yl]oxycyclobutyl]piperazine-1-carboxylate (50 mg, 78.9 μmol) and in TFA (1 mL) was added TfOH (508 mg, 3.39 mmol), then the reaction mixture was stirred at 70° C. for 2 hrs. On completion, the reaction mixture was concentrated in vacuo to give the title compound (40 mg, 96% yield, TFA) as brown oil. LC-MS (ESI+) m/z 414.2 (M+H)$^+$.

Tert-butyl (3R,4S)-4-(azetidin-3-yloxy)-3-fluoropiperidine-1-carboxylate (Intermediate CQH)

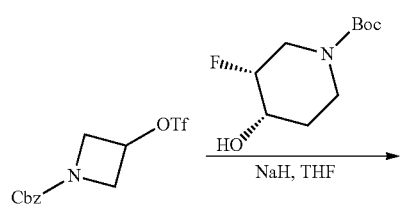

Step 1—Tert-butyl (3R,4S)-4-(1-benzyloxycarbonylazetidin-3-yl)oxy-3-fluoro-piperidine-1-carboxylate. To a mixture of benzyl tert-butyl (3R,4S)-3-fluoro-4-hydroxy-piperidine-1-carboxylate (1.45 g, 6.63 mmol, CAS #1174020-42-8) in THF (10 mL) was added NaH (589 mg, 14.7 mmol, 60% dispersion in mineral oil) at 0° C., then the mixture was stirred at 25° C. for 1 hr. Then, KI (244 mg, 1.47 mmol) and benzyl 3-(trifluoromethylsulfonyloxy)azetidine-1-carboxylate (2.50 g, 7.37 mmol, synthesized via Step 1 of Intermediate CNN) was added and the mixture was stirred at 50° C. for 16 hrs. On completion, the reaction was cooled to rt, and the mixture was quenched with H$_2$O (2 mL) slowly at 0° C. Then HCl (1M, 3 mL) was added at 0° C. to adjust the pH=7, and the mixture was stirred at 25° C. for 0.5 hr. Then the mixture was extracted with EA (20 mL×3). The combined organic layers were washed with saturated NaCl (10 mL), dried over anhydrous Na$_2$SO$_4$, filtered and concentrated in vacuo to give the crude product. The crude product was purified by column chromatography (SiO$_2$, PE:EA=10:1 to 1:1), then the residue was purified by reverse phase (0.1% FA condition) to give the title compound (0.92 g, 30% yield) as yellow solid. $^1$H NMR (400 MHz, DMSO-d$_6$) δ 7.38-7.31 (m, 5H), 5.03 (s, 2H), 4.84-4.66 (m, 1H), 4.49-4.45 (m, 1H), 4.19-4.00 (m, 3H), 3.77 (s, 3H), 3.67-3.51 (m, 1H), 3.18-2.74 (m, 2H), 1.70-1.55 (m, 2H), 1.47-1.31 (m, 9H). LC-MS (ESI$^+$) m/z 309.1 (M−100+H)$^+$.

Step 2—Tert-butyl (3R,4S)-4-(azetidin-3-yloxy)-3-fluoro-piperidine-1-carboxylate. To a solution of Pd/C (1.50 g, 10 wt %) in THF (10 mL) was added tert-butyl (3R,4S)-4-(1-benzyloxycarbonylazetidin-3-yl)oxy-3-fluoro-piperidine-1-carboxylate (1.50 g, 3.67 mmol), then the mixture was degassed and purged with H$_2$ three times. Then the mixture was stirred at 25° C. for 2 hrs under H$_2$ (15 psi) atmosphere. On completion, the reaction was filtered to give a filtrate, which was then concentrated in vacuo to give the title compound (1.00 g, 96% yield) as yellow liquid. $^1$H NMR (400 MHz, DMSO-d$_6$) δ 4.78-4.59 (m, 1H), 4.41-4.30 (m, 1H), 4.01 (t, J=9.6 Hz, 1H), 3.88-3.74 (s, 1H), 3.56-3.42 (m, 3H), 3.42-3.34 (m, 2H), 3.14-2.75 (m, 2H), 2.18 (s, 1H), 1.66-1.47 (m, 2H), 1.38 (s, 9H). LC-MS (ESI$^+$) m/z 274.9 (M+H)$^+$.

3-[4-[3-[[(3R,4S)-3-Fluoro-4-piperidyl]oxy]azetidin-1-yl]-3-methyl-2-oxo-benzimidazol-1-yl] piperidine-2,6-dione (Intermediate CQI)

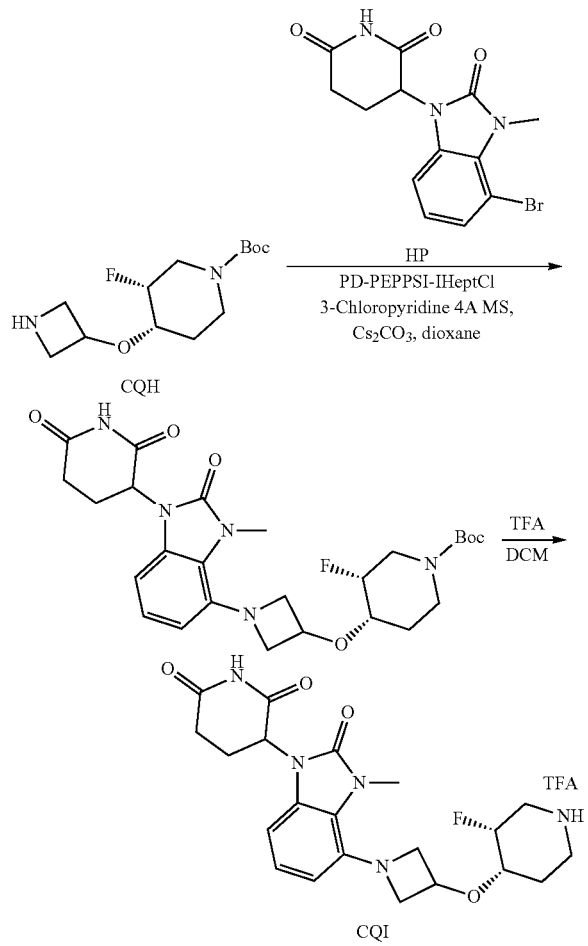

Step 1—Tert-butyl (3R,4S)-4-[1-[1-(2,6-dioxo-3-piperidyl)-3-methyl-2-oxo-benzimidazol-4-yl]azetidin-3-yl]oxy-3-fluoro-piperidine-1-carboxylate. A mixture of 3-(4-bromo-3-methyl-2-oxo-benzimidazol-1-yl)piperidine-2,6-dione (677 mg, 2.00 mmol, Intermediate HP), tert-butyl (3R,4S)-4-(azetidin-3-yloxy)-3-fluoro-piperidine-1-carboxylate (500 mg, 1.82 mmol, Intermediate CQH), Cs$_2$CO$_3$ (1.78 g, 5.47 mmol), 4 Å molecular sieves (514 mg, 1.82 mmol) and 1,3-bis[2,6-bis(1-propylbutyl)phenyl]-4,5-dichloro-2H-imidazol-1-ium-2-ide; 3-chloropyridine dichloropalladium (177 mg, 182 µmol) in dioxane (10 mL) was degassed and purged with N$_2$ three times. Then the mixture was stirred at 100° C. for 16 hrs under N$_2$ atmosphere. On completion, the reaction was cooled to rt, filtered and concentrated in vacuo to give a residue. The residue was purified by column chromatography (SiO$_2$, PE:EA=50:1 to 5:1, P1:Rf=0.5) and then the residue was purified by reverse phase (FA condition) to give the title compound (345 mg, 34% yield) as yellow solid. $^1$H NMR (400 MHz, DMSO-d$_6$) δ 13.12-12.31 (m, 1H), 11.08 (s, 1H), 8.13 (s, 1H), 6.98-6.68 (m, 3H), 5.32 (dd, J=5.2, 12.6 Hz, 1H), 4.87-4.71 (m, 1H), 4.54 (t, J=5.8 Hz, 1H), 4.09-4.02 (m, 4H), 3.91-3.78 (m, 1H), 3.63 (t, J=5.6 Hz, 3H), 2.97-2.83 (m, 2H), 2.73-2.61 (m, 2H), 1.73-1.67 (m, 1H), 1.65-1.57 (m, 1H), 1.39 (s, 9H), 1.17 (t, J=7.2 Hz, 2H). LC-MS (ESI$^+$) m/z 532.2 (M+H)$^+$.

Step 2—3-[4-[3-[[(3R,4S)-3-Fluoro-4-piperidyl]oxy]azetidin-1-yl]-3-methyl-2-oxo-benzimidazol-1-yl] piperidine-2,6-dione. To a solution of tert-butyl (3R,4S)-4-[1-[1-(2,6-dioxo-3-piperidyl)-3-methyl-2-oxo-benzimidazol-4-yl]azetidin-3-yl]oxy-3-fluoro-piperidine-1-carboxylate (100 mg, 188 µmol) in DCM (1 mL) was added TFA (0.2 mL) at 0° C. The mixture was stirred at 25° C. for 0.5 hr. On completion, the reaction mixture was concentrated in vacuo to give the title compound (101 mg, 98% yield, TFA) as black brown liquid. LC-MS (ESI$^+$) m/z 432.2 (M+H)$^+$.

3-[4-[3-Methoxy-3-(piperazin-1-ylmethyl)cyclobutyl]-3-methyl-2-oxo-benzimidazol-1-yl] piperidine-2,6-dione (Intermediate CQJ)

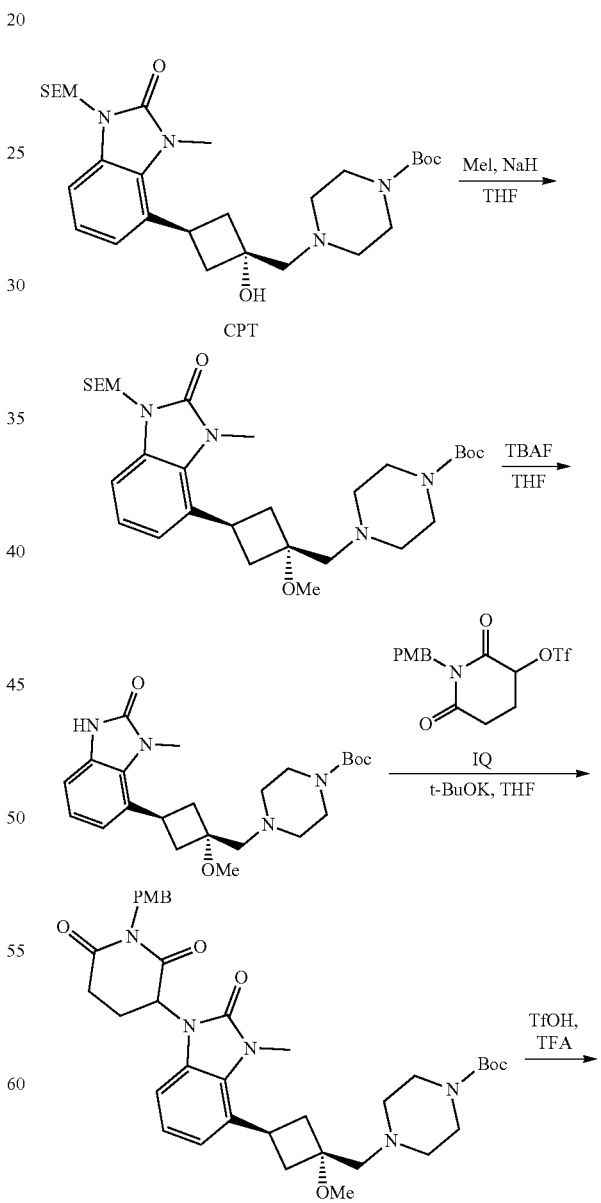

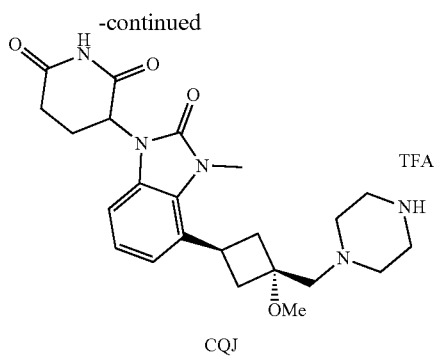

CQJ

Step 1—Tert-butyl 4-[[1-methoxy-3-[3-methyl-2-oxo-1-(2-trimethylsilylethoxymethyl)benzimidazol-4-yl]cyclobutyl]methyl]piperazine-1-carboxylate. To a solution of tert-butyl 4-[[1-hydroxy-3-[3-methyl-2-oxo-1-(2-trimethylsilylethoxymethyl)benzimidazol-4-yl]cyclobutyl]methyl] piperazine-1-carboxylate (200 mg, 365 µmol, Intermediate CPT) in THF (5 mL) was added NaH (29.2 mg, 731 µmol, 60% dispersion in mineral oil) at 0° C., then the mixture was stirred at 20° C. for 1 hr. Next, CH₃I (259 mg, 1.83 mmol) was added dropwise at 20° C., then the mixture was stirred at 20° C. for 9 hrs. On completion, the reaction mixture was quenched with saturated NH₄Cl (5 ml) aqueous, and then extracted with ethyl acetate (5 mL×3). The combined organic layers were washed with brine (5 mL), dried over Na₂SO₄ and filtered. The filtrate was concentrated in vacuo to give a residue. The residue was purified by column chromatography (SiO₂, petroleum ether/ethyl acetate=10/0 to 0/1) to give the title compound (100 mg, 48% yield) as a light yellow oil. ¹H NMR (400 MHz, CDCl₃) δ 7.12 (td, J=8.0, 16.4 Hz, 3H), 5.34 (s, 2H), 4.28-4.14 (m, 1H), 3.68 (s, 3H), 3.66-3.61 (m, 2H), 3.46 (d, J=4.8 Hz, 4H), 3.35 (s, 3H), 2.65-2.55 (m, 2H), 2.53 (s, 2H), 2.49 (s, 4H), 2.40-2.27 (m, 2H), 1.49 (s, 9H), 0.98-0.92 (m, 2H), 0.00 (s, 9H); LC-MS (ESI⁺) m/z 561.3 (M+H)⁺.

Step 2—Tert-butyl 4-[[1-methoxy-3-(3-methyl-2-oxo-1H-benzimidazol-4-yl)cyclobutyl]methyl] piperazine-1-carboxylate. A solution of tert-butyl 4-[[1-methoxy-3-[3-methyl-2-oxo-1-(2-trimethylsilylethoxymethyl)benzimidazol-4-yl]cyclobutyl]methyl]piperazine-1-carboxylate (100 mg, 178 µmol) in TBAF (3 mL) and THF (3 mL) was stirred at 70° C. for 12 hrs. On completion, the reaction mixture was poured into water (10 mL), and then extracted with ethyl acetate (10 mL×3). The combined organic layers were washed with brine (10 mL), dried over sodium sulfate and filtered. The filtrate was concentrated in vacuo to give a residue. The residue was purified by column chromatography (SiO₂, petroleum ether/ethyl acetate=10/1 to 0/1) to give the title compound (45.0 mg, 29% yield) as a light yellow oil. ¹H NMR (400 MHz, CD₃OD) δ 7.10-7.02 (m, 2H), 6.93 (dd, J=0.8, 7.6 Hz, 1H), 3.66 (s, 2H), 3.61 (s, 3H), 3.44-3.37 (m, 8H), 3.34 (s, 3H), 2.61 (s, 1H), 2.35-2.24 (m, 4H), 1.45 (s, 9H); LC-MS (ESI⁺) m/z 431.2 (M+H)⁺.

Step 3—Tert-butyl 4-[[1-methoxy-3-[1-[1-[(4-methoxyphenyl)methyl]-2,6-dioxo-3-piperidyl]-3-methyl-2-oxo-benzimidazol-4-yl]cyclobutyl]methyl]piperazine-1-carboxylate. To a solution of tert-butyl 4-[[1-methoxy-3-(3-methyl-2-oxo-1H-benzimidazol-4-yl)cyclobutyl]methyl] piperazine-1-carboxylate (45.0 mg, 104 µmol) in THF (2 mL) was added t-BuOK (29.3 mg, 261 µmol) at −10° C. and the mixture was stirred for 0.5 h. Then [1-[(4-methoxyphenyl)methyl]-2,6-dioxo-3-piperidyl] trifluoromethanesulfonate (79.7 mg, 209 µmol, Intermediate IQ) was added and the mixture was stirred at −10° C. for 0.5 hrs. On completion, the reaction mixture was poured into water (10 mL), and then extracted with ethyl acetate (10 mL×3). The combined organic layers were washed with brine (10 mL), dried over sodium sulfate and filtered. The filtrate was concentrated in vacuo to give a residue. The crude product was purified by reversed-phase (0.1% FA condition) to give the title compound (35.0 mg, 50% yield) as a white solid. ¹H NMR (400 MHz, CDCl₃) δ 7.37 (d, J=8.4 Hz, 2H), 7.09 (d, J=8.0 Hz, 1H), 6.94 (t, J=7.6 Hz, 1H), 6.83 (d, J=8.4 Hz, 2H), 6.40 (d, J=7.6 Hz, 1H), 5.21 (dd, J=5.2, 12.8 Hz, 1H), 5.03-4.82 (m, 2H), 4.18 (t, J=8.8 Hz, 1H), 3.80 (s, 3H), 3.67 (s, 3H), 3.46 (s, 4H), 3.33 (s, 3H), 3.09-2.95 (m, 1H), 2.89-2.76 (m, 1H), 2.65 (d, J=4.4 Hz, 1H), 2.63-2.40 (m, 8H), 2.39-2.26 (m, 2H), 2.22-2.08 (m, 1H), 1.47 (s, 9H); LC-MS (ESI⁺) m/z 662.3 (M+H)⁺.

Step 4—3-[4-[3-Methoxy-3-(piperazin-1-ylmethyl)cyclobutyl]-3-methyl-2-oxo-benzimidazol-1-yl]piperidine-2,6-dione. A solution of tert-butyl 4-[[1-methoxy-3-[1-[1-[(4-methoxyphenyl)methyl]-2,6-dioxo-3-piperidyl]-3-methyl-2-oxo-benzimidazol-4-yl]cyclobutyl]methyl]piperazine-1-carboxylate (35.0 mg, 52.8 µmol) in TFA (0.5 mL) and TfOH (0.1 mL) was stirred at 70° C. for 0.5 hr. On completion, the filtrate was concentrated in vacuo to give the title compound (29.0 mg, 98% yield, TFA) as a black brown oil. LC-MS (ESI⁺) m/z 442.1 (M+H)⁺.

Azetidin-3-yloxy-tert-butyl-dimethyl-silane (Intermediate CQK)

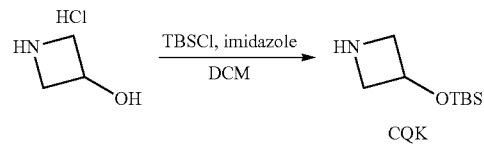 [SMILES: Cl ; OC1CNC1 ; CC(C)(C)[Si](C)(C)OC1CNC1]

To a solution of azetidin-3-ol (5 g, 45.6 mmol, HCl, CAS #45347-82-8) in DCM (100 mL) was added imidazole (9.32 g, 136 mmol), then TBSCl (13.7 g, 91.2 mmol) was added at 0° C., then the mixture was stirred at 25° C. for 16 hr. On completion, the mixture was diluted with water (10 mL) and extracted with DCM (20 ml). The combined organic layers were washed with NH₄Cl (20 mL), dried over Na₂SO₄, filtered and concentrated in vacuo to give the title compound (6 g, 70% yield) as a white solid. ¹H NMR (400 MHz, CDCl₃) δ 4.61 (d, J=5.4 Hz, 1H), 3.82-3.55 (m, 5H), 0.90-0.86 (m, 9H), 0.03 (s, 6H).

3-[3-Methyl-2-oxo-4-(3-oxoazetidin-1-yl)benzimidazol-1-yl]piperidine-2,6-dione (Intermediate CQL)

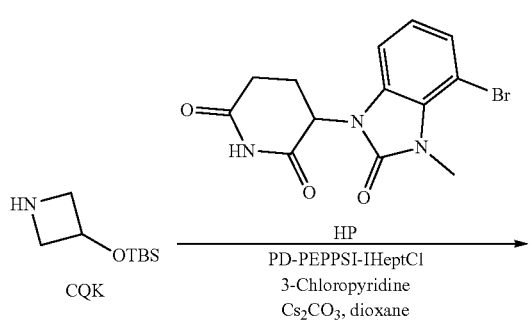

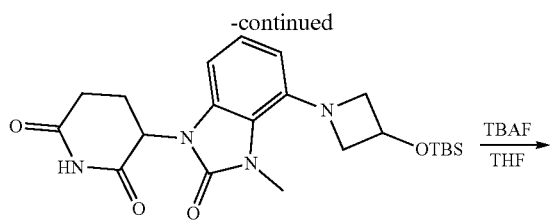

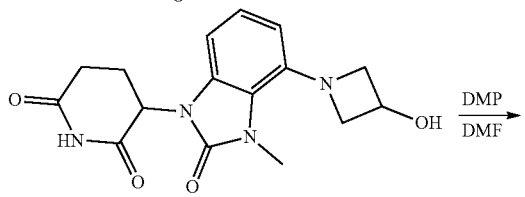

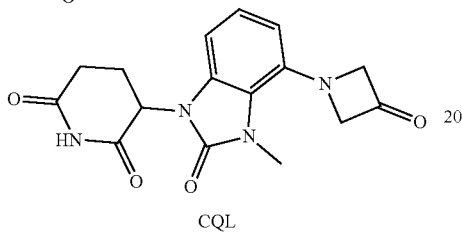

CQL

Step 1—3-[4-[3-[Tert-butyl(dimethyl)silyl]oxyazetidin-1-yl]-3-methyl-2-oxo-benzimidazol-1-yl] piperidine-2,6-dione. To a solution of azetidin-3-yloxy-tert-butyl-dimethyl-silane (3.32 g, 17.7 mmol, Intermediate CQK), 3-(4-bromo-3-methyl-2-oxo-benzimidazol-1-yl)piperidine-2,6-dione (4 g, 11.8 mmol, Intermediate HP) in dioxane (15 mL) was added 1,3-bis[2,6-bis(1-propylbutyl)phenyl]-4,5-dichloro-2H-imidazol-1-ium-2-ide; 3-chloropyridine dichloropalladium (1.15 g, 1.18 mmol) and $Cs_2CO_3$ (11.5 g, 35.5 mmol). The mixture was stirred at 100° C. for 16 hrs. On completion, the mixture was filtered and concentrated in vacuo to give a residue. The mixture was purified by reverse phase (FA condition) to give the title compound (2 g, 38% yield) as a white solid. $^1$H NMR (400 MHz, $CDCl_3$) δ 8.48-8.31 (m, 1H), 6.99 (t, J=8.0 Hz, 1H), 6.73 (d, J=8.4 Hz, 1H), 6.48 (d, J=8.0 Hz, 1H), 5.21 (dd, J=5.4, 12.4 Hz, 1H), 4.70-4.66 (m, 1H), 4.04-3.95 (m, 2H), 3.73 (s, 3H), 3.66 (t, J=6.0 Hz, 2H), 2.99-2.65 (m, 3H), 2.25-2.14 (m, 1H), 0.91 (s, 9H), 0.09 (s, 6H); LC-MS (ESI$^+$) m/z 445.1 (M+H)$^+$.

Step 2—3-[4-(3-Hydroxyazetidin-1-yl)-3-methyl-2-oxo-benzimidazol-1-yl]piperidine-2,6-dione. A mixture of 3-[4-[3-[tert-butyl(dimethyl)silyl]oxyazetidin-1-yl]-3-methyl-2-oxo-benzimidazol-1-yl] piperidine-2,6-dione (950 mg, 2.14 mmol) and TBAF (1 M, 3.21 mL) in THF (10 mL) was stirred at 25° C. for 2 hr. On completion, the mixture was concentrated in vacuo to give a residue. The mixture was purified by column chromatography ($SiO_2$, Petroleum ether/Ethyl acetate=5/1 to 0/1) to give the title compound (700 mg, 98% yield) as a yellow solid. $^1$H NMR (400 MHz, $CDCl_3$) δ 9.28-8.74 (m, 1H), 8.05 (s, 1H), 6.56 (d, J=2.0 Hz, 2H), 3.80 (s, 3H), 3.75 (s, 3H), 3.20-3.18 (m, 6H), 1.50 (s, 9H), 1.39 (t, J=7.2 Hz, 10H), 1.27 (t, J=7.2 Hz, 3H); LC-MS (ESI$^+$) m/z 331.0 (M+H)$^+$.

Step 3—3-[3-Methyl-2-oxo-4-(3-oxoazetidin-1-yl)benzimidazol-1-yl]piperidine-2,6-dione. To a solution of 3-[4-(3-hydroxyazetidin-1-yl)-3-methyl-2-oxo-benzimidazol-1-yl] piperidine-2,6-dione (300 mg, 908 µmol) in DMF (2 mL) was added DMP (462 mg, 1.09 mmol). The mixture was stirred at 25° C. for 1 hr. On completion, the mixture was quenched with $Na_2S_2O_3$ (5 ml) and $NaHCO_3$ (5 ml). The mixture was extracted with DCM (10 ml) and the organic layer was concentrated in vacuo to give a residue. The mixture was purified by reverse phase (FA condition) to give the title compound (246 mg, 82% yield) as a yellow solid. $^1$H NMR (400 MHz, $CDCl_3$) δ 8.13 (s, 1H), 7.10-7.03 (m, 1H), 6.88 (d, J=8.0 Hz, 1H), 6.59 (d, J=7.8 Hz, 1H), 5.22 (dd, J=5.6, 12.4 Hz, 1H), 4.73 (s, 3H), 3.78 (s, 3H), 3.02-2.69 (m, 4H), 2.30-2.19 (m, 1H); LC-MS (ESI$^+$) m/z 329.0 (M+H)$^+$.

Tert-butyl 4-((1R,4r)-4-(4-(5-((1R,4R)-2-oxa-5-azabicyclo[2.2.1]heptan-5-yl)pyrazolo[1,5-a]pyrimidine-3-carboxamido)-3-(difluoromethyl)-1H-pyrazol-1-yl)cyclohexyl)piperazine-1-carboxylate (Intermediate CQM) Tert-butyl 4-((1S,4s)-4-(4-(5-((1R,4R)-2-oxa-5-azabicyclo[2.2.1]heptan-5-yl)pyrazolo [1,5-a]pyrimidine-3-carboxamido)-3-(difluoromethyl)-1H-pyrazol-1-yl)cyclohexyl)piperazine-1-carboxylate (Intermediate CQN)

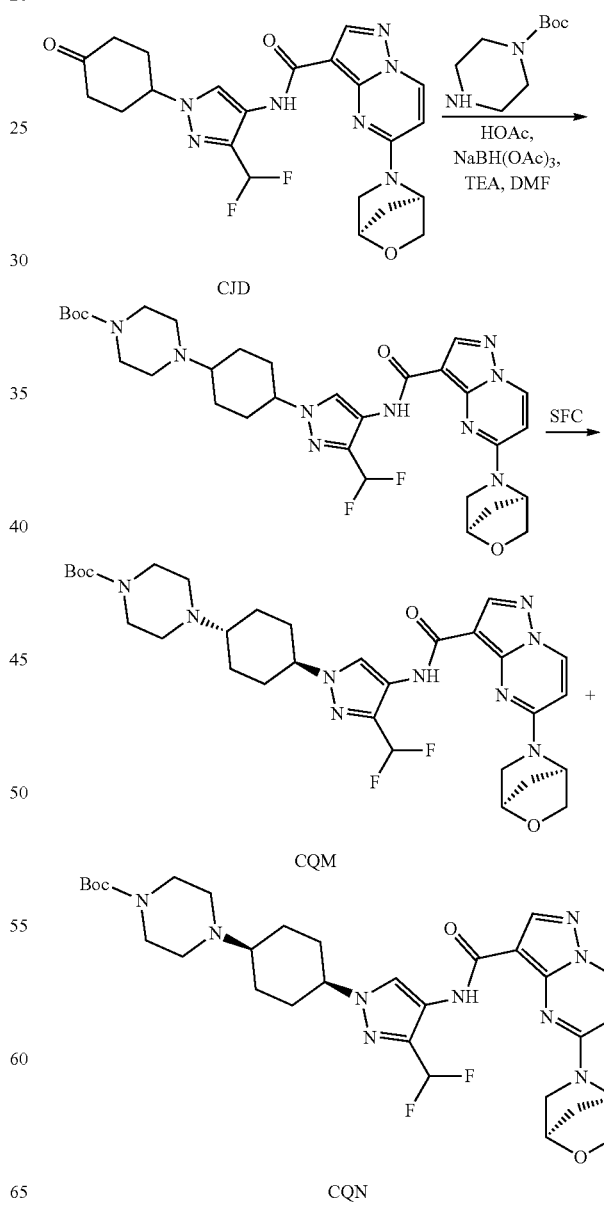

Step 1—Tert-butyl 4-[4-[3-(difluoromethyl)-4-[[5-[(1R,4R)-2-oxa-5-azabicyclo[2.2.1]heptan-5-yl]pyrazolo[1,5-a]pyrimidine-3-carbonyl]amino]pyrazol-1-yl]cyclohexyl]piperazine-1-carboxylate. To a solution of tert-butyl piperazine-1-carboxylate (126 mg, 676 μmol, CAS #57260-71-6) in DMF (5 mL) was added AcOH (73.8 mg, 1.23 mmol) at 25° C. until pH stabilized at 5-6. Subsequently, N-[3-(difluoromethyl)-1-(4-oxocyclohexyl)pyrazol-4-yl]-5-[(1R,4R)-2-oxa-5-azabicyclo[2.2.1]heptan-5-yl]pyrazolo[1,5-a]pyrimidine-3-carboxamide (290 mg, 615 μmol, from Intermediate CJD) was added and the mixture was stirred at 50° C. for 1 hr. Next, NaBH(OAc)₃ (195 mg, 922 μmol) was added one portion and the mixture was stirred at 50° C. for 3 hrs. On completion, the reaction mixture was quenched with H₂O (0.2 mL) at 20° C., then filtered and the organic phase was concentrated to give a residue. The residue was purified by reversed phase (0.1% FA condition) and prep-TLC (SiO₂, DCM:MeOH=10:1) to give the title compound (140 mg, 35% yield) as an off-white solid. ¹H NMR (400 MHz, DMSO-d₆) δ 9.53-9.45 (m, 1H), 8.78 (d, J=8.0 Hz, 1H), 8.43-8.34 (m, 1H), 8.25 (d, J=5.6 Hz, 1H), 7.30-6.95 (m, 1H), 6.89-6.42 (m, 1H), 5.32-5.01 (m, 1H), 4.77 (d, J=17.6 Hz, 1H), 4.36-4.11 (m, 1H), 3.86-3.70 (m, 2H), 3.67-3.42 (m, 2H), 3.30 (s, 4H), 2.48-2.42 (m, 3H), 2.41-2.34 (m, 2H), 2.24-2.13 (m, 1H), 2.12-2.02 (m, 2H), 2.01-1.88 (m, 2H), 1.87 (s, 1H), 1.83-1.72 (m, 2H), 1.62-1.51 (m, 1H), 1.42 (s, 1H), 1.39 (d, J=1.6 Hz, 9H); LC-MS (ESI⁺) m/z 642.2 (M+H)⁺.

Step 2—Tert-butyl 4-((1R,4r)-4-(4-(5-((1R,4R)-2-oxa-5-azabicyclo[2.2.1]heptan-5-yl)pyrazolo[1,5-a]pyrimidine-3-carboxamido)-3-(difluoromethyl)-1H-pyrazol-1-yl)cyclohexyl)piperazine-1-carboxylate and Tert-butyl 4-((1S,4s)-4-(4-(5-((1R,4R)-2-oxa-5-azabicyclo[2.2.1]heptan-5-yl)pyrazolo[1,5-a]pyrimidine-3-carboxamido)-3-(difluoromethyl)-1H-pyrazol-1-yl)cyclohexyl)piperazine-1-carboxylate. Tert-butyl 4-[4-[3-(difluoromethyl)-4-[[5-[(1R,4R)-2-oxa-5-azabicyclo[2.2.1]heptan-5-yl]pyrazolo[1,5-a]pyrimidine-3-carbonyl]amino]pyrazol-1-yl]cyclohexyl]piperazine-1-carboxylate was purified by SFC purification (column: DAICEL CHIRALPAK AD (250 mm*30 mm, 10 um); mobile phase: [CO₂-ACN/MeOH (0.1% NH₃H₂O)]; B %: 45%, isocratic elution mode) to give tert-butyl 4-((1R,4r)-4-(4-(5-((1R,4R)-2-oxa-5-azabicyclo[2.2.1]heptan-5-yl)pyrazolo[1,5-a]pyrimidine-3-carboxamido)-3-(difluoromethyl)-1H-pyrazol-1-yl)cyclohexyl)piperazine-1-carboxylate (65.0 mg, 46% yield, 99% ee, t_R=1.461) as a yellow solid (¹H NMR (400 MHz, DMSO-d₆) δ 9.49 (d, J=6.0 Hz, 1H), 8.78 (d, J=7.6 Hz, 1H), 8.38 (d, J=4.4 Hz, 1H), 8.25 (d, J=5.6 Hz, 1H), 7.28-6.94 (m, 1H), 6.90-6.39 (m, 1H), 5.35-5.03 (m, 1H), 4.77 (d, J=17.6 Hz, 1H), 4.28-4.07 (t, J=11.2 Hz, 1H), 3.85-3.71 (m, 2H), 3.66-3.42 (m, 2H), 3.28 (s, 4H), 2.45 (s, 4H), 2.15-2.03 (m, 3H), 2.03-1.92 (m, 2H), 1.92-1.82 (m, 2H), 1.82-1.70 (m, 2H), 1.41 (s, 2H), 1.39 (s, 9H); LC-MS (ESI⁺) m/z 642.3 (M+H)⁺) and tert-butyl 4-((1S,4s)-4-(4-(5-((1R,4R)-2-oxa-5-azabicyclo[2.2.1]heptan-5-yl)pyrazolo[1,5-a]pyrimidine-3-carboxamido)-3-(difluoromethyl)-1H-pyrazol-1-yl)cyclohexyl)piperazine-1-carboxylate (45.0 mg, 32% yield, 100% ee, t_R=0.766) as a yellow solid (¹H NMR (400 MHz, DMSO-d₆) δ 9.51 (d, J=6.0 Hz, 1H), 8.78 (d, J=7.6 Hz, 1H), 8.39 (d, J=3.6 Hz, 1H), 8.25 (d, J=5.6 Hz, 1H), 7.30-6.98 (m, 1H), 6.90-6.40 (m, 1H), 5.35-5.04 (m, 1H), 4.77 (d, J=16.4 Hz, 1H), 4.32 (d, J=0.8 Hz, 1H), 3.85-3.72 (m, 2H), 3.68-3.42 (m, 2H), 3.32-3.31 (m, 4H), 2.37 (s, 4H), 2.26-2.20 (m, 1H), 2.20-2.10 (m, 2H), 2.04-1.91 (m, 2H), 1.88-1.73 (m, 4H), 1.61-1.52 (m, 2H), 1.39 (s, 9H); LC-MS (ESI⁺) m/z 642.2 (M+H)⁺).

N-[3-(difluoromethyl)-1-(4-piperazin-1-ylcyclohexyl)pyrazol-4-yl]-5-[(1R,4R)-2-oxa-5-azabicyclo[2.2.1]heptan-5-yl]pyrazolo[1,5-a]pyrimidine-3-carboxamide (Intermediate CQO)

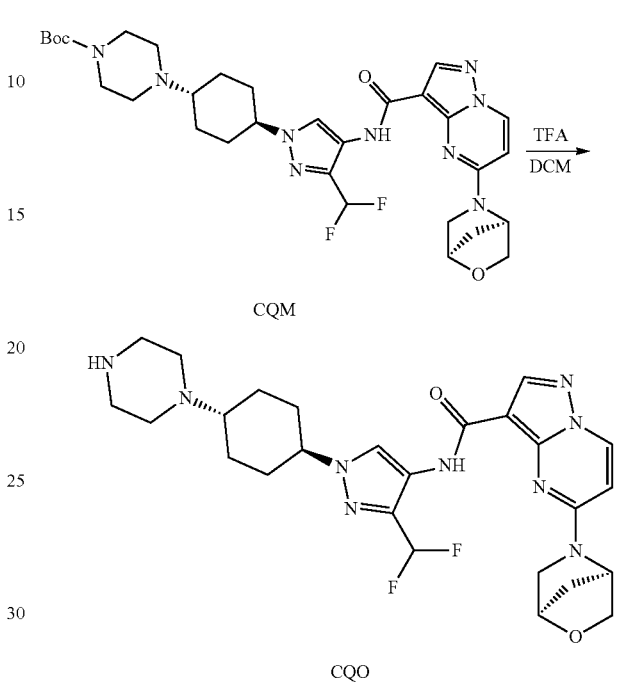

Tert-butyl 4-[4-[3-(difluoromethyl)-4-[[5-[(1R,4R)-2-oxa-5-azabicyclo[2.2.1]heptan-5-yl]pyrazolo [1,5-a]pyrimidine-3-carbonyl]amino]pyrazol-1-yl]cyclohexyl]piperazine-1-carboxylate (60.0 mg, 93.5 μmol, Intermediate CQM) was dissolved in DCM (1 mL) and TFA (0.3 mL), then the mixture was stirred as 25° C. for 1 hr. On completion, the reaction mixture was concentrated to give the title compound (60.0 mg, 97% yield, TFA) as an off-white solid. LC-MS (ESI⁺) m/z 542.2 (M+H)⁺.

Tert-butyl (3R,4R)-4-(azetidin-3-yloxy)-3-fluoropiperidine-1-carboxylate (Intermediate CQP)

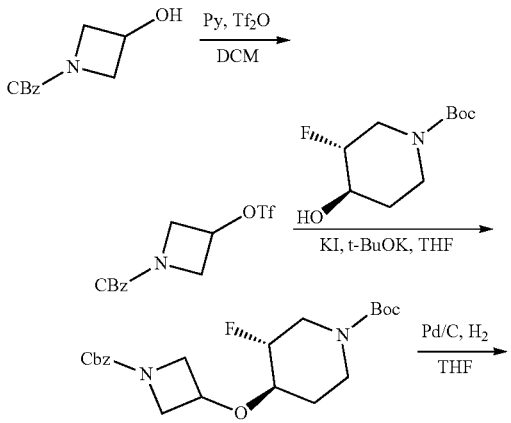

-continued

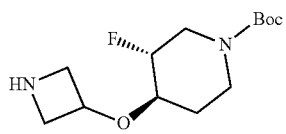

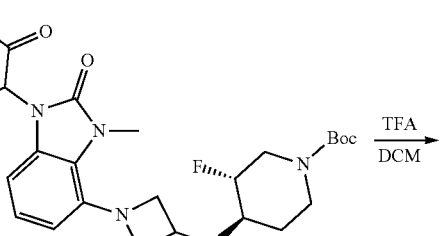

Step 1—Tert-butyl (3R,4R)-4-(1-benzyloxycarbonylazetidin-3-yl)oxy-3-fluoro-piperidine-1-carboxylate. To a solution of tert-butyl (3R,4R)-3-fluoro-4-hydroxy-piperidine-1-carboxylate (3.00 g, 1.37 mmol, CAS #1174020-43-9) in THF (20 mL) was added t-BuOK (2.79 g, 2.49 mmol) at −10° C., and the mixture was stirred at −10° C. for 1 hr. Then benzyl 3-(trifluoromethylsulfonyloxy)azetidine-1-carboxylate (4.22 g, 1.24 mmol, synthesized via Step 1 of Intermediate CNN) and KI (4.13 mg, 249 µmol) was added, and the mixture was stirred at −10° C. for 2 hrs. On completion, the reaction mixture was concentrated in vacuo to give a residue. Then the residue was purified by flash silica gel chromatography ($SiO_2$, Petroleum ether/Ethyl acetate=3/1) to give a residue. The residue was re-purified by reverse phase (0.1% FA condition) to give the title compound (300 mg, 6% yield) as yellow oil. $^1$H NMR (400 MHz, DMSO-$d_6$) δ 7.41-7.28 (m, 5H), 5.03 (s, 2H), 4.52-4.33 (m, 2H), 4.13 (s, 2H), 3.77 (s, 3H), 3.61-3.49 (m, 2H), 3.31 (s, 1H), 3.25-3.01 (m, 2H), 1.85 (d, J=4.0, 8.4 Hz, 1H), 1.39 (s, 9H); LC-MS (ESI$^+$) m/z 309.1 (M−100+H)$^+$.

Step 2—Tert-butyl (3R,4R)-4-(azetidin-3-yloxy)-3-fluoro-piperidine-1-carboxylate. To a solution of tert-butyl (3R,4R)-4-(1-benzyloxycarbonylazetidin-3-yl)oxy-3-fluoro-piperidine-1-carboxylate (370 mg, 906 µmol) in THF (4 mL) was added Pd/C (370 mg, 10 wt %) under $N_2$ atmosphere. The suspension was degassed and purged with $H_2$ three times. Then the mixture was stirred at 25° C. for 2 hrs under $H_2$ (15 psi). On completion, the reaction mixture was filtered to give the filtrate and concentrated in vacuo to give the title compound (240 mg, 77% yield) as yellow oil. LC-MS (ESI$^+$) m/z 274.9 (M+H)$^+$.

3-[4-[3-[[(3R,4R)-3-Fluoro-4-piperidyl]oxy]azetidin-1-yl]-3-methyl-2-oxo-benzimidazol-1-yl]piperidine-2,6-dione (Intermediate CQQ)

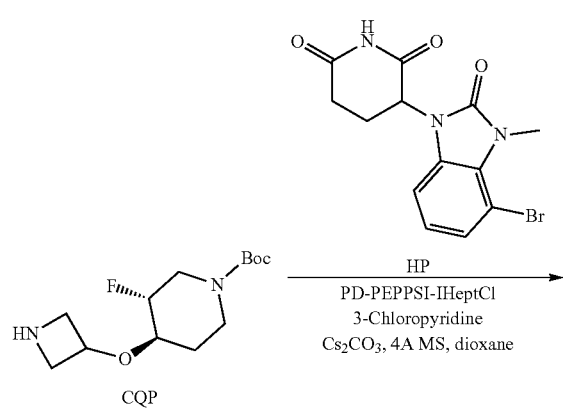

Step 1—Tert-butyl (3R,4R)-4-[1-[1-(2,6-dioxo-3-piperidyl)-3-methyl-2-oxo-benzimidazol-4-yl]azetidin-3-yl]oxy-3-fluoro-piperidine-1-carboxylate. To a solution of tert-butyl (3R,4R)-4-(azetidin-3-yloxy)-3-fluoro-piperidine-1-carboxylate (169 mg, 616 µmol, Intermediate CQP) and 3-(4-bromo-3-methyl-2-oxo-benzimidazol-1-yl)piperidine-2,6-dione (187 mg, 554 µmol, Intermediate HP) in dioxane (8 mL) was added $Cs_2CO_3$ (602 mg, 1.85 mmol), 4 Å molecular sieves (500 mg) and PD-PEPPSI-IHeptCl 3-Chloropyridine (59.9 mg, 61.6 µmol). The mixture was then stirred at 100° C. for 6 hrs under $N_2$. On completion, the reaction mixture was filtered to give the filtrate and concentrated in vacuo to give a residue. The residue was purified by column chromatography ($SiO_2$, PE:EA=5:1) to give the title compound (100 mg, 31% yield) as yellow oil. $^1$H NMR (400 MHz, DMSO-$d_6$) δ 11.07 (s, 1H), 6.99-6.93 (m, 1H), 6.76 (d, J=8.0 Hz, 1H), 6.69 (d, J=8.0 Hz, 1H), 5.32 (d, J=5.2, 12.4 Hz, 1H), 4.56 (t, J=6.0 Hz, 1H), 4.50-4.36 (m, 1H), 4.09-4.02 (m, 2H), 3.64 (d, J=6.0 Hz, 3H), 3.56 (s, 3H), 3.29 (s, 1H), 3.18-3.11 (m, 1H), 2.91-2.83 (m, 1H), 2.73-2.59 (m, 4H), 2.00-1.86 (m, 2H), 1.44 (d, J=4.4, 8.8 Hz, 1H), 1.39 (s, 9H); LC-MS (ESI$^+$) m/z 532.2 (M+H)$^+$.

Step 2—3-[4-[3-[[(3R,4R)-3-Fluoro-4-piperidyl]oxy]azetidin-1-yl]-3-methyl-2-oxo-benzimidazol-1-yl]piperidine-2,6-dione. To a solution of tert-butyl (3R,4R)-4-[1-[1-(2,6-dioxo-3-piperidyl)-3-methyl-2-oxo-benzimidazol-4-yl]azetidin-3-yl]oxy-3-fluoro-piperidine-1-carboxylate (100 mg, 188 µmol) in DCM (1 mL) was added TFA (3.07 g, 26.9 mmol), then the mixture was stirred at 25° C. for 1 hr. On completion, the reaction mixture was concentrated in vacuo to give the title compound (60.0 mg, 78% yield, TFA) as brown oil. LC-MS (ESI$^+$) m/z 432.1 (M+H)$^+$.

719

Tert-butyl (3S,4S)-4-(azetidin-3-yloxy)-3-fluoro-piperidine-1-carboxylate (Intermediate CQR)

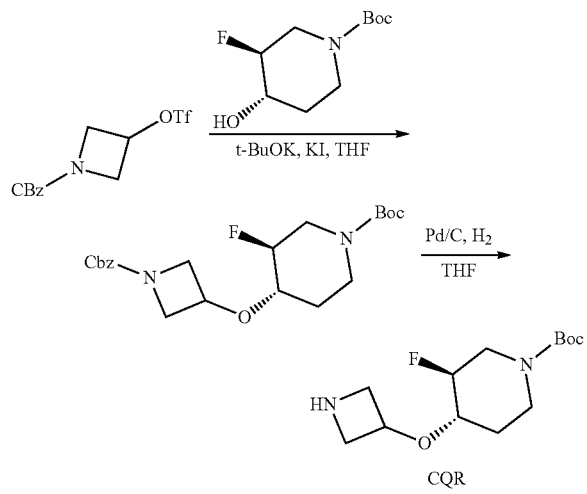

Step 1—N-[2-[4-[[2-[1-(2,6-dioxo-3-piperidyl)-3-methyl-2-oxo-benzimidazol-4-yl]-5,5-difluoro-2,7-diazaspiro[3.5]nonan-7-yl]methyl]cyclohexyl]indazol-5-yl]-6-(trifluoromethyl)pyridine-2-carboxamide. To a solution of tert-butyl (3S,4S)-3-fluoro-4-hydroxy-piperidine-1-carboxylate (3.60 g, 10.6 mmol, CAS #1174020-44-0) in DMF (10 mL) was added tBuOK (2.30 g, 21.2 mmol). The mixture was stirred at −10° C. for 0.5 hr, then benzyl 3-(trifluoromethylsulfonyloxy)azetidine-1-carboxylate (3.6 mg, 10.6 mmol, synthesized via Step 1 of Intermediate CNN) and KI (360 mg, 2.1 mmol) was added and the mixture was stirred at −10° C. for 2 hrs. On completion, the mixture was quenched with water (0.2 mL) and concentrated in vacuo to give a residue. The residue was purified by reverse phase (0.1% FA condition) to give the title compound (300 mg, 7% yield) as a white solid. $^1$H NMR (400 MHz, CDCl$_3$) δ 7.42-7.29 (m, 5H), 5.10 (s, 2H), 4.51-4.44 (m, 1H), 4.55-4.25 (m, 1H), 4.22-4.20 (m, 2H), 4.10-3.99 (m, 1H), 3.96-3.90 (m, 2H), 3.77 (d, J=13.6 Hz, 1H), 3.50-3.40 (m, 1H), 3.21-3.07 (m, 1H), 3.06-2.96 (m, 1H), 1.97-1.93 (m, 1H), 1.56-1.52 (m, 1H), 1.46 (s, 9H); LC-MS (ESI$^+$) m/z 309.0 (M−100+H)$^+$.

Step 2—Tert-butyl (3S,4S)-4-(azetidin-3-yloxy)-3-fluoro-piperidine-1-carboxylate. To a solution of tert-butyl (3S,4S)-4-(1-benzyloxycarbonylazetidin-3-yl)oxy-3-fluoro-piperidine-1-carboxylate (250 mg, 612 μmol) in THF (1 mL) was added Pd/C (2.00 g, 10 wt %). The mixture was then stirred at 25° C. under H$_2$ (15 Psi) for 3 hrs. On completion, the mixture was filtered and concentrated in vacuo to give the title compound (167 mg, 99% yield) as black oil. $^1$H NMR (400 MHz, CDCl$_3$) δ 4.54-4.46 (m, 1H), 4.45-4.23 (m, 1H), 4.15-3.85 (m, 1H), 3.81-3.71 (m, 2H), 3.70-3.67 (m, 2H), 3.53-3.38 (m, 1H), 3.20-3.18 (m, 1H), 3.14-3.02 (m, 1H), 1.97-1.91 (m, 1H), 1.57-1.49 (m, 1H), 1.46 (s, 9H); LC-MS (ESI$^+$) m/z 274.9 (M+H)$^+$.

720

3-[4-[3-[[(3S,4S)-3-fluoro-4-piperidyl]oxy]azetidin-1-yl]-3-methyl-2-oxo-benzimidazol-1-yl] piperidine-2,6-dione (Intermediate CQS)

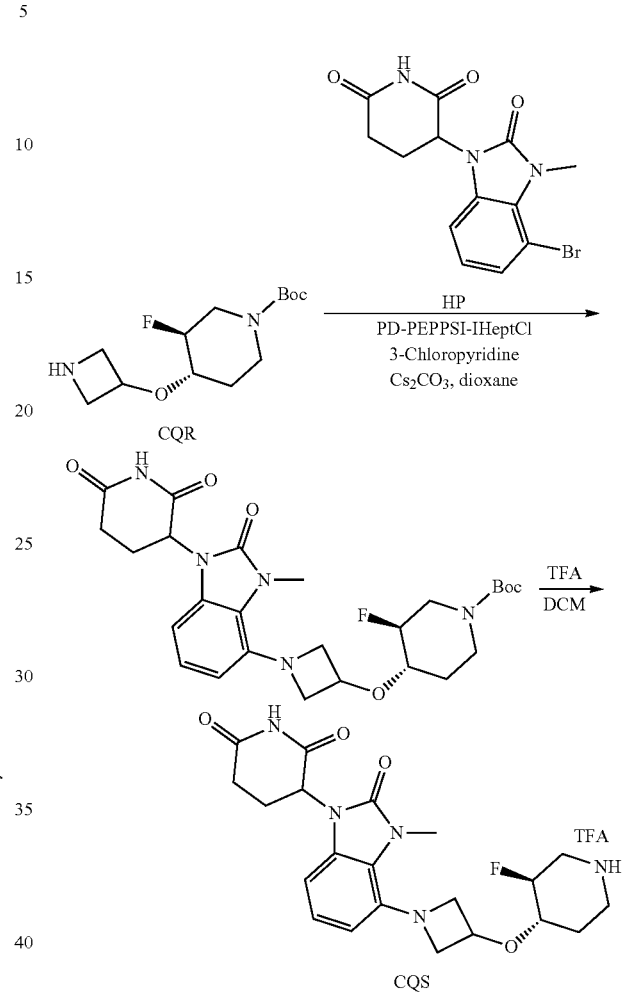

Step 1—Tert-butyl (3S,4S)-4-[1-[1-(2,6-dioxo-3-piperidyl)-3-methyl-2-oxo-benzimidazol-4-yl] azetidin-3-yl]oxy-3-fluoro-piperidine-1-carboxylate. A mixture of 3-(4-bromo-3-methyl-2-oxo-benzimidazol-1-yl)piperidine-2,6-dione (123 mg, 364 μmol, Intermediate HP), tert-butyl (3S,4S)-4-(azetidin-3-yloxy)-3-fluoro-piperidine-1-carboxylate (100 mg, 364 μmol, Intermediate CQR), 1,3-bis[2,6-bis(1-propylbutyl)phenyl]-4,5-dichloro-2H-imidazol-1-ium-2-ide; 3-chloropyridine dichloropalladium (35.4 mg, 36.4 μmol), and Cs$_2$CO$_3$ (356 mg, 1.09 mmol) in dioxane (1 mL) was degassed and purged with N$_2$ three times. Then the mixture was stirred at 100° C. for 3 hrs under N$_2$ atmosphere. On completion, the mixture was filtered and concentrated in vacuo to give a residue. The residue was purified by reverse phase (0.1% FA condition) to give the title compound (33.0 mg, 17% yield) as white solid. $^1$H NMR (400 MHz, CDCl$_3$) δ 8.01 (s, 1H), 7.05 (t, J=8.0 Hz, 1H), 6.81 (d, J=8.0 Hz, 1H), 6.57 (d, J=7.6 Hz, 1H), 5.24-5.15 (m, 1H), 4.68-4.59 (m, 1H), 4.44-4.42 (m, 2H), 4.25 (dd, J=4.0, 6.0 Hz, 2H), 3.93-3.87 (m, 2H), 3.81 (d, J=4.4 Hz, 1H), 3.78 (s, 3H), 3.71 (t, J=4.8 Hz, 1H), 3.55-3.50 (m, 1H), 3.08-2.91 (m, 3H), 2.83-2.66 (m, 2H), 2.26-2.20 (m, 1H), 2.01-1.95 (m, 1H), 1.47 (s, 9H). LC-MS (ESI$^+$) m/z 532.1 (M+H)$^+$.

Step 2—3-[4-[3-[[(3S,4S)-3-fluoro-4-piperidyl]oxy]azetidin-1-yl]-3-methyl-2-oxo-benzimidazol-1-yl] piperidine-2,6-dione. To a solution of tert-butyl (3S,4S)-4-[1-[1-(2,6-dioxo-3-piperidyl)-3-methyl-2-oxo-benzimidazol-4-yl]azetidin-3-yl]oxy-3-fluoro-piperidine-1-carboxylate (33.0 mg, 62.0 µmol) in DCM (0.5 mL) was added TFA (1.01 g, 8.89 mmol). The mixture was then stirred at 25° C. for 1 hr. On completion, the mixture was filtered and concentrated in vacuo to give the title compound (33.8 mg, TFA) as white solid. LC-MS (ESI+) m/z 432.1 (M+H)+.

N-[2-(4-formylcyclohexyl)pyrazolo[3,4-c]pyridin-5-yl]-5-[(1R,4R)-2-oxa-5-azabicyclo[2.2.1]heptan-5-yl]pyrazolo[1,5-a]pyrimidine-3-carboxamide (Intermediate CQT)

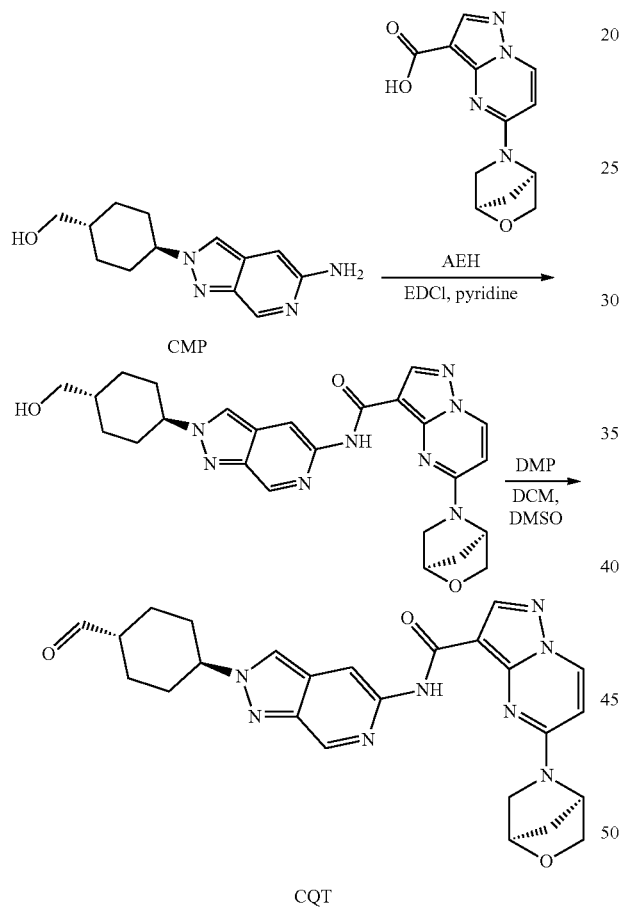

Step 1—N-[2-[4-(hydroxymethyl)cyclohexyl]pyrazolo[3,4-c]pyridin-5-yl]-5-[(1R,4R)-2-oxa-5-azabicyclo[2.2.1]heptan-5-yl]pyrazolo[1,5-a]pyrimidine-3-carboxamide. A mixture of [4-(5-aminopyrazolo[3,4-c]pyridin-2-yl)cyclohexyl]methanol (244 mg, 863 µmol, HCl, Intermediate CMP), 5-[(1R,4R)-2-oxa-5-azabicyclo[2.2.1]heptan-5-yl]pyrazolo[1,5-a]pyrimidine-3-carboxylic acid (269 mg, 1.04 mmol, Intermediate AEH) and EDCI (199 mg, 1.04 mmol) in pyridine (5 mL) was stirred at 60° C. for 0.5 hr. On completion, the reaction mixture was concentrated under reduced pressure and extracted with ethyl acetate (25 mL×3). Then the mixture was precipitated with water to give the residue at aqueous phase, the filtered solid was dried to give the title compound (270 mg, 64% yield) as a pink solid. 1H NMR (400 MHz, DMSO-d6) δ 10.68-10.44 (m, 1H), 8.98 (s, 1H), 8.82 (d, J=7.6 Hz, 1H), 8.50 (s, 1H), 8.39 (d, J=8.0 Hz, 1H), 8.29 (d, J=3.6 Hz, 1H), 6.94-6.47 (m, 1H), 5.41-5.01 (m, 1H), 4.83 (d, J=11.6 Hz, 1H), 4.58-4.43 (m, 2H), 3.96-3.83 (m, 1H), 3.77-3.60 (m, 2H), 3.30 (d, J=6.0 Hz, 2H), 2.17 (d, J=9.6 Hz, 2H), 2.11-1.99 (m, 2H), 1.98-1.88 (m, 4H), 1.59-1.42 (m, 1H), 1.28-1.05 (m, 3H); LC-MS (ESI+) m/z 489.2 (M+H)+.

Step 2—N-[2-(4-formylcyclohexyl)pyrazolo[3,4-c]pyridin-5-yl]-5-[(1R,4R)-2-oxa-5-azabicyclo[2.2.1]heptan-5-yl]pyrazolo[1,5-a]pyrimidine-3-carboxamide. To a mixture of N-[2-[4-(hydroxymethyl)cyclohexyl]pyrazolo[3,4-c]pyridin-5-yl]-5-[(1R,4R)-2-oxa-5-azabicyclo[2.2.1]heptan-5-yl]pyrazolo[1,5-a]pyrimidine-3-carboxamide (270 mg, 552 µmol) in DMSO (0.4 mL) and DCM (1 mL) was added DMP (305 mg, 718 µmol, 223 µL) at 25° C., then the mixture was stirred at 35° C. for 2 hrs. On completion, the mixture was quenched with saturated solution of Na2S2O3 (20 mL) and saturated solution NaHCO3, and the mixture was extracted with dichloromethane (25 mL×3). The combined organic phase was dried over anhydrous sodium sulfate, filtered and concentrated to give the title compound (268 mg, 99% yield) as a yellow solid. 1H NMR (400 MHz, DMSO-d6) δ 10.64-10.46 (m, 1H), 9.64 (s, 1H), 8.98 (s, 1H), 8.82 (d, J=7.6 Hz, 1H), 8.50 (s, 1H), 8.40 (d, J=8.4 Hz, 1H), 8.29 (d, J=3.6 Hz, 1H), 6.99-6.43 (m, 1H), 5.75 (s, 1H), 5.41-5.07 (m, 1H), 4.83 (d, J=10.8 Hz, 1H), 4.55 (tt, J=3.6, 12.0 Hz, 1H), 4.09-3.63 (m, 4H), 2.24 (dd, J=2.8, 12.4 Hz, 2H), 2.17-1.93 (m, 6H), 1.46 (dq, J=3.2, 12.8 Hz, 2H); LC-MS (ESI+) m/z 487.1 (M+H)+.

3-[5-(5,5-Difluoro-2,7-diazaspiro[3.5]nonan-2-yl)-4-fluoro-3-methyl-2-oxo-benzimidazol-1-yl]piperidine-2,6-dione (Intermediate CQU)

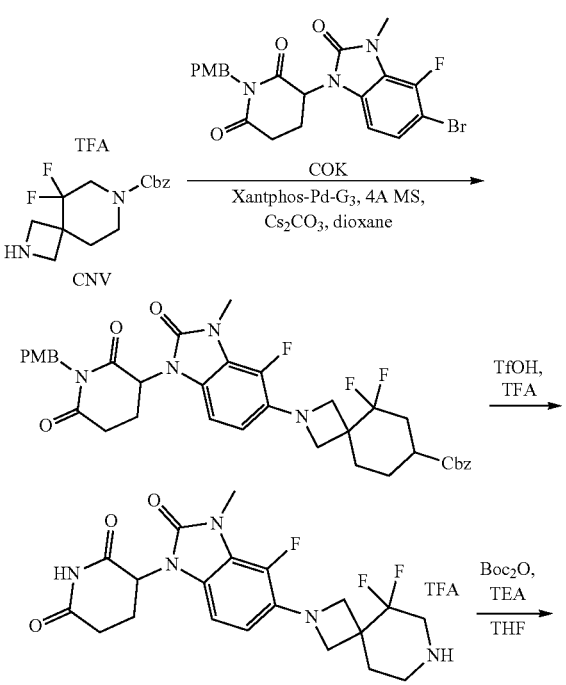

-continued

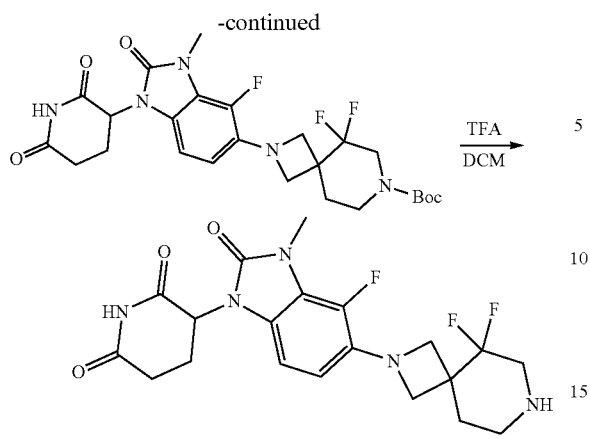

Step 1—Benzyl 5,5-difluoro-2-[4-fluoro-1-[1-[(4-methoxyphenyl)methyl]-2,6-dioxo-3-piperidyl]-3-methyl-2-oxo-benzimidazol-5-yl]-2,7-diazaspiro[3.5]nonane-7-carboxylate. To a solution of benzyl 5,5-difluoro-2,7-diazaspiro[3.5]nonane-7-carboxylate (800 mg, 1.95 mmol, TFA, Intermediate CNV) in dioxane (10 mL) was added 3-(5-bromo-4-fluoro-3-methyl-2-oxo-benzimidazol-1-yl)-1-[(4-methoxyphenyl)methyl]piperidine-2,6-dione (928 mg, 1.95 mmol, Intermediate COK), $Cs_2CO_3$ (1.91 g, 5.85 mmol), 1,3-bis[2,6-bis(1-propylbutyl)phenyl]-4,5-dichloro-2H-imidazol-1-ium-2-ide; 3-chloropyridine dichloropalladium (189 mg, 194 μmol), and 4 Å molecular sieves (40 mg). The mixture was stirred at 100° C. for 16 hrs. On completion, the reaction mixture was filtered and the filtrate was concentrated in vacuo. The residue was purified by column chromatography ($SiO_2$, PE:EA=5:1 to PE:EA=1:1, PE:EA=1:1, P1:Rf=0.24) to give the title compound (860 mg, 63% yield) as a yellow solid. LC-MS (ESI$^+$) m/z 692.2 (M+H)$^+$.

Step 2—3-[5-(5,5-Difluoro-2,7-diazaspiro[3.5]nonan-2-yl)-4-fluoro-3-methyl-2-oxo-benzimidazol-1-yl]piperidine-2,6-dione. To a solution of benzyl 5,5-difluoro-2-[4-fluoro-1-[1-[(4-methoxyphenyl)methyl]-2,6-dioxo-3-piperidyl]-3-methyl-2-oxo-benzimidazol-5-yl]-2,7-diazaspiro[3.5]nonane-7-carboxylate (800 mg, 1.16 mmol) in TFA (3 mL) was added TfOH (1.02 g, 6.78 mmol, 0.6 mL). The mixture was then stirred at 70° C. for 2 hrs. On completion, the reaction mixture was concentrated in vacuo to give the title compound (637 mg, 99% yield, TFA) as a brown oil. LC-MS (ESI+) m/z 438.1 (M+H)$^+$.

Step 3—Tert-butyl 2-[1-(2,6-dioxo-3-piperidyl)-4-fluoro-3-methyl-2-oxo-benzimidazol-5-yl]-5,5-difluoro-2,7-diazaspiro[3.5]nonane-7-carboxylate. To a solution of 3-[5-(5,5-difluoro-2,7-diazaspiro[3.5]nonan-2-yl)-4-fluoro-3-methyl-2-oxo-benzimidazol-1-yl]piperidine-2,6-dione (630 mg, 1.14 mmol, TFA) in DCM (5 mL) was added $Boc_2O$ (374 mg, 1.71 mmol) and TEA (115 mg, 1.14 mmol). The mixture was then stirred at 25° C. for 1 hr. On completion, the residue was diluted with water (10 mL) and extracted with water (2×10 mL). The combined organic layers was washed with brine (15 mL) and dried over $Na_2SO_4$, filtered and the filtrate was concentrated in vacuo. The residue was triturated with (PE:EA=10:1) to give the title compound (580 mg, 94% yield) as a yellow solid. $^1$H NMR (400 MHz, DMSO-$d_6$) δ 11.08 (s, 1H), 6.81 (d, J=8.4 Hz, 1H), 6.25 (t, J=8.4 Hz, 1H), 5.30 (d, J=5.2, 12.8 Hz, 1H), 3.95 (d, J=7.2 Hz, 2H), 3.74 (d, J=7.2 Hz, 2H), 3.65 (t, J=11.2 Hz, 2H), 3.47-3.38 (m, 5H), 2.94-2.79 (m, 1H), 2.73-2.56 (m, 2H), 2.09-1.93 (m, 3H), 1.41 (s, 9H); LC-MS (ESI+) m/z 537.8 (M+H)$^+$.

Step 4—3-[5-(5,5-Difluoro-2,7-diazaspiro[3.5]nonan-2-yl)-4-fluoro-3-methyl-2-oxo-benzimidazol-1-yl]piperidine-2,6-dione. To a solution of tert-butyl 2-[1-(2,6-dioxo-3-piperidyl)-4-fluoro-3-methyl-2-oxo-benzimidazol-5-yl]-5,5-difluoro-2,7-diazaspiro[3.5]nonane-7-carboxylate (50.0 mg, 93.0 μmol) in DCM (0.5 mL) was added TFA (307 mg, 2.69 mmol). The mixture was then stirred at 25° C. for 1 hr. On completion, the reaction mixture was concentrated in vacuo to give the title compound (50.0 mg, 97% yield, TFA) as a brown oil. LC-MS (ESI+) m/z 438.0 (M+H)$^+$.

3-[4-Fluoro-5-[3-[[(3R,4S)-3-fluoro-4-piperidyl]oxymethyl]azetidin-1-yl]-3-methyl-2-oxo-benzimidazol-1-yl]piperidine-2,6-dione (Intermediate CQV)

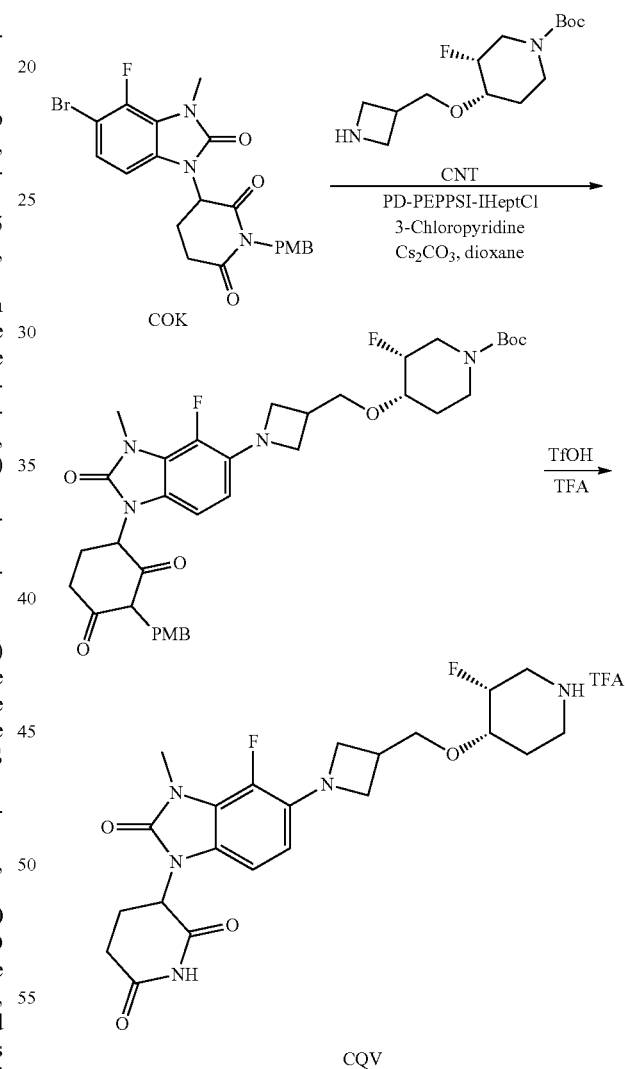

Step 1—Tert-butyl(3R,4S)-3-fluoro-4-[[1-[4-fluoro-1-[1-[(4-methoxyphenyl)methyl]-2,6-dioxo-3-piperidyl]-3-methyl-2-oxo-benzimidazol-5-yl]azetidin-3-yl]methoxy]piperidine-1-carboxylate. A mixture of tert-butyl (3R,4S)-4-(azetidin-3-ylmethoxy)-3-fluoro-piperidine-1-carboxylate (332 mg, 1.15 mmol, Intermediate CNT), 3-(5-bromo-4-fluoro-3-methyl-2-oxo-benzimidazol-1-yl)-1-[(4-methoxyphenyl)methyl]piperidine-2,6-dione (500 mg, 1.05 mmol, Intermediate COK), PD-PEPPSI-IHeptCl 3-Chloropyridine (102 mg, 104 μmol), and Cs₂CO₃ (684 mg, 2.10 mmol) in dioxane (10 mL) was stirred at 100° C. for 16 hrs under N₂. On completion, the reaction mixture was filtered and the filtrate was concentrated in vacuo to give a residue. The residue was purified by flash silica gel chromatography (SiO₂, Petroleum ether/Ethyl acetate=1/1, P1:Rf=0.2) to give the title compound (442 mg, 61% yield) as light yellow solid. ¹H NMR (400 MHz, DMSO-d₆) δ 7.18 (d, J=8.4 Hz, 2H), 6.84 (d, J=8.4 Hz, 2H), 6.65 (d, J=8.4 Hz, 1H), 6.14 (t, J=8.4 Hz, 1H), 5.43 (dd, J=5.6, 13.2 Hz, 1H), 4.88 (d, J=2.0 Hz, 1H), 4.85-4.70 (m, 3H), 4.06-3.95 (m, 2H), 3.91 (t, J=7.6 Hz, 2H), 3.71 (s, 3H), 3.69 (d, J=3.2 Hz, 1H), 3.58 (t, J=5.6 Hz, 3H), 3.09-2.97 (m, 2H), 2.95-2.75 (m, 5H), 2.70-2.60 (m, 1H), 2.06-1.98 (m, 1H), 1.72-1.66 (m, 1H), 1.63-1.52 (m, 2H), 1.37 (s, 9H); LC-MS (ESI⁺) m/z 684.5 (M+H)⁺.

Step 2—3-[4-Fluoro-5-[3-[[(3R,4S)-3-fluoro-4-piperidyl]oxymethyl]azetidin-1-yl]-3-methyl-2-oxo-benzimidazol-1-yl]piperidine-2,6-dione. To a solution of tert-butyl (3R,4S)-3-fluoro-4-[[1-[4-fluoro-1-[1-[(4-methoxyphenyl)methyl]-2,6-dioxo-3-piperidyl]-3-methyl-2-oxo-benzimidazol-5-yl]azetidin-3-yl]methoxy]piperidine-1-carboxylate (100 mg, 146 μmol) in TFA (3 mL) was added TfOH (1.70 g, 11.3 mmol) dropwise at 25° C., then the reaction mixture was stirred at 70° C. for 2 hrs. On completion, the reaction mixture was concentrated in vacuo to give the title compound (84.0 mg, 99% yield, TFA) as light yellow oil. LC-MS (ESI+) m/z 464.2 (M+H)⁺.

3-[3-Methyl-2-oxo-4-(4-piperidyloxy)benzimidazol-1-yl]piperidine-2,6-dione (Intermediate CQW)

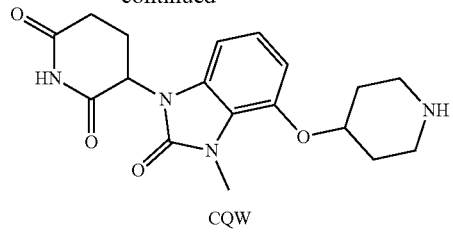

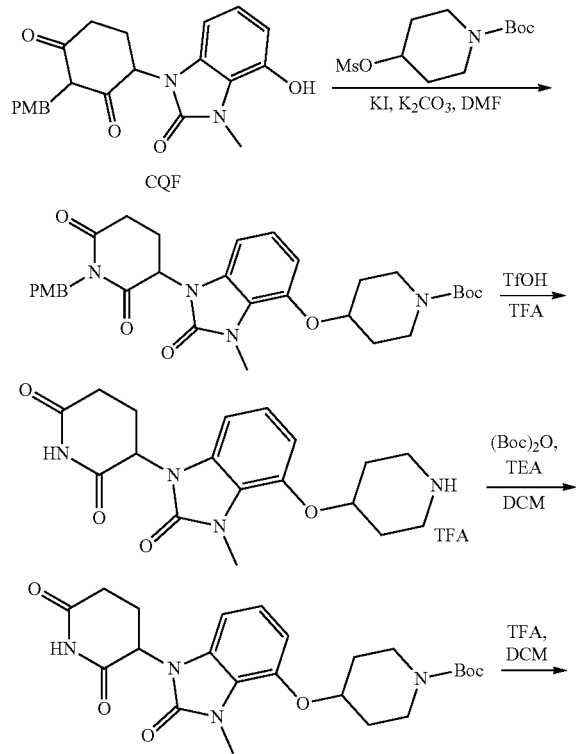

Step 1—Tert-butyl4-[1-[1-[(4-methoxyphenyl)methyl]-2,6-dioxo-3-piperidyl]-3-methyl-2-oxo-benzimidazol-4-yl]oxypiperidine-1-carboxylate. To a solution of 3-(4-hydroxy-3-methyl-2-oxo-benzimidazol-1-yl)-1-[(4-methoxyphenyl)methyl] piperidine-2,6-dione (1 g, 2.53 mmol, Intermediate CQF) in DMF (10 mL) was added KI (83.9 mg, 505 μmol), tert-butyl 4-methylsulfonyloxypiperidine-1-carboxylate (1.06 g, 3.79 mmol, CAS #141399-51-4), and K₂CO₃ (699 mg, 5.06 mmol) at 25° C. Then the reaction mixture was stirred at 90° C. for 12 hrs. On completion, the reaction mixture was quenched with H₂O (20 mL) under stirring. The residue was diluted with water (20 mL) and extracted with EA (30 mL×3). The combined organic layer was dried over Na₂SO₄, filtered and concentrated in vacuo to give a residue. The residue was purified by reverse phase (0.1% FA condition) to give the title compound (1.15 g, 78% yield) as light yellow solid. ¹H NMR (400 MHz, DMSO-d6) δ=7.22 (d, J=8.6 Hz, 2H), 6.95-6.79 (m, 5H), 5.44-5.44 (m, 1H), 4.86-4.75 (m, 2H), 3.73 (s, 3H), 3.64-3.59 (m, 2H), 3.55 (s, 3H), 3.32-3.27 (m, 2H), 3.08-2.99 (m, 1H), 2.80-2.66 (m, 2H), 2.08-2.00 (m, 2H), 1.97-1.91 (m, 2H), 1.69-1.62 (m, 2H), 1.42 (s, 9H). LC-MS (ESI+) m/z 523.2 (M+H)⁺.

Step 2—3-[3-Methyl-2-oxo-4-(4-piperidyloxy)benzimidazol-1-yl]piperidine-2,6-dione. To a solution of tert-butyl 4-[1-[1-[(4-methoxyphenyl)methyl]-2,6-dioxo-3-piperidyl]-3-methyl-2-oxo-benzimidazol-4-yl]oxypiperidine-1-carboxylate (1.05 g, 1.81 mmol) in TFA (10 mL) was added TfOH (5.94 g, 3.50 mL) dropwise at 25° C., then the reaction mixture was stirred at 70° C. for 2 hrs. On completion, the reaction mixture was concentrated in vacuo to give the title compound (857 mg, 99% yield, TFA) as brown oil. LC-MS (ESI+) m/z 359.1 (M+H)⁺.

Step 3—Tert-butyl4-[1-(2,6-dioxo-3-piperidyl)-3-methyl-2-oxo-benzimidazol-4-yl]oxypiperidine-1-carboxylate. To a solution of 3-[3-methyl-2-oxo-4-(4-piperidyloxy)benzimidazol-1-yl]piperidine-2,6-dione (898 mg, 1.90 mmol TFA) in DCM (10 mL) was added TEA (577 mg, 5.70 mmol) and (Boc)₂O (622 mg, 2.85 mmol) dropwise at 0° C. Then the reaction mixture was stirred at 25° C. for 2 hrs. On completion, the reaction mixture was quenched with H₂O (20 mL) under stirring. The residue was diluted with water (20 mL) and extracted with EA (30 mL×3). The combined organic layer was dried over Na₂SO₄, filtered and concentrated in vacuo to give a residue. The residue was purified by reverse phase (0.1% FA condition) to give the title compound (650 mg, 75% yield) as light yellow solid. ¹H NMR (400 MHz, DMSO-d6) δ 11.10 (s, 1H), 6.99-6.93 (m, 1H), 6.82 (d, J=8.4 Hz, 1H), 6.75 (d, J=7.6 Hz, 1H), 5.34 (dd, J=5.4, 12.8 Hz, 1H), 4.70-4.68 (m, 1H), 3.64-3.59 (m, 2H), 3.54 (s, 3H), 3.32-3.26 (m, 2H), 2.69-2.58 (m, 2H), 2.00-1.91 (m, 3H), 1.67-1.64 (m, 3H), 1.42 (s, 9H). LC-MS (ESI+) m/z 403.1 (M+H−56)⁺.

Step 4—3-[3-Methyl-2-oxo-4-(4-piperidyloxy)benzimidazol-1-yl]piperidine-2,6-dione. To a solution of tert-butyl 4-[1-(2,6-dioxo-3-piperidyl)-3-methyl-2-oxo-benzimidazol- 4-yl]oxy piperidine-1-carboxylate (150 mg, 327 µmol) in DCM (1 mL) was added a TFA (921 mg, 600.00 µL) dropwise at 0° C., then the reaction mixture was stirred at 25° C. for 0.14 hr. On completion, the reaction mixture was concentrated in vacuo to give the title compound (154 mg, 99% yield, TFA) as light yellow oil. LC-MS (ESI+) m/z 359.1 (M+H)+.

N-[2-(4-oxocyclohexyl)pyrazolo[3,4-c]pyridin-5-yl]-6-(trifluoromethyl)pyridine-2-carboxamide (Intermediate CQX)

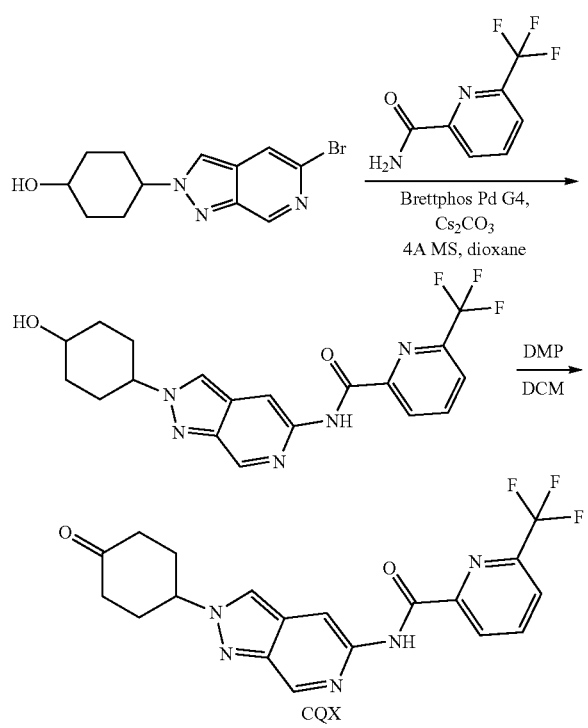

Step 1—N-[2-(4-hydroxycyclohexyl)pyrazolo[3,4-c]pyridin-5-yl]-6-(trifluoromethyl)pyridine-2-carboxamide. A mixture of 6-(trifluoromethyl)pyridine-2-carboxamide (385 mg, 2.03 mmol, CAS #22245-84-7), 4-(5-bromopyrazolo[3,4-c]pyridin-2-yl)cyclohexanol (600 mg, 2.03 mmol, synthesized via Step 1 of Intermediate CPO), 4 Å molecular sieves (100 mg), dicyclohexyl-[3,6-dimethoxy-2-(2,4,6-triisopropylphenyl)phenyl]phosphane methanesulfonate [2-[2-(methylamino)phenyl]phenyl]palladium (186 mg, 202 µmol) and Cs$_2$CO$_3$ (1.98 g, 6.08 mmol) in DMF (20 mL) was degassed and purged with N$_2$ three times. Then the mixture was stirred at 130° C. for 16 hrs under N$_2$ atmosphere. On completion, the reaction mixture was filtered and concentrated in vacuo to give a residue. The residue was purified by reverse phase (FA condition) to give the title compound (410 mg, 45% yield) as gray solid. $^1$H NMR (400 MHz, DMSO-d$_6$) δ 10.17 (s, 1H), 9.08-9.02 (m, 1H), 8.60-8.57 (m, 1H), 8.47 (d, J=7.2 Hz, 2H), 8.42-8.38 (m, 1H), 8.21 (d, J=7.6 Hz, 1H), 4.61-4.54 (m, 1H), 4.06-3.98 (m, 1H), 3.90 (s, 1H), 2.34-2.30 (m, 1H), 2.13 (d, J=10.4 Hz, 1H), 1.91-1.77 (m, 3H), 1.65 (s, 1H), 1.48-1.36 (m, 1H), 1.19-1.16 (m, 1H). LC-MS (ESI+) m/z 406.0 (M+H)+.

Step 2—N-[2-(4-oxocyclohexyl)pyrazolo[3,4-c]pyridin-5-yl]-6-(trifluoromethyl)pyridine-2-carboxamide. To a solution of N-[2-(4-hydroxycyclohexyl)pyrazolo[3,4-c]pyridin-5-yl]-6-(trifluoromethyl)pyridine-2-carboxamide (200 mg, 493 µmol) in DCM (2 mL) was added DMP (272 mg, 641 µmol) at 0° C. The mixture was stirred at 25° C. for 0.5 hrs. On completion, the mixture was diluted with DCM (2 mL) and quenched by addition Na$_2$S$_2$O$_2$ (1 mL) and saturated NaHCO$_3$ (1 mL). Then the combined organic layer were dried over anhydrous Na$_2$SO$_4$, filtered and concentrated in vacuo to give the title compound (190 mg, 90% yield) as yellow solid. LC-MS (ESI+) m/z 404.0 (M+H)+.

N-[2-(4-oxocyclohexyl)indazol-5-yl]-6-(trifluoromethyl)pyridine-2-carboxamide (Intermediate CQY)

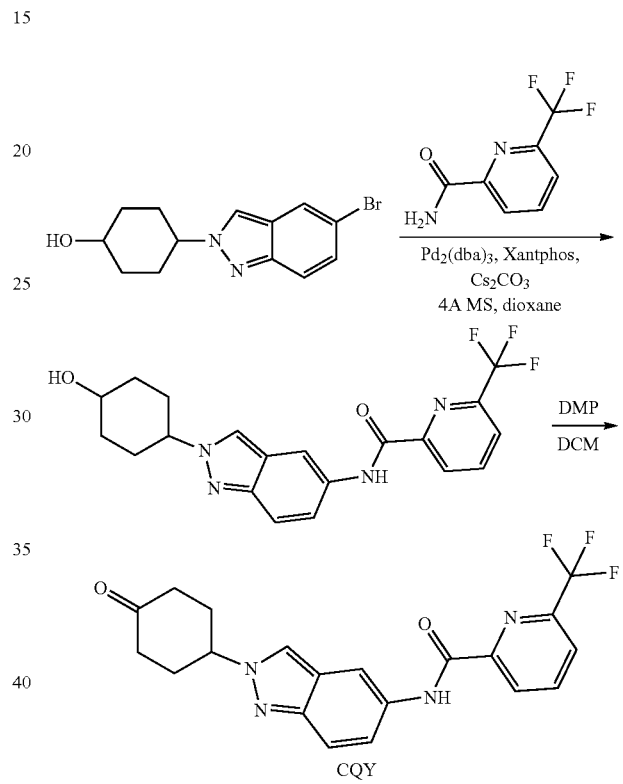

Step 1—3-[4-Fluoro-5-[3-[[(3R,4S)-3-fluoro-4-piperidyl]oxymethyl]azetidin-1-yl]-3-methyl-2-oxo-benzimidazol-1-yl]piperidine-2,6-dione. To a solution of 4-(5-bromoindazol-2-yl)cyclohexanol (2.12 g, 7.18 mmol, synthesized via Step 1 of Intermediate CLV) and 6-(trifluoromethyl) pyridine-2-carboxamide (1.50 g, 7.90 mmol) in dioxane (30 mL) was added Cs$_2$CO$_3$ (4.68 g, 14.3 mmol), 4 Å molecular sieves (60 mg), and BrettPhos (Pd, G$_4$) (330 mg, 359 µmol) at 25° C., then the reaction mixture was stirred at 100° C. for 8 hrs under N$_2$. On completion, the reaction mixture was concentrated in vacuo to give a residue. The residue was purified by column chromatography (SiO$_2$, DCM:MeOH=50:1 to DCM:MeOH=15:1, P1:Rf=0.6) to give the title compound (2.4 g, 82% yield) as light yellow solid. $^1$H NMR (400 MHz, DMSO-d$_6$) δ 10.4 (s, 1H), 8.43-8.39 (m, 2H), 8.39-8.33 (m, 1H), 8.33-8.29 (m, 1H), 8.19-8.15 (m, 1H), 7.65-7.60 (m, 1H), 7.58-7.54 (m, 1H), 4.74-4.52 (m, 1H), 4.47 (tt, J=3.6, 11.1 Hz, 1H), 2.32 (dq, J=3.2, 12.0 Hz, 2H), 2.03-1.95 (m, 1H), 1.92-1.76 (m, 4H), 1.70-1.60 (m, 2H). LC-MS (ESI+) m/z 405.1 (M+H)+.

Step 2—N-[2-(4-oxocyclohexyl)indazol-5-yl]-6-(trifluoromethyl)pyridine-2-carboxamide. To a solution of N-[2-(4- hydroxycyclohexyl)indazol-5-yl]-6-(trifluoromethyl)pyridine-2-carboxamide (500 mg, 1.24 mmol) in DCM (20 mL) was added DMP (629 mg, 1.48 mmol) dropwise at 0° C. for 2 hrs. On completion, the reaction mixture was quenched with sat. $Na_2S_2O_3$ solution (3 mL) and $NaHCO_3$ solution (3 mL) under stirring. The residue was diluted with water (3 mL) and extracted with EA (3 mL×3). The combined organic layer was dried over $Na_2SO_4$, filtered and concentrated in vacuo to give a residue. The residue was purified by column chromatography ($SiO_2$, DCM:MeOH=50:1 to DCM:MeOH=15:1, P1:Rf=0.6) to give the title compound (490 mg, 98% yield) as light yellow solid. LC-MS (ESI+) m/z 403.1 (M+H)+.

Tert-butyl (3R,4R)-4-(azetidin-3-ylmethoxy)-3-fluoro-piperidine-1-carboxylate (Intermediate CQZ)

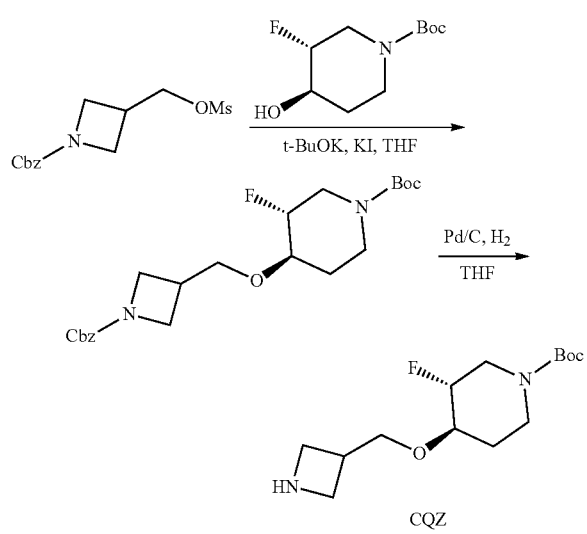

Step 1—Tert-butyl (3R,4R)-4-[(1-benzyloxycarbonylazetidin-3-yl)methoxy]-3-fluoro-piperidine-1-carboxylate. To a mixture of tert-butyl (3R,4R)-3-fluoro-4-hydroxy-piperidine-1-carboxylate (5.00 g, 22.8 mmol, CAS #1174020-43-9) in THF (50 mL) was added t-BuOK (1 M, 34.2 mL) at 0° C., then the mixture was stirred at 0° C. for 1 hr under $N_2$. Next, benzyl 3-(methylsulfonyloxymethyl)azetidin-1-carboxylate (6.83 g, 22.8 mmol, synthesized via Step 1 of Intermediate CNP) and KI (757 mg, 4.56 mmol) in THF (70 mL) were added at 0° C., and the mixture was stirred at 25° C. for 12 hrs under $N_2$. On completion, the reaction mixture was concentrated under reduced pressure to remove solvent. The mixture was diluted with water (50 mL) and extracted with ethyl acetate (25 mL×3). The combined organic phase was dried over anhydrous sodium sulfate, filtered and concentrated to give a residue. The residue was purified by column chromatography ($SiO_2$, Petroleum ether/Ethyl acetate=10:1 to 2:1, EA=25%) to give the title compound (1.60 g, 16% yield) as yellow oil. $^1$H NMR (400 MHz, $CDCl_3$) δ 7.40-7.28 (m, 5H), 5.10 (s, 2H), 4.50-4.29 (m, 1H), 4.08 (t, J=8.4 Hz, 2H), 3.91-3.81 (m, 1H), 3.79-3.74 (m, 2H), 3.70 (d, J=6.4 Hz, 2H), 3.66-3.46 (m, 2H), 3.34-3.13 (m, 2H), 2.85-2.75 (m, 1H), 1.95 (ddd, J=3.6, 6.8, 14.0 Hz, 1H), 1.58-1.51 (m, 1H), 1.46 (s, 9H); LC-MS (ESI+) m/z 445.1 (M+Na)+.

Step 2—Tert-butyl (3R,4R)-4-(azetidin-3-ylmethoxy)-3-fluoro-piperidine-1-carboxylate. To a mixture of tert-butyl (3R,4R)-4-[(1-benzyloxycarbonylazetidin-3-yl)methoxy]-3-fluoro-piperidine-1-carboxylate (1.00 g, 2.37 mmol) in THF (20 mL) was added Pd/C (500 mg, 469 μmol, 10 wt %) at 25° C., then the mixture was stirred at 25° C. for 16 hrs under $H_2$ (15 Psi). On completion, the mixture was filtered and concentrated to give the title compound (682 mg, 100% yield) as black oil. $^1$H NMR (400 MHz, $CDCl_3$) δ 4.51-4.32 (m, 1H), 3.96-3.76 (m, 2H), 3.76-3.65 (m, 3H), 3.65-3.50 (m, 2H), 3.50-3.38 (m, 2H), 3.38-3.10 (m, 2H), 3.00-2.92 (m, 1H), 2.45 (s, 1H), 2.02-1.93 (m, 1H), 1.62-1.54 (m, 1H), 1.47-1.46 (m, 9H); LC-MS (ESI+) m/z 289.1 (M+H)+.

3-[4-Fluoro-5-[3-[[(3R,4R)-3-fluoro-4-piperidyl]oxymethyl]azetidin-1-yl]-3-methyl-2-oxo-benzimidazol-1-yl]piperidine-2,6-dione (Intermediate CRA)

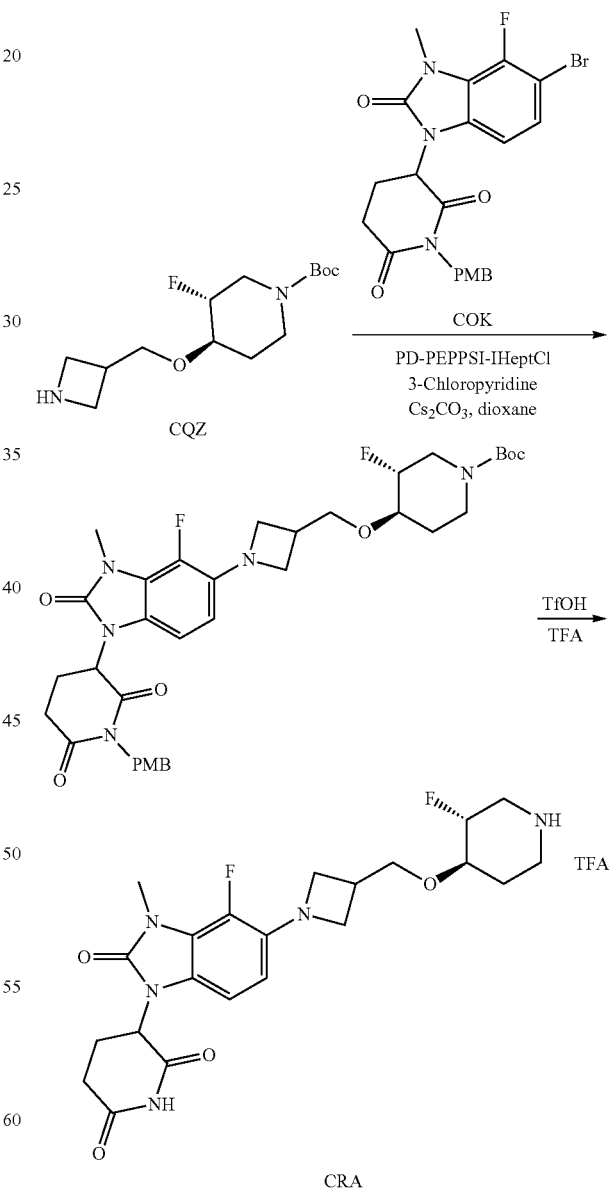

Step 1—Tert-butyl (3R,4R)-3-fluoro-4-[[1-[4-fluoro-1-[1-[(4-methoxyphenyl)methyl]-2,6-dioxo-3-piperidyl]-3-methyl-2-oxo-benzimidazol-5-yl]azetidin-3-yl]methoxy]piperidine-1-carboxylate. To a solution of tert-butyl (3R,4R)-4-(azetidin-3-ylmethoxy)-3-fluoro-piperidine-1-carboxylate (425 mg, 693 µmol, Intermediate CQZ), 3-(5-bromo-4-fluoro-3-methyl-2-oxo-benzimidazol-1-yl)-1-[(4-methoxyphenyl)methyl]piperidine-2,6-dione (688 mg, 578 µmoll, Intermediate COK) and $Cs_2CO_3$ (941 mg, 1.16 mmol), and 4 Å molecular sieves in dioxane (10 mL) were added 1,3-bis[2,6-bis(1-propylbutyl)phenyl]-4,5-dichloro-2H-imidazol-1-ium-2-ide 3-chloropyridine dichloropalladium (196 mg, 115 µmol) at 25° C. The mixture was degassed and purged with $N_2$ three times, and then the mixture was stirred at 100° C. for 16 hrs under $N_2$ atmosphere. On completion, the mixture was filtered and concentrated to give a residue. The residue was purified by reversed phase flash (0.1% FA condition) to give the title compound (240 mg, 23% yield) as a yellow solid. $^1$H NMR (400 MHz, DMSO-$d_6$) δ 8.17 (s, 1H), 7.20 (d, J=8.8 Hz, 2H), 6.85 (d, J=8.8 Hz, 2H), 6.66 (d, J=8.0 Hz, 1H), 6.15 (t, J=8.4 Hz, 1H), 5.44 (d, J=5.2, 13.2 Hz, 1H), 4.86-4.68 (m, 2H), 4.57-4.34 (m, 1H), 3.92 (t, J=7.6 Hz, 2H), 3.75 (d, J=7.2 Hz, 1H), 3.72 (s, 3H), 3.68 (s, 1H), 3.59 (t, J=5.2 Hz, 4H), 3.40 (s, 2H), 3.25-3.16 (m, 1H), 3.09-2.99 (m, 1H), 2.94-2.79 (m, 2H), 2.79-2.65 (m, 2H), 2.01 (d, J=7.2 Hz, 1H), 1.93-1.81 (m, 1H), 1.44 (s, 2H), 1.39 (s, 9H); LC-MS (ESI$^+$) m/z 684.2 (M+H)$^+$.

Step 2—3-[4-Fluoro-5-[3-[[(3R,4R)-3-fluoro-4-piperidyl]oxymethyl]azetidin-1-yl]-3-methyl-2-oxo-benzimidazol-1-yl]piperidine-2,6-dione. To a solution of tert-butyl (3R,4R)-3-fluoro-4-[[1-[4-fluoro-1-[1-[(4-methoxyphenyl)methyl]-2,6-dioxo-3-piperidyl]-3-methyl-2-oxo-benzimidazol-5-yl]azetidin-3-yl]methoxy]piperidine-1-carboxylate (180 mg, 263 µmol) in TFA (3 mL) and TfOH (0.6 mL) was stirred at 70° C. for 0.5 hr. On completion, the reaction mixture was concentrated under reduced pressure to give the title compound (151 mg, 99% yield, TFA) as a red oil. LC-MS (ESI$^+$) m/z 463.9 (M+H)$^+$.

4-Chloro-3-methyl-1H-imidazo[4,5-c]pyridin-2-one (Intermediate CRB)

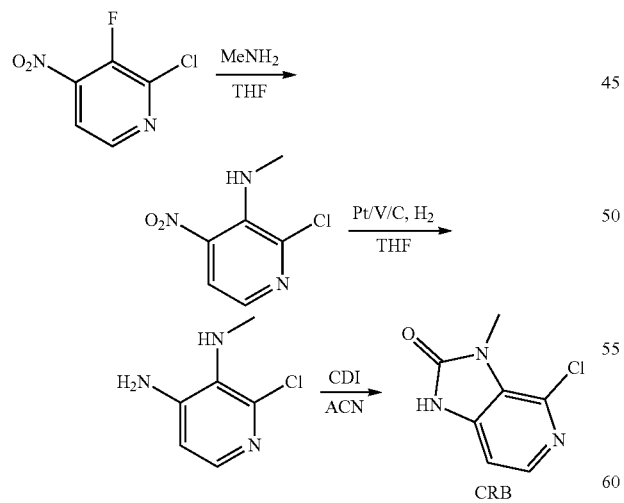

Step 1—2-Chloro-N-methyl-4-nitro-pyridin-3-amine. To a solution of 2-chloro-3-fluoro-4-nitro-pyridine (20.0 g, 113 mmol, CAS #109613-90-3) in THF (200 mL) was added methanamine (17.5 g, 169 mmol, 30% solution) at 0° C. under $N_2$ over 30 mins. The reaction was then stirred at 0° C. for 1 hr. Then the reaction was stirred at 25° C. for 16 hrs. On completion, the reaction was diluted with EtOAc (400 mL). The mixture was washed with water (200 mL×3), the combined organic phase was dried over anhydrous sodium sulfate, filtered and concentrated to give the title compound (21.3 g, 95% yield) was as yellow solid. $^1$H NMR (400 MHz, DMSO-$d_6$) δ 7.79-7.57 (m, 2H), 6.87 (d, J=4.4 Hz, 1H), 2.70 (d, J=5.2 Hz, 3H).

Step 2—2-Chloro-N3-methyl-pyridine-3,4-diamine. To a solution of 2-chloro-N-methyl-4-nitro-pyridin-3-amine (21.0 g, 111 mmol) in MeOH (400 mL) was added Pt/V/C (4.20 g, 16.0 mmol) and $H_2$ (225 mg, 111 mmol, 15 psi). The mixture was stirred at 25° C. for 16 hrs. On completion, the mixture was filtered and concentrated to give the title compound (17.4 g, 98% yield) as black oil. $^1$H NMR (400 MHz, DMSO-$d_6$) δ 7.52 (d, J=5.2 Hz, 1H), 6.52 (d, J=5.2 Hz, 1H), 5.99 (s, 2H), 3.73 (d, J=5.6 Hz, 1H), 2.56 (d, J=5.6 Hz, 3H).

Step 3—4-Chloro-3-methyl-1H-imidazo[4,5-c]pyridin-2-one. A mixture of 2-chloro-N3-methyl-pyridine-3,4-diamine (17.4 g, 110 mmol) and CDI (21.5 g, 132 mmol) in ACN (200 mL) was degassed and purged with $N_2$ three times. Then the mixture was stirred at 85° C. for 16 hrs under $N_2$ atmosphere. On completion, the mixture was filtered and concentrated to give the title compound (15.0 g, 73% yield) as white solid. $^1$H NMR (400 MHz, DMSO-$d_6$) δ 11.70 (s, 1H), 7.95 (d, J=5.2 Hz, 1H), 7.06 (d, J=5.2 Hz, 1H), 3.52 (s, 3H).

3-Methyl-4-piperazin-1-yl-1H-imidazo[4,5-c]pyridin-2-one (Intermediate CRC)

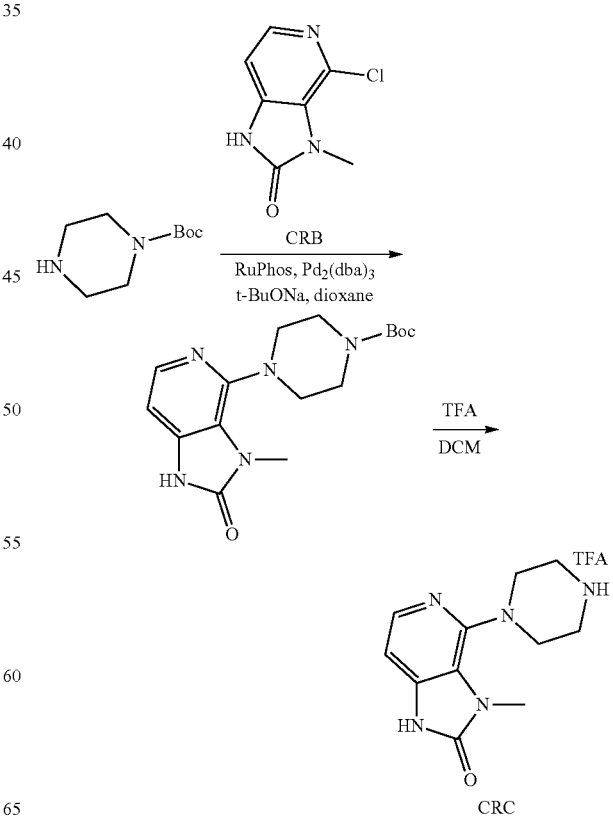

Step 1—Tert-butyl 4-(3-methyl-2-oxo-1H-imidazo[4,5-c]pyridin-4-yl)piperazine-1-carboxylate. A mixture of 4-chloro-3-methyl-1H-imidazo[4,5-c]pyridin-2-one (5.00 g, 27.2 mmol, Intermediate CRB), tert-butyl piperazine-1-carboxylate (6.59 g, 35.4 mmol, CAS #143238-38-4), RuPhos (1.27 g, 2.72 mmol), Pd$_2$(dba)$_3$ (1.25 g, 1.36 mmol) and t-BuONa (7.85 g, 81.7 mmol) in dioxane (2 mL) was degassed and purged with N$_2$ three times. Then the mixture was stirred at 100° C. for 2 hrs under N$_2$ atmosphere. On completion, the mixture was filtered and concentrated to give a residue. The residue was purified by column chromatography (SiO$_2$, DCM/MeOH=1/0 to 60/1) to give the title compound (5.15 g, 51% yield) as yellow solid. $^1$H NMR (400 MHz, DMSO-d$_6$) δ 11.29 (s, 1H), 7.86 (d, J=5.2 Hz, 1H), 6.81 (d, J=5.2 Hz, 1H), 3.50 (s, 7H), 2.99 (t, J=4.8 Hz, 4H), 1.42 (s, 9H); LC-MS (ESI$^+$) m/z 334.1 (M+H)$^+$.

Step 2—3-Methyl-4-piperazin-1-yl-1H-imidazo[4,5-c]pyridin-2-one. To a solution of tert-butyl 4-(3-methyl-2-oxo-1H-imidazo[4,5-c]pyridin-4-yl)piperazine-1-carboxylate (2.50 g, 7.50 mmol) in DCM (30 mL) was added TFA (6 mL). The mixture was stirred at 25° C. for 0.5 hr. On completion, the mixture was filtered and concentrated to give the title compound (2.50 g, 96% yield, TFA) as a yellow oil. LC-MS (ESI$^+$) m/z 234.1 (M+H)$^+$.

Tert-butyl (4R)-3,3-difluoro-4-[4-(3-methyl-2-oxo-1H-imidazo[4,5-c]pyridin-4-yl)piperazin-1-yl]piperidine-1-carboxylate (Intermediate CRD) and tert-butyl (4S)-3,3-difluoro-4-[4-(3-methyl-2-oxo-1H-imidazo[4,5-c]pyridin-4-yl)piperazin-1-yl]piperidine-1-carboxylate (Intermediate CRE)

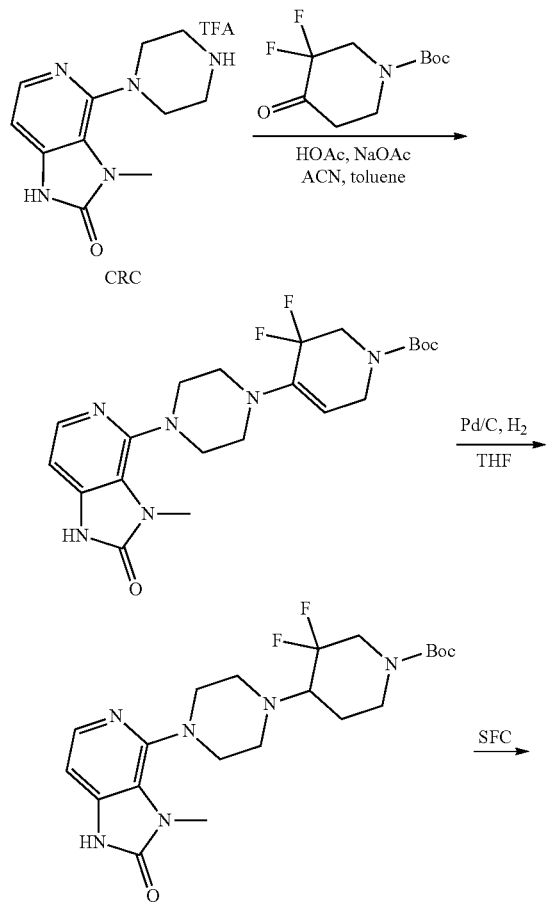

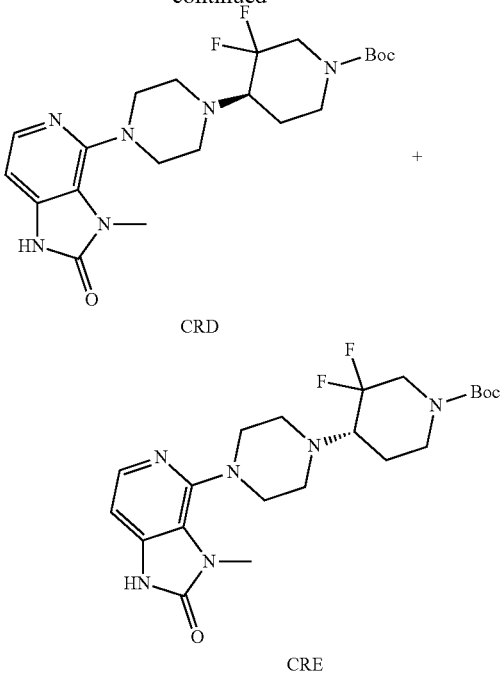

Step 1—Tert-butyl 3,3-difluoro-4-[4-(3-methyl-2-oxo-1H-imidazo[4,5-c]pyridin-4-yl)piperazin-1-yl]-2,6-dihydropyridine-1-carboxylate. To a mixture of 3-methyl-4-piperazin-1-yl-1H-imidazo[4,5-c]pyridin-2-one (2.50 g, 7.20 mmol, TFA, Intermediate CRC) in ACN (30 mL) and toluene (20 mL) was added NaOAc (1.18 g, 14.4 mmol) at 25° C. until the pH stabilized at 5. Then tert-butyl 3,3-difluoro-4-oxo-piperidine-1-carboxylate (3.39 g, 14.4 mmol, CAS #1215071-17-2) was added at 25° C. The resulting reaction mixture was stirred at 110° C. for 24 hrs. On completion, the mixture was filtered and concentrated to give a residue. The residue was diluted with EA (150 mL) and H$_2$O (120 mL). The mixture was filtered and concentrated to give the title compound (3.80 g, 99% yield) as yellow solid. LC-MS (ESI$^+$) m/z 451. (M+H)$^+$.

Step 2—Tert-butyl 3,3-difluoro-4-[4-(3-methyl-2-oxo-1H-imidazo[4,5-c]pyridin-4-yl)piperazin-1-yl] piperidine-1-carboxylate. To a solution of tert-butyl 3,3-difluoro-4-[4-(3-methyl-2-oxo-1H-imidazo[4,5-c]pyridin-4-yl)piperazin-1-yl]-2,6-dihydropyridine-1-carboxylate (3.80 g, 8.44 mmol) in THF (80 mL) was added Pd/C (3.50 g, 3.29 mmol, 10 wt %) under H$_2$ (15 Psi). The mixture was stirred at 25° C. for 16 hrs. On completion, the mixture was filtered and concentrated to give a residue. The residue was purified by column chromatography (SiO$_2$, DCM/MeOH=80/1 to 40/1) to give the title compound (2.30 g, 60% yield) as white solid. $^1$H NMR (400 MHz, DMSO-d$_6$) δ 11.24 (s, 1H), 7.86 (d, J=5.2 Hz, 1H), 6.78 (d, J=5.2 Hz, 1H), 4.03 (s, 2H), 3.49 (s, 3H), 3.17-3.04 (m, 2H), 3.01 (s, 4H), 2.90 (d, J=3.6 Hz, 5H), 1.86-1.64 (m, 2H), 1.40 (s, 9H); LC-MS (ESI$^+$) m/z 453.1 (M+H)$^+$.

Step 3—Tert-butyl (4R)-3,3-difluoro-4-[4-(3-methyl-2-oxo-1H-imidazo[4,5-c]pyridin-4-yl)piperazin-1-yl]piperidine-1-carboxylate and Tert-butyl (4S)-3,3-difluoro-4-[4-(3-methyl-2-oxo-1H-imidazo[4,5-c]pyridin-4-yl)piperazin-1-yl]piperidine-1-carboxylate. Tert-butyl 3,3-difluoro-4-[4-(3-methyl-2-oxo-1H-imidazo[4,5-c]pyridin-4-yl)piperazin-1-yl]piperidine-1-carboxylate (2.30 g, 5.08 mmol) was separated by SFC (column: DAICEL CHIRALPAK AD (250 mm*50 mm, 10 um); mobile phase: [CO$_2$-EtOH (0.1% NH$_3$H$_2$O)]; B %: 55%, isocratic elution mode) to give tert-butyl (4R)-3,3-difluoro-4-[4-(3-methyl-2-oxo-1H-imidazo[4,5-c]pyridin-4-yl)piperazin-1-yl]piperidine-1-carboxylate (1.00 g, 41% yield, 100% ee, t$_R$=0.58) as a white solid ($^1$H NMR (400 MHz, DMSO-d$_6$) δ 11.72-10.78 (m, 1H), 7.86 (d, J=5.2 Hz, 1H), 6.78 (d, J=5.2 Hz, 1H), 4.03 (d, J=7.2 Hz, 3H), 3.49 (s, 3H), 3.12 (d, J=12.4 Hz, 2H), 3.01 (s, 4H), 2.90 (d, J=3.6 Hz, 4H), 1.82-1.67 (m, 2H), 1.40 (s, 9H); LC-MS (ESI$^+$) m/z 453.2 (M+H)$^+$) and tert-butyl (4S)-3,3-difluoro-4-[4-(3-methyl-2-oxo-1H-imidazo[4,5-c]pyridin-4-yl)piperazin-1-yl]piperidine-1-carboxylate (1.00 g, 41% yield, 99% ee, t$_R$=1.389) as a white solid ($^1$H NMR (400 MHz, DMSO-d$_6$) δ 11.72-10.78 (m, 1H), 7.86 (d, J=5.2 Hz, 1H), 6.78 (d, J=5.2 Hz, 1H), 4.03 (d, J=7.2 Hz, 3H), 3.49 (s, 3H), 3.12 (d, J=12.4 Hz, 2H), 3.01 (s, 4H), 2.90 (d, J=3.6 Hz, 4H), 1.82-1.67 (m, 2H), 1.40 (s, 9H); LC-MS (ESI$^+$) m/z 453.2 (M+H)$^+$). The absolute stereochemistry of the enantiomers was assigned arbitrarily.

3-[4-[4-[(4R)-3,3-difluoro-4-piperidyl]piperazin-1-yl]-3-methyl-2-oxo-imidazo[4,5-c] pyridin-1-yl] piperidine-2,6-dione (Intermediate CRF)

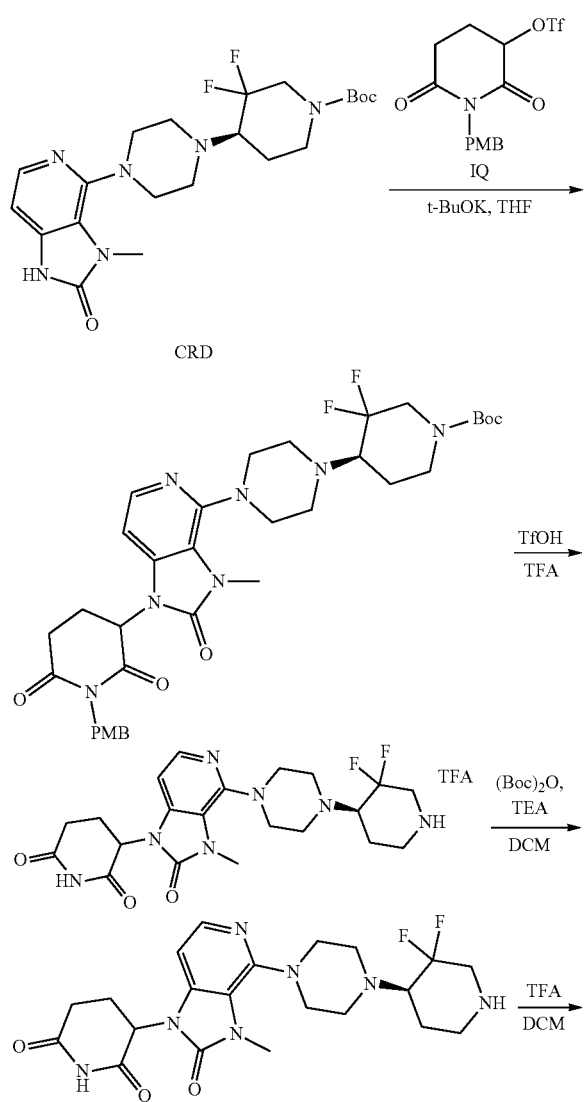

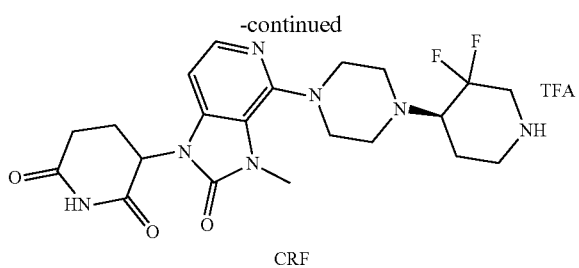

CRF

Step 1—Tert-butyl (4R)-3,3-difluoro-4-[4-[1-[1-[(4-methoxyphenyl)methyl]-2,6-dioxo-3-piperidyl]-3-methyl-2-oxo-imidazo[4,5-c]pyridin-4-yl]piperazin-1-yl]piperidine-1-carboxylate. A mixture of tert-butyl (4R)-3,3-difluoro-4-[4-(3-methyl-2-oxo-1H-imidazo[4,5-c]pyridin-4-yl) piperazin-1-yl]piperidine-1-carboxylate (900 mg, 1.98 mmol, Intermediate CRD) and t-BuOK (334 mg, 2.99 mmol) in THF (10 mL) was stirred at 0° C. for 30 min. Then a solution of [1-[(4-methoxyphenyl)methyl]-2,6-dioxo-3-piperidyl] trifluoromethanesulfonate (1.52 g, 3.98 mmol, Intermediate IQ) in THF (5 mL) was added and the reaction mixture was stirred at 0° C. for 1 hr. On completion, the reaction was diluted with EtOAc (100 mL). The mixture was washed with water (30 mL×3). The combined organic phase was dried over anhydrous sodium sulfate, filtered and concentrated to give are residue. The residue was purified by column chromatography (SiO$_2$, DCM/Ethyl acetate=3/1 to 1/1) to give the title compound (1.12 g, 50% yield) as yellow solid. $^1$H NMR (400 MHz, DMSO-d$_6$) δ 7.90 (d, J=5.6 Hz, 1H), 7.21 (d, J=8.4 Hz, 2H), 6.92-6.79 (m, 3H), 5.54 (dd, J=5.2, 13.0 Hz, 1H), 4.16-3.95 (m, 2H), 3.74-3.68 (m, 3H), 3.57 (s, 3H), 3.17-2.99 (m, 7H), 2.90 (d, J=8.8 Hz, 5H), 2.86-2.66 (m, 3H), 2.49-2.47 (m, 1H), 2.13-2.03 (m, 1H), 1.87-1.65 (m, 2H), 1.41 (s, 9H); LC-MS (ESI$^+$) m/z 684.5 (M+H)$^+$.

Step 2—3-[4-[4-[(4R)-3,3-difluoro-4-piperidyl]piperazin-1-yl]-3-methyl-2-oxo-imidazo[4,5-c] pyridine-1-yl]piperidine-2,6-dione. To a solution of tert-butyl (4R)-3,3-difluoro-4-[4-[1-[1-[(4-methoxyphenyl)methyl]-2,6-dioxo-3-piperidyl]-3-methyl-2-oxo-imidazo[4,5-c]pyridin-4-yl]piperazin-1-yl]piperidine-1-carboxylate (500 mg, 731 μmol) in TFA (1.5 mL) was added TfOH (0.3 mL). The mixture was then stirred at 70° C. for 2 hrs. On completion, the mixture was concentrated to give the title compound (400 mg, 94% yield, TFA) as a black oil. LC-MS (ESI$^+$) m/z 464.0 (M+H)$^+$.

Step 3—Tert-butyl (4R)-4-[4-[1-(2,6-dioxo-3-piperidyl)-3-methyl-2-oxo-imidazo[4,5-c]pyridin-4-yl]piperazin-1-yl]-3,3-difluoro-piperidine-1-carboxylate. To a solution of 3-[4-[4-[(4R)-3,3-difluoro-4-piperidyl]piperazin-1-yl]-3-methyl-2-oxo-imidazo [4,5-c]pyridin-1-yl]piperidine-2,6-dione (400 mg, 692 μmol, TFA) in DCM (4 mL) was added TEA (210 mg, 2.08 mmol) and tert-butoxycarbonyl tert-butyl carbonate (226 mg, 1.04 mmol). The mixture was stirred at 25° C. for 16 hrs. On completion, the mixture was quenched with ice water (100 ml) and extracted with EA (35 ml×3). The combined organic phase was washed with H$_2$O (75 mL), dried over anhydrous sodium sulfate, filtered and concentrated to give a residue. The residue was purified by column chromatography (SiO$_2$, DCM/MeOH=80/1 to 60/1) to give the title compound (180 mg, 48% yield) as brown solid. $^1$H NMR (400 MHz, DMSO-d$_6$) δ 11.14 (s, 1H), 7.93 (d, J=5.2 Hz, 1H), 6.98 (d, J=5.2 Hz, 1H), 5.39 (dd, J=5.2, 12.8 Hz, 1H), 4.03 (d, J=7.2 Hz, 2H), 3.57 (s, 3H), 3.16-2.99

(m, 6H), 2.97-2.81 (m, 6H), 2.76-2.57 (m, 2H), 2.09-1.98 (m, 1H), 1.87-1.66 (m, 2H), 1.40 (s, 9H); LC-MS (ESI⁺) m/z 564.3 (M+H)⁺.

Step 4—3-[4-[4-[(4R)-3,3-difluoro-4-piperidyl]piperazin-1-yl]-3-methyl-2-oxo-imidazo[4,5-c] pyridine-1-yl]piperidine-2,6-dione. To a solution of tert-butyl (4R)-4-[4-[1-(2,6-dioxo-3-piperidyl)-3-methyl-2-oxo-imidazo[4,5-c] pyridin-4-yl]piperazin-1-yl]-3,3-difluoro-piperidine-1-carboxylate (50.0 mg, 88.7 µmol) in DCM (1 mL) was added TFA (0.2 mL). The mixture was then stirred at 25° C. for 0.5 hr. On completion, the mixture was filtered and concentrated to give the title compound (50.0 mg, 97% yield, TFA) as a black oil. LC-MS (ESI⁺) m/z 464.2 (M+H)⁺.

3-[4-[4-[(4S)-3,3-difluoro-4-piperidyl]piperazin-1-yl]-3-methyl-2-oxo-imidazo[4,5-c] pyridin-1-yl] piperidine-2,6-dione (Intermediate CRG)

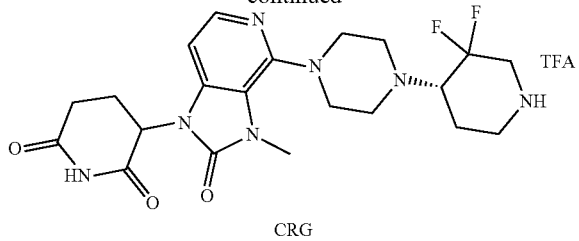

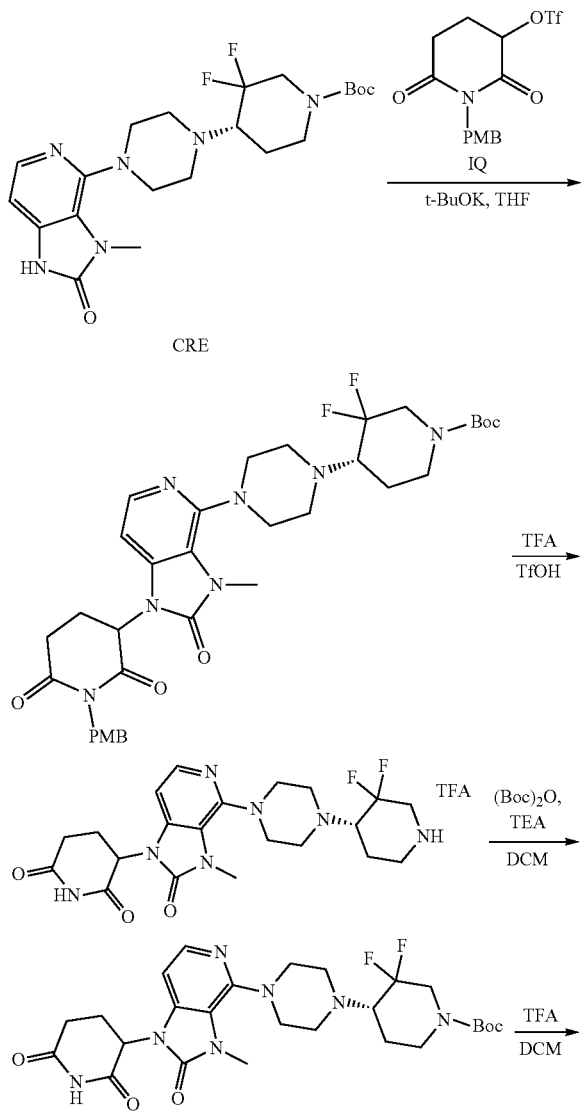

Step 1—Tert-butyl (4S)-3,3-difluoro-4-[4-[1-[1-[(4-methoxyphenyl)methyl]-2,6-dioxo-3-piperidyl]-3-methyl-2-oxo-imidazo[4,5-c]pyridin-4-yl]piperazin-1-yl]piperidine-1-carboxylate. A mixture of tert-butyl (4S)-3,3-difluoro-4-[4-(3-methyl-2-oxo-1H-imidazo[4,5-c]pyridin-4-yl) piperazin-1-yl]piperidine-1-carboxylate (900 mg, 1.99 mmol, Intermediate CRE) and t-BuOK (334 mg, 2.98 mmol) in THF (9 mL) was stirred at 0° C. for 30 min. Then a solution of [1-[(4-methoxyphenyl)methyl]-2,6-dioxo-3-piperidyl] trifluoromethanesulfonate (1.52 g, 3.98 mmol, Intermediate IQ) in THF (5 mL) was added. The reaction mixture was stirred at 0° C. for 1 hr. On completion, the mixture was diluted with EA (10 ml) and water (5 mL) at 0° C. and extracted with EA (15 mL×3). The combined organic phase was dried over anhydrous sodium sulfate, filtered and concentrated to give a residue. The residue was purified by column chromatography (SiO₂, DCM/EA=3:1 to 1:1) to give the compound (1.35 g, 96% yield) as a yellow solid. LC-MS (ESI⁺) m/z 684.3 (M+H)⁺.

Step 2—3-[4-[4-[(4S)-3,3-difluoro-4-piperidyl]piperazin-1-yl]-3-methyl-2-oxo-imidazo[4,5-c]pyridin-1-yl]piperidine-2,6-dione. To a solution of tert-butyl (4S)-3,3-difluoro-4-[4-[1-[1-[(4-methoxyphenyl)methyl]-2,6-dioxo-piperidyl]-3-methyl-2-oxo-imidazo[4,5-c]pyridin-4-yl] piperazin-1-yl]piperidine-1-carboxylate (400 mg, 585 µmol) in TfOH (0.2 mL) was added TFA (1 mL). The mixture was stirred at 70° C. for 2 hrs. On completion, the mixture was concentrated in vacuo to give the title compound (337 mg, 87% yield, TFA) as brown oil. LC-MS (ESI⁺) m/z 464.1 (M+H)⁺.

Step 3—Tert-butyl (4S)-4-[4-[1-(2,6-dioxo-3-piperidyl)-3-methyl-2-oxo-imidazo[4,5-c]pyridin-4-yl] piperazin-1-yl]-3,3-difluoro-piperidine-1-carboxylate. To a solution of 3-[4-[4-[(4S)-3,3-difluoro-4-piperidyl]piperazin-1-yl]-3-methyl-2-oxo-imidazo[4,5-c]pyridin-1-yl]piperidine-2,6-dione (337 mg, 583 µmol, TFA) in DCM (4 mL) was added TEA (177 mg, 1.75 mmol) and (Boc)₂O (191 mg, 875 µmol). The mixture was stirred at 25° C. for 2 hrs. On completion, the residue was diluted with water (20 mL), then the residue was extracted with DCM (10×3 mL). The combined organic layer was washed with brine (10 mL), dried over Na₂SO₄, filtered and the filtrate was concentrated in vacuo to give the title compound (180 mg, 54% yield) as a brown solid. ¹H NMR (400 MHz, DMSO-d₆) δ 11.14 (s, 1H), 7.93 (d, J=5.2 Hz, 1H), 6.98 (d, J=5.2 Hz, 1H), 5.39 (dd, J=5.2, 12.8 Hz, 1H), 4.13-3.96 (m, 2H), 3.57 (s, 3H), 3.18-3.10 (m, 1H), 3.04 (s, 5H), 2.94-2.87 (m, 5H), 2.72-2.60 (m, 2H), 2.05-1.97 (m, 1H), 1.86-1.78 (m, 1H), 1.72 (dd, J=3.2, 12.4 Hz, 1H), 1.60-1.54 (m, 1H), 1.40 (s, 9H); LC-MS (ESI⁺) m/z 564.2 (M+H)⁺.

Step 4—3-[4-[4-[(4S)-3,3-difluoro-4-piperidyl]piperazin-1-yl]-3-methyl-2-oxo-imidazo[4,5-c] pyridin-1-yl]piperidine-2,6-dione. To a solution of tert-butyl (4S)-4-[4-[1-(2,6-dioxo-3-piperidyl)-3-methyl-2-oxo-imidazo[4,5-c] pyridin-4-yl]piperazin-1-yl]-3,3-difluoro-piperidine-1- carboxylate (50 mg, 88.7 μmol) in DCM (1 mL) was added TFA (0.2 mL). The mixture was stirred at 25° C. for 1 hr. On completion, the reaction mixture was concentrated in vacuo to give the title compound (51 mg, 89% yield, TFA) as brown oil. LC-MS (ESI⁺) m/z 464.1 (M+H)⁺.

3-[5-Fluoro-3-methyl-2-oxo-4-(3-oxoazetidin-1-yl)benzimidazol-1-yl]piperidine-2,6-dione (Intermediate CRH)

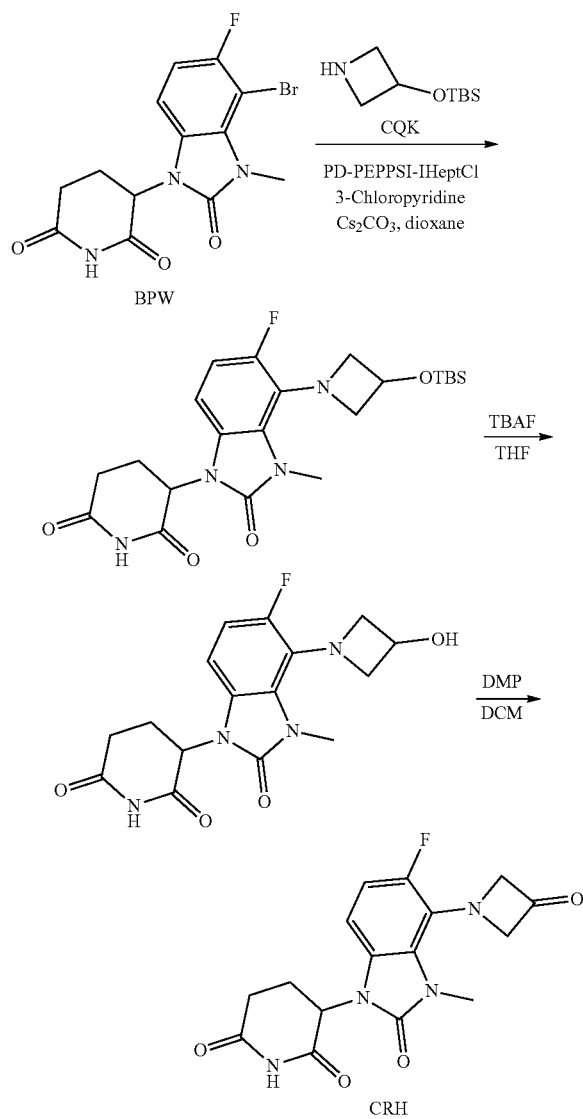

Step 1—3-[4-[3-[Tert-butyl(dimethyl)silyl]oxyazetidin-1-yl]-5-fluoro-3-methyl-2-oxo-benzimidazol-1-yl]piperidine-2,6-dione. A mixture of 3-(4-bromo-5-fluoro-3-methyl-2-oxo-benzimidazol-1-yl)piperidine-2,6-dione (500 mg, 1.40 mmol, Intermediate BPW), azetidin-3-yloxy-tert-butyl-dimethyl-silane (394 mg, 2.11 mmol, Intermediate CQK), 1,3-bis[2,6-bis(1-propylbutyl)phenyl]-4,5-dichloro-2H-imidazol-1-ium-2-ide; 3-chloropyridine; dichloropalladium (136 mg, 140 μmol), Cs₂CO₃ (1.37 g, 4.21 mmol) and 4 Å molecular sieves (500 mg) in dioxane (10 mL) was degassed and purged with N₂ three times. Then the mixture was stirred at 100° C. for 12 hrs under N₂ atmosphere. On completion, the reaction mixture was concentrated in vacuo to give a residue. Then the mixture was poured into water (50 mL) and extracted with ethyl acetate (50 mL×3). The combined organic layers were washed with brine (50 mL), dried over Na₂SO₄ and filtered. The filtrate was concentrated in vacuo to give a residue. The residue was purified by reversed phase (0.1% FA condition) to give the title compound (170 mg, 26% yield) as a brown solid. ¹H NMR (400 MHz, CDCl₃) δ 8.09 (s, 1H), 6.89-6.65 (m, 1H), 6.48 (dd, J=3.6, 8.8 Hz, 1H), 5.18 (dd, J=5.2, 12.8 Hz, 1H), 4.67 (t, J=5.6 Hz, 1H), 4.10-3.93 (m, 4H), 3.74 (s, 3H), 2.99-2.61 (m, 3H), 2.30-2.12 (m, 1H), 0.93 (s, 9H), 0.09 (s, 6H); LC-MS (ESI⁺) m/z 463.2 (M+H)⁺.

Step 2—3-[5-Fluoro-4-(3-hydroxyazetidin-1-yl)-3-methyl-2-oxo-benzimidazol-1-yl]piperidine-2,6-dione. To a solution of 3-[4-[3-[tert-butyl(dimethyl)silyl]oxyazetidin-1-yl]-5-fluoro-3-methyl-2-oxo-benzimidazol-1-yl]piperidine-2,6-dione (140 mg, 302 μmol) in THF (3 mL) was added TBAF (1 M, 605 μL). The mixture was stirred at 20° C. for 2 hrs. On completion, the reaction mixture was poured into water (50 mL) and extracted with ethyl acetate (50 mL×3). The combined organic layers were washed with brine (50 mL), dried over Na₂SO₄, filtered and concentrated in vacuo to give a residue. The crude product was triturated with DCM (5 mL) and filtered to give the title compound (100 mg, 93% yield) as a brown solid. ¹H NMR (400 MHz, DMSO-d₆) δ 11.09 (s, 1H), 6.96-6.77 (m, 2H), 5.58 (d, J=6.0 Hz, 1H), 5.32 (dd, J=5.2, 12.8 Hz, 1H), 4.58-4.43 (m, 1H), 4.05-3.95 (m, 2H), 3.93-3.84 (m, 2H), 3.60 (s, 3H), 2.94-2.79 (m, 1H), 2.74-2.56 (m, 2H), 2.00-1.94 (m, 1H); LC-MS (ESI⁺) m/z 349.1 (M+H)⁺.

Step 3—3-[5-Fluoro-3-methyl-2-oxo-4-(3-oxoazetidin-1-yl)benzimidazol-1-yl]piperidine-2,6-dione. To a solution of 3-[5-fluoro-4-(3-hydroxyazetidin-1-yl)-3-methyl-2-oxo-benzimidazol-1-yl] piperidine-2,6-dione (90.0 mg, 258 μmol) in DCM (3 mL) was added DMP (164 mg, 387 μmol). The mixture was stirred at 20° C. for 2 hrs. On completion, the reaction mixture was quenched with saturated NaHCO₃ (5 mL) and saturated Na₂S₂O₃ (5 mL), and the mixture was stirred at 25° C. for 0.5 hr. Then the organic layer was extracted with DCM (10 mL×3). The combined organic layers were washed with brine (10 mL), dried over Na₂SO₄, filtered, and concentrated in vacuo to give the title compound (88.0 mg, 98% yield) as a brown solid. ¹H NMR (400 MHz, DMSO-d₆) δ 11.10 (s, 1H), 7.08-6.88 (m, 2H), 5.36 (dd, J=5.2, 12.8 Hz, 1H), 4.85 (s, 4H), 3.67 (s, 3H), 2.97-2.78 (m, 1H), 2.73-2.58 (m, 2H), 2.04-1.93 (m, 1H); LC-MS (ESI⁺) m/z 369.0 (M+Na)⁺.

N-[3-(difluoromethyl)-1-(4-formylcyclohexyl)pyrazol-4-yl]-5-(2-oxa-6-azaspiro[3.3]heptan-6-yl)pyrazolo[1,5-a]pyrimidine-3-carboxamide (Intermediate CRI)

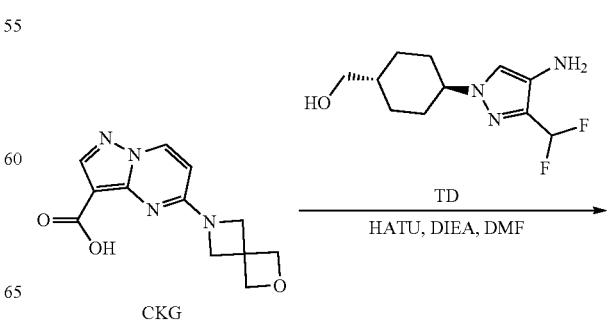

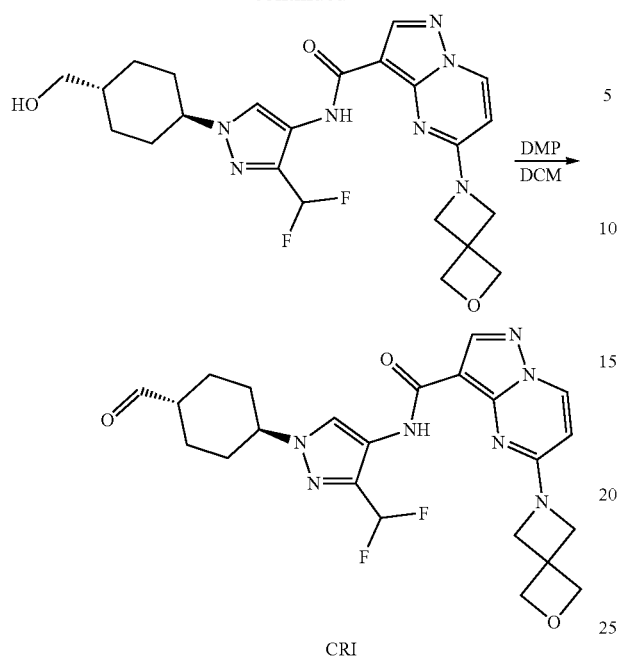

CRI

Step 1—N-[3-(difluoromethyl)-1-[4-(hydroxymethyl)cyclohexyl]pyrazol-4-yl]-5-(2-oxa-6-azaspiro[3.3]heptan-6-yl)pyrazolo[1,5-a]pyrimidine-3-carboxamide. To a solution of 5-(2-oxa-6-azaspiro[3.3]heptan-6-yl)pyrazolo[1,5-a]pyrimidine-3-carboxylic acid (900 mg, 3.46 mmol, Intermediate CKG) in pyridine (1 mL) was added EDCI (795 mg, 4.15 mmol) and [4-[4-amino-3-(difluoromethyl)pyrazol-1-yl]cyclohexyl]methanol (848 mg, 3.46 mmol, Intermediate TD). The mixture was stirred at 50° C. for 2 hrs. On completion, the reaction mixture was added dropwise to H$_2$O (80 mL) at 20° C. Then the mixture was filtered and the cake was dried in vacuo to give the title compound (1.50 g, 88% yield) as a white solid. $^1$H NMR (400 MHz, DMSO-d$_6$) δ 9.68 (s, 1H), 8.74 (d, J=7.6 Hz, 1H), 8.37 (s, 1H), 8.24 (s, 1H), 7.32-6.98 (m, 1H), 6.36 (d, J=7.6 Hz, 1H), 4.73 (s, 4H), 4.48 (t, J=5.2 Hz, 1H), 4.37 (s, 4H), 4.22-4.12 (m, J=4.0, 8.0, 11.6 Hz, 1H), 3.26 (t, J=5.6 Hz, 2H), 2.08-2.01 (m, 2H), 1.86 (d, J=12.0 Hz, 2H), 1.80-1.65 (J=3.2, 12.4 Hz, 2H), 1.52-1.37 (m, 1H), 1.18-1.01 (m, 2H); LC-MS (ESI$^+$) m/z 488.1 (M+H)$^+$.

Step 2—N-[3-(difluoromethyl)-1-(4-formylcyclohexyl)pyrazol-4-yl]-5-(2-oxa-6-azaspiro[3.3]heptan-6-yl)pyrazolo[1,5-a]pyrimidine-3-carboxamide. To a solution of N-[3-(difluoromethyl)-1-[4-(hydroxymethyl)cyclohexyl]pyrazol-4-yl]-5-(2-oxa-6-azaspiro[3.3]heptan-6-yl)pyrazolo[1,5-a]pyrimidine-3-carboxamide (1.35 g, 2.77 mmol) in DCM (20 mL) was added DMP (1.53 g, 3.60 mmol). The mixture was stirred at 25° C. for 1 hr. On completion, the reaction mixture was quenched with Na$_2$S$_2$O$_3$ (20 mL) and NaHCO$_3$ (20 mL) at 25° C., and then extracted with DCM (20 mL×3). The combined organic phase was washed with saturated sodium chloride solution (30 mL×2), dried over anhydrous sodium sulfate, filtered and concentrated to give a residue. The crude product was triturated with DCM/PE (2/1) (20 mL) at 25° C. for 30 mins, then filtered and dried in vacuo to give the title compound (1.05 g, 78% yield) as an off-white solid. LC-MS (ESI$^+$) m/z 486.0 (M+H)$^+$.

The following intermediates were synthesized as described in WO 2020/010227 and WO 2020/264499, the contents of each of which are herein incorporated by reference:

3-(4-Bromo-3-methyl-2-oxo-2,3-dihydro-1H-benzo[d]imidazol-1-yl)piperidine-2,6-dione (Intermediate HP)

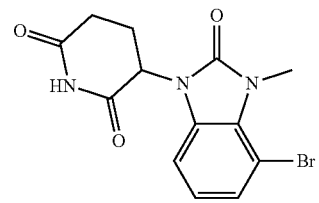

HP 3-(Difluoromethyl)-4-nitro-1H-pyrazole (Intermediate HS)

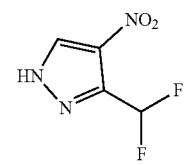

HS

[4-[4-Amino-3-(difluoromethyl)pyrazol-1-yl]cyclohexyl]methanol (Intermediate TD

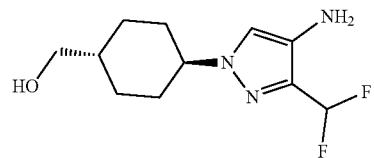

TD 1-(2,6-dioxo-3-piperidyl)-3-methyl-2-oxo-benzimidazole-4-carbaldehyde (Intermediate WW)

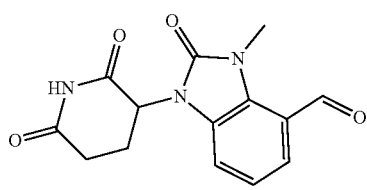

WW

N-[3-(difluoromethyl)-1-(4-formylcyclohexyl)pyrazol-4-yl]-5-morpholino-pyrazolo[1,5-a]pyrimidine-3-carboxamide (Intermediate ABC)

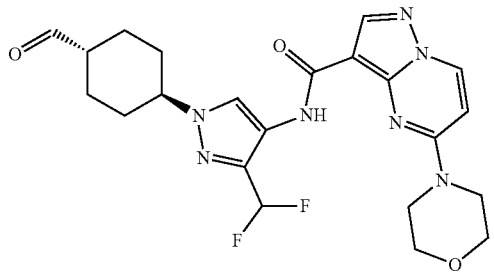

ABC

Tert-butyl N-[3-(difluoromethyl)-1-(4-formylcyclohexyl)pyrazol-4-yl]carbamate (Intermediate ABM)

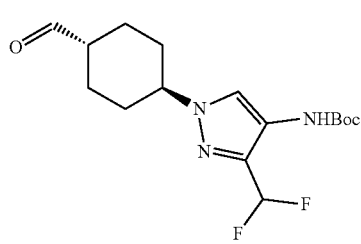

ABM

5-[(1R,4R)-2-oxa-5-azabicyclo[2.2.1]heptan-5-yl]pyrazolo[1,5-a]pyrimidine-3-carboxylic acid (Intermediate AEH)

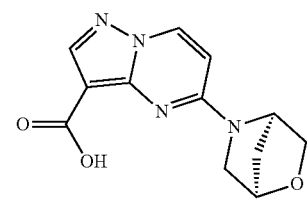

AEH 3-(4-(Azetidin-3-yl)-3-methyl-2-oxo-2,3-dihydro-1H-benzo[d]imidazol-1-yl)piperidine-2,6-dione (Intermediate BRF)

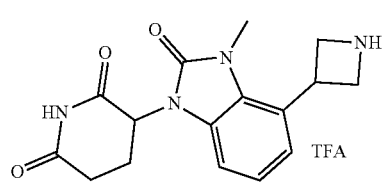

BRF

The following intermediates were synthesized as described in WO 2022/147456, the contents of which are herein incorporated by reference:

N-[3-(difluoromethyl)-1-(4-formylcyclohexyl)pyrazol-4-yl]-5-[(1R,4R)-2-oxa-5-azabicyclo [2.2.1]heptan-5-yl]pyrazolo[1,5-a]pyrimidine-3-carboxamide (Intermediate AJB)

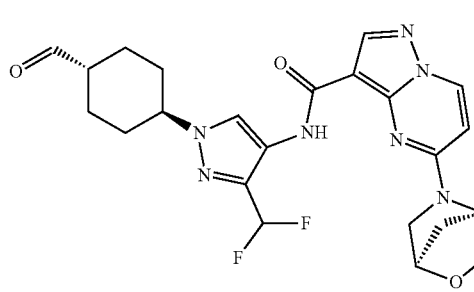

AJB

N-[6-(difluoromethyl)-2-(4-formylcyclohexyl)indazol-5-yl]-6-(trifluoromethyl) pyridine-2-carboxamide (Intermediate ALU)

ALU

[4-(5-Amino-6-methoxy-indazol-2-yl)cyclohexyl]methanol (Intermediate ATE)

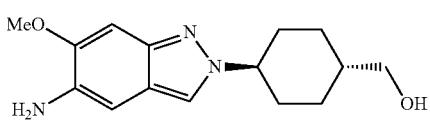

ATE

745

N-[2-(4-formylcyclohexyl)-6-methoxy-indazol-5-yl]-6-(trifluoromethyl)pyridine-2-carboxamide (Intermediate ATJ)

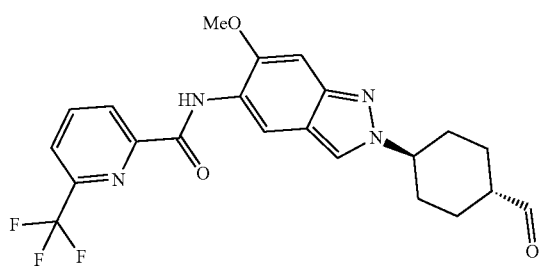

3-(3-Methyl-2-oxo-4-(piperidin-4-yl)-2,3-dihydro-1H-benzo[d]imidazol-1-yl)piperidine-2,6-dione (Intermediate AZK)

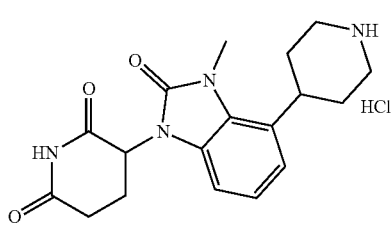

3-(3-Methyl-2-oxo-4-piperazin-1-yl-benzimidazol-1-yl)piperidine-2,6-dione (Intermediate BAI)

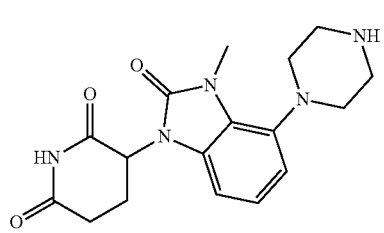

746

N-[3-(difluoromethyl)-1-(4-formylcyclohexyl) pyrazol-4-yl] pyrazolo [1,5-a]pyrimidine-3-carboxamide (Intermediate BHI)

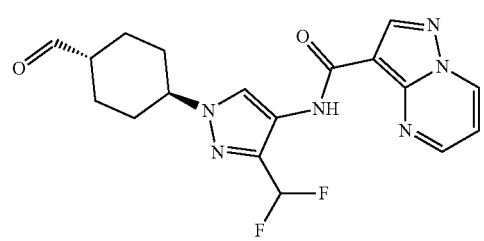

Tert-butyl N-[2-(4-formylcyclohexyl)-6-methoxy-indazol-5-yl]carbamate (Intermediate BGT)

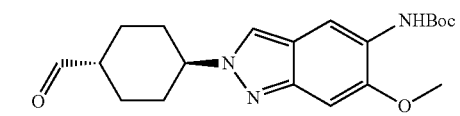

N-[3-(difluoromethyl)-1-[4-(hydroxymethyl)cyclohexyl]pyrazol-4-yl]pyrazolo[1,5-a] pyrimidine-3-carboxamide (Intermediate BIK)

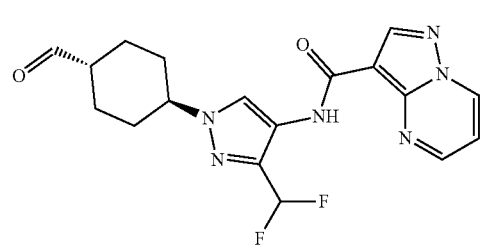

3-(4-Bromo-5-fluoro-3-methyl-2-oxo-benzimidazol-1-yl)piperidine-2,6-dione (Intermediate BPW)

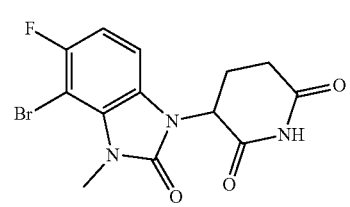

747

3-(5-methoxy-3-methyl-2-oxo-4-(piperidin-4-yl)-2,
3-dihydro-1H-benzo[d]imidazol-1-yl) piperidine-2,
6-dione (Intermediate BRE)

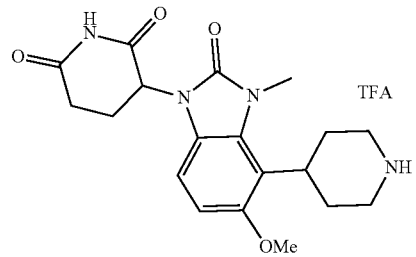

N-[2-(4-formylcyclohexyl)indazol-5-yl]-6-(trifluoromethyl)pyridine-2-carboxamide (Intermediate BRP)

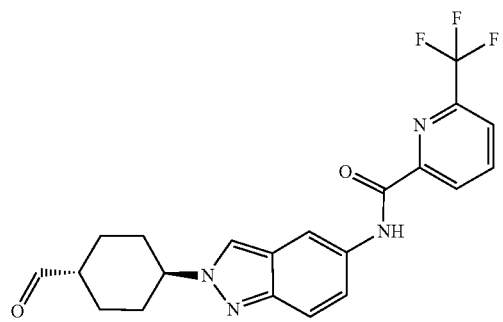

N-[2-(4-formylcyclohexyl)pyrazolo[3,4-c]pyridin-5-yl]-6-(trifluoromethyl)pyridine-2-carboxamide (Intermediate BRR)

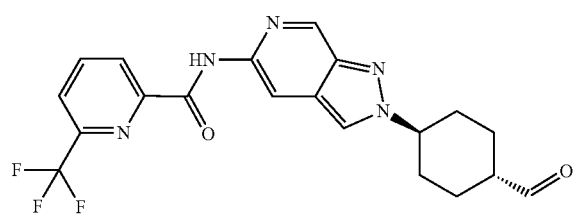

748

1-[8-[4-(Methylamino)-1-piperidyl]-4-isoquinolyl]
hexahydropyrimidine-2,4-dione (Intermediate BSA)

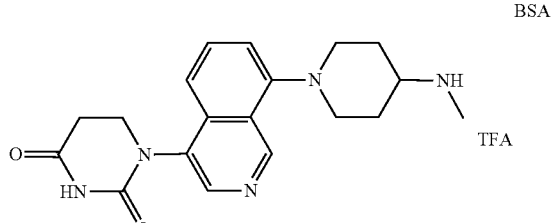

N-[2-(4-formylcyclohexyl)-6-methyl-indazol-5-yl]-
6-(trifluoromethyl)pyridine-2-carboxamide (Intermediate BSC)

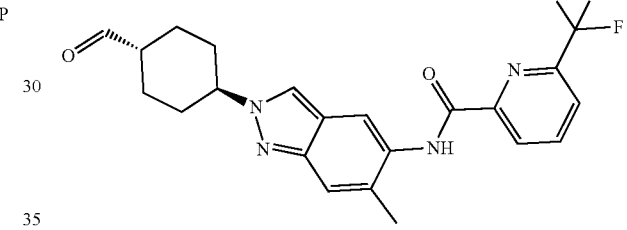

3-[3-Methyl-4-[4-(methylamino)-1-piperidyl]-2-oxo-
benzimidazol-1-yl]piperidine-2,6-dione (Intermediate BSF)

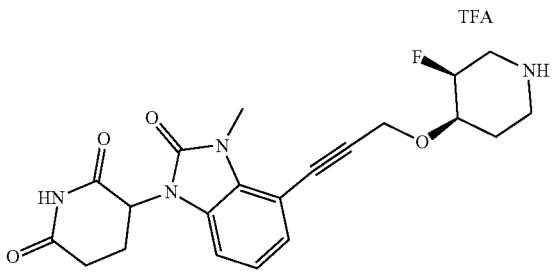

749

3-[4-[3-[[(3R, 4R)-3-fluoro-4-piperidyl]oxy]prop-1-ynyl]-3-methyl-2-oxo-benzimidazol-1-yl]piperidine-2,6-dione (Intermediate BSG)

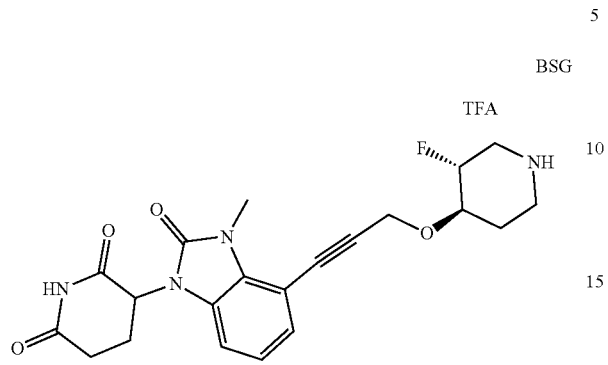

BSG

N-[2-(4-formylcyclohexyl)indazol-5-yl]-6-(trifluoromethyl)pyridine-2-carboxamide (Intermediate BTW)

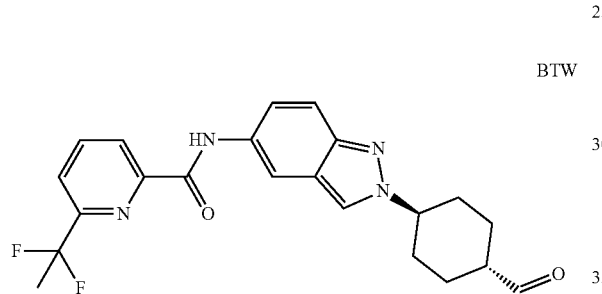

BTW

Tert-butyl N-[2-(4-formylcyclohexyl)indazol-5-yl]carbamate (Intermediate BUO)

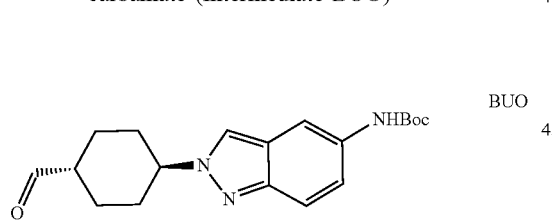

BUO

5-Chloro-N-[2-(4-formylcyclohexyl)indazol-5-yl]pyridine-3-carboxamide (Intermediate BUT)

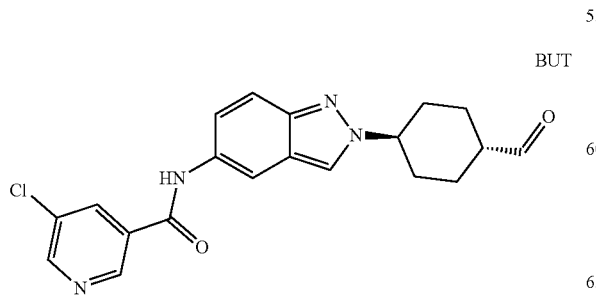

BUT

750

6-Cyano-N-[2-(4-formylcyclohexyl)indazol-5-yl]pyridine-2-carboxamide (Intermediate BVH)

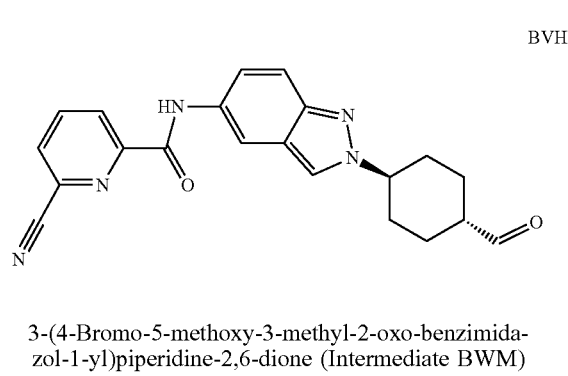

BVH 3-(4-Bromo-5-methoxy-3-methyl-2-oxo-benzimidazol-1-yl)piperidine-2,6-dione (Intermediate BWM)

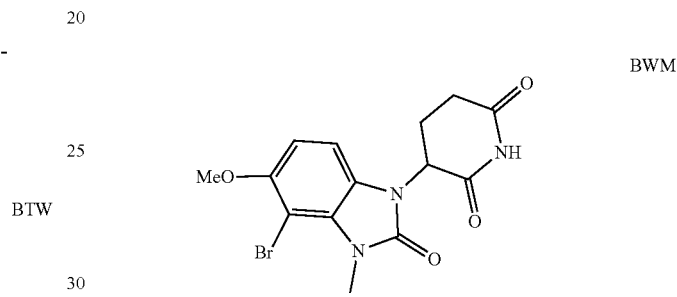

BWM

3-[4-[3-[[(3S,4R)-3-Fluoro-4-piperidyl]oxy]prop-1-ynyl]-5-methoxy-3-methyl-2-oxo-benzimidazol-1-yl]piperidine-2, 6-dione (Intermediate BWN)

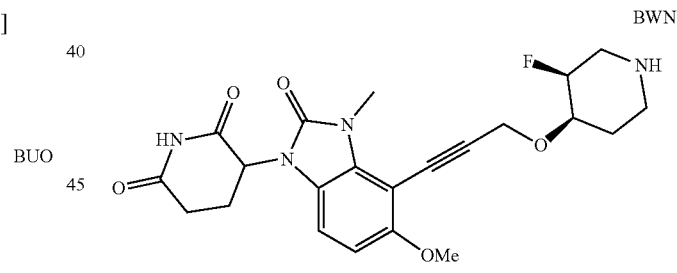

BWN

5-Cyano-N-[2-(4-formylcyclohexyl)-5-methoxy-1,3-benzothiazol-6-yl]pyridine-3-carboxamide (Intermediate BXG)

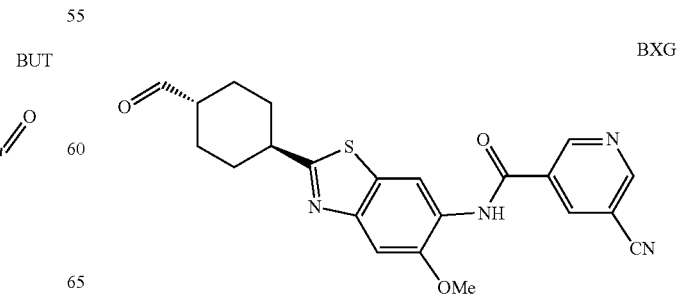

BXG

751
N-[6-cyano-2-(4-formylcyclohexyl)indazol-5-yl]-6-(trifluoromethyl)pyridine-2-carboxamide (Intermediate BXI)

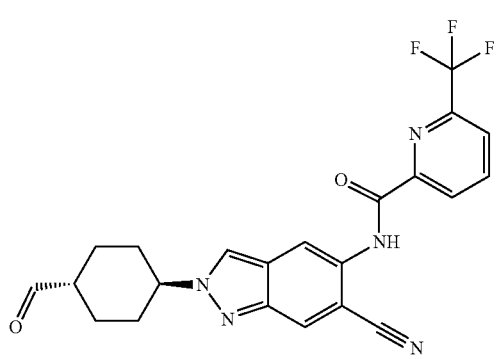

BXI 752
3-[3-Methyl-4-[3-[(2S)-2-methylpiperazin-1-yl]prop-1-ynyl]-2-oxo-benzimidazol-1-yl]piperidine-2,6-dione (Intermediate BXU)

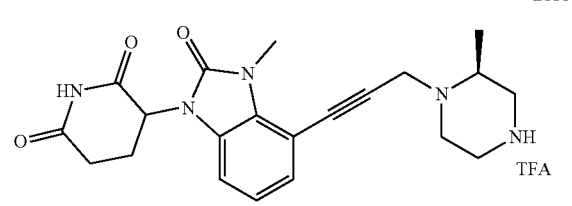

BXU

3-[3-methyl-2-oxo-4-[3-(piperazin-1-ylmethyl)cyclobutyl]benzimidazol-1-yl]piperidine-2,6-dione (Intermediate CBA)

3-(3-methyl-2-oxo-4-(3-(piperidin-4-yloxy)prop-1-yn-1-yl)-2,3-dihydro-1H-benzo[d]imidazol-1-yl)piperidine-2,6-dione (Intermediate BXN)

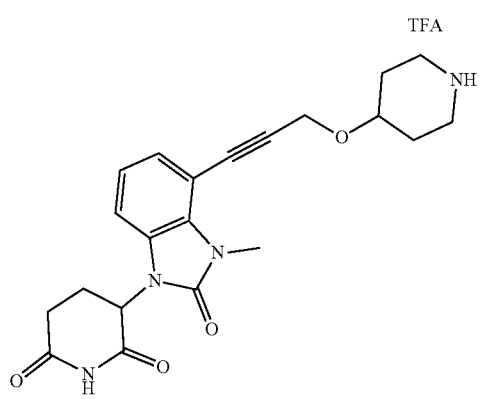

BXN

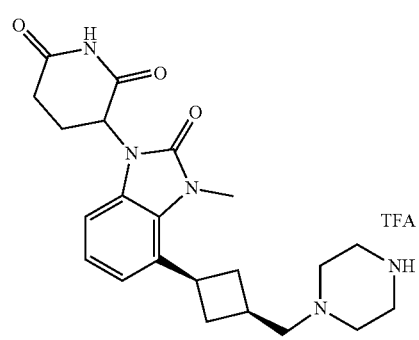

CBA

3-[4-(3,9-Diazaspiro[5.5]undecan-3-yl)-3-methyl-2-oxo-benzimidazol-1-yl]piperidine-2,6-dione (Intermediate BXR)

3-[3-Methyl-2-oxo-4-(3-piperazin-1-ylprop-1-ynyl)benzimidazol-1-yl]piperidine-2,6-dione (Intermediate CBD)

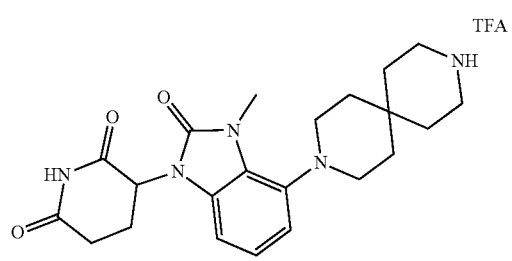

BXR

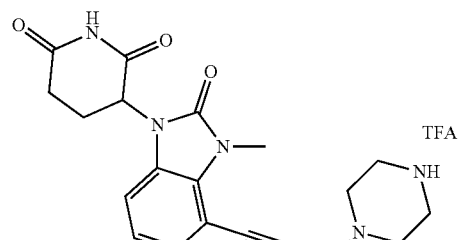

CBD

753

3-[4-(azetidin-3-yl)-3-methyl-2-oxo-benzimidazol-1-yl]piperidine-2,6-dione (Intermediate CBL)

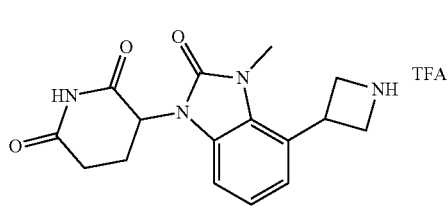
CBL 3-(5-methoxy-3-methyl-2-oxo-4-piperazin-1-yl-benzimidazol-1-yl)piperidine-2,6-dione (Intermediate CCS)

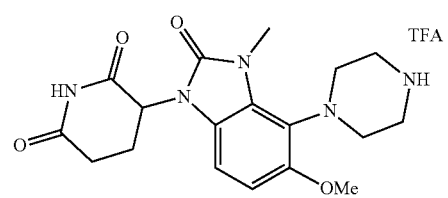
CCS

Tert-butyl 4-((1r,3r)-3-(1-(2,6-dioxopiperidin-3-yl)-3-methyl-2-oxo-2,3-dihydro-1H-benzo[d]imidazol-4-yl)cyclobutoxy)piperidine-1-carboxylate (Intermediate CFS)

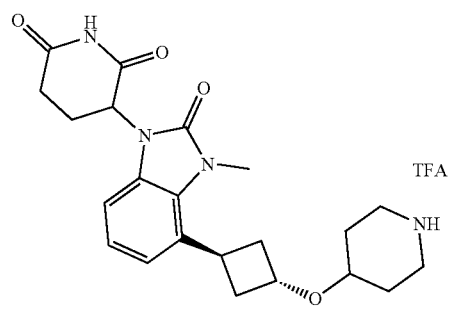
CFS

3-[3-Methyl-2-oxo-4-[3-(piperazin-1-ylmethyl)-1-bicyclo[1.1.1]pentanyl]benzimidazol-1-yl] piperidine-2,6-dione (Intermediate CGM)

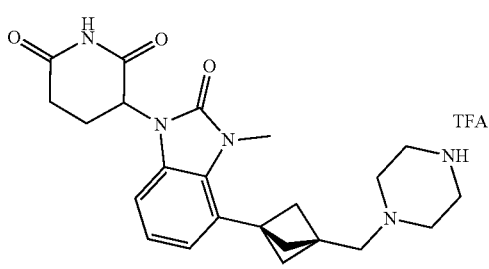
CGM

754

3-[3-Cyclopropyl-2-oxo-4-(3-piperazin-1-ylprop-1-ynyl)benzimidazol-1-yl]piperidine-2,6-dione (Intermediate CGO)

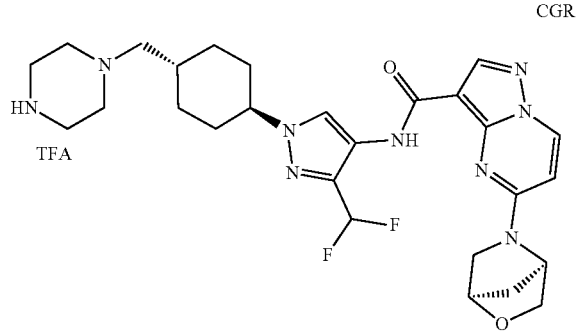 [SMILES: O=C(Nc1cn([C@H]2CC[C@H](CN3CCNCC3)CC2)nc1C(F)F)c1cnn2ccc(N3C[C@H]4C[C@@H]3CO4)nc12]
CGO

N-[3-(difluoromethyl)-1-[4-(piperazin-1-ylmethyl)cyclohexyl]pyrazol-4-yl]-5-[(1R,4R)-2-oxa-5-azabicyclo[2.2.1]heptan-5-yl]pyrazolo[1,5-a]pyrimidine-3-carboxamide (Intermediate CGR)

CGR

3-[4-[3-[(3,3-Difluoro-4-piperidyl)oxy]prop-1-ynyl]-3-methyl-2-oxo-benzimidazol-1-yl]piperidine-2,6-dione (Intermediate CHD)

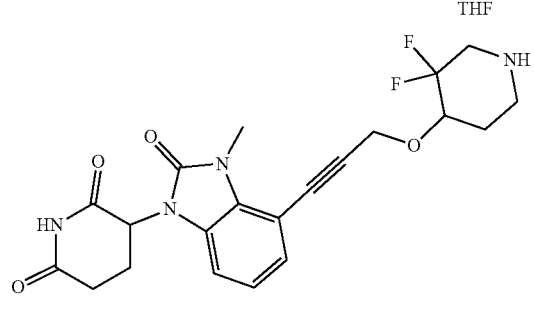
CHD

755

3-[4-[3-[[(3S, 4R)-3-Fluoro-4-piperidyl] oxy]prop-1-ynyl]-3-methyl-2-oxo-benzimidazol-1-yl] piperidine-2,6-dione (Intermediate CHH)

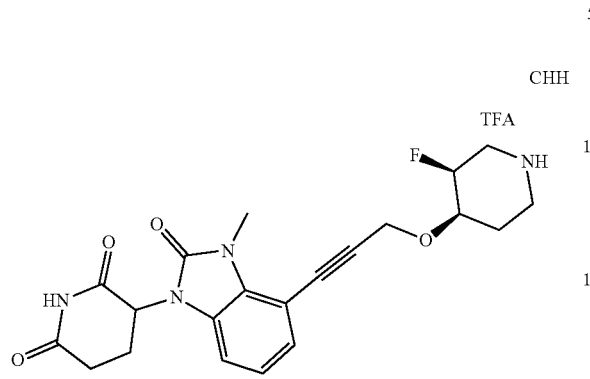

3-[4-[3-[[(3R,4S)-3-fluoro-4-piperidyl]oxy]prop-1-ynyl]-3-methyl-2-oxo-benzimidazol-1-yl]piperidine-2,6-dione (Intermediate CHI)

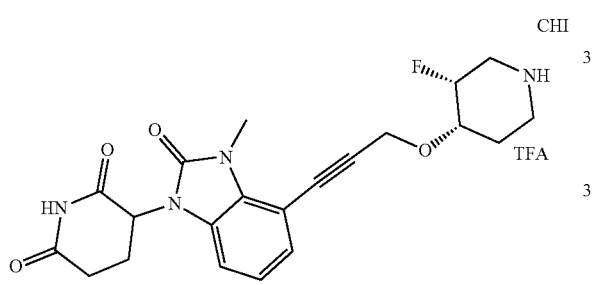

3-[3-Methyl-4-[3-[[(3S,4S)-3-methyl-4-piperidyl]oxy]prop-1-ynyl]-2-oxo-benzimidazol-1-yl]piperidine-2,6-dione (Intermediate CHJ)

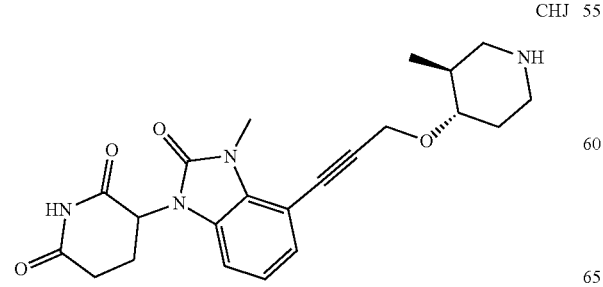

756

1-[8-(3-Piperazin-1-ylprop-1-ynyl)-4-isoquinolyl]hexahydropyrimidine-2,4-dione (Intermediate CHK)

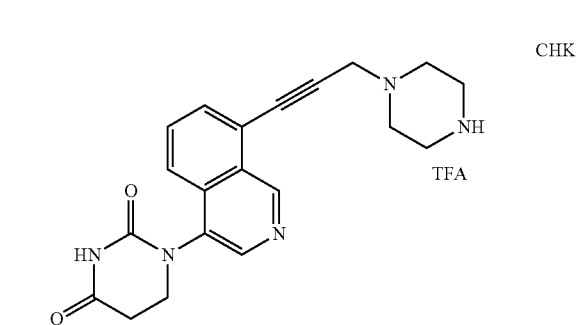 [SMILES: O=C1CCN(c2cncc3c(C#CCN4CCNCC4)cccc23)C(=O)N1]

3-[5-Methoxy-3-methyl-2-oxo-4-(3-piperazin-1-ylprop-1-ynyl)benzimidazol-1-yl]piperidine-2,6-dione (Intermediate CHL)

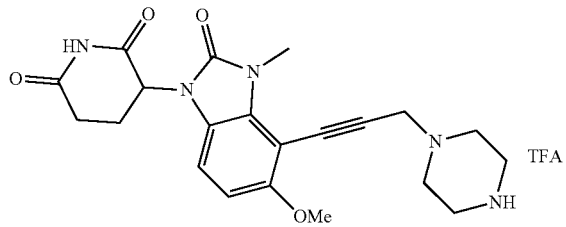

1-[8-[3-[[(3S,4R)-3-fluoro-4-piperidyl]oxy]prop-1-ynyl]-4-isoquinolyl]hexahydropyrimidine-2,4-dione (Intermediate CHN)

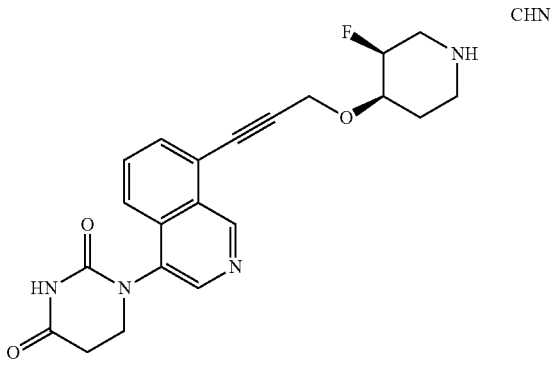 [SMILES: O=C1CCN(c2cncc3c(C#CCO[C@@H]4CCNC[C@@H]4F)cccc23)C(=O)N1]

757

3-[3-Methyl-4-[3-[(2R)-2-methylpiperazin-1-yl]prop-1-ynyl]-2-oxo-benzimidazol-1-yl]piperidine-2,6-dione (Intermediate CHO)

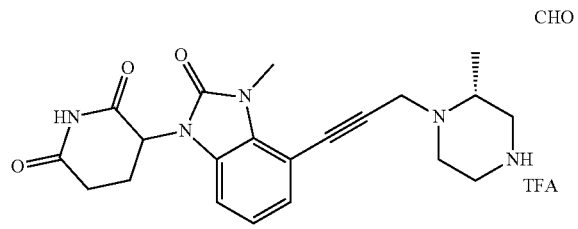 [SMILES: C[C@@H]1CNCCN1CC#Cc1cccc2c1n(C)c(=O)n2C1CCC(=O)NC1=O]
CHO
TFA

3-[4-[3-[[(3R,4S)-3-fluoro-4-piperidyl]oxy]prop-1-ynyl]-5-methoxy-3-methyl-2-oxo-benzimidazol-1-yl]piperidine-2,6-dione (Intermediate CIB)

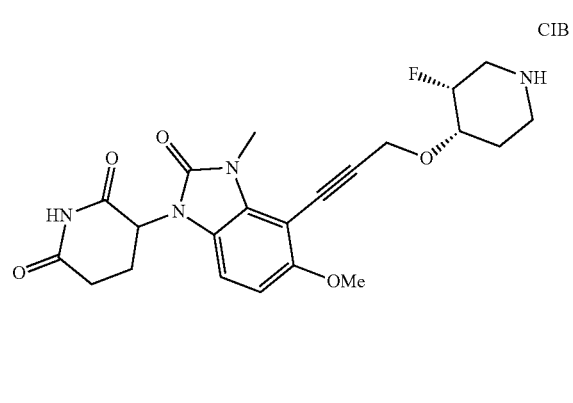 [SMILES: COc1ccc2c(c1C#CCO[C@H]1CCNC[C@H]1F)n(C)c(=O)n2C1CCC(=O)NC1=O]
CIB

1-[8-[3-[[(3R,4R)-3-methyl-4-piperidyl]oxy]prop-1-ynyl]-4-isoquinolyl] hexahydropyrimidine-2,4-dione (Intermediate CID)

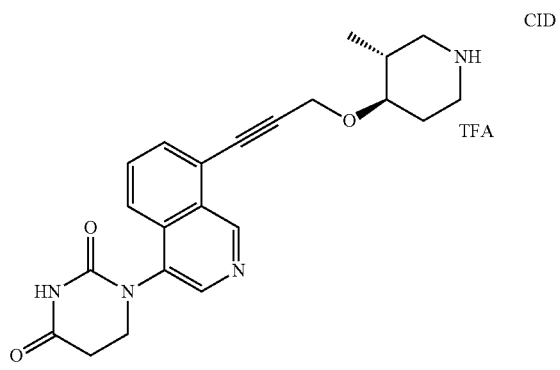 [SMILES: C[C@@H]1CNCC[C@H]1OCC#Cc1cccc2c(N3CCC(=O)NC3=O)cncc12]
CID
TFA

758

3-[5-methoxy-3-methyl-4-[3-[[(3S,4S)-3-methyl-4-piperidyl]oxy]prop-1-ynyl]-2-oxo-benzimidazol-1-yl]piperidine-2,6-dione (Intermediate CIF)

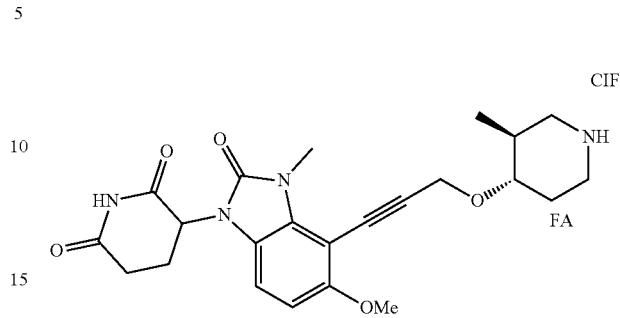
CIF
FA

3-[3-Methyl-2-oxo-4-[4-(4-piperidyl)piperazin-1-yl]benzimidazol-1-yl]piperidine-2,6-dione (Intermediate CIL)

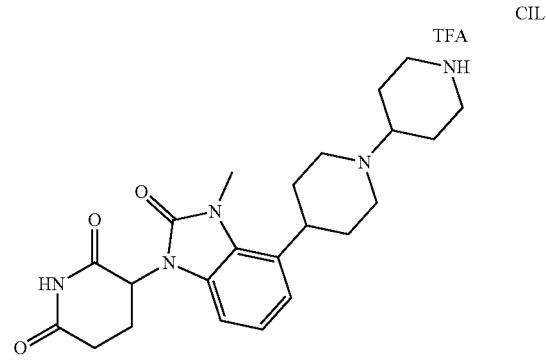 [SMILES: Cn1c(=O)n(C2CCC(=O)NC2=O)c2cccc(C3CCN(C4CCNCC4)CC3)c21]
CIL
TFA

3-[3-Methyl-2-oxo-4-[3-(piperazin-1-ylmethyl)cyclobutyl]benzimidazol-1-yl]piperidine-2,6-dione (Intermediate CIP)

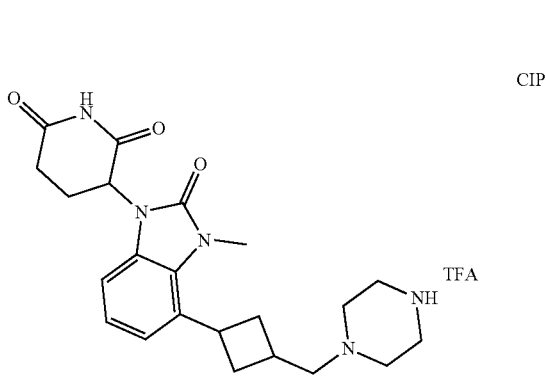 [SMILES: Cn1c(=O)n(C2CCC(=O)NC2=O)c2cccc(C3CC(CN4CCNCC4)C3)c21]
CIP
TFA

759

3-[3-Methyl-2-oxo-4-(4-piperazin-1-yl-1-piperidyl)benzimidazol-1-yl]piperidine-2,6-dione (Intermediate CIR)

760

3-[3-Methyl-2-oxo-4-[3-(piperazin-1-ylmethyl)cyclobutyl]benzimidazol-1-yl]piperidine-2,6-dione (Intermediate CIX)

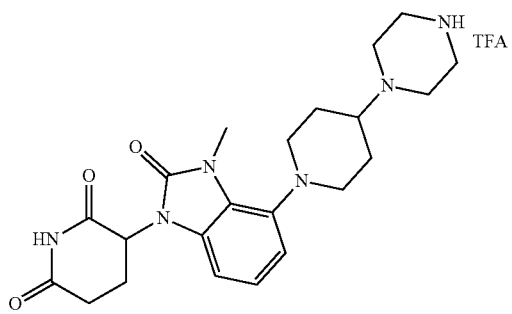

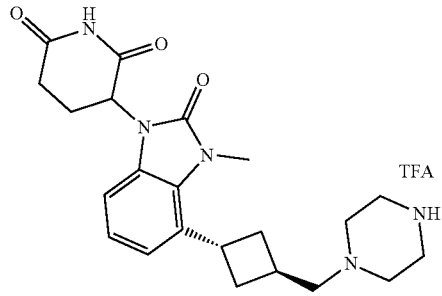

Example 1 (Method 1): Synthesis of N-[3-(difluoromethyl)-1-[4-[[4-[3-[1-(2,6-dioxo-3-piperidyl)-3-methyl-2-oxo-benzimidazol-4-yl]prop-2-ynyl]piperazin-1-yl]methyl]cyclohexyl]pyrazol-4-yl]-5-pyrrolidin-1-yl-pyrazolo[1,5-a]pyrimidine-3-carboxamide

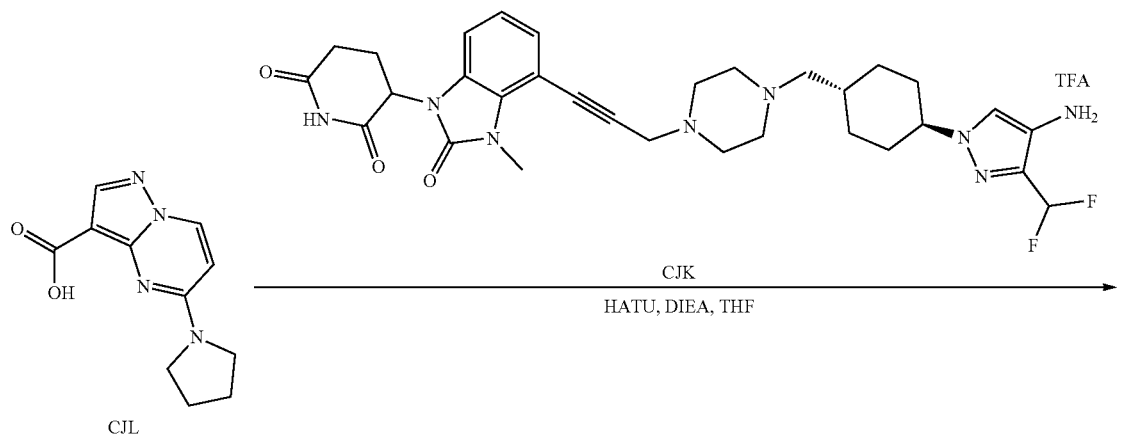

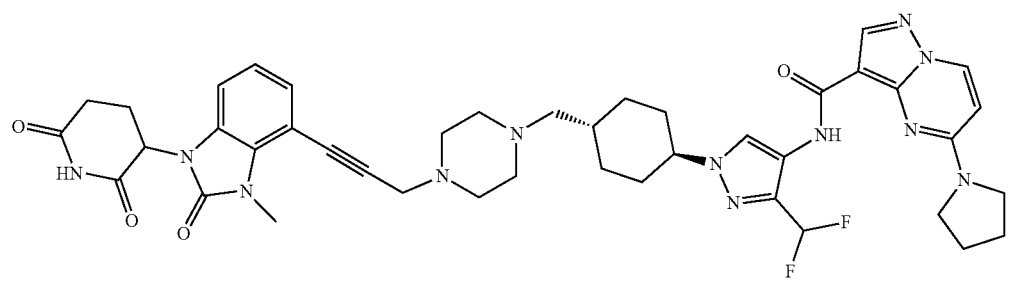

I-103

A mixture of 5-pyrrolidin-1-ylpyrazolo [1,5-a]pyrimidine-3-carboxylic acid (30.0 mg, 129 umol, Intermediate CJL), HATU (54.0 mg, 142 umol) and DIEA (90 uL) in THF (2 mL) was stirred at 40° C. for 2 hours. Then 3-[4-[3-[4-[[4-[4-amino-3-(difluoromethyl)pyrazol-1-yl]cyclohexyl]methyl]piperazin-1-yl]prop-1-ynyl]-3-methyl-2-oxo-benzimidazol-1-yl]piperidine-2,6-dione (93.4 mg, 129 umol, TFA, Intermediate CJK) was added, the mixture was stirred at 40° C. for 16 hours. On completion, the reaction mixture was quenched with water (0.05 mL) and purified by prep-HPLC (column: Phenomenex C18 150×25 mm×10 um; mobile phase: [water(NH$_4$HCO$_3$)-ACN]) to give the title compound (25.6 mg, 24% yield, 100% purity) as white solid. $^1$H NMR (400 MHz, DMSO-d$_6$) δ 11.11 (s, 1H), 9.56 (s, 1H), 8.74 (d, J=7.6 Hz, 1H), 8.37 (s, 1H), 8.23 (s, 1H), 7.25-6.93 (m, 4H), 6.56 (d, J=7.6 Hz, 1H), 5.39 (dd, J=5.2, 12.8 Hz, 1H), 4.22-4.11 (m, 1H), 3.64 (s, 5H), 3.57 (s, 4H), 2.94-2.82 (m, 1H), 2.77-2.70 (m, 1H), 2.70-2.63 (m, 2H), 2.62-2.54 (m, 4H), 2.45-2.35 (m, 3H), 2.12 (d, J=7.2 Hz, 2H), 2.06-1.94 (m, 7H), 1.89 (d, J=12.0 Hz, 2H), 1.79-1.67 (m, 2H), 1.63-1.50 (m, 1H), 1.11-0.96 (m, 2H); LC-MS (ESI$^+$) m/z 823.2 (M+H)$^+$.

TABLE 2

Compounds synthesized via Method 1, with the corresponding amine and acid coupling.

| I-#[a] | Amine | Acid | LCMS (ES+) m/z (M + H)$^+$ | 1HNMR (400 MHz, DMSO-d$_6$) δ |
|---|---|---|---|---|
| I-100 | CJK | CJJ | 837.3 | 11.11 (s, 1H), 9.38 (s, 1H), 8.72 (d, J = 8.0 Hz, 1H), 8.37 (s, 1H), 8.24 (s, 1H), 7.24-7.05 (m, 3H), 7.04-6.88 (m, 2H), 5.45-5.32 (m, 1H), 4.24-4.10 (m, 1H), 3.79-3.75 (m, 4H), 3.64 (s, 3H), 3.57 (s, 2H), 2.89-2.84 (m, 2H), 2.61-2.54 (m, 8H), 2.12-2.08 (m, 2H), 2.06-1.98 (m, 3H), 1.93-1.85 (m, 2H), 1.81-1.64 (m, 5H), 1.60-1.56 (m, 5H), 1.10-0.95 (m, 2H) |
| I-106 | CJK | CJM | 809.4 | 11.11 (s, 1H), 9.70 (s, 1H), 8.73 (d, J = 7.6 Hz, 1H), 8.36 (s, 1H), 8.23 (s, 1H), 7.23-6.94 (m, 4H), 6.34 (d, J = 7.6 Hz, 1H), 5.39 (d, J = 5.6, 12.8 Hz, 1H), 4.28-4.12 (m, 5H), 3.65 (s, 3H), 3.57 (s, 2H), 2.93-2.83 (m, 1H), 2.73-2.64 (m, 2H), 2.56 (s, 4H), 2.45-2.31 (m, 6H), 2.13 (d, J = 7.2 Hz, 2H), 2.07-1.99 (m, 3H), 1.89 (d, J = 10.4 Hz, 2H), 1.78-1.67 (m, 2H), 1.62-1.52 (m, 1H), 1.10-0.96 (m, 2H) |
| I-108 | CJK | CJW | 850.4 | 11.19-11.07 (m, 1H), 9.72 (s, 1H), 8.49 (d, J = 7.6 Hz, 1H), 8.36 (d, J = 0.8 Hz, 1H), 7.17-6.99 (m, 5H), 6.92 (d, J = 2.8 Hz, 1H), 6.75-6.25 (m, 1H), 5.44-5.35 (m, 1H), 5.27-4.93 (m, 1H), 4.81-4.68 (m, 1H), 4.21-4.08 (m, 1H), 3.82-3.76 (m, 1H), 3.64 (s, 3H), 3.60-3.53 (m, 4H), 2.93-2.84 (m, 2H), 2.72-2.64 (m, 3H), 2.45-2.38 (m, 3H), 2.18-2.08 (m, 3H), 2.07-1.94 (m, 6H), 1.93-1.81 (m, 4H), 1.77-1.68 (m, 2H), 1.61-1.53 (m, 1H), 1.08-0.99 (m, 2H) |
| I-150 | CJO | CJR | 836.6 | 11.08 (s, 1H), 9.93 (s, 1H), 9.22 (s, 1H), 9.02 (d, J = 2.0 Hz, 1H), 8.59 (s, 1H), 8.31 (s, 1H), 8.04 (s, 1H), 7.08 (s, 1H), 7.02-6.92 (m, 2H), 6.89-6.82 (m, 1H), 5.35 (dd, J = 5.2, 12.8 Hz, 1H), 4.46-4.32 (m, 1H), 3.87 (s, 3H), 3.63 (s, 3H), 3.30 (s, 3H), 2.93 (s, 3H), 2.89 (d, J = 4.4 Hz, 5H), 2.65-2.55 (m, 4H), 2.44-2.40 (m, 1H), 2.21-2.10 (m, 2H), 2.06-1.83 (m, 6H), 1.79-1.64 (m, 4H), 1.60-1.43 (m, 4H), 1.21-1.06 (m, 2H) |
| I-151 | CJO | CJQ | 852.4 | 11.08 (s, 1H), 10.04 (s, 1H), 9.38 (s, 1H), 9.24 (d, J = 2.0 Hz, 1H), 8.77 (s, 1H), 8.31 (s, 1H), 8.03 (s, 1H), 7.09 (s, 1H), 6.99-6.95 (m, 2H), 6.91-6.83 (m, 1H), 5.41-5.29 (m, 1H), 4.49-4.32 (m, 1H), 3.88 (s, 3H), 3.63 (s, 3H), 3.41 (s, 3H), 2.88-2.87 (m, 7H), 2.30-2.25 (m, 1H), 2.20-2.09 (m, 3H), 2.04-1.83 (m, 7H), 1.80-1.63 (m, 6H), 1.61-1.41 (m, 5H), 1.19-1.07 (m, 2H) |
| I-156[b] | CJO | CJX | 799.1 | 11.07 (s, 1H), 10.07 (s, 1H), 9.27 (d, J = 2.0 Hz, 1H), 9.22 (d, J = 2.0 Hz, 1H), 8.77 (t, J = 2.0 Hz, 1H), 8.43 (s, 1H), 8.14 (s, 1H), 6.99-6.94 (m, 2H), 6.89-6.83 (m, 1H), 6.33 (s, 1H), 5.34 (dd, J = 5.6, 13.2 Hz, 1H), 3.89 (s, 3H), 3.63 (s, 3H), 2.92-2.83 (m, 5H), 2.73-2.61 (m, 3H), 2.39-2.31 (m, 4H), 2.15 (d, J = 6.8 Hz, 2H), 2.09-1.95 (m, 3H), 1.93-1.82 (m, 2H), 1.73-1.61 (m, 4H), 1.58-1.41 (m, 7H), 1.10-0.94 (m, 2H) |
| I-157 | CJO | CJN | 811.9 | 11.09 (s, 1H), 9.29 (s, 1H), 8.54 (s, 1H), 8.27 (s, 1H), 8.15 (s, 1H), 7.11 (s, 1H), 7.02-6.93 (m, 2H), 6.90-6.82 (m, 1H), 5.35 (dd, J = 5.2, 12.4 Hz, 1H), 4.36 (d, J = 3.2 Hz, 1H), 3.94 (d, J = 2.4 Hz, 6H), 3.63 (s, 3H), 2.88 (s, 5H), 2.73-2.57 (m, 3H), 2.42 (s, 3H), 2.27-2.09 (m, 4H), 2.02-1.83 (m, 5H), 1.77-1.59 (m, 5H), 1.58-1.39 (m, 4H), 1.18-1.02 (m, 2H) |
| I-225 | CJK | CJU | 837.6 | 11.13 (s, 1H), 9.69 (s, 1H), 8.74 (d, J = 7.6 Hz, 1H), 8.37 (s, 1H), 8.23 (s, 1H), 7.25-6.96 (m, 4H), 6.36 (d, J = 7.6 Hz, 1H), 5.40 (dd, J = 5.2, 12.4 Hz, 1H), 4.25-4.13 (m, 1H), 3.90 (d, J = 13.2 Hz, 4H), 3.66 (s, 5H), 3.16-2.82 (m, 5H), 2.78-2.58 (m, 6H), 2.13-1.97 (m, 4H), 1.90 (d, J = 12.0 Hz, 2H), 1.84-1.69 (m, 3H), 1.32 (s, 6H), 1.30-1.22 (m, 6H), 1.20-1.02 (m, 2H) |
| I-241 | CLA | CKX | 758.5 | 11.08 (s, 1H), 10.03 (s, 1H), 9.37 (dd, J = 1.6, 7.2 Hz, 1H), 8.86 (dd, J = 1.6, 4.4 Hz, 1H), 8.70 (s, 1H), 8.36 (s, 1H), 7.32 (dd, J = 4.4, 7.2 Hz, 1H), 7.14 (t, J = 54.1 Hz, 1H), 7.00-6.94 (m, 1H), 6.92-6.88 (m, 1H), 6.86 (d, J = 8.0 Hz, 1H), 5.34 (dd, J = 5.6, 12.4 Hz, 1H), 4.27-4.08 (m, 1H), 3.63 (s, 3H), 3.19-3.07 (m, |

TABLE 2-continued

Compounds synthesized via Method 1, with the corresponding amine and acid coupling.

| I-#[a] | Amine | Acid | LCMS (ES+) m/z (M + H)+ | 1HNMR (400 MHz, DMSO-$d_6$) δ |
|---|---|---|---|---|
| | | | | 3H), 2.92-2.82 (m, 1H), 2.79-2.62 (m, 4H), 2.28-2.21 (m, 1H), 2.17 (s, 3H), 2.12-2.04 (m, 2H), 2.03-1.97 (m, 1H), 1.95-1.80 (m, 3H), 1.79-1.68 (m, 2H), 1.60-1.48 (m, 1H), 1.43-1.33 (m, 1H), 1.31-1.20 (m, 2H), 1.16-1.00 (m, 2H), 0.99-0.91 (m, 3H) |
| I-286 | CJK | CJY | 865.3 | 11.12 (s, 1H), 9.33 (s, 1H), 8.82 (d, J = 8.0 Hz, 1H), 8.38 (s, 1H), 8.29 (s, 1H), 7.28-6.98 (m, 4H), 6.93 (d, J = 8.0 Hz, 1H), 5.40 (dd, J = 5.2, 12.6 Hz, 1H), 4.58-4.27 (m, 2H), 4.25-4.10 (m, 1H), 3.93 (dd, J = 2.4, 12.0 Hz, 1H), 3.71-3.53 (m, 7H), 3.11 (t, J = 11.6 Hz, 2H), 2.90 (d, J = 4.8 Hz, 1H), 2.87-2.80 (m, 1H), 2.80-2.74 (m, 1H), 2.71 (dd, J = 4.4, 12.4 Hz, 1H), 2.68-2.56 (m, 5H), 2.19 (s, 2H), 2.14-1.96 (m, 4H), 1.89 (d, J = 12.0 Hz, 2H), 1.74 (dt, J = 10.4, 12.0 Hz, 3H), 1.60 (d, J = 2.8 Hz, 1H), 1.19 (d, J = 6.0 Hz, 3H), 1.11-1.01 (m, 2H) |
| I-295 | CJK | CKD | 887.3 | 11.10 (s, 1H), 9.25 (s, 1H), 8.91 (d, J = 7.6 Hz, 1H), 8.35 (d, J = 12.0 Hz, 2H), 7.17-6.94 (m, 5H), 5.39 (d, J = 5.6, 12.4 Hz, 1H), 4.27 (s, 4H), 4.22-4.14 (m, 1H), 3.65 (s, 3H), 3.57 (s, 2H), 3.25 (s, 2H), 3.06-2.96 (m, 1H), 2.89 (s, 1H), 2.76-2.63 (m, 3H), 2.61-2.53 (m, 5H), 2.40 (s, 3H), 2.13 (d, J = 7.2 Hz, 2H), 2.06-1.98 (m, 3H), 1.89 (d, J = 10.4 Hz, 2H), 1.79-1.68 (m, 2H), 1.63-1.53 (m, 1H), 1.09-0.98 (m, 2H) |
| I-296 | CJK | CKM | 879.4 | 11.18-11.04 (m, 1H), 9.37 (s, 1H), 8.75 (d, J = 8.0 Hz, 1H), 8.38 (s, 1H), 8.28-8.23 (m, 1H), 7.26-7.09 (m, 3H), 7.04-6.99 (m, 1H), 6.94 (d, J = 8.0 Hz, 1H), 5.43-5.36 (m, 1H), 4.40-4.35 (m, 4H), 4.22-4.13 (m, 1H), 3.78-3.71 (m, 4H), 3.65 (s, 3H), 3.58-3.55 (m, 2H), 2.93-2.83 (m, 1H), 2.60-2.55 (m, 5H), 2.43-2.37 (m, 3H), 2.13 (d, J = 6.8 Hz, 2H), 2.02 (s, 4H), 1.93-1.84 (m, 7H), 1.77-1.69 (m, 2H), 1.62-1.55 (m, 1H), 1.10-1.00 (m, 2H) |
| I-315 | CJK | CKG | 851.4 | 11.11 (s, 1H), 9.69 (s, 1H), 8.75 (d, J = 7.6 Hz, 1H), 8.37 (s, 1H), 8.24 (s, 1H), 7.18-7.01 (m, 4H), 6.37 (d, J = 7.6 Hz, 1H), 5.39 (dd, J = 5.2, 12.8 Hz, 1H), 4.73 (s, 4H), 4.38 (s, 4H), 4.24-4.16 (m, 1H), 3.65 (s, 3H), 3.62-3.53 (m, 1H), 3.10-2.97 (m, 1H), 2.95-2.82 (m, 2H), 2.77-2.60 (m, 6H), 2.46-2.35 (m, 2H), 2.18-2.12 (m, 1H), 2.11-1.96 (m, 4H), 1.94-1.86 (m, 2H), 1.81-1.69 (m, 2H), 1.68-1.49 (m, 1H), 1.28-1.20 (m, 1H), 1.17-0.99 (m, 2H) |
| I-320 | CJK | CKP | 865.5 | 11.12 (s, 1H), 9.73-9.43 (m, 1H), 8.76 (d, J = 7.2 Hz, 1H), 8.38 (s, 1H), 8.25 (s, 1H), 7.19-6.99 (m, 4H), 6.56 (d, J = 7.6 Hz, 1H), 5.39 (dd, J = 5.2, 12.8 Hz, 1H), 4.66-4.51 (m, 4H), 4.26-4.09 (m, 1H), 3.87 (d, J = 11.6 Hz, 2H), 3.65 (s, 5H), 3.57 (s, 4H), 2.95-2.82 (m, 2H), 2.68 (d, J = 2.4 Hz, 2H), 2.60 (s, 2H), 2.42-2.31 (m, 4H), 2.29 (d, J = 6.8 Hz, 1H), 2.13 (d, J = 7.2 Hz, 2H), 2.03 (d, J = 5.2 Hz, 3H), 1.93-1.84 (m, 2H), 1.80-1.67 (m, 2H), 1.63-1.52 (m, 1H), 1.10-0.98 (m, 2H) |
| I-339 | CJK | CKJ | 865.5 | 11.11 (s, 1H), 9.40 (s, 1H), 8.80 (d, J = 7.6 Hz, 1H), 8.37 (s, 1H), 8.26 (s, 1H), 7.24-7.07 (m, 3H), 7.04-6.96 (m, 1H), 6.83 (d, J = 8.0 Hz, 1H), 5.39 (dd, J = 5.4, 12.4 Hz, 1H), 4.97 (d, J = 3.2 Hz, 1H), 4.69-4.56 (m, 1H), 4.24-4.09 (m, 1H), 3.77-3.70 (m, 1H), 3.64 (s, 5H), 3.57 (s, 3H), 2.94-2.83 (m, 1H), 2.76-2.69 (m, 1H), 2.57 (s, 6H), 2.45-2.35 (m, 3H), 2.15-2.10 (m, 2H), 2.08-1.97 (m, 7H), 1.92-1.85 (m, 2H), 1.79-1.68 (m, 2H), 1.63-1.52 (m, 1H), 1.09-0.99 (m, 2H) |
| I-405 | CJK | CJZ | 853.3 | 11.12 (s, 1H), 9.29 (s, 1H), 8.83 (d, J = 8.0 Hz, 1H), 8.38 (s, 1H), 8.29 (s, 1H), 7.26-6.98 (m, 4H), 6.92 (d, J = 8.0 Hz, 1H), 5.40 (dd, J = 5.2, 12.4 Hz, 1H), 4.24-4.14 (m, 1H), 3.87 (s, 2H), 3.80-3.74 (m, 4H), 3.65 (s, 3H), 3.59 (s, 2H), 2.88 (dd, J = 5.2, 16.4 Hz, 1H), 2.73 (d, J = 4.4 Hz, 1H), 2.71-2.67 (m, 1H), 2.65 (d, J = 4.6 Hz, 2H), 2.61 (s, 4H), 2.30-2.14 (m, 2H), 2.04 (d, J = 8.0 Hz, 4H), 1.89 (d, J = 11.6 Hz, 2H), 1.83-1.49 (m, 4H), 1.12-1.01 (m, 2H), 0.79-0.74 (m, 2H), 0.68-0.64 (m, 2H) |
| I-406 | CJK | CKA | 853.1 | 11.12 (s, 1H), 9.33 (s, 1H), 8.83 (d, J = 8.0 Hz, 1H), 8.38 (s, 1H), 8.28 (s, 1H), 7.29-6.97 (m, 4H), 6.93 (d, J = 8.0 Hz, 1H), 5.39 (dd, J = 5.2, 12.8 Hz, 1H), 4.57-4.27 (m, 2H), 4.25-4.12 (m, 1H), 3.99-3.86 (m, 1H), 3.65 (s, 3H), 3.64-3.50 (m, 4H), 3.26 (d, J = 2.8 Hz, 1H), 3.10 (t, J = 12.4 Hz, 1H), 2.95-2.80 (m, 2H), 2.80-2.54 (m, 7H), 2.47-2.33 (m, 2H), 2.27-1.95 (m, 5H), 1.94-1.83 (m, 2H), 1.81-1.68 (m, 2H), 1.68-1.47 (m, 1H), 1.19 (d, J = 6.4 Hz, 3H), 1.14-0.98 (m, 2H) |

TABLE 2-continued

Compounds synthesized via Method 1, with the corresponding amine and acid coupling.

| I-#[a] | Amine | Acid | LCMS (ES+) m/z (M + H)+ | 1HNMR (400 MHz, DMSO-$d_6$) δ |
|---|---|---|---|---|
| I-414 | CJK | CKN | 845.2 | 11.12 (s, 1H), 9.63 (s, 1H), 8.92 (d, J = 7.2 Hz, 1H), 8.37 (s, 1H), 8.33 (s, 1H), 7.32-6.96 (m, 4H), 6.54 (d, J = 7.6 Hz, 1H), 5.39 (dd, J = 5.2, 12.4 Hz, 1H), 4.66 (t, J = 11.6 Hz, 4H), 4.25-4.11 (m, 1H), 3.65 (s, 3H), 3.61 (s, 2H), 3.43-3.35 (m, 2H), 2.94-2.83 (m, 1H), 2.77-2.67 (m, 2H), 2.67-2.54 (m, 6H), 2.39-2.20 (m, 2H), 2.09-1.97 (m, 3H), 1.95-1.85 (m, 2H), 1.81-1.68 (m, 2H), 1.67-1.55 (m, 1H), 1.15-0.97 (m, 2H) |
| I-418 | CJK | COW | 879.4 | 11.13 (s, 1H), 9.62-9.51 (m, 1H), 8.96-8.82 (m, 1H), 8.77 (d, J = 7.6 Hz, 1H), 8.40 (s, 1H), 7.22-7.00 (m, 4H), 6.63-6.51 (m, 1H), 5.45-5.33 (m, 1H), 4.31-4.15 (m, 1H), 3.88-3.80 (m, 2H), 3.77-3.72 (m, 2H), 3.67 (s, 3H), 3.65-3.63 (m, 2H), 3.61-3.53 (m, 5H), 3.09-2.97 (m, 6H), 2.89 (s, 2H), 2.80-2.62 (m, 5H), 2.06 (td, J = 6.4, 12.8 Hz, 4H), 1.97-1.88 (m, 5H), 1.79 (d, J = 12.0 Hz, 2H), 1.24-1.15 (m, 2H) |
| I-429 | CJK | CKC | 867.4 | 11.11 (s, 1H), 9.27 (s, 1H), 8.82 (d, J = 8.0 Hz, 1H), 8.38 (s, 1H), 8.28 (s, 1H), 7.19-7.08 (m, 2H), 7.05-6.92 (m, 2H), 5.39 (d, J = 5.6, 12.8 Hz, 1H), 4.54-4.33 (m, 1H), 4.24-4.11 (m, 1H), 3.64 (s, 4H), 3.57 (s, 2H), 2.95-2.82 (m, 1H), 2.76-2.62 (m, 4H), 2.61-2.51 (m, 8H), 2.41 (s, 3H), 2.12 (d, J = 6.8 Hz, 2H), 2.06-1.97 (m, 3H), 1.94-1.84 (m, 2H), 1.80-1.66 (m, 2H), 1.64-1.52 (m, 1H), 1.22-1.16 (m, 6H), 1.10-0.97 (m, 2H) |
| I-430 | CJK | CKB | 867.2 | 11.12 (s, 1H), 9.30 (s, 1H), 8.80 (d, J = 8.0 Hz, 1H), 8.39 (s, 1H), 8.27 (s, 1H), 7.29-6.88 (m, 5H), 5.39 (dd, J = 5.6, 12.8 Hz, 1H), 4.26-4.14 (m, 1H), 4.13-4.00 (m, 2H), 3.98-3.83 (m, 2H), 3.65 (s, 3H), 3.63-3.57 (m, 2H), 3.50 (dd, J = 6.8, 13.2 Hz, 3H), 2.95-2.82 (m, 2H), 2.78-2.56 (m, 6H), 2.48-2.36 (m, 2H), 2.23-2.13 (m, 1H), 2.11-1.97 (m, 4H), 1.89 (d, J = 11.2 Hz, 2H), 1.81-1.69 (m, 2H), 1.68-1.49 (m, 1H), 1.17 (d, J = 6.4 Hz, 6H), 1.11-0.98 (m, 2H) |
| I-509 | CMB | CKG | 877.3 | 11.09 (s, 1H), 9.70 (s, 1H), 8.75 (d, J = 7.6 Hz, 1H), 8.38 (s, 1H), 8.25 (s, 1H), 7.29-7.02 (m, 1H), 7.02-6.97 (m, 2H), 6.95-6.93 (m, 1H), 6.37 (d, J = 7.6 Hz, 1H), 5.40-5.33 (m, 1H), 4.74 (s, 4H), 4.39 (s, 4H), 4.26-4.17 (m, 1H), 3.62 (s, 3H), 3.24-3.17 (m, 4H), 3.09-2.98 (m, 1H), 2.92-2.84 (m, 2H), 2.64 (s, 2H), 2.44 (s, 3H), 2.08-1.98 (m, 6H), 1.92-1.88 (m, 1H), 1.84-1.74 (m, 3H), 1.61-1.53 (m, 1H), 1.10-0.99 (m, 2H) |
| I-512 | CMB | CJL | 849.5 | 11.24-10.83 (m, 1H), 9.57 (s, 1H), 8.74 (d, J = 7.6 Hz, 1H), 8.39 (s, 1H), 8.36-8.21 (m, 1H), 7.25-6.92 (m, 4H), 6.56 (d, J = 7.6 Hz, 1H), 5.36 (dd, J = 5.2, 12.4 Hz, 1H), 4.25-4.14 (m, 1H), 3.70-3.59 (m, 5H), 3.59-3.50 (m, 2H), 3.27-3.12 (m, 4H), 3.09-2.95 (m, 1H), 2.94-2.83 (m, 2H), 2.75-2.53 (m, 3H), 2.44 (s, 3H), 2.10-1.95 (m, 9H), 1.94-1.87 (m, 1H), 1.85-1.69 (m, 3H), 1.63-1.50 (m, 1H), 1.12-0.97 (m, 2H) |
| I-515 | CMB | CJJ | 863.4 | 11.09 (s, 1H), 9.39 (s, 1H), 8.72 (d, J = 8.0 Hz, 1H), 8.39 (s, 1H), 8.24 (s, 1H), 7.23-6.96 (m, 3H), 6.95-6.87 (m, 2H), 5.35 (d, J = 12.4 Hz, 1H), 4.20 (s, 1H), 3.79 (s, 4H), 3.62 (s, 3H), 3.25-3.21 (m, 4H), 3.18-3.15 (m, 1H), 3.09-2.96 (m, 2H), 2.93-2.83 (m, 2H), 2.64 (s, 2H), 2.43 (s, 3H), 2.39-2.31 (m, 1H), 2.07-1.98 (m, 4H), 1.93-1.86 (m, 1H), 1.83-1.72 (m, 3H), 1.67 (d, J = 4.4 Hz, 2H), 1.60 (d, J = 4.0 Hz, 4H), 1.04 (d, J = 12.0Hz, 2H) |
| I-522 | CMB | CMD | 865.5 | 11.16 (s, 1H), 9.47 (s, 1H), 8.90 (d, J = 8.0 Hz, 1H), 8.45 (s, 1H), 8.36 (s, 1H), 7.34-6.95 (m, 5H), 5.43 (m, J = 5.2, 12.8 Hz, 1H), 4.35-4.19 (m, 1H), 3.89-3.84 (m, 1H), 3.79 (m, J = 4.4 Hz, 4H), 3.69 (s, 3H), 3.34-3.17 (m, 4H), 3.15-3.04 (m, 1H), 3.00-2.90 (m, 2H), 2.84-2.76 (m, 1H), 2.72-2.61 (m, 4H), 2.50 (s, 4H), 2.18-2.02 (m, 5H), 2.01-1.93 (m, 1H), 1.93-1.76 (m, 3H), 1.69-1.56 (m, 1H), 1.17-1.04 (m, 2H) |
| I-523 | CMB | CMG | 877.3 | 11.17-11.00 (m, 1H), 9.50 (d, J = 6.0 Hz, 1H), 8.78 (d, J = 7.6 Hz, 1H), 8.39 (d, J = 4.4 Hz, 1H), 8.26 (d, J = 5.6 Hz, 1H), 7.27-7.09 (m, 1H), 7.02-6.97 (m, 2H), 6.94 (d, J = 7.2 Hz, 1H), 6.89-6.43 (m, 1H), 5.36 (dd, J = 5.2, 12.8 Hz, 1H), 5.28 (s, 1H), 4.77 (d, J = 16.4 Hz, 1H), 4.26-4.14 (m, 1H), 3.84-3.73 (m, 2H), 3.62 (s, 3H), 3.60 (s, 1H), 3.43 (s, 1H), 3.21 (d, J = 16.0 Hz, 3H), 3.08-2.84 (m, 4H), 2.73-2.60 (m, 2H), 2.43 (s, 3H), 2.09-1.87 (m, 9H), 1.84-1.70 (m, 3H), 1.61-1.51 (m, 1H), 1.09-0.99 (m, 2H) |
| I-528 | CMB | CJZ | 879.4 | 11.09 (s, 1H), 9.33 (s, 1H), 8.82 (d, J = 8.0 Hz, 1H), 8.39 (s, 1H), 8.29 (s, 1H), 7.33-6.85 (m, 5H), 5.36 (dd, J = 5.2, 12.4 Hz, 1H), 4.61-4.06 (m, 3H), 4.00-3.89 (m, 1H), 3.72-3.51 (m, 5H), 3.25-3.03 (m, 5H), 3.01-2.74 (m, 3H), 2.73-2.55 (m, 2H), 2.44 (s, 4H), 2.16-1.96 (m, 5H), 1.94-1.87 (m, 1H), 1.85-1.70 (m, 3H), 1.63-1.49 (m, 1H), 1.30-1.13 (m, 4H), 1.11-0.96 (m, 2H) |
| I-529 | CMB | CKA | 879.6 | 11.09 (s, 1H), 9.34 (s, 1H), 8.83 (d, J = 8.0 Hz, 1H), 8.39 (s, 1H), 7.33-6.83 (m, 5H), 5.36 (dd, J = 4.4, 12.8 Hz, 1H), 4.54-4.26 |

TABLE 2-continued

Compounds synthesized via Method 1, with the corresponding amine and acid coupling.

| I-#[a] | Amine | Acid | LCMS (ES+) m/z (M + H)+ | 1HNMR (400 MHz, DMSO-$d_6$) δ |
|---|---|---|---|---|
| | | | | (m, 2H), 4.25-4.14 (m, 1H), 4.00-3.84 (m, 1H), 3.62 (s, 3H), 3.60-3.53 (m, 1H), 3.26-3.08 (m, 5H), 3.07-2.96 (m, 1H), 2.95-2.84 (m, 2H), 2.84-2.69 (m, 2H), 2.65-2.58 (m, 2H), 2.44 (s, 3H), 2.11-1.98 (m, 5H), 1.97-1.85 (m, 2H), 1.84-1.69 (m, 3H), 1.66-1.49 (m, 1H), 1.19 (d, J = 6.0 Hz, 4H), 1.12-0.95 (m, 2H) |
| I-530 | CMB | CMA | 893.5 | 11.10 (s, 1H), 9.29 (s, 1H), 8.81 (d, J = 8.0 Hz, 1H), 8.40 (s, 1H), 8.28 (s, 1H), 7.29-7.02 (m, 1H), 7.02-6.97 (m, 2H), 6.93 (d, J = 8.0 Hz, 2H), 5.36 (dd, J = 5.6, 12.4 Hz, 1H), 4.27-4.15 (m, 1H), 3.82-3.72 (m, 4H), 3.67 (s, 2H), 3.62 (s, 3H), 3.28-3.12 (m, 4H), 3.09-2.97 (m, 1H), 2.94-2.83 (m, 2H), 2.80-2.60 (m, 3H), 2.44 (s, 3H), 2.10-1.94 (m, 5H), 1.92-1.69 (m, 4H), 1.63-1.51 (m, 1H), 1.20 (s, 6H), 1.12-0.97 (m, 2H) |
| I-533 | CMB | CKB | 893.3 | 0.97-1.10 (m, 2 H) 1.17 (d, J = 6.4 Hz, 6 H) 1.51-1.64 (m, 1 H) 1.70-1.86 (m, 3 H) 1.87-1.95 (m, 1 H) 1.96-2.08 (m, 5 H) 2.44 (s, 3 H) 2.61-2.72 (m, 3 H) 2.83-2.94 (m, 2 H) 2.96-3.10 (m, 1 H) 3.13-3.28 (m, 4 H) 3.51 (br dd, J = 13.2, 6.8 Hz, 3 H) 3.62 (s, 3 H) 3.87-3.94 (m, 1 H) 4.03-4.12 (m, 2 H) 4.15-4.26 (m, 1 H) 5.36 (br dd, J = 12.8, 5.2 Hz, 1 H) 6.89-7.03 (m, 4 H) 7.11-7.30 (m, 1 H) 8.28 (s, 1 H) 8.40 (s, 1 H) 8.80 (d, J = 8.0 Hz, 1 H) 9.31 (s, 1 H) 11.05-11.14 (m, 1 H) |
| I-534 | CMB | CMH | 877.3 | 11.19 (s, 1H), 9.65 (s, 1H), 8.95 (d, J = 7.6 Hz, 1H), 8.50 (s, 1H), 8.41 (s, 1H), 7.18-7.02 (m, 4H), 6.73 (d, J = 8.0 Hz, 1H), 5.46 (d, J = 12.0 Hz, 1H), 4.84-4.72 (m, 2H), 4.45 (d, J = 10.8 Hz, 1H), 4.31 (s, 1H), 4.16 (d, J = 12.0 Hz, 1H), 3.97 (d, J = 11.2 Hz, 1H), 3.88 (d, J = 10.4 Hz, 1H), 3.73 (s, 3H), 3.35-3.25 (m, J = 16 Hz, 12 Hz, 5H), 3.20-3.07 (m, 1H), 3.06-2.87 (m, 4H), 2.81 (s, 1H), 2.76 (d, J = 11.2 Hz, 2H), 2.19-2.08 (m, 5H), 2.04 (d, J = 8.4 Hz, 2H), 1.96-1.77 (m, 4H), 1.66 (d, J = 3.2 Hz, 1H), 1.15 (d, J = 13.2 Hz, 2H) |
| I-703 | CJK | CLF | 875.6 | 11.12 (s, 1H), 9.30 (s, 1H), 8.96 (d, J = 8.0 Hz, 1H), 8.37 (d, J = 16.8 Hz, 2H), 7.29-6.95 (m, 5H), 5.39 (d, J = 5.2, 12.4 Hz, 1H), 4.33 (t, J = 8.8 Hz, 2H), 4.28-4.13 (m, 3H), 3.94 (d, J = 4.4 Hz, 2H), 3.71-3.55 (m, 5H), 2.94-2.79 (m, 2H), 2.77-2.51 (m, 10H), 2.11-1.94 (m, 4H), 1.90 (d, J = 11.2 Hz, 2H), 1.83-1.59 (m, 3H), 1.19-0.98 (m, 2H) |
| I-714 | CMJ | CKD | 920.2 | 11.12 (s, 1H), 9.25 (s, 1H), 8.92 (d, J = 8.0 Hz, 1H), 8.36 (d, J = 12.8 Hz, 2H), 7.22-6.98 (m, 5H), 5.40 (dd, J = 5.6, 12.8 Hz, 1H), 4.60-4.55 (m, 2H), 4.53-4.37 (m, 1H), 4.27 (s, 4H), 4.20-4.14 (m, 1H), 3.64 (s, 3H), 3.27 (d, J = 1.6 Hz, 4H), 3.05-2.99 (m, 1H), 2.91-2.84 (m, 1H), 2.75-2.63 (m, 4H), 2.18 (d, J = 6.8 Hz, 2H), 2.11-2.08 (m, 1H), 2.07-1.99 (m, 5H), 1.88 (dd, J = 2.0, 9.8 Hz, 2H), 1.78-1.69 (m, 2H), 1.60-1.53 (m, 1H), 1.48-1.41 (m, 1H), 1.08-0.99 (m, 2H) |
| I-715 | CML | CKD | 920.4 | 11.12 (s, 1H), 9.25 (s, 1H), 8.92 (d, J = 7.8 Hz, 1H), 8.37 (s, 1H), 8.34 (s, 1H), 7.25-7.01 (m, 5H), 5.40 (dd, J = 5.6, 12.4 Hz, 1H), 4.61-4.55 (m, 2H), 4.27 (s, 4H), 3.64 (s, 3H), 3.29-3.24 (m, 6H), 3.06-3.01 (m, 1H), 2.97-2.76 (m, 2H), 2.73-2.63 (m, 3H), 2.18 (d, J = 6.4 Hz, 2H), 2.10-1.98 (m, 6H), 1.91-1.85 (m, 2H), 1.79-1.71 (m, 2H), 1.63-1.55 (m, 1H), 1.50-1.41 (m, 1H), 1.07-0.96 (m, 2H) |
| I-723 | COJ | CKP | 946.8 | 11.22-10.95 (m, 1H), 9.75-9.41 (m, 1H), 8.86-8.65 (m, 1H), 8.48-8.31 (m, 1H), 8.25 (s, 1H), 7.34-7.04 (m, 1H), 7.01-6.86 (m, 3H), 6.56 (d, J = 7.6 Hz, 1H), 5.47-5.27 (m, 1H), 4.64-4.47 (m, 4H), 4.27-4.10 (m, 1H), 3.97-3.79 (m, 2H), 3.65-3.60 (m, 4H), 2.99 (dd, J = 2.8, 11.6 Hz, 3H), 2.90 (d, J = 9.6 Hz, 6H), 2.86-2.81 (m, 2H), 2.71-2.59 (m, 2H), 2.37-2.16 (m, 6H), 2.11-1.96 (m, 5H), 1.92-1.85 (m, 2H), 1.83-1.73 (m, 4H), 1.66-1.55 (m, 1H), 1.00 (s, 2H) |
| I-735 | COJ | CKG | 932.4 | 11.09 (s, 1H), 9.69 (s, 1H), 8.76 (d, J = 7.2 Hz, 1H), 8.37 (s, 1H), 8.25 (s, 1H), 7.29-7.02 (m, 1H), 7.01-6.85 (m, 3H), 6.38 (d, J = 7.6 Hz, 1H), 5.35 (dd, J = 5.2, 12.8 Hz, 1H), 4.74 (s, 4H), 4.39 (s, 4H), 4.23-4.13 (m, 1H), 3.63 (s, 3H), 3.06-2.98 (m, 2H), 2.95-2.78 (m, 10H), 2.75-2.68 (m, 1H), 2.64-2.58 (m, 1H), 2.27-2.15 (m, 3H), 2.10-1.97 (m, 4H), 1.91-1.84 (m, 2H), 1.83-1.70 (m, 4H), 1.65-1.52 (m, 1H), 1.10-0.98 (m, 2H) |

[a]Coupling was run for 8-18 hr from 25° C.-50° C. TEA and other bases and solvents could be employed for the coupling. The final products were isolated under standard purification techniques including reverse HPLC, silica gel chromatography, and prep-TLC with appropriate solvent conditions.
[b]POCl$_3$ in pyridine was used in place of HATU for the coupling, which was run at rt for 2.5 hr.

Example 2 (Method 2): Synthesis of N-[3-(difluoromethyl)-1-[4-[[(3S,4R)-4-[3-[1-(2,6-dioxo-3-piperidyl)-5-methoxy-3-methyl-2-oxo-benzimidazol-4-yl]prop-2-ynoxy]-3-fluoro-1-piperidyl]methyl]cyclohexyl]pyrazol-4-yl]-5-1[(1R,4R)-2-oxa-5-azabicyclo[2.2.1]heptan-5-yl]pyrazolo[1,5-a]pyrimidine-3-carboxamide

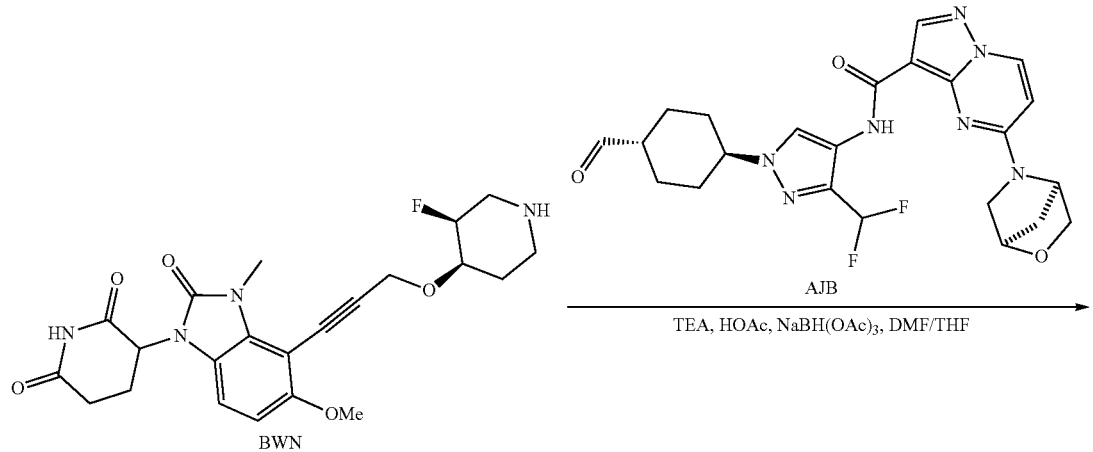

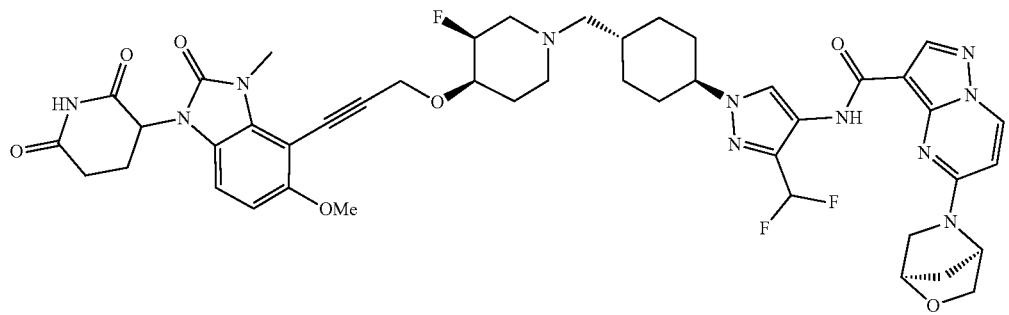

I-1

To a solution of 3-[4-[3-[[(3S,4R)-3-fluoro-4-piperidyl]oxy] prop-1-ynyl]-5-methoxy-3-methyl-2-oxo-benzimidazol-1-yl]piperidine-2,6-dione (35 mg, 78.7 umol, Intermediate CFJ), and N-[3-(difluoromethyl)-1-(4-formyl cyclohexyl)pyrazol-4-yl]-5-[(1R)-2-oxa-5-azabicyclo [2.2.1]heptan-5-yl]pyrazolo[1,5-a]pyrimidine-3-carboxamide (38.2 mg, 78.7 umol, Intermediate AFB) in a mix solvent of THF (4 mL) and DMF (1 mL) was added TEA (15.9 mg, 157 umol) at −10° C., then the mixture was stirred at −10° C. for 5 min. Next, HOAc (14.1 mg, 236 umol) was added to above solution, and the mixture was stirred at 25 min. Finally, NaBH(OAc)₃ (33.3 mg, 157 umol) was added and the mixture was stirred at −10° C. for 8.5 hrs. On completion, the mixture was quenched with H₂O (0.5 mL) and concentrated in vacuo. The crude product was purified by prep-HPLC (column: Phenomenex luna C 18 150*25 mm*10 um; mobile phase: [water (0.225% FA)-ACN]; B %: 17%-47%, 10 min) to give the title compound (41.6 mg, 55% yield) as a white solid. $^1$H NMR (400 MHz, DMSO-d$_6$) δ 11.10 (s, 1H), 9.50 (d, J=6.0 Hz, 1H), 8.78 (d, J=7.6 Hz, 1H), 8.38 (d, J=4.4 Hz, 1H), 8.25 (d, J=5.6 Hz, 1H), 7.26-6.95 (m, 2H), 6.88-6.43 (m, 2H), 5.35 (dd, J=5.2, 12.8 Hz, 1H), 5.29-5.05 (m, 1H), 4.93-4.72 (m, 2H), 4.56 (s, 2H), 4.24-4.12 (m, 1H), 3.85-3.72 (m, 6H), 3.62 (s, 3H), 3.61-3.58 (m, 1H), 3.44 (d, J=10.4 Hz, 1H), 2.95-2.82 (m, 2H), 2.75-2.68 (m, 1H), 2.68-2.62 (m, 2H), 2.15 (s, 3H), 2.09-1.99 (m, 4H), 1.99-1.80 (m, 5H), 1.80-1.68 (m, 3H), 1.66-1.51 (m, 1H), 1.11-0.96 (m, 2H). LC-MS (ESI$^+$) m/z 914.5 (M+H)$^+$.

TABLE 3

Compounds synthesized via Method 2, with the reductive amination of the corresponding amines and aldehydes.

| I-#[a] | Amine | Aldehyde | LCMS (ES+) m/z (M + H)+ | $^1$HNMR (400 MHZ, DMSO-d6) δ |
|---|---|---|---|---|
| I-4 | CGO | AJB | 877.9 | 11.09 (s, 1H), 9.49 (d, J = 6.4 Hz, 1H), 8.78 (d, J = 7.8 Hz, 1H), 8.38 (d, J = 4.0 Hz, 1H), 8.25 (d, J = 5.4 Hz, 1H), 7.27-6.95 (m, 4H), 6.66 (d, J = 7.8, 164.4 Hz, 1H), 5.33 (d, J = 5.5, 12.4 Hz, 1H), 5.27 (s, 1H), 4.76 (d, J = 18.8 Hz, 1H), 4.25-4.12 (m, 1H), 3.84-3.72 (m, 2H), 3.65-3.54 (m, 3H), 3.44 (d, J = 9.6 Hz, 1H), 3.16-3.05 (m, 2H), 2.95-2.77 (m, 2H), 2.74-2.55 (m, 6H), 2.33 (td, J = 1.6, 3.7 Hz, 2H), 2.08-1.96 (m, 5H), 1.95-1.68 (m, 6H), 1.65-1.54 (m, 1H), 1.14-1.00 (m, 6H) |
| I-6 | CGR | CCX | 863.1 | 10.53 (s, 1H), 9.50 (d, J = 6.0 Hz, 1H), 9.33 (s, 1H), 8.77 (d, J = 7.6 Hz, 1H), 8.58-8.54 (m, 1H), 8.39 (d, J = 4.4 Hz, 1H), 8.25 (d, J = 5.6 Hz, 1H), 7.87-7.82 (m, 1H), 7.79 (t, J = 7.6 Hz, 1H), 7.65 (d, J = 7.2 Hz, 1H), 7.26-6.94 (m, 1H), 6.88-6.41 (m, 1H), 5.30-5.04 (m, 1H), 4.81-4.72 (m, 1H), 4.44 (t, J = 8.0 Hz, 1H), 4.24-4.12 (m, 1H), 3.92 (m, J = 5.2, 10.0, 12.4 Hz, 1H), 3.85-3.77 (m, 2H), 3.76-3.66 (m, 2H), 3.66-3.56 (m, 2H), 3.44 (d, J = 10.0 Hz, 2H), 2.98 (m, J = 6.0, 10.0, 16.4 Hz, 2H), 2.76 (td, J = 5.4, 16.6 Hz, 3H), 2.43-2.34 (m, 5H), 2.18 (s, 3H), 2.08-1.85 (m, 8H), 1.83-1.66 (m, 3H), 1.59 (d, J = 2.8 Hz, 1H), 1.11-0.98 (m, 2H) |
| I-8 | CGM | AJB | 893.5 | 11.09 (d, J = 2.0 Hz, 1H), 9.54-9.44 (m, 1H), 8.78 (d, J = 7.6 Hz, 1H), 8.38 (d, J = 4.4 Hz, 2H), 8.25 (d, J = 5.6 Hz, 1H), 7.15-6.95 (m, 3H), 6.90-6.42 (m, 2H), 5.37 (m, J = 5.6, 12.4 Hz, 1H), 5.29-5.05 (m, 1H), 4.77 (d, J = 17.6 Hz, 1H), 4.25-4.12 (m, 1H), 3.85-3.77 (m, 2H), 3.74 (d, J = 7.6 Hz, 1H), 3.66-3.58 (m, 2H), 3.57 (s, 3H), 3.44 (d, J = 10.8 Hz, 2H), 2.94-2.82 (m, 1H), 2.78-2.69 (m, 1H), 2.65-2.57 (m, 1H), 2.37 (s, 2H), 2.18-2.09 (m, 9H), 2.07-1.93 (m, 6H), 1.93-1.84 (m, 3H), 1.81-1.65 (m, 3H), 1.60-1.52 (m, 1H), 1.09-0.98 (m, 2H) |
| I-9 | BXU | AJB | 865.4 | 11.12 (s, 1H), 9.50 (d, J = 6.8 Hz, 1H), 9.12-8.94 (m, 1H), 8.78 (d, J = 7.6 Hz, 1H), 8.39 (d, J = 4.0 Hz, 1H), 8.25 (d, J = 5.6 Hz, 1H), 6.96 (s, 4H), 6.69-6.63 (dd, J = 7.6, 164.4 Hz, 1H), 5.40 (dd, J = 5.2, 12.4 Hz, 1H), 5.17 (d, J = 78.8 Hz, 1H), 4.76 (d, J = 22.8 Hz, 1H), 4.22 (t, J = 10.0 Hz, 1H), 3.96 (d, J = 17.6 Hz, 1H), 3.84-3.71 (m, 3H), 3.68 (s, 3H), 3.65-3.43 (m, 4H), 3.04-2.85 (m, 6H), 2.78-2.68 (m, 2H), 2.13-1.84 (m, 9H), 1.84-1.72 (m, 2H), 1.25-1.14 (m, 2H), 1.10 (d, J = 6.0 Hz, 3H) |
| I-18 | CHD | AJB | 902.4 | 11.12 (s, 1H), 9.50 (d, J = 6.0 Hz, 1H), 8.78 (d, J = 7.6 Hz, 1H), 8.38 (d, J = 4.0 Hz, 1H), 8.27-8.21 (m, 1H), 7.24-6.96 (m, 3H), 6.89-6.43 (m, 1H), 5.40 (dd, J = 4.8, 12.4 Hz, 1H), 5.30-5.05 (m, 1H), 4.77 (d, J = 17.2 Hz, 1H), 4.62 (s, 1H), 4.22-4.12 (m, 1H), 3.93-3.84 (m, 1H), 3.83-3.72 (m, 2H), 3.64 (s, 2H), 3.62-3.58 (m, 1H), 3.44 (d, J = 9.6 Hz, 2H), 3.00-2.78 (m, 2H), 2.76-2.52 (m, 4H), 2.36-2.17 (m, 3H), 2.15-1.84 (m, 8H), 1.83-1.26 (m, 5H), 1.16-0.96 (m, 2H) |
| I-22 | BSF | AJB | 884.4 | 11.12 (s, 1H), 9.50 (d, J = 6.4 Hz, 1H), 8.78 (d, J = 7.6 Hz, 1H), 8.38 (d, J = 4.4 Hz, 1H), 8.25 (d, J = 5.6 Hz, 1H), 7.32-6.94 (m, 4H), 6.89-6.38 (m, 1H), 5.40 (dd, J = 5.6, 12.8 Hz, 1H), 5.30-5.04 (m, 1H), 4.94-4.71 (m, 2H), 4.55 (s, 2H), 4.26-4.08 (m, 1H), 3.88-3.68 (m, 3H), 3.64 (s, 3H), 3.62-3.55 (m, 1H), 3.49-3.39 (m, 2H), 2.93-2.80 (m, 2H), 2.77-2.68 (m, 1H), 2.65 (m, 1H), 2.44-2.34 (m, 1H), 2.15 (m, 3H), 2.08-1.99 (m, 4H), 1.96 (m,, 1H), 1.88 (m, 2H), 1.83-1.67 (m, 4H), 1.63-1.51 (m, 1H), 1.11-0.93 (m, 2H) |
| I-23 | BSG | AJB | 884.3 | 11.11 (s, 1H), 9.49 (d, J = 6.0 Hz, 1H), 8.76 (d, J = 8.0 Hz, 1H), 8.37 (d, J = 4.4 Hz, 1H), 8.24 (d, J = 5.6 Hz, 1H), 7.26-6.92 (m, 4H), 6.87-6.40 (m, 1H), 5.39 (dd, J = 5.6, 12.8 Hz, 1H), 5.29-5.00 (m, 1H), 4.75 (d, J = 18.0 Hz, 1H), 4.59-4.35 (m, 3H), 4.21-4.08 (m, 1H), 3.83-3.73 (m, 2H), 3.63 (m, 3H), 3.59 (m, 2H), 3.43 (m, 2H), 3.05-2.95 (m, 1H), 2.92-2.83 (m, 1H), 2.70 (m, 2H), 2.64 (m, 1H), 2.16 (m, 2H), 2.11-2.07 (m, 1H), 2.04-1.98 (m, 4H), 1.97-1.91 (m, 2H), 1.86 (m, 2H), 1.78-1.66 (m, 2H), 1.63-1.50 (m, 1H), 1.48-1.35 (m, 1H), 1.10-0.92 (m, 2H) |
| I-31 | CBD | AJB | 851.6 | 11.11 (s, 1H), 9.49 (d, J = 6.4 Hz, 1H), 8.77 (d, J = 7.6 Hz, 1H), 8.37 (d, J = 4.4 Hz, 1H), 8.25 (d, J = 5.2 Hz, 1H), 8.22 (s, 1H), 7.26-6.94 (m, 4H), 6.88-6.40 (m, 1H), 5.36-5.39 (m, 1H), 5.30-5.03 (m, 1H), 4.74-4.78 (m, 1H), 4.22-4.12 (m, 1H), 3.85-3.77 (m, 2H), 3.72-3.74 (m, 1H), 3.64 (s, 3H), 3.62-3.55 (m, 4H), 2.94-2.83 (m, 1H), 2.76-2.63 (m, 2H), 2.62-2.53 (m, 4H), 2.38-2.40 (m, 2H), 2.11-2.12 (m, 2H), 2.08-1.96 (m, 5H), 1.95-1.84 (m, 3H), 1.78-1.67 (m, 2H), 1.62-1.50 (m, 1H), 1.09-0.97 (m, 2H) |

TABLE 3-continued

Compounds synthesized via Method 2, with the reductive amination of the corresponding amines and aldehydes.

| I-#[a] | Amine | Aldehyde | LCMS (ES+) m/z (M + H)+ | 1HNMR (400 MHZ, DMSO-d6) δ |
|---|---|---|---|---|
| I-35 | CHH | AJB | 884.3 | 11.12 (s, 1H), 9.49 (d, J = 6.4 Hz, 1H), 8.78 (d, J = 7.6 Hz, 1H), 8.38 (d, J = 4.4 Hz, 1H), 8.26 (d, J = 5.6 Hz 1H), 7.26-6.95 (m, 4H), 6.90-6.40 (m, 1H), 5.45-5.36 (m, 1H), 5.30-5.05 (m, 1H), 4.90-4.72 (m, 2H), 4.55 (s, 2H), 4.22-4.12 (m, 1H), 3.85-3.70 (m, 3H), 3.64 (s, 3H), 3.62-3.56 (m, 2H), 3.49-3.40 (m, 1H), 2.96-2.82 (m, 2H), 2.77-2.68 (m, 1H), 2.65-2.55 (m, 2H), 2.15 (d, J = 7.2 Hz, 2H), 2.04 (d, J = 8.4 Hz, 4H), 1.99-1.82 (m, 4H), 1.82-1.67 (m, 4H), 1.63-1.50 (m, 1H), 1.08-0.97 (m, 2H) |
| I-36 | CHI | AJB | 884.4 | 11.12 (s, 1H), 9.50 (d, J = 6.0 Hz, 1H), 8.78 (d, J = 7.6 Hz, 1H), 8.38 (d, J = 4.4 Hz, 1H), 8.25 (d, J = 5.6 Hz, 1H), 7.29-6.94 (m, 4H), 6.89-6.42 (m, 1H), 5.40 (dd, J = 5.2, 12.8 Hz, 1H), 5.30-5.04 (m, 1H), 4.92-4.72 (m, 2H), 4.55 (s, 2H), 4.17 (t, J = 1.6, 10.0 Hz, 1H), 3.87-3.70 (m, 3H), 3.64 (s, 3H), 3.62-3.57 (m, 1H), 3.44 (d, J = 10.0 Hz, 2H), 2.95-2.82 (m, 2H), 2.77-2.68 (m, 1H), 2.64-2.59 (m, 1H), 2.47-2.34 (m, 1H), 2.15 (m, 3H), 2.04 (m, 4H), 1.96 (m, 1H), 1.88 (m, 2H), 1.83-1.66 (m, 4H), 1.58 (m, 1H), 1.03 (m, 2H) |
| I-38 | CHK | AJB | 833.4 | 10.57 (s, 1 H) 9.58 (s, 1 H) 9.49 (d, J = 6.0 Hz, 1 H) 8.78 (d, J = 7.6 Hz, 1 H) 8.65 (s, 1 H) 8.37 (d, J = 4.0 Hz, 1 H) 8.25 (d, J = 5.6 Hz, 1 H) 8.03 (d, J = 8.4 Hz, 1 H) 7.86-7.90 (m, 1 H) 7.78-7.84 (m, 1 H) 6.97-7.24 (m, 1 H) 6.44-6.87 (m, 1 H) 5.07-5.28 (m, 1 H) 4.76 (d, J = 17.2 Hz, 1 H) 4.13-4.21 (m, 1 H) 3.96 (ddd, J = 12.0, 10.0, 4.8 Hz, 1 H) 3.76-3.85 (m, 2 H) 3.73-3.75 (m, 2 H) 3.68-3.73 (m, 1 H) 3.63 (d, J = 10.8 Hz, 1 H) 3.59 (s, 1 H) 3.44 (d, J = 10.0 Hz, 1 H) 2.99 (ddd, J = 16.4, 10.4, 6.4 Hz, 1 H) 2.77 (t, J = 5.2 Hz, 1 H) 2.70-2.75 (m, 1 H) 2.67 (dd, J = 3.6, 2.0 Hz, 4 H) 2.52 (s, 2 H) 2.14 (d, J = 7.2 Hz, 2 H) 1.98-2.09 (m, 3 H) 1.94-1.98 (m, 1 H) 1.90 (d, J = 12.8 Hz, 2 H) 1.66-1.80 (m, 2 H) 1.53-1.65 (m, 1 H) 0.95-1.11 (m, 2 H) |
| I-39 | CHL | AJB | 881.4 | 10.99-11.16 (m, 1 H) 9.49 (d, J = 6.0 Hz, 1 H) 8.78 (d, J = 7.6 Hz, 1 H) 8.37 (d, J = 4.0 Hz, 1 H) 8.25 (d, J = 5.6 Hz, 1 H) 6.96-7.26 (m, 2 H) 6.42-6.89 (m, 2 H) 5.30-5.39 (m, 1 H) 5.07-5.28 (m, 1 H) 4.72-4.80 (m, 1 H) 4.13-4.21 (m, 1 H) 3.78-3.89 (m, 4 H) 3.72-3.77 (m, 1 H) 3.62 (s, 3 H) 3.57-3.59 (m, 1 H) 3.52-3.57 (m, 2 H) 3.46 (s, 1 H) 2.82-2.93 (m, 1 H) 2.68-2.75 (m, 1 H) 2.63 (d, J = 4.8 Hz, 1 H) 2.57 (d, J = 1.2 Hz, 4 H) 2.52 (s, 2 H) 2.36-2.43 (m, 2 H) 2.12 (d, J = 7.2 Hz, 2 H) 1.94-2.06 (m, 5 H) 1.89 (d, J = 12.8 Hz, 2 H) 1.67-1.80 (m, 2 H) 1.52-1.64 (m, 1 H) 0.97-1.09 (m, 2 H) |
| I-41 | CHN | AJB | 866.5 | 10.58 (s, 1H), 9.59 (br s, 1H), 9.50 (br d, J = 6.5 Hz, 1H), 9.46-9.11 (m, 1H), 8.79 (d, J = 7.6 Hz, 1H), 8.67 (s, 1H), 8.39 (br d, J = 3.6 Hz, 1H), 8.25 (d, J = 5.6 Hz, 1H), 8.07 (d, J = 7.6 Hz, 1H), 7.93-7.88 (m, 1H), 7.87-7.80 (m, 1H), 7.25-6.97 (m, 1H), 6.88-6.45 (m, 1H), 5.43-5.07 (m, 2H), 4.81-4.69 (m, 3H), 4.39-4.07 (m, 2H), 3.97 (ddd, J = 5.0, 10.1, 12.0 Hz, 2H), 3.85-3.77 (m, 2H), 3.76-3.67 (m, 2H), 3.67-3.56 (m, 2H), 3.45 (d, J = 9.4 Hz, 1H), 3.00 (ddd, J = 6.4, 10.0, 16.5 Hz, 2H), 2.76 (td, J = 5.2, 16.8 Hz, 1H), 2.22-2.16 (m, 1H), 2.15-2.00 (m, 4H), 1.96 (br d, J = 16.4 Hz, 2H), 1.92-1.73 (m, 5H), 1.28-0.99 (m, 2H) |
| I-42 | CHO | AJB | 865.6 | 11.11 (s, 1H), 9.49 (d, J = 6.0 Hz, 1H), 8.77 (d, J = 8.0 Hz, 1H), 8.37 (d, J = 4.4 Hz, 1H), 8.25 (d, J = 5.6 Hz, 1H), 7.18-6.94 (m, 4H), 6.90-6.39 (m, 1H), 5.39 (dd, J = 5.2, 12.8 Hz, 1H), 5.30-5.04 (m, 1H), 4.76 (d, J = 17.2 Hz, 1H), 4.24-4.08 (m, 1H), 3.87-3.72 (m, 3H), 3.66 (s, 3H), 3.64 (s, 1H), 3.62-3.56 (m, 2H), 3.44 ( d, J = 10.4 Hz, 1H), 2.95-2.82 (m, 1H), 2.79-2.66 (m, 4H), 2.66-2.58 (m, 2H), 2.57-2.53 (m, 1H), 2.52 ( d, J = 2.0 Hz, 1H), 2.09 ( d, J = 7.2 Hz, 2H), 2.06-1.92 (m, 6H), 1.88 (d, J = 11.6 Hz, 2H), 1.79-1.67 (m, 3H), 1.63-1.49 (m, 1H), 1.01 (d, J = 6.0 Hz, 3H) |
| I-51 | CIB | AJB | 914.4 | 11.11 (s, 1H), 9.50 (d, J = 6.0 Hz, 1H), 8.79 (d, J = 7.6 Hz, 1H), 8.39 (d, J = 4.0 Hz, 1H), 8.26 (d, J = 5.6 Hz, 1H), 7.27-6.96 (m, 2H), 6.90-6.41 (m, 2H), 5.39-5.31 (m, 1H), 5.31-5.05 (m, 1H), 4.90 (s, 1H), 4.77 (d, J = 16.8 Hz, 2H), 4.56 (s, 2H), 4.22-4.13 (m, 1H), 3.80 (s, 3H), 3.74 (d, J = 7.6 Hz, 2H), 3.63 (s, 3H), 2.95-2.81 (m, 3H), 2.69-2.58 (m, 4H), 2.16 (m, 2H), 2.09-1.94 (m, 6H), 1.93-1.79 (m, 4H), 1.78-1.68 (m, 3H), 1.63-1.52 (m, 1H), 1.11-0.97 (m, 2H) |
| I-55 | CID | AJB | 862.5 | 10.59 (s, 1 H) 9.59 (s, 1 H) 9.51 (d, J = 6.8 Hz, 1 H) 8.79 (d, J = 7.6 Hz, 1 H) 8.67 (s, 1 H) 8.40 (d, J = 4.0 Hz, 1 H) 8.26 (d, J = 5.6 Hz, 1 H) 8.07 (d, J = 8.4 Hz, 1 H) 7.81-7.92 (m, 2 H) 7.11 (d, J = 3.6 Hz, 1 H) 6.44-6.90 (m, 1 H) 5.06-5.30 (m, 1 H) 4.75 (s, 1 H) 4.69 (d, J = 11.2 Hz, 2 H) 4.23 (s, 1 H) 3.98 (ddd, J = |

TABLE 3-continued

Compounds synthesized via Method 2, with the reductive amination of the corresponding amines and aldehydes.

| I-#[a] | Amine | Aldehyde | LCMS (ES+) m/z (M + H)+ | $^1$HNMR (400 MHZ, DMSO-d6) δ |
|---|---|---|---|---|
| | | | | 12.0, 10.2, 5.2 Hz, 1 H) 3.70-3.84 (m, 3 H) 3.63 (s, 1 H) 3.60 (s, 1 H) 3.41-3.55 (m, 2 H) 3.16-3.25 (m, 1 H) 2.99 (dd, J = 10.0, 6.0 Hz, 3 H) 2.72-2.83 (m, 2 H) 2.07 (d, J = 8.0 Hz, 3 H) 1.99 (s, 1 H) 1.87-1.96 (m, 4 H) 1.79 (s, 4 H) 1.08-1.31 (m, 3 H) 1.04 (s, 3 H) |
| I-58 | CIF | AJB | 910.4 | 11.10 (s, 1H), 9.50 (d, J = 6.0 Hz, 1H), 8.78 (d, J = 7.6 Hz, 1H), 8.38 (d, J = 4.4 Hz, 1H), 8.25 (d, J = 5.6 Hz, 1H), 7.26-6.95 (m, 2H), 6.86 (d, J = 7.6 Hz, 2H), 5.34 (dd, J = 5.2, 12.4 Hz, 1H), 5.30-5.01 (m, 1H), 4.77 (d, J = 17.6 Hz, 1H), 4.58-4.39 (m, 2H), 4.24-4.11 (m, 1H), 3.80-3.79 (m, 3H), 3.77-3.71 (m, 1H), 3.62 (s, 3H), 3.59 (s, 1H), 3.14-3.08 (m, 2H), 2.90-2.80 (m, 2H), 2.75 (d, J = 8.8 Hz, 1H), 2.65-2.57 (m, 2H), 2.14-1.97 (m, 8H), 1.96-1.84 (m, 4H), 1.78-1.69 (m, 2H), 1.67-1.54 (m, 3H), 1.41-1.28 (m, 1H), 1.09-0.97 (m, 2H), 0.93 (d, J = 6.0 Hz, 3H) |
| I-62 | CIL | AJB | 896.6 | 11.08 (s, 1H), 9.50 (d, J = 6.0 Hz, 1H), 8.78 (d, J = 7.6 Hz, 1H), 8.38 (d, J = 4.4 Hz, 1H), 8.27-8.25 (m, 1H), 7.25-6.44 (m, 5H), 5.35 (dd, J = 5.2, 12.8 Hz, 1H), 5.30-5.06 (m, 1H), 4.77 (d, J = 16.8 Hz, 1H), 4.24-4.11 (m, 1H), 3.83-3.72 (m, 2H), 3.65-3.59 (m, 5H), 2.98 (dd, J = 2.8, 7.2 Hz, 2H), 2.94-2.76 (m, 7H), 2.74-2.58 (m, 3H), 2.52 (d, J = 2.0 Hz, 1H), 2.25-2.17 (m, 1H), 2.10 (d, J = 7.2 Hz, 2H), 2.07-2.00 (m, 2H), 2.00-1.94 (m, 2H), 1.93-1.81 (m, 5H), 1.81-1.69 (m, 4H), 1.61-1.51 (m, 1H), 1.50-1.37 (m, 2H), 1.11-0.97 (m, 2H) |
| I-66 | CIP | AJB | 881.6 | 11.09 (s, 1H), 9.50 (d, J = 6.0 Hz, 1H), 8.77 (d, J = 7.6 Hz, 1H), 8.38 (d, J = 4.4 Hz, 1H), 8.25 (d, J = 5.6 Hz, 1H), 7.26-6.95 (m, 4H), 6.88-6.42 (m, 1H), 5.40-5.31 (m, 1H), 5.29-5.04 (m, 1H), 4.76 (d, J = 17.2 Hz, 1H), 4.21-4.14 (m, 1H), 4.01-3.91 (m, 1H), 3.85-3.78 (m, 2H), 3.73 (d, J = 7.6 Hz, 2H), 3.65-3.59 (m, 5H), 3.51 (s, 3H), 3.44 (d, J = 10.4 Hz, 2H), 2.94-2.82 (m, 1H), 2.76-2.58 (m, 4H), 2.44 (d, J = 5.6 Hz, 4H), 2.32 (dd, J = 1.6, 3.6 Hz, 1H), 2.16 (d, J = 7.2 Hz, 2H), 2.06-1.99 (m, 3H), 1.99-1.93 (m, 2H), 1.88 (d, J = 11.2 Hz, 3H), 1.79-1.67 (m, 2H), 1.57 (s, 1H), 1.03 (q, J = 11.6 Hz, 2H) |
| I-67[b] | CHJ | AJB | 880.4 | 11.12 (s, 1H), 9.49 (d, J = 6.0 Hz, 1H), 8.78 (d, J = 8.0 Hz, 1H), 8.38 (d, J = 4.4 Hz, 1H), 8.25 (d, J = 5.6 Hz, 1H), 7.28-6.95 (m, 4H), 6.89-6.43 (m, 1H), 5.40 (dd, J = 5.2, 12.4 Hz, 1H), 5.30-5.05 (m, 1H), 4.77 (d, J = 17.2 Hz, 1H), 4.57-4.41 (m, 2H), 4.24-4.10 (m, 1H), 3.85-3.72 (m, 2H), 3.65 (s, 3H), 3.62-3.58 (m, 1H), 3.44 (d, J = 8.4 Hz, 1H), 3.12-3.04 (m, 1H), 2.94-2.80 (m, 2H), 2.77-2.60 (m, 3H), 2.10-1.97 (m, 7H), 1.96-1.84 (m, 4H), 1.80-1.70 (m, 2H), 1.69-1.60 (m, 2H), 1.60-1.49 (m, 1H), 1.42-1.30 (m, 1H), 1.09-0.96 (m, 2H), 0.93 (d, J = 6.0 Hz, 3H) |
| I-69 | CIR | AJB | 896.4 | 11.1 (s, 1H), 9.51 (d, J = 6.4 Hz, 1H), 8.78 (d, J = 7.6 Hz, 1H), 8.40 (d, J = 4.0 Hz, 1H), 8.26 (d, J = 5.6 Hz, 1H), 7.26-6.96 (m, 2H), 6.93-6.44 (m, 3H), 5.36 (dd, J = 5.4, 12.4 Hz, 1H), 5.18 (d, J = 80.4 Hz, 1H), 4.83-4.72 (m, 1H), 4.21 (s, 1H), 3.83-3.72 (m, 2H), 3.63 (s, 4H), 3.59 (s, 1H), 3.56-3.50 (m, 1H), 3.45 (d, J = 10.0 Hz, 1H), 3.23 (s, 2H), 3.12-2.84 (m, 6H), 2.73-2.70 (m, 3H), 2.66-2.54 (m, 2H), 2.30-2.13 (m, 4H), 2.09-2.04 (m, 2H), 2.02 (d, J = 10.4 Hz, 1H), 2.00-1.89 (m, 5H), 1.86-1.75 (m, 3H), 1.74-1.56 (m, 2H), 1.24-1.04 (m, 2H) |
| I-73[b] | CHJ | AJB | 880.4 | 11.12 (s, 1H), 9.49 (d, J = 6.4 Hz, 1H), 8.78 (d, J = 7.6 Hz, 1H), 8.38 (d, J = 4.0 Hz, 1H), 8.25 (d, J = 5.6 Hz, 1H), 7.28-6.93 (m, 4H), 6.89-6.41 (m, 1H), 5.40 (dd, J = 5.2, 12.7 Hz, 1H), 5.30-5.05 (m, 1H), 4.76 (d, J = 18.0 Hz, 1H), 4.59-4.41 (m, 2H), 4.25-4.12 (m, 1H), 3.85-3.72 (m, 2H), 3.65 (s, 3H), 3.63-3.57 (m, 1H), 3.44 (d, J = 10.0 Hz, 1H), 3.15-3.08 (m, 1H), 2.95-2.77 (m, 3H), 2.74-2.59 (m, 2H), 2.20-2.08 (m, 3H), 2.07-1.94 (m, 6H), 1.88 (d, J = 12.4 Hz, 2H), 1.74 (q, J = 11.2 Hz, 3H), 1.67-1.52 (m, 2H), 1.46-1.33 (m, 1H), 1.12-0.97 (m, 2H), 0.94 (d, J = 6.4 Hz, 3H) |
| I-78 | CBA | AJB | 881.9 | 11.08 (s, 1H), 9.50 (d, J = 6.0 Hz, 1H), 8.78 (d, J = 7.6 Hz, 1H), 8.38 (d, J = 4.4 Hz, 1H), 8.25 (d, J = 5.6 Hz, 1H), 7.12-6.95 (m, 4H), 6.88-6.43 (m, 1H), 5.37-5.33 (m, 1H), 5.30-5.05 (m, 1H), 4.78-4.74 (m, 1H), 4.25-4.13 (m, 1H), 3.99-3.95 (m, 1H), 3.84-3.78 (m, 2H), 3.74-3.72 (m, 1H), 3.65-3.58 (m, 2H), 3.57 (s, 3H), 3.45-3.43 (m, 2H), 2.94-2.82 (m, 2H), 2.75-2.69 (m, 2H), 2.66-2.56 (m, 4H), 2.52-2.51 (m, 2H), 2.46 (s, 2H), 2.28-2.15 (m, 2H), 2.08-1.86 (m, 10H), 1.80-1.68 (m, 2H), 1.65-1.55 (m, 1H), 1.12-0.98 (m, 2H) |
| I-79 | CIX | AJB | 881.8 | 11.09 (s, 1H), 9.50 (d, J = 5.6 Hz, 1H), 8.78 (d, J = 7.6 Hz, 1H), 8.38 (d, J = 4.0 Hz, 1H), 8.25 (d, J = 5.6 Hz, 1H), 7.25-6.95 (m, |

TABLE 3-continued

Compounds synthesized via Method 2, with the reductive amination of the corresponding amines and aldehydes.

| I-#[a] | Amine | Aldehyde | LCMS (ES+) m/z (M + H)+ | $^1$HNMR (400 MHZ, DMSO-d6) δ |
|---|---|---|---|---|
| | | | | 4H), 6.89-6.43 (m, 1H), 5.38-5.33 (m, 1H), 5.29-5.05 (m, 1H), 4.78-4.74 (m, 1H), 4.22-4.09 (m, 2H), 3.84-3.77 (m, 2H), 3.74-3.72 (m, 1H), 3.65-3.56 (m, 2H), 3.51 (s, 3H), 3.45-3.42 (m, 2H), 2.94-2.83 (m, 1H), 2.77-2.57 (m, 5H), 2.43-2.27 (m, 6H), 2.19-2.09 (m, 4H), 2.08-1.84 (m, 8H), 1.79-1.67 (m, 2H), 1.57 (s, 1H), 1.07-0.98 (m, 2H) |
| I-82 | CFS | AJB | 882.8 | 11.09 (s, 1H), 9.50 (d, J = 6.0 Hz, 1H), 8.78 (d, J = 7.6 Hz, 1H), 8.38 (d, J = 4.4 Hz, 1H), 8.25 (d, J = 5.6 Hz, 1H), 7.27-6.95 (m, 4H), 6.90-6.41 (m, 1H), 5.36 (dd, J = 5.2, 12.4 Hz, 1H), 5.30-5.03 (m, 1H), 4.84-4.70 (m, 1H), 4.28-4.12 (m, 2H), 4.11-4.01 (m, 1H), 3.86-3.71 (m, 2H), 3.66-3.55 (m, 2H), 3.50 (s, 3H), 3.44 (d, J = 10.4 Hz, 1H), 2.96-2.82 (m, 1H), 2.76-2.61 (m, 4H), 2.46-2.35 (m, 3H), 2.15 (d, J = 6.0 Hz, 2H), 2.08-1.93 (m, 7H), 1.92-1.66 (m, 7H), 1.63-1.52 (m, 1H), 1.51-1.39 (m, 2H), 1.11-0.95 (m, 2H) |
| I-83 | BXR | CJI | 792.6 | 11.08 (s, 1H), 9.79 (s, 1H), 9.00 (s, 1H), 8.79 (d, J = 2.4 Hz, 1H), 8.30 (s, 1H), 8.24-8.16 (m, 1H), 8.04 (s, 1H), 7.08 (s, 1H), 7.01-6.92 (m, 2H), 6.90-6.82 (m, 1H), 5.34 (dd, J = 5.6, 12.4 Hz, 1H), 4.43-4.29 (m, 1H), 3.87 (s, 3H), 3.63 (s, 3H), 2.88 (s, 5H), 2.76-2.62 (m, 2H), 2.40-2.34 (m, 4H), 2.20-2.09 (m, 4H), 2.04-1.93 (m, 3H), 1.92-1.83 (m, 2H), 1.78-1.60 (m, 5H), 1.57-1.38 (m, 4H), 1.22-1.02 (m, 2H) |
| I-94 | BXR | BXG | 816 | 11.08 (s, 1H), 10.13 (s, 1H), 9.31 (d, J = 2.0 Hz, 1H), 9.22 (d, J = 2.0 Hz, 1H), 8.80 (d, J = 2.0 Hz, 1H), 8.41 (s, 1H), 7.66 (s, 1H), 7.00-6.93 (m, 2H), 6.90-6.83 (m, 1H), 5.34 (dd, J = 5.2, 12.4 Hz, 1H), 3.93 (s, 3H), 3.63 (s, 3H), 3.10-3.01 (m, 1H), 2.93-2.82 (m, 5H), 2.76-2.58 (m, 3H), 2.46 (s, 2H), 2.29-2.12 (m, 4H), 2.03-1.87 (m, 3H), 1.80-1.37 (m, 12H), 1.15-1.01 (m, 2H) |
| I-98 | CBD | ABC | 839.3 | 11.11 (s, 1H), 9.39 (s, 1H), 8.82 (d, J = 8.0 Hz, 1H), 8.37 (s, 1H), 8.28 (s, 1H), 7.24-6.94 (m, 4H), 6.90 (d, J = 8.0 Hz, 1H), 5.39 (dd, J = 5.6, 12.4 Hz, 1H), 4.25-4.11 (m, 1H), 3.79 (s, 4H), 3.72 (d, J = 4.4 Hz, 4H), 3.64 (s, 3H), 3.56 (s, 2H), 2.96-2.81 (m, 1H), 2.77-2.62 (m, 2H), 2.62-2.52 (m, 5H), 2.45-2.34 (m, 3H), 2.12 (d, J = 7.2 Hz, 2H), 2.08-1.97 (m, 3H), 1.88 (d, J = 12.0 Hz, 2H), 1.80-1.66 (m, 2H), 1.57 (s, 1H), 1.13-0.94 (m, 2H) |
| I-133 | CBL | CJH | 739.4 | 11.10 (s, 1 H) 10.80 (s, 1 H) 8.71 (s, 1 H) 8.49 (s, 1 H) 8.11-8.19 (m, 2 H) 7.85 (d, J = 7.2 Hz, 1 H) 7.14-7.21 (m, 2 H) 6.98-7.09 (m, 2 H) 5.36 (d, J = 4.8 Hz, 1 H) 4.42-4.59 (m, 2 H) 4.17-4.34 (m, 1 H) 4.00 (s, 3 H) 3.92 (d, J = 10.8 Hz, 1 H) 3.64-3.80 (m, 2 H) 3.53-3.61 (m, 1 H) 3.49 (s, 3 H) 2.81-2.93 (m, 1 H) 2.69-2.76 (m, 1 H) 2.56-2.65 (m, 4 H) 2.43 (s, 2 H) 2.10-2.19 (m, 1 H) 1.97 (d, J = 4.8 Hz, 1 H) 1.75-1.84 (m, 6 H) 1.51-1.59 (m, 1 H) 1.39-1.48 (m, 1 H) |
| I-159 | CJP | AJB | 911.5 | 11.09 (s, 1H), 9.50 (d, J = 6.2 Hz, 1H), 8.78 (d, J = 7.6 Hz, 1H), 8.39 (d, J = 4.4 Hz, 1H), 8.29-8.12 (m, 1H), 7.11 (d, J = 3.6 Hz, 1H), 6.99-6.93 (m, 1H), 6.88 (t, J = 8.8 Hz, 3H), 5.34-5.30 (m, 1H), 5.30-5.05 (m, 1H), 4.77-4.75 (m, 1H), 4.24-4.13 (m, 1H), 3.87-3.75 (m, 2H), 3.62 (s, 3H), 3.56-3.48 (m, 2H), 3.12-3.04 (m, 2H), 2.97-2.70 (m, 6H), 2.68-2.59 (m, 2H), 2.26-2.23 (m, 3H), 2.09-1.94 (m, 7H), 1.93-1.82 (m, 5H), 1.81-1.67 (m, 3H), 1.60-1.56 (m, 5H), 1.06-1.01 (m, 2H) |
| I-164 | CJT | AJB | 910.6 | 11.09 (s, 1H), 9.50 (d, J = 6.0 Hz, 1H), 8.78 (d, J = 7.6 Hz, 1H), 8.39 (d, J = 4.0 Hz, 1H), 8.26 (d, J = 5.6 Hz, 1H), 7.28-7.07 (m, 1H), 7.01-6.43 (m, 4H), 5.35 (d, J = 5.6, 12.8 Hz, 1H), 5.18 (d, J = 8.0 Hz, 1H), 4.77 (d, J = 20.0 Hz, 1H), 4.20 (t, J = 10.4 Hz, 1H), 3.88-3.64 (m, 3H), 3.62 (s, 3H), 3.61-3.42 (m, 2H), 3.12 (d, J = 8.8 Hz, 2H), 2.90-2.85 (m, 2H), 2.79-2.54 (m, 9H), 2.46-2.19 (m, 4H), 2.12-1.57 (m, 14H), 1.34 (d, J = 11.2 Hz, 2H), 1.21-0.95 (m, 2H) |
| I-189 | BAI | AJB | 813.4 | 11.08 (s, 1H), 9.50 (d, J = 6.0 Hz, 1H), 8.78 (d, J = 7.6 Hz, 1H), 8.39 (d, J = 4.4 Hz, 1H), 8.26 (d, J = 5.6 Hz, 1H), 7.26-7.00 (m, 1H), 7.00-6.88 (m, 3H), 6.87-6.43 (m, 1H), 5.35 (dd, J = 5.2, 12.8 Hz, 1H), 5.30-5.05 (m, 1H), 4.84-4.69 (m, 1H), 4.29-4.13 (m, 1H), 3.84-3.71 (m, 2H), 3.63 (s, 3H), 3.60 (s, 1H), 3.45 (d, J = 10.0 Hz, 1H), 3.08-2.82 (m, 7H), 2.69-2.62 (m, 2H), 2.62-2.57 (m, 2H), 2.30-2.17 (m, 2H), 2.11-1.88 (m, 8H), 1.84-1.71 (m, 2H), 1.70-1.60 (m, 1H), 1.18-1.01 (m, 2H) |
| I-200[c,d] | BAI | CJD | 799.2 | 11.14-11.03 (m, 1H), 9.50 (d, J = 6.4 Hz, 1H), 8.78 (d, J = 7.6 Hz, 1H), 8.40 (d, J = 4.4 Hz, 1H), 8.26 (d, J = 5.6 Hz, 1H), 7.27-6.99 (m, 1H), 6.99-6.88 (m, 3H), 6.87-6.43 (m, 1H), 5.35 (dd, J = 5.6, 12.4 Hz, 1H), 5.30-5.05 (m, 1H), 4.82-4.72 (m, 1H), |

TABLE 3-continued

Compounds synthesized via Method 2, with the reductive amination of the corresponding amines and aldehydes.

| I-#[a] | Amine | Aldehyde | LCMS (ES+) m/z (M + H)+ | $^1$HNMR (400 MHZ, DMSO-d6) δ |
|---|---|---|---|---|
| | | | | 4.27-4.16 (m, 1H), 3.84-3.71 (m, 2H), 3.65-3.58 (m, 4H), 3.46 (d, J = 3.2 Hz, 1H), 3.10-2.96 (m, 2H), 2.95-2.77 (m, 5H), 2.71 (d, J = 4.4 Hz, 1H), 2.68-2.62 (m, 2H), 2.59 (s, 1H), 2.43 (s, 1H), 2.15-2.07 (m, 2H), 2.04-1.90 (m, 5H), 1.87-1.73 (m, 2H), 1.54-1.41 (m, 2H) |
| I-201[e] | CIL | CJD | 882.5 | 11.08 (s, 1H), 9.52 (d, J = 6.0 Hz, 1H), 8.78 (d, J = 7.6 Hz, 1H), 8.40 (d, J = 3.6 Hz, 1H), 8.26 (d, J = 5.6 Hz, 1H), 7.29-7.00 (m, 1H), 7.00-6.87 (m, 3H), 6.87-6.43 (m, 1H), 5.39-5.31 (m, 1H), 5.30-5.06 (m, 1H), 4.77 (d, J = 15.6 Hz, 1H), 4.33 (s, 1H), 3.84-3.78 (m, 2H), 3.74 (d, J = 7.6 Hz, 1H), 3.62 (s, 3H), 3.60 (s, 1H), 3.05 (d, J = 10.4 Hz, 3H), 2.98-2.79 (m, 6H), 2.74-2.58 (m, 4H), 2.30 (s, 1H), 2.26-2.13 (m, 3H), 2.07-1.91 (m, 5H), 1.89-1.73 (m, 6H), 1.65-1.51 (m, 2H), 1.51-1.37 (m, 2H)) |
| I-203[e,f] | CIR | CJD | 882.3 | 11.08 (s, 1H), 9.50 (d, J = 6.0 Hz, 1H), 8.77 (dd, J = 2.0, 7.6 Hz, 1H), 8.38 (d, J = 4.8 Hz, 1H), 8.26 (d, J = 5.6 Hz, 1H), 7.25-6.98 (m, 1H), 6.97-6.41 (m, 4H), 5.35 (dd, J = 5.6, 12.4 Hz, 1H), 5.17 (d, J = 84.8 Hz, 1H), 4.77 (d, J = 15.4 Hz, 1H), 4.23-4.11 (m, 1H), 3.86-3.69 (m, 3H), 3.67-3.55 (m, 6H), 3.44 (d, J = 10.0 Hz, 2H), 3.12 (d, J = 10.8 Hz, 2H), 2.95-2.82 (m, 1H), 2.77-2.52 (m, 8H), 2.38-2.21 (m, 2H), 2.17-1.82 (m, 9H), 1.82-1.69 (m, 2H), 1.59 (d, J = 10.4 Hz, 2H), 1.48-1.31 (m, 2H) |
| I-258 | CKI | AJB | 816.6 | 10.49 (s, 1H), 9.49 (d, J = 6.4 Hz, 1H), 8.78 (d, J = 7.6 Hz, 1H), 8.38 (d, J = 4.4 Hz, 1H), 8.25 (d, J = 5.6 Hz, 1H), 7.62 (d, J = 2.0 Hz, 1H), 7.57 (d, J = 8.4 Hz, 1H), 7.43 (dd, J = 2.0, 8.4 Hz, 1H), 7.25-6.95 (m, 1H), 6.89-6.43 (m, 1H), 5.30-5.06 (m, 1H), 4.81-4.72 (m, 1H), 4.23-4.12 (m, 1H), 3.85-3.75 (m, 2H), 3.75-3.70 (m, 1H), 3.70-3.61 (m, 1H), 3.61-3.56 (m, 2H), 3.54 (s, 2H), 3.52-3.39 (m, 2H), 2.76-2.70 (m, 2H), 2.56 (d, J = 2.8 Hz, 5H), 2.27-2.11 (m, 2H), 2.09-1.96 (m, 4H), 1.96-1.84 (m, 3H), 1.79-1.67 (m, 2H), 1.66-1.53 (m, 1H), 1.12-0.97 (m, 2H) |
| I-337 | CBD | CKF | 851.3 | 11.10 (s, 1H), 9.52 (s, 1H), 8.86 (d, J = 7.6 Hz, 1H), 8.37 (s, 1H), 8.30 (s, 1H), 7.23-6.91 (m, 4H), 6.74 (d, J = 8.0 Hz, 1H), 5.39 (dd, J = 5.2, 12.8 Hz, 1H), 4.82-4.65 (m, 2H), 4.25-4.10 (m, 1H), 4.24-4.11 (m, 1H), 3.87-3.76 (m, 3H), 3.65 (s, 3H), 3.56 (s, 2H), 3.24-3.17 (m, 2H), 2.94-2.82 (m, 1H), 2.78-2.68 (m, 1H), 2.67-2.59 (m, 2H), 2.58-2.52 (m, 3H), 2.47-2.33 (m, 3H), 2.16-2.09 (m, 2H), 2.07-1.98 (m, 3H), 1.94-1.83 (m, 3H), 1.80-1.67 (m, 2H), 1.64-1.51 (m, 1H), 1.11-0.96 (m, 2H) |
| I-340[e,g] | CBD | CJD | 837.1 | 11.11 (s, 1H), 9.50 (d, J = 6.4 Hz, 1H), 8.78 (d, J = 7.6 Hz, 1H), 8.38 (d, J = 2.4 Hz, 1H), 8.24 (d, J = 5.6 Hz, 1H), 7.36-6.95 (m, 4H), 6.89-6.40 (m, 1H), 5.45-5.32 (dd, J = 5.2, 12.4 Hz, 1H), 5.31-5.04 (m, 1H), 4.77 (d, J = 17.2 Hz, 1H), 4.30 (d, J = 1.2 Hz, 1H), 3.83-3.73 (m, 2H), 3.65 (s, 3H), 3.62-3.58 (m, 2H), 3.55 (s, 2H), 3.43 (s, 2H), 2.94-2.83 (m, 1H), 2.75-2.63 (m, 2H), 2.59 (s, 6H), 2.24-2.08 (m, 3H), 2.06-1.93 (m, 3H), 1.93-1.82 (m, 2H), 1.80-1.70 (m, 2H), 1.63-1.47 (m, 2H) |
| I-343 | COP | AJB | 877.4 | 11.12 (s, 1H), 9.50 (d, J = 6.0 Hz, 1H), 8.78 (d, J = 7.6 Hz, 1H), 8.38 (d, J = 4.4 Hz, 1H), 8.25 (d, J = 5.6 Hz, 1H), 7.25-6.92 (m, 4H), 6.88-6.41 (m, 1H), 5.45-5.34 (dd, J = 5.6, 12.4 Hz, 1H), 5.31-5.04 (m, 1H), 4.76 (d, J = 18.4 Hz, 1H), 4.23-4.11 (m, 1H), 3.84-3.71 (m, 2H), 3.65 (s, 3H), 3.62-3.56 (m, 2H), 3.44 (d, J = 10.4 Hz, 1H), 3.41-3.39 (m, 2H), 3.28 (s, 2H), 2.96-2.82 (m, 1H), 2.77-2.66 (m, 1H), 2.57 (d, J = 8.0 Hz, 2H), 2.15 (d, J = 9.6 Hz, 2H), 2.09 (d, J = 7.2 Hz, 2H), 2.07-1.93 (m, 5H), 1.92-1.80 (m, 4H), 1.78-1.66 (m, 4H), 1.59-1.44 (m, 1H), 1.09-0.95 (m, 2H) |
| I-348 | CKL | AJB | 893.5 | 11.11 (s, 1H), 9.49 (d, J = 6.0 Hz, 1H), 8.78 (d, J = 7.6 Hz, 1H), 8.37 (d, J = 4.4 Hz, 1H), 8.25 (d, J = 5.6 Hz, 1H), 7.27-6.92 (m, 4H), 6.66 (d, J = 8.0, 1H), 5.39 (d, J = 5.2, 1H), 5.17 (d, J = 82.8 Hz, 1H), 4.84-4.69 (m, 1H), 4.25-4.07 (m, 1H), 3.86-3.79 (m, 3H), 3.74 (s, 1H), 3.68 (s, 3H), 3.65-3.58 (m, 2H), 3.44 (d, J = 10.0 Hz, 2H), 2.96-2.83 (m, 3H), 2.76-2.68 (m, 2H), 2.66-2.53 (m, 8H), 2.07-1.87 (m, 7H), 1.78-1.66 (m, 2H), 1.53-1.39 (m, 1H), 1.12-0.99 (m, 2H) |

TABLE 3-continued

Compounds synthesized via Method 2, with the reductive amination of the corresponding amines and aldehydes.

| I-#[a] | Amine | Aldehyde | LCMS (ES+) m/z (M + H)+ | $^1$HNMR (400 MHZ, DMSO-d6) δ |
|---|---|---|---|---|
| I-349 | COR | AJB | 893.3 | 11.12 (s, 1H), 9.50 (d, J = 6.0 Hz, 1H), 8.78 (d, J = 7.6 Hz, 1H), 8.38 (d, J = 4.4 Hz, 1H), 8.25 (d, J = 5.6 Hz, 1H), 7.29-7.04 (m, 3H), 7.03-6.96 (m, 1H), 6.90-6.41 (m, 1H), 5.39 (dd, J = 5.2, 12.4 Hz, 1H), 5.31-5.03 (m, 1H), 4.77 (d, J = 17.6 Hz, 1H), 4.26-4.13 (m, 1H), 3.92 (s, 2H), 3.85 (d, J = 9.6 Hz, 2H), 3.80 (s, 1H), 3.76-3.65 (m, 3H), 3.63 (s, 3H), 3.59 (s, 1H), 3.44 (d, J = 9.6 Hz, 1H), 2.89 (s, 3H), 2.80-2.69 (m, 3H), 2.66-2.56 (m, 3H), 2.15 (d, J = 5.6 Hz, 2H), 2.03 (t, J = 10.8 Hz, 4H), 1.98-1.90 (m, 3H), 1.81-1.71 (m, 2H), 1.63 (s, 1H), 1.13-0.98 (m, 2H) |
| I-362 | CGR | CAG | 909.3 | 11.09 (s, 1H), 9.50 (d, J = 6.4 Hz, 1H), 8.78 (d, J = 8.0 Hz, 1H), 8.38 (d, J = 4.4 Hz, 1H), 8.25 (d, J = 5.6 Hz, 1H), 7.26-6.91 (m, 4H), 6.90-6.40 (m, 1H), 5.36 (dd, J = 5.6, 12.4 Hz, 1H), 5.30-5.01 (m, 1H), 4.85-4.70 (m, 1H), 4.25-4.11 (m, 1H), 3.80 (s, 1H), 3.74 (d, J = 7.6 Hz, 1H), 3.65-3.59 (m, 2H), 3.57 (s, 3H), 3.17 (s, 1H), 2.93-2.85 (m, 1H), 2.74-2.62 (m, 2H), 2.41-2.30 (m, 6H), 2.12 (t, J = 7.6 Hz, 4H), 2.09-1.94 (m, 6H), 1.93-1.84 (m, 6H), 1.83-1.66 (m, 3H), 1.65-1.47 (m, 4H), 1.15-0.95 (m, 4H) |
| I-370 | BXN | CKR | 860.4 | 11.12 (s, 1H), 9.61 (d, J = 4.8 Hz, 1H), 8.98 (d, J = 2.8 Hz, 1H), 8.81 (dd, J = 1.6, 7.6 Hz, 1H), 8.30 (d, J = 5.6 Hz, 1H), 7.80 (d, J = 8.0 Hz, 2H), 7.46 (d, J = 8.0 Hz, 2H), 7.44-7.20 (m, 1H), 7.18 (s, 2H), 7.06-6.99 (m, 1H), 6.68 (dd, J = 8.0, 165.6 Hz, 1H), 5.40 (dd, J = 5.2, 12.4 Hz, 1H), 5.20 (d, J = 85.6 Hz, 1H), 4.79 (d, J = 13.2 Hz, 1H), 4.48 (s, 2H), 3.83 (s, 2H), 3.75 (d, J = 7.6 Hz, 1H), 3.64 (s, 5H), 2.96-2.80 (m, 2H), 2.77-2.60 (m, 5H), 2.24-2.14 (m, 1H), 2.12-1.95 (m, 4H), 1.94-1.86 (m, 2H), 1.59-1.46 (m, 2H) |
| I-374 | COT | AJB | 886.2 | 11.18-11.05 (m, 1H), 9.50 (d, J = 6.0 Hz, 1H), 8.78 (d, J = 7.6 Hz, 1H), 8.38 (d, J = 4.0 Hz, 1H), 8.25 (d, J = 5.6 Hz, 1H), 7.25-6.95 (m, 4H), 6.89-6.41 (m, 1H), 5.44-5.34 (m, 1H), 5.30-5.05 (m, 1H), 4.77 (d, J = 17.2 Hz, 1H), 4.26-4.08 (m, 1H), 3.83-3.73 (m, 2H), 3.63 (s, 3H), 3.61-3.56 (m, 1H), 3.45 (d, J = 10.4 Hz, 1H), 3.10-3.02 (m, 1H), 2.93-2.79 (m, 3H), 2.72-2.66 (m, 1H), 2.64 (d, J = 5.2 Hz, 1H), 2.60 (s, 1H), 2.56 (s, 1H), 2.22 (d, J = 5.6 Hz, 2H), 2.13-1.94 (m, 8H), 1.92-1.84 (m, 2H), 1.80-1.70 (m, 2H), 1.66-1.47 (m, 2H), 1.13-0.97 (m, 2H) |
| I-383 | CKT | AJB | 828.4 | 11.10 (s, 1H), 9.50 (d, J = 6.4 Hz, 1H), 8.79 (d, J = 7.6 Hz, 1H), 8.38 (d, J = 4.0 Hz, 1H), 8.30-8.20 (m, 1H), 7.26-6.90 (m, 4H), 6.90-6.42 (m, 1H), 5.41-5.31 (m, 1H), 5.30-5.04 (m, 1H), 4.84-4.69 (m, 1H), 4.25-4.10 (m, 1H), 3.85-3.72 (m, 3H), 3.63 (d, J = 9.2 Hz, 2H), 3.59 (s, 1H), 3.57 (s, 3H), 3.44 (d, J = 11.2 Hz, 2H), 3.16-3.07 (m, 1H), 3.00-2.94 (m, 1H), 2.87-2.75 (m, 2H), 2.67-2.63 (m, 2H), 2.13 (d, J = 7.2 Hz, 2H), 2.06-1.97 (m, 5H), 1.93 (d, J = 10.8 Hz, 2H), 1.90-1.84 (m, 2H), 1.80-1.67 (m, 2H), 1.64-1.53 (m, 1H), 1.12-0.95 (m, 2H) |
| I-385 | CKV | AJB | 842.3 | 11.09 (s, 1H), 9.50 (d, J = 6.4 Hz, 1H), 8.78 (d, J = 7.6 Hz, 1H), 8.38 (d, J = 4.4 Hz, 1H), 8.25 (d, J = 5.6 Hz, 1H), 7.26-6.93 (m, 3H), 6.91-6.39 (m, 2H), 5.44-5.31 (m, 1H), 5.17 (d, J = 81.2 Hz, 1H), 4.76 (d, J = 17.6 Hz, 1H), 4.26-4.11 (m, 1H), 3.85-3.79 (m, 2H), 3.79-3.61 (m, 1H), 3.59 (s, 1H), 3.56 (s, 3H), 3.54-3.48 (m, 1H), 3.48-3.41 (m, 2H), 3.12-3.01 (m, 1H), 2.95-2.83 (m, 2H), 2.79-2.68 (m, 2H), 2.68-2.61 (m, 2H), 2.11 (d, J = 7.2 Hz, 2H), 2.07-1.93 (m, 6H), 1.89 (d, J = 11.6 Hz, 2H), 1.80-1.66 (m, 5H), 1.64-1.52 (m, 1H), 1.12-0.95 (m, 2H) |
| I-400 | CKW | CKR | 846.9 | 11.07 (s, 1H), 9.61 (d, J = 4.4 Hz, 1H), 8.98 (d, J = 3.2 Hz, 1H), 8.81 (d, J = 7.6 Hz, 1H), 8.30 (d, J = 5.2 Hz, 1H), 7.80(d, J = 8.4 Hz, 2H), 7.46 (d, J = 8.4 Hz, 1H), 7.44-7.15 (m, 1H), 6.98-6.45 (m, 4H), 5.36-5.08 (m, 2H), 4.79 (d, J = 13.2 Hz, 1H), 3.84 (s, 1H), 3.75 (d, J = 7.6 Hz, 1H), 3.67-3.62 (m, 2H), 3.57 (d, J = 8.0 Hz, 6H), 3.52-3.45 (m, 3H), 2.95-2.81 (m, 1H), 2.74-2.57 (m, 4H), 2.37 (s, 3H), 2.09-1.91 (m, 3H), 1.79 (t, J = 4.4 Hz, 4H) |
| I-421[c,g] | CBD | CJD | 837.3 | 11.12 (s, 1H), 9.49 (d, J = 6.0 Hz, 1H), 8.78 (d, J = 7.6 Hz, 1H), 8.38 (d, J = 4.4 Hz, 1H), 8.25 (d, J = 5.6 Hz, 1H), 7.26-6.96 (m, 4H), 6.89-6.40 (m, 1H), 5.48-5.34 (dd, J = 5.6, 12.4 Hz, 1H), 5.31-5.03 (m, 1H), 4.76 (d, J = 16.0 Hz, 1H), 4.18 (t, J = 10.4 Hz, 1H), 3.83-3.72 (m, 2H), 3.64 (s, 3H), 3.63-3.57 (m, 2H), 3.55 (s, 2H), 3.44 (d, J = 10.4 Hz, 2H), 2.94-2.84 (m, 1H), 2.78-2.63 (m, 2H), 2.56 (s, 6H), 2.40-2.32 (m, 1H), 2.08-2.00 (m, 3H), 1.98 (s, 1H), 1.96-1.83 (m, 3H), 1.83-1.69 (m, 2H), 1.48-1.33 (m, 2H) |
| I-425[e] | CIL | CJD | 882.5 | 11.09 (s, 1H), 9.50 (d, J = 5.6 Hz, 1H), 8.78 (d, J = 7.6 Hz, 1H), 8.38 (d, J = 4.4 Hz, 1H), 8.26 (d, J = 5.6 Hz, 1H), 7.25-7.00 (m, |

TABLE 3-continued

Compounds synthesized via Method 2, with the reductive amination of the corresponding amines and aldehydes.

| I-#[a] | Amine | Aldehyde | LCMS (ES+) m/z (M + H)+ | 1HNMR (400 MHZ, DMSO-d6) δ |
|---|---|---|---|---|
| | | | | 1H), 6.98-6.87 (m, 3H), 6.86-6.44 (m, 1H), 5.39-5.31 (m, 1H), 5.29-5.05 (m, 1H), 4.77 (d, J = 16.4 Hz, 1H), 4.23-4.13 (m, 1H), 3.84-3.79 (m, 2H), 3.74 (d, J = 7.6 Hz, 1H), 3.62 (s, 3H), 3.59 (s, 1H), 2.91 (d, J = 9.6 Hz, 5H), 2.72-2.58 (m, 5H), 2.43-2.45 (m, 2H), 2.29-2.16 (m, 4H), 2.10-2.05 (m, 3H), 1.98-1.97 (m, 3H), 1.90-1.85 (m, 2H), 1.84-1.74 (m, 4H), 1.49-1.36 (m, 4H |
| I-484 | CLC | CLU | 823.3 | 11.09 (s, 1H), 9.48 (s, 1H), 8.75 (d, J = 7.6 Hz, 1H), 8.39 (s, 1H), 8.25 (s, 1H), 7.25-6.91 (m, 4H), 6.75 (d, J = 8.0 Hz, 1H), 5.36 (dd, J = 5.2, 12.5 Hz, 1H), 4.35-4.05 (m, 1H), 3.62 (s, 3H), 3.23 (s, 8H), 3.17 (s, 2H), 3.06 (dd, J = 5.6, 11.3 Hz, 1H), 2.89 (t, J = 12.0 Hz, 3H), 2.75-2.62 (m, 2H), 2.43 (s, 3H), 2.10-1.97 (m, 5H), 1.91-1.72 (m, 4H), 1.65-1.49 (m, 1H), 1.13-0.95 (m, 2H) |
| I-485 | CLC | BIK | 780.3 | 11.10 (s, 1H), 10.04 (s, 1H), 9.38 (dd, J = 1.6, 7.2 Hz, 1H), 8.87 (dd, J = 1.6, 4.4 Hz, 1H), 8.70 (s, 1H), 8.38 (s, 1H), 7.32 (dd, J = 4.4, 6.8 Hz, 1H), 7.29-7.02 (m, 1H), 7.01-6.89 (m, 3H), 5.43-5.29 (m, 1H), 4.29-4.16 (m, 1H), 3.62 (s, 3H), 3.24 (s, 4H), 3.10-3.00 (m, 1H), 2.94-2.83 (m, 2H), 2.76-2.61 (m, 2H), 2.44 (s, 3H), 2.11-1.97 (m, 5H), 1.95-1.67 (m, 5H), 1.63-1.51 (m, 1H), 1.12-0.97 (m, 2H) |
| I-502 | CLC | AJB | 877.1 | 11.10 (s, 1H), 9.50 (d, J = 6.0 Hz, 1H), 8.79 (d, J = 7.6 Hz, 1H), 8.39 (d, J = 4.4 Hz, 1H), 8.26 (d, J = 5.6 Hz, 1H), 7.03 (s, 1H), 7.02-6.97 (m, 2H), 6.96-6.92 (m, 1H), 6.89-6.43 (m, 1H), 5.43-5.32 (m, 1H), 5.31-5.05 (m, 1H), 4.84-4.69 (m, 1H), 4.28-4.14 (m, 1H), 3.84-3.72 (m, 1H), 3.65-3.58 (m, 4H), 3.45 (d, J = 10.0 Hz, 1H), 3.24 (s, 1H), 3.18 (d, J = 10.4 Hz, 2H), 2.95-2.84 (m, 2H), 2.71 (d, J = 2.4 Hz, 1H), 2.68-2.63 (m, 2H), 2.59 (s, 1H), 2.44 (s, 3H), 2.35-2.31 (m, 1H), 2.11-1.96 (m, 7H), 1.96-1.87 (m, 2H), 1.85-1.70 (m, 3H), 1.63-1.51 (m, 1H), 1.11-0.97 (m, 2H) |
| I-545 | CLX | ALU | 811.3 | 11.10 (s, 1H), 10.49 (s, 1H), 8.61-8.52 (m, 1H), 8.51-8.36 (m, 3H), 8.23 (dd, J = 0.8, 7.6 Hz, 1H), 7.99 (s, 1H), 7.40-7.21 (m, 1H), 7.20-6.95 (m, 3H), 5.39 (dd, J = 5.2, 12.4 Hz, 1H), 4.92-4.45 (m, 2H), 3.63-3.53 (m, 3H), 3.49-3.36 (m, 2H), 2.99-2.81 (m, 2H), 2.75-2.63 (m, 2H), 2.36-2.29 (m, 2H), 2.27-2.08 (m, 4H), 2.06-1.89 (m, 6H), 1.88-1.64 (m, 2H), 1.28-1.06 (m, 2H) |
| I-547 | CLX | ATJ | 791.4 | 11.10 (s, 1H), 10.50 (s, 1H), 8.69 (s, 1H), 8.48-8.38 (m, 2H), 8.34 (s, 1H), 8.24-8.20 (m, 1H), 7.20-7.15 (m, 1H), 7.09-6.99 (m, 2H), 5.39 (dd, J = 5.2, 12.8 Hz, 1H), 4.87-4.65 (m, 1H), 4.45-4.32 (m, 1H), 3.99 (s, 3H), 3.58 (s, 3H), 3.48-3.40 (m, 1H), 2.94-2.84 (m, 2H), 2.74-2.63 (m, 2H), 2.60 (s, 1H), 2.34-2.29 (m, 2H), 2.18-2.10 (m, 4H), 2.01-1.87 (m, 6H), 1.85-1.63 (m, 2H), 1.14 (d, J = 12.4 Hz, 2H) |
| I-548 | CLX | BXI | 786.4 | 11.10 (s, 1H), 10.64 (s, 1H), 8.63 (s, 1H), 8.49-8.35 (m, 3H), 8.29-8.19 (m, 2H), 7.21-6.95 (m, 3H), 5.38 (dd, J = 5.2, 12.7 Hz, 1H), 4.92-4.50 (m, 2H), 3.65-3.53 (m, 3H), 3.51-3.34 (m, 2H), 2.99-2.81 (m, 2H), 2.80-2.61 (m, 3H), 2.37-2.27 (m, 2H), 2.25-2.08 (m, 4H), 2.05-1.72 (m, 7H), 1.28-1.00 (m, 2H) |
| I-549 | CLX | BRR | 762.2 | 11.13-10.89 (m, 1H), 10.20 (s, 1H), 9.06 (s, 1H), 8.63-8.58 (m, 1H), 8.51-8.46 (m, 2H), 8.45-8.38 (m, 1H), 8.23 (dd, J = 0.8, 7.6 Hz, 1H), 7.25-6.80 (m, 4H), 5.39 (dd, J = 5.2, 12.4 Hz, 1H), 4.87-4.65 (m, 1H), 4.63-4.54 (m, 1H), 3.64-3.52 (m, 3H), 3.51 (s, 2H), 2.95-2.83 (m, 2H), 2.75-2.63 (m, 2H), 2.33-2.30 (m, 2H), 2.24-2.13 (m, 4H), 2.02-1.97 (m, 5H), 1.85-1.68 (m, 2H), 1.21-1.10 (m, 2H) |
| I-550 | CLX | BSC | 775.3 | 11.10 (s, 1H), 10.13 (s, 1H), 8.47-8.34 (m, 3H), 8.26-8.15 (m, 2H), 7.52 (s, 1H), 7.17 (d, J = 8.0 Hz, 1H), 7.11-6.95 (m, 2H), 5.39 (dd, J = 5.2, 12.8 Hz, 1H), 4.91-4.61 (m, 1H), 4.50-4.36 (m, 1H), 3.58 (s, 3H), 3.49-3.40 (m, 1H), 2.96-2.83 (m, 2H), 2.77-2.63 (m, 2H), 2.60 (s, 1H), 2.41 (s, 3H), 2.32 (dd, J = 2.0, 3.6 Hz, 2H), 2.21-2.10 (m, 4H), 2.05-1.90 (m, 6H), 1.86-1.78 (m, 1H), 1.75-1.64 (m, 1H), 1.24-1.08 (m, 2H) |
| I-553 | CLX | BRP | 761.3 | 11.11 (s, 1H), 10.37 (s, 1H), 8.44-8.33 (m, 3H), 8.30 (d, J = 1.2 Hz, 1H), 8.19-8.15 (m, 1H), 7.64-7.60 (m, 1H), 7.58-7.53 (m, 1H), 7.18 (m, J = 1.2, 7.8 Hz, 1H), 7.09-7.01 (m, 2H), 5.39 (m, J = 5.6, 12 Hz, 1H), 4.90-4.66 (m, 1H), 4.50-4.42 (m, 1H), 3.60-3.56 (m, 3H), 3.19-3.07 (m, 1H), 2.97-2.84 (m, 2H), 2.75-2.59 (m, 3H), 2.37-2.28 (m, 2H), 2.21-2.10 (m, 4H), 2.05-1.91 (m, 6H), 1.87-1.66 (m, 2H), 1.25-1.07 (m, 2H) |
| I-555 | COY | BRP | 790.4 | 11.11 (m, 1H), 10.37 (s, 1H), 8.43-8.34 (m, 3H), 8.30 (s, 1H), 8.18 (m, 7.4 Hz, 1H), 7.65-7.60 (m, 1H), 7.58-7.54 (m, 1H), 7.02-6.97 (m, 2H), 6.92 (m, 1H), 5.37 (m, 12.6 Hz, 1H), 4.93- |

TABLE 3-continued

Compounds synthesized via Method 2, with the reductive amination of the corresponding amines and aldehydes.

| I-#[a] | Amine | Aldehyde | LCMS (ES+) m/z (M + H)+ | 1HNMR (400 MHZ, DMSO-d6) δ |
|---|---|---|---|---|
| | | | | 4.71 (m, 1H), 4.50-4.42 (m, 1H), 3.62 (s, 3H), 3.10 (d, J = 11.2 Hz, 1H), 2.92-2.84 (m, 2H), 2.79-2.62 (m, 5H), 2.39 (s, 4H), 2.18 (m, 2H), 2.08-1.91 (m, 6H), 1.82-1.76 (m, 1H), 1.76-1.68 (m, 1H), 1.66-1.59 (m, 1H), 1.20-1.11 (m, 2H) |
| I-562 | CLZ | BHI | 792.5 | 11.08 (s, 1H), 10.04 (s, 1H), 9.38 (dd, J = 1.6, 7.2 Hz, 1H), 8.87 (dd, J = 1.6, 4.4 Hz, 1H), 8.70 (s, 1H), 8.38 (s, 1H), 7.32 (dd, J = 4.4, 6.8 Hz, 1H), 7.28 (s, 1H), 6.89 (d, J = 8.4 Hz, 1H), 6.69 (d, J = 8.8 Hz, 1H), 5.38-5.20 (m, 1H), 4.88-4.59 (m, 1H), 4.28-4.14 (m, 1H), 3.79 (s, 3H), 3.56 (s, 3H), 2.91-2.84 (m, 2H), 2.70-2.62 (m, 5H), 2.43-2.39 (m, 2H), 2.38-2.33 (m, 3H), 2.10-2.03 (m, 2H), 2.01-1.90 (m, 3H), 1.83-1.50 (m, 6H), 1.13-0.99 (m, 2H) |
| I-576 | CPB | AJB | 881.4 | 11.11-11.05 (m, 1H), 9.49 (d, J = 5.6 Hz, 1H), 8.77 (d, J = 8.0 Hz, 1H), 8.37 (d, J = 3.6 Hz, 1H), 8.25 (d, J = 5.2 Hz, 1H), 6.97 (s, 3H), 6.93-6.40 (m, 3H), 5.40-5.32 (m, 1H), 5.29-5.05 (m, 1H), 4.76 (d, J = 16.8 Hz, 1H), 4.20-4.12 (m, 1H), 3.83-3.77 (m, 2H), 3.59 (s, 4H), 3.55 (s, 3H), 3.10 (d, J = 8.0 Hz, 4H), 2.76-2.59 (m, 4H), 2.12 (d, J = 6.0 Hz, 3H), 2.06-1.95 (m, 8H), 1.91-1.81 (m, 5H), 1.79-1.67 (m, 3H), 1.60-1.53 (m, 1H), 1.07-0.98 (m, 2H) |
| I-578 | CQD | AJB | 895.6 | 11.0 (s, 1H), 9.50 (m, J = 6.0 Hz, 1H), 8.77 (d, J = 7.6 Hz, 1H), 8.38 (d, J = 4.4 Hz, 1H), 8.25 (m, J = 5.6 Hz, 1H), 7.23 (m, J = 7.6 Hz, 1H), 7.14-7.08 (m, 1H), 7.08-7.03 (m, 1H), 7.03-6.98 (m, 1H), 6.87-6.43 (m, 1H), 6.45 (d, J = 7.6 Hz, 1H), 5.36 (m, J = 5.6, 12.8 Hz, 1H), 5.17 (m, J = 84.8 Hz, 1H), 4.76 (m, J = 18.4 Hz, 1H), 4.25-4.13 (m, 1H), 4.12-4.03 (m, 1H), 3.87-3.77 (m, 2H), 3.76-3.69 (m, 1H), 3.65-3.59 (m, 2H), 3.50 (s, 3H), 2.92-2.83 (m, 1H), 2.78-2.69 (m, 1H), 2.64 (m, J = 5.2 Hz, 2H), 2.61 (m, 2H), 2.47-2.37 (m, 3H), 2.31 (m, 5H), 2.14 (m, J = 6.8 Hz, 2H), 2.06-2.00 (m, 3H), 1.98 (m, 1H), 1.95-1.85 (m, 1H), 1.79-1.69 (m, 2H), 1.62-1.54 (m, 1H), 1.15-0.95 (m, 2H) |
| I-580 | CPU | AJB | 897.4 | 11.08 (s, 1H), 9.50 (d, J = 5.6 Hz, 1H), 8.78 (d, J = 7.6 Hz, 1H), 8.38 (d, J = 3.6 Hz, 1H), 8.25 (d, J = 5.2 Hz, 1H), 7.27-7.09 (m, 2H), 7.05 (t, J = 7.6 Hz, 1H), 6.97 (d, J = 7.2 Hz, 1H), 6.89-6.42 (m, 1H), 5.36 (dd, J = 5.2, 11.6 Hz, 1H), 5.28 (s, 1H), 4.77 (d, J = 18.8 Hz, 1H), 4.18 (t, J = 10.8 Hz, 1H), 3.80 (s, 2H), 3.74 (s, 1H), 3.59 (s, 3H), 3.55 (s, 3H), 3.45 (s, 1H), 2.95-2.81 (m, 2H), 2.73-2.59 (m, 8H), 2.43 (d, J = 0.8 Hz, 2H), 2.31 (d, J = 13.2 Hz, 1H), 2.24-2.13 (m, 4H), 2.07-1.94 (m, 5H), 1.90 (d, J = 12.8 Hz, 2H), 1.80-1.68 (m, 2H), 1.60 (d, J = 7.2 Hz, 1H), 1.11-0.97 (m, 2H) |
| I-581 | CNO | AJB | 901.4 | 11.07 (s, 1H), 9.50 (d, J = 6.0 Hz, 1H), 8.84-8.23 (m, 2H), 7.26-6.85 (m, 2H), 6.81-6.43 (m, 2H), 5.39-5.05 (m, 2H), 4.82-4.71 (m, 1H), 4.69-4.49 (m, 1H), 4.28-4.14 (m, 1H), 4.13-3.99 (m, 2H), 3.84-3.72 (m, 2H), 3.69-3.55 (m, 6H), 3.47-3.37 (m, 4H), 3.29-2.90 (m, 3H), 2.90-2.83 (m, 1H), 2.76-2.54 (m, 6H), 2.23-2.00 (m, 5H), 2.00-1.83 (m, 4H), 1.82-1.48 (m, 3H), 1.30-0.94 (m, 2H) |
| I-585 | CNQ | AJB | 915.4 | 11.07 (s, 1H), 9.50 (d, J = 6.4 Hz, 1H), 8.78 (d, J = 7.2 Hz, 1H), 8.38 (d, J = 4.4 Hz, 1H), 8.27-8.20 (m, 1H), 7.26-6.91 (m, 2H), 6.89-6.41 (m, 3H), 5.36-5.03 (m, 2H), 4.89-4.65 (m, 2H), 4.23-4.10 (m, 1H), 3.90 (t, J = 7.2 Hz, 2H), 3.84-3.65 (m, 5H), 3.65-3.58 (m, 4H), 3.57 (s, 3H), 2.93-2.55 (m, 7H), 2.14 (d, J = 7.2 Hz, 3H), 2.08-1.93 (m, 5H), 1.93-1.83 (m, 2H), 1.81-1.62 (m, 4H), 1.61-1.47 (m, 1H), 1.10-0.95 (m, 2H) |
| I-587 | CNS | AJB | 915.4 | 11.07 (s, 1H), 9.50 (d, J = 6.4 Hz, 1H), 8.78 (d, J = 7.6 Hz, 1H), 8.38 (d, J = 4.4 Hz, 1H), 8.25 (d, J = 5.6 Hz, 1H), 7.28-6.92 (m, 2H), 6.89-6.43 (m, 3H), 5.32 (dd, J = 5.2, 12.8 Hz, 1H), 5.28-5.06 (m, 1H), 4.82-4.70 (m, 1H), 4.52-4.32 (m, 1H), 4.22-4.12 (m, 1H), 3.89 (t, J = 7.2 Hz, 2H), 3.84-3.71 (m, 4H), 3.65-3.58 (m, 2H), 3.57 (s, 4H), 3.47-3.35 (m, 2H), 3.03-2.95 (m, 1H), 2.93-2.76 (m, 2H), 2.73-2.65 (m, 2H), 2.64-2.57 (m, 1H), 2.16 (d, J = 7.2 Hz, 2H), 2.10-1.94 (m, 8H), 1.91-1.84 (m, 2H), 1.81-1.68 (m, 2H), 1.62-1.51 (m, 1H), 1.47-1.35 (m, 1H), 1.09-0.96 (m, 2H) |
| I-588 | CNU | AJB | 915.4 | 11.07 (s, 1H), 9.50 (d, J = 6.0 Hz, 1H), 8.78 (d, J = 7.4 Hz, 1H), 8.38 (d, J = 4.0 Hz, 1H), 8.25 (d, J = 5.6 Hz, 1H), 7.26-6.41 (m, 5H), 5.32 (dd, J = 5.2, 12.4 Hz, 1H), 5.28 (s, 1H), 4.86-4.67 (m, 2H), 4.22-4.11 (m, 1H), 3.90 (t, J = 6.8 Hz, 2H), 3.85-3.77 (m, 2H), 3.76-3.69 (m, 2H), 3.66-3.61 (m, 1H), 3.60-3.58 (m, 2H), 3.57 (s, 3H), 3.47-3.42 (m, 1H), 2.94-2.86 (m, 1H), 2.85-2.76 (m, 2H), 2.75-2.64 (m, 2H), 2.62-2.53 (m, 3H), 2.13 (d, J = 6.8 |

TABLE 3-continued

Compounds synthesized via Method 2, with the reductive amination of the corresponding amines and aldehydes.

| I-#[a] | Amine | Aldehyde | LCMS (ES+) m/z (M + H)+ | 1HNMR (400 MHZ, DMSO-d6) δ |
|---|---|---|---|---|
| | | | | Hz, 3H), 2.12-1.90 (m, 5H), 1.87 (d, J = 12.4 Hz, 2H), 1.83-1.62 (m, 4H), 1.60-1.50 (m, 1H), 1.08-0.96 (m, 2H) |
| I-597 | CNB | AJB | 868.4 | 11.08 (s, 1H), 9.49 (d, J = 6.0 Hz, 1H), 8.78 (d, J = 7.6 Hz, 1H), 8.38-8.24 (m, 2H), 7.25-6.95 (m, 4H), 6.88-6.43 (m, 1H), 5.35 (dd, J = 5.2, 12.8 Hz, 1H), 5.29-5.05 (m, 1H), 4.77 (d, J = 18.0 Hz, 1H), 4.21-4.10 (m, 1H), 4.06-3.92 (m, 2H), 3.84-3.72 (m, 2H), 3.65-3.58 (m, 2H), 3.56 (s, 3H), 3.55-3.47 (m, 4H), 2.94-2.84 (m, 1H), 2.78-2.58 (m, 5H), 2.41-2.34 (m, 2H), 2.26 (d, J = 6.4 Hz, 2H), 2.06-1.89 (m, 7H), 1.88-1.80 (m, 1H), 1.77-1.63 (m, 2H), 1.39-1.26 (m, 1H), 1.12-0.98 (m, 2H) |
| I-605 | CMW | AJB | 898.3 | 11.07 (s, 1H), 9.50 (d, J = 6.0 Hz, 1H), 8.78 (d, J = 7.6 Hz, 1H), 8.38 (d, J = 4.4 Hz, 1H), 8.25 (d, J = 5.6 Hz, 1H), 7.26-6.98 (m, 1H), 6.96 (t, J = 8.4 Hz, 1H), 6.88-6.42 (m, 3H), 5.37-5.30 (m, 1H), 5.28-5.05 (m, 1H), 4.77 (d, J = 17.2 Hz, 1H), 4.23-4.11 (m, 1H), 3.87-3.69 (m, 5H), 3.63 (d, J = 8.0 Hz, 3H), 3.59 (s, 1H), 3.56 (s, 3H), 2.93-2.82 (m, 1H), 2.74-2.69 (m, 1H), 2.67 (s, 2H), 2.65-2.56 (m, 4H), 2.42-2.30 (m, 4H), 2.11 (d, J = 7.2 Hz, 2H), 2.08-1.92 (m, 6H), 1.92-1.84 (m, 2H), 1.81-1.66 (m, 2H), 1.64-1.50 (m, 1H), 1.11-0.97 (m, 2H) |
| I-613 | CLO | CMN | 761.2 | 11.15-11.08 (m, 1H), 10.43 (s, 1H), 8.41 (s, 1H), 8.35-8.32 (m, 1H), 8.32-8.25 (m, 2H), 7.99 (dd, J = 2.4, 6.0 Hz, 1H), 7.66-7.60 (m, 1H), 7.58-7.52 (m, 1H), 7.23-6.94 (m, 4H), 5.47-5.36 (m, 1H), 4.52-4.39 (m, 1H), 3.92-3.76 (m, 1H), 3.57 (s, 3H), 3.27-3.23 (m, 1H), 3.07-2.99 (m, 1H), 2.96-2.84 (m, 1H), 2.79-2.69 (m, 1H), 2.69-2.58 (m, 2H), 2.36-2.24 (m, 4H), 2.24-2.11 (m, 3H), 2.05-1.89 (m, 6H), 1.22-1.10 (m, 2H) |
| I-614 | CLO | CMQ | 726.3 | 11.10 (s, 1H), 10.41 (s, 1H), 9.05 (s, 1H), 8.59 (s, 1H), 8.49 (d, J = 1.2 Hz, 1H), 8.05-7.98 (m, 2H), 7.58 (d, J = 7.6 Hz, 1H), 7.15-7.06 (m, 3H), 5.42-5.40 (m, 1H), 4.61-4.54 (m, 1H), 3.92-3.79 (m, 1H), 3.57 (s, 3H), 3.02 (d, J = 7.6 Hz, 1H), 2.95-2.86 (m, 1H), 2.73 (d, J = 3.6 Hz, 1H), 2.64 (s, 3H), 2.39-2.27 (m, 5H), 2.21 (d, J = 8.8 Hz, 3H), 2.08-1.95 (m, 6H), 1.89 (d, J = 8.4 Hz, 1H), 1.76-1.69 (m, 1H), 1.21-1.13 (m, 2H) |
| I-615 | CLO | CMX | 737.3 | 11.10 (s, 1H), 10.26 (s, 1H), 9.07 (s, 1H), 8.60 (s, 1H), 8.49-8.42 (m, 2H), 8.39-8.31 (m, 2H), 7.15-7.11 (m, 1H), 7.10-7.03 (m, 2H), 5.45-5.34 (m, 1H), 4.65-4.53 (m, 1H), 3.93-3.83 (m, 1H), 3.83-3.75 (m, 1H), 3.57 (s, 3H), 3.09-2.97 (m, 2H), 2.96-2.81 (m, 2H), 2.75-2.69 (m, 1H), 2.66-2.59 (m, 2H), 2.36 (s, 1H), 2.31-2.17 (m, 4H), 2.03-1.96 (m, 4H), 1.94-1.87 (m, 1H), 1.73 (td, J = 5.2, 10.4 Hz, 1H), 1.23-1.12 (m, 2H) |
| I-616 | CLO | CMS | 762.4 | 11.12 (s, 1H), 10.32 (s, 1H), 9.11-9.01 (m, 1H), 8.62 (s, 1H), 8.51 (s, 1H), 8.40-8.30 (m, 2H), 8.03 (d, J = 7.6 Hz, 1H), 7.20 (s, 1H), 7.14-7.05 (m, 3H), 5.45-5.37 (m, 1H), 4.71-4.53 (m, 1H), 3.92-3.78 (m, 1H), 3.58 (s, 3H), 3.29-3.19 (m, 2H), 3.03 (d, J = 7.6 Hz, 1H), 2.93-2.85 (m, 1H), 2.80-2.62 (m, 3H), 2.37-2.28 (m, 3H), 2.27-2.17 (m, 3H), 2.04-1.97 (m, 4H), 1.93-1.86 (m, 1H), 1.74-1.67 (m, 1H), 1.34-1.04 (m, 2H) |
| I-625 | CMO | BVH | 718.3 | 11.12 (s, 1H), 10.61 (s, 1H), 8.42 (s, 1H), 8.40 (d, J = 2.4 Hz, 1H), 8.34 (s, 1H), 8.31 (d, J = 2.0 Hz, 1H), 7.62 (d, J = 1.2 Hz, 2H), 7.19 (d, J = 8.4 Hz, 1H), 7.09-7.01 (m, 2H), 5.40 (dd, J = 5.2, 12.3 Hz, 1H), 4.94-4.64 (m, 1H), 4.51-4.44 (m, 1H), 3.59 (s, 3H), 3.10 (d, J = 2.8 Hz, 1H), 2.95-2.88 (m, 2H), 2.69-2.65 (m, 3H), 2.35-2.29 (m, 3H), 2.21-2.16 (m, 3H), 2.04-1.98 (m, 4H), 1.95-1.89 (m, 2H), 1.87-1.79 (m, 1H), 1.76-1.68 (m, 1H), 1.28-1.08 (m, 3H) |
| I-629 | CMO | CMN | 743.4 | 11.12 (s, 1H), 10.44 (d, J = 0.8 Hz, 1H), 8.41 (s, 1H), 8.35-8.28 (m, 3H), 8.00 (d, J = 7.2 Hz, 1H), 7.63 (d, J = 11.6 Hz, 1H), 7.61 (m, 1H), 7.57-6.94 (m, 4H), 5.43 (d, 1H), 4.51 (d, 1H), 4.01-3.62 (m, 2H), 3.01 (d, J = 5.6 Hz, 3H), 2.86-2.66 (m, 2H), 2.69-2.66 (m, 4H), 2.42-2.31 (m, 4H), 2.23-2.01 (m, 4H), 2.03-1.99 (m, 6H), 1.22-1.11 (m, 2H) |
| I-633 | CMO | CMQ | 708.3 | 11.08 (s, 1H), 10.41 (s, 1H), 9.04 (s, 1H), 8.64-8.43 (m, 2H), 8.07-7.94 (m, 2H), 7.57 (d, J = 7.6 Hz, 1H), 7.22-7.12 (m, 1H), 7.10-6.99 (m, 2H), 5.39 (dd, J = 5.2, 12.4 Hz, 1H), 4.89-4.65 (m, 1H), 4.63-4.50 (m, 1H), 3.58 (s, 3H), 3.51-3.39 (m, 1H), 3.37-3.32 (m, 1H), 2.96-2.83 (m, 2H), 2.78-2.68 (m, 1H), 2.64 (s, 4H), 2.37-2.26 (m, 2H), 2.24-2.08 (m, 4H), 2.05-1.89 (m, 6H), 1.88-1.79 (m, 1H), 1.76-1.66 (m, 1H), 1.25-1.09 (m, 2H) |
| I-637 | CMO | CMX | 719.6 | 11.10 (s, 1H), 10.26 (s, 1H), 9.08 (s, 1H), 8.61 (s, 1H), 8.49-8.44 (m, 2H), 8.38-8.31 (m, 2H), 7.18 (d, J = 7.2 Hz, 1H), 7.11-6.96 (m, 2H), 5.39 (dd, J = 5.6, 12.8 Hz, 1H), 4.92-4.68 (m, 1H), 4.66-4.52 (m, 1H), 3.58 (s, 3H), 3.52-3.44 (m, 1H), 2.98-2.82 (m, |

TABLE 3-continued

Compounds synthesized via Method 2, with the reductive amination of the corresponding amines and aldehydes.

| I-#[a] | Amine | Aldehyde | LCMS (ES+) m/z (M + H)+ | ¹HNMR (400 MHZ, DMSO-d6) δ |
|---|---|---|---|---|
| | | | | 2H), 2.79-2.69 (m, 1H), 2.63 (d, J = 18.0 Hz, 2H), 2.33 (dd, J = 2.4, 4.0 Hz, 2H), 2.26-2.15 (m, 3H), 2.12 (dd, J = 9.6, 11.6 Hz, 1H), 2.06-1.91 (m, 6H), 1.89-1.77 (m, 1H), 1.77-1.66 (m, 1H), 1.26-1.11 (m, 2H) |
| I-638 | CMM | CMX | 719.3 | 11.11 (s, 1H), 10.26 (s, 1H), 9.07 (s, 1H), 8.61 (s, 1H), 8.52-8.42 (m, 2H), 8.41-8.28 (m, 2H), 7.18 (d, J = 6.4 Hz, 1H), 7.11-6.97 (m, 2H), 5.39 (dd, J = 4.0, 11.2 Hz, 1H), 4.91-4.65 (m, 1H), 4.64-4.51 (m, 1H), 3.58 (s, 3H), 3.51-3.44 (m, 1H), 2.98-2.83 (m, 2H), 2.80-2.69 (m, 1H), 2.65-2.58 (m, 2H), 2.36-2.28 (m, 2H), 2.27-2.10 (m, 4H), 2.06-1.92 (m, 6H), 1.89-1.78 (m, 1H), 1.76-1.66 (m, 1H), 1.26-1.09 (m, 2H) |
| I-641 | CMO | CMS | 744.2 | 11.10 (s, 1H), 10.31 (s, 1H), 9.06 (s, 1H), 8.61 (s, 1H), 8.50 (d, J = 1.2 Hz, 1H), 8.42-8.28 (m, 2H), 8.02 (d, J = 7.6 Hz, 1H), 7.35-6.97 (m, 4H), 5.39 (dd, J = 5.2, 12.0 Hz, 1H), 4.90-4.65 (m, 1H), 4.64-4.52 (m, 1H), 3.58 (s, 3H), 3.51-3.42 (m, 1H), 2.96-2.83 (m, 2H), 2.79-2.69 (m, 1H), 2.65-2.57 (m, 2H), 2.35-2.30 (m, 2H), 2.26-2.15 (m, 3H), 2.13-2.08 (m, 1H), 2.05-1.90 (m, 6H), 1.88-1.79 (m, 1H), 1.76-1.65 (m, 1H), 1.28-1.09 (m, 2H) |
| I-656 | CMO | BRR | 762.2 | 11.1 (s, 1H), 10.2 (s, 1H), 9.07 (s, 1H), 8.61 (s, 1H), 8.51-8.47 (m, 2H), 8.41 (t, J = 7.6 Hz, 1H), 8.23 (d, J = 7.6 Hz, 1H), 7.17 (d, J = 8.0 Hz, 1H), 7.09-6.99 (m, 2H), 5.39 (dd, J = 5.2, 12.4 Hz, 1H), 4.85-4.55 (m, 2H), 3.58 (s, 3H), 3.47-3.43 (m, 1H), 2.95-2.86 (m, 2H), 2.77-2.58 (m, 3H), 2.32 (d, J = 1.6 Hz, 2H), 2.22-2.10 (m, 4H), 2.01 (d, J = 10.4 Hz, 4H), 1.97-1.90 (m, 2H), 1.88-1.79 (m, 1H), 1.76-1.67 (m, 1H), 1.23-1.15 (m, 2H) |
| I-660 | CPG | AJB | 938.5 | 11.08 (s, 1H), 9.49 (d, J = 5.2 Hz, 1H), 8.78 (d, J = 7.6 Hz, 1H), 8.37 (d, J = 4.0 Hz, 1H), 8.25 (d, J = 5.6 Hz, 1H), 7.11-6.43 (m, 5H), 5.34 (d, J = 5.2, 12.4 Hz, 1H), 5.17 (d, J = 82.0 Hz, 1H), 4.76 (d, J = 18.0 Hz, 1H), 4.20-4.12 (m, 1H), 3.85-3.77 (m, 3H), 3.73 (d, J = 8.0 Hz, 1H), 3.62 (s, 3H), 3.59 (s, 1H), 3.44 (s, 4H), 3.01 (d, J = 6.4 Hz, 2H), 2.91 (d, J = 6.8 Hz, 4H), 2.74-2.56 (m, 3H), 2.35-2.25 (m, 5H), 2.20 (d, J = 7.2, 12.4 Hz, 2H), 2.08-1.92 (m, 6H), 1.91-1.79 (m, 3H), 1.79-1.63 (m, 3H), 1.37-1.26 (m, 1H), 1.05 (q, J = 11.6 Hz, 2H) |
| I-669 | CNW | AJB | 889.6 | 11.07 (s, 1H), 9.49 (d, J = 6.0 Hz, 1H), 8.77 (d, J = 7.6 Hz, 1H), 8.54-8.13 (m, 2H), 7.29-6.94 (m, 2H), 6.89-6.41 (m, 3H), 5.46-4.99 (m, 2H), 4.91-4.65 (m, 1H), 4.31-4.09 (m, 1H), 4.05-3.89 (m, 2H), 3.85-3.71 (m, 2H), 3.69-3.60 (m, 3H), 3.60-3.54 (m, 3H), 2.96-2.81 (m, 1H), 2.76-2.55 (m, 7H), 2.20 (d, J = 6.8 Hz, 2H), 2.12-1.94 (m, 7H), 1.92-1.83 (m, 2H), 1.82-1.68 (m, 2H), 1.67-1.55 (m, 1H), 1.17-0.93 (m, 2H) |
| I-670 | CQG | AJB | 883.7 | 11.08 (s, 1H), 9.49 (d, J = 6.0 Hz, 1H), 8.78 (d, J = 7.6 Hz, 1H), 8.38 (d, J = 4.4 Hz, 1H), 8.25 (d, J = 5.6 Hz, 1H), 7.28-6.96 (m, 1H), 6.96-6.89 (m, 1H), 6.88-6.58 (m, 2H), 6.56-6.41 (m, 1H), 5.33 (dd, J = 5.6, 12.8 Hz, 1H), 5.29-5.05 (m, 1H), 4.91-4.51 (m, 2H), 4.17 (t, J = 9.6 Hz, 1H), 3.80 (s, 1H), 3.65-3.52 (m, 6H), 3.00-2.84 (m, 2H), 2.73-2.61 (m, 3H), 2.43-2.27 (m, 7H), 2.24-1.82 (m, 13H), 1.80-1.67 (m, 2H), 1.63-1.50 (m, 1H), 1.14-0.94 (m, 2H) |
| I-671 | CPM | BRP | 816.3 | 11.08 (s, 1H), 10.35 (s, 1H), 8.43-8.32 (m, 3H), 8.29 (s, 1H), 8.17 (d, J = 7.2 Hz, 1H), 7.64-7.51 (m, 2H), 7.19 (d, J = 7.2 Hz, 1H), 7.10-6.97 (m, 2H), 5.36 (d, J = 5.2, 12.0 Hz, 1H), 4.47-4.20 (m, 3H), 3.73-3.63 (m, 2H), 3.52 (s, 3H), 3.00-2.94 (m, 1H), 2.90-2.82 (m, 1H), 2.75-2.64 (m, 4H), 2.38-2.29 (m, 2H), 2.21 (d, J = 6.0 Hz, 2H), 2.15 (d, J = 8.4 Hz, 2H), 2.05-1.87 (m, 7H), 1.83-1.76 (m, 1H), 1.67-1.59 (m, 1H), 1.24-1.07 (m, 3H) |
| I-672 | CPY | BRR | 817.4 | 11.08 (s, 1H), 10.19 (s, 1H), 9.06 (s, 1H), 8.60 (s, 1H), 8.50-8.47 (m, 2H), 8.44-8.39 (m, 1H), 8.23 (d, J = 7.8 Hz, 1H), 7.19 (d, J = 7.2 Hz, 1H), 7.08-7.02 (m, 2H), 5.39-5.34 (m, 1H), 4.61-4.40 (m, 2H), 4.36-4.19 (m, 2H), 3.76-3.63 (m, 3H), 3.52 (s, 3H), 2.71-2.66 (m, 3H), 2.35-2.30 (m, 2H), 2.22-2.16 (m, 4H), 2.01-1.93 (m, 6H), 1.82-1.58 (m, 3H), 1.25-1.08 (m, 4H) |
| I-673 | CPM | AJB | 885.4 | 11.08 (s, 1H), 9.50 (d, J = 6.0 Hz, 1H), 8.77 (d, J = 8.0 Hz, 1H), 8.38 (d, J = 4.4 Hz, 1H), 8.25 (d, J = 5.6 Hz, 1H), 7.25-6.95 (m, 4H), 6.65 (dd, J = 8.0, 164.4 Hz, 1H), 5.36 (d, J = 5.2, 12.4 Hz, 1H), 5.17 (d, J = 84.4 Hz, 1H), 4.77 (d, J = 16.8 Hz, 1H), 4.65 (d, J = 48.8 Hz, 1H), 4.28-4.12 (m, 2H), 3.83-3.72 (m, 2H), 3.70-3.58 (m, 4H), 3.52 (s, 3H), 3.44 (d, J = 10.0 Hz, 2H), 3.25 (s, 2H), 2.93-2.84 (m, 2H), 2.70 (dd, J = 4.8, 12.8 Hz, 1H), 2.62 (d, J = 17.2 Hz, 2H), 2.42-2.32 (m, 1H), 2.15 (d, J = 7.2 Hz, 2H), 2.07-1.86 (m, 7H), 1.74 (q, J = 12.0 Hz, 2H), 1.63-1.49 (m, 3H), 1.10-0.94 (m, 2H) |

TABLE 3-continued

Compounds synthesized via Method 2, with the reductive amination of the corresponding amines and aldehydes.

| I-#[a] | Amine | Aldehyde | LCMS (ES+) m/z (M + H)[+] | $^1$HNMR (400 MHZ, DMSO-d6) δ |
|---|---|---|---|---|
| I-674 | CND | CNM | 884.3 | 11.07 (s, 1H), 9.33 (s, 1H), 8.82 (d, J = 8.0 Hz, 1H), 8.38 (s, 1H), 8.28 (s, 1H), 7.13 (t, J = 53.6 Hz, 1H), 6.97-6.93 (m, 1H), 6.92 (d, J = 3.2 Hz, 1H), 6.72 (d, J = 7.6 Hz, 1H), 6.64 (d, J = 8.0 Hz, 1H), 5.36-5.27 (m, 1H), 4.48-4.36 (m, 1H), 4.23-4.13 (m, 1H), 4.00-3.87 (m, 3H), 3.60 (dd, J = 2.8, 6.8 Hz, 2H), 3.56 (s, 3H), 3.51-3.44 (m, 3H), 3.16-3.06 (m, 2H), 2.93-2.74 (m, 4H), 2.57 (s, 2H), 2.42-2.35 (m, 6H), 2.11 (d, J = 7.2 Hz, 2H), 2.06-1.95 (m, 4H), 1.92-1.87 (m, 2H), 1.80-1.67 (m, 3H), 1.61-1.53 (m, 1H), 1.19 (d, J = 6.0 Hz, 3H), 1.09-0.98 (m, 2H) |
| I-675 | CNK | AJB | 912.2 | 11.10-10.98 (m, 1H), 9.49 (d, J = 6.0 Hz, 1H), 8.78 (d, J = 7.6 Hz, 1H), 8.38 (d, J = 4.4 Hz, 1H), 8.25 (d, J = 5.6 Hz, 1H), 7.27-6.93 (m, 1H), 6.87-6.43 (m, 2H), 6.45 (d, J = 8.0 Hz, 1H), 5.30-5.06 (m, 2H), 4.76 (d, J = 17.2 Hz, 1H), 4.18-4.16 (m, 1H), 3.99-3.92 (m, 2H), 3.86 (s, 3H), 3.80 (s, 1H), 3.70 (t, J = 6.0 Hz, 2H), 3.60 (s, 3H), 3.47-3.42 (m, 2H), 2.93-2.76 (m, 3H), 2.63 (d, J = 7.2 Hz, 4H), 2.43-2.31 (m, 7H), 2.11 (d, J = 7.2 Hz, 2H), 2.04 (d, J = 8.8 Hz, 3H), 1.98-1.84 (m, 5H), 1.78-1.69 (m, 2H), 1.62-1.54 (m, 1H), 1.09-0.99 (m, 2H) |
| I-676 | CNJ | AJB | 900.4 | 11.08 (s, 1H), 9.49 (d, J = 5.6 Hz, 1H), 8.78 (d, J = 7.6 Hz, 1H), 8.38 (d, J = 4.4 Hz, 1H), 8.25 (d, J = 5.6 Hz, 1H), 7.24-6.97 (m, 1H), 6.91-6.32 (m, 3H), 5.37-5.05 (m, 2H), 4.77 (d, J = 16.4 Hz, 1H), 4.24-4.10 (m, 1H), 4.02 (t, J = 6.4 Hz, 2H), 3.88-3.75 (m, 2H), 3.66 (s, 2H), 3.61 (s, 3H), 2.97-2.74 (m, 3H), 2.62 (d, J = 6.8 Hz, 3H), 2.44-2.28 (m, 8H), 2.10 (d, J = 6.8 Hz, 2H), 2.08-1.92 (m, 6H), 1.89 (dd, J = 1.6, 12.8 Hz, 2H), 1.80-1.69 (m, 2H), 1.62-1.49 (m, 1H), 1.09-0.97 (m, 2H) |
| I-677 | BAI | CPP | 761.3 | 11.08 (s, 1H), 10.20 (s, 1H), 9.07 (s, 1H), 8.61 (s, 1H), 8.53-8.46 (m, 2H), 8.45-8.38 (m, 1H), 8.23 (d, J = 8.0 Hz, 1H), 7.04-6.85 (m, 3H), 5.35 (dd, J = 5.2, 12.8 Hz, 1H), 4.65-4.50 (m, 1H), 4.21 (d, J = 1.6 Hz, 1H), 3.64 (s, 3H), 2.98-2.84 (m, 6H), 2.72-2.58 (m, 4H), 2.38 (s, 2H), 2.36-2.23 (m, 3H), 2.05-1.93 (m, 3H), 1.79 (d, J = 13.2 Hz, 2H), 1.68-1.56 (m, 2H) |
| I-678 | CNH | AJB | 900.4 | 11.07 (s, 1H), 9.49 (d, J = 6.0 Hz, 1H), 8.78 (d, J = 7.6 Hz, 1H), 8.38 (d, J = 4.4 Hz, 1H), 8.25 (d, J = 5.6 Hz, 1H), 7.27-7.08 (m, 1H), 7.02-6.94 (m, 1H), 6.87-6.43 (m, 3H), 5.29-5.37 (m, 1H), 5.09-4.78 (m, 2H), 4.24-4.10 (m, 1H), 3.80 (s, 1H), 3.72 (d, J = 7.2 Hz, 2H), 3.63 (d, J = 9.2 Hz, 2H), 3.56 (s, 3H), 3.45 (d, J = 10.0 Hz, 2H), 2.94-2.83 (m, 1H), 2.72-2.64 (m, 2H), 2.57 (s, 6H), 2.44-2.26 (m, 4H), 2.14-1.82 (m, 10H), 1.79-1.68 (m, 2H), 1.58 (d, J = 6.4 Hz, 1H), 1.11-0.97 (m, 2H) |
| I-679 | CNF | AJB | 914.5 | 11.08 (s, 1H), 9.50 (d, J = 6.4 Hz, 1H), 8.78 (d, J = 7.6 Hz, 1H), 8.39 (d, J = 4.4 Hz, 1H), 8.26 (d, J = 5.6 Hz, 1H), 7.14-6.42 (m, 5H), 5.35 (dd, J = 5.2, 12.8 Hz, 1H), 5.29-5.04 (m, 1H), 4.77 (d, J = 17.2 Hz, 2H), 4.24-4.11 (m, 1H), 3.81 (s, 1H), 3.62 (s, 3H), 3.59 (s, 1H), 3.45 (d, J = 9.6 Hz, 1H), 3.15 (d, J = 6.4 Hz, 1H), 3.07-2.96 (m, 2H), 2.94-2.74 (m, 8H), 2.74-2.61 (m, 3H), 2.59 (s, 1H), 2.18 (s, 2H), 2.06-1.85 (m, 9H), 1.81-1.70 (m, 3H), 1.64-1.49 (m, 2H), 1.13-0.96 (m, 2H) |
| I-680 | CND | CNE | 884.6 | 11.07 (s, 1H), 9.34 (s, 1H), 8.83 (d, J = 8.0 Hz, 1H), 8.40 (d, J = 3.2 Hz, 1H), 8.28 (s, 1H), 7.33-6.90 (m, 3H), 6.84-6.60 (m, 2H), 5.44-5.20 (m, 1H), 4.58-4.29 (m, 2H), 4.27-4.14 (m, 1H), 4.08-3.98 (m, 1H), 3.97-3.85 (m, 2H), 3.68-3.56 (m, 6H), 3.55-3.41 (m, 5H), 3.15-2.94 (m, 7H), 2.91-2.74 (m, 3H), 2.74-2.67 (m, 2H), 2.65-2.58 (m, 2H), 2.28-2.18 (m, 2H), 2.13-2.03 (m, 2H), 2.02-1.95 (m, 1H), 1.95-1.84 (m, 3H), 1.84-1.71 (m, 2H), 1.19 (d, J = 6.4 Hz, 3H) |
| I-681 | CPN | AJB | 885.3 | 11.08 (s, 1H), 9.49 (d, J = 6.0 Hz, 1H), 8.78 (d, J = 8.0 Hz, 1H), 8.38 (d, J = 4.4 Hz, 1H), 8.27-8.23 (m, 1H), 7.26-6.96 (m, 4H), 6.86 (d, J = 8.0 Hz, 1H), 5.36 (d, J = 5.4, 12.6 Hz, 1H), 5.28 (s, 1H), 4.77 (d, J = 17.6 Hz, 1H), 4.47-4.26 (m, 1H), 4.25-4.12 (m, 2H), 3.83-3.69 (m, 3H), 3.67-3.57 (m, 3H), 3.51 (s, 3H), 3.44 (d, J = 10.0 Hz, 2H), 2.99-2.91 (m, 1H), 2.87 (dd, J = 5.2, 16.4 Hz, 1H), 2.75-2.66 (m, 2H), 2.65-2.59 (m, 1H), 2.30 (d, J = 10.0 Hz, 1H), 2.17 (d, J = 7.2 Hz, 2H), 2.08-1.93 (m, 7H), 1.90-1.83 (m, 2H), 1.81-1.67 (m, 3H), 1.58 (s, 1H), 1.26-1.15 (m, 1H), 1.11-0.96 (m, 2H) |
| I-682 | CMY | AJB | 903.3 | 11.08 (s, 1H), 9.50 (d, J = 5.6 Hz, 1H), 8.78 (d, J = 7.8 Hz, 1H), 8.38 (d, J = 4.0 Hz, 1H), 8.25 (d, J = 5.2 Hz, 1H), 7.25-7.20 (m, 1H), 7.14-6.95 (m, 3H), 6.89-6.42 (m, 1H), 5.37 (dd, J = 5.6, 12.4 Hz, 1H), 5.30-5.04 (m, 1H), 4.77 (d, J = 17.6 Hz, 1H), 4.24 (d, J = 7.2 Hz, 1H), 4.22-4.11 (m, 1H), 3.84-3.72 (m, 3H), 3.69-3.56 (m, 3H), 3.52 (s, 3H), 3.45 (d, J = 9.6 Hz, 1H), 2.95-2.79 |

TABLE 3-continued

Compounds synthesized via Method 2, with the reductive amination of the corresponding amines and aldehydes.

| I-#[a] | Amine | Aldehyde | LCMS (ES+) m/z (M + H)+ | 1HNMR (400 MHZ, DMSO-d6) δ |
|---|---|---|---|---|
| | | | | (m, 2H), 2.74-2.59 (m, 4H), 2.38-2.23 (m, 2H), 2.21 (d, J = 6.8 Hz, 2H), 2.10-1.92 (m, 6H), 1.88 (d, J = 12.0 Hz, 2H), 1.75 (q, J = 11.2 Hz, 3H), 1.63-1.53 (m, 2H), 1.09-0.97 (m, 2H) |
| I-683 | CPJ | AJB | 914.5 | 11.08 (s, 1H), 9.50 (d, J = 6.4 Hz, 1H), 8.78 (d, J = 7.6 Hz, 1H), 8.39 (d, J = 4.4 Hz, 1H), 8.26 (d, J = 5.6 Hz, 1H), 7.14-6.42 (m, 5H), 5.35 (dd, J = 5.2, 12.8 Hz, 1H), 5.29-5.04 (m, 1H), 4.77 (d, J = 17.2 Hz, 2H), 4.24-4.11 (m, 1H), 3.81 (s, 1H), 3.62 (s, 3H), 3.59 (s, 1H), 3.45 (d, J = 9.6 Hz, 1H), 3.15 (d, J = 6.4 Hz, 1H), 3.07-2.96 (m, 2H), 2.94-2.74 (m, 8H), 2.74-2.61 (m, 3H), 2.59 (s, 1H), 2.18 (s, 2H), 2.06-1.85 (m, 9H), 1.81-1.70 (m, 3H), 1.64-1.49 (m, 2H), 1.13-0.96 (m, 2H) |
| I-687 | CCS | CMX | 732.4 | 11.06 (s, 1H), 10.25 (s, 1H), 9.07 (s, 1H), 8.60 (s, 1H), 8.48-8.43 (m, 2H), 8.37-8.31 (m, 2H), 6.87 (d, J = 8.8 Hz, 1H), 6.68 (d, J = 8.8 Hz, 1H), 5.30 (dd, J = 5.2, 12.8 Hz, 1H), 4.62-4.54 (m, 1H), 3.78 (s, 3H), 3.62 (s, 3H), 3.57-3.44 (m, 3H), 2.84-2.74 (m, 5H), 2.26-2.14 (m, 7H), 2.03-1.91 (m, 6H), 1.21-1.11 (m, 2H) |
| I-688 | CMU | BRR | 772.3 | 11.10 (s, 1H), 10.20 (s, 1H), 9.06 (s, 1H), 8.60 (s, 1H), 8.49 (d, J = 1.2 Hz, 1H), 8.48 (s, 1H), 8.45-8.39 (m, 1H), 8.24 (d, J = 8.0 Hz, 1H), 7.04 (t, J = 6.4 Hz, 3H), 5.39 (dd, J = 5.2, 12.4 Hz, 1H), 4.63-4.50 (m, 1H), 4.17-4.09 (m, 2H), 3.83 (s, 2H), 3.62 (s, 3H), 2.98-2.82 (m, 2H), 2.76-2.61 (m, 5H), 2.44-2.30 (m, 2H), 2.19 (d, J = 9.2 Hz, 2H), 2.07-1.85 (m, 6H), 1.62-1.47 (m, 1H), 1.25-1.13 (m, 2H) |
| I-689 | CMU | BRP | 771.3 | 11.09 (s, 1H), 10.34 (s, 1H), 8.42-8.33 (m, 3H), 8.28 (d, J = 1.2 Hz, 1H), 8.20-8.14 (m, 1H), 7.63-7.58 (m, 1H), 7.56-7.51 (m, 1H), 7.07-6.96 (m, 3H), 5.37 (dd, J = 5.6, 12.6 Hz, 1H), 4.49-4.36 (m, 1H), 4.14-4.05 (m, 2H), 3.83-3.74 (m, 1H), 3.61 (s, 3H), 3.47 (s, 1H), 3.15 (d, J = 7.2 Hz, 1H), 3.06 (d, J = 7.2 Hz, 1H), 2.93-2.83 (m, 1H), 2.77-2.58 (m, 4H), 2.40-2.33 (m, 2H), 2.31-2.24 (m, 1H), 2.13 (d, J = 8.8 Hz, 2H), 2.04-1.97 (m, 1H), 1.90 (t, J = 10.8 Hz, 4H), 1.47-1.33 (m, 1H), 1.22-1.04 (m, 2H) |
| I-690 | CMO | CLV | 777.4 | 11.10 (s, 1H), 10.36 (s, 1H), 8.42 (s, 1H), 8.42-8.34 (m, 2H), 8.31 (s, 1H), 8.18 (dd, J = 0.8, 7.4 Hz, 1H), 7.67-7.61 (m, 1H), 7.59-7.53 (m, 1H), 7.19 (d, J = 7.6 Hz, 1H), 7.12-7.02 (m, 2H), 5.46-5.34 (m, 1H), 4.93-4.71 (m, 1H), 4.51-4.40 (m, 1H), 4.21 (s, 1H), 3.59 (s, 3H), 3.02-2.87 (m, 2H), 2.75-2.60 (m, 3H), 2.44-2.40 (m, 2H), 2.39-2.20 (m, 4H), 2.07-1.76 (m, 8H), 1.59 (t, J = 11.6 Hz, 2H) |
| I-693 | BAI | CMS | 727.4 | 11.09 (s, 1H), 10.31 (s, 1H), 9.06 (s, 1H), 8.60 (s, 1H), 8.50 (d, J = 1.2 Hz, 1H), 8.41-8.27 (m, 2H), 8.01 (d, J = 7.2 Hz, 1H), 7.19 (t, J = 54.8 Hz, 1H), 7.03-6.85 (m, 3H), 5.36 (dd, J = 5.6, 12.8 Hz, 1H), 4.65-4.52 (m, 1H), 3.64 (s, 3H), 3.13-2.77 (m, 7H), 2.76-2.57 (m, 3H), 2.42-2.12 (m, 5H), 2.08-1.88 (m, 5H), 1.83-1.63 (m, 1H), 1.29-1.10 (m, 2H) |
| I-694 | CMT | BRR | 763.3 | 11.09 (s, 1H), 10.23-10.16 (m, 1H), 9.06 (s, 1H), 8.61 (s, 1H), 8.51-8.46 (m, 2H), 8.44-8.39 (m, 1H), 8.23 (dd, J = 0.8, 7.6 Hz, 1H), 6.99-6.93 (m, 1H), 6.91-6.84 (m, 1H), 5.35 (dd, J = 5.2, 12.8 Hz, 1H), 4.64-4.52 (m, 1H), 3.64 (s, 3H), 3.26-3.25 (m, 1H), 2.97 (d, J = 10.8 Hz, 1H), 2.87-2.83 (m, 2H), 2.74-2.58 (m, 3H), 2.53-2.52 (m, 1H), 2.29-2.16 (m, 6H), 2.04-1.90 (m, 5H), 1.74-1.63 (m, 1H), 1.24-1.10 (m, 2H) |
| I-701 | CMC | AJB | 932.4 | 11.08 (s, 1H), 9.50 (d, J = 6.4 Hz, 1H), 8.78 (d, J = 7.6 Hz, 1H), 8.39 (d, J = 4.4 Hz, 1H), 8.26 (d, J = 5.6 Hz, 1H), 7.27-6.99 (m, 1H), 6.99-6.91 (m, 2H), 6.90-6.42 (m, 2H), 5.35 (dd, J = 5.6, 12.8 Hz, 1H), 5.30-5.05 (m, 1H), 4.82-4.71 (m, 1H), 4.23-4.12 (m, 1H), 3.84-3.72 (m, 2H), 3.63 (s, 3H), 3.61-3.42 (m, 2H), 3.06-2.95 (m, 3H), 2.94-2.88 (m, 5H), 2.86-2.80 (m, 2H), 2.75-2.67 (m, 1H), 2.65-2.57 (m, 2H), 2.27-2.14 (m, 3H), 2.09-1.94 (m, 6H), 1.94-1.68 (m, 7H), 1.64-1.51 (m, 1H), 1.12-0.96 (m, 2H) |
| I-702 | CLD | CKR | 861.2 | 11.15-11.05 (m, 1H), 9.61 (d, J = 4.0 Hz, 1H), 8.96 (d, J = 3.6 Hz, 1H), 8.85-8.62 (m, 1H), 8.45-8.34 (m, 3H), 7.77 (d, J = 8.0 Hz, 2H), 7.42 (d, J = 8.3 Hz, 2H), 7.07-6.87 (m, 4H), 5.37-5.30 (m, 2H), 4.84-4.69 (m, 1H), 3.81 (d, J = 19.6 Hz, 4H), 3.64 (s, 3H), 2.97-2.89 (m, 6H), 2.03-1.96 (m, 6H), 1.67 (s, 4H), 1.48-1.45 (m, 1H), 1.24-1.23 (m, 2H), 0.87-0.82 (m, 2H) |

TABLE 3-continued

Compounds synthesized via Method 2, with the reductive amination of the corresponding amines and aldehydes.

| I-#[a] | Amine | Aldehyde | LCMS (ES+) m/z (M + H)+ | 1HNMR (400 MHZ, DMSO-d6) δ |
|---|---|---|---|---|
| I-704 | CLI | ATJ | 807.2 | 1.13-1.26 (m, 3H) 1.66-1.83 (m, 1H) 1.86-2.06 (m, 6H) 2.12-2.19 (m, 2H) 2.68-2.78 (m, 5H) 2.85-2.94 (m, 3H) 2.98-3.06 (m, 2H) 3.98 (s, 3H) 4.33-4.46 (m, 1H) 5.38 (dd, J = 12.8, 5.20 Hz, 1H) 6.54 (s, 1H) 7.10-7.20 (m, 3H) 7.26 (s, 1H) 8.22 (d, J = 7.6 Hz, 1H) 8.34 (s, 1H) 8.37-8.43 (m, 1H) 8.44-8.49 (m, 1H) 8.69 (s, 1H) 10.51 (s, 1H) 11.11 (s, 1H) |
| I-705 | CLO | BXI | 804.3 | 11.21-10.98 (m, 1H), 10.64 (s, 1H), 8.64 (s, 1H), 8.51-8.35 (m, 3H), 8.31-8.14 (m, 2H), 7.22-6.93 (m, 3H), 5.46-5.34 (m, 1H), 4.66-4.52 (m, 1H), 3.92-3.75 (m, 1H), 3.57 (s, 3H), 3.25-3.20 (m, 1H), 3.06-2.98 (m, 1H), 2.96-2.83 (m, 1H), 2.79-2.69 (m, 1H), 2.65-2.60 (m, 2H), 2.38-2.31 (m, 3H), 2.31-2.24 (m, 2H), 2.23-2.17 (m, 2H), 2.03-1.96 (m, 4H), 1.93-1.85 (m, 1H), 1.79-1.66 (m, 1H), 1.22-1.10 (m, 2H) |
| I-706 | CLL | BRP | 759.4 | 11.11 (s, 1H), 10.36 (s, 1H), 8.42-8.29 (m, 4H), 8.17 (dd, J = 1.2, 7.6 Hz, 1H), 7.64-7.53 (m, 2H), 7.13-7.01 (m, 2H), 6.92 (d, J = 7.8 Hz, 1H), 6.11 (s, 1H), 5.45-5.37 (m, 1H), 5.20 (s, 1H), 4.54-4.39 (m, 1H), 3.30 (s, 3H), 3.21 (d, J = 2.4 Hz, 1H), 3.13-3.04 (m, 1H), 2.97-2.86 (m, 2H), 2.74 (s, 1H), 2.71 (s, 1H), 2.61 (s, 1H), 2.37 (d, J = 7.2 Hz, 2H), 2.18 (d, J = 10.4 Hz, 2H), 1.99 (d, J = 10.8 Hz, 5H), 1.26-1.10 (m, 3H) |
| I-707 | CLN | BRP | 759.3 | 11.10 (s, 1H), 10.37 (s, 1H), 8.45-8.33 (m, 3H), 8.31 (s, 1H), 8.18 (d, J = 7.6 Hz, 1H), 7.67-7.50 (m, 2H), 7.12-6.91 (m, 3H), 5.46-5.28 (m, J = 5.2, 12.4 Hz, 1H), 5.27-4.58 (m, 1H), 4.57-4.39 (m, 1H), 3.90-3.71 (m, 1H), 3.63 (s, 3H), 3.44 (s, 2H), 3.22-3.01 (m, 2H), 2.95-2.85 (m, 1H), 2.77-2.69 (m, 1H), 2.63 (d, J = 17.6 Hz, 2H), 2.19 (d, J = 9.2 Hz, 3H), 2.10-1.52 (m, 9H), 1.35-1.09 (m, 2H) |
| I-708 | CLO | BRP | 779.4 | 11.10 (s, 1H), 10.35 (s, 1H), 8.45-8.25 (m, 4H), 8.17 (d, J = 8.0 Hz, 1H), 7.72-7.46 (m, 2H), 7.17-7.00 (m, 3H), 5.50-5.28 (m, 1H), 4.54-4.36 (m, 1H), 3.96-3.73 (m, 1H), 3.57 (s, 3H), 3.07-2.99 (m, 1H), 2.96-2.82 (m, 1H), 2.80-2.69 (m, 1H), 2.65-2.59 (m, 2H), 2.28 (s, 1H), 2.23-2.12 (m, 3H), 2.06-1.85 (m, 7H), 1.79-1.65 (m, 1H), 1.22-1.05 (m, 2H) |
| I-709 | CLS | BRP | 761.3 | 10.55 (d, J = 10.4 Hz, 1H), 10.36 (s, 1H), 9.70 (s, 1H), 8.58 (d, J = 2.0 Hz, 1H), 8.45-8.28 (m, 4H), 8.18 (dd, J = 1.2, 7.6 Hz, 1H), 8.05-7.94 (m, 1H), 7.90-7.74 (m, 2H), 7.68-7.50 (m, 2H), 4.47 (s, 2H), 3.95 (d, J = 4.8 Hz, 1H), 3.79-3.59 (m, 1H), 3.25-3.20 (m, 1H), 3.10-3.03 (m, 1H), 3.01-2.93 (m, 1H), 2.82-2.71 (m, 2H), 2.44-2.36 (m, 4H), 2.19 (dd, J = 2.0, 9.2 Hz, 2H), 2.00 (d, J = 12.0 Hz, 3H), 1.95 (s, 2H), 1.78-1.68 (m, 1H), 1.23-1.13 (m, 2H) |
| I-710 | CLC | ATJ | 838.3 | 11.10 (s, 1H), 10.50 (s, 1H), 8.69 (s, 1H), 8.50-8.44 (m, 1H), 8.44-8.37 (m, 1H), 8.34 (s, 1H), 8.22 (dd, J = 0.8, 7.6 Hz, 1H), 7.16 (s, 1H), 7.08-6.90 (m, 3H), 5.37 (dd, J = 5.6, 12.8 Hz, 1H), 4.46-4.30 (m, 1H), 3.98 (s, 3H), 3.63 (s, 3H), 3.27-3.12 (m, 4H), 3.12-2.96 (m, 2H), 2.95-2.83 (m, 2H), 2.78-2.69 (m, 1H), 2.65-2.58 (m, 2H), 2.45 (s, 3H), 2.21-2.11 (m, 2H), 2.08-2.00 (m, 2H), 1.97-1.78 (m, 4H), 1.68-1.54 (m, 1H), 1.20-1.01 (m, 2H) |
| I-711 | AZK | CLV | 758.3 | 11.09 (s, 1H), 10.36 (s, 1H), 8.49-8.15 (m, 5H), 7.67-7.51 (m, 2H), 7.15-6.90 (m, 3H), 5.37 (br dd, J = 5.2, 12.4 Hz, 1H), 4.51-4.33 (m, 1H), 3.59 (s, 3H), 3.22-3.14 (m, 2H), 3.07 (br d, J = 11.2 Hz, 2H), 2.95-2.83 (m, 1H), 2.78-2.68 (m, 1H), 2.62 (br d, J = 18.4 Hz, 1H), 2.40-2.25 (m, 6H), 2.04-1.89 (m, 3H), 1.87-1.70 (m, 6H), 1.68-1.51 (m, 2H) |
| I-712 | CME | AJB | 938.9 | 11.12-10.94 (m, 1H), 9.48 (m, J = 5.6 Hz, 1H), 8.77 (d, J = 8.0 Hz, 1H), 8.42-8.31 (m, 1H), 8.24 (d, J = 5.6 Hz, 1H), 7.24-6.90 (m, 2H), 6.88-6.40 (m, 3H), 5.30-5.03 (m, 2H), 4.80-4.70 (m, 1H), 4.19-4.10 (m, 1H), 3.79-3.72 (m, 2H), 3.61 (m, 2H), 3.06 (m, 4H), 2.99 (m, J = 7.6 Hz, 2H), 2.90 (m, J = 6.4 Hz, 2H), 2.88-2.81 (m, 1H), 2.79-2.55 (m, 10H), 2.28 (m, J = 7.2, 16.8 Hz, 4H), 2.22-2.15 (m, 1H), 2.06-1.91 (m, 6H), 1.86-1.59 (m, 6H), 1.37-1.26 (m, 1H), 1.10-0.98 (m, 2H) |
| I-713 | CLL | BXI | 784.3 | 11.11 (s, 1H), 10.64 (s, 1H), 8.64 (s, 1H), 8.48-8.36 (m, 3H), 8.28-8.20 (m, 2H), 7.14-6.90 (m, 3H), 6.11 (s, 1H), 5.40 (d, J = 5.2, 12.4 Hz, 1H), 5.35-5.18 (m, 1H), 4.70-4.46 (m, 1H), 3.35 (s, 1H), 3.30 (s, 3H), 3.09 (s, 1H), 2.98-2.85 (m, 1H), 2.80-2.63 (m, 3H), 2.37 (d, J = 7.2 Hz, 2H), 2.27-2.16 (m, 2H), 2.09-1.94 (m, 5H), 1.84-1.68 (m, 1H), 1.30-1.13 (m, 2H) |
| I-716 | CLO | BVH | 736.2 | 11.12 (s, 1H), 10.61 (s, 1H), 8.43-8.38 (m, 2H), 8.35-8.27 (m, 3H), 7.61 (d, J = 0.8 Hz, 2H), 7.16-7.02 (m, 3H), 5.48-5.35 (m, 1H), 4.52-4.39 (m, 1H), 3.90-3.78 (m, 1H), 3.57 (s, 3H), 3.05- |

TABLE 3-continued

Compounds synthesized via Method 2, with the reductive amination of the corresponding amines and aldehydes.

| I-#[a] | Amine | Aldehyde | LCMS (ES+) m/z (M + H)+ | $^1$HNMR (400 MHZ, DMSO-d6) δ |
|---|---|---|---|---|
| | | | | 2.99 (m, 1H), 2.95-2.80 (m, 2H), 2.73 (s, 2H), 2.36-2.27 (m, 4H), 2.24-2.14 (m, 3H), 2.06-1.92 (m, 6H), 1.75-1.65 (m, 1H), 1.20-1.10 (m, 2H) |
| I-717 | CMM | BRR | 762.4 | 11.12 (s, 1H), 10.21 (s, 1H), 9.07 (s, 1H), 8.62 (s, 1H), 8.49 (d, J = 8.4 Hz, 2H), 8.45-8.39 (m, 1H), 8.24 (d, J = 8.0 Hz, 1H), 7.19-7.01 (m, 3H), 5.46-5.35 (m, 1H), 4.90-4.45 (m, 2H), 3.58 (s, 3H), 2.94-2.83 (m, 2H), 2.79-2.63 (m, 4H), 2.35-2.29 (m, 2H), 2.26-2.17 (m, 3H), 2.08-1.95 (m, 6H), 1.88-1.61 (m, 2H), 1.41-1.07 (m, 3H) |
| I-718 | COA | AJB | 914.4 | 11.10 (s, 1H), 9.51 (d, J = 6.4 Hz, 1H), 8.79 (d, J = 7.6 Hz, 1H), 8.40 (s, 1H), 8.26 (d, J = 5.6 Hz, 1H), 7.26-7.10 (m, 2H), 7.05 (t, J = 7.6 Hz, 1H), 6.99 (d, J = 7.6 Hz, 1H), 6.91-6.41 (m, 1H), 5.36 (dd, J = 5.2, 12.8 Hz, 1H), 5.30-5.07 (m, 1H), 4.82-4.72 (m, 1H), 4.27-4.14 (m, 2H), 3.90-3.78 (m, 3H), 3.77-3.67 (m, 3H), 3.66-3.58 (m, 2H), 3.53 (d, J = 4.8 Hz, 4H), 3.45 (d, J = 10.0 Hz, 1H), 3.19-2.95 (m, 3H), 2.94-2.84 (m, 1H), 2.76-2.62 (m, 3H), 2.60 (s, 1H), 2.41-2.27 (m, 3H), 2.25-2.13 (m, 3H), 2.06 (s, 3H), 2.03 (s, 1H), 2.01-1.93 (m, 3H), 1.92-1.82 (m, 3H), 1.82-1.70 (m, 2H) |
| I-719 | CLO | COC | 848.5 | 11.11 (s, 1H), 10.07-9.78 (m, 1H), 8.81 (d, J = 7.6 Hz, 1H), 8.45-8.17 (m, 3H), 7.61 (d, J = 9.2 Hz, 1H), 7.25-7.18 (m, 1H), 7.16-6.99 (m, 3H), 6.92-6.47 (m, 1H), 5.46-5.34 (m, 1H), 5.26-4.75 (m, 2H), 4.49-4.35 (m, 1H), 4.00-3.88 (m, 1H), 3.87-3.74 (m, 3H), 3.71-3.66 (m, 1H), 3.57 (s, 3H), 3.04-2.99 (m, 1H), 2.94-2.85 (m, 1H), 2.75-2.69 (m, 1H), 2.69-2.59 (m, 3H), 2.35-2.32 (m, 2H), 2.31-2.23 (m, 2H), 2.20-2.14 (m, 2H), 2.07-1.88 (m, 8H), 1.74-1.66 (m, 1H), 1.57-1.50 (m, 1H), 1.22-1.10 (m, 2H) |
| I-720 | COH | AJB | 932.5 | 11.09 (s, 1H), 9.50 (d, J = 6.4 Hz, 1H), 8.78 (d, J = 7.6 Hz, 1H), 8.39 (d, J = 4.4 Hz, 1H), 8.26 (d, J = 5.6 Hz, 1H), 7.26-6.99 (m, 1H), 6.99-6.91 (m, 2H), 6.89-6.44 (m, 2H), 5.35 (dd, J = 5.2, 12.4 Hz, 1H), 5.30-5.05 (m, 1H), 4.77 (d, J = 17.2 Hz, 1H), 4.18 (t, J = 10.8 Hz, 1H), 3.83-3.70 (m, 2H), 3.63 (s, 3H), 3.60-3.43 (m, 2H), 3.01-2.83 (m, 10H), 2.75-2.57 (m, 3H), 2.26-2.15 (m, 3H), 2.09-1.94 (m, 6H), 1.93-1.83 (s, 3H), 1.83-1.68 (m, 4H), 1.64-1.53 (m, 1H), 1.10-0.99 (m, 2H) |
| I-721 | COG | AJB | 932.4 | 11.08 (s, 1H), 9.50 (d, J = 6.0 Hz, 1H), 8.78 (d, J = 7.6 Hz, 1H), 8.39 (d, J = 4.0 Hz, 1H), 8.26 (d, J = 5.6 Hz, 1H), 7.25-6.92 (m, 3H), 6.90-6.44 (m, 2H), 5.35 (dd, J = 5.2, 12.4 Hz, 1H), 5.30-5.06 (m, 1H), 4.77 (d, J = 17.2 Hz, 1H), 4.23-4.13 (m, 1H), 3.84-3.72 (m, 2H), 3.63 (s, 3H), 3.59 (s, 1H), 3.48-3.42 (m, 1H), 3.01-2.84 (m, 10H), 2.75-2.67 (m, 1H), 2.64-2.58 (m, 2H), 2.27-2.15 (m, 3H), 2.08-1.94 (m, 6H), 1.93-1.84 (m, 3H), 1.83-1.70 (m, 4H), 1.63-1.53 (m, 1H), 1.10-0.98 (m, 2H) |
| I-722 | COI | AJB | 914.6 | 11.09 (s, 1H), 9.50 (d, J = 6.3 Hz, 1H), 8.78 (d, J = 8.0 Hz, 1H), 8.38 (d, J = 4.4 Hz, 1H), 8.26 (d, J = 5.6 Hz, 1H), 7.28-7.09 (m, 2H), 7.08-7.02 (m, 1H), 6.99 (d, J = 7.4 Hz, 1H), 6.66 (dd, J = 8.0, 165.0 Hz, 1H), 5.36 (dd, J = 5.6, 12.8 Hz, 1H), 5.18 (d, J = 82.4 Hz, 1H), 4.87-4.71 (m, 2H), 4.26-4.13 (m, 2H), 3.85-3.72 (m, 2H), 3.64-3.56 (m, 2H), 3.53 (s, 3H), 3.48-3.43 (m, 1H), 2.94-2.80 (m, 2H), 2.73-2.62 (m, 3H), 2.35-2.29 (m, 3H), 2.19-2.14 (m, 4H), 2.08-1.93 (m, 6H), 1.92-1.85 (m, 2H), 1.81-1.67 (m, 4H), 1.62-1.52 (m, 1H), 1.11-0.97 (m, 2H) |
| I-724 | COL | AJB | 900.4 | 11.09 (s, 1H), 9.50 (d, J = 6.4 Hz, 1H), 8.79 (dd, J = 1.6, 7.6 Hz, 1H), 8.42-8.12 (m, 2H), 7.26-6.96 (m, 1H), 6.90-6.43 (m, 2H), 6.21 (t, J = 8.4 Hz, 1H), 5.33-5.05 (m, 2H), 4.77 (d, J = 19.6 Hz, 1H), 4.24-4.15 (m, 1H), 3.99 (t, J = 6.4 Hz, 2H), 3.85-3.71 (m, 3H), 3.65-3.58 (m, 2H), 3.56-3.51 (m, 2H), 3.47-3.41 (m, 4H), 3.00-2.83 (m, 4H), 2.80-2.57 (m, 9H), 2.10-1.93 (m, 6H), 1.89 (d, J = 12.8 Hz, 2H), 1.81-1.69 (m, 2H), 1.68-1.59 (m, 1H), 1.15-0.99 (m, 2H) |
| I-725 | COM | AJB | 933.4 | 11.08 (s, 1H), 9.50 (d, J = 6.0 Hz, 1H), 8.78 (d, J = 8.0 Hz, 1H), 8.41-8.13 (m, 2H), 7.25-6.96 (m, 1H), 6.88-6.44 (m, 2H), 6.22 (t, J = 8.0 Hz, 1H), 5.31-5.07 (m, 2H), 4.80-4.73 (m, 1H), 4.27-4.15 (m, 1H), 3.94 (t, J = 6.8 Hz, 2H), 3.84-3.67 (m, 5H), 3.65-3.58 (m, 4H), 3.44 (s, 3H), 3.15-2.99 (m, 2H), 2.92-2.84 (m, 2H), 2.72-2.57 (m, 3H), 2.17-2.02 (m, 5H), 2.02-1.92 (m, 4H), 1.92-1.82 (m, 4H), 1.81-1.68 (m, 3H), 1.25-1.01 (m, 2H) |
| I-726 | CLL | ALU | 809.3 | 11.11 (s, 1H), 10.64 (s, 1H), 8.64 (s, 1H), 8.48-8.36 (m, 3H), 8.28-8.20 (m, 2H), 7.14-6.90 (m, 3H), 6.11 (s, 1H), 5.40 (d, J = 5.2, 12.4 Hz, 1H), 5.35-5.18 (m, 1H), 4.70-4.46 (m, 1H), 3.35 (s, 1H), 3.30 (s, 3H), 3.09 (s, 1H), 2.98-2.85 (m, 2H), 2.80-2.63 |

TABLE 3-continued

Compounds synthesized via Method 2, with the reductive amination of the corresponding amines and aldehydes.

| I-#[a] | Amine | Aldehyde | LCMS (ES+) m/z (M + H)+ | $^1$HNMR (400 MHZ, DMSO-d6) δ |
|---|---|---|---|---|
| | | | | (m, 3H), 2.37 (d, J = 7.2 Hz, 2H), 2.27-2.16 (m, 2H), 2.09-1.94 (m, 5H), 1.84-1.68 (m, 1H), 1.30-1.13 (m, 2H) |
| I-727 | CMO | CPZ | 707.4 | 11.12 (s, 1H), 10.39 (s, 1H), 8.40 (s, 1H), 8.35 (s, 1H), 7.97-7.93 (m, 2H), 7.63-7.57 (m, 2H), 7.56-7.53 (m, 1H), 7.19 (d, J = 7.6 Hz, 1H), 7.09-7.02 (m, 2H), 5.40 (dd, J = 5.2, 12.4 Hz, 1H), 4.90-4.65 (m, 1H), 4.49-4.41 (m, 1H), 3.59 (s, 3H), 3.10 (s, 1H), 2.95-2.86 (m, 2H), 2.65 (s, 3H), 2.35-2.31 (m, 2H), 2.24-2.09 (m, 5H), 2.06-1.88 (m, 8H), 1.87-1.79 (m, 1H), 1.75-1.68 (m, 1H), 1.20-1.13 (m, 2H) |
| I-728 | CQI | AJB | 901.6 | 11.08 (s, 1H), 9.50 (d, J = 6.4 Hz, 1H), 8.78 (d, J = 7.6 Hz, 1H), 8.38 (d, J = 4.0 Hz, 1H), 8.25 (d, J = 5.6 Hz, 1H), 7.11 (d, J = 3.6 Hz, 1H), 7.26-6.94 (m, 1H), 7.00-6.93 (m, 1H), 6.86 (d, J = 7.6 Hz, 1H), 6.76 (d, J = 7.6 Hz, 1H), 6.69 (d, J = 8.0 Hz, 1H), 6.45 (d, J = 8.0 Hz, 1H), 7.24 (d, J = 3.6 Hz, 1H), 6.88-6.42 (m, 1H), 6.71-6.42 (m, 1H), 5.32 (dd, J = 5.2, 12.8 Hz, 1H), 5.28 (s, 1H), 5.28-5.07 (m, 1H), 5.07 (s, 1H), 4.77 (d, J = 17.6 Hz, 1H), 4.54 (d, J = 7.6 Hz, 1H), 4.21-4.14 (m, 1H), 4.06 (s, 2H), 3.85-3.78 (m, 2H), 3.73 (d, J = 7.4 Hz, 1H), 3.63 (d, J = 8.8 Hz, 3H), 3.59 (s, 1H), 3.57 (s, 3H), 3.43 (s, 3H), 2.94-2.82 (m, 2H), 2.73-2.62 (m, 3H), 2.14 (d, J = 2.4 Hz, 2H), 2.03 (s, 1H), 1.98 (s, 1H), 1.87 (d, J = 11.6 Hz, 2H), 1.78-1.72 (m, 2H), 1.07-1.01 (m, 1H) |
| I-729 | CQJ | AJB | 911.4 | 11.09 (s, 1H), 9.49 (d, J = 6.0 Hz, 1H), 8.78 (d, J = 7.6 Hz, 1H), 8.38 (d, J = 4.4 Hz, 1H), 8.25 (d, J = 5.6 Hz, 1H), 7.32-7.07 (m, 2H), 7.05-6.96 (m, 2H), 6.66 (dd, J = 7.6, 165.2 Hz, 1H), 5.36 (dd, J = 5.2, 12.4 Hz, 1H), 5.29-4.92 (m, 1H), 4.77 (d, J = 17.6 Hz, 1H), 4.14 (dd, J = 8.8, 16.8 Hz, 2H), 3.82-3.73 (m, 2H), 3.62 (s, 1H), 3.59 (s, 1H), 3.54 (s, 3H), 3.43 (s, 2H), 3.21 (s, 3H), 2.92-2.84 (m, 1H), 2.73-2.61 (m, 2H), 2.45 (s, 5H), 2.38-2.29 (m, 4H), 2.25-2.19 (m, 2H), 2.10 (d, J = 7.2 Hz, 2H), 2.05-1.94 (m, 5H), 1.88 (d, J = 11.2 Hz, 2H), 1.73 (q, J = 11.6 Hz, 2H), 1.61-1.51 (m, 1H), 1.08-0.97 (m, 2H) |
| I-730[c] | CQO | CQL | 854.4 | 11.08 (s, 1H), 9.50 (d, J = 5.6 Hz, 1H), 8.78 (d, J = 7.6 Hz, 1H), 8.38 (d, J = 4.4 Hz, 1H), 8.25 (d, J = 5.6 Hz, 1H), 7.29-6.91 (m, 2H), 6.89-6.41 (m, 3H), 5.41-5.03 (m, 2H), 4.77 (d, J = 16.0 Hz, 1H), 4.25-4.11 (m, 1H), 3.89 (d, J = 2.4 Hz, 2H), 3.83-3.71 (m, 2H), 3.65-3.59 (m, 3H), 3.58-3.53 (m, 3H), 3.50-3.39 (m, 1H), 3.18 (t, J = 6.4 Hz, 1H), 2.94-2.81 (m, 1H), 2.63 (s, 2H), 2.59 (s, 4H), 2.43-2.20 (m, 5H), 2.11-1.87 (m, 7H), 1.82-1.70 (m, 2H), 1.40 (q, J = 11.2 Hz, 2H) |
| I-732 | CQQ | AJB | 901.3 | 11.07 (s, 1H), 9.50 (d, J = 6.4 Hz, 1H), 8.78 (d, J = 8.0 Hz, 1H), 8.38 (d, J = 4.4 Hz, 1H), 8.25 (d, J = 5.6 Hz, 1H), 7.11 (d, J = 3.2 Hz, 1H), 7.00-6.84 (m, 2H), 6.79-6.42 (m, 3H), 5.32 (d, J = 4.4, 12.4 Hz, 1H), 5.28-5.06 (m, 1H), 4.76 (d, J = 18.8 Hz, 1H), 4.55 (t, J = 6.0 Hz, 1H), 4.50-4.34 (m, 1H), 4.20-4.13 (m, 1H), 4.09-4.00 (m, 2H), 3.80 (s, 1H), 3.66-3.60 (m, 3H), 3.56 (s, 3H), 3.45 (d, J = 9.2 Hz, 2H), 3.10-2.98 (m, 2H), 2.89-2.83 (m, 1H), 2.74-2.65 (m, 3H), 2.17 (d, J = 6.4 Hz, 2H), 2.01 (dd, J = 3.6, 5.6 Hz, 4H), 1.87 (dd, J = 3.6, 11.2 Hz, 3.2H), 1.81-1.68 (m, 3H), 1.61-1.36 (m, 3H), 1.07-0.99 (m, 2H) |
| I-733 | CQS | AJB | 901.2 | 11.08 (s, 1H), 9.50 (d, J = 6.0 Hz, 1H), 8.78 (d, J = 7.6 Hz, 1H), 8.38 (d, J = 4.4 Hz, 1H), 8.25 (d, J = 5.6 Hz, 1H), 7.26-6.93 (m, 2H), 6.89-6.43 (m, 3H), 5.32 (dd, J = 5.6, 12.4 Hz, 1H), 5.29-5.05 (m, 1H), 4.77 (d, J = 18.0 Hz, 1H), 4.59-4.52 (m, 1H), 4.51-4.31 (m, 1H), 4.22-4.12 (m, 1H), 4.10-4.01 (m, 2H), 3.83-3.72 (m, 2H), 3.61 (d, J = 12.0 Hz, 3H), 3.56 (s, 3H), 3.51-3.37 (m, 2H), 3.09-3.00 (m, 1H), 2.93-2.82 (m, 1H), 2.75-2.61 (m, 3H), 2.17 (d, J = 6.4 Hz, 2H), 2.06-1.93 (m, 8H), 1.91-1.84 (m, 2H), 1.80-1.69 (m, 2H), 1.63-1.52 (m, 1H), 1.49-1.38 (m, 1H), 1.09-0.98 (m, 2H) |
| I-734 | CLO | CQT | 849.3 | 11.11 (s, 1H), 10.69-10.48 (m, 1H), 8.99 (s, 1H), 8.83 (d, J = 7.6 Hz, 1H), 8.51 (s, 1H), 8.43-8.37 (m, 1H), 8.30 (d, J = 5.2 Hz, 1H), 7.17-7.02 (m, 3H), 6.94-6.47 (m, 1H), 5.50-5.37 (m, 1H), 5.35 (s, 1H), 4.90-4.76 (m, 1H), 4.60-4.48 (m, 1H), 3.93-3.84 (m, 2H), 3.78-3.72 (m, 2H), 3.57 (s, 3H), 3.27-3.18 (m, 2H), 3.04-3.00 (m, 1H), 2.95-2.85 (m, 2H), 2.71-2.63 (m, 3H), 2.37-2.28 (m, 4H), 2.23-2.18 (m, 2H), 2.10-1.98 (m, 6H), 1.93-1.88 (m, 1H), 1.77-1.67 (m, 1H), 1.24-1.11 (m, 2H) |
| I-736[h] | CMY | CJD | 889.7 | 11.09 (s, 1H), 9.50 (d, J = 6.0 Hz, 1H), 8.78 (d, J = 7.6 Hz, 1H), 8.38 (d, J = 4.4 Hz, 1H), 8.25 (d, J = 5.6 Hz, 1H), 7.30-7.09 (m, 2H), 7.09-6.99 (m, 2H), 6.90-6.41 (m, 1H), 5.37 (dd, J = 5.2, 12.8 Hz, 1H), 5.29-5.05 (m, 1H), 4.77 (d, J = 16.4 Hz, 1H), 4.26 (t, J = 7.6 Hz, 1H), 4.22-4.12 (m, 1H), 3.80 (s, 1H), 3.83-3.71 |

TABLE 3-continued

Compounds synthesized via Method 2, with the reductive amination of the corresponding amines and aldehydes.

| I-#[a] | Amine | Alde-hyde | LCMS (ES+) m/z (M + H)+ | 1HNMR (400 MHZ, DMSO-d6) δ |
|---|---|---|---|---|
| | | | | (m, 2H), 3.70-3.56 (m, 3H), 3.52 (s, 3H), 3.44 (d, J = 10.4 Hz, 1H), 3.01-2.82 (m, 2H), 2.79-2.57 (m, 6H), 2.46-2.30 (m, 2H), 2.12-2.04 (m, 2H), 2.04-1.93 (m, 3H), 1.86 (d, J = 12.0 Hz, 2H), 1.81-1.68 (m, 3H), 1.56-1.39 (m, 3H) |
| I-737 | CQU | BRR | 839.3 | 11.08 (s, 1H), 10.20 (s, 1H), 9.06 (s, 1H), 8.60 (s, 1H), 8.54-8.34 (m, 3H), 8.23 (d, J = 7.2 Hz, 1H), 6.81 (d, J = 8.4 Hz, 1H), 6.28 (t, J = 8.4 Hz, 1H), 5.30 (d, J = 5.2, 12.8 Hz, 1H), 4.65-4.48 (m, 1H), 3.93 (d, J = 7.2 Hz, 2H), 3.71 (d, J = 7.2 Hz, 2H), 3.44 (d, J = 1.2 Hz, 3H), 2.94-2.83 (m, 1H), 2.77-2.57 (m, 6H), 2.25 (d, J = 7.2 Hz, 2H), 2.22-2.14 (m, 2H), 2.09-1.91 (m, 7H), 1.74-1.58 (m, 1H), 1.22-1.03 (m, 2H) |
| I-738 | CQV | AJB | 933.4 | 11.09 (s, 1H), 9.51 (d, J = 6.0 Hz, 1H), 8.79 (d, J = 7.6 Hz, 1H), 8.39 (d, J = 4.4 Hz, 1H), 8.26 (d, J = 5.6 Hz, 1H), 7.27-6.96 (m, 1H), 6.90-6.43 (m, 2H), 6.22 (t, J = 8.4 Hz, 1H), 5.33-5.27 (m, 1H), 5.09-4.68 (m, 2H), 4.25-4.11 (m, 1H), 3.94 (t, J = 6.8 Hz, 2H), 3.85-3.73 (m, 2H), 3.74-3.67 (m, 2H), 3.61 (d, J = 10.4 Hz, 3H), 3.58-3.46 (m, 2H), 3.44 (s, 3H), 2.95-2.76 (m, 3H), 2.70-2.58 (m, 4H), 2.38-2.25 (m, 1H), 2.13 (d, J = 7.2 Hz, 3H), 2.09-1.95 (m, 5H), 1.92-1.85 (m, 2H), 1.84-1.71 (m, 3H), 1.71-1.63 (m, 1H), 1.57 (d, J = 7.6 Hz, 1H), 1.10-0.96 (m, 2H) |
| I-739[h] | CQW | CJD | 814.5 | 11.09 (s, 1H), 9.50 (d, J = 5.8 Hz, 1H), 8.79 (d, J = 7.8 Hz, 1H), 8.39 ( d, J = 4.4 Hz, 1H), 8.26 (d, J = 5.4 Hz, 1H), 7.31-7.03 (m, 1H), 6.95 (t, J = 8.4 Hz, 1H), 6.89-6.44 (m, 3H), 5.34 (J = 5.4, 12.6 Hz, 1H), 5.29-5.06 (m, 1H), 4.77 (J = 16.8 Hz, 1H), 4.57-4.46 (m, 1H), 4.25-4.13 (m, 1H), 3.84-3.72 (m, 2H), 3.67-3.58 (m, 2H), 3.56 (s, 3H), 3.45 (d, J = 10.0 Hz, 1H), 2.96-2.83 (m, 1H), 2.77 (s, 2H), 2.72-2.59 (m, 2H), 2.17-1.86 (m, 10H), 1.85-1.59 (m, 5H), 1.47 (J = 11.2 Hz, 2H) |
| I-740[h] | CQW | CQX | 746.1 | 11.21-10.89 (m, 1H), 10.20 (s, 1H), 9.06 (s, 1H), 8.60 (s, 1H), 8.54-8.45 (m, 2H), 8.41 (t, J = 8.0 Hz, 1H), 8.23 (d, J = 7.2 Hz, 1H), 6.99-6.92 (m, 1H), 6.81 (d, J = 8.0 Hz, 1H), 6.73 (d, J = 8.0 Hz, 1H), 5.33 (dd, J = 6.0, 12.4 Hz, 1H), 4.55 (dd, J = 2.8, 12.4 Hz, 2H), 3.57 (s, 3H), 2.80 (d, J = 4.4 Hz, 3H), 2.70-2.63 (m, 4H), 2.26-2.19 (m, 2H), 2.07-1.88 (m, 8H), 1.79-1.70 (m, 2H), 1.61-1.50 (m, 2H) |
| I-741[h] | CQW | CQY | 745.4 | 11.09 (s, 1H), 10.36 (s, 1H), 8.44-8.33 (m, 3H), 8.29 (s, 1H), 8.17 (d, J = 7.6 Hz, 1H), 7.65-7.51 (m, 2H), 6.99-6.89 (m, 1H), 6.84-6.77 (m, 1H), 6.76-6.69 (m, 1H), 5.34 (dd, J = 5.2, 12.4 Hz, 1H), 4.52 (s, 1H), 4.49-4.36 (m, 1H), 3.60-3.53 (m, 3H), 2.94-2.76 (m, 3H), 2.75-2.57 (m, 3H), 2.42-2.35 (m, 1H), 2.24-2.14 (m, 2H), 2.08-1.82 (m, 8H), 1.74 (d, J = 7.6 Hz, 2H), 1.65-1.49 (m, 2H) |
| I-742 | CRA | AJB | 933.2 | 11.08 (s, 1H), 9.50 (d, J = 6.4 Hz, 1H), 8.78 (d, J = 7.6 Hz, 1H), 8.38 (d, J = 4.4 Hz, 1H), 8.29-8.12 (m, 1H), 7.11 (t, J = 3.2, 53.2 Hz, 1H), 6.89-6.41 (m, 2H), 6.21 (s, 1H), 5.32-5.03 (m, 2H), 4.77 (d, J = 17.6 Hz, 1H), 4.56-4.27 (m, 1H), 4.25-4.10 (m, 1H), 3.92 (t, J = 7.2 Hz, 2H), 3.84-3.70 (m, 4H), 3.69-3.54 (m, 4H), 3.43 (d, J = 1.6 Hz, 3H), 3.03-2.94 (m, 1H), 2.92-2.81 (m, 2H), 2.72-2.65 (m, 2H), 2.58 (s, 2H), 2.16 (d, J = 6.0 Hz, 2H), 2.08-1.92 (m, 8H), 1.87 (d, J = 12.4 Hz, 2H), 1.82-1.67 (m, 2H), 1.63-1.48 (m, 1H), 1.46-1.32 (m, 1H), 1.09-0.94 (m, 2H) |
| I-743 | CRF | AJB | 933.6 | 11.14 (s, 1H), 9.50 (d, J = 6.0 Hz, 1H), 8.78 (d, J = 7.6 Hz, 1H), 8.39 (d, J = 4.4 Hz, 1H), 8.26 (d, J = 5.6 Hz, 1H), 7.93 (d, J = 5.6 Hz, 1H), 7.27-6.93 (m, 2H), 6.66 (dd, J = 7.6, 165.6 Hz, 1H), 5.39 (dd, J = 5.2, 12.4 Hz, 1H), 5.18 (d, J = 82.8 Hz, 1H), 4.77 (d, J = 16.8 Hz, 1H), 4.24-4.10 (m, 1H), 3.88-3.69 (m, 2H), 3.65-3.54 (m, 4H), 3.49-3.40 (m, 1H), 3.04 (s, 4H), 2.95-2.84 (m, 6H), 2.75-2.58 (m, 3H), 2.27-2.14 (m, 3H), 2.12-1.95 (m, 6H), 1.94-1.70 (m, 7H), 1.66-1.52 (m, 1H), 1.13-0.94 (m, 2H) |
| I-744 | CRG | AJB | 933.6 | 11.22-11.04 (m, 1H), 9.50 (d, J = 5.6 Hz, 1H), 8.78 (d, J = 7.6 Hz, 1H), 8.38 (d, J = 4.4 Hz, 1H), 8.26 (d, J = 5.2 Hz, 1H), 7.93 (d, J = 5.6 Hz, 1H), 7.26-6.95 (m, 2H), 6.66 (dd, J = 7.6, 164.4 Hz, 1H), 5.38 (dd, J = 5.2, 12.0 Hz, 1H), 5.18 (d, J = 82.8 Hz, 1H), 4.77 (d, J = 17.6 Hz, 1H), 4.25-4.09 (m, 1H), 3.83-3.73 (m, 2H), 3.66-3.59 (m, 2H), 3.57 (s, 3H), 3.08-3.00 (m, 5H), 2.97-2.81 (m, 8H), 2.71-2.63 (m, 3H), 2.24-2.14 (m, 3H), 2.08-2.01 (m, 4H), 1.92-1.85 (m, 2H), 1.83-1.67 (m, 4H), 1.62-1.53 (m, 1H), 1.10-0.98 (m, 2H) |
| I-745[c] | CQO | CRH | 872.5 | 11.09 (s, 1H), 9.50 (d, J = 5.6 Hz, 1H), 8.78 (d, J = 7.6 Hz, 1H), 8.39 (d, J = 3.2 Hz, 1H), 8.26 (d, J = 5.6 Hz, 1H), 7.26-6.97 (m, 1H), 6.91-6.44 (m, 3H), 5.35-5.07 (m, 2H), 4.77 (d, J = 18.8 Hz, 1H), 4.26-4.15 (m, 1H), 3.94 (d, J = 6.2 Hz, 2H), 3.87 (s, |

TABLE 3-continued

Compounds synthesized via Method 2, with the reductive amination of the corresponding amines and aldehydes.

| I-#[a] | Amine | Aldehyde | LCMS (ES+) m/z (M + H)+ | 1HNMR (400 MHZ, DMSO-d6) δ |
|---|---|---|---|---|
| | | | | 2H), 3.80 (s, 2H), 3.60 (s, 5H), 3.44 (d, J = 9.2 Hz, 1H), 3.30 (s, 3H), 2.94-2.76 (m, 2H), 2.65 (d, J = 17.2 Hz, 3H), 2.33 (s, 4H), 2.11-2.05 (m, 2H), 1.96 (d, J = 11.2 Hz, 5H), 1.83-1.73 (m, 2H), 1.51-1.36 (m, 2H) |
| I-746 | COH | CRI | 932.5 | 11.09 (s, 1H), 9.69 (s, 1H), 8.75 (d, J = 7.6 Hz, 1H), 8.38 (s, 1H), 8.25 (s, 1H), 7.31-7.01 (m, 1H), 7.00-6.86 (m, 3H), 6.37 (d, J = 7.6 Hz, 1H), 5.35 (dd, J = 5.2, 12.8 Hz, 1H), 4.74 (s, 4H), 4.38 (s, 4H), 4.18 (t, J = 11.6 Hz, 1H), 3.63 (s, 3H), 3.07-2.75 (m, 12H), 2.75-2.66 (m, 1H), 2.65-2.57 (m, 1H), 2.28-2.13 (m, 3H), 2.12-1.95 (m, 4H), 1.94-1.69 (m, 6H), 1.65-1.50 (m, 1H), 1.13-0.94 (m, J = 12.8 Hz, 2H) |
| I-747 | COG | CRI | 932.3 | 11.15-10.99 (m, 1H), 9.69 (s, 1H), 8.76 (d, J = 7.6 Hz, 1H), 8.37 (s, 1H), 8.25 (s, 1H), 7.16 (t, J = 53.6 Hz, 1H), 7.01-6.91 (m, 2H), 6.88 (d, J = 7.2 Hz, 1H), 6.38 (d, J = 7.6 Hz, 1H), 5.35 (dd, J = 5.2, 12.8 Hz, 1H), 4.74 (s, 4H), 4.39 (s, 4H), 4.24-4.09 (m, 1H), 3.63 (s, 3H), 2.79 (s, 12H), 2.73 (s, 1H), 2.59 (s, 1H), 2.27-2.14 (m, 3H), 2.10-1.97 (m, 4H), 1.93-1.72 (m, 6H), 1.65-1.52 (m, 1H), 1.12-0.98 (m, 2H) |
| I-748 | CND | AJB | 882.3 | 11.07 (s, 1H), 9.50 (d, J = 6.0 Hz, 1H), 8.77 (d, J = 7.6 Hz, 1H), 8.38 (d, J = 4.4 Hz, 1H), 8.25 (d, J = 5.6 Hz, 1H), 7.19 (s, 1H), 6.86 (d, J = 8.0 Hz, 1H), 6.75-6.42 (m, 2H), 5.37-5.01 (m, 2H), 4.76 (d, J = 18.0 Hz, 1H), 4.23-4.12 (m, 1H), 3.93 (t, J = 6.8 Hz, 2H), 3.83-3.72 (m, 2H), 3.66-3.59 (m, 2H), 3.56 (s, 3H), 3.52-3.46 (m, 5H), 2.93-2.79 (m, 2H), 2.71-2.56 (m, 4H), 2.46-2.26 (m, 6H), 2.13 (d, J = 7.2 Hz, 2H), 2.09-1.93 (m, 5H), 1.88 (d, J = 12.0 Hz, 2H), 1.81-1.65 (m, 2H), 1.65-1.50 (m, 1H), 1.11-0.96 (m, 2H) |

[a]For Method 2, when the amine is the HCl salt, TEA was added to free base the salt, followed by HOAc to adjust the pH to 3-4. Other standard reductive amination conditions could be applied, including NaBH3CN with 4Å molecular sieves, TEA, AcOH, in DMF, and KOAc could also be used in place of the TEA/HOAc combination. The reductive amination was run anywhere from 2-16 hrs and the reaction temperature was run anywhere from −15° C. to 60° C. The final products were isolated under standard purification techniques including reverse HPLC, silica gel chromatography, and prep-TLC with appropriate solvent conditions.

[b]The product of the coupling was further separated by SFC (column: REGIS(S,S)WHELK-O1(250 mm*25 mm, 10 um); mobile phase: [Neu-ETOH]; B%: 70%-70%, 3;30 min) and then by prep-HPLC (column: Phenomenex luna C18 150*25 mm* 10 um;mobile phase: [water(0.225% FA)-ACN]; B%: 18%-48%, 10 min). Absolute stereochemistry of the diastereomers was assigned arbitrarily.

[c]Ketone used in place of aldehyde for the reductive coupling.

[d]The product of the reductive amination was further separated by HPLC to give the chiral compound. The absolute stereochemistry was assigned arbitrarily.

[e]The product of the coupling was separated by SFC (column: DAICEL CHIRALCEL OD(250 mm*30 mm, 10 um); mobile phase: [ACN/MeOH(0.1% NH3H2O)]; B%: 60%-60%, A4.73; 66 min) and then prep-HPLC (column: Phenomenex luna C18 150*25 mm* 10 um;mobile phase: [water(FA)-ACN]; B%: 2%-32%, 10 min). The absolute stereochemistry of the diastereomers was assigned arbitrarily.

[f]Prep HPLC was used to separate the cis and trans diastereomer, where the isomers were confirmed by 2D NMR.

[g]The product of the reductive amination was further separated SFC (column: DAICEL CHIRALPAK AD(250 mm*30 mm, 10 um); mobile phase: [ACN/IPA(0.1% NH3H2O)]; B%: 60%-60%, A7; 91 min) and prep-HPLC purification (column: Phenomenex Luna C18 150*25 mm*10 um; mobile phase: [water(FA)-ACN]; B%: 7%-37%, 8 min). The absolute stereochemistry of the diastereomers was assigned arbitrarily.

[h]The product of the coupling was purified by standard techniques such as prep-TLC, then the cis/trans isomers were further obtained by separation with prep-HPLC to give the chiral compound. The cis/trans configurations were assigned arbitrarily.

Examples 3: Syntheses of N-[3-(difluoromethyl)-1-[4-[[4-[3-[1-[(3R)-2,6-dioxo-3-piperidyl]-3-methyl-2-oxo-benzimidazol-4-yl]prop-2-ynyl]piperazin-1-yl]methyl]cyclohexyl]pyrazol-4-yl]-5-[(1R,4R)-2-oxa-5-azabicyclo[2.2.1]heptan-5-yl]pyrazolo[1,5-a]pyrimidine-3-carboxamide (I-71) and N-[3-(difluoromethyl)-1-[4-[[4-[3-[1-[(3S)-2,6-dioxo-3-piperidyl]-3-methyl-2-oxo-benzimidazol-4-yl]prop-2-ynyl]piperazin-1-yl]methyl]cyclohexyl]pyrazol-4-yl]-5-[(1R,4R)-2-oxa-5-azabicyclo[2.2.1]heptan-5-yl]pyrazolo[1,5-a]pyrimidine-3-carboxamide (I-72)

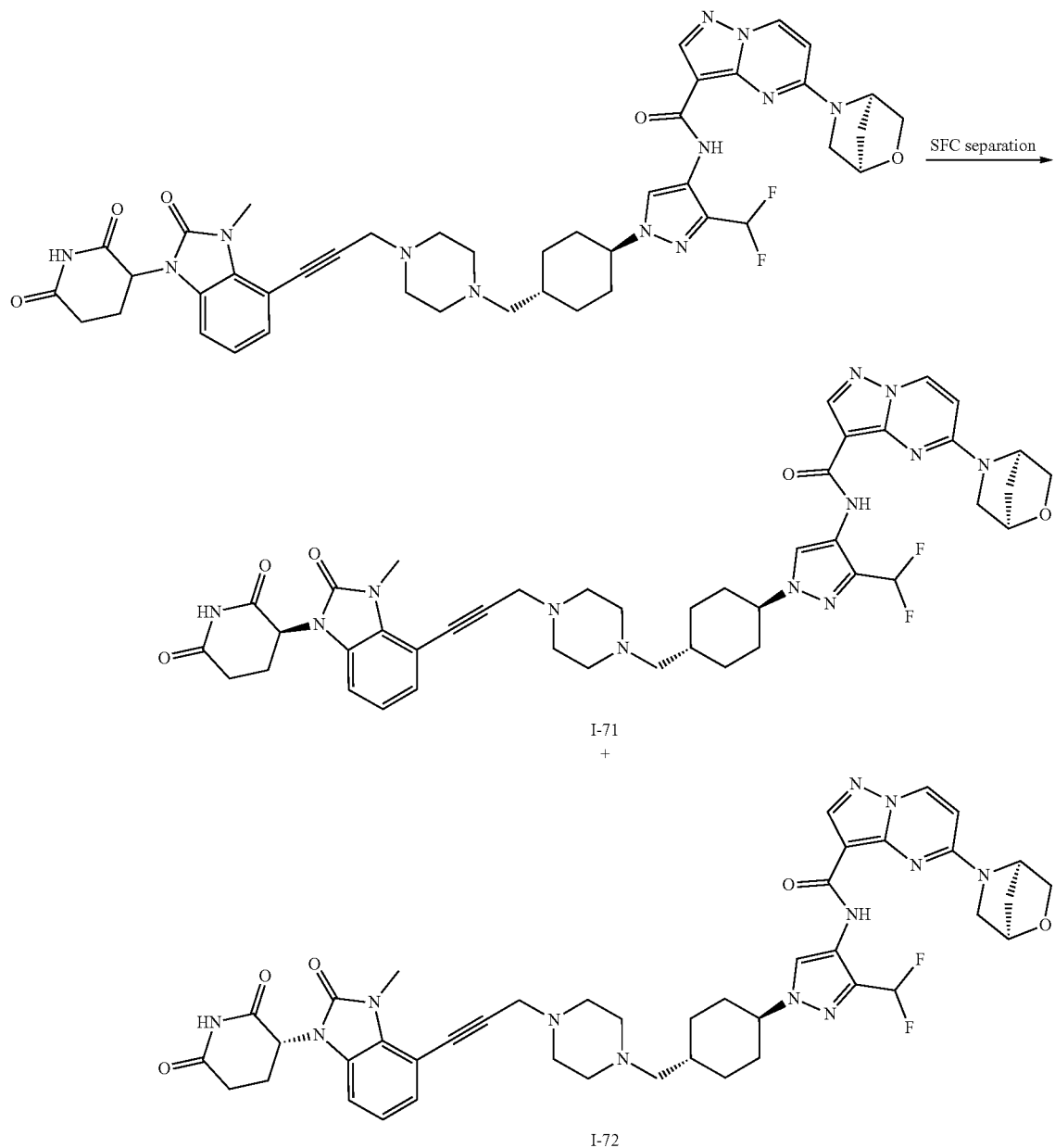

I-71

+

I-72

N-[3-(difluoromethyl)-1-[4-[[4-[3-[1-(2,6-dioxo-3-piperidyl)-3-methyl-2-oxo-benzimidazol-4-yl]prop-2-ynyl]piperazin-1-yl]methyl]cyclohexyl]pyrazol-4-yl]-5-[(1R,4R)-2-oxa-5-azabicyclo[2.2.1]heptan-5-yl]pyrazolo[1,5-a]pyrimidine-3-carboxamide (100 mg, 117 umol, Example I-31) was purified by SFC separation (column: REGIS (S,S)WHELK-O1 (250 mm*25 mm, 10 um); mobile phase: [0.1% NH$_3$H$_2$O MEOH]; B %, 10 min) to -[3-(difluoromethyl)-1-[4-[[4-[3-[1-[(3R)-2,6-dioxo-3-piperidyl]-3-methyl-2-oxo-benzimidazol-4-yl]prop-2-ynyl]piperazin-1-yl]methyl]cyclohexyl]pyrazol-4-yl]-5-[(1R,4R)-2-oxa-5-azabicyclo[2.2.1]heptan-5-yl]pyrazolo[1,5-a]pyrimidine-3-carboxamide (31.8 mg, 31% yield, FA salt, peak 1) as a white solid ($^1$H NMR (400 MHz, DMSO-d$_6$) δ11.11 (s, 1H), 9.49 (d, J=6.0 Hz, 1H), 8.77 (d, J=7.6 Hz, 1H), 8.37 (d, J=4.4 Hz, 1H), 8.25 (d, J=5.6 Hz, 1H), 7.26-6.95 (m, 4H), 6.65 (d, J=7.6 Hz, 1H), 5.39 (d, J=5.6 Hz, 1H), 5.27 (s, 1H), 4.76 (d, J=16.4 Hz, 1H), 4.24-4.09 (m, 1H), 3.86-3.67 (m, 3H), 3.64 (s, 3H), 3.62-3.54 (m, 4H), 2.93-2.84 (m, 1H), 2.76-2.63 (m, 2H), 2.56 (s, 4H), 2.40 (d, J=1.6 Hz, 3H), 2.12 (d, J=7.2 Hz, 2H), 2.05-1.86 (m, 7H), 1.79-1.67 (m, 2H), 1.63-1.51 (m, 1H), 1.10-0.96 (m, 2H); LC-MS (ESI+) m/z 851.4 (M+H)$^+$; and N-[3-(difluoromethyl)-1-[4-[[4-[3-[1-[(3S)-2,6-dioxo-3-piperidyl]-3-methyl-2-oxo-benzimidazol-4-yl]prop-2-ynyl]piperazin-1-yl]methyl]cyclohexyl]pyrazol-4-yl]-5-[(1R,4R)-2-oxa-5-azabicyclo[2.2.1]heptan-5-yl]pyrazolo[1,5-a]pyrimidine-3-carboxamide (column: REGIS(S,S) WHELK-O1 (250 mm*25 mm, 10 um); mobile phase: [0.1% NH$_3$H$_2$O IPA]; B %: 60%-60%, 4.8; 70 min) to (24.0 mg, 24% yield, FA salt, peak 2) as a white solid (1H NMR (400 MHz, DMSO-d$_6$) δ11.12 (s, 1H), 9.50 (d, J=6.0 Hz, 1H), 8.78 (d, J=7.6 Hz, 1H), 8.38 (d, J=4.4 Hz, 1H), 8.25 (d, J=5.6 Hz, 1H), 7.17-6.98 (m, 4H), 6.66 (d, J=7.6 Hz, 1H), 5.39 (d, J=5.2 Hz, 1H), 5.18 (d, J=81.6 Hz, 1H), 4.77 (d, J=17.2 Hz, 1H), 4.26-4.08 (m, 1H), 3.82-3.73 (m, 2H), 3.65 (s, 3H), 3.63-3.55 (m, 4H), 3.45 (d, J=9.6 Hz, 1H), 2.95-2.83 (m, 1H), 2.73-2.64 (m, 2H), 2.57 (s, 4H), 2.45-2.37 (m, 3H), 2.13 (d, J=7.2 Hz, 2H), 2.05-1.87 (m, 7H), 1.79-1.69 (m, 2H), 1.64-1.51 (m, 1H), 1.11-0.96 (m, 2H); LC-MS (ESI+) m/z 851.3 (M+H)$^+$). Absolute stereochemistry of the diastereomer was assigned arbitrarily.

Example 4: Synthesis of N-[1-[4-[cyano-[4-[3-[1-(2,6-dioxo-3-piperidyl)-3-methyl-2-oxo-benzimidazol-4-yl]prop-2-ynoxy]-1-piperidyl]methyl]cyclohexyl]-3-(difluoromethyl)pyrazol-4-yl]-5-[(1R,4R)-2-oxa-5-azabicyclo[2.2.1]heptan-5-yl]pyrazolo[1,5-a]pyrimidine-3-carboxamide (I-193)

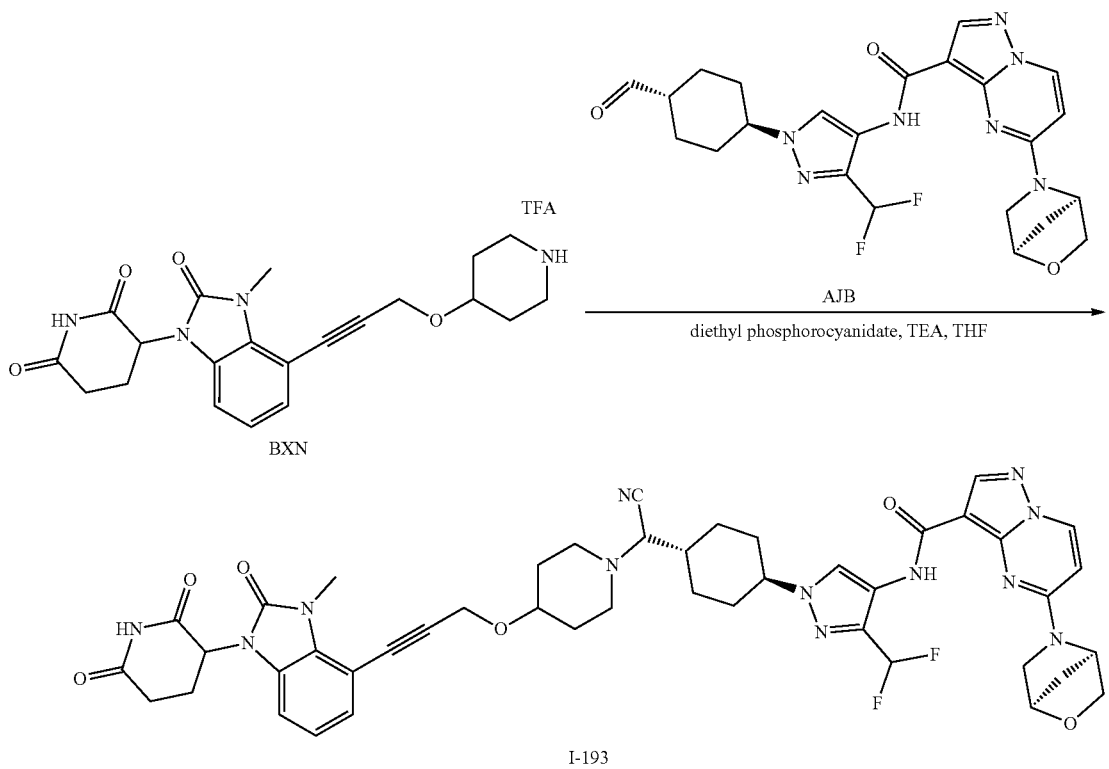

To a solution of 3-[3-methyl-2-oxo-4-[3-(4-piperidyloxy)prop-1-ynyl]benzimidazol-1-yl] piperidine-2,6-dione (50 mg, 97.9 umol, TFA, Intermediate BXN), diethoxyphosphorylformonitrile (15.9 mg, 97.9 umol) and TEA (8.26 mg, 81.6 umol) in THF (1 mL) was added N-[3-(difluoromethyl)-1-(4-formylcyclohexyl)pyrazol-4-yl]-5-[(1R,4R)-2-oxa-5-azabicyclo[2.2.1]heptan-5-yl]pyrazolo[1,5-a]pyrimidine-3-carboxamide (39.6 mg, 81.6 umol, Intermediate AJB) in THF (1 mL). The mixture was then stirred at 25° C. for 3 hrs. On completion, the mixture was concentrated to give a residue. The residue was purified by column chromatography (SiO$_2$, DCM/MeOH=100/1 to 10/1) then normal phase HPLC (column: Welch Ultimate XB-CN 150*40 mm*10 um; mobile phase: [Heptane-EtOH]; B %: 70%-90%, 15 min) to give the title compound (29.5 mg, 38% yield) as a white solid. $^1$H NMR (400 MHz, DMSO-d$_6$) δ 11.12 (s, 1H), 9.50 (d, J=6.4 Hz, 1H), 8.78 (d, J=7.6 Hz, 1H), 8.40 (d, J=4.4 Hz, 1H), 8.26 (d, J=5.6 Hz, 1H), 7.27-7.08 (m, 3H), 7.07-6.99 (m, 1H), 6.66 (dd, J=7.6, 164.8 Hz, 1H), 5.40 (dd, J=5.6, 12.6 Hz, 1H), 5.18 (d, J=82.4 Hz, 1H), 4.77 (d, J=18.8 Hz, 1H), 4.50 (s, 2H), 4.26-4.11 (m, 1H), 3.84-3.71 (m, 2H), 3.65 (s, 3H), 3.63-3.53 (m, 3H), 2.96-2.85 (m, 1H), 2.80-2.63 (m, 4H), 2.46-2.35 (m, 2H), 2.15-2.01 (m, 5H), 1.98-1.75 (m, 7H), 1.65-1.50 (m, 2H), 1.32-1.18 (m, 2H), 1.12-1.00 (m, 1H); LC-MS (ESI$^+$) m/z 891.4 (M+H)$^+$.

Example 5: IRAK4 MSD Degradation in OCI-LY10

Degradation of IRAK4 in OCI-LY10 was quantitatively measured using Meso Scale Discovery technology. OCI-LY10 cells were seeded in 96-well plates (Corning 3799) with a density of 300,000 cells per well in 100 µL fresh media. Compounds were then added to the assay plates with a final top concentration of 1 to 10 µM in a 1:3 dilution series with total of 8 doses. The assay plates were then incubated for 4 to 24 hours at 37° C. under 5% $CO_2$. The assay plates were then centrifuged for 5 minutes and the cell pellets were treated with 100 µL/well RIPA lysis buffer (Boston Bio-Products BP-115D) with proteinase inhibitors. To prepare MSD assay plates (Meso Scale Discovery Catalog number L15XA-3), the plates were coated with 2 µg/mL capture antibody (mouse Anti-IRAK4 antibody [2H9], ab119942) in PBS, at 40 µL/well. The plates were then incubated overnight at 4° C., washed 3 times with 150 µL/well TBST buffer (Cell Signaling Technology, Catalog number 9997S) and blocked with 150 µL/well blocking buffer (Meso Scale Discovery Catalog number R93BA-4). Cell lysates were then added to MSD assay plates and the plates were incubated at room temperature for 1 hour. The plates were then washed 3 times with 150 µL/well TBST buffer and 25 µL/well primary detection antibody (rabbit Anti-IRAK4 antibody [Y279], from Abcam. Catalog number ab32511, 1 µg/mL). The assay plates were then incubated at room temperature for 1 hour, washed 3 times with 150 µL/well TBST buffer and 25 µL/well secondary detection antibody, SULFO-TAG anti-rabbit antibody were added (anti-rabbit antibody from Meso Scale Discovery, Catalog number R32AB-1, 1 µg/mL). The assay plates were then incubated at room temperature for 1 hour, washed 3 times with 150 µL/well TBST buffer, and 150 µL/well MSD reading buffer (Meso Scale Discovery catalog number R92TC-2) was added. The plates were then analyzed by a MSD reader (Meso Scale Discovery, Model Quick Plex SQ 120). The data was then analyzed by software Prism 7.0 from GraphPad and the dose-depended IRAK4 degradation were fit using a three-parameter logistic equation to calculate $DC_{50}$.

IRAK4 MSD degradation results in OCI-LY10 cells for compounds of the invention are presented in Table 4. The letter codes for IRAK4 $DC_{50}$ include: A (<0.01 µM); B (0.01 to <0.1 µM); C (0.1 to 0.2 µM); and D (>0.2 µM or not tested).

TABLE 4

IRAK4 MSD Degradation in OCI-LY10 Results

| I-# | IRAK4 degradation in OCI-LY10 at 4 hrs: $DC_{50}$ (µM) | IRAK4 degradation in OCI-LY10 at 24 hrs: $DC_{50}$ (µM) |
| --- | --- | --- |
| I-1 | B | D |
| I-2 | A | D |
| I-3 | A | D |
| I-4 | A | D |
| I-5 | A | D |
| I-6 | A | D |
| I-7 | A | D |
| I-8 | A | D |
| I-9 | B | D |
| I-10 | A | D |
| I-11 | D | D |
| I-12 | D | D |
| I-13 | D | D |
| I-14 | D | D |
| I-15 | D | D |
| I-16 | A | D |
| I-17 | B | D |
| I-18 | B | D |
| I-19 | C | D |
| I-20 | A | D |
| I-21 | A | D |
| I-22 | B | D |
| I-23 | B | D |
| I-24 | B | D |
| I-25 | B | A |
| I-26 | B | D |
| I-27 | B | D |
| I-28 | A | D |
| I-29 | A | D |
| I-30 | B | D |
| I-31 | A | D |
| I-32 | D | D |
| I-33 | A | D |
| I-34 | A | D |
| I-35 | B | D |
| I-36 | B | D |
| I-37 | A | A |
| I-38 | A | A |
| I-39 | A | D |
| I-40 | A | D |
| I-41 | A | D |
| I-42 | B | D |
| I-43 | D | D |
| I-44 | B | D |
| I-45 | B | D |
| I-46 | A | D |
| I-47 | D | D |
| I-48 | B | D |
| I-49 | B | D |
| I-50 | B | D |
| I-51 | B | D |
| I-52 | A | D |
| I-53 | A | D |
| I-54 | A | D |
| I-55 | B | D |
| I-56 | A | D |
| I-57 | B | D |
| I-58 | A | D |
| I-59 | A | D |
| I-60 | A | D |
| I-61 | A | D |
| I-62 | A | D |
| I-63 | A | D |
| I-64 | A | D |
| I-65 | A | D |
| I-66 | A | D |
| I-67 | A | D |
| I-68 | A | D |
| I-69 | A | D |
| I-70 | A | D |
| I-71 | B | D |
| I-72 | A | D |
| I-73 | B | D |

TABLE 4-continued

IRAK4 MSD Degradation in OCI-LY10 Results

| I-# | IRAK4 degradation in OCI-LY10 at 4 hrs: $DC_{50}$ (μM) | IRAK4 degradation in OCI-LY10 at 24 hrs: $DC_{50}$ (μM) |
|---|---|---|
| I-74 | A | D |
| I-75 | A | D |
| I-76 | A | D |
| I-77 | A | D |
| I-78 | A | D |
| I-79 | A | D |
| I-80 | B | D |
| I-81 | A | D |
| I-82 | D | D |
| I-83 | D | D |
| I-84 | D | D |
| I-85 | D | D |
| I-86 | D | D |
| I-87 | A | A |
| I-88 | B | D |
| I-89 | D | D |
| I-90 | D | D |
| I-91 | D | C |
| I-92 | D | D |
| I-93 | B | B |
| I-94 | D | D |
| I-95 | D | D |
| I-96 | D | D |
| I-97 | A | D |
| I-98 | A | D |
| I-99 | B | D |
| I-100 | B | D |
| I-101 | A | D |
| I-102 | B | D |
| I-103 | A | D |
| I-104 | B | D |
| I-105 | D | D |
| I-106 | A | D |
| I-107 | B | B |
| I-108 | D | D |
| I-109 | B | D |
| I-110 | B | B |
| I-111 | A | D |
| I-112 | B | D |
| I-113 | D | A |
| I-114 | A | D |
| I-115 | B | D |
| I-116 | D | B |
| I-117 | D | B |
| I-118 | D | B |
| I-119 | D | D |
| I-120 | D | D |
| I-121 | C | D |
| I-122 | D | B |
| I-123 | D | D |
| I-124 | D | D |
| I-125 | D | D |
| I-126 | D | D |
| I-127 | C | D |
| I-128 | B | D |
| I-129 | A | D |
| I-130 | D | B |
| I-131 | D | D |
| I-132 | D | D |
| I-133 | D | D |
| I-134 | D | D |
| I-135 | D | D |
| I-136 | D | D |
| I-137 | D | B |
| I-138 | D | A |
| I-139 | D | B |
| I-140 | D | B |
| I-141 | D | B |
| I-142 | D | A |
| I-143 | D | A |
| I-144 | A | A |
| I-145 | A | A |
| I-146 | D | B |
| I-147 | C | D |
| I-148 | B | D |
| I-149 | A | D |
| I-150 | B | D |
| I-151 | D | D |
| I-152 | D | D |
| I-153 | D | D |
| I-154 | D | D |
| I-155 | A | D |
| I-156 | D | B |
| I-157 | A | D |
| I-158 | A | D |
| I-159 | A | D |
| I-160 | A | A |
| I-161 | A | D |
| I-162 | A | D |
| I-163 | A | D |
| I-165 | A | D |
| I-164 | A | D |
| I-166 | B | D |
| I-167 | D | B |
| I-168 | D | D |
| I-169 | D | D |
| I-170 | D | B |
| I-171 | D | B |
| I-172 | D | B |
| I-173 | D | B |
| I-174 | D | D |
| I-175 | D | D |
| I-176 | D | D |
| I-177 | D | D |
| I-178 | D | D |
| I-179 | D | D |
| I-180 | D | D |
| I-181 | D | D |
| I-182 | D | D |
| I-183 | D | D |
| I-184 | D | D |
| I-185 | D | D |
| I-186 | D | D |
| I-187 | D | D |
| I-188 | A | D |
| I-189 | B | D |
| I-190 | B | D |
| I-191 | B | D |
| I-192 | D | D |
| I-193 | D | D |
| I-194 | D | D |
| I-195 | D | D |
| I-196 | D | B |
| I-197 | B | D |
| I-198 | B | B |
| I-199 | D | B |
| I-200 | B | D |
| I-201 | A | D |
| I-202 | A | D |
| I-203 | D | D |
| I-204 | A | D |
| I-205 | D | D |
| I-206 | D | D |
| I-207 | D | D |
| I-208 | D | D |
| I-209 | D | D |
| I-210 | D | D |
| I-211 | D | D |
| I-212 | D | D |
| I-213 | D | D |
| I-214 | D | D |
| I-215 | D | D |

TABLE 4-continued

IRAK4 MSD Degradation in OCI-LY10 Results

| I-# | IRAK4 degradation in OCI-LY10 at 4 hrs: $DC_{50}$ (μM) | IRAK4 degradation in OCI-LY10 at 24 hrs: $DC_{50}$ (μM) |
|---|---|---|
| I-216 | D | D |
| I-217 | D | D |
| I-218 | C | D |
| I-219 | D | D |
| I-220 | D | D |
| I-221 | D | B |
| I-222 | D | B |
| I-223 | D | B |
| I-224 | D | B |
| I-225 | D | A |
| I-226 | D | A |
| I-227 | D | B |
| I-228 | D | A |
| I-229 | D | B |
| I-230 | D | B |
| I-231 | D | D |
| I-232 | D | D |
| I-233 | D | D |
| I-234 | D | C |
| I-235 | D | B |
| I-236 | D | A |
| I-237 | D | B |
| I-238 | D | D |
| I-239 | D | D |
| I-240 | D | D |
| I-241 | D | C |
| I-242 | D | D |
| I-243 | D | D |
| I-244 | D | D |
| I-245 | D | B |
| I-246 | D | D |
| I-247 | D | A |
| I-248 | D | B |
| I-249 | D | D |
| I-250 | D | B |
| I-251 | D | D |
| I-252 | D | B |
| I-253 | D | D |
| I-254 | D | D |
| I-255 | D | D |
| I-256 | D | D |
| I-257 | D | D |
| I-258 | D | D |
| I-259 | D | D |
| I-260 | D | D |
| I-261 | D | D |
| I-262 | D | D |
| I-263 | D | D |
| I-264 | D | D |
| I-265 | D | D |
| I-266 | D | D |
| I-267 | D | D |
| I-268 | D | D |
| I-269 | D | D |
| I-270 | D | B |
| I-271 | D | A |
| I-272 | D | A |
| I-273 | D | A |
| I-274 | D | A |
| I-275 | D | A |
| I-276 | D | A |
| I-277 | D | A |
| I-278 | D | A |
| I-279 | D | D |
| I-280 | D | D |
| I-281 | D | D |
| I-282 | D | B |
| I-283 | D | B |
| I-284 | D | D |
| I-285 | D | D |
| I-286 | D | A |
| I-287 | D | A |
| I-288 | D | D |
| I-289 | D | D |
| I-290 | D | A |
| I-291 | D | A |
| I-292 | D | A |
| I-293 | D | D |
| I-294 | D | A |
| I-295 | D | A |
| I-296 | B | D |
| I-297 | D | D |
| I-298 | D | A |
| I-299 | D | A |
| I-300 | D | A |
| I-301 | D | D |
| I-302 | D | D |
| I-303 | D | A |
| I-304 | D | A |
| I-305 | D | D |
| I-306 | D | D |
| I-307 | D | A |
| I-308 | D | A |
| I-309 | D | A |
| I-310 | D | D |
| I-311 | D | D |
| I-312 | D | D |
| I-313 | D | D |
| I-314 | D | D |
| I-315 | D | A |
| I-316 | D | B |
| I-317 | D | D |
| I-318 | B | D |
| I-319 | D | A |
| I-320 | A | D |
| I-321 | D | A |
| I-322 | D | D |
| I-323 | D | D |
| I-324 | D | D |
| I-325 | D | D |
| I-326 | B | D |
| I-327 | D | A |
| I-328 | B | D |
| I-329 | B | D |
| I-330 | D | D |
| I-331 | B | D |
| I-332 | A | D |
| I-333 | D | D |
| I-334 | D | D |
| I-335 | D | D |
| I-336 | D | D |
| I-337 | D | A |
| I-338 | D | A |
| I-339 | A | D |
| I-340 | D | D |
| I-341 | D | D |
| I-342 | A | D |
| I-343 | D | A |
| I-344 | D | D |
| I-345 | B | D |
| I-348 | C | D |
| I-349 | B | D |
| I-351 | D | D |
| I-352 | B | D |
| I-353 | D | D |
| I-354 | D | D |
| I-355 | B | D |
| I-356 | D | A |
| I-357 | D | A |
| I-358 | D | D |
| I-359 | D | D |
| I-360 | D | A |

TABLE 4-continued

IRAK4 MSD Degradation in OCI-LY10 Results

| I-# | IRAK4 degradation in OCI-LY10 at 4 hrs: $DC_{50}$ (μM) | IRAK4 degradation in OCI-LY10 at 24 hrs: $DC_{50}$ (μM) |
|---|---|---|
| I-361 | D | D |
| I-362 | A | D |
| I-363 | D | D |
| I-364 | D | D |
| I-365 | D | D |
| I-366 | D | D |
| I-367 | D | D |
| I-368 | D | D |
| I-369 | A | D |
| I-370 | B | D |
| I-371 | D | D |
| I-372 | D | D |
| I-373 | D | D |
| I-374 | B | D |
| I-375 | D | D |
| I-376 | D | D |
| I-377 | D | D |
| I-378 | D | D |
| I-379 | D | D |
| I-380 | D | D |
| I-381 | D | D |
| I-382 | D | D |
| I-383 | D | D |
| I-384 | D | D |
| I-385 | A | D |
| I-386 | D | D |
| I-387 | A | D |
| I-388 | D | D |
| I-389 | B | D |
| I-390 | D | D |
| I-391 | D | D |
| I-392 | D | D |
| I-393 | D | D |
| I-394 | D | D |
| I-395 | D | D |
| I-396 | D | D |
| I-397 | D | D |
| I-398 | D | D |
| I-399 | A | D |
| I-400 | B | D |
| I-401 | D | D |
| I-402 | D | D |
| I-403 | D | D |
| I-404 | D | D |
| I-405 | D | D |
| I-406 | D | A |
| I-407 | D | D |
| I-408 | D | D |
| I-409 | D | D |
| I-410 | D | D |
| I-411 | D | D |
| I-412 | D | D |
| I-413 | D | D |
| I-414 | C | D |
| I-415 | D | D |
| I-416 | D | D |
| I-417 | D | D |
| I-418 | B | D |
| I-419 | B | D |
| I-420 | D | D |
| I-421 | B | D |
| I-422 | D | D |
| I-423 | D | D |
| I-424 | D | D |
| I-425 | A | D |
| I-426 | B | D |
| I-427 | D | A |
| I-428 | D | A |
| I-429 | D | D |
| I-430 | D | A |
| I-431 | D | A |
| I-432 | D | A |
| I-433 | D | A |
| I-434 | D | A |
| I-435 | D | D |
| I-436 | D | D |
| I-437 | B | D |
| I-438 | D | D |
| I-439 | A | D |
| I-440 | A | A |
| I-441 | A | A |
| I-442 | B | A |
| I-443 | D | D |
| I-444 | D | D |
| I-445 | D | D |
| I-446 | D | D |
| I-447 | D | A |
| I-448 | D | D |
| I-449 | D | D |
| I-450 | D | D |
| I-451 | D | D |
| I-452 | D | D |
| I-453 | D | D |
| I-454 | D | D |
| I-455 | D | D |
| I-456 | D | D |
| I-457 | D | D |
| I-458 | D | D |
| I-459 | D | D |
| I-460 | D | D |
| I-461 | D | D |
| I-462 | D | D |
| I-463 | D | D |
| I-464 | D | D |
| I-465 | D | D |
| I-466 | D | D |
| I-467 | D | D |
| I-468 | D | D |
| I-469 | D | D |
| I-470 | D | D |
| I-471 | D | D |
| I-472 | D | D |
| I-473 | D | D |
| I-474 | D | D |
| I-475 | D | D |
| I-476 | D | D |
| I-477 | D | D |
| I-478 | D | D |
| I-479 | D | D |
| I-480 | D | D |
| I-481 | D | D |
| I-482 | D | D |
| I-483 | D | D |
| I-484 | D | B |
| I-485 | D | B |
| I-486 | D | D |
| I-487 | D | D |
| I-488 | D | D |
| I-489 | D | D |
| I-490 | D | D |
| I-491 | D | D |
| I-492 | D | D |
| I-493 | D | D |
| I-494 | D | D |
| I-495 | D | D |
| I-496 | D | D |
| I-497 | D | D |
| I-498 | D | D |
| I-499 | D | D |
| I-500 | D | D |
| I-501 | D | D |
| I-502 | D | D |

TABLE 4-continued

IRAK4 MSD Degradation in OCI-LY10 Results

| I-# | IRAK4 degradation in OCI-LY10 at 4 hrs: DC$_{50}$ (μM) | IRAK4 degradation in OCI-LY10 at 24 hrs: DC$_{50}$ (μM) |
|---|---|---|
| I-503 | D | D |
| I-504 | D | D |
| I-505 | D | D |
| I-506 | D | D |
| I-507 | D | D |
| I-508 | D | D |
| I-509 | D | B |
| I-510 | D | B |
| I-511 | D | B |
| I-512 | D | B |
| I-513 | D | D |
| I-514 | D | D |
| I-515 | D | B |
| I-516 | D | D |
| I-517 | D | D |
| I-518 | D | D |
| I-519 | D | D |
| I-520 | D | D |
| I-521 | D | D |
| I-522 | D | B |
| I-523 | D | B |
| I-524 | D | B |
| I-525 | D | A |
| I-526 | D | B |
| I-527 | D | B |
| I-528 | D | B |
| I-529 | D | B |
| I-530 | D | B |
| I-531 | D | D |
| I-532 | D | D |
| I-533 | D | D |
| I-534 | D | B |
| I-535 | D | D |
| I-536 | D | D |
| I-537 | D | D |
| I-538 | D | D |
| I-539 | D | D |
| I-540 | D | D |
| I-541 | D | D |
| I-542 | D | D |
| I-543 | D | D |
| I-544 | D | B |
| I-545 | D | A |
| I-546 | D | D |
| I-547 | D | A |
| I-548 | D | A |
| I-549 | D | A |
| I-550 | D | A |
| I-551 | D | D |
| I-552 | D | B |
| I-553 | D | A |
| I-554 | D | B |
| I-555 | D | B |
| I-556 | D | D |
| I-557 | D | D |
| I-558 | D | D |
| I-559 | D | D |
| I-560 | D | D |
| I-561 | D | D |
| I-562 | D | A |
| I-563 | D | D |
| I-564 | D | D |
| I-565 | D | D |
| I-566 | D | D |
| I-567 | D | D |
| I-568 | D | D |
| I-569 | D | D |
| I-570 | D | D |
| I-571 | D | D |
| I-572 | D | D |
| I-573 | D | D |
| I-574 | D | D |
| I-575 | D | D |
| I-576 | D | A |
| I-577 | D | D |
| I-578 | D | A |
| I-579 | D | D |
| I-580 | D | A |
| I-581 | D | A |
| I-582 | D | D |
| I-583 | D | D |
| I-584 | D | D |
| I-585 | D | A |
| I-586 | D | A |
| I-587 | D | A |
| I-588 | D | A |
| I-589 | D | D |
| I-590 | D | D |
| I-591 | D | D |
| I-592 | D | D |
| I-593 | D | D |
| I-594 | D | D |
| I-595 | D | D |
| I-596 | D | D |
| I-597 | D | A |
| I-598 | D | A |
| I-599 | D | A |
| I-600 | D | D |
| I-601 | D | D |
| I-602 | D | D |
| I-603 | D | D |
| I-604 | D | D |
| I-605 | D | A |
| I-606 | D | A |
| I-607 | D | B |
| I-608 | D | D |
| I-609 | D | D |
| I-610 | D | D |
| I-611 | D | D |
| I-612 | D | D |
| I-613 | D | A |
| I-614 | D | A |
| I-615 | D | A |
| I-616 | D | A |
| I-617 | D | A |
| I-618 | D | A |
| I-619 | D | A |
| I-620 | D | D |
| I-621 | D | D |
| I-622 | D | D |
| I-623 | D | D |
| I-624 | D | D |
| I-625 | D | A |
| I-626 | D | D |
| I-627 | D | D |
| I-628 | D | D |
| I-629 | D | A |
| I-630 | D | D |
| I-631 | D | D |
| I-632 | D | D |
| I-633 | D | A |
| I-634 | D | D |
| I-635 | D | D |
| I-636 | D | D |
| I-637 | D | A |
| I-638 | D | A |
| I-639 | D | D |
| I-640 | D | D |
| I-641 | D | A |
| I-642 | D | D |
| I-643 | D | D |
| I-644 | D | D |

TABLE 4-continued

IRAK4 MSD Degradation in OCI-LY10 Results

| I-# | IRAK4 degradation in OCI-LY10 at 4 hrs: DC$_{50}$ (μM) | IRAK4 degradation in OCI-LY10 at 24 hrs: DC$_{50}$ (μM) |
|---|---|---|
| I-645 | D | A |
| I-646 | D | D |
| I-647 | D | D |
| I-648 | D | D |
| I-649 | D | A |
| I-650 | D | D |
| I-651 | D | D |
| I-652 | D | D |
| I-653 | D | A |
| I-654 | D | D |
| I-655 | D | D |
| I-656 | D | A |
| I-657 | D | D |
| I-658 | D | D |
| I-659 | D | D |
| I-660 | D | A |
| I-661 | D | D |
| I-662 | D | D |
| I-663 | D | D |
| I-664 | D | D |
| I-665 | D | D |
| I-666 | D | D |
| I-667 | D | D |
| I-668 | D | B |
| I-669 | D | A |
| I-670 | D | A |
| I-671 | D | A |
| I-672 | D | A |
| I-673 | D | A |
| I-674 | D | A |
| I-675 | D | A |
| I-676 | D | A |
| I-677 | D | A |
| I-678 | D | A |
| I-679 | D | A |
| I-680 | D | A |
| I-681 | D | A |
| I-682 | D | A |
| I-683 | D | A |
| I-684 | D | A |
| I-685 | D | A |
| I-686 | D | B |
| I-687 | D | A |
| I-688 | D | A |
| I-689 | D | A |
| I-690 | D | A |
| I-691 | D | D |
| I-692 | D | A |
| I-693 | D | A |
| I-694 | D | A |
| I-695 | D | A |
| I-696 | D | A |
| I-697 | D | A |
| I-698 | D | D |
| I-699 | D | D |
| I-700 | D | D |
| I-701 | D | A |
| I-702 | D | B |
| I-703 | D | A |
| I-704 | D | B |
| I-705 | D | A |
| I-706 | D | B |
| I-707 | D | A |
| I-708 | D | B |
| I-709 | D | B |
| I-710 | D | B |
| I-711 | D | A |
| I-712 | D | A |
| I-713 | D | A |
| I-714 | D | A |
| I-715 | D | A |
| I-716 | D | A |
| I-717 | D | A |
| I-718 | D | A |
| I-719 | D | A |
| I-720 | D | A |
| I-721 | D | A |
| I-722 | D | A |
| I-723 | D | A |
| I-724 | D | A |
| I-725 | D | D |
| I-726 | D | A |
| I-727 | D | A |
| I-728 | D | A |
| I-729 | D | A |
| I-730 | D | A |
| I-731 | D | A |
| I-732 | D | A |
| I-733 | D | A |
| I-734 | D | A |
| I-735 | D | A |
| I-736 | D | A |
| I-737 | D | B |
| I-738 | D | A |
| I-739 | D | A |
| I-740 | D | A |
| I-741 | D | A |
| I-742 | D | A |
| I-743 | D | A |
| I-744 | D | A |
| I-745 | D | A |
| I-746 | D | D |
| I-747 | D | D |
| I-748 | D | D |
| I-749 | D | D |
| I-750 | D | D |
| I-751 | D | D |
| I-752 | D | D |
| I-753 | D | D |
| I-754 | D | D |
| I-755 | D | D |
| I-756 | D | D |
| I-757 | D | D |
| I-758 | D | D |
| I-759 | D | D |
| I-760 | D | D |
| I-761 | D | D |
| I-762 | D | D |
| I-763 | D | D |
| I-764 | D | D |
| I-765 | D | D |
| I-766 | D | D |
| I-767 | D | D |
| I-768 | D | D |
| I-769 | D | D |
| I-770 | D | D |
| I-771 | D | D |
| I-772 | D | D |
| I-773 | D | D |
| I-774 | D | D |
| I-775 | D | D |
| I-776 | D | D |
| I-777 | D | D |
| I-778 | D | D |
| I-779 | D | D |
| I-780 | D | D |
| I-781 | D | D |
| I-782 | D | D |
| I-783 | D | D |
| I-784 | D | D |
| I-785 | D | D |
| I-786 | D | D |

TABLE 4-continued

IRAK4 MSD Degradation in OCI-LY10 Results

| I-# | IRAK4 degradation in OCI-LY10 at 4 hrs: $DC_{50}$ (μM) | IRAK4 degradation in OCI-LY10 at 24 hrs: $DC_{50}$ (μM) |
| --- | --- | --- |
| I-787 | D | D |
| I-788 | D | D |
| I-789 | D | D |
| I-790 | D | D |
| I-791 | D | D |
| I-792 | D | D |
| I-793 | D | D |
| I-794 | D | D |
| I-795 | D | D |
| I-796 | D | D |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The invention claimed is:

1. A compound selected from:

I-93

I-252 or a pharmaceutically acceptable salt thereof.

2. A pharmaceutical composition comprising a compound of claim 1, and a pharmaceutically acceptable carrier, adjuvant, or vehicle.

3. The pharmaceutical composition of claim 2, further comprising an additional therapeutic agent.

4. A method of degrading IRAK4 protein kinase in a patient or biological sample comprising administering to said patient, or contacting said biological sample with a compound of claim 1, or a pharmaceutical composition thereof.

5. A method of treating an IRAK4-mediated disorder, disease, or condition in a patient comprising administering to said patient a compound of claim 1, or a pharmaceutical composition thereof.

6. The method of claim 5, further comprising administration of an additional therapeutic agent.

7. A method of treating an autoimmune disease, an inflammatory disorder, or an immunodeficiency disorder in a patient comprising administering to said patient a compound of claim 1, or a pharmaceutical composition thereof.

8. The method of claim 7, wherein the disease or disorder is systemic lupus erythematosus, rheumatoid arthritis, polychondritis, scleroderma, Wegener granulomatosis, dermatomyositis, chronic active hepatitis, myasthenia gravis, Steven-Johnson syndrome, idiopathic sprue, ulcerative colitis, Crohn's disease, irritable bowel syndrome, celiac disease, periodontitis, hyaline membrane disease, kidney disease, glomerular disease, alcoholic liver disease, endocrine ophthalmopathy, Grave's disease, sarcoidosis, alveolitis, chronic hypersensitivity pneumonitis, multiple sclerosis, primary biliary cirrhosis, uveitis, Sjogren's syndrome, vernal keratoconjunctivitis, interstitial lung fibrosis, psoriatic arthritis, systemic juvenile idiopathic arthritis, nephritis, diverticulitis, interstitial cystitis, glomerulonephritis, chronic granulomatous disease, endometriosis, leptospirosis renal disease, glaucoma, retinal disease, aging, headache, pain, complex regional pain syndrome, cardiac hypertrophy, muscle wasting, catabolic disorders, obesity, fetal growth retardation, hypercholesterolemia, heart disease, chronic heart failure, mesothelioma, anhidrotic ectodermal dysplasia, Behcet's disease, incontinentia pigmenti, Paget's disease, pancreatitis, hereditary periodic fever syndrome, asthma, acute lung injury, acute respiratory distress syndrome, eosinophilia, hypersensitivities, anaphylaxis, nasal sinusitis, silica induced diseases, COPD, pulmonary disease, cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, Type 1 diabetes, Type 2 diabetes, appendicitis, atopic dermatitis, allergy, blepharitis, bronchiolitis, bronchitis, bursitis, cervicitis, cholangitis, cholecystitis, chronic graft rejection, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonia, polymyositis, proctitis, prostatitis, pyelonephritis, rhinitis, salpingitis, sinusitis, stomatitis, synovitis, tendonitis, tonsillitis, vaginitis, vasculitis, vulvitis, alopecia areata, erythema multiforma, dermatitis herpetiformis, scleroderma, vitiligo, hypersensitivity angiitis, urticaria, bullous pemphigoid, *Pemphigus vulgaris, Pemphigus foliaceus*, paraneoplastic pemphigus, epidermolysis bullosa acquisita, acute and chronic gout, chronic gouty arthritis, psoriasis, psoriatic arthritis, rheumatoid arthritis, juvenile rheumatoid arthritis, cryopyrin associated periodic syndrome, adult onset Still's disease, macrophage activation syndrome, primary and secondary hemophagocytic lymphohistiocytosis, familial Mediterranean fever, NLRP12 autoinflammatory syndrome, or osteoarthritis.

9. The method of claim 7, wherein the disease or disorder is ocular allergy, conjunctivitis, keratoconjunctivitis sicca, vernal conjunctivitis, allergic rhinitis, chronic rhinosinusitis with nasal polyps (CRSwNP), hemolytic anemia, aplastic anemia, pure red cell anemia, idiopathic thrombocytopenia, eosinophilia, hypereosinophilia, Loffler's syndrome, eosinophilic pneumonia, tropical eosinophilia, bronchopulmonary aspergillosis, polyarteritis nodosa, Churg-Strauss syndrome, eosinophilic granuloma, eosinophilic asthma, eosinophilic COPD, psoriasis, generalized pustular psoriasis, psoriasis vulgaris, contact dermatitis, atopic dermatitis, alopecia areata, erythema multiforma, dermatitis, herpetiformis, scleroderma, vitiligo, hypersensitivity angiitis, urticaria, bullous pemphigoid, lupus, erythematosus, systemic lupus erythematosus, *Pemphigus vulgaris, Pemphigus foliaceus*, paraneoplastic pemphigus, epidermolysis bullosa acquisita, acne vulgaris, hidradenitis suppurativa, Sweet Syndrome, pyoderma gangrenosum, allergic conditions of the skin, acute and chronic gout, chronic gouty arthritis, psoriasis, psoriatic arthritis, rheumatoid arthritis, juvenile rheumatoid arthritis, cryopyrin associated periodic syndrome, adult onset Still's disease, macrophage activation syndrome, primary and secondary hemophagocytic lymphohistiocytosis, familial Mediterranean fever, or NLRP12 autoinflammatory syndrome.

* * * * *